(12) United States Patent
Takasaki et al.

(10) Patent No.: US 9,145,415 B2
(45) Date of Patent: Sep. 29, 2015

(54) NITROGEN-CONTAINING HETEROCYCLIC COMPOUND OR SALT THEREOF

(71) Applicant: FUJIFILM Corporation, Tokyo (JP)

(72) Inventors: Masaru Takasaki, Ashigarakami-gun (JP); Toshiaki Tsujino, Ashigarakami-gun (JP); Shintarou Tanabe, Ashigarakami-gun (JP); Megumi Ookubo, Ashigarakami-gun (JP); Kimihiko Sato, Ashigarakami-gun (JP); Atsush Hirai, Ashigarakami-gun (JP); Daisuke Terada, Ashigarakami-gun (JP); Shinsuke Inuki, Ashigarakami-gun (JP); Shinsuke Mizumoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/516,337

(22) Filed: Oct. 16, 2014

(65) Prior Publication Data
US 2015/0045339 A1    Feb. 12, 2015

Related U.S. Application Data

(63) Continuation of application No. PCT/JP2013/061273, filed on Apr. 16, 2013.

(30) Foreign Application Priority Data

Apr. 17, 2012  (JP) .................................. 2012-094184
Mar. 15, 2013  (JP) .................................. 2013-082479

(51) Int. Cl.

| | |
|---|---|
| *A61K 31/505* | (2006.01) |
| *C07D 471/04* | (2006.01) |
| *C07D 403/12* | (2006.01) |
| *C07D 401/14* | (2006.01) |
| *C07D 213/74* | (2006.01) |
| *C07D 401/12* | (2006.01) |
| *C07D 405/12* | (2006.01) |
| *C07D 239/48* | (2006.01) |
| *C07D 239/49* | (2006.01) |
| *C07D 409/12* | (2006.01) |
| *C07D 401/06* | (2006.01) |
| *C07D 403/04* | (2006.01) |
| *C07D 403/14* | (2006.01) |
| *C07D 413/04* | (2006.01) |
| *C07D 413/12* | (2006.01) |
| *C07D 413/14* | (2006.01) |
| *C07D 417/12* | (2006.01) |
| *A61K 31/44* | (2006.01) |

(52) U.S. Cl.
CPC ............ *C07D 471/04* (2013.01); *C07D 213/74* (2013.01); *C07D 239/48* (2013.01); *C07D 239/49* (2013.01); *C07D 401/06* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 409/12* (2013.01); *C07D 413/04* (2013.01); *C07D 413/12* (2013.01); *C07D 413/14* (2013.01); *C07D 417/12* (2013.01); *A61K 31/44* (2013.01); *A61K 31/505* (2013.01)

(58) Field of Classification Search
CPC .. C07D 239/42; C07D 213/72; C07D 213/73; C07D 213/74; C07D 403/12; C07D 471/04; C07D 401/12; C07D 405/12; C07D 239/48; C07D 239/49; C07D 409/12; C07D 403/04; C07D 401/06; C07D 417/12; C07D 413/14; C07D 413/12; C07D 413/04; C07D 403/14; C07D 401/14; A61K 31/44; A61K 31/505
USPC ........... 544/298, 330, 331; 546/309; 514/272, 514/275
See application file for complete search history.

(56) References Cited

U.S. PATENT DOCUMENTS

| | | | | |
|---|---|---|---|---|
| 8,703,767 B2 * | 4/2014 | Bearss et al. | ................ | 514/234.2 |
| 2012/0035168 A1 * | 2/2012 | Brandl et al. | .............. | 514/230.5 |
| 2012/0149722 A1 * | 6/2012 | Lee et al. | ....................... | 514/272 |
| 2013/0059847 A1 * | 3/2013 | Bearss et al. | ................ | 514/234.2 |

FOREIGN PATENT DOCUMENTS

| | | |
|---|---|---|
| JP | 2009-515851 A | 4/2009 |
| WO | WO 9109856 A1 * | 7/1991 |
| WO | 2006/135713 A2 | 12/2006 |
| WO | WO 2007/054550 A1 | 5/2007 |
| WO | WO 2007/109120 A2 | 9/2007 |
| WO | 2009/095399 A2 | 8/2009 |

(Continued)

OTHER PUBLICATIONS

CAS Registry Nos. 1208542-16-8; 1211912-67-2; and 1370823-68-9.*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
J. Cools et al., 64 Cancer Research, 6385-6389 (2004).*
K.W. Pratz et al., 115 Blood, 1425-1432 (2010).*
D.G. Gilliland et al., 100 Blood, 1532-1542 (2002).*

(Continued)

*Primary Examiner* — Alexander R Pagano
(74) *Attorney, Agent, or Firm* — Birch, Stewart, Kolasch & Birch, LLP

(57) ABSTRACT

The object is to provide an Fms-like tyrosine kinase 3 (FLT3) inhibitor useful as a therapeutic agent for acute myeloid leukemia (AML). A novel nitrogen-containing heterocyclic compound represented by the general formula [1] or a salt thereof is provided. The compound or a salt thereof of the present invention can be used as an active ingredient of a pharmaceutical composition for a treatment of a disease or condition relating to FLT3, such as acute myeloid leukemia (AML) and acute promyelocytic leukemia (APL).

20 Claims, No Drawings

(56) References Cited

FOREIGN PATENT DOCUMENTS

| WO | WO 2010/129053 A2 | 11/2010 |
| WO | WO 2012064706 A1 * | 5/2012 |
| WO | WO 2012061303 A1 * | 10/2012 |
| WO | WO 2012135801 A1 * | 10/2012 |
| WO | WO 2012150952 A1 * | 11/2012 |

OTHER PUBLICATIONS deVries et al., 92 Haematologica, 1557-1560 (2007).*
D. Gilliland et al., 100 Blood 1532-1542 (2002).*
American Cancer Society, "Cancer Facts and Figures", 2012, pp. 9-24.
Brown et al., "FLT3 Inhibitors: a paradigm for the development therapeutics for paediatric cancer", European Journal of Cancer, 2004, vol. 40, pp. 707-721.
Choudhary et al., "AML-associated Flt3 kinase domain mutations show signal transduction differences compared with Flt3 ITD mutations", Blood, Jul. 2005, vol. 106, No. 1, pp. 265-273
International Search Report issued in PCT/JP2013/061273, mailed on Jun. 4, 2013.
Kiyoi et al., "Mechanism of constitutive activation of FLT3 with internal tandem duplication in the juxtamembrane domain", Oncogene, 2002, vol. 21, pp. 2555-2563.
PCT/ISA/237—Issued in PCT/JP2013/061273, mailed on Jun. 4, 2013.
Yokota et al., "Internal tandem duplication of the FLT3 gene is preferentially seen in acute myeloid leukemia and myelodysplastic syndrome among various hematological malignancies. A study on a large series of patients and cell lines", Leukemia, 1997, vol. 11, pp. 1605-1609.
International Preliminary Report on Patentability dated Oct. 30, 2014, issued in PCT/JP2013/061273 (Forms PCT/IB/326, PCT/IB/373, PCT/ISA/237 and PCT/IB/338).
Chinese Office Action issued in Chinese Patent Application No. 201380020839.X on Jul. 3, 2015.
Extended European Search Report issued in European Patent Application No. 13778349.4 on Aug. 26, 2015.

* cited by examiner

NITROGEN-CONTAINING HETEROCYCLIC COMPOUND OR SALT THEREOF

CROSS REFERENCE TO RELATED APPLICATIONS

This application is a Continuation of PCT International Application No. PCT/JP2013/061273, filed on Apr. 16, 2013, which claims priority under 35 U.S.C. 119 (a) to Patent Application No. 2012-094184 and Patent Application No. 2013-082479, filed in Japan on Apr. 17, 2012 and Mar. 15, 2013 respectively, all of which are hereby expressly incorporated by reference into the present application.

TECHNICAL FIELD

The present invention relates to a nitrogen-containing heterocyclic compound or a salt thereof that is useful as an Fms-like tyrosine kinase 3 inhibitor.

BACKGROUND ART

The Fms-like tyrosine kinase 3 (FLT3) is a protein belonging to the class III of receptor type tyrosine kinases, and it has five immnunoglobulin-like motifs in the N-terminus extracellular domain, and two kinase domains at the C-terminus. Expression of FLT3 is observed on normal CD34-positive human bone marrow precursor cells and dendritic cell progenitors, and it plays an important role for proliferation, differentiation, and so forth of these cells (Non-patent document 1). Further, the ligand (FL) of FLT3 is expressed in bone marrow stromal cells and T cells, and is one of the cytokines that affect the cytogenesis of many kinds of hematogenous systems, and stimulate proliferation of stem cells, precursor cells, dendritic cells, and natural killer cells through interactions with other growth factors.

FLT3 is dimerized upon binding of FL, and activated by autophosphorylation. As a result, phosphorylation of PI3 as well as AKT and ERK in the RAS signal transduction pathway is induced. FLT3 plays an important role for proliferation and differentiation of hematopoietic cells.

In normal bone marrow, expression of FLT3 is limited to early precursor cells, but in blood carcinoma, FLT3 is expressed at a high concentration, or FLT3 causes a mutation and thereby contributes to proliferation and malignant alteration of carcinoma through activation of the aforementioned signal transduction pathway. The blood carcinoma include, for example, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, myelodysplastic syndrome (MDS), and myeloproliferative disorder (MPD).

As for AML among the various kinds of blood carcinoma, several existing therapies are effective to a certain extent, but relapse and resistance are frequently observed, and it is still such an intractable carcinoma as the five-year survival rate for that carcinoma is about 24% (in the United States) (Non-patent document 2). One of the causes of the relapse and resistance thereof is gene mutation of the AML cells, and especially, gene mutation of FLT3 is confirmed most frequently. It is known that the FLT3 gene mutation includes internal tandem duplication (ITD) mutation observed near the membrane (Non-patent document 3) and activation mutation of the tyrosine kinase moiety (Non-patent document 4), and FLT3 is constantly activated even in the absence of the ligand to accelerate proliferation of cancer cells.

It is reported that the ITD mutation, in particular, is observed in about 30% of AML patients, and vital prognosis of the patients having this mutation is poor (Non-patent document 5).

It is thought that suppression of both the activation of FLT3 and the activation thereof by gene mutation is important for the treatment of AML and improvement of prognosis, and development of FLT3 inhibitor is conducted.

For example, AC220 (Ambit) is a compound that selectively inhibits a type III tyrosine kinase (FLT3, c-KIT, FMS, PDGFR), and it is developed with targeting AML (Patent document 1).

Further, drugs showing superior sustainability are also being developed by covalently bonding such an inhibitory compound to a biological protein. For example, Afatinib (BIBW2992) is reported as an EGFR inhibitor having acrylic group in the molecule (Patent document 2).

PRIOR ART REFERENCES

Patent Documents

Patent document 1: WO2007/109120 A2

Patent document 2: Japanese Patent Unexamined Publication (Kohyo) No. 2009-515851

Non-Patent Documents

Non-patent document 1: Brown P. et al., European Journal of Cancer, vol. 40, pp. 707-721, 2004

Non-patent document 2: American Cancer Society, Cancer Facts and Figures, pp. 9-24, 2012

Non-patent document 3: Yokota S. et al., Leukemia, vol. 11, pp. 1605-1609, 1997

Non-patent document 4: Choudhary C. et al., Blood, vol. 106, pp. 265-273, 2005

Non-patent document 5: Kiyoi H. et al., Oncogene, vol. 21, pp. 2555-2563, 2002

SUMMARY OF THE INVENTION

Object to be Achieved by the Invention

FLT3 inhibitor useful as a therapeutic agent for AML is strongly desired.

Means for Achieving the Object

The inventors of the present invention conducted various researches in order to solve the aforementioned problem, as a result, found that a compound represented by the general formula [1]:

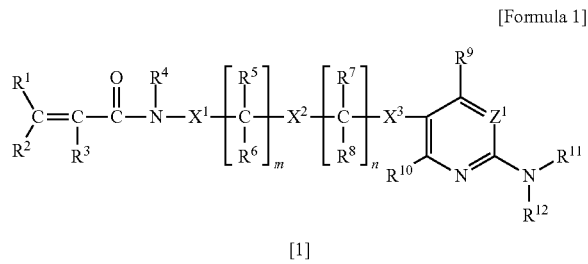

[1]

(in the formula, $R^1$ represents hydrogen atom or a $C_{1-6}$ alkyl group which may be substituted, $R^2$ represents hydrogen atom, a $C_{1-6}$ alkyl group which may be substituted, a $C_{2-6}$ alkenyl group which may be substituted or a $C_{2-6}$ alkynyl group which may be substituted, $R^3$ represents hydrogen atom, a $C_{1-6}$ alkyl group which may be substituted, a $C_{2-6}$ alkenyl group which may be substituted or a $C_{2-6}$ alkynyl group which may be substituted, or $R^2$ and $R^3$ may bind together to form an atomic bond, $R^4$ represents hydrogen atom, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted or an imino protecting group, m of $R^5$ are the same or different, and represent hydrogen atom or a $C_{1-6}$ alkyl group which may be substituted, m of $R^6$ are the same or different, and represent hydrogen atom or a $C_{1-6}$ alkyl group which may be substituted, or $R^5$ and $R^6$ binding to the same carbon atom may bind together to form a $C_{2-6}$ alkylene group which may be substituted, an O—($C_{1-6}$ alkylene) group which may be substituted, an N($R^{13}$)—($C_{1-6}$ alkylene) group which may be substituted (in the formula, $R^{13}$ represents hydrogen atom, a $C_{1-6}$ alkyl group which may be substituted or an imino protecting group), a ($C_{1-3}$ alkylene)-O—($C_{1-3}$ alkylene) group which may be substituted or a ($C_{1-3}$ alkylene)-N($R^{13}$)—($C_{1-3}$ alkylene) group which may be substituted (in the formula, $R^{13}$ has the same meanings as that defined above), n of $R^7$ are the same or different, and represent hydrogen atom or a $C_{1-6}$ alkyl group which may be substituted, n of $R^8$ are the same or different, and represent hydrogen atom or a $C_{1-6}$ alkyl group which may be substituted, or $R^7$ and $R^8$ binding to the same carbon atom may bind together to form a $C_{2-6}$ alkylene group which may be substituted, an O—($C_{1-6}$ alkylene) group which may be substituted, an N($R^{14}$)—($C_{1-6}$ alkylene) group which may be substituted (in the formula, $R^{14}$ represents hydrogen atom, a $C_{1-6}$ alkyl group which may be substituted or an imino protecting group), a ($C_{1-3}$ alkylene)-O—($C_{1-3}$ alkylene) group which may be substituted or a ($C_{1-3}$ alkylene)-N($R^{14}$)—($C_{1-3}$ alkylene) group which may be substituted (in the formula, $R^{14}$ has the same meaning as that defined above), $R^9$ represents a $C_{1-6}$ alkyl group which may be substituted, a $C_{3-8}$ cycloalkyl group which may be substituted, an aryl group which may be substituted, a $C_{1-6}$ alkoxy group which may be substituted, a heterocyclic group which may be substituted or N($R^{15}$)($R^{16}$) (in the formula, $R^{15}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, and $R^{16}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted, or $R^{15}$ and $R^{16}$ may form a cyclic amino group which may be substituted together with the nitrogen atom to which they bind), $R^{10}$ represents hydrogen atom, a halogen atom, a $C_{1-6}$ alkyl group which may be substituted, a $C_{3-8}$ cycloalkyl group which may be substituted, an aryl group which may be substituted, a $C_{1-6}$ alkoxy group which may be substituted or a heterocyclic group which may be substituted, $R^{11}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, $R^{12}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a heterocyclic group which may be substituted or a carbamoyl group which may be substituted, $X^1$ represents a group represented by the general formula [2]:

[Formula 2]

$$-X^4-X^5-$$ [2]

(in the formula, $X^4$ represents a divalent alicyclic hydrocarbon group which may be substituted, a divalent aromatic hydrocarbon group which may be substituted, a divalent heterocyclic group which may be substituted, a group represented by the general formula [3]

[3]

(in the formula, p of $R^{17}$ are the same or different, and represent hydrogen atom or a $C_{1-6}$ alkyl group which may be substituted, or one $R^{17}$ selected from p of $R^{17}$ may bind with $R^4$ to form a $C_{1-6}$ alkylene group which may be substituted, a ($C_{1-3}$ alkylene)-O group which may be substituted, a ($C_{1-3}$ alkylene)-N($R^{19}$) group which may be substituted (in the formula, $R^{19}$ represents hydrogen atom, a $C_{1-6}$ alkyl group which may be substituted or an imino protecting group), a ($C_{1-3}$ alkylene)-O—($C_{1-3}$ alkylene) group which may be substituted or a ($C_{1-3}$ alkylene)-N($R^{19}$)—($C_{1-3}$ alkylene) group which may be substituted (in the formula, $R^{19}$ has the same meanings as that defined above), p of $R^{18}$ are the same or different, and represent hydrogen atom or a $C_{1-6}$ alkyl group which may be substituted, or $R^{17}$ and $R^{18}$ binding to the same carbon atom may bind together to form a $C_{2-6}$ alkylene group which may be substituted, an O—($C_{1-6}$ alkylene) group which may be substituted, an N($R^{20}$)—($C_{1-6}$ alkylene) group which may be substituted (in the formula, $R^{20}$ represents hydrogen atom, a $C_{1-6}$ alkyl group which may be substituted or an imino protecting group), a ($C_{1-3}$ alkylene)-O—($C_{1-3}$ alkylene) group which may be substituted or a ($C_{1-3}$ alkylene)-N($R^{20}$)—($C_{1-3}$ alkylene) group which may be substituted (in the formula, $R^{20}$ has the same meanings as that defined above), and p represents an integer of 1 to 6), or an atomic bond, and $X^5$ represents oxygen atom, N($R^{21}$) (in the formula, $R^{21}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group, or $R^{21}$ may bind with $R^4$ to form a $C_{1-6}$ alkylene group which may be substituted), C(═O), C(═O)—N($R^{21}$) (in the formula, $R^{21}$ has the same meaning as that defined above), or an atomic bond), $X^2$ represents a $C_{1-6}$ alkylene group which may be substituted, a divalent alicyclic hydrocarbon group which may be substituted, a divalent aromatic hydrocarbon group which may be substituted or a divalent heterocyclic group which may be substituted, $X^3$ represents a $C_{1-6}$ alkylene group which may be substituted, a $C_{2-6}$ alkenylene group which may be substituted, a $C_{2-6}$ alkynylene group which may be substituted, an O—($C_{1-6}$ alkylene) group which may be substituted, an $S(O)_q$—($C_{1-6}$ alkylene) group which may be substituted (in the formula, q represents 0, 1 or 2), an $N(R^{22})$—($C_{1-6}$ alkylene) group which may be substituted (in the formula, $R^{22}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group), $N(R^{22})$—C(═O) (in the formula, $R^{22}$ has the same meaning as that defined above), or an atomic bond, $Z^1$ represents nitrogen atom or $C(R^{23})$ (in the formula, $R^{23}$ represents hydrogen atom, a halogen atom, a $C_{1-6}$ alkyl group which may be substituted, a $C_{3-8}$ cycloalkyl group which may be substituted, an aryl group which may be substituted, a $C_{1-6}$ alkoxy group which may be substituted or a heterocyclic group which may be substituted), m represents an integer of 0 to 6, and n represents an integer of 0 to 6) or a salt thereof is useful as an FLT3 inhibitor, and accomplished the present invention.

The present invention provides the followings.

(1) A compound represented by the general formula [1] defined above or a salt thereof.
(2) The compound or a salt thereof according to (1), wherein $Z^1$ is nitrogen atom.
(3) The compound or a salt thereof according to (1) or (2), wherein $X^3$ is a $C_{2-6}$ alkynylene group which may be substituted or $N(R^{22})$—C(═O) (in the formula, $R^{22}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group).
(4) The compound or a salt thereof according to (1) or (2), wherein $X^3$ is ethynylene group.
(5) The compound or a salt thereof according to any one of (1) to (4), wherein $R^1$ is hydrogen atom, and $R^2$ is a $C_{1-6}$ alkyl group which may be substituted.
(6) The compound or a salt thereof according to any one of (1) to (4), wherein $R^1$ is hydrogen atom, and $R^2$ is a $C_{1-6}$ alkyl group substituted with a di($C_{1-6}$ alkyl)amino group.
(7) The compound or a salt thereof according to any one of (1) to (6), wherein $R^9$ is $N(R^{15})(R^{16})$ (in the formula, $R^{15}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, and $R^{16}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted, or $R^{15}$ and $R^{16}$ may form a cyclic amino group which may be substituted together with the nitrogen atom to which they bind).
(8) The compound or a salt thereof according to (7), wherein $R^{15}$ is hydrogen atom, and $R^{16}$ is a $C_{1-6}$ alkyl group which may be substituted.
(9) The compound or a salt thereof according to any one of (1) to (8), wherein $R^{11}$ is hydrogen atom, and $R^{12}$ is an aryl group which may be substituted or a heterocyclic group which may be substituted.
(10) The compound or a salt thereof according to any one of (1) to (8), wherein $R^{11}$ is hydrogen atom, and $R^{12}$ is phenyl group which may be substituted, pyridyl group which may be substituted, pyrazolyl group which may be substituted, thienyl group which may be substituted, oxazolyl group which may be substituted, thiazolyl group which may be substituted, isothiazolyl group which may be substituted, indazolyl group which may be substituted, pyrazolopyridinyl group which may be substituted, quinolyl group which may be substituted, isoquinolyl group which may be substituted, cinnolinyl group which may be substituted, phthalazinyl group which may be substituted, quinoxalinyl group which may be substituted, benzofuranyl group which may be substituted or benzothiazolyl group which may be substituted.
(11) The compound or a salt thereof according to any one of (1) to (10), wherein $R^4$ is hydrogen atom or a $C_{1-6}$ alkyl group which may be substituted.
(12) The compound or a salt thereof according to any one of (1) to (10), wherein $R^4$ is hydrogen atom or methyl group.
(13) The compound or a salt thereof according to any one of (1) to (12), wherein $X^2$ is a $C_{1-6}$ alkylene group which may be substituted or a divalent alicyclic hydrocarbon group which may be substituted.
(14) The compound or a salt thereof according to any one of (1) to (13), wherein $X^1$ is a group represented by the general formula [2]:

[Formula 4]

$$-X^4-X^5-\qquad [2]$$

(in the formula, $X^4$ represents a group represented by the general formula [3]

[Formula 5]

[3]

(in the formula, p of $R^{17}$ are the same or different, and represent hydrogen atom or a $C_{1-6}$ alkyl group which may be substituted, p of $R^{18}$ are the same or different, and represent hydrogen atom or a $C_{1-6}$ alkyl group which may be substituted, and p represents an integer of 1 to 6), and $X^5$ represents C(═O)—$N(R^{21})$ (in the formula, $R^{2'}$ represents hydrogen atom)).
(15) The compound or a salt thereof according to any one of (1) to (14), wherein $R^3$ is hydrogen atom or a $C_{1-6}$ alkyl group which may be substituted.
(16) The compound or a salt thereof according to any one of (1) to (15), wherein $R^5$, $R^6$, $R^7$ and $R^8$ are hydrogen atoms.
(17) The compound or a salt thereof according to any one of (1) to (16), wherein $R^{10}$ is hydrogen atom.
(18) A compound represented by the general formula [1]-(1):

[Formula 6]

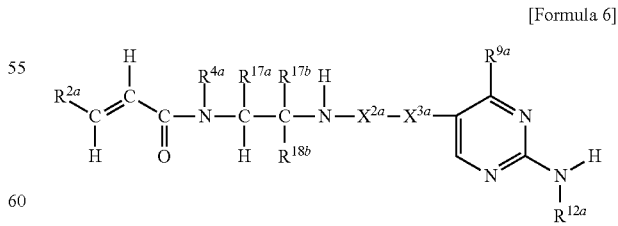

[1]-(1)

(in the formula,
$R^{2a}$ represents hydrogen atom or a $C_{1-6}$ alkyl group which may be substituted, $R^{4a}$ represents hydrogen atom or a $C_{1-6}$ alkyl group which may be substituted, $R^{17a}$ represents hydrogen atom or a $C_{1-6}$ alkyl group which may be substituted, provided that $R^{17a}$ may form a divalent nitrogen-containing heterocyclic group which may be substituted together with $R^{4a}$, the nitrogen atom to which $R^{4a}$ binds, and the carbon atom to which $R^{17a}$ binds, $R^{17b}$ and $R^{18b}$ are the same or different, and represent hydrogen atom or a $C_{1-6}$ alkyl group which may be substituted, provided that $R^{17b}$ and $R^{18b}$ may form C(=O) together with the carbon atom to which they bind, or $R^{17b}$ and $R^{18b}$ may form a heterocyclic group which may be substituted together with the carbon atom to which they bind, $R^{9a}$ represents a $C_{1-6}$ alkyl group which may be substituted, a $C_{1-6}$ alkoxy group which may be substituted, a heterocyclic group which may be substituted or $N(R^{15})(R^{16})$ (in the formula, $R^{15}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, and $R^{16}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted, or $R^{15}$ and $R^{16}$ may form a cyclic amino group which may be substituted together with the nitrogen atom to which they bind), $R^{12a}$ represents a $C_{1-6}$ alkyl group which may be substituted, an aryl group which may be substituted or a heterocyclic group which may be substituted, $X^{2a}$ represents a $C_{1-6}$ alkylene group which may be substituted, a divalent alicyclic hydrocarbon group which may be substituted or a divalent aromatic hydrocarbon group which may be substituted, and $X^{3a}$ represents a $C_{2-6}$ alkynylene group which may be substituted or $N(R^{22})$—C(=O) (in the formula, $R^{22}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group) or a salt thereof.

(19) The compound or a salt thereof according to (18), wherein $R^{2a}$ is a $C_{1-6}$ alkyl group which may be substituted, substituent of the $C_{1-6}$ alkyl group which may be substituted as $R^{2a}$ is a halogen atom, hydroxyl group, a $C_{1-6}$ alkylamino group which may be substituted with one or more groups selected from the substituent group A-3, a di($C_{1-6}$ alkyl) amino group which may be substituted with one or more groups selected from the substituent group A-3 or a heterocyclic group which may be substituted with one or more groups selected from the substituent group A-3, and the substituent group A-3 consists of a halogen atom, hydroxyl group which may be protected, and a $C_{1-6}$ alkyl group which may be substituted with hydroxyl group.

(20) The compound or a salt thereof according to (18) or (19), wherein $R^{4a}$ is hydrogen atom or a $C_{1-6}$ alkyl group.

(21) The compound or a salt thereof according to any one of (18) to (20), wherein $R^{17a}$ is hydrogen atom or a $C_{1-6}$ alkyl group.

(22) The compound or a salt thereof according to any one of (18) to (21), wherein $R^{17b}$ and $R^{18b}$ are a $C_{1-6}$ alkyl group, or $R^{17b}$ and $R^{18b}$ form C(=O) together with the carbon atom to which they bind.

(23) The compound or a salt thereof according to any one of (18) to (22), wherein $R^{9a}$ is $N(R^{15})(R^{16})$ (in the formula, $R^{15}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, and $R^{16}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted, or $R^{15}$ and $R^{16}$ may form a cyclic amino group which may be substituted together with the nitrogen atom to which they bind).

(24) The compound or a salt thereof according to any one of (18) to (23), wherein $R^{12a}$ is an aryl group which may be substituted.

(25) The compound or a salt thereof according to any one of (18) to (24), wherein $X^{2a}$ is a $C_{1-6}$ alkylene group which may be substituted or a divalent alicyclic hydrocarbon group which may be substituted.

(26) The compound or a salt thereof according to any one of (18) to (25), wherein $X^{3a}$ is a $C_{2-6}$ alkynylene group which may be substituted.

(27) A pharmaceutical composition containing the compound or a salt thereof according to any one of (1) to (26).

(28) The pharmaceutical composition according to (27), which is for treatment of a disease or condition relating to FLT3.

(29) The pharmaceutical composition according to (27), which is for treatment of acute myeloid leukemia.

(30) An FLT3 inhibitor containing the compound or salt thereof according to any one of (1) to (26).

The present invention also provides the followings.

(a) A compound represented by the general formula [1] defined above or a salt thereof, which is for use as a drug.

(b) A compound represented by the general formula [1] or a salt thereof, which is for use in treatment of a disease or condition relating to FLT3, preferably for use in treatment of acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, myelodysplastic syndrome (MDS), or myeloproliferative disorder (MPD), more preferably for use in treatment of AML or APL, further preferably for use in treatment of AML.

(c) A pharmaceutical composition containing a compound represented by the general formula [1] or a salt thereof together with a pharmaceutically acceptable additive.

(d) Use of a compound represented by the general formula [1] or a salt thereof for manufacture of a drug for use in treatment of a disease or condition relating to FLT3, preferably for use in treatment of acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, myelodysplastic syndrome (MDS), or myeloproliferative disorder (MPD), more preferably for use in treatment of AML or APL, further preferably for use in treatment of AML.

(e) A method for treatment of a disease or condition relating to FLT3, preferably for treatment of acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, myelodysplastic syndrome (MDS), or myeloproliferative disorder (MPD), more preferably for treatment of AML or APL, further preferably for treatment of AML, which comprises the step of administering a therapeutically effective amount of a compound represented by the general formula [1] or a salt thereof to an object (mammal including human) in need of such treatment.

Effect of the Invention

The nitrogen-containing heterocyclic compound or a salt thereof of the present invention has superior antitumor activity, and is useful as an FLT3 inhibitor.

BEST MODE FOR CARRYING OUT THE INVENTION

Hereafter, the present invention will be explained in detail.
The terms used for the present invention have the following meanings unless especially specified.

The halogen atom means fluorine atom, chlorine atom, bromine atom, or iodine atom.

The $C_{1-6}$ alkyl group means a linear or branched $C_{1-6}$ alkyl group such as methyl, ethyl, propyl, isopropyl, butyl, sec-butyl, isobutyl, tert-butyl, pentyl, isopentyl, and hexyl groups.

The $C_{1-3}$ alkyl group means methyl, ethyl, propyl, or isopropyl group.

The $C_{2-6}$ alkenyl group means a linear or branched $C_{2-6}$ alkenyl group such as vinyl, allyl, propenyl, isopropenyl, butenyl, isobutenyl, 1,3-butadienyl, pentenyl, and hexenyl groups.

The $C_{2-6}$ alkynyl group means a linear or branched $C_{2-6}$ alkynyl group such as ethynyl, propynyl, butynyl, pentynyl, and hexynil groups.

The $C_{3-8}$ cycloalkyl group means a $C_{3-8}$ cycloalkyl groups such as cyclopropyl, cyclobutyl, cyclopentyl, and cyclohexyl groups.

The aryl group means phenyl or naphthyl group.

The ar($C_{1-6}$ alkyl) group means an ar($C_{1-6}$ alkyl) group such as benzyl, diphenylmethyl, trityl, phenethyl, and naphthylmethyl groups.

The $C_{1-6}$ alkoxy group means a linear, cyclic, or branched $C_{1-6}$ alkyloxy group such as methoxy, ethoxy, propoxy, isopropoxy, cyclopropoxy, butoxy, isobutoxy, sec-butoxy, tert-butoxy, cyclobutoxy, pentyloxy, and hexyloxy groups.

The $C_{1-3}$ alkoxy group means methoxy, ethoxy, propoxy, or isopropoxy group.

The ($C_{1-6}$ alkoxy)-($C_{1-6}$ alkyl) group means a ($C_{1-6}$ alkyloxy)-($C_{1-6}$ alkyl) group such as methoxymethyl and 1-ethoxyethyl groups.

The ar($C_{1-6}$ alkoxy)-($C_{1-6}$ alkyl) group means an ar($C_{1-6}$ alkyloxy)-($C_{1-6}$ alkyl) group such as benzyloxymethyl and phenethyloxymethyl groups.

The $C_{2-6}$ alkanoyl group means a linear or branched $C_{2-6}$ alkanoyl group such as acetyl, propionyl, valeryl, isovaleryl, and pivaloyl groups.

The aroyl group means benzoyl or naphthoyl group.

The heterocyclylcarbonyl group means nicotinoyl, thenoyl, pyrrolidinocarbonyl, or furoyl group.

The (α-substituted)aminoacetyl group means an (α-substituted)aminoacetyl group derived from an amino acid (examples include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, and hydroxyproline), of which N-terminus may be protected.

The acyl group means formyl group, succinyl group, glutaryl group, maleoyl group, phthaloyl group, a $C_{2-6}$ alkanoyl group, aroyl group, a heterocyclylcarbonyl group, or an (α-substituted)aminoacetyl group.

The acyl($C_{1-6}$ alkyl) group means an acyl($C_{1-6}$ alkyl) group such as acetylmethyl, benzoylmethyl, and 1-benzoylethyl groups.

The acyloxy($C_{1-6}$ alkyl) group means an acyloxy($C_{1-6}$ alkyl) group such as acetoxymethyl, propionyloxymethyl, pivaloyloxymethyl, benzoyloxymethyl, and 1-(benzoyloxy)ethyl groups.

The $C_{1-6}$ alkoxycarbonyl group means a linear or branched $C_{1-6}$ alkyloxycarbonyl group such as methoxycarbonyl, ethoxycarbonyl, isopropoxycarbonyl, tert-butoxycarbonyl, and 1,1-dimethylpropoxycarbonyl groups.

The ar($C_{1-6}$ alkoxy)carbonyl group means an ar($C_{1-6}$ alkyl) oxycarbonyl group such as benzyloxycarbonyl and phenethyloxycarbonyl groups.

The aryloxycarbonyl group means phenyloxycarbonyl or naphthyloxycarbonyl group.

The $C_{1-6}$ alkylamino group means a linear or branched $C_{1-6}$ alkylamino group such as methylamino, ethylamino, propylamino, isopropylamino, butylamino, sec-butylamino tert-butylamino, pentylamino, and hexylamino groups.

The $C_{1-3}$ alkylamino group means methylamino, ethylamino, propylamino, or isopropylamino group.

The di($C_{1-6}$ alkyl)amino group means a linear or branched di($C_{1-6}$ alkyl)amino group such as dimethylamino, diethylamino, dipropylamino, diisopropylamino, dibutylamino, di(tert-butyl)amino, dipentylamino, dihexylamino, (ethyl)(methyl)amino," and (methyl)(propyl)amino groups.

The di($C_{1-3}$ alkyl)amino group means a linear or branched di($C_{1-3}$ alkyl)amino group such as dimethylamino, diethylamino, dipropylamino, diisopropylamino, (methyl)(ethyl)amino," and (methyl)(propyl)amino groups.

The $C_{1-6}$ alkylsulfonyl group means a $C_{1-6}$ alkylsulfonyl groups such as methylsulfonyl, ethylsulfonyl, and propylsulfonyl groups.

The arylsulfonyl group means benzenesulphonyl, p-toluenesulfonyl, or naphthalenesulfonyl group.

The $C_{1-6}$ alkylsulfonyloxy group means a $C_{1-6}$ alkylsulfonyloxy groups such as methylsulfonyloxy and ethylsulfonyloxy groups.

The arylsulfonyloxy group means benzenesulfonyloxy or p-toluenesulfonyloxy group.

The $C_{1-6}$ alkylsulfonylamino group means a $C_{1-6}$ alkylsulfonylamino groups such as methylsulfonylamino and ethylsulfonylamino groups.

The cyclic amino group means a cyclic amino group having a ring containing one or more nitrogen atoms as heteroatoms, which may further contain one or more atoms selected from oxygen atom and sulfur atoms, such as azetidinyl, pyrrolidinyl, pyrrolinyl, pyrrolyl, piperidinyl, tetrahydropyridyl, homopiperidinyl, imidazolidinyl, imidazolinyl, imidazolyl, pyrazolidinyl, pyrazolinyl, pyrazolyl, piperazinyl, homopiperazinyl, triazolyl, tetrazolyl, morpholinyl, thiomorpholinyl, tetrahydroquinolinyl, tetrahydroisoquinolinyl, and quinuclidinyl.

The monocyclic nitrogen-containing heterocyclic group means a monocyclic nitrogen-containing heterocyclic group containing only nitrogen atom as a heteroatom constituting the ring, such as azetidinyl, pyrrolidinyl, pyrrolinyl, pyrrolyl, piperidyl, tetrahydropyridyl, pyridyl, homopiperidinyl, octahydroazocinyl, imidazolidinyl, imidazolinyl, imidazolyl, pyrazolidinyl, pyrazolinyl, pyrazolyl, piperazinyl, pyrazinyl, pyridazinyl, pyrimidinyl, homopiperazinyl, triazolyl, and tetrazolyl groups.

The monocyclic oxygen-containing heterocyclic group means tetrahydrofuranyl, furanyl, tetrahydropyranyl, or pyranyl group.

The monocyclic sulfur-containing heterocyclic group means thienyl group.

The monocyclic nitrogen and oxygen-containing heterocyclic group means a monocyclic nitrogen and oxygen-containing heterocyclic group containing only nitrogen atom and oxygen atom as heteroatoms constituting the ring, such as oxazolyl, isoxazolyl, oxadiazolyl, and morpholinyl groups.

The monocyclic nitrogen and sulfur-containing heterocyclic group means a monocyclic nitrogen and sulfur-containing heterocyclic group containing only nitrogen atom and sulfur atom as heteroatoms constituting the ring, such as thiazolyl, isothiazolyl, thiadiazolyl, thiomorpholinyl, 1-oxidothiomorpholinyl, and 1,1-dioxidothiomorpholinyl groups.

The monocyclic heterocyclic group means a monocyclic nitrogen-containing heterocyclic group, a monocyclic oxygen-containing heterocyclic group, a monocyclic sulfur-containing heterocyclic group, a monocyclic nitrogen and oxygen-containing heterocyclic group, or a monocyclic nitrogen and sulfur-containing heterocyclic group.

The bicyclic nitrogen-containing heterocyclic group means a bicyclic nitrogen-containing heterocyclic group containing only nitrogen atom as a heteroatom constituting the ring, such as indolinyl, indolyl, isoindolinyl, isoindolyl, benzimidazolyl, indazolyl, benzotriazolyl, pyrazolopyridinyl, quinolyl, tetrahydroquinolinyl, quinolyl, tetrahydroisoquinolinyl, isoquinolinyl, quinolidinyl, cinnolinyl, phthalazinyl, quinazolinyl, dihydroquinoxalinyl, quinoxalinyl, naphthylidinyl, purinyl, pteridinyl, and quinuclidinyl groups.

The bicyclic oxygen-containing heterocyclic group means a bicyclic oxygen-containing heterocyclic group containing only oxygen atom as a heteroatom constituting the ring, such as 2,3-dihydrobenzofuranyl, benzofuranyl, isobenzofuranyl, cromanyl, chromenyl, isocromanyl, 1,3-benzodioxolyl, 1,3-benzodioxanyl, and 1,4-benzodioxanyl groups.

The bicyclic sulfur-containing heterocyclic group means a bicyclic sulfur-containing heterocyclic group containing only sulfur atom as a heteroatom constituting the ring, such as 2,3-dihydrobenzothienyl and benzothienyl groups.

The bicyclic nitrogen and oxygen-containing heterocyclic group means a bicyclic nitrogen and oxygen-containing heterocyclic group containing only nitrogen atom and oxygen atom as heteroatoms constituting the ring, such as benzoxazolyl, benzoisoxazolyl, benzoxadiazolyl, benzomorpholinyl, dihydropyranopyridyl, dihydrodioxynopyridyl, and dihydropyridoxadinyl groups.

The bicyclic nitrogen and sulfur-containing heterocyclic group means a bicyclic nitrogen and sulfur-containing heterocyclic group containing only nitrogen atom and sulfur atom as heteroatoms constituting the ring, such as benzothiazolyl, benzoisothiazolyl, and benzothiadiazolyl groups.

The bicyclic heterocyclic group means a bicyclic nitrogen-containing heterocyclic group, a bicyclic oxygen-containing heterocyclic group, a bicyclic sulfur-containing heterocyclic group, a bicyclic nitrogen and oxygen-containing heterocyclic group, or a bicyclic nitrogen and sulfur-containing heterocyclic group.

The heterocyclic group means a monocyclic heterocyclic group or a bicyclic heterocyclic group.

The $C_{1-6}$ alkylene group means a linear or branched $C_{1-6}$ alkylene group such as methylene, ethylene, propylene, butylene, and hexylene groups.

The $C_{2-6}$ alkylene group means a linear or branched $C_{2-6}$ alkylene group such as ethylene, propylene, butylene, and hexylene groups.

The $C_{1-3}$ alkylene group means methylene, ethylene, or propylene group.

The $C_{2-6}$ alkenylene group means a linear or branched $C_{2-6}$ alkenylene group such as vinylene, propenylene, butenylene, and pentenylene groups.

The $C_{2-6}$ alkynylene group means a linear or branched $C_{2-6}$ alkynylene group such as ethynylene, propynylene, butynylene, and pentynylene groups.

The divalent alicyclic hydrocarbon group means a group formed by eliminating two hydrogen atoms from an alicyclic hydrocarbon ring, such as 1,2-cyclobutylene, 1,3-cyclobutylene, 1,2-cyclopentylene, 1,3-cyclopentylene, 1,2-cyclohexylene, 1,4-cyclohexylene, bicyclo(3.2.1)octylene, bicyclo(2.2.0)hexylene, and bicyclo(5.2.0)nonylene groups.

The divalent 4-, 5- or 6-membered alicyclic hydrocarbon residue means a group formed by eliminating two hydrogen atoms from a 4-, 5- or 6-membered alicyclic hydrocarbon ring, such as 1,2-cyclobutylene, 1,3-cyclobutylene, 1,2-cyclopentylene, 1,3-cyclopentylene, 1,2-cyclohexylene, 1,3-cyclohexylene, 1,4-cyclohexylene, bicyclo(3.2.1)octylene, and bicyclo(2.2.0)hexylene.

The divalent aromatic hydrocarbon group means a group formed by removing two hydrogen atoms from an aromatic hydrocarbon ring, such as phenylene, indenylene, naphthylene, fluorenylene, phenanthrenylene, anthrylene, and pyrenylene groups.

The divalent nitrogen-containing heterocyclic group means a group formed by removing two hydrogen atoms from nitrogen-containing heterocyclic ring, such as azetidinediyl, pyrrolidinediyl, pyrrolinediyl, piperidinediyl, tetrahydropyridinediyl, homopiperidinediyl, imidazolidinediyl, imidazolinediyl, pyrazolidinediyl, piperazinediyl, and homopiperazinediyl.

The divalent heterocyclic group means a group formed by removing two hydrogen atoms from a heterocyclic ring, such as pyrrolinediyl, furandiyl, thiophenediyl, pyrazinediyl, pyridinediyl, and pyrimidinediyl groups.

The silyl group means trimethylsilyl, triethylsilyl, or tributylsilyl group.

Examples of the leaving group include a halogen atom, a $C_{1-6}$ alkylsulfonyloxy group, and an arylsulfonyloxy group. The $C_{1-6}$ alkylsulfonyloxy group, and arylsulfonyloxy group may be substituted.

The amino protecting group may be any group that can be used as a usual protective group of amino group. Examples include, for example, the groups mentioned in T. W. Greene et al., Protective Groups in Organic Synthesis, 4 th Edition, pp. 696-926, 2007, John Wiley & Sons, Inc. Specific examples include an ar($C_{1-6}$ alkyl) group, a ($C_{1-6}$ alkoxy)($C_{1-6}$ alkyl) group, an acyl group, a $C_{1-6}$ alkoxycarbonyl group, an ar($C_{1-6}$ alkoxy)carbonyl group, aryloxycarbonyl group, a $C_{1-6}$ alkylsulfonyl group, an arylsulfonyl group, and a silyl group.

The imino protecting group may be any group that can be used as a usual protective group of imino group. Examples include, for example, the groups mentioned in T. W. Greene et al., Protective Groups in Organic Synthesis, 4 th Edition, pp. 696-868, 2007, John Wiley & Sons, Inc. Specific examples include an ar($C_{1-6}$ alkyl) group, a ($C_{1-6}$ alkoxy)($C_{1-6}$ alkyl) group, an acyl group, a $C_{1-6}$ alkoxycarbonyl group, an ar($C_{1-6}$ alkoxy)carbonyl group, an aryloxycarbonyl group, a $C_{1-6}$ alkylsulfonyl group, an arylsulfonyl group, and a silyl group.

The hydroxyl protecting group may be any group that can be used as a usual protective group of hydroxyl group. Examples include, for example, the groups mentioned in T.

W. Greene et al., Protective Groups in Organic Synthesis, 4 th Edition, pp. 16-299, 2007, John Wiley & Sons, Inc. Specific examples include a $C_{1-6}$ alkyl group, a $C_{2-6}$ alkenyl group, an ar($C_{1-6}$ alkyl) group, a ($C_{1-6}$ alkoxy)($C_{1-6}$ alkyl) group, an ar($C_{1-6}$ alkoxy)($C_{1-6}$ alkyl) group, an acyl group, a $C_{1-6}$ alkoxycarbonyl group, an ar($C_{1-6}$ alkoxy)carbonyl group, a $C_{1-6}$ alkylsulfonyl group, an arylsulfonyl group, a silyl group, tetrahydrofuranyl group, and tetrahydropyranyl group.

The carboxyl protecting group may be any group that can be used as a usual protective group of carboxyl group. Examples include, for example, the groups mentioned in T. W. Greene et al., Protective Groups in Organic Synthesis, 4 th Edition, pp. 533-643, 2007, John Wiley & Sons, Inc. Specific examples include a $C_{1-6}$ alkyl group, a $C_{2-6}$ alkenyl group, an aryl group, an ar($C_{1-6}$ alkyl) group, a ($C_{1-6}$ alkoxy)($C_{1-6}$ alkyl) group, an ar($C_{1-6}$ alkoxy)($C_{1-6}$ alkyl) group, an acyl($C_{1-6}$ alkyl) group, an acyloxy($C_{1-6}$ alkyl) group, and a silyl group.

The halogenated hydrocarbon means methylene chloride, chloroform, or dichloroethane.

The ether means diethyl ether, diisopropyl ether, dioxane, tetrahydrofuran, anisole, ethylene glycol dimethyl ether, diethylene glycol dimethyl ether, or diethylene glycol diethyl ether.

The alcohol means methanol, ethanol, propanol, 2-propanol, butanol, or 2-methyl-2-propanol.

The ketone means acetone, 2-butanone, 4-methyl-2-pentanone, or methyl isobutyl ketone.

The ester means methyl acetate, ethyl acetate, propyl acetate, or butyl acetate.

The amide means N,N-dimethylformamide, N,N-dimethylacetamide, or N-methylpyrrolidone.

The nitrile means acetonitrile or propionitrile.

The sulfoxide means dimethyl sulfoxide or sulfolane.

The aromatic hydrocarbon means benzene, toluene, or xylene.

The inorganic base means sodium hydroxide, potassium hydroxide, tert-butoxysodium, tert-butoxypotassium, sodium hydrogencarbonate, sodium carbonate, potassium carbonate, or cesium carbonate.

The organic base means triethylamine, N,N-diisopropylethylamine, 1,8-diazabicyclo(5.4.0)undec-7-ene (DBU), 4-dimethylaminopyridine, or N-methylmorpholine.

The palladium catalyst means metal palladium such as palladium/carbon and palladium black; an inorganic palladium salt such as palladium chloride; an organic palladium salt such as palladium acetate; an organic palladium complex such as tetrakis(triphenylphosphine)palladium(0), bis(triphenylphosphine)palladium(II) dichloride, 1,1'-bis-(diphenylphosphino)fenocenepalladium(II) dichloride, (E)-di(μ-acetato)bis(o-(di-o-tolylphosphino)benzyl)dipalladium (II), and tris(dibenzylideneacetone)dipalladium(0); or a polymer-immobilized organic palladium complex such as polymer-supported bis(acetato)triphenylphosphinepalladium(II) and polymer-supported di(acetate)dicyclohexylphenylphosphinepalladium(II).

The ligand means a trialkylphosphine such as trimethylphosphine and tri-tert-butylphosphine; a tricycloalkylphosphine such as tricyclohexylphosphine; a triarylphosphine such as triphenylphosphine and tritolylphosphine; a trialkyl phosphite such as trimethyl phosphite, triethyl phosphite and tributyl phosphite; a tricycloalkyl phosphite such as tricyclohexyl phosphite; a triaryl phosphite such as triphenyl phosphite; an imidazolium salt such as 1,3-bis(2,4,6-trimethylphenyl)imidazolium chloride; a diketone such as acetylacetone and octafluoroacetylacetone; an amine such as trimethylamine, triethylamine, tripropylamine, and triisopropylamine; 1,1'-bis-(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, 4,5'-bis(diphenylphosphino)-9,9'-dimethylxanthene, or 2-(di-tert-butylphosphino)biphenyl.

Examples of the salt of the compound of Formula [1] include a usually known salt of a basic group such as an amino group, or an acidic group such as hydroxyl group or carboxyl group.

Examples of the salt of the basic group include salts with a mineral acid such as hydrochloric acid, hydrobromic acid, nitric acid, and sulfuric acid; salts with an organic carboxylic acid such as formic acid, acetic acid, citric acid, oxalic acid, fumaric acid, maleic acid, succinic acid, malic acid, tartaric acid, aspartic acid, trichloroacetic acid, and trifluoroacetic acid; and salts with a sulfonic acid such as methanesulfonic acid, benzenesulfonic acid, p-toluenesulfonic acid, mesitylenesulfonic acid, and naphthalenesulfonic acid.

Examples of the salt of an acidic group include salts with an alkali metal such as sodium or potassium; salts with an alkaline earth metal such as calcium or magnesium; ammonium salts; and salts with an nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Among the aforementioned salts, preferred examples of the salt include pharmacologically acceptable salts.

The compound of the present invention is a compound represented by the general formula [1]:

[Formula 7]

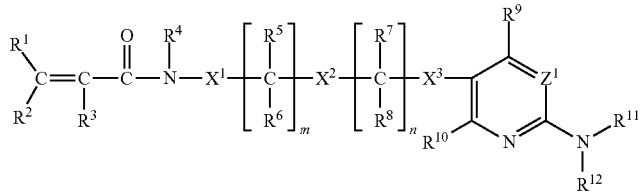

[1]

(in the formula, $R^1$, $R^2$, $R^3$, $R^4$, $R^5$, $R^6$, $R^7$, $R^8$, $R^9$, $R^{10}$, $R^{11}$, $R^{12}$, $X^1$, $X^2$, $X^3$, $Z^1$, m and n have the same meanings as those defined above).

$R^1$ represents hydrogen atom or a $C_{1-6}$ alkyl group which may be substituted, preferably hydrogen atom.

Regardless of the types of the other substituents, the $C_{1-6}$ alkyl group as $R^1$ may be substituted with one or more groups selected from a halogen atom, cyano group, amino group which may be protected, and hydroxyl group which may be protected. The $C_{1-6}$ alkyl group mentioned above is preferably a $C_{1-3}$ alkyl group.

$R^2$ represents hydrogen atom, a $C_{1-6}$ alkyl group which may be substituted, a $C_{2-6}$ alkenyl group which may be substituted or a $C_{2-6}$ alkynyl group which may be substituted, preferably hydrogen atom or a $C_{1-6}$ alkyl group which may be substituted, more preferably a $C_{1-6}$ alkyl group which may be substituted. The $C_{1-6}$ alkyl group which may be substituted mentioned above is preferably a $C_{1-3}$ alkyl group which may be substituted, more preferably methyl group or ethyl group which may be substituted, further preferably methyl group which may be substituted.

Regardless of the types of the other substituents, the $C_{1-6}$ alkyl group, $C_{2-6}$ alkenyl group or $C_{2-6}$ alkynyl group as $R^2$ may be substituted with one or more substituents selected from a halogen atom, cyano group, amino group which may be protected, hydroxyl group which may be protected, a $C_{1-6}$ alkoxy group which may be substituted with one or more groups selected from the substituent group A, an acyl group which may be substituted with one or more groups selected from the substituent group A, a $C_{1-6}$ alkoxycarbonyl group which may be substituted with one or more groups selected from the substituent group A, a $C_{1-6}$ alkylamino group which may be substituted with one or more groups selected from the substituent group A, a di($C_{1-6}$ alkyl)amino group which may be substituted with one or more groups selected from the substituent group A, a $C_{1-6}$ alkylsulfonyl group which may be substituted with one or more groups selected from the substituent group A, a $C_{1-6}$ alkylsulfonylamino group which may be substituted with one or more groups selected from the substituent group A, and a heterocyclic group which may be substituted with one or more groups selected from the substituent group A.

The substituent group A consists of a halogen atom, cyano group, amino group which may be protected, hydroxyl group which may be protected, a $C_{1-6}$ alkyl group which may be substituted with one or more groups selected from the substituent group B, a $C_{3-8}$ cycloalkyl group which may be substituted with one or more groups selected from the substituent group B, an aryl group which may be substituted with one or more groups selected from the substituent group B, a $C_{1-6}$ alkoxy group which may be substituted with one or more groups selected from the substituent group B, a $C_{1-6}$ alkylamino group which may be substituted with one or more groups selected from the substituent group B, a di($C_{1-6}$ alkyl)amino group which may be substituted with one or more groups selected from the substituent group B, a heterocyclic group which may be substituted with one or more groups selected from the substituent group B, and oxo group.

The substituent group B consists of a halogen atom, cyano group, amino group which may be protected, hydroxyl group which may be protected, a $C_{1-6}$ alkyl group which may be substituted with a halogen atom or hydroxyl group, a $C_{1-6}$ alkoxy group which may be substituted with a halogen atom or hydroxyl group, an aryl group, a heterocyclic group, and oxo group.

The substituent of the $C_{1-6}$ alkyl group which may be substituted, the $C_{2-6}$ alkenyl group which may be substituted or the $C_{2-6}$ alkynyl group which may be substituted as $R^2$ is preferably a halogen atom, hydroxyl group, a $C_{1-6}$ alkylamino group which may be substituted with one or more groups selected from the substituent group A-1, a di($C_{1-6}$ alkyl) amino group which may be substituted with one or more groups selected from the substituent group A-1, or a heterocyclic group which may be substituted with one or more groups selected from the substituent group A-1.

The halogen atom mentioned above is preferably fluorine atom, chlorine atom or bromine atom, more preferably bromine atom.

The $C_{1-6}$ alkylamino group is preferably a $C_{1-3}$ alkylamino group, more preferably methylamino group or ethylamino group, further preferably methylamino group.

The di($C_{1-6}$ alkyl)amino group is preferably a di($C_{1-3}$ alkyl) amino group, more preferably dimethylamino group, diethylamino group or (methyl)(ethyl)amino group, further preferably dimethylamino group.

The heterocyclic group is preferably azetidinyl group, piperazinyl group or morpholinyl group.

The substituent group A-1 consists of a halogen atom, hydroxyl group which may be protected, and a $C_{1-6}$ alkyl group which may be substituted with hydroxyl group. The halogen atom mentioned above is preferably fluorine atom, chlorine atom or bromine atom, more preferably fluorine atom.

The $C_{1-6}$ alkyl group is preferably a $C_{1-3}$ alkyl group, more preferably methyl group or ethyl group, further preferably methyl group.

$R^2$ is preferably a $C_{1-6}$ alkyl group substituted with a substituent selected from the group consisting of a $C_{1-6}$ alkylamino group which may be substituted with one or more groups selected from the substituent group A-1 and a di($C_{1-6}$ alkyl)amino group which may be substituted with one or more groups selected from the substituent group A-1, more preferably a $C_{1-6}$ alkyl group substituted with a substituent selected from the group consisting of a $C_{1-6}$ alkylamino group and a di($C_{1-6}$ alkyl)amino group, further preferably a $C_{1-6}$ alkyl group substituted with a di($C_{1-6}$ alkyl)amino group.

The $C_{1-6}$ alkyl group substituted with a di($C_{1-6}$ alkyl)amino group mentioned above is preferably a $C_{1-3}$ alkyl group substituted with a di($C_{1-3}$ alkyl)amino group, more preferably methyl group or ethyl group substituted with a di($C_{1-3}$ alkyl) amino group, further preferably a di($C_{1-3}$ alkyl)aminomethyl group.

The di($C_{1-3}$ alkyl)aminomethyl group is preferably diethylaminomethyl group or dimethylaminomethyl group, more preferably dimethylaminomethyl group.

$R^3$ is hydrogen atom, a $C_{1-6}$ alkyl group which may be substituted, a $C_{2-6}$ alkenyl group which may be substituted or a $C_{2-6}$ alkynyl group which may be substituted, and $R^2$ and $R^3$ may bind together to form an atomic bond. $R^3$ is preferably hydrogen atom, a $C_{1-6}$ alkyl group, a $C_{2-6}$ alkenyl group, or a $C_{2-6}$ alkynyl group, or $R^2$ and $R^3$ preferably bind together to form an atomic bond, and $R^3$ is more preferably hydrogen atom or a $C_{1-6}$ alkyl group, further preferably hydrogen atom.

Regardless of the types of the other substituents, the $C_{1-6}$ alkyl group, $C_{2-6}$ alkenyl group, or $C_{2-6}$ alkynyl group as $R^3$ may be substituted with one or more groups selected from a halogen atom, cyano group, amino group which may be protected and hydroxyl group which may be protected.

$R^4$ is hydrogen atom, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted or an imino protecting group, preferably hydrogen atom or a $C_{1-6}$ alkyl group, more preferably a $C_{1-6}$ alkyl group.

The $C_{1-6}$ alkyl group mentioned above is preferably a $C_{1-3}$ alkyl group, more preferably methyl group or ethyl group, further preferably methyl group.

Regardless of the types of the other substituents, the $C_{1-6}$ alkyl group, $C_{2-6}$ alkenyl group, $C_{2-6}$ alkynyl group or $C_{3-8}$ cycloalkyl group as $R^4$ may be substituted with one or more groups selected from a halogen atom, cyano group, amino group which may be protected, hydroxyl group which may be protected, an aryl group which may be substituted with one or more groups selected from the substituent group A, and a heterocyclic group which may be substituted with one or more groups selected from the substituent group A.

m of $R^5$ are the same or different, and represent hydrogen atom or a $C_{1-6}$ alkyl group which may be substituted, preferably hydrogen atom or a $C_{1-6}$ alkyl group, more preferably hydrogen atom.

m of $R^6$ are the same or different, and represent hydrogen atom or a $C_{1-6}$ alkyl group which may be substituted, or $R^5$ and $R^6$ binding to the same carbon atom may bind together to form a $C_{2-6}$ alkylene group which may be substituted, an O—($C_{1-6}$ alkylene) group which may be substituted, an $N(R^{13})$—($C_{1-6}$ alkylene) group which may be substituted (in the formula, $R^{13}$ has the same meaning as that defined above), a ($C_{1-3}$ alkylene)-O—($C_{1-3}$ alkylene) group which may be substituted or a ($C_{1-3}$ alkylene)-$N(R^{13})$—($C_{1-3}$ alkylene) group which may be substituted (in the formula, $R^{13}$ has the same meanings as that defined above), and $R^6$ preferably represents hydrogen atom or a $C_{1-6}$ alkyl group, more preferably hydrogen atom.

n of $R^7$ are the same or different, and represent hydrogen atom or a $C_{1-6}$ alkyl group which may be substituted, preferably hydrogen atom or a $C_{1-6}$ alkyl group, more preferably hydrogen atom.

n of $R^8$ are the same or different, and represent hydrogen atom or a $C_{1-6}$ alkyl group which may be substituted, or $R^7$ and $R^8$ binding to the same carbon atom may bind together to form a $C_{2-6}$ alkylene group which may be substituted, an O—($C_{1-6}$ alkylene) group which may be substituted, an $N(R^{14})$—($C_{1-6}$ alkylene) group which may be substituted (in the formula, $R^{14}$ has the same meaning as that defined above), a ($C_{1-3}$ alkylene)-O—($C_{1-3}$ alkylene) group which may be substituted or a ($C_{1-3}$ alkylene)-$N(R^{14})$—($C_{1-3}$ alkylene) group which may be substituted (in the formula, $R^{14}$ has the same meanings as that defined above), and $R^8$ preferably represents hydrogen atom or a $C_{1-6}$ alkyl group, more preferably hydrogen atom.

Regardless of the types of the other substituents, the $C_{1-6}$ alkyl group as $R^5$, $R^6$, $R^7$ or $R^8$ may be substituted with one or more groups selected from a halogen atom, cyano group, amino group which may be protected, hydroxyl group which may be protected, a $C_{1-6}$ alkoxy group which may be substituted with one or more groups selected from the substituent group A, an aryl group which may be substituted with one or more groups selected from the substituent group A, and a heterocyclic group which may be substituted with one or more groups selected from the substituent group A.

Regardless of the types of the other substituents, the $C_{2-6}$ alkylene group, O—($C_{1-6}$ alkylene) group, $N(R^{13})$—($C_{1-6}$ alkylene) group (in the formula, $R^{13}$ has the same meaning as that defined above), ($C_{1-3}$ alkylene)-O—($C_{1-3}$ alkylene) group, or ($C_{1-3}$ alkylene)-$N(R^{13})$—($C_{1-3}$ alkylene) group (in the formula, $R^{13}$ has the same meanings as that defined above) formed by $R^5$ and $R^6$ binding together may be substituted with one or more groups selected from a halogen atom, cyano group, amino group which may be protected, hydroxyl group which may be protected and oxo group.

Regardless of the types of the other substituents, the $C_{1-6}$ alkyl group as $R^{13}$ or $R^{14}$ may be substituted with one or more groups selected from a halogen atom, cyano group, amino group which may be protected, and hydroxyl group which may be protected.

Regardless of the types of the other substituents, the $C_{2-6}$ alkylene group, O—($C_{1-6}$ alkylene) group, $N(R^{14})$—($C_{1-6}$ alkylene) group (in the formula, $R^{14}$ has the same meanings as that defined above), ($C_{1-3}$ alkylene)-O—($C_{1-3}$ alkylene) group, or ($C_{1-3}$ alkylene)-$N(R^{14})$—($C_{1-3}$ alkylene) group (in the formula, $R^{14}$ has the same meanings as that defined above) formed by $R^7$ and $R^8$ binding together may be substituted with one or more groups selected from a halogen atom, cyano group, amino group which may be protected, hydroxyl group which may be protected, and oxo group.

$R^9$ is a $C_{1-6}$ alkyl group which may be substituted, a $C_{3-8}$ cycloalkyl group which may be substituted, an aryl group which may be substituted, a $C_{1-6}$ alkoxy group which may be substituted, a heterocyclic group which may be substituted, or $N(R^{15})(R^{16})$ (in the formula, $R^{15}$ and $R^{16}$ have the same meanings as those defined above), preferably a $C_{1-6}$ alkoxy group which may be substituted, a heterocyclic group which may be substituted, or $N(R^{15})(R^{16})$ (in the formula, $R^{15}$ and $R^{16}$ have the same meanings as those defined above), more preferably a $C_{1-6}$ alkoxy group which may be substituted or $N(R^{15})(R^{16})$ (in the formula, $R^{15}$ and $R^{16}$ have the same meanings as those defined above), further preferably $N(R^{15})(R^{16})$ (in the formula, $R^{15}$ and $R^{16}$ have the same meanings as those defined above).

Regardless of the types of the other substituents, the $C_{1-6}$ alkyl group, $C_{3-8}$ cycloalkyl group, aryl group, $C_{1-6}$ alkoxy group or heterocyclic group as $R^9$ may be substituted with one or more groups selected from a halogen atom, cyano group, amino group which may be protected, and hydroxyl group which may be protected.

Regardless of the types of the other substituents, the $C_{1-6}$ alkyl group, $C_{2-6}$ alkenyl group, $C_{2-6}$ alkynyl group, or $C_{3-8}$ cycloalkyl group as $R^{15}$ may be substituted with one or more groups selected from a halogen atom, cyano group, amino group which may be protected, and hydroxyl group which may be protected.

Regardless of the types of the other substituents, the $C_{1-6}$ alkyl group, $C_{2-6}$ alkenyl group, $C_{2-6}$ alkynyl group, $C_{3-8}$ cycloalkyl group, aryl group, or heterocyclic group as $R^{16}$ may be substituted with one or more groups selected from a halogen atom, cyano group, amino group which may be protected, hydroxyl group which may be protected, a $C_{1-6}$ alkyl group which may be substituted with one or more groups selected from the substituent group A, a $C_{3-6}$ cycloalkyl group which may be substituted with one or more groups selected from the substituent group A, an aryl group which may be substituted with one or more groups selected from the substituent group A, a $C_{1-6}$ alkoxy group which may be substituted with one or more groups selected from the substituent group A, an acyl group which may be substituted with one or more groups selected from the substituent group A, a $C_{1-6}$ alkoxycarbonyl group which may be substituted with one or more groups selected from the substituent group A, a $C_{1-6}$ alkylamino group which may be substituted with one or more groups selected from the substituent group A, a di($C_{1-6}$ alkyl)amino group which may be substituted with one or more groups selected from the substituent group A, a $C_{1-6}$ alkylsulfonyl group which may be substituted with one or more groups selected from the substituent group A, a $C_{1-6}$ alkylsulfonylamino group which may be substituted with one or more groups selected from the substituent group A, and a heterocyclic group which may be substituted with one or more groups selected from the substituent group A.

Regardless of the types of the other substituents, the cyclic amino group formed by $R^{15}$ and $R^{16}$ together with the nitrogen atom to which they bind may be substituted with one or more groups selected from a halogen atom, cyano group, amino group which may be protected, hydroxyl group which may be protected, and oxo group.

Preferred examples of the $C_{1-6}$ alkoxy group which may be substituted mentioned above as $R^9$ include unsubstituted alkoxy groups, such as methoxy group, ethoxy group, propoxy group, butoxy group, pentoxy group, cyclopropoxy group, cyclobutoxy group, and cyclopentoxy group, more preferably ethoxy group, propoxy group, butoxy group, and cyclopropoxy group.

Preferred examples of the heterocyclic group which may be substituted as $R^9$ include azetidinyl group, pyrrolidinyl group, pyrazolyl group, piperazinyl group, triazolyl group, morpholinyl group, and so forth. Preferred examples of the substituent of the heterocyclic group include a halogen atom such as fluorine atom and a $C_{1-3}$ alkyl group such as methyl group.

$R^{15}$ is preferably hydrogen atom, a $C_{1-6}$ alkyl group which may be substituted or a $C_{3-8}$ cycloalkyl group which may be substituted, more preferably hydrogen atom, a $C_{1-6}$ alkyl group or a $C_{3-8}$ cycloalkyl group, further preferably hydrogen atom.

The $C_{1-6}$ alkyl group mentioned above is preferably a $C_{1-3}$ alkyl group, and the $C_{3-8}$ cycloalkyl group is preferably cyclopropyl group.

$R^{16}$ is preferably a $C_{1-6}$ alkyl group which may be substituted, a $C_{3-8}$ cycloalkyl group which may be substituted, an aryl group which may be substituted or a heterocyclic group which may be substituted, more preferably a $C_{1-6}$ alkyl group which may be substituted, a $C_{3-8}$ cycloalkyl group which may be substituted or an aryl group which may be substituted, further preferably a $C_{1-6}$ alkyl group which may be substituted or a $C_{3-8}$ cycloalkyl group which may be substituted, particularly preferably a $C_{1-6}$ alkyl group which may be substituted.

Preferred examples of the substituent of the $C_{1-6}$ alkyl group which may be substituted include a halogen atom such as fluorine atom; cyano group; a $C_{1-3}$ alkoxy group such as methoxy group; a di($C_{1-3}$ alkyl)amino group such as dimethylamino; an aryl group such as phenyl group; and a heterocyclic group such as tetrahydropyranyl group, thienyl group and morpholinyl group, and more preferred examples include a halogen atom such as fluorine atom; and a $C_{1-3}$ alkoxy group such as methoxy group. In addition, a $C_{1-6}$ alkyl group not having any substituent can also be preferably used.

The $C_{1-6}$ alkyl group mentioned above is preferably a $C_{1-3}$ alkyl group, more preferably ethyl group or propyl group, further preferably propyl group.

Preferred examples of the $C_{3-8}$ cycloalkyl group include those not having any substituent. For example, cyclopropyl group, cyclobutyl group and cyclopentyl group are preferred, and cyclopropyl group is more preferred.

Preferred examples of the substituent of the aryl group which may be substituted include a halogen atom such as fluorine atom; cyano group; a $C_{1-3}$ alkyl group such as methyl group, ethyl group and propyl group; and a $C_{1-3}$ alkoxy group such as methoxy group and ethoxy group. In addition, an aryl group not having any substituent can also be preferably used. The aryl group mentioned above is preferably phenyl group.

Preferred examples of the heterocyclic group which may be substituted include a $C_{1-3}$ alkoxy group such as methoxy group and ethoxy group. In addition, a heterocyclic group not having any substituent can also be preferably used. The heterocyclic group mentioned above is preferably pyridyl group or quinolyl group.

$R^{10}$ is hydrogen atom, a halogen atom, a $C_{1-6}$ alkyl group which may be substituted, a $C_{3-8}$ cycloalkyl group which may be substituted, an aryl group which may be substituted, a $C_{1-6}$ alkoxy group which may be substituted or a heterocyclic group which may be substituted, preferably hydrogen atom, a $C_{1-6}$ alkyl group which may be substituted or an aryl group which may be substituted, more preferably hydrogen atom or a $C_{1-6}$ alkyl group, further preferably hydrogen atom.

Regardless of the types of the other substituents, the $C_{1-6}$ alkyl group, $C_{3-8}$ cycloalkyl group, aryl group, $C_{1-6}$ alkoxy group or heterocyclic group as $R^{10}$ may be substituted with one or more groups selected from a halogen atom, cyano group, amino group which may be protected, and hydroxyl group which may be protected.

Preferred examples of the substituent of the aryl group which may be substituted include a halogen atom such as fluorine atom and chlorine atom, and the aryl group is preferably phenyl group.

$R^{11}$ is hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, preferably hydrogen atom.

Regardless of the types of the other substituents, the $C_{1-6}$ alkyl group, $C_{2-6}$ alkenyl group, $C_{2-6}$ alkynyl group or $C_{3-8}$ cycloalkyl group as $R^{11}$ may be substituted with one or more groups selected from a halogen atom, cyano group, amino group which may be protected, hydroxyl group which may be protected, a $C_{1-6}$ alkyl group which may be substituted with one or more groups selected from the substituent group A, an aryl group which may be substituted with one or more groups selected from the substituent group A, a $C_{1-6}$ alkoxy group which may be substituted with one or more groups selected from the substituent group A, a $C_{1-6}$ alkylamino group which may be substituted with one or more groups selected from the substituent group A, a di($C_{1-6}$ alkyl)amino group which may be substituted with one or more groups selected from the substituent group A, and a heterocyclic group which may be substituted with one or more groups selected from the substituent group A.

$R^{12}$ is a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted, a heterocyclic group which may be substituted or a carbamoyl group which may be substituted, preferably a $C_{1-6}$ alkyl group which may be substituted, a $C_{3-8}$ cycloalkyl group which may be substituted, an aryl group which may be substituted or a heterocyclic group which may be substituted, more preferably an aryl group which may be substituted or a heterocyclic group which may be substituted, further preferably an aryl group which may be substituted.

Regardless of the types of the other substituents, the $C_{1-6}$ alkyl group, $C_{2-6}$ alkenyl group, $C_{2-6}$ alkynyl group, $C_{3-8}$ cycloalkyl group, aryl group, heterocyclic group, or carbamoyl group as $R^{12}$ may be substituted with one or more groups selected from a halogen atom, cyano group, amino group which may be protected, hydroxyl group which may be protected, a carbamoyl group which may be substituted with one or more groups selected from the substituent group A, a $C_{1-6}$ alkyl group which may be substituted with one or more groups selected from the substituent group A, an aryl group which may be substituted with one or more groups selected from the substituent group A, a $C_{1-6}$ alkoxy group which may be substituted with one or more groups selected from the substituent group A, an acyl group which may be substituted with one or more groups selected from the substituent group A, a $C_{1-6}$ alkoxycarbonyl group which may be substituted with one or more groups selected from the substituent group A, a $C_{1-6}$ alkylamino group which may be substituted with one or more groups selected from the substituent group A, a di($C_{1-6}$ alkyl)amino group which may be substituted with one or more groups selected from the substituent group A, a $C_{1-6}$ alkylsulfonyl group which may be substituted with one or more groups selected from the substituent group A, a $C_{1-6}$ alkylsulfonylamino group which may be substituted with one or more groups selected from the substituent group A, and a heterocyclic group which may be substituted with one or more groups selected from the substituent group A.

The substituent of the $C_{1-6}$ alkyl group which may be substituted, $C_{3-8}$ cycloalkyl group which may be substituted, aryl group which may be substituted, heterocyclic group which may be substituted, or carbamoyl group which may be substituted as $R^{12}$ is preferably a halogen atom, cyano group, amino group which may be protected, hydroxyl group which may be protected, a carbamoyl group which may be substituted with one or more groups selected from the substituent group A-2, a $C_{1-6}$ alkyl group which may be substituted with one or more groups selected from the substituent group A-2, a $C_{1-6}$ alkoxy group which may be substituted with one or more groups selected from the substituent group A-2, a $C_{1-6}$ alkylamino group which may be substituted with one or more groups selected from the substituent group A-2, a di($C_{1-6}$ alkyl)amino group which may be substituted with one or more groups selected from the substituent group A-2, or a heterocyclic group which may be substituted with one or more groups selected from the substituent group A-2.

The substituent group A-2 consists of a halogen atom, a $C_{1-6}$ alkyl group, a $C_{3-8}$ cycloalkyl group, a $C_{1-6}$ alkoxy group, and a heterocyclic group.

The $C_{1-6}$ alkyl group which may be substituted as $R^{12}$ is preferably a substituted $C_{1-6}$ alkyl group, more preferably a substituted $C_{1-3}$ alkyl group, further preferably a substituted methyl group or a substituted ethyl group.

The substituent of the substituted $C_{1-6}$ alkyl group is preferably hydroxyl group; a heterocyclic group such as pyridyl group, pyrrolidinyl group and morpholinyl group; or a di($C_{1-6}$ alkyl)amino group such as dimethylamino group. In particular, a $C_{1-6}$ alkyl group substituted with a heterocyclic group such as pyridyl group, pyrrolidinyl group and morpholinyl group is preferred.

The aryl group which may be substituted as $R^{12}$ is preferably a substituted aryl group, more preferably a substituted phenyl group.

The substituent of the substituted phenyl group is preferably a halogen atom; cyano group; amino group protected with an acyl group; a carbamoyl group which may be substituted with one or more groups selected from a $C_{1-6}$ alkyl group and a $C_{3-8}$ cycloalkyl group; a $C_{1-6}$ alkyl group which may be substituted with one or more groups selected from a halogen atom and a heterocyclic group; a $C_{1-6}$ alkoxy group which may be substituted with a halogen atom; or a heterocyclic group, more preferably a halogen atom; cyano group; a $C_{1-6}$ alkyl group which may be substituted with one or more groups selected from a halogen atom and a heterocyclic group; or a $C_{1-6}$ alkoxy group which may be substituted with a halogen atom, further preferably cyano group, a $C_{1-6}$ alkyl group, or a $C_{1-6}$ alkoxy group, particularly preferably cyano group.

The halogen atom mentioned above is preferably fluorine atom or chlorine atom, more preferably fluorine atom.

The $C_{1-6}$ alkyl group is preferably a $C_{1-3}$ alkyl group, more preferably methyl group or ethyl group, further preferably methyl group.

Preferred examples of the $C_{3-8}$ cycloalkyl group include cyclopropyl group.

The $C_{1-6}$ alkoxy group is preferably methoxy group, ethoxy group or propoxy group, more preferably methoxy group or ethoxy group, further preferably methoxy group.

Preferred examples of the heterocyclic group include pyrazolyl group and triazolyl group.

When the aryl group is phenyl group, it is preferred that the phenyl group does not have any substituent at the o-position, but has a substituent at the m- and/or p-position, it is more preferred that the phenyl group does not have any substituent at the o-position, but has a substituent at the m- or p-position, and it is still more preferred that the phenyl group has a substituent only at the p-position.

Preferred substituents at the m-position or p-position are as described above.

The heterocyclic group which may be substituted as $R^{12}$ is preferably pyridyl group which may be substituted, pyrazolyl group which may be substituted, thienyl group which may be substituted, oxazolyl group which may be substituted, thiazolyl group which may be substituted, isothiazolyl group which may be substituted, indazolyl group which may be substituted, pyrazolopyridinyl group which may be substituted, quinolyl group which may be substituted, isoquinolyl group which may be substituted, cinnolinyl group which may be substituted, phthalazinyl group which may be substituted, quinoxalinyl group which may be substituted, benzofuranyl group which may be substituted, or benzothiazolyl group which may be substituted, more preferably pyridyl group which may be substituted, indazolyl group which may be substituted, or pyrazolopyridinyl group which may be substituted, further preferably pyridyl group which may be substituted.

The substituent of the pyridyl group which may be substituted is preferably a halogen atom, a $C_{1-6}$ alkyl group, a $C_{1-6}$ alkoxy group, a $C_{1-6}$ alkylamino group or a heterocyclic group, more preferably a halogen atom or a $C_{1-6}$ alkoxy group.

The halogen atom mentioned above is preferably fluorine atom or chlorine atom, more preferably fluorine atom.

The $C_{1-6}$ alkyl group is preferably a $C_{1-3}$ alkyl group, more preferably methyl group or ethyl group, further preferably methyl group.

The $C_{1-6}$ alkoxy group is preferably methoxy group, ethoxy group or propoxy group, more preferably methoxy group or ethoxy group, further preferably methoxy group.

The $C_{1-6}$ alkylamino group is preferably methylamino group, ethylamino group or propylamino group, more preferably methylamino group or ethylamino group, further preferably methylamino group.

Preferred examples of the heterocyclic group include morpholinyl group.

When $R^{12}$ is pyridyl group which may be substituted, preferably it is a pyridyl group represented by the following formula [I]-(1) or [I]-(2):

[Formula 8]

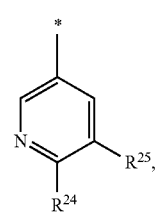

[I]-(1)

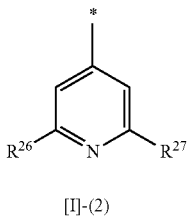

[I]-(2)

(in the formulas, $R^{24}$, $R^{25}$, $R^{26}$ and $R^{27}$ are the same or different, and represent hydrogen atom, a halogen atom, a $C_{1-6}$ alkyl group, a $C_{1-6}$ alkoxy group, a $C_{1-6}$ alkylamino group or a heterocyclic group, and * represents binding position), more preferably a pyridyl group represented by the formula [I]-(2).

Preferred examples of $R^{24}$, $R^{25}$, $R^{26}$ and $R^{27}$ are the same as those mentioned above as substituent of the pyridyl group which may be substituted. It is more preferred that one of $R^{24}$ and $R^{25}$, or one of $R^{26}$ and $R^{27}$ represents hydrogen atom.

The substituent of the pyridyl group which may be substituted is preferably a halogen atom; a $C_{1-6}$ alkyl group which may be substituted with a $C_{1-6}$ alkoxy group; a $C_{1-6}$ alkoxy group; or a di($C_{1-6}$ alkyl)amino group, more preferably a $C_{1-6}$ alkyl group which may be substituted with a $C_{1-6}$ alkoxy group; or a $C_{1-6}$ alkoxy group.

The halogen atom mentioned above is preferably fluorine atom or chlorine atom, more preferably fluorine atom.

The $C_{1-6}$ alkoxy group is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

Preferred examples of the di($C_{1-6}$ alkyl)amino group include a di($C_{1-3}$ alkyl)amino group such as dimethylamino group.

When $R^{12}$ is indazolyl group which may be substituted, it is preferably an indazolyl group represented by any one of the following formulas [II]-(1) to [II]-(4):

[Formula 9]

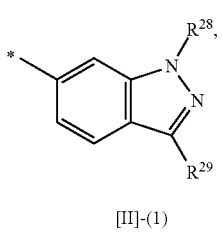

[II]-(1)

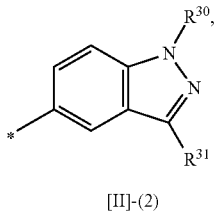

[II]-(2)

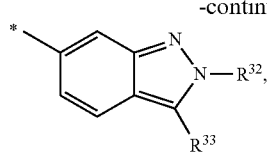

[II]-(3)

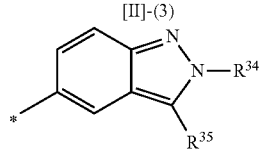

[II]-(4)

(in the formula, $R^{28}$, $R^{30}$, $R^{32}$ and $R^{34}$ are the same or different, and represent hydrogen atom; or a $C_{1-6}$ alkyl group which may be substituted with a $C_{1-6}$ alkoxy group, $R^{29}$, $R^{31}$, $R^{33}$ and $R^{35}$ are the same or different, and represent hydrogen atom; a halogen atom; a $C_{1-6}$ alkyl group which may be substituted with a $C_{1-6}$ alkoxy group; a $C_{1-6}$ alkoxy group; or a di($C_{1-6}$ alkyl)amino group, and * represents binding position), more preferably an indazolyl group represented by the formula [II]-(1) or [II]-(2), further preferably an indazolyl group represented by the formula [II]-(1).

The $C_{1-6}$ alkoxy group mentioned above is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

The halogen atom is preferably fluorine atom or chlorine atom, more preferably fluorine atom.

Preferred examples of the di($C_{1-6}$ alkyl)amino group include a di($C_{1-3}$ alkyl)amino group such as dimethylamino group.

$R^{28}$, $R^{32}$ and $R^{34}$ preferably represent hydrogen atom; or a $C_{1-3}$ alkyl group which may be substituted with a $C_{1-3}$ alkoxy group, more preferably hydrogen atom, methyl group, ethyl group or methoxyethyl group, further preferably hydrogen atom or methyl group, particularly preferably hydrogen atom.

$R^{29}$, $R^{31}$, $R^{33}$ and $R^{35}$ preferably represent hydrogen atom, a $C_{1-6}$ alkyl group or a $C_{1-6}$ alkoxy group, more preferably hydrogen atom, methyl group or methoxy group, further preferably hydrogen atom or methyl group, particularly preferably hydrogen atom.

The substituent of the indazolyl group which may be substituted is preferably a $C_{1-6}$ alkyl group which may be substituted with a $C_{1-6}$ alkoxy group; or a $C_{1-6}$ alkoxy group.

The $C_{1-6}$ alkoxy group mentioned above is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

When $R^{12}$ is pyrazolopyridinyl group which may be substituted, $R^{12}$ is preferably a pyrazolopyridinyl group represented by any one of the following formulas [III]-(1) to [III]-(4):

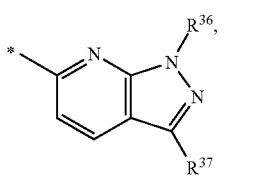

[III]-(1)

[III]-(2)

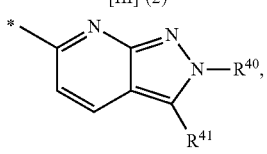

[III]-(3)

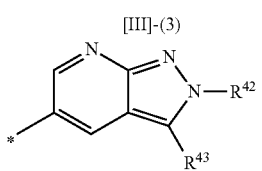

[III]-(4)

(in the formula, $R^{36}$, $R^{38}$, $R^{40}$ and $R^{42}$ are the same or different, and represent hydrogen atom; or a $C_{1-6}$ alkyl group which may be substituted with a $C_{1-6}$ alkoxy group, $R^{37}$, $R^{39}$, $R^{41}$ and $R^{43}$ are the same or different, and represent hydrogen atom; a $C_{1-6}$ alkyl group which may be substituted with a $C_{1-6}$ alkoxy group; or a $C_{1-6}$ alkoxy group, and * represents binding position), more preferably a pyrazolopyridinyl group represented by the formula [III]-(1) or [III]-(2), further preferably a pyrazolopyridinyl group represented by the formula [III]-(2).

The $C_{1-6}$ alkoxy group mentioned above is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

$R^{36}$, $R^{38}$, $R^{40}$ and $R^{42}$ are preferably hydrogen atom; or a $C_{1-3}$ alkyl group which may be substituted with a $C_{1-3}$ alkoxy group, more preferably hydrogen atom, methyl group, ethyl group, methoxyethyl group or methoxy group, further preferably hydrogen atom or methyl group, particularly preferably hydrogen atom.

$R^{37}$, $R^{39}$, $R^{41}$ and $R^{43}$ are preferably hydrogen atom, a $C_{1-6}$ alkyl group or a $C_{1-6}$ alkoxy group, more preferably hydrogen atom, methyl group or methoxy group, further preferably hydrogen atom.

Preferred examples of the substituent of the pyrazolyl group which may be substituted as $R^{12}$ include a $C_{1-6}$ alkyl group such as methyl group.

Preferred examples of the substituent of the thienyl group which may be substituted as $R^{12}$ include cyano group and a heterocyclic group such as carbamoyl group.

Preferred examples of the substituent of the oxazolyl group which may be substituted as $R^{12}$ include a $C_{1-6}$ alkyl group such as butyl group.

Preferred examples of the substituent of the thiazolyl group which may be substituted as $R^{12}$ include cyano group.

Preferred examples of the substituent of the isothiazolyl group which may be substituted as $R^{12}$ include a $C_{1-6}$ alkyl group such as methyl group.

Preferred examples of the substituent of the benzothiazolyl group which may be substituted as $R^{12}$ include a $C_{1-6}$ alkyl group such as methyl group.

As the isoquinolyl group which may be substituted, cinnolinyl group which may be substituted, phthalazinyl group which may be substituted, quinoxalinyl group which may be substituted and benzofuranyl group which may be substituted as $R^{12}$, those not having any substituent are also preferred.

Preferred examples of the substituent of the carbamoyl group which may be substituted as $R^{12}$ include a heterocyclic group such as pyridyl group.

$X^1$ is a group represented by the general formula [2]:

$$—X^4—X^5— \qquad [2]$$

(in the formula, $X^4$ and $X^5$ have the same meanings as those defined above).

$X^4$ is a divalent alicyclic hydrocarbon group which may be substituted, a divalent aromatic hydrocarbon group which may be substituted, a divalent heterocyclic group which may be substituted, a group represented by the general formula [3]:

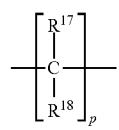

[3]

(in the formula, $R^{17}$, $R^{18}$ and p have the same meanings as those defined above) or an atomic bond.

Regardless of the types of the other substituents, the divalent alicyclic hydrocarbon group, divalent aromatic hydrocarbon group or divalent heterocyclic group as $X^4$ may be substituted with one or more groups selected from a halogen atom, cyano group, amino group which may be protected, hydroxyl group which may be protected and oxo group.

When $X^4$ is a divalent alicyclic hydrocarbon group which may be substituted, preferred examples of the divalent alicyclic hydrocarbon group include cyclohexylene group, and an unsubstituted alicyclic hydrocarbon group is also preferred.

When $X^4$ is a divalent aromatic hydrocarbon group which may be substituted, preferred examples of the divalent aromatic hydrocarbon group include phenylene group, and an unsubstituted aromatic hydrocarbon group is also preferred.

When $X^4$ is a divalent a heterocyclic group, preferred examples of the divalent heterocyclic group include pyridinediyl group, and an unsubstituted heterocyclic group is also preferred.

When $X^4$ is a group represented by the general formula [3]:

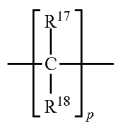

[Formula 13]

[3]

(in the formula, $R^{17}$, $R^{18}$ and p have the same meanings as those defined above), p of $R^{17}$ are the same or different, and represent hydrogen atom or a $C_{1-6}$ alkyl group which may be substituted, or one $R^{17}$ among p of $R^{17}$ may bind with $R^4$ to form a $C_{1-6}$ alkylene group which may be substituted, a ($C_{1-3}$ alkylene)-O group which may be substituted, a ($C_{1-3}$ alkylene)-N($R^{19}$) group which may be substituted (in the formula, $R^{19}$ has the same meaning as that defined above), a ($C_{1-3}$ alkylene)-O—($C_{1-3}$ alkylene) group which may be substituted or a ($C_{1-3}$ alkylene)-N($R^{19}$)—($C_{1-3}$ alkylene) group which may be substituted (in the formula, $R^{19}$ has the same meaning as that defined above), p of $R^{18}$ are the same or different, and represent hydrogen atom or a $C_{1-6}$ alkyl group which may be substituted, or $R^{17}$ and $R^{18}$ binding to the same carbon atom may bind together to form a $C_{2-6}$ alkylene group which may be substituted, an O—($C_{1-6}$ alkylene) group which may be substituted, an N($R^{20}$)—($C_{1-6}$ alkylene) group which may be substituted (in the formula, $R^{20}$ has the same meaning as that defined above), a ($C_{1-3}$ alkylene)-O—($C_{1-3}$ alkylene) group which may be substituted, or a ($C_{1-3}$ alkylene)-N($R^{20}$)—($C_{1-3}$ alkylene) group which may be substituted (in the formula, $R^{20}$ has the same meaning as that defined above), and p has the same meaning as that defined above.

p of $R^{17}$ are the same or different, and preferably represent hydrogen atom or a $C_{1-6}$ alkyl group which may be substituted, or bind with $R^4$ to represent a $C_{1-6}$ alkylene group which may be substituted or a ($C_{1-3}$ alkylene)-N($R^{19}$)—($C_{1-3}$ alkylene) group which may be substituted (in the formula, $R^{19}$ has the same meaning as that defined above).

The $C_{1-6}$ alkyl group of the $C_{1-6}$ alkyl group which may be substituted mentioned above is preferably methyl group, ethyl group, propyl group or butyl group, more preferably methyl group, ethyl group or propyl group, further preferably methyl group or ethyl group, particularly preferably methyl group.

Regardless of the types of the other substituents, the $C_{1-6}$ alkyl group as $R^{17}$ may be substituted with one or more groups selected from a halogen atom, cyano group, amino group which may be protected and hydroxyl group which may be protected. Preferred examples of the substituent of the $C_{1-6}$ alkyl group which may be substituted include a halogen atom such as fluorine atom; hydroxyl group; a $C_{1-3}$ alkoxy group such as methoxy group; and an aryl group such as phenyl group.

Regardless of the types of the other substituents, the $C_{1-6}$ alkylene group, ($C_{1-3}$ alkylene)-O group, ($C_{1-3}$ alkylene)-N($R^{19}$) group (in the formula, $R^{19}$ has the same meaning as that defined above), ($C_{1-3}$ alkylene)-O—($C_{1-3}$ alkylene) group or ($C_{1-3}$ alkylene)-N($R^{19}$)—($C_{1-3}$ alkylene) group (in the formula, $R^{19}$ has the same meaning as that defined above) formed by $R^4$ and $R^{17}$ binding together may be substituted with one or more groups selected from a halogen atom, cyano group, amino group which may be protected, hydroxyl group which may be protected and oxo group.

The $C_{1-6}$ alkylene group of the $C_{1-6}$ alkylene group which may be substituted formed by $R^{17}$ together with $R^4$ is preferably a $C_{1-3}$ alkylene, more preferably ethylene group.

Preferred examples of the substituent of the $C_{1-6}$ alkylene group which may be substituted include a halogen atom such as fluorine atom; hydroxyl group; a $C_{1-3}$ alkyl group such as methyl group; and a $C_{1-3}$ alkoxy group such as methoxy group.

The $C_{1-3}$ alkylene of the ($C_{1-3}$ alkylene)-N($R^{19}$)—($C_{1-3}$ alkylene) group which may be substituted (in the formula, $R^{19}$ has the same meaning as that defined above) formed by $R^{17}$ together with $R^4$ is preferably a $C_{1-3}$ alkylene group, more preferably ethylene group or trimethylene group. In addition, an unsubstituted ($C_{1-3}$ alkylene)-N($R^{19}$)—($C_{1-3}$ alkylene) group (in the formula, $R^{19}$ has the same meaning as that defined above) is also preferred.

p of $R^{18}$ are the same or different, and preferably represent hydrogen atom or a $C_{1-6}$ alkyl group which may be substituted, or $R^{17}$ and $R^{18}$ binding to the same carbon atom may bind together to represent a ($C_{1-3}$ alkylene)-O—($C_{1-3}$ alkylene) group which may be substituted.

Regardless of the types of the other substituents, the $C_{2-6}$ alkylene group, O—($C_{1-6}$ alkylene) group, N($R^{20}$)—($C_{1-6}$ alkylene) group (in the formula, $R^{20}$ has the same meaning as that defined above), ($C_{1-3}$ alkylene)-O—($C_{1-3}$ alkylene) group or ($C_{1-3}$ alkylene)-N($R^{20}$)—($C_{1-3}$ alkylene) group (in the formula, $R^{20}$ has the same meaning as that defined above) formed by $R^{17}$ and $R^{18}$ binding together may be substituted with one or more groups selected from a halogen atom, cyano group, amino group which may be protected, hydroxyl group which may be protected and oxo group.

Regardless of the types of the other substituents, the $C_{1-6}$ alkyl group as $R^{18}$ may be substituted with one or more groups selected from a halogen atom, cyano group, amino group which may be protected, hydroxyl group which may be protected, a $C_{1-6}$ alkoxy group which may be substituted with one or more groups selected from the substituent group A, an aryl group which may be substituted with one or more groups selected from the substituent group A and a heterocyclic group which may be substituted with one or more groups selected from the substituent group A.

Regardless of the types of the other substituents, the $C_{1-6}$ alkyl group as $R^{19}$ or $R^{20}$ may be substituted with one or more groups selected from a halogen atom, cyano group, amino group which may be protected and hydroxyl group which may be protected.

The $C_{1-6}$ alkylene group of the $C_{1-6}$ alkylene group which may be substituted formed by $R^{17}$ together with $R^4$ mentioned above is preferably a $C_{1-3}$ alkylene, more preferably ethylene group.

Preferred examples of the substituent of the $C_{1-6}$ alkylene group which may be substituted include a halogen atom such as fluorine atom; hydroxyl group; a $C_{1-3}$ alkyl group such as methyl group; and a $C_{1-3}$ alkoxy group such as methoxy group.

The $C_{1-3}$ alkylene group of the ($C_{1-3}$ alkylene)-O—($C_{1-3}$ alkylene) group which may be substituted formed by $R^{17}$ and $R^{18}$ binding to the same carbon atom and binding together is preferably ethylene group. In addition, an unsubstituted ($C_{1-3}$ alkylene)-O—($C_{1-3}$ alkylene) group is also preferred.

$X^5$ represents oxygen atom, N($R^{21}$) (in the formula, $R^{21}$ has the same meaning as that defined above), C(=O), C(=O)—N($R^{21}$) (in the formula, $R^{21}$ has the same meaning as that defined above) or an atomic bond.

Regardless of the types of the other substituents, the $C_{1-6}$ alkyl group, $C_{2-6}$ alkenyl group or $C_{2-6}$ alkynyl group as $R^{21}$ may be substituted with one or more groups selected from a halogen atom, cyano group, amino group which may be protected and hydroxyl group which may be protected.

$R^{21}$ of $N(R^{21})$ is preferably hydrogen atom, or $R^{21}$ preferably binds with $R^4$ to form a $C_{1-6}$ alkylene group which may be substituted.

The $C_{1-6}$ alkylene group mentioned above is preferably a $C_{1-3}$ alkylene group, more preferably ethylene group or trimethylene group.

$R^{21}$ of $C(=O)$—$N(R^{21})$ is preferably hydrogen atom.

Regardless of the types of the other substituents, the $C_{1-6}$ alkylene group formed by $R^4$ and $R^{21}$ binding together may be substituted with one or more groups selected from a halogen atom, cyano group, amino group which may be protected, hydroxyl group which may be protected and oxo group.

p is an integer of 1 to 6, preferably an integer of 1 to 4, more preferably an integer of 1 to 3, further preferably 1 or 2, particularly preferably 1.

Regardless of the types of the other substituents, the $C_{1-6}$ alkyl group, $C_{2-6}$ alkenyl group or $C_{2-6}$ alkynyl group as $R^{22}$ may be substituted with one or more groups selected from a halogen atom, cyano group, amino group which may be protected and hydroxyl group which may be protected.

Regardless of the types of the other substituents, the $C_{1-6}$ alkyl group, $C_{3-8}$ cycloalkyl group, aryl group, $C_{1-6}$ alkoxy group or heterocyclic group as $R^{23}$ may be substituted with one or more groups selected from a halogen atom, cyano group, amino group which may be protected, hydroxyl group which may be protected and oxo group.

$X^2$ is a $C_{1-6}$ alkylene group which may be substituted, a divalent alicyclic hydrocarbon group which may be substituted, a divalent aromatic hydrocarbon group which may be substituted or a divalent heterocyclic group which may be substituted.

Regardless of the types of the other substituents, the $C_{1-6}$ alkylene group, divalent alicyclic hydrocarbon group, divalent aromatic hydrocarbon group or divalent heterocyclic group as $X^2$ may be substituted with one or more groups selected from a halogen atom, cyano group, amino group which may be protected, hydroxyl group which may be protected, a $C_{1-6}$ alkyl group which may be substituted with one or more groups selected from the substituent group A, a $C_{1-6}$ alkoxy group which may be substituted with one or more groups selected from the substituent group A and oxo group.

When $X^2$ is a $C_{1-6}$ alkylene group which may be substituted, the $C_{1-6}$ alkylene group of the $C_{1-6}$ alkylene group which may be substituted is preferably methylene group, ethylene group or trimethylene group, more preferably trimethylene group.

The substituent of the $C_{1-6}$ alkylene group of the $C_{1-6}$ alkylene group which may be substituted is preferably oxo group or a $C_{1-6}$ alkyl group, more preferably a $C_{1-3}$ alkyl group, further preferably methyl group or ethyl group, particularly preferably methyl group. In addition, as the $C_{1-6}$ alkylene group which may be substituted, an unsubstituted $C_{1-6}$ alkylene group is preferred.

When $X^2$ is a divalent alicyclic hydrocarbon group which may be substituted, the divalent alicyclic hydrocarbon group of the divalent alicyclic hydrocarbon group which may be substituted is preferably cyclobutylene group, cyclopentylene group or cyclohexylene group, more preferably cyclobutylene group or cyclohexylene group, further preferably cyclobutylene group.

The cyclobutylene group mentioned above is preferably

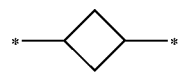

[Formula 14]

(in the formula, * represents binding position), more preferably

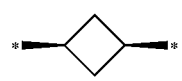

[Formula 15]

(in the formula, * represents binding position).

The cyclopentylene group is preferably

[Formula 16]

(in the formula, * represents binding position), more preferably

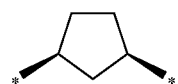 or 

[Formula 17]

(in the formula, * represents binding position), more preferably

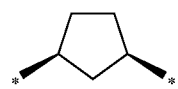

[Formula 18]

(in the formula, * represents binding position).

The cyclohexylene group is preferably

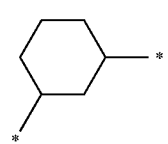

[Formula 19]

(in the formula, * represents binding position), more preferably

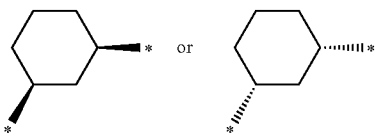

[Formula 20]

(in the formula, * represents binding position), still more preferably

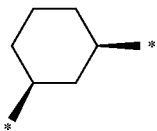

[Formula 21]

(in the formula, * represents binding position).

In addition, as the divalent alicyclic hydrocarbon group which may be substituted, an unsubstituted divalent alicyclic hydrocarbon group is preferred.

When $X^2$ is an aromatic hydrocarbon group which may be substituted, the aromatic hydrocarbon group of the aromatic hydrocarbon group which may be substituted is preferably phenylene group.

The phenylene group mentioned above is preferably

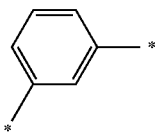

[Formula 22]

(in the formula, * represents binding position).

When $X^2$ is an aromatic hydrocarbon group which may be substituted, the substituent of the aromatic hydrocarbon group which may be substituted is preferably a halogen atom; a $C_{1-6}$ alkyl group which may be substituted with a halogen atom; or a $C_{1-6}$ alkoxy group.

The halogen atom mentioned above is preferably fluorine atom or chlorine atom, more preferably fluorine atom.

The $C_{1-6}$ alkyl group is preferably a $C_{1-3}$ alkyl group, more preferably methyl group or ethyl group, further preferably methyl group.

The $C_{1-6}$ alkoxy group is preferably methoxy group, ethoxy group or propoxy group, more preferably methoxy group or ethoxy group, further preferably methoxy group.

In addition, as the divalent aromatic hydrocarbon group which may be substituted, an unsubstituted divalent aromatic hydrocarbon group is preferred.

When $X^2$ is a divalent heterocyclic group which may be substituted, the heterocyclic group of the divalent heterocyclic group which may be substituted is preferably pyrrolidinediyl group, piperidinediyl group, tetrahydropyridinediyl group, pyridinediyl group, isoxazolediyl group, oxadiazoldiyl group, benzoimidazolediyl group or benzooxazolediyl group, more preferably pyrrolidinediyl group, piperidinediyl group, tetrahydropyridinediyl group, pyridinediyl group, isoxazolediyl group or oxadiazoldiyl group, further preferably piperidinediyl group, tetrahydropyridinediyl group or pyridinediyl group, particularly preferably pyridinediyl group.

In addition, as the divalent heterocyclic group which may be substituted, an unsubstituted divalent heterocyclic group is preferred.

$X^3$ is a $C_{1-6}$ alkylene group which may be substituted, a $C_{2-6}$ alkenylene group which may be substituted, a $C_{2-6}$ alkynylene group which may be substituted, an O—($C_{1-6}$ alkylene) group which may be substituted, an $S(O)_q$—($C_{1-6}$ alkylene) group which may be substituted (in the formula, q represents 0, 1 or 2), an $N(R^{22})$—($C_{1-6}$ alkylene) group which may be substituted (in the formula, $R^{22}$ has the same meaning as that defined above), $N(R^{22})$—C(=O) (in the formula, $R^{22}$ has the same meaning as that defined above) or an atomic bond.

Regardless of the types of the other substituents, the $C_{1-6}$ alkylene group, $C_{2-6}$ alkenylene group, $C_{2-6}$ alkynylene group, O—($C_{1-6}$ alkylene) group, $S(O)_q$—($C_{1-6}$ alkylene) group or $N(R^{22})$—($C_{1-6}$ alkylene) group (in the formula, $R^{22}$ and q have the same meanings as those defined above) as $X^3$ may be substituted with one or more groups selected from a halogen atom, cyano group, amino group which may be protected, hydroxyl group which may be protected and oxo group.

The compounds wherein $X^3$ is a $C_{2-6}$ alkynylene group which may be substituted or $N(R^{22})$—C(=O) (in the formula, $R^{22}$ has the same meaning as that defined above) are preferred, and the compounds wherein $X^3$ is ethynylene group are more preferred.

$X^3$ is preferably a $C_{1-6}$ alkylene group, a $C_{2-6}$ alkenylene group, a $C_{2-6}$ alkynylene group, an $S(O)_q$—($C_{1-6}$ alkylene) group (in the formula, q has the same meaning as that defined above), $N(R^{22})$—C(=O) (in the formula, $R^{22}$ has the same meaning as that defined above) or an atomic bond, more preferably a $C_{2-6}$ alkynylene group or $N(R^{22})$—C(=O) (in the formula, $R^{22}$ has the same meaning as that defined above), further preferably a $C_{2-6}$ alkynylene group.

As for $X^3$, the $C_{1-6}$ alkylene group is preferably ethylene group, the $C_{2-6}$ alkenylene group is preferably ethenylene group, the $C_{2-6}$ alkynylene group is preferably ethynylene group, the $C_{1-6}$ alkylene group of the O—($C_{1-6}$ alkylene) group is preferably methylene group, the $C_{1-6}$ alkylene group of the $S(O)_q$—($C_{1-6}$ alkylene) group (in the formula, q has the same meaning as that defined above) is preferably methylene group, q is preferably an integer of 0, the $C_{1-6}$ alkylene group of the $N(R^{22})$—($C_{1-6}$ alkylene) group (in the formula, $R^{22}$ has the same meaning as that defined above) is preferably methylene group, $R^{22}$ of $N(R^{22})$—($C_{1-6}$ alkylene) group (in the formula, $R^{22}$ has the same meaning as that defined above) is preferably hydrogen atom, and $R^{22}$ of $N(R^{22})$—C(=O) (in the formula, $R^{22}$ has the same meaning as that defined above) is preferably hydrogen atom.

$Z^1$ is nitrogen atom or $C(R^{23})$ (in the formula, $R^{23}$ has the same meaning as that defined above), preferably nitrogen atom.

m is an integer of 0 to 6, preferably an integer of 0 to 3, more preferably an integer of 0 to 2, further preferably an integer of 0 or 1, particularly preferably an integer of 0.

n is an integer of 0 to 6, preferably an integer of 0 to 3, more preferably an integer of 0 to 2, further preferably an integer of 0 or 1, particularly preferably an integer of 0.

As the compound of the present invention represented by the general formula [1], preferred compounds include the following compounds.

The compounds wherein $R^1$ is hydrogen atom are preferred.

The compounds wherein $R^2$ is hydrogen atom or a $C_{1-6}$ alkyl group which may be substituted are preferred, the compounds wherein $R^2$ is a $C_{1-6}$ alkyl group which may be substituted are more preferred, and the compounds wherein $R^2$ is a $C_{1-6}$ alkyl group substituted with a di($C_{1-6}$ alkyl)amino group are further preferred.

The compounds wherein $R^3$ is hydrogen atom or a $C_{1-6}$ alkyl group which may be substituted are preferred, and the compounds wherein $R^3$ is hydrogen atom are more preferred.

The compounds wherein $R^4$ is hydrogen atom or a $C_{1-6}$ alkyl group which may be substituted are preferred, and the compounds wherein $R^4$ is a $C_{1-6}$ alkyl group are more preferred.

The compounds wherein $R^5$, $R^6$, $R^7$ and $R^8$ are hydrogen atom or a $C_{1-6}$ alkyl group are preferred, and the compounds wherein $R^5$, $R^6$, $R^7$ and $R^8$ are hydrogen atoms are more preferred.

The compounds wherein $R^9$ is $N(R^{15})(R^{16})$ (in the formula, $R^1$ and $R^{16}$ have the same meanings as those defined above) are preferred.

The compounds wherein $R^{10}$ is hydrogen atom are preferred.

The compounds wherein $R^{11}$ is hydrogen atom are preferred.

The compounds wherein $R^{12}$ is an aryl group which may be substituted or a heterocyclic group which may be substituted are preferred, the compounds wherein $R^{12}$ is phenyl group which may be substituted, pyridyl group which may be substituted, oxazolyl group which may be substituted, pyrazolyl group which may be substituted, thiazolyl group which may be substituted, isoquinolyl group which may be substituted or cinnolyl group which may be substituted are preferred.

The compounds wherein $X^1$ is $—X^4—X^5—$ (in the formula, $X^4$ and $X^5$ have the same meanings as those defined above) are preferred, and the compounds wherein $X^1$ is $—X^4—X^5—$ (in the formula, $X^4$ represents a group represented by the general formula [3]:

[Formula 23]

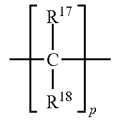

[3]

(in the formula, $R^{17}$, $R^{18}$ and p have the same meanings as those defined above), and $X^5$ represents $C(=O)—NH$) are more preferred.

The compounds wherein $X^2$ is a $C_{1-6}$ alkylene group which may be substituted or a divalent alicyclic hydrocarbon group which may be substituted are preferred, and the compounds wherein $X^2$ is a $C_{1-6}$ alkylene group which may be substituted or a divalent 4-, 5- or 6-membered ring alicyclic hydrocarbon group which may be substituted are more preferred.

The compounds wherein $Z^1$ is nitrogen atom are preferred.

As the compounds of the present invention, those represented by the following general formula [1]-(1):

[Formula 24]

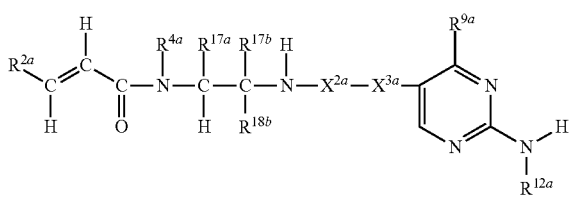

[1]-(1)

(in the formula, $R^{2a}$, $R^{4a}$, $R^{17a}$, $R^{17b}$, $R^{18b}$, $R^{9a}$, $R^{12a}$, $X^{2a}$, and $X^{3a}$ have the same meanings as those defined above) are preferred.

$R^{2a}$ is hydrogen atom or a $C_{1-6}$ alkyl group which may be substituted, preferably a $C_{1-6}$ alkyl group which may be substituted.

The $C_{1-6}$ alkyl group which may be substituted mentioned above is preferably a $C_{1-3}$ alkyl group which may be substituted, more preferably methyl group or ethyl group which may be substituted, further preferably methyl group which may be substituted.

The substituent of the $C_{1-6}$ alkyl group which may be substituted as $R^{2a}$ is preferably a halogen atom, hydroxyl group, a $C_{1-6}$ alkylamino group which may be substituted with one or more substituents selected from the substituent group A-3, a di($C_{1-6}$ alkyl)amino group which may be substituted with one or more substituents selected from the substituent group A-3 or a heterocyclic group which may be substituted with one or more substituents selected from the substituent group A-3.

The halogen atom mentioned above is preferably fluorine atom, chlorine atom or bromine atom, more preferably bromine atom.

The $C_{1-6}$ alkylamino group is preferably a $C_{1-3}$ alkylamino group, more preferably a $C_{1-2}$ alkylamino group, further preferably methylamino group.

The di($C_{1-6}$ alkyl)amino group is preferably a di($C_{1-3}$ alkyl)amino group, more preferably a di($C_{1-2}$ alkyl)amino group, further preferably dimethylamino group.

The heterocyclic group is preferably azetidinyl group, piperazinyl group or morpholinyl group.

The substituent group A-3 consists of a halogen atom, hydroxyl group which may be protected and a $C_{1-6}$ alkyl group which may be substituted with hydroxyl group.

The halogen atom mentioned above is preferably fluorine atom, chlorine atom or bromine atom, more preferably fluorine atom.

The $C_{1-6}$ alkyl group is preferably a $C_{1-3}$ alkyl group, more preferably methyl group or ethyl group, further preferably methyl group.

The substituent of the $C_{1-6}$ alkyl group which may be substituted as $R^{2a}$ is more preferably a $C_{1-6}$ alkylamino group which may be substituted with one or more groups selected from the substituent group A-1 or a di($C_{1-6}$ alkyl)amino group which may be substituted with one or more groups selected from the substituent group A-1, still more preferably a $C_{1-6}$ alkylamino group or a di($C_{1-6}$ alkyl)amino group, further preferably a di($C_{1-6}$ alkyl)amino group.

As the $C_{1-6}$ alkyl group substituted with a di($C_{1-6}$ alkyl) amino group mentioned above is preferably a $C_{1-3}$ alkyl group substituted with a di($C_{1-3}$ alkyl)amino group, more preferably methyl group or ethyl group substituted with a di($C_{1-3}$ alkyl) amino group, further preferably a di($C_{1-3}$ alkyl)aminomethyl group.

The di($C_{1-3}$ alkyl)aminomethyl group is preferably diethylaminomethyl group or dimethylaminomethyl group, more preferably dimethylaminomethyl group.

$R^{4a}$ is hydrogen atom or a $C_{1-6}$ alkyl group which may be substituted, preferably hydrogen atom or a $C_{1-6}$ alkyl group, more preferably a $C_{1-6}$ alkyl group.

The $C_{1-6}$ alkyl group is preferably a $C_{1-3}$ alkyl group, more preferably methyl group or ethyl group, further preferably methyl group.

$R^{17a}$ is hydrogen atom or a $C_{1-6}$ alkyl group which may be substituted, provided that $R^{17a}$ may form a divalent nitrogen-containing heterocyclic group which may be substituted together with $R^{4a}$, the nitrogen atom to which $R^{4a}$ binds, and the carbon atom to which $R^{17a}$ binds, and $R^{17a}$ is preferably hydrogen atom or a $C_{1-6}$ alkyl group, more preferably a $C_{1-6}$ alkyl group.

In addition, when $R^{17a}$ is a $C_{1-6}$ alkyl group, it is preferably

[Formula 25]

(in the formula, * is the binding position on the nitrogen atom side, and ** is the binding position on the carbon atom side).

The $C_{1-6}$ alkyl group of the $C_{1-6}$ alkyl group which may be substituted mentioned above is preferably methyl group, ethyl group, propyl group or butyl group, more preferably methyl group, ethyl group or propyl group, further preferably methyl group or ethyl group, particularly preferably methyl group.

The substituent of the $C_{1-6}$ alkyl group which may be substituted is preferably a halogen atom such as fluorine atom; hydroxyl group; a $C_{1-6}$ alkoxy group such as methoxy group; or an aryl group such as phenyl group.

The divalent nitrogen-containing heterocyclic group of the divalent nitrogen-containing heterocyclic group which may be substituted formed by $R^{17a}$, $R^{4a}$, the nitrogen atom to which $R^{4a}$ binds and the carbon atom to which $R^{17a}$ binds binding together is preferably azetidinediyl group, pyrrolidinediyl group, piperidinediyl group, homopiperidinediyl group, piperazinediyl group or homopiperazinediyl group, more preferably azetidinediyl group or pyrrolidinediyl group.

The substituent of the divalent nitrogen-containing heterocyclic group which may be substituted is preferably a halogen atom such as fluorine atom; hydroxyl group; a $C_{1-3}$ alkyl group such as methyl group; or a $C_{1-6}$ alkoxy group such as methoxy group. In addition, an unsubstituted divalent nitrogen-containing heterocyclic group is also preferred.

$R^{17b}$ and $R^{18b}$ are the same or different, and represent hydrogen atom or a $C_{1-6}$ alkyl group which may be substituted, provided that, $R^{17b}$ and $R^{18b}$ may form C(=O) together with the carbon atom to which they bind, or $R^{17b}$ and $R^{18b}$ may form a divalent heterocyclic group which may be substituted together with the carbon atom to which they bind, preferably $R^{17b}$ and $R^{18b}$ represent a $C_{1-6}$ alkyl group, or $R^{17b}$ and $R^{18b}$ form C(=O) together with the carbon atom to which they bind, more preferably $R^{17b}$ and $R^{18b}$ form C(=O) together with the carbon atom to which they bind.

The $C_{1-6}$ alkyl group mentioned above is preferably a $C_{1-3}$ alkyl group, more preferably methyl group or ethyl group, further preferably methyl group.

The heterocyclic group is preferably tetrahydropyranediyl group. In addition, as the heterocyclic group which may be substituted, an unsubstituted heterocyclic group is also preferred.

The substituent of the $C_{1-6}$ alkyl group which may be substituted is preferably a halogen atom such as fluorine atom; hydroxyl group; or a $C_{1-6}$ alkoxy group such as methoxy group.

$R^{9a}$ is a $C_{1-6}$ alkyl group which may be substituted, a $C_{1-6}$ alkoxy group which may be substituted, a heterocyclic group which may be substituted or $N(R^{15})(R^{16})$ (in the formula, $R^{15}$ and $R^{16}$ have the same meanings as those defined above), preferably a $C_{1-6}$ alkoxy group which may be substituted, a heterocyclic group which may be substituted or $N(R^{15})(R^{16})$ (in the formula, $R^{15}$ and $R^{16}$ have the same meanings as those defined above), more preferably a $C_{1-6}$ alkoxy group which may be substituted or $N(R^{15})(R^{16})$, further preferably $N(R^{15})(R^{16})$ (in the formula, $R^{15}$ and $R^{16}$ have the same meanings as those defined above).

Preferred examples of the $C_{1-6}$ alkoxy group which may be substituted mentioned above include those not having any substituent, for example, methoxy group, ethoxy group, propoxy group, butoxy group, pentyloxy group, cyclopropoxy group, cyclobutoxy group, cyclopentyloxy group and so forth, preferably ethoxy group, propoxy group, butoxy group, and cyclopropoxy group.

Preferred examples of the heterocyclic group which may be substituted include azetidinyl group, pyrrolidinyl group, pyrazolyl group, piperazinyl group, triazolyl group, morpholinyl group, and so forth. Preferred examples of the substituent of the heterocyclic group include a halogen atom such as fluorine atom and a $C_{1-3}$ alkyl group such as methyl group.

$R^{15}$ of $N(R^{15})(R^{16})$ (in the formula, $R^{15}$ and $R^{16}$ have the same meanings as those defined above) is preferably hydrogen atom, a $C_{1-6}$ alkyl group which may be substituted or a $C_{3-8}$ cycloalkyl group which may be substituted, more preferably hydrogen atom, a $C_{1-6}$ alkyl group or a $C_{3-8}$ cycloalkyl group, further preferably hydrogen atom.

The $C_{1-6}$ alkyl group mentioned above is preferably a $C_{1-3}$ alkyl group, and preferred examples of the $C_{3-8}$ cycloalkyl group include cyclopropyl.

$R^{16}$ of $N(R^{15})(R^{16})$ (in the formula, $R^{15}$ and $R^{16}$ have the same meanings as those defined above) is preferably a $C_{1-6}$ alkyl group which may be substituted, a $C_{3-8}$ cycloalkyl group which may be substituted, an aryl group which may be substituted or a heterocyclic group which may be substituted, more preferably a $C_{1-6}$ alkyl group which may be substituted, a $C_{3-8}$ cycloalkyl group which may be substituted or an aryl group which may be substituted, further preferably a $C_{1-6}$ alkyl group which may be substituted or a $C_{3-8}$ cycloalkyl group which may be substituted, particularly preferably a $C_{1-6}$ alkyl group which may be substituted.

Preferred examples of the substituent of the $C_{1-6}$ alkyl group which may be substituted include a halogen atom such as fluorine atom; cyano group; a $C_{1-3}$ alkoxy group such as methoxy group; a di($C_{1-3}$ alkyl)amino group such as dimethylamino; an aryl group such as phenyl group; and a heterocyclic group such as tetrahydropyranyl group, thienyl group and morpholinyl group, and it is preferably a halogen atom such as fluorine atom; or a $C_{1-3}$ alkoxy group such as methoxy group. In addition, a $C_{1-6}$ alkyl group not having any substituent can also be preferably used.

The $C_{1-6}$ alkyl group mentioned above is preferably a $C_{1-6}$ alkyl group, more preferably ethyl group or propyl group, further preferably propyl group.

Preferred examples of the $C_{3-8}$ cycloalkyl group include those not having any substituent. For example, such a $C_{3-5}$ cycloalkyl group as cyclopropyl group, cyclobutyl group and cyclopentyl group is preferred, and cyclopropyl group is more preferred.

Preferred examples of the substituent of the heterocyclic group which may be substituted include a $C_{1-3}$ alkoxy group such as methoxy group and ethoxy group. In addition, a heterocyclic group not having any substituent can also be preferably used. The heterocyclic group is preferably pyridyl group or quinolyl group.

$R^{12a}$ is a $C_{1-6}$ alkyl group which may be substituted, an aryl group which may be substituted or a heterocyclic group which may be substituted, preferably an aryl group which may be substituted or a heterocyclic group which may be substituted, more preferably an aryl group which may be substituted.

The substituent of the $C_{1-6}$ alkyl group which may be substituted as $R^{12a}$ is preferably a halogen atom, cyano group, amino group which may be protected, hydroxyl group which may be protected, a carbamoyl group which may be substituted with one or more groups selected from the substituent group A-4, a $C_{1-6}$ alkyl group which may be substituted with one or more groups selected from the substituent group A-4, a $C_{1-6}$ alkoxy group which may be substituted with one or more groups selected from the substituent group A-4, a $C_{1-6}$ alkylamino group which may be substituted with one or more groups selected from the substituent group A-4, a di($C_{1-6}$ alkyl)amino group which may be substituted with one or more groups selected from the substituent group A-4, or a heterocyclic group which may be substituted with one or more groups selected from the substituent group A-4.

The substituent group A-4 consists of a halogen atom, a $C_{1-6}$ alkyl group, a $C_{3-8}$ cycloalkyl group, a $C_{1-6}$ alkoxy group and a heterocyclic group.

The $C_{1-6}$ alkyl group which may be substituted as $R^{12a}$ is preferably a substituted $C_{1-6}$ alkyl group, more preferably a substituted $C_{1-3}$ alkyl group, further preferably a substituted methyl group or ethyl group.

The substituent of the substituted $C_{1-6}$ alkyl group is preferably hydroxyl group; a heterocyclic group such as pyridyl group, pyrrolidinyl group and morpholinyl group; or a di($C_{1-6}$ alkyl)amino group such as dimethylamino group. In particular, a $C_{1-6}$ alkyl group substituted with a heterocyclic group such as pyridyl group, pyrrolidinyl group and morpholinyl group is preferred.

The aryl group which may be substituted as $R^{12a}$ is preferably a substituted aryl group, more preferably a substituted phenyl group.

The substituent of the substituted phenyl group is preferably a halogen atom; cyano group; amino group protected with an acyl group; a carbamoyl group which may be substituted with one or more groups selected from a $C_{1-6}$ alkyl group and a $C_{3-8}$ cycloalkyl group; a $C_{1-6}$ alkyl group which may be substituted with one or more groups selected from a halogen atom and a heterocyclic group; a $C_{1-6}$ alkoxy group which may be substituted with a halogen atom; or a heterocyclic group, more preferably a halogen atom; cyano group; a $C_{1-6}$ alkyl group which may be substituted with one or more groups selected from a halogen atom and a heterocyclic group; or a $C_{1-6}$ alkoxy group which may be substituted with a halogen atom, further preferably cyano group, a $C_{1-6}$ alkyl group or a $C_{1-6}$ alkoxy group, particularly preferably cyano group.

The halogen atom mentioned above is preferably fluorine atom or chlorine atom, more preferably fluorine atom.

The $C_{1-6}$ alkyl group is preferably a $C_{1-3}$ alkyl group, more preferably methyl group or ethyl group, further preferably methyl group.

Preferred examples of the $C_{3-8}$ cycloalkyl group include cyclopropyl group.

The $C_{1-6}$ alkoxy group is preferably methoxy group, ethoxy group or propoxy group, more preferably methoxy group or ethoxy group, further preferably methoxy group.

Preferred examples of the heterocyclic group include pyrazolyl group and triazolyl group.

When the aryl group is phenyl group, it is preferred that the phenyl group does not have any substituent at the o-position, but has a substituent at the m- and/or p-position, it is more preferred that the phenyl group does not have any substituent at the o-position, but has a substituent at the m- or p-position, and it is still more preferred that the phenyl group has a substituent only at the p-position.

Preferred substituents at the m-position or p-position are as described above.

The heterocyclic group which may be substituted as $R^{12a}$ is preferably pyridyl group which may be substituted, pyrazolyl group which may be substituted, thienyl group which may be substituted, oxazolyl group which may be substituted, thiazolyl group which may be substituted, isothiazolyl group which may be substituted, indazolyl group which may be substituted, pyrazolopyridinyl group which may be substituted, quinolyl group which may be substituted, isoquinolyl group which may be substituted, cinnolinyl group which may be substituted, phthalazinyl group which may be substituted, quinoxalinyl group which may be substituted, benzofuranyl group which may be substituted or benzothiazolyl group which may be substituted, more preferably pyridyl group which may be substituted, indazolyl group which may be substituted or pyrazolopyridinyl group which may be substituted, further preferably pyridyl group which may be substituted.

The substituent of the pyridyl group which may be substituted is preferably a halogen atom, a $C_{1-6}$ alkyl group, a $C_{1-6}$ alkoxy group, $C_{1-6}$ alkylamino group or a heterocyclic group, more preferably a halogen atom or a $C_{1-6}$ alkoxy group.

The halogen atom mentioned above is preferably fluorine atom or chlorine atom, more preferably fluorine atom.

The $C_{1-6}$ alkyl group is preferably a $C_{1-3}$ alkyl group, more preferably methyl group or ethyl group, further preferably methyl group.

The $C_{1-6}$ alkoxy group is preferably methoxy group, ethoxy group or propoxy group, more preferably methoxy group or ethoxy group, further preferably methoxy group.

The $C_{1-6}$ alkylamino group is preferably methylamino group, ethylamino group or propylamino group, more preferably methylamino group or ethylamino group, further preferably methylamino group.

Preferred examples of the heterocyclic group include morpholinyl group.

When $R^{12a}$ is pyridyl group which may be substituted, preferably it is a pyridyl group represented by the following formula [I]-(1) or [I]-(2):

[Formula 26]

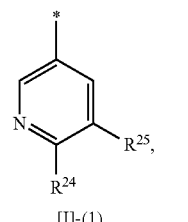

[I]-(1)

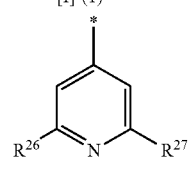

[I]-(2)

(in the formulas, $R^{24}$, $R^{25}$, $R^{26}$ and $R^{27}$ have the same meanings as those defined above), more preferably a pyridyl group represented by the formula [I]-(2).

Preferred examples of $R^{24}$, $R^{25}$, $R^{26}$ and $R^{27}$ are the same as those mentioned above as substituent of the pyridyl group which may be substituted. It is more preferred that one of $R^{24}$ and $R^{25}$, or one of $R^{26}$ and $R^{27}$ is hydrogen atom.

The substituent of the pyridyl group which may be substituted is preferably a halogen atom; a $C_{1-6}$ alkyl group which may be substituted with a $C_{1-6}$ alkoxy group; a $C_{1-6}$ alkoxy group; or a di($C_{1-6}$ alkyl)amino group, more preferably a $C_{1-6}$ alkyl group which may be substituted with a $C_{1-6}$ alkoxy group; or a $C_{1-6}$ alkoxy group.

The halogen atom mentioned above is preferably fluorine atom or chlorine atom, more preferably fluorine atom.

The $C_{1-6}$ alkoxy group is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

Preferred examples of the di($C_{1-6}$ alkyl)amino group include a di($C_{1-3}$ alkyl)amino group such as dimethylamino group.

When $R^{12a}$ is indazolyl group which may be substituted, it is preferably an indazolyl group represented by any one of the following formulas [II]-(1) to [II]-(4):

[Formula 27]

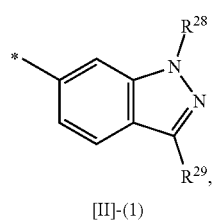

[II]-(1)

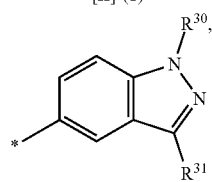

[II]-(2)

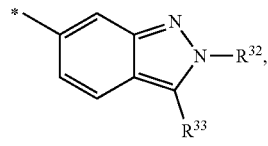

[II]-(3)

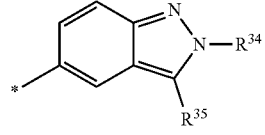

[II]-(4)

(in the formula, $R^{28}$, $R^{29}$, $R^{30}$, $R^{31}$, $R^{32}$, $R^{33}$, $R^{34}$, $R^{35}$ and * have the same meanings as those defined above), more preferably an indazolyl group represented by the formula [II]-(1) or [II]-(2), further preferably an indazolyl group represented by the formula [II]-(1).

The $C_{1-6}$ alkoxy group mentioned above is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

The halogen atom is preferably fluorine atom or chlorine atom, more preferably fluorine atom.

Preferred examples of the di($C_{1-6}$ alkyl)amino group include a di($C_{1-3}$ alkyl)amino group such as dimethylamino group.

$R^{28}$, $R^{30}$, $R^{32}$ and $R^{34}$ preferably represent hydrogen atom; or a $C_{1-3}$ alkyl group which may be substituted with a $C_{1-3}$ alkoxy group, more preferably hydrogen atom, methyl group, ethyl group or methoxyethyl group, further preferably hydrogen atom or methyl group, particularly preferably hydrogen atom.

$R^{29}$, $R^{31}$, $R^{33}$ and $R^{35}$ preferably represent hydrogen atom, a $C_{1-6}$ alkyl group or a $C_{1-6}$ alkoxy group, more preferably hydrogen atom, methyl group or methoxy group, further preferably hydrogen atom or methyl group, particularly preferably hydrogen atom.

The substituent of the indazolyl group which may be substituted is preferably a $C_{1-6}$ alkyl group which may be substituted with a $C_{1-6}$ alkoxy group; or a $C_{1-6}$ alkoxy group.

The $C_{1-6}$ alkoxy group is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

When $R^{12a}$ is pyrazolopyridinyl group which may be substituted, $R^{12a}$ is preferably a pyrazolopyridinyl group represented by any one of the following formulas [III]-(1) to [III]-(4):

[Formula 28]

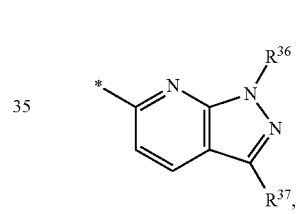

[III]-(1)

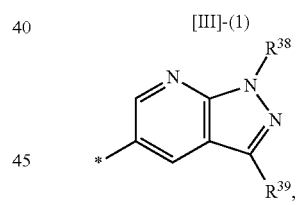

[III]-(2)

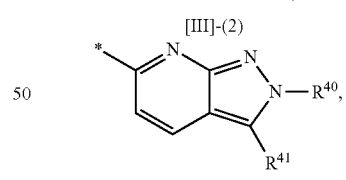

[III]-(3)

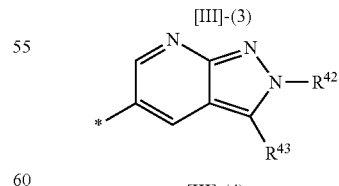

[III]-(4)

(in the formula, $R^{36}$, $R^{37}$, $R^{38}$, $R^{39}$, $R^{40}$, $R^{41}$, $R^{42}$, $R^{43}$ and * have the same meanings as those defined above), more preferably a pyrazolopyridinyl group represented by the formula [III]-(1) or [III]-(2), further preferably a pyrazolopyridinyl group represented by the formula [III]-(2).

The $C_{1-6}$ alkoxy group mentioned above is preferably methoxy group, ethoxy group or propoxy group, more preferably methoxy group or ethoxy group, further preferably methoxy group.

The $C_{1-6}$ alkyl group is preferably a $C_{1-3}$ alkyl group, more preferably methyl group or ethyl group, further preferably methyl group.

$R^{36}$, $R^{38}$, $R^{40}$ and $R^{42}$ preferably represent hydrogen atom; or a $C_{1-3}$ alkyl group which may be substituted with a $C_{1-3}$ alkoxy group, more preferably hydrogen atom, methyl group, ethyl group, methoxyethyl group or methoxy group, further preferably hydrogen atom or methyl group, particularly preferably hydrogen atom.

$R^{37}$, $R^{39}$, $R^{41}$ and $R^{43}$ preferably represent hydrogen atom, a $C_{1-6}$ alkyl group or a $C_{1-6}$ alkoxy group, more preferably hydrogen atom, methyl group or methoxy group, further preferably hydrogen atom.

Preferred examples of the substituent of the pyrazolyl group which may be substituted as $R^{12a}$ include a $C_{1-6}$ alkyl group such as methyl group.

Preferred examples of the substituent of the thienyl group which may be substituted as $R^{12a}$ include cyano group and a heterocyclic group such as carbamoyl group.

Preferred examples of the substituent of the oxazolyl group which may be substituted as $R^{12a}$ include a $C_{1-6}$ alkyl group such as butyl group.

Preferred examples of the substituent of the thiazolyl group which may be substituted as $R^{12a}$ include cyano group.

Preferred examples of the substituent of the isothiazolyl group which may be substituted as $R^{12a}$ include a $C_{1-6}$ alkyl group such as methyl group.

Preferred examples of the substituent of the benzothiazolyl group which may be substituted as $R^{12a}$ include a $C_{1-6}$ alkyl group such as methyl group.

As the isoquinolyl group which may be substituted, cinnolinyl group which may be substituted, phthalazinyl group which may be substituted, quinoxalinyl group which may be substituted and benzofuranyl group which may be substituted as $R^{12a}$, those not having any substituent are also preferred.

Preferred examples of the substituent of the carbamoyl group which may be substituted as $R^{12a}$ include a heterocyclic group such as pyridyl group.

$X^{2a}$ is a $C_{1-6}$ alkylene group which may be substituted, a divalent alicyclic hydrocarbon group which may be substituted or a divalent aromatic hydrocarbon group which may be substituted, preferably a $C_{1-6}$ alkylene group which may be substituted or a divalent alicyclic hydrocarbon group which may be substituted, more preferably a $C_{1-6}$ alkylene group which may be substituted.

When $X^{2a}$ is a $C_{1-6}$ alkylene group which may be substituted, the $C_{1-6}$ alkylene group of the $C_{1-6}$ alkylene group which may be substituted is preferably methylene group, ethylene group or trimethylene group, more preferably trimethylene group.

The substituent of the $C_{1-6}$ alkylene group of the $C_{1-6}$ alkylene group which may be substituted is preferably a $C_{1-6}$ alkyl group, more preferably a $C_{1-3}$ alkyl group, further preferably methyl group or ethyl group, particularly preferably methyl group. In addition, as the $C_{1-6}$ alkylene group which may be substituted, an unsubstituted $C_{1-6}$ alkylene group is preferred.

When $X^{2a}$ is a divalent alicyclic hydrocarbon group which may be substituted, the divalent alicyclic hydrocarbon group of the divalent alicyclic hydrocarbon group which may be substituted is preferably cyclobutylene group, cyclopentylene group or cyclohexylene group, more preferably cyclobutylene group or cyclohexylene group, further preferably cyclobutylene group.

The cyclobutylene group mentioned above is preferably

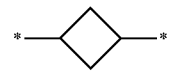

[Formula 29]

(in the formula, * represents binding position), more preferably

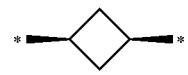

[Formula 30]

(in the formula, * represents binding position).

The cyclopentylene group is preferably

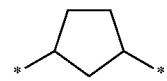

[Formula 31]

(in the formula, * represents binding position), more preferably

[Formula 32]

(in the formula, * represents binding position), more preferably

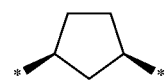

[Formula 33]

(in the formula, * represents binding position).

The cyclohexylene group is preferably

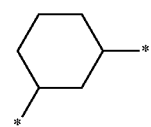

[Formula 34]

(in the formula, * represents binding position), more preferably

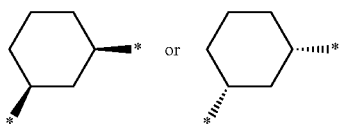

[Formula 35]

(in the formula, * represents binding position), still more preferably

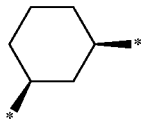

[Formula 36]

(in the formula, * represents binding position).

In addition, as the divalent alicyclic hydrocarbon group which may be substituted, an unsubstituted divalent alicyclic hydrocarbon group is preferred.

When $X^{2a}$ is an aromatic hydrocarbon group which may be substituted, the aromatic hydrocarbon group of the aromatic hydrocarbon group which may be substituted is preferably phenylene group.

The phenylene group mentioned above is preferably

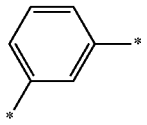

[Formula 37]

(in the formula, * represents binding position).

When $X^{2a}$ is an aromatic hydrocarbon group which may be substituted, the substituent of the aromatic hydrocarbon group which may be substituted is preferably a halogen atom; a $C_{1-6}$ alkyl group which may be substituted with a halogen atom; or a $C_{1-6}$ alkoxy group which may be substituted with a halogen atom.

The halogen atom mentioned above is preferably fluorine atom or chlorine atom, more preferably fluorine atom.

The $C_{1-6}$ alkyl group is preferably a $C_{1-3}$ alkyl group, more preferably methyl group or ethyl group, further preferably methyl group.

The $C_{1-6}$ alkoxy group is preferably methoxy group, ethoxy group or propoxy group, more preferably methoxy group or ethoxy group, further preferably methoxy group.

In addition, as the divalent aromatic hydrocarbon group which may be substituted, an unsubstituted divalent aromatic hydrocarbon group is preferred.

$X^{3a}$ is a $C_{2-6}$ alkynylene group which may be substituted or $N(R^{22})$—$C(=O)$ (in the formula, $R^{22}$ has the same meaning as that defined above), preferably a $C_{2-6}$ alkynylene group which may be substituted.

The $C_{2-6}$ alkynylene group mentioned above is preferably ethynylene group, $R^{22}$ of $N(R^{22})$—$C(=O)$ (in the formula, $R^{22}$ has the same meaning as that defined above) is preferably hydrogen atom.

In addition, as the $C_{2-6}$ alkynylene group which may be substituted, an unsubstituted $C_{2-6}$ alkynylene group is preferred.

Examples of preferred compounds among the compounds of the present invention include the following compounds.

(S,E)-N-(3-(2-(4-(Dimethylamino)-N-methyl-2-butenamido)propanamido)phenyl)-4-(propylamino)-2-((2-(pyridin-4-yl)ethyl)amino)pyrimidine-5-carboxamide [Compound No. 2-12]

(S,E)-2-((4-Carbamoylphenyl)amino)-N-(3-(2-(4-(dimethylamino)-N-methyl-2-butenamido)propanamido)phenyl)-4-(propylamino)pyrimidine-5-carboxamide [Compound No. 3-1]

(E)-2-((4-Carbamoylphenyl)amino)-N-(3-(2-(4-(dimethylamino)-N-methyl-2-butenamido)actamido)cyclohexyl)-4-(propylamino)pyrimidine-5-carboxamide [Compound No. 3-4]

(S,E)-2-((4-Carbamoylphenyl)amino)-N-(3-(2-(4-(diethylamino)-N-methyl-2-butenamido)propanamido)phenyl)-4-(propylamino)pyrimidine-5-carboxamide [Compound No. 4-8]

(S,E)-2-((4-Carbamoylphenyl)amino)-N-(3-(2-(4-(dimethylamino)-N-methyl-2-butenamido)propaneamido)propyl)-4-(propylamino)pyrimidine-5-carboxamide [Compound No. 5-1]

(S,E)-N-(3-(2-(4-(Dimethylamino)-N-methyl-2-butenamido)propanamido)phenyl)-2-(isoquinolin-6-ylamino)-4-(propylamino)pyrimidine-5-carboxamide [Compound No. 6-9]

(S,E)-2-(Cinnolin-6-ylamino)-N-(3-(2-(4-(dimethylamino)-N-methyl-2-butenamido)propanamido)phenyl)-4-(propylamino)pyrimidine-5-carboxamide [Compound No. 6-11]

(S,E)-4-(Dimethylamino)-N-(1-((5-(2-((3-fluorophenyl)amino)-4-(propylamino)pyrimidin-5-yl)-4-pentyn-1-yl)amino)-1-oxopropan-2-yl)-N-methyl-2-butenamide [Compound No. 7-1]

(S,E)-N-(1-((5-(2-((3-Cyanophenyl)amino)-4-(propylamino)pyrimidin-5-yl)-4-pentyn-1-yl)amino)-1-oxopropan-2-yl)-4-(dimethylamino)-N-methyl-2-butenamide [Compound No. 7-3]

(S,E)-4-((5-(5-(2-(4-(Dimethylamino)-N-methyl-2-butenamido)propaneamido)-1-pentyn-1-yl)-4-(propylamino)pyrimidin-2-yl)amino)benzamide [Compound No. 7-4]

(S,E)-N-(1-((5-(2-((4-Cyanophenyl)amino)-4-(propylamino)pyrimidin-5-yl)-4-pentyn-1-yl)amino)-1-oxopropan-2-yl)-4-(dimethylamino)-N-methyl-2-butenamide [Compound No. 7-5]

(E)-4-(Dimethylamino)-N-(2-((5-(2-((4-fluorophenyl)amino)-4-(propylamino)pyrimidin-5-yl)-4-pentyn-1-yl)amino)-2-oxoethyl)-N-methyl-2-butenamide [Compound No. 7-8]

(E)-N-(2-((5-(2-((4-Cyanophenyl)amino)-4-(propylamino)pyrimidin-5-yl)-4-pentyn-1-yl)amino)-2-oxoethyl)-4-(dimethylamino)-N-methyl-2-butenamide [Compound No. 7-9]

(S,E)-4-(Dimethylamino)-N-(1-((5-(2-(3-fluorophenyl)amino)-4-(propylamino)pyrimidin-5-yl)-4-pentyn-1-yl)amino)-1-oxobutan-2-yl)-N-methyl-2-butenamide [Compound No. 7-17]

(S,E)-4-(Dimethylamino)-N-(1-((5-(2-((3-fluoro-4-methoxyphenyl)amino)-4-(propylamino)pyrimidin-5-yl)-4-pentyn-1-yl)amino)-1-oxopropan-2-yl)-N-methyl-2-butenamide [Compound No. 7-20]

(S,E)-4-(Dimethylamino)-N-(1-((5-(2-((6-fluoropyridin-3-yl)amino)-4-(propylamino)pyrimidin-5-yl)-4-pentyn-1-yl)amino)-1-oxopropan-2-yl)-N-methyl-2-butenamide [Compound No. 7-21]

(S,E)-4-(Dimethylamino)-N-(1-((5-(2-((6-fluoropyridin-3-yl)amino)-4-(4-methoxyphenyl)amino)pyrimidin-5-yl)-

4-pentyn-1-yl)amino)-1-oxopropan-2-yl)-N-methyl-2-butenamide [Compound No. 7-22]

(E)-4-(Dimethylamino)-N-(2-((5-(2-((3-fluorophenyl)amino)-4-(propylamino)pyrimidin-5-yl)-4-pentyn-1-yl)amino)-2-oxoethyl)-N-methyl-2-butenamide [Compound No. 7-24]

(S,E)-N-(5-(2-((4-Cyanophenyl)amino)-4-(propylamino)pyrimidin-5-yl)-4-pentyn-1-yl)-1-(4-(dimethylamino)-2-butenoyl)pyrrolidine-2-carboxamide [Compound No. 7-33]

(S,E)-N-(1-((5-(4-(Cyclopropylamino)-2-((3-fluoro-4-methoxyphenyl)amino)pyrimidin-5-yl)-4-pentyn-1-yl)amino)-1-oxopropan-2-yl)-4-(dimethylamino)-N-methyl-2-butenamide [Compound No. 7-42]

(S,E)-4-(Dimethylamino)-N-(1-((5-(2-((3-fluoro-4-methoxyphenyl)amino)-4-((3-fluoropropyl)amino)pyrimidin-5-yl)-4-pentyn-1-yl)amino)-1-oxopropan-2-yl)-N-methyl-2-butenamide [Compound No. 7-56]

(S,E)-N-(1-((5-(2-((4-Cyanophenyl)amino)-4-(propylamino)pyrimidin-5-yl)-4-pentyn-1-yl)amino)-3-hydroxy-1-oxopropan-2-yl)-4-(dimethylamino)-N-methyl-2-butenamide [Compound No. 7-62]

(2S,4R)-1-((E)-4-(Dimethylamino)-2-butenoyl)-N-(5-(2-((3-fluorophenyl)amino)-4-(propylamino)pyrimidin-5-yl)-4-pentyn-1-yl)-4-hydroxypyrrolidine-2-carboxamide [Compound No. 7-66]

(2S,4S)-1-((E)-4-(Dimethylamino)-2-butenoyl)-4-fluoro-N-(5-(2-((3-fluorophenyl)amino)-4-(methylamino)pyrimidin-5-yl)-4-pentyn-1-yl)pyrrolidine-2-carboxamide [Compound No. 7-72]

(2S,4S)-1-((E)-4-(Dimethylamino)-2-butenoyl)-N-(5-(2-((3-fluorophenyl)amino)-4-(methylamino)pyrimidin-5-yl)-4-pentyn-1-yl)-4-methoxypyrrolidine-2-carboxamide [Compound No. 7-73]

(2S,4S)-1-((E)-4-(Dimethylamino)-2-butenoyl)-4-fluoro-N-(5-(2-((4 -fluorophenyl)amino)-4-(methylamino)pyrimidin-5-yl)-4-pentyn-1-yl)pyrrolidine-2-carboxamide [Compound No. 7-80]

(2S,4R)-1-((E)-4-(Dimethylamino)-2-butenoyl)-4-fluoro-N-(5-(2-((4-fluorophenyl)amino)-4-(methylamino)pyrimidin-5-yl)-4-pentyn-1-yl)pyrrolidine-2-carboxamide [Compound No. 7-81]

(2S,4S)-1-((E)-4-(Dimethylamino)-2-butenoyl)-N-(5-(2-(4-fluorophenyl)amino)-4-(methylamino)pyrimidin-5-yl)-4-pentyn-1-yl)-4-methoxypyrrolidine-2-carboxamide [Compound No. 7-82]

(2S,4R)-1-((E)-4-(Dimethylamino)-2-butenoyl)-N-(5-(2-((4-fluorophenyl)amino)-4-(methylamino)pyrimidin-5-yl)-4-pentyn-1-yl)-4-methoxypyrrolidine-2-carboxamide [Compound No. 7-83]

(S,E)-1-(4-(Dimethylamino)-2-butenoyl)-N-(5-(2-((4-fluorophenyl)amino)-4-(methylamino)pyrimidin-5-yl)-4-pentyn-1-yl)azetidine-2-carboxamide [Compound No. 7-86]

(2S,4S)—N-(5-(2-((4-Cyanophenyl)amino)-4-(methylamino)pyrimidin-5-yl)-4-pentyn-1-yl)-1-((E)-4-(dimethylamino)-2-butenoyl)-4-fluoropyrrolidine-2-carboxamide [Compound No. 7-87]

(E)-N-(2-((5-(2-((4-Cyanophenyl)amino)-4-(methylamino)pyrimidin-5-yl)-4-pentyn-1-yl)amino)-2-oxoethyl)-4-(dimethylamino)-N-methyl-2-butenamide [Compound No. 7-88]

(S,E)-4-(Dimethylamino)-N-(1-((3-((2-((3-fluorophenyl)amino)-4-(propylamino)pyrimidin-5-yl)ethynyl)phenyl)amino)-1-oxopropan-2-yl)-N-methyl-2-butenamide [Compound No. 8-1]

(S,E)-4-((5-((3-(2-(4-(Dimethylamino)-N-methyl-2-butenamido)propanamido)phenyl)ethynyl)-4-(propylamino)pyrimidin-2-yl)amino)benzamide [Compound No. 8-2]

(S,E)-N-1-((5-(2-((4-Cyanophenyl)amino)-4-(pyrrolidin-1-yl)pyrimidin-5-yl)-4-pentyn-1-yl)amino)-1-oxopropan-2-yl)-4-(dimethylamino)-N-methyl-2-butenamide [Compound No. 9-1]

(S,E)-4-(Dimethylamino)-N-(1-((5-(2-((2-fluoropyridin-4-yl)amino)-4-(pyrrolidin-1-yl)pyrimidin-5-yl)-4-pentyn-1-yl)amino)-1-oxopropan-2-yl)-N-methyl-2-butenamide [Compound No. 9-12]

(S,E)-4-(Dimethylamino)-N-(1-((5-(2-((2-fluoropyridin-4-yl)amino)-4-(propylamino)pyrimidin-5-yl)-4-pentyn-1-yl)amino)-1-oxopropan-2-yl)-N-methyl-2-butenamide [Compound No. 9-13]

(S,E)-N-(1-((5-(4-(Cyclopropylamino)-2-((2-fluoropyridin-4-yl)amino)pyrimidin-5-yl)-4-pentyn-1-yl)amino)-1-oxopropan-2-yl)-4-(dimethylamino)-N-methyl-2-butenamide [Compound No. 9-15]

(S,E)-4-(Dimethylamino)-N-methyl-N-(1-((5-(2-((3-methylisothiazol-5-yl)amino)-4-(propylamino)pyrimidin-5-yl)-4-pentyn-1-yl)amino)-1-oxopropan-2-yl)-2-butenamide [Compound No. 9-30]

(S,E)-4-(Dimethylamino)-N-(1-((5-(4-(3-methoxypropyl)amino)-2-((2-methoxypyridin-4-yl)amino)pyrimidin-5-yl)-4-pentyn-1-yl)amino)-1-oxopropan-2-yl)-N-methyl-2-butenamide [Compound No. 9-31]

(S,E)-1-(4-(Dimethylamino)-2-butenoyl)-N-(5-(4-((3-methoxypropyl)amino)-2-((methoxypyridin-4-yl)amino)pyrimidin-5-yl)-4-pentyn-1-yl)pyrrolidine-2-carboxamide [Compound No. 9-32]

(2S,4S)-1-((E)-4-(Dimethylamino)-2-butenoyl)-4-fluoro-N-(5-(4-((3-methoxypropyl)amino)-2-((methoxypyridin-4-yl)amino)pyrimidin-5-yl)-4-pentyn-1-yl)pyrrolidine-2-carboxamide [Compound No. 9-34]

(S,E)-1-(4-(Dimethylamino)-2-butenoyl)-N-(5-(2-((2-methoxypyridin-4-yl)amino)-4-(propylamino)pyrimidin-5-yl)-4-pentyn-1-yl)pyrrolidine-2-carboxamide [Compound No. 9-35]

(2S,4S)-1-((E)-4-(Dimethylamino)-2-butenoyl)-4-fluoro-N-(5-(2-((2-methoxypyridin-4-yl)amino)-4-(propylamino)pyrimidin-5-yl)-4-pentyn-1-yl)pyrrolidine-2-carboxamide [Compound No. 9-37]

(E)-4-(Dimethylamino)-N-(2-((5-(2-((2-methoxypyridin-4-yl)amino)-4-(propylamino)pyrimidin-5-yl)-4-pentyn-1-yl)amino)-2-oxoethyl)-N-methyl-2-butenamide [Compound No. 9-38]

(S,E)-4-(Dimethylamino)-N-(1-((5-(2-((3-fluorophenyl)amino)-4-((4-methoxyphenyl)amino)pyrimidin-5-yl)-4-pentyn-1-yl)amino)-1-oxopropan-2-yl)-N-methyl-2-butenamide [Compound No. 10-3]

(S,E)-4-(Dimethylamino)-N-(1-((5-(2-((3-fluorophenyl)amino)-4-morpholinopyrimidin-5-yl)-4-pentyn-1-yl)amino)-1-oxopropan-2-yl)-N-methyl-2-butenamide [Compound No. 10-5]

(E)-4-(Dimethylamino)-N-(2-((5-(2-((4-fluorophenyl)amino)-4-(3-fluoropropyl)amino)pyrimidin-5-yl)-4-pentyn-1-yl)amino)-2-oxoethyl)-N-methyl-2-butenamide [Compound No. 10-21]

(S,E)-N-(1-((5-(2-((4-Cyanophenyl)amino)-4-(cyclopropylamino)pyrimidin-5-yl)-4-pentyn-1-yl)amino)-1-oxopropan-2-yl)-4-(dimethylamino))-N-methyl-2-butenamide [Compound No. 10-25]

(S,E)-N-(1-((5-(2-((4-Cyanophenyl)amino)-4-((3-fluoropropyl)amino)pyrimidin-5-yl)-4-pentyn-1-yl)amino)-1-oxopropan-2-yl)-4-(dimethylamino))-N-methyl-2-butenamide [Compound No. 10-29]

(S,E)-4-(Dimethylamino))-N-(1-((5-(4-(ethylamino)-2-((1-methyl-1H-indazol-5-yl)amino)pyrimidin-5-yl)-4-pentyn-1-yl)amino)-1-oxopropan-2-yl)-N-methyl-2-butenamide [Compound No. 10-53]

(S,E)-N-(1-((5-(4-(Cyclopropylamino)-2-((1-methyl-1H-indazol-5-yl)amino)pyrimidin-5-yl)-4-pentyn-1-yl)amino)-1-oxopropan-2-yl)-4-(dimethylamino))-N-methyl-2-butenamide [Compound No. 10-54]

(S,E)-4-(Dimethylamino))-N-methyl-N-(1-((5-(2-((1-methyl-1H-indazol-5-yl)amino)-4-(methylamino)pyrimidin-5-yl)-4-pentyn-1-yl)amino)-1-oxopropan-2-yl)-2-butenamide [Compound No. 10-56]

(S,E)-N-(5-(2-((1H-Indazol-5-yl)amino)-4-(methylamino)pyrimidin-5-yl)-4-pentyn-1-yl)-1-(4-(dimethylamino)-2-butenoyl)pyrrolidine-2-carboxamide [Compound No. 10-66]

(S,E)-N-(5-(2-((1H-Indazol-5-yl)amino)-4-(ethylamino)pyrimidin-5-yl)-4-pentyn-1-yl)-1-(4-(dimethylamino)-2-butenoyl)pyrrolidine-2-carboxamide [Compound No. 10-67]

(S,E)-N-(5-(2-((1H-Indazol-5-yl)amino)-4-((3-methoxypropyl)amino)pyrimidin-5-yl)-4-pentyn-1-yl)-1-(4-(dimethylamino)-2-butenoyl)pyrrolidine-2-carboxamide [Compound No. 10-68]

(E)-4-(Dimethylamino)-N—((S)-1-(((1S,3R)-3-((2-((3-fluorophenyl)amino)-4-(propylamino)pyrimidin-5-yl)ethynyl)cyclohexyl)amino)-1-oxopropan-2-yl)-N-methyl-2-butenamide [Compound No. 13-1]

(E)-4-(Dimethylamino)-N—((S)-1-(((1S,3R)-3-((2-((3-fluorophenyl)amino)-4-(propylamino)pyrimidin-5-yl)ethynyl)cyclobutyl)amino)-1-oxopropan-2-yl)-N-methyl-2-butenamide [Compound No. 13-8]

(E)-N—((S)-1-(((1S,3R)-3-((2-((4-Cyanophenyl)amino)-4-(methylamino)pyrimidin-5-yl)ethynyl)cyclobutyl)amino)-1-oxopropan-2-yl)-4-(dimethylamino)-N-methyl-2-butenamide [Compound No. 13-9]

(E)-4-(Dimethylamino)-N—((S)-1-(((1S,3R)-3-((2-((3-fluorophenyl)amino)-4-(methylamino)pyrimidin-5-yl)ethynyl)cyclobutyl)amino)-1-oxopropan-2-yl)-N-methyl-2-butenamide [Compound No. 13-13]

(E)-N—((S)-1-(((1S,3R)-3-((2-((4-Cyanophenyl)amino)-4-(methylamino)pyrimidin-5-yl)ethynyl)cyclobutyl)amino)-1-oxopropan-2-yl)-4-(dimethylamino)-N-methyl-2-butenamide [Compound No. 13-14]

(E)-N—((S)-1-(((1S,3R)-3-((2-((3-Cyanophenyl)amino)-4-(methylamino)pyrimidin-5-yl)ethynyl)cyclobutyl)amino)-1-oxopropan-2-yl)-4-(dimethylamino)-N-methyl-2-butenamide [Compound No. 13-15]

(E)-4-(Dimethylamino)-N—((S)-1-(((1S,3R)-3-((2-((3-fluoro-4-methoxyphenyl)amino)-4-(methylamino)pyrimidin-5-yl)ethynyl)cyclobutyl)amino)-1-oxopropan-2-yl)-N-methyl-2-butenamide [Compound No. 13-16]

(E)-4-(Dimethylamino)-N—((S)-1-(((1S,3R)-3-((2-((4-fluorophenyl)amino)-4-(methylamino)pyrimidin-5-yl)ethynyl)cyclobutyl)amino)-1-oxopropan-2-yl)-N-methyl-2-butenamide [Compound No. 13-19]

(E)-N—((S)-1-(((1S,3R)-3-((2-((3-Cyanophenyl)amino)-4-(cyclopropylamino)pyrimidin-5-yl)ethynyl)cyclobutyl)amino)-1-oxopropan-2-yl)-4-(dimethylamino)-N-methyl-2-butenamide [Compound No. 13-20]

(E)-4-(Dimethylamino)-N—((S)-1-(((1S*,3R*)-3-((2-((2-fluoropyridin-4-yl)amino)-4-(propylamino)pyrimidin-5-yl)ethynyl)cyclobutyl)amino)-1-oxopropan-2-yl)-N-methyl-2-butenamide [Compound No. 14-4]

(E)-4-(Dimethylamino)-N—((S)-1-(((1S,3R)-3-((2-((2-methoxypyridin-4-yl)amino)-4-(propylamino)pyrimidin-5-yl)ethynyl)cyclobutyl)amino)-1-oxopropan-2-yl)-N-methyl-2-butenamide [Compound No. 14-6]

(E)-N—((S)-1-(((1S,3R)-3-((2-((4-Cyanophenyl)amino)-4-(methylamino)pyrimidin-5-yl)ethynyl)cyclohexyl)amino)-1-oxopropan-2-yl)-4-(dimethylamino)-N-methyl-2-butenamide [Compound No. 15-5]

(E)-N—((S)-1-(((1S*,3R*)-3-((2-((4-Cyanophenyl)amino)-4-(cyclopropylamino)pyrimidin-5-yl)ethynyl)cyclobutyl)amino)-1-oxopropan-2-yl)-4-(dimethylamino)-N-methyl-2-butenamide [Compound No. 15-8]

(E)-N—((S)-1-(((1S*,3R*)-3-((4-(Cyclopropylamino)-2-((4-fluorophenyl)amino)pyrimidin-5-yl)ethynyl)cyclobutyl)amino)-1-oxopropan-2-yl)-4-(dimethylamino)-N-methyl-2-butenamide [Compound No. 15-9]

(E)-N—((S)-1-(((1S*,3R*)-3-((4-(Cyclopropylamino)-2-((3-fluoro-4-methoxyphenyl)amino)pyrimidin-5-yl)ethynyl)cyclobutyl)amino)-1-oxopropan-2-yl)-4-(dimethylamino)-N-methyl-2-butenamide [Compound No. 15-10]

(E)-4-(Dimethylamino)-N—((S)-1-(((1S,3R)-3-((2-((3-fluorophenyl)amino)-4-((3-fluoropropyl)amino)pyrimidin-5-yl)ethynyl)cyclobutyl)amino)-1-oxopropan-2-yl)-N-methyl-2-butenamide [Compound No. 15-13]

(E)-N—((S)-1-(((1S,3R)-3-((2-((4-Cyanophenyl)amino)-4-((3-fluoropropyl)amino)pyrimidin-5-yl)ethynyl)cyclobutyl)amino)-1-oxopropan-2-yl)-4-(dimethylamino)-N-methyl-2-butenamide [Compound No. 15-14]

(E)-4-(Dimethylamino)-N—((S)-1-(((1S,3R)-3-((2-((3-fluorophenyl)amino)-4-((3-methoxypropyl)amino)pyrimidin-5-yl)ethynyl)cyclobutyl)amino)-1-oxopropan-2-yl)-N-methyl-2-butenamide [Compound No. 15-15]

(E)-N—((S)-1-(((1S,3R)-3-((2-((4-Cyanophenyl)amino)-4-((3-methoxypropyl)amino)pyrimidin-5-yl)ethynyl)cyclobutyl)amino)-1-oxopropan-2-yl)-4-(dimethylamino)-N-methyl-2-butenamide [Compound No. 15-16]

(E)-4-(Dimethylamino)-N—((S)-1-(((1S,3R)-3-((2-((3-fluoro-4-methoxyphenyl)amino)-4-(methylamino)pyrimidin-5-yl)ethynyl)cyclohexyl)amino)-1-oxopropan-2-yl)-N-methyl-2-butenamide [Compound No. 21-32]

(S,E)-4-(Dimethylamino)-N-methyl-N-(1-((5-(2-((2-methylpyridin-4-yl)amino)-4-(propylamino)pyrimidin-5-yl)-4-pentyn-1-yl)amino)-1-oxopropan-2-yl)-2-butenamide [Compound No. 22-1]

(S,E)-N-(1-((5-(2-(Benzo[d]thiazol-6-ylamino)-4-(propylamino)pyrimidin-5-yl)-4-pentyn-1-yl)amino)-1-oxopropan-2-yl)-4-(dimethylamino)-N-methyl-2-butenamide [Compound No. 22-6]

(S,E)-1-(4-(Dimethylamino)-2-butenoyl)-N-(5-(2-((1-methyl-1H-indazol-5-yl)amino)-4-(propylamino)pyrimidin-5-yl)-4-pentyn-1-yl)pyrrolidine-2-carboxamide [Compound No. 22-31]

(S,E)-1-(4-(Dimethylamino)-2-butenoyl)-N-(5-(2-((1-methyl-1H-pyrazolo[3,4-b]pyridin-5-yl)amino)-4-(propylamino)pyrimidin-5-yl)-4-pentyn-1-yl)pyrrolidine-2-carboxamide [Compound No. 22-43]

(S,E)-1-(4-(Dimethylamino)-2-butenoyl)-N-(5-(2-((1-(2-methoxyethyl)-1H-pyrazolo[3,4-b]pyridin-5-yl)amino)-4-(propylamino)pyrimidin-5-yl)-4-pentyn-1-yl)pyrrolidine-2-carboxamide [Compound No. 22-44]

(S,E)-4-(Dimethylamino)-N-methyl-N-(1-((5-(2-((3-methyl-1H-pyrazolo[3,4-b]pyridin-5-yl)amino)-4-(propylamino)pyrimidin-5-yl)-4-pentyn-1-yl)amino)-1-oxopropan-2-yl)-2-butenamide [Compound No. 22-51]

(S,E)-1-(4-(Dimethylamino)-2-butenoyl)-N-(5-(2-((3-methyl-1H-pyrazolo[3,4-b]pyridin-5-yl)amino)-4-(propylamino)pyrimidin-5-yl)-4-pentyn-1-yl)pyrrolidine-2-carboxamide [Compound No. 22-56]

(S,E)-1-(4-(Dimethylamino)-2-butenoyl)-N-(5-(2-((3-methoxy-1H-pyrazolo[3,4-b]pyridin-5-yl)amino)-4-(propylamino)pyrimidin-5-yl)-4-pentyn-1-yl)pyrrolidine-2-carboxamide [Compound No. 22-57]

When there are isomers (for example, optical isomers, geometrical isomers, tautomers etc.) of the compounds of the general formula [1] and salts thereof, they fall within the scope of the present invention, and anhydrides, solvates, hydrates and crystals of various forms thereof also fall within the scope of the present invention.

The compounds of the present invention represented by the general formula [1] have superior FLT3 inhibition activity, and are useful for treatment of a disease or condition relating to FLT3. The treatment means prophylactic treatment, therapeutic treatment etc.

The prophylactic treatment means a treatment for inhibiting onset, reducing risk of onset, retarding onset, etc.

The therapeutic treatment means a treatment for improving a target disease or condition, or suppressing (maintaining or retarding) aggravation of the disease or condition.

The disease or condition relating to FLT3 means any diseases and conditions that can be treated by inhibiting FLT3. Examples include, for example, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large cell lymphoma (ALCL), prolymphocytic leukemia (PML), juvenile myelomonocytic leukemia (JMML), adult T cell ALL, myelodysplastic syndrome (MDS), and myeloproliferative disorder (MPD), AML and APL are preferred examples, and AML is a more preferred example.

The compounds of the present invention represented by the general formula [1] are also useful as seed compounds, lead compounds, or intermediates for searching for a compound useful for prophylactic or therapeutic treatment of FLT3-related diseases.

Hereafter, the methods for preparing the compounds of the present invention will be explained.

The compounds of the present invention are prepared by a combination of per se known methods, and for example, they can be prepared by the preparation methods shown below.

[Preparation Method 1]

[Formula 38]

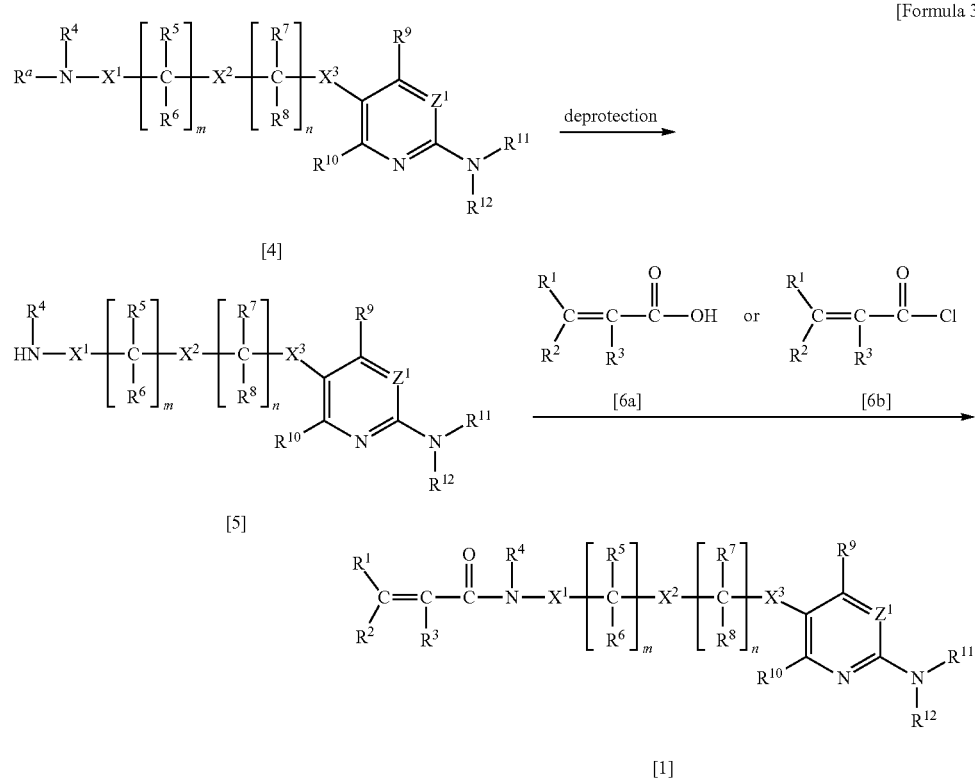

(In the formula, $R^a$ represents an amino protecting group or an imino protecting group; and $R^1$, $R^2$, $R^3$, $R^4$, $R^5$, $R^6$, $R^7$, $R^8$, $R^9$, $R^{10}$, $R^{11}$, $R^{12}$, $X^1$, $X^2$, $X^3$, $Z^1$, m and n have the same meanings as those defined above.)

(1-1)

The compounds of the general formula [5] can be prepared by carrying out deprotection of a compound of the general formula [4].

This reaction can be performed by, for example, the method described in T. W. Greene et al., Protective Groups in Organic Synthesis, 4 th Edition, pp. 696-926, 2007, John Wiley & Sons, Inc.

(1-2)

As the compounds of the general formula [6 a], for example, crotonic acid, 4-dimethylaminocrotonic acid, and so forth are known.

The compounds of the general formula [1] can be prepared by reacting a compound of the general formula [5] with a compound of the general formula [6 a] in the presence of a condensing agent or an acid halide, and a base.

This reaction can be performed by, for example, the method described in Chemical Reviews, vol. 97, p. 2243, 1997, Chemical Synthesis of Natural Product Peptides: Coupling Methods for the Incorporation of Noncoded Amino Acids into Peptides, or Tetrahedron, vol. 60, p. 2447, 2004, Recent development of peptide coupling reagents in organic synthesis.

The solvent used for this reaction is not particularly limited, so long as a solvent that does not affect the reaction is chosen, and examples include, for example, halogenated hydrocarbons, ethers, esters, amides, nitriles, sulfoxides, and aromatic hydrocarbons, and these solvents may be used as a mixture.

Preferred examples of the solvent include amides, and N,N-dimethylformamide is more preferred.

Although amount of the solvent to be used is not particularly limited, it may be 1- to 500-fold amount (v/w) with respect to the compound of the general formula [5].

Examples of the base used for this reaction include inorganic bases and organic bases.

Amount of the base to be used may be 1- to 50-fold molar amount, preferably 1- to 10-fold molar amount, with respect to the compound of the general formula [5].

Examples of the condensing agent used for this reaction include, for example, carbodiimides such as N,N'-dicyclohexylcarbodiimide and 1-ethyl-3-(3-dimethylaminopropyl)carbodiimide; carbonyl compounds such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium hexafluorophosphate; O-(7-azabenzotriazol-1-yl)-1,1,3,3-tetramethyluronium hexafluorophosphate; and so forth.

Examples of the acid halide used for this reaction include, for example, carboxylic acid halides such as acetyl chloride and trifluoroacetyl chloride; sulfonic acid halides such as methanesulfonyl chloride and para-toluenesulfonyl chloride; chloroformic acid esters such as ethyl chloroformate and isobutyl chloroformate, and so forth.

Amount of the compound of the general formula [6 a] to be used is not particularly limited, and it may be 1- to 10-fold amount (v/w) with respect to the compound of the general formula [5].

This reaction may be performed at −30 to 150° C., preferably 0 to 100° C., for 30 minutes to 48 hours.

(1-3)

As the compounds of the general formula [6 b], for example, acrylic acid chloride, and so forth are known.

The compounds of the general formula [1] can be prepared by reacting a compound of the general formula [5] with a compound of the general formula [6 b] in the presence of a base.

The compounds of the general formula [6 b] can be prepared by reacting a compound of the general formula [6 a] with thionyl chloride, oxalyl chloride, or the like.

The solvent used for this reaction is not particularly limited, so long as a solvent that does not affect the reaction is chosen. Examples include, for example, halogenated hydrocarbons, ethers, esters, amides, aromatic hydrocarbons, and acetonitrile, and a mixture of these solvents may also be used.

Preferred examples of the solvent include amides, and N,N-dimethylformamide is preferred.

Although amount of the solvent to be used is not particularly limited, it may be 1- to 500-fold amount (v/w) with respect to the compound of the general formula [5].

Examples of the base used for this reaction include inorganic bases and organic bases.

Amount of the base to be used may be 1- to 50-fold molar amount, preferably 1- to 5-fold molar amount, with respect to the compound of the general formula [5].

This reaction may be performed at −30 to 150° C., preferably 0 to 100° C., for 30 minutes to 48 hours.

Next, the method for preparing the compounds of the general formula [4], which are starting materials for the production of the compounds of the present invention, will be explained.

[Preparation Method 2]

[Formula 39]

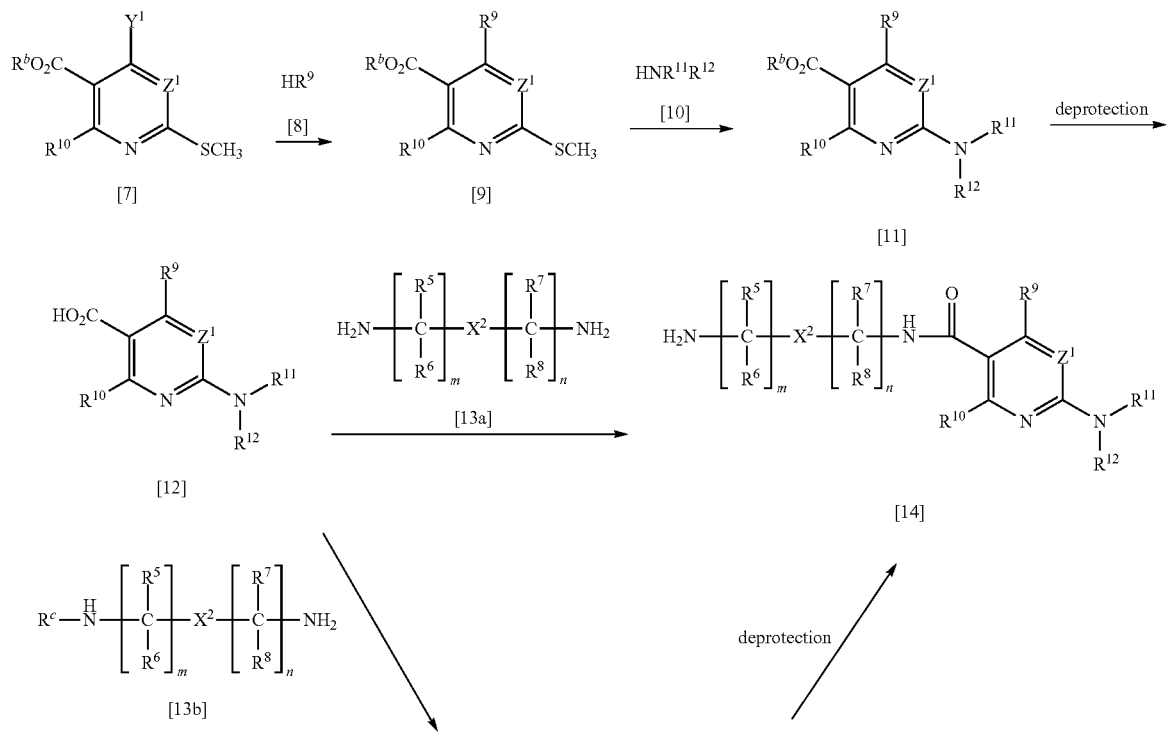

-continued

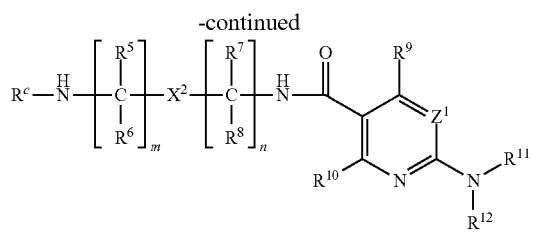

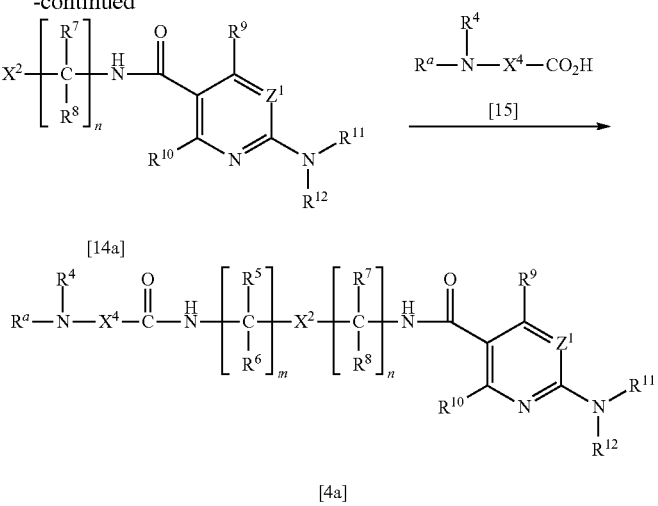

(In the formula, $R^b$ represents a carboxy protecting group; $R^C$ represents an amino protecting group; $Y^1$ represents a leaving group; and $R^4$, $R^5$, $R^6$, $R^7$, $R^8$, $R^9$, $R^{10}$, $R^{11}$, $R^{12}$, $R^a$, $X^2$, $X^4$, $Z^1$, m, and n have the same meanings as those defined above.)

(2-1)

As the compounds of the general formula [7], for example, ethyl 4-chloro-2-(methylthio)pyrimidine-5-carboxylate and so forth are known.

As the compounds of the general formula [8], for example, propylamine and so forth are known.

The compounds of the general formula [9] can be prepared by reacting a compound of the general formula [7] with a compound of the general formula [8] in the presence of a base.

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and a mixture of these solvents may also be used.

Preferred examples of the solvent include ethers, and tetrahydrofuran is more preferred.

Although amount of the solvent to be used is not particularly limited, it may be 1- to 500-fold amount (v/w) with respect to the compound of the general formula [7].

Amount of the compound of the general formula [8] to be used may be 1- to 50-fold molar amount, preferably 1- to 5-fold molar amount, with respect to the compound of the general formula [7].

Examples of the base used for this reaction include inorganic bases and organic bases.

Amount of the base to be used may be 1- to 50-fold molar amount, preferably 1- to 5-fold molar amount, with respect to the compound of the general formula [7].

This reaction may be performed at −30 to 150° C., preferably 0 to 100° C., for 30 minutes to 48 hours.

(2-2)

As the compounds of the general formula [10], for example, 4-(2-aminoethyl)pyridine, 4-aminobenzamide, and so forth are known.

The compounds of the general formula [11] can be prepared by oxidizing a compound of the general formula [9] with a peroxy acid, and then reacting the resultant with a compound of the general formula [10] in the presence of a base.

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and a mixture of these solvents may also be used.

Preferred examples of the solvent include amides, and N-methylpyrrolidone is more preferred.

Although amount of the solvent to be used is not particularly limited, it may be 1- to 500-fold amount (v/w) with respect to the compound of the general formula [9].

Examples of the peroxy acid used for this reaction include hydrogen peroxide, peracetic acid, and meta-chloroperbenzoic acid, and meta-chloroperbenzoic acid is more preferred.

Amount of the peroxy acid to be used may be 1- to 50-fold molar amount, preferably 1- to 5-fold molar amount, with respect to the compound of the general formula [9].

Amount of the compound of the general formula [10] to be used may be 1- to 50-fold molar amount, preferably 1- to 5-fold molar amount, with respect to the compound of the general formula [9].

Examples of the base used for this reaction include inorganic bases and organic bases.

Amount of the base to be used may be 1- to 50-fold molar amount, preferably 1- to 5-fold molar amount, with respect to the compound of the general formula [9].

This reaction may be performed at −30 to 150° C., preferably 0 to 100° C., for 30 minutes to 48 hours.

(2-3)

The compounds of the general formula [12] can be prepared by carrying out deprotection of a compound of the general formula [11].

This reaction can be performed by the method described in T. W. Greene et al., Protective Groups in Organic Synthesis, 4 th edition, pp. 533-643, 2007, John Wiley & Sons, Inc.

(2-4)

As the compounds of the general formula [13 a], for example, 1,3-phenylenediamine, 1,3-cyclohexanediamine, 1,3-diaminopentane, and so forth are known.

The compounds of the general formula [14] can be prepared by reacting a compound of the general formula [12] with a compound of the general formula [13 a] in the presence of a condensing agent.

This reaction can be performed in a manner similar to that of the preparation method (1-2).

(2-5)

As the compounds of the general formula [13 b], for example, N-Boc-1,3-propanediamine, 1-benzyl-3-aminopyrrolidine, and so forth are known.

The compounds of the general formula [13 b] can be prepared from a compound of the general formula [13 a] by a method similar to the method described in T. W. Greene et al., Protective Groups in Organic Synthesis, 4 th edition, pp. 696-926, 2007, John Wiley & Sons, Inc.

The compounds of the general formula [14] can also be prepared by reacting a compound of the general formula [12] with a compound of the general formula [13 b] in the presence of a condensing agent, and then performing deprotection of the resultant compound.

This reaction can be performed in a manner similar to that of the preparation method (1-2) and the preparation method (1-1).

(2-6)

As the compounds of the general formula [15], for example, N-Boc-L-alanine and so forth are known.

The compounds of the general formula [4 a] can be prepared by reacting a compound of the general formula [14] with a compound of the general formula [15] in the presence of a condensing agent or an acid halide.

This reaction can be performed in a manner similar to that of the preparation method (1-2).

[Preparation Method 3]

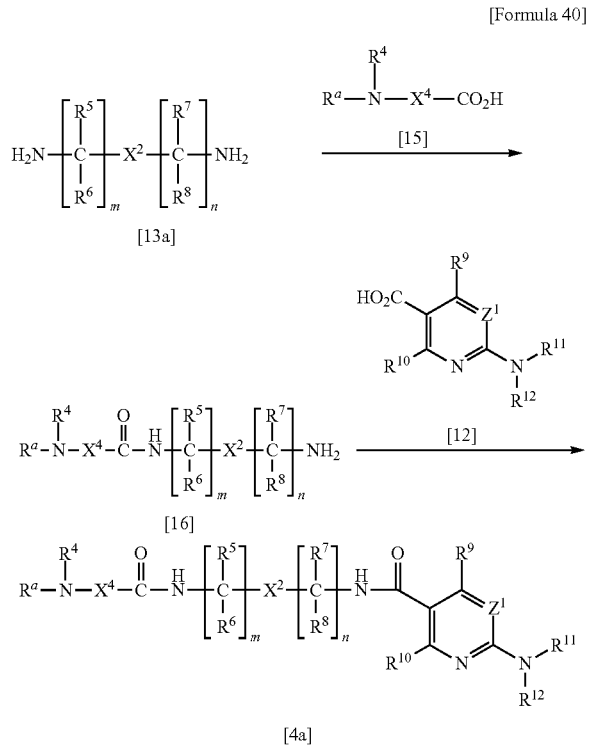

[Formula 40]

(In the formula, $R^4$, $R^5$, $R^6$, $R^7$, $R^8$, $R^9$, $R^{10}$, $R^{11}$, $R^{12}$, $R^a$, $X^2$, $X^4$, $Z^1$, m, and n have the same meanings as those defined above.)

(3-1)

The compounds of the general formula [16] can be prepared by reacting a compound of the general formula [13 a] with a compound of the general formula [15] in the presence of a condensing agent or an acid halide.

This reaction can be performed in a manner similar to that of the preparation method (1-2).

(3-2)

The compounds of the general formula [4 a] can be prepared by reacting a compound of the general formula [16] with a compound of the general formula [12] in the presence of a condensing agent or an acid halide.

This reaction can be performed in a manner similar to that of the preparation method (1-2).

[Preparation Method 4]

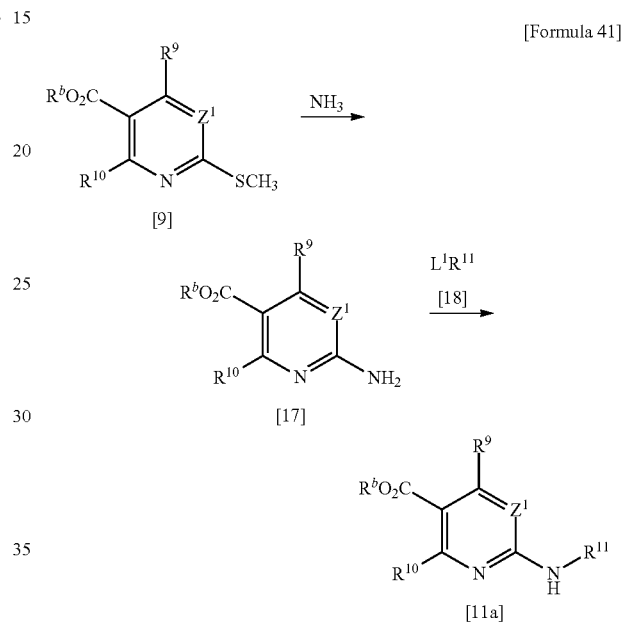

[Formula 41]

(In the formula, $L^1$ represents a leaving group; and $R^9$, $R^{10}$, $R^{11}$, $R^b$, and $Z^1$ have the same meanings as those defined above.)

(4-1)

The compounds of the general formula [17] can be prepared by oxidizing a compound of the general formula [9] with a peroxy acid, and then reacting the resultant with ammonia.

This reaction can be performed in a manner similar to that of the preparation method (2-2).

(4-2)

As the compounds of the general formula [18], for example, 4-bromobenzonitrile and so forth are known.

The compounds of the general formula [11 a] can be prepared by reacting a compound of the general formula [17] with a compound of the general formula [18] in the presence of a palladium catalyst, a ligand, and a base.

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and a mixture of these solvents may also be used.

Preferred examples of the solvent include ethers, and 1,4-dioxane is more preferred.

Although amount of the solvent to be used is not particularly limited, it may be 1- to 500-fold amount (v/w) with respect to the compound of the general formula [17].

Amount of the catalyst to be used may be 0.001- to 2-fold molar amount, preferably 0.01- to 0.5-fold molar amount, with respect to the compound of the general formula [17].

Amount of the ligand to be used may be 0.001- to 2-fold molar amount, preferably 0.01- to 0.5-fold molar amount, with respect to the compound of the general formula [17].

Examples of the base used for this reaction include inorganic bases and organic bases.

Amount of the base to be used may be 1- to 50-fold molar amount, preferably 1- to 5-fold molar amount, with respect to the compound of the general formula [17].

This reaction may be performed at 0 to 150° C., preferably 20 to 120° C., for 30 minutes to 48 hours.

For this reaction, a microwave reactor may be used.

[Preparation Method 5]

[Formula 42]

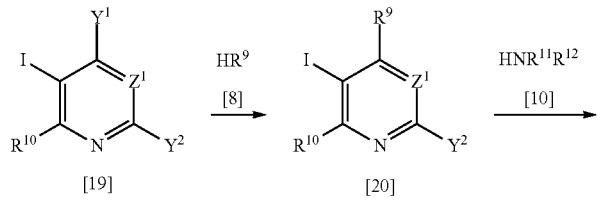

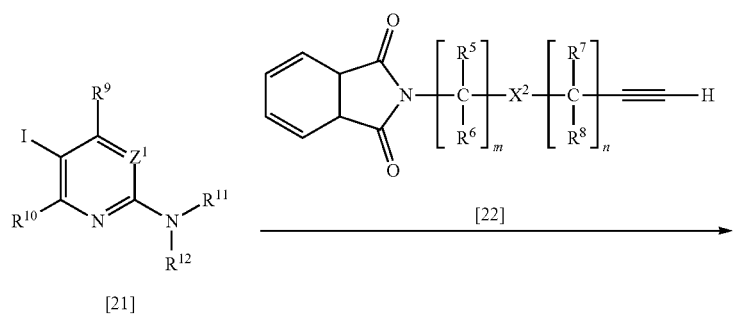

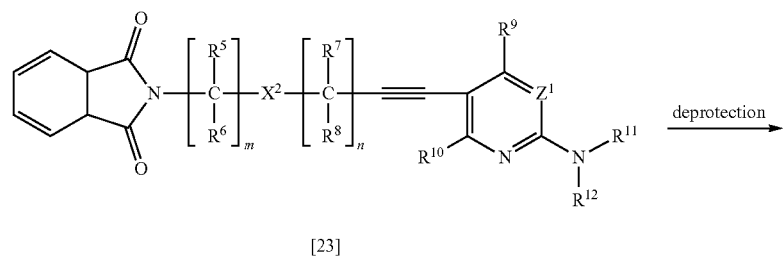

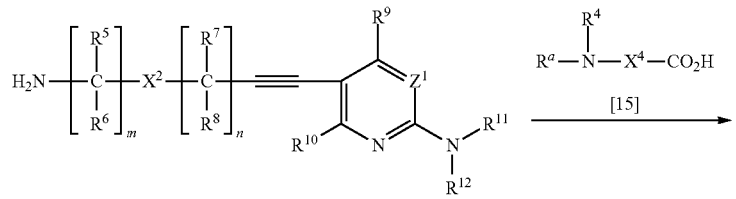

(In the formula, $Y^2$ represents a leaving group; and $R^4$, $R^5$, $R^6$, $R^7$, $R^8$, $R^9$, $R^{10}$, $R^{11}$, $R^{12}$, $R^a$, $X^2$, $X^4$, $Y^1$, $Z^1$, m, and n have the same meanings as those defined above.)

(5-1)

The compounds of the general formula [20] can be prepared by reacting a compound of the general formula [19] with a compound of the general formula [8].

This reaction can be performed in a manner similar to that of the preparation method (2-1).

(5-2)

The compounds of the general formula [21] can be prepared by reacting a compound of the general formula [20] with a compound of the general formula [10].

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and a mixture of these solvents may also be used.

Preferred examples of the solvent include amides, and N-methylpyrrolidone is more preferred.

Although amount of the solvent to be used is not particularly limited, it may be 1- to 500-fold amount (v/w) with respect to the compound of the general formula [20].

Amount of the compound of the general formula [10] to be used may be 1- to 50-fold molar amount, preferably 1- to 5-fold molar amount, with respect to the compound of the general formula [20].

For this reaction, a proton acid is preferably used.

As the proton acid, camphorsulfonic acid is preferred.

Amount of the proton acid to be used may be 1- to 50-fold molar amount, preferably 1- to 10-fold molar amount, with respect to the compound of the general formula [20].

This reaction may be performed at −30 to 150° C., preferably 0 to 100° C., for 30 minutes to 48 hours.

(5-3)

The compounds of the general formula [23] can be prepared by reacting a compound of the general formula [21] with a compound of the general formula [22] in the presence of a palladium catalyst, a copper salt, and a base.

The solvent used for this reaction is not particularly limited, so long as a solvent that does not affect the reaction is chosen. Examples include, for example, halogenated hydrocarbons, ethers, esters, amides, nitriles, sulfoxides, and aromatic hydrocarbons, and a mixture of these solvents may also be used.

Preferred examples of the solvent include amides, and N,N-dimethylformamide is more preferred.

Although amount of the solvent to be used is not particularly limited, it may be 1- to 500-fold amount (v/w) with respect to the compound of the general formula [21].

Amount of the compound of the general formula [22] to be used may be 1- to 50-fold molar amount, preferably 1- to 5-fold molar amount, with respect to the compound of the general formula [21].

Amount of the catalyst used may be 0.0001- to 2-fold molar amount, preferably 0.001- to 0.2-fold molar amount, with respect to the compound of the general formula [21].

Examples of the copper salt used for this reaction include copper(I) chloride, copper(I) bromide, copper(I) iodide, and copper(II) acetate.

Amount of the copper salt to be used may be 0.0001- to 2-fold molar amount, preferably 0.001- to 0.2-fold molar amount, with respect to the compound of the general formula [21].

Examples of the base used for this reaction include organic bases.

Amount of the base to be used may be 0.1- to 50-fold molar amount, preferably 1- to 10-fold molar amount, with respect to the compound of the general formula [21].

This reaction may be performed at −30 to 150° C., preferably 0 to 100° C., for 30 minutes to 48 hours.

(5-4)

The compounds of the general formula [24] can be prepared by carrying out deprotection of a compound of the general formula [23].

This reaction can be performed by the method described in T. W. Greene et al., Protective Groups in Organic Synthesis, 4 th edition, pp. 790-793, 2007, John Wiley & Sons, Inc.

(5-5)

The compounds of the general formula [4 b] can be prepared by reacting a compound of the general formula [24] with a compound of the general formula [15] in the presence of a condensing agent or an acid halide.

This reaction can be performed in a manner similar to that of the preparation method (1-2).

[Preparation Method 6]

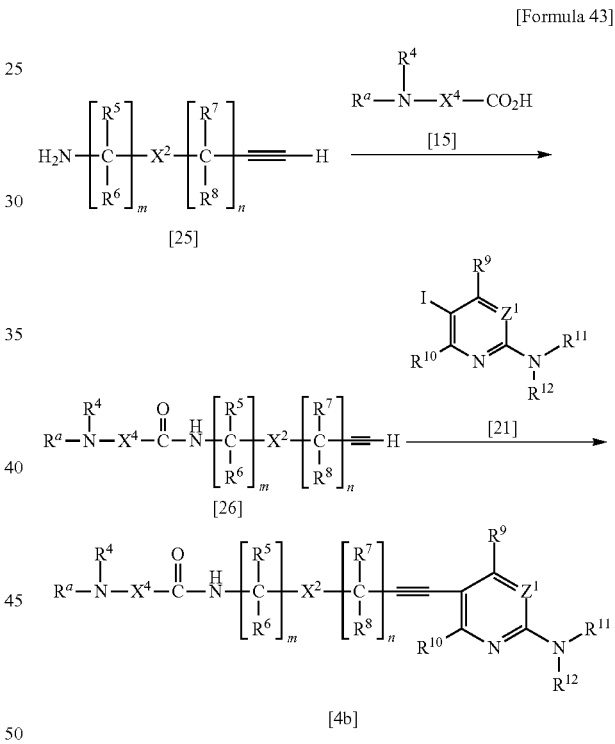

[Formula 43]

(In the formula, $R^4$, $R^5$, $R^6$, $R^7$, $R^8$, $R^9$, $R^{10}$, $R^{11}$, $R^{12}$, $R^a$, $X^2$, $X^4$, $Z^1$, m, and n have the same meanings as those defined above.)

(6-1)

The compounds of the general formula [26] can be prepared by reacting a compound of the general formula [25] with a compound of the general formula [15] in the presence of a condensing agent or an acid halide.

This reaction can be performed in a manner similar to that of the preparation method (1-2).

(6-2)

The compounds of the general formula [4 b] can be prepared by reacting a compound of the general formula [26] with a compound of the general formula [21].

This reaction can be performed in a manner similar to that of the preparation method (5-3).

[Preparation Method 7]

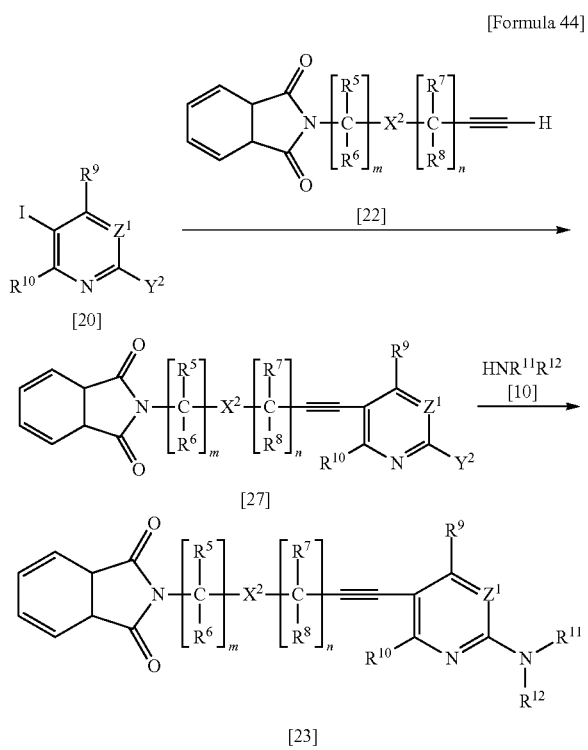

[Formula 44]

(In the formula, $R^5$, $R^6$, $R^7$, $R^8$, $R^9$, $R^{10}$, $R^{11}$, $R^{12}$, $Z^2$, $Y^2$, $Z^1$, m, and n have the same meanings as those defined above.)

(7-1)

The compounds of the general formula [27] can be prepared by reacting a compound of the general formula [20] with a compound of the general formula [22].

This reaction can be performed in a manner similar to that of the preparation method (5-3).

(7-2)

The compounds of the general formula [23] can be prepared by reacting a compound of the general formula [27] with a compound of the general formula [10].

This reaction can be performed in a manner similar to that of the preparation method (5-2).

When there are isomers (for example, optical isomers, geometrical isomers, tautomers, etc.) of the compounds used in the aforementioned preparation methods, these isomers can also be used.

Further, when there are solvates, hydrates and crystals of various forms thereof, these solvates, hydrates and crystals of various forms can also be used.

As for the compounds used in the aforementioned preparation methods having, for example, amino group, hydroxyl group, carboxyl group or the like, these groups can be protected with usual protective groups beforehand, and after the reactions, the protective groups can be eliminated by a known method.

The compounds obtained by the aforementioned preparation methods can be derived into other compounds by a per se known reaction such as condensation, addition, oxidation, reduction, rearrangement, substitution, halogenation, dehydration, hydrolysis, or an appropriate combination of these.

When the compounds of the present invention are used as a drug, they may be optionally mixed with pharmaceutical additives usually used for preparation of drugs, such as excipients, carriers, diluents, stabilizers, preservatives, buffering agents, corrigents, suspending agents, emulsifiers, flavoring agents, dissolving aids, colorants, and thickeners, as well as other active ingredients. The drugs can be orally or parenterally administered by a conventional method in the form of tablet, capsule, fine particle preparation, syrup, granule, pill, suspension, emulsion, solution, powdery preparation, suppository, eye drop, nose drop, ear drop, patch, ointment, injection, or the like. Administration method, dose, and frequency of administration can be appropriately chosen according to age, weight, and symptoms of patients. The compounds can usually be orally or parenterally administered (for example, injection, drip infusion, administration to the rectum part, etc.) to an adult at a daily dose of 0.01 to 1000 mg/kg at one time a day, or several times a day as divided portions.

Next, usefulness of typical compounds of the present invention will be explained with reference to the following test examples.

Test Example 1

FLT3 Inhibition Test

The FLT3 inhibition test was performed for the compounds of the present invention by the method described below.

For the FLT3 enzyme inhibition test, glutathione S-transferase (GST)-fused human FLT3 protein (intracellular region, 564 to 993 aa) produced by using a baculovirus expression system (Carna Biosciences) was used.

A reaction mixture in a volume of 9 μL containing the FLT3 protein and a test compound of a predetermined concentration (1.2 μg of FLT3, 100 mM HEPES, 10 mM $MgCl_2$, 25 mM NaCl, 0.01% BSA, 1 mM DTT, pH 7.5) was left standing at 25° C. for 15 minutes. Then, 3 μL (final concentration 0.25 μM) of a substrate peptide, biotin-AAA-AEEEEYFEL-VAKKK (Toray Industries), and 3 μL (final concentration 50 μM) of ATP (Sigma-Aldrich) were added to the reaction mixture, and the mixture was shaken for 2 minutes, and then further left standing at 25° C. for 30 minutes to allow the enzymatic reaction.

Then, 30 μL of an enzymatic reaction termination solution containing Streptavidin-Xlent (Cisbio) and Mab PT66-K (Cisbio) (5 μg/mL streptavidin, 0.19 μg/mL PT66-K, 30 mM HEPES (pH 7.0), 150 mM KF, 75 mM EDTA, 0.15% BSA, 0.075% Tween 20) was added to the reaction mixture to arrest the enzymatic reaction, and the reaction mixture was left standing at room temperature for 1 hour to allow the antigen-antibody reaction. Then, phosphorylation of the substrate peptide was measured by measuring time decomposition fluorescence at 615 nm and 665 nm using Envision (PerkinElmer).

Test Example 2

Leukemia Cell Proliferation Inhibition Test

A leukemia cell proliferation inhibition test was performed for the compounds of the present invention by using the leukemia cell strains MV4-11 (ATCC Number, CRL-9591) and Molm-13 (DSMZ Number, ACC554).

The leukemia cell proliferation inhibition test was performed by the method described below.

For the purpose of measuring proliferation inhibition attained with a compound, the total cell count was quantified on the basis of the total cellular ATP concentration using the ATPlite (PerkinElmer) reagent utilizing firefly luciferase. The Molm-13 or MV4-11 cells were added to the RPMI medium containing penicillin and streptomycin (penn/strep) and 10% FBS at a density of $2\times10^5$ cells/ml, and 50 μL (10,000 cells) of the cell suspension was inoculated to each well of a 96-well plate (Corning).

A serially diluted solution of a compound or 0.1% DMSO (solvent control) in a volume of 50 μL was added to the cells, and then the cells were cultured for 72 hours under the standard cell proliferation conditions (37° C., 5% $CO_2$) to allow proliferation of the cells. In order to measure the proliferation of the total cells, equal volume of the ATPlite reaction mixture was added to each well in accordance with the instructions attached to ATPlite, and then luminescence count of the well was measured (relative light unit, RLU).

The RLU signal observed with the DMSO solvent control after 72 hours of the culture was defined as a signal indicating 0% inhibition, and the $GI_{50}$ value for the proliferation inhibition corresponds to a concentration of a compound that provides 50% inhibition based on the proliferation of the total cells contained in the DMSO solvent control. Each data point was obtained from samples in duplicate. The $GI_{50}$ values were calculated by the non-linear regression fitting (Fit Model (205)) according to a sigmoid dose-reaction equation using the XLfit software.

The results are shown below.

TABLE 1

| IC50 | FLT3 (WT) enzyme inhibition activity Evaluation | MV4-11 cell proliferation inhibition effect Evaluation | MOLM13 cell proliferation inhibition effect Evaluation |
| --- | --- | --- | --- |
| Lower than 0.01 μM | +++ | +++ | +++ |
| 0.01 to 0.1 μM | ++ | ++ | ++ |
| 0.1 to 1 μM | + | + | + |
| Higher than 1 μM | − | − | − |

TABLE 2

| Compound No. | FLT3 (WT) enzyme inhibition activity | MV4-11 cell proliferation inhibition effect | MOLM13 cell proliferation inhibition effect |
| --- | --- | --- | --- |
| 1-1 | +++ | ++ | ++ |
| 1-2 | +++ | +++ | ++ |
| 1-3 | +++ | +++ | +++ |
| 1-4 | +++ | +++ | ++ |
| 1-5 | ++ | ++ | ++ |
| 1-6 | +++ | ++ | ++ |
| 1-7 | +++ | ++ | +++ |
| 1-8 | +++ | +++ | ++ |
| 1-9 | +++ | +++ | ++ |
| 1-10 | +++ | +++ | +++ |
| 1-11 | +++ | ++ | ++ |
| 1-12 | +++ | +++ | ++ |
| 2-1 | +++ | ++ | ++ |
| 2-2 | +++ | ++ | ++ |
| 2-3 | +++ | ++ | ++ |
| 2-4 | +++ | +++ | ++ |
| 2-5 | +++ | ++ | ++ |
| 2-6 | ++ | ++ | ++ |
| 2-7 | +++ | ++ | + |
| 2-8 | +++ | ++ | ++ |
| 2-9 | +++ | +++ | +++ |
| 2-10 | +++ | + | + |
| 2-11 | +++ | ++ | ++ |
| 2-12 | +++ | +++ | +++ |
| 2-13 | +++ | ++ | ++ |
| 2-14 | +++ | ++ | ++ |
| 2-15 | +++ | + | + |
| 2-16 | +++ | ++ | + |
| 2-17 | ++ | + | + |
| 2-18 | ++ | − | − |
| 2-19 | ++ | − | − |
| 2-20 | +++ | ++ | ++ |
| 2-21 | ++ | ++ | ++ |
| 2-23 | +++ | ++ | +++ |
| 2-24 | +++ | ++ | ++ |
| 2-25 | ++ | + | + |
| 2-26 | ++ | + | + |
| 2-27 | ++ | + | + |
| 2-28 | + | + | + |
| 2-29 | ++ | + | + |
| 3-1 | +++ | +++ | +++ |
| 3-2 | +++ | ++ | ++ |
| 3-3 | +++ | ++ | ++ |
| 3-4 | +++ | +++ | +++ |
| 3-6 | +++ | + | − |
| 3-7 | +++ | ++ | ++ |

TABLE 3

| Compound No. | FLT3 (WT) enzyme inhibition activity | MV4-11 cell proliferation inhibition effect | MOLM13 cell proliferation inhibition effect |
| --- | --- | --- | --- |
| 3-8 | +++ | ++ | ++ |
| 3-9 | +++ | ++ | ++ |
| 3-10 | +++ | + | + |
| 3-11 | +++ | +++ | ++ |
| 3-12 | +++ | ++ | ++ |
| 3-13 | +++ | ++ | ++ |
| 3-15 | +++ | + | + |
| 3-17 | +++ | + | − |
| 3-18 | +++ | − | − |
| 3-19 | +++ | ++ | + |
| 3-20 | +++ | ++ | + |
| 3-21 | +++ | + | + |
| 3-24 | +++ | ++ | + |
| 3-25 | +++ | ++ | + |
| 3-27 | +++ | ++ | ++ |
| 3-28 | +++ | + | + |
| 3-29 | +++ | ++ | ++ |
| 3-30 | +++ | +++ | ++ |
| 3-31 | +++ | + | + |
| 4-1 | +++ | ++ | ++ |
| 4-2 | +++ | +++ | +++ |
| 4-3 | +++ | +++ | +++ |
| 4-4 | +++ | +++ | +++ |
| 4-5 | +++ | +++ | +++ |
| 4-7 | +++ | +++ | +++ |
| 4-8 | +++ | +++ | +++ |
| 4-9 | +++ | +++ | +++ |
| 4-10 | +++ | +++ | +++ |
| 4-13 | +++ | ++ | ++ |
| 4-14 | +++ | +++ | +++ |
| 4-15 | +++ | ++ | + |
| 5-1 | +++ | +++ | +++ |
| 5-2 | +++ | ++ | ++ |
| 5-3 | +++ | ++ | ++ |
| 5-4 | +++ | + | + |
| 5-5 | +++ | ++ | ++ |
| 6-1 | +++ | +++ | ++ |
| 6-2 | ++ | ++ | + |
| 6-3 | +++ | ++ | ++ |
| 6-4 | +++ | +++ | +++ |
| 6-5 | +++ | ++ | ++ |
| 6-6 | +++ | +++ | +++ |
| 6-7 | +++ | ++ | ++ |
| 6-8 | +++ | +++ | +++ |

TABLE 3-continued

| Compound No. | FLT3 (WT) enzyme inhibition activity | MV4-11 cell proliferation inhibition effect | MOLM13 cell proliferation inhibition effect |
|---|---|---|---|
| 6-9 | +++ | +++ | +++ |
| 6-10A | +++ | ++ | + |
| 6-10B | +++ | +++ | +++ |
| 6-11 | +++ | +++ | +++ |

TABLE 4

| Compound No. | FLT3 (WT) enzyme inhibition activity | MV4-11 cell proliferation inhibition effect | MOLM13 cell proliferation inhibition effect |
|---|---|---|---|
| 6-12 | +++ | ++ | + |
| 6-13 | +++ | + | + |
| 6-14 | +++ | +++ | ++ |
| 6-15 | +++ | + | + |
| 6-16 | ++ | + | ++ |
| 6-17 | ++ | + | + |
| 6-18 | +++ | ++ | ++ |
| 6-19 | ++ | ++ | ++ |
| 6-21 | ++ | + | + |
| 6-23 | ++ | + | + |
| 7-1 | +++ | +++ | +++ |
| 7-2 | +++ | +++ | +++ |
| 7-3 | +++ | +++ | +++ |
| 7-4 | +++ | +++ | +++ |
| 7-5 | +++ | +++ | +++ |
| 7-6 | +++ | ++ | ++ |
| 7-7 | +++ | +++ | +++ |
| 7-8 | +++ | +++ | +++ |
| 7-9 | +++ | +++ | +++ |
| 7-10 | +++ | ++ | ++ |
| 7-11 | +++ | ++ | ++ |
| 7-12 | ++ | + | + |
| 7-14 | +++ | +++ | ++ |
| 7-15 | ++ | +++ | +++ |
| 7-16 | ++ | +++ | +++ |
| 7-17 | +++ | +++ | +++ |
| 7-18 | +++ | ++ | ++ |
| 7-19 | +++ | +++ | +++ |
| 7-20 | +++ | +++ | +++ |
| 7-21 | +++ | +++ | +++ |
| 7-22 | +++ | +++ | +++ |
| 7-23 | +++ | +++ | ++ |
| 7-24 | +++ | +++ | +++ |
| 7-25 | +++ | +++ | ++ |
| 7-27 | +++ | ++ | +++ |
| 7-28 | +++ | +++ | +++ |
| 7-29 | +++ | ++ | + |
| 7-31 | +++ | +++ | +++ |
| 7-32 | +++ | +++ | +++ |
| 7-33 | +++ | +++ | +++ |
| 7-34 | +++ | +++ | +++ |
| 7-35 | +++ | +++ | +++ |
| 7-36 | +++ | +++ | ++ |
| 7-37 | +++ | +++ | +++ |
| 7-38 | +++ | ++ | ++ |
| 7-39 | +++ | +++ | +++ |
| 7-40 | +++ | +++ | +++ |
| 7-41 | +++ | +++ | +++ |

TABLE 5

| Compound No. | FLT3 (WT) enzyme inhibition activity | MV4-11 cell proliferation inhibition effect | MOLM13 cell proliferation inhibition effect |
|---|---|---|---|
| 7-42 | +++ | +++ | +++ |
| 7-43 | +++ | +++ | +++ |
| 7-44 | +++ | +++ | +++ |
| 7-45 | +++ | +++ | +++ |
| 7-46 | +++ | +++ | ++ |
| 7-47 | +++ | +++ | +++ |
| 7-48 | +++ | +++ | +++ |
| 7-49 | +++ | +++ | +++ |
| 7-50 | +++ | +++ | +++ |
| 7-51 | +++ | +++ | +++ |
| 7-52 | +++ | +++ | +++ |
| 7-53 | ++ | +++ | +++ |
| 7-54 | ++ | +++ | +++ |
| 7-55 | +++ | +++ | +++ |
| 7-56 | +++ | +++ | +++ |
| 7-57 | +++ | +++ | +++ |
| 7-58 | +++ | +++ | +++ |
| 7-59 | +++ | +++ | +++ |
| 7-60 | +++ | +++ | +++ |
| 7-61 | +++ | +++ | +++ |
| 7-62 | +++ | +++ | +++ |
| 7-63 | +++ | +++ | +++ |
| 7-64 | +++ | +++ | +++ |
| 7-65 | +++ | +++ | +++ |
| 7-66 | +++ | +++ | +++ |
| 7-67 | +++ | +++ | +++ |
| 7-68 | +++ | +++ | +++ |
| 7-69 | +++ | +++ | +++ |
| 7-70 | +++ | +++ | +++ |
| 7-71 | +++ | +++ | +++ |
| 7-72 | +++ | +++ | +++ |
| 7-73 | +++ | +++ | +++ |
| 7-74 | +++ | +++ | +++ |
| 7-75 | +++ | +++ | +++ |
| 7-76 | +++ | +++ | +++ |
| 7-77 | +++ | +++ | +++ |
| 7-78 | +++ | +++ | ++ |
| 7-79 | +++ | +++ | +++ |
| 7-80 | +++ | +++ | +++ |
| 7-81 | +++ | +++ | +++ |
| 7-82 | +++ | +++ | +++ |
| 7-83 | +++ | +++ | +++ |
| 7-84 | +++ | +++ | +++ |
| 7-85 | +++ | +++ | +++ |
| 7-86 | +++ | +++ | +++ |
| 7-87 | +++ | +++ | +++ |
| 7-88 | +++ | +++ | +++ |
| 7-89 | +++ | +++ | +++ |

TABLE 6

| Compound No. | FLT3 (WT) enzyme inhibition activity | MV4-11 cell proliferation inhibition effect | MOLM13 cell proliferation inhibition effect |
|---|---|---|---|
| 7-90 | +++ | + | + |
| 7-91 | +++ | + | + |
| 7-92 | +++ | +++ | +++ |
| 7-93 | +++ | +++ | +++ |
| 7-94 | ++ | ++ | ++ |
| 7-95 | ++ | − | − |
| 7-96 | ++ | + | − |
| 8-1 | +++ | +++ | +++ |
| 8-2 | +++ | +++ | +++ |
| 8-3 | +++ | +++ | ++ |
| 8-4 | +++ | ++ | ++ |
| 8-5 | +++ | ++ | ++ |
| 8-6 | +++ | +++ | +++ |
| 8-7 | +++ | +++ | ++ |
| 8-9 | +++ | ++ | ++ |
| 8-10 | +++ | +++ | ++ |
| 8-11 | +++ | +++ | +++ |
| 8-12 | +++ | ++ | ++ |

TABLE 6-continued

| Compound No. | FLT3 (WT) enzyme inhibition activity | MV4-11 cell proliferation inhibition effect | MOLM13 cell proliferation inhibition effect |
|---|---|---|---|
| 8-13 | +++ | ++ | ++ |
| 8-14 | +++ | +++ | ++ |
| 8-15 | ++ | + | + |
| 8-16 | ++ | ++ | + |
| 8-18 | +++ | ++ | ++ |
| 8-19 | +++ | ++ | ++ |
| 8-20 | ++ | ++ | + |
| 8-21 | ++ | + | + |
| 8-22 | +++ | ++ | ++ |
| 8-23 | +++ | ++ | ++ |
| 9-1 | +++ | +++ | +++ |
| 9-2 | +++ | ++ | ++ |
| 9-3 | +++ | +++ | ++ |
| 9-4 | +++ | ++ | ++ |
| 9-5 | +++ | ++ | ++ |
| 9-6 | +++ | +++ | +++ |
| 9-7 | +++ | +++ | +++ |
| 9-8 | +++ | +++ | ++ |
| 9-9 | +++ | +++ | +++ |
| 9-10 | +++ | +++ | +++ |
| 9-11 | +++ | +++ | +++ |
| 9-12 | +++ | +++ | +++ |
| 9-13 | +++ | +++ | +++ |
| 9-14 | +++ | +++ | +++ |
| 9-15 | +++ | +++ | +++ |
| 9-16 | +++ | +++ | +++ |
| 9-17 | +++ | +++ | +++ |
| 9-18 | +++ | +++ | +++ |
| 9-19 | +++ | +++ | +++ |
| 9-20 | +++ | +++ | +++ |

TABLE 7

| Compound No. | FLT3 (WT) enzyme inhibition activity | MV4-11 cell proliferation inhibition effect | MOLM13 cell proliferation inhibition effect |
|---|---|---|---|
| 9-21 | +++ | +++ | ++ |
| 9-22 | +++ | +++ | ++ |
| 9-23 | ++ | ++ | + |
| 9-25 | +++ | +++ | +++ |
| 9-26 | +++ | +++ | +++ |
| 9-27 | +++ | +++ | +++ |
| 9-28 | +++ | +++ | +++ |
| 9-29 | +++ | +++ | +++ |
| 9-30 | +++ | +++ | +++ |
| 9-31 | +++ | +++ | +++ |
| 9-32 | +++ | +++ | +++ |
| 9-33 | +++ | +++ | +++ |
| 9-34 | +++ | +++ | +++ |
| 9-35 | +++ | +++ | +++ |
| 9-36 | +++ | +++ | +++ |
| 9-37 | +++ | +++ | +++ |
| 9-38 | +++ | +++ | +++ |
| 9-39 | +++ | +++ | +++ |
| 9-40 | ++ | ++ | ++ |
| 10-1 | +++ | +++ | ++ |
| 10-2 | +++ | +++ | +++ |
| 10-3 | +++ | +++ | +++ |
| 10-4 | +++ | +++ | +++ |
| 10-5 | +++ | +++ | +++ |
| 10-6 | +++ | +++ | +++ |
| 10-7 | +++ | +++ | +++ |
| 10-8 | +++ | +++ | ++ |
| 10-9 | +++ | ++ | ++ |
| 10-10 | +++ | +++ | +++ |
| 10-11 | +++ | +++ | ++ |
| 10-12 | +++ | +++ | ++ |
| 10-13 | +++ | +++ | +++ |
| 10-14 | +++ | +++ | +++ |
| 10-15 | +++ | +++ | +++ |

TABLE 7-continued

| Compound No. | FLT3 (WT) enzyme inhibition activity | MV4-11 cell proliferation inhibition effect | MOLM13 cell proliferation inhibition effect |
|---|---|---|---|
| 10-16 | +++ | +++ | +++ |
| 10-17 | +++ | +++ | ++ |
| 10-18 | +++ | +++ | +++ |
| 10-19 | +++ | +++ | +++ |
| 10-20 | +++ | +++ | +++ |
| 10-21 | +++ | +++ | +++ |
| 10-22 | +++ | +++ | +++ |
| 10-23 | +++ | +++ | +++ |
| 10-24 | +++ | +++ | +++ |
| 10-25 | +++ | +++ | +++ |
| 10-26 | +++ | +++ | ++ |
| 10-27 | +++ | +++ | +++ |
| 10-28 | +++ | +++ | ++ |
| 10-29 | +++ | +++ | +++ |

TABLE 8

| Compound No. | FLT3 (WT) enzyme inhibition activity | MV4-11 cell proliferation inhibition effect | MOLM13 cell proliferation inhibition effect |
|---|---|---|---|
| 10-30 | +++ | +++ | ++ |
| 10-31 | +++ | +++ | ++ |
| 10-32 | +++ | +++ | +++ |
| 10-33 | +++ | +++ | +++ |
| 10-34 | +++ | +++ | +++ |
| 10-35 | +++ | +++ | ++ |
| 10-36 | +++ | +++ | +++ |
| 10-37 | +++ | +++ | +++ |
| 10-38 | +++ | +++ | ++ |
| 10-39 | +++ | +++ | +++ |
| 10-40 | +++ | +++ | +++ |
| 10-41 | +++ | +++ | +++ |
| 10-42 | +++ | +++ | +++ |
| 10-43 | +++ | ++ | ++ |
| 10-44 | +++ | +++ | +++ |
| 10-45 | +++ | +++ | +++ |
| 10-46 | +++ | +++ | +++ |
| 10-47 | +++ | +++ | +++ |
| 10-48 | +++ | +++ | +++ |
| 10-49 | +++ | +++ | +++ |
| 10-50 | +++ | +++ | +++ |
| 10-51 | +++ | +++ | +++ |
| 10-52 | +++ | +++ | +++ |
| 10-53 | +++ | +++ | +++ |
| 10-54 | +++ | +++ | +++ |
| 10-55 | +++ | +++ | +++ |
| 10-56 | +++ | +++ | +++ |
| 10-57 | +++ | +++ | +++ |
| 10-58 | +++ | +++ | +++ |
| 10-59 | +++ | +++ | +++ |
| 10-60 | +++ | +++ | +++ |
| 10-61 | +++ | +++ | +++ |
| 10-62 | +++ | +++ | +++ |
| 10-63 | +++ | +++ | +++ |
| 10-64 | +++ | +++ | +++ |
| 10-65 | +++ | +++ | +++ |
| 10-66 | +++ | +++ | +++ |
| 10-67 | +++ | +++ | +++ |
| 10-68 | +++ | +++ | +++ |
| 10-69 | +++ | +++ | +++ |
| 10-70 | +++ | +++ | +++ |
| 10-71 | +++ | +++ | +++ |
| 10-72 | +++ | +++ | +++ |
| 10-73 | +++ | +++ | +++ |
| 10-74 | +++ | +++ | +++ |
| 10-75 | +++ | +++ | +++ |
| 11-1 | ++ | ++ | ++ |
| 11-3 | ++ | + | + |

TABLE 9

| Compound No. | FLT3 (WT) enzyme inhibition activity | MV4-11 cell proliferation inhibition effect | MOLM13 cell proliferation inhibition effect |
|---|---|---|---|
| 11-8 | +++ | ++ | ++ |
| 11-9 | +++ | ++ | ++ |
| 11-10 | +++ | +++ | ++ |
| 11-11 | +++ | ++ | ++ |
| 12-1 | +++ | +++ | +++ |
| 12-2 | +++ | +++ | ++ |
| 12-3 | +++ | +++ | +++ |
| 12-5 | +++ | ++ | ++ |
| 12-6 | ++ | ++ | + |
| 12-9 | +++ | ++ | ++ |
| 12-10 | +++ | ++ | + |
| 12-11 | ++ | ++ | ++ |
| 12-12 | ++ | ++ | +++ |
| 12-13 | +++ | +++ | +++ |
| 12-14 | +++ | +++ | +++ |
| 13-1 | +++ | +++ | +++ |
| 13-2 | +++ | ++ | ++ |
| 13-3 | +++ | +++ | ++ |
| 13-4 | +++ | +++ | +++ |
| 13-5 | +++ | +++ | +++ |
| 13-6 | +++ | +++ | +++ |
| 13-7 | +++ | +++ | +++ |
| 13-8 | +++ | +++ | +++ |
| 13-9 | +++ | +++ | +++ |
| 13-10 | +++ | +++ | +++ |
| 13-11 | +++ | +++ | +++ |
| 13-12 | +++ | +++ | +++ |
| 13-13 | +++ | +++ | +++ |
| 13-14 | +++ | +++ | +++ |
| 13-15 | +++ | +++ | +++ |
| 13-16 | +++ | +++ | +++ |
| 13-17 | +++ | +++ | +++ |
| 13-18 | +++ | +++ | +++ |
| 13-19 | +++ | +++ | +++ |
| 13-20 | +++ | +++ | +++ |
| 13-21 | +++ | +++ | +++ |
| 13-22 | +++ | +++ | +++ |
| 14-1 | +++ | +++ | +++ |
| 14-2 | +++ | +++ | +++ |
| 14-3 | +++ | +++ | +++ |
| 14-4 | +++ | +++ | +++ |
| 14-5 | +++ | +++ | +++ |
| 14-6 | +++ | +++ | +++ |
| 15-1 | +++ | +++ | +++ |
| 15-2 | +++ | +++ | ++ |
| 15-3 | +++ | +++ | +++ |
| 15-4 | +++ | +++ | +++ |
| 15-5 | +++ | +++ | +++ |

TABLE 10

| Compound No. | FLT3 (WT) enzyme inhibition activity | MV4-11 cell proliferation inhibition effect | MOLM13 cell proliferation inhibition effect |
|---|---|---|---|
| 15-6 | +++ | +++ | +++ |
| 15-7 | +++ | +++ | +++ |
| 15-8 | +++ | +++ | +++ |
| 15-9 | +++ | +++ | +++ |
| 15-10 | +++ | +++ | +++ |
| 15-11 | +++ | +++ | +++ |
| 15-12 | +++ | +++ | +++ |
| 15-13 | +++ | +++ | +++ |
| 15-14 | +++ | +++ | +++ |
| 15-15 | +++ | +++ | +++ |
| 15-16 | +++ | +++ | +++ |
| 16-1 | +++ | ++ | + |
| 16-2 | +++ | ++ | + |
| 16-3 | +++ | + | + |
| 17-1 | +++ | +++ | +++ |
| 17-2 | +++ | +++ | +++ |
| 17-3 | +++ | ++ | ++ |
| 18-1 | +++ | ++ | ++ |
| 18-2 | +++ | +++ | ++ |
| 19-1 | +++ | + | + |
| 20-1 | ++ | +++ | +++ |
| 20-2 | ++ | ++ | ++ |
| 20-3 | ++ | +++ | +++ |
| 20-4 | +++ | ++ | ++ |
| 21-1 | +++ | +++ | +++ |
| 21-2 | +++ | +++ | +++ |
| 21-3 | +++ | +++ | +++ |
| 21-4 | +++ | +++ | ++ |
| 21-5 | + | − | + |
| 21-6 | +++ | +++ | +++ |
| 21-7 | +++ | +++ | +++ |
| 21-8 | ++ | ++ | ++ |
| 21-9 | +++ | +++ | +++ |
| 21-10 | +++ | ++ | ++ |
| 21-12 | +++ | +++ | +++ |
| 21-13 | +++ | +++ | +++ |
| 21-14 | +++ | ++ | ++ |
| 21-15 | +++ | +++ | ++ |
| 21-16 | +++ | +++ | +++ |
| 21-17 | +++ | +++ | ++ |
| 21-18 | ++ | ++ | ++ |
| 21-19 | +++ | +++ | +++ |
| 21-20 | +++ | +++ | +++ |
| 21-21 | +++ | +++ | +++ |
| 21-22 | +++ | +++ | +++ |
| 21-27 | +++ | +++ | +++ |
| 21-28 | +++ | +++ | +++ |
| 21-29 | +++ | +++ | +++ |

TABLE 11

| Compound No. | FLT3 (WT) enzyme inhibition activity | MV4-11 cell proliferation inhibition effect | MOLM13 cell proliferation inhibition effect |
|---|---|---|---|
| 21-30 | +++ | +++ | +++ |
| 21-31 | +++ | +++ | +++ |
| 21-32 | +++ | +++ | +++ |
| 21-33 | +++ | +++ | +++ |
| 21-34 | +++ | +++ | +++ |
| 21-35 | +++ | ++ | ++ |
| 21-36 | +++ | +++ | +++ |
| 21-37 | +++ | +++ | +++ |
| 21-38 | +++ | +++ | +++ |
| 21-39 | +++ | +++ | +++ |
| 21-40 | +++ | +++ | +++ |
| 21-41 | +++ | +++ | +++ |
| 21-42 | +++ | +++ | +++ |
| 21-43 | +++ | +++ | +++ |
| 21-44 | +++ | ++ | ++ |
| 21-45 | +++ | +++ | +++ |
| 21-46 | +++ | +++ | +++ |
| 21-47 | +++ | +++ | +++ |
| 21-48 | +++ | ++ | +++ |
| 21-49 | ++ | +++ | +++ |
| 21-50 | +++ | +++ | +++ |
| 21-51 | +++ | +++ | +++ |
| 21-52 | +++ | +++ | +++ |
| 21-53 | +++ | +++ | +++ |
| 21-54 | ++ | ++ | + |
| 21-55 | +++ | +++ | +++ |
| 21-56 | ++ | + | + |
| 22-1 | +++ | +++ | +++ |
| 22-2 | +++ | +++ | +++ |
| 22-3 | +++ | ++ | ++ |
| 22-4 | +++ | +++ | +++ |
| 22-5 | ++ | + | ++ |

TABLE 11-continued

| Compound No. | FLT3 (WT) enzyme inhibition activity | MV4-11 cell proliferation inhibition effect | MOLM13 cell proliferation inhibition effect |
|---|---|---|---|
| 22-6 | +++ | +++ | +++ |
| 22-7 | +++ | ++ | ++ |
| 22-8 | +++ | +++ | ++ |
| 22-9 | +++ | ++ | ++ |
| 22-10 | +++ | +++ | +++ |
| 22-11 | +++ | +++ | +++ |
| 22-12 | +++ | +++ | +++ |
| 22-13 | ++ | + | ++ |
| 22-14 | +++ | +++ | +++ |
| 22-15 | +++ | ++ | ++ |
| 22-16 | ++ | ++ | ++ |
| 22-17 | +++ | +++ | +++ |
| 22-18 | +++ | +++ | +++ |
| 22-19 | +++ | +++ | +++ |
| 22-20 | +++ | +++ | +++ |
| 22-22 | +++ | +++ | +++ |

TABLE 12

| Compound No. | FLT3 (WT) enzyme inhibition activity | MV4-11 cell proliferation inhibition effect | MOLM13 cell proliferation inhibition effect |
|---|---|---|---|
| 22-23 | +++ | +++ | +++ |
| 22-24 | ++ | ++ | ++ |
| 22-25 | +++ | +++ | +++ |
| 22-26 | +++ | ++ | ++ |
| 22-27 | +++ | +++ | +++ |
| 22-28 | +++ | +++ | +++ |
| 22-29 | +++ | +++ | +++ |
| 22-30 | +++ | +++ | +++ |
| 22-31 | +++ | +++ | +++ |
| 22-32 | +++ | +++ | +++ |
| 22-33 | +++ | +++ | +++ |
| 22-36 | +++ | +++ | +++ |
| 22-37 | +++ | +++ | +++ |
| 22-38 | +++ | +++ | +++ |
| 22-39 | +++ | +++ | +++ |
| 22-40 | +++ | +++ | +++ |
| 22-41 | +++ | +++ | +++ |
| 22-42 | +++ | +++ | +++ |
| 22-43 | +++ | +++ | +++ |
| 22-44 | +++ | +++ | +++ |
| 22-45 | +++ | +++ | +++ |
| 22-46 | +++ | +++ | +++ |
| 22-47 | +++ | +++ | +++ |
| 22-50 | +++ | ++ | +++ |
| 22-51 | +++ | +++ | +++ |
| 22-55 | +++ | +++ | +++ |
| 22-56 | +++ | +++ | +++ |
| 22-57 | +++ | +++ | +++ |
| 22-58 | +++ | +++ | +++ |
| 22-59 | +++ | +++ | +++ |
| 22-60 | +++ | +++ | +++ |
| 22-61 | +++ | +++ | +++ |
| 22-62 | +++ | +++ | +++ |
| 22-63 | +++ | +++ | +++ |
| 22-64 | +++ | +++ | +++ |
| 22-65 | +++ | +++ | +++ |
| 22-66 | +++ | +++ | +++ |
| 22-67 | +++ | +++ | +++ |
| 22-68 | +++ | +++ | +++ |

The compounds of the present invention had superior FLT3 inhibition activity and leukemia cell strain proliferation inhibition activity.

EXAMPLES

Hereafter, the present invention will be explained with reference to examples. However, the present invention is not limited by these examples.

Unless especially indicated, an automatic purification system, ISOLERA (produced by Biotage), was used for the purification by column chromatography.

Unless especially indicated, SNAP KP-Sil Cartridge (produced by Biotage) was used as the carrier for silica gel column chromatography, and SNAP KP-NH Cartridge (produced by Biotage) was used as the carrier for basic silica gel column chromatography.

The mixing ratios of the eluents are indicated in terms of volume ratio. For example, an indication of "eluent, 75 to 0% hexane in ethyl acetate" means that an eluent consisting of 75% hexane and 25% ethyl acetate was continuously changed to an eluent consisting of 0% hexane and 100% ethyl acetate at last.

As the microwave synthesizer, Initiator Sixty (produced by Biotage) was used.

As the continuous flow hydrogenation reactor, H-Cube (produced by ThalesNano) was used.

As the supercritical fluid chromatography (SFC) purification system, SFC30 (produced by Waters) was used.

The NMR spectra were measured by using tetramethylsilane as an internal standard and Bruker AV300 (produced by Bruker), and all the δ values are indicated in terms of ppm.

The MS spectra were measured by using ACQUITY SQD LC/MS System (produced by Waters).

The abbreviations used in the examples have the following meanings.

Boc: tert-butoxycarbonyl
DMSO-d$_6$: deuterated dimethyl sulfoxide
TBS: tert-butyldimethylsilyl Example 1

1

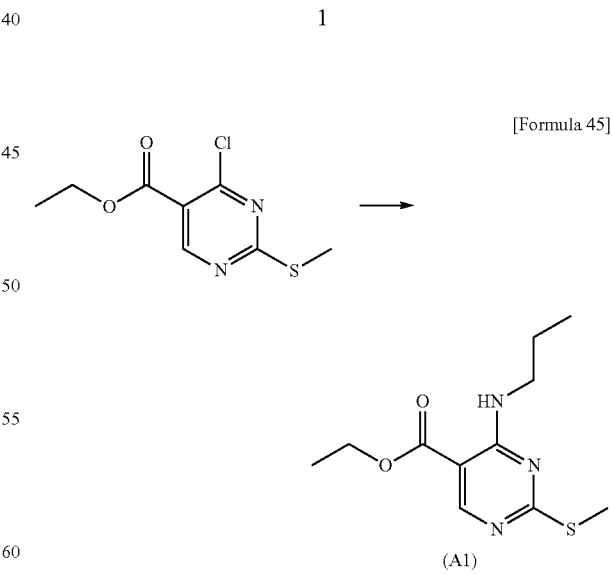

[Formula 45]

(A1)

To a solution of 4-chloro-2-(methylthio)pyrimidine-5-carboxylic acid ethyl ester (11.6 g) in tetrahydrofuran (100 mL), triethylamine (8.4 mL) and propylamine (5.1 mL) were added under ice cooling, and the mixture was stirred at room temperature for 30 minutes. To the reaction mixture, 1.0 mol/L aqueous hydrochloric acid and ethyl acetate were added. The organic layer was separated, washed successively with saturated aqueous sodium hydrogencarbonate and saturated aqueous sodium chloride, and then dried over anhydrous magnesium sulfate, and the solvent was evaporated under reduced pressure to obtain oily 2-(methylthio)-4-(propylamino)pyrimidine-5-carboxylic acid ethyl ester (A1, 11.7 g).

¹H-NMR (CDCl₃) δ: 8.61 (1H, s), 8.27 (1H, brs), 4.32 (2H, q, J=7.0 Hz), 3.55-3.48 (2H, m), 2.53 (3H, s), 1.73-1.60 (2H, m), 1.37 (3H, t, J=7.3 Hz), 0.99 (3H, t, J=7.6 Hz)

2

[Formula 46]

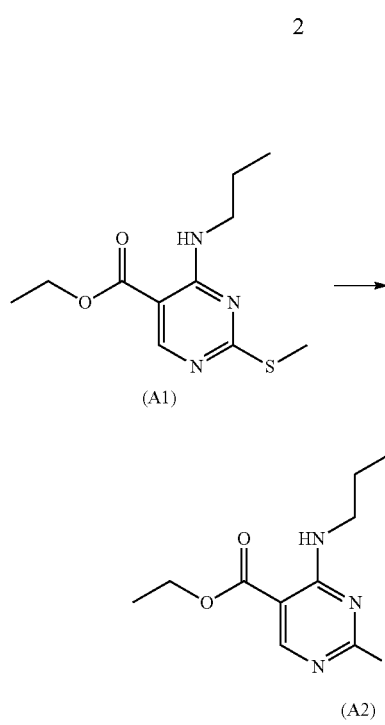

To a solution of 2-(methylthio)-4-(propylamino)pyrimidine-5-carboxylic acid ethyl ester (A1, 9.0 g) in N-methylpyrrolidone (88 mL), meta-chloroperbenzoic acid (70 to 75% wt, 10.8 g) was added portionwise under ice cooling, and the mixture was stirred at room temperature for 45 minutes. To the reaction mixture, meta-chloroperbenzoic acid (70 to 75% wt, 2.5 g) was added at room temperature, and the mixture was stirred at the same temperature for 3 hours. To the reaction mixture, saturated aqueous sodium hydrogencarbonate and ethyl acetate were added. The organic layer was separated, washed with saturated aqueous sodium chloride, and then dried over anhydrous magnesium sulfate, and the solvent was evaporated under reduced pressure. To a solution of the obtained residue in N-methylpyrrolidone (35 mL), N,N-diisopropylethylamine (11.9 mL) and 4-(2-aminoethyl)pyridine (6.3 mL) were added at room temperature, and the mixture was stirred at 100° C. for 4 hours. The reaction mixture was cooled to room temperature, and then poured into water (400 mL). The solid matter was taken by filtration, washed with water, and then dried under reduced pressure to obtain 4-(propylamino)-2-((2-(pyridin-4-yl)ethyl)amino)pyrimidine-5-carboxylic acid ethyl ester (A2, 9.2 g) as yellow solid.

3

[Formula 47]

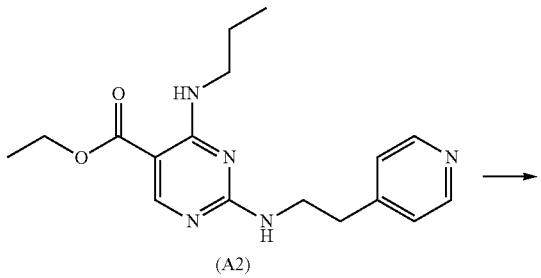

A mixture of 4-(propylamino)-2-((2-(pyridin-4-yl)ethyl) amino)pyrimidine-5-carboxylic acid ethyl ester (A2, 9.2 g), ethanol (115 mL), tetrahydrofuran (58 mL) and 2.0 mol/L aqueous sodium hydroxide (115 mL) was stirred at 40° C. for 4 hours, and then further stirred at 60° C. for 3 hours. The reaction mixture was cooled to room temperature, then 12 mol/L aqueous hydrochloric acid (19.5 mL) was added to the mixture (pH 5 to 6), and the organic solvent was evaporated under reduced pressure. The solid matter was taken by filtration, washed with water, and then dried under reduced pressure to obtain 4-(propylamino)-2-((2-(pyridin-4-yl)ethyl) amino)pyrimidine-5-carboxylic acid (A3, 9.3 g) as white solid.

MS m/z (M−H): 300.3

4

[Formula 48]

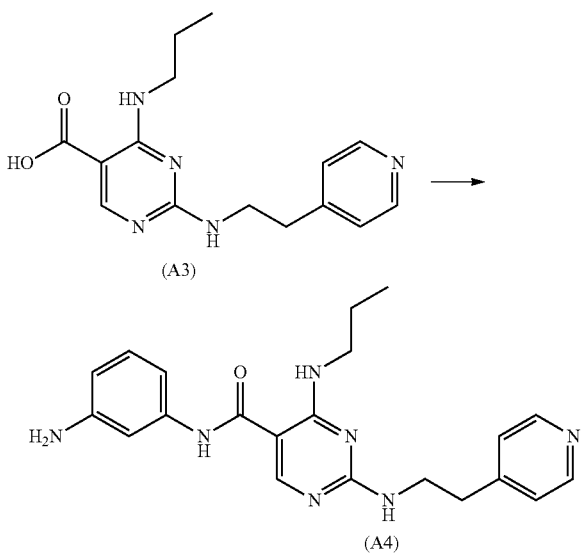

To a suspension of 4-(propylamino)-2-((2-(pyridin-4-yl) ethyl)amino)pyrimidine-5-carboxylic acid (A3, 1.12 g), 1-ethyl-3-(3-dimethylaminopropyl)carbodiimide hydrochloride (843 mg) and 1-hydroxybenzotriazole monohydrate (595 mg) in N,N-dimethylformamide (20 mL), N,N-diisopropylethylamine (2.0 mL) was added at room temperature, and the mixture was stirred at 40° C. for 2 hours (Reaction mixture A).

To a solution of 1,3-phenylenediamine (1.73 g) in N,N-dimethylformamide (10 mL), Reaction mixture A mentioned above was added at room temperature, and the mixture was stirred at the same temperature for 4 hours. To the reaction mixture, saturated aqueous sodium hydrogencarbonate and ethyl acetate were added. The organic layer was separated, and the aqueous layer was extracted with ethyl acetate. The organic layer and the extract were combined, washed with saturated aqueous sodium chloride, and then dried over anhydrous magnesium sulfate, and the solvent was evaporated under reduced pressure. The obtained residue was purified by basic silica gel column chromatography to obtain N-(3-aminophenyl)-4-(propylamino)-2-((2-(pyridin-4-yl)ethyl)amino)pyrimidine-5-carboxamide (A4, 950 mg) as white solid.

$^1$H-NMR (DMSO-d$_6$) δ: 9.50 (1H, brs), 8.74 (1H, brs), 8.56-8.42 (3H, m), 7.37 (1H, brs), 7.25 (2H, d, J=5.3 Hz), 6.98-6.88 (2H, m), 6.72 (1H, d, J=9.2 Hz), 6.27 (1H, d, J=9.2 Hz), 5.02 (2H, s), 3.58-3.50 (2H, m), 3.44-3.34 (2H, m), 2.88 (2H, t, J=6.9 Hz), 1.62-1.50 (2H, m), 0.91 (3H, t, J=7.3 Hz)

To N-Boc-L-alanine (57 mg), 1-ethyl-3-(3-dimethylaminopropyl)carbodiimide hydrochloride (115 mg) and 1-hydroxybenzotriazole monohydrate (81 mg), N,N-dimethylformamide (2 mL) was added at room temperature, and the mixture was stirred at the same temperature for 2 hours. To the reaction mixture, N,N-diisopropylethylamine (153 μL) and N-(3-aminophenyl)-4-(propylamino)-2-((2-(pyridin-4-yl)ethyl)amino)pyrimidine-5-carboxamide (A4, 98 mg) were added at room temperature, and the mixture was stirred at the same temperature for 5 hours. To the reaction mixture, saturated aqueous sodium hydrogencarbonate and ethyl acetate were added. The organic layer was separated, washed with saturated aqueous sodium chloride, and then dried over anhydrous magnesium sulfate, and the solvent was evaporated under reduced pressure. The obtained residue was purified by basic silica gel column chromatography (eluent, 98 to 90% ethyl acetate in methanol) to obtain oily (S)-tert-butyl (1-oxo-1-((3-(4-(propylamino)-2-((2-(pyridin-4-yl)ethyl)amino)pyrimidine-5-carboxamido)phenyl)amino)propan-2-yl)carbamate (A5, 137 mg).

MS m/z (M+H): 563.4

[Formula 49]

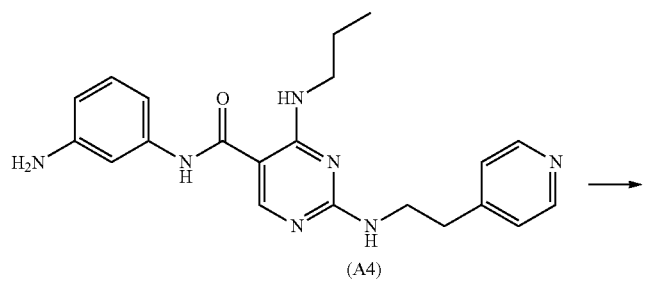

(A4)

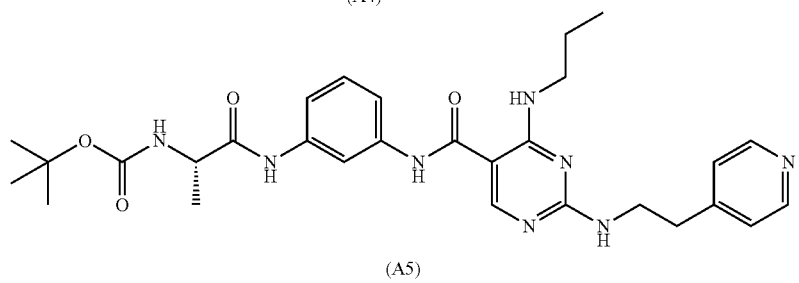

(A5)

[Formula 50]

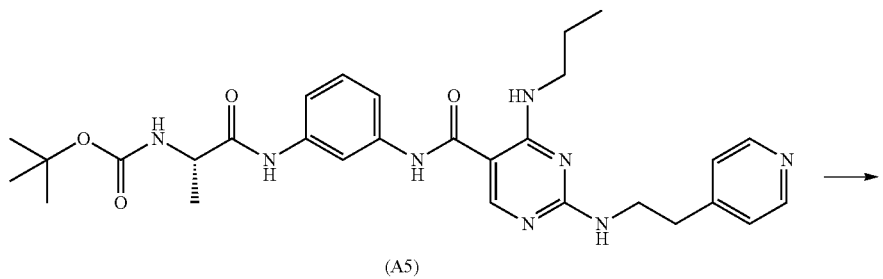

(A5)

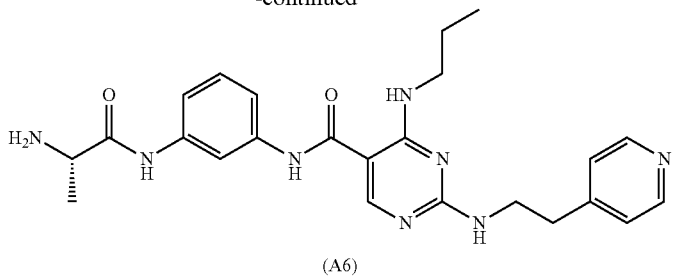

(A6)

To a solution of (S)-tert-butyl (1-oxo-1-((3-(4-(propylamino)-2-((2-(pyridin-4-yl)ethyl)amino)pyrimidine-5-carboxamido)phenyl)amino)propan-2-yl)carbamate (A5, 137 mg) in chloroform (2 mL), trifluoroacetic acid (2 mL) was added at room temperature, and the mixture was stirred at the same temperature for 3 hours. The solvent was evaporated under reduced pressure, and to the obtained residue, saturated aqueous sodium hydrogencarbonate and ethyl acetate were added. The organic layer was separated, and the aqueous layer was extracted with ethyl acetate. The organic layer and the extract were combined, washed with saturated aqueous sodium chloride, and then dried over anhydrous magnesium sulfate, and the solvent was evaporated under reduced pressure. To the obtained residue, ethyl acetate was added, and the solid matter was taken by filtration, and dried under reduced pressure to obtain (S)—N-(3-(2-aminopropanamido)phenyl)-4-(propylamino)-2-((2-(pyridin-4-yl)ethyl)amino)pyrimidine-5-carboxamide (A6, 75 mg) as white solid.

7

[Formula 51]

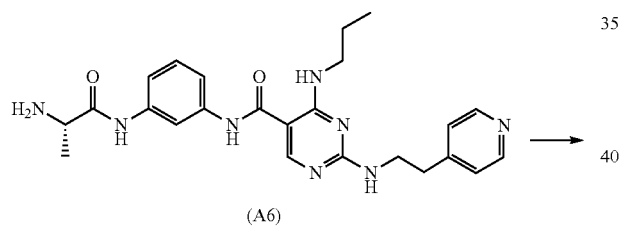

(A6)

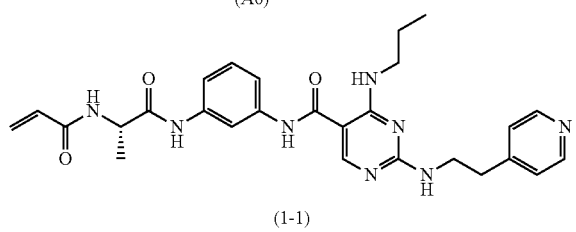

(1-1)

To a solution of (S)—N-(3-(2-aminopropanamido)phenyl)-4-(propylamino)-2-((2-(pyridin-4-yl)ethyl)amino)pyrimidine-5-carboxamide (A6, 23.1 mg) in N,N-dimethylformamide (1 mL), triethylamine (28 μL) and acryloyl chloride (6 μL) were added under ice cooling, and the mixture was stirred at the same temperature for 2 hours. To the reaction mixture, acryloyl chloride (2 μL) was added under ice cooling, and the mixture was stirred at the same temperature for 30 minutes. To the reaction mixture, saturated aqueous sodium hydrogencarbonate and ethyl acetate were added. The organic layer was separated, washed with saturated aqueous sodium chloride, and then dried over anhydrous magnesium sulfate, and the solvent was evaporated under reduced pressure. The obtained residue was purified by basic silica gel column chromatography to obtain (S)—N-(3-(2-(acrylylamido)propanamido)phenyl)-4-(propylamino)-2-((2-(pyridin-4-yl)ethyl)amino)pyrimidine-5-carboxamide (1-1, 8.9 mg) as white solid.

$^1$H-NMR (CD$_3$OD) δ: 8.44-8.36 (3H, m), 7.91 (1H, s), 7.36-7.24 (5H, m), 6.36 (1H, dd, J=17.2, 9.9 Hz), 6.24 (1H, dd, J=17.2, 2.6 Hz), 5.69 (1H, dd, J=9.6, 2.3 Hz), 4.60-4.52 (1H, m), 3.69 (2H, t, J=6.9 Hz), 3.46 (2H, brs), 2.99 (2H, t, J=7.3 Hz), 1.72-1.60 (2H, m), 1.46 (3H, d, J=7.3 Hz), 0.99 (3H, t, J=7.3 Hz)

8

[Formula 52]

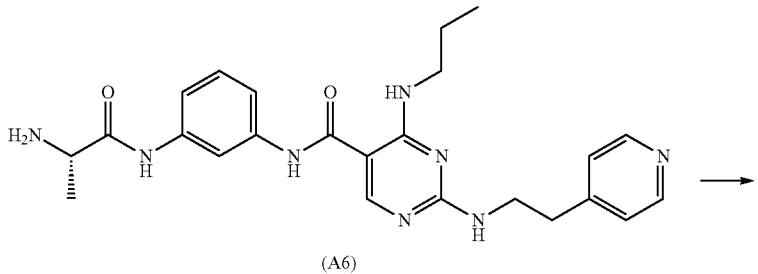

(A6)

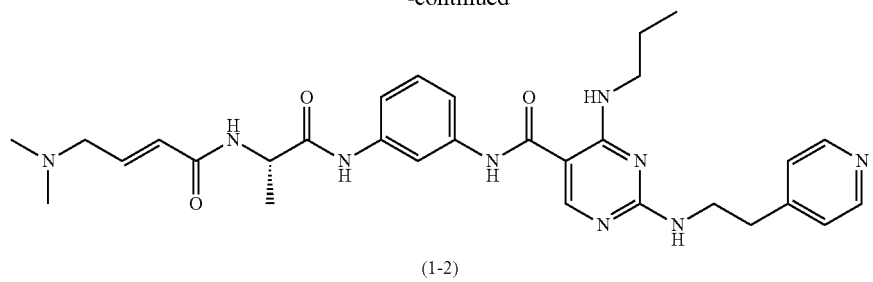

(1-2)

To a solution of (S)—N-(3-(2-aminopropanamido)phenyl)-4-(propylamino)-2-((2-(pyridin-4-yl)ethyl)amino)pyrimidine-5-carboxamide (A6, 21 mg), 4-dimethylaminocrotonic acid hydrochloride (16 mg) and 1-ethyl-3-(3-dimethylaminopropyl)carbodiimide hydrochloride (38 mg) in N,N-dimethylformamide (2 mL), triethylamine (40 μL) was added at room temperature, and the mixture was stirred at 50° C. for 30 minutes. The reaction mixture was cooled to room temperature, and then saturated aqueous sodium hydrogencarbonate and ethyl acetate were added to the mixture. The organic layer was separated, washed with water, and then dried over anhydrous sodium sulfate, and the solvent was evaporated under reduced pressure. The obtained residue was purified by silica gel column chromatography (eluent, 95% chloroform/5% methanol) to obtain (S,E)-N-(3-(2-(4-(dimethylamino)-2-butenamido)propanamido)phenyl)-4-(propylamino)-2-((2-(pyridin-4-yl)ethyl)amino)pyrimidine-5-carboxamide (1-2, 11 mg).

$^1$H-NMR (CDCl$_3$) δ: 9.15 (1H, brs), 8.66 (1H, brs), 8.50-8.49 (2H, m), 8.35-8.32 (2H, m), 7.69 (1H, brs), 7.42-7.40 (1H, m), 7.22-7.19 (2H, m), 7.13 (2H, d, J=5.3 Hz), 6.89-6.84 (2H, m), 6.02 (1H, d, J=15.2 Hz), 5.50 (1H, brs), 4.75 (1H, q, J=6.6 Hz), 3.72-3.67 (2H, m), 3.42 (2H, s), 3.03 (2H, d, J=5.9 Hz), 2.91 (2H, t, J=6.9 Hz), 2.22 (6H, s), 1.66-1.61 (2H, m), 1.44 (3H, d, J=6.6 Hz), 0.97 (3H, t, J=7.3 Hz)

U.S. Pat. No. 6,344,465 B1, 4-(propylamino)-2-((2-(pyridin-4-yl)ethyl)amino)pyrimidine-5-carboxylic acid (A3, 627 mg), 1-ethyl-3-(3-dimethylaminopropyl)carbodiimide hydrochloride (545 mg) and 1-hydroxybenzotriazole monohydrate (377 mg), N,N-dimethylformamide (15 mL) and triethylamine (766 μL) were added at room temperature, the reaction vessel was sealed, and then the mixture was stirred at 100° C. for 40 minutes by using a microwave reaction system. The reaction mixture was cooled to room temperature, and then saturated aqueous sodium hydrogencarbonate and ethyl acetate were added to the mixture. The organic layer was separated, and dried over anhydrous sodium sulfate, and the solvent was evaporated under reduced pressure. The obtained residue was purified by silica gel column chromatography (eluent, 97 to 96% ethyl acetate in methanol) to obtain 4-(propylamino)-2-((2-(pyridin-4-yl)ethyl)amino)-N-(3-(2,2,2-trifluoro-N-methylacetamido)phenyl)pyrimidine-5-carboxamide (A7, 186 mg).

$^1$H-NMR (CDCl$_3$) δ: 8.89 (1H, brs), 8.49 (2H, d, J=5.9 Hz), 8.35 (1H, s), 7.82-7.28 (3H, m), 7.16 (2H, d, J=7.6 Hz), 7.00 (1H, d, J=7.9 Hz), 6.68 (1H, brs), 5.35 (1H, brs), 3.75-3.65 (2H, m), 3.48-3.40 (2H, m), 3.36 (3H, s), 2.94 (2H, t, J=8.9 Hz), 1.67-1.62 (2H, m), 1.00 (3H, t, J=7.3 Hz)

2

Example 2

1

[Formula 53]

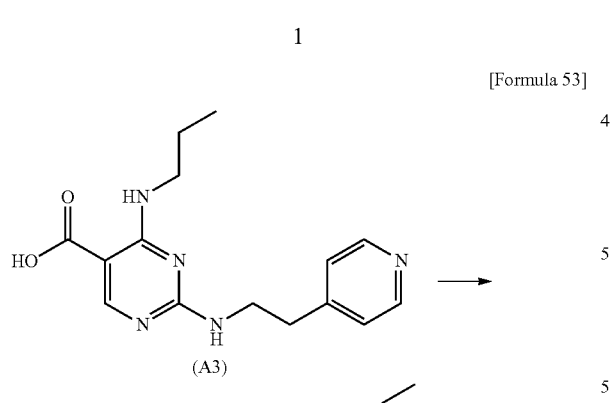

(A3)

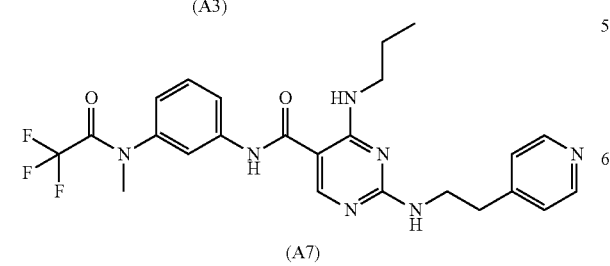

(A7)

[Formula 54]

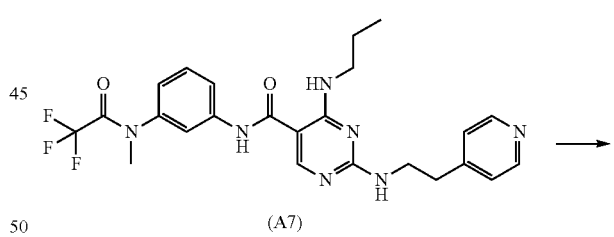

(A7)

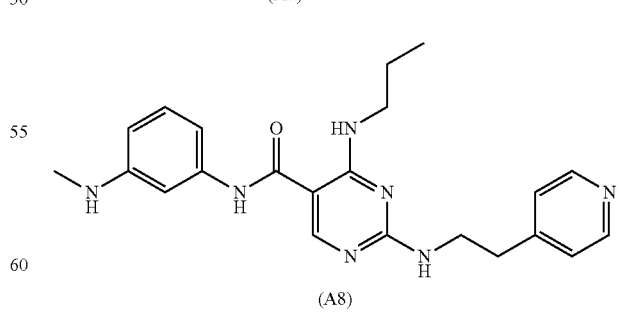

(A8)

To N-(3-aminophenyl)-2,2,2-trifluoro-N-methylactamide (302 mg) synthesized according to the method described in To a solution of 4-(propylamino)-2-((2-(pyridin-4-yl)ethyl)amino)-N-(3-(2,2,2-trifluoro-N-methylacetamido)phenyl)pyrimidine-5-carboxamide (A7, 186 mg) in methanol (4 mL) and water (2 mL), potassium carbonate (92 mg) was added at room temperature, and the mixture was stirred at the same temperature for 13 hours and 30 minutes. To the reaction mixture, water and chloroform were added. The organic layer was separated, washed successively with water and saturated aqueous sodium chloride, and then dried over anhydrous sodium sulfate, and the solvent was evaporated under reduced pressure to obtain N-(3-(methylamino)phenyl)-4-(propylamino)-2-((2-(pyridin-4-yl)ethyl)amino)pyrimidine-5-carboxamide (A8, 141 mg).

MS m/z (M−H): 406.3

3

In the same manner as that of Example 1, (4), Intermediates (A9) to (A12) were obtained.

TABLE 13

| Compound No. | Structure | Physicochemical data |
| --- | --- | --- |
| A9 | 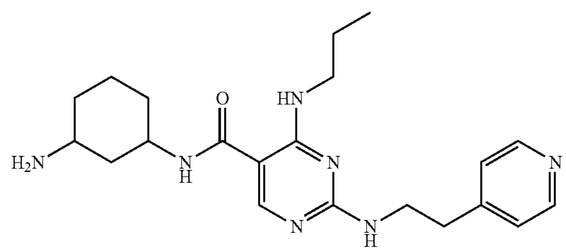 [SMILES: CCCNc1nc(NCCc2ccncc2)ncc1C(=O)NC1CCCC(N)C1] | MS m/z (M + H): 398.3 |
| A10 | 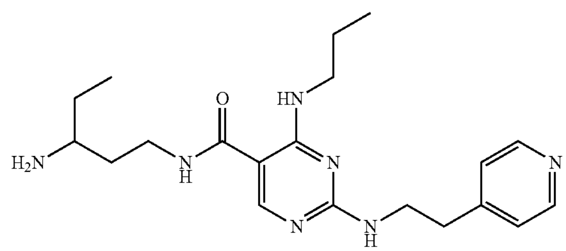 [SMILES: CCCNc1nc(NCCc2ccncc2)ncc1C(=O)NCCC(N)CC] | MS m/z (M + H): 386.4 |
| A11 | 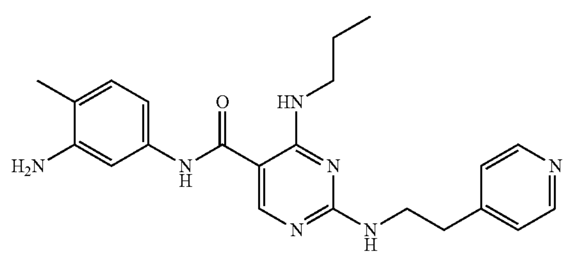 [SMILES: CCCNc1nc(NCCc2ccncc2)ncc1C(=O)Nc1ccc(C)c(N)c1] | MS m/z (M + H): 406.3 |
| A12 | 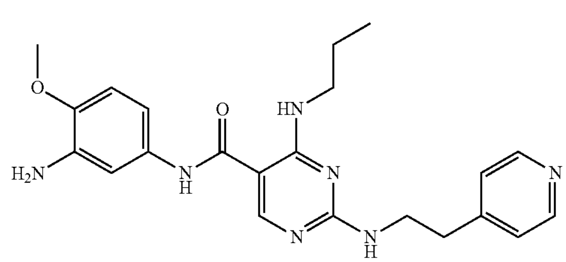 [SMILES: CCCNc1nc(NCCc2ccncc2)ncc1C(=O)Nc1ccc(OC)c(N)c1] | MS m/z (M + H): 422.2 |

4

In the same manner as that of Example 1, (5), Intermediates (A13) to (A20) were obtained.

TABLE 14

| Compound No. | Structure | Physicochemical data |
|---|---|---|
| A13 | 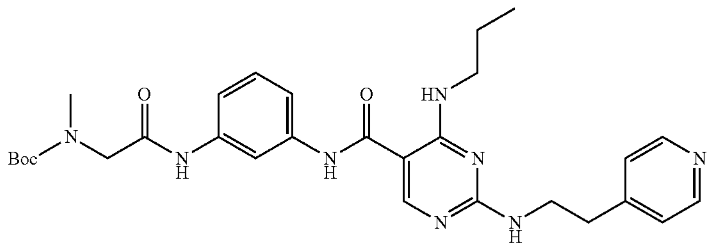 [SMILES: CCCNc1nc(NCCc2ccncc2)ncc1C(=O)Nc1cccc(NC(=O)CN(C)C(=O)OC(C)(C)C)c1] | MS m/z (M + H): 563.4 |
| A14 | 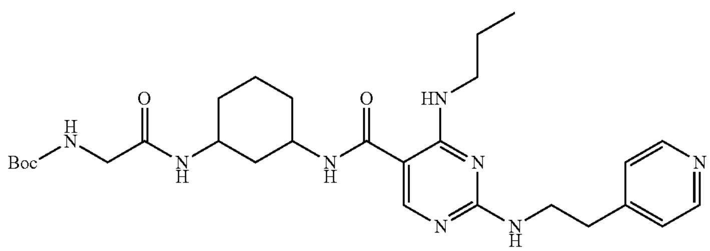 [SMILES: CCCNc1nc(NCCc2ccncc2)ncc1C(=O)NC1CCCC(NC(=O)CNC(=O)OC(C)(C)C)C1] | MS m/z (M + H): 555.4 |
| A15 | 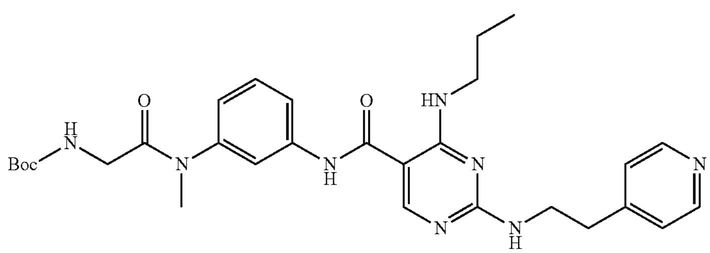 [SMILES: CCCNc1nc(NCCc2ccncc2)ncc1C(=O)Nc1cccc(N(C)C(=O)CNC(=O)OC(C)(C)C)c1] | — |
| A16 | 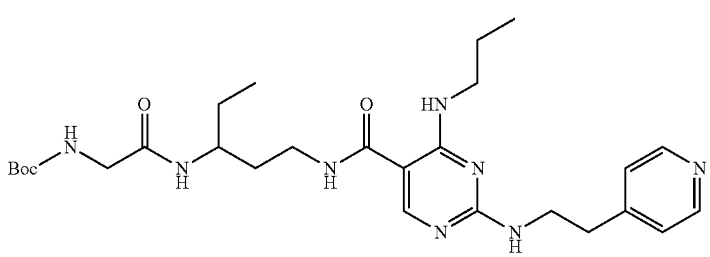 [SMILES: CCCNc1nc(NCCc2ccncc2)ncc1C(=O)NCCC(CC)NC(=O)CNC(=O)OC(C)(C)C] | MS m/z (M + H): 543.4 |
| A17 | 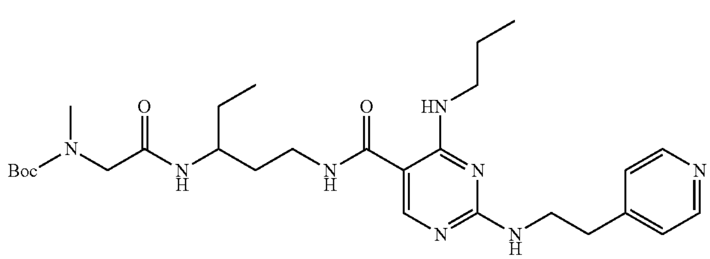 [SMILES: CCCNc1nc(NCCc2ccncc2)ncc1C(=O)NCCC(CC)NC(=O)CN(C)C(=O)OC(C)(C)C] | MS m/z (M + H): 557.5 |

TABLE 14-continued

| Compound No. | Structure | Physicochemical data |
|---|---|---|
| A18 | 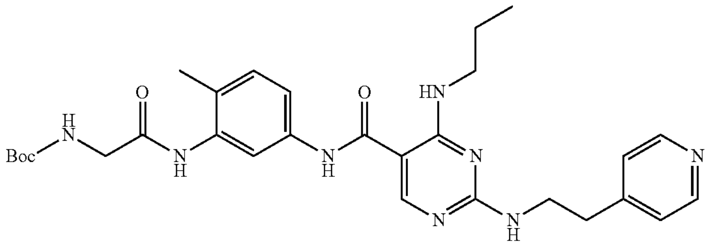 [SMILES: CCCNc1nc(NCCc2ccncc2)ncc1C(=O)Nc1ccc(C)c(NC(=O)CNC(=O)OC(C)(C)C)c1] | MS m/z (M + H): 563.4 |
| A19 | 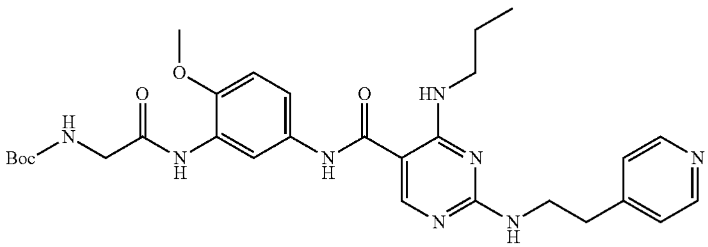 [SMILES: CCCNc1nc(NCCc2ccncc2)ncc1C(=O)Nc1ccc(OC)c(NC(=O)CNC(=O)OC(C)(C)C)c1] | — |
| A20 | 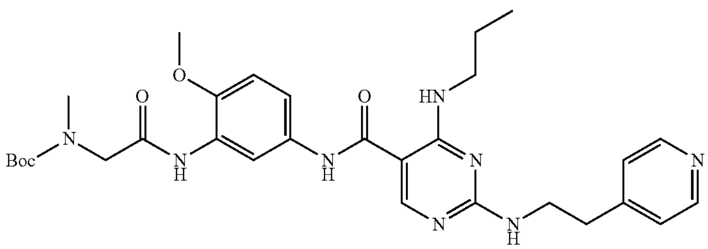 [SMILES: CCCNc1nc(NCCc2ccncc2)ncc1C(=O)Nc1ccc(OC)c(NC(=O)CN(C)C(=O)OC(C)(C)C)c1] | — |

In the same manner as that of Example 1, (6), Intermediates (A21) to (A28) were obtained.

TABLE 15

| Compound No. | Structure | Physicochemical data |
|---|---|---|
| A21 | 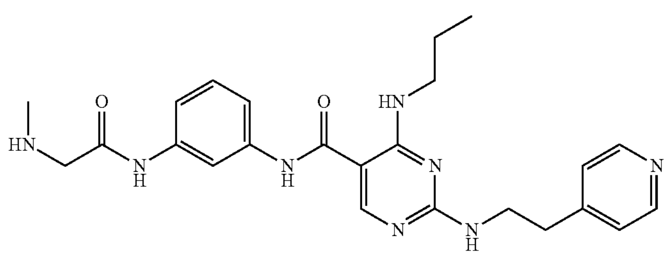 [SMILES: CCCNc1nc(NCCc2ccncc2)ncc1C(=O)Nc1cccc(NC(=O)CNC)c1] | MS m/z (M + H): 463.3 |
| A22 | 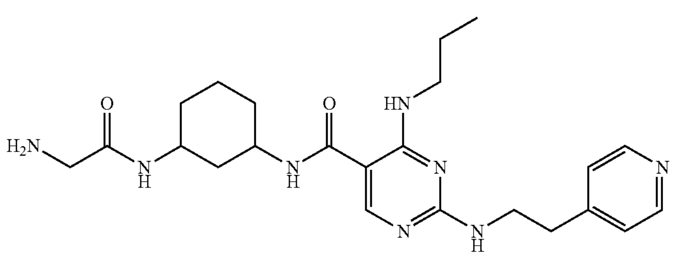 [SMILES: CCCNc1nc(NCCc2ccncc2)ncc1C(=O)NC1CCCC(NC(=O)CN)C1] | MS m/z (M + H): 455.4 |

TABLE 15-continued

| Compound No. | Structure | Physicochemical data |
| --- | --- | --- |
| A23 | 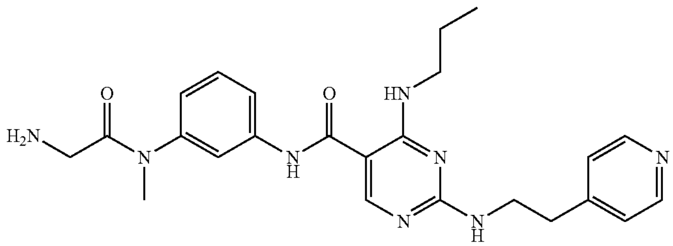 [SMILES: CCCNc1nc(NCCc2ccncc2)ncc1C(=O)Nc1cccc(N(C)C(=O)CN)c1] | — |
| A24 | 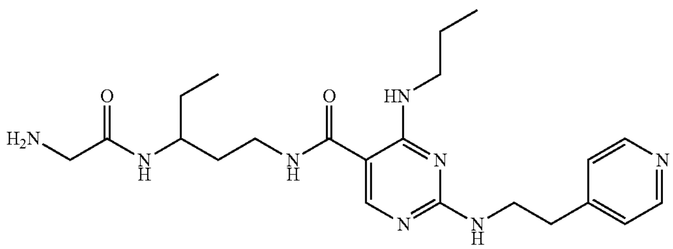 [SMILES: CCCNc1nc(NCCc2ccncc2)ncc1C(=O)NCCC(CC)NC(=O)CN] | — |
| A25 | 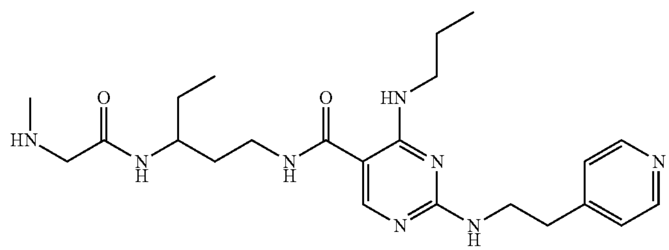 [SMILES: CCCNc1nc(NCCc2ccncc2)ncc1C(=O)NCCC(CC)NC(=O)CNC] | — |
| A26 | 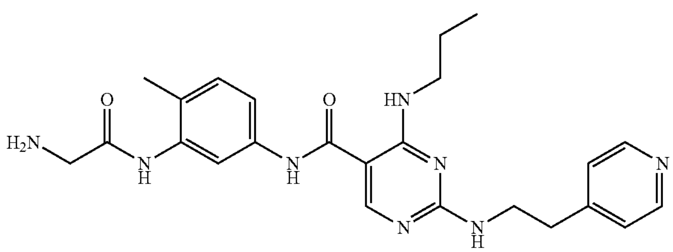 [SMILES: CCCNc1nc(NCCc2ccncc2)ncc1C(=O)Nc1ccc(C)c(NC(=O)CN)c1] | — |
| A27 | 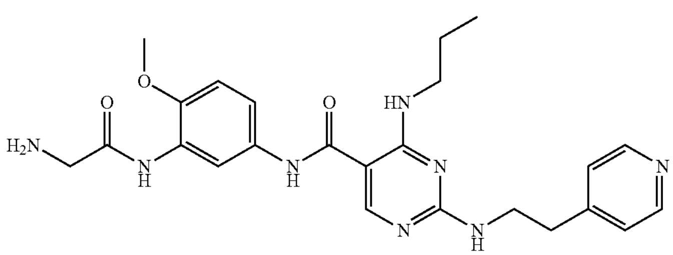 [SMILES: CCCNc1nc(NCCc2ccncc2)ncc1C(=O)Nc1ccc(OC)c(NC(=O)CN)c1] | — |
| A28 | 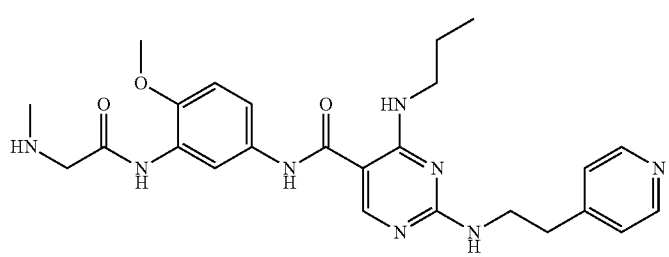 [SMILES: CCCNc1nc(NCCc2ccncc2)ncc1C(=O)Nc1ccc(OC)c(NC(=O)CNC)c1] | MS m/z (M + H): 493.3 |

Example 3

In the same manner as that of Example 1, (7) or Example 1, (8), Compounds (1-3) to (1-12) were obtained.

TABLE 16

| Compound No. | Structure | Physicochemical data |
| --- | --- | --- |
| 1-3 | 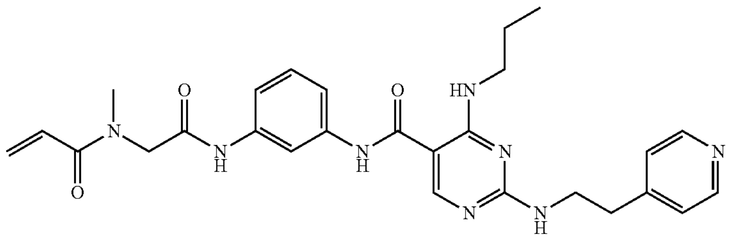 [SMILES: C=CC(=O)N(C)CC(=O)Nc1cccc(NC(=O)c2cnc(NCCc3ccncc3)nc2NCCC)c1] | $^1$H-NMR (CDCl$_3$) δ: 8.52-8.46 (2H, m), 8.31 (1H, s), 7.67 (1H, s), 7.44-7.36 (1H, m), 7.25-7.14 (4H, m), 6.63 (1H, dd, J = 16.8, 10.2 Hz), 6.39 (1H, d, J = 16.5 Hz), 5.80 (1H, d, J = 10.2 Hz), 4.17 (2H, s), 3.68 (2H, t, J = 7.3 Hz), 3.43 (2H, s), 3.25 (3H, s), 2.93 (2H, t, J = 7.3 Hz), 1.70-1.60 (2H, m), 0.98 (3H, t, J = 7.3 Hz) |
| 1-4 | 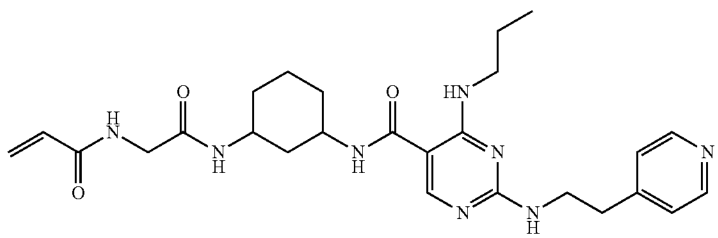 [SMILES: C=CC(=O)NCC(=O)NC1CCCC(NC(=O)c2cnc(NCCc3ccncc3)nc2NCCC)C1] | MS m/z [M + H]: 509.4 |
| 1-5 | 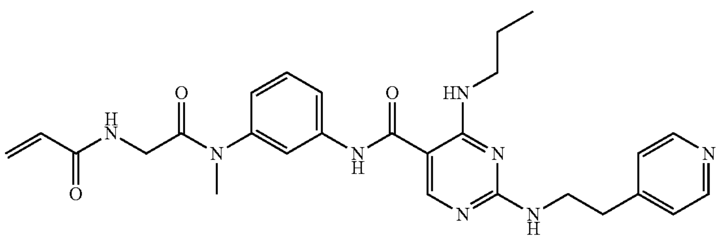 [SMILES: C=CC(=O)NCC(=O)N(C)c1cccc(NC(=O)c2cnc(NCCc3ccncc3)nc2NCCC)c1] | $^1$H-NMR (CDCl$_3$) δ: 8.62 (1H, brs), 8.53-8.52 (2H, m), 8.23 (1H, brs), 8.04 (1H, brs), 7.65 (1H, s), 7.48-7.33 (2H, m), 7.17 (2H, d, J = 3.0 Hz), 6.94 (1H, d, J = 10.1 Hz), 6.68 (1H, s), 6.24-6.14 (2H, m), 5.63 (1H, d, J = 9.9 Hz), 5.46 (1H, brs), 3.88 (2H, d, J = 4.0 Hz), 3.72-3.70 (2H, m), 3.51-3.40 (2H, m), 3.32 (3H, s), 2.93 (2H, t, J = 6.9 Hz), 1.70-1.66 (2H, m), 0.99 (3H, t, J = 7.6 Hz) |
| 1-6 | 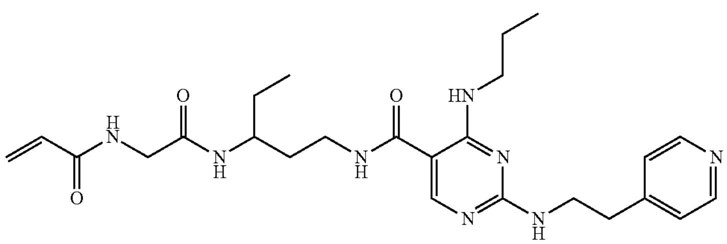 [SMILES: C=CC(=O)NCC(=O)NC(CC)CCNC(=O)c1cnc(NCCc2ccncc2)nc1NCCC] | $^1$H-NMR (CDCl$_3$) δ: 8.85 (1H, brs), 8.51 (2H, d, J = 5.9 Hz), 8.29 (1H, s), 7.38 (1H, brs), 7.15 (2H, d, J = 5.9 Hz), 6.92 (1H, brs), 6.57 (1H, d, J = 9.2 Hz), 6.32 (1H, dd, J = 17.0, 2.0 Hz), 6.20 (1H, dd, J = 17.0, 10.0 Hz), 5.71 (1H, dd, J = 10.0, 2.0 Hz), 5.36 (1H, brs), 4.05 (2H, dd, J = 5.3, 2.6 Hz), 3.90-3.71 (2H, m), 3.68 (2H, q, J = 6.8 Hz), 3.48-3.35 (2H, m), 2.92 (3H, t, J = 6.9 Hz), 1.95-1.80 (1H, m), 1.70-1.35 (5H, m), 0.98 (3H, t, J = 7.6 Hz), 0.90 (3H, t, J = 7.6 Hz) |

TABLE 17

| Compound No. | Structure | Physicochemical data |
| --- | --- | --- |
| 1-7 | 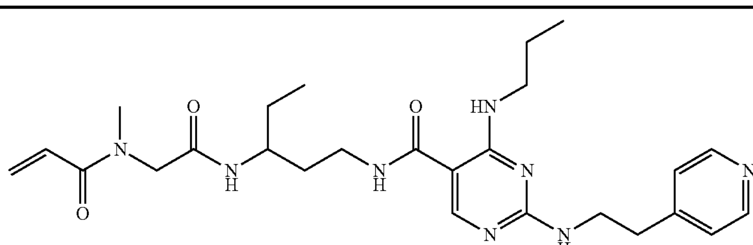 | $^1$H-NMR (CDCl$_3$) δ: 8.86 (1H, brs), 8.51 (2H, dd, J = 4.6, 1.3 Hz), 8.33 (1H, s), 7.47 (1H, brs), 7.16 (2H, d, J = 5.9 Hz), 6.62 (1H, dd, J = 16.8, 10.2 Hz), 6.42-6.33 (2H, m), 5.79 (1H, dd, J = 10.2, 1.7 Hz), 5.23 (1H, s), 4.16 (1H, d, J = 14.2 Hz), 3.95 (1H, d, J = 14.2 Hz), 3.86-3.77 (2H, m), 3.68 (2H, q, J = 6.8 Hz), 3.41 (2H, d, J = 5.3 Hz), |

TABLE 17-continued

| Compound No. | Structure | Physicochemical data |
|---|---|---|
| | | 3.22 (3H, s), 2.94-2.83 (3H, m), 1.90-1.78 (1H, m), 1.71-1.31 (5H, m), 0.98 (3H, t, J = 7.4 Hz), 0.88 (3H, t, J = 7.4 Hz) |
| 1-8 | 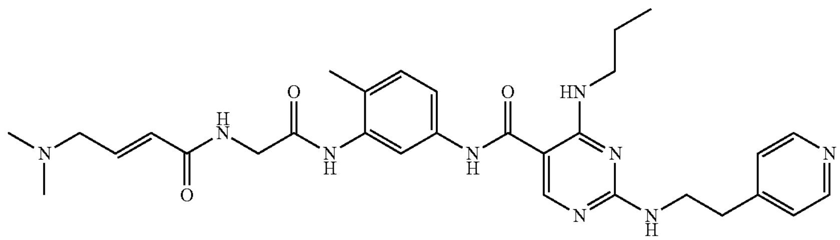 [SMILES: CCCNc1nc(NCCc2ccncc2)ncc1C(=O)Nc1ccc(C)c(NC(=O)CNC(=O)/C=C/CN(C)C)c1] | ¹H-NMR (CD₃OD) δ: 8.42 (3H, d, J = 5.3 Hz), 8.23 (2H, brs), 7.71 (1H, s), 7.34-7.31 (2H, m), 7.20-7.17 (1H, m), 6.78-6.75 (1H, m), 6.44 (1H, d, J = 15.2 Hz), 4.16 (1H, s), 3.88 (2H, d, J = 6.6 Hz), 3.70 (2H, t, J = 6.6 Hz), 3.47-3.40 (2H, m), 3.00 (2H, t, J = 6.9 Hz), 2.85 (6H, s), 2.23 (3H, s), 1.68-1.63 (2H, m), 0.99 (3H, t, J = 7.3 Hz) |
| 1-9 | 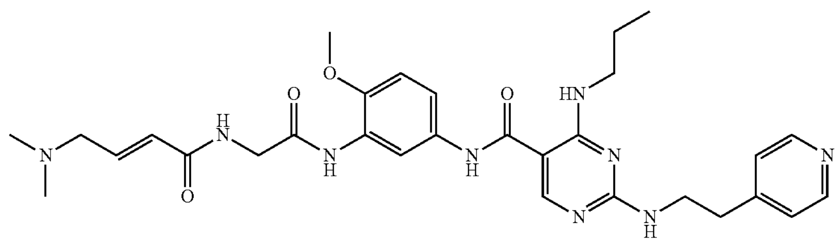 [SMILES: CCCNc1nc(NCCc2ccncc2)ncc1C(=O)Nc1ccc(OC)c(NC(=O)CNC(=O)/C=C/CN(C)C)c1] | ¹H-NMR (CDCl₃) δ: 8.70 (1H, brs), 8.52-8.51 (2H, m), 8.42-8.39 (2H, m), 8.33 (1H, brs), 8.27 (1H, brs), 7.52-7.49 (1H, m), 7.14-7.13 (2H, m), 6.94-6.84 (3H, m), 6.05 (1H, d, J = 15.2 Hz), 5.25 (1H, s), 4.15 (2H, brs), 3.86 (3H, s), 3.67 (2H, brs), 3.44 (2H, brs), 3.07 (2H, d, J = 5.9 Hz), 2.90 (2H, t, J = 5.6 Hz), 2.26 (6H, s), 1.67-1.62 (2H, m), 0.97 (3H, t, J = 7.3 Hz) |
| 1-10 | 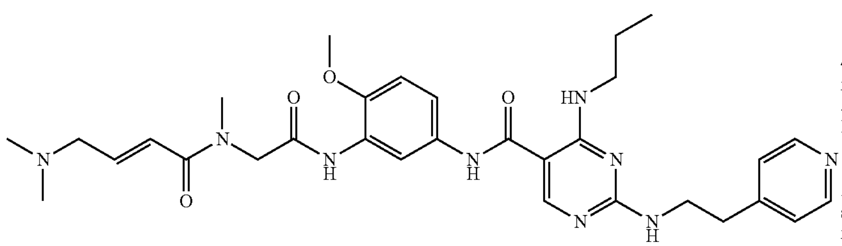 | ¹H-NMR (CDCl₃) δ: 8.65 (2H, brs), 8.52 (2H, d, J = 4.3 Hz), 8.29-8.25 (2H, m), 7.85 (1H, brs), 7.46 (1H, d, J = 8.9 Hz), 7.16 (2H, d, J = 5.9 Hz), 7.00-6.93 (1H, m), 6.84 (1H, d, J = 8.6 Hz), 6.49 (1H, d, J = 15.2 Hz), 5.32 (1H, brs), 4.21 (2H, s), 3.85 (3H, s), 3.70-3.68 (2H, m), 3.43 (2H, brs), 3.22 (3H, s), 3.17-3.11 (2H, m), 2.92 (2H, t, J = 6.9 Hz), 2.27 (3H, s), 2.21 (3H, s), 1.66-1.61 (2H, m), 0.97 (3H, t, J = 7.3 Hz) |

TABLE 18

| Compound No. | Structure | Physicochemical data |
|---|---|---|
| 1-11 | 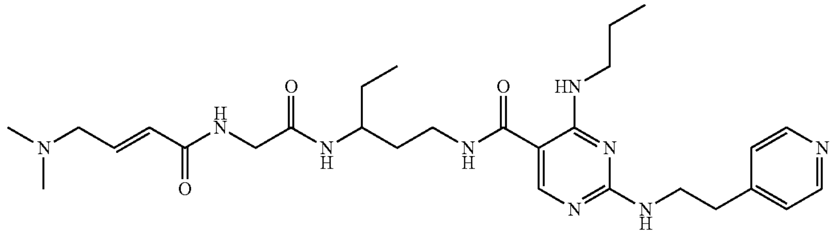 [SMILES: CCCNc1nc(NCCc2ccncc2)ncc1C(=O)NCCC(CC)NC(=O)CNC(=O)/C=C/CN(C)C] | ¹H-NMR (CDCl₃) δ: 8.86 (1H, brs), 8.51 (2H, dd, J = 4.3, 1.7 Hz), 8.30 (1H, s), 7.45 (1H, brs,) 7.16 (2H, d, J = 5.9 Hz), 6.94 (1H, brs), 6.84 (1H, dt, J = 15.6, 6.1 Hz), 6.74 (1H, d, J = 9.2 Hz), 6.06 (1H, d, J = 15.6 Hz), 5.50 (1H, brs), 4.04 (2H, t, J = 5.0 Hz), 3.85-3.64 (4H, m), 3.42 (2H, d, J = 5.3 Hz), 3.06 (2H, dd, J = 5.9, 1.3 Hz, 2.92 (3H, t, J = 6.9 Hz), 2.24 (6H, s), 1.91-1.82 (1H, m), 1.71-1.37 (5H, m), 0.98 (3H, t, J = 7.4 Hz), 0.89 (3H, t, J = 7.4 Hz) |

TABLE 18-continued

| Compound No. | Structure | Physicochemical data |
|---|---|---|
| 1-12 | 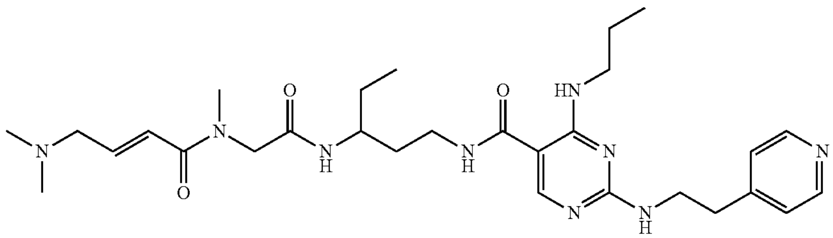 [SMILES: CCCNc1nc(NCCc2ccncc2)ncc1C(=O)NCCC(CC)NC(=O)CN(C)C(=O)/C=C/CN(C)C] | $^1$H-NMR (CDCl$_3$) δ: 8.87 (1H, brs), 8.51 (2H, dd, J = 4.6, 1.3 Hz), 8.33 (1H, s), 7.51 (1H, brs), 7.16 (2H, d, J = 5.9 Hz), 6.93 (1H, dt, J = 15.2, 5.9 Hz), 6.49-6.40 (2H, m), 5.35 (1H, brs), 4.16 (1H, d, J = 14.5 Hz), 3.92 (1H, d, J = 14.5 Hz), 3.84-3.72 (2H, m), 3.68 (2H, q, J = 6.8 Hz), 3.44 (2H, t, J = 10.6 Hz), 3.21(3H, s), 3.10 (2H, d, J = 5.9 Hz), 2.94-2.79 (3H, m), 2.26 (6H, s), 1.88-1.80 (1H, m), 1.70-1.33 (5H, m), 0.98 (3H, t, J = 7.4 Hz), 0.88 (3H, t, J = 7.4 Hz) |

Example 4

1

[Formula 55]

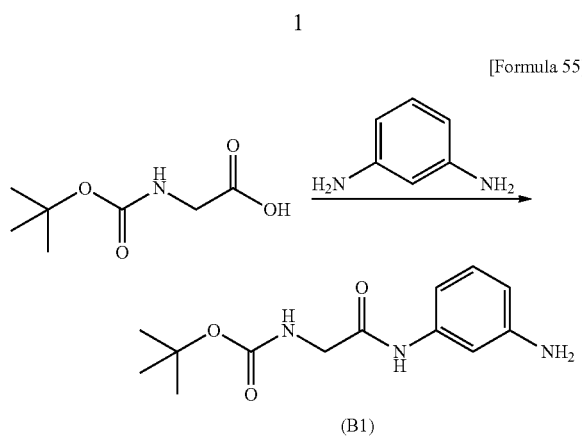

(B1)

To a solution of N-Boc-glycine (3.50 g) in N,N-dimethylactamide (20 mL), carbonyldiimidazole (3.34 g) was added at room temperature, and the mixture was stirred at the same temperature for 1 hour (Reaction mixture A).

To a solution of 1,3-phenylenediamine (3.24 g) in N,N-dimethylactamide (20 mL), Reaction mixture A was added dropwise at room temperature, and the mixture was stirred at the same temperature for 2 hours. To the reaction mixture, saturated aqueous sodium chloride and ethyl acetate were added. The organic layer was separated, washed successively with saturated aqueous sodium hydrogencarbonate and saturated aqueous sodium chloride, and then dried over anhydrous magnesium sulfate, and the solvent was evaporated under reduced pressure. The obtained residue was purified by basic silica gel column chromatography to obtain oily tert-butyl (2-((3-aminophenyl)amino)-2-oxoethyl)carbamate (B1, 3.20 g).

$^1$H-NMR (CDCl$_3$) δ: 7.98 (1H, s), 7.12 (1H, s), 7.08 (1H, t, J=7.9 Hz), 6.68 (1H, d, J=7.9 Hz), 6.44 (1H, d, J=7.9 Hz), 5.22 (1H, s), 3.90 (2H, d, J=5.9 Hz), 3.69 (2H, brs), 1.48 (9H, s)

2

[Formula 56]

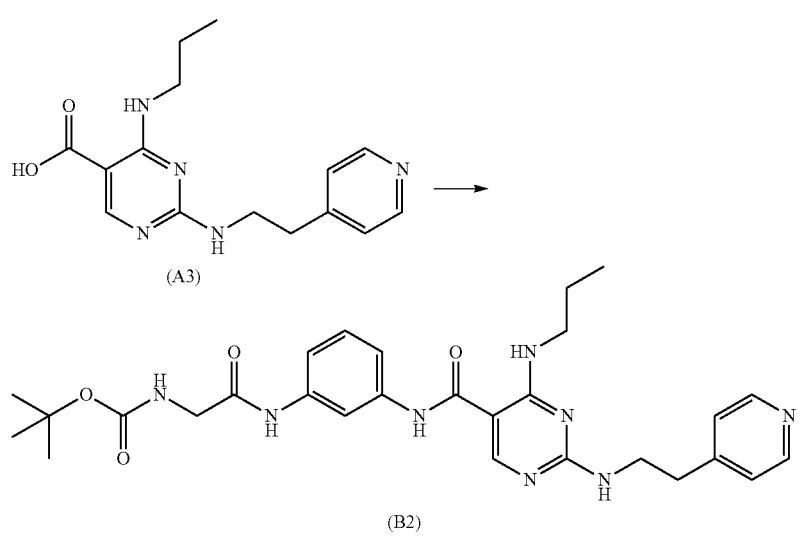

(B2)

To a suspension of 4-(propylamino)-2-((2-(pyridin-4-yl)ethyl)amino)pyrimidine-5-carboxylic acid (A3, 301 mg) in N,N-dimethylformamide (3 mL), 1-ethyl-3-(3-dimethylaminopropyl)carbodiimide hydrochloride (211 mg) and 1-hydroxybenzotriazole monohydrate (162 mg) were added at room temperature, and the mixture was stirred at the same temperature for 2 hours. To the reaction mixture, a solution of N,N-diisopropylethylamine (511 μL) and tert-butyl (2-((3-aminophenyl)amino)-2-oxoethyl)carbamate (B1, 292 mg) in N,N-dimethylformamide (2 mL) was added at room temperature, and the mixture was stirred at the same temperature for 5 hours. To the reaction mixture, saturated aqueous sodium chloride and ethyl acetate were added. The organic layer was separated, washed with saturated aqueous sodium chloride, and then dried over anhydrous magnesium sulfate, and the solvent was evaporated under reduced pressure. The obtained residue was purified by silica gel column chromatography (eluent, 100 to 93% ethyl acetate in methanol) to obtain oily tert-butyl (2-oxo-2-((3-(4-(propylamino)-2-((2-(pyridin-4-yl)ethyl)amino)pyrimidine-5-carboxamido)phenyl)amino)ethyl)carbamate (B2, 437 mg).

MS m/z (M−H): 547.2

2.4 Hz), 4.08 (2H, s), 3.78-3.62 (2H, m), 3.57-3.41 (2H, br), 3.01 (2H, t, J=7.2 Hz), 1.76-1.53 (2H, m), 0.99 (3H, t, J=7.5 Hz)

4

[Formula 58]

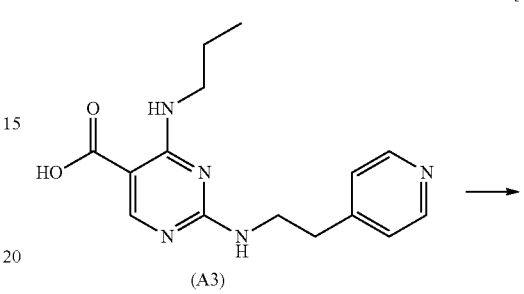

(A3)

3

[Formula 57]

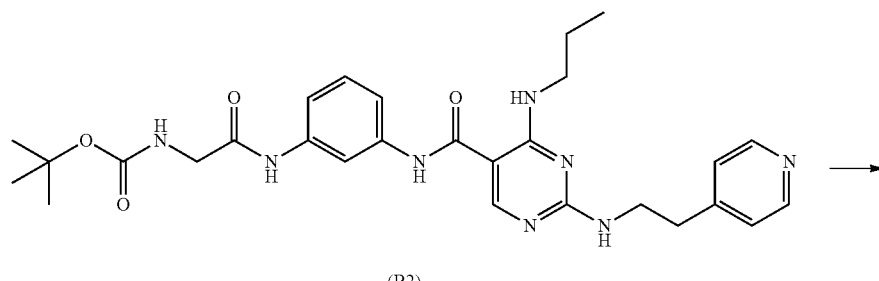

(B2)

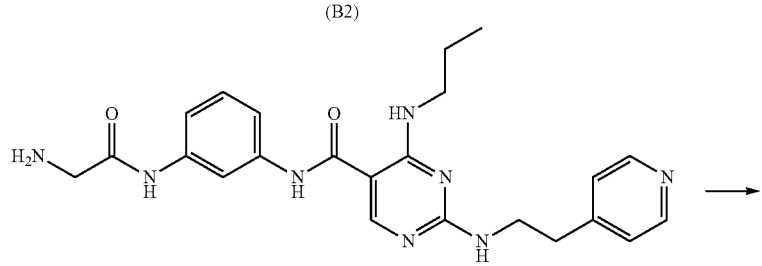

(B26)

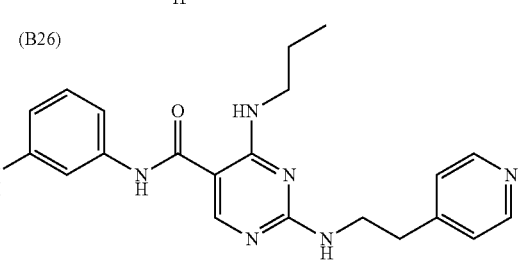

(2-1)

In the same manner as that of Example 1, (6) and Example 1, (7), N-(3-(2-(acrylylamido)acetamido)phenyl)-4-(propylamino)-2-((2-(pyridin-4-yl)ethyl)amino)pyrimidine-5-carboxamide (2-1) was obtained from tert-butyl (2-oxo-2-((3-(4-(propylamino)-2-((2-(pyridin-4-yl)ethyl)amino)pyrimidine-5-carboxamido)phenyl)amino)ethyl)carbamate (B2).

$^1$H-NMR (CD$_3$OD) δ: 8.43 (2H, dd, J=4.5, 1.5 Hz), 8.38 (1H, s), 7.93 (1H, s), 7.38-7.21 (5H, m), 6.33 (1H, dd, J=17.1, 9.8 Hz), 6.28 (1H, dd, J=17.1, 2.1 Hz), 5.71 (1H, dd, J=9.6,

-continued

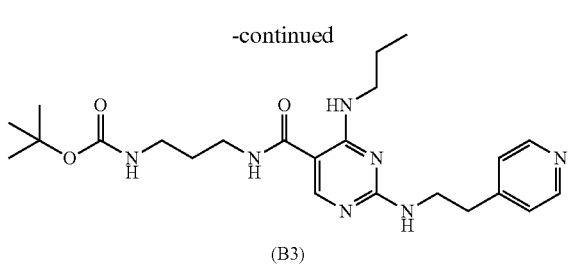

(B3)

To 4-(propylamino)-2-((2-(pyridin-4-yl)ethyl)amino)pyrimidine-5-carboxylic acid (A3, 452 mg), 1-ethyl-3-(3-dimethylaminopropyl)carbodiimide hydrochloride (575 mg) and 1-hydroxybenzotriazole monohydrate (405 mg), N,N-dimethylformamide (10 mL) was added at room temperature, and the mixture was stirred at 40° C. for 2 hours. The reaction mixture was cooled to room temperature, then N,N-diisopropylethylamine (765 µL) and N-Boc-1,3-propanediamine (330 mg) were added to the mixture, and the mixture was stirred at the same temperature for 2 hours. To the reaction mixture, saturated aqueous sodium hydrogencarbonate and ethyl acetate were added. The organic layer was separated, washed successively with water and saturated aqueous sodium chloride, and then dried over anhydrous magnesium sulfate, and the solvent was evaporated under reduced pressure. The obtained residue was purified by basic silica gel column chromatography (eluent, 100 to 95% ethyl acetate in methanol) to obtain tert-butyl (3-(4-(propylamino)-2-((2-(pyridin-4-yl)ethyl)amino)pyrimidine-5-carboxamido)propyl)carbamate (B3, 481 mg) as white solid.

MS m/z (M+H): 458.4

5

[Formula 59]

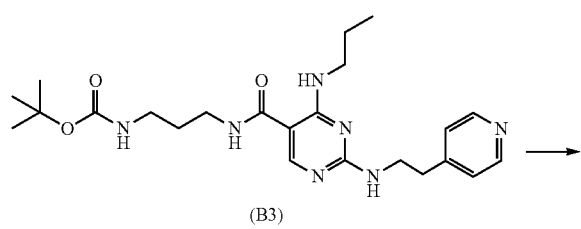

(B3)

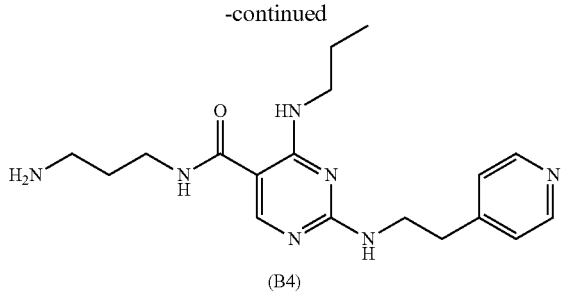

(B4)

To a solution of tert-butyl (3-(4-(propylamino)-2-((2-(pyridin-4-yl)ethyl)amino)pyrimidine-5-carboxamido)propyl)carbamate (B3, 281 mg) in chloroform (2 mL), trifluoroacetic acid (2 mL) was added at room temperature, and the mixture was stirred at the same temperature for 30 minutes. To the reaction mixture, saturated aqueous sodium hydrogencarbonate and ethyl acetate were added. The organic layer was separated, and the aqueous layer was extracted three times with chloroform. The organic layer and the extracts were combined, washed with saturated aqueous sodium chloride, and then dried over anhydrous sodium sulfate, and the solvent was evaporated under reduced pressure. The obtained residue was purified by basic silica gel column chromatography (eluent, 85 to 70% ethyl acetate in methanol) to obtain N-(3-aminopropyl)-4-(propylamino)-2-((2-(pyridin-4-yl)ethyl)amino)pyrimidine-5-carboxamide (B4, 142 mg) as white solid.

$^1$H-NMR (CDCl$_3$) δ: 8.89 (1H, brs), 8.51 (2H, dd, J=6.0, 1.5 Hz), 8.09 (1H, s), 8.09 (1H, brs), 7.15 (2H, d, J=6.0 Hz), 5.37 (1H, brs), 3.67 (2H, q, J=6.6 Hz), 3.52-3.41 (4H, m), 2.91 (4H, t, J=6.6 Hz), 1.74-1.59 (6H, m), 0.98 (3H, t, J=7.5 Hz)

6

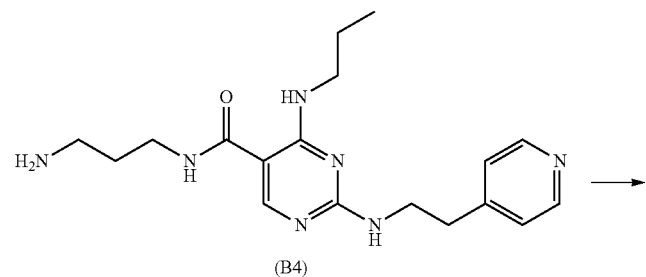

(B4)

[Formula 60]

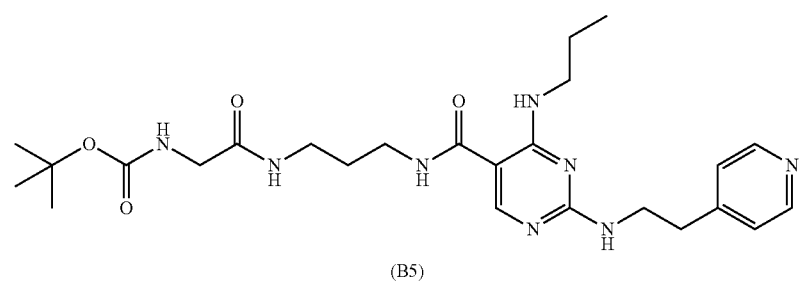

(B5)

To N-(3-aminopropyl)-4-(propylamino)-2-((2-(pyridin-4-yl)ethyl)amino)pyrimidine-5-carboxamide (B4, 57 mg), N-Boc-glycine (44 mg), 1-ethyl-3-(3-dimethylaminopropyl)carbodiimide hydrochloride (127 mg) and 1-hydroxybenzotriazole monohydrate (102 mg), N,N-dimethylformamide (2 mL) and triethylamine (46 μL) were added at room temperature, and the mixture was stirred at the same temperature for 7 hours. To the reaction mixture, saturated aqueous sodium hydrogencarbonate and ethyl acetate were added. The organic layer was separated, and the aqueous layer was extracted with ethyl acetate. The organic layer and the extract were combined, washed successively with water and saturated aqueous sodium chloride, and then dried over anhydrous sodium sulfate, and the solvent was evaporated under reduced pressure. The obtained residue was purified by basic silica gel column chromatography (eluent, 95 to 90% ethyl acetate in methanol) to obtain amorphous tert-butyl (2-oxo-2-((3-(4-(propylamino)-2-((2-(pyridin-4-yl)ethyl)amino)pyrimidine-5-carboxamido)propyl)amino)ethyl)carbamate (B5, 83 mg).

MS m/z (M+H): 515.4

$^1$H-NMR (CDCl$_3$) δ: 8.78 (1H, brs), 8.49 (2H, dd, J=4.3, 1.7 Hz), 8.20 (1H, s), 7.30 (1H, brs), 7.20-7.10 (4H, m), 6.30 (1H, dd, J=17.0, 2.0 Hz), 6.20 (1H, dd, J=17.0, 10.0 Hz), 5.68 (1H, dd, J=10.0, 2.0 Hz), 5.61 (1H, brs), 4.01 (2H, d, J=5.9 Hz), 3.68 (2H, q, J=6.8 Hz), 3.46-3.29 (6H, m), 2.91 (2H, t, J=6.9 Hz), 1.75-1.59 (4H, m), 0.98 (3H, t, J=7.6 Hz)

Example 5

1

[Formula 62]

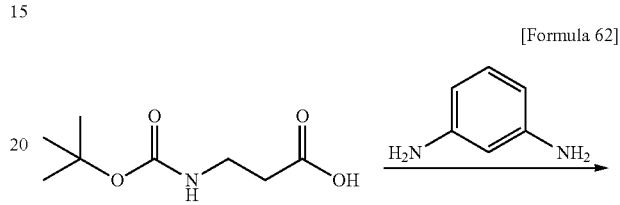

[Formula 61]

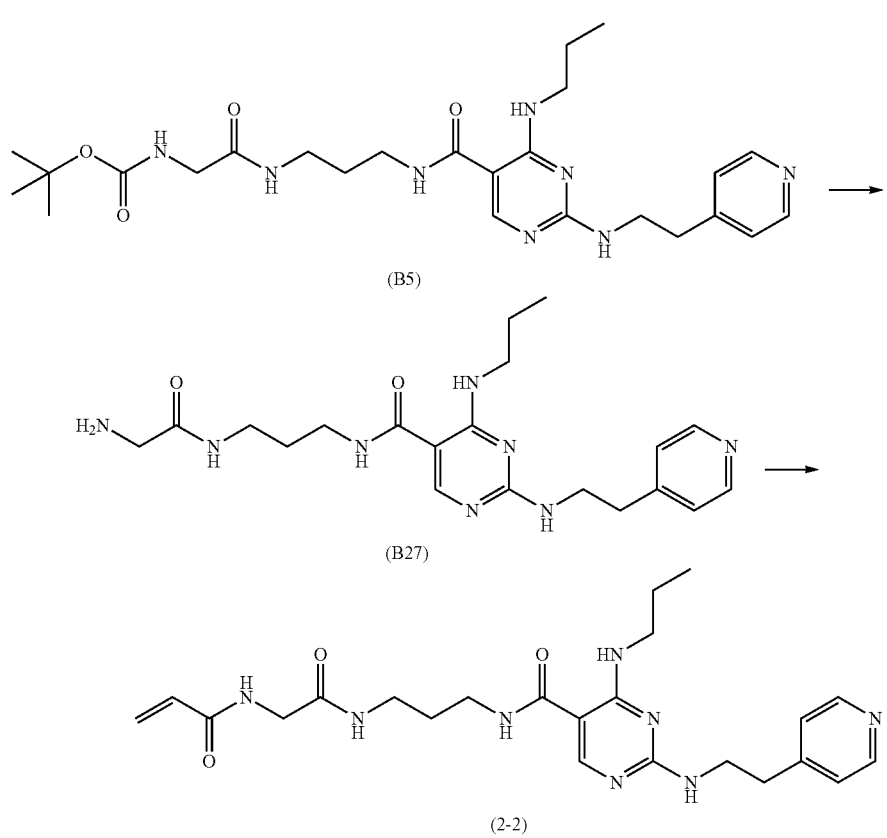

In the same manner as that of Example 1, (6) and Example 1, (7), N-(3-(2-(acrylylamido)actamido)propyl)-4-(propylamino)-2-((2-(pyridin-4-yl)ethyl)amino)pyrimidine-5-carboxamide (2-2) was obtained from tert-butyl (2-oxo-2-((3-(4-(propylamino)-2-((2-(pyridin-4-yl)ethyl)amino)pyrimidine-5-carboxamido)propyl)amino)ethyl)carbamate (B5).

-continued

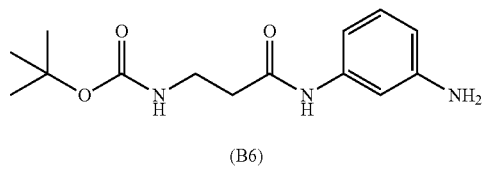

(B6)

To a solution of N-Boc-β-alanine (1.00 g) in N,N-dimethylactamide (5 mL), carbonyldiimidazole (888 mg) was added at room temperature, and the mixture was stirred at the same temperature for 1 hour and 20 minutes. To the reaction mixture, a solution of 1,3-phenylenediamine (1.15 g) in N,N-dimethylactamide (5 mL) was added at room temperature, and the mixture was stirred at the same temperature for 18 hours. To the reaction mixture, saturated aqueous sodium hydrogencarbonate and ethyl acetate were added. The organic layer was separated, washed with saturated aqueous sodium chloride, and then dried over anhydrous magnesium sulfate, and the solvent was evaporated under reduced pressure. The obtained residue was purified by silica gel column chromatography to obtain tert-butyl (3-((3-aminophenyl)amino)-3-oxopropyl)carbamate (B6, 978 mg).

$^1$H-NMR (CDCl$_3$) δ: 7.65 (1H, s), 7.14 (1H, s), 7.07 (2H, t, J=7.9 Hz), 6.71 (1H, d, J=7.9 Hz), 6.43 (1H, d, J=7.9 Hz), 5.19 (1H, s), 3.70 (1H, brs), 3.48-3.46 (2H, m), 2.56 (2H, t, J=5.9 Hz), 1.43 (9H, s)

2

[Formula 63]

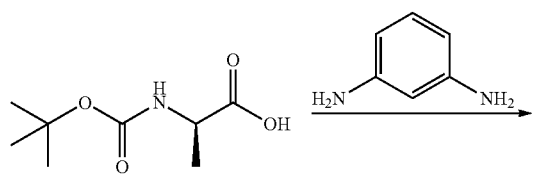

(B7)

By using N-Boc-D-alanine, amorphous (R)-tert-butyl (1-((3-aminophenyl)amino)-1-oxopropan-2-yl)carbamate (B7) was obtained in the same manner as that of Example 5, (1).

$^1$H-NMR (CDCl$_3$) δ: 8.19 (1H, s), 7.14 (1H, s), 7.07 (1H, t, J=7.9 Hz), 6.69 (1H, d, J=7.9 Hz), 6.43 (1H, d, J=7.9 Hz), 4.95 (1H, brs), 4.32-4.20 (1H, m), 3.69 (2H, brs), 1.46 (9H, s), 1.42 (3H, d, J=6.6 Hz)

3

[Formula 64]

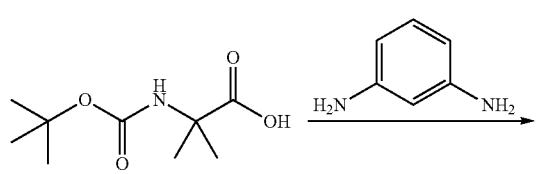

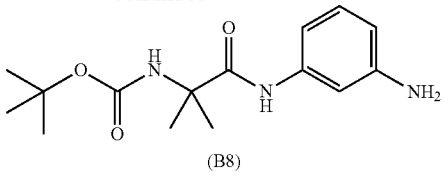

(B8)

To a solution of 2-(tert-butoxycarbonylamino)isobutyric acid (203 mg), 1-ethyl-3-(3-dimethylaminopropyl)carbodiimide hydrochloride (211 mg) and 1-hydroxybenzotriazole monohydrate (149 mg) in N,N-dimethylformamide (3 mL), N,N-diisopropylethylamine (510 μL) was added at room temperature, and the mixture was stirred at the same temperature for 1 hour and 30 minutes. To the reaction mixture, a solution of 1,3-phenylenediamine (260 mg) in N,N-dimethylformamide (2 mL) was added at room temperature, and the mixture was stirred at 80° C. for 1 hour and 30 minutes. The reaction mixture was cooled to room temperature, and then saturated aqueous sodium hydrogencarbonate and ethyl acetate were added to the mixture. The organic layer was separated, washed with saturated aqueous sodium chloride, and then dried over anhydrous magnesium sulfate, and the solvent was evaporated under reduced pressure. The obtained residue was purified by silica gel column chromatography to obtain tert-butyl (1-((3-aminophenyl)amino)-2-methyl-1-oxopropan-2-yl)carbamate (B8, 195 mg) as white solid.

MS m/z (M+H): 294.2

4

[Formula 65]

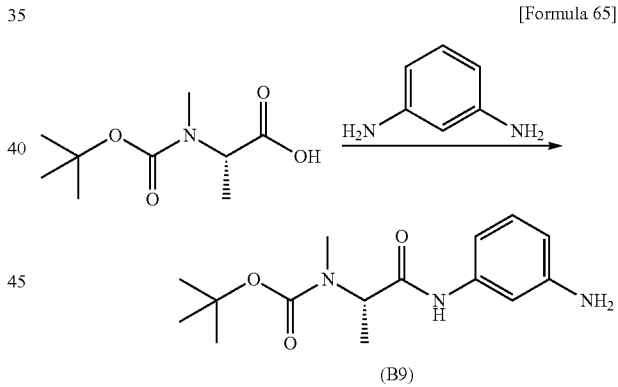

(B9)

To N-Boc-N-methyl-L-alanine (1.02 g), 1-ethyl-3-(3-dimethylaminopropyl)carbodiimide hydrochloride (1.92 g) and 1-hydroxybenzotriazole monohydrate (1.35 g), N,N-dimethylformamide (15 mL) was added at room temperature, and the mixture was stirred at the same temperature for 1 hour. To the reaction mixture, a solution of N,N-diisopropylethylamine (2.6 mL) and 1,3-phenylenediamine (1.35 g) in N,N-dimethylformamide (4 mL) was added at room temperature, and the mixture was stirred at 40° C. for 3 hours. The reaction mixture was cooled to room temperature, and then saturated aqueous sodium hydrogencarbonate and ethyl acetate were added to the mixture. The organic layer was separated, washed successively with water and saturated aqueous sodium chloride, and then dried over anhydrous magnesium sulfate, and the solvent was evaporated under reduced pressure. The obtained residue was purified by silica gel column chromatography (eluent, 60 to 25% hexane in ethyl acetate)

to obtain amorphous (S)-tert-butyl (1-((3-aminophenyl)amino)-1-oxopropan-2-yl)(methyl)carbamate (B9, 967 mg).

MS m/z (M+H): 294.2

5

[Formula 66]

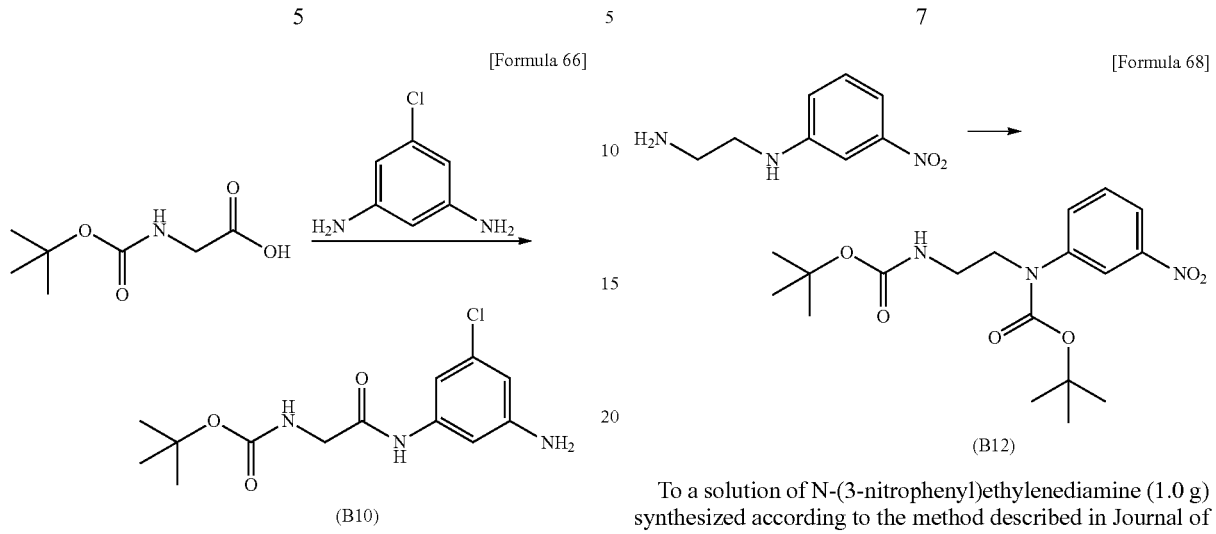

(B10)

To a solution of 5-chloro-1,3-phenylenediamine (1.22 g), N-Boc-glycine (500 mg) and (1-cyano-2-ethoxy-2-oxoethylideneaminoxy)dimethylamino-morpholino-carbenium hexafluorophosphate (1.83 g) in N,N-dimethylformamide (5 mL), N-methylmorpholine (628 μL) was added at room temperature, and the mixture was stirred at 130° C. for 5 hours. The reaction mixture was cooled to room temperature, and then saturated aqueous sodium hydrogencarbonate and ethyl acetate were added to the mixture. The organic layer was separated, and the aqueous layer was extracted with ethyl acetate. The organic layer and the extract were combined, washed successively with water and saturated aqueous sodium chloride, and then dried over anhydrous sodium sulfate, and the solvent was evaporated under reduced pressure. The obtained residue was purified by basic silica gel column chromatography (eluent, 70 to 40% hexane in ethyl acetate) to obtain tert-butyl (2-((3-amino-5-chlorophenyl)amino)-2-oxoethyl)carbamate (B10, 273 mg) as yellow solid.

MS m/z (M+H): 300.1, 303.1

6

[Formula 67]

By using 4,6-dimethyl-1,3-phenylenediamine, oily tert-butyl (2-((5-amino-2,4-dimethylphenyl)amino)-2-oxoethyl)carbamate (B11) was obtained in the same manner as that of Example 5, (5).

$^1$H-NMR (CDCl$_3$) δ: 7.83 (1H, brs), 7.37 (1H, s), 6.84 (1H, s), 5.17 (1H, brs), 3.91 (2H, d, J=6.0 Hz), 3.54 (2H, brs), 2.13 (3H, s), 2.10 (3H, s), 1.48 (9H, s)

7

[Formula 68]

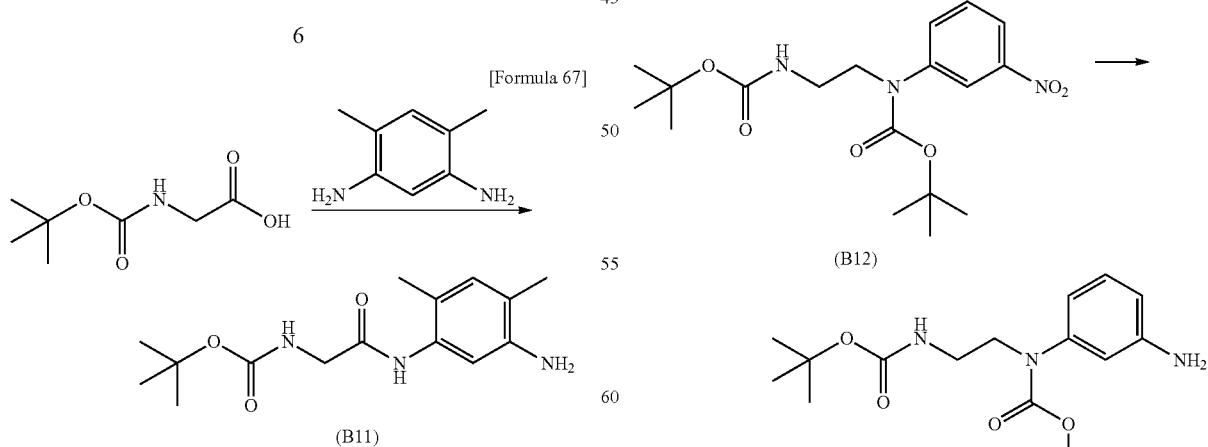

(B12)

To a solution of N-(3-nitrophenyl)ethylenediamine (1.0 g) synthesized according to the method described in Journal of Organic Chemistry, 1992, vol. 57, pp. 6257-6265 and 4-dimethylaminopyridine (674 mg) in acetonitrile (10 mL), triethylamine (3.8 mL) and di-tert-butyl dicarbonate (4.8 g) were added at room temperature, and the mixture was stirred at the same temperature for 13 hours. To the reaction mixture, water and ethyl acetate were added. The organic layer was separated, and the aqueous layer was extracted with ethyl acetate. The organic layer and the extract were combined, washed successively with water and saturated aqueous sodium chloride, and then dried over anhydrous sodium sulfate, and the solvent was evaporated under reduced pressure. The obtained residue was purified by silica gel column chromatography (eluent, 90 to 80% hexane in ethyl acetate) to obtain oily tert-butyl (2-((tert-butoxycarbonyl)amino)ethyl)(3-nitrophenyl)carbamate (B12, 1.0 g).

8

[Formula 69]

(B13)

To a suspension of 10% palladium-carbon (500 mg) in methanol (4 mL), tert-butyl (2-(((tert-butoxycarbonyl)amino)ethyl)(3-nitrophenyl)carbamate (B12, 500 mg) was added at room temperature, and the mixture was stirred at room temperature for 1 hour and 30 minutes under a hydrogen atmosphere. To the reaction mixture, methanol was added, the insoluble matter was removed by filtration through Cerite, and then the solvent was evaporated under reduced pressure. The obtained residue was purified by basic silica gel column chromatography (eluent, 75 to 70% hexane in ethyl acetate) to obtain tert-butyl(3-aminophenyl)(2-(((tert-butoxycarbonyl)amino)ethyl)carbamate (B13, 140 mg).

MS m/z (M+H): 352.3

9

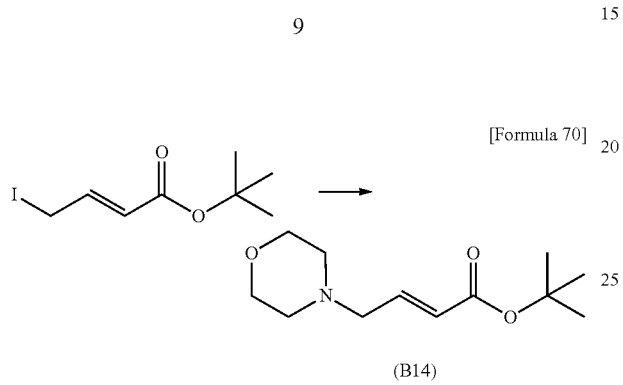

(B14)

[Formula 70]

To a solution of 4-iodocrotonic acid tert-butyl ester (310 mg) synthesized according to the method described in Journal of Medicinal Chemistry, 2005, vol. 48, pp. 1107-1131 in tetrahydrofuran (3 mL), morpholine (200 μL) was added under ice cooling, and the mixture was stirred at room temperature for 13 hours. To the reaction mixture, saturated aqueous sodium hydrogencarbonate and ethyl acetate were added. The organic layer was separated, washed successively with water and saturated aqueous sodium chloride, and then dried over anhydrous sodium sulfate, and the solvent was evaporated under reduced pressure to obtain (E)-tert-butyl 4-morpholino-2-butenoate (B14, 180 mg).

$^1$H-NMR (CDCl$_3$) δ: 6.85-6.80 (1H, m), 5.91 (1H, d, J=15.9 Hz), 3.86-3.62 (4H, m), 3.10 (2H, d, J=3.0 Hz), 2.60-2.35 (4H, m), 1.51 (9H, s)

10

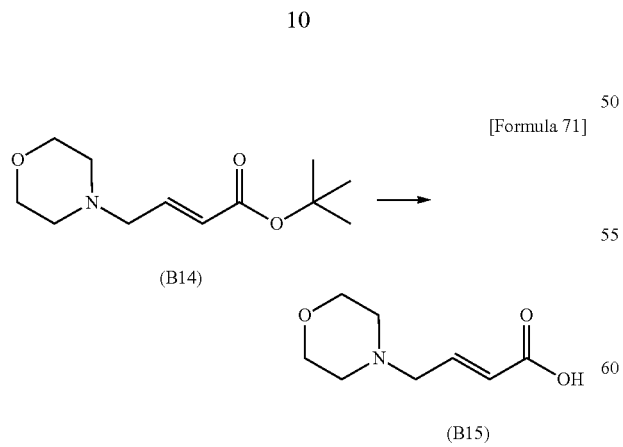

(B14)

(B15)

[Formula 71]

To (E)-tert-butyl 4-morpholino-2-butenoate (B14, 179 mg), 1.0 mol/L aqueous hydrochloric acid (4 mL) was added at room temperature, and the mixture was stirred for 1 hour and 40 minutes under reflux by heating. The reaction mixture was cooled to room temperature, and then toluene was added to the mixture, and the solvent was evaporated under reduced pressure. To the obtained residue, ethyl acetate was added. The solid matter was taken by filtration, washed with chloroform, and then dried under reduced pressure to obtain (E)-4-morpholino-2-butenoic acid (B15) hydrochloride (134 mg).

$^1$H-NMR (DMSO-d$_6$) δ: 6.89-6.84 (1H, m), 6.18 (1H, d, J=15.9 Hz), 3.94-3.92 (4H, m), 3.16-2.92 (2H, m), 2.58-2.44 (4H, m)

11

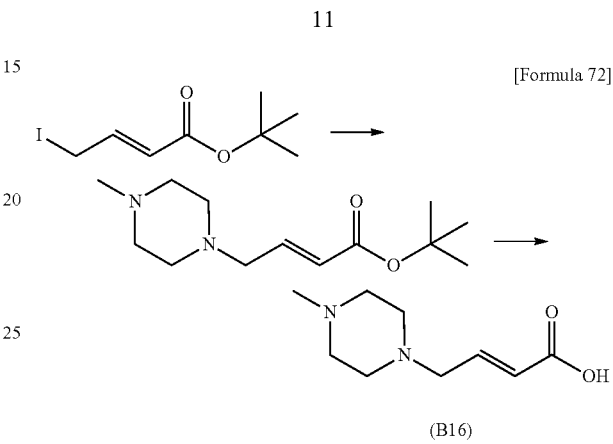

(B16)

[Formula 72]

By using N-methylpiperazine, (E)-4-(4-methylpiperazin-1-yl)-2-butenoic acid (B16) hydrochloride was obtained in the same manner as that of Example 5, (9) and Example 5, (10).

$^1$H-NMR (DMSO-d$_6$) δ: 6.91-6.73 (1H, m), 6.20 (1H, d, J=15.2 Hz), 4.00-3.00 (10H, m), 2.82 (3H, s)

12

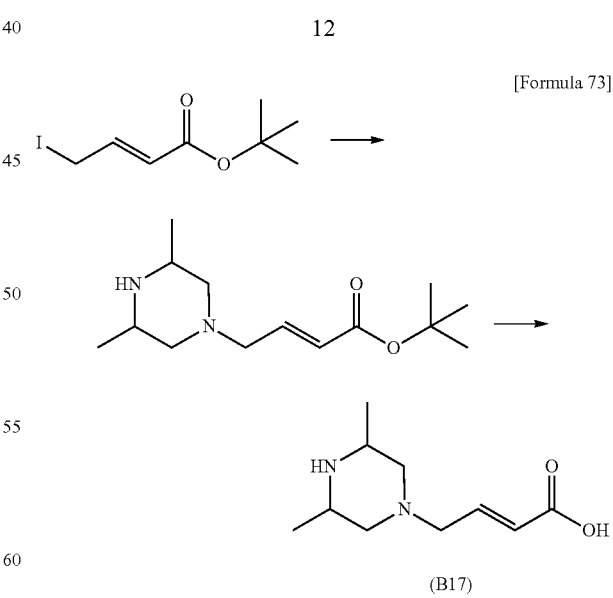

(B17)

[Formula 73]

By using 2,6-dimethylpiperazine, (E)-4-(3,5-dimethylpiperazin-1-yl)-2-butenoic acid (B17) hydrochloride was obtained in the same manner as that of Example 5, (9) and Example 5, (10).

13

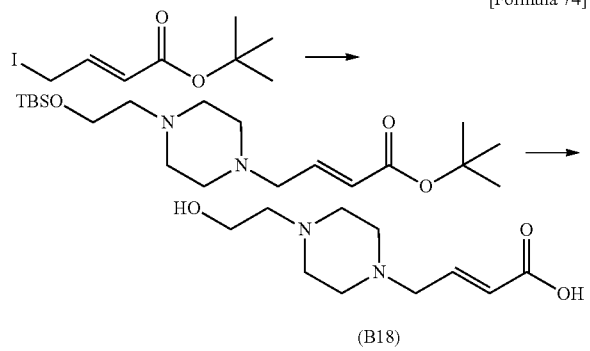

[Formula 74]

By using 1-(2-(tert-butyldimethylsilyloxy)ethyl)piperazine, (E)-4-(4-(2-hydroxyethyl)piperazin-1-yl)-2-butenoic acid (B18) hydrochloride was obtained in the same manner as that of Example 5, (9) and Example 5, (10).

$^1$H-NMR (DMSO-$d_6$) δ: 6.87-6.82 (1H, m), 6.24 (1H, d, J=15.2 Hz), 4.51-3.17 (14H, m)

14

By using 4-(propylamino)-2-((2-(pyridin-4-yl)ethyl)amino)pyrimidine-5-carboxylic acid (A3), Intermediates (B19) to (B25) were obtained in the same manner as that of Example 4, (2).

TABLE 19

| Compound No. | Structure | Physicochemical data |
|---|---|---|
| B19 | 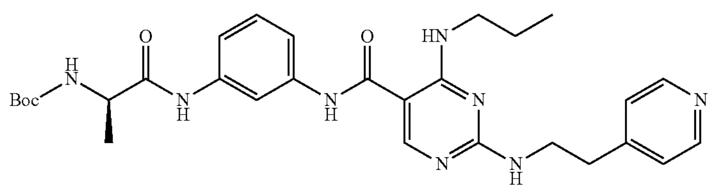 [SMILES: CCCNc1nc(NCCc2ccncc2)ncc1C(=O)Nc1cccc(NC(=O)[C@@H](C)NC(=O)OC(C)(C)C)c1] | MS m/z (M + H): 563.5 |
| B20 | 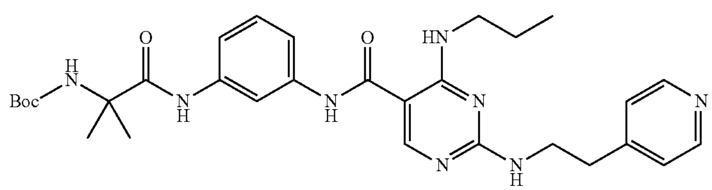 [SMILES: CCCNc1nc(NCCc2ccncc2)ncc1C(=O)Nc1cccc(NC(=O)C(C)(C)NC(=O)OC(C)(C)C)c1] | MS m/z (M + H): 577.5 |
| B21 | 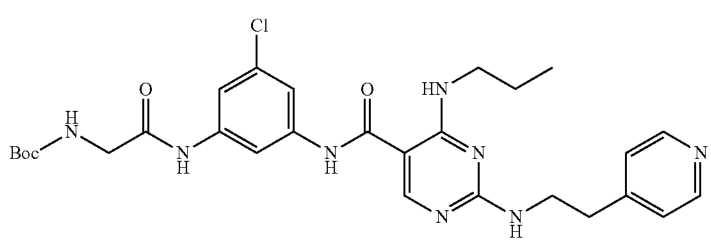 [SMILES: CCCNc1nc(NCCc2ccncc2)ncc1C(=O)Nc1cc(Cl)cc(NC(=O)CNC(=O)OC(C)(C)C)c1] | — |
| B22 | 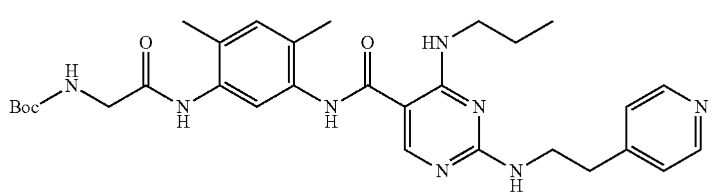 [SMILES: CCCNc1nc(NCCc2ccncc2)ncc1C(=O)Nc1cc(NC(=O)CNC(=O)OC(C)(C)C)c(C)cc1C] | — |
| B23 | 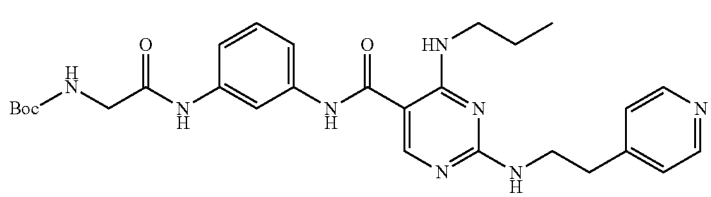 [SMILES: CCCNc1nc(NCCc2ccncc2)ncc1C(=O)Nc1cccc(NC(=O)CNC(=O)OC(C)(C)C)c1] | — |

TABLE 19-continued

| Compound No. | Structure | Physicochemical data |
| --- | --- | --- |
| B24 | 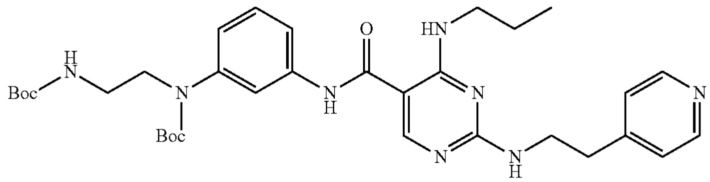 [SMILES: CCCNc1nc(NCCc2ccncc2)ncc1C(=O)Nc1cccc(N(CCNC(=O)OC(C)(C)C)C(=O)OC(C)(C)C)c1] | MS m/z (M + H): 635.5 |
| B25 | 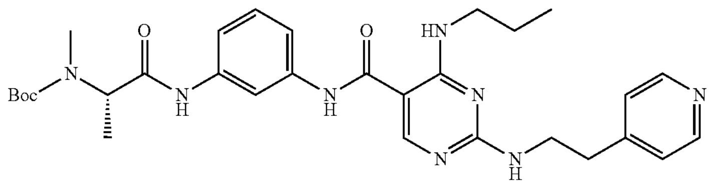 [SMILES: CCCNc1nc(NCCc2ccncc2)ncc1C(=O)Nc1cccc(NC(=O)[C@H](C)N(C)C(=O)OC(C)(C)C)c1] | MS m/z (M + H): 577.3 |

15

In the same manner as that of Example 1, (6), Intermediates (B28) to (B34) were obtained.

TABLE 20

| Compound No. | Structure | Physicochemical data |
| --- | --- | --- |
| B28 | 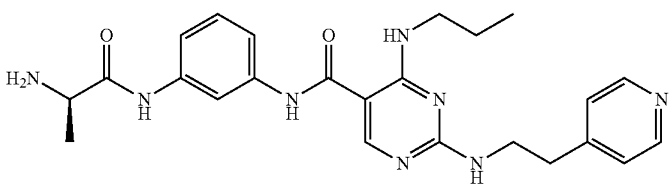 [SMILES: CCCNc1nc(NCCc2ccncc2)ncc1C(=O)Nc1cccc(NC(=O)[C@@H](C)N)c1] | — |
| B29 | 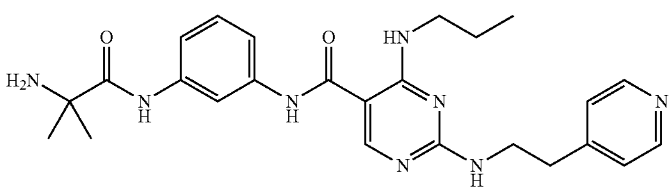 [SMILES: CCCNc1nc(NCCc2ccncc2)ncc1C(=O)Nc1cccc(NC(=O)C(C)(C)N)c1] | MS m/z (M + H): 477.3 |
| B30 | 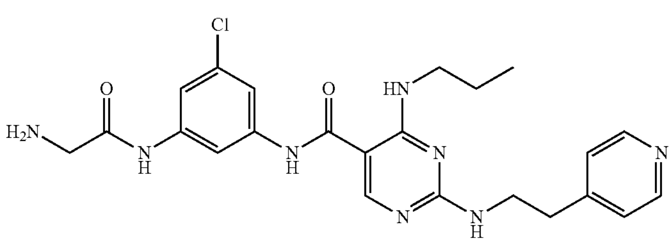 [SMILES: CCCNc1nc(NCCc2ccncc2)ncc1C(=O)Nc1cc(Cl)cc(NC(=O)CN)c1] | — |
| B31 | 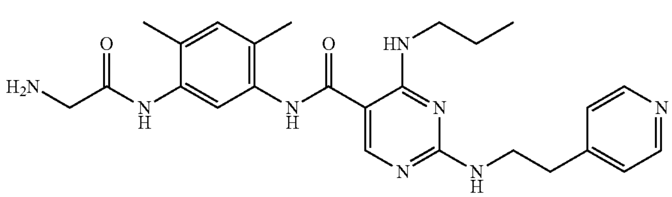 [SMILES: CCCNc1nc(NCCc2ccncc2)ncc1C(=O)Nc1cc(NC(=O)CN)c(C)cc1C] | — |

TABLE 20-continued

| Compound No. | Structure | Physicochemical data |
|---|---|---|
| B32 | 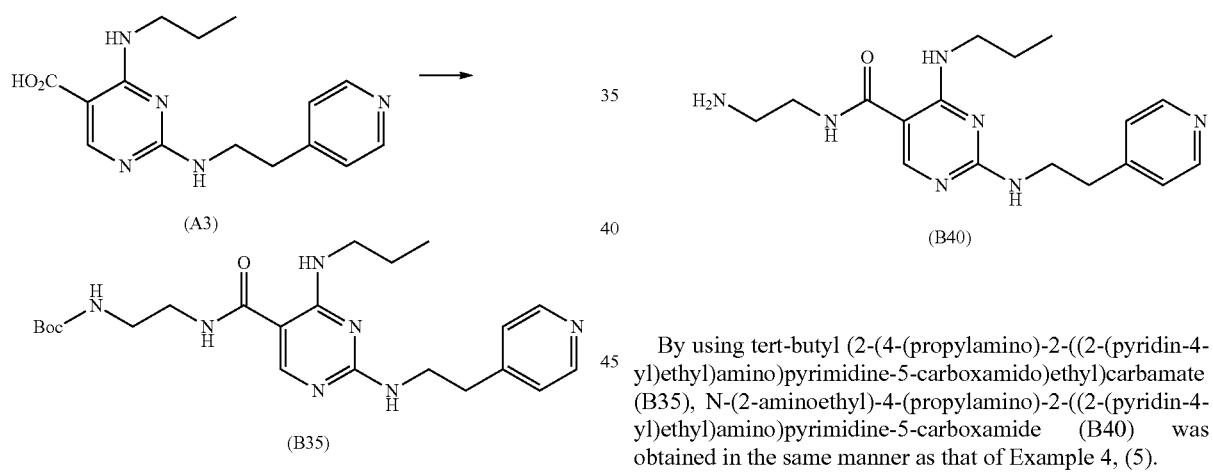 | — |
| B33 | 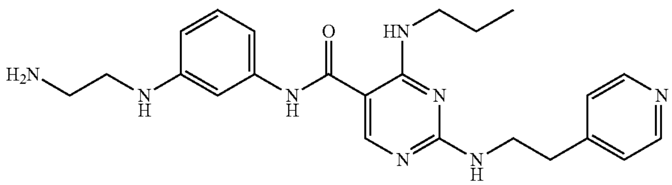 [SMILES: CCCNc1nc(NCCc2ccncc2)ncc1C(=O)Nc1cccc(NCCN)c1] | MS m/z (M + H): 435.4 |
| B34 | 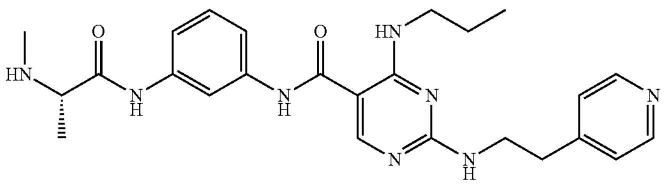 [SMILES: CCCNc1nc(NCCc2ccncc2)ncc1C(=O)Nc1cccc(NC(=O)[C@H](C)NC)c1] | MS m/z (M + H): 477.2 |

16

[Formula 75]

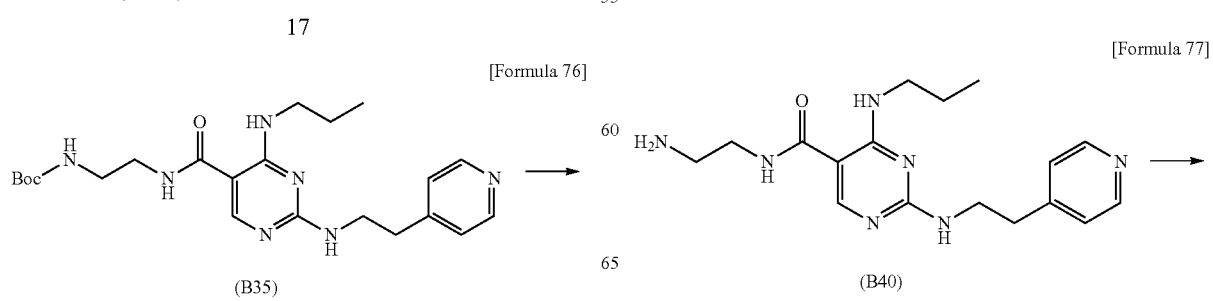

By using 4-(propylamino)-2-((2-(pyridin-4-yl)ethyl)amino)pyrimidine-5-carboxylic acid (A3), tert-butyl (2 (4-(propylamino)-2-((2-(pyridin-4-yl)ethyl)amino)pyrimidine-5-carboxamido)ethyl)carbamate (B35) was obtained in the same manner as that of Example 4, (4).

MS m/z (M+H): 444.3

17

[Formula 76]

By using tert-butyl (2-(4-(propylamino)-2-((2-(pyridin-4-yl)ethyl)amino)pyrimidine-5-carboxamido)ethyl)carbamate (B35), N-(2-aminoethyl)-4-(propylamino)-2-((2-(pyridin-4-yl)ethyl)amino)pyrimidine-5-carboxamide (B40) was obtained in the same manner as that of Example 4, (5).

MS m/z (M+H): 344.3

18

[Formula 77]

-continued

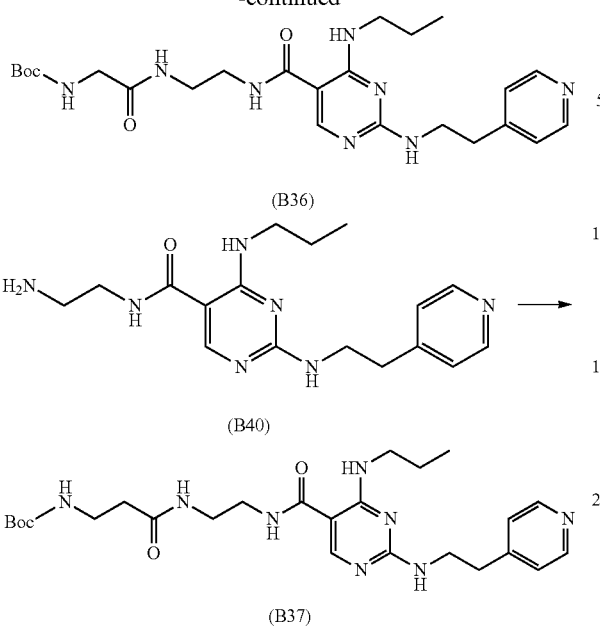

(B36)

(B40)

(B37)

By using N-(2-aminoethyl)-4-(propylamino)-2-((2-(pyridin-4-yl)ethyl)amino)pyrimidine-5-carboxamide (B40), tert-butyl (2-oxo-2-((2-(4-(propylamino)-2-((2-(pyridin-4-yl)ethyl)amino)pyrimidine-5-carboxamido)ethyl)amino)ethyl)carbamate (B36) and tert-butyl (3-oxo-3-((2-(4-(propylamino)-2-((2-(pyridin-4-yl)ethyl)amino)pyrimidine-5-carboxamido)ethyl)amino)propyl)carbamate (B37) were obtained in the same manner as that of Example 4, (6).

19

[Formula 78]

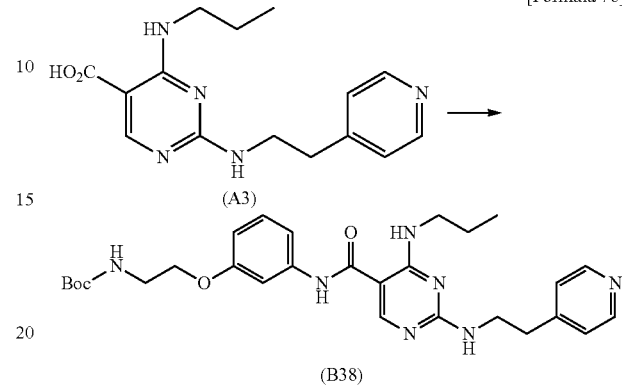

(A3)

(B38)

By using 4-(propylamino)-2-((2-(pyridin-4-yl)ethyl)amino)pyrimidine-5-carboxylic acid (A3), tert-butyl (2-(3-(4-(propylamino)-2-((2-(pyridin-4-yl)ethyl)amino)pyrimidine-5-carboxamido)phenoxy)ethyl)carbamate (B38) was obtained in the same manner as that of Example 4, (4).

20

In the same manner as that of Example 1, (6), Intermediates (B41) to (B44) were obtained.

TABLE 21

| Compound No. | Structure | Physicochemical data |
|---|---|---|
| B41 | 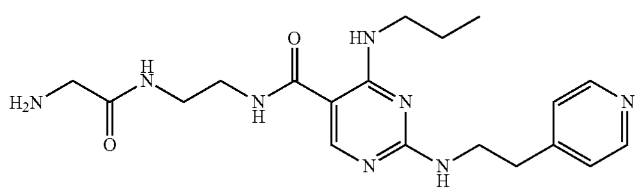 [SMILES: CCCNc1nc(NCCc2ccncc2)ncc1C(=O)NCCNC(=O)CN] | — |
| B42 | 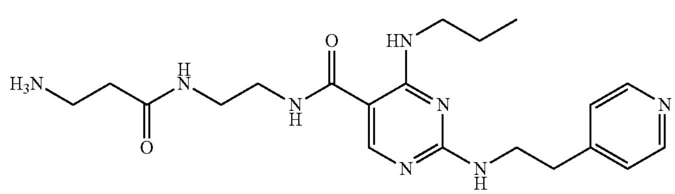 [SMILES: CCCNc1nc(NCCc2ccncc2)ncc1C(=O)NCCNC(=O)CCN] | MS m/z (M + H): 415.3 |
| B43 | 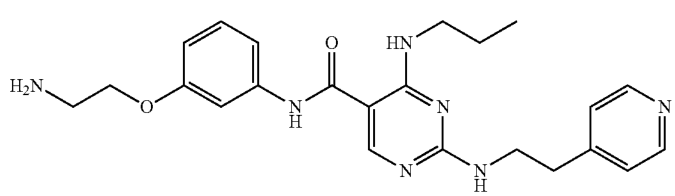 [SMILES: CCCNc1nc(NCCc2ccncc2)ncc1C(=O)Nc1cccc(OCCN)c1] | MS m/z (M + H): 436.3 |

TABLE 21-continued

| Compound No. | Structure | Physicochemical data |
|---|---|---|
| B44 | 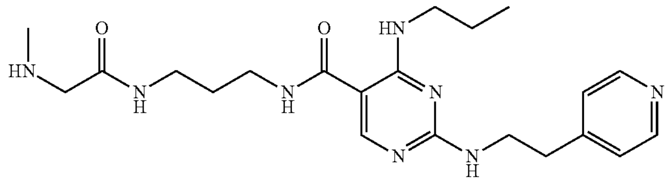 [SMILES: CCCNc1nc(NCCc2ccncc2)ncc1C(=O)NCCCNC(=O)CNC] | — |

Example 6

In the same manner as that of Example 1, (7) or Example 1, (8), Compounds (2-3) to (2-29) were obtained.

TABLE 22

| Compound No. | Structure | Physicochemical data |
|---|---|---|
| 2-3 | 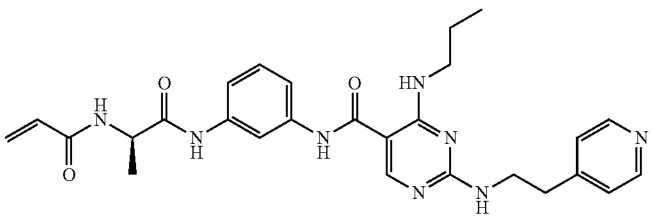 [SMILES: C=CC(=O)N[C@H](C)C(=O)Nc1cccc(NC(=O)c2cnc(NCCc3ccncc3)nc2NCCC)c1] | $^1$H-NMR (CDCl$_3$) δ: 8.73 (1H, brs), 8.49 (2H, d, J = 3.0 Hz), 8.29 (1H, s), 7.78 (1H, s), 7.42-7.34 (1H, m), 7.28-7.24 (1H, m), 7.20 (2H, d, J = 5.9 Hz), 6.34 (1H, d, J = 16.2 Hz), 6.18 (1H, dd, J = 16.8, 10.2 Hz), 5.72 (1H, d, J = 10.2 Hz), 4.64 (1H, d, J = 7.3 Hz), 3.69 (2H, t, J = 6.9 Hz), 3.48-3.38 (2H, m), 2.96 (2H, t, J = 7.3 Hz), 1.72-1.60 (2H, m), 1.46 (3H, d, J = 7.3 Hz), 0.99 (3H, t, J = 7.6 Hz) |
| 2-4 | 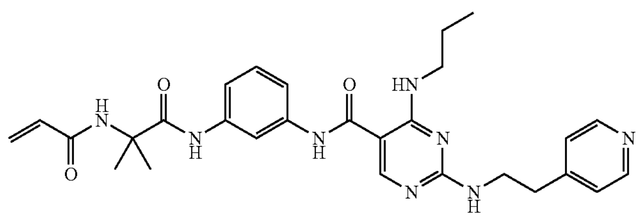 [SMILES: C=CC(=O)NC(C)(C)C(=O)Nc1cccc(NC(=O)c2cnc(NCCc3ccncc3)nc2NCCC)c1] | $^1$H-NMR (CDCl$_3$) δ: 9.30 (1H, s), 8.65 (1H, brs), 8.49 (2H, d, J = 5.8 Hz), 8.34-8.22 (2H, m), 7.73 (1H, s), 7.36 (1H, d, J = 7.9 Hz), 7.26-7.12 (4H, m), 6.53 (1H, s), 6.30 (1H, d, J = 17.2 Hz), 6.14 (1H, dd, J = 17.2, 10.2 Hz), 5.66 (1H, dd, J = 10.2, 1.7 Hz), 5.55 (1H, brs), 3.70-3.60 (2H, m), 3.42 (2H, brs), 2.89 (2H, t, J = 7.3 Hz), 1.68-1.58 (8H, m), 0.97 (3H, t, J = 7.3 Hz) |
| 2-5 | 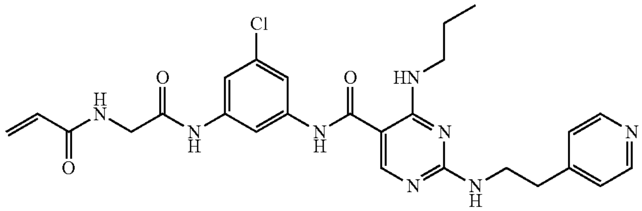 [SMILES: C=CC(=O)NCC(=O)Nc1cc(Cl)cc(NC(=O)c2cnc(NCCc3ccncc3)nc2NCCC)c1] | $^1$H-NMR (CDCl$_3$ + CD$_3$OD) δ: 8.47 (2H, dd, J = 4.3, 1.7 Hz), 8.30 (1H, s), 7.62 (1H, t, J = 2.0 Hz), 7.52 (1H, t, J = 1.7 Hz), 7.39 (1H, d, J = 2.0 Hz), 7.22 (2H, d, J = 5.9 Hz), 6.35 (1H, dd, J = 17.0, 2.0 Hz), 6.24 (1H, dd, J = 17.0, 10.0 Hz), 5.74 (1H, dd, J = 10.0, 2.0 Hz), 4.07 (2H, s), 3.69 (2H, t, J = 6.9 Hz), 3.45 (2H, brs), 2.96 (2H, t, J = 7.3 Hz), 1.70-1.61 (2H, m), 1.00 (3H, t, J = 7.3 Hz) |
| 2-6 | 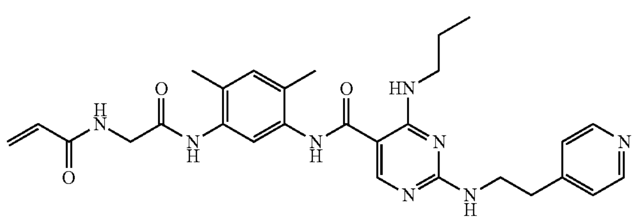 [SMILES: C=CC(=O)NCC(=O)Nc1cc(NC(=O)c2cnc(NCCc3ccncc3)nc2NCCC)c(C)cc1C] | $^1$H-NMR (CDCl$_3$) δ: 8.65 (1H, brs), 8.52 (2H, dd, J = 4.3, 1.7 Hz), 8.35 (1H, s), 8.32 (1H, brs), 7.93 (1H, brs), 7.83 (1H, brs), 7.15 (2H, d, J = 5.9 Hz), 7.03 (1H, brs), 7.00 (1H, s), 6.35 (1H, dd, J = 17.0, 2.0 Hz), 6.18 (1H, dd, J = 17.0, 10.0 Hz), 5.70 (1H, dd, J = 10.0, 2.0 Hz), 5.36 (1H, brs), 4.08 (2H, d, J = 5.9 Hz), 3.69 (2H, q, J = 6.8 Hz), 3.42 (2H, br), 2.92 (2H, t, J = 6.9 Hz), 2.16 (3H, s), 2.15 (3H, s), 1.68-1.58 (2H, m), 0.95 (3H, t, J = 7.6 Hz) |

TABLE 23

| Compound No. | Structure | Physicochemical data |
|---|---|---|
| 2-7 | 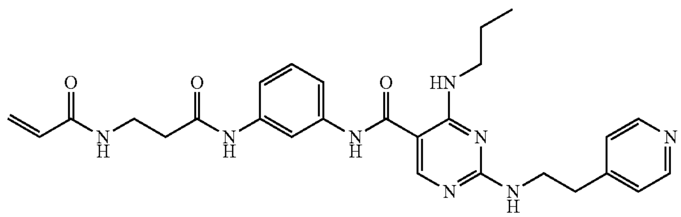 [SMILES: C=CC(=O)NCCC(=O)Nc1cccc(NC(=O)c2cnc(NCCc3ccncc3)nc2NCCC)c1] | $^1$H-NMR (CD$_3$OD) δ: 8.41-8.39 (3H, m), 7.91 (1H, s), 7.31-7.24 (5H, m), 6.23-6.19 (2H, m), 5.64 (1H, dd, J = 7.3, 4.6 Hz), 3.68 (2H, t, J = 6.9 Hz), 3.59 (2H, t, J = 6.6 Hz), 3.45 (2H, s), 2.99 (2H, t, J = 6.9 Hz), 2.69-2.60 (2H, m), 1.68-1.63 (2H, m), 0.99 (3H, t, J = 7.6 Hz) |
| 2-8 | 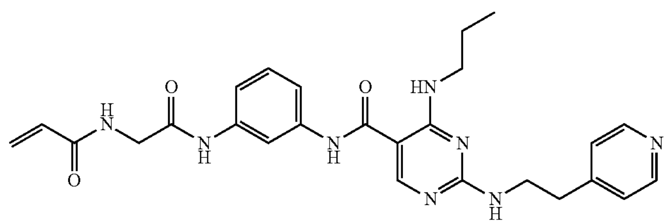 | MS m/z [M + H]: 489.3 |
| 2-9 | 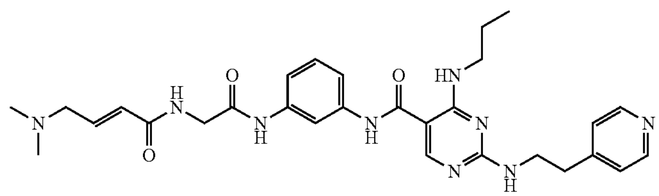 [SMILES: CCCNc1nc(NCCc2ccncc2)ncc1C(=O)Nc1cccc(NC(=O)CNC(=O)/C=C/CN(C)C)c1] | $^1$H-NMR (CD$_3$OD) δ: 8.42-8.39 (3H, m), 7.91-7.90 (1H, m), 7.34-7.22 (5H, m), 6.81 (1H, dt, J = 15.9, 6.6 Hz), 6.19 (1H, d, J = 15.9 Hz), 4.10-4.07 (2H, m), 3.68 (2H, t, J = 7.3 Hz), 3.47-3.43 (2H, m), 3.14 (2H, d, J = 6.6 Hz), 2.99 (2H, t, J = 6.9 Hz), 2.28 (6H, s), 1.67-1.62 (2H, m), 0.99 (3H, t, J = 7.3 Hz) |
| 2-10 | 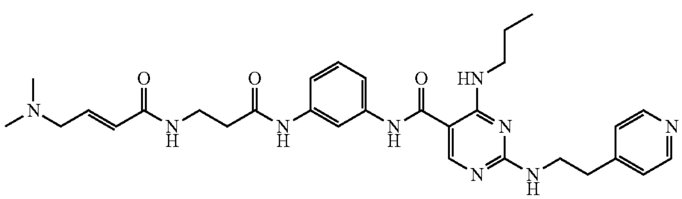 [SMILES: CCCNc1nc(NCCc2ccncc2)ncc1C(=O)Nc1cccc(NC(=O)CCNC(=O)/C=C/CN(C)C)c1] | $^1$H-NMR (CD$_3$OD) δ: 8.42-8.39 (3H, m), 7.92-7.89 (1H, m), 7.34-7.08 (5H, m), 6.78-6.73 (1H, m), 6.08 (1H, d, J = 15.2 Hz), 3.68 (2H, t, J = 6.9 Hz), 3.59 (2H, d, J = 6.6 Hz), 3.49-3.46 (2H, m), 3.09 (2H, d, J = 6.6 Hz), 2.98 (2H, t, J = 6.9 Hz), 2.62 (2H, t, J = 6.9 Hz), 2.24 (6H, s), 1.67-1.62 (2H, m), 0.98 (3H, t, J = 7.6 Hz) |
| 2-11 | 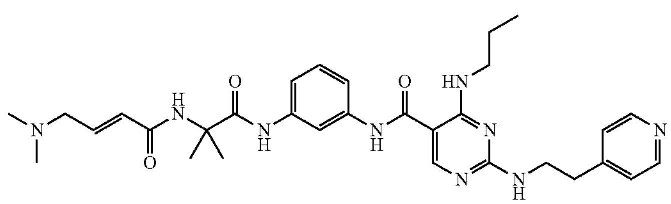 [SMILES: CCCNc1nc(NCCc2ccncc2)ncc1C(=O)Nc1cccc(NC(=O)C(C)(C)NC(=O)/C=C/CN(C)C)c1] | $^1$H-NMR (CDCl$_3$) δ: 9.55 (1H, brs), 8.68 (1H, brs), 8.53 (2H, d, J = 4.6 Hz), 8.25 (1H, brs), 7.80 (1H, brs), 7.70 (1H, brs), 7.31-7.22 (5H, m), 6.90-6.87 (1H, m), 6.00 (1H, d, J = 15.2 Hz), 5.94 (1H, brs), 5.26 (1H, brs), 3.71-3.69 (2H, m), 3.49-3.44 (2H, m), 3.07 (2H, d, J = 5.9 Hz), 2.95-2.90 (2H, m), 2.26 (6H, s), 1.67 (6H, s), 1.64-1.63 (2H, m), 0.98 (3H, t, J = 7.6 Hz) |

TABLE 24

| Compound No. | Structure | Physicochemical data |
|---|---|---|
| 2-12 | 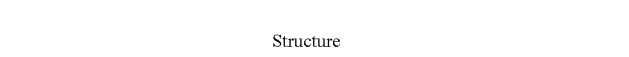 | $^1$H-NMR (CDCl$_3$) δ: 8.89 (1H, s), 8.66 (1H, brs), 8.51 (2H, d, J = 5.9 Hz), 8.22 (1H, brs), 8.08 (1H, brs), 7.79 (1H, s), 7.34 (1H, d, J = 7.9 Hz), 7.26-7.12 (4H, m), 6.96 (1H, dt, J = 15.2, 5.9 Hz), 6.43 (1H, d, J = 15.2 Hz), 5.64 (1H, brs), 5.29 (1H, q, J = 7.0 Hz), 3.67 (2H, q, J = 6.4 Hz), 3.43 (2H, brs), 3.09 (2H, d, J = 4.6 Hz), 3.03 (3H, s), 2.91 (2H, t, J = 7.3 Hz), 2.26 (6H, s), 1.70-1.58 (2H, m), 1.41 (3H, d, J = 7.3 Hz), 0.97 (3H, t, J = 7.6 Hz) |

TABLE 24-continued

| Compound No. | Structure | Physicochemical data |
|---|---|---|
| 2-13 | 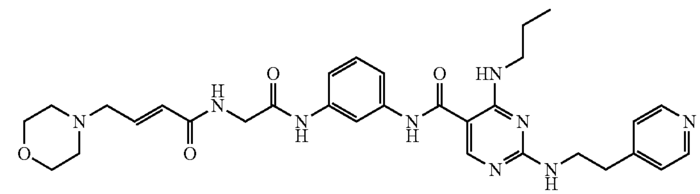 [SMILES: CCCNc1nc(NCCc2ccncc2)ncc1C(=O)Nc1cccc(NC(=O)CNC(=O)/C=C/CN2CCOCC2)c1] | ¹H-NMR (CD₃OD) δ: 8.42-8.39 (3H, m), 7.90 (1H, d, J = 3.3 Hz), 7.34-7.22 (5H, m), 6.80 (1H, dt, J = 15.4, 6.4 Hz), 6.22 (1H, d, J = 15.9 Hz), 4.08 (2H, s), 3.70-3.67 (6H, m), 3.43-3.38 (2H, m), 3.17 (2H, d, J = 6.6 Hz), 2.99 (2H, t, J = 6.9 Hz), 2.49-2.48 (4H, m), 1.67-1.63 (2H, m), 0.99 (3H, t, J = 7.3 Hz) |
| 2-14 | 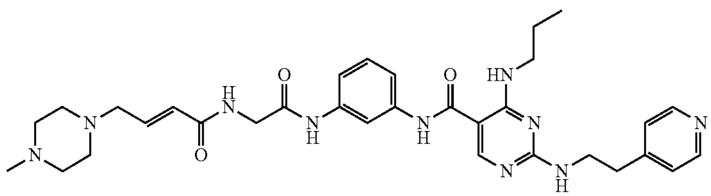 [SMILES: CCCNc1nc(NCCc2ccncc2)ncc1C(=O)Nc1cccc(NC(=O)CNC(=O)/C=C/CN2CCN(C)CC2)c1] | ¹H-NMR (CDCl₃) δ: 9.29 (1H, brs), 8.67 (2H, brs), 8.48-8.45 (2H, m), 8.38 (1H, s), 7.66 (1H, s), 7.37-7.18 (5H, m), 6.84-6.82 (1H, m), 6.01 (1H, d, J = 15.9 Hz), 5.78 (1H, brs), 5.36 (1H, brs), 4.08 (2H, brs), 3.66 (2H, brs), 3.41 (2H, brs), 3.07-3.06 (2H, m), 2.91-2.87 (2H, m), 2.45-2.41 (4H, m), 2.25 (3H, s), 1.99-1.96 (4H, m), 1.63 (2H, brs), 0.96-0.90 (3H, m) |
| 2-15 | 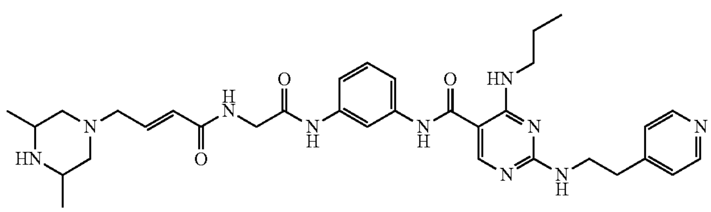 [SMILES: CCCNc1nc(NCCc2ccncc2)ncc1C(=O)Nc1cccc(NC(=O)CNC(=O)/C=C/CN2CC(C)NC(C)C2)c1] | ¹H-NMR (CD₃OD) δ: 8.41-8.40 (3H, m), 7.91-7.90 (1H, m), 7.34-7.22 (5H, m), 6.81 (1H, dt, J = 15.6, 6.4 Hz), 6.21 (1H, d, J = 15.9 Hz), 4.08 (2H, s), 3.70-3.61 (2H, m), 3.48-3.41 (2H, m), 3.16 (2H, d, J = 6.4 Hz), 2.94-2.87 (6H, m), 1.71-1.59 (4H, m), 1.06 (6H, d, J = 6.6 Hz), 0.99 (3H, t, J = 7.3 Hz) |

TABLE 25

| Compound No. | Structure | Physicochemical data |
|---|---|---|
| 2-16 | 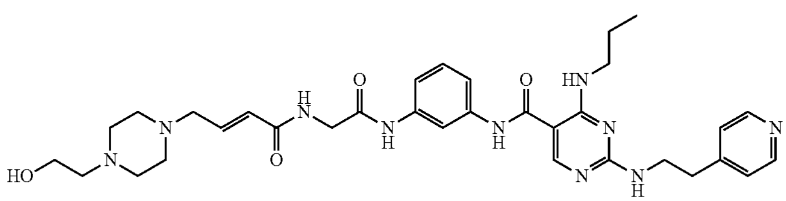 [SMILES: CCCNc1nc(NCCc2ccncc2)ncc1C(=O)Nc1cccc(NC(=O)CNC(=O)/C=C/CN2CCN(CCO)CC2)c1] | ¹H-NMR (CD₃OD) δ: 8.42-8.40 (3H, m), 7.91-7.88 (1H, m), 7.32-7.28 (5H, m), 6.83-6.78 (1H, m), 6.21 (1H, d, J = 15.2 Hz), 4.07-4.06 (2H, m), 3.65-3.60 (4H, m), 3.44 (2H, brs), 3.19-3.17 (2H, m), 3.01-2.97 (2H, m), 2.88-2.54 (10H, m), 1.66-1.63 (2H, m), 0.99 (3H, t, J = 14.5 Hz) |
| 2-17 | 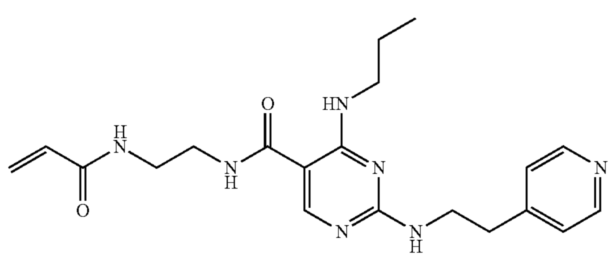 [SMILES: C=CC(=O)NCCNC(=O)c1cnc(NCCc2ccncc2)nc1NCCC] | ¹H-NMR (CDCl₃) δ: 8.75 (1H, brs), 8.50 (2H, dd, J = 4.3, 1.7 Hz), 7.99 (1H, brs), 7.15 (3H, d, J = 5.9 Hz), 6.79 (1H, brs), 6.29 (1H, dd, J = 17.0, 2.0 Hz), 6.11 (1H, dd, J = 17.0, 10.0 Hz), 5.81 (1H, brs), 5.64 (1H, dd, J = 10.0, 2.0 Hz), 3.67 (2H, q, J = 6.6 Hz), 3.54 (4H, brs), 3.48-3.38 (2H, m), 2.91 (2H, t, J = 6.9 Hz), 1.70-1.58 (2H, m), 0.98 (3H, t, J = 7.3 Hz) |
| 2-18 | 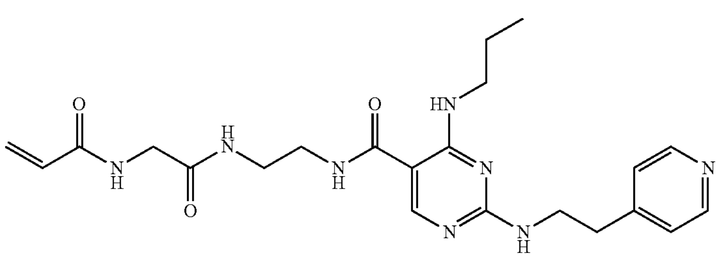 [SMILES: C=CC(=O)NCC(=O)NCCNC(=O)c1cnc(NCCc2ccncc2)nc1NCCC] | ¹H-NMR (CDCl₃ + CD₃OD) δ: 8.76 (1H, brs), 8.48 (2H, d, J = 5.9 Hz), 8.15 (1H, s), 7.51 (1H, brs), 7.31 (1H, brs), 7.22 (1H, brs), 7.13 (2H, d, J = 5.9 Hz), 6.31-6.11 (2H, m), 5.78 (1H, brs), 5.65 (1H, dd, J = 9.9, 2.0 Hz), 3.95 (2H, d, J = 5.3 Hz), 3.66 (2H, q, J = 6.9 Hz), 3.46-3.39 (4H, m), 2.90 (2H, t, J = 6.9 Hz), 2.06-2.04 (2H, m), 1.69-1.57 (2H, m), 0.97 (3H, t, J = 7.3 Hz) |

TABLE 25-continued

| Compound No. | Structure | Physicochemical data |
|---|---|---|
| 2-19 | 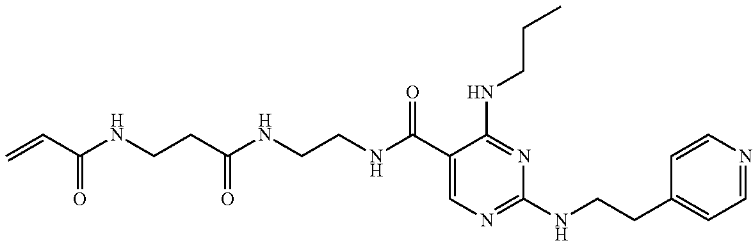 [SMILES: C=CC(=O)NCCC(=O)NCCNC(=O)c1cnc(NCCc2ccncc2)nc1NCCC] | ¹H-NMR (CDCl₃ + CD₃OD) δ: 8.79 (1H, brs), 8.49 (2H, d, J = 5.9 Hz), 8.16 (1H, s), 7.36 (1H, brs), 7.15 (3H, t, J = 5.9 Hz), 6.96 (1H, brs), 6.25-6.02 (2H, m), 5.81 (1H, brs), 5.58 (1H, d, J = 9.9 Hz), 3.68 (2H, d, J = 6.9 Hz), 3.57 (2H, d, J = 5.3 Hz), 3.51-3.38 (4H, m), 2.92 (2H, t, J = 6.9 Hz), 2.46 (2H, d, J = 5.3 Hz), 2.13 (2H, s), 1.68-1.60 (2H, m), 0.98 (3H, t, J = 7.3 Hz) |
| 2-20 | 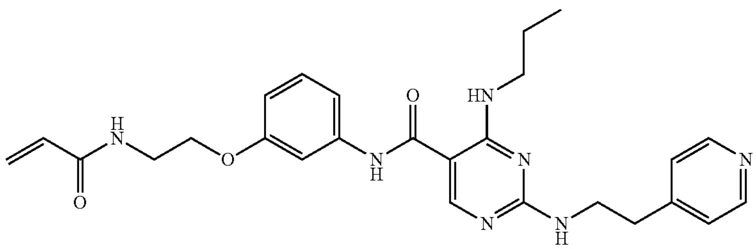 [SMILES: C=CC(=O)NCCOc1cccc(NC(=O)c2cnc(NCCc3ccncc3)nc2NCCC)c1] | ¹H-NMR (CDCl₃) δ: 8.64 (1H, brs), 8.52 (3H, d, J = 5.9 Hz), 8.20 (1H, brs), 7.76 (1H, brs), 7.29-7.23 (3H, m), 7.16 (1H, d, J = 5.9 Hz), 6.98 (1H, d, J = 7.9 Hz), 6.66 (1H, d, J = 8.6 Hz), 6.29-6.14 (2H, m), 5.67 (1H, d, J = 9.9 Hz), 5.41 (1H, brs), 4.09 (2H, t, J = 5.0 Hz), 3.78-3.67 (4H, m), 3.47-3.44 (2H, m), 2.93 (2H, t, J = 6.9 Hz), 1.71-1.64 (2H, m), 0.99 (3H, t, J = 7.6 Hz) |

TABLE 26

| Compound No. | Structure | Physicochemical data |
|---|---|---|
| 2-21 | 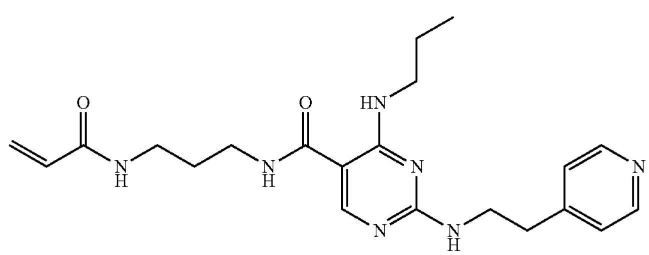 [SMILES: C=CC(=O)NCCCNC(=O)c1cnc(NCCc2ccncc2)nc1NCCC] | ¹H-NMR (CDCl₃ + CD₃OD) δ: 8.79 (1H, brs), 8.51 (2H, d, J = 5.9 Hz), 8.20 (1H, s), 7.14 (2H, d, J = 5.9 Hz), 7.13 (1H, brs), 6.37 (1H, brs), 6.34-6.08 (2H, m), 5.67 (1H, d, J = 9.9 Hz), 5.58 (1H, brs), 3.68 (2H, q, J = 6.9 Hz), 3.45-3.38 (4H, m), 2.92 (2H, t, J = 6.9 Hz), 2.04 (2H, t, J = 3.0 Hz), 1.77-1.59 (4H, m), 0.99 (3H, t, J = 7.3 Hz) |
| 2-23 | 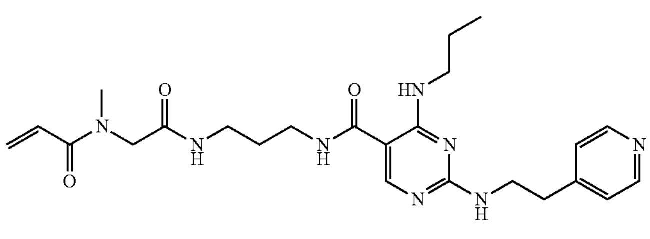 [SMILES: C=CC(=O)N(C)CC(=O)NCCCNC(=O)c1cnc(NCCc2ccncc2)nc1NCCC] | ¹H-NMR (CDCl₃) δ: 8.51 (2H, d, J = 5.9 Hz), 8.20 (1H, brs), 7.15 (2H, d, J = 5.9 Hz), 6.63 (1H, dd, J = 16.5, 10.6 Hz), 6.37 (1H, dd, J = 16.8, 1.7 Hz), 5.77 (1H, dd, J = 10.6, 2.0 Hz), 4.06 (2H, s), 3.67 (2H, q, J = 6.6 Hz), 3.46-3.28 (6H, m), 3.21 (3H, s), 2.92 (2H, t, J = 6.9 Hz), 1.74-1.60 (4H, m), 0.98 (3H, t, J = 7.6 Hz) |
| 2-24 | 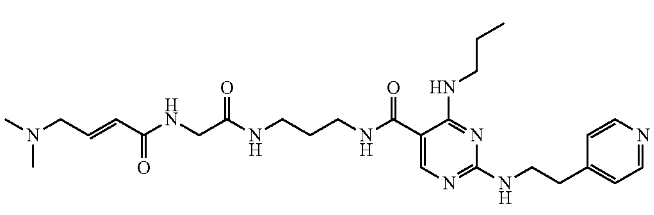 [SMILES: CCCNc1nc(NCCc2ccncc2)ncc1C(=O)NCCCNC(=O)CNC(=O)/C=C/CN(C)C] | ¹H-NMR (CDCl₃) δ: 8.78 (1H, brs), 8.51 (2H, d, J = 5.9 Hz), 8.21 (1H, s), 7.15 (2H, d, J = 5.9 Hz), 7.05 (2H, brs), 6.92-6.81 (1H, m), 6.73 (1H, brs), 6.04 (1H, d, J = 15.2 Hz), 5.41 (1H, brs), 4.00 (2H, d, J = 5.3 Hz), 3.72-3.68 (2H, m), 3.50-3.32 (6H, m), 3.06 (2H, d, J = 5.9 Hz), 2.92 (2H, t, J = 7.3 Hz), 2.24 (6H, s), 1.90 (2H, brs), 1.73-1.59 (2H, m), 0.98 (3H, t, J = 7.3 Hz) |

TABLE 26-continued

| Compound No. | Structure | Physicochemical data |
|---|---|---|
| 2-25 | 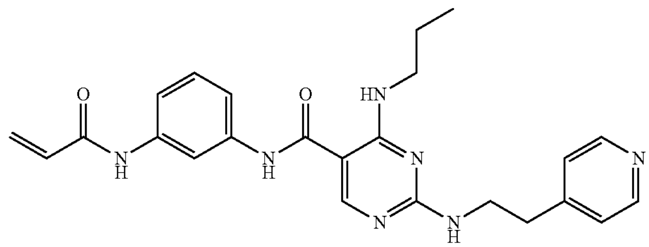 [SMILES: C=CC(=O)Nc1cccc(NC(=O)c2cnc(NCCc3ccncc3)nc2NCCC)c1] | ¹H-NMR (CD₃OD) δ: 8.93-8.87 (1H, m), 8.42 (2H, dd, J = 3.6, 1.2 Hz), 8.40 (1H, s), 8.00 (1H, s), 7.91 (1H, s), 7.42-7.13 (7H, m), 6.44 (1H, dd, J = 12.6, 7.5 Hz), 6.36 (1H, dd, J = 12.6, 1.5 Hz), 5.77 (1H, dd, J = 7.2, 1.5 Hz), 3.70 (2H, t, J = 5.1 Hz), 3.56-3.38 (2H, m), 3.00 (2H, t, J = 5.1 Hz), 1.74-1.56 (2H, m), 1.00 (3H, t, J = 5.7 Hz) |

TABLE 27

| Compound No. | Structure | Physicochemical data |
|---|---|---|
| 2-26 | 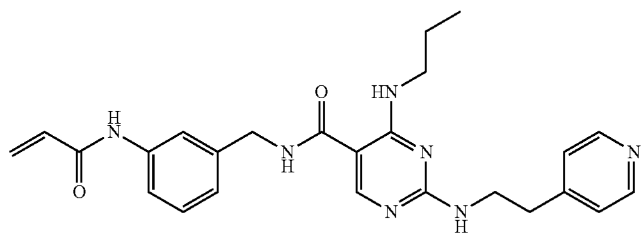 [SMILES: C=CC(=O)Nc1cccc(CNC(=O)c2cnc(NCCc3ccncc3)nc2NCCC)c1] | ¹H-NMR (DMSO-d₆) δ: 10.11 (1H, s), 8.98-8.84 (1H, m), 8.76-8.62 (1H, m), 8.45 (2H, dd, J = 4.5, 1.8 Hz), 8.42 (1H, s), 7.59 (1H, d, J = 8.1 Hz), 7.53 (1H, s), 7.34-7.21 (4H, m), 6.98 (1H, d, J = 7.8 Hz), 6.41 (1H, dd, J = 16.8, 9.9 Hz), 6.25 (1H, dd, J = 17.1, 2.1 Hz), 5.73 (1H, dd, J = 9.9, 2.1 Hz), 4.37 (2H, d, J = 4.8 Hz), 3.60-3.41 (2H, m), 3.44-3.26 (2H, m), 2.86 (2H, t, J = 7.2 Hz), 0.88 (3H, t, J = 7.5 Hz) |
| 2-27 | 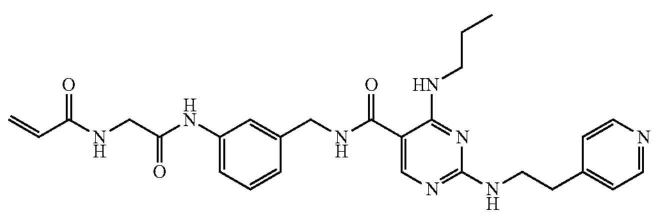 [SMILES: C=CC(=O)NCC(=O)Nc1cccc(CNC(=O)c2cnc(NCCc3ccncc3)nc2NCCC)c1] | MS m/z (M + H): 517.2 |
| 2-28 | 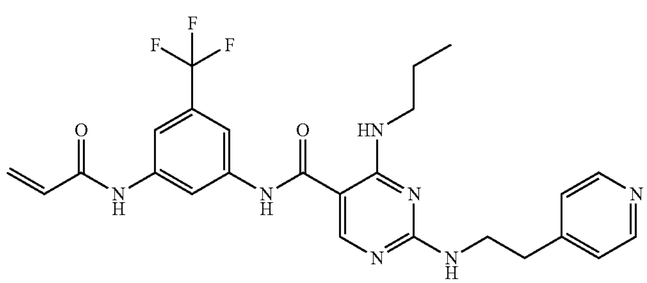 [SMILES: C=CC(=O)Nc1cc(NC(=O)c2cnc(NCCc3ccncc3)nc2NCCC)cc(C(F)(F)F)c1] | ¹H-NMR (CD₃OD) δ: 8.47-8.37 (3H, m), 8.23 (1H, s), 8.28-8.10 (1H, m), 7.78 (1H, s), 7.71 (1H, s), 7.35 (2H, d, J = 5.9 Hz), 6.50-6.34 (2H, m), 5.81 (1H, dd, J = 8.4, 3.5 Hz), 3.70 (2H, t, J = 6.9 Hz), 3.53-3.41 (2H, m), 3.00 (2H, t, J = 7.1 Hz), 1.74-1.56 (2H, m), 1.00 (3H, t, J = 7.3 Hz) |
| 2-29 | 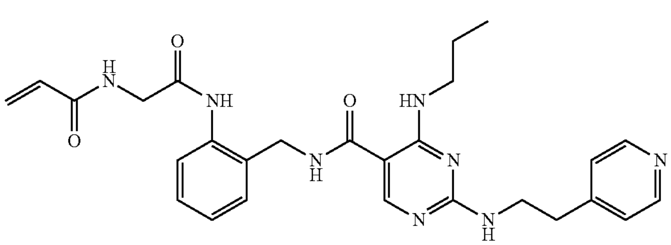 [SMILES: C=CC(=O)NCC(=O)Nc1ccccc1CNC(=O)c1cnc(NCCc2ccncc2)nc1NCCC] | ¹H-NMR (CD₃OD) δ: 8.40 (2H, dd, J = 4.6, 1.7 Hz), 8.21 (1H, s), 7.64 (1H, dd, J = 8.3, 0.9 Hz), 7.39-7.16 (5H, m), 6.33 (1H, dd, J = 17.1, 9.6 Hz), 6.26 (1H, dd, J = 16.8, 2.3 Hz), 5.69 (1H, dd, J = 9.6, 2.3 Hz), 4.64-4.56 (1H, m), 4.38 (2H, s), 4.13 (2H, s), 3.65 (2H, t, J = 7.1 Hz), 3.48-3.36 (2H, m), 3.34 (3H, s), 2.96 (2H, t, J = 7.1 Hz), 1.71-1.56 (2H, m), 0.96 (3H, J = 7.8 Hz) |

Example 7

[Formula 79]

1

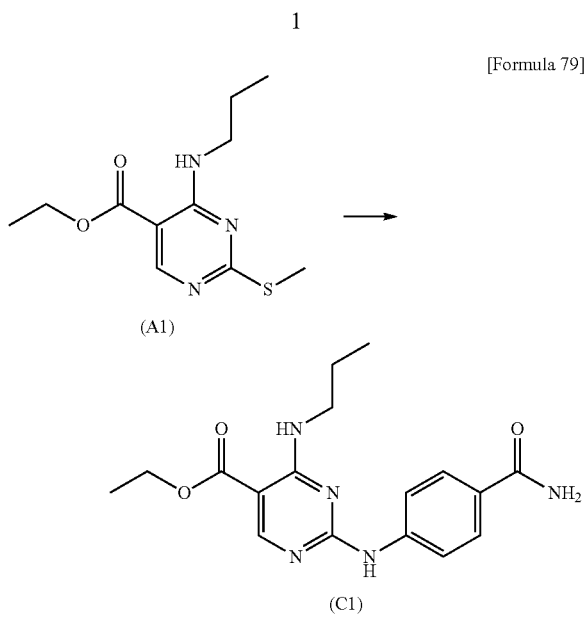

To a solution of 2-(methylthio)-4-(propylamino)pyrimidine-5-carboxylic acid ethyl ester (A1, 7.0 g) in chloroform (100 mL), meta-chloroperbenzoic acid (70 to 75% wt, 13.5 g) was added under ice cooling, and the mixture was stirred at room temperature for 30 minutes. The reaction mixture was cooled on ice, and then saturated aqueous sodium hydrogencarbonate and chloroform were added to the mixture. The organic layer was separated, and the aqueous layer was extracted with chloroform. The organic layer and the extract were combined, washed with saturated aqueous sodium chloride, and then dried over anhydrous sodium sulfate, and the solvent was evaporated under reduced pressure. To a solution of the obtained residue in N-methylpyrrolidone (100 mL), 4-aminobenzamide (5.3 g) and (1S)-(+)-10-camphorsulfonic acid (19.1 g) were added at room temperature, and the mixture was stirred at 110° C. for 3 hours. The reaction mixture was cooled to room temperature, and then poured into ice water. The solid matter was taken by filtration, washed with water, and then dried under reduced pressure to obtain ethyl 2-((4-carbamoylphenyl)amino)-4-(propylamino)pyrimidine-5-carboxylate (C1, 8.1 g) as white solid.

MS m/z (M+H): 344.2

2

[Formula 80]

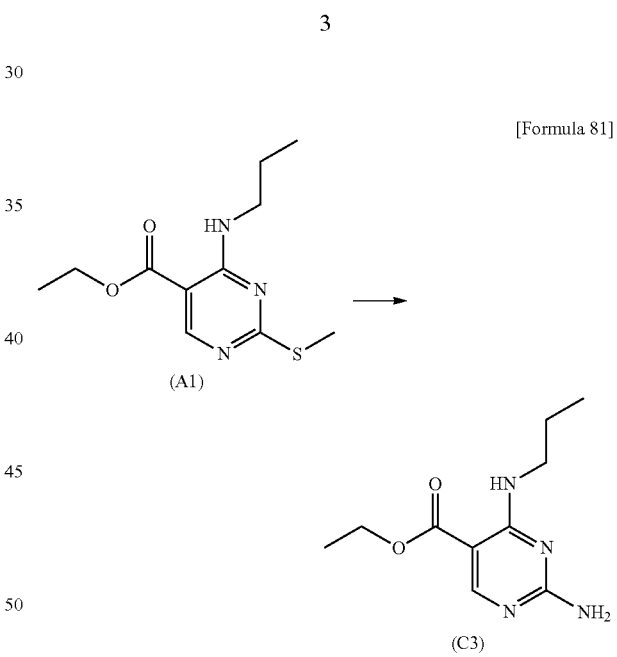

To a solution of ethyl 2-((4-carbamoylphenyl)amino)-4-(propylamino)pyrimidine-5-carboxylate (C1, 8.0 g) in tetrahydrofuran (240 mL) and methanol (240 mL), water (40 mL) and 5.0 mol/L aqueous sodium hydroxide (48 mL) were added at room temperature, and the mixture was stirred at 60° C. for 3 hours. The reaction mixture was cooled on ice, then 12 mol/L aqueous hydrochloric acid was added to the mixture until pH of the mixture became 2, and the reaction mixture was poured into ice water (2000 mL). The solid matter was taken by filtration, washed with water, and then dried under reduced pressure to obtain 2-((4-carbamoylphenyl)amino)-4-(propylamino)pyrimidine-5-carboxylic acid (C2, 4.0 g) as white solid.

3

[Formula 81]

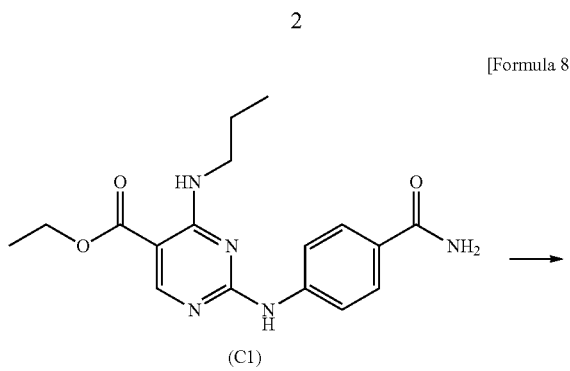

To a solution of 2-(methylthio)-4-(propylamino)pyrimidine-5-carboxylic acid ethyl ester (A1, 11.7 g) in N-methylpyrrolidone (90 mL), meta-chloroperbenzoic acid (70 to 75% wt, 20.8 g) was added under ice cooling, and the mixture was stirred at room temperature for 40 minutes. To the reaction mixture, N,N-diisopropylethylamine (23.9 mL) and 10% aqueous ammonia (60.0 mL) were added at room temperature, and the mixture was stirred at the same temperature for 1 hour. The reaction mixture was poured into water (400 mL). The solid matter was taken by filtration, washed with water, and then dried under reduced pressure to obtain ethyl 2-amino-4-(propylamino)pyrimidine-5-carboxylate (C3, 8.0 g).

MS m/z (M+H): 225.1

4

[Formula 82]

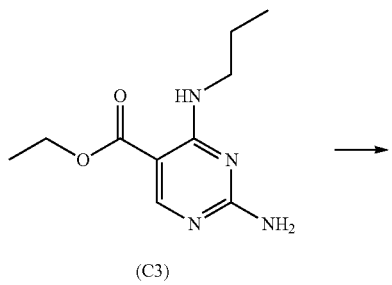
(C3)

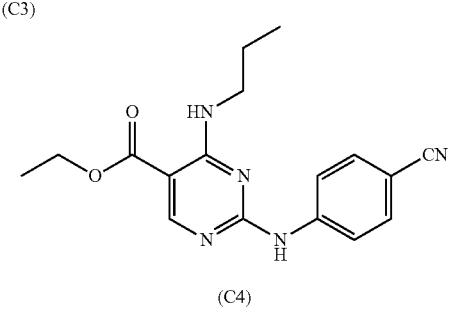
(C4)

To a solution of tris(dibenzylideneacetone)dipalladium(0) (1.14 g) and 4,5'-bis(diphenylphosphino)-9,9'-dimethylxanthene (1.45 g) in 1,4-dioxane (150 mL), ethyl 2-amino-4-(propylamino)pyrimidine-5-carboxylate (C3, 5.61 g), 4-bromobenzonitrile (6.83 g) and cesium carbonate (24.40 g) were added at room temperature, and the mixture was stirred at 100° C. for 11 hours and 30 minutes under a nitrogen atmosphere. The reaction mixture was cooled to room temperature, then the insoluble matter was removed by filtration through Cerite, and then 1.0 mol/L aqueous hydrochloric acid and ethyl acetate were added. The organic layer was separated, washed successively with 1.0 mol/L aqueous hydrochloric acid, saturated aqueous sodium hydrogencarbonate and saturated aqueous sodium chloride, and then dried over anhydrous magnesium sulfate, and the solvent was evaporated under reduced pressure. To the obtained residue, ethyl acetate was added, and the solid matter was taken by filtration to obtain ethyl 2-((4-cyanophenyl)amino)-4-(propylamino)pyrimidine-5-carboxylate (C4, 2.68 g).

MS m/z (M+H): 326.1

5

[Formula 83]

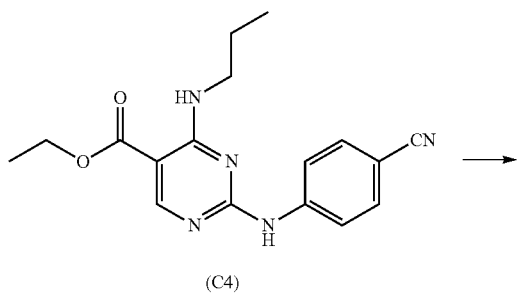
(C4)

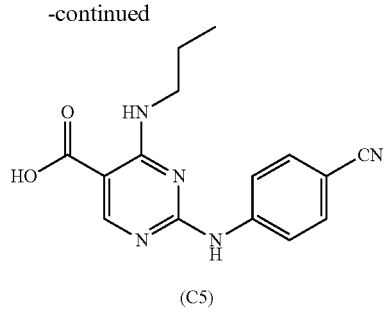
(C5)

To a solution of ethyl 2-((4-cyanophenyl)amino)-4-(propylamino)pyrimidine-5-carboxylate (C4, 0.90 g) in ethanol (10 mL) and tetrahydrofuran (5 mL), 2.0 mol/L aqueous sodium hydroxide (2.8 mL) was added at room temperature, and the mixture was stirred at 50° C. for 5 hours. The reaction mixture was cooled to room temperature, and then 1.0 mol/L aqueous hydrochloric acid was added to the reaction mixture until the mixture became acidic. The solid matter was taken by filtration, washed with water, and then dried under reduced pressure to obtain 2-((4-cyanophenyl)amino)-4-(propylamino)pyrimidine-5-carboxylic acid (C5, 738 mg).

MS m/z (M+H): 298.2

6

[Formula 84]

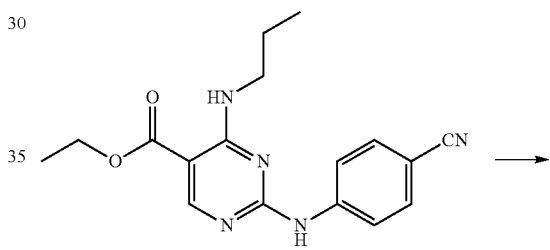
(C4)

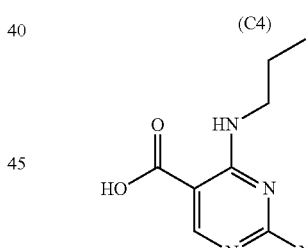
(C5)

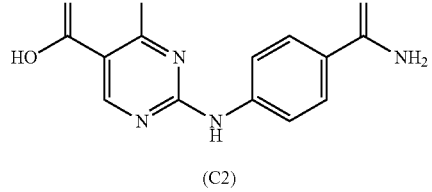
(C2)

To a solution of ethyl 2-((4-cyanophenyl)amino)-4-(propylamino)pyrimidine-5-carboxylate (C4, 800 mg) in tetrahydrofuran (25 mL) and methanol (25 mL), water (2 mL) and 4.0 mol/L aqueous sodium hydroxide (8 mL) were added at room temperature, and the mixture was stirred at 55° C. for 1 hour and 20 minutes. The reaction mixture was cooled to room temperature, and then 35% aqueous hydrogen peroxide (8 mL) was added to the mixture, and the mixture was stirred at the same temperature for 45 minutes. To the reaction mixture, 3.0 mol/L aqueous hydrochloric acid was added until the reaction mixture was neutralized. The solid matter was taken by filtration, and dried under reduced pressure to obtain 2-((4-carbamoylphenyl)amino)-4-(propylamino)pyrimidine-5-carboxylic acid (C2, 500 mg) as white solid.

MS m/z (M+H): 316.2

7

[Formula 85]

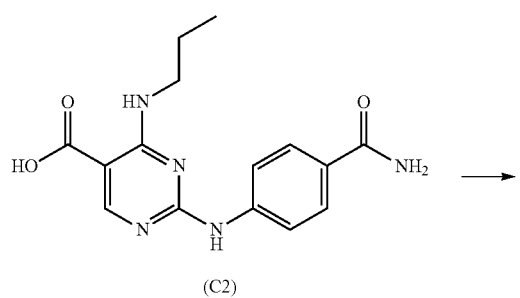

(C2)

To 2-((4-carbamoylphenyl)amino)-4-(propylamino)pyrimidine-5-carboxylic acid (C2, 400 mg), 1-ethyl-3-(3-dimethylaminopropyl)carbodiimide hydrochloride (970 mg) and 1-hydroxybenzotriazole monohydrate (780 mg), N,N-dimethylformamide (5 mL) and N,N-diisopropylethylamine (430 µL) were added at room temperature, and the mixture was stirred at the same temperature for 1 hour. To the reaction mixture, 1,3-phenylenediamine (418 mg) was added at room temperature, and the mixture was stirred at the same temperature for 16 hours. To the reaction mixture, saturated aqueous sodium hydrogencarbonate and ethyl acetate were added. The organic layer was separated, washed successively with water and saturated aqueous sodium chloride, and then dried over anhydrous sodium sulfate, and the solvent was evaporated under reduced pressure. The obtained residue was purified by basic silica gel column chromatography (eluent, 95% ethyl acetate/5% methanol) to obtain N-(3-aminophenyl)-2-((4-carbamoylphenyl)amino)-4-(propylamino)pyrimidine-5-carboxamide (C6, 272 mg) as pale yellow solid.

MS m/z (M+H): 406.2

8

[Formula 86]

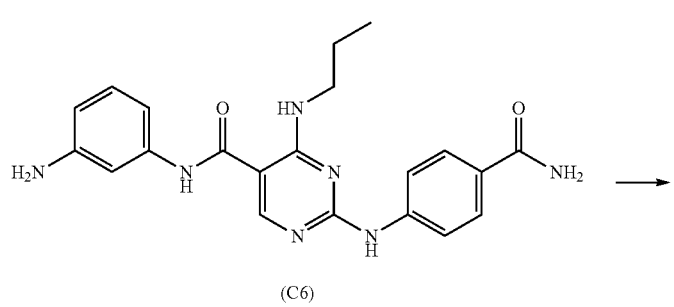

(C6)

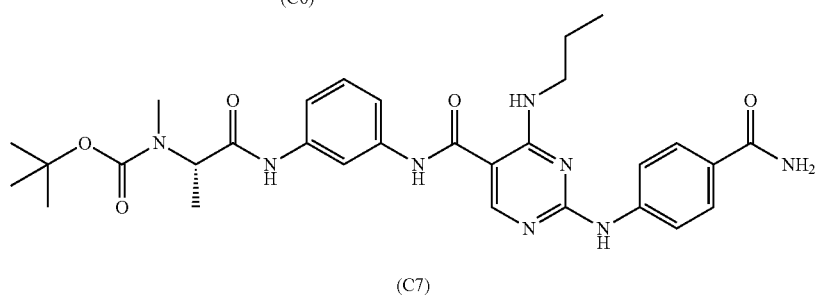

(C7)

-continued

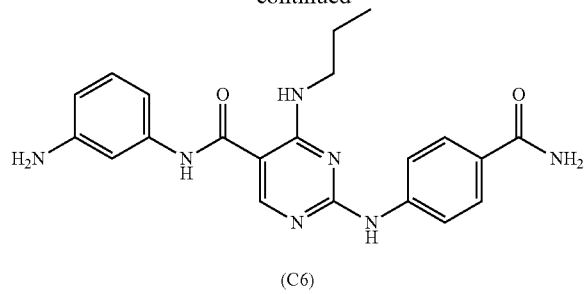

(C6)

To N-(3-aminophenyl)-2-((4-carbamoylphenyl)amino)-4-(propylamino)pyrimidine-5-carboxamide (C6, 272 mg), N-Boc-N-methyl-L-alanine (164 mg), 1-ethyl-3-(3-dimethylaminopropyl)carbodiimide hydrochloride (515 mg) and 1-hydroxybenzotriazole monohydrate (411 mg), N,N-dimethylformamide (5 mL) and N,N-diisopropylethylamine (228 µL) were added at room temperature, and the mixture was stirred at the same temperature for 7 hours. To the reaction mixture, water and ethyl acetate were added. The organic layer was separated, and the aqueous layer was extracted with ethyl acetate. The organic layer and the extract were combined, washed successively with water and saturated aqueous sodium chloride, and then dried over anhydrous sodium sulfate, and the solvent was evaporated under reduced pressure. The obtained residue was purified by basic silica gel column chromatography (eluent, 98 to 95% ethyl acetate in methanol) to obtain (S)-tert-butyl (1-((3-(2-(4-carbamoylphenyl)amino)-4-(propylamino)pyrimidine-5-carboxamido)phenyl)amino)-1-oxopropan-2-yl)(methyl)carbamate (C7, 339 mg) as white solid.

MS m/z (M+H): 591.3

(methyl)carbamate (B9, 323 mg) were added to the mixture at room temperature, and the mixture was stirred at the same temperature for 30 minutes, and then further stirred at 50° C. for 1 hour and 30 minutes. The reaction mixture was cooled to room temperature, and then saturated aqueous sodium hydrogencarbonate and ethyl acetate were added to the mixture. The organic layer was separated, washed successively with water and saturated aqueous sodium chloride, and then dried over anhydrous sodium sulfate, and the solvent was evaporated under reduced pressure. The obtained residue was puri-

9

[Formula 87]

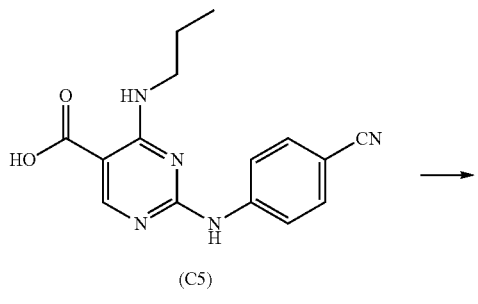

(C5)

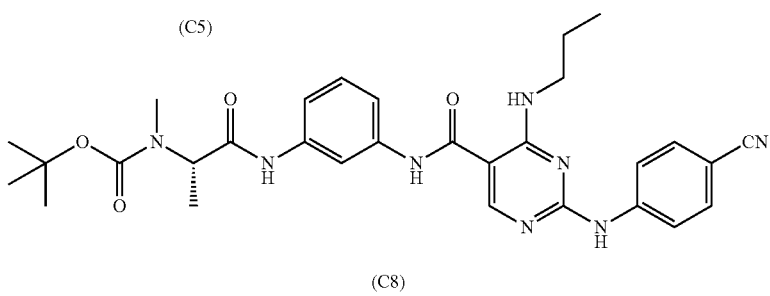

(C8)

To 2-((4-cyanophenyl)amino)-4-(propylamino)pyrimidine-5-carboxylic acid (C5, 297 mg), 1-ethyl-3-(3-dimethylaminopropyl)carbodiimide hydrochloride (383 mg) and 1-hydroxybenzotriazole monohydrate (270 mg), N,N-dimethylformamide (7.5 mL) was added at room temperature, and the mixture was stirred at 50° C. for 1 hour and 20 minutes. The reaction mixture was cooled to room temperature, and then N,N-diisopropylethylamine (697 μL) and (S)-tert-butyl (1-((3-aminophenyl)amino)-1-oxopropan-2-yl)

fied by silica gel column chromatography (eluent, 40 to 10% hexane in ethyl acetate) to obtain (S)-tert-butyl (1-((3-(2-((4-cyanophenyl)amino)-4-(propylamino)pyrimidine-5-carboxamido)phenyl)amino)-1-oxopropan-2-yl)(methyl)carbamate (C8, 325 mg).

MS m/z (M+H): 573.3

10

[Formula 88]

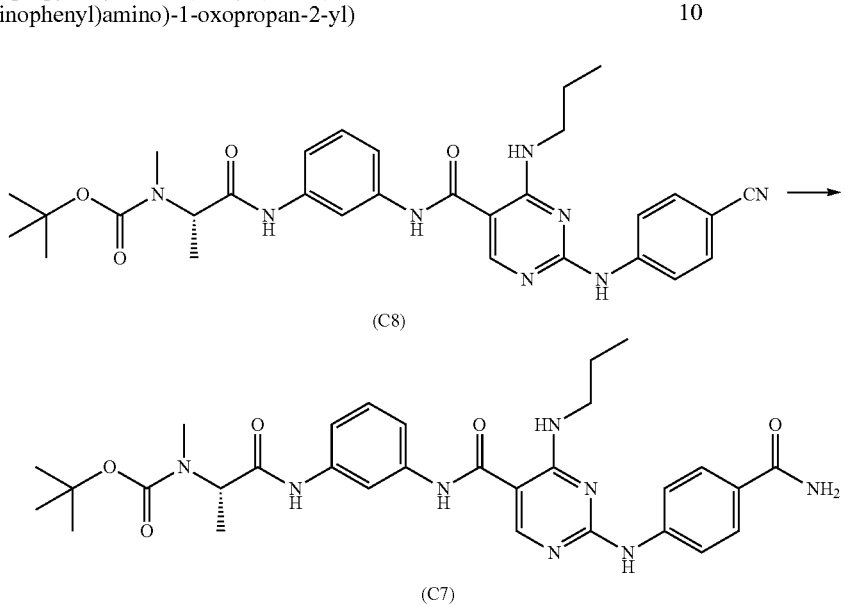

To a solution of (S)-tert-butyl (1-((3-(2-((4-cyanophenyl)amino)-4-(propylamino)pyrimidine-5-carboxamido)phenyl)amino)-1-oxopropan-2-yl)(methyl)carbamate (C8, 173 mg) in ethanol (4 mL) and dimethyl sulfoxide (2 mL), 2.0 mol/L aqueous sodium hydroxide (0.45 mL) and 35% aqueous hydrogen peroxide (87 µL) were added at room temperature, and the mixture was stirred at the same temperature for 1 hour. To the reaction mixture, water (15 mL) was added. The solid matter was taken by filtration, washed successively with water and ethyl acetate, and then dried under reduced pressure to obtain (S)-tert-butyl (1-((3-(2-((4-carbamoylphenyl)amino)-4-(propylamino)pyrimidine-5-carboxamido)phenyl)amino)-1-oxopropan-2-yl)(methyl)carbamate (C7, 102 mg) as white solid.

MS m/z (M+H): 591.3

11

[Formula 89]

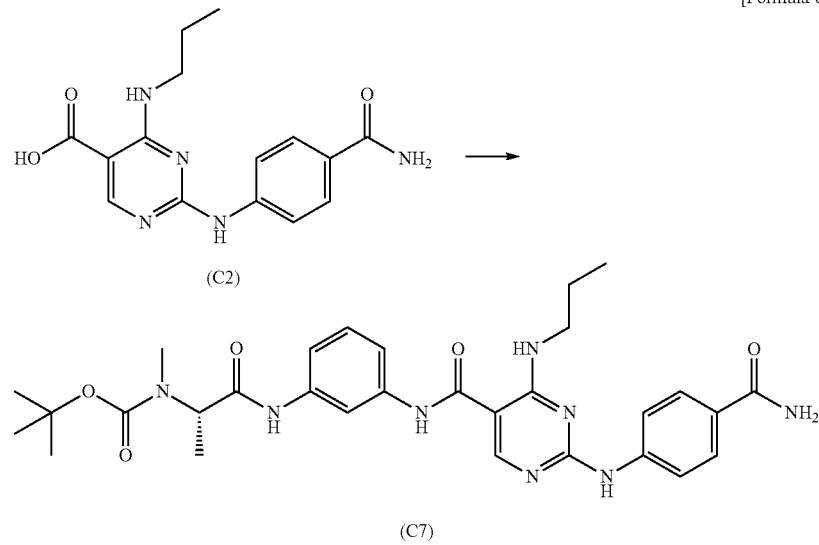

By using 2-((4-carbamoylphenyl)amino)-4-(propylamino)pyrimidine-5-carboxylic acid (C2) and (S)-tert-butyl (1-((3-aminophenyl)amino)-1-oxopropan-2-yl)(methyl)carbamate (B9), (S)-tert-butyl (1-((3-(2-((4-carbamoylphenyl)amino)-4-(propylamino)pyrimidine-5-carboxamido)phenyl)amino)-1-oxopropan-2-yl)(methyl)carbamate (C7) was obtained as white solid in the same manner as that of Example 7, (9).

MS m/z (M+H): 591.3

12

[Formula 90]

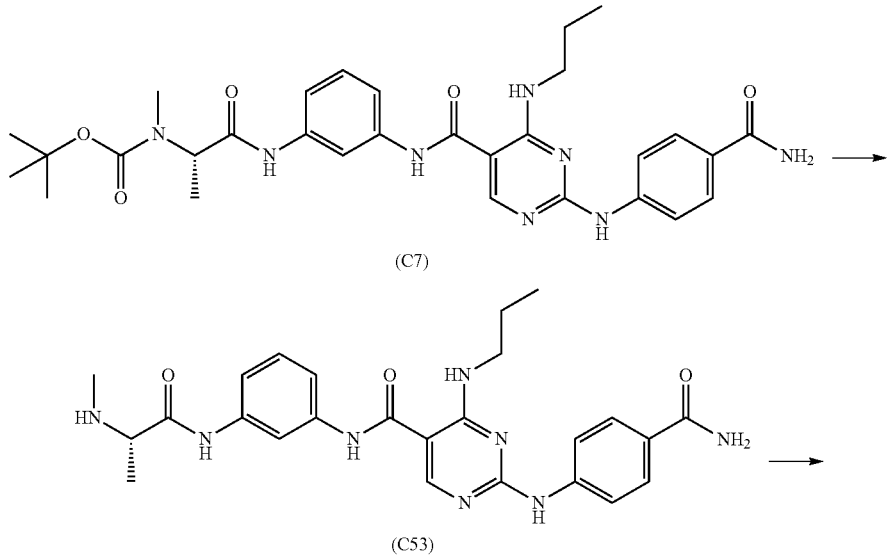

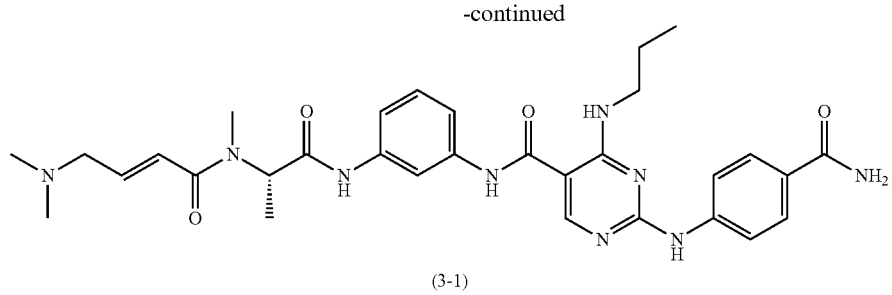

(3-1)

By using (S)-tert-butyl (1-((3-(2-((4-carbamoylphenyl)amino)-4-(propylamino)pyrimidine-5-carboxamido)phenyl)amino)-1-oxopropan-2-yl)(methyl)carbamate (C7), (S,E)-2-((4-carbamoylphenyl)amino)-N-(3-(2-(4-(dimethylamino)-N-methyl-2-butenamido)propanamido)phenyl)-4-(propylamino)pyrimidine-5-carboxamide (3-1) was obtained as white solid in the same manner as that of Example 1, (6) and Example 1, (8).

$^1$H-NMR (DMSO-d$_6$) δ: 10.02 (1H, s), 9.95 (1H, s), 9.88 (1H, s), 8.83 (1H, brs), 8.72 (1H, s), 8.08 (1H, s), 7.90 (2H, d, J=8.6 Hz), 7.86-7.78 (3H, m), 7.36-7.14 (4H, m), 6.70-6.52 (2H, m), 5.14-5.06 (1H, m), 3.52-3.42 (2H, m), 3.08-3.02 (5H, m), 2.15 (6H, s), 1.72-1.58 (2H, m), 1.36 (3H, d, J=6.6 Hz), 0.97 (3H, t, J=7.3 Hz)

Example 8

1

[Formula 91]

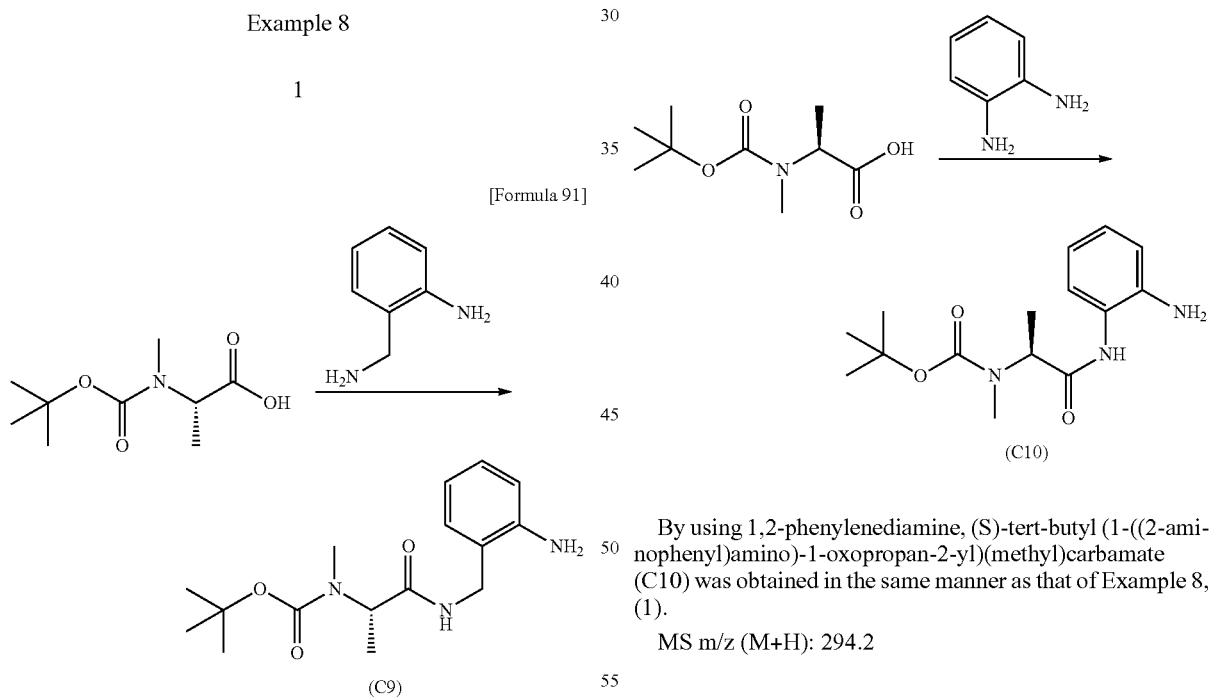

(C9)

To a solution of N-Boc-N-methyl-L-alanine (200 mg), 2-aminobenzylamine (240 mg), 1-ethyl-3-(3-dimethylaminopropyl)carbodiimide hydrochloride (755 mg) and 1-hydroxybenzotriazole monohydrate (603 mg) in N,N-dimethylformamide (4 mL), N,N-diisopropylethylamine (355 µL) was added at room temperature, and the mixture was stirred at the same temperature for 9 hours. To the reaction mixture, water and ethyl acetate were added. The organic layer was separated, and the aqueous layer was extracted with ethyl acetate. The organic layer and the extract were combined, washed successively with water and saturated aqueous sodium chloride, and then dried over anhydrous sodium sulfate, and the solvent was evaporated under reduced pressure. The obtained residue was purified by silica gel column chromatography (eluent, 75 to 50% hexane in ethyl acetate) to obtain oily (S)-tert-butyl (1-((2-aminobenzyl)amino)-1-oxopropan-2-yl)(methyl)carbamate (C9, 47 mg).

MS m/z (M+H): 308.2

2

[Formula 92]

(C10)

By using 1,2-phenylenediamine, (S)-tert-butyl (1-((2-aminophenyl)amino)-1-oxopropan-2-yl)(methyl)carbamate (C10) was obtained in the same manner as that of Example 8, (1).

MS m/z (M+H): 294.2

3

[Formula 93]

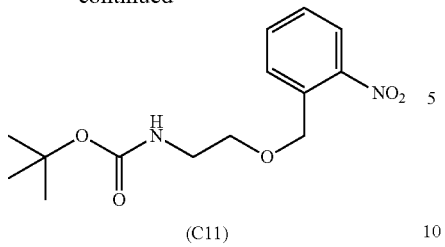

(C11)

To a solution of N-Boc-ethanolamine (477 mg) in tetrahydrofuran (10 mL), sodium hydride (118 mg, 60 wt %) was added under ice cooling, and the mixture was stirred at the same temperature for 1 hour under a nitrogen atmosphere. To the reaction mixture, 2-nitrobenzyl bromide (500 mg) was added under ice cooling, and the mixture was stirred at the same temperature for 1 hour, and then further stirred at room temperature for 4 hours. To the reaction mixture, saturated aqueous sodium hydrogencarbonate and ethyl acetate were added. The organic layer was separated, washed successively with water and saturated aqueous sodium chloride, and then dried over anhydrous sodium sulfate, and the solvent was evaporated under reduced pressure. The obtained residue was purified by silica gel column chromatography (eluent, 80 to 70% hexane in ethyl acetate) to obtain oily tert-butyl (2-((2-nitrobenzyl)oxy)ethyl)carbamate (C11, 154 mg).

4

[Formula 94]

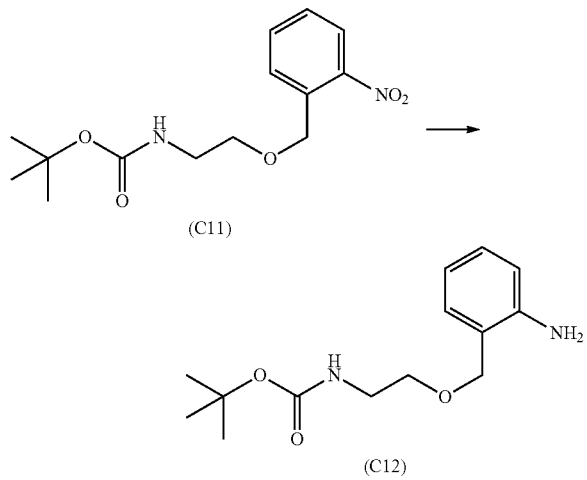

To a solution of tert-butyl (2-((2-nitrobenzyl)oxy)ethyl)carbamate (C11, 154 mg) in ethanol (5 mL) and water (1 mL), iron powder (174 mg) and ammonium chloride (167 mg) were added at room temperature, and the mixture was stirred at 80° C. for 2 hours. The reaction mixture was cooled to room temperature, and then ethyl acetate was added to the reaction mixture. The insoluble matter was removed by filtration through Cerite, and then the solvent was evaporated under reduced pressure. The obtained residue was purified by basic silica gel column chromatography (eluent, 75% hexane/25% ethyl acetate) to obtain oily tert-butyl (2-((2-aminobenzyl)oxy)ethyl)carbamate (C12, 60 mg).

MS m/z (M+H): 267.2

5

[Formula 95]

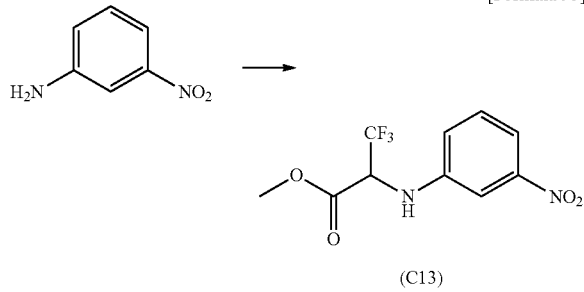

To a solution of methyl trifluoropyruvate (500 mg) and 3-nitroaniline (442 mg) in methylene chloride (32 mL), titanium tetrachloride (350 µL) was added at room temperature, and the mixture was stirred at the same temperature for 20 minutes. To the reaction mixture, sodium triacetoxyborohydride (1.35 g) was added at room temperature, and the mixture was stirred at the same temperature for 2 hours. To the reaction mixture, water and methylene chloride were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 20% hexane in ethyl acetate) to obtain methyl 3,3,3-trifluoro-2-((3-nitrophenyl)amino)propanoate (C13, 391 mg).

$^1$H-NMR (CDCl$_3$) δ: 8.13 (1H, dt), 7.81 (1H, t), 7.59 (1H, t), 7.28-7.23 (1H, m), 3.78 (3H, s)

6

[Formula 96]

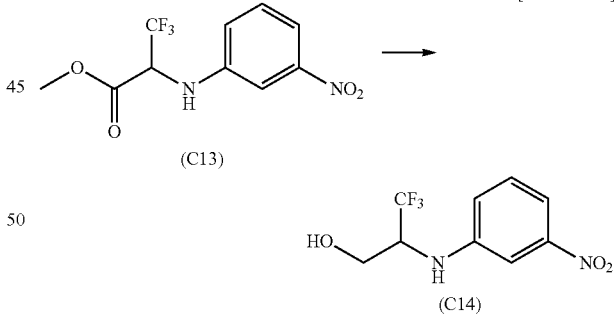

To a solution of methyl 3,3,3-trifluoro-2-((3-nitrophenyl)amino)propanoate (C13, 297 mg) in ethanol (10 mL), sodium borohydride (121 mg) was added at room temperature, and the mixture was stirred at the same temperature for 4 hours. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 50% hexane in ethyl acetate) to obtain 3,3,3-trifluoro-2-((3-nitrophenyl)amino)propan-1-ol (C14, 197 mg).

$^1$H-NMR (CDCl$_3$) δ: 7.65 (1H, dd), 7.55 (1H, t), 7.35 (1H, t), 7.01 (1H, dd), 4.16-3.90 (3H, m)

7

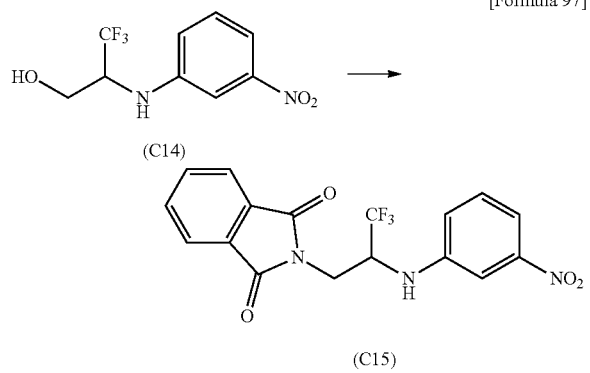

[Formula 97]

(C14)

(C15)

To a solution of 3,3,3-trifluoro-2-((3-nitrophenyl)amino)propan-1-ol (C14, 171 mg), phthalimide (201 mg) and triphenylphosphine (305 mg) in tetrahydrofuran (7 mL), a 40% solution of diethyl azodicarboxylate in toluene (526 μL) was added under ice cooling, and the mixture was stirred at the same temperature for 40 minutes. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 70% hexane in ethyl acetate) to obtain 2-(3,3,3-trifluoro-2-((3-nitrophenyl)amino)propyl)isoindoline-1,3-dione (C15, 209 mg).

$^1$H-NMR (CDCl$_3$) δ: 7.90-7.69 (4H, m), 7.50 (1H, dd), 7.43 (1H, t), 7.22 (1H, t), 6.90 (1H, dd), 4.50-4.35 (1H, m), 4.19-4.00 (2H, m)

8

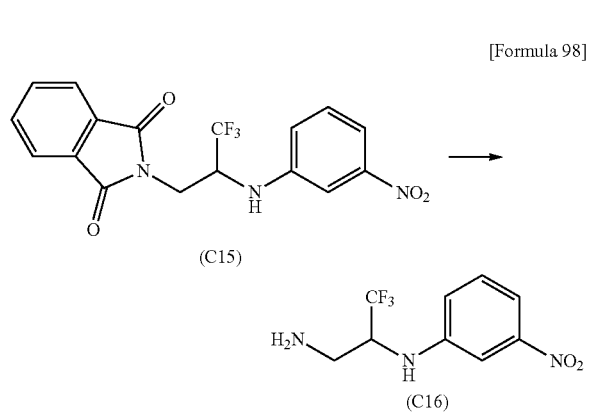

[Formula 98]

(C15)

(C16)

To a solution of 2-(3,3,3-trifluoro-2-((3-nitrophenyl)amino)propyl)isoindoline-1,3-dione (C15, 209 mg) in ethanol (3 mL) and tetrahydrofuran (3 mL), hydrazine monohydrate (132 μL) was added at room temperature, and the mixture was stirred at the same temperature for 19 hours. The insoluble matter was removed by filtration, and then the solvent was evaporated under reduced pressure to obtain 3,3,3-trifluoro-N$^2$-(3-nitrophenyl)propane-1,2-diamine (C16, 106 mg).

9

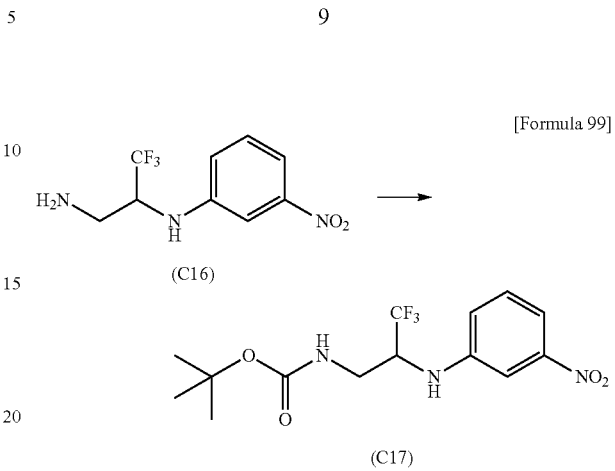

[Formula 99]

(C16)

(C17)

To a solution of 3,3,3-trifluoro-N$^2$-(3-nitrophenyl)propane-1,2-diamine (C16, 106 mg) in tetrahydrofuran (4 mL), triethylamine (90 μL) and di-tert-butyl dicarbonate (140 mg) were added at room temperature, and the mixture was stirred at the same temperature for 4 hours. To the reaction mixture, water and ethyl acetate were added. The organic layer was separated, washed with saturated aqueous sodium chloride, and then dried over anhydrous sodium sulfate, and the solvent was evaporated under reduced pressure to obtain tert-butyl (3,3,3-trifluoro-2-((3-nitrophenyl)amino)propyl)carbamate (C17, 202 mg).

$^1$H-NMR (CDCl$_3$) δ: 7.63 (1H, dd), 7.50 (1H, t), 7.32 (1H, t), 6.96 (1H, dd), 4.98-4.76 (1H, m), 3.68-3.44 (2H, m), 1.55 (9H, s)

10

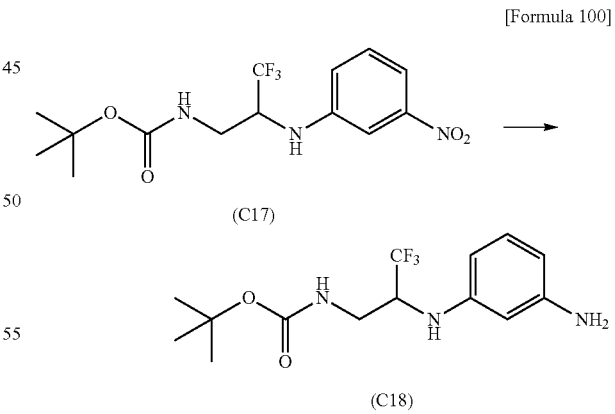

[Formula 100]

(C17)

(C18)

To 10% palladium-carbon (50 mg) and ammonium formate (135 mg), a solution of tert-butyl (3,3,3-trifluoro-2-((3-nitrophenyl)amino)propyl)carbamate (C17, 100 mg) in methanol (2 mL) was added at room temperature, and the mixture was stirred at the same temperature for 3 hours. The insoluble matter was removed by filtration through Cerite, and then the solvent was evaporated under reduced pressure. To the obtained residue, ethyl acetate and water were added.

The organic layer was separated, washed with saturated aqueous sodium chloride, and then dried over anhydrous sodium sulfate, and the solvent was evaporated under reduced pressure to obtain tert-butyl (2-((3-aminophenyl)amino)-3,3,3-trifluoropropyl)carbamate (C18, 45 mg).

MS m/z (M+H): 320.1

11

[Formula 101]

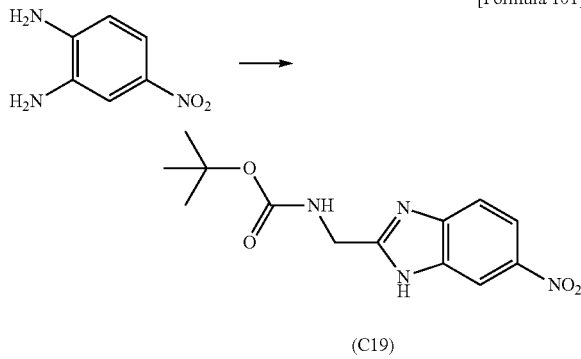

(C19)

To a solution of N-Boc-glycine (571 mg) in tetrahydrofuran (16 mL), isobutyl chloroformate (428 μL) and N-methylmorpholine (358 μL) were added under ice cooling, and the mixture was stirred at the same temperature for 20 minutes. To the reaction mixture, 4-nitro-1,2-phenylenediamine (500 mg) was added under ice cooling, and the mixture was stirred at room temperature for 3 hours and 30 minutes. To the reaction mixture, acetic acid (16 mL) was added, and the mixture was stirred at 70° C. for 3 hours and 30 minutes. The reaction mixture was cooled to room temperature, and then water and ethyl acetate were added to the reaction mixture. The organic layer was separated, washed successively with saturated aqueous sodium hydrogencarbonate and saturated aqueous sodium chloride, and then dried over anhydrous sodium sulfate, and the solvent was evaporated under reduced pressure. The obtained residue was purified by silica gel column chromatography (eluent, 100 to 0% hexane in ethyl acetate) to obtain tert-butyl ((6-nitro-1H-benzo[d]imidazol-2-yl)methyl)carbamate (C19, 782 mg).

MS m/z (M+H): 293.1

12

[Formula 102]

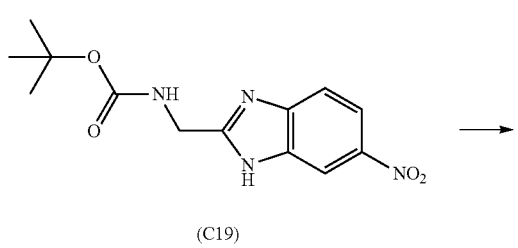

(C19)

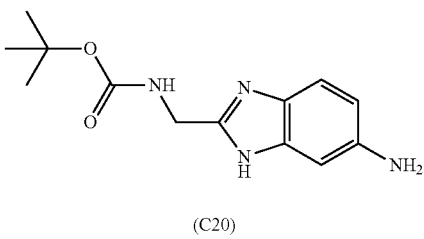

(C20)

To 10% palladium-carbon (50 mg) and ammonium formate (228 mg), a solution of tert-butyl ((6-nitro-1H-benzo[d]imidazol-2-yl)methyl)carbamate (C19, 106 mg) in methanol (4 mL) was added at room temperature, and the mixture was stirred at room temperature for 1 hour and 30 minutes. The insoluble matter was removed by filtration through Cerite, and then the solvent was evaporated under reduced pressure. To the obtained residue, ethyl acetate and water were added. The organic layer was separated, washed with saturated aqueous sodium chloride, and then dried over anhydrous sodium sulfate, and the solvent was evaporated under reduced pressure to obtain tert-butyl ((6-amino-1H-benzo[d]imidazol-2-yl)methyl)carbamate (C20, 100 mg).

MS m/z (M+H): 263.2

13

[Formula 103]

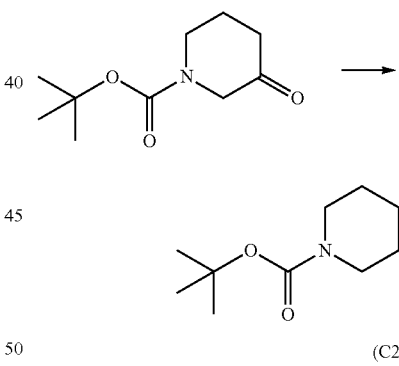

(C21)

To a solution of 1-Boc-3-piperidinone (256 mg) and 3-nitroaniline (190 mg) in methylene chloride (7 mL), sodium triacetoxyborohydride (438 mg) and acetic acid (80 μL) were added at room temperature, and the mixture was stirred at the same temperature for 15 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 50% hexane in ethyl acetate) to obtain tert-butyl 3-((3-nitrophenyl)amino)piperidine-1-carboxylate (C21, 229 mg).

MS m/z (M+H): 322.1

14

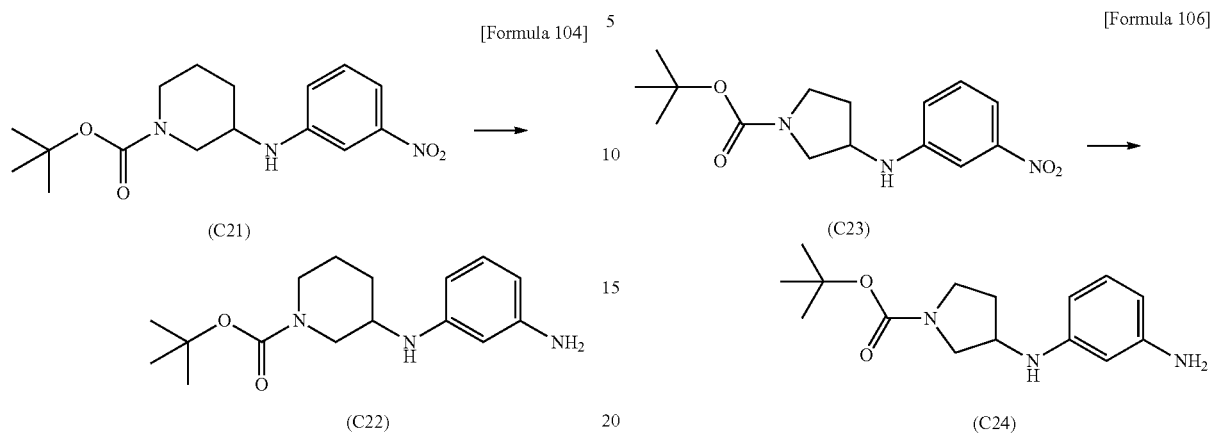

To 10% palladium-carbon (100 mg), a solution of tert-butyl 3-((3-nitrophenyl)amino)piperidine-1-carboxylate (C21, 229 mg) in tetrahydrofuran (10 mL) and methanol (4 mL) was added at room temperature, and the mixture was stirred at room temperature for 1 hour under a hydrogen atmosphere. The insoluble matter was removed by filtration through Cerite, and then the solvent was evaporated under reduced pressure to obtain tert-butyl 3-((3-aminophenyl)amino)piperidine-1-carboxylate (C22, 211 mg).

MS m/z (M+H): 292.2

15

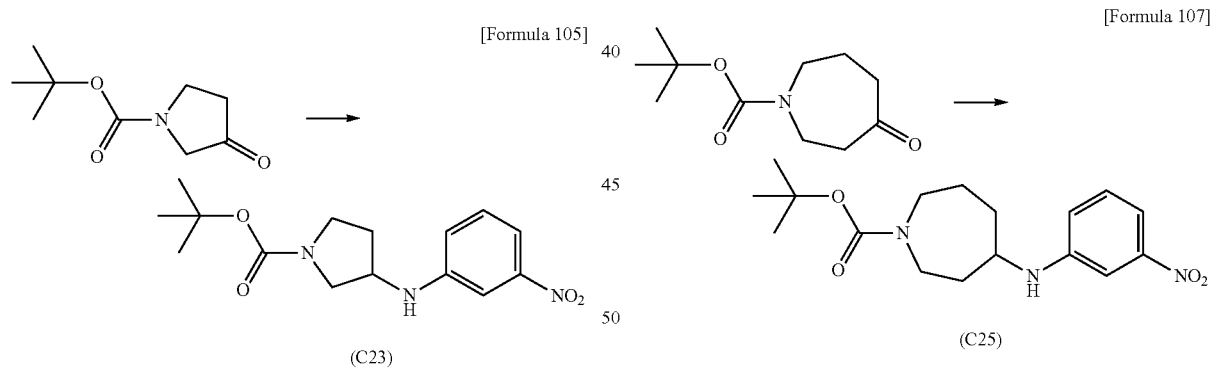

To a solution of 1-(tert-butoxycarbonyl)-3-pyrrolidinone (220 mg) and 3-nitroaniline (164 mg) in methylene chloride (3 mL), sodium triacetoxyborohydride (375 mg) and acetic acid (67 μL) were added at room temperature, and the mixture was stirred at the same temperature for 10 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 50% hexane in ethyl acetate) to obtain tert-butyl 3-((3-nitrophenyl)amino)pyrrolidine-1-carboxylate (C23, 210 mg).

16

To 10% palladium-carbon (100 mg), a solution of tert-butyl 3-((3-nitrophenyl)amino)pyrrolidine-1-carboxylate (C23, 210 mg) in tetrahydrofuran (10 mL) and methanol (10 mL) was added at room temperature, and the mixture was stirred at the same temperature for 1 hour under a hydrogen atmosphere. The insoluble matter was removed by filtration through Cerite, and then the solvent was evaporated under reduced pressure to obtain tert-butyl 3-((3-aminophenyl)amino)pyrrolidine-1-carboxylate (C24, 231 mg).

MS m/z (M+H): 278.2

17

To a solution of N-Boc-hexahydro-1H-azepin-4-one (141 mg) and 3-nitroaniline (91 mg) in methylene chloride (3 mL), sodium triacetoxyborohydride (210 mg) and acetic acid (38 μL) were added at room temperature, and the mixture was stirred at the same temperature for 10 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 30% hexane in ethyl acetate) to obtain tert-butyl 4-((3-nitrophenyl)amino)azepane-1-carboxylate (C25, 157 mg).

MS m/z (M+H): 336.2

18

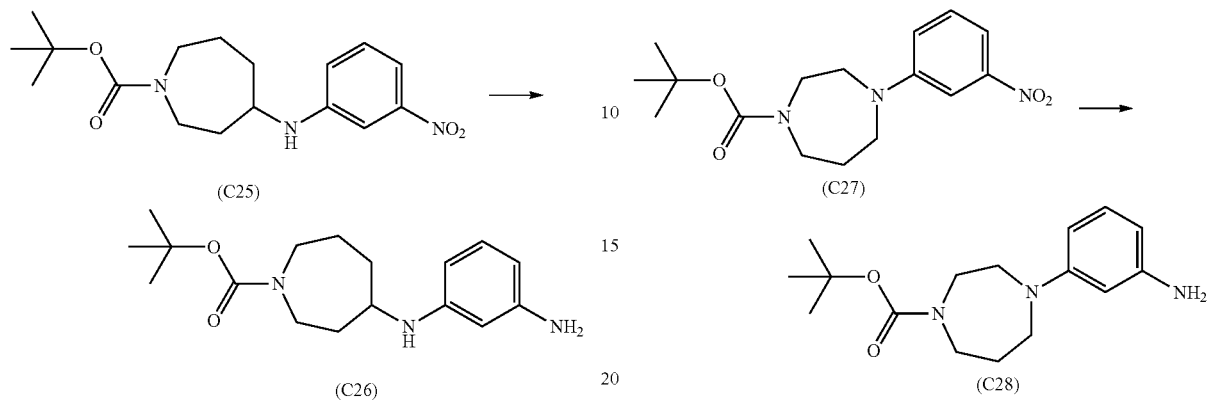

To 10% palladium-carbon (30 mg), a solution of tert-butyl 4-((3-nitrophenyl)amino)azepane-1-carboxylate (C25, 78 mg) in tetrahydrofuran (2 mL) and methanol (2 mL) was added at room temperature, and the mixture was stirred at the same temperature for 1 hour under a hydrogen atmosphere. The insoluble matter was removed by filtration through Cerite, and then the solvent was evaporated under reduced pressure to obtain tert-butyl 4-((3-aminophenyl)amino)azepane-1-carboxylate (C26, 64 mg).

19

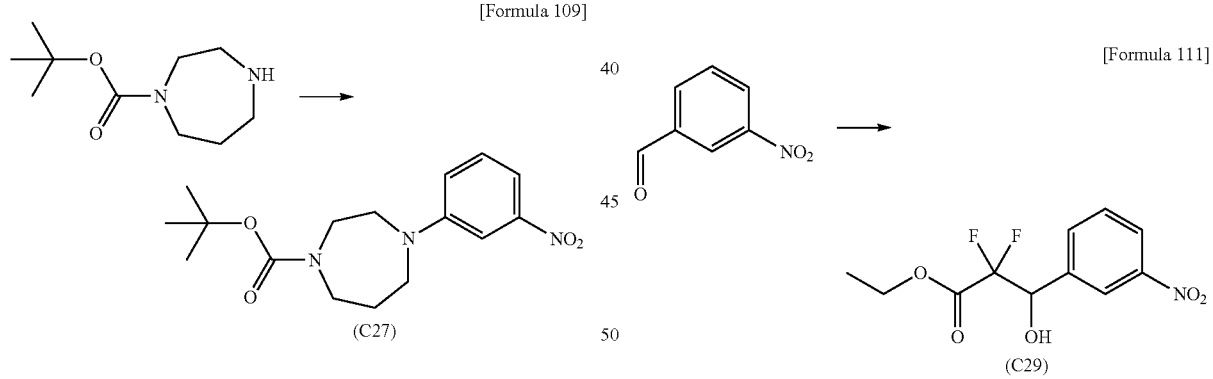

To a solution of 1-Boc-hexahydro-1,4-diazepine (150 mg), 3-bromonitrobenzene (125 mg) and cesium carbonate (507 mg) in 1,4-dioxane (3 mL), bis[di-tert-butyl(4-dimethylaminophenyl)phosphine]dichloropalladium(II) (26 mg) was added at room temperature, and the mixture was stirred at 80° C. for 2 hours. The reaction mixture was cooled to room temperature, and then water and ethyl acetate were added to the mixture. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 70% hexane in ethyl acetate) to obtain tert-butyl 4-(3-nitrophenyl)-1,4-diazepane-1-carboxylate (C27, 15 mg).

MS m/z (M+H): 322.1

20

To 10% palladium-carbon (10 mg), a solution of tert-butyl 4-(3-nitrophenyl)-1,4-diazepane-1-carboxylate (C27, 15 mg) in tetrahydrofuran (2 mL) and methanol (2 mL) was added at room temperature, and the mixture was stirred at the same temperature for 1 hour under a hydrogen atmosphere. The insoluble matter was removed by filtration through Cerite, and then the solvent was evaporated under reduced pressure to obtain tert-butyl 4-(3-aminophenyl)-1,4-diazepane-1-carboxylate (C28, 12 mg).

MS m/z (M+H): 292.2

21

To a suspension of zinc (962 mg) in tetrahydrofuran (25 mL), trimethylsilyl chloride (1 drop) and ethyl bromodifluoroacetate (2.2 mL) were added at room temperature, and the mixture was stirred for 5 minutes under reflux by heating. To the reaction mixture, 3-nitrobenzaldehyde (695 mg) was added, and the mixture was stirred for 30 minutes under reflux by heating. The reaction mixture was cooled to room temperature, and then ethyl acetate and 1.0 mol/L aqueous hydrochloric acid were added to the mixture. The organic layer was separated, washed successively with 1.0 mol/L aqueous hydrochloric acid and saturated aqueous sodium chloride, and then dried over anhydrous sodium sulfate, and the solvent was evaporated under reduced pressure. The obtained residue was purified by silica gel column chromatography (eluent, 100 to 60% hexane in ethyl acetate) to obtain ethyl 2,2-difluoro-3-hydroxy-3-(3-nitrophenyl)propanoate (C29, 1.02 g).

$^1$H-NMR (CDCl$_3$) δ: 8.37-8.34 (1H, brs), 8.28-8.24 (1H, m), 7.84-7.78 (1H, m), 7.60 (1H, t), 5.38-5.27 (1H, m), 7.36 (2H, q), 1.34 (3H, t)

22

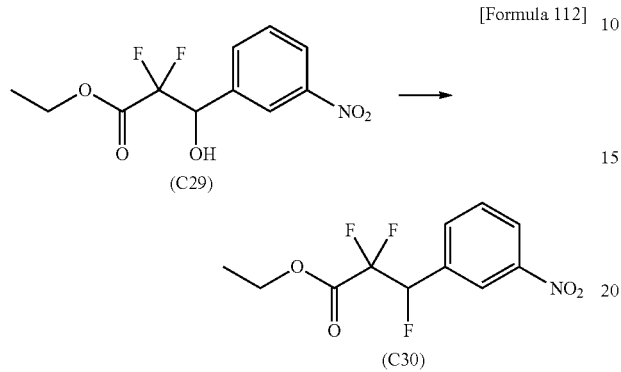

[Formula 112]

To a solution of ethyl 2,2-difluoro-3-hydroxy-3-(3-nitrophenyl)propanoate (C29, 1.02 g) in methylene chloride (22 mL), bis(2-methoxyethyl)aminosulfur trifluoride (1.6 mL) was added under ice cooling, and the mixture was stirred at room temperature for 16 hours. To the reaction mixture, ethyl acetate and water were added. The organic layer was separated, washed successively with 1.0 mol/L aqueous hydrochloric acid, saturated aqueous sodium hydrogencarbonate and saturated aqueous sodium chloride, and then dried over anhydrous sodium sulfate, and the solvent was evaporated under reduced pressure to obtain ethyl 2,2,3-trifluoro-3-(3-nitrophenyl)propanoate (C30, 1.19 g).

$^1$H-NMR (CDCl$_3$) δ: 8.36 (2H, m), 7.81-7.77 (1H, m), 7.69-7.62 (1H, m), 6.05-5.82 (1H, m), 4.41 (2H, q), 1.38 (3H, t)

23

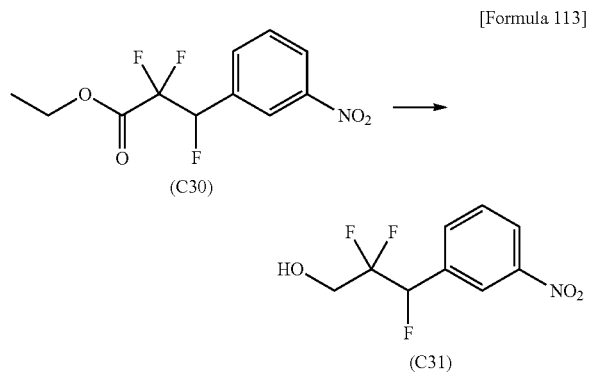

[Formula 113]

To a solution of ethyl 2,2,3-trifluoro-3-(3-nitrophenyl)propanoate (C30, 1.19 g) in ethanol (43 mL), sodium borohydride (811 mg) was added under ice cooling, and the mixture was stirred at room temperature for 40 minutes. To the reaction mixture, ethyl acetate and 1.0 mol/L aqueous hydrochloric acid were added. The organic layer was separated, washed successively with saturated aqueous sodium hydrogencarbonate and saturated aqueous sodium chloride, and then dried over anhydrous sodium sulfate, and the solvent was evaporated under reduced pressure. The obtained residue was purified by silica gel column chromatography (eluent, 100 to 40% hexane in ethyl acetate) to obtain 2,2,3-trifluoro-3-(3-nitrophenyl)propan-1-ol (C31, 829 mg).

$^1$H-NMR (CDCl$_3$) δ: 8.36-8.28 (2H, m), 7.82-7.77 (1H, m), 7.64 (1H, t), 5.98-5.74 (1H, m), 4.19-3.84 (2H, m)

24

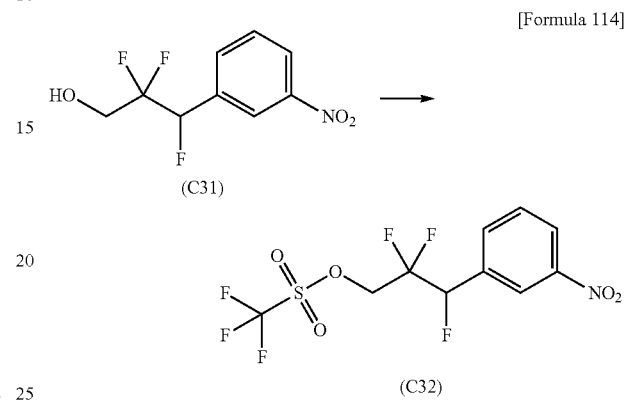

[Formula 114]

To a suspension of 2,2,3-trifluoro-3-(3-nitrophenyl)propan-1-ol (C31, 500 mg), anhydrous sodium sulfate (500 mg) and pyridine (256 µL) in methylene chloride (20 mL), trifluoromethanesulfonic anhydride (521 µL) was added under ice cooling, and the mixture was stirred at the same temperature for 1 hour. To the reaction mixture, 10% aqueous citric acid and methylene chloride were added. The organic layer was separated, washed successively with saturated aqueous sodium hydrogencarbonate and saturated aqueous sodium chloride, and then dried over anhydrous sodium sulfate, and the solvent was evaporated under reduced pressure to obtain 2,2,3-trifluoro-3-(3-nitrophenyl)propyl trifluoromethanesulfonate (C32, 709 mg).

25

[Formula 115]

To 2,2,3-trifluoro-3-(3-nitrophenyl)propyl trifluoromethanesulfonate (C32, 709 mg) and potassium phthalimide (1.07 g), N-methylpyrrolidone (4 mL) was added at room temperature, and the mixture was stirred at 80° C. for 3 hours. The reaction mixture was cooled to room temperature, and then ethyl acetate and saturated aqueous sodium hydrogencarbonate were added to the mixture. The organic layer was separated, washed successively with water and saturated aqueous sodium chloride, and then dried over anhydrous sodium sulfate, and the solvent was evaporated under reduced pressure. The obtained residue was purified by silica gel column chromatography (eluent, 100 to 30% hexane in ethyl acetate) to obtain 2-(2,2,3-trifluoro-3-(3-nitrophenyl)propyl)isoindoline-1,3-dione (C33, 531 mg).

¹H-NMR (CDCl₃) δ: 8.37-8.27 (2H, m), 7.95-7.75 (5H, m), 7.63 (1H, t), 5.98-5.62 (1H, m), 4.41-4.26 (2H, m)

26

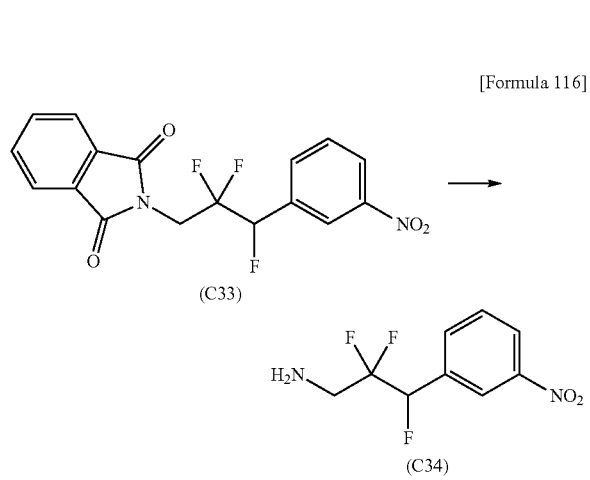

To a solution of 2-(2,2,3-trifluoro-3-(3-nitrophenyl)propyl)isoindoline-1,3-dione (C33, 531 mg) in ethanol (4 mL) and tetrahydrofuran (4 mL), hydrazine monohydrate (349 µL) was added at room temperature, and the mixture was stirred at the same temperature for 18 hours. The insoluble matter was removed by filtration, and then the solvent was evaporated under reduced pressure to obtain 2,2,3-trifluoro-3-(3-nitrophenyl)propan-1-amine (C34, 224 mg).

27

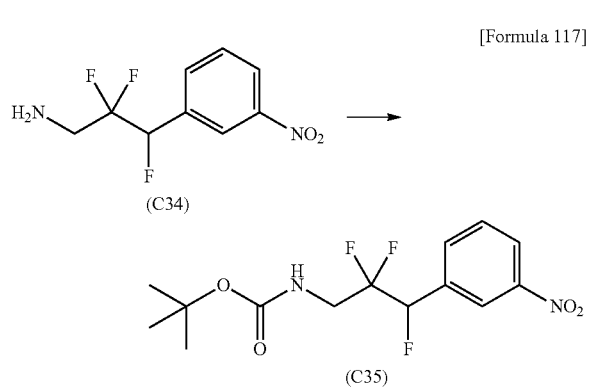

To a solution of 2,2,3-trifluoro-3-(3-nitrophenyl)propan-1-amine (C34, 224 mg) in tetrahydrofuran (5 mL), triethylamine (200 µL) and di-tert-butyl dicarbonate (313 mg) were added at room temperature, and the mixture was stirred at the same temperature for 7 hours. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 50% hexane in ethyl acetate) to obtain tert-butyl (2,2,3-trifluoro-3-(3-nitrophenyl)propyl)carbamate (C35, 182 mg).

¹H-NMR (CDCl₃) δ: 8.33-8.27 (2H, m), 7.79 (1H, d), 7.63 (1H, t), 5.78-5.54 (1H, m), 3.96-3.58 (2H, m), 1.47 (9H, s)

28

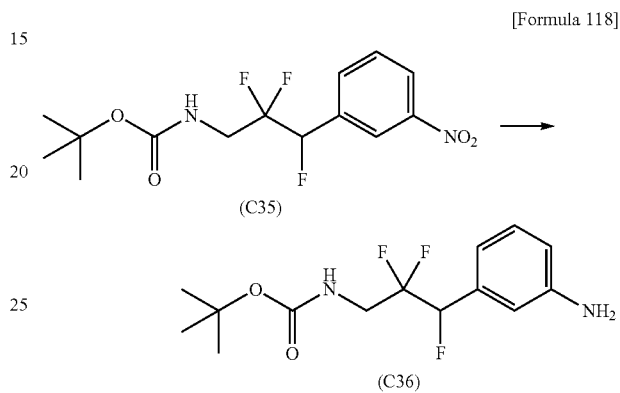

To 10% palladium-carbon (40 mg), a solution of tert-butyl (2,2,3-trifluoro-3-(3-nitrophenyl)propyl)carbamate (C35, 80 mg) in tetrahydrofuran (5 mL) and methanol (5 mL) was added at room temperature, and the mixture was stirred at room temperature for 1 hour under a hydrogen atmosphere. The insoluble matter was removed by filtration through Cerite, and then the solvent was evaporated under reduced pressure to obtain tert-butyl (3-(3-aminophenyl)-2,2,3-trifluoropropyl)carbamate (C36, 88 mg).

MS m/z (M+H): 305.1

29

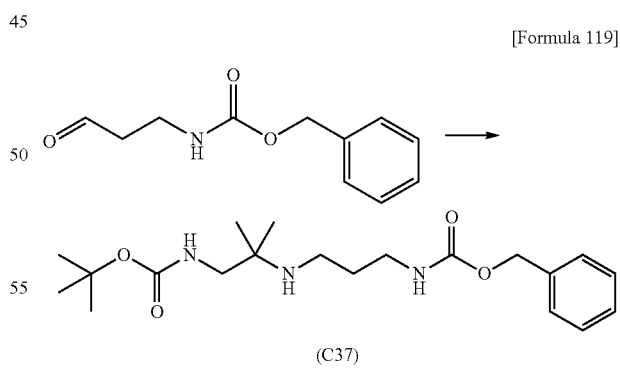

To a solution of tert-butyl (2-amino-2-methylpropyl)carbamate 50 mg) and 3-((benzyloxycarbonyl)amino)propionaldehyde (60 mg) in methylene chloride (3 mL), sodium triacetoxyborohydride (83 mg) and acetic acid (15 µL) were added at room temperature, and the mixture was stirred at the same temperature for 15 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 0% hexane in ethyl acetate) to obtain tert-butyl (2-((3-((benzyloxycarbonyeamino)propyl)amino)-2-methylpropyl)carbamate (C37, 93 mg).

MS m/z (M+H): 380.3

30

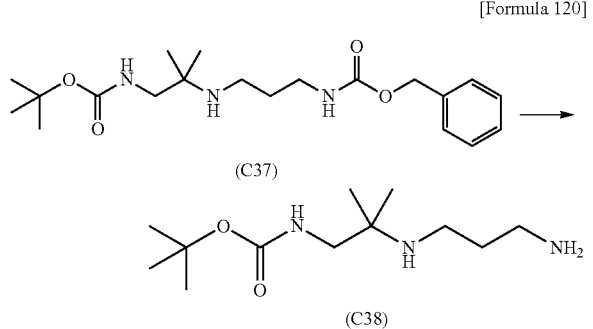

(C37)

(C38)

To 10% palladium-carbon (50 mg), a solution of tert-butyl (2-((3-((benzyloxycarbonyeamino)propyl)amino)-2-methylpropyl)carbamate (C37, 93 mg) in methanol (5 mL) was added at room temperature, and the mixture was stirred at room temperature for 2 hours and 30 minutes under a hydrogen atmosphere. The insoluble matter was removed by filtration through Cerite, and then the solvent was evaporated under reduced pressure to obtain tert-butyl (2-((3-aminopropyl)amino)-2-methylpropyl)carbamate (C38, 56 mg).

$^1$H-NMR (CDCl$_3$) δ: 3.06 (2H, d), 2.80 (2H, t), 2.60 (2H, t), 1.68-1.55 (2H, m), 1.06 (6H, s)

31

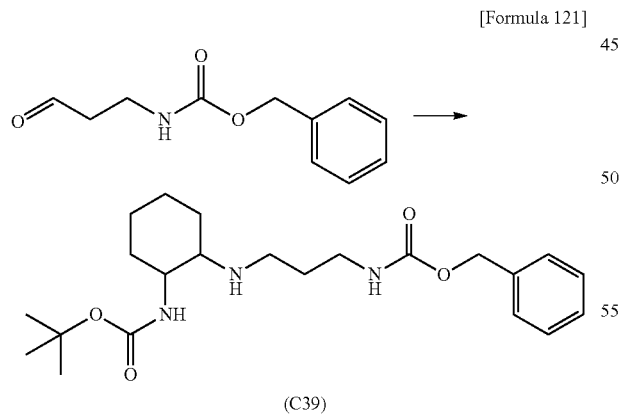

(C39)

To a solution of N-(tert-butoxycarbonyl)-1,2-cyclohexanediamine (200 mg) and 3-((benzyloxycarbonyl)amino) propionaldehyde (65 mg) in methylene chloride (4 mL), sodium triacetoxyborohydride (133 mg) and acetic acid (18 μL) were added at room temperature, and the mixture was stirred at the same temperature for 5 hours and 30 minutes. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 0% hexane in ethyl acetate) to obtain tert-butyl (2-((3-((benzyloxycarbonyl)amino)propyl)amino)cyclohexyl)carbamate (C39, 137 mg).

MS m/z (M+H): 406.3

32

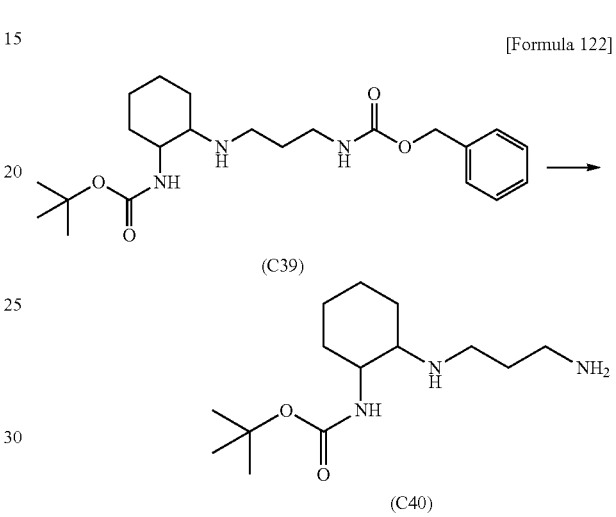

(C39)

(C40)

To 10% palladium-carbon (50 mg), a solution of tert-butyl (2-((3-((benzyloxycarbonyl)amino)propyl)amino)cyclohexyl)carbamate (C39, 137 mg) in methanol (5 mL) was added at room temperature, and the mixture was stirred at room temperature for 4 hours under a hydrogen atmosphere. The insoluble matter was removed by filtration through Cerite, and then the solvent was evaporated under reduced pressure to obtain tert-butyl (2-((3-aminopropyl)amino)cyclohexyl)carbamate (C40, 101 mg).

33

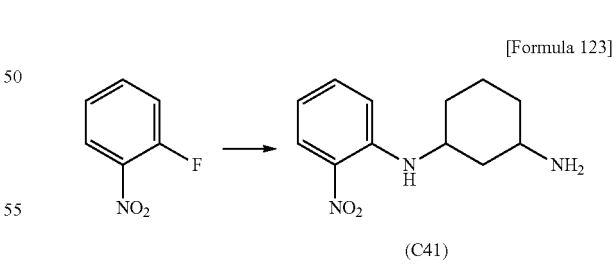

(C41)

To a suspension of 2-fluoronitrobenzene (197 mg) and potassium carbonate (193 mg) in acetonitrile (4 mL), 1,3-cyclohexanediamine (480 mg) was added at room temperature, and the mixture was stirred for 10 hours and 30 minutes under reflux by heating. The reaction mixture was cooled to room temperature, and then ethyl acetate and water were added to the reaction mixture. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 80% ethyl acetate in methanol) to obtain $N^1$-(2-nitrophenyl)cyclohexane-1,3-diamine (C41, 162 mg).

MS m/z (M+H): 236.1

34

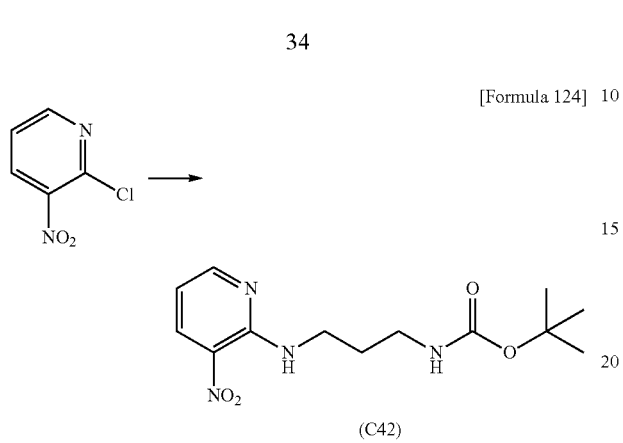

[Formula 124]

(C42)

To 2-chloro-3-nitropyridine (92 mg), tert-butyl(3-aminopropyl)carbamate (102 mg) and potassium carbonate (161 mg), acetonitrile (1.2 mL) was added at room temperature, and the mixture was stirred at the same temperature for 4 hours. To the reaction mixture, ethyl acetate and water were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 0% hexane in ethyl acetate) to obtain tert-butyl (3-((3-nitropyridin-2-yl)amino)propyl)carbamate (C42, 186 mg).

MS m/z (M+H): 297.2

35

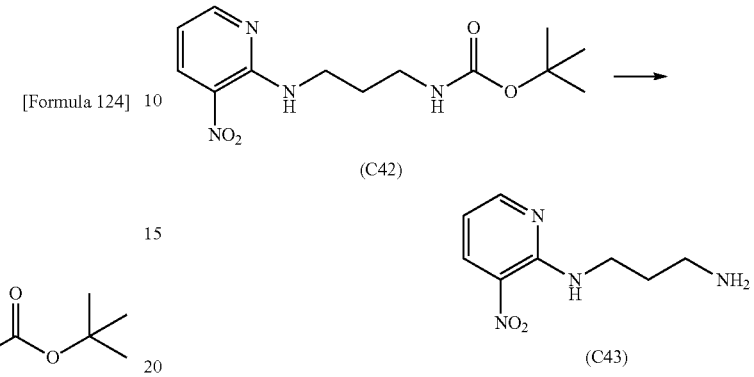

[Formula 125]

(C42)

(C43)

To tert-butyl (3-((3-nitropyridin-2-yl)amino)propyl)carbamate (C42, 53 mg), a 4.0 mol/L solution of hydrochloric acid in dioxane (2 mL) and water (100 μL) were added at room temperature, and the mixture was stirred at the same temperature for 1 hour. To the reaction mixture, diisopropyl ether were added, the solvent was removed by decantation, and then the residue was dried under reduced pressure to obtain $N^1$-(3-nitropyridin-2-yl)propane-1,3-diamine (C43) hydrochloride (113 mg).

MS m/z (M+H): 197.1

36

In the same manner as that of Example 1, (4) or Example 7, (9), Intermediates (C44) to (C46) were obtained.

TABLE 28

| Compound No. | Structure | Physicochemical data |
|---|---|---|
| C44 | ![structure] | — |
| C45 | ![structure] | — |

TABLE 28-continued

| Compound No. | Structure | Physicochemical data |
|---|---|---|
| C46 | 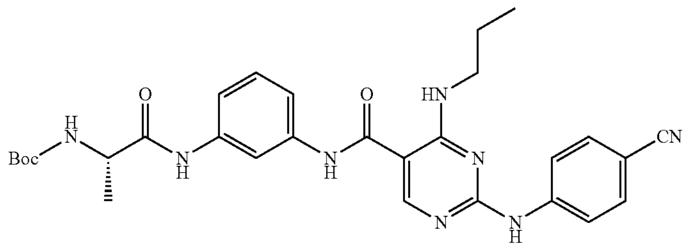 [SMILES: CCCNc1nc(Nc2ccc(C#N)cc2)ncc1C(=O)Nc1cccc(NC(=O)[C@H](C)NC(=O)OC(C)(C)C)c1] | MS m/z (M + H): 559.3 |

37

By using Intermediates (C45) and (C46), Intermediates (C47) and (C48) were obtained in the same manner as that of Example 7, (10).

TABLE 29

| Compound No. | Structure | Physicochemical data |
|---|---|---|
| C47 | 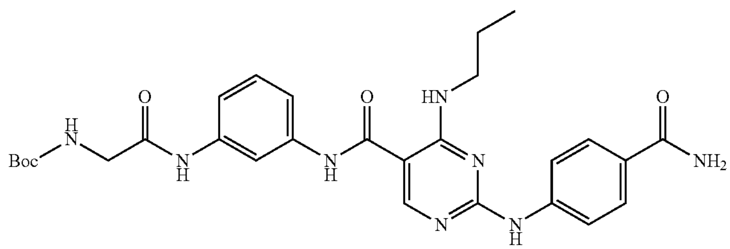 [SMILES: CCCNc1nc(Nc2ccc(C(N)=O)cc2)ncc1C(=O)Nc1cccc(NC(=O)CNC(=O)OC(C)(C)C)c1] | MS m/z (M + H): 563.3 |
| C48 | 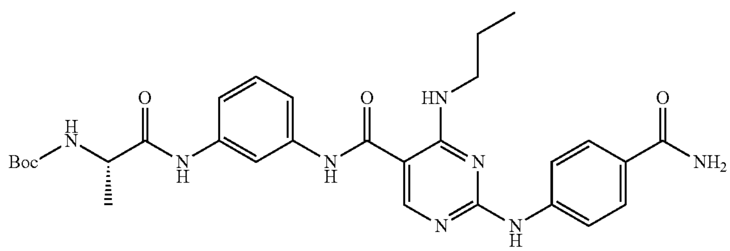 [SMILES: CCCNc1nc(Nc2ccc(C(N)=O)cc2)ncc1C(=O)Nc1cccc(NC(=O)[C@H](C)NC(=O)OC(C)(C)C)c1] | MS m/z (M + H): 577.3 |

38

By using Intermediates (C44), Intermediates (C49) and (C50) were obtained in the same manner as that of Example 1, (5).

TABLE 30

| Compound No. | Structure | Physicochemical data |
|---|---|---|
| C49 | 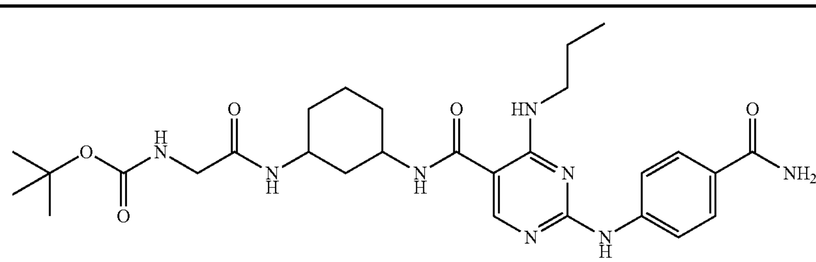 | — |

TABLE 30-continued

| Compound No. | Structure | Physicochemical data |
|---|---|---|
| C50 | 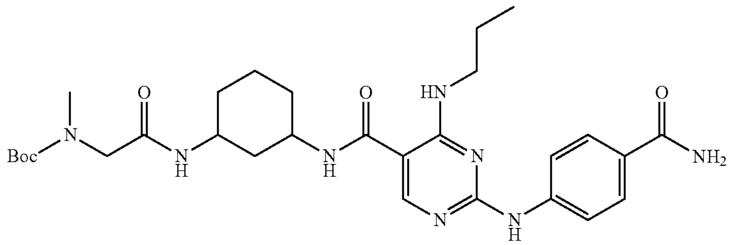 [SMILES: CCCNc1nc(Nc2ccc(C(N)=O)cc2)ncc1C(=O)NC1CCCC(NC(=O)CN(C)C(=O)OC(C)(C)C)C1] | MS m/z (M + H): 583.4 |

39

In the same manner as that of Example 1, (6), Intermediates (C51) to (C55) were obtained.

TABLE 31

| Compound No. | Structure | Physicochemical data |
|---|---|---|
| C51 | 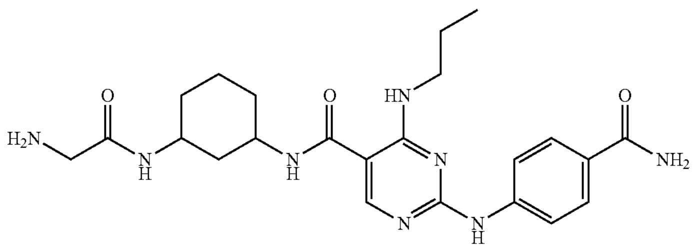 [SMILES: CCCNc1nc(Nc2ccc(C(N)=O)cc2)ncc1C(=O)NC1CCCC(NC(=O)CN)C1] | MS m/z (M + H): 469.3 |
| C52 | 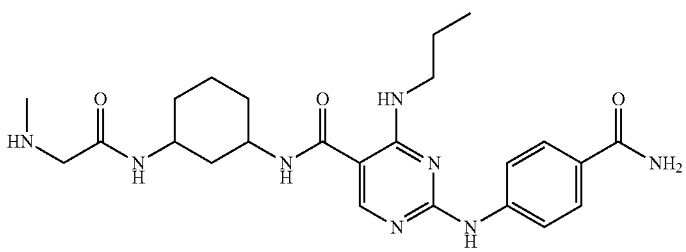 [SMILES: CCCNc1nc(Nc2ccc(C(N)=O)cc2)ncc1C(=O)NC1CCCC(NC(=O)CNC)C1] | MS m/z (M + H): 483.3 |
| C53 | 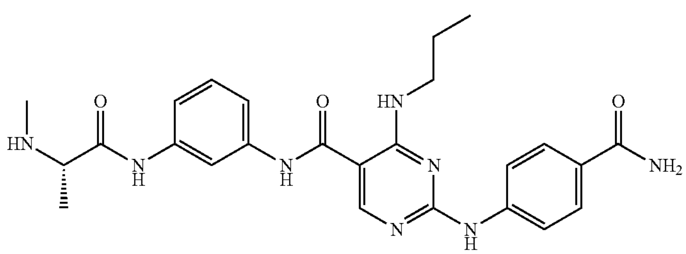 [SMILES: CCCNc1nc(Nc2ccc(C(N)=O)cc2)ncc1C(=O)Nc1cccc(NC(=O)[C@H](C)NC)c1] | MS m/z (M + H): 491.3 |
| C54 | 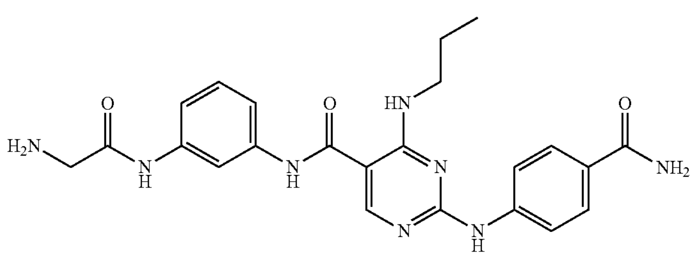 [SMILES: CCCNc1nc(Nc2ccc(C(N)=O)cc2)ncc1C(=O)Nc1cccc(NC(=O)CN)c1] | — |

TABLE 31-continued

| Compound No. | Structure | Physicochemical data |
|---|---|---|
| C55 | 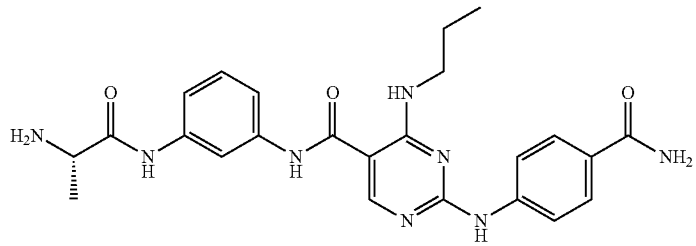 [SMILES: CCCNc1nc(Nc2ccc(C(N)=O)cc2)ncc1C(=O)Nc1cccc(NC(=O)[C@H](C)N)c1] | MS m/z (M + H): 477.3 |

40

In the same manner as that of Example 7, (7), Intermediates (C56) and (C57) were obtained.

TABLE 32

| Compound No. | Structure | Physicochemical data |
|---|---|---|
| C56 | 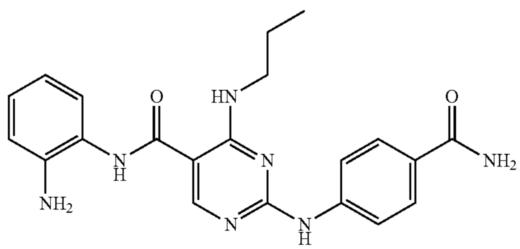 [SMILES: CCCNc1nc(Nc2ccc(C(N)=O)cc2)ncc1C(=O)Nc1ccccc1N] | — |
| C57 | 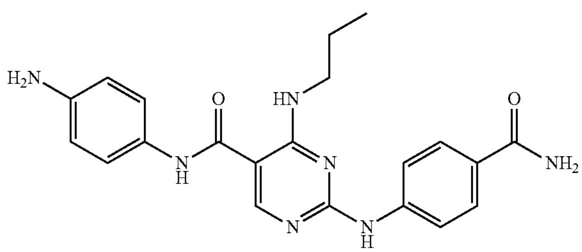 [SMILES: CCCNc1nc(Nc2ccc(C(N)=O)cc2)ncc1C(=O)Nc1ccc(N)cc1] | — |

41

In the same manner as that of Example 7, (11), Intermediates (C58) to (C76) were obtained.

TABLE 33

| Compound No. | Structure | Physicochemical data |
|---|---|---|
| C58 | 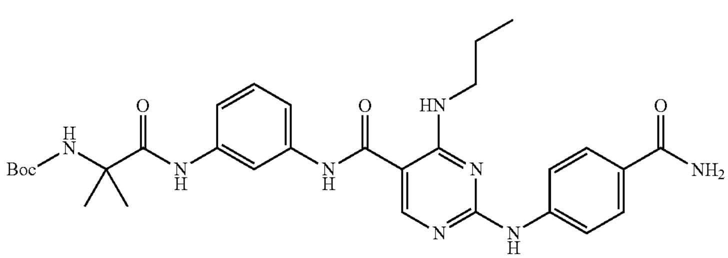 [SMILES: CCCNc1nc(Nc2ccc(C(N)=O)cc2)ncc1C(=O)Nc1cccc(NC(=O)C(C)(C)NC(=O)OC(C)(C)C)c1] | — |

TABLE 33-continued

| Compound No. | Structure | Physicochemical data |
|---|---|---|
| C59 | 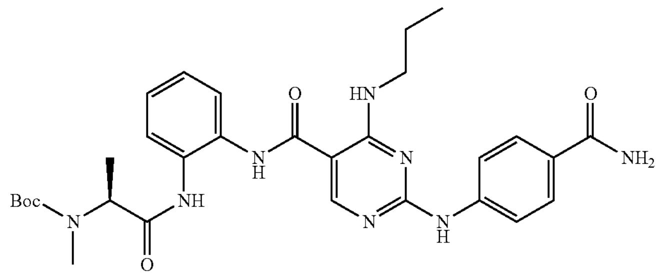 [SMILES: CCCNc1nc(Nc2ccc(C(N)=O)cc2)ncc1C(=O)Nc1ccccc1NC(=O)[C@H](C)N(C)C(=O)OC(C)(C)C] | — |
| C60 | 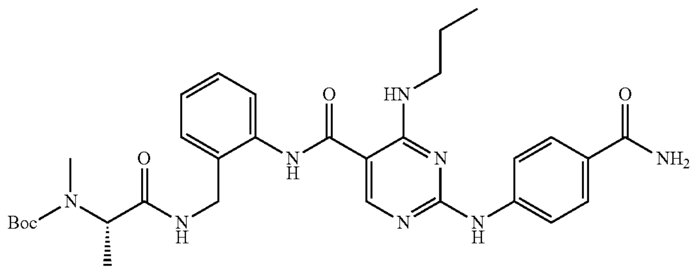 [SMILES: CCCNc1nc(Nc2ccc(C(N)=O)cc2)ncc1C(=O)Nc1ccccc1CNC(=O)[C@H](C)N(C)C(=O)OC(C)(C)C] | — |
| C61 | 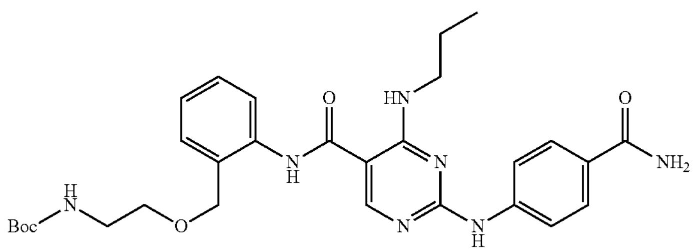 [SMILES: CCCNc1nc(Nc2ccc(C(N)=O)cc2)ncc1C(=O)Nc1ccccc1COCCNC(=O)OC(C)(C)C] | — |
| C62 | 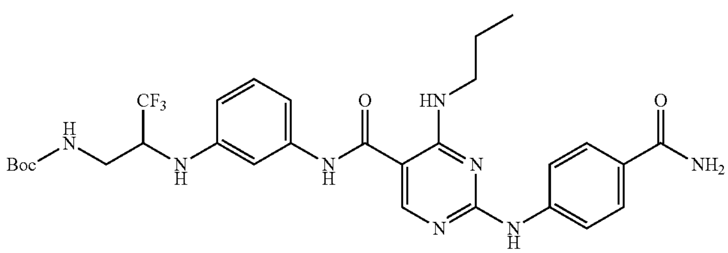 [SMILES: CCCNc1nc(Nc2ccc(C(N)=O)cc2)ncc1C(=O)Nc1cccc(NC(CNC(=O)OC(C)(C)C)C(F)(F)F)c1] | — |
| C63 | 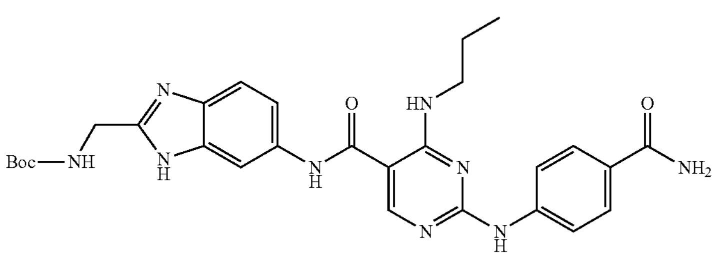 [SMILES: CCCNc1nc(Nc2ccc(C(N)=O)cc2)ncc1C(=O)Nc1ccc2nc(CNC(=O)OC(C)(C)C)[nH]c2c1] | — |
| C64 | 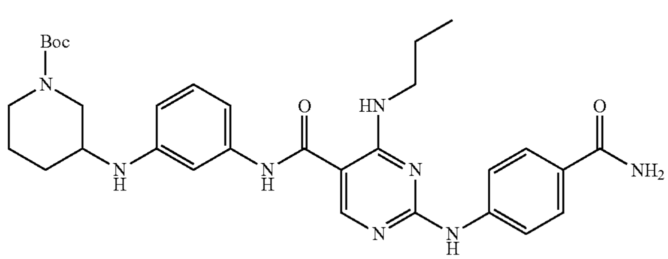 [SMILES: CCCNc1nc(Nc2ccc(C(N)=O)cc2)ncc1C(=O)Nc1cccc(NC2CCCN(C(=O)OC(C)(C)C)C2)c1] | — |

TABLE 33-continued
| Compound No. | Structure | Physicochemical data |
|---|---|---|
| C65 | 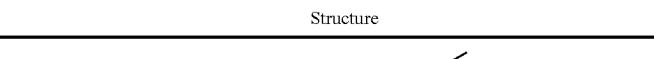 | — |
TABLE 34
| Compound No. | Structure | Physicochemical data |
|---|---|---|
| C66 | 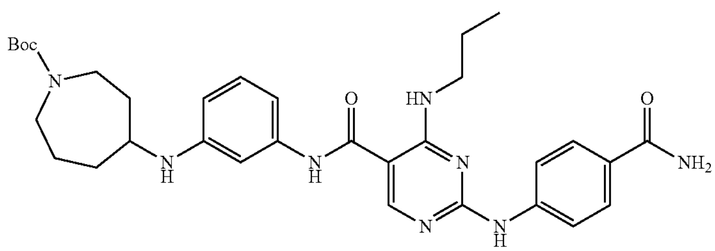 [SMILES: CCCNc1nc(Nc2ccc(C(N)=O)cc2)ncc1C(=O)Nc1cccc(NC2CCCN(C(=O)OC(C)(C)C)CC2)c1] | — |
| C67 | 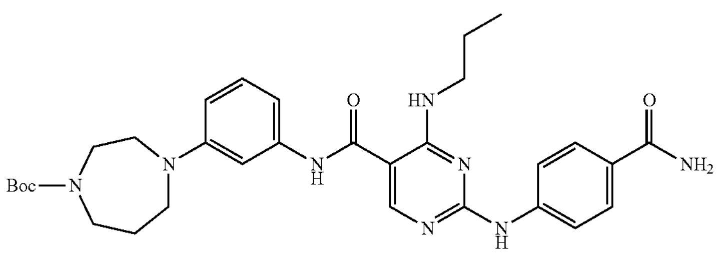 [SMILES: CCCNc1nc(Nc2ccc(C(N)=O)cc2)ncc1C(=O)Nc1cccc(N2CCCN(C(=O)OC(C)(C)C)CC2)c1] | — |
| C68 | 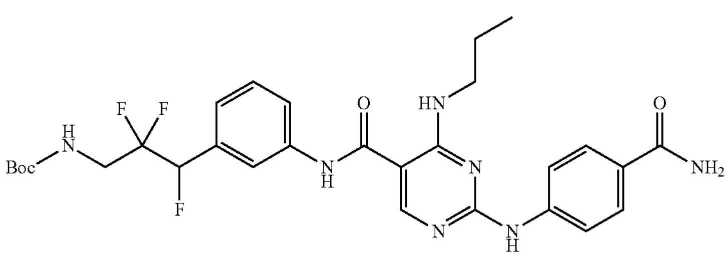 [SMILES: CCCNc1nc(Nc2ccc(C(N)=O)cc2)ncc1C(=O)Nc1cccc(C(F)C(F)(F)CNC(=O)OC(C)(C)C)c1] | — |
| C69 | 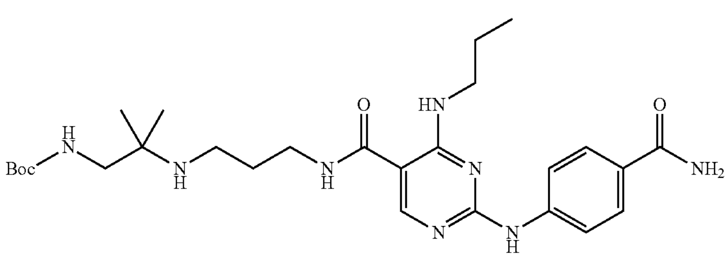 [SMILES: CCCNc1nc(Nc2ccc(C(N)=O)cc2)ncc1C(=O)NCCCNC(C)(C)CNC(=O)OC(C)(C)C] | — |

TABLE 34-continued

| Compound No. | Structure | Physicochemical data |
|---|---|---|
| C70 | 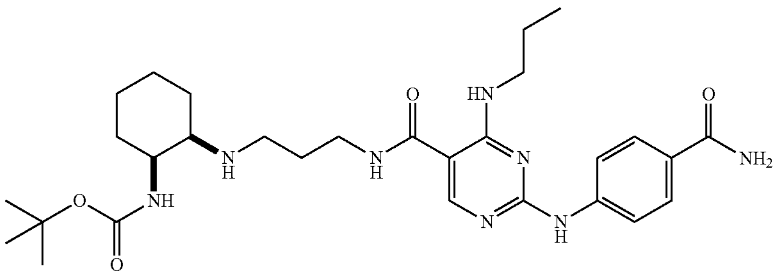 | — |
| C71 | 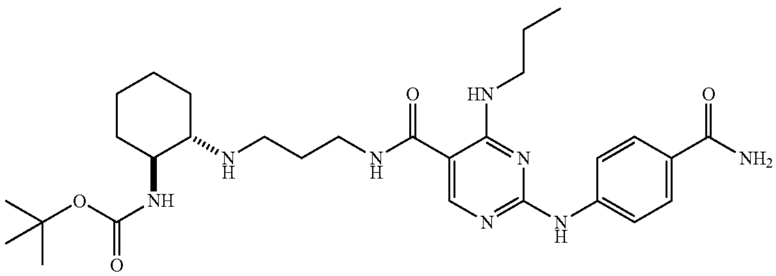 [SMILES: CCCNc1nc(Nc2ccc(C(N)=O)cc2)ncc1C(=O)NCCCN[C@H]1CCCC[C@@H]1NC(=O)OC(C)(C)C] | — |
| C72 | 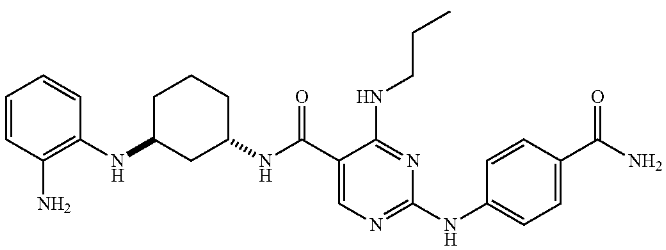 | — |
| C73 | 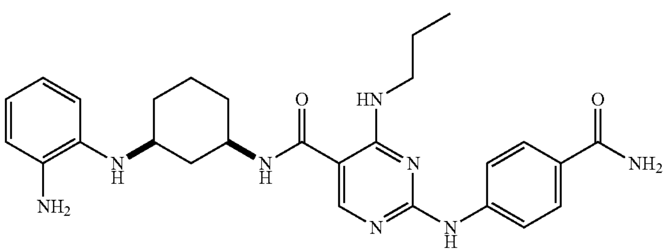 | — |

TABLE 35

| Compound No. | Structure | Physicochemical data |
|---|---|---|
| C74 | 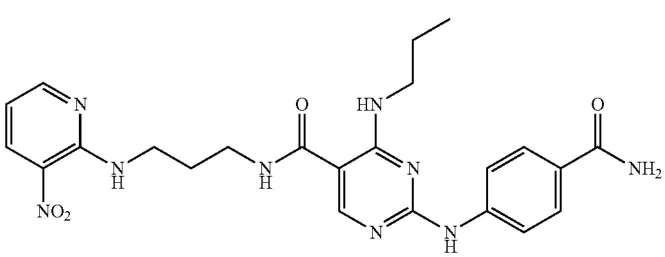 | — |

TABLE 35-continued

| Compound No. | Structure | Physicochemical data |
|---|---|---|
| C75 | 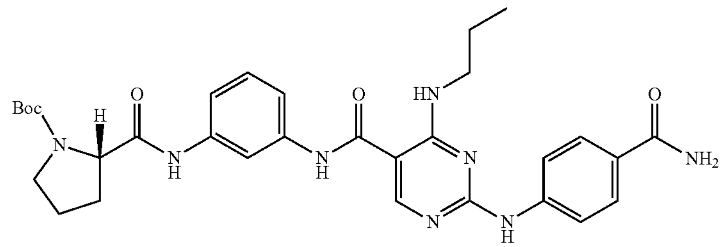 [SMILES: CCCNc1nc(Nc2ccc(C(N)=O)cc2)ncc1C(=O)Nc1cccc(NC(=O)[C@@H]2CCCN2C(=O)OC(C)(C)C)c1] | — |
| C76 | 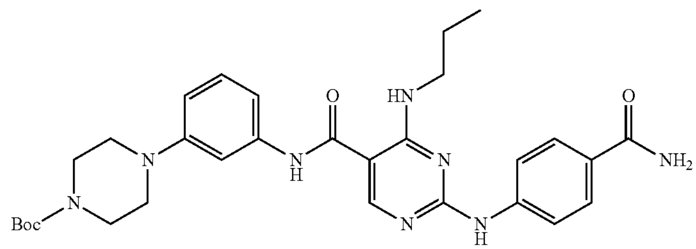 [SMILES: CCCNc1nc(Nc2ccc(C(N)=O)cc2)ncc1C(=O)Nc1cccc(N2CCN(C(=O)OC(C)(C)C)CC2)c1] | — |

42

In the same manner as that of Example 1, (6), Intermediates (C77) to (C92) were obtained.

TABLE 36

| Compound No. | Structure | Physicochemical data |
|---|---|---|
| C77 | 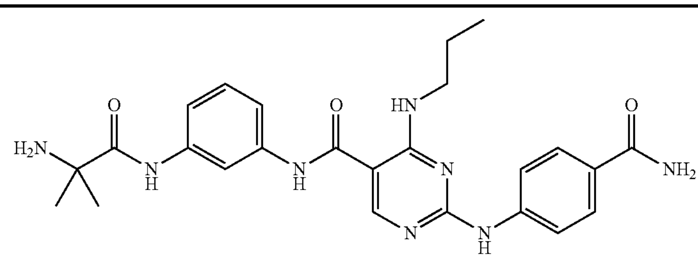 | MS m/z (M + H): 491.2 |
| C78 | 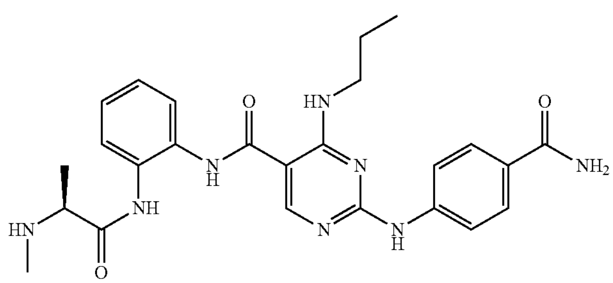 [SMILES: CCCNc1nc(Nc2ccc(C(N)=O)cc2)ncc1C(=O)Nc1ccccc1NC(=O)[C@H](C)NC] | — |
| C79 | 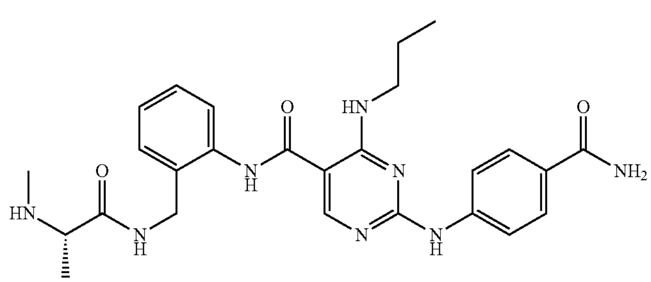 [SMILES: CCCNc1nc(Nc2ccc(C(N)=O)cc2)ncc1C(=O)Nc1ccccc1CNC(=O)[C@H](C)NC] | — |

TABLE 36-continued
| Compound No. | Structure | Physicochemical data |
|---|---|---|
| C80 | 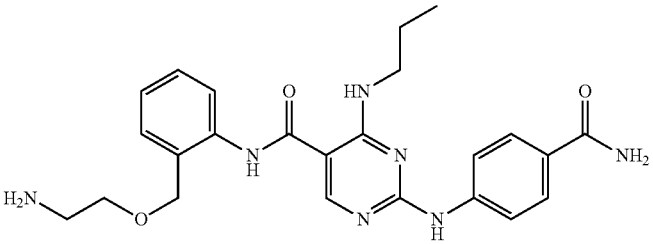 [SMILES: CCCNc1nc(Nc2ccc(C(N)=O)cc2)ncc1C(=O)Nc1ccccc1COCCN] | — |
| C81 | 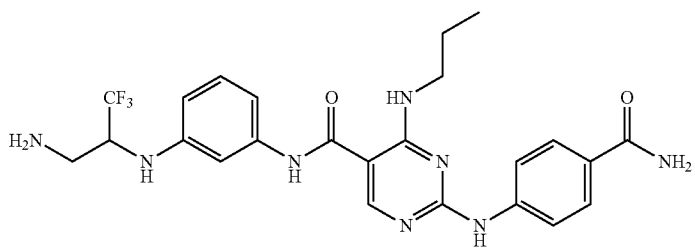 [SMILES: CCCNc1nc(Nc2ccc(C(N)=O)cc2)ncc1C(=O)Nc1cccc(NC(CN)C(F)(F)F)c1] | — |
| C82 | 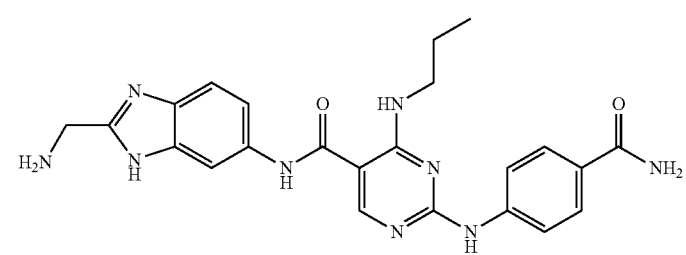 [SMILES: CCCNc1nc(Nc2ccc(C(N)=O)cc2)ncc1C(=O)Nc1ccc2nc(CN)[nH]c2c1] | — |
| C83 | 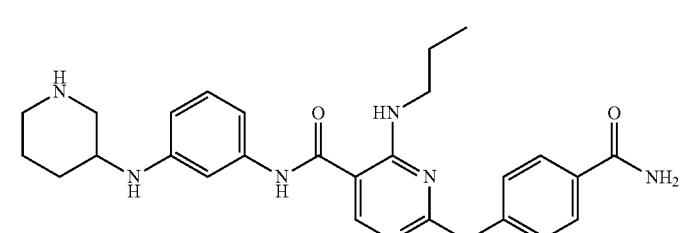 | — |
| C84 | 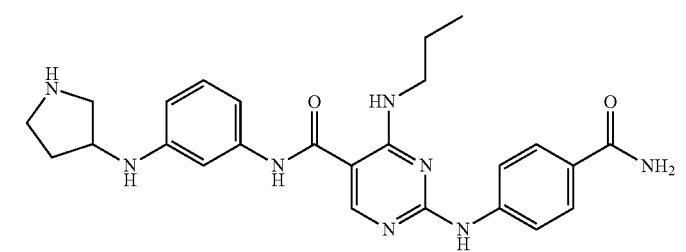 [SMILES: CCCNc1nc(Nc2ccc(C(N)=O)cc2)ncc1C(=O)Nc1cccc(NC2CCNC2)c1] | — |

TABLE 37
| Compound No. | Structure | Physicochemical data |
|---|---|---|
| C85 | 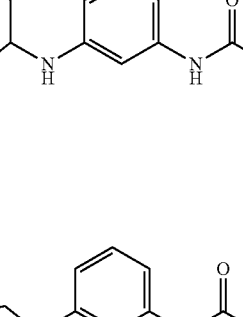 | — |
| C86 | 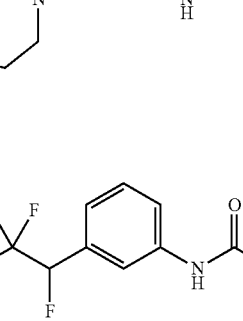 | — |
| C87 | 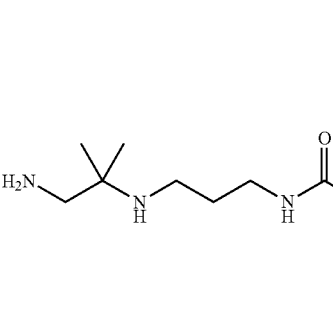 | — |
| C88 | 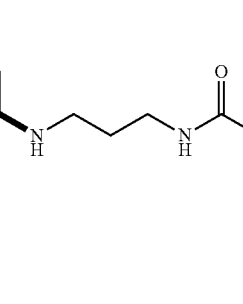 | — |
| C89 | 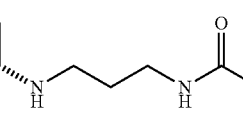 | — |
| C90 | 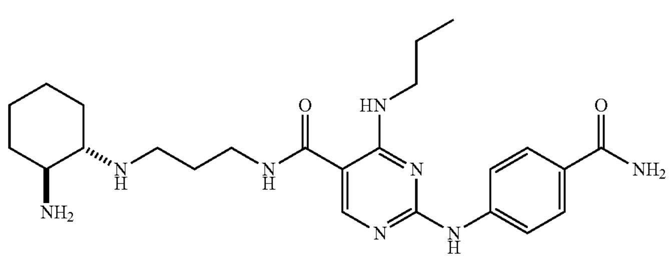 | — |

TABLE 37-continued
| Compound No. | Structure | Physicochemical data |
|---|---|---|
| C91 | 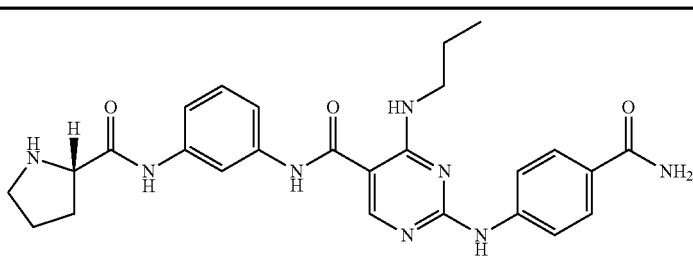 | MS m/z (M + H): 503.2 |
| C92 | 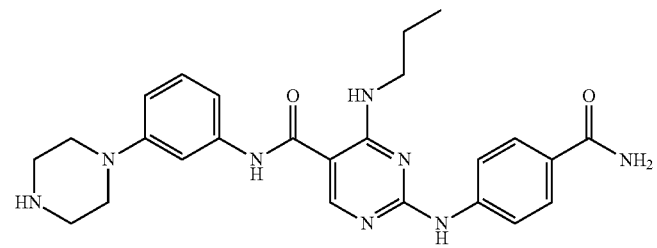 [SMILES: CCCNc1nc(Nc2ccc(C(N)=O)cc2)ncc1C(=O)Nc1cccc(N2CCNCC2)c1] | — |
43
By using Intermediates (C72) to (C74), Intermediates (C93) to (C95) were obtained in the same manner as that of Example 8, (10).
TABLE 38
| Compound No. | Structure | Physicochemical data |
|---|---|---|
| C93 | 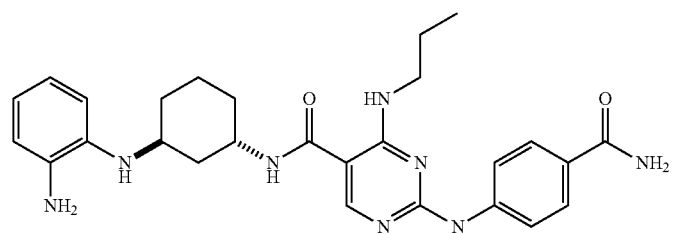 | — |
| C94 | 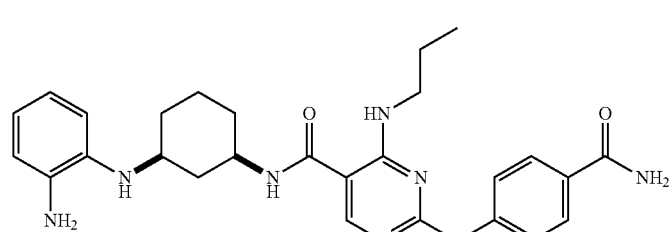 | — |
| C95 | 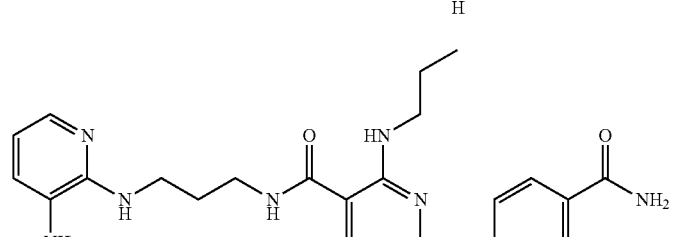 | — |

Example 9

In the same manner as that of Example 7, Compounds (3-2) to (3-31) were obtained.

TABLE 39

| Compound No. | Structure | Physicochemical data |
|---|---|---|
| 3-2 | 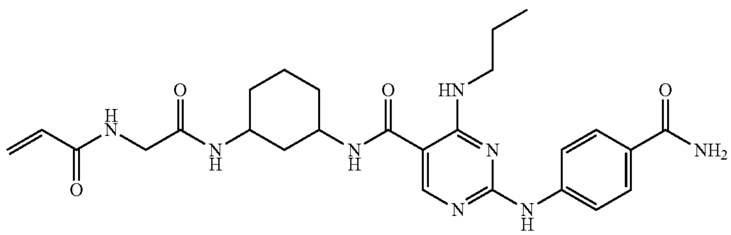 [SMILES: C=CC(=O)NCC(=O)NC1CCCC(NC(=O)c2cnc(Nc3ccc(C(N)=O)cc3)nc2NCCC)C1] | $^1$H-NMR (DMSO-d$_6$) δ: 9.77 (1H, s), 9.03 (1H, t, J = 5.6 Hz), 8.52 (1H, s), 8.33-8.29 (1H, m), 8.11 (1H, d, J = 7.8 Hz), 7.92-7.78 (6H, m), 7.15 (1H, s), 6.32 (1H, dd, J = 16.8, 10.2 Hz), 6.08 (1H, dd, J = 16.8, 2.6 Hz), 5.60 (1H, dd, J = 10.2, 2.6 Hz), 3.75-3.38 (6H, m), 1.98-1.94 (1H, m), 1.76-1.56 (5H, m), 1.35-1.03 (4H, m), 0.96 (3H, t, J = 7.3 Hz) |
| 3-3 | 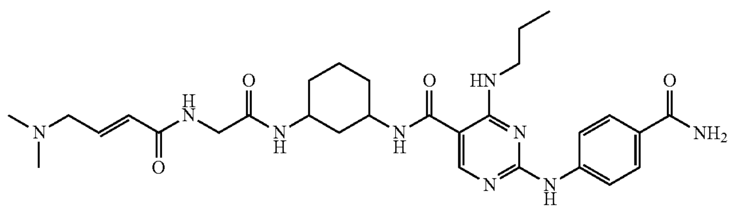 [SMILES: CCCNc1nc(Nc2ccc(C(N)=O)cc2)ncc1C(=O)NC1CCCC(NC(=O)CNC(=O)/C=C/CN(C)C)C1] | $^1$H-NMR (CDCl$_3$ + CD$_3$OD) δ: 8.26 (1H, s), 7.85-7.78 (4H, m), 6.80 (1H, dt, J = 15.2, 6.4 Hz), 6.08 (1H, d, J = 15.2 Hz), 3.93-3.82 (4H, m), 3.49 (2H, d, J = 5.3 Hz), 3.18-3.11 (2H, m), 2.28 (6H, s), 1.75-1.61 (4H, m), 1.30-1.01 (9H, m) |
| 3-4 | 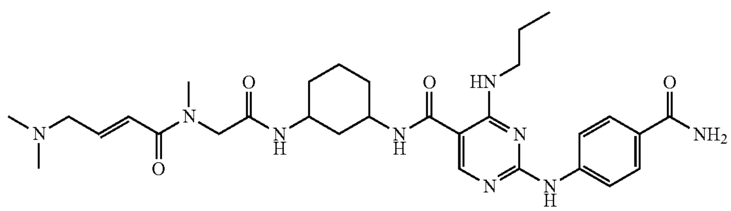 [SMILES: CCCNc1nc(Nc2ccc(C(N)=O)cc2)ncc1C(=O)NC1CCCC(NC(=O)CN(C)C(=O)/C=C/CN(C)C)C1] | $^1$H-NMR (DMSO-d$_6$) δ: 9.76 (1H, s), 9.04 (1H, t, J = 5.3 Hz), 8.52 (1H, s), 8.06 (1H, dd, J = 25.1, 7.9 Hz), 7.88-7.78 (6H, m), 7.15 (1H, s), 6.61-6.31 (2H, m), 3.95 (2H, d, J = 15.9 Hz), 3.75-3.38 (4H, m), 3.03 (3H, m), 2.96 (2H, d, J = 5.3 Hz), 2.15 (3H, s), 2.09 (3H, s), 1.96 (1H, d, J = 12.6 Hz), 1.75-1.56 (5H, m), 1.34-1.15 (4H, m), 0.96 (3H, t, J = 7.3 Hz) |
| 3-5 | 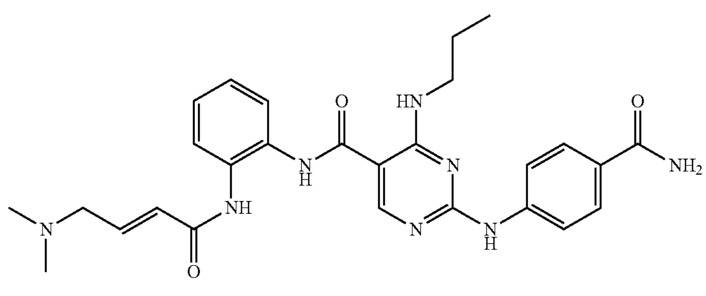 [SMILES: CCCNc1nc(Nc2ccc(C(N)=O)cc2)ncc1C(=O)Nc1ccccc1NC(=O)/C=C/CN(C)C] | $^1$H-NMR (CDCl$_3$ + CD$_3$OD) δ: 8.49 (1H, s), 7.80 (4H, s), 7.72 (1H, d, J = 8.6 Hz), 7.31-7.25 (2H, m), 7.23-7.18 (1H, m), 6.95 (1H, dt, J = 10.6, 4.8 Hz), 6.20 (1H, d, J = 15.9 Hz), 3.49 (2H, t, J = 7.3 Hz), 3.15 (2H, d, J = 4.6 Hz), 2.31 (6H, s), 1.70 (2H, dd, J = 13.9, 7.3 Hz), 1.02 (3H, t, J = 7.3 Hz) |
| 3-6 | 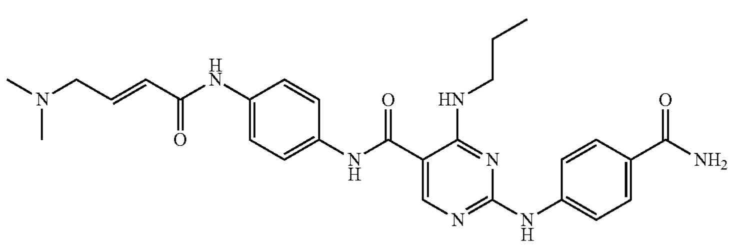 [SMILES: CCCNc1nc(Nc2ccc(C(N)=O)cc2)ncc1C(=O)Nc1ccc(NC(=O)/C=C/CN(C)C)cc1] | $^1$H-NMR (CDCl$_3$ + CD$_3$OD) δ: 8.48 (1H, s), 7.87-7.78 (4H, m), 7.64-7.51 (4H, m), 6.89 (1H, dt, J = 15.4, 6.3 Hz), 6.20 (1H, d, J = 15.4 Hz), 3.52 (2H, dd, J = 12.9, 6.9 Hz), 3.18 (2H, d, J = 7.3 Hz), 2.33 (6H, s), 1.79-1.67 (2H, m), 1.04 (3H, t, J = 7.3 Hz) |
| 3-7 | 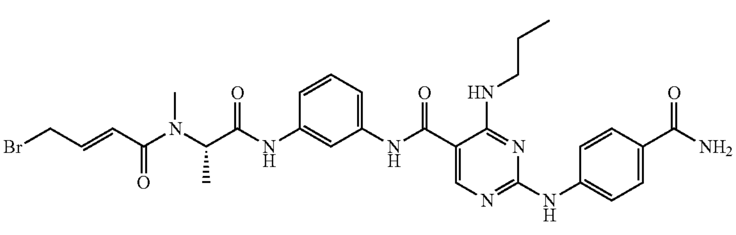 [SMILES: CCCNc1nc(Nc2ccc(C(N)=O)cc2)ncc1C(=O)Nc1cccc(NC(=O)[C@H](C)N(C)C(=O)/C=C/CBr)c1] | $^1$H-NMR (CD$_3$OD) δ: 8.56 (1H, s), 7.95 (1H, s), 7.90-7.83 (4H, m), 7.31-7.29 (3H, m), 6.32 (1H, dt, J = 6.3, 1.7 Hz), 6.10 (1H, q, J = 6.3 Hz), 5.15 (1H, q, J = 7.0 Hz), 3.53 (2H, t, J = 7.3 Hz), 3.45 (2H, dd, J = 6.3, 1.7 Hz), 3.11 (3H, s), 1.78-1.66 (2H, m), 1.46 (3H, d, J = 7.3 Hz), 1.04 (3H, t, J = 7.3 Hz) |

TABLE 40

| Compound No. | Structure | Physicochemical data |
|---|---|---|
| 3-8 | 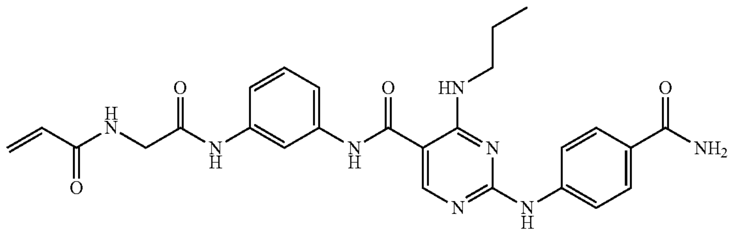 [SMILES: C=CC(=O)NCC(=O)Nc1cccc(NC(=O)c2cnc(Nc3ccc(C(N)=O)cc3)nc2NCCC)c1] | ¹H-NMR (DMSO-d₆) δ: 10.07 (1H, s), 10.03 (1H, s), 9.88 (1H, s), 8.83 (1H, t, J = 5.6 Hz), 8.72 (1H, s), 8.48 (1H, t, J = 5.9 Hz), 8.06 (1H, s), 7.90 (2H, d, J = 9.2 Hz), 7.86-7.78 (3H, m), 7.36-7.14 (4H, m), 6.36 (1H, dd, J = 17.2, 9.9 Hz), 6.12 (1H, dd, J = 17.2, 2.6 Hz), 5.64 (1H, dd, J = 9.9, 2.0 Hz), 3.98 (2H, d, J = 5.9 Hz), 3.47 (2H, q, J = 6.6 Hz), 1.72-1.58 (2H, m), 0.98 (3H, t, J = 7.3 Hz) |
| 3-9 | 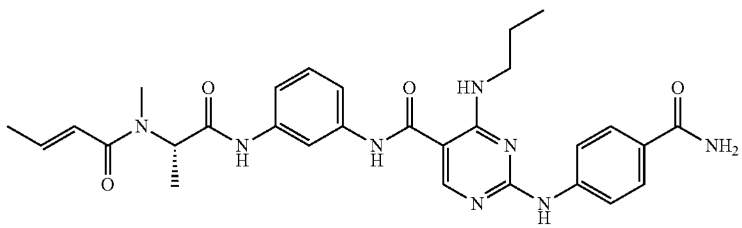 [SMILES: C/C=C/C(=O)N(C)[C@@H](C)C(=O)Nc1cccc(NC(=O)c2cnc(Nc3ccc(C(N)=O)cc3)nc2NCCC)c1] | ¹H-NMR (DMSO-d₆) δ: 10.01 (1H, s), 9.94, 9.84 (2H, m), 8.83 (1H, brs), 8.72 (1H, s), 8.07 (1H, s), 7.90 (2H, d, J = 8.6 Hz), 7.86-7.78 (3H, m), 7.36-7.16 (4H, m), 6.76-6.66 (1H, m), 6.49 (1H, d, J = 14.5 Hz), 5.16-5.04 (1H, m), 3.47 (2H, q, J = 6.6 Hz), 3.04 (3H, s), 1.86 (3H, d, J = 6.6 Hz), 1.72-1.58 (2H, m), 1.35 (3H, d, J = 7.3 Hz), 0.98 (3H, t, J = 7.6 Hz) |
| 3-10 | 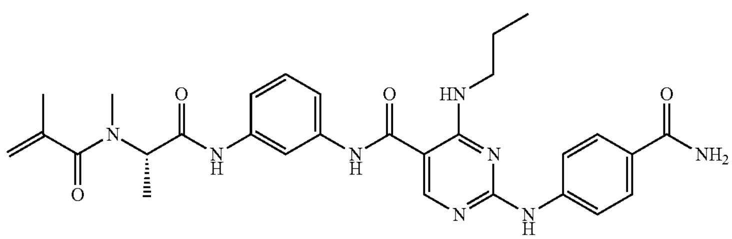 [SMILES: C=C(C)C(=O)N(C)[C@@H](C)C(=O)Nc1cccc(NC(=O)c2cnc(Nc3ccc(C(N)=O)cc3)nc2NCCC)c1] | ¹H-NMR (DMSO-d₆) δ: 10.04-9.94 (2H, m), 9.88 (1H, s), 8.83 (1H, brs), 8.72 (1H, s), 8.08 (1H, s), 7.90 (2H, d, J = 8.6 Hz), 7.86-7.78 (3H, m), 7.36-7.16 (4H, m), 5.21 (1H, s), 5.10-4.90 (2H, m), 3.52-3.42 (2H, m), 3.00 (3H, brs), 1.87 (3H, s), 1.70-1.60 (2H, m), 1.48-1.38 (3H, m), 0.98 (3H, t, J = 7.3 Hz) |
| 3-11 | 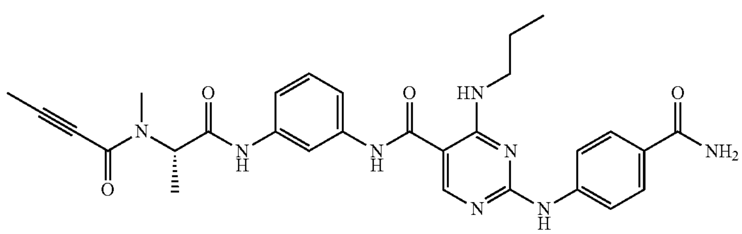 [SMILES: CC#CC(=O)N(C)[C@@H](C)C(=O)Nc1cccc(NC(=O)c2cnc(Nc3ccc(C(N)=O)cc3)nc2NCCC)c1] | MS m/z [M + H]: 557.3 |
| 3-12 | 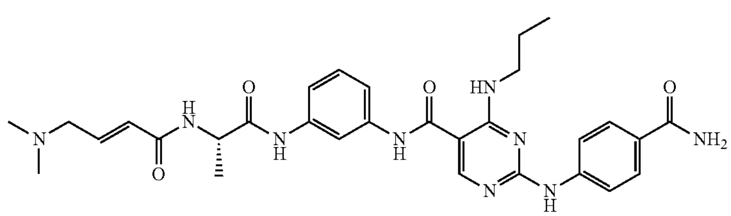 [SMILES: CCCNc1nc(Nc2ccc(C(N)=O)cc2)ncc1C(=O)Nc1cccc(NC(=O)[C@H](C)NC(=O)/C=C/CN(C)C)c1] | MS m/z [M + H]: 588.3 |
| 3-13 | 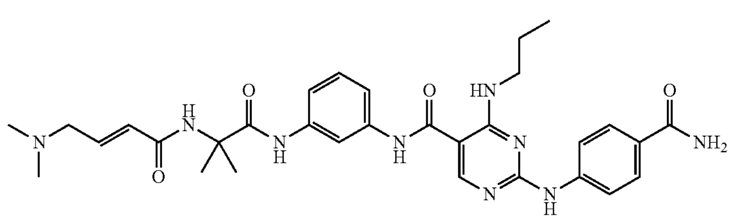 [SMILES: CCCNc1nc(Nc2ccc(C(N)=O)cc2)ncc1C(=O)Nc1cccc(NC(=O)C(C)(C)NC(=O)/C=C/CN(C)C)c1] | MS m/z [M + H]: 602.3 |

TABLE 41

| Compound No. | Structure | Physicochemical data |
|---|---|---|
| 3-14 | 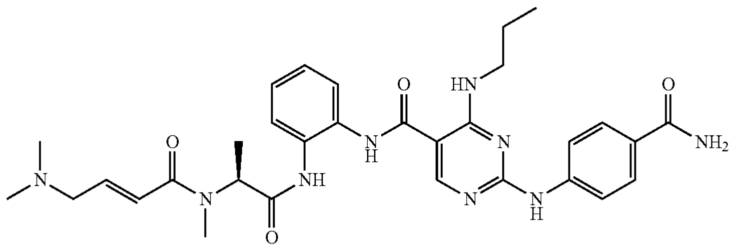 [SMILES: CCCNc1nc(Nc2ccc(C(N)=O)cc2)ncc1C(=O)Nc1ccccc1NC(=O)[C@H](C)N(C)C(=O)/C=C/CN(C)C] | ¹H-NMR (CDCl₃) δ: 9.07 (1H, s), 9.00 (1H, s), 8.85 (1H, t, J = 5.3 Hz), 8.54 (1H, s), 8.23 (1H, s), 7.76 (4H, s), 7.61 (1H, d, J = 7.3 Hz), 7.47 (1H, d, J = 6.6 Hz), 7.23-7.14 (2H, m), 6.90 (1H, dt, J = 15.2, 5.9 Hz), 6.36 (1H, d, J = 15.2 Hz), 6.21 (1H, brs), 5.26 (1H, q, J = 7.0 Hz), 3.45 (2H, q, J = 6.4 Hz), 3.04-3.02 (5H, m), 2.42 (1H, brs), 2.20 (6H, s), 1.66 (2H, dt, J = 14.4, 7.0 Hz), 1.44 (3H, d, J = 7.3 Hz), 0.99 (3H, t, J = 7.6 Hz) |
| 3-15 | 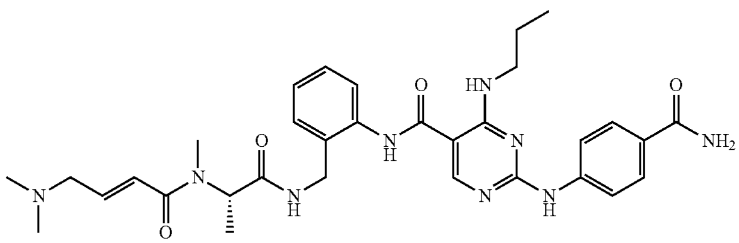 [SMILES: CCCNc1nc(Nc2ccc(C(N)=O)cc2)ncc1C(=O)Nc1ccccc1CNC(=O)[C@H](C)N(C)C(=O)/C=C/CN(C)C] | ¹H-NMR (CDCl₃) δ: 10.44 (1H, s), 9.06 (1H, t, J = 5.6 Hz), 8.92 (1H, s), 8.19 (1H, s), 7.75-7.74 (5H, m), 7.58 (1H, t, J = 6.3 Hz), 7.35-7.23 (2H, m), 7.11 (1H, t, J = 7.3 Hz), 6.90 (1H, dt, J = 15.2, 5.9 Hz), 6.37 (1H, d, J = 15.2 Hz), 6.16 (1H, brs), 5.15 (1H, q, J = 7.0 Hz), 4.38-4.18 (2H, m), 3.51 (2H, dd, J = 13.2, 6.6 Hz), 3.09 (2H, d, J = 5.3 Hz), 2.89 (3H, s), 2.70 (1H, brs), 2.26 (6H, s), 1.77-1.64 (2H, m), 1.37-1.30 (3H, m), 1.02 (3H, t, J = 7.3 Hz) |
| 3-16 | 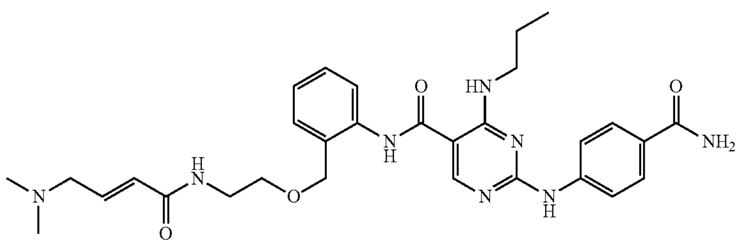 [SMILES: CCCNc1nc(Nc2ccc(C(N)=O)cc2)ncc1C(=O)Nc1ccccc1COCCNC(=O)/C=C/CN(C)C] | ¹H-NMR (CDCl₃ + CD₃OD) δ: 8.38 (1H, s), 8.11 (1H, d, J = 7.9 Hz), 7.82 (4H, s), 7.39 (1H, t, J = 7.6 Hz), 7.23 (1H, d, J = 7.3 Hz), 7.11 (1H, t, J = 7.6 Hz), 6.75 (1H, dt, J = 15.6, 6.1Hz), 5.95 (1H, d, J = 15.6 Hz), 4.67 (2H, s), 3.65 (2H, t, J = 5.0 Hz), 3.56-3.49 (4H, m), 3.01 (2H, t, J = 3.3 Hz), 2.21 (6H, s), 1.79-1.67 (2H, m), 1.04 (3H, t, J = 7.6 Hz) |
| 3-17 | 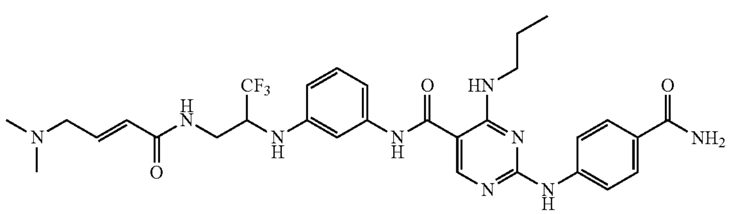 [SMILES: CCCNc1nc(Nc2ccc(C(N)=O)cc2)ncc1C(=O)Nc1cccc(NC(CNC(=O)/C=C/CN(C)C)C(F)(F)F)c1] | ¹H-NMR (CD₃OD) δ: 8.53 (1H, s), 7.86 (4H, brs), 7.41-7.35 (2H, m), 7.11-7.04 (1H, m), 6.51-6.46 (1H, m), 6.03 (1H, dt), 5.44 (1H, d), 4.97-4.76 (3H, m), 3.53 (2H, t), 3.06 (2H, d), 2.21 (6H, s), 1.77-1.66 (2H, m), 1.04 (3H, t) |

TABLE 42

| Compound No. | Structure | Physicochemical data |
|---|---|---|
| 3-18 | 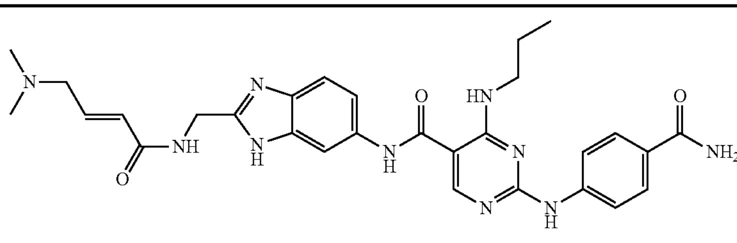 | ¹H-NMR (CD₃OD) δ: 8.59 (1H, s), 7.97-7.88 (1H, m), 7.86 (4H, d), 7.53-7.46 (1H, m), 7.39-7.31 (1H, m), 6.84 (1H, dt), 6.18 (1H, dt), 3.53 (2H, t), 3.17-3.08 (2H, m), 3.24 (2H, t), 2.24 (6H, s), 1.82-1.59 (2H, m), 1.04 (3H, t) |

TABLE 42-continued

| Compound No. | Structure | Physicochemical data |
|---|---|---|
| 3-19 | 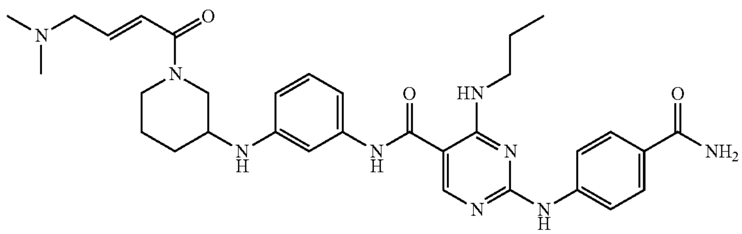 [SMILES: CCCNc1nc(Nc2ccc(C(N)=O)cc2)ncc1C(=O)Nc1cccc(NC2CCCN(C(=O)/C=C/CN(C)C)C2)c1] | ¹H-NMR (CD₃COCD₃) δ: 8.67 (1H, s), 8.00 (2H, d), 7.92 (2H, d), 7.33-6.89 (3H, m), 6.69-6.57 (1H, m), 6.51-6.40 (2H, m), 4.09-3.99 (3H, m), 3.59 (4H, m), 3.34-3.00 (2H, m), 2.13 (6H, s), 1.87-1.50 (6H, m), 1.03 (3H, t) |
| 3-20 | 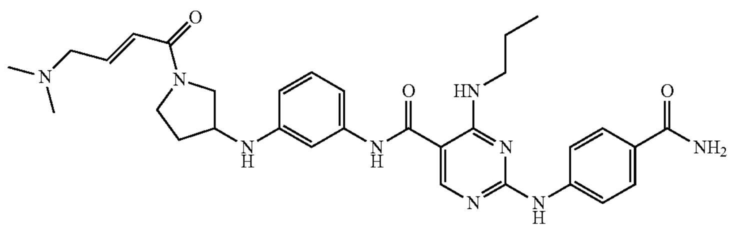 [SMILES: CCCNc1nc(Nc2ccc(C(N)=O)cc2)ncc1C(=O)Nc1cccc(NC2CCN(C(=O)/C=C/CN(C)C)C2)c1] | ¹H-NMR (CD₃COCD₃) δ: 8.64 (1H, s), 8.00 (2H, d), 7.92 (2H, d), 7.25-6.90 (3H, m), 6.79-6.67 (1H, m), 6.48-6.31 (2H, m), 4.11-3.39 (7H, m), 3.02 (2H, t), 2.18 (6H, s), 2.18-2.12 (2H, m), 1.77-1.67 (2H, m), 1.03 (3H, t) |
| 3-21 | 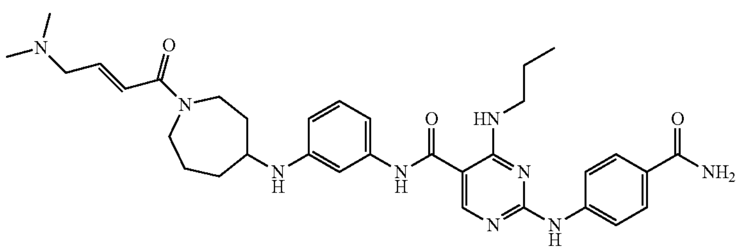 [SMILES: CCCNc1nc(Nc2ccc(C(N)=O)cc2)ncc1C(=O)Nc1cccc(NC2CCCN(C(=O)/C=C/CN(C)C)CC2)c1] | ¹H-NMR (CD₃COCD₃) δ: 8.63 (1H, s), 8.00 (2H, d), 7.92 (2H, d), 7.11-7.06 (1H, m), 7.05-7.0 (1H, m), 6.96-6.90 (1H, m), 6.81-6.69 (1H, m), 6.57 (1H, dt), 6.36 (1H, d), 3.82-3.40 (7H, m), 3.04 (2H, d), 2.17 (6H, s), 2.08-2.03 (4H, m), 1.80-1.66 (4H, m), 1.04 (3H, t) |
| 3-22 | 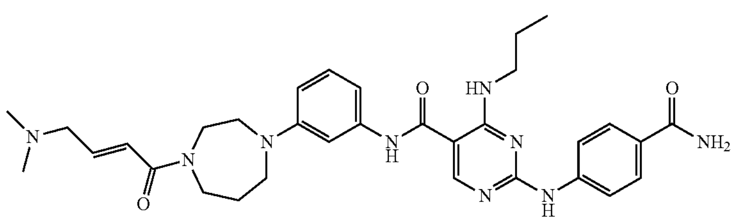 [SMILES: CCCNc1nc(Nc2ccc(C(N)=O)cc2)ncc1C(=O)Nc1cccc(N2CCCN(C(=O)/C=C/CN(C)C)CC2)c1] | ¹H-NMR (CD₃COCD₃) δ: 8.56 (1H, s), 8.01 (2H, d), 7.93 (2H, d), 7.24-7.19 (1H, m), 7.15-7.03 (2H, m), 6.60-6.51 (3H, m), 3.87-3.43 (10H, m), 3.06-2.94 (2H, m), 2.17 (6H, s), 1.74 (2H, dt), 1.41 (2H, dd), 1.03 (3H, t) |
| 3-23 | 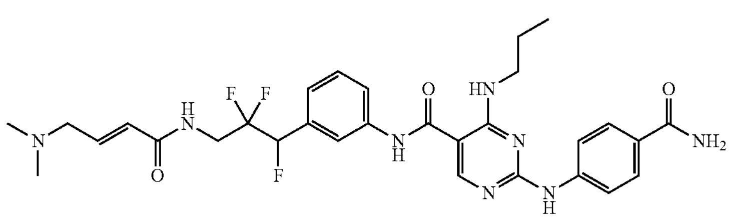 [SMILES: CCCNc1nc(Nc2ccc(C(N)=O)cc2)ncc1C(=O)Nc1cccc(C(F)C(F)(F)CNC(=O)/C=C/CN(C)C)c1] | ¹H-NMR (CD₃COCD₃) δ: 8.73 (1H, s), 8.01 (2H, d), 7.94 (2H, d), 7.60-7.52 (1H, m), 7.47-7.40 (1H, m), 7.27-7.22 (1H, m), 6.76 (1H, m), 6.18 (1H, m), 5.83 (1H, m), 4.00-3.84 (1H, m), 3.83-3.69 (1H, m), 3.61-3.53 (1H, m), 3.01 (1H, m), 2.17 (6H, s), 1.81-1.67 (2H, m), 1.03 (3H, t) |
| 3-24 | 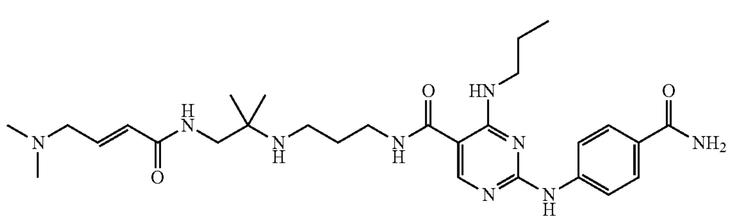 [SMILES: CCCNc1nc(Nc2ccc(C(N)=O)cc2)ncc1C(=O)NCCCNC(C)(C)CNC(=O)/C=C/CN(C)C] | ¹H-NMR (CD₃OD) δ: 8.40 (1H, s), 7.86-7.83 (4H, brs), 6.75 (1H, dt), 6.13 (1H, d), 3.50 (2H, t), 3.39 (2H, t), 3.32-3.28 (2H, t), 3.09 (2H, d), 2.66 (2H, t), 2.23 (6H, s), 1.80-1.61 (4H, m), 1.10 (6H, s), 1.03 (3H, t) |

TABLE 43

| Compound No. | Structure | Physicochemical data |
|---|---|---|
| 3-25 | 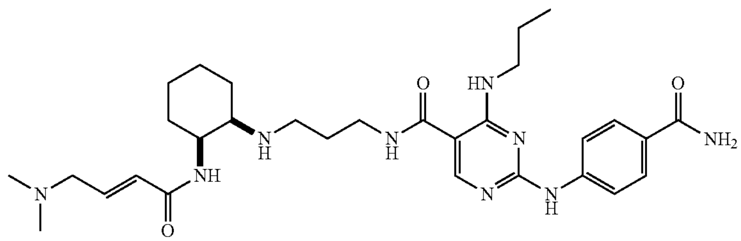 | ¹H-NMR (CD₃OD) δ: 8.38 (1H, s), 7.86-7.83 (1H, brs), 6.73 (1H, dt), 6.18 (1H, d), 3.50 (2H, t), 3.40-3.31 (4H, m), 3.05 (2H, d), 2.31-2.11 (3H, m), 2.20 (6H, s), 1.80-1.45 (8H, m), 1.04-0.93 (4H, m), 1.03 (3H, t) |
| 3-26 | 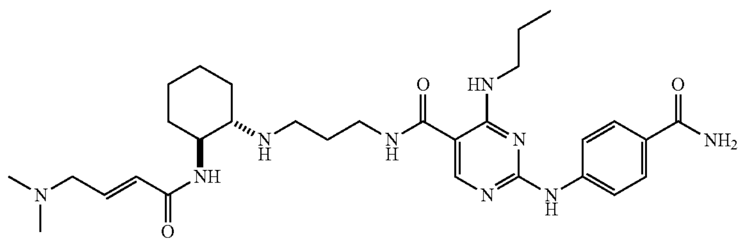 | ¹H-NMR (CD₃OD) δ: 8.45 (1H, s), 8.36 (4H, s), 6.74 (1H, dt), 6.08 (1H, d), 3.50 (2H, t), 3.41-3.28 (3H, m), 3.06 (2H, m), 2.32-2.10 (3H, m), 2.22 (6H, s), 1.80-1.63 (8H, m), 1.05-0.90 (4H, m), 1.03 (3H, t) |
| 3-27 | 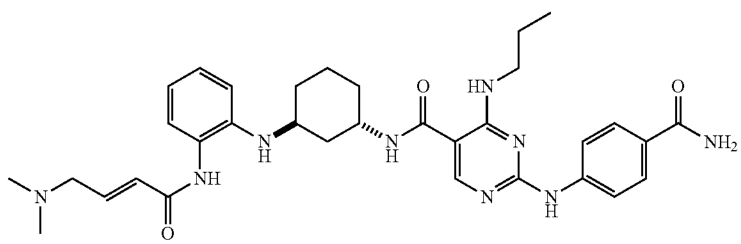 | ¹H-NMR (CD₃COCD₃) δ: 8.48 (1H, s), 7.98 (2H, d), 7.91 (2H, d), 7.33 (1H, dd), 7.04 (1H, t), 6.88 (1H, dt), 6.78 (1H, d), 6.63 (1H, t), 6.37 (1H, d), 4.09-3.98 (1H, m), 3.55-3.43 (3H, m), 3.07 (2H, d), 2.05 (6H, s), 1.96-1.50 (8H, m), 1.01 (3H, t) |
| 3-28 | 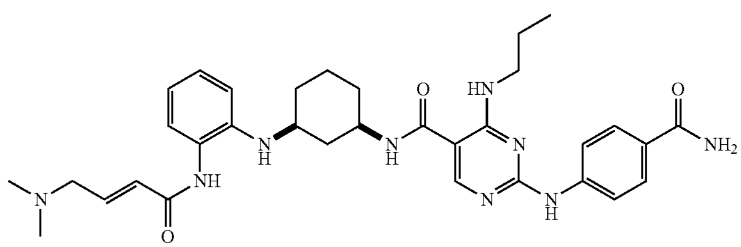 | ¹H-NMR (CD₃COCD₃) δ: 8.51 (1H, s), 7.98 (2H, d), 7.91 (2H, d), 7.33 (1H, dd), 7.04 (1H, t), 6.88 (1H, dt), 6.78 (1H, d), 6.63 (1H, t), 6.37 (1H, d), 4.37-4.25 (1H, m), 3.90-3.77 (1H, m), 3.54-3.45 (2H, m), 3.07 (2H, d), 2.05 (6H, s), 1.96-1.50 (8H, m), 1.01 (3H, t) |
| 3-29 | 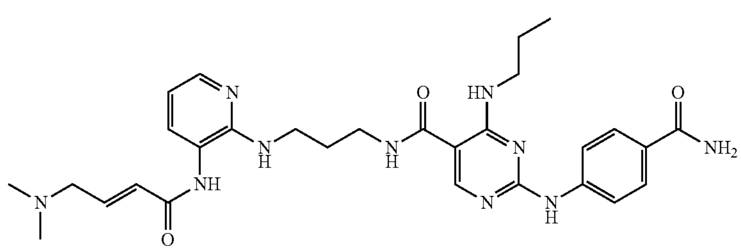 [SMILES: CCCNc1nc(Nc2ccc(C(N)=O)cc2)ncc1C(=O)NCCCNc1ncccc1NC(=O)/C=C/CN(C)C] | ¹H-NMR (CD₃OD) δ: 8.37 (1H, s), 7.93-7.90 (1H, m), 7.85-7.83 (4H, brs), 7.50-7.45 (1H, m), 6.90 (1H, dt), 6.63-6.56 (1H, m), 3.54-3.37 (4H, m), 3.23-3.12 (4H, m), 2.15 (6H, s), 1.98-1.83 (2H, m), 1.75-1.65 (2H, m), 1.03 (3H, t) |
| 3-30 | 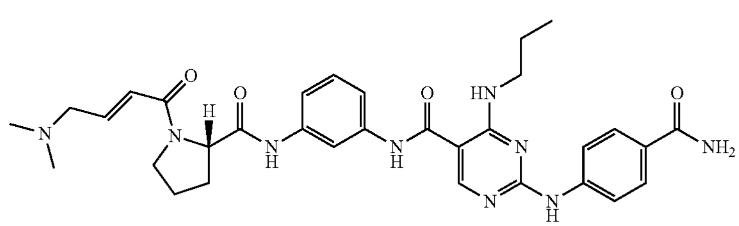 [SMILES: CCCNc1nc(Nc2ccc(C(N)=O)cc2)ncc1C(=O)Nc1cccc(NC(=O)[C@@H]2CCCN2C(=O)/C=C/CN(C)C)c1] | ¹H-NMR (DMSO-d₆) δ: 10.06-9.98 (2H, m), 9.88 (1H, s), 8.84 (1H, brs), 8.72 (1H, s), 8.09 (1H, s), 7.92-7.78 (5H, m), 7.34-7.14 (4H, m), 6.66-6.54 (1H, m), 6.43 (1H, d, J = 15.2 Hz), 4.54-4.48 (1H, m), 3.74-3.58 (2H, m), 3.52-3.42 (2H, m), 3.04 (2H, d, J = 5.3 Hz), 2.16 (6H, s), 2.00-1.86 (4H, m), 1.70-1.60 (2H, m), 0.98 (3H, t, J = 7.6 Hz) |

TABLE 43-continued

| Compound No. | Structure | Physicochemical data |
|---|---|---|
| 3-31 | 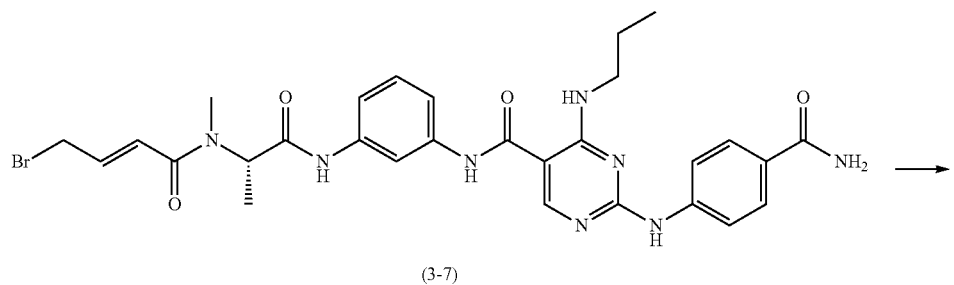 | $^1$H-NMR (CD$_3$COCD$_3$) δ: 8.68 (1H, s), 8.01 (2H, d), 7.93 (2H, d), 7.47-7.43 (1H, m), 7.28-7.17 (2H, m), 6.81-6.59 (3H, m), 3.83-3.72 (4H, brs), 3.61-3.52 (2H, m), 3.25-3.16 (4H, brs), 3.05 (2H, d), 2.19 (6H, s), 1.74 (2H, dt), 1.03 (3H, t) |

Example 10

[Formula 126]

(3-7)

(4-1)

To a solution of (S,E)-N-(3-(2-(4-bromo-N-methyl-2-butenamido)propanamido)phenyl)-2-((4-carbamoylphenyl)amino)-4-(propylamino)pyrimidine-5-carboxamide (3-7, 100 mg) in N,N-dimethylformamide (2 mL), piperazine (135 mg) was added at room temperature, and the mixture was stirred at the same temperature for 1 hour and 40 minutes. The solvent was evaporated under reduced pressure, and the obtained residue was purified by basic silica gel column chromatography (eluent, 85% ethyl acetate/15% methanol) to obtain (S,E)-2-((4-carbamoylphenyl)amino)-N-(3-(2-(N-methyl-4-(piperazin-1-yl)-2-butenamido)propanamido)phenyl)-4-(propylamino)pyrimidine-5-carboxamide (4-1, 57 mg) as white solid.

$^1$H-NMR (CDCl$_3$+CD$_3$OD) δ: 8.45 (1H, s), 7.84-7.76 (5H, m), 7.45 (1H, d, J=7.9 Hz), 7.32-7.23 (2H, m), 6.95 (1H, dt, J=15.2, 6.3 Hz), 6.47 (1H, d, J=15.2 Hz), 5.28 (1H, q, J=7.3 Hz), 3.50 (2H, t, J=7.3 Hz), 3.18 (2H, d, J=6.3 Hz), 3.07 (3H, s), 2.90-2.85 (4H, m), 2.48 (4H, brs), 1.78-1.66 (2H, m), 1.43 (3H, d, J=7.3 Hz), 1.03 (3H, t, J=7.3 Hz)

Example 11

In the same manner as that of Example 10, Compounds (4-2) to (4-15) were obtained.

TABLE 44

| Compound No. | Structure | Physicochemical data |
|---|---|---|
| 4-2 | 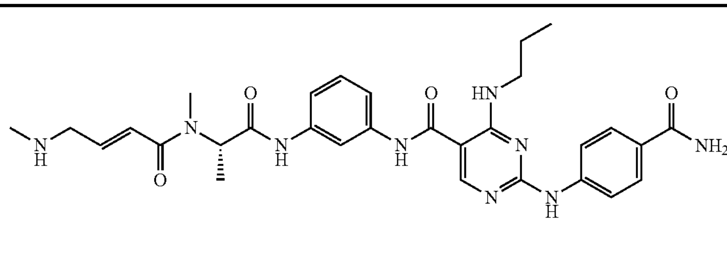 | $^1$H-NMR (CDCl$_3$ + CD$_3$OD) δ: 8.46 (1H, s), 7.90-7.75 (5H, m), 7.42-7.27 (3H, m), 6.96 (1H, d, J = 14.5 Hz), 6.46 (1H, d, J = 14.5 Hz), 5.28 (1H, d, J = 7.3 Hz), 3.50-3.28 (4H, m), 3.08 (3H, s), 2.44 (3H, s), 1.73-1.63 (2H, m), 1.44 (3H, d, J = 6.6 Hz), 1.03 (3H, t, J = 7.3 Hz) |

TABLE 44-continued

| Compound No. | Structure | Physicochemical data |
|---|---|---|
| 4-3 | 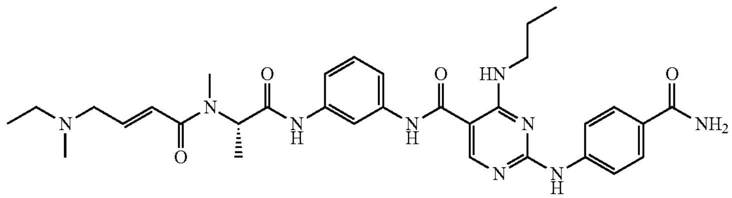 [SMILES: CCCNc1nc(Nc2ccc(C(N)=O)cc2)ncc1C(=O)Nc1cccc(NC(=O)[C@H](C)N(C)C(=O)/C=C/CN(C)CC)c1] | ¹H-NMR (CDCl₃ + CD₃OD) δ: 8.45 (1H, s), 7.80-7.75 (5H, m), 7.46 (1H, d, J = 6.6 Hz), 7.31-7.27 (2H, m), 6.96 (1H, dt, J = 15.0, 5.9 Hz), 6.46 (1H, d, J = 15.0 Hz), 5.29 (1H, q, J = 6.8 Hz), 3.49 (2H, t, J = 7.3 Hz), 3.21 (2H, d, J = 5.9 Hz), 3.07 (3H, s), 2.52-2.45 (2H, m), 2.27 (3H, s), 1.71-1.63 (2H, m), 1.43 (3H, d, J = 6.8 Hz), 1.12-0.90 (6H, m) |
| 4-4 | 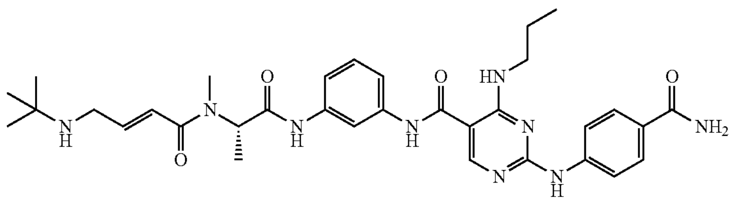 [SMILES: CCCNc1nc(Nc2ccc(C(N)=O)cc2)ncc1C(=O)Nc1cccc(NC(=O)[C@H](C)N(C)C(=O)/C=C/CNC(C)(C)C)c1] | ¹H-NMR (CDCl₃ + CD₃OD) δ: 8.46 (1H, s), 7.84-7.75 (5H, m), 7.45 (1H, d, J = 7.3 Hz), 7.34-7.24 (2H, m), 7.00 (1H, dt, J = 15.2, 6.3 Hz), 6.47 (1H, d, J = 15.2 Hz), 5.29 (1H, q, J = 6.6 Hz), 3.51-3.39 (4H, m), 3.08 (3H, s), 1.77-1.65 (2H, m), 1.43 (3H, d, J = 6.6 Hz), 1.15 (9H, s), 1.03 (3H, t, J = 7.3 Hz) |
| 4-5 | 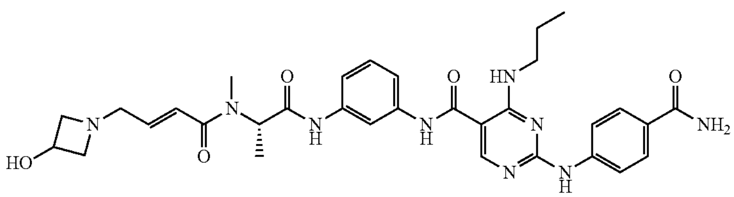 [SMILES: CCCNc1nc(Nc2ccc(C(N)=O)cc2)ncc1C(=O)Nc1cccc(NC(=O)[C@H](C)N(C)C(=O)/C=C/CN2CC(O)C2)c1] | ¹H-NMR (CDCl₃ + CD₃OD) δ: 8.45 (1H, s), 7.84-7.75 (5H, m), 7.45 (1H, d, J = 7.3 Hz), 7.30-7.24 (2H, m), 6.83 (1H, dt, J = 15.9, 5.1 Hz), 6.40 (1H, d, J = 15.9 Hz), 5.27 (1H, q, J = 7.3 Hz), 4.46-4.38 (1H, m), 3.72-3.66 (2H, m), 3.50 (2H, t, J = 7.3 Hz), 3.23-3.27 (2H, m), 3.07 (3H, s), 2.99 (2H, t, J = 7.3 Hz), 1.78-1.66 (2H, m), 1.43 (3H, d, J = 6.6 Hz), 1.03 (3H, t, J = 7.3 Hz) |
| 4-6 | 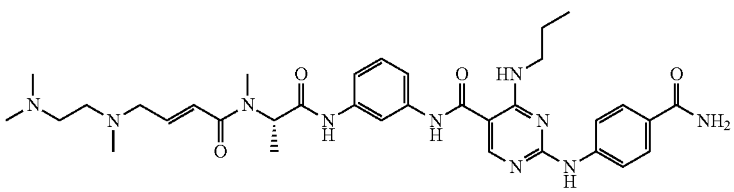 [SMILES: CCCNc1nc(Nc2ccc(C(N)=O)cc2)ncc1C(=O)Nc1cccc(NC(=O)[C@H](C)N(C)C(=O)/C=C/CN(C)CCN(C)C)c1] | MS m/z [M + H]: 659.4 |

TABLE 45

| Compound No. | Structure | Physicochemical data |
|---|---|---|
| 4-7 | 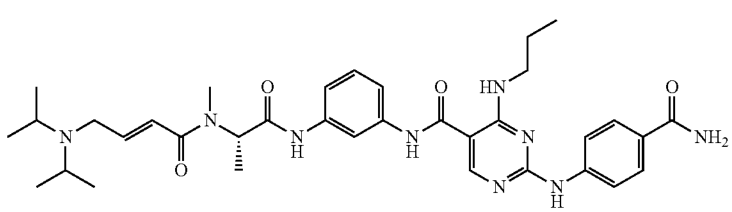 [SMILES: CCCNc1nc(Nc2ccc(C(N)=O)cc2)ncc1C(=O)Nc1cccc(NC(=O)[C@H](C)N(C)C(=O)/C=C/CN(C(C)C)C(C)C)c1] | ¹H-NMR (CD₃OD) δ: 8.56 (1H, s), 7.93 (1H, s), 7.89-7.82 (4H, m), 7.30-7.23 (3H, m), 6.87 (1H, dt, J = 15.0, 7.0 Hz), 6.67 (1H, d, J = 15.0 Hz), 5.19 (1H, q, J = 7.0 Hz), 3.52 (2H, t, J = 7.3 Hz), 3.35-3.30 (2H, m), 3.14 (3H, s), 3.10-3.01 (2H, m), 1.71 (2H, dt, J = 14.5, 7.3 Hz), 1.47 (3H, d, J = 7.0 Hz), 1.06-1.01 (15H, m) |
| 4-8 | 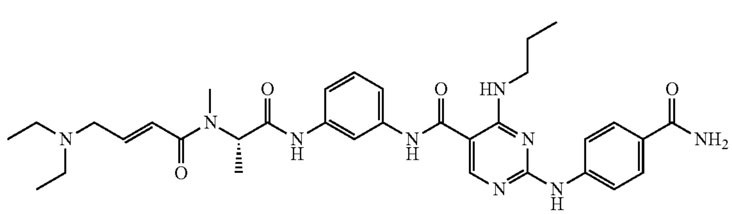 [SMILES: CCCNc1nc(Nc2ccc(C(N)=O)cc2)ncc1C(=O)Nc1cccc(NC(=O)[C@H](C)N(C)C(=O)/C=C/CN(CC)CC)c1] | ¹H-NMR (CDCl₃ + CD₃OD) δ: 8.44 (1H, s), 7.82-7.75 (5H, m), 7.46 (1H, dt, J = 4.5, 2.2 Hz), 7.31-7.27 (2H, m), 6.99 (1H, dt, J = 15.2, 6.3 Hz), 6.47 (1H, d, J = 15.2 Hz), 5.30 (1H, q, J = 7.0 Hz), 3.47 (2H, t, J = 7.3 Hz), 3.28 (2H, d, J = 6.3 Hz), 3.07 (3H, s), 2.56 (4H, q, J = 7.3 Hz), 1.76-1.64 (2H, m), 1.43 (3H, d, J = 7.3 Hz), 1.08-0.99 (9H, m) |

TABLE 45-continued

| Compound No. | Structure | Physicochemical data |
|---|---|---|
| 4-9 | 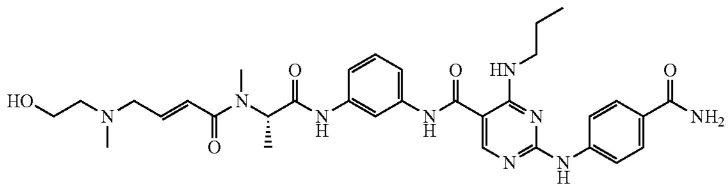 [SMILES: CCCNc1nc(Nc2ccc(C(N)=O)cc2)ncc1C(=O)Nc1cccc(NC(=O)[C@H](C)N(C)C(=O)/C=C/CN(C)CCO)c1] | ¹H-NMR (CDCl₃ + CD₃OD) δ: 8.45 (1H, s), 7.91-7.76 (5H, m), 7.43 (1H, s), 7.34-7.28 (2H, m), 6.94 (1H, d, J = 14.5 Hz), 6.49 (1H, d, J = 14.5 Hz), 5.29 (1H, d, J = 6.6 Hz), 3.65-3.27 (6H, m), 3.07 (3H, s), 2.70-2.43 (2H, m), 2.32 (3H, s), 1.72-1.67 (2H, m), 1.44 (3H, d, J = 7.3 Hz), 1.02 (3H, t, J = 7.3 Hz) |
| 4-10 | 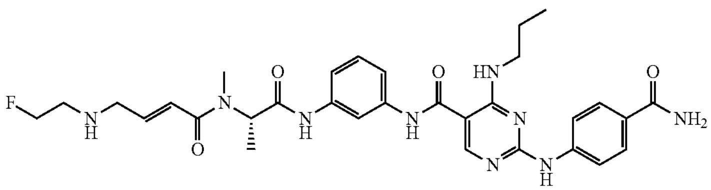 [SMILES: CCCNc1nc(Nc2ccc(C(N)=O)cc2)ncc1C(=O)Nc1cccc(NC(=O)[C@H](C)N(C)C(=O)/C=C/CNCCF)c1] | ¹H-NMR (CD₃OD) δ: 8.55 (1H, s), 7.99 (1H, s), 7.89-7.82 (4H, m), 7.30-7.28 (3H, m), 6.86 (1H, dt, J = 15.6, 5.9 Hz), 6.63 (1H, d, J = 15.6 Hz), 5.19 (1H, q, J = 7.0 Hz), 4.60 (1H, dd, J = 9.9, 4.6 Hz), 4.44 (1H, dd, J = 9.9, 4.6 Hz), 3.54-3.46 (4H, m), 3.16 (3H, s), 2.95 (1H, t, J = 4.6 Hz), 2.86 (1H, t, J = 4.6 Hz), 1.78-1.65 (2H, m), 1.47 (3H, d, J = 7.3 Hz), 1.03 (3H, t, J = 7.3 Hz) |
| 4-11 | 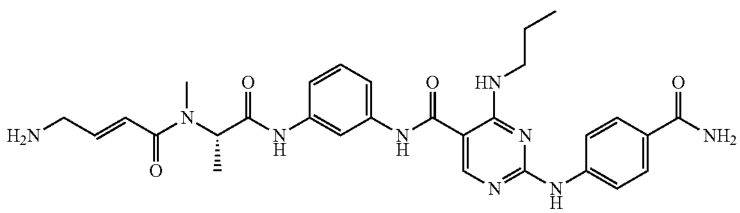 [SMILES: CCCNc1nc(Nc2ccc(C(N)=O)cc2)ncc1C(=O)Nc1cccc(NC(=O)[C@H](C)N(C)C(=O)/C=C/CN)c1] | ¹H-NMR (CDCl₃ + CD₃OD) δ: 8.44 (1H, s), 7.82-7.76 (5H, m), 7.44 (1H, d, J = 7.3 Hz), 7.31-7.22 (2H, m), 7.02 (1H, dt, J = 15.2, 5.1 Hz), 6.44 (1H, d, J = 15.2 Hz), 5.29 (1H, q, J = 7.3 Hz), 3.53-3.43 (4H, m), 3.08 (3H, s), 1.76-1.64 (2H, m), 1.43 (3H, d, J = 7.3 Hz), 1.02 (3H, t, J = 7.3 Hz) |

TABLE 46

| Compound No. | Structure | Physicochemical data |
|---|---|---|
| 4-12 | 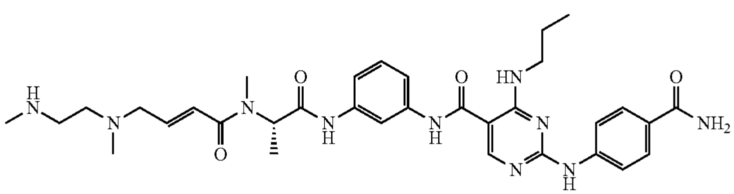 [SMILES: CCCNc1nc(Nc2ccc(C(N)=O)cc2)ncc1C(=O)Nc1cccc(NC(=O)[C@H](C)N(C)C(=O)/C=C/CN(C)CCNC)c1] | MS m/z [M + H]: 645.5 |
| 4-13 | 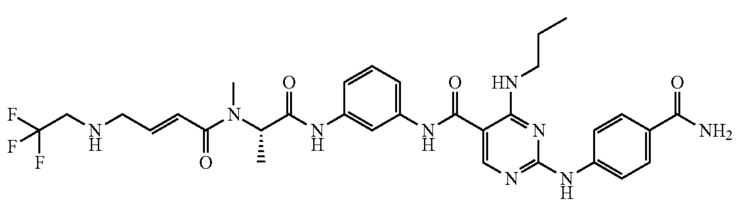 [SMILES: CCCNc1nc(Nc2ccc(C(N)=O)cc2)ncc1C(=O)Nc1cccc(NC(=O)[C@H](C)N(C)C(=O)/C=C/CNCC(F)(F)F)c1] | ¹H-NMR (CDCl₃ + CD₃OD) δ: 8.47 (1H, s), 7.82-7.79 (5H, m), 7.38-7.33 (3H, m), 6.92 (1H, d, J = 15.2 Hz), 6.54 (1H, d, J = 15.2 Hz), 5.28 (1H, d, J = 7.3 Hz), 3.56-3.48 (4H, m), 3.22 (2H, q, J = 9.0 Hz), 3.10 (3H, s), 1.78-1.66 (2H, m), 1.45 (3H, d, J = 7.3 Hz), 1.03 (3H, t, J = 7.6 Hz) |
| 4-14 | 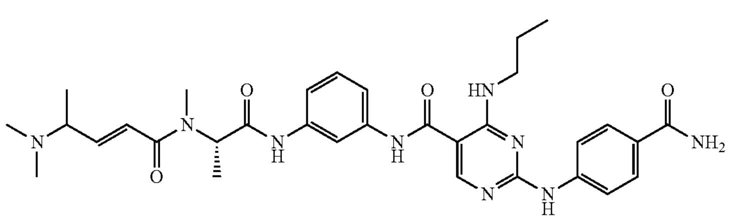 [SMILES: CCCNc1nc(Nc2ccc(C(N)=O)cc2)ncc1C(=O)Nc1cccc(NC(=O)[C@H](C)N(C)C(=O)/C=C/C(C)N(C)C)c1] | ¹H-NMR (CDCl₃) δ: 8.43 (1H, s), 7.80-7.73 (5H, m), 7.43 (1H, t, J = 2.3 Hz), 7.27 (2H, d, J = 5.3 Hz), 6.91 (1H, dd, J = 15.2, 7.9 Hz), 6.36 (1H, d, J = 15.2 Hz), 5.30 (1H, q, J = 7.3 Hz), 3.49-3.43 (2H, m), 3.17-3.02 (4H, m), 2.26 (6H, s), 1.74-1.62 (2H, m), 1.43 (3H, d, J = 7.3 Hz), 1.21 (3H, d, J = 7.3 Hz), 1.00 (3H, t, J = 7.3 Hz) |

TABLE 46-continued

| Compound No. | Structure | Physicochemical data |
|---|---|---|
| 4-15 | 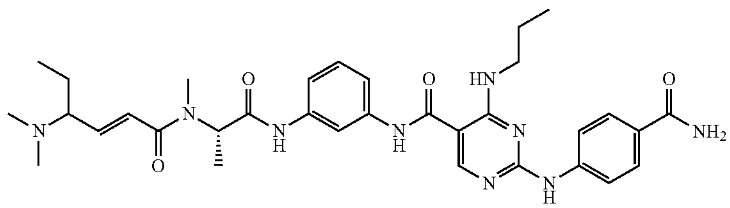 [SMILES: CCCNc1nc(Nc2ccc(C(N)=O)cc2)ncc1C(=O)Nc1cccc(NC(=O)[C@H](C)N(C)C(=O)/C=C/C(CC)N(C)C)c1] | $^1$H-NMR (CDCl$_3$) δ: 8.42 (1H, s), 7.80-7.73 (5H, m), 7.43 (1H, d, J = 3.3 Hz), 7.28 (2H, t, J = 5.9 Hz), 6.83 (1H, dd, J = 15.2, 9.2 Hz), 6.34 (1H, d, J = 15.2 Hz), 5.30 (1H, q, J = 6.8 Hz), 3.48-3.40 (2H, m), 3.09 (3H, s), 2.88-2.78 (1H, m), 2.27 (6H, d, J = 2.6 Hz), 1.72-1.64 (3H, m), 1.55-1.43 (4H, m), 1.00 (3H, t, J = 7.6 Hz), 0.88 (3H, dt, J = 7.4, 3.1 Hz) |

Example 12

1

[Formula 127]

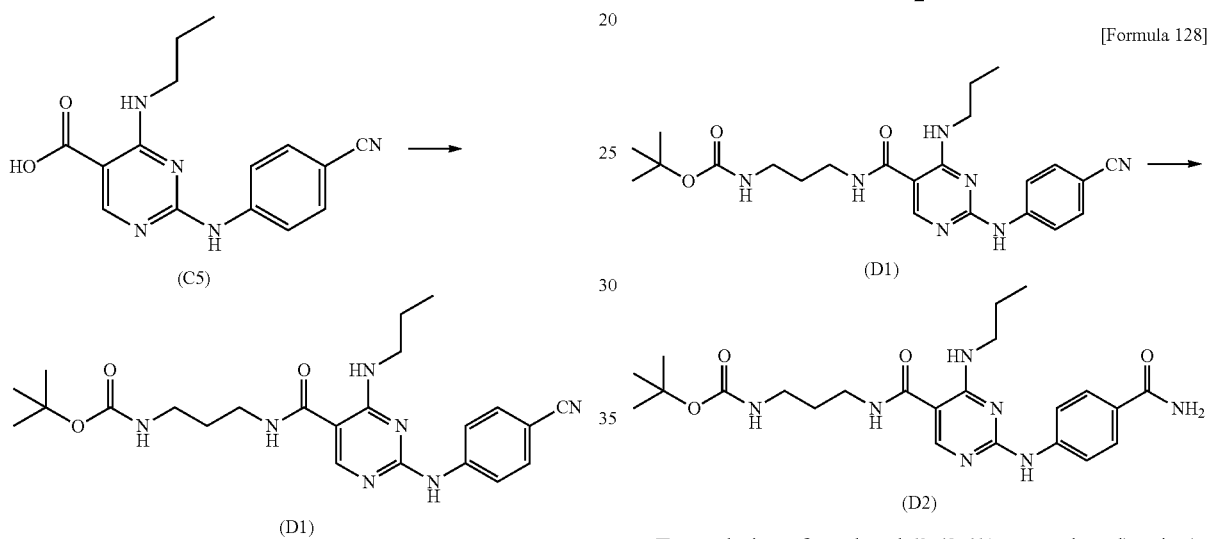

To 2-((4-cyanophenyl)amino)-4-(propylamino)pyrimidine-5-carboxylic acid (C5, 328 mg), N-Boc-1,3-propanediamine (289 μL), 1-ethyl-3-(3-dimethylaminopropyl)carbodiimide hydrochloride (846 mg), and 1-hydroxybenzotriazole monohydrate (676 mg), N,N-dimethylformamide (10 mL) and triethylamine (306 μL) were added at room temperature, and the mixture was stirred at the same temperature for 2 hours. To the reaction mixture, saturated aqueous sodium hydrogencarbonate and ethyl acetate were added. The organic layer was separated, washed successively with water and saturated aqueous sodium chloride, and then dried over anhydrous sodium sulfate, and the solvent was evaporated under reduced pressure. The obtained residue was purified by basic silica gel column chromatography (eluent, 50 to 30% hexane in ethyl acetate) to obtain tert-butyl (3-(2-((4-cyanophenyl)amino)-4-(propylamino)pyrimidine-5-carboxamido)propyl)carbamate (D1, 224 mg) as white solid.

2

[Formula 128]

To a solution of tert-butyl (3-(2-((4-cyanophenyl)amino)-4-(propylamino)pyrimidine-5-carboxamido)propyl)carbamate (D1, 220 mg) in ethanol (4 mL) and dimethyl sulfoxide (4 mL), 1.0 mol/L aqueous sodium hydroxide (2.4 mL) and 35% aqueous hydrogen peroxide (750 μL) were added at room temperature, and the mixture was stirred at the same temperature for 30 minutes. To the reaction mixture, water was added. The solid matter was taken by filtration, washed with water, and then dried under reduced pressure to obtain tert-butyl (3-(2-((4-carbamoylphenyl)amino)-4-(propylamino)pyrimidine-5-carboxamido)propyl)carbamate (D2, 195 mg) as white solid.

MS m/z (M+H): 472.3

3

[Formula 129]

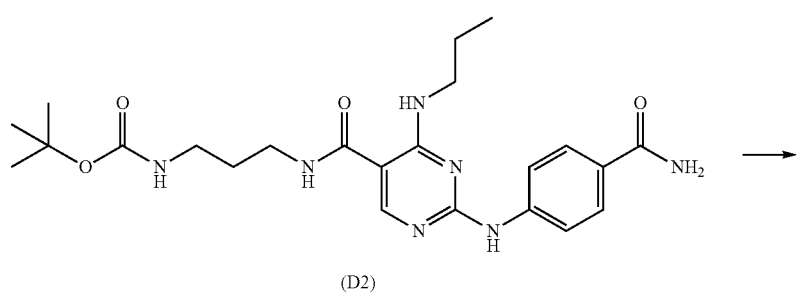

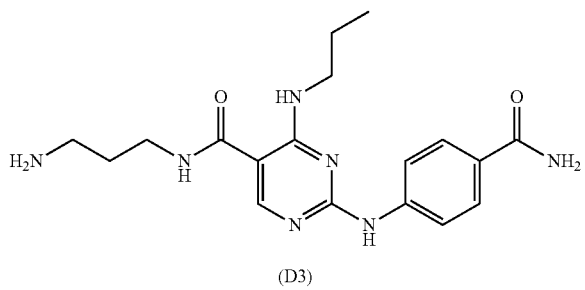

(D3)

To a suspension of tert-butyl (3-(2-((4-carbamoylphenyl)amino)-4-(propylamino)pyrimidine-5-carboxamido)propyl)carbamate (D2, 190 mg) in chloroform (8 mL) and methanol (2 mL), trifluoroacetic acid (1 mL) was added at room temperature, and the mixture was stirred at the same temperature for 30 minutes. The solvent was evaporated under reduced pressure to obtain N-(3-aminopropyl)-2-(4-carbamoylphenyl)amino)-4-(propylamino)pyrimidine-5-carboxamide (D3) trifluoroacetate (280 mg).

MS m/z (M+H): 372.3

4

[Formula 130]

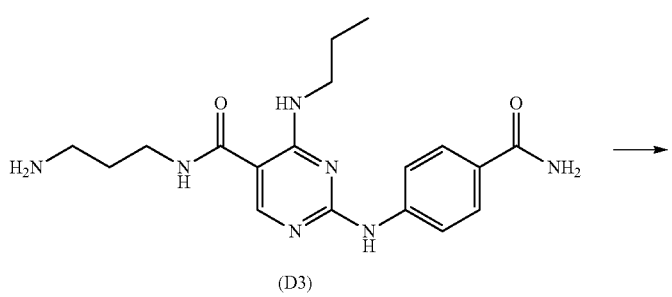

(D3)

→

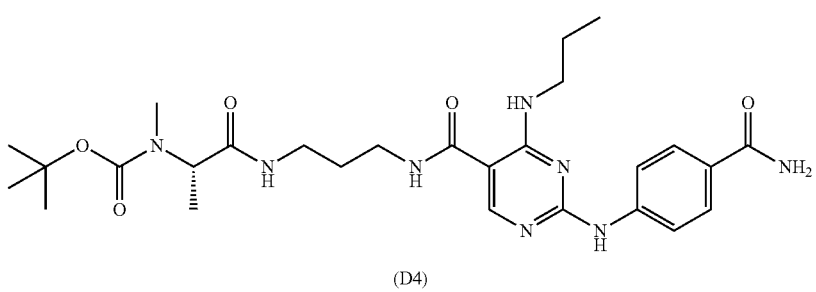

(D4)

To N-(3-aminopropyl)-2-(4-carbamoylphenyl)amino)-4-(propylamino)pyrimidine-5-carboxamide (D3) trifluoroacetate (100 mg), N-Boc-N-methyl-L-alanine (47 mg), 1-ethyl-3-(3-dimethylaminopropyl)carbodiimide hydrochloride (128 mg) and 1-hydroxybenzotriazole monohydrate (102 mg), N,N-dimethylformamide (2 mL) and triethylamine (116 μL) were added at room temperature, and the mixture was stirred at the same temperature for 1 hour. To the reaction mixture, water and ethyl acetate were added. The organic layer was separated, washed successively with water and saturated aqueous sodium chloride, and then dried over anhydrous sodium sulfate, and the solvent was evaporated under reduced pressure to obtain (S)-tert-butyl (1-((3-(2-((4-carbamoylphenyl)amino)-4-(propylamino)pyrimidine-5-carboxamido)propyl)amino)-1-oxopropan-2-yl)(methyl)carbamate (D4, 103 mg) as white solid.

MS m/z (M+H): 557.3

[Formula 131]

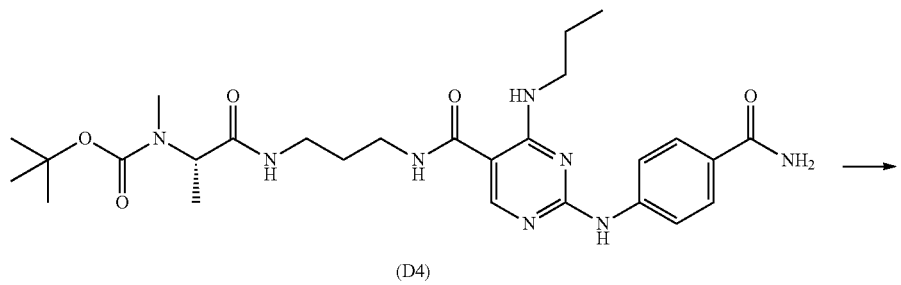

(D4)

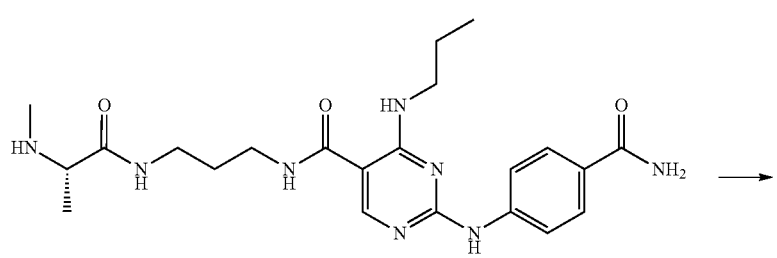

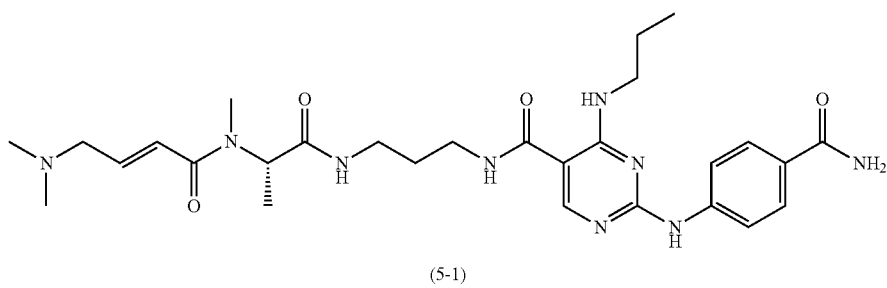

(5-1)

By using (S)-tert-butyl (1-((3-(2-((4-carbamoylphenyl)amino)-4-(propylamino)pyrimidine-5-carboxamido)propyl)amino)-1-oxopropan-2-yl)(methyl)carbamate (D4), (S,E)-2-((4-carbamoylphenyl)amino)-N-(3-(2-(4-(dimethylamino)-N-methyl-2-butenamido)propaneamido)propyl)-4-(propylamino)pyrimidine-5-carboxamide (5-1) was obtained as white solid in the same manner as that of Example 1, (6) and Example 1, (8).

$^1$H-NMR (DMSO-d$_6$) δ: 9.76 (1H, s), 9.05 (1H, brs), 8.50 (1H, s), 8.28 (1H, brs), 7.88-7.78 (6H, m), 7.15 (1H, s), 6.66-6.50 (2H, m), 4.99 (1H, d, J=6.6 Hz), 3.46-3.39 (2H, m), 3.25-2.75 (10H, m), 2.14 (6H, s), 1.66-1.61 (4H, m), 1.30-1.22 (2H, m), 0.96 (3H, t, J=7.6 Hz)

Example 13

1

By using Intermediates (D3), Intermediates (D5) and (D6) were obtained in the same manner as that of Example 12, (4).

TABLE 47

| Compound No. | Structure | Physicochemical data |
|---|---|---|
| D5 | 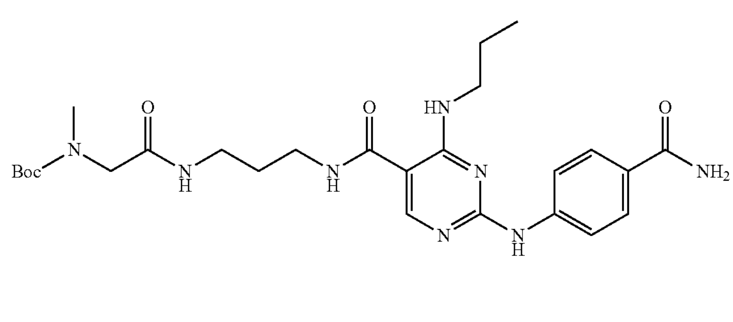 [SMILES: CCCNc1nc(Nc2ccc(C(N)=O)cc2)ncc1C(=O)NCCCNC(=O)CN(C)C(=O)OC(C)(C)C] | MS m/z (M + H): 543.4 |

TABLE 47-continued

| Compound No. | Structure | Physicochemical data |
|---|---|---|
| D6 | (structure) | — |

By using Intermediates (D4) to (D6), Compounds (5-2) to (5-5) were obtained in the same manner as that of Example 1, (6) to (8).

TABLE 48

| Compound No. | Structure | Physicochemical data |
|---|---|---|
| 5-2 | (structure) | MS m/z (M + H): 497.4 |
| 5-3 | (structure) | $^1$H-NMR (CDCl$_3$ + CD$_3$OD) δ: 8.34 (1H, s), 7.80 (4H, s), 6.63 (1H, dd, J = 16.5, 10.6 Hz), 6.35 (1H, d, J = 16.5 Hz), 5.80 (1H, d, J = 10.6 Hz), 5.15 (1H, q, J = 6.8 Hz), 3.38-3.29 (6H, m), 3.06 (3H, s), 1.75-1.68 (4H, m), 1.40 (3H, d, J = 6.8 Hz), 1.03 (3H, t, J = 7.3 Hz) |
| 5-4 | (structure) | $^1$H-NMR (CDCl$_3$ + CD$_3$OD) δ: 8.37 (1H, s), 7.83 (4H, d, J = 2.6 Hz), 6.80 (1H, dt, J = 15.6, 6.4 Hz), 6.09 (1H, d, J = 15.6 Hz), 4.47 (1H, q, J = 7.3 Hz), 3.49 (2H, t, J = 7.3 Hz), 3.36-3.28 (4H, m), 3.19-3.10 (2H, m), 2.25 (6H, s), 1.80-1.63 (4H, m), 1.41 (3H, d, J = 7.3 Hz), 1.04 (3H, t, J = 7.6 Hz) |
| 5-5 | (structure) | $^1$H-NMR (CDCl$_3$ + CD$_3$OD) δ: 8.35 (1H, s), 7.86-7.80 (4H, m), 6.90-6.81 (1H, m), 6.55 (1H, d, J = 15.2 Hz), 4.09 (2H, s), 3.50 (2H, t, J = 6.3 Hz), 3.36-3.31 (4H, m), 3.22 (3H, s), 3.18-3.08 (2H, m), 2.28 (6H, s), 1.76-1.61 (4H, m), 1.05 (3H, t, J = 7.3 Hz) |

Example 14

1

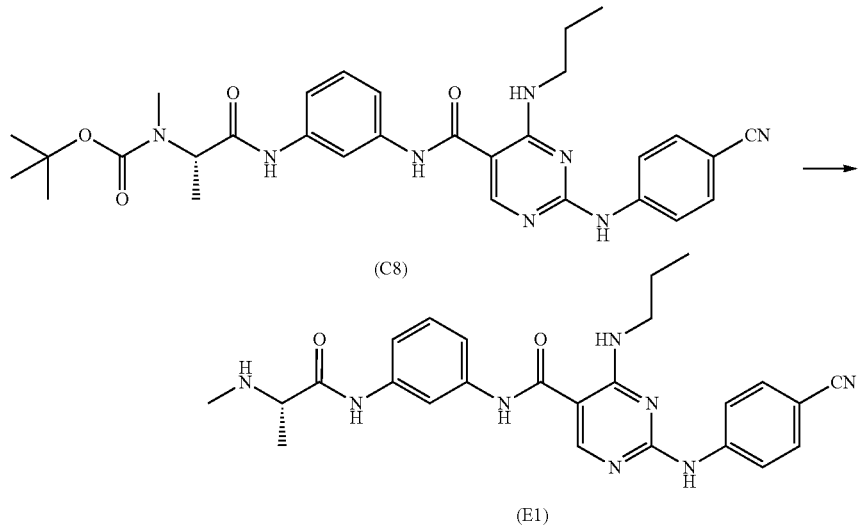

To a suspension of (S)-tert-butyl (1-((3-(2-((4-cyanophenyl)amino)-4-(propylamino)pyrimidine-5-carboxamido)phenyl)amino)-1-oxopropan-2-yl)(methyl)carbamate (C8, 325 mg) in 1,4-dioxane (6 mL), a 4.0 mol/L solution of hydrochloric acid in 1,4-dioxane (6 mL) was added at room temperature, and the mixture was stirred at the same temperature for 4 hours. The solvent was evaporated under reduced pressure, ethyl acetate was added to the obtained residue, and the solid matter was taken by filtration to obtain (S)-2-((4-cyanophenyl)amino)-N-(3-(2-(methylamino)propanamido)phenyl)-4-(propylamino)pyrimidine-5-carboxamide (E1) dihydrochloride (302 mg).

MS m/z (M+H): 473.2

2

To a solution of (S)-2-((4-cyanophenyl)amino)-N-(3-(2-(methylamino)propanamido)phenyl)-4-(propylamino)pyrimidine-5-carboxamide (E1) dihydrochloride (58 mg), 4-dimethylaminocrotonic acid hydrochloride (33 mg) and 1-ethyl-3-(3-dimethylaminopropyl)carbodiimide hydrochloride (38 mg) in N,N-dimethylformamide (1 mL), N,N-diisopropylethylamine (174 μL) was added at room temperature, and the mixture was stirred at the same temperature for 15 hours. To the reaction mixture, saturated aqueous sodium hydrogencarbonate was added. The solid matter was taken by filtration, washed with water, and then dried under reduced pressure. The obtained solid matter was purified by basic silica gel column chromatography (eluent, 98 to 88% ethyl acetate in methanol) to obtain (S,E)-2-((4-cyanophenyl)amino)-N-(3-(2-(4-(dimethylamino)-N-methyl-2-butenamido)propanamido)phenyl)-4-(propylamino)pyrimidine-5-carboxamide (6-1, 41 mg) as white solid.

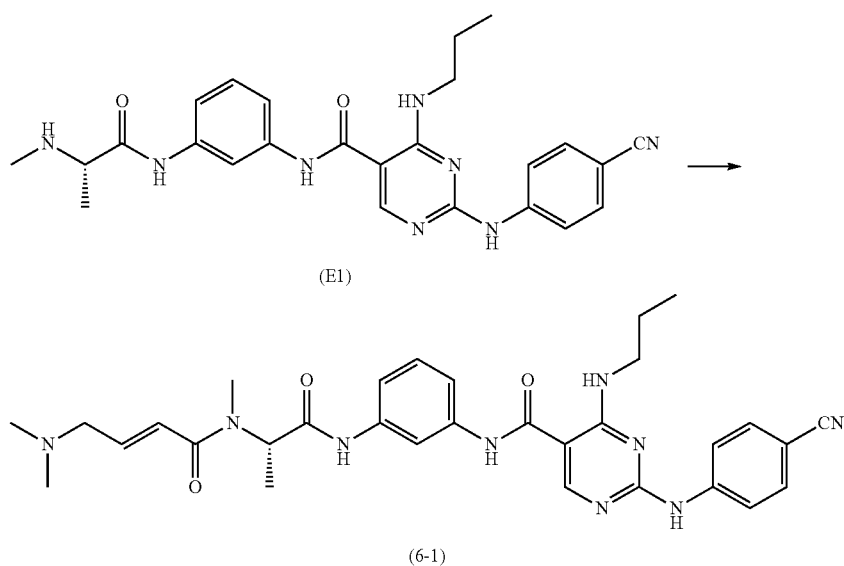

$^1$H-NMR (CDCl$_3$) δ: 8.84 (1H, s), 8.79 (1H, brs), 8.38 (1H, s), 7.85 (2H, s), 7.79 (2H, d, J=8.6 Hz), 7.59 (2H, d, J=8.6 Hz), 7.50 (1H, s), 7.36 (1H, d, J=7.9 Hz), 7.30-7.24 (1H, m), 7.15 (1H, d, J=7.9 Hz), 6.99 (1H, dt, J=15.2, 5.9 Hz), 6.44 (1H, d, J=15.2 Hz), 5.30 (1H, q, J=6.9 Hz), 3.52-3.42 (2H, m), 3.11 (2H, d, J=4.6 Hz), 3.03 (3H, s), 2.27 (6H, s), 1.76-1.66 (2H, m), 1.43 (3H, d, J=7.3 Hz), 1.02 (3H, t, J=6.9 Hz)

Example 15

1

[Formula 134]

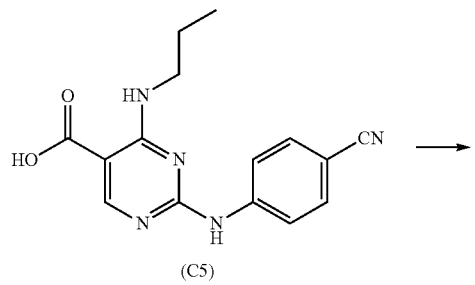

(C5)

→

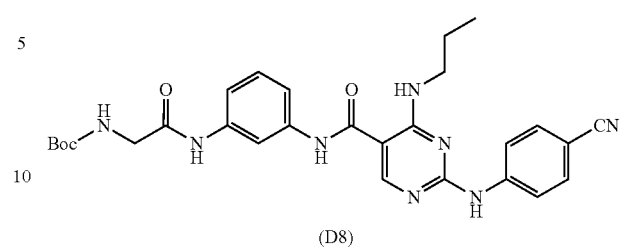

(D8)

By using tert-butyl (2-((3-aminophenyl)amino)-2-oxoethyl)carbamate (B1) and 2-((4-cyanophenyl)amino)-4-(propylamino)pyrimidine-5-carboxylic acid (C5), tert-butyl (2-((3-(2-((4-cyanophenyl)amino)-4-(propylamino) pyrimidine-5-carboxamido)phenyl)amino)-2-oxoethyl) carbamate (D8) was obtained in the same manner as that of Example 12, (1).

2

[Formula 135]

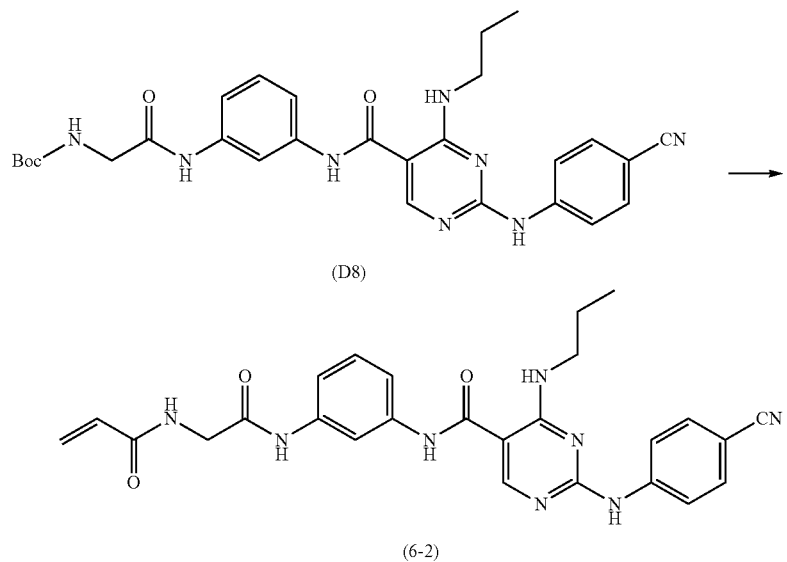

By using tert-butyl (2-((3-(2-((4-cyanophenyl)amino)-4-(propylamino)pyrimidine-5-carboxamido)phenyl)amino)-2-oxoethyl)carbamate (D8), N-(3-(2-(acrylylamido)acetamido)phenyl)-2-((4-cyanophenyl)amino)-4-(propylamino) pyrimidine-5-carboxamide (6-2) was obtained as white solid in the same manner as that of Example 1, (6) and Example 1, (7).

MS m/z[M+H]: 499.3

Example 16

1

By using Intermediates (C3), Intermediate (E2) was obtained in the same manner as that of Example 7, (4).

By using Intermediates (A1), Intermediate (E3) was obtained in the same manner as that of Example 7, (1).

TABLE 49

| Compound No. | Structure | Physicochemical data |
|---|---|---|
| E2 | ethyl 4-(propylamino)-2-((3-cyanophenyl)amino)pyrimidine-5-carboxylate | — |
| E3 | ethyl 4-(propylamino)-2-((3-fluorophenyl)amino)pyrimidine-5-carboxylate | MS m/z (M + H): 319.2 |

(2) By using Intermediates (E2) and (E3), Intermediates (E27) and (E28) were obtained in the same manner as that of Example 7, (5).

TABLE 50

| Compound No. | Structure | Physicochemical data |
|---|---|---|
| E27 | 4-(propylamino)-2-((3-cyanophenyl)amino)pyrimidine-5-carboxylic acid | MS m/z (M + H): 298.1 |
| E28 | 4-(propylamino)-2-((3-fluorophenyl)amino)pyrimidine-5-carboxylic acid | MS m/z (M + H): 290.1 |

(3) By using Intermediates (E27) and (E28), Intermediates (E29) and (E30) were obtained in the same manner as that of Example 7, (9).

TABLE 51

| Compound No. | Structure | Physicochemical data |
|---|---|---|
| E29 | 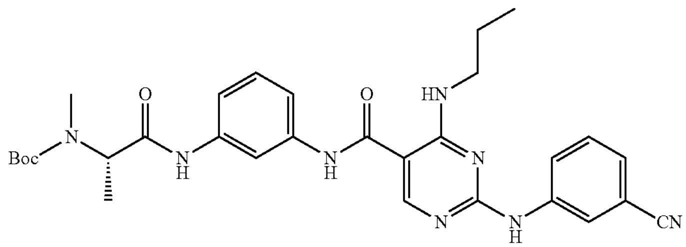 [SMILES: CCCNc1nc(Nc2cccc(C#N)c2)ncc1C(=O)Nc1cccc(NC(=O)[C@H](C)N(C)C(=O)OC(C)(C)C)c1] | MS m/z (M + H): 573.3 |
| E30 | 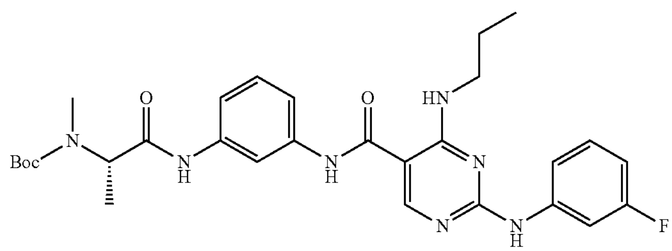 [SMILES: CCCNc1nc(Nc2cccc(F)c2)ncc1C(=O)Nc1cccc(NC(=O)[C@H](C)N(C)C(=O)OC(C)(C)C)c1] | MS m/z (M + H): 566.3 |

[Formula 136]

By using (S)-tert-butyl (1-((3-(2-((3-cyanophenyl)amino)-4-(propylamino)pyrimidine-5-carboxamido)phenyl)amino)-1-oxopropan-2-yl)(methyl)carbamate (E29), (S,E)-2-((3-cyanophenyl)amino)-N-(3-(2-(4-(dimethylamino)-N-methyl-2-butenamido)propanamido)phenyl)-4-(propylamino)pyrimidine-5-carboxamide (6-3) was obtained as white solid in the same manner as that of Example 14, (1) and Example 14, (2).

$^1$H-NMR (DMSO-d$_6$) δ: 10.03 (1H, s), 10.00 (1H, s), 9.95 (1H, s), 8.86 (1H, brs), 8.73 (1H, s), 8.47 (1H, s), 8.08 (1H, s), 7.95 (1H, d, J=7.9 Hz), 7.50 (1H, t, J=7.9 Hz), 7.40 (1H, d, J=7.3 Hz), 7.36-7.20 (3H, m), 6.68-6.54 (2H, m), 5.14-5.06 (1H, m), 3.46 (2H, q, J=6.6 Hz), 3.05 (5H, brs), 2.15 (6H, s), 1.70-1.58 (2H, m), 1.36 (3H, d, J=7.3 Hz), 0.97 (3H, t, J=7.3 Hz)

Example 17

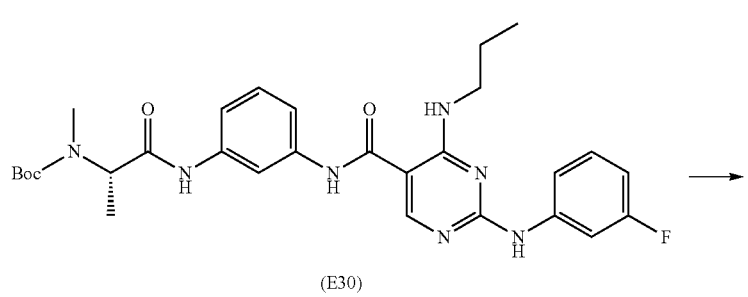

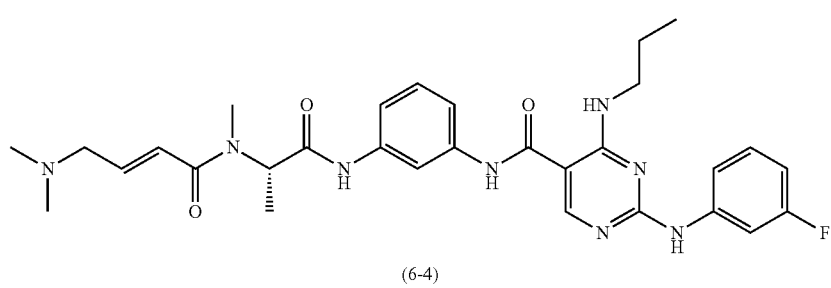

By using (S)-tert-butyl (1-((3-(2-((3-fluorophenyl) amino)-4-(propylamino)pyrimidine-5-carboxamido)phenyl) amino)-1-oxopropan-2-yl)(methyl)carbamate (E30), (S,E)-N-(3-(2-(4-(dimethylamino)-N-methyl-2-butenamido) propanamido)phenyl)-2-((3-fluorophenyl)amino)-4-(propylamino)pyrimidine-5-carboxamide (6-4) was obtained as white solid in the same manner as that of Example 14, (1) and Example 14, (2).

$^1$H-NMR (CDCl$_3$) δ: 8.86 (1H, s), 8.76 (1H, brs), 8.37 (1H, s), 7.97 (1H, s), 7.84-7.78 (2H, m), 7.47 (1H, s), 7.36 (1H, d, J=7.9 Hz), 7.28-7.10 (4H, m), 6.98 (1H, dt, J=15.2, 5.9 Hz), 6.75-6.68 (1H, m), 6.43 (1H, d, J=15.2 Hz), 5.30 (1H, q, J=7.0 Hz), 3.52-3.44 (2H, m), 3.10 (2H, d, J=4.6 Hz), 3.03 (3H, s), 2.26 (6H, s), 1.74-1.64 (2H, m), 1.42 (3H, d, J=6.6 Hz), 1.01 (3H, t, J=7.6 Hz)

Example 18

1

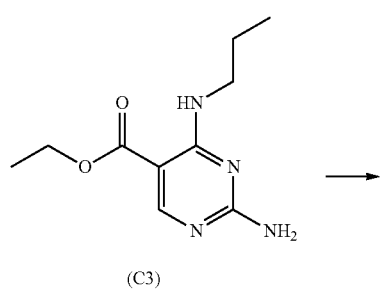

2

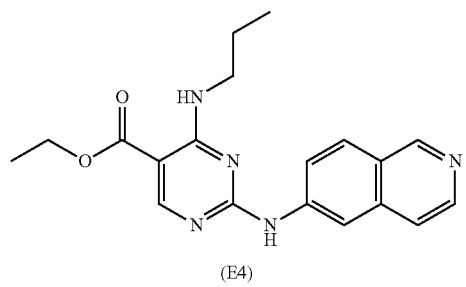

By using 6-bromoisoquinoline, ethyl 2-((isoquinolin-6-yl) amino)-4-(propylamino)pyrimidine-5-carboxylate (E4) was obtained in the same manner as that of Example 7, (4).

MS m/z (M+H): 352.2

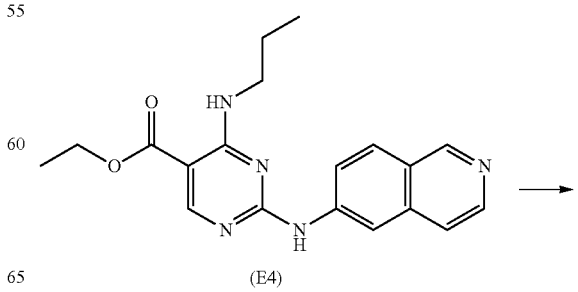

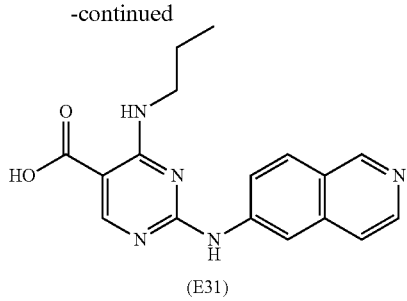

(E31)

By using ethyl 2-((isoquinolin-6-yl)amino)-4-(propylamino)pyrimidine-5-carboxylate (E4), 2-((isoquinolin-6-yl)amino)-4-(propylamino)pyrimidine-5-carboxylic acid (E31) was obtained in the same manner as that of Example 7, (5).
MS m/z (M+H): 324.2

3

[Formula 140]

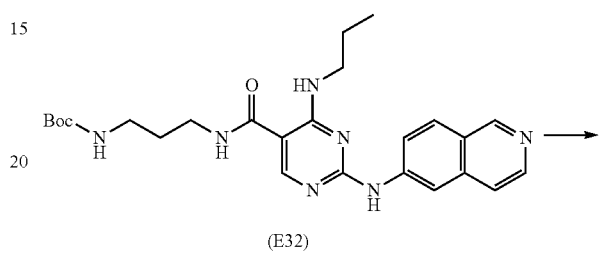

By using 2-((isoquinolin-6-yl)amino)-4-(propylamino)pyrimidine-5-carboxylic acid (E31), tert-butyl (3-(2-((isoquinolin-6-yl)amino)-4-(propylamino)pyrimidine-5-carboxamido)propyl)carbamate (E32) was obtained in the same manner as that of Example 12, (1).
MS m/z (M+H): 480.3

4

[Formula 141]

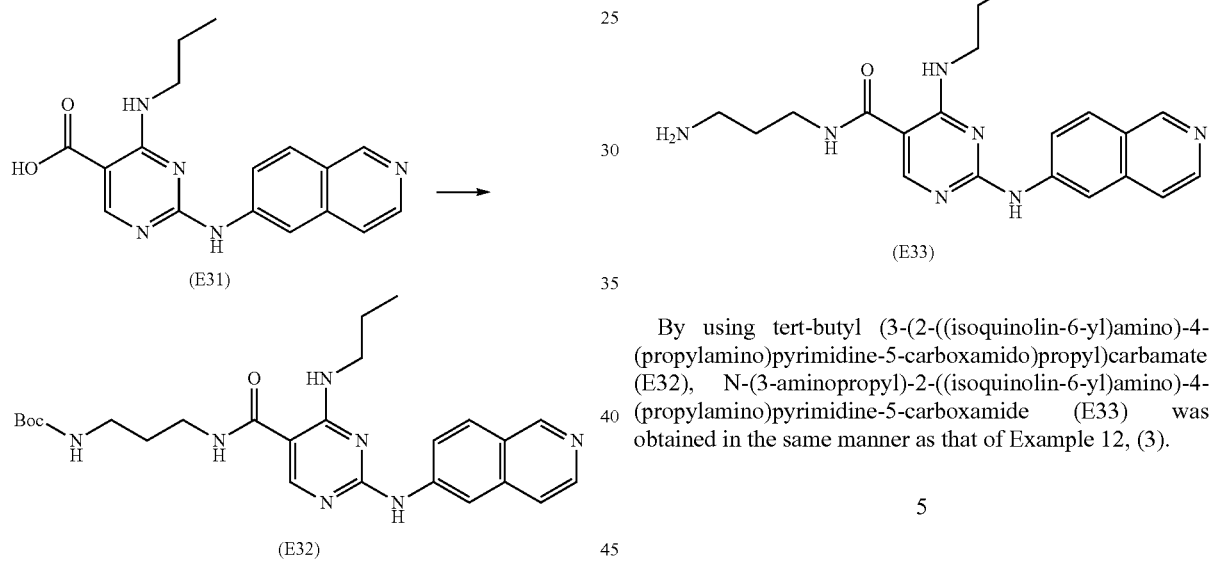

By using tert-butyl (3-(2-((isoquinolin-6-yl)amino)-4-(propylamino)pyrimidine-5-carboxamido)propyl)carbamate (E32), N-(3-aminopropyl)-2-((isoquinolin-6-yl)amino)-4-(propylamino)pyrimidine-5-carboxamide (E33) was obtained in the same manner as that of Example 12, (3).

5

In the same manner as that of Example 12, (4), Intermediates (E34) to (E38) were obtained.

TABLE 52

| Compound No. | Structure | Physicochemical data |
| --- | --- | --- |
| E34 | 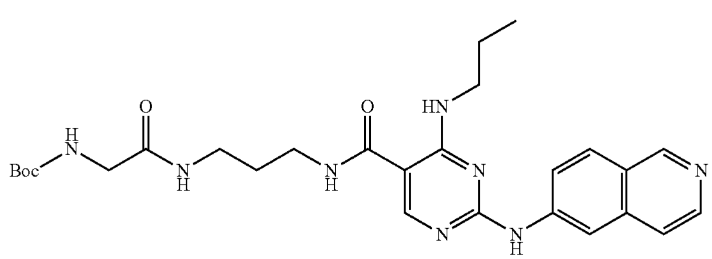 [SMILES: CCCNc1nc(Nc2ccc3cnccc3c2)ncc1C(=O)NCCCNC(=O)CNC(=O)OC(C)(C)C] | MS m/z (M + H): 537.3 |

TABLE 52-continued
| Compound No. | Structure | Physicochemical data |
|---|---|---|
| E35 | 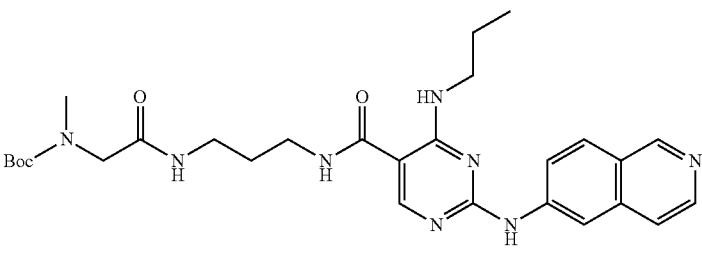 | — |
| E36 | 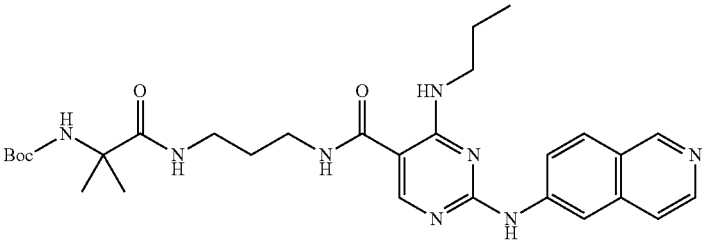 [SMILES: CCCNc1nc(Nc2ccc3cnccc3c2)ncc1C(=O)NCCCNC(=O)C(C)(C)NC(=O)OC(C)(C)C] | — |
| E37 | 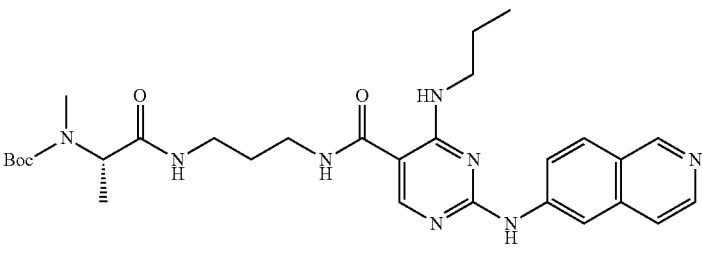 [SMILES: CCCNc1nc(Nc2ccc3cnccc3c2)ncc1C(=O)NCCCNC(=O)[C@H](C)N(C)C(=O)OC(C)(C)C] | — |
| E38 | 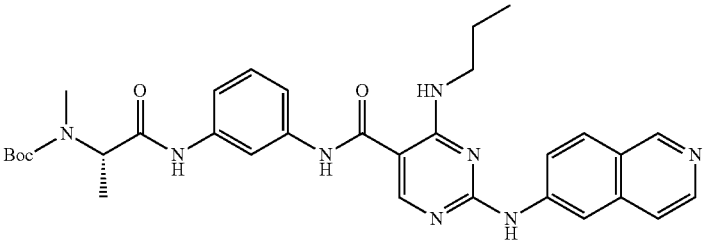 [SMILES: CCCNc1nc(Nc2ccc3cnccc3c2)ncc1C(=O)Nc1cccc(NC(=O)[C@H](C)N(C)C(=O)OC(C)(C)C)c1] | MS m/z (M + H): 599.3 |
In the same manner as that of Example 1 or Example 14, Compounds (6-5) to (6-9) were obtained.
TABLE 53
| Compound No. | Structure | Physicochemical data |
|---|---|---|
| 6-5 | 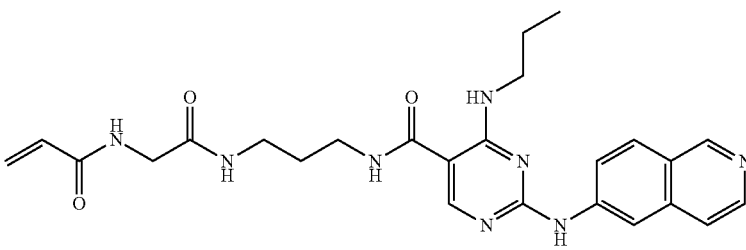 | $^1$H-NMR (DMSO-$d_6$) δ: 10.02 (1H, s), 9.11 (2H, brs), 8.62 (1H, s), 8.56 (1H, s), 8.40-8.30 (3H, m), 8.02-7.92 (2H, m), 7.86 (1H, dd, J = 8.9, 1.7 Hz), 7.58 (1H, d, J = 5.9 Hz), 6.32 (1H, dd, J = 17.2, 9.9 Hz), 6.10 (1H, dd, J = 17.2, 2.6 Hz), 5.61 (1H, dd, J = 10.2, 2.3 Hz), 3.76 (2H, d, J = 5.9 Hz), 3.56-3.46 (2H, m), 3.28-3.20 (2H, m), 3.18-3.08 (2H, m), 1.74-1.60 (4H, m), 0.99 (3H, t, J = 7.6 Hz) |

TABLE 53-continued

| Compound No. | Structure | Physicochemical data |
|---|---|---|
| 6-6 | 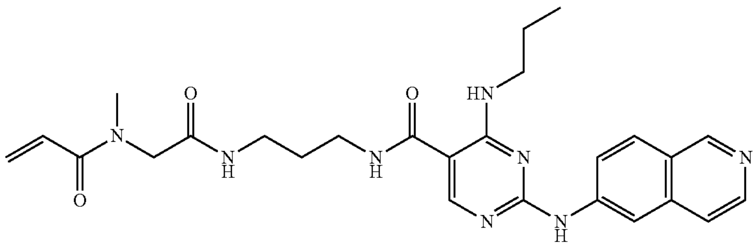 [SMILES: C=CC(=O)N(C)CC(=O)NCCCNC(=O)c1cnc(Nc2ccc3cnccc3c2)nc1NCCC] | ¹H-NMR (CDCl₃) δ: 9.10 (1H, s), 9.01 (1H, brs), 8.48-8.42 (3H, m), 7.87 (1H, d, J = 9.2 Hz), 7.70 (1H, brs), 7.62 (1H, dd, J = 9.2, 2.0 Hz), 7.53 (1H, d, J = 5.3 Hz), 7.45 (1H, brs), 6.97 (1H, brs), 6.64 (1H, dd, J = 16.8, 10.2 Hz), 6.40 (1H, dd, J = 16.5, 2.0 Hz), 5.80 (1H, dd, J = 10.2, 1.7 Hz), 4.08 (2H, s), 3.58-3.50 (2H, m), 3.44-3.34 (4H, m), 3.22 (3H, s), 1.82-1.70 (4H, m), 1.06 (3H, t, J = 7.3 Hz) |
| 6-7 | 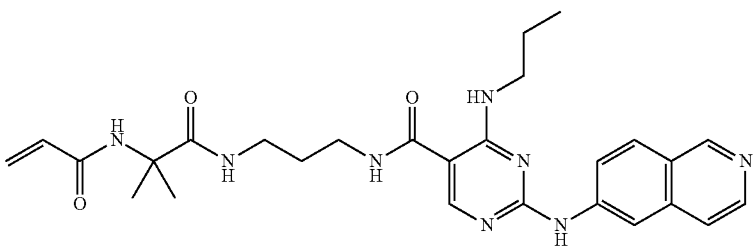 [SMILES: C=CC(=O)NC(C)(C)C(=O)NCCCNC(=O)c1cnc(Nc2ccc3cnccc3c2)nc1NCCC] | ¹H-NMR (CDCl₃) δ: 9.07 (1H, s), 9.03 (1H, t, J = 5.6 Hz), 8.51 (1H, s), 8.46 (1H, s), 8.40 (1H, d, J = 5.3 Hz), 8.14 (1H, brs), 7.84 (1H, d, J = 8.6 Hz), 7.71 (1H, brs), 7.62 (1H, dd, J = 8.6, 2.0 Hz), 7.50 (1H, d, J = 5.3 Hz), 7.22 (1H, t, J = 6.3 Hz), 6.87 (1H, s), 6.28 (1H, dd, J = 17.2, 2.0 Hz), 6.17 (1H, dd, J = 16.8, 9.6 Hz), 5.63 (1H, dd, J = 9.9, 2.0 Hz), 3.53 (2H, q, J = 6.6 Hz), 3.46-3.36 (4H, m), 1.80-1.70 (4H, m), 1.61 (6H, s), 1.05 (3H, t, J (3H, t, J = 7.6 Hz) |
| 6-8 | 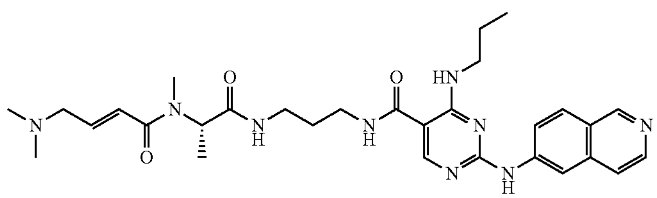 [SMILES: CCCNc1nc(Nc2ccc3cnccc3c2)ncc1C(=O)NCCCNC(=O)[C@H](C)N(C)C(=O)/C=C/CN(C)C] | MS m/z (M + H) δ: 576.3 |
| 6-9 | 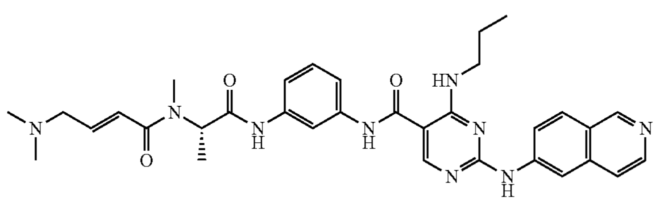 [SMILES: CCCNc1nc(Nc2ccc3cnccc3c2)ncc1C(=O)Nc1cccc(NC(=O)[C@H](C)N(C)C(=O)/C=C/CN(C)C)c1] | ¹H-NMR (DMSO-d₆) δ: 10.13 (1H, s), 10.06 (1H, s), 9.95 (1H, s), 9.12 (1H, s), 8.88 (1H, brs), 8.77 (1H, s), 8.65 (1H, s), 8.39 (1H, d, J = 5.9 Hz), 8.10 (1H, s), 8.02 (1H, d, J = 9.2 Hz), 7.89 (1H, d, J = 9.2 Hz), 7.60 (1H, d, J = 5.9 Hz), 7.38-7.22 (3H, m), 6.70-6.54 (2H, m), 5.16-5.06 (1H, m), 3.56 (2H, q, J = 6.6 Hz), 3.05 (3H, s), 2.14 (6H, s), 1.78-1.64 (2H, m), 1.37 (3H, d, J = 7.3 Hz), 1.00 (3H, t, J = 7.6 Hz) |

Example 19

1

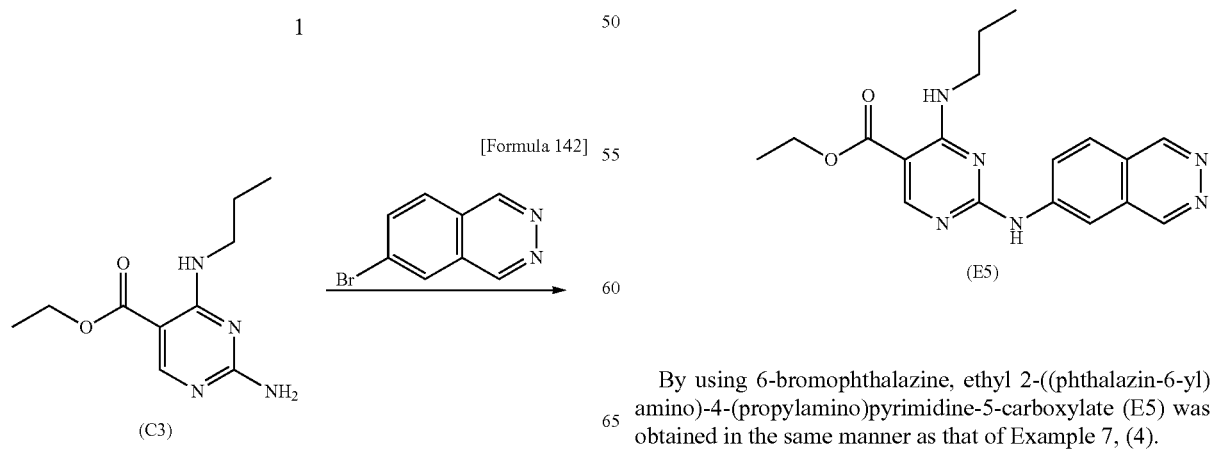

[Formula 142]

By using 6-bromophthalazine, ethyl 2-((phthalazin-6-yl)amino)-4-(propylamino)pyrimidine-5-carboxylate (E5) was obtained in the same manner as that of Example 7, (4).

MS m/z (M+H): 353.2

2

[Formula 143]

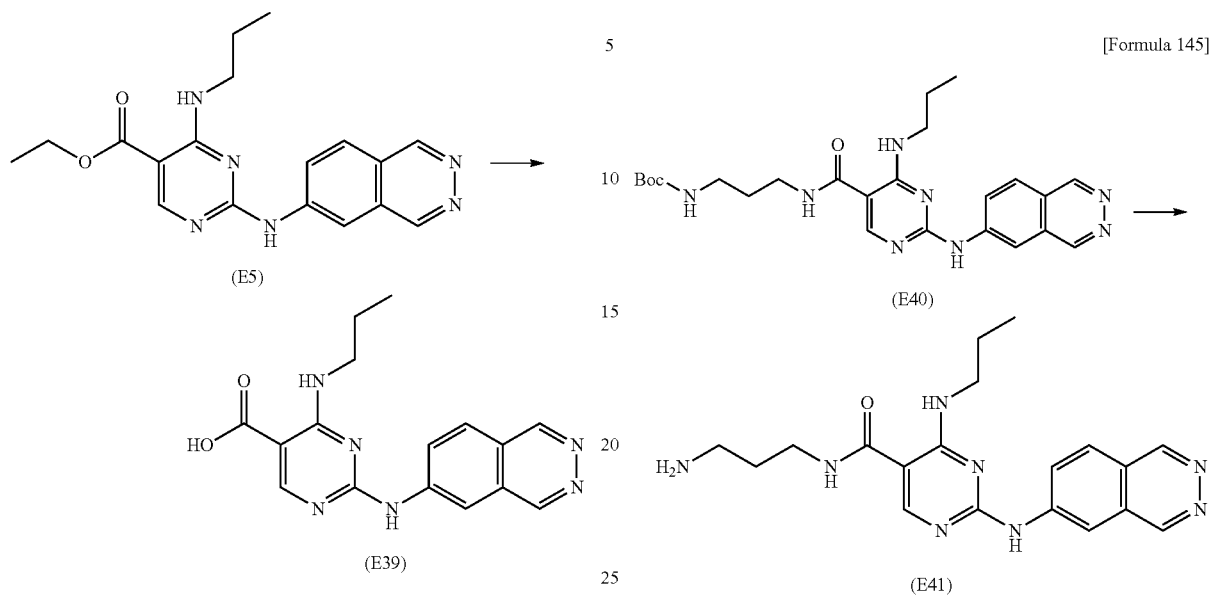

By using ethyl 2-((phthalazin-6-yl)amino)-4-(propylamino)pyrimidine-5-carboxylate (E5), 2-((phthalazin-6-yl)amino)-4-(propylamino)pyrimidine-5-carboxylic acid (E39) was obtained in the same manner as that of Example 7, (5).
MS m/z (M+H): 325.2

3

[Formula 144]

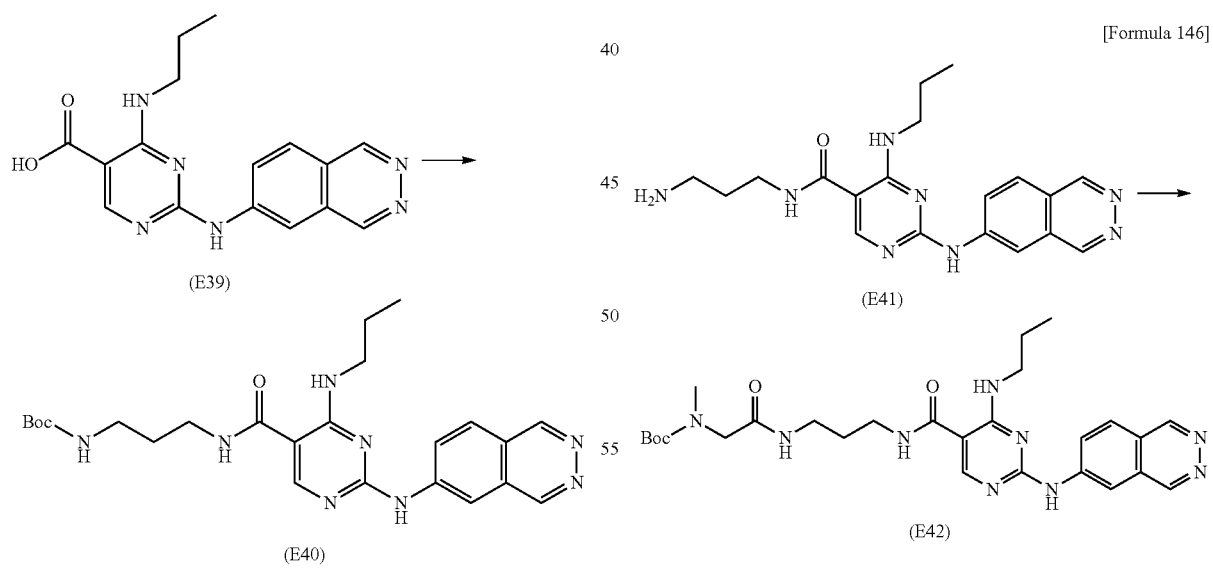

By using 2-((phthalazin-6-yl)amino)-4-(propylamino)pyrimidine-5-carboxylic acid (E39), tert-butyl (3-(2-((phthalazin-6-yl)amino)-4-(propylamino)pyrimidine-5-carboxamido)propyl)carbamate (E40) was obtained in the same manner as that of Example 12, (1).
MS m/z (M+H): 481.3

4

[Formula 145]

By using tert-butyl (3-(2-((phthalazin-6-yl)amino)-4-(propylamino)pyrimidine-5-carboxamido)propyl)carbamate (E40), N-(3-aminopropyl)-2-((phthalazin-6-yl)amino)-4-(propylamino)pyrimidine-5-carboxamide (E41) was obtained in the same manner as that of Example 12, (3).
MS m/z (M+H): 381.3

5

[Formula 146]

By using N-(3-aminopropyl)-2-((phthalazin-6-yl)amino)-4-(propylamino)pyrimidine-5-carboxamide (E41), tert-butyl methyl(2-oxo-2-((3-(2-((phthalazin-6-yl)amino)-4-(propylamino)pyrimidine-5-carboxamido)propyl)amino)ethyl)carbamate (E42) was obtained in the same manner as that of Example 12, (4).
MS m/z (M+H): 552.3

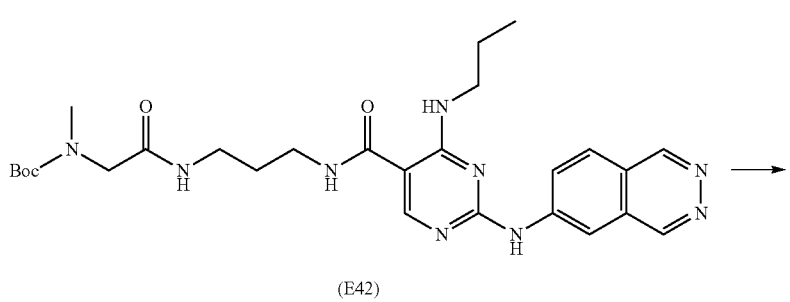

(E42)

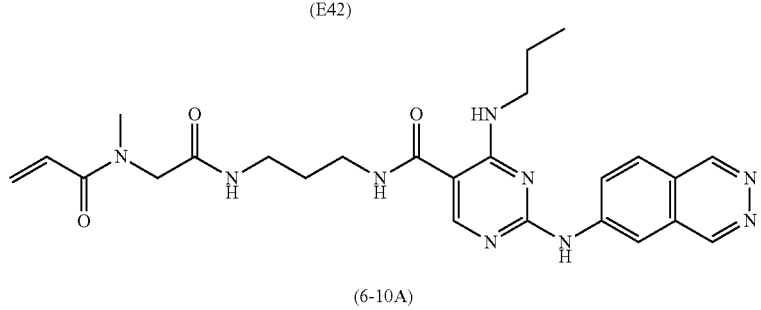

(6-10A)

By using tert-butyl methyl(2-oxo-2-((3-(2-((phthalazin-6-yl)amino)-4-(propylamino)pyrimidine-5-carboxamido)propyl)amino)ethyl)carbamate (E42), N-(3-(2-(N-methylacrylylamido)actamido)propyl)-2-((phthalazin-6-yl)amino)-4-(propylamino)pyrimidine-5-carboxamide (6-10 A) was obtained in the same manner as that of Example 1.

MS m/z [M+H]: 506.3

Example 20

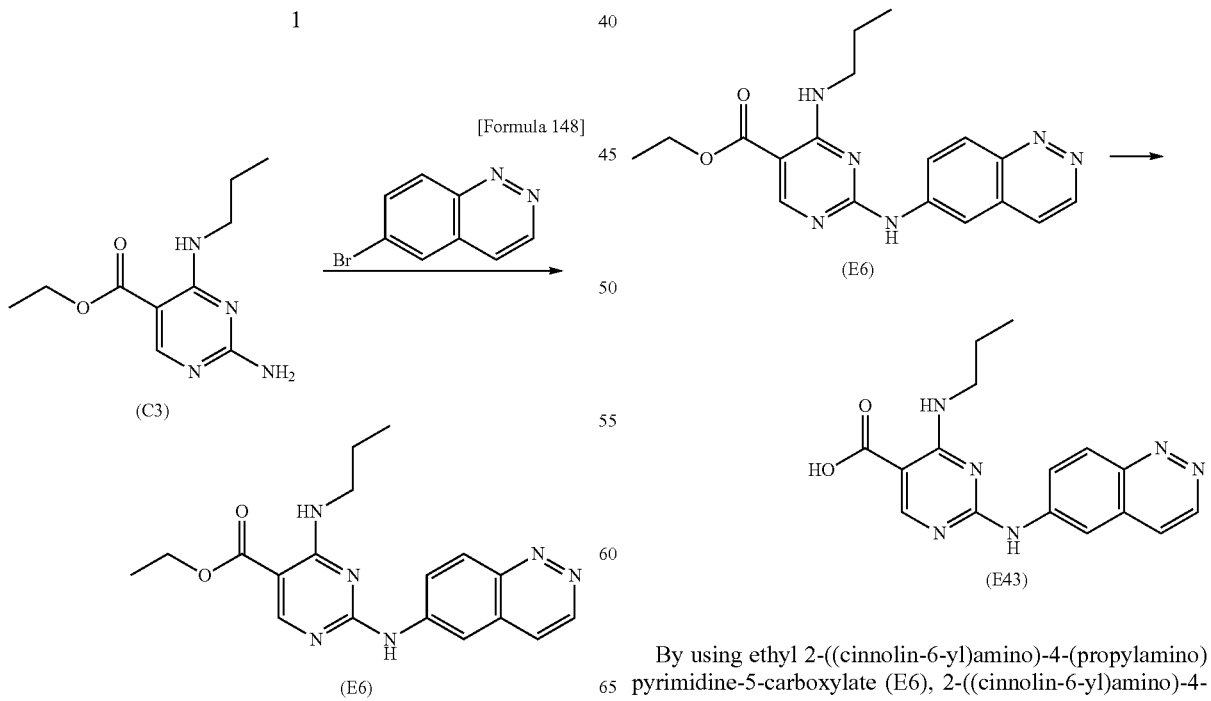

By using 6-bromocinnoline, ethyl 2-((cinnolin-6-yl)amino)-4-(propylamino)pyrimidine-5-carboxylate (E6) was obtained in the same manner as that of Example 7, (4).

MS m/z (M+H): 353.2

By using ethyl 2-((cinnolin-6-yl)amino)-4-(propylamino)pyrimidine-5-carboxylate (E6), 2-((cinnolin-6-yl)amino)-4-(propylamino)pyrimidine-5-carboxylic acid (E43) was obtained in the same manner as that of Example 7, (5).

3

[Formula 150]

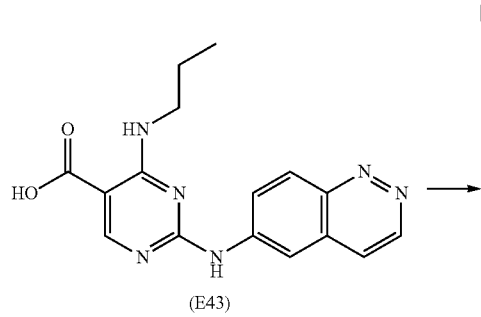

(E43)

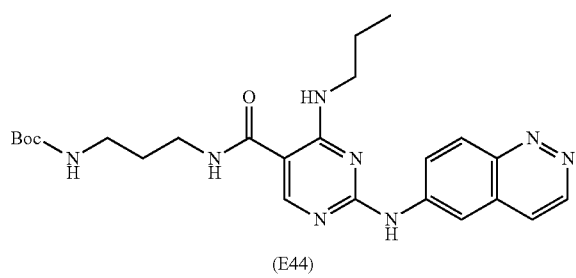

(E44)

By using 2-((cinnolin-6-yl)amino)-4-(propylamino)pyrimidine-5-carboxylic acid (E43), tert-butyl (3-(2-((cinnolin-6-yl)amino)-4-(propylamino)pyrimidine-5-carboxamido)propyl)carbamate (E44) was obtained in the same manner as that of Example 12, (1).

4

[Formula 151]

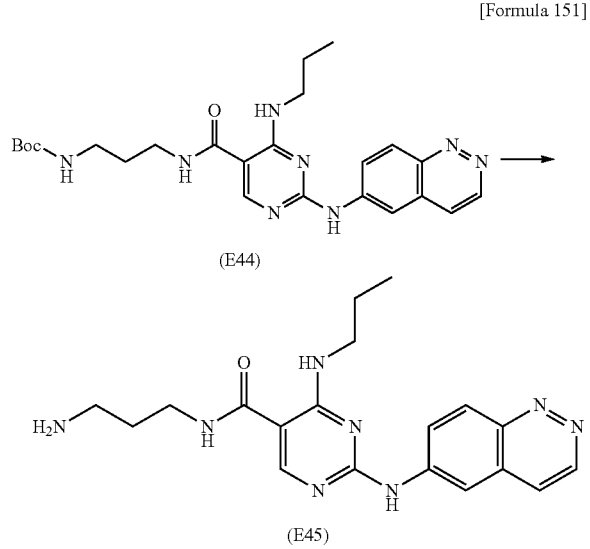

By using tert-butyl (3-(2-((cinnolin-6-yl)amino)-4-(propylamino)pyrimidine-5-carboxamido)propyl)carbamate (E44), N-(3-aminopropyl)-2-((cinnolin-6-yl)amino)-4-(propylamino)pyrimidine-5-carboxamide (E45) was obtained in the same manner as that of Example 12, (3).

5

[Formula 152]

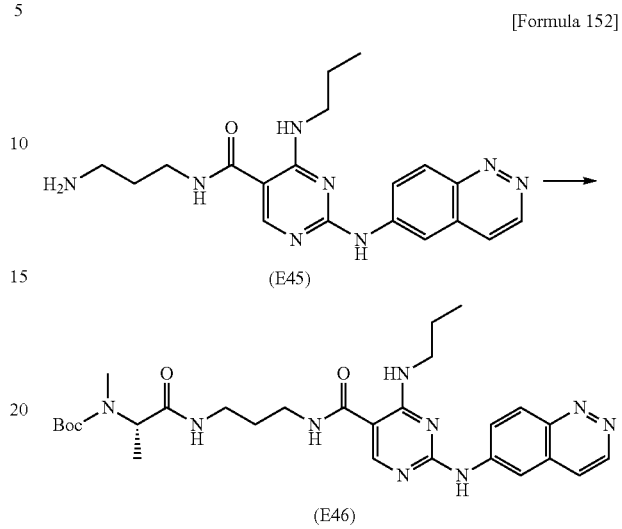

By using N-(3-aminopropyl)-2-((cinnolin-6-yl)amino)-4-(propylamino)pyrimidine-5-carboxamide (E45), (S)-tert-butyl (1-((3-(2-((cinnolin-6-yl)amino)-4-(propylamino)pyrimidine-5-carboxamido)propyl)amino)-1-oxopropan-2-yl)(methyl)carbamate (E46) was obtained in the same manner as that of Example 12, (4).

6

[Formula 153]

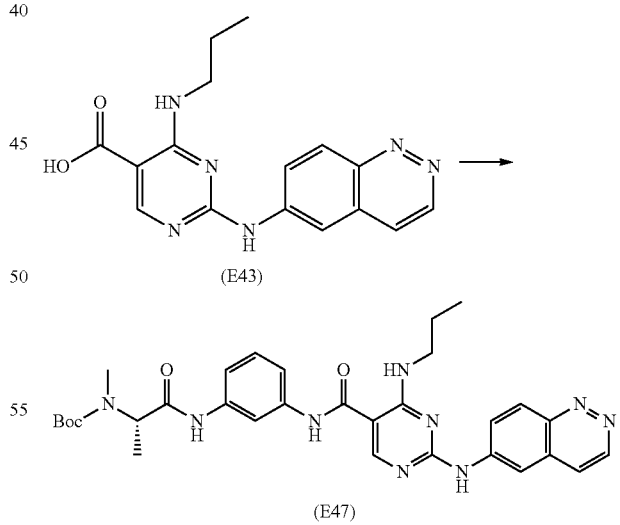

By using 2-((cinnolin-6-yl)amino)-4-(propylamino)pyrimidine-5-carboxylic acid (E43), (S)-tert-butyl (1-((3-(2-((cinnolin-6-yl)amino)-4-(propylamino)pyrimidine-5-carboxamido)phenyl)amino)-1-oxopropan-2-yl)(methyl)carbamate (E47) was obtained in the same manner as that of Example 7, (9).

7

By using Intermediates (E46) and (E47), Compounds (6-10 B) and (6-11) were obtained in the same manner as that of Example 1 or Example 14.

reaction mixture was poured into water. The solid matter was taken by filtration, and dried under reduced pressure to obtain ethyl 2-((phenoxycarbonyl)amino)-4-(propylamino)pyrimidine-5-carboxylate (E7, 2.89 g) as white solid.

MS m/z[M+H]: 345.2

TABLE 54

| Compound No. | Structure | Physicochemical data |
|---|---|---|
| 6-10B | 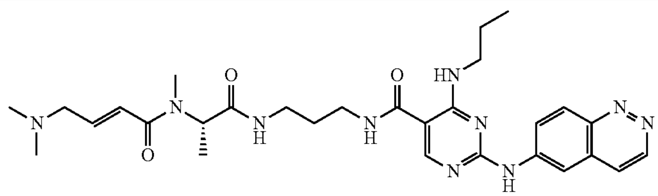 [SMILES: CCCNc1nc(Nc2ccc3nnccc3c2)ncc1C(=O)NCCCNC(=O)[C@H](C)N(C)C(=O)/C=C/CN(C)C] | $^1$H-NMR (DMSO-$d_6$) δ: 10.24 (1H, s), 9.16 (1H, s), 8.68 (1H, d), 8.58 (1H, s), 8.40-8.30 (2H, m), 8.08 (1H, dd), 7.93 (1H, d), 3.57-3.38 (4H, m), 3.35-2.98 (5H, m), 2.93 (3H, s), 2.15 (6H, s), 1.75-1.60 (4H, m), 1.23 (3H, d), 0.99 (3H, t) |
| 6-11 | 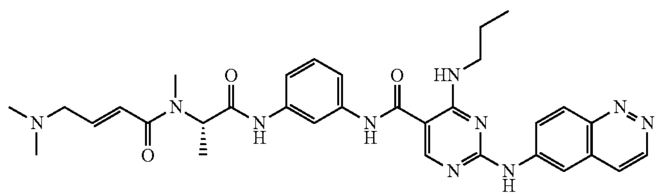 [SMILES: CCCNc1nc(Nc2ccc3nnccc3c2)ncc1C(=O)Nc1cccc(NC(=O)[C@H](C)N(C)C(=O)/C=C/CN(C)C)c1] | $^1$H-NMR (DMSO-$d_6$) δ: 10.35 (1H, s), 10.10 (1H, s), 9.96 (1H, s), 9.18 (1H, d), 8.89 (1H, t), 8.79 (1H, s), 8.71 (1H, d), 8.34 (1H, d), 8.14-8.09 (2H, m), 7.95 (1H, d), 7.37-7.22 (3H, m), 6.66-6.54 (2H, m), 3.57 (2H, q), 3.07-3.02 (5H, brs), 2.16 (6H, s), 2.16-2.11 (1H, m), 1.71 (2H, dt), 1.36 (3H, d), 1.00 (3H, t) |

Example 21

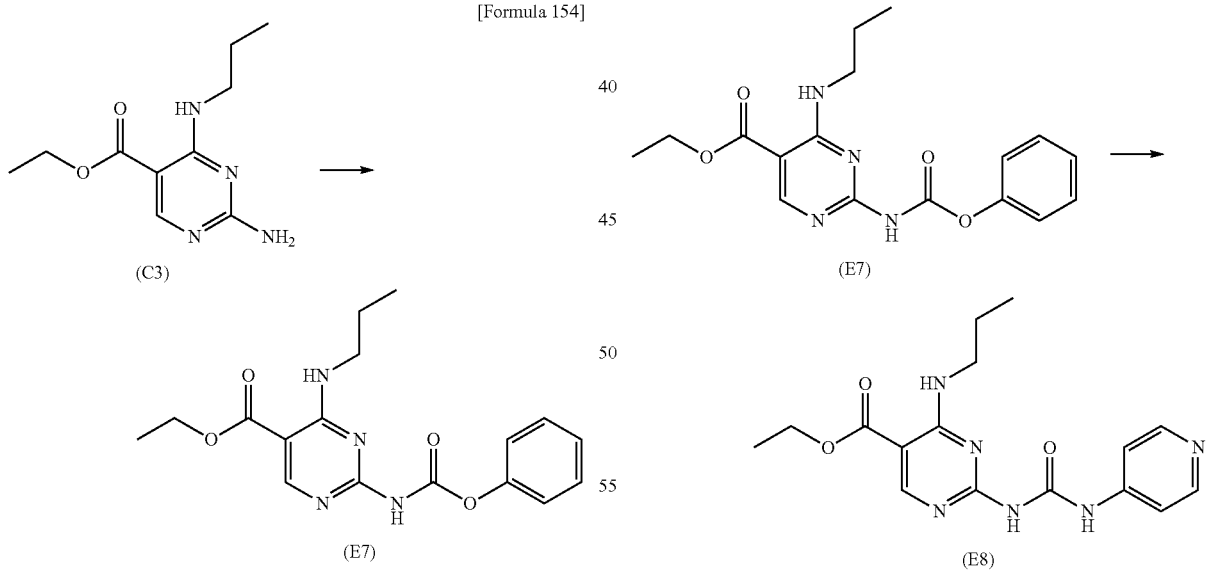

[Formula 154]

(C3)

[Formula 155]

(E7)

(E7)

(E8)

To a solution of ethyl 2-amino-4-(propylamino)pyrimidine-5-carboxylate (C3, 5.00 g) and pyridine (2.2 mL) in N,N-dimethylformamide (45 mL), phenyl chloroformate (3.1 mL) was added dropwise under ice cooling, and the mixture was stirred at the same temperature for 40 minutes. To the reaction mixture, pyridine (1.0 mL) and phenyl chloroformate (1.5 mL) were added under ice cooling, and the mixture was stirred at the same temperature for 40 minutes. The To ethyl 2-((phenoxycarbonyl)amino)-4-(propylamino) pyrimidine-5-carboxylate (E7, 2.89 g) and 4-aminopyridine (3.16 g), N,N-dimethylformamide (30 mL) was added at room temperature, and the mixture was stirred at 70° C. for 30 minutes. The reaction mixture was cooled to room temperature, and then the reaction mixture was poured into water (300 mL). The solid matter was taken by filtration, and purified by silica gel column chromatography (eluent, ethyl acetate) to obtain ethyl 4-(propylamino)-2-(3-(pyridin-4-yl)ureido)pyrimidine-5-carboxylate (E8, 830 mg) as white solid.

MS m/z [M+H]: 345.2

3

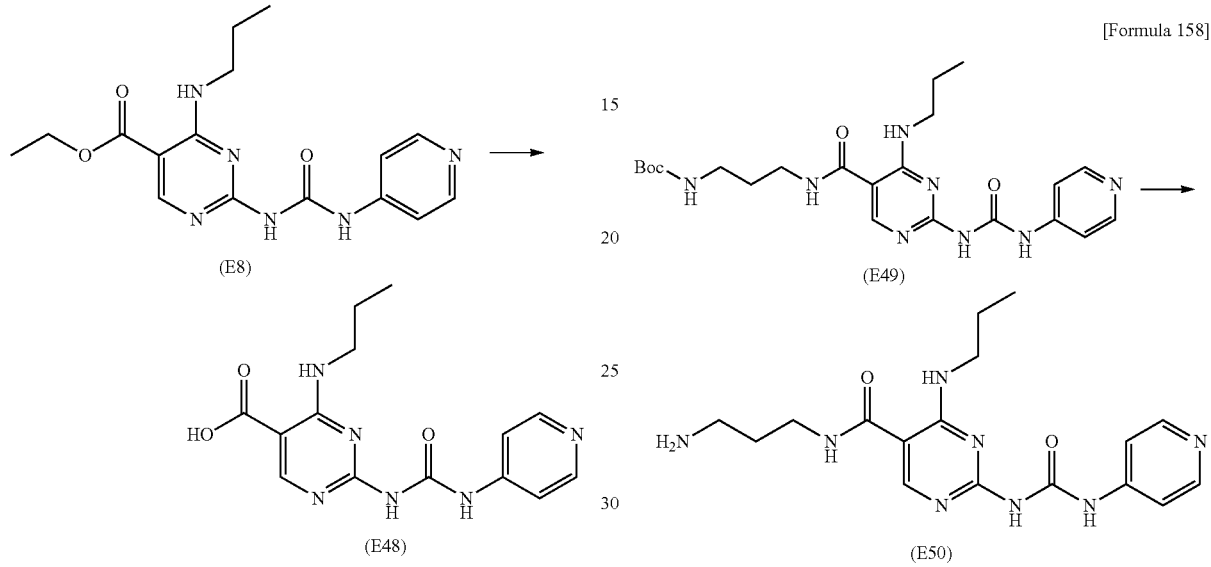

By using ethyl 4-(propylamino)-2-(3-(pyridin-4-yl)ureido)pyrimidine-5-carboxylate (E8), 4-(propylamino)-2-(3-(pyridin-4-yl)ureido)pyrimidine-5-carboxylic acid (E48) was obtained in the same manner as that of Example 7, (5).

MS m/z (M+H): 317.2

4

By using 4-(propylamino)-2-(3-(pyridin-4-yl)ureido)pyrimidine-5-carboxylic acid (E48), tert-butyl (3-(4-(propylamino)-2-(3-(pyridin-4-yl)ureido)pyrimidine-5-carboxamido)propyl)carbamate (E49) was obtained in the same manner as that of Example 12, (1).

MS m/z (M+H): 473.3

5

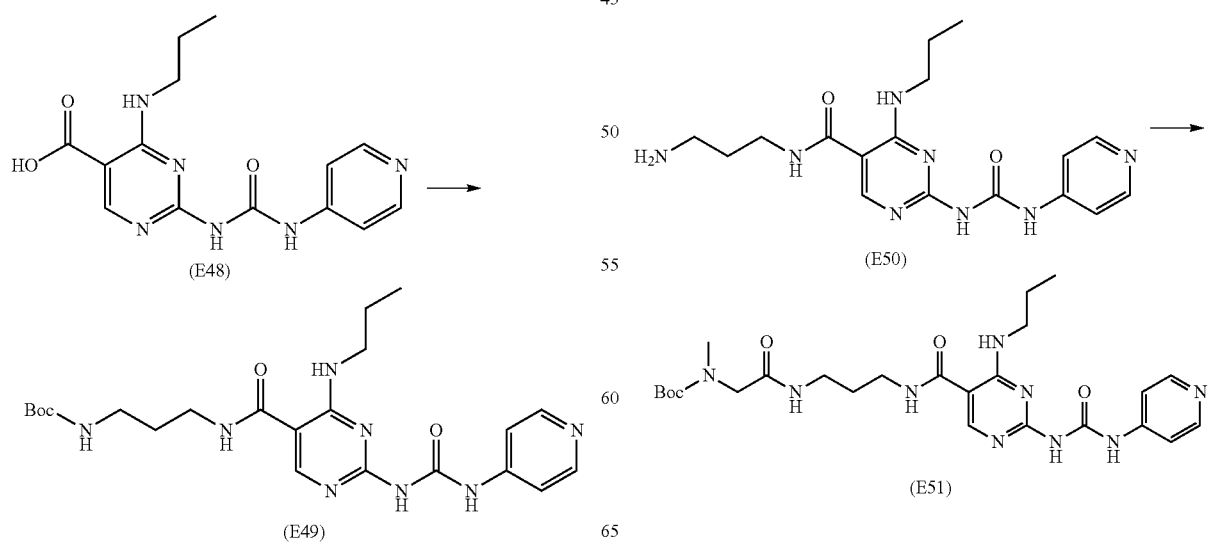

By using tert-butyl (3-(4-(propylamino)-2-(3-(pyridin-4-yl)ureido)pyrimidine-5-carboxamido)propyl)carbamate (E49), N-(3-aminopropyl)-4-(propylamino)-2-(3-(pyridin-4-yl)ureido)pyrimidine-5-carboxamide (E50) was obtained in the same manner as that of Example 12, (3).

6

By using N-(3-aminopropyl)-4-(propylamino)-2-(3-(pyridin-4-yl)ureido)pyrimidine-5-carboxamide (E50), tert-butyl methyl (2-oxo-2-((3-(4-(propylamino)-2-(3-(pyridin-4-yl)ureido)pyrimidine-5-carboxamido)propyl)amino)ethyl)carbamate (E51) was obtained in the same manner as that of Example 12, (4).

MS m/z (M+H): 544.3

7

[Formula 160]

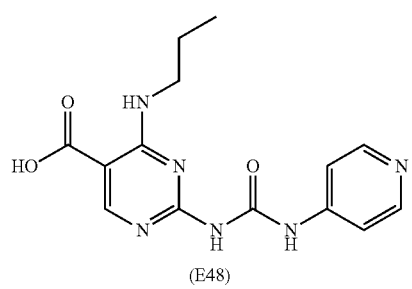

(E48)

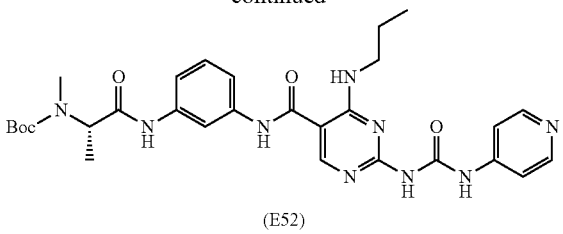

(E52)

By using 4-(propylamino)-2-(3-(pyridin-4-yl)ureido)pyrimidine-5-carboxylic acid (E48), (S)-tert-butyl methyl(1-oxo-1-((3-(4-(propylamino)-2-(3-(pyridin-4-yl)ureido)pyrimidine-5-carboxamido)phenyl)amino)propan-2-yl)carbamate (E52) was obtained in the same manner as that of Example 7, (9).

MS m/z (M+H): 592.3

8

In the same manner as that of Example 1 or Example 14, Compounds (6-12) to (6-15) were obtained.

TABLE 55

| Compound No. | Structure | Physicochemical data |
|---|---|---|
| 6-12 | 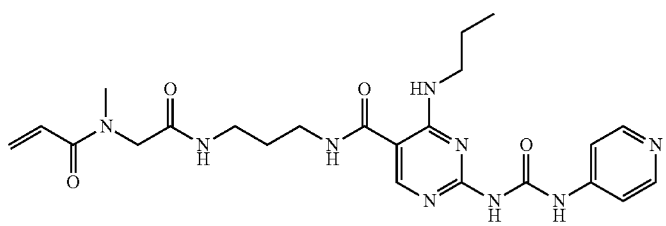 [SMILES: C=CC(=O)N(C)CC(=O)NCCCNC(=O)c1cnc(NC(=O)Nc2ccncc2)nc1NCCC] | 1H-NMR (CD$_3$OD) δ: 8.47-8.46 (1H, m), 8.39-8.38 (2H, m), 7.63-7.62 (2H, m), 6.81-6.62 (1H, m), 6.27-6.21 (1H, m), 5.78-5.72 (1H, m), 4.12-3.99 (2H, m), 3.50 (2H, t, J = 6.9 Hz), 3.37 (2H, t, J = 6.9 Hz), 3.21 (3H, s), 3.14-3.04 (2H, m), 1.93-1.64 (4H, m), 1.14 = 0.90 (3H, m) |
| 6-13 | 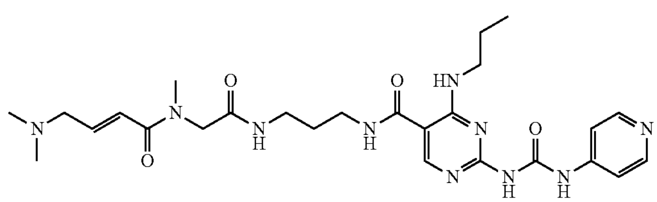 [SMILES: CCCNc1nc(NC(=O)Nc2ccncc2)ncc1C(=O)NCCCNC(=O)CN(C)C(=O)/C=C/CN(C)C] | 1H-NMR (CDCl$_3$) δ: 11.66 (1H, brs), 9.12 (1H, brs), 8.44-8.42 (3H, m), 7.85-7.71 (1H, m), 7.38 (2H, brs), 7.24-7.11 (1H, m), 6.91-6.89 (1H, m), 6.47 (1H, d, J = 15.2 Hz), 4.10 (2H, s), 3.41-3.28 (6H, m), 3.22 (3H, s), 3.13-3.08 (2H, m), 2.47 (1H, brs), 2.24 (6H, s), 1.72-1.65 (4H, m), 1.00 (3H, t, J = 6.3 Hz) |
| 6-14 | 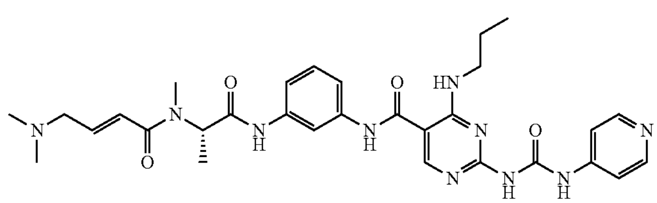 [SMILES: CCCNc1nc(NC(=O)Nc2ccncc2)ncc1C(=O)Nc1cccc(NC(=O)[C@H](C)N(C)C(=O)/C=C/CN(C)C)c1] | MS m/z[M + H]: 603.3 |
| 6-15 | 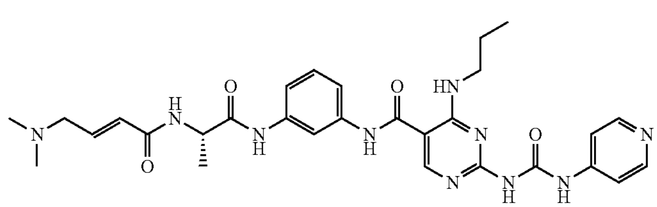 [SMILES: CCCNc1nc(NC(=O)Nc2ccncc2)ncc1C(=O)Nc1cccc(NC(=O)[C@H](C)NC(=O)/C=C/CN(C)C)c1] | 1H-NMR (CD$_3$OD) δ: 8.65 (1H, s), 8.38 (2H, d, J = 4.6 Hz), 7.94 (1H, s), 7.58 (2H, d, J = 4.6 Hz), 7.38-7.24 (3H, m), 6.82 (1H, dt, J = 15.4, 6.4 Hz), 6.16 (1H, d, J = 15.9 Hz), 4.61 (1H, q, J = 7.0 Hz), 3.51 2H, t, J = 7.3 Hz), 3.17-3.13 (2H, m), 2.29 (6H, s), 1.80-1.70 (2H, m), 1.47 (3H, d, J = 6.6 Hz), 1.06 (3H, t, J = 8.0 Hz) |

Example 23

1

[Formula 161]

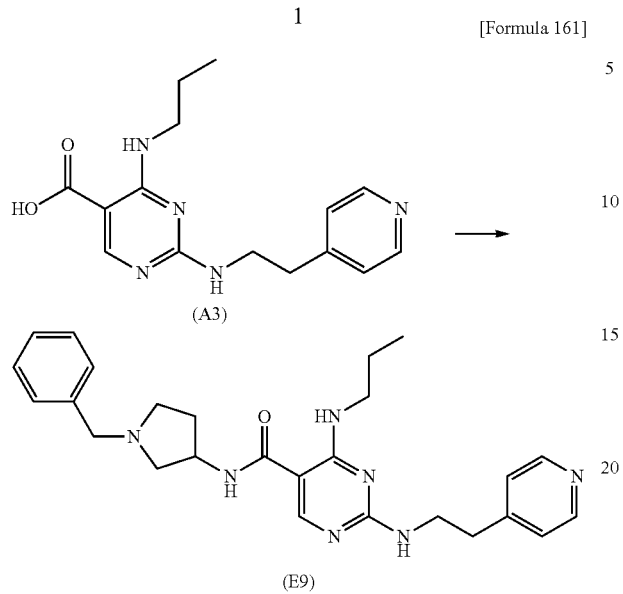

To a solution of 4-(propylamino)-2-((2-(pyridin-4-yl)ethyl)amino)pyrimidine-5-carboxylic acid (A3, 90 mg) in N,N-dimethylformamide (2 mL), 1-ethyl-3-(3-dimethylaminopropyl)carbodiimide hydrochloride (63 mg) and 1-hydroxybenzotriazole monohydrate (45 mg) were added at room temperature, and the mixture was stirred at the same temperature for 2 hours and 30 minutes. To the reaction mixture, N,N-diisopropylethylamine (153 µL) and 1-benzyl-3-aminopyrrolidine (53 mg) were added at room temperature, and the mixture was stirred at the same temperature for 2 hours. To the reaction mixture, water was added. The solid matter was taken by filtration, washed with water, and then dried under reduced pressure. The obtained solid matter was purified by basic silica gel column chromatography to obtain N-(1-benzylpyrrolidin-3-yl)-4-(propylamino)-2-((2-(pyridin-4-yl)ethyl)amino)pyrimidine-5-carboxamide (E9, 117 mg).

MS m/z (M+H): 460.3

2

[Formula 162]

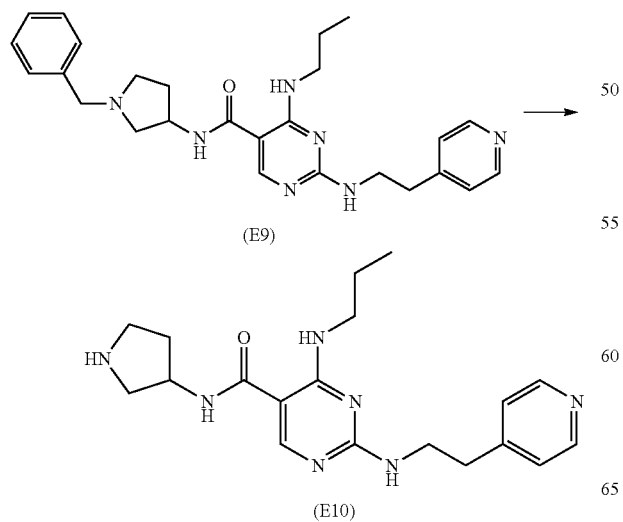

To a suspension of 10% palladium-carbon (12 mg) in methanol (1 mL), a solution of ammonium formate (64 mg) and N-(1-benzylpyrrolidin-3-yl)-4-(propylamino)-2-((2-(pyridin-4-yl)ethyl)amino)pyrimidine-5-carboxamide (E9, 117 mg) in methanol (4 mL) was added at room temperature, and the mixture was stirred for 5 hours and 30 minutes under reflux by heating. The reaction mixture was cooled to room temperature, and then methanol was added to the mixture. The insoluble matter was removed by filtration through Cerite, and then the solvent was evaporated under reduced pressure. The obtained residue was purified by basic silica gel column chromatography to obtain 4-(propylamino)-2-((2-(pyridin-4-yl)ethyl)amino)-N-(pyrrolidin-3-yl)pyrimidine-5-carboxamide (E10, 85 mg).

3

[Formula 163]

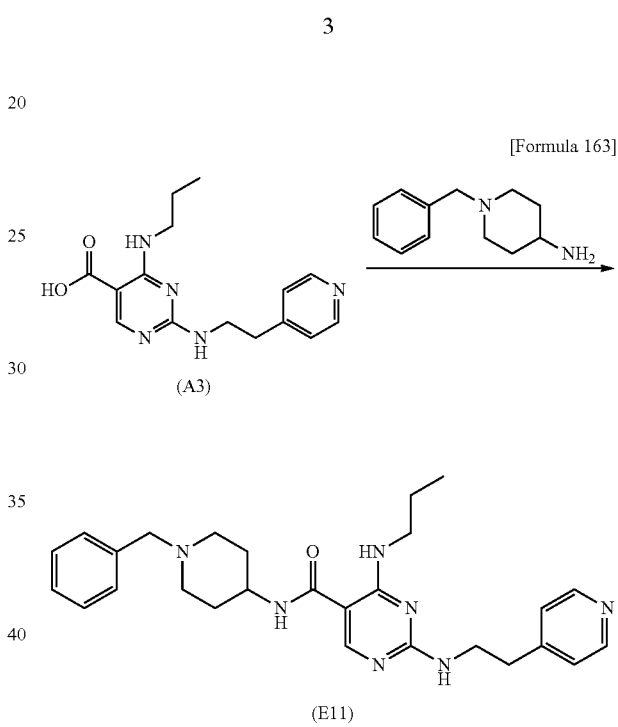

By using 4-amino-1-benzylpiperazine, N-(1-benzylpiperidin-4-yl)-4-(propylamino)-2-((2-(pyridin-4-yl)ethyl)amino)pyrimidine-5-carboxamide (E11) was obtained in the same manner as that of Example 23, (1).

MS m/z (M+H): 474.4

4

[Formula 164]

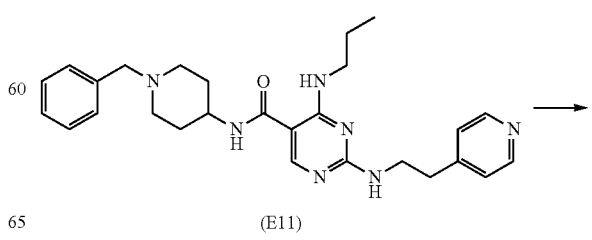

229

-continued

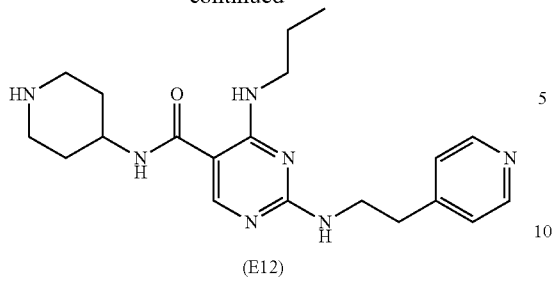

(E12)

By using N-(1-benzylpiperidin-4-yl)-4-(propylamino)-2-((2-(pyridin-4-yl)ethyl)amino)pyrimidine-5-carboxamide

230

(E11), N-(piperidin-4-yl)-4-(propylamino)-2-((2-(pyridin-4-yl)ethyl)amino)pyrimidine-5-carboxamide (E12) was obtained in the same manner as that of Example 23, (2).

MS m/z (M+H): 384.3

5

By using Intermediates (E10) and (E12), Intermediates (E53) and (E54) were obtained in the same manner as that of Example 12, (4).

TABLE 56

| Compound No. | Structure | Physicochemical data |
|---|---|---|
| E53 | 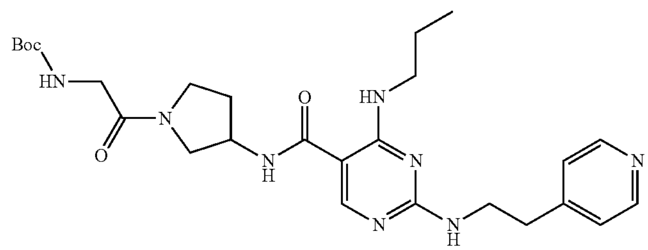 [SMILES: CCCNc1nc(NCCc2ccncc2)ncc1C(=O)NC1CCN(C(=O)CNC(=O)OC(C)(C)C)C1] | — |
| E54 | 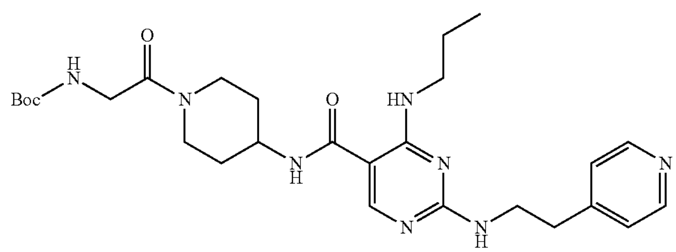 [SMILES: CCCNc1nc(NCCc2ccncc2)ncc1C(=O)NC1CCN(C(=O)CNC(=O)OC(C)(C)C)CC1] | — |

6

In the same manner as that of Example 1, Compounds (6-16) to (6-19) were obtained.

TABLE 57

| Compound No. | Structure | Physicochemical data |
|---|---|---|
| 6-16 | 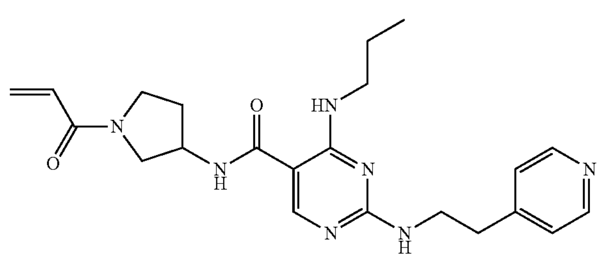 [SMILES: C=CC(=O)N1CCC(NC(=O)c2cnc(NCCc3ccncc3)nc2NCCC)C1] | $^1$H-NMR (CD$_3$OD) δ: 8.40 (2H, d, J = 6.4 Hz), 8.24 (1H, s), 7.31 (2H, d, J = 6.4 Hz), 6.68-6.50 (1H, m), 6.32-6.20 (1H, m), 5.78-5.68 (1H, m), 4.60-4.44 (1H, m), 4.00-3.26 (8H, m), 2.97 (2H, t, J = 6.9 Hz), 2.36-2.16 (1H, m), 2.12-1.94 (1H, m), 1.64 (2H, q, J = 7.3 Hz), 0.98 (3H, t, J = 7.6 Hz) |

TABLE 57-continued

| Compound No. | Structure | Physicochemical data |
|---|---|---|
| 6-17 | 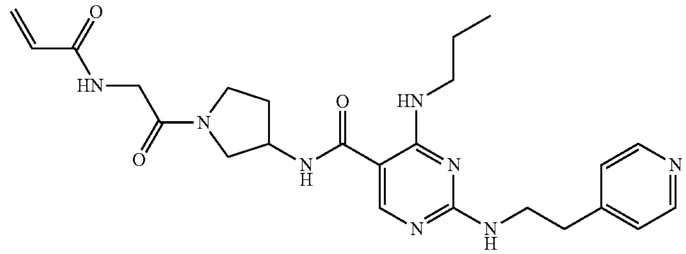 [SMILES: C=CC(=O)NCC(=O)N1CCC(NC(=O)c2cnc(NCCc3ccncc3)nc2NCCC)C1] | $^1$H-NMR (CDCl$_3$) δ: 8.76 (1H, brs), 8.49 (2H, d, J = 5.9 Hz), 8.16 (1H, brs), 7.13 (2H, d, J = 5.3 Hz), 7.12-7.04 (1H, m), 6.95 (1H, brs), 6.29 (1H, d, J = 17.2 Hz), 6.18 (1H, dd, J = 17.2, 9.9 Hz), 5.65 (1H, d, J = 9.9 Hz), 5.62-5.44 (1H, m), 4.68-4.56 (1H, m), 4.16-4.06 (1H, m), 4.00-3.84 (1H, m), 3.80-3.38 (8H, m), 2.90 (2H, t, J = 6.9 Hz), 2.36-2.08 (2H, m), 1.72-1.58 (2H, m), 0.99 (3H, t, J = 7.3 Hz) |
| 6-18 | 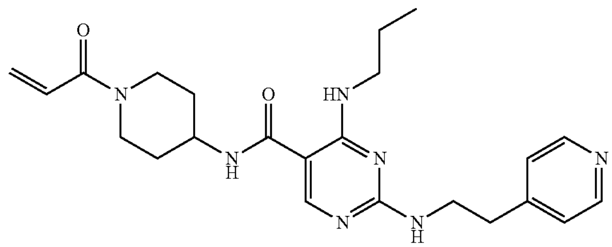 [SMILES: C=CC(=O)N1CCC(NC(=O)c2cnc(NCCc3ccncc3)nc2NCCC)CC1] | $^1$H-NMR (CDCl$_3$) δ: 8.70 (1H, brs), 8.51 (2H, d, J = 5.9 Hz), 8.05 (1H, brs), 7.15 (2H, d, J = 5.9 Hz), 6.59 (1H, dd, J = 16.5, 10.6 Hz), 6.27 (1H, dd, J = 16.5, 2.0 Hz), 5.97 (1H, d, J = 7.3 Hz), 5.69 (1H, dd, J = 10.2, 1.7 Hz), 5.30 (1H, s), 4.70-4.60 (1H, m), 4.20-4.06 (1H, m), 4.05-3.96 (1H, m), 3.68 (2H, q, J = 6.6 Hz), 3.42 (2H, brs), 3.28-3.14 (1H, m), 2.91 (2H, t, J = 6.9 Hz), 2.86-2.76 (1H, m), 2.16-1.98 (2H, m), 1.72-1.58 (2H, m), 1.50-1.36 (2H, m), 0.99 (3H, t, J = 7.6 Hz) |
| 6-19 | 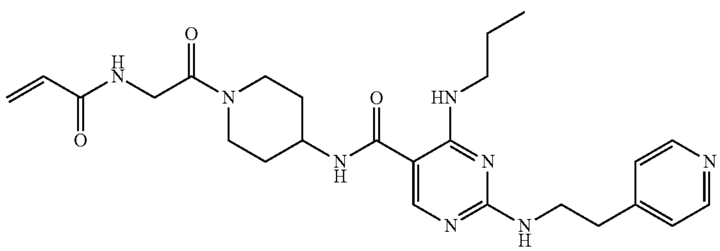 [SMILES: C=CC(=O)NCC(=O)N1CCC(NC(=O)c2cnc(NCCc3ccncc3)nc2NCCC)CC1] | $^1$H-NMR (CDCl$_3$) δ: 8.70 (1H, brs), 8.51 (2H, d, J = 5.9 Hz), 8.02 (1H, brs), 7.15 (2H, d, J = 5.9 Hz), 6.79 (1H, brs), 6.31 (1H, dd, J = 16.8, 1.7 Hz), 6.19 (1H, dd, J = 17.2, 9.9 Hz), 5.93 (1H, d, J = 7.3 Hz), 5.68 (1H, dd, J = 9.9, 2.0 Hz), 5.36 (1H, brs), 4.59 (1H, d, J = 13.9 Hz), 4.26-4.04 (3H, m), 3.79 (1H, d, J = 12.6 Hz), 3.68 (2H, q, J = 6.6 Hz), 3.42 (2H, brs), 3.18 (1H, t, J = 11.6 Hz), 2.94-2.78 (3H, m), 2.18-2.02 (2H, m), 1.70-1.60 (2H, m), 1.52-1.36 (2H, m), 0.99 (3H, t, J = 7.3 Hz) |

Example 24

1

[Formula 165]

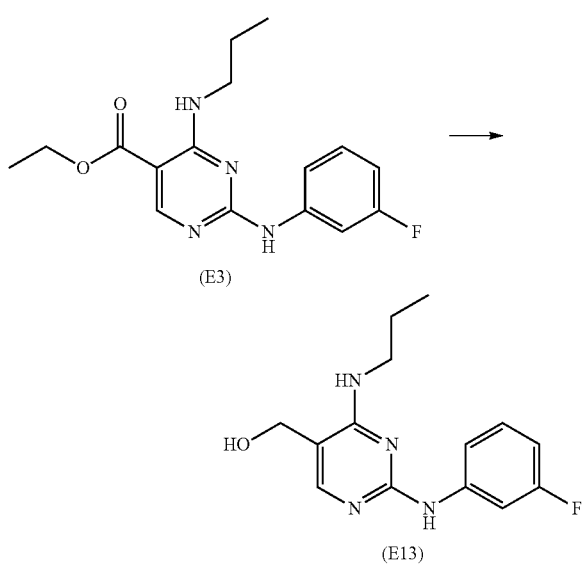

To a suspension of lithium aluminum hydride (160 mg) in tetrahydrofuran (14 mL), ethyl 2-((3-fluorophenyl)amino)-4-(propylamino)pyrimidine-5-carboxylate (E3, 450 mg) was added under ice cooling, and the mixture was stirred at the same temperature for 1 hour and 30 minutes. To the reaction mixture, lithium aluminum hydride (80 mg) was added under ice cooling, and the mixture was stirred at the same temperature for 1 hour. To the reaction mixture, ethyl acetate and an aqueous solution of the Rochell salt were added at room temperature, and the mixture was stirred at the same temperature for 2 hours and 30 minutes. The insoluble matter was removed by filtration through Cerite. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 90% ethyl acetate in methanol) to obtain (2-((3-fluorophenyl)amino)-4-(propylamino)pyrimidin-5-yl)methanol (E13, 212 mg).

MS m/z (M+H): 277.2

2

[Formula 166]

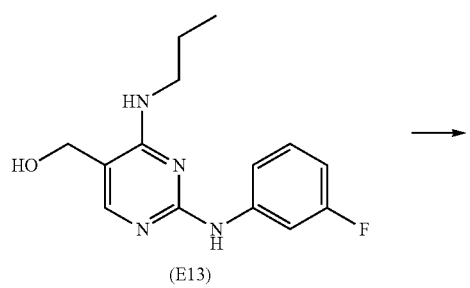

To a solution of (2-((3-fluorophenyl)amino)-4-(propylamino)pyrimidin-5-yl)methanol (E13, 26 mg) in chloroform (2 mL), manganese dioxide (41 mg) was added at room temperature, and the mixture was stirred at 50° C. for 4 hours. The reaction mixture was cooled to room temperature, then the insoluble matter was removed by filtration through Cerite, and then the solvent was evaporated under reduced pressure. The obtained residue was purified by silica gel column chromatography (eluent, 70 to 40% hexane in ethyl acetate) to obtain 2-((3-fluorophenyl)amino)-4-(propylamino)pyrimidine-5-carbaldehyde (E14, 26 mg).

MS m/z (M+H): 275.1

3

[Formula 167]

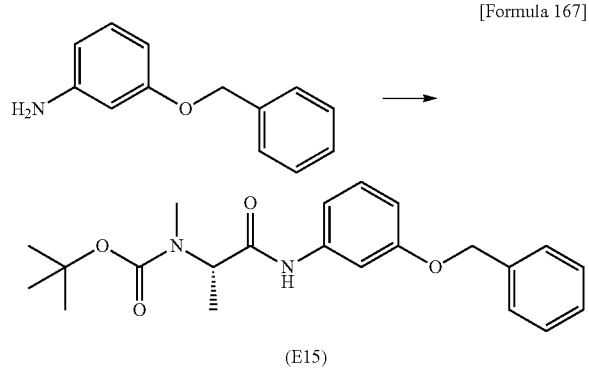

To a solution of N-Boc-N-methyl-L-alanine (561 mg) in tetrahydrofuran (14 mL), isobutyl chloroformate (362 µL) and N-methylmorpholine (303 µL) were added under ice cooling, and the mixture was stirred at the same temperature for 30 minutes. To the reaction mixture, 3-benzyloxyaniline (500 mg) was added under ice cooling, and the mixture was stirred at room temperature for 30 minutes. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 70% hexane in ethyl acetate) to obtain (S)-tert-butyl (1-((3-(benzyloxy)phenyl)amino)-1-oxopropan-2-yl)(methyl)carbamate (E15, 903 mg).

MS m/z (M+H): 385.2

4

[Formula 168]

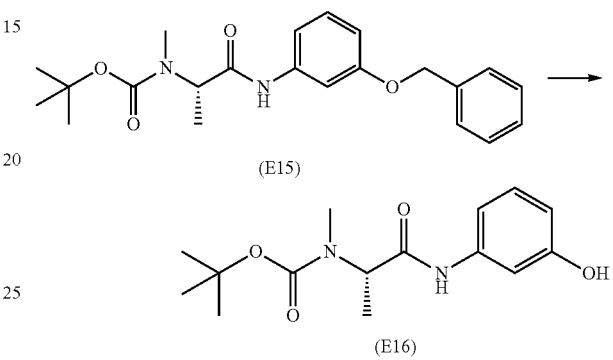

To 10% palladium-carbon (100 mg), a solution of (S)-tert-butyl (1-((3-(benzyloxy)phenyl)amino)-1-oxopropan-2-yl)(methyl)carbamate (E15, 166 mg) in methanol (4 mL) and tetrahydrofuran (2 mL) was added at room temperature, and the mixture was stirred at the same temperature for 5 hours and 30 minutes under a hydrogen atmosphere. The insoluble matter was removed by filtration through Cerite, and then the solvent was evaporated under reduced pressure to obtain (S)-tert-butyl (1-((3-hydroxyphenyl)amino)-1-oxopropan-2-yl)(methyl)carbamate (E16, 136 mg).

MS m/z (M+H): 295.2

5

[Formula 169]

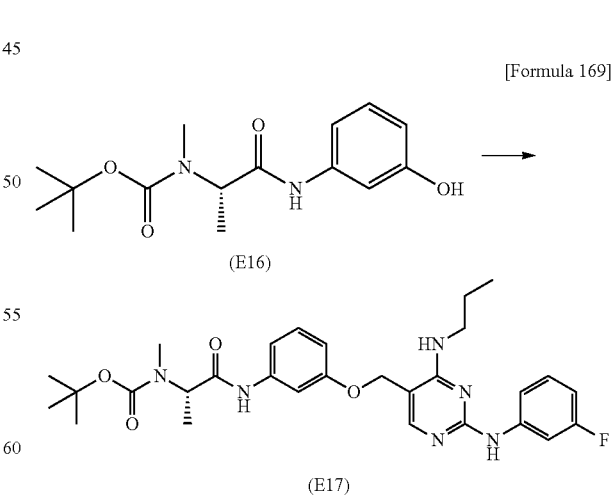

To a solution of (S)-tert-butyl (1-((3-hydroxyphenyl)amino)-1-oxopropan-2-yl)(methyl)carbamate (E16, 68 mg), a solution of (2-(3-fluorophenyl)amino)-4-(propylamino)pyrimidin-5-yl)methanol (E13, 50 mg) and triphenylphosphine (52 mg) in tetrahydrofuran (2 mL), a 40% solution of diethyl azodicarboxylate in toluene (86 µL) was added under ice cooling, and the mixture was stirred at the same temperature for 15 minutes, and then stirred at room temperature for 2 hours. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 70 to 0% hexane in ethyl acetate) to obtain (S)-tert-butyl (1-((3-((2-((3-fluorophenyl)amino)-4-(propylamino)pyrimidin-5-yl)methoxy)phenyl)amino)-1-oxopropan-2-yl)(methyl)carbamate (E17, 54 mg).

MS m/z (M+H): 553.3

6

[Formula 170]

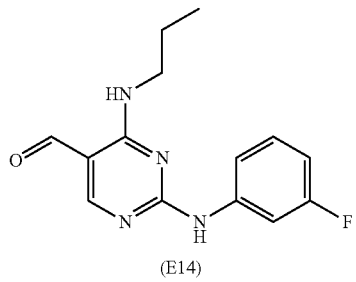
(E14)

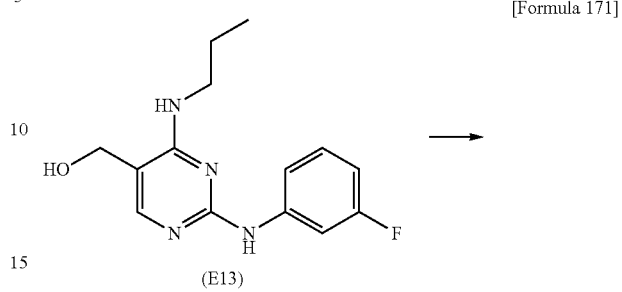
(E13)

To a solution of (S)-tert-butyl (1-((3-aminophenyl)amino)-1-oxopropan-2-yl)(methyl)carbamate (B9, 28 mg) and 2-((3-fluorophenyl)amino)-4-(propylamino)pyrimidine-5-carbaldehyde (E14, 24 mg) in methylene chloride (2 mL), sodium triacetoxyborohydride (28 mg) and acetic acid (50 µL) were added at room temperature, and the mixture was stirred at the same temperature for 5 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 60 to 0% hexane in ethyl acetate) to obtain (S)-tert-butyl (1-((3-(((2-((3-fluorophenyl)amino)-4-(propylamino)pyrimidin-5-yl)methyl)amino)phenyl)amino)-1-oxopropan-2-yl)(methyl)carbamate (E18, 33 mg).

MS m/z (M+H): 552.3

7

[Formula 171]

(E19)

To a solution of (2-((3-fluorophenyl)amino)-4-(propylamino)pyrimidin-5-yl)methanol (E13, 20 mg) and 3-nitrothiophenol (17 mg) in tetrahydrofuran (1 mL), tributylphosphine (36 µL) and 1,1'-(azodicarbonyl)dipiperidine (28 mg) were added under ice cooling, and the mixture was stirred at room temperature for 6 hours and 30 minutes. To the reaction mixture, tributylphosphine (36 µL) and 1,1'-(azodicarbonyl)dipiperidine (28 mg) were added at room temperature, and the mixture was stirred at the same temperature for 8 hours and 30 minutes. The solvent was evaporated under reduced pressure, and then the obtained residue was purified by basic silica gel column chromatography (eluent, 88 to 40% hexane in ethyl acetate) to obtain $N^2$-(3-fluorophenyl)-5-(((3-nitrophenyl)thio)methyl)-$N^4$-propylpyrimidine-2,4-diamine (E19, 19 mg) as yellow solid.

MS m/z (M+H): 414.3

8

[Formula 172]

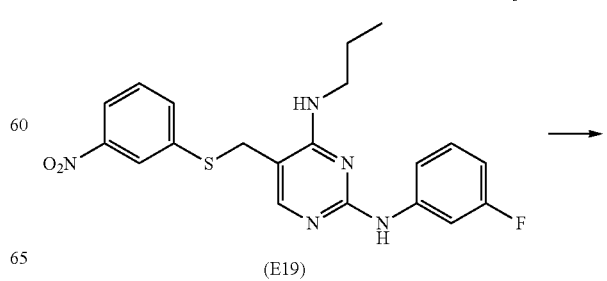
(E19)

237

-continued

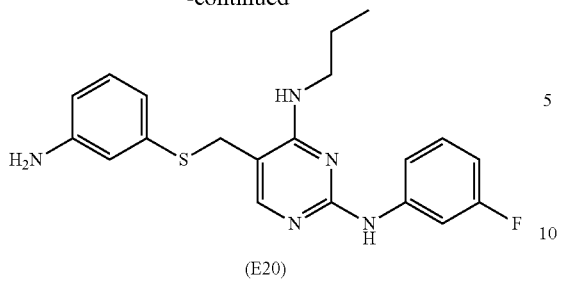

(E20)

To a solution of $N^2$-(3-fluorophenyl)-5-(((3-nitrophenyl)thio)methyl)-$N^4$-propylpyrimidine-2,4-diamine (E19, 160 mg) in ethanol (4 mL) and ethyl acetate (8 mL), tin(II) chloride (739 mg) was added at room temperature, and the mixture was stirred at 70° C. for 1 hour. The reaction mixture was cooled to room temperature, and then water and ethyl acetate were added to the mixture. The organic layer was separated, washed successively with water and saturated aqueous sodium chloride, and then dried over anhydrous magnesium sulfate, and the solvent was evaporated under reduced pressure to obtain 5-(((3-aminophenyl)thio)methyl)-$N^2$-(3-fluorophenyl)-$N^4$-propylpyrimidine-2,4-diamine (E20).

MS m/z (M+H): 384.3

9

[Formula 173]

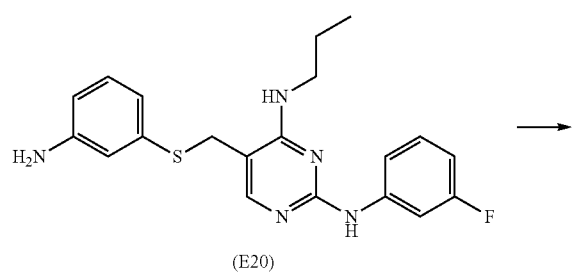

(E20)

238

-continued

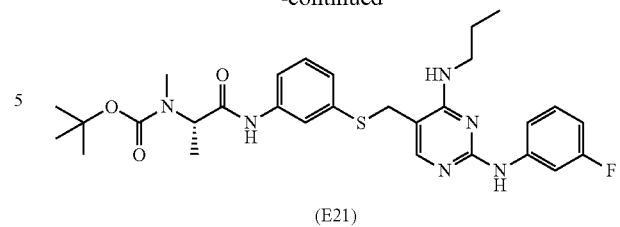

(E21)

To 5-(((3-aminophenyl)thio)methyl)-$N^2$-(3-fluorophenyl)-$N^4$-propylpyrimidine-2,4-diamine (E20) obtained above, N-Boc-N-methyl-L-alanine (179 mg), 1-ethyl-3-(3-dimethylaminopropyl)carbodiimide hydrochloride (169 mg) and 1-hydroxybenzotriazole monohydrate (119 mg), N,N-dimethylformamide (2.5 mL) and N,N-diisopropylethylamine (299 µL) were added at room temperature, and the mixture was stirred at 40° C. for 11 hours. The reaction mixture was cooled to room temperature, and then saturated aqueous sodium hydrogencarbonate and ethyl acetate were added to the mixture. The organic layer was separated, washed successively with water, saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 88 to 28% hexane in ethyl acetate) to obtain oily (S)-tert-butyl (1-((3-(((2-((3-fluorophenyl)amino)-4-(propylamino)pyrimidin-5-yl)methyl)thio)phenyl)amino)-1-oxopropan-2-yl)(methyl)carbamate (E21, 47 mg).

MS m/z (M+H): 569.4

10

In the same manner as that of Example 1 or Example 14, Compounds (6-20) to (6-22) were obtained.

TABLE 58

| Compound No. | Structure | Physicochemical data |
|---|---|---|
| 6-20 | 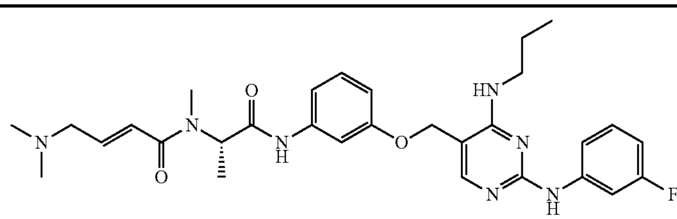 | $^1$H-NMR (CDCl$_3$) δ: 7.78 (1H, s), 7.77-7.75 (1H, m), 7.50 (1H, s), 7.25-6.90 (4H, m), 6.71-6.63 (1H, m), 6.46-6.39 (1H, m), 5.48 (1H, dt), 5.28 (1H, d), 4.88 (2H, s), 3.52-3.43 (3H, m), 3.11 (2H, d), 3.01 (3H, s), 2.28 (6H, s), 1.74-1.62 (2H, m), 1.43 (3H, d), 1.00 (3H, t) |
| 6-21 | 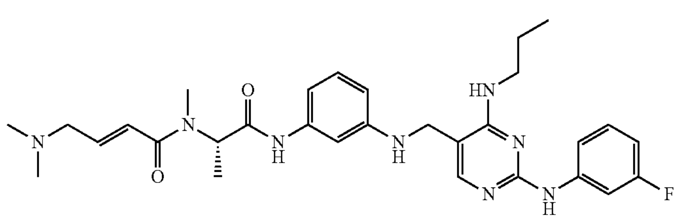 [SMILES: CCCNc1nc(Nc2cccc(F)c2)ncc1CNc1cccc(NC(=O)[C@H](C)N(C)C(=O)/C=C/CN(C)C)c1] | $^1$H-NMR (CDCl$_3$) δ: 7.85-7.78 (1H, m), 7.83 (1H, s), 7.26-7.07 (3H, m), 7.00-6.94 (1H, m), 6.82-6.76 (1H, m), 6.71-6.63 (1H, m), 6.50-6.43 (1H, m), 5.83-5.73 (1H, m), 5.33-5.24 (1H, m), 4.06 (2H, d), 3.49-3.40 (3H, m), 3.11 (3H, d), 3.01 (3H, s), 2.27 (6H, s), 1.71-1.57 (2H, m), 1.42 (3H, d), 0.96 (3H, t) |

TABLE 58-continued

| Compound No. | Structure | Physicochemical data |
|---|---|---|
| 6-22 | [structure] | ¹H-NMR (CDCl$_3$) δ: 8.88 (1H, s), 7.78 (1H, dt, J = 11.5, 2.0 Hz), 7.71 (1H, s), 7.67 (1H, s), 7.36-6.95 (7H, m), 6.65 (1H, td, J = 8.3, 2.0 Hz), 6.42 (1H, d, J = 15.2 Hz), 5.45(1H, t, J = 5.3 Hz), 5.28 (1H, q, J = 6.6 Hz), 3.92 (2H, s), 3.55-3.45 (2H, m), 3.11 (2H, d, J = 5.9 Hz), 3.01 (3H, s), 2.27 (6H, s), 1.77-1.63 (2H, m), 1.42 (3H, d, J = 7.3Hz), 1.02 (3H, t, J = 7.3 Hz) |

Example 25

1

[Formula 174]

(E3)

To a solution of ethyl 2-((3-fluorophenyl)amino)-4-(propylamino)pyrimidine-5-carboxylate (E3, 247 mg) in ethanol (3 mL) and tetrahydrofuran (1.5 mL), 2.0 mol/L aqueous sodium hydroxide (0.78 mL) was added at room temperature, and the mixture was stirred at 50° C. for 1 hour. To the reaction mixture, 2.0 mol/L aqueous sodium hydroxide (0.39 mL) was added at 50° C., and the mixture was stirred at the same temperature for 3 hours. The reaction mixture was cooled to room temperature, and then 1.0 mol/L aqueous hydrochloric acid was added to the reaction mixture until the mixture became acidic. The solid matter was taken by filtration, washed with water, and then dried under reduced pressure to obtain 2-((3-fluorophenyl)amino)-4-(propylamino) pyrimidine-5-carboxylic acid (E22, 130 mg).

MS m/z (M+H): 290.1

2

[Formula 175]

(E22)

(E23)

To 2-((3-fluorophenyl)amino)-4-(propylamino)pyrimidine-5-carboxylic acid (E22, 19 mg), thionyl chloride (2 mL) was added at room temperature, and the mixture was stirred for 2 hours under reflux by heating. The reaction mixture was cooled to room temperature, and then toluene was added to the mixture. The solvent was evaporated under reduced pressure to obtain 2-((3-fluorophenyl)amino)-4-(propylamino) pyrimidine-5-carbonyl chloride (E23) as white solid.

3

[Formula 176]

(E23)

-continued

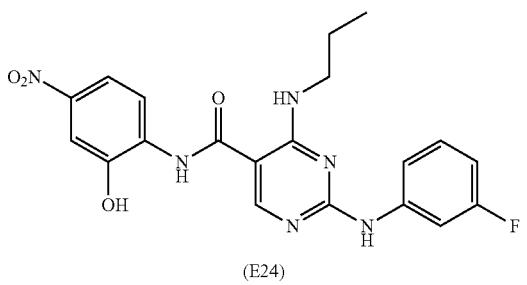
(E24)

To 2-((3-fluorophenyl)amino)-4-(propylamino)pyrimidine-5-carbonyl chloride (E23) obtained above and 2-amino-5-nitrophenol (15 mg), 1,4-dioxane (1.5 mL) was added at room temperature, the reaction vessel was sealed, and then by using a microwave reaction system, the mixture was stirred at 210° C. for 30 minutes. The reaction mixture was cooled to room temperature, and then saturated aqueous sodium hydrogencarbonate and ethyl acetate were added to the reaction mixture. The organic layer was separated, washed successively with saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 88 to 20% hexane in ethyl acetate) to obtain 2-((3-fluorophenyl)amino)-N-(2-hydroxy-4-nitrophenyl)-4-(propylamino)pyrimidine-5-carboxamide (E24, 11 mg) as yellow solid.

MS m/z (M+H): 427.3

4

[Formula 177]

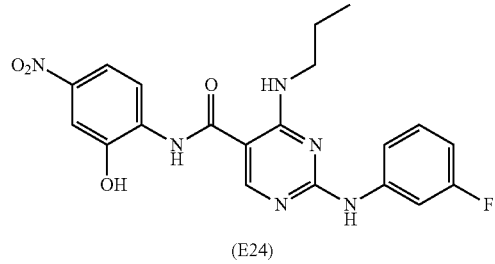
(E24)

→

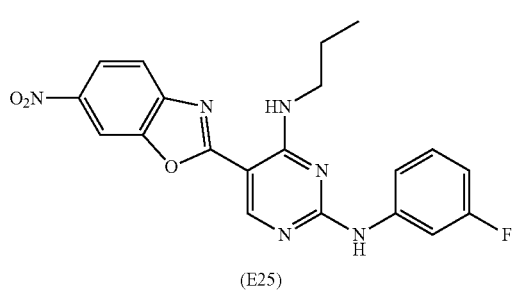
(E25)

To 2-((3-fluorophenyl)amino)-N-(2-hydroxy-4-nitrophenyl)-4-(propylamino)pyrimidine-5-carboxamide (E24, 11 mg) and p-toluenesulfonic acid monohydrate (15 mg), xylene (1.5 mL) was added at room temperature, and the mixture was stirred at 155° C. for 4 hours. The reaction mixture was cooled to room temperature, and then purified by silica gel column chromatography (eluent, 100 to 80% ethyl acetate in methanol). To the obtained solid matter, saturated aqueous sodium hydrogencarbonate and ethyl acetate were added. The organic layer was separated, washed successively with saturated aqueous sodium hydrogencarbonate and saturated aqueous sodium chloride, and then dried over anhydrous magnesium sulfate, and the solvent was evaporated under reduced pressure. To the obtained residue, ethyl acetate were added, and the solid matter was taken by filtration to obtain $N^2$-(3-fluorophenyl)-5-(6-nitrobenzo[d]oxazol-2-yl)-$N^4$-propylpyrimidine-2,4-diamine (E25) as yellow solid.

MS m/z (M+H): 409.3

5

[Formula 178]

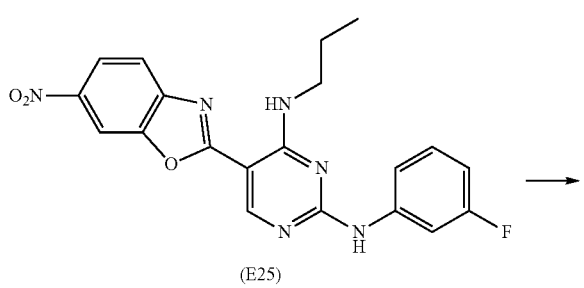
(E25)

→

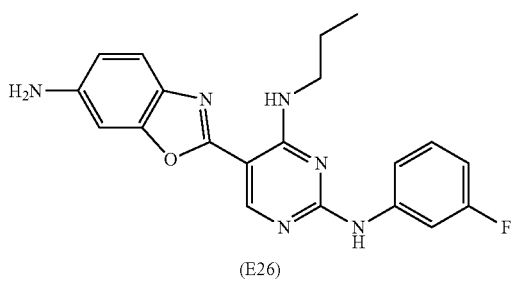
(E26)

To a solution of $N^2$-(3-fluorophenyl)-5-(6-nitrobenzo[d]oxazol-2-yl)-$N^4$-propylpyrimidine-2,4-diamine (E25) obtained above in ethanol (1.5 mL) and ethyl acetate (1.5 mL), tin(II) chloride (49 mg) was added at room temperature, and the mixture was stirred at 70° C. for 50 minutes. The reaction mixture was cooled to room temperature, and then saturated aqueous sodium hydrogencarbonate and ethyl acetate were added to the reaction mixture. The organic layer was separated, washed with saturated aqueous sodium chloride, and then dried over anhydrous magnesium sulfate to obtain 5-(6-aminobenzo[d]oxazol-2-yl)-$N^2$-(3-fluorophenyl)-$N^4$-propylpyrimidine-2,4-diamine (E26).
[Formula 179]
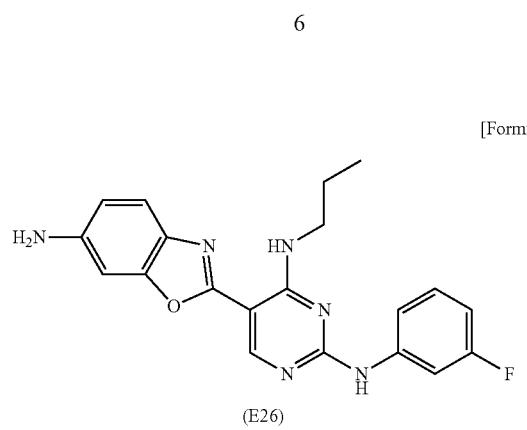
(E26)
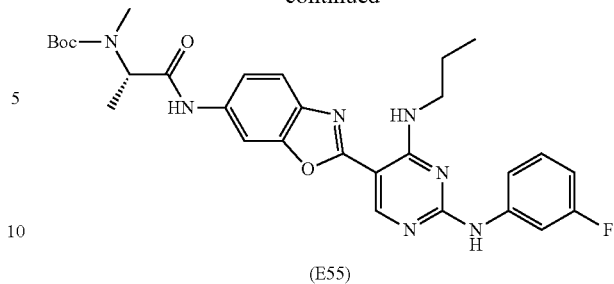
(E55)
By using 5-(6-aminobenzo[d]oxazol-2-yl)-$N^2$-(3-fluorophenyl)-$N^4$-propylpyrimidine-2,4-diamine (E26), (S)-tert-butyl (1-((2-(2-(((3-fluorophenyl)amino)-4-(propylamino)pyrimidin-5-yl)benzo[d]oxazol-6-yl)amino)-1-oxopropan-2-yl)(methyl)carbamate (E55) was obtained in the same manner as that of Example 1, (5).
[Formula 180]
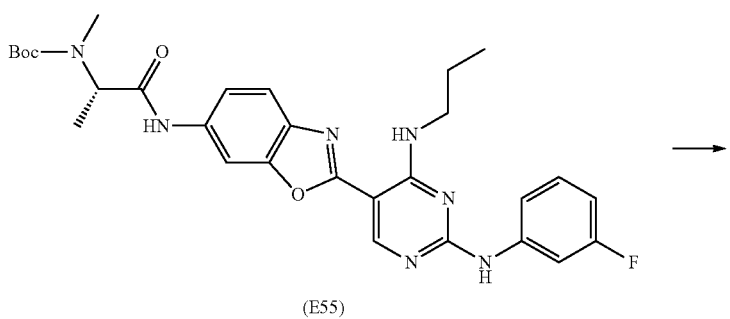
(E55)
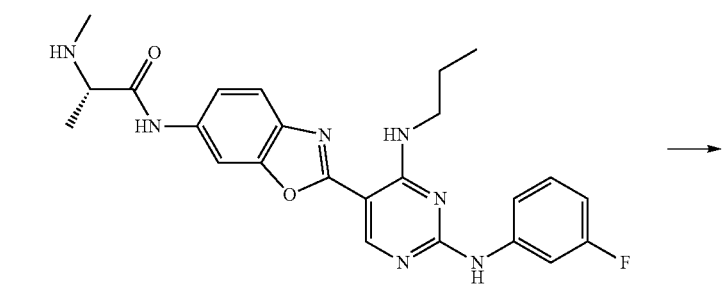
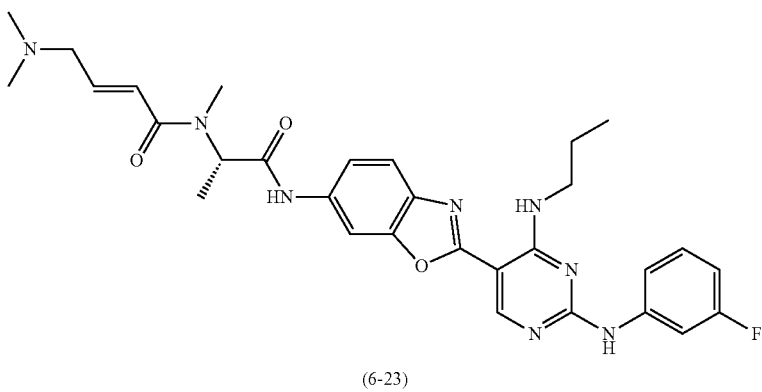
(6-23)

By using (S)-tert-butyl (1-((2-(2-((3-fluorophenyl)amino)-4-(propylamino)pyrimidin-5-yl)benzo[d]oxazol-6-yl)amino)-1-oxopropan-2-yl)(methyl)carbamate (E55), (S,E)-4-(dimethylamino)-N-(1-((2-(2-((3-fluorophenyl)amino)-4-(propylamino)pyrimidin-5-yl)benzo[d]oxazol-6-yl)amino)-1-oxopropan-2-yl)-N-methyl-2-butenamide (6-23) was obtained in the same manner as that of Example 1, (6) and Example 1, (8).

$^1$H-NMR (CDCl$_3$) δ: 9.00-8.93 (2H, m), 8.79 (1H, s), 8.11 (1H, d, J=2.0 Hz), 7.88 (1H, d, J=10.6 Hz), 7.54 (1H, d, J=8.6 Hz), 7.27-7.13 (4H, m), 7.02 (1H, dt, J=15.2, 5.9 Hz), 6.74 (1H, td, J=7.9, 2.0 Hz), 6.45 (1H, d, J=15.2 Hz), 5.40-5.26 (1H, m), 3.71-3.61 (2H, m), 3.12 (2H, dd, J=5.9, 1.3 Hz), 3.05 (3H, s), 2.28 (6H, s), 1.88-1.75 (2H, m), 1.46 (3H, d, J=6.6 Hz), 1.09 (3H, t, J=7.6 Hz)

Example 35

1

[Formula 181]

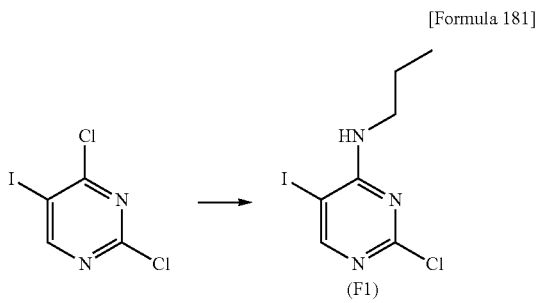

To a solution of 2,4-dichloro-5-iodopyrimidine (5.77 g) synthesized according to the method described in WO2008/155140 A1 and N,N-diisopropylethylamine (7.86 mL) in tetrahydrofuran (83 mL), propylamine (3.55 mL) was added under ice cooling, and the mixture was stirred at room temperature for 1 hour. To the reaction mixture, water and ethyl acetate were added. The organic layer was separated, and the aqueous layer was extracted with ethyl acetate. The organic layer and the extract were combined, washed successively with 1.0 mol/L aqueous hydrochloric acid, water, saturated aqueous sodium hydrogencarbonate and saturated aqueous sodium chloride, and then dried over anhydrous magnesium sulfate. The solvent was evaporated under reduced pressure to obtain oily 2-chloro-5-iodo-N-propylpyrimidin-4-amine (F1, 6.44 g).

MS m/z (M+H): 298.3

2

[Formula 182]

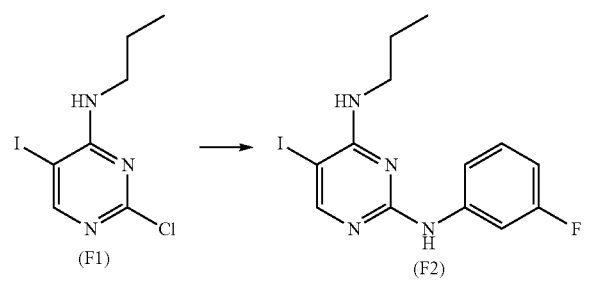

To a solution of 2-chloro-5-iodo-N-propylpyrimidin-4-amine (F1, 596 mg) and 3-fluoroaniline (1.11 g) in N-methylpyrrolidone (10 mL), (1S)-(+)-10-camphorsulfonic acid (2.32 g) was added at room temperature, and the mixture was stirred at 40 to 50° C. for 6 hours. The reaction mixture was cooled to room temperature, and then saturated aqueous sodium hydrogencarbonate was added to the reaction mixture. The solid matter was taken by filtration, washed with water, and then dried under reduced pressure to obtain N$^2$-(3-fluorophenyl)-5-iodo-N$^4$-propylpyrimidine-2,4-diamine (F2, 685 mg) as white solid.

MS m/z (M+H): 373.0

3

[Formula 183]

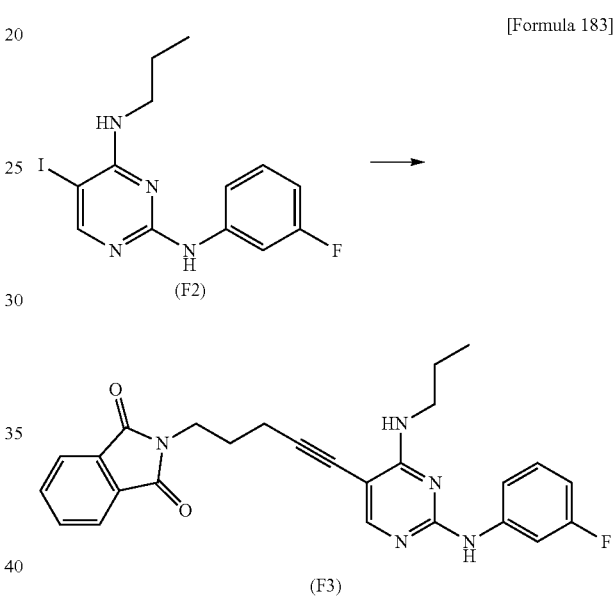

To a solution of N$^2$-(3-fluorophenyl)-5-iodo-N$^4$-propylpyrimidine-2,4-diamine (F2, 2.50 g), bis(triphenylphosphine)palladium(II) dichloride (472 mg) and copper(I) iodide (256 mg) in N,N-dimethylformamide (60 mL), triethylamine (4.7 mL) and N-(4-pentynyl)phthalimide (2.15 g) were added at room temperature, and the mixture was stirred at the same temperature for 2 hours. To the reaction mixture, water and ethyl acetate were added. The organic layer was separated, and the aqueous layer was extracted with ethyl acetate. The organic layer and the extract were combined, washed successively with water, saturated aqueous ammonium chloride and saturated aqueous sodium chloride, and then dried over anhydrous magnesium sulfate, and the solvent was evaporated under reduced pressure. To the obtained residue, hexane and ethyl acetate were added. The solid matter was taken by filtration, and dried under reduced pressure to obtain 2-(5-(2-((3-fluorophenyl)amino)-4-(propylamino)pyrimidin-5-yl)-4-pentyn-1-yl)isoindoline-1,3-dione (F3, 1.44 g) as yellow solid.

MS m/z (M+H): 458.8

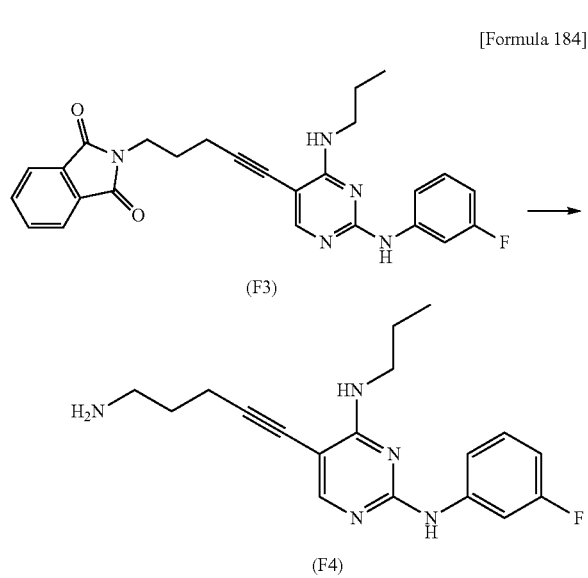

(F3)

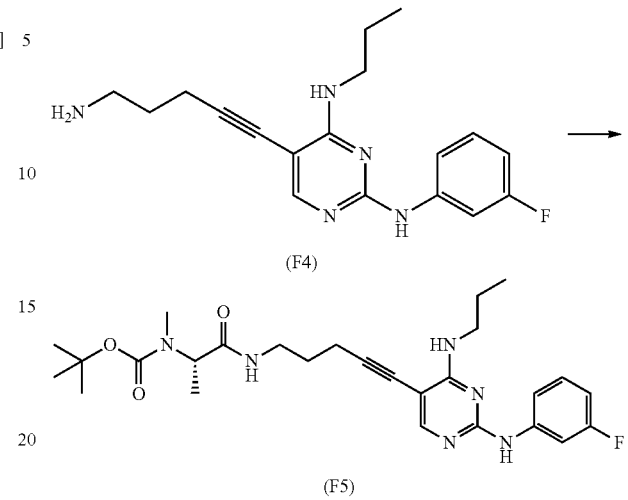

(F4)

(F4)

To a solution of 2-(5-(2-((3-fluorophenyl)amino)-4-(propylamino)pyrimidin-5-yl)-4-pentyn-1-yl)isoindoline-1,3-dione (F3, 2.51 g) in tetrahydrofuran (20 mL) and ethanol (10 mL), hydrazine monohydrate (5.1 mL) was added at room temperature, and the mixture was stirred for 10 minutes under reflux by heating. To the reaction mixture, ethanol (10 mL) was added, and the mixture was stirred at room temperature for 3 hours and 20 minutes. To the reaction mixture, diisopropyl ether was added, the insoluble matter was removed by filtration, and then water was added to the filtrate. The organic layer was separated, washed successively with saturated aqueous sodium hydrogencarbonate and saturated aqueous sodium chloride, and then dried over anhydrous magnesium sulfate. The solvent was evaporated under reduced pressure to obtain 5-(5-amino-1-pentyn-1-yl)-$N^2$-(3-fluorophenyl)-$N^4$-propylpyrimidine-2,4-diamine (F4, 1.10 g) as white solid.

MS m/z (M+H): 328.2

(F5)

To a solution of 5-(5-amino-1-pentyn-1-yl)-$N^2$-(3-fluorophenyl)-$N^4$-propylpyrimidine-2,4-diamine (F4, 91 mg), N-Boc-N-methyl-L-alanine (113 mg), 1-ethyl-3-(3-dimethylaminopropyl)carbodiimide hydrochloride (107 mg) and 1-hydroxybenzotriazole monohydrate (75 mg) in N,N-dimethylformamide (2 mL), N,N-diisopropylethylamine (194 μL) was added at room temperature, and the mixture was stirred at the same temperature for 4 hours and 20 minutes. To the reaction mixture, saturated aqueous sodium hydrogencarbonate and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 75 to 25% hexane in ethyl acetate) to obtain oily (S)-tert-butyl (1-((5-(2-(3-fluorophenyl)amino)-4-(propylamino)pyrimidin-5-yl)-4-pentyn-1-yl)amino)-1-oxopropan-2-yl)(methyl)carbamate (F5, 103 mg).

MS m/z (M+H): 513.3

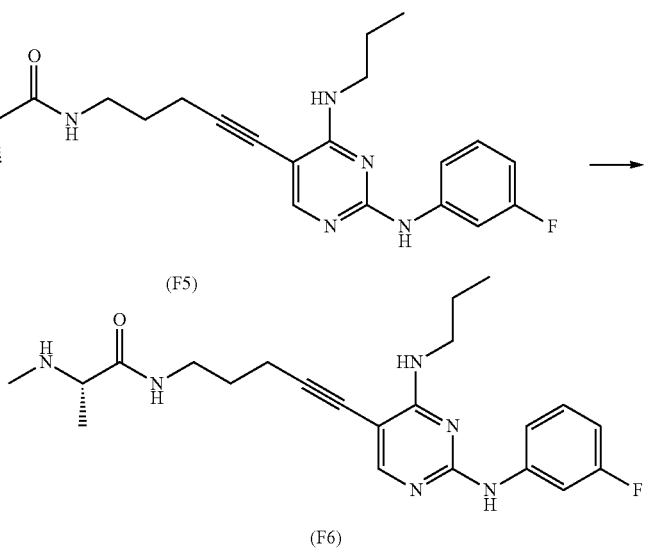

(F5)

(F6)

To a solution of (S)-tert-butyl (1-((5-(2-((3-fluorophenyl)amino)-4-(propylamino)pyrimidin-5-yl)-4-pentyn-1-yl)amino)-1-oxopropan-2-yl)(methyl)carbamate (F5, 103 mg) in 1,4-dioxane (2 mL), a 4.0 mol/L solution of hydrochloric acid in 1,4-dioxane (2 mL) was added at room temperature, and the mixture was stirred at the same temperature for 2 hours. The solvent was evaporated under reduced pressure. The obtained solid matter was washed with ethyl acetate, and then dried under reduced pressure to obtain (S)—N-(5-(2-((3-fluorophenyl)amino)-4-(propylamino)pyrimidin-5-yl)-4-pentyn-1-yl)-2-(methylamino)propanamide (F6) dihydrochloride (94 mg) as white solid.

MS m/z (M+H): 413.2

7

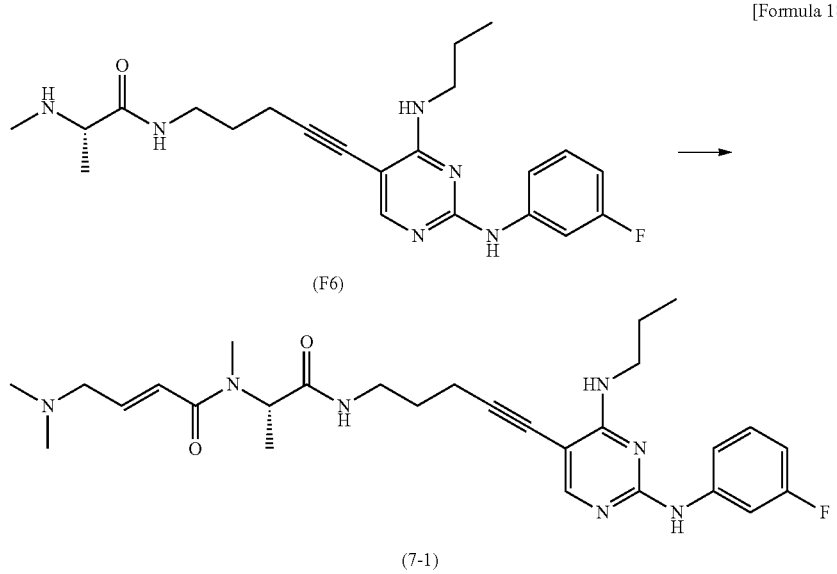

To a solution of 4-dimethylaminocrotonic acid hydrochloride (307 mg) in N,N-dimethylformamide (9 mL), N-methylmorpholine (682 µL) was added under ice cooling, and the mixture was stirred at the same temperature for 5 minutes. Then, isobutyl chloroformate (204 µL) was added to the mixture under ice cooling, and the mixture was stirred at the same temperature for 3 minutes. To the reaction mixture, (S)—N-(5-(2-((3-fluorophenyl)amino)-4-(propylamino)pyrimidin-5-yl)-4-pentyn-1-yl)-2-(methylamino)propanamide (F6) dihydrochloride (300 mg) was added under ice cooling, and the mixture was stirred at the same temperature for 1 hour and 30 minutes. To the reaction mixture, saturated aqueous sodium hydrogencarbonate (10 drops) were added, and the solvent was evaporated under reduced pressure. The obtained residue was purified by basic silica gel column chromatography (eluent, 100 to 90% ethyl acetate in methanol) to obtain (S,E)-4-(dimethylamino)-N-(1-((5-(2-((3-fluorophenyl)amino)-4-(propylamino)pyrimidin-5-yl)-4-pentyn-1-yl)amino)-1-oxopropan-2-yl)-N-methyl-2-butenamide (7-1, 208 mg).

$^1$H-NMR (CDCl$_3$) δ: 7.96 (1H, s), 7.82 (1H, dt, J=11.9, 2.3 Hz), 7.26-7.16 (1H, m), 7.11-7.06 (1H, m), 7.08-7.04 (1H, m), 6.94 (1H, dt, J=15.2, 5.9 Hz), 6.67 (1H, dt, J=7.9, 2.3 Hz), 6.59-6.48 (1H, m), 6.42 (1H, d, J=15.2 Hz), 6.31-6.22 (1H, m), 5.18 (1H, q, J=7.3 Hz), 3.55-3.47 (2H, m), 3.49-3.39 (2H, m), 3.10 (2H, d, J=5.9 Hz), 2.99 (3H, s), 2.44 (2H, t, J=6.6 Hz), 2.27 (6H, s), 1.81-1.69 (2H, m), 1.71-1.64 (2H, m), 1.36 (3H, d, J=7.3 Hz), 1.01 (3H, t, J=7.9 Hz)

Example 36

1 [Formula 188]

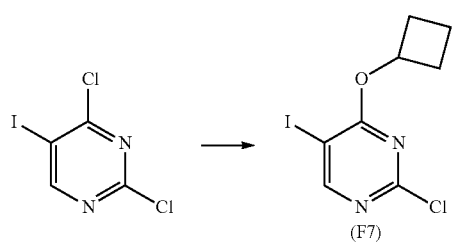

To a solution of cyclobutanol (117 µL) in tetrahydrofuran (2 mL), tert-butoxypotassium (100 mg) was added at room

[Formula 187]

temperature, and the mixture was stirred under reflux by heating. The reaction mixture was cooled to room temperature (Reaction mixture A).

To a solution of 2,4-dichloro-5-iodopyrimidine (205 mg) in N,N-dimethylformamide (2 mL), Reaction mixture A mentioned above was added under ice cooling, and the mixture was stirred at the same temperature for 2 hours. To the reaction mixture, water and ethyl acetate were added. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain 2-chloro-4-cyclobutoxy-5-iodopyrimidine (F7).

MS m/z (M+H): 311.0

2 [Formula 189]

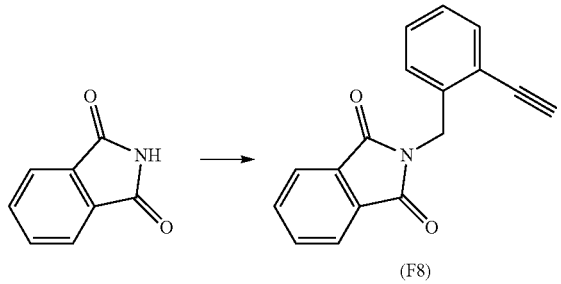

To a solution of 2-ethynylbenzyl alcohol (1.00 g), phthalimide (2.20 g) and triphenylphosphine (3.96 g) in tetrahydrofuran (30 mL), a solution of diisopropyl azodicarboxylate (1.9 mol/L) in toluene (7.9 mL) was added under ice cooling, and the mixture was stirred at room temperature for 5 hours. The solvent was evaporated under reduced pressure, and the obtained residue was purified by silica gel column chromatography (eluent, 96 to 66% hexane in ethyl acetate) to obtain 2-(2-ethynylbenzyl)isoindoline-1,3-dione (F8, 1.44 g) as pale orange solid.

MS m/z (M+H): 262.2

3

[Formula 190]

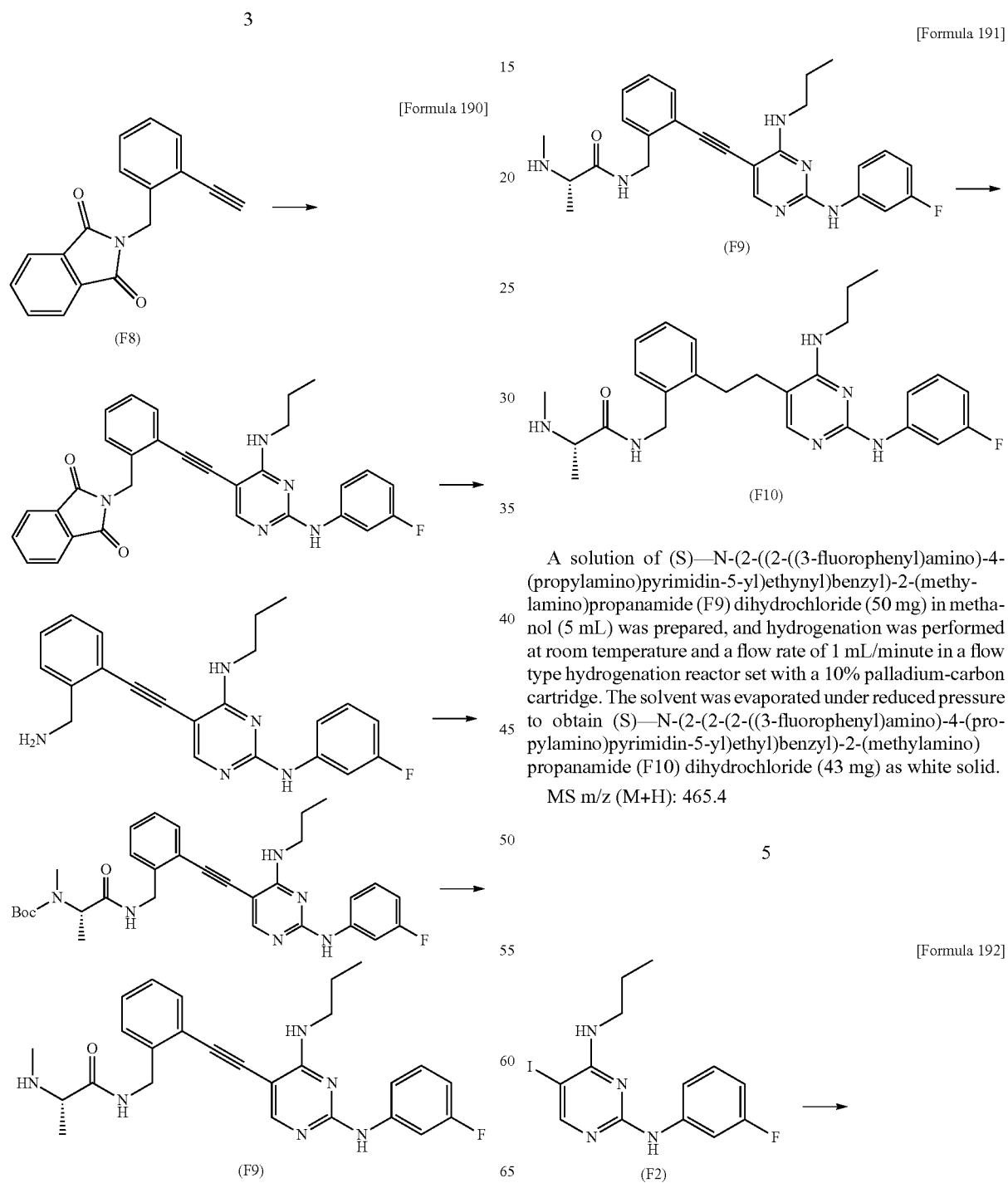

In the same manner as that of Example 35, (3) to (6), (S)—N-(2-((2-((3-fluorophenyl)amino)-4-(propylamino)pyrimidin-5-yl)ethynyl)benzyl)-2-(methylamino)propanamide (F9) dihydrochloride was obtained from 2-(2-ethynylbenzyl)isoindoline-1,3-dione (F8).

MS m/z (M+H): 461.4

4

[Formula 191]

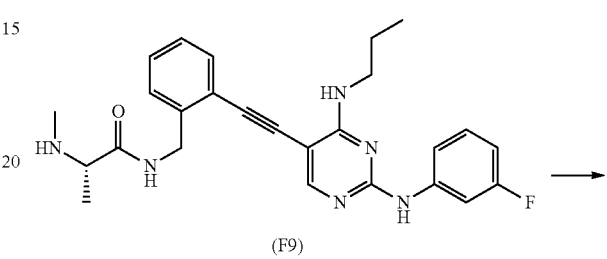

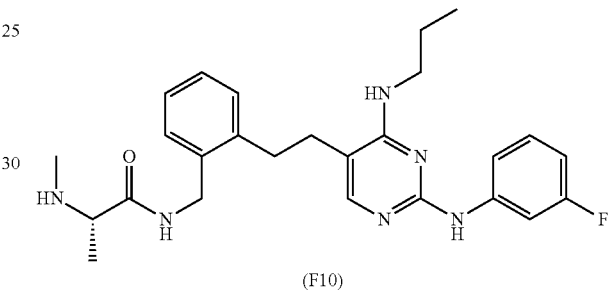

A solution of (S)—N-(2-((2-((3-fluorophenyl)amino)-4-(propylamino)pyrimidin-5-yl)ethynyl)benzyl)-2-(methylamino)propanamide (F9) dihydrochloride (50 mg) in methanol (5 mL) was prepared, and hydrogenation was performed at room temperature and a flow rate of 1 mL/minute in a flow type hydrogenation reactor set with a 10% palladium-carbon cartridge. The solvent was evaporated under reduced pressure to obtain (S)—N-(2-(2-(2-((3-fluorophenyl)amino)-4-(propylamino)pyrimidin-5-yl)ethyl)benzyl)-2-(methylamino)propanamide (F10) dihydrochloride (43 mg) as white solid.

MS m/z (M+H): 465.4

5

[Formula 192]

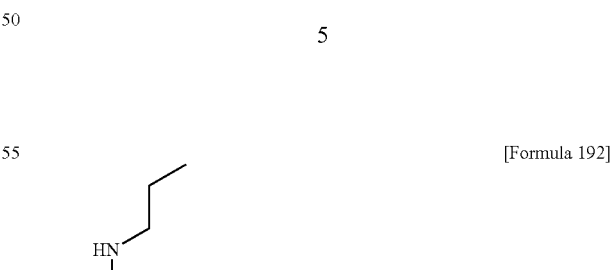

-continued

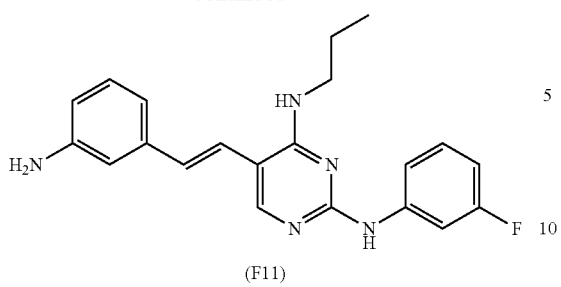

(F11)

To a solution of 3-vinylaniline (19 µL), $N^2$-(3-fluorophenyl)-5-iodo-$N^4$-propylpyrimidine-2,4-diamine (F2, 51 mg) and palladium(II) acetate (3 mg) in acetonitrile (1.5 mL), triethylamine (68 µL) was added at room temperature, and the mixture was stirred at the same temperature for 1 hour, and then stirred at 80° C. for 14 hours. The reaction mixture was cooled to room temperature, and then the solvent was evaporated under reduced pressure. The obtained residue was purified by silica gel column chromatography (eluent, 50% hexane in ethyl acetate) to obtain (E)-5-(3-aminostyryl)-$N^2$-(3-fluorophenyl)-$N^4$-propylpyrimidine-2,4-diamine (F11, 14 mg).

MS m/z (M+H): 364.3

6

[Formula 193]

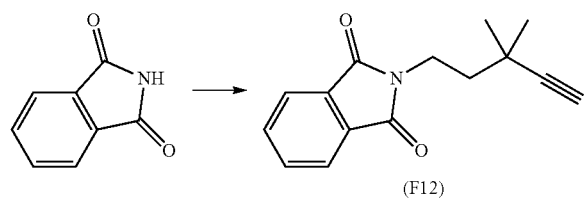

(F12)

To a solution of 3,3-dimethyl-4-pentyn-1-ol (6.3 g) synthesized according to the method described in Chemistry A European Journal, 2005, 11, pp. 308-320, triphenylphosphine (29.4 g), and phthalimide (16.5 g) in tetrahydrofuran (200 mL), a 2.2 mol/L solution of diethyl azodicarboxylate in toluene (51 mL) was added dropwise under ice cooling, and the mixture was stirred at the same temperature. To the reaction mixture, water and ethyl acetate were added. The organic layer was separated, washed successively with water and saturated aqueous sodium chloride, and then dried over anhydrous sodium sulfate, and the solvent was evaporated under reduced pressure. To the obtained residue, ethyl acetate were added, the insoluble matter was removed by filtration, and then the solvent was evaporated under reduced pressure. The obtained residue was purified by silica gel column chromatography to obtain 2-(3,3-dimethyl-4-pentyn-1-yl)isoindoline-1,3-dione (F12, 7.1 g) as pale yellow solid.

MS m/z (M+H): 242.1

7

[Formula 194]

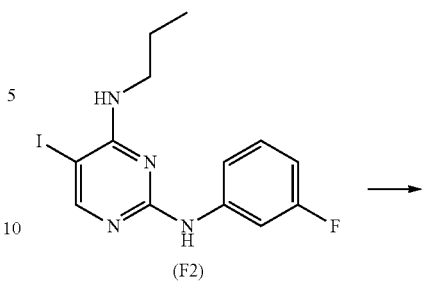

(F2)

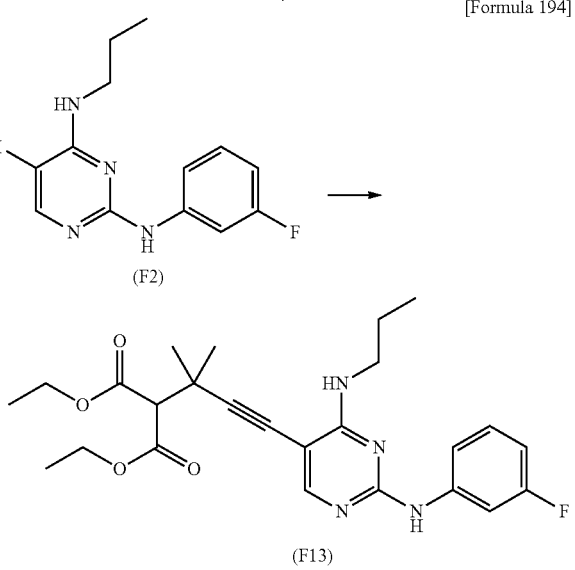

(F13)

To a solution of diethyl 2-(2-methyl-3-butyn-2-yl)malonate synthesized according to the method described in Chemistry A European Journal, 2005, 11, pp. 308-320 (3.3 g), $N^2$-(3-fluorophenyl)-5-iodo-$N^4$-propylpyrimidine-2,4-diamine (F2, 868 mg), bis(triphenylphosphine)palladium(II) dichloride (161 mg) and copper(I) iodide (88 mg) in N,N-dimethylformamide (15 mL), triethylamine (1.6 mL) was added at room temperature, and the mixture was stirred at the same temperature for 2 hours and 30 minutes. To the reaction mixture, tetrakis(triphenylphosphine)palladium(0) (132 mg) was added at room temperature, and the mixture was stirred at the same temperature for 1 hour and 40 minutes. To the reaction mixture, ethyl acetate and saturated aqueous ammonium chloride were added. The organic layer was separated, washed successively with saturated aqueous ammonium chloride, water and saturated aqueous sodium chloride, and then dried over anhydrous sodium sulfate, and the solvent was evaporated under reduced pressure. The obtained residue was purified by silica gel column chromatography (eluent, 94 to 64% hexane in ethyl acetate) to obtain diethyl 2-(4-(2-((3-fluorophenyl)amino)-4-(propylamino)pyrimidin-5-yl)-2-methyl-3-butyn-2-yl)malonate (F13, 803 mg) as yellow solid.

MS m/z (M+H): 471.4

8

[Formula 195]

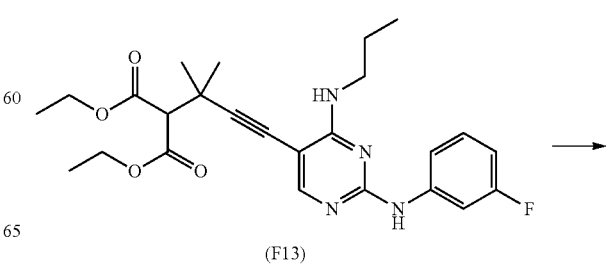

(F13)

-continued

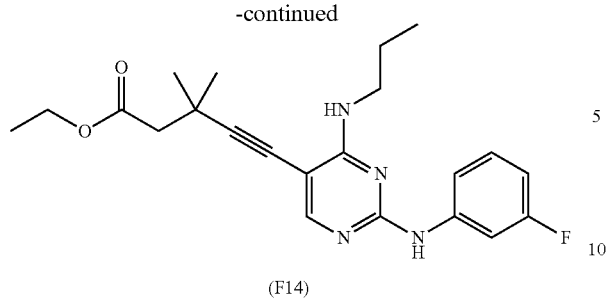

(F14)

To diethyl 2-(4-(2-((3-fluorophenyl)amino)-4-(propylamino)pyrimidin-5-yl)-2-methyl-3-butyn-2-yl)malonate (F13, 400 mg) and sodium bromide (437 mg), water (140 μL) and dimethyl sulfoxide (10 mL) were added at room temperature, the reaction vessel was sealed, and then by using a microwave reaction system, the mixture was stirred at 190° C. for 30 minutes. The reaction mixture was cooled to room temperature, and then ethyl acetate and water were added to the reaction mixture. The organic layer was separated, washed successively with water and saturated aqueous sodium chloride, and then dried over anhydrous sodium sulfate, and the solvent was evaporated under reduced pressure. The obtained residue was purified by silica gel column chromatography (eluent, 94 to 64% hexane in ethyl acetate) to obtain ethyl 5-(2-(3-fluorophenyl)amino)-4-(propylamino)pyrimidin-5-yl)-3,3-dimethyl-4-pentynoate (F14, 64 mg).

MS m/z (M+H): 399.4

9

[Formula 196]

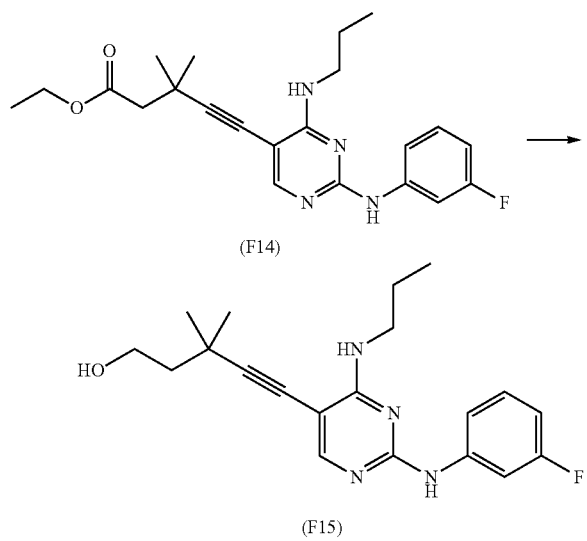

(F14)

(F15)

To a solution of ethyl 5-(2-((3-fluorophenyl)amino)-4-(propylamino)pyrimidin-5-yl)-3,3-dimethyl-4-pentynoate (F14, 120 mg) in tetrahydrofuran (4 mL), lithium aluminum hydride (114 mg) was added under ice cooling, and the mixture was stirred at the same temperature for 5 minutes, and then stirred at room temperature for 1 hour. The reaction mixture was cooled on ice, and then saturated aqueous sodium sulfate was added, and the mixture was stirred at room temperature. To the reaction mixture, ethyl acetate was added.

The organic layer was separated, washed with saturated aqueous sodium chloride, and then dried over anhydrous magnesium sulfate, and the solvent was evaporated under reduced pressure. The obtained residue was purified by silica gel column chromatography (eluent, 88 to 28% hexane in ethyl acetate) to obtain 5-(2-(3-fluorophenyl)amino)-4-(propylamino)pyrimidin-5-yl)-3,3-dimethyl-4-pentyn-1-ol (F15, 75 mg) as white solid.

MS m/z (M+H): 357.3

10

[Formula 197]

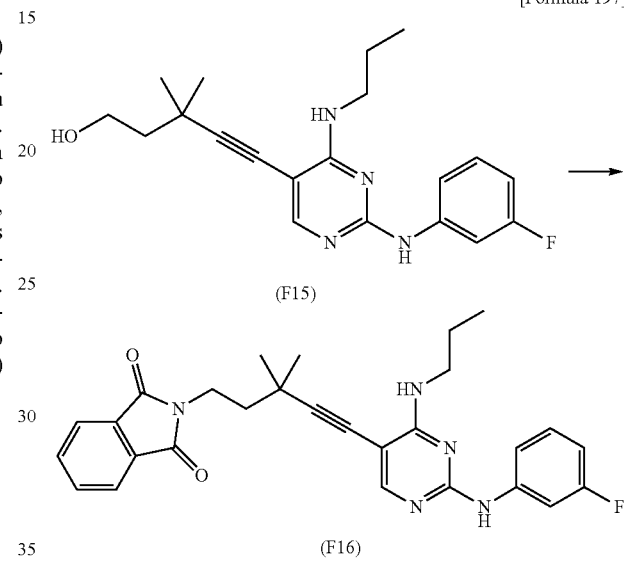

(F15)

(F16)

To a solution of 5-(2-((3-fluorophenyl)amino)-4-(propylamino)pyrimidin-5-yl)-3,3-dimethyl-4-pentyn-1-ol (F15, 75 mg), phthalimide (93 mg) and triphenylphosphine (165 mg) in tetrahydrofuran (3.5 mL), a 1.9 mol/L solution of diisopropyl azodicarboxylate in toluene (332 μL) was added under ice cooling, and the mixture was stirred at room temperature for 1 hour. The solvent was evaporated under reduced pressure, and the obtained residue was purified by silica gel column chromatography (eluent, 92 to 52% hexane in ethyl acetate) to obtain 2-(5-(2-((3-fluorophenyl)amino)-4-(propylamino)pyrimidin-5-yl)-3,3-dimethyl-4-pentyn-1-yl)isoindoline-1,3-dione (F16, 129 mg) as pale yellow solid.

MS m/z (M+H): 486.4

11

[Formula 198]

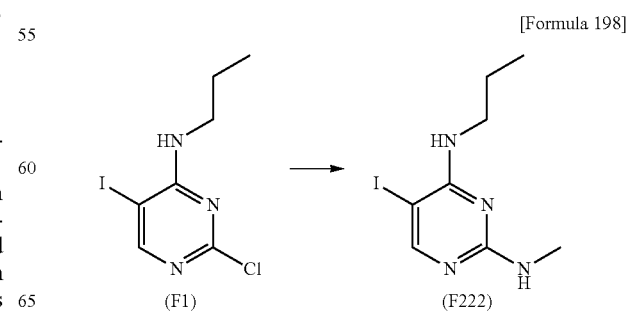

(F1)

(F222)

To a solution of 2-chloro-5-iodo-N-propylpyrimidin-4-amine (F1, 46.3 mg) in tetrahydrofuran (0.5 mL), a 9.8 mol/L solution of methylamine in methanol (0.5 mL) was added at room temperature, the reaction vessel was sealed, and then by using a microwave reaction system, the mixture was stirred at 80° C. for 30 minutes. The reaction mixture was cooled to room temperature, and then the solvent was evaporated under reduced pressure. The obtained residue was purified by silica gel column chromatography (eluent, 40 to 27% hexane in ethyl acetate) to obtain 5-iodo-$N^2$-methyl-$N^4$-propylpyrimidine-2,4-diamine (F222, 32.4 mg) as white solid.

MS m/z (M+H): 293.1

12

By using 2,4-dichloro-5-iodopyrimidine, Intermediates (F17) to (F22) and Intermediates (F176) to (F186) were obtained in the same manner as that of Example 35, (1) or Example 36, (1).

TABLE 59

| Compound No. | Structure | Physicochemical data |
|---|---|---|
| F17 | 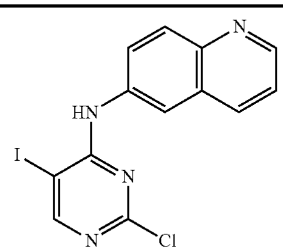 | — |
| F18 | 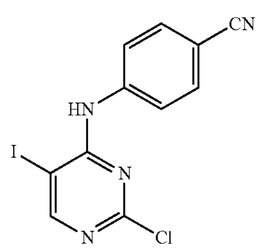 [SMILES: N#Cc1ccc(Nc2nc(Cl)ncc2I)cc1] | — |
| F19 | 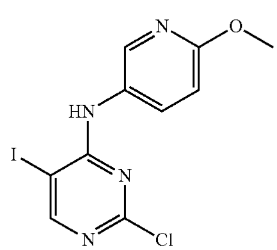 [SMILES: COc1ccc(Nc2nc(Cl)ncc2I)cn1] | MS m/z (M − H): 363.0 |
| F20 | 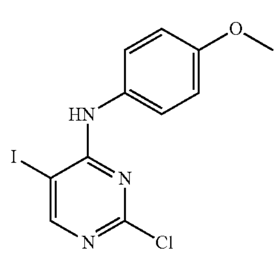 [SMILES: COc1ccc(Nc2nc(Cl)ncc2I)cc1] | — |

TABLE 59-continued

| Compound No. | Structure | Physicochemical data |
|---|---|---|
| F21 | 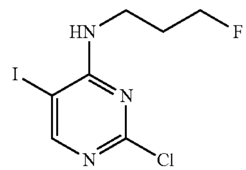 [SMILES: FCCCNc1nc(Cl)ncc1I] | — |
| F22 | 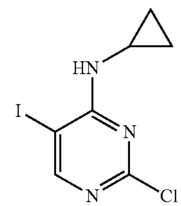 [SMILES: Clc1ncc(I)c(NC2CC2)n1] | — |
| F176 | 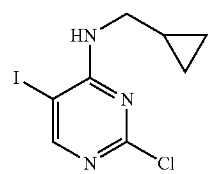 [SMILES: Clc1ncc(I)c(NCC2CC2)n1] | MS m/z (M − H): 308.0 |
| F177 | 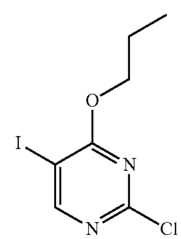 | MS m/z (M + H): 299.0 |
| F178 | 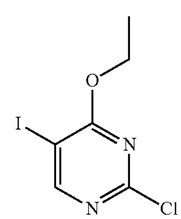 | MS m/z (M + H): 285.0 |
| F179 | 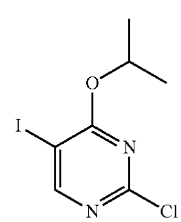 | MS m/z (M + H): 299.0 |
| F180 | 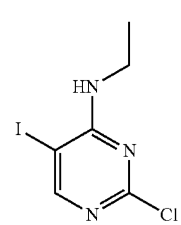 | MS m/z (M + H): 284.0 |

TABLE 60

| Compound No. | Structure | Physicochemical data |
|---|---|---|
| F181 | 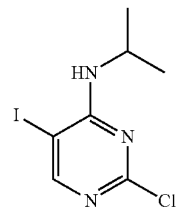 | MS m/z (M + H): 298.0 |
| F182 | 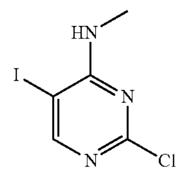 | MS m/z (M + H): 270.0 |
| F183 | 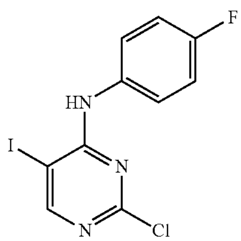 [SMILES: Fc1ccc(Nc2nc(Cl)ncc2I)cc1] | MS m/z (M + H): 350.0 |
| F184 | 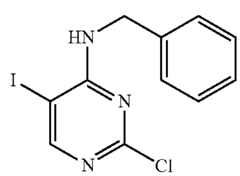 [SMILES: Clc1ncc(I)c(NCc2ccccc2)n1] | MS m/z (M + H): 346.0 |
| F185 | 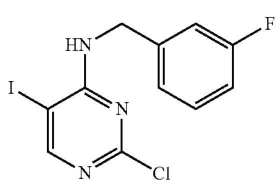 [SMILES: Fc1cccc(CNc2nc(Cl)ncc2I)c1] | MS m/z (M + H): 364.0 |
| F186 | 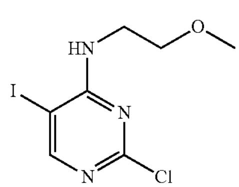 | MS m/z (M + H): 314.0 |

TABLE 61

| Compound No. | Structure | Physicochemical data |
|---|---|---|
| F23 | 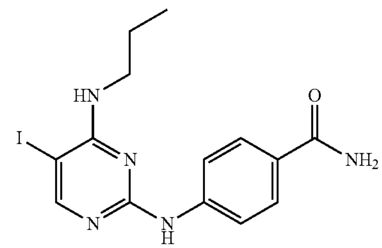 [SMILES: CCCNc1nc(Nc2ccc(C(N)=O)cc2)ncc1I] | — |
| F24 | 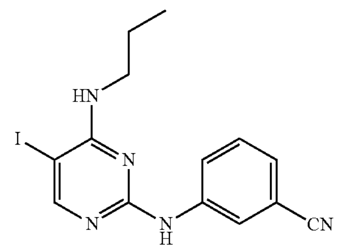 [SMILES: CCCNc1nc(Nc2cccc(C#N)c2)ncc1I] | — |
| F25 | 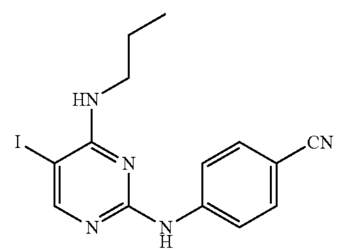 [SMILES: CCCNc1nc(Nc2ccc(C#N)cc2)ncc1I] | MS m/z (M + H): 380.2 |
| F26 | 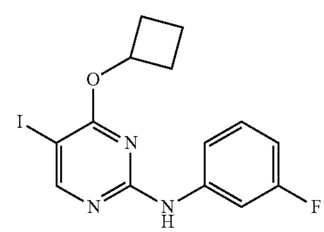 [SMILES: Fc1cccc(Nc2ncc(I)c(OC3CCC3)n2)c1] | — |
| F27 | 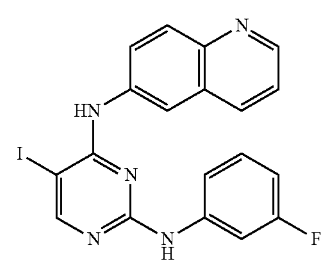 [SMILES: Fc1cccc(Nc2ncc(I)c(Nc3ccc4ncccc4c3)n2)c1] | — |
| F28 | 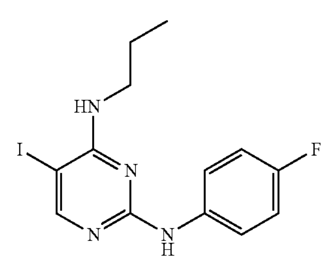 [SMILES: CCCNc1nc(Nc2ccc(F)cc2)ncc1I] | MS m/z (M + H): 373.1 |

In the same manner as that of Example 35, (2) or Example 36, (11), Intermediates (F23) to (F39), Intermediates (F187) to (F234), and Intermediates (F327) were obtained.

TABLE 61-continued

| Compound No. | Structure | Physicochemical data |
|---|---|---|
| F29 | 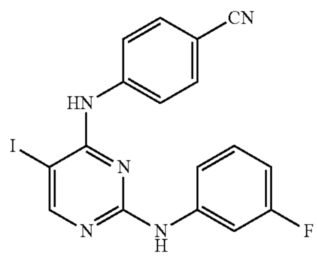 [SMILES: N#Cc1ccc(Nc2nc(Nc3cccc(F)c3)ncc2I)cc1] | — |
| F30 | 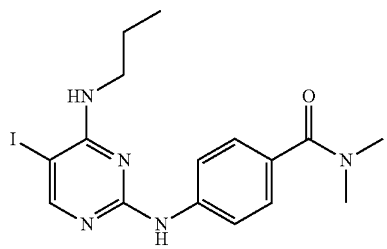 [SMILES: CCCNc1nc(Nc2ccc(C(=O)N(C)C)cc2)ncc1I] | — |

TABLE 62

| Compound No. | Structure | Physicochemical data |
|---|---|---|
| F31 | | — |
| F32 | | — |
| F33 | | — |
| F34 | 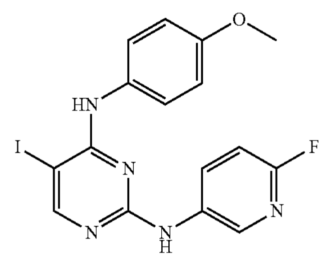 [SMILES: COc1ccc(Nc2nc(Nc3ccc(F)nc3)ncc2I)cc1] | — |
| F35 | 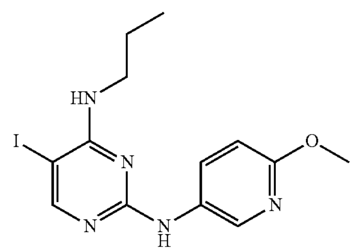 [SMILES: CCCNc1nc(Nc2ccc(OC)nc2)ncc1I] | — |
| F36 | 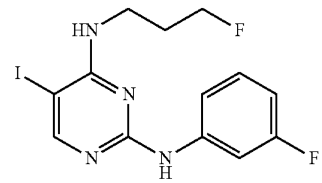 [SMILES: FCCCNc1nc(Nc2cccc(F)c2)ncc1I] | — |
| F37 | 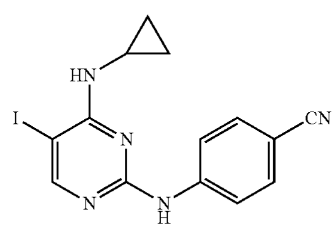 [SMILES: N#Cc1ccc(Nc2ncc(I)c(NC3CC3)n2)cc1] | — |
| F38 | 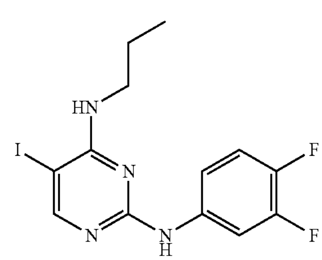 [SMILES: CCCNc1nc(Nc2ccc(F)c(F)c2)ncc1I] | — |
| F39 | 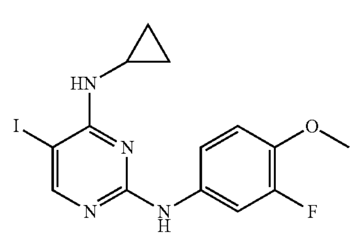 [SMILES: COc1ccc(Nc2ncc(I)c(NC3CC3)n2)cc1F] | — |

TABLE 63

| Compound No. | Structure | Physico-chemical data |
|---|---|---|
| F187 | 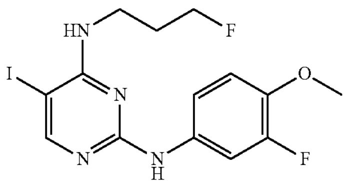 [SMILES: COc1ccc(Nc2ncc(I)c(NCCCF)n2)cc1F] | MS m/z (M + H): 421.3 |
| F188 | 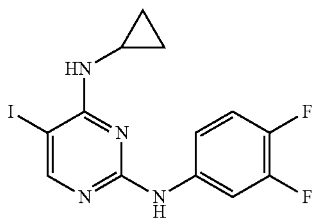 [SMILES: Fc1ccc(Nc2ncc(I)c(NC3CC3)n2)cc1F] | MS m/z (M + H): 389.4 |
| F189 | 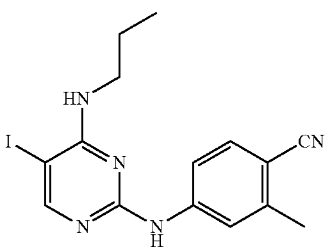 [SMILES: CCCNc1nc(Nc2ccc(C#N)c(C)c2)ncc1I] | MS m/z (M + H): 394.1 |
| F190 | 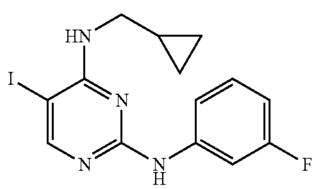 [SMILES: Fc1cccc(Nc2ncc(I)c(NCC3CC3)n2)c1] | MS m/z (M − H): 383.2 |
| F191 | 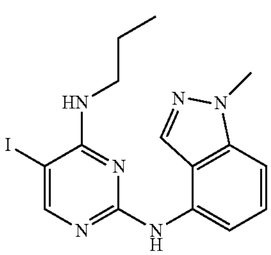 [SMILES: CCCNc1nc(Nc2cccc3c2cnn3C)ncc1I] | MS m/z (M + H): 409.1 |
| F192 | 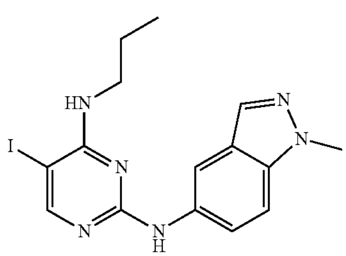 [SMILES: CCCNc1nc(Nc2ccc3c(cnn3C)c2)ncc1I] | MS m/z (M + H): 409.1 |

TABLE 63-continued

| Compound No. | Structure | Physico-chemical data |
|---|---|---|
| F193 | | MS m/z (M + H): 409.1 |
| F194 | | MS m/z (M + H): 459.2 |
| F195 | | MS m/z (M + H): 409.1 |

TABLE 64

| Compound No. | Structure | Physico-chemical data |
|---|---|---|
| F196 | 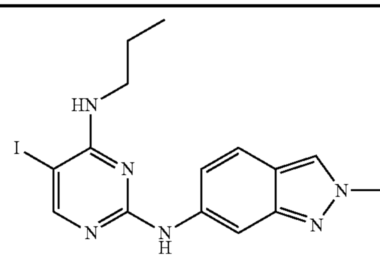 | MS m/z (M + H): 409.1 |
| F197 | 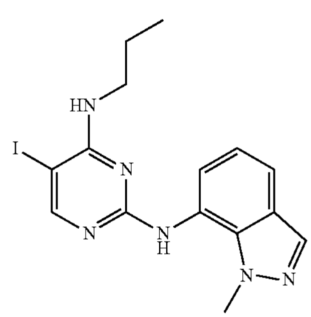 [SMILES: CCCNc1nc(Nc2cccc3cnn(C)c23)ncc1I] | MS m/z (M + H): 409.1 |

TABLE 64-continued

| Compound No. | Structure | Physicochemical data |
|---|---|---|
| F198 | 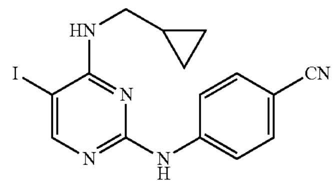 [SMILES: N#Cc1ccc(Nc2ncc(I)c(NCC3CC3)n2)cc1] | — |
| F199 | 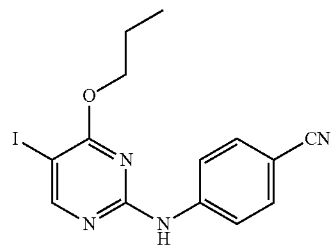 [SMILES: CCCOc1nc(Nc2ccc(C#N)cc2)ncc1I] | MS m/z (M + H): 381.1 |
| F200 | 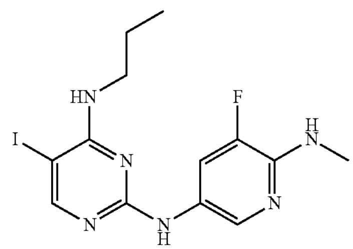 [SMILES: CCCNc1nc(Nc2cnc(NC)c(F)c2)ncc1I] | MS m/z (M + H): 403.1 |
| F201 | 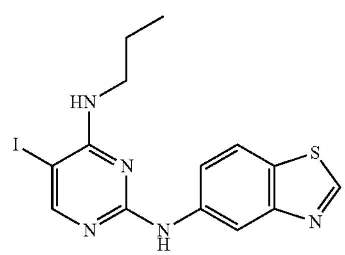 [SMILES: CCCNc1nc(Nc2ccc3scnc3c2)ncc1I] | MS m/z (M + H): 412.1 |
| F202 | 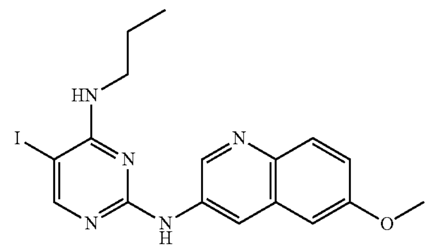 [SMILES: CCCNc1nc(Nc2cnc3ccc(OC)cc3c2)ncc1I] | MS m/z (M + H): 436.1 |
| F203 | 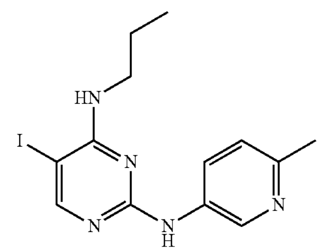 [SMILES: CCCNc1nc(Nc2ccc(C)nc2)ncc1I] | MS m/z (M + H): 370.1 |
| F204 | 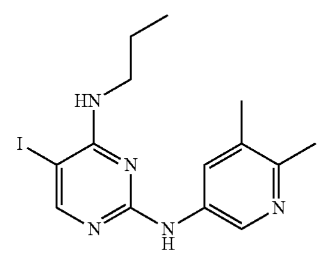 [SMILES: CCCNc1nc(Nc2cnc(C)c(C)c2)ncc1I] | MS m/z (M + H): 384.1 |

TABLE 65

| Compound No. | Structure | Physicochemical data |
|---|---|---|
| F205 | 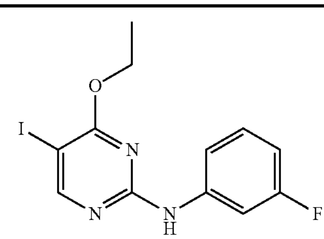 | MS m/z (M + H): 360.2 |
| F206 | 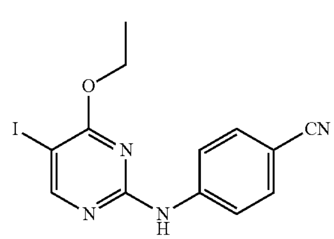 [SMILES: CCOc1nc(Nc2ccc(C#N)cc2)ncc1I] | MS m/z (M + H): 367.1 |

TABLE 65-continued

| Compound No. | Structure | Physicochemical data |
|---|---|---|
| F207 | 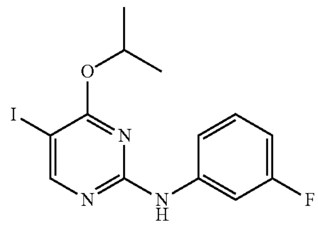 [SMILES: CC(C)Oc1nc(Nc2cccc(F)c2)ncc1I] | MS m/z (M + H): 374.1 |
| F208 | 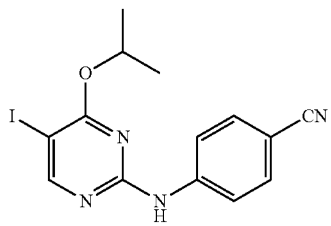 [SMILES: CC(C)Oc1nc(Nc2ccc(C#N)cc2)ncc1I] | MS m/z (M + H): 381.1 |
| F209 | 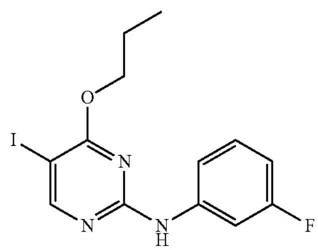 | MS m/z (M + H): 360.2 |
| F210 | 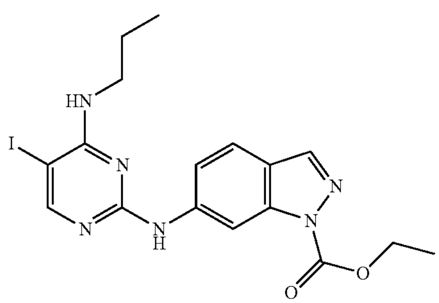 [SMILES: CCCNc1nc(Nc2ccc3cnn(C(=O)OCC)c3c2)ncc1I] | MS m/z (M + H): 467.1 |
| F211 | 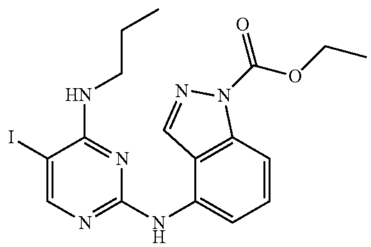 [SMILES: CCCNc1nc(Nc2cccc3c2cnn3C(=O)OCC)ncc1I] | MS m/z (M + H): 467.2 |
| F212 | 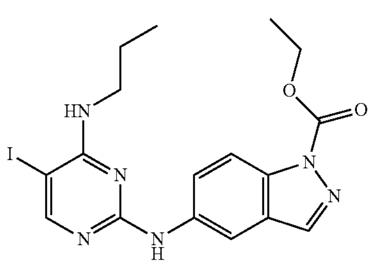 [SMILES: CCCNc1nc(Nc2ccc3c(cnn3C(=O)OCC)c2)ncc1I] | MS m/z (M + H): 467.2 |

TABLE 65-continued

| Compound No. | Structure | Physicochemical data |
|---|---|---|
| F213 | 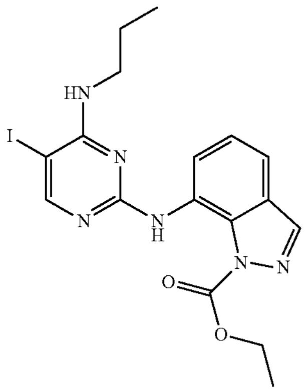 [SMILES: CCCNc1nc(Nc2cccc3cnn(C(=O)OCC)c23)ncc1I] | MS m/z (M + H): 467.2 |

TABLE 66

| Compound No. | Structure | Physicochemical data |
|---|---|---|
| F214 | 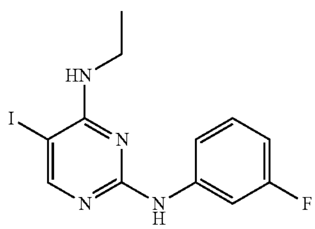 [SMILES: CCNc1nc(Nc2cccc(F)c2)ncc1I] | MS m/z (M + H): 359.1 |
| F215 | 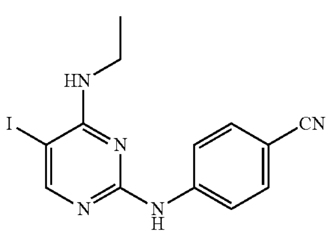 | MS m/z (M + H): 366.1 |
| F216 | 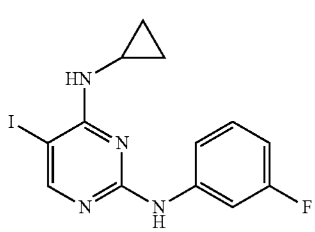 [SMILES: Fc1cccc(Nc2ncc(I)c(NC3CC3)n2)c1] | MS m/z (M + H): 371.2 |
| F217 | 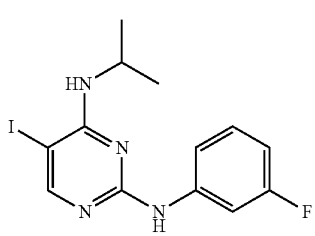 [SMILES: CC(C)Nc1nc(Nc2cccc(F)c2)ncc1I] | MS m/z (M + H): 373.1 |
| F218 | | — |
| F219 | | MS m/z (M + H): 352.1 |
| F220 | | MS m/z (M + H): 375.1 |
| F221 | | MS m/z (M + H): 395.1 |

TABLE 66-continued

| Compound No. | Structure | Physicochemical data |
|---|---|---|
| F222 | 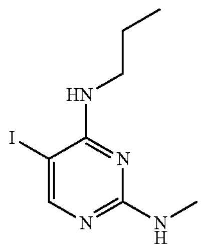 | MS m/z (M + H): 293.1 |

TABLE 67

| Compound No. | Structure | Physicochemical data |
|---|---|---|
| F223 | 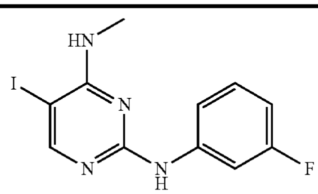 | MS m/z (M + H): 345.1 |
| F224 | 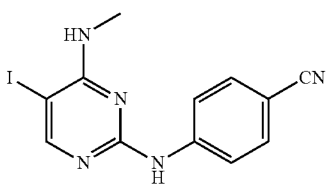 [SMILES: CNc1nc(Nc2ccc(C#N)cc2)ncc1I] | — |
| F225 | 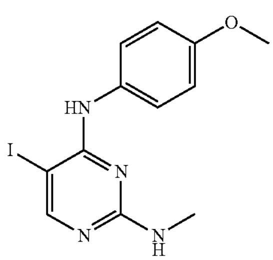 [SMILES: CNc1ncc(I)c(Nc2ccc(OC)cc2)n1] | MS m/z (M + H): 357.1 |
| F226 | 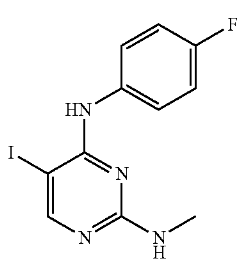 [SMILES: CNc1ncc(I)c(Nc2ccc(F)cc2)n1] | MS m/z (M + H): 345.1 |
| F227 | 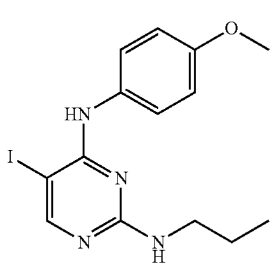 [SMILES: CCCNc1ncc(I)c(Nc2ccc(OC)cc2)n1] | MS m/z (M + H): 385.1 |

TABLE 67-continued

| Compound No. | Structure | Physicochemical data |
|---|---|---|
| F228 | 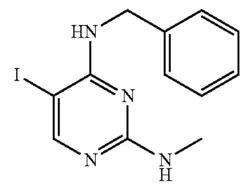 [SMILES: CNc1ncc(I)c(NCc2ccccc2)n1] | MS m/z (M + H): 341.1 |
| F229 | 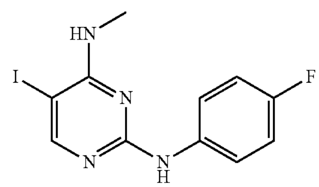 [SMILES: CNc1nc(Nc2ccc(F)cc2)ncc1I] | MS m/z (M − H): 343.1 |
| F230 | 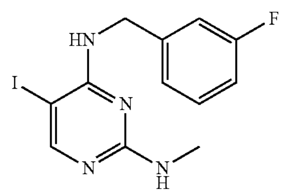 [SMILES: CNc1ncc(I)c(NCc2cccc(F)c2)n1] | MS m/z (M + H): 359.1 |

TABLE 68

| Compound No. | Structure | Physicochemical data |
|---|---|---|
| F231 | 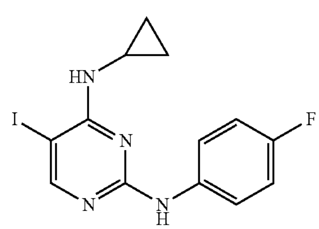 [SMILES: Fc1ccc(Nc2ncc(I)c(NC3CC3)n2)cc1] | MS m/z (M + H): 371.1 |
| F232 | 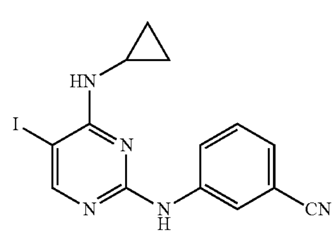 [SMILES: N#Cc1cccc(Nc2ncc(I)c(NC3CC3)n2)c1] | MS m/z (M + H): 378.1 |

TABLE 68-continued
| Compound No. | Structure | Physicochemical data |
|---|---|---|
| F233 | 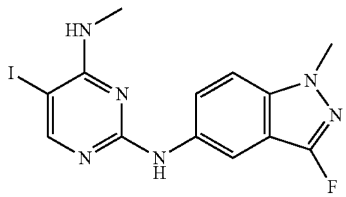 [SMILES: CNc1nc(Nc2ccc3c(c2)c(F)nn3C)ncc1I] | MS m/z (M + H): 399.1 |
| F234 | 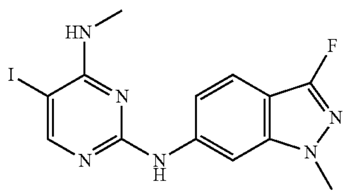 [SMILES: CNc1nc(Nc2ccc3c(F)nn(C)c3c2)ncc1I] | MS m/z (M + H): 399.1 |
| F227 |  | — |
In the same manner as that of Example 35, (3), Intermediates (F40) to (F56) and Intermediates (F235) to (F241) were obtained.
TABLE 69
| Compound No. | Structure | Physicochemical data |
|---|---|---|
| F40 | 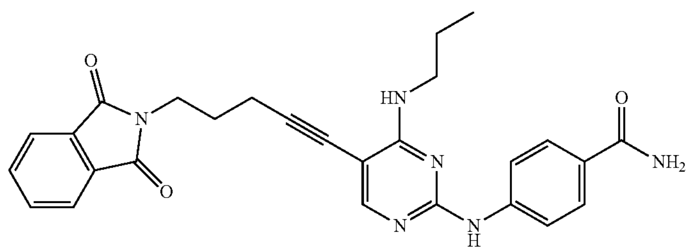 [SMILES: CCCNc1nc(Nc2ccc(C(N)=O)cc2)ncc1C#CCCCN1C(=O)c2ccccc2C1=O] | MS m/z (M + H): 483.2 |
| F41 | 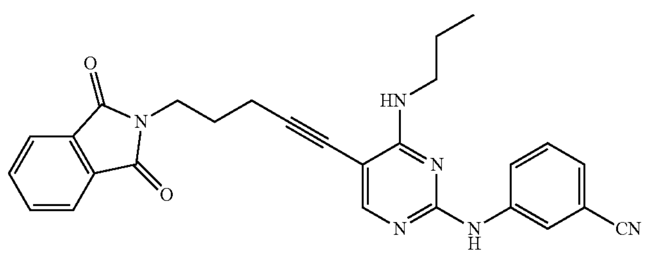 [SMILES: CCCNc1nc(Nc2cccc(C#N)c2)ncc1C#CCCCN1C(=O)c2ccccc2C1=O] | — |
| F42 | 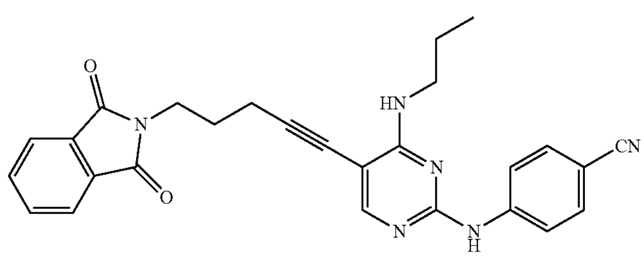 [SMILES: CCCNc1nc(Nc2ccc(C#N)cc2)ncc1C#CCCCN1C(=O)c2ccccc2C1=O] | MS m/z (M + H): 465.3 |
| F43 | 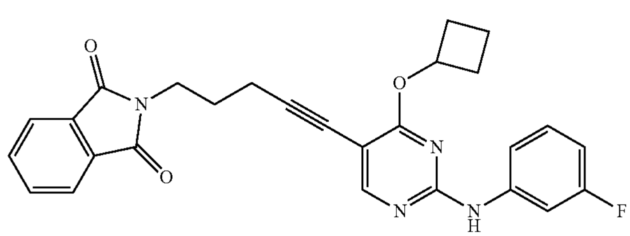 [SMILES: O=C1c2ccccc2C(=O)N1CCCC#Cc1cnc(Nc2cccc(F)c2)nc1OC1CCC1] | — |

TABLE 69-continued

| Compound No. | Structure | Physicochemical data |
|---|---|---|
| F44 | 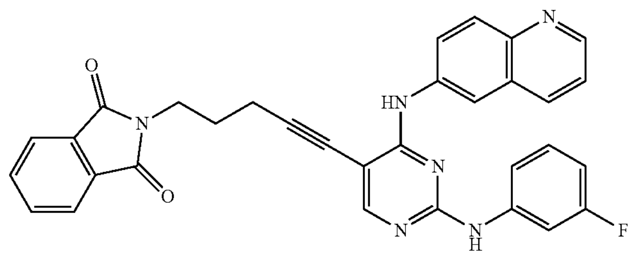 [SMILES: O=C1c2ccccc2C(=O)N1CCCC#Cc1cnc(Nc2cccc(F)c2)nc1Nc1ccc2ncccc2c1] | — |
| F45 | 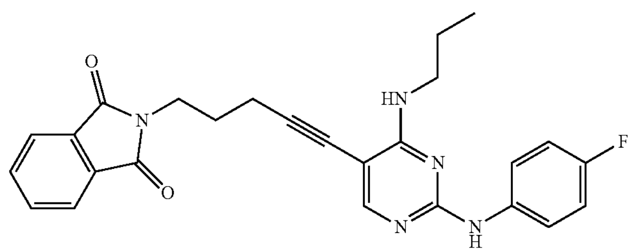 [SMILES: CCCNc1nc(Nc2ccc(F)cc2)ncc1C#CCCCN1C(=O)c2ccccc2C1=O] | MS m/z (M + H): 458.3 |
| F46 | 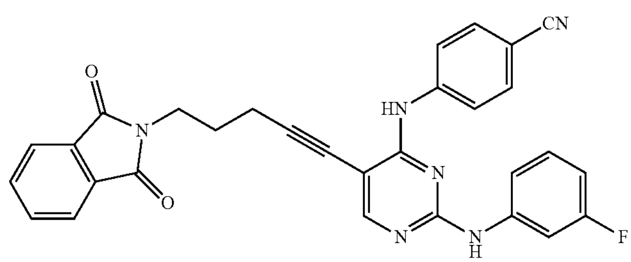 [SMILES: N#Cc1ccc(Nc2nc(Nc3cccc(F)c3)ncc2C#CCCCN2C(=O)c3ccccc3C2=O)cc1] | — |
| F47 | 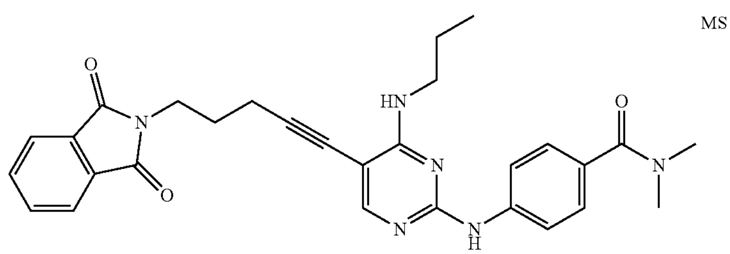 | MS m/z (M + H): 511.4 |

TABLE 70

| Compound No. | Structure | Physicochemical data |
|---|---|---|
| F48 | 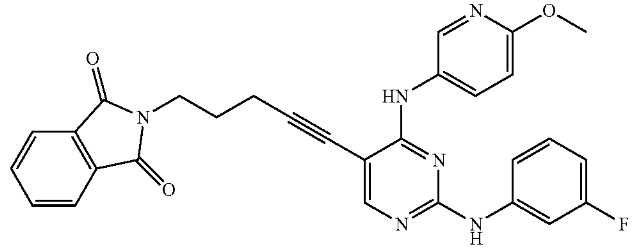 [SMILES: COc1ccc(Nc2nc(Nc3cccc(F)c3)ncc2C#CCCCN2C(=O)c3ccccc3C2=O)cn1] | — |

TABLE 70-continued

| Compound No. | Structure | Physicochemical data |
|---|---|---|
| F49 | 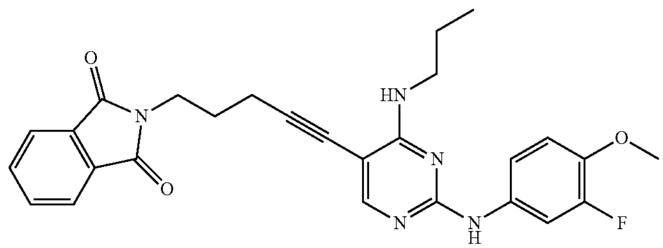 [SMILES: CCCNc1nc(Nc2ccc(OC)c(F)c2)ncc1C#CCCCN1C(=O)c2ccccc2C1=O] | — |
| F50 | 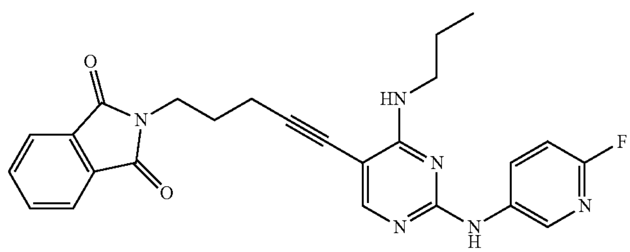 | — |
| F51 | 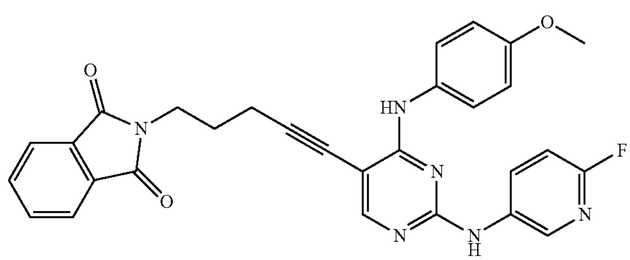 [SMILES: COc1ccc(Nc2nc(Nc3ccc(F)nc3)ncc2C#CCCCN2C(=O)c3ccccc3C2=O)cc1] | — |
| F52 | 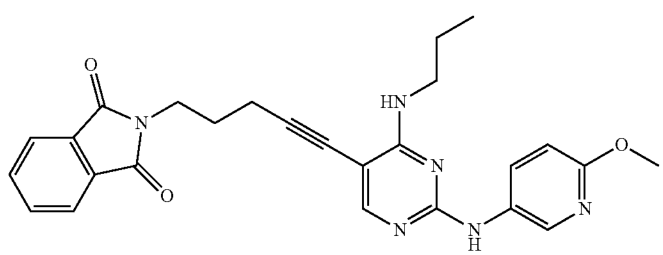 [SMILES: CCCNc1nc(Nc2ccc(OC)nc2)ncc1C#CCCCN1C(=O)c2ccccc2C1=O] | — |
| F53 | 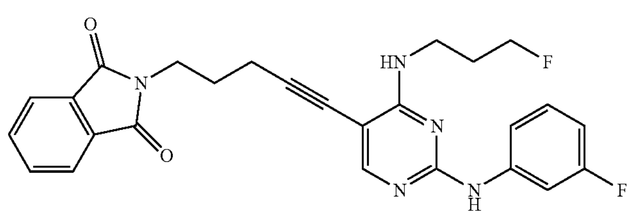 [SMILES: O=C1c2ccccc2C(=O)N1CCCC#Cc1cnc(Nc2cccc(F)c2)nc1NCCCF] | — |
| F54 | 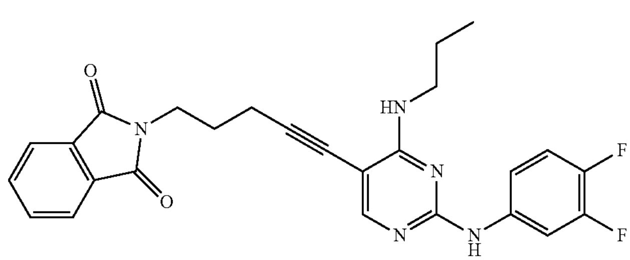 [SMILES: CCCNc1nc(Nc2ccc(F)c(F)c2)ncc1C#CCCCN1C(=O)c2ccccc2C1=O] | — |

TABLE 70-continued

| Compound No. | Structure | Physicochemical data |
|---|---|---|
| F55 | 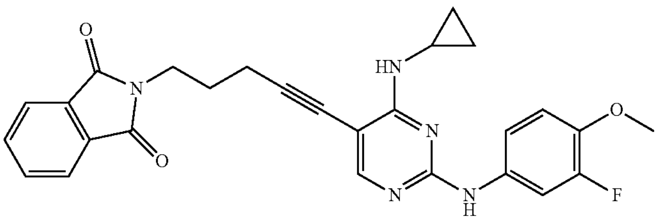 [SMILES: COc1ccc(Nc2ncc(C#CCCCN3C(=O)c4ccccc4C3=O)c(NC3CC3)n2)cc1F] | — |
| F56 | 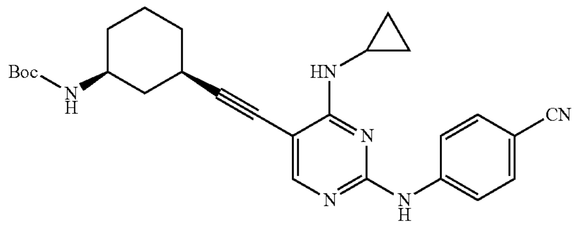 [SMILES: CC(C)(C)OC(=O)N[C@H]1CCC[C@@H](C#Cc2cnc(Nc3ccc(C#N)cc3)nc2NC2CC2)C1] | — |
| F235 | 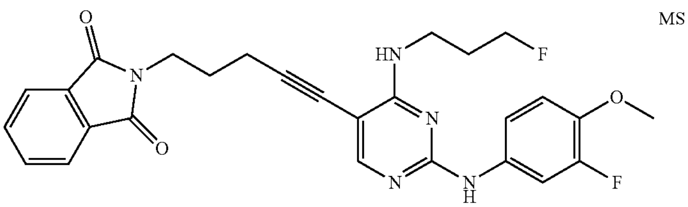 | MS m/z (M − H): 504.3 |

TABLE 71

| Compound No. | Structure | Physicochemical data |
|---|---|---|
| F236 | 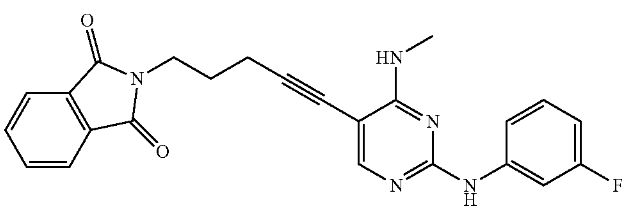 [SMILES: CNc1nc(Nc2cccc(F)c2)ncc1C#CCCCN1C(=O)c2ccccc2C1=O] | — |
| F237 | 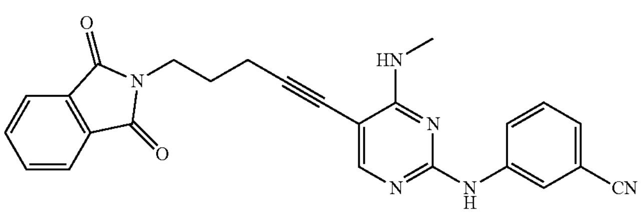 [SMILES: CNc1nc(Nc2cccc(C#N)c2)ncc1C#CCCCN1C(=O)c2ccccc2C1=O] | MS m/z (M + H): 437.3 |
| F238 | 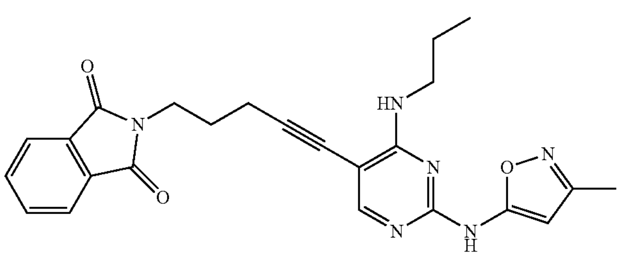 | MS m/z (M + H): 445.3 |

TABLE 71-continued

| Compound No. | Structure | Physicochemical data |
|---|---|---|
| F239 | 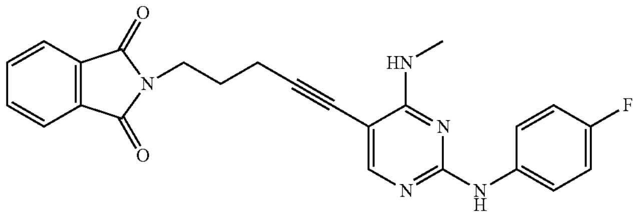 [SMILES: CNc1nc(Nc2ccc(F)cc2)ncc1C#CCCCN1C(=O)c2ccccc2C1=O] | MS m/z (M + H): 430.3 |
| F240 | 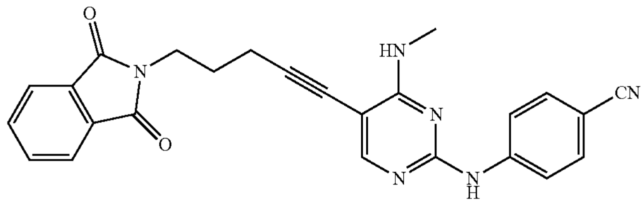 [SMILES: CNc1nc(Nc2ccc(C#N)cc2)ncc1C#CCCCN1C(=O)c2ccccc2C1=O] | MS m/z (M + H): 437.3 |
| F241 | 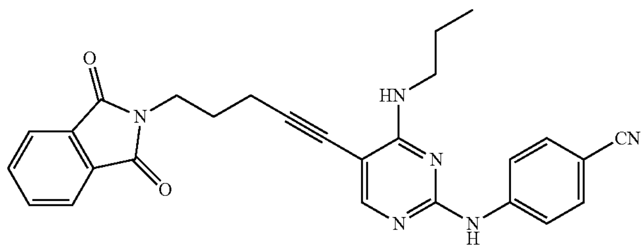 | MS m/z (M + H): 437.4 |

In the same manner as that of Example 35, (4), Intermediates (F57) to (F73), Intermediates (F242) to (F248), and Intermediates (F328) were obtained.

TABLE 72

| Compound No. | Structure | Physicochemical data |
|---|---|---|
| F57 | 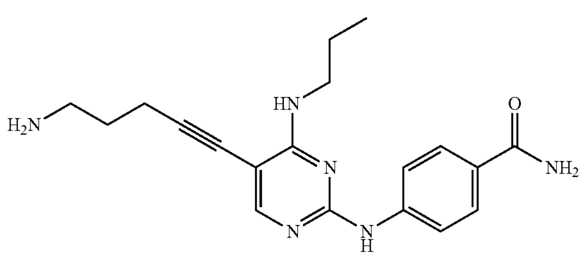 [SMILES: CCCNc1nc(Nc2ccc(C(N)=O)cc2)ncc1C#CCCCN] | MS m/z (M + H): 353.2 |
| F58 | 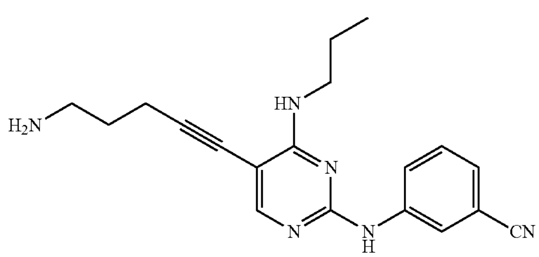 [SMILES: CCCNc1nc(Nc2cccc(C#N)c2)ncc1C#CCCCN] | — |

TABLE 72-continued

| Compound No. | Structure | Physicochemical data |
|---|---|---|
| F59 | 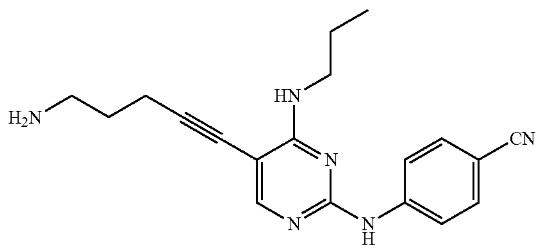 [SMILES: CCCNc1nc(Nc2ccc(C#N)cc2)ncc1C#CCCCN] | MS m/z (M + H): 335.3 |
| F60 | 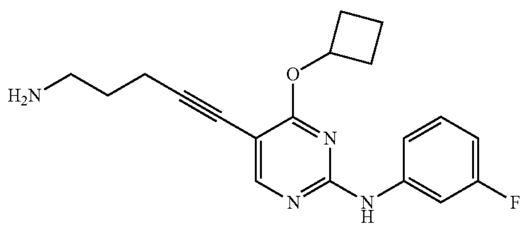 [SMILES: NCCCC#Cc1cnc(Nc2cccc(F)c2)nc1OC1CCC1] | — |
| F61 | 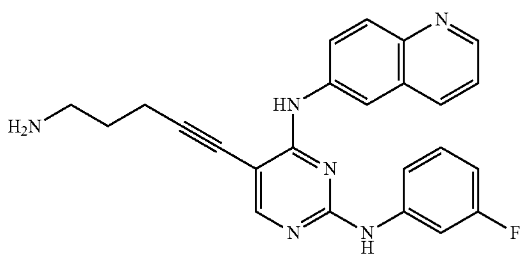 [SMILES: NCCCC#Cc1cnc(Nc2cccc(F)c2)nc1Nc1ccc2ncccc2c1] | — |
| F62 | 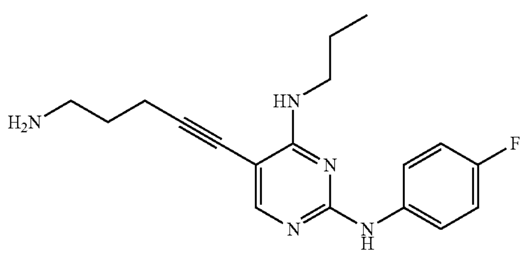 [SMILES: CCCNc1nc(Nc2ccc(F)cc2)ncc1C#CCCCN] | — |
| F63 | 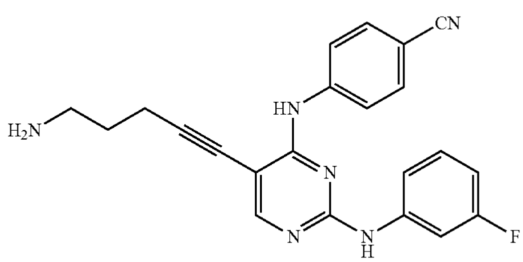 [SMILES: N#Cc1ccc(Nc2nc(Nc3cccc(F)c3)ncc2C#CCCCN)cc1] | — |
| F64 | 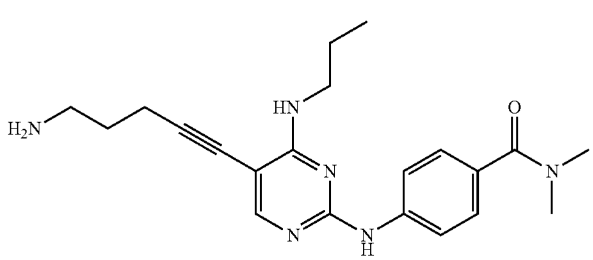 [SMILES: CCCNc1nc(Nc2ccc(C(=O)N(C)C)cc2)ncc1C#CCCCN] | MS m/z (M + H): 381.4 |

TABLE 73

| Compound No. | Structure | Physicochemical data |
|---|---|---|
| F65 | 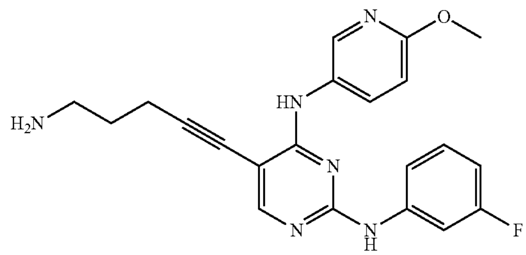 [SMILES: COc1ccc(Nc2nc(Nc3cccc(F)c3)ncc2C#CCCCN)cn1] | — |
| F66 | 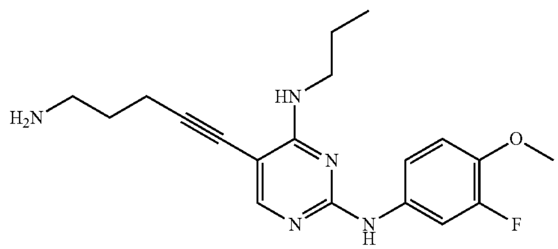 [SMILES: CCCNc1nc(Nc2ccc(OC)c(F)c2)ncc1C#CCCCN] | — |
| F67 | 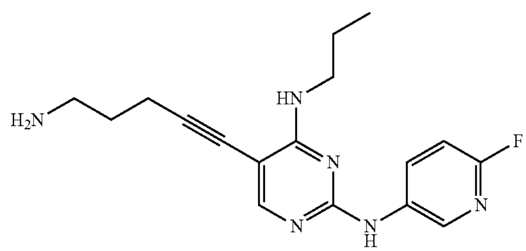 [SMILES: CCCNc1nc(Nc2ccc(F)nc2)ncc1C#CCCCN] | — |
| F68 | 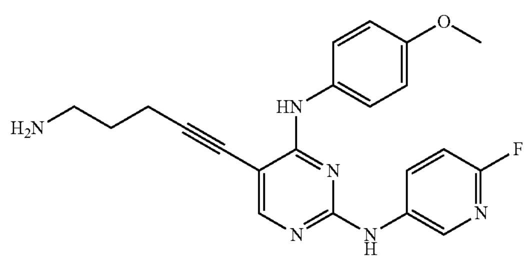 [SMILES: COc1ccc(Nc2nc(Nc3ccc(F)nc3)ncc2C#CCCCN)cc1] | — |
| F69 | 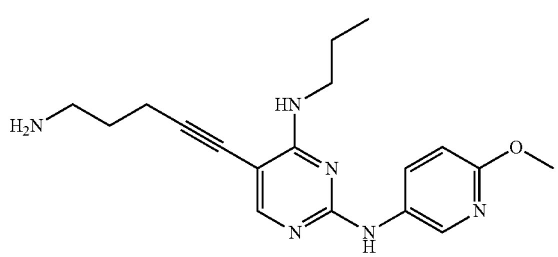 [SMILES: CCCNc1nc(Nc2ccc(OC)nc2)ncc1C#CCCCN] | — |
| F70 | 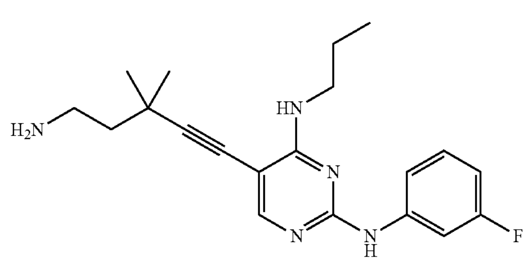 [SMILES: CCCNc1nc(Nc2cccc(F)c2)ncc1C#CC(C)(C)CCN] | — |

TABLE 73-continued

| Compound No. | Structure | Physicochemical data |
|---|---|---|
| F71 | 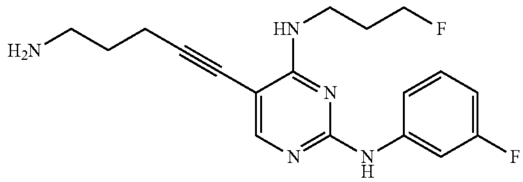 [SMILES: NCCCC#Cc1cnc(Nc2cccc(F)c2)nc1NCCCF] | — |
| F72 | 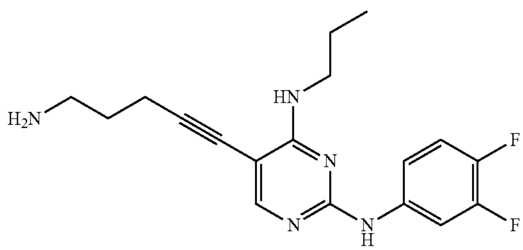 [SMILES: CCCNc1nc(Nc2ccc(F)c(F)c2)ncc1C#CCCCN] | — |
| F73 | 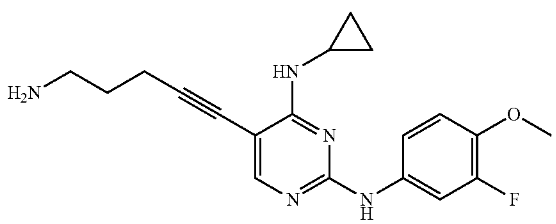 [SMILES: COc1ccc(Nc2ncc(C#CCCCN)c(NC3CC3)n2)cc1F] | — |

TABLE 74

| Compound No. | Structure | Physicochemical data |
|---|---|---|
| F242 | 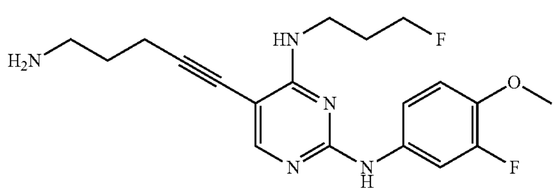 [SMILES: COc1ccc(Nc2ncc(C#CCCCN)c(NCCCF)n2)cc1F] | MS m/z (M + H): 376.3 |
| F243 | 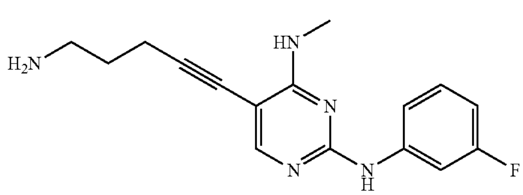 [SMILES: CNc1nc(Nc2cccc(F)c2)ncc1C#CCCCN] | MS m/z (M + H): 300.2 |
| F244 | 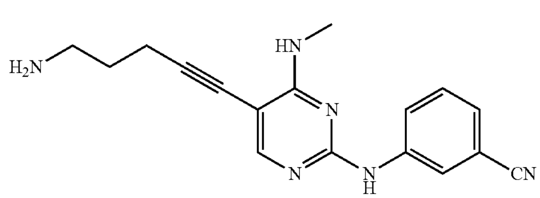 [SMILES: CNc1nc(Nc2cccc(C#N)c2)ncc1C#CCCCN] | MS m/z (M + H): 307.2 |

TABLE 74-continued
| Compound No. | Structure | Physicochemical data |
|---|---|---|
| F245 | 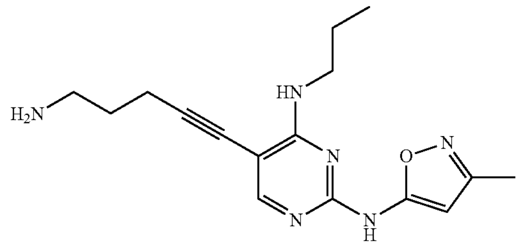 [SMILES: CCCNc1nc(Nc2cc(C)no2)ncc1C#CCCCN] | — |
| F246 | 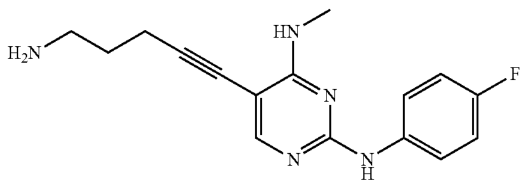 [SMILES: CNc1nc(Nc2ccc(F)cc2)ncc1C#CCCCN] | MS m/z (M + H): 300.3 |
| F247 | 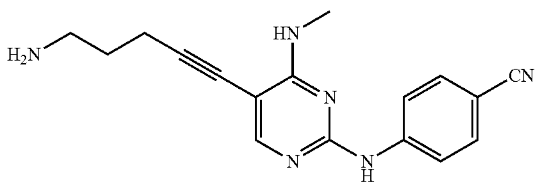 [SMILES: CNc1nc(Nc2ccc(C#N)cc2)ncc1C#CCCCN] | MS m/z (M + H): 307.3 |
| F248 | 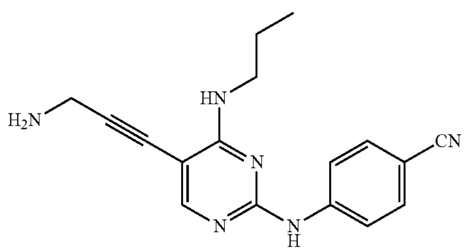 [SMILES: CCCNc1nc(Nc2ccc(C#N)cc2)ncc1C#CCN] | MS m/z (M + H): 307.3 |
| F328 | 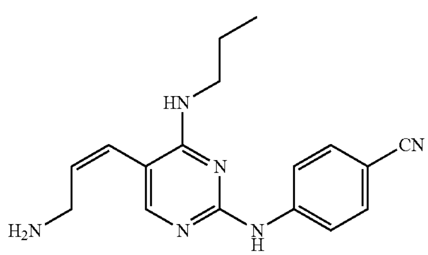 [SMILES: CCCNc1nc(Nc2ccc(C#N)cc2)ncc1/C=C\CN] | MS m/z (M + H): 309.3 |
[Formula 199]
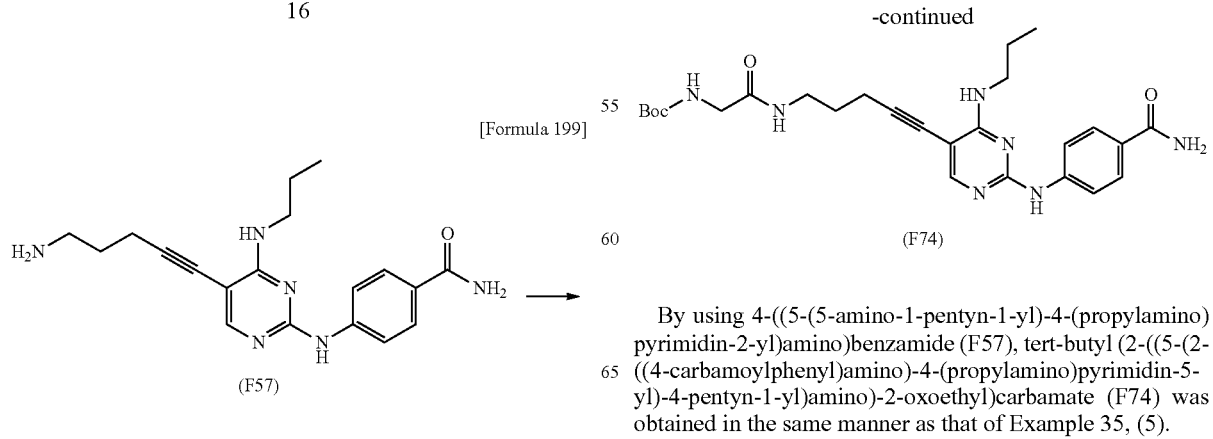
By using 4-((5-(5-amino-1-pentyn-1-yl)-4-(propylamino)pyrimidin-2-yl)amino)benzamide (F57), tert-butyl (2-((5-(2-((4-carbamoylphenyl)amino)-4-(propylamino)pyrimidin-5-yl)-4-pentyn-1-yl)amino)-2-oxoethyl)carbamate (F74) was obtained in the same manner as that of Example 35, (5).

[Formula 200]

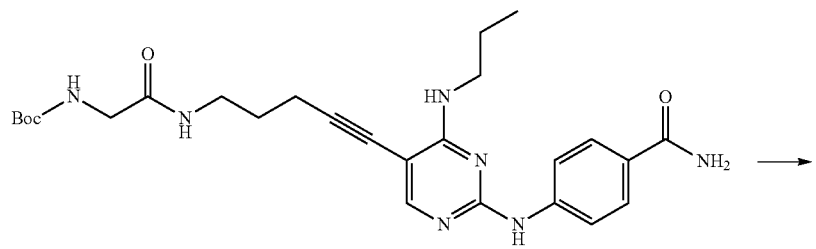

(F74)

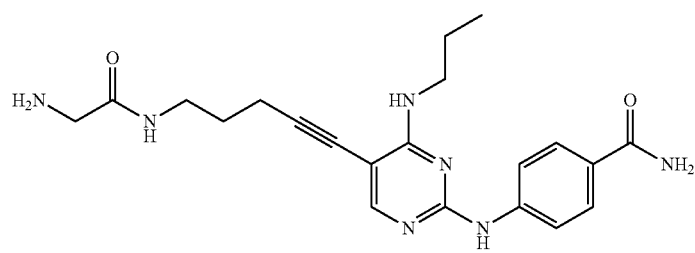

(F75)

By using tert-butyl (2-((5-(2-((4-carbamoylphenyl)amino)-4-(propylamino)pyrimidin-5-yl)-4-pentyn-1-yl)amino)-2-oxoethyl)carbamate (F74), 4-((5-(5-(2-aminoactamido)-1-pentyn-1-yl)-4-(propylamino)pyrimidin-2-yl)amino)benzamide (F75) dihydrochloride was obtained in the same manner as that of Example 35, (6).

A mixed solution of 4-((5-(5-(2-aminoactamido)-1-pentyn-1-yl)-4-(propylamino)pyrimidin-2-yl)amino)benzamide (F75) dihydrochloride (100 mg) in methanol (60 mL) and acetic acid (4 mL) was prepared, and hydrogenation was performed at room temperature and a flow rate of 1 mL/minute in a flow type hydrogenation reactor set with a 10% palladium-carbon cartridge. The solvent was evaporated under reduced pressure to obtain 4-((5-(5-(2-aminoactamido)pentyl)-4-(propylamino)pyrimidin-2-yl)amino)benzamide (F76) dihydrochloride (90 mg) as white solid.

MS m/z (M+H): 414.3

[Formula 201]

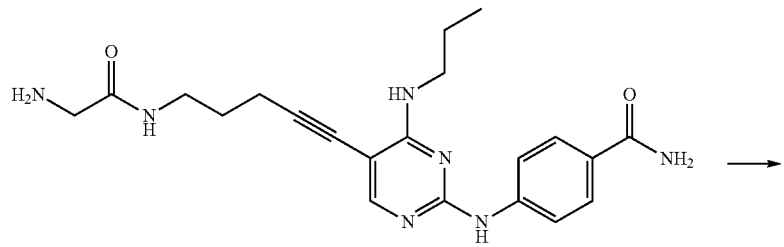

(F75)

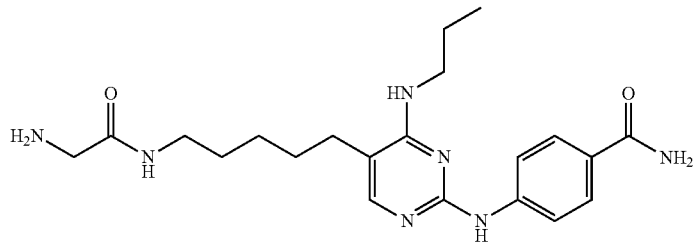

(F76)

19

[Formula 202]

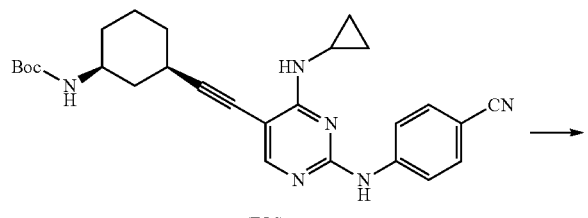

(F56)

↓

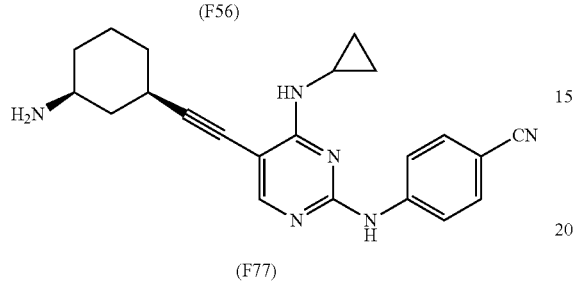

(F77)

By using tert-butyl ((1S,3R)-3-((2-((4-cyanophenyl)amino)-4-(cyclopropylamino)pyrimidin-5-yl)ethynyl)cyclohexyl)carbamate (F56), 4-((5-(((1S,3R)-3-aminocyclohexyl)ethynyl)-4-(cyclopropylamino)pyrimidin-2-yl)amino)benzonitrile (F77) dihydrochloride was obtained in the same manner as that of Example 35, (6).

20

In the same manner as that of Example 35, (5), Intermediates (F78) to (F126), Intermediates (F249) to (F287), Intermediates (F329) and (F330) were obtained.

TABLE 75

| Compound No. | Structure | Physicochemical data |
|---|---|---|
| F78 | 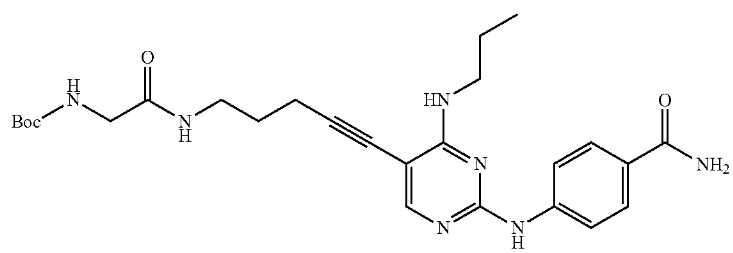 [SMILES: CCCNc1nc(Nc2ccc(C(N)=O)cc2)ncc1C#CCCCNC(=O)CNC(=O)OC(C)(C)C] | — |
| F79 | 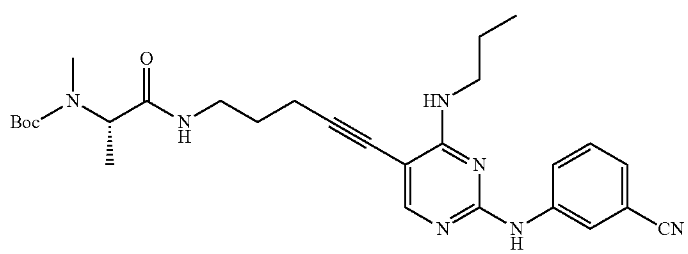 [SMILES: CCCNc1nc(Nc2cccc(C#N)c2)ncc1C#CCCCNC(=O)[C@H](C)N(C)C(=O)OC(C)(C)C] | — |
| F80 | 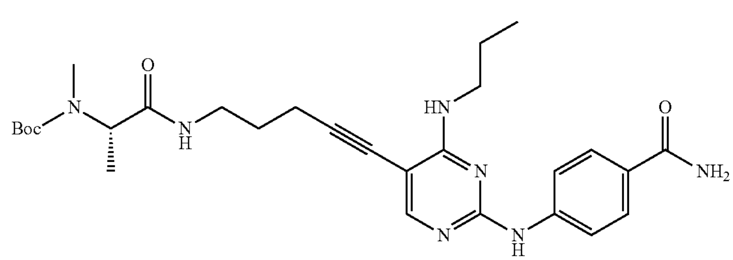 [SMILES: CCCNc1nc(Nc2ccc(C(N)=O)cc2)ncc1C#CCCCNC(=O)[C@H](C)N(C)C(=O)OC(C)(C)C] | MS m/z (M + H): 538.3 |

TABLE 75-continued

| Compound No. | Structure | Physicochemical data |
|---|---|---|
| F81 | 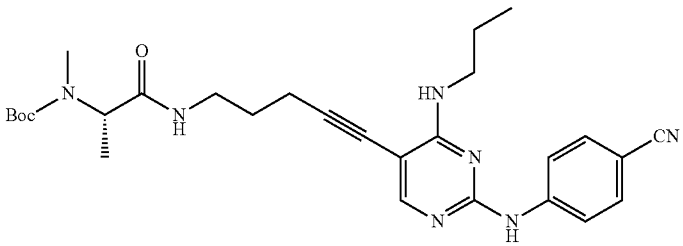 [SMILES: CCCNc1nc(Nc2ccc(C#N)cc2)ncc1C#CCCCNC(=O)[C@H](C)N(C)C(=O)OC(C)(C)C] | MS m/z (M + H): 520.4 |
| F82 | 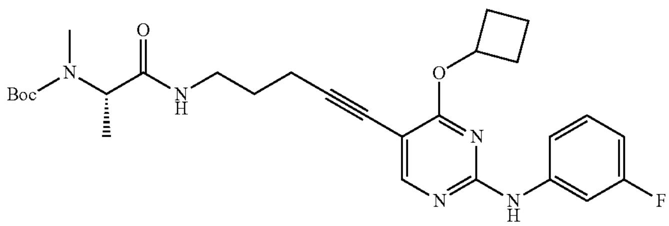 [SMILES: C[C@@H](C(=O)NCCCC#Cc1cnc(Nc2cccc(F)c2)nc1OC1CCC1)N(C)C(=O)OC(C)(C)C] | — |
| F83 | 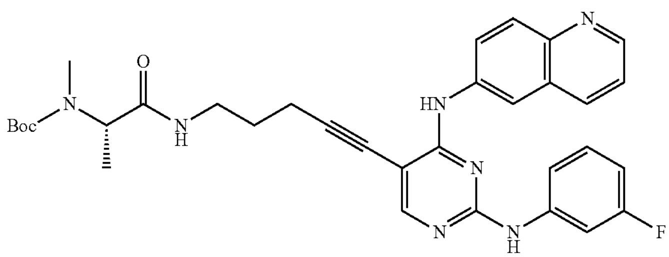 [SMILES: C[C@@H](C(=O)NCCCC#Cc1cnc(Nc2cccc(F)c2)nc1Nc1ccc2ncccc2c1)N(C)C(=O)OC(C)(C)C] | — |
| F84 | 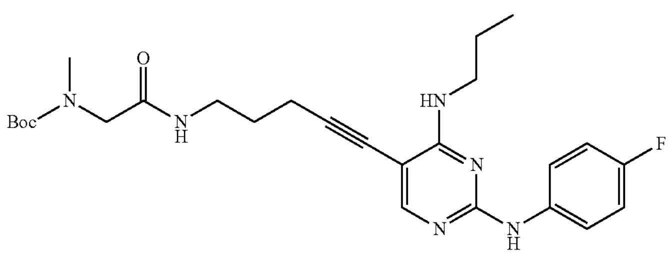 [SMILES: CCCNc1nc(Nc2ccc(F)cc2)ncc1C#CCCCNC(=O)CN(C)C(=O)OC(C)(C)C] | MS m/z (M + H): 499.4 |
| F85 | 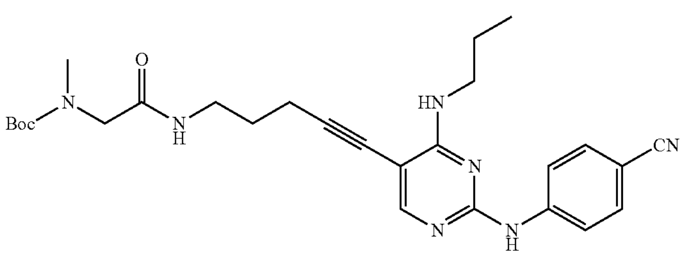 [SMILES: CCCNc1nc(Nc2ccc(C#N)cc2)ncc1C#CCCCNC(=O)CN(C)C(=O)OC(C)(C)C] | MS m/z (M + H): 506.4 |
| F86 | 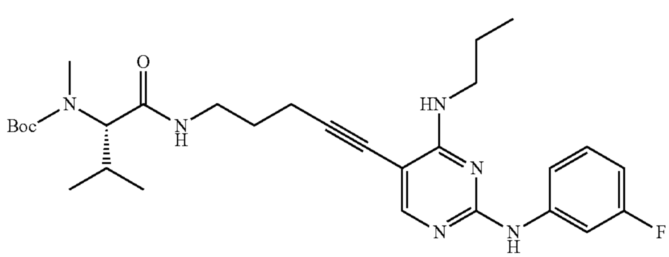 [SMILES: CCCNc1nc(Nc2cccc(F)c2)ncc1C#CCCCNC(=O)[C@H](C(C)C)N(C)C(=O)OC(C)(C)C] | MS m/z (M + H): 541.5 |

TABLE 75-continued
| Compound No. | Structure | Physicochemical data |
|---|---|---|
| F87 | 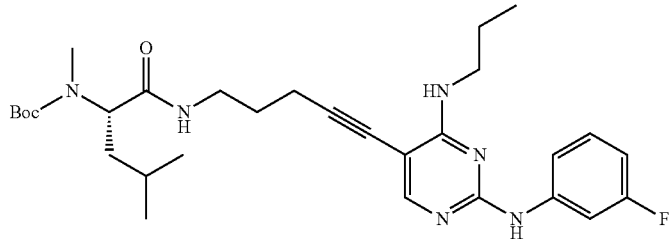 [SMILES: CCCNc1nc(Nc2cccc(F)c2)ncc1C#CCCCNC(=O)[C@H](CC(C)C)N(C)C(=O)OC(C)(C)C] | MS m/z (M + H): 555.5 |
| F88 | 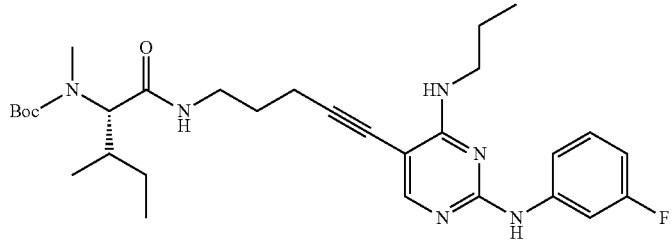 [SMILES: CCCNc1nc(Nc2cccc(F)c2)ncc1C#CCCCNC(=O)[C@H](C(C)CC)N(C)C(=O)OC(C)(C)C] | — |
TABLE 76
| Compound No. | Structure | Physicochemical data |
|---|---|---|
| F89 | 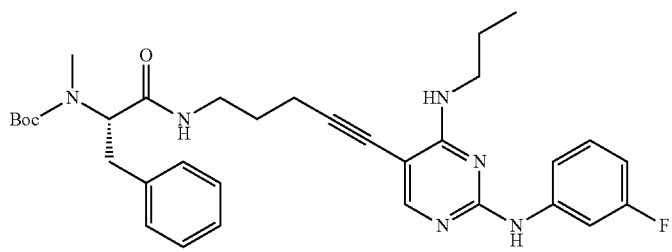 [SMILES: CCCNc1nc(Nc2cccc(F)c2)ncc1C#CCCCNC(=O)[C@H](Cc1ccccc1)N(C)C(=O)OC(C)(C)C] | — |
| F90 | 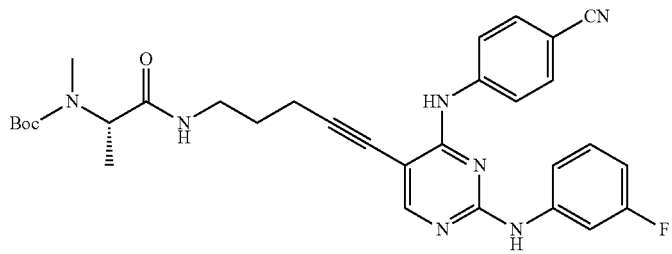 [SMILES: C[C@@H](C(=O)NCCCC#Cc1cnc(Nc2cccc(F)c2)nc1Nc1ccc(C#N)cc1)N(C)C(=O)OC(C)(C)C] | — |
| F91 | 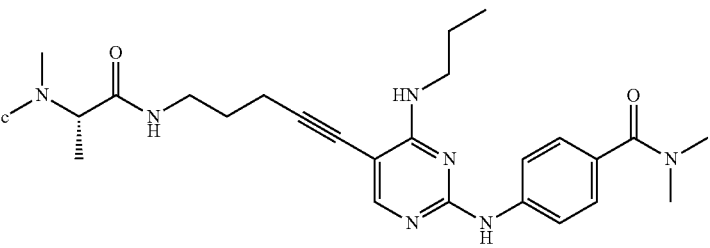 | MS m/z (M + H): 566.5 |

TABLE 76-continued

| Compound No. | Structure | Physicochemical data |
| --- | --- | --- |
| F92 | 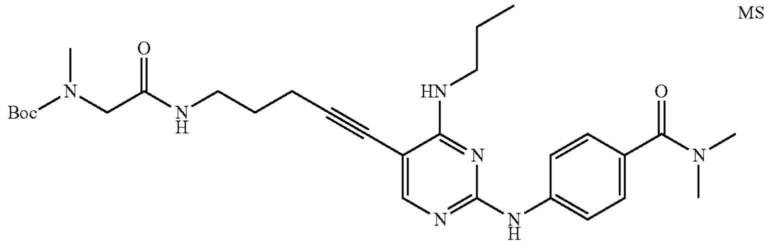 | MS m/z (M + H): 552.5 |
| F93 | 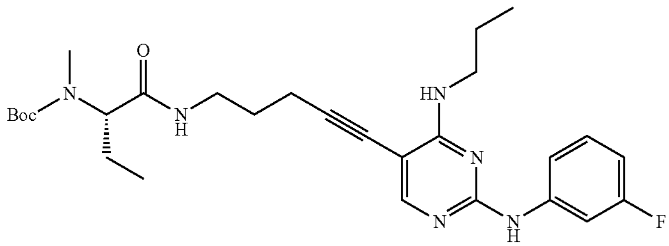 [SMILES: CCCNc1nc(Nc2cccc(F)c2)ncc1C#CCCCNC(=O)[C@H](CC)N(C)C(=O)OC(C)(C)C] | — |
| F94 | 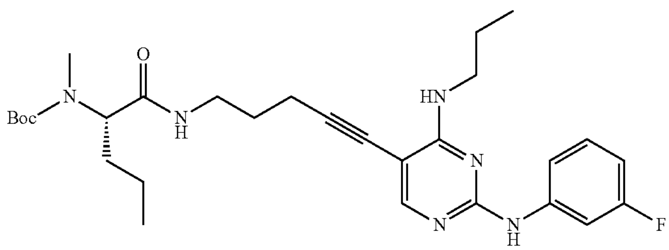 [SMILES: CCCNc1nc(Nc2cccc(F)c2)ncc1C#CCCCNC(=O)[C@H](CCC)N(C)C(=O)OC(C)(C)C] | — |
| F95 | 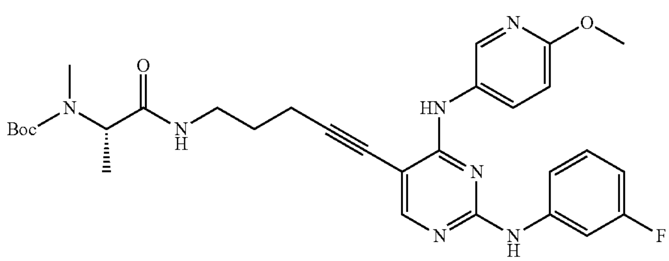 [SMILES: COc1ccc(Nc2nc(Nc3cccc(F)c3)ncc2C#CCCCNC(=O)[C@H](C)N(C)C(=O)OC(C)(C)C)cn1] | — |
| F96 | 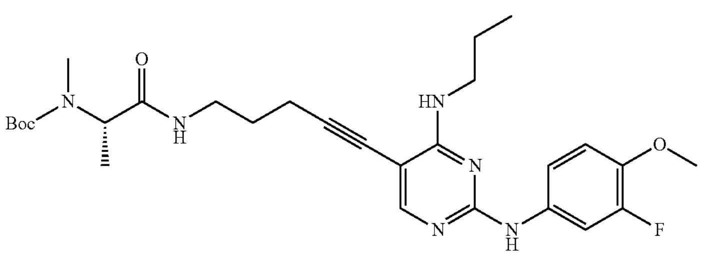 [SMILES: CCCNc1nc(Nc2ccc(OC)c(F)c2)ncc1C#CCCCNC(=O)[C@H](C)N(C)C(=O)OC(C)(C)C] | — |
| F97 | 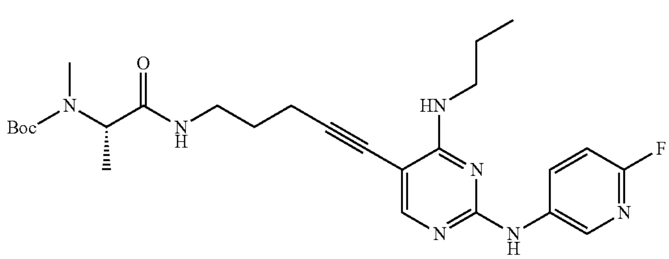 [SMILES: CCCNc1nc(Nc2ccc(F)nc2)ncc1C#CCCCNC(=O)[C@H](C)N(C)C(=O)OC(C)(C)C] | — |

TABLE 76-continued

| Compound No. | Structure | Physicochemical data |
|---|---|---|
| F98 | 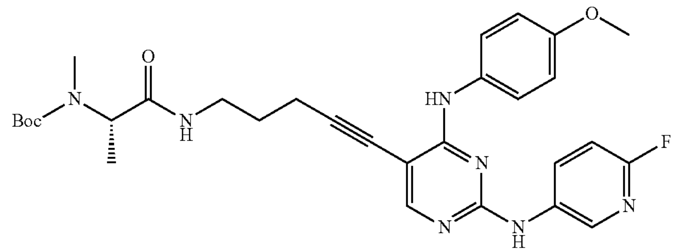 [SMILES: COc1ccc(Nc2nc(Nc3ccc(F)nc3)ncc2C#CCCCNC(=O)[C@H](C)N(C)C(=O)OC(C)(C)C)cc1] | — |

TABLE 77

| Compound No. | Structure | Physicochemical data |
|---|---|---|
| F99 | 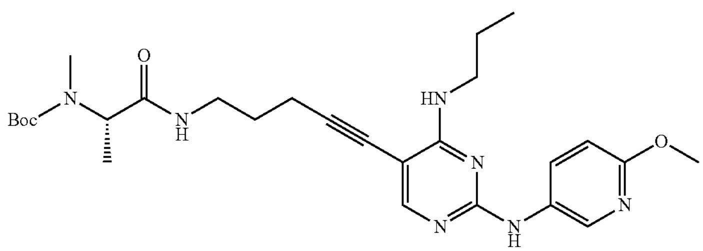 [SMILES: CCCNc1nc(Nc2ccc(OC)nc2)ncc1C#CCCCNC(=O)[C@H](C)N(C)C(=O)OC(C)(C)C] | — |
| F100 | 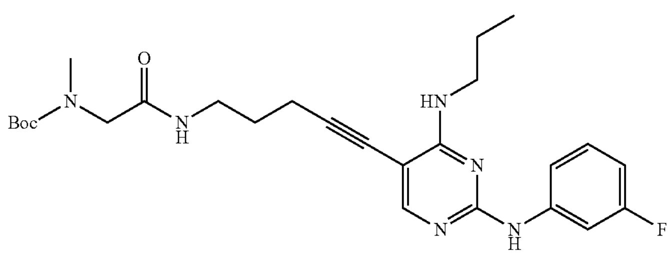 [SMILES: CCCNc1nc(Nc2cccc(F)c2)ncc1C#CCCCNC(=O)CN(C)C(=O)OC(C)(C)C] | — |
| F101 | 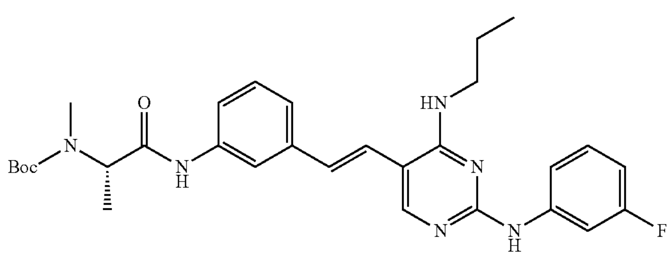 [SMILES: CCCNc1nc(Nc2cccc(F)c2)ncc1/C=C/c1cccc(NC(=O)[C@H](C)N(C)C(=O)OC(C)(C)C)c1] | — |
| F102 | 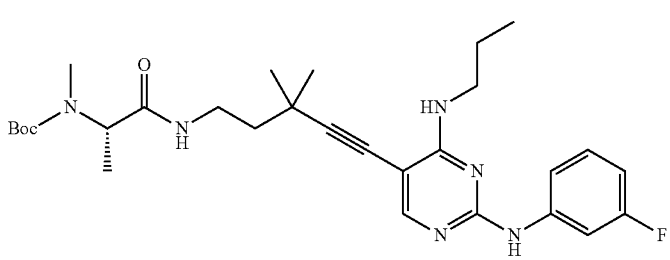 [SMILES: CCCNc1nc(Nc2cccc(F)c2)ncc1C#CC(C)(C)CCNC(=O)[C@H](C)N(C)C(=O)OC(C)(C)C] | — |

TABLE 77-continued
| Compound No. | Structure | Physicochemical data |
|---|---|---|
| F103 | 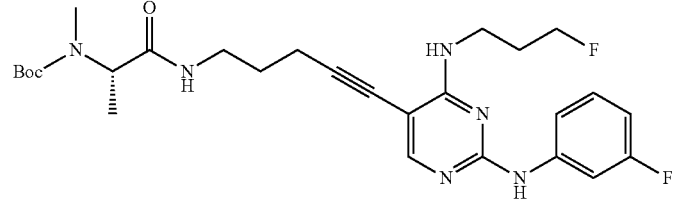 [SMILES: C[C@@H](C(=O)NCCCC#Cc1cnc(Nc2cccc(F)c2)nc1NCCCF)N(C)C(=O)OC(C)(C)C] | — |
| F104 | 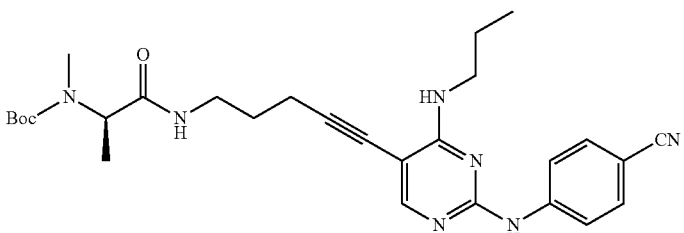 | MS m/z (M + H): 520.4 |
| F105 | 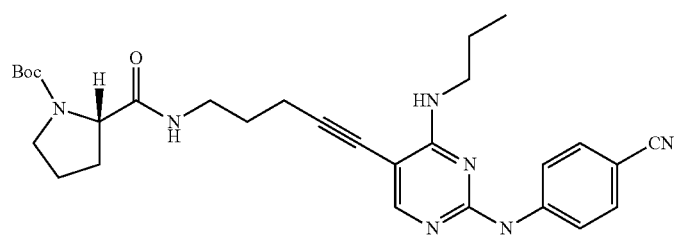 | MS m/z (M + H): 532.4 |
| F106 | 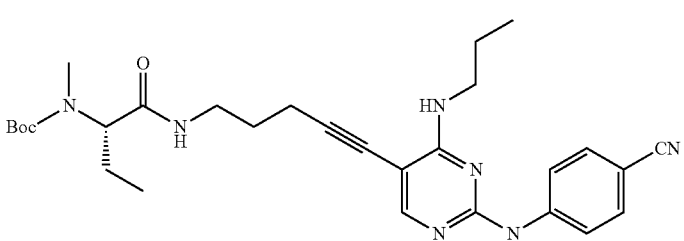 | — |
| F107 | 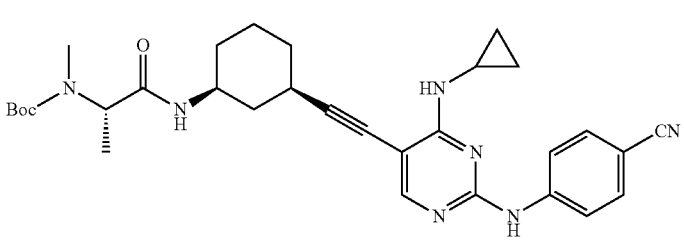 [SMILES: C[C@@H](C(=O)N[C@H]1CCC[C@@H](C#Cc2cnc(Nc3ccc(C#N)cc3)nc2NC2CC2)C1)N(C)C(=O)OC(C)(C)C] | — |
| F108 | 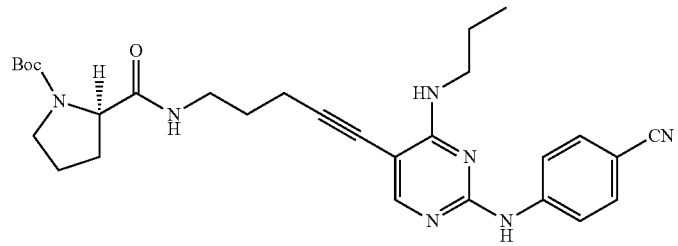 [SMILES: CCCNc1nc(Nc2ccc(C#N)cc2)ncc1C#CCCCNC(=O)[C@H]1CCCN1C(=O)OC(C)(C)C] | — |

TABLE 78
| Compound No. | Structure | Physicochemical data |
|---|---|---|
| F109 | 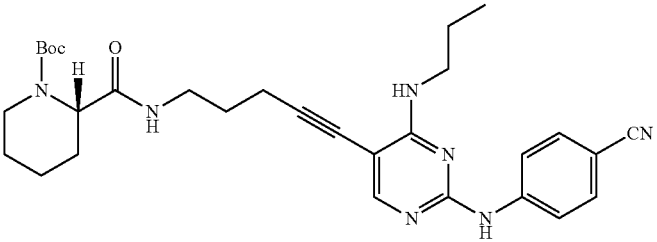 [SMILES: CCCNc1nc(Nc2ccc(C#N)cc2)ncc1C#CCCCNC(=O)[C@@H]1CCCCN1C(=O)OC(C)(C)C] | — |
| F110 | 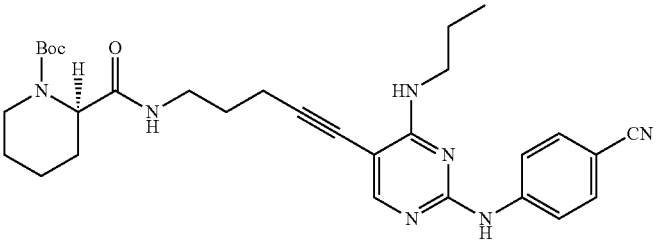 [SMILES: CCCNc1nc(Nc2ccc(C#N)cc2)ncc1C#CCCCNC(=O)[C@H]1CCCCN1C(=O)OC(C)(C)C] | — |
| F111 | 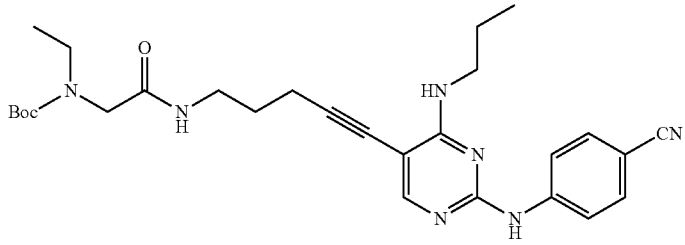 [SMILES: CCCNc1nc(Nc2ccc(C#N)cc2)ncc1C#CCCCNC(=O)CN(CC)C(=O)OC(C)(C)C] | — |
| F112 | 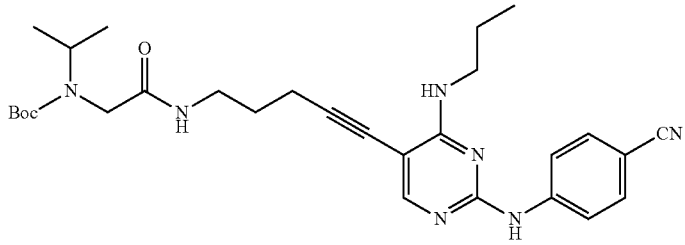 [SMILES: CCCNc1nc(Nc2ccc(C#N)cc2)ncc1C#CCCCNC(=O)CN(C(=O)OC(C)(C)C)C(C)C] | — |
| F113 | 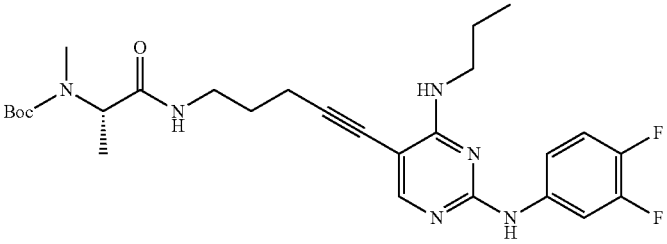 [SMILES: CCCNc1nc(Nc2ccc(F)c(F)c2)ncc1C#CCCCNC(=O)[C@H](C)N(C)C(=O)OC(C)(C)C] | — |
| F114 | 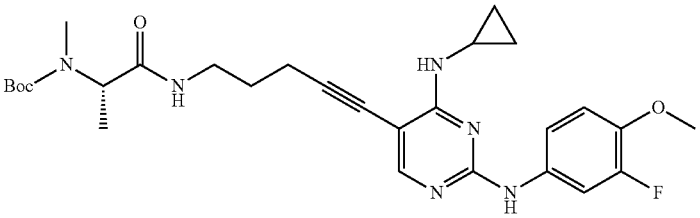 [SMILES: COc1ccc(Nc2ncc(C#CCCCNC(=O)[C@H](C)N(C)C(=O)OC(C)(C)C)c(NC3CC3)n2)cc1F] | — |

TABLE 78-continued
| Compound No. | Structure | Physicochemical data |
|---|---|---|
| F115 | 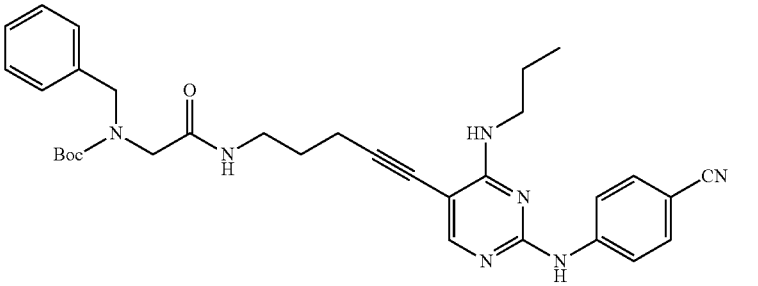 [SMILES: CCCNc1nc(Nc2ccc(C#N)cc2)ncc1C#CCCCNC(=O)CN(Cc1ccccc1)C(=O)OC(C)(C)C] | — |
| F116 | 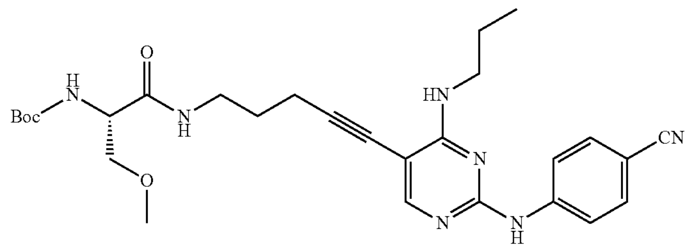 [SMILES: CCCNc1nc(Nc2ccc(C#N)cc2)ncc1C#CCCCNC(=O)[C@H](COC)NC(=O)OC(C)(C)C] | — |
| F117 | 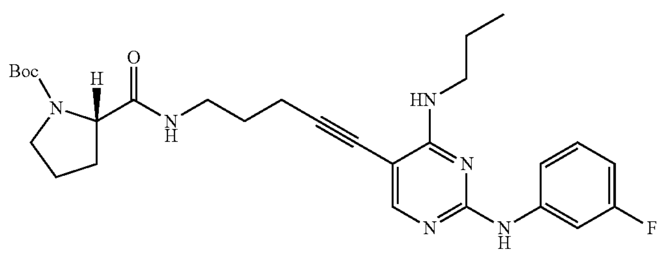 [SMILES: CCCNc1nc(Nc2cccc(F)c2)ncc1C#CCCCNC(=O)[C@@H]1CCCN1C(=O)OC(C)(C)C] | — |
TABLE 79
| Compound No. | Structure | Physicochemical data |
|---|---|---|
| F118 | 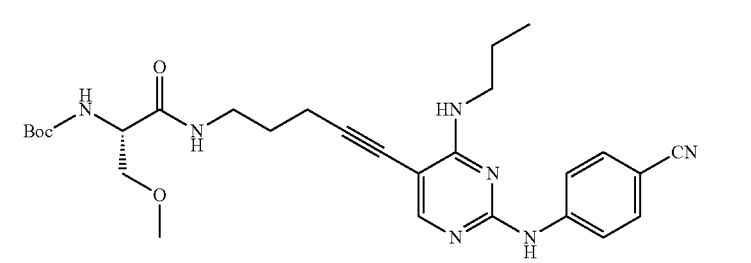 | — |
| F119 | 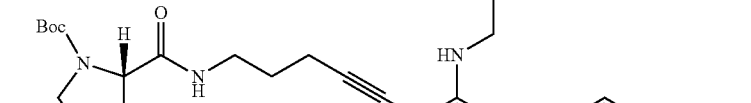 | — |

TABLE 79-continued

| Compound No. | Structure | Physicochemical data |
|---|---|---|
| F120 | 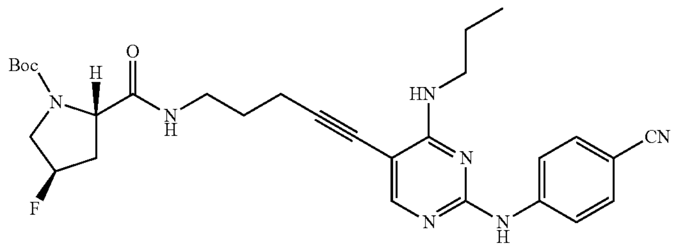 [SMILES: CCCNc1nc(Nc2ccc(C#N)cc2)ncc1C#CCCCNC(=O)[C@@H]1C[C@@H](F)CN1C(=O)OC(C)(C)C] | — |
| F121 | 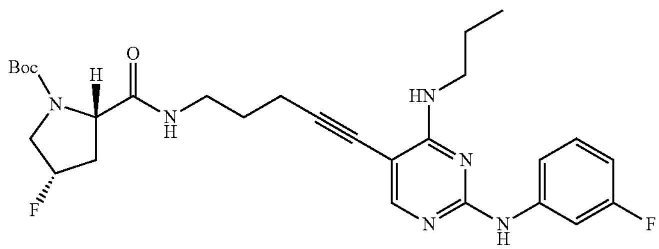 [SMILES: CCCNc1nc(Nc2cccc(F)c2)ncc1C#CCCCNC(=O)[C@@H]1C[C@H](F)CN1C(=O)OC(C)(C)C] | — |
| F122 | 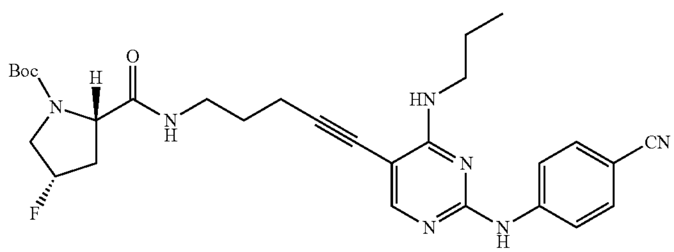 [SMILES: CCCNc1nc(Nc2ccc(C#N)cc2)ncc1C#CCCCNC(=O)[C@@H]1C[C@H](F)CN1C(=O)OC(C)(C)C] | — |
| F123 | 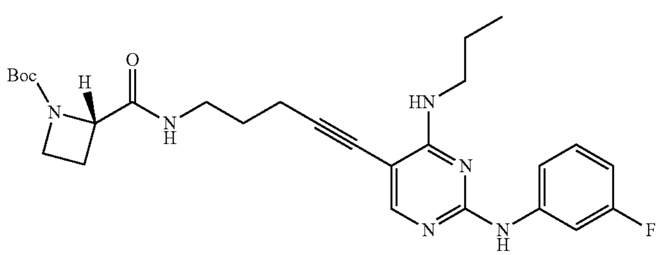 [SMILES: CCCNc1nc(Nc2cccc(F)c2)ncc1C#CCCCNC(=O)[C@@H]1CCN1C(=O)OC(C)(C)C] | — |
| F124 | 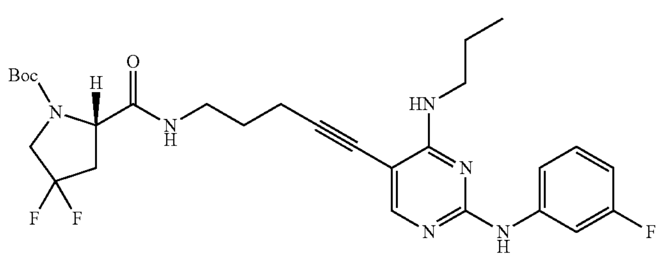 [SMILES: CCCNc1nc(Nc2cccc(F)c2)ncc1C#CCCCNC(=O)[C@@H]1CC(F)(F)CN1C(=O)OC(C)(C)C] | — |
| F125 | 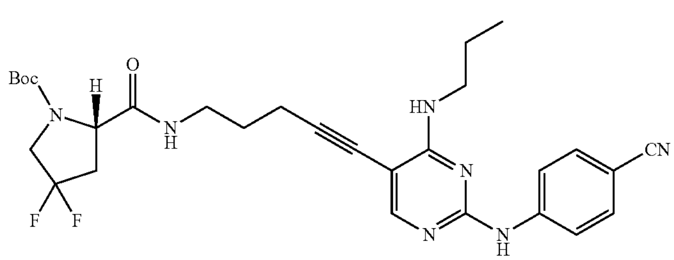 [SMILES: CCCNc1nc(Nc2ccc(C#N)cc2)ncc1C#CCCCNC(=O)[C@@H]1CC(F)(F)CN1C(=O)OC(C)(C)C] | — |

TABLE 79-continued
| Compound No. | Structure | Physicochemical data |
|---|---|---|
| F126 | 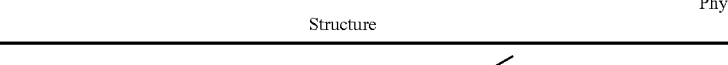 | — |
TABLE 80
| Compound No. | Structure | Physicochemical data |
|---|---|---|
| F249 | 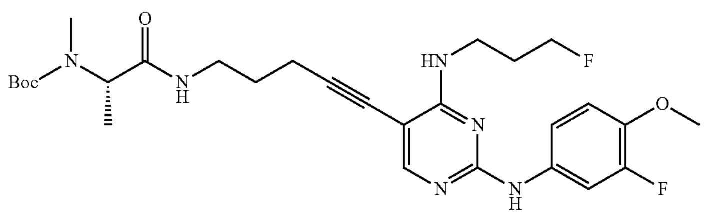 [SMILES: COc1ccc(Nc2ncc(C#CCCCNC(=O)[C@H](C)N(C)C(=O)OC(C)(C)C)c(NCCCF)n2)cc1F] | MS m/z (M + H): 561.2 |
| F250 | 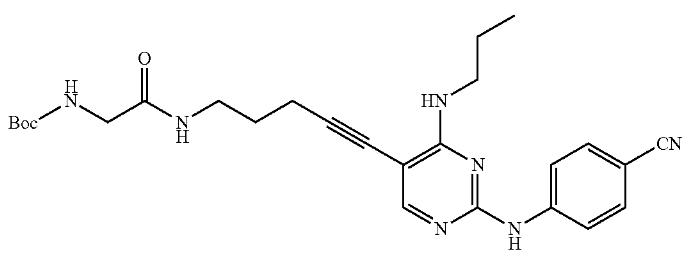 [SMILES: CCCNc1nc(Nc2ccc(C#N)cc2)ncc1C#CCCCNC(=O)CNC(=O)OC(C)(C)C] | — |
| F251 | 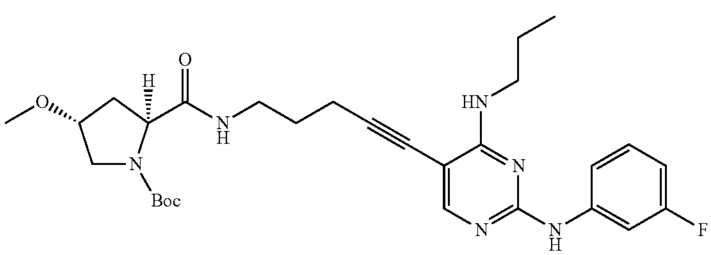 [SMILES: CCCNc1nc(Nc2cccc(F)c2)ncc1C#CCCCNC(=O)[C@@H]1C[C@@H](OC)CN1C(=O)OC(C)(C)C] | MS m/z (M + H): 555.4 |
| F252 | 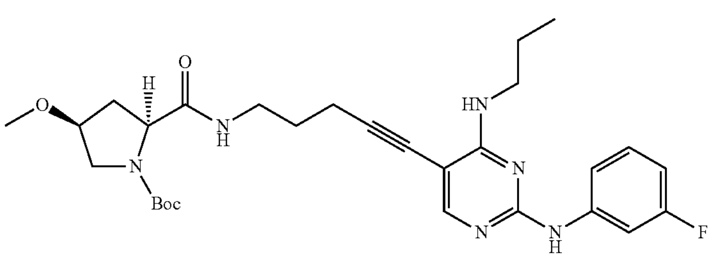 [SMILES: CCCNc1nc(Nc2cccc(F)c2)ncc1C#CCCCNC(=O)[C@@H]1C[C@H](OC)CN1C(=O)OC(C)(C)C] | MS m/z (M + H): 555.4 |

TABLE 80-continued
| Compound No. | Structure | Physicochemical data |
|---|---|---|
| F253 | 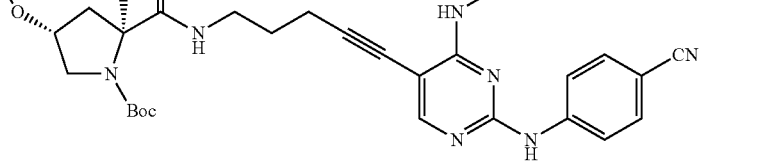 | MS m/z (M + H): 562.4 |
| F254 | 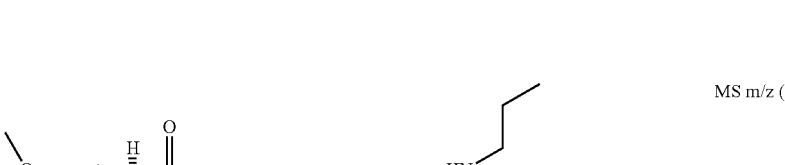 | MS m/z (M + H): 562.4 |
| F255 | 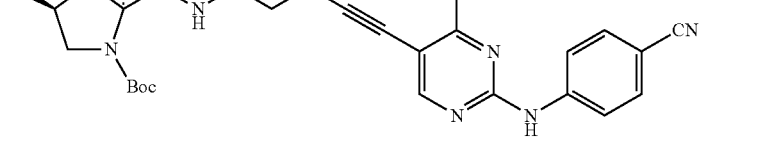 | — |
| F256 | 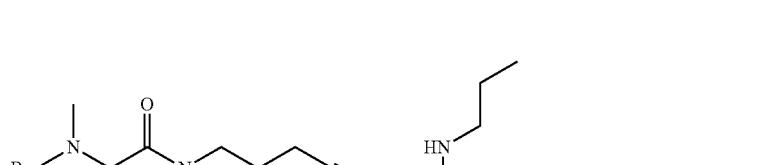 | — |
| F257 | 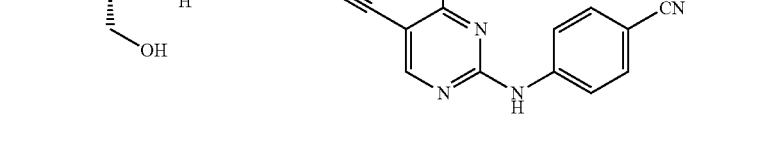 | MS m/z (M + H): 534.4 |

TABLE 81
| Compound No. | Structure | Physicochemical data |
|---|---|---|
| F258 | 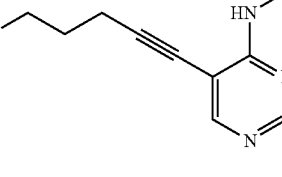 | MS m/z (M + H): 548.4 |
| F259 | 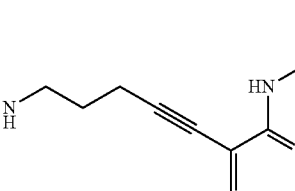 | MS m/z (M + H): 541.4 |
| F260 | 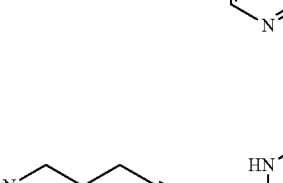 | MS m/z (M + H): 541.4 |
| F261 | 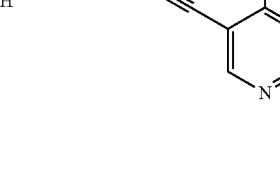 | MS m/z (M + H): 548.4 |
| F262 | 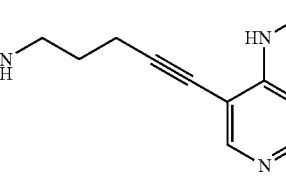 | MS m/z (M + H): 548.4 |
| F263 | 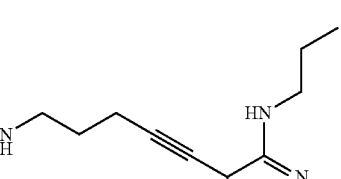 | MS m/z (M + H): 548.5 |

TABLE 81-continued

| Compound No. | Structure | Physicochemical data |
|---|---|---|
| F264 | 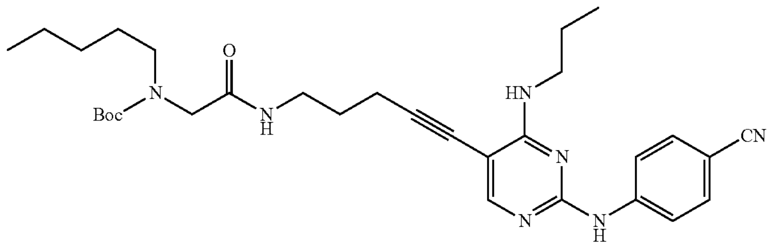 [SMILES: CCCCCN(CC(=O)NCCCC#Cc1cnc(Nc2ccc(C#N)cc2)nc1NCCC)C(=O)OC(C)(C)C] | MS m/z (M + H): 562.4 |
| F265 | 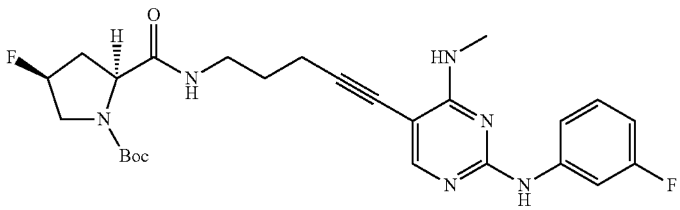 [SMILES: CNc1nc(Nc2cccc(F)c2)ncc1C#CCCCNC(=O)[C@@H]1C[C@H](F)CN1C(=O)OC(C)(C)C] | MS m/z (M + H): 515.4 |
| F266 | 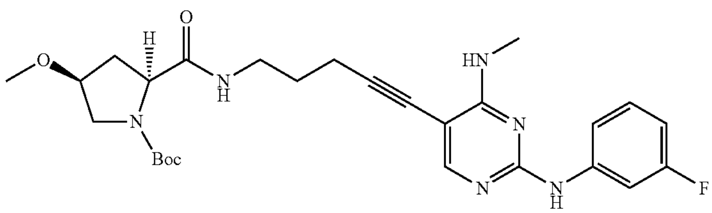 [SMILES: CNc1nc(Nc2cccc(F)c2)ncc1C#CCCCNC(=O)[C@@H]1C[C@H](OC)CN1C(=O)OC(C)(C)C] | MS m/z (M + H): 527.4 |
| F267 | 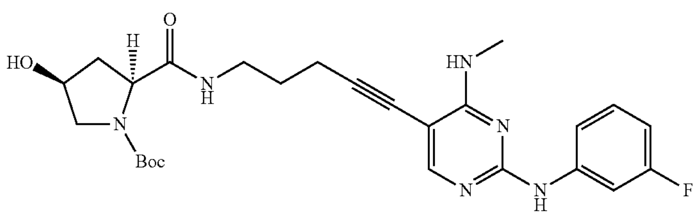 [SMILES: CNc1nc(Nc2cccc(F)c2)ncc1C#CCCCNC(=O)[C@@H]1C[C@H](O)CN1C(=O)OC(C)(C)C] | MS m/z (M + H): 513.4 |

TABLE 82

| Compound No. | Structure | Physicochemical data |
|---|---|---|
| F268 | 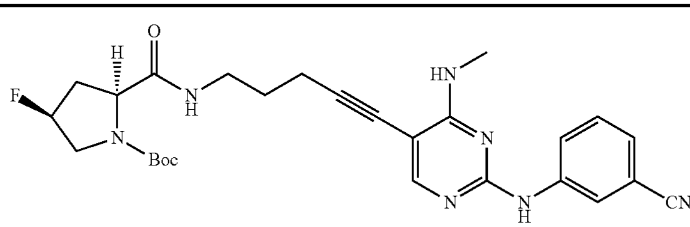 | MS m/z (M + H): 522.4 |
| F269 | 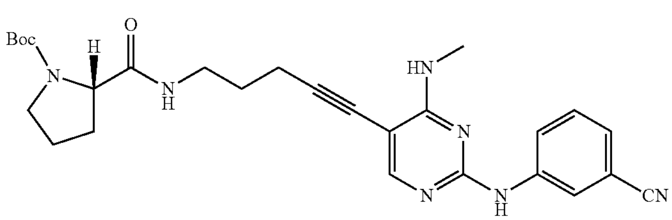 [SMILES: CNc1nc(Nc2cccc(C#N)c2)ncc1C#CCCCNC(=O)[C@@H]1CCCN1C(=O)OC(C)(C)C] | MS m/z (M − H): 502.4 |

TABLE 82-continued

| Compound No. | Structure | Physicochemical data |
|---|---|---|
| F270 | 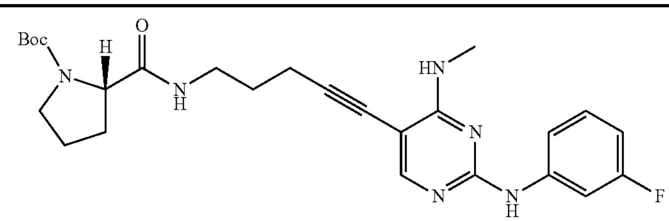 | MS m/z (M + H): 497.4 |
| F271 | 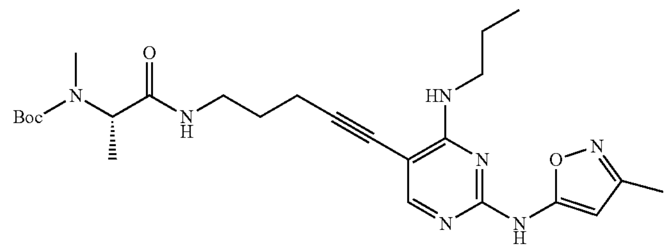 [SMILES: CCCNc1nc(Nc2cc(C)no2)ncc1C#CCCCNC(=O)[C@H](C)N(C)C(=O)OC(C)(C)C] | MS m/z (M + H): 500.4 |
| F272 | 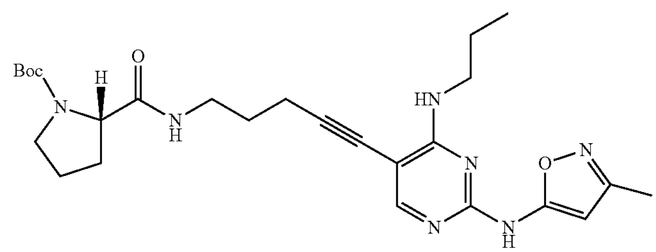 [SMILES: CCCNc1nc(Nc2cc(C)no2)ncc1C#CCCCNC(=O)[C@@H]1CCCN1C(=O)OC(C)(C)C] | MS m/z (M + H): 512.4 |
| F273 | 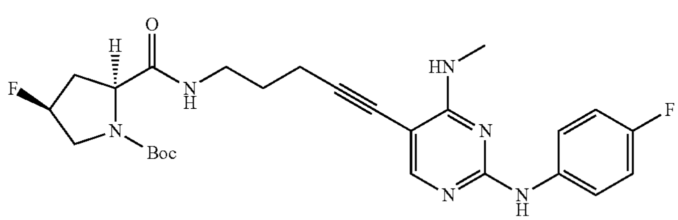 [SMILES: CNc1nc(Nc2ccc(F)cc2)ncc1C#CCCCNC(=O)[C@@H]1C[C@H](F)CN1C(=O)OC(C)(C)C] | MS m/z (M + H): 515.4 |
| F274 | 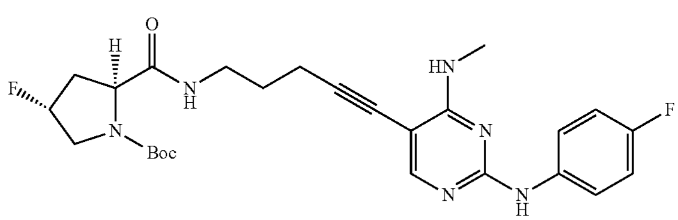 [SMILES: CNc1nc(Nc2ccc(F)cc2)ncc1C#CCCCNC(=O)[C@@H]1C[C@@H](F)CN1C(=O)OC(C)(C)C] | MS m/z (M + H): 515.4 |
| F275 | 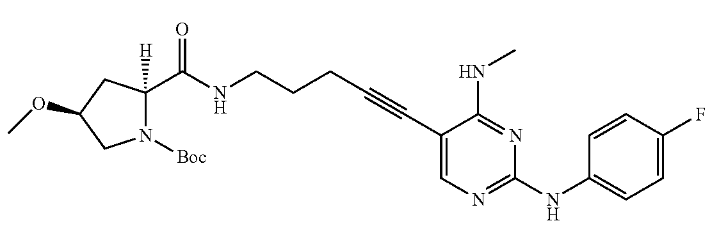 [SMILES: CNc1nc(Nc2ccc(F)cc2)ncc1C#CCCCNC(=O)[C@@H]1C[C@H](OC)CN1C(=O)OC(C)(C)C] | MS m/z (M + H): 527.5 |
| F276 | 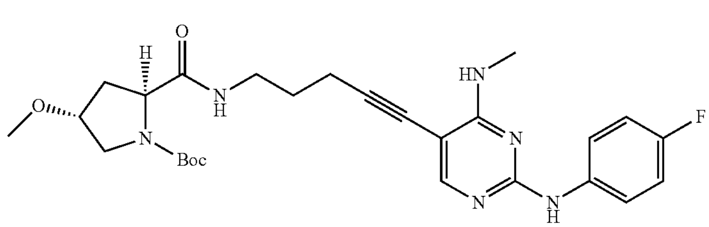 [SMILES: CNc1nc(Nc2ccc(F)cc2)ncc1C#CCCCNC(=O)[C@@H]1C[C@@H](OC)CN1C(=O)OC(C)(C)C] | MS m/z (M + H): 527.5 |

TABLE 82-continued
| Compound No. | Structure | Physicochemical data |
|---|---|---|
| F277 | 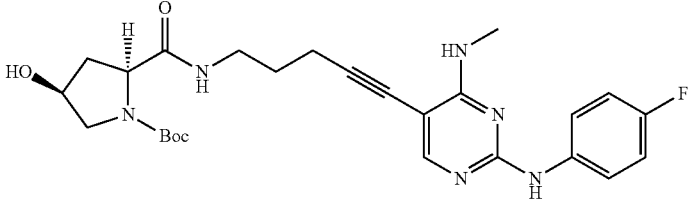 [SMILES: CNc1nc(Nc2ccc(F)cc2)ncc1C#CCCCNC(=O)[C@@H]1C[C@H](O)CN1C(=O)OC(C)(C)C] | MS m/z (M + H): 513.4 |
TABLE 83
| Compound No. | Structure | Physicochemical data |
|---|---|---|
| F278 | 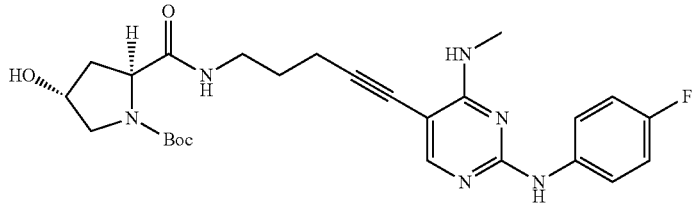 [SMILES: CNc1nc(Nc2ccc(F)cc2)ncc1C#CCCCNC(=O)[C@@H]1C[C@@H](O)CN1C(=O)OC(C)(C)C] | MS m/z (M + H): 513.4 |
| F279 | 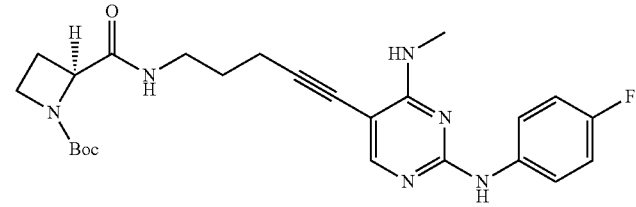 [SMILES: CNc1nc(Nc2ccc(F)cc2)ncc1C#CCCCNC(=O)[C@@H]1CCN1C(=O)OC(C)(C)C] | MS m/z (M + H): 483.4 |
| F280 | 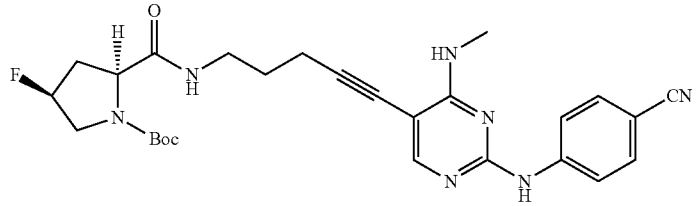 [SMILES: CNc1nc(Nc2ccc(C#N)cc2)ncc1C#CCCCNC(=O)[C@@H]1C[C@H](F)CN1C(=O)OC(C)(C)C] | MS m/z (M + H): 522.4 |
| F281 | 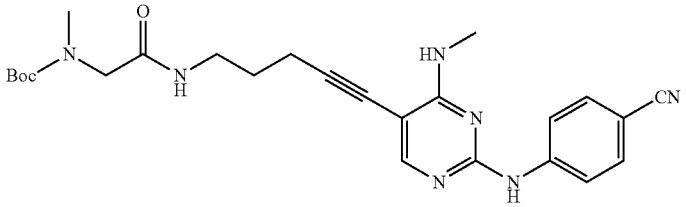 [SMILES: CNc1nc(Nc2ccc(C#N)cc2)ncc1C#CCCCNC(=O)CN(C)C(=O)OC(C)(C)C] | MS m/z (M + H): 478.4 |
| F282 | 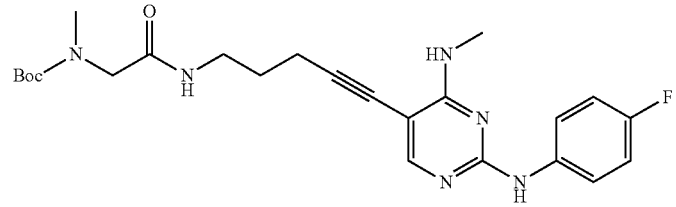 [SMILES: CNc1nc(Nc2ccc(F)cc2)ncc1C#CCCCNC(=O)CN(C)C(=O)OC(C)(C)C] | MS m/z (M + H): 471.4 |

TABLE 83-continued

| Compound No. | Structure | Physicochemical data |
|---|---|---|
| F283 | 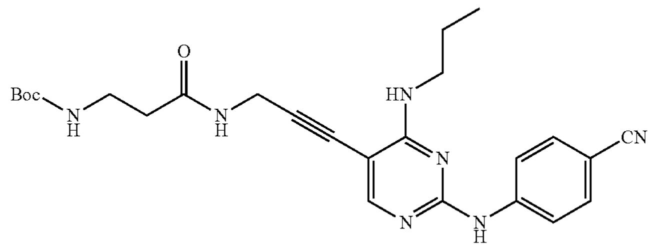 [SMILES: CCCNc1nc(Nc2ccc(C#N)cc2)ncc1C#CCNC(=O)CCNC(=O)OC(C)(C)C] | MS m/z (M + H): 478.5 |
| F284 | 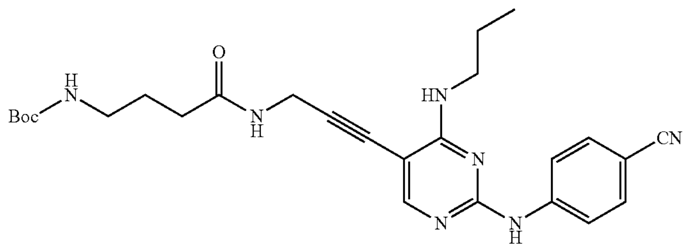 [SMILES: CCCNc1nc(Nc2ccc(C#N)cc2)ncc1C#CCNC(=O)CCCNC(=O)OC(C)(C)C] | MS m/z (M + H): 492.5 |
| F285 | 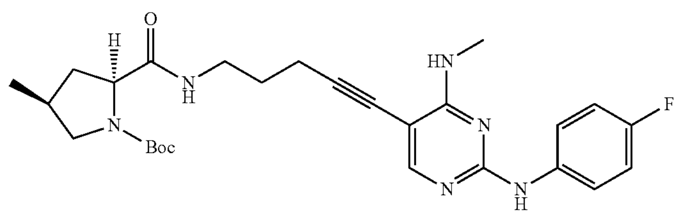 [SMILES: CNc1nc(Nc2ccc(F)cc2)ncc1C#CCCCNC(=O)[C@@H]1C[C@H](C)CN1C(=O)OC(C)(C)C] | MS m/z (M + H): 511.4 |
| F286 | 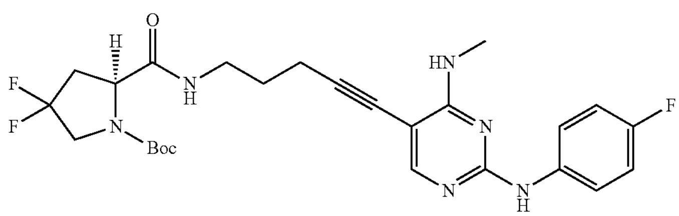 [SMILES: CNc1nc(Nc2ccc(F)cc2)ncc1C#CCCCNC(=O)[C@@H]1CC(F)(F)CN1C(=O)OC(C)(C)C] | MS m/z (M + H): 533.4 |
| F287 | 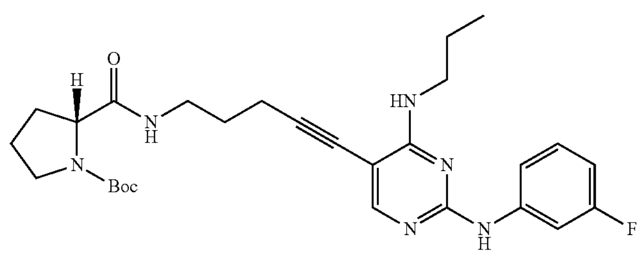 [SMILES: CCCNc1nc(Nc2cccc(F)c2)ncc1C#CCCCNC(=O)[C@H]1CCCN1C(=O)OC(C)(C)C] | MS m/z (M + H): 525.4 |

TABLE 84

| Compound No. | Structure | Physicochemical data |
|---|---|---|
| F329 | 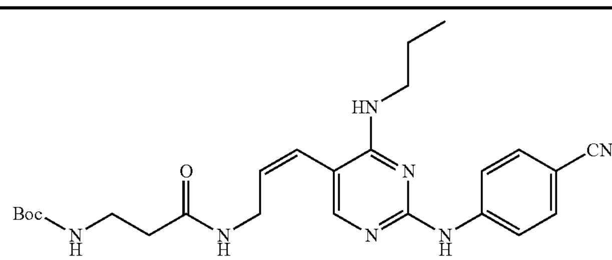 | MS m/z (M + H): 480.5 |

TABLE 84-continued

| Compound No. | Structure | Physicochemical data |
|---|---|---|
| F330 | 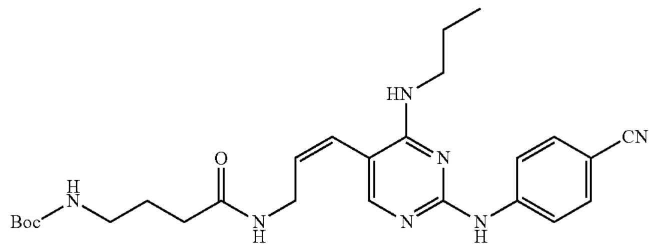 [SMILES: CCCNc1nc(Nc2ccc(C#N)cc2)ncc1/C=C\CNC(=O)CCCNC(=O)OC(C)(C)C] | MS m/z (M + H): 494.5 |

21

In the same manner as that of Example 35, (6), Intermediates (F127) to (F175), Intermediates (F288) to (F326), Intermediates (F331) and (F332) were obtained.

TABLE 85

| Compound No. | Structure | Physicochemical data |
|---|---|---|
| F127 | 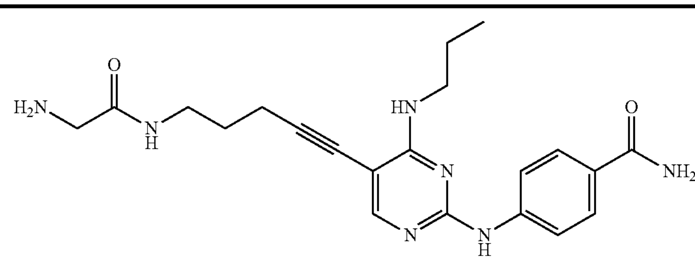 | — |
| F128 | 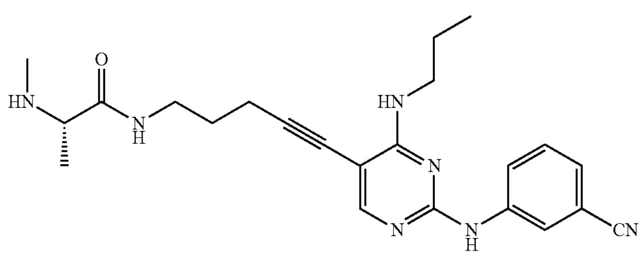 [SMILES: CCCNc1nc(Nc2cccc(C#N)c2)ncc1C#CCCCNC(=O)[C@H](C)NC] | — |
| F129 | 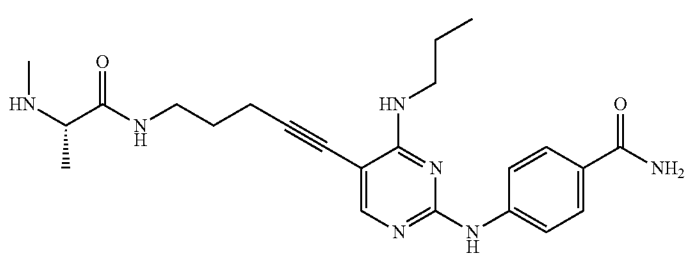 [SMILES: CCCNc1nc(Nc2ccc(C(N)=O)cc2)ncc1C#CCCCNC(=O)[C@H](C)NC] | MS m/z (M + H): 438.3 |
| F130 | 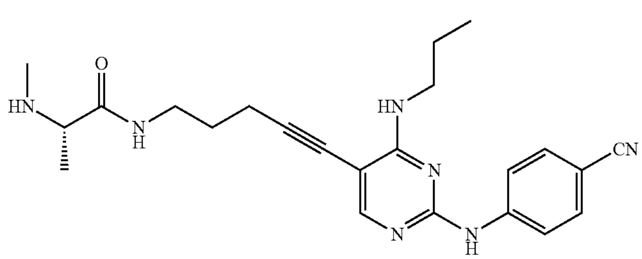 [SMILES: CCCNc1nc(Nc2ccc(C#N)cc2)ncc1C#CCCCNC(=O)[C@H](C)NC] | MS m/z (M + H): 420.4 |

TABLE 85-continued

| Compound No. | Structure | Physicochemical data |
|---|---|---|
| F131 | 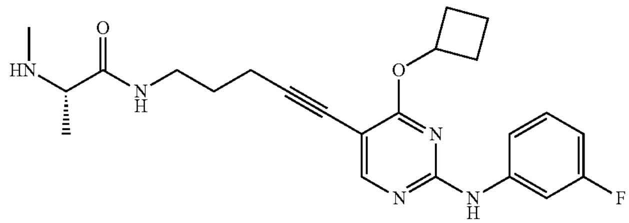 [SMILES: CN[C@@H](C)C(=O)NCCCC#Cc1cnc(Nc2cccc(F)c2)nc1OC1CCC1] | — |
| F132 | 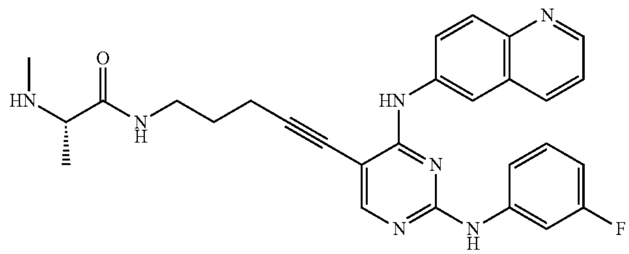 [SMILES: CN[C@@H](C)C(=O)NCCCC#Cc1cnc(Nc2cccc(F)c2)nc1Nc1ccc2ncccc2c1] | — |
| F133 | 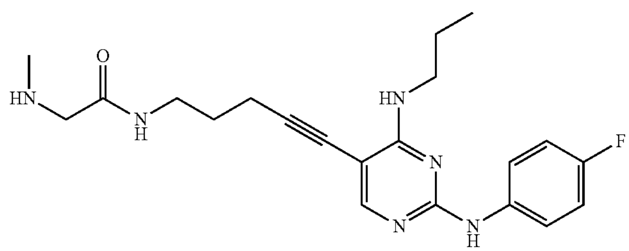 [SMILES: CCCNc1nc(Nc2ccc(F)cc2)ncc1C#CCCCNC(=O)CNC] | MS m/z (M + H): 399.3 |
| F134 | 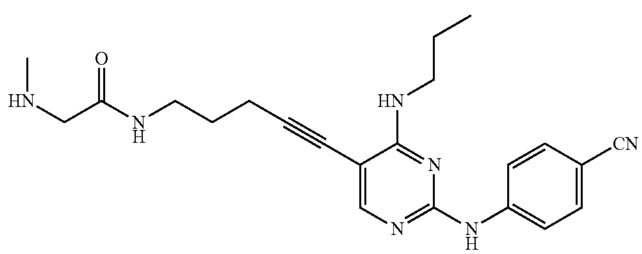 [SMILES: CCCNc1nc(Nc2ccc(C#N)cc2)ncc1C#CCCCNC(=O)CNC] | MS m/z (M + H): 406.4 |
| F135 | 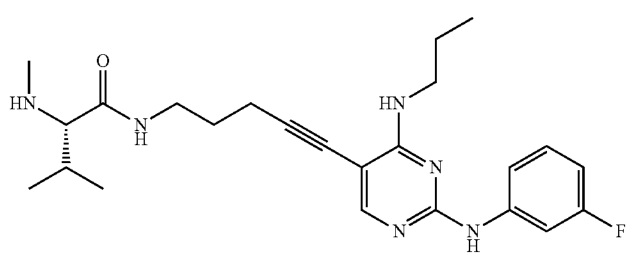 [SMILES: CCCNc1nc(Nc2cccc(F)c2)ncc1C#CCCCNC(=O)[C@@H](NC)C(C)C] | — |
| F136 | 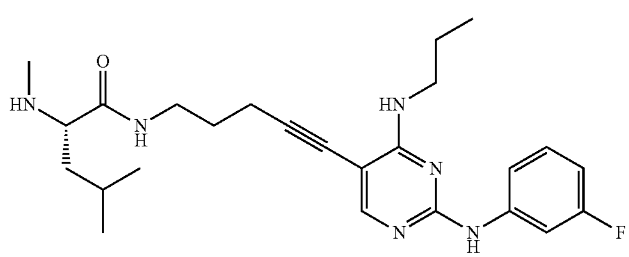 [SMILES: CCCNc1nc(Nc2cccc(F)c2)ncc1C#CCCCNC(=O)[C@H](CC(C)C)NC] | — |

TABLE 86

| Compound No. | Structure | Physicochemical data |
|---|---|---|
| F137 | 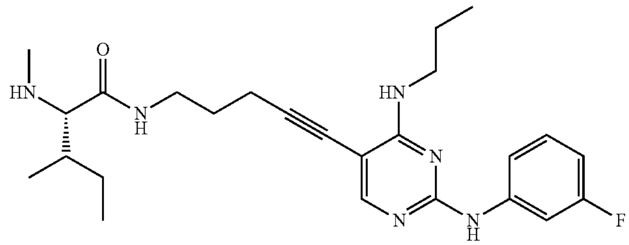 [SMILES: CCCNc1nc(Nc2cccc(F)c2)ncc1C#CCCCNC(=O)[C@@H](NC)C(C)CC] | — |
| F138 | 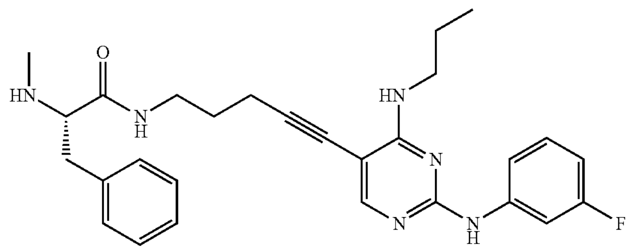 [SMILES: CCCNc1nc(Nc2cccc(F)c2)ncc1C#CCCCNC(=O)[C@H](Cc1ccccc1)NC] | — |
| F139 | 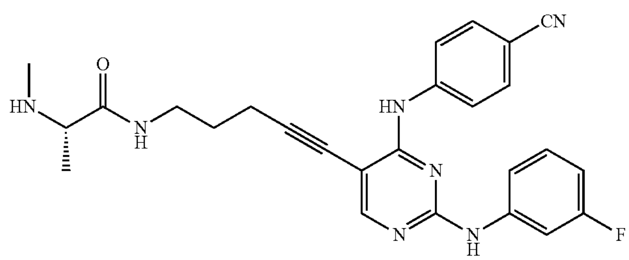 [SMILES: CN[C@@H](C)C(=O)NCCCC#Cc1cnc(Nc2cccc(F)c2)nc1Nc1ccc(C#N)cc1] | — |
| F140 | 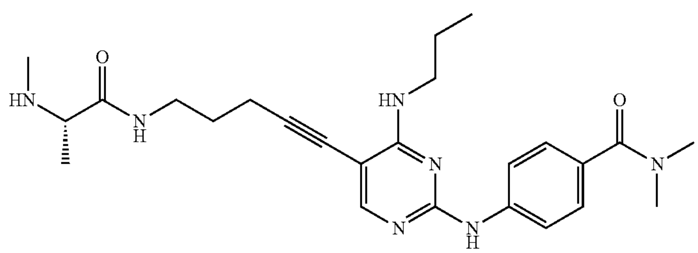 [SMILES: CCCNc1nc(Nc2ccc(C(=O)N(C)C)cc2)ncc1C#CCCCNC(=O)[C@H](C)NC] | — |
| F141 | 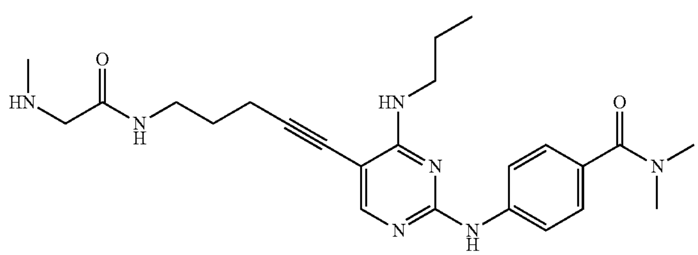 [SMILES: CCCNc1nc(Nc2ccc(C(=O)N(C)C)cc2)ncc1C#CCCCNC(=O)CNC] | — |
| F142 | 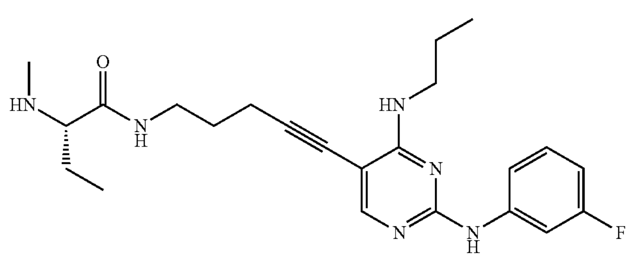 | — |

TABLE 86-continued

| Compound No. | Structure | Physicochemical data |
|---|---|---|
| F143 | 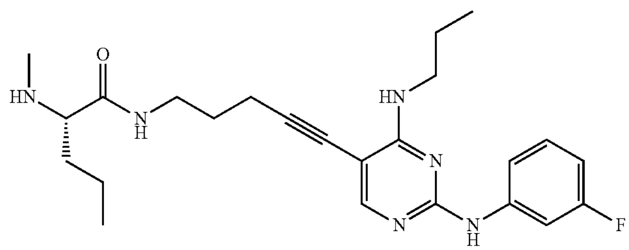 [SMILES: CCCNc1nc(Nc2cccc(F)c2)ncc1C#CCCCNC(=O)[C@H](CCC)NC] | — |
| F144 | 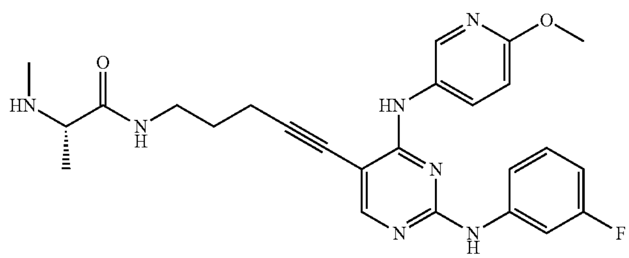 [SMILES: CN[C@@H](C)C(=O)NCCCC#Cc1cnc(Nc2cccc(F)c2)nc1Nc1ccc(OC)nc1] | — |
| F145 | 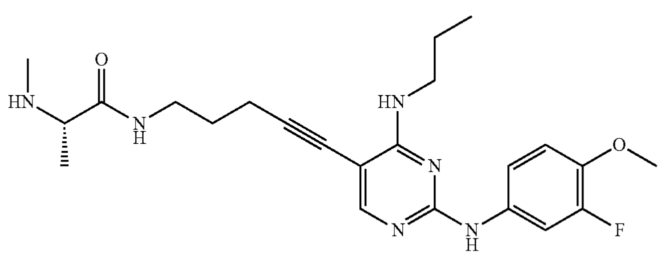 [SMILES: CCCNc1nc(Nc2ccc(OC)c(F)c2)ncc1C#CCCCNC(=O)[C@H](C)NC] | — |
| F146 | 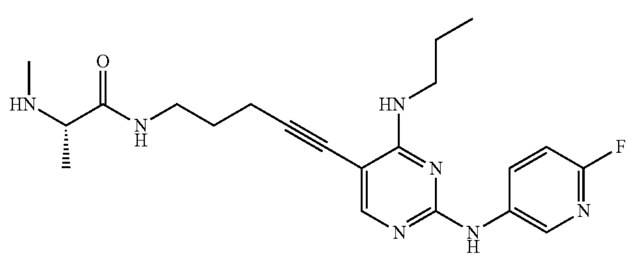 [SMILES: CCCNc1nc(Nc2ccc(F)nc2)ncc1C#CCCCNC(=O)[C@H](C)NC] | — |
| F147 | 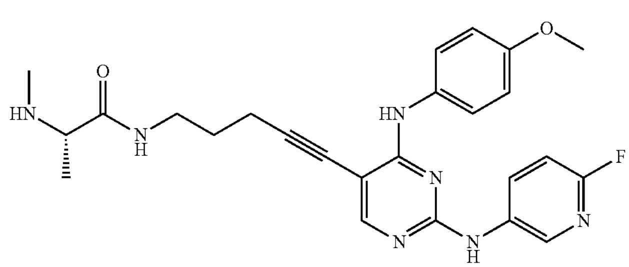 [SMILES: CN[C@@H](C)C(=O)NCCCC#Cc1cnc(Nc2ccc(F)nc2)nc1Nc1ccc(OC)cc1] | — |

TABLE 87
| Compound No. | Structure | Physicochemical data |
|---|---|---|
| F148 | 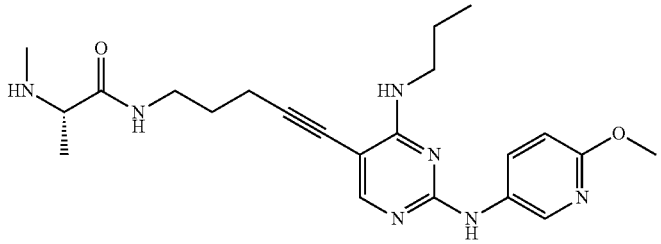 [SMILES: CCCNc1nc(Nc2ccc(OC)nc2)ncc1C#CCCCNC(=O)[C@H](C)NC] | — |
| F149 | 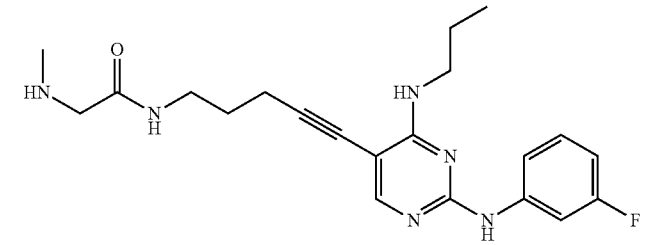 [SMILES: CCCNc1nc(Nc2cccc(F)c2)ncc1C#CCCCNC(=O)CNC] | — |
| F150 | 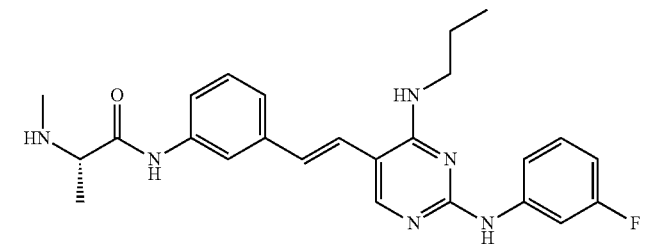 [SMILES: CCCNc1nc(Nc2cccc(F)c2)ncc1/C=C/c1cccc(NC(=O)[C@H](C)NC)c1] | — |
| F151 | 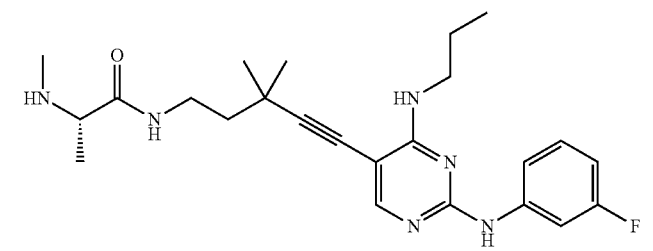 | — |
| F152 | 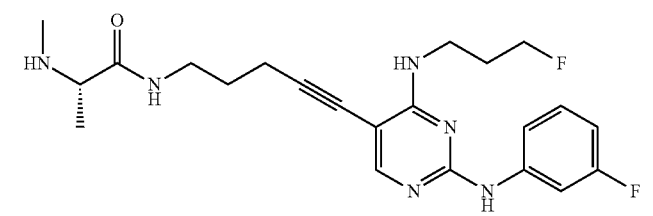 [SMILES: CN[C@@H](C)C(=O)NCCCC#Cc1cnc(Nc2cccc(F)c2)nc1NCCCF] | — |
| F153 | 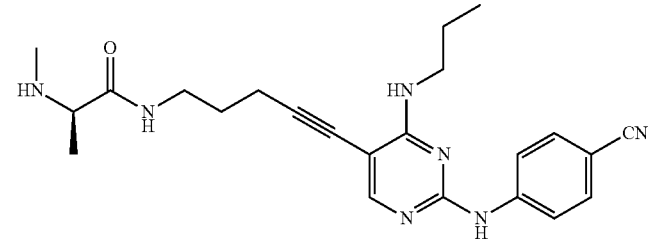 [SMILES: CCCNc1nc(Nc2ccc(C#N)cc2)ncc1C#CCCCNC(=O)[C@@H](C)NC] | — |

TABLE 87-continued
| Compound No. | Structure | Physicochemical data |
|---|---|---|
| F154 | 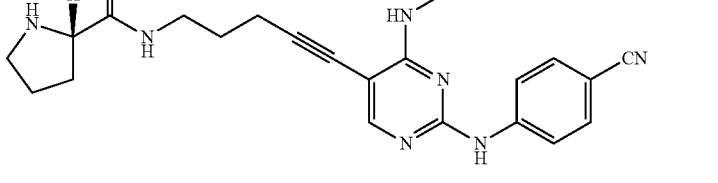 | — |
| F155 | 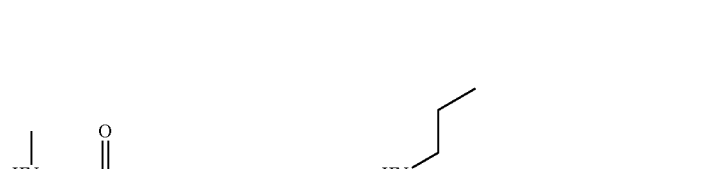 | — |
| F156 | 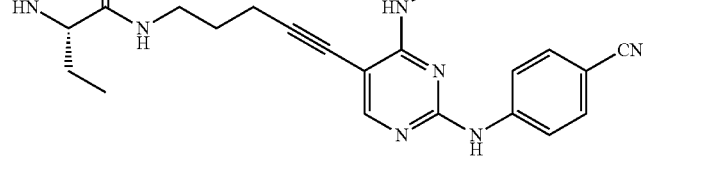 | — |
| F157 | 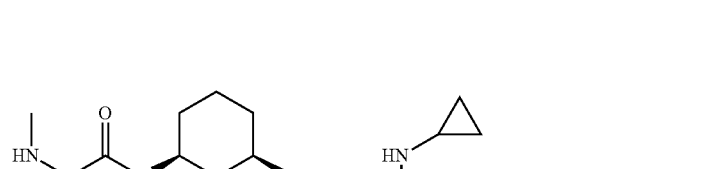 | — |
| F158 | 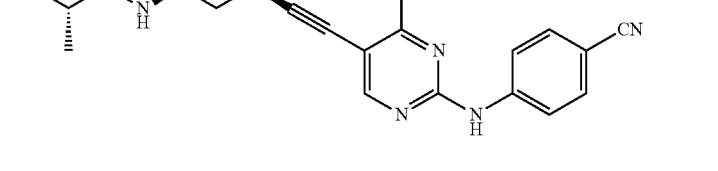 | — |

TABLE 88
| Compound No. | Structure | Physicochemical data |
|---|---|---|
| F159 | 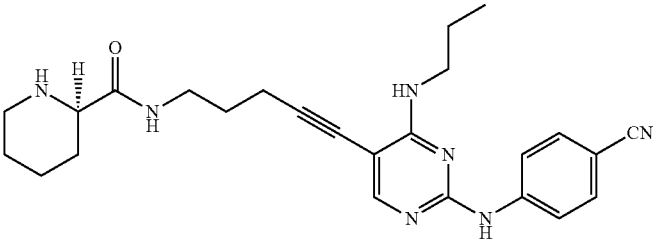 [SMILES: CCCNc1nc(Nc2ccc(C#N)cc2)ncc1C#CCCCNC(=O)[C@H]1CCCCN1] | — |
| F160 | 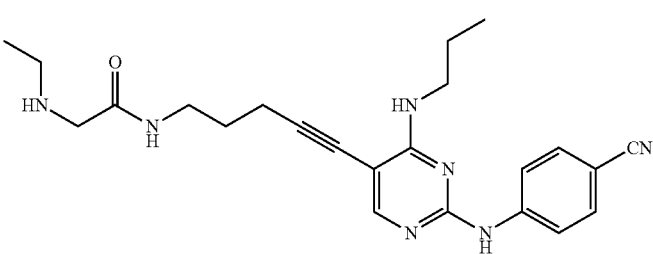 [SMILES: CCCNc1nc(Nc2ccc(C#N)cc2)ncc1C#CCCCNC(=O)CNCC] | — |
| F161 | 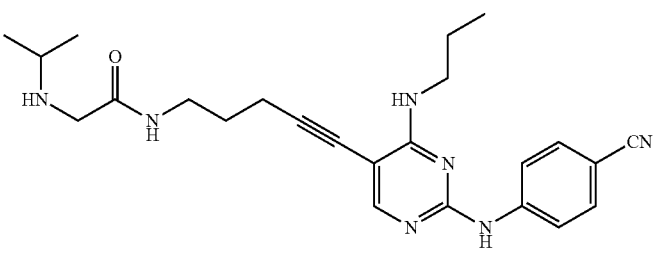 [SMILES: CCCNc1nc(Nc2ccc(C#N)cc2)ncc1C#CCCCNC(=O)CNC(C)C] | — |
| F162 | 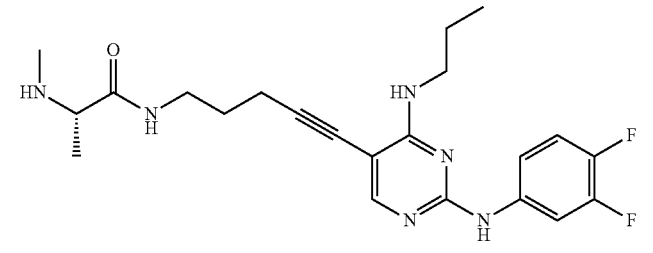 [SMILES: CCCNc1nc(Nc2ccc(F)c(F)c2)ncc1C#CCCCNC(=O)[C@H](C)NC] | — |
| F163 | 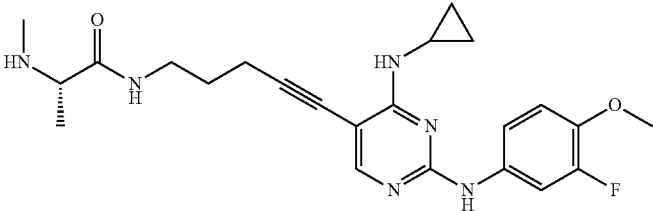 [SMILES: CN[C@@H](C)C(=O)NCCCC#Cc1cnc(Nc2ccc(OC)c(F)c2)nc1NC1CC1] | — |
| F164 | 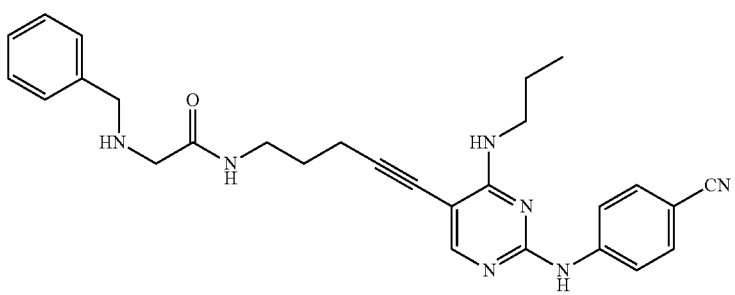 [SMILES: CCCNc1nc(Nc2ccc(C#N)cc2)ncc1C#CCCCNC(=O)CNCc1ccccc1] | — |

TABLE 88-continued

| Compound No. | Structure | Physicochemical data |
|---|---|---|
| F165 | 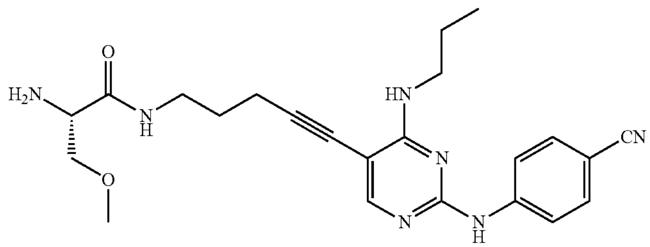 [SMILES: CCCNc1nc(Nc2ccc(C#N)cc2)ncc1C#CCCCNC(=O)[C@@H](N)COC] | — |
| F166 | 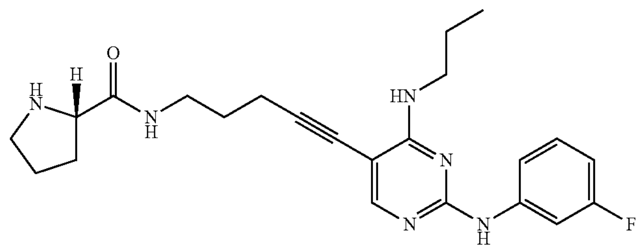 [SMILES: CCCNc1nc(Nc2cccc(F)c2)ncc1C#CCCCNC(=O)[C@@H]1CCCN1] | — |
| F167 | 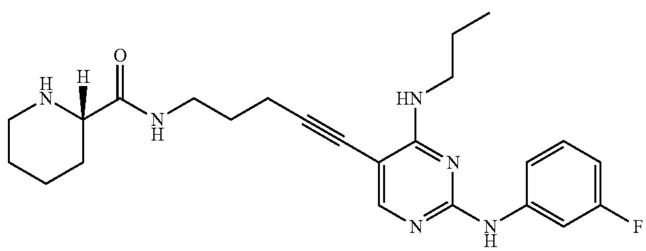 [SMILES: CCCNc1nc(Nc2cccc(F)c2)ncc1C#CCCCNC(=O)[C@@H]1CCCCN1] | — |
| F168 | 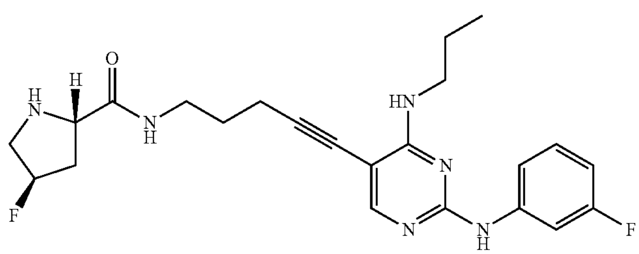 [SMILES: CCCNc1nc(Nc2cccc(F)c2)ncc1C#CCCCNC(=O)[C@@H]1C[C@@H](F)CN1] | — |

TABLE 89

| Compound No. | Structure | Physicochemical data |
|---|---|---|
| F169 | 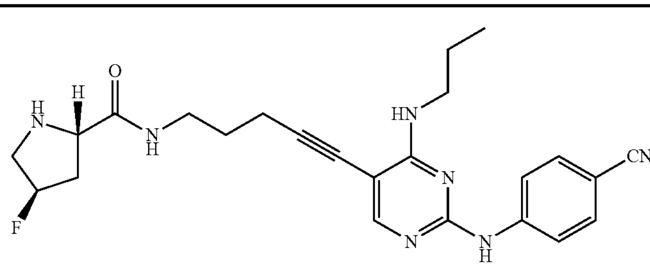 | — |

TABLE 89-continued

| Compound No. | Structure | Physicochemical data |
|---|---|---|
| F170 | 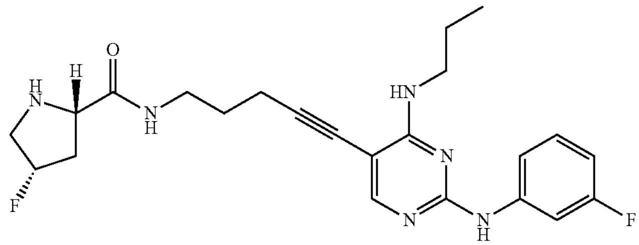 [SMILES: CCCNc1nc(Nc2cccc(F)c2)ncc1C#CCCCNC(=O)[C@@H]1C[C@H](F)CN1] | — |
| F171 | 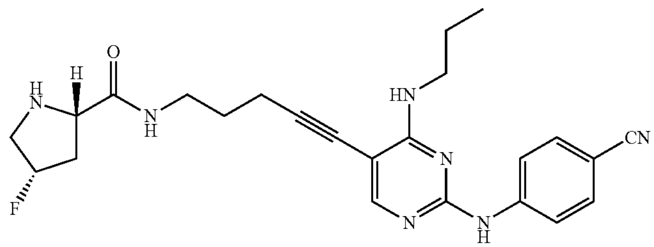 [SMILES: CCCNc1nc(Nc2ccc(C#N)cc2)ncc1C#CCCCNC(=O)[C@@H]1C[C@H](F)CN1] | — |
| F172 | 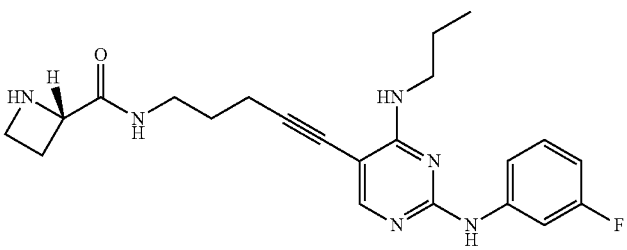 [SMILES: CCCNc1nc(Nc2cccc(F)c2)ncc1C#CCCCNC(=O)[C@@H]1CCN1] | — |
| F173 | 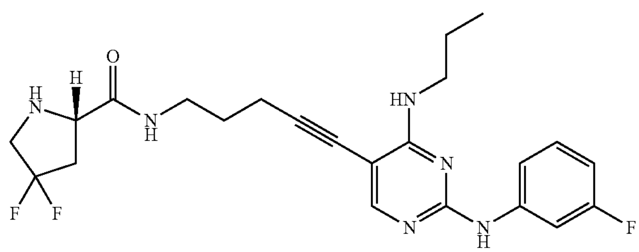 [SMILES: CCCNc1nc(Nc2cccc(F)c2)ncc1C#CCCCNC(=O)[C@@H]1CC(F)(F)CN1] | — |
| F174 | 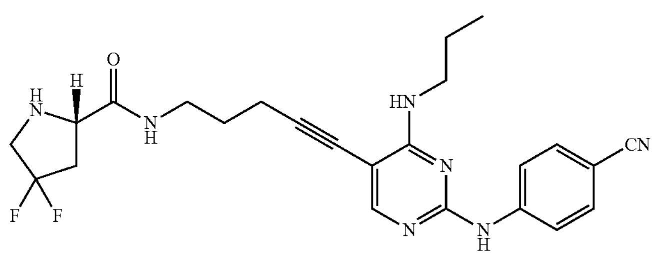 [SMILES: CCCNc1nc(Nc2ccc(C#N)cc2)ncc1C#CCCCNC(=O)[C@@H]1CC(F)(F)CN1] | — |
| F175 | 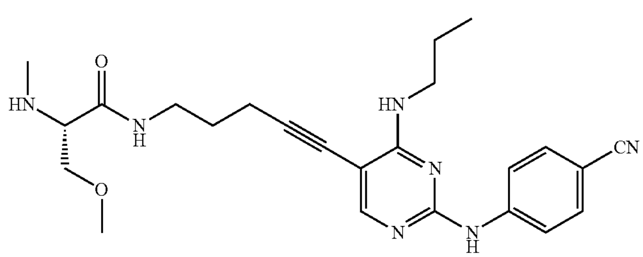 [SMILES: CCCNc1nc(Nc2ccc(C#N)cc2)ncc1C#CCCCNC(=O)[C@H](COC)NC] | — |

TABLE 89-continued

| Compound No. | Structure | Physicochemical data |
|---|---|---|
| F288 | 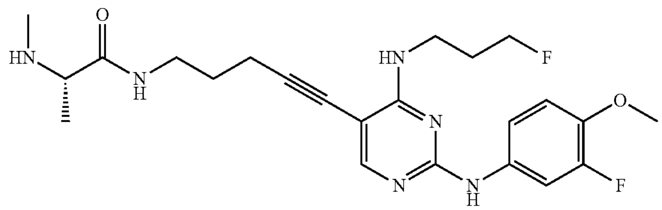 [SMILES: CN[C@@H](C)C(=O)NCCCC#Cc1cnc(Nc2ccc(OC)c(F)c2)nc1NCCCF] | MS m/z (M + H): 461.3 |
| F289 | 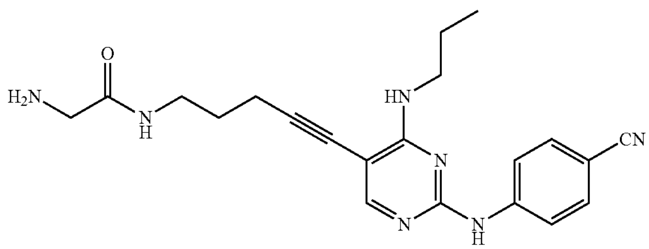 [SMILES: CCCNc1nc(Nc2ccc(C#N)cc2)ncc1C#CCCCNC(=O)CN] | — |

TABLE 90

| Compound No. | Structure | Physicochemical data |
|---|---|---|
| F290 | 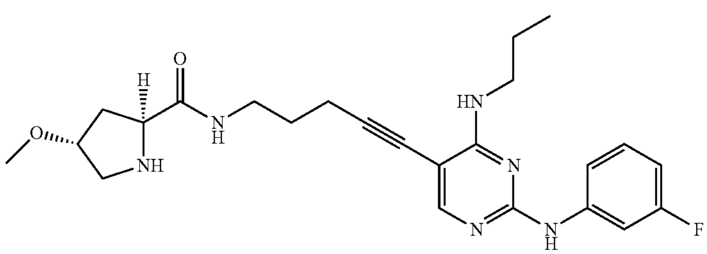 [SMILES: CCCNc1nc(Nc2cccc(F)c2)ncc1C#CCCCNC(=O)[C@@H]1C[C@@H](OC)CN1] | MS m/z (M + H): 455.3 |
| F291 | 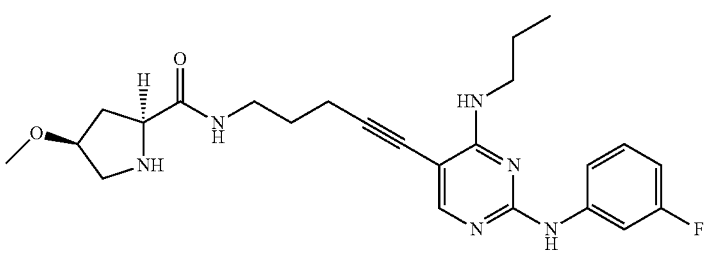 [SMILES: CCCNc1nc(Nc2cccc(F)c2)ncc1C#CCCCNC(=O)[C@@H]1C[C@H](OC)CN1] | MS m/z (M + H): 455.3 |
| F292 | 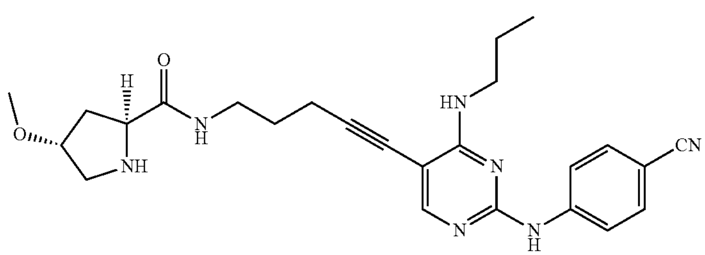 [SMILES: CCCNc1nc(Nc2ccc(C#N)cc2)ncc1C#CCCCNC(=O)[C@@H]1C[C@@H](OC)CN1] | MS m/z (M + H): 462.3 |

TABLE 90-continued

| Compound No. | Structure | Physicochemical data |
|---|---|---|
| F293 | 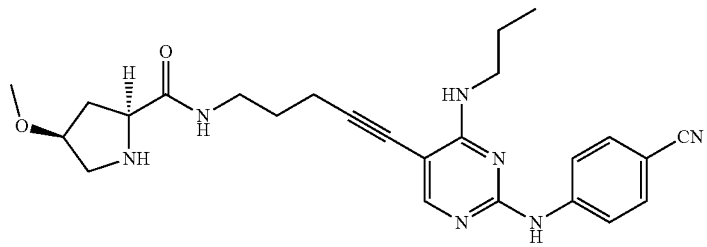 [SMILES: CCCNc1nc(Nc2ccc(C#N)cc2)ncc1C#CCCCNC(=O)[C@@H]1C[C@H](OC)CN1] | MS m/z (M + H): 462.3 |
| F294 | 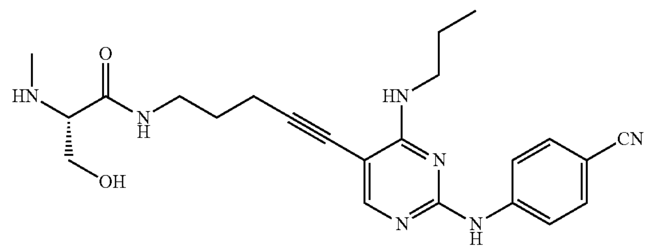 [SMILES: CCCNc1nc(Nc2ccc(C#N)cc2)ncc1C#CCCCNC(=O)[C@H](CO)NC] | — |
| F295 | 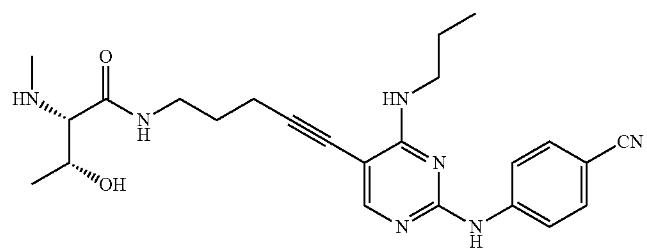 [SMILES: CCCNc1nc(Nc2ccc(C#N)cc2)ncc1C#CCCCNC(=O)[C@@H](NC)[C@@H](C)O] | — |
| F296 | 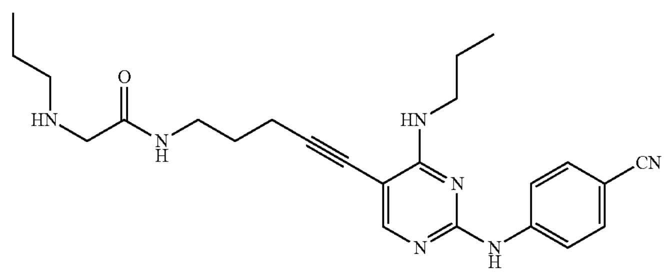 [SMILES: CCCNCC(=O)NCCCC#Cc1cnc(Nc2ccc(C#N)cc2)nc1NCCC] | — |
| F297 | 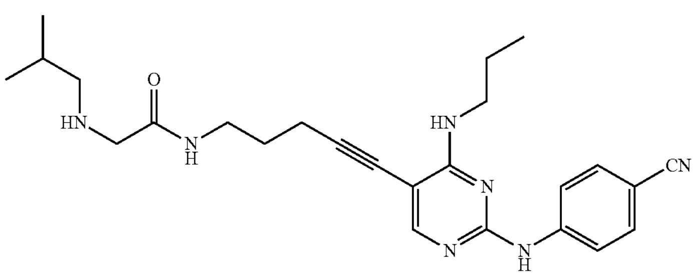 [SMILES: CCCNc1nc(Nc2ccc(C#N)cc2)ncc1C#CCCCNC(=O)CNCC(C)C] | — |
| F298 | 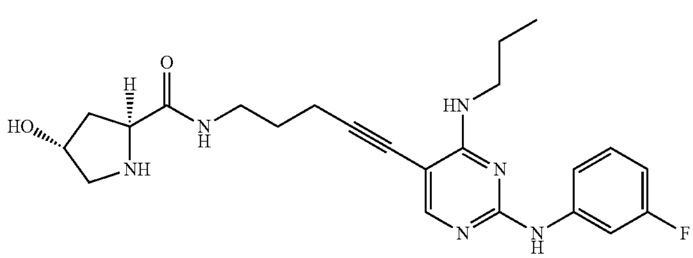 [SMILES: CCCNc1nc(Nc2cccc(F)c2)ncc1C#CCCCNC(=O)[C@@H]1C[C@@H](O)CN1] | MS m/z (M + H): 441.3 |

TABLE 91

| Compound No. | Structure | Physicochemical data |
|---|---|---|
| F299 | 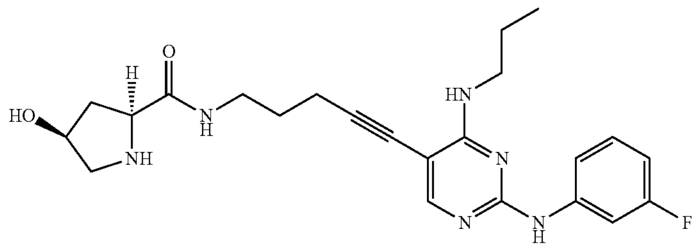 [SMILES: CCCNc1nc(Nc2cccc(F)c2)ncc1C#CCCCNC(=O)[C@@H]1C[C@H](O)CN1] | MS m/z (M + H): 441.3 |
| F300 | 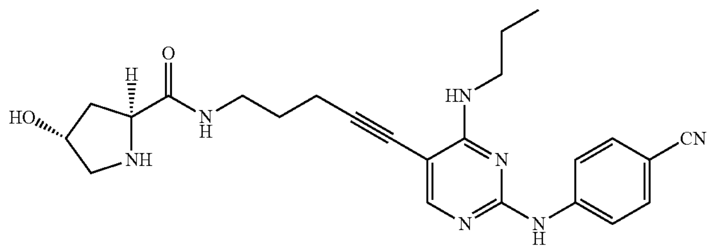 [SMILES: CCCNc1nc(Nc2ccc(C#N)cc2)ncc1C#CCCCNC(=O)[C@@H]1C[C@@H](O)CN1] | MS m/z (M + H): 448.3 |
| F301 | 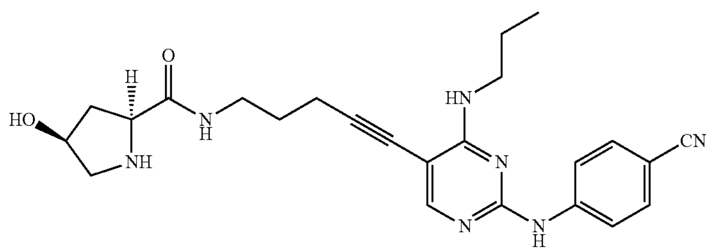 [SMILES: CCCNc1nc(Nc2ccc(C#N)cc2)ncc1C#CCCCNC(=O)[C@@H]1C[C@H](O)CN1] | MS m/z (M + H): 448.3 |
| F302 | 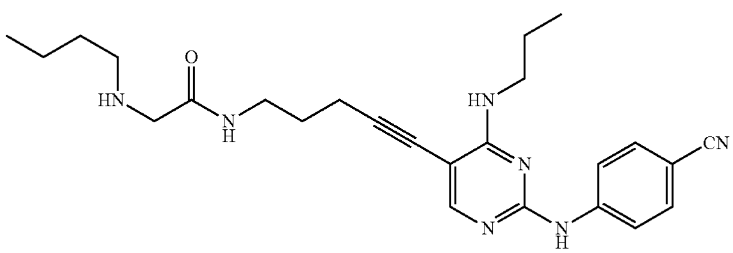 [SMILES: CCCCNCC(=O)NCCCC#Cc1cnc(Nc2ccc(C#N)cc2)nc1NCCC] | — |
| F303 | 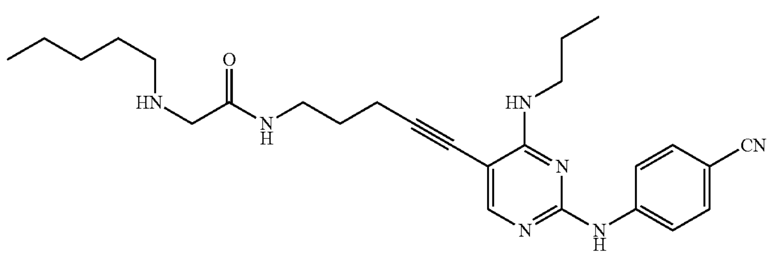 [SMILES: CCCCCNCC(=O)NCCCC#Cc1cnc(Nc2ccc(C#N)cc2)nc1NCCC] | — |
| F304 | 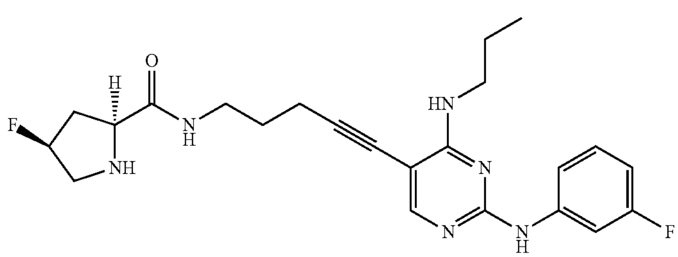 | MS m/z (M + H): 415.3 |

TABLE 91-continued

| Compound No. | Structure | Physicochemical data |
|---|---|---|
| F305 | 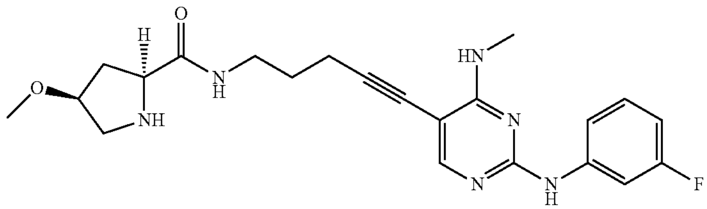 [SMILES: CNc1nc(Nc2cccc(F)c2)ncc1C#CCCCNC(=O)[C@@H]1C[C@H](OC)CN1] | — |
| F306 | 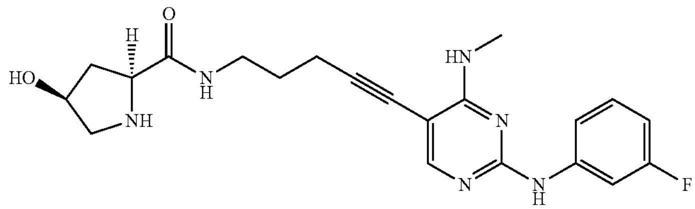 [SMILES: CNc1nc(Nc2cccc(F)c2)ncc1C#CCCCNC(=O)[C@@H]1C[C@H](O)CN1] | — |
| F307 | 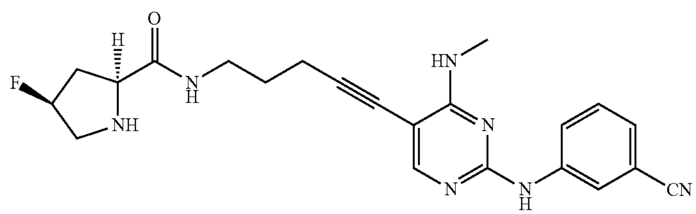 [SMILES: CNc1nc(Nc2cccc(C#N)c2)ncc1C#CCCCNC(=O)[C@@H]1C[C@H](F)CN1] | MS m/z (M + H): 422.3 |
| F308 | 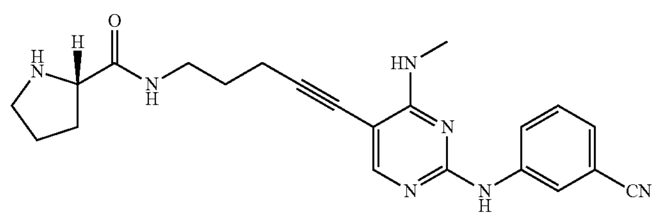 [SMILES: CNc1nc(Nc2cccc(C#N)c2)ncc1C#CCCCNC(=O)[C@@H]1CCCN1] | — |

TABLE 92

| Compound No. | Structure | Physicochemical data |
|---|---|---|
| F309 | 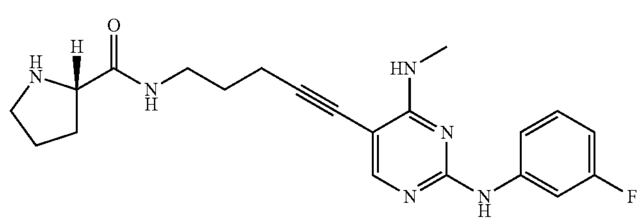 [SMILES: CNc1nc(Nc2cccc(F)c2)ncc1C#CCCCNC(=O)[C@@H]1CCCN1] | — |
| F310 | 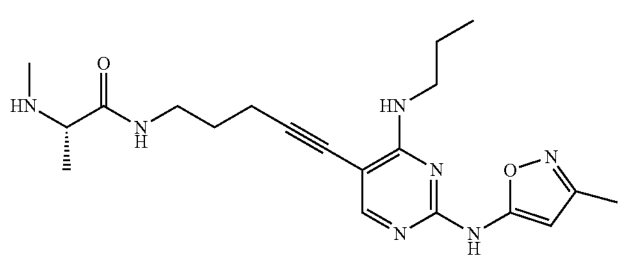 [SMILES: CCCNc1nc(Nc2cc(C)no2)ncc1C#CCCCNC(=O)[C@H](C)NC] | MS m/z (M + H): 400.4 |

TABLE 92-continued
| Compound No. | Structure | Physicochemical data |
|---|---|---|
| F311 | 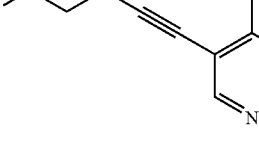 | MS m/z (M + H): 412.3 |
| F312 | 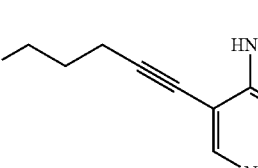 | MS m/z (M + H): 415.3 |
| F313 | 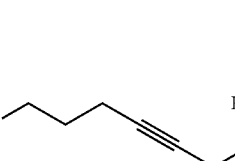 | MS m/z (M + H): 415.3 |
| F314 | 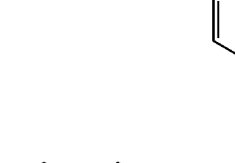 | MS m/z (M + H): 427.4 |
| F315 | 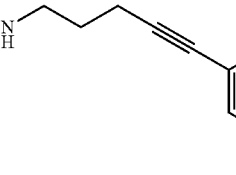 | MS m/z (M + H): 427.4 |
| F316 | 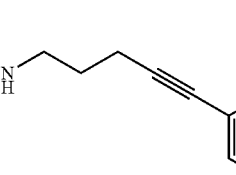 | MS m/z (M + H): 413.3 |
| F317 | 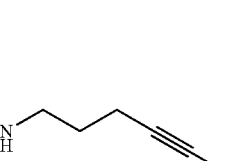 | Ms m/z (M + H): 413.3 |

TABLE 92-continued

| Compound No. | Structure | Physicochemical data |
|---|---|---|
| F318 | 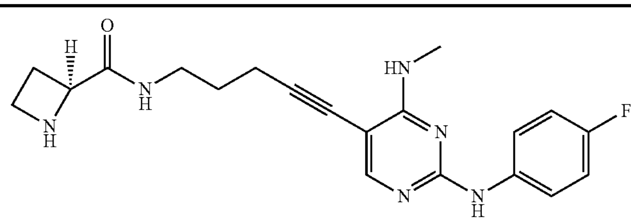 | MS m/z (M + H): 383.3 |

TABLE 93

| Compound No. | Structure | Physicochemical data |
|---|---|---|
| F319 | 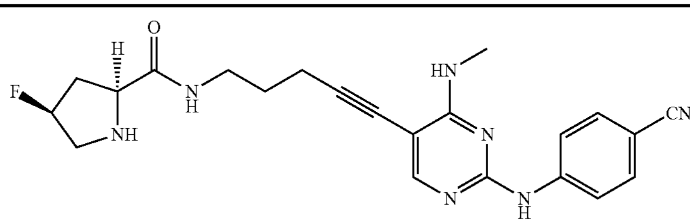 | MS m/z (M + H): 422.2 |
| F320 | 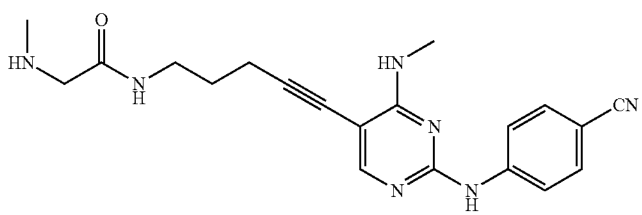 [SMILES: CNCC(=O)NCCCC#Cc1cnc(Nc2ccc(C#N)cc2)nc1NC] | MS m/z (M + H): 378.3 |
| F321 | 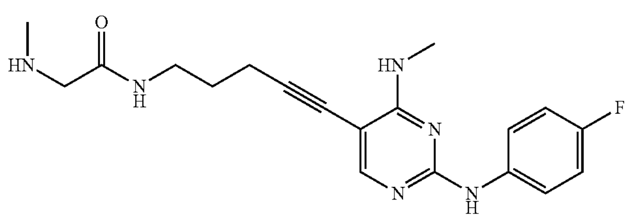 [SMILES: CNCC(=O)NCCCC#Cc1cnc(Nc2ccc(F)cc2)nc1NC] | MS m/z (M + H): 371.3 |
| F322 | 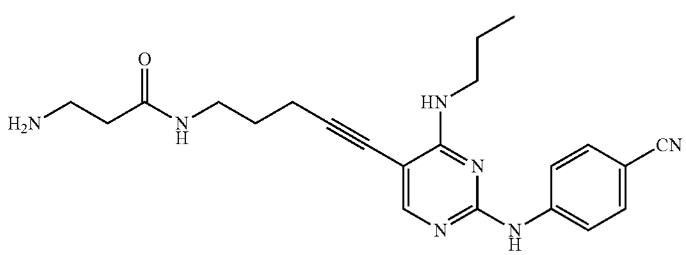 [SMILES: CCCNc1nc(Nc2ccc(C#N)cc2)ncc1C#CCCCNC(=O)CCN] | — |
| F323 | 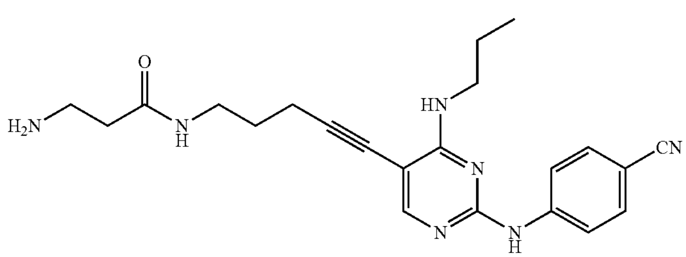 [SMILES: CCCNc1nc(Nc2ccc(C#N)cc2)ncc1C#CCCCNC(=O)CCN] | — |

TABLE 93-continued

| Compound No. | Structure | Physicochemical data |
|---|---|---|
| F324 | 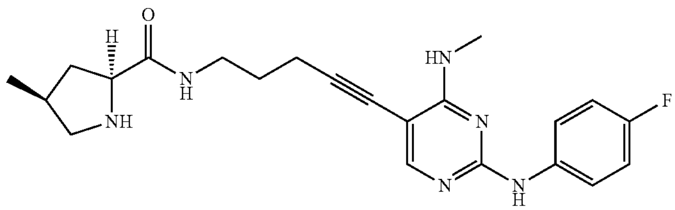 [SMILES: CNc1nc(Nc2ccc(F)cc2)ncc1C#CCCCNC(=O)[C@@H]1C[C@H](C)CN1] | MS m/z (M + H): 411.3 |
| F325 | 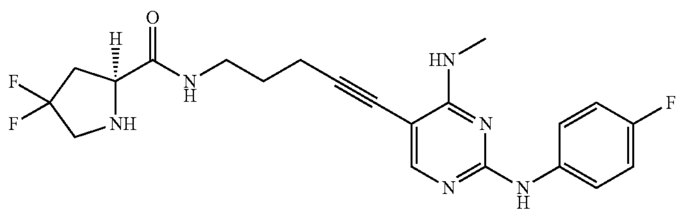 [SMILES: CNc1nc(Nc2ccc(F)cc2)ncc1C#CCCCNC(=O)[C@@H]1CC(F)(F)CN1] | MS m/z (M + H): 433.3 |
| F326 | 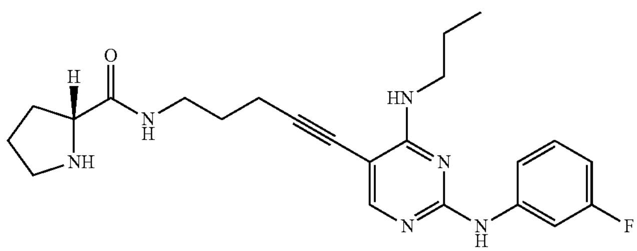 [SMILES: CCCNc1nc(Nc2cccc(F)c2)ncc1C#CCCCNC(=O)[C@H]1CCCN1] | MS m/z (M + H): 425.3 |
| F331 | 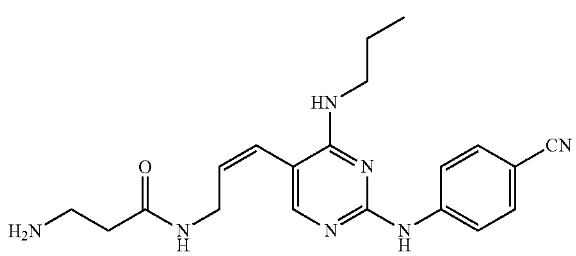 [SMILES: CCCNc1nc(Nc2ccc(C#N)cc2)ncc1/C=C\CNC(=O)CCN] | — |
| F332 | 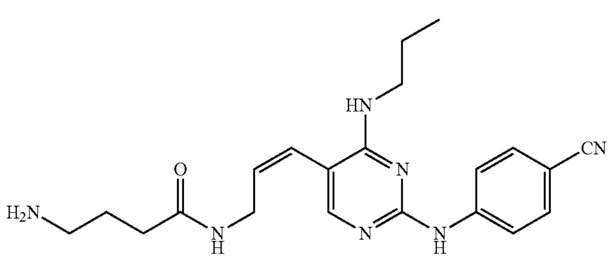 [SMILES: CCCNc1nc(Nc2ccc(C#N)cc2)ncc1/C=C\CNC(=O)CCCN] | — |

Example 37

In the same manner as that of Example 35, Compounds (7-2) to (7-96) were obtained.

TABLE 94

| Compound No. | Structure | Physicochemical data |
|---|---|---|
| 7-2 | 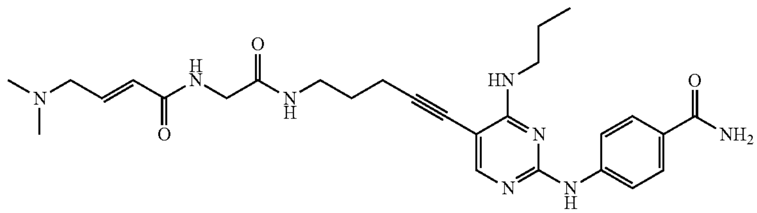 [SMILES: CCCNc1nc(Nc2ccc(C(N)=O)cc2)ncc1C#CCCCNC(=O)CNC(=O)/C=C/CN(C)C] | ¹H-NMR (CD₃OD) δ: 7.88 (1H, s), 7.81 (4H, s), 6.81-6.76 (1H, m), 6.15 (1H, d, J = 15.9 Hz), 3.91 (2H, s), 3.55-3.46 (2H, m), 3.41 (2H, t, J = 6.6 Hz), 3.13 (2H, dd, J = 6.6, 1.3 Hz), 2.52 (2H, t, J = 6.6 Hz), 2.26 (6H, s), 1.77-1.69 (4H, m), 0.99 (3H, t, J = 7.3 Hz) |
| 7-3 | 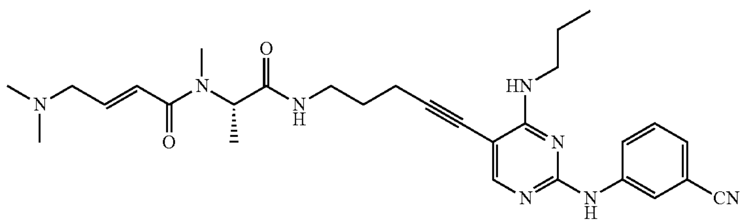 [SMILES: CCCNc1nc(Nc2cccc(C#N)c2)ncc1C#CCCCNC(=O)[C@H](C)N(C)C(=O)/C=C/CN(C)C] | ¹H-NMR (CDCl₃) δ: 8.41-8.32 (1H, m), 8.09 (1H, s), 7.96 (1H, s), 7.62 (1H, d, J = 9.2 Hz), 7.37-7.34 (1H, m), 7.24 (1H, d, J = 7.3 Hz), 6.94 (1H, dt, J = 15.2, 5.9 Hz), 6.81 (1H, t, J = 5.9 Hz), 6.52-6.24 (2H, m), 5.21 (1H, q, J = 7.0 Hz), 3.54-3.41 (4H, m), 3.11 (2H, d, J = 5.3 Hz), 3.02 (3H, s), 2.45 (2H, t, J = 6.6 Hz), 2.27 (6H, s), 1.80-1.73 (4H, m), 1.37 (3H, d, J = 7.0 Hz), 1.02 (3H, t, J = 7.6 Hz) |
| 7-4 | 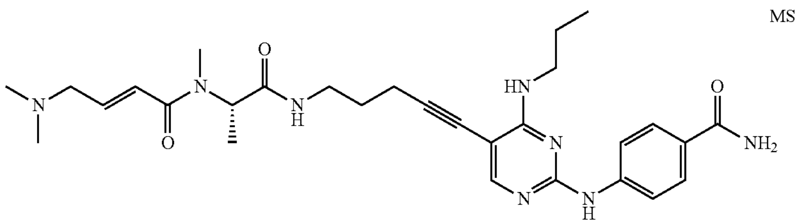 | MS m/z (M + H): 549.3 |
| 7-5 | 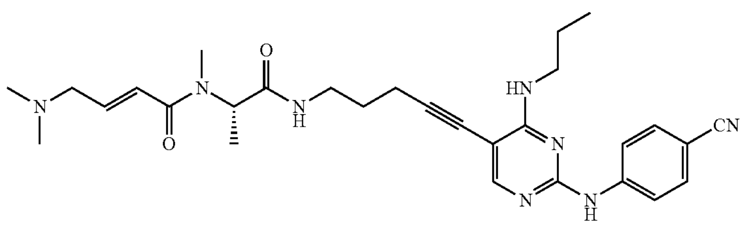 [SMILES: CCCNc1nc(Nc2ccc(C#N)cc2)ncc1C#CCCCNC(=O)[C@H](C)N(C)C(=O)/C=C/CN(C)C] | ¹H-NMR (CDCl₃) δ: 8.05 (1H, s), 7.97 (1H, s), 7.79 (2H, d, J = 8.6 Hz), 7.56 (2H, d, J = 9.2 Hz), 6.94 (1H, dt, J = 15.2, 5.3 Hz), 6.71 (1H, t, J = 5.6 Hz), 6.44-6.42 (2H, m), 5.20 (1H, q, J = 7.3 Hz), 3.49-3.45 (4H, m), 3.11 (2H, d, J = 5.3 Hz), 3.01 (3H, s), 2.45 (2H, t, J = 6.6 Hz), 2.27 (6H, s), 1.77-1.66 (4H, m), 1.36 (3H, d, J = 7.3 Hz), 1.00 (3H, t, J = 7.3 Hz) |
| 7-6 | 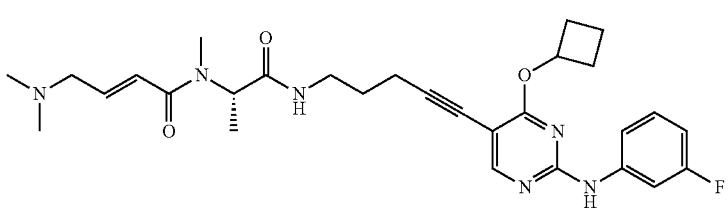 [SMILES: C[C@@H](C(=O)NCCCC#Cc1cnc(Nc2cccc(F)c2)nc1OC1CCC1)N(C)C(=O)/C=C/CN(C)C] | ¹H-NMR (CDCl₃) δ: 8.21 (1H, s), 7.71 (1H, dt, J = 11.7, 2.3 Hz), 7.29-7.21 (1H, m), 7.14-7.06 (2H, m), 6.93 (1H, dt, J = 15.2, 5.9 Hz), 6.73 (1H, dt, J = 8.3, 2.3 Hz), 6.57-6.47 (1H, m), 6.47-6.35 (1H, m), 5.29-5.15 (2H, m), 3.40 (2H, q, J = 6.6 Hz), 3.14-3.04 (2H, m), 2.99 (3H, s), 2.56-2.44 (4H, m), 2.32-2.18 (8H, m), 1.94-1.67 (4H, m), 1.35 (3H, d, J = 6.6 Hz) |

TABLE 95

| Compound No. | Structure | Physicochemical data |
|---|---|---|
| 7-7 | 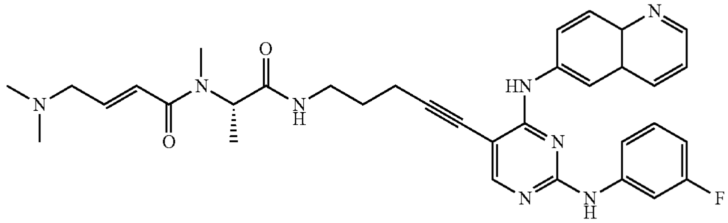 [SMILES: C[C@@H](C(=O)NCCCC#Cc1cnc(Nc2cccc(F)c2)nc1NC1=CC2C=CC=NC2C=C1)N(C)C(=O)/C=C/CN(C)C] | ¹H-NMR (CDCl₃) δ: 8.84 (1H, dd, J = 4.3, 1.7 Hz), 8.38-8.31 (2H, m), 8.20 (1H, s), 8.10-8.02 (2H, m), 7.97 (1H, dd, J = 9.2, 2.0 Hz), 7.63-7.54 (1H, m), 7.38 (1H, dd, J = 8.3, 4.3 Hz), 7.31 (1H, s), 7.21-7.14 (2H, m), 6.93 (1H, dt, J = 15.2, 5.9 Hz), 6.75-6.59 (2H, m), 6.41 (1H, d, J = 15.2 Hz), 5.20 (1H, q, J = 7.0 Hz), 3.59-3.46 (2H, m), 3.10 (2H, d, J = 5.9 Hz), 2.97 (3H, s), 2.52 (2H, t, J = 5.6 Hz), 2.26 (6H, s), 1.86-1.74 (2H, m), 1.36 (3H, d, J = 7.0 Hz) |

TABLE 95-continued

| Compound No. | Structure | Physicochemical data |
|---|---|---|
| 7-8 | 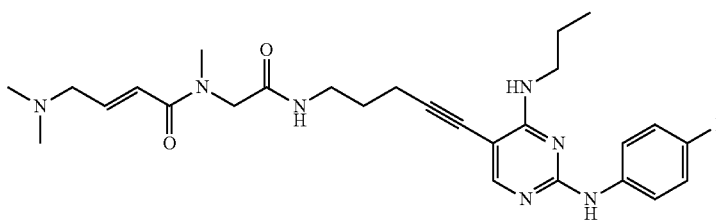 | ¹H-NMR (CDCl₃) δ: 7.95 (1H, s), 7.60-7.52 (2H, m), 7.04-6.90 (3H, m), 6.88 (1H, s), 6.57 (1H, brs), 6.46 (1H, d, J = 15.2 Hz), 6.03 (1H, brs), 4.03 (2H, s), 3.50-3.40 (4H, m), 3.20 (3H, s), 3.10 (2H, d, J = 5.9 Hz), 2.47 (2H, t, J = 6.6 Hz), 2.27 (6H, s), 1.82-1.64 (4H, m), 0.98 (3H, t, J = 7.3 Hz) |
| 7-9 | 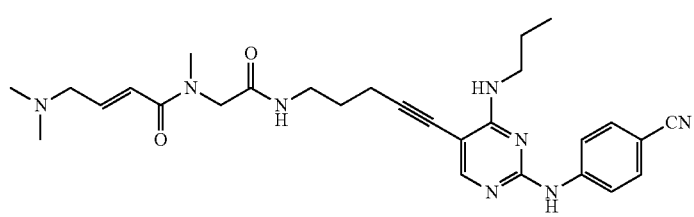 [SMILES: CCCNc1nc(Nc2ccc(C#N)cc2)ncc1C#CCCCNC(=O)CN(C)C(=O)/C=C/CN(C)C] | ¹H-NMR (CDCl₃) δ: 7.98 (1H, s), 7.76 (2H, d, J = 9.2 Hz), 7.57 (2H, d, J = 8.6 Hz), 7.20 (1H, s), 6.96 (1H, dt, J = 15.2, 5.9 Hz), 6.59 (1H, brs), 6.47 (1H, d, J = 15.2 Hz), 6.27 (1H, brs), 4.04 (2H, s), 3.54-3.40 (4H, m), 3.20 (3H, s), 3.10 (2H, d, J = 5.9 Hz), 2.48 (2H, t, J = 6.9 Hz), 2.27 (6H, s), 1.82-1.66 (4H, m), 1.00 (3H, t, J = 7.3 Hz) |
| 7-10 | 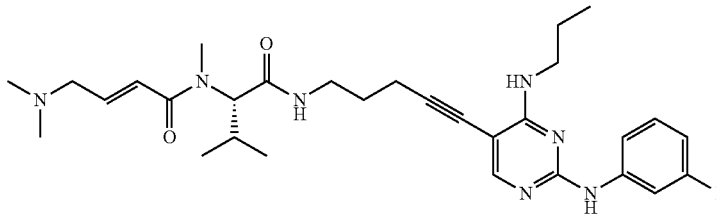 | ¹H-NMR (CDCl₃) δ: 7.95 (1H, s), 7.83 (1H, d, J = 11.9 Hz), 7.22-6.88 (4H, m), 6.68 (1H, t, J = 8.3 Hz), 6.46-6.41 (3H, m), 4.52 (1H, d, J = 11.2 Hz), 3.54-3.41 (4H, m), 3.10 (2H, d, J = 5.9 Hz), 3.05 (3H, s), 2.43 (2H, t, J = 6.6 Hz), 2.37-2.27 (7H, m), 1.76-1.66 (4H, m), 1.00 (6H, t, J = 7.3 Hz), 0.86 (3H, d, J = 6.6 Hz) |
| 7-11 | 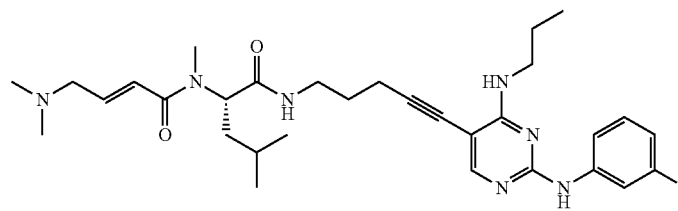 | ¹H-NMR (CDCl₃) δ: 7.96 (1H, s), 7.83 (1H, dt, J = 12.1, 2.3 Hz), 7.25-7.07 (3H, m), 6.94 (1H, dt, J = 15.2, 5.9 Hz), 6.67 (1H, dt, J = 8.3, 2.3 Hz), 6.51 (1H, brs), 6.42 (1H, d, J = 15.2 Hz), 6.33 (1H, t, J = 5.9 Hz), 5.11 (1H, t, J = 7.6 Hz), 3.54-3.42 (4H, m), 3.10 (2H, d, J = 5.9 Hz), 2.99 (3H, s), 2.45 (2H, d, J = 7.6 Hz), 2.27 (6H, s), 1.79-1.59 (6H, m), 1.56-1.43 (1H, m), 1.03-0.90 (9H, m) |

TABLE 96

| Compound No. | Structure | Physicochemical data |
|---|---|---|
| 7-12 | 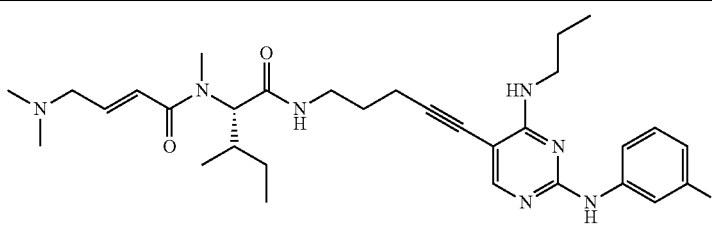 | ¹H-NMR (CDCl₃) δ: 7.95 (1H, s), 7.83 (1H, dt, J = 12.1, 2.1 Hz), 7.38 (1H, s), 7.20 (1H, q, J = 7.7 Hz), 7.11 (1H, d, J = 8.3 Hz), 6.92 (1H, dt, J = 15.2, 5.9 Hz), 6.67 (1H, dt, J = 8.3, 1.8 Hz), 6.53 (1H, t, J = 5.9 Hz), 6.46-6.37 (2H, m), 4.63 (1H, d, J = 11.2 Hz), 3.53-3.40 (4H, m), 3.10 (2H, dd, J = 5.9, 2.1 Hz), 3.05 (3H, s), 2.43 (2H, t, J = 6.6 Hz), 2.27 (6H, s), 2.21-2.05 (2H, m), 1.78-1.66 (4H, m), 1.43-1.31 (1H, m), 1.02-0.85 (9H, m) |
| 7-13 | 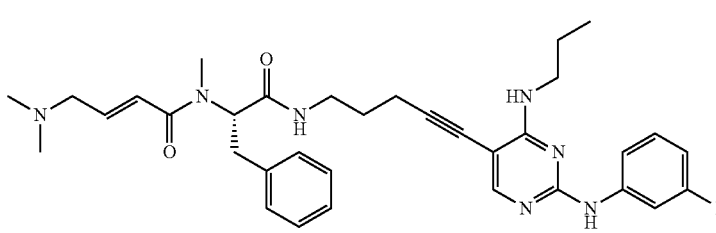 | ¹H-NMR (CDCl₃) δ: 7.93 (1H, s), 7.83 (1H, dt, J = 12.1, 2.1 Hz), 7.32-7.09 (8H, m), 6.87 (1H, dt, J = 15.2, 5.9 Hz), 6.67 (1H, dt, J = 8.1, 2.1 Hz), 6.53 (1H, t, J = 5.9 Hz), 6.35-6.30 (2H, m), 5.33 (1H, t, J = 7.6 Hz), 3.57-3.31 (5H, m), 3.08-2.94 (6H, m), 2.32 (2H, t, J = 5.0 Hz), 2.25 (6H, s), 1.81-1.63 (4H, m), 1.02 (3H, t, J = 7.6 Hz) |

TABLE 96-continued

| Compound No. | Structure | Physicochemical data |
|---|---|---|
| 7-14 | 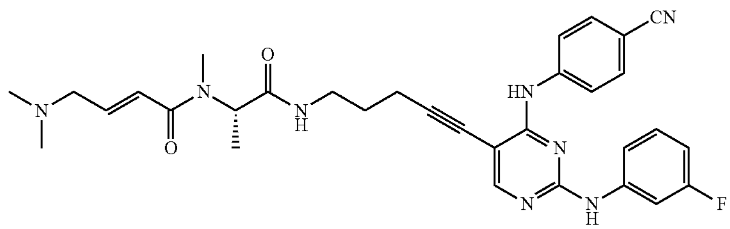 [SMILES: C[C@@H](C(=O)NCCCC#Cc1cnc(Nc2cccc(F)c2)nc1Nc1ccc(C#N)cc1)N(C)C(=O)/C=C/CN(C)C] | ¹H-NMR (CDCl₃) δ: 8.44 (1H, s), 8.21 (1H, s), 8.00-7.91 (3H, m), 7.60 (2H, d, J = 8.6 Hz), 7.30-7.17 (2H, m), 7.12-7.06 (1H, m), 6.94 (1H, dt, J = 15.2, 5.9 Hz), 6.75 (1H, dt, J = 8.3, 2.4 Hz), 6.67-6.58 (1H, m), 6.43 (1H, d, J = 15.2 Hz), 5.19 (1H, q, J = 7.0 Hz), 3.58-3.45 (2H, m), 3.11 (2H, d, J = 4.6 Hz), 2.98 (3H, s), 2.56-2.46 (2H, m), 2.27 (6H, s), 1.84-1.70 (2H, m), 1.36 (3H, d, J = 7.0 Hz) |
| 7-15 | 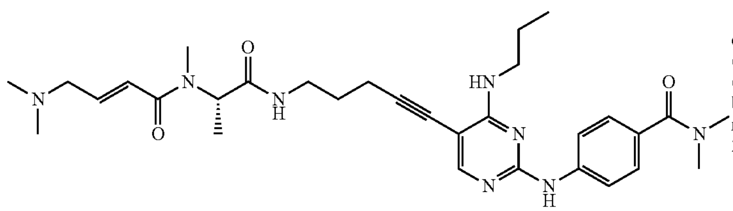 | ¹H-NMR (CDCl₃) δ: 7.97 (1H, s), 7.67 (2H, d, J = 8.6 Hz), 7.40 (2H, d, J = 8.6 Hz), 7.03 (1H, s), 6.94 (1H, dt, J = 15.2, 5.9 Hz), 6.52 (1H, brs), 6.42 (1H, d, J = 15.2 Hz), 6.25 (1H, brs), 5.18 (1H, q, J = 7.3 Hz), 3.54-3.40 (4H, m), 3.10 (2H, d, J = 6.6 Hz), 3.07 (6H, brs), 2.99 (3H, s), 2.49-2.39 (2H, m), 2.27 (6H,S), 1.77-1.68 (4H, m), 1.36 (3H, d, J = 7.3 Hz), 1.00 (3H, t, J = 7.6 Hz) |
| 7-16 | 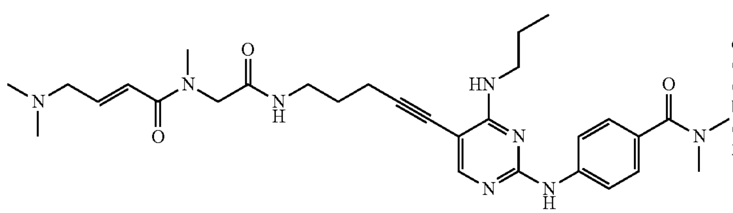 | ¹H-NMR (CDCl₃) δ: 7.97 (1H, s), 7.68 (2H, d, J = 8.6 Hz), 7.40 (2H, d, J = 8.6 Hz), 7.34 (1H, s), 6.95 (1H, dt, J = 15.2, 5.9 Hz), 6.69 (1H, brs), 6.46 (1H, d, J = 15.2 Hz), 6.13 (1H, brs), 4.04 (2H, s), 3.52-3.40 (4H, m), 3.20 (3H, s), 3.10 (2H, d, J = 6.6 Hz), 3.07 (6H, s), 2.47 (2H, t, J = 6.6 Hz), 2.26 (6H, s), 1.82-1.66 (4H, m), 0.99 (3H, t, J = 7.6 Hz) |

TABLE 97

| Compound No. | Structure | Physicochemical data |
|---|---|---|
| 7-17 | 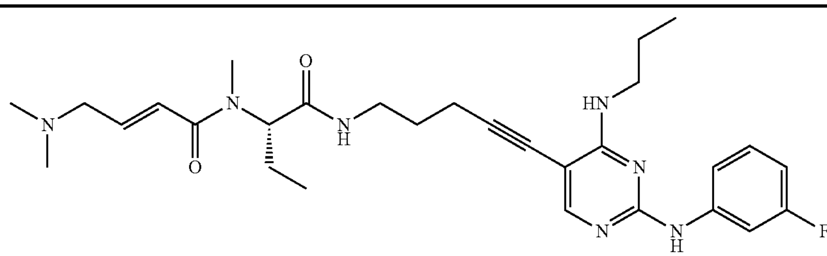 | ¹H-NMR (CDCl₃) δ: 7.95 (1H, s), 7.83 (1H, dt, J = 12.1, 2.3Hz), 7.26-7.17 (3H, m), 6.94 (1H, dt, J = 15.2, 5.9Hz), 6.67 (1H, dt, J = 8.1, 2.3Hz), 6.56 (1H, t, J = 5.9Hz), 6.44 (1H, d, J = 15.2Hz), 6.32 (1H, t, J = 5.6Hz), 4.91 (1H, t, J = 7.6Hz), 3.54-3.41 (4H, m), 3.11 (2H, dd, J = 5.9, 1.3Hz), 3.00 (3H, s), 2.43 (2H, t, J = 6.6Hz), 2.27 (6H, s), 2.04-1.65 (6H, m), 1.00 (3H, t, J = 7.3Hz), 0.90 (3H, t, J = 7.3Hz) |

TABLE 97-continued

| Compound No. | Structure | Physicochemical data |
|---|---|---|
| 7-18 | 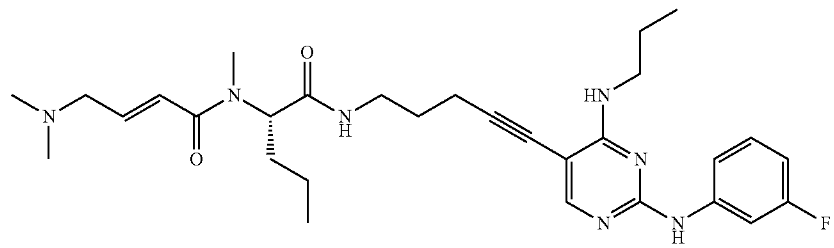 [SMILES: CCCNc1nc(Nc2cccc(F)c2)ncc1C#CCCCNC(=O)[C@H](CCC)N(C)C(=O)/C=C/CN(C)C] | ¹H-NMR (CDCl₃) δ: 7.96 (1H, s), 7.83 (1H, dt, J = 12.1, 2.2Hz), 7.36 (1H, s), 7.21 (1H, q, J = 7.7Hz), 7.10 (1H, d, J = 9.2Hz), 6.93 (1H, dt, J = 15.2, 5.9Hz), 6.67 (1H, dt, J = 8.1, 2.2Hz), 6.58 (1H, t, J = 5.9Hz), 6.43 (1H, d, J = 15.2Hz), 6.33 (1H, t, J = 5.6Hz), 5.01 (1H, t, J = 7.6Hz), 3.54-3.40 (4H, m), 3.10 (2H, d, J = 5.3Hz), 3.00 (3H, s), 2.43 (2H, t, J = 6.6Hz), 2.27 (6H, s), 1.96-1.60 (6H, m), 1.35-1.21 (2H, m), 1.00 (3H, t, J = 7.6Hz), 0.94 (3H, t, J = 7.6Hz) |
| 7-19 | 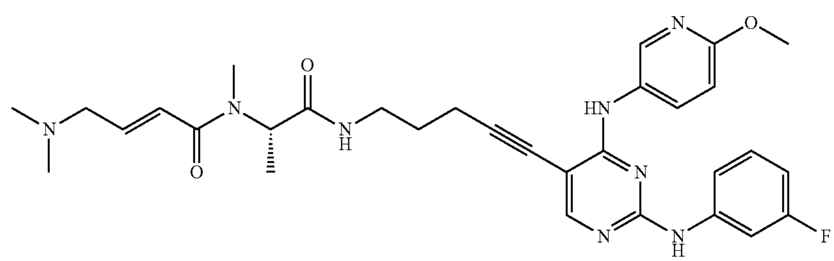 [SMILES: COc1ccc(Nc2nc(Nc3cccc(F)c3)ncc2C#CCCCNC(=O)[C@H](C)N(C)C(=O)/C=C/CN(C)C)cn1] | ¹H-NMR (CDCl₃) δ: 8.39 (1H, d, J = 2.6Hz), 8.22 (1H, s), 8.12 (1H, s), 7.91 (1H, dd, J = 9.2, 2.6Hz), 7.56 (1H, dt, J = 11.7, 2.3Hz), 7.16 (1H, q, J = 7.5Hz), 7.06 (1H, s), 7.01 (1H, dd, J = 8.6, 2.3Hz), 6.93 (1H, dt, J = 15.2, 5.9Hz), 6.78 (1H, d, J = 9.2Hz), 6.66 (1H, dt, J = 8.3, 2.3Hz), 6.64-6.55 (1H, m), 6.46-6.35 (1H, m), 5.16 (1H, q, J = 7.0Hz), 3.96 (3H, s), 3.51 (2H, q, J = 6.2Hz), 3.09 (2H, dd, J = 5.9, 1.3Hz), 2.95 (3H, s), 2.52-2.42 (2H, m), 2.26 (6H, s), 1.80-1.69 (2H, m), 1.32 (3H, d, J = 7.0Hz) |
| 7-20 | 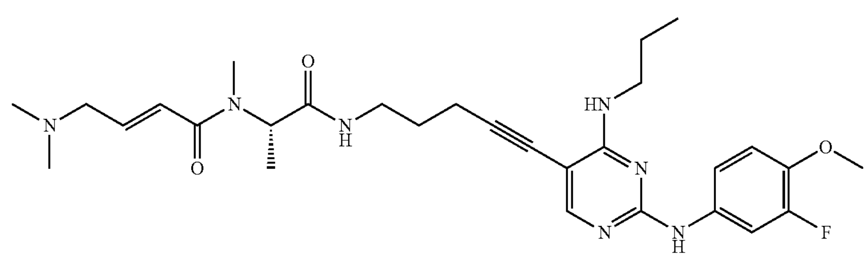 | ¹H-NMR (CDCl₃) δ: 7.93 (1H, s), 7.77 (1H, dd, J = 13.9, 2.6Hz), 7.08-7.00 (1H, m), 6.98-6.86 (3H, m), 6.59-6.49 (1H, m), 6.42 (1H, d, J = 15.2Hz), 6.26-6.16 (1H, m), 5.18 (1H, q, J = 7.0Hz), 3.87 (3H, s), 3.51-3.40 (4H, m), 3.10 (2H, d, J = 5.9Hz), 2.99 (3H, s), 2.43 (2H, t, J = 6.6Hz), 2.27 (6H, s), 1.80-1.62 (4H, m), 1.35 (3H, d, J = 7.0Hz), 0.99 (3H, t, J = 7.3Hz) |

TABLE 98

| Compound No. | Structure | Physicochemical data |
|---|---|---|
| 7-21 | 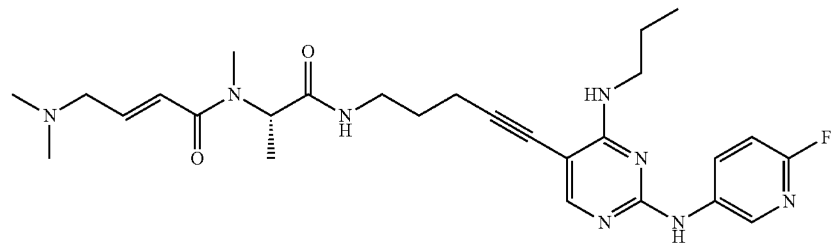 [SMILES: CCCNc1nc(Nc2ccc(F)nc2)ncc1C#CCCCNC(=O)[C@H](C)N(C)C(=O)/C=C/CN(C)C] | ¹H-NMR (CDCl₃) δ: 8.40 (1H, s), 8.25-8.19 (2H, m), 7.95 (1H, s), 7.00-6.85 (2H, m), 6.72 (1H, d, J = 5.9Hz), 6.43 (1H, d, J = 15.2Hz), 6.32 (1H, t, J = 5.6Hz), 5.20 (1H, q, J = 7.0Hz), 3.49-3.40 (4H, m), 3.10 (2H, dd, J = 5.9, 1.3Hz), 3.01 (3H, s), 2.46-2.39 (2H, m), 2.27 (6H, s), 1.77-1.65 (4H, m), 1.36 (3H, d, J = 7.3Hz), 0.98 (3H, t, J = 7.5Hz) |
| 7-22 | 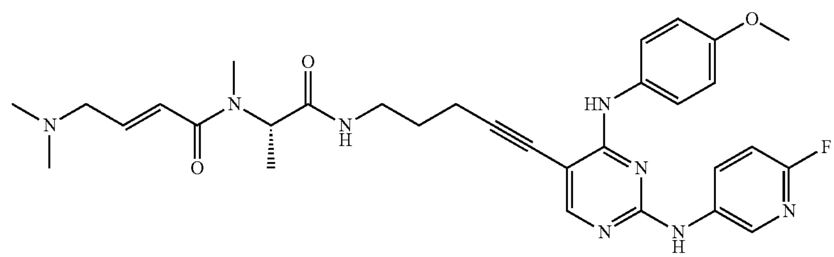 [SMILES: COc1ccc(Nc2nc(Nc3ccc(F)nc3)ncc2C#CCCCNC(=O)[C@H](C)N(C)C(=O)/C=C/CN(C)C)cc1] | ¹H-NMR (CDCl₃) δ: 8.39-8.17 (2H, m), 8.17-8.05 (2H, m), 8.09 (2H, s), 7.53-7.41 (2H, m), 6.96-6.73 (4H, m), 6.41 (1H, d, J = 15.2Hz), 5.19 (1H, q, J = 7.2Hz), 3.82 (3H, s), 3.57-3.41 (2H, m), 3.09 (2H, d, J = 5.9Hz), 2.97 (3H, s), 2.60-2.42 (2H, m), 2.25 (6H, s), 1.88-1.68 (2H, m), 1.33 (3H, d, J = 7.2Hz) |
| 7-23 | 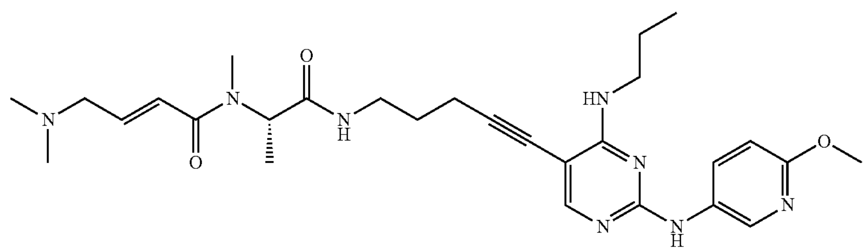 | ¹H-NMR (CDCl₃) δ: 8.24 (1H, d, J = 2.6Hz), 7.99 (1H, dd, J = 8.6, 2.6Hz), 7.93 (1H, s), 6.94 (1H, dt, J = 15.2, 5.9Hz), 6.79 (1H, s), 6.72 (1H, d, J = 8.6Hz), 6.57-6.48 (1H, m), 6.42 (1H, d, J = 15.2Hz), 6.20-6.09 (1H, m), 5.18 (1H, q, J = 6.8Hz), 3.92 (3H, s), 3.50-3.37 (4H, m), 3.10 (2H, d, J = 5.9Hz), 2.99 (3H, s), 2.43 (2H, t, J = 6.9Hz), 2.27 (6H, s), 1.80-1.66 (4H, m), 1.35 (3H, d, J = 6.8Hz), 0.97 (3H, t, J = 7.6Hz) |
| 7-24 | 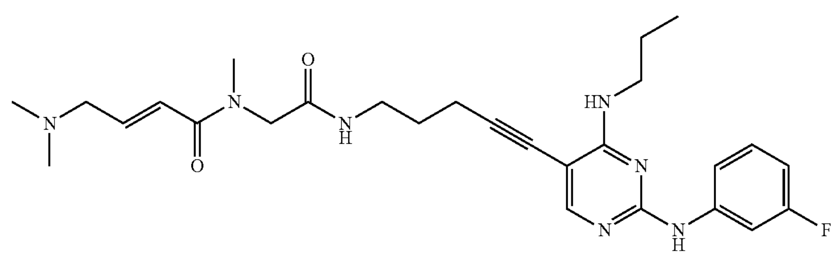 [SMILES: CCCNc1nc(Nc2cccc(F)c2)ncc1C#CCCCNC(=O)CN(C)C(=O)/C=C/CN(C)C] | ¹H-NMR (CDCl₃) δ: 7.96 (1H, s), 7.81 (1H, dt, J = 11.9, 2.3Hz), 7.26-7.16 (1H, m), 7.11-7.07 (1H, m), 7.09-7.06 (1H, m), 6.95 (1H, dt, J = 15.2, 5.9Hz), 6.67 (1H, dt, J = 8.6, 2.6Hz), 6.62-6.55 (1H, m), 6.48 (1H, d, J = 15.2Hz), 6.20-6.10 (1H, m), 4.04 (2H, s), 3.55-3.46 (2H, m), 3.48-3.40 (2H, m), 3.20 (3H, s), 3.13 (2H, d, J = 5.9Hz), 2.48 (2H, t, J = 6.6Hz), 2.29 (6H, s), 1.86-1.75 (2H, m), 1.76-1.64 (2H, m), 1.00 (3H, t, J = 7.3Hz) |

TABLE 98-continued

| Compound No. | Structure | Physicochemical data |
|---|---|---|
| 7-25 | 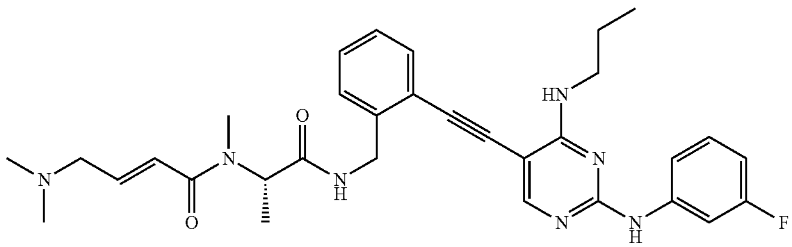 [SMILES: CCCNc1nc(Nc2cccc(F)c2)ncc1C#Cc1ccccc1CNC(=O)[C@H](C)N(C)C(=O)/C=C/CN(C)C] | ¹H-NMR (CDCl₃) δ: 8.13 (1H, s), 7.84 (1H, dt, J = 11.9, 2.0Hz), 7.51-7.45 (1H, m), 7.28-7.18 (4H, m), 7.14-7.08 (2H, m), 6.93-6.85 (1H, m), 6.70 (1H, td, J = 8.6, 2.6Hz), 6.48-6.40 (1H, m), 6.34 (1H, d, J = 15.2Hz), 5.21 (1H, q, J = 7.3Hz), 4.65 (1H, dd, J = 15.2, 7.2Hz), 4.53 (1H, dd, J = 15.2, 6.6Hz), 3.60-3.49 (2H, m), 3.06 (2H, d, J = 5.9Hz), 2.88 (3H, s), 2.24 (6H, s), 1.83-1.69 (2H, m), 1.33 (3H, d, J = 7.3Hz), 1.03 (3H, t, J = 7.6Hz) |

TABLE 99

| Compound No. | Structure | Physicochemical data |
|---|---|---|
| 7-26 | 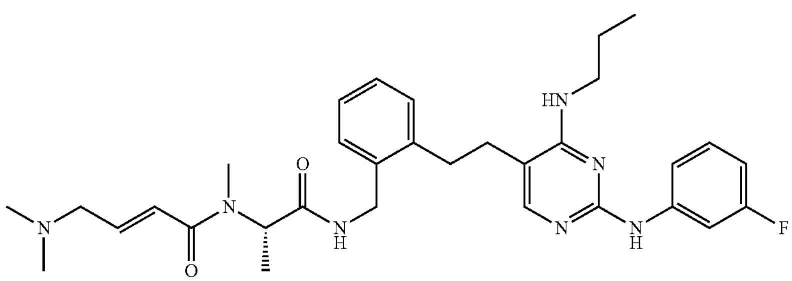 [SMILES: CCCNc1nc(Nc2cccc(F)c2)ncc1CCc1ccccc1CNC(=O)[C@H](C)N(C)C(=O)/C=C/CN(C)C] | ¹H-NMR (CDCl₃) δ: 7.84 (1H, dt, J = 12.5, 2.6Hz), 7.70 (1H, s), 7.25-7.04 (7H, m), 6.98-6.91 (1H, m), 6.91 (1H, dt, J = 15.2, 5.9Hz), 6.64 (1H, td, J = 8.6, 2.6Hz), 6.39 (1H, d, J = 15.2Hz), 5.66-5.58 (1H, m), 5.20 (1H, q, J = 7.3Hz), 4.43 (2H, d, J = 6.6Hz), 3.45-3.34 (2H, m), 3.09 (2H, d, J = 5.9Hz), 2.94 (3H, s), 2.86 (2H, t, J = 7.3Hz), 2.65-2.55 (2H, m), 2.26 (6H, s), 1.65-1.54 (2H, m), 1.35 (3H, d, J = 7.3Hz), 0.97 (3H, t, J = 7.3Hz) |
| 7-27 | 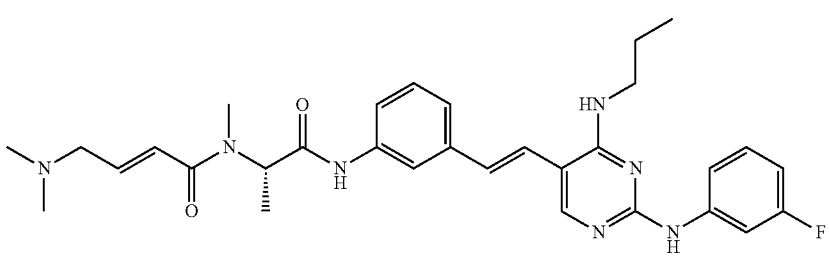 [SMILES: CCCNc1nc(Nc2cccc(F)c2)ncc1/C=C/c1cccc(NC(=O)[C@H](C)N(C)C(=O)/C=C/CN(C)C)c1] | ¹H-NMR (CDCl₃) δ: 8.83 (1H, s), 8.04 (1H, s), 7.84 (1H, dt, J = 11.9, 2.3Hz), 7.74 (1H, s), 7.36 (1H, d, J = 7.9Hz), 7.31-7.09 (4H, m), 7.00 (1H, dt, J = 15.2, 5.9Hz), 6.80 (2H, s), 6.67 (1H, td, J = 7.9, 2.0Hz), 6.45 (1H, d, J = 15.2Hz), 5.48-5.25 (2H, m), 5.26-5.15 (1H, m), 3.57-3.47 (2H, m), 3.11 (2H, d, J = 5.9Hz), 3.05 (3H, s), 2.27 (6H, s), 1.82-1.69 (2H, m), 1.45 (3H, d, J = 7.3Hz), 1.03 (3H, t, J = 7.6Hz) |

TABLE 99-continued

| Compound No. | Structure | Physicochemical data |
|---|---|---|
| 7-28 | 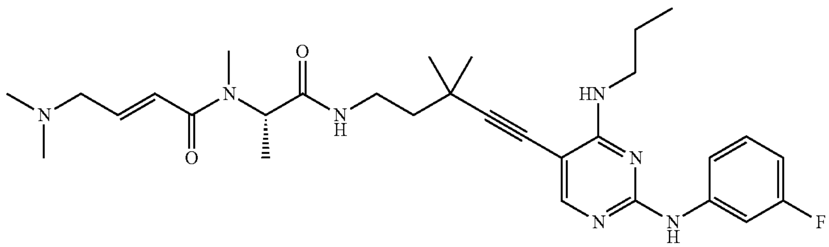 [SMILES: CCCNc1nc(Nc2cccc(F)c2)ncc1C#CC(C)(C)CCNC(=O)[C@H](C)N(C)C(=O)/C=C/CN(C)C] | ¹H-NMR (CDCl₃) δ: 7.96 (1H, s), 7.82 (1H, dt, J = 11.9, 2.0Hz), 7.27-7.16 (1H, m), 7.10-7.05 (2H, m), 6.93 (1H, dt, J = 15.2, 5.9Hz), 6.67 (1H, dt, J = 7.9, 2.0Hz), 6.60-6.51 (1H, m), 6.41 (1H, d, J = 15.2Hz), 6.11-6.00 (1H, m), 5.17 (1H, q, J = 7.3Hz), 3.55-3.47 (2H, m), 3.49-3.35 (2H, m), 3.10 (2H, d, J = 5.9Hz), 2.98 (3H, s), 2.27 (6H, s), 1.75-1.62 (2H, m), 1.34 (3H, d, J = 7.3Hz), 1.34-1.24 (2H, m), 1.30 (6H, s), 1.00 (3H, t, J = 7.6Hz) |
| 7-29 | 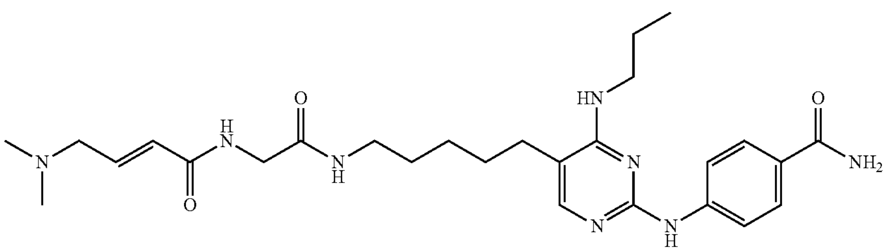 [SMILES: CCCNc1nc(Nc2ccc(C(N)=O)cc2)ncc1CCCCCNC(=O)CNC(=O)/C=C/CN(C)C] | ¹H-NMR (CD₃OD) δ: 7.80 (4H, s), 7.60 (1H, s), 6.78 (1H, dt, J = 15.9, 6.6Hz), 6.14 (1H, d, J = 15.9Hz), 3.88 (2H, s), 3.47 (2H, t, J = 7.3Hz), 3.20 (2H, t, J = 6.9Hz), 3.11 (2H, dd, J = 6.6, 1.3Hz), 2.36 (2H, t, J = 7.6Hz), 2.26 (6H, s), 1.72-1.67 (2H, m), 1.61-1.51 (4H, m), 1.41-1.35 (2H, m), 1.00 (3H, t, J = 7.6Hz) |

TABLE 100

| Compound No. | Structure | Physicochemical data |
|---|---|---|
| 7-31 | 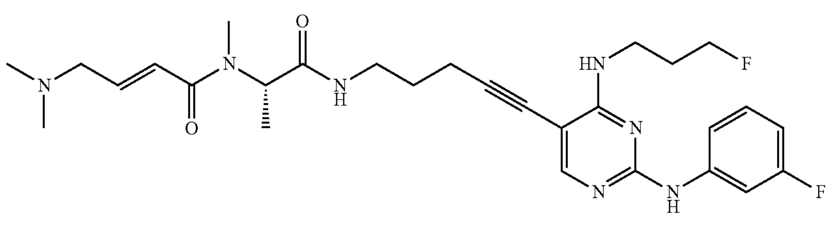 [SMILES: C[C@@H](C(=O)NCCCC#Cc1cnc(Nc2cccc(F)c2)nc1NCCCF)N(C)C(=O)/C=C/CN(C)C] | ¹H-NMR (CDCl₃) δ: 7.97 (1H, s), 7.77 (1H, dt, J = 12.1, 2.1Hz), 7.21 (1H, dt, J = 8.3, 6.6Hz), 7.17 (1H, s), 7.10 (1H, dd, J = 8.3, 2.1Hz), 6.94 (1H, dt, J = 15.2, 5.9Hz), 6.68 (1H, dt, J = 8.3, 2.1Hz), 6.65-6.60 (1H, m), 6.60-6.52 (1H, m), 6.45-6.40 (1H, m), 5.19 (1H, q, J = 7.3Hz), 4.60 (2H, dt, J = 47.3, 5.6Hz), 3.71 (2H, q, J = 6.6Hz), 3.46 (2H, q, J = 6.4Hz), 3.10 (2H, dd, J = 5.9, 1.3Hz), 3.00 (3H, s), 2.43 (2H, t, J = 6.3Hz), 2.27 (6H, s), 2.21-2.04 (2H, m), 1.80-1.66 (2H, m), 1.36 (3H, d, J = 7.3Hz) |

| Compound No. | Structure | Physicochemical data |
|---|---|---|
| 7-32 | 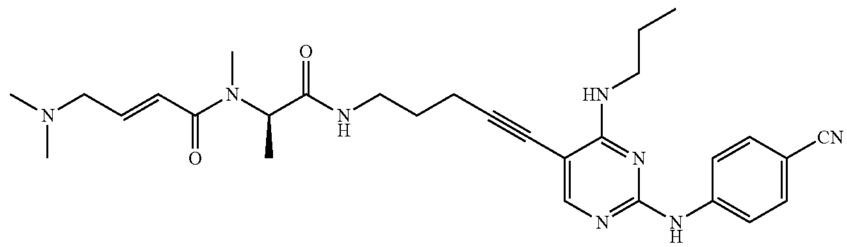 [SMILES: CCCNc1nc(Nc2ccc(C#N)cc2)ncc1C#CCCCNC(=O)[C@@H](C)N(C)C(=O)/C=C/CN(C)C] | ¹H-NMR (CDCl₃) δ: 7.98 (1H, s), 7.77 (2H, d, J = 9.2Hz), 7.60-7.48 (3H, m), 6.94 (1H, dt, J = 15.2, 5.9Hz), 6.60 (1H, brs), 6.48-6.34 (2H, m), 5.19 (1H, q, J = 7.0Hz), 3.56-3.40 (4H, m), 3.10 (2H, dd, J = 5.9, 1.3Hz), 3.00 (3H, s), 2.50-2.38 (2H, m), 2.27 (6H, s), 1.88-1.64 (4H, m), 1.36 (3H, d, J = 7.3Hz), 1.00 (3H, t, J = 7.6Hz) |
| 7-33 | 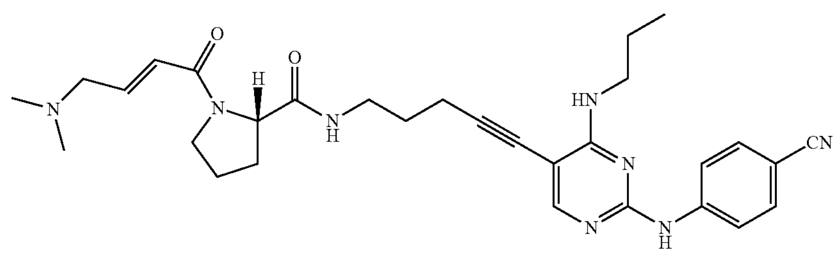 [SMILES: CCCNc1nc(Nc2ccc(C#N)cc2)ncc1C#CCCCNC(=O)[C@@H]1CCCN1C(=O)/C=C/CN(C)C] | ¹H-NMR (CDCl₃) δ: 7.97 (1H, s), 7.77 (2H, d, J = 8.6Hz), 7.56 (2H, d, J = 8.6Hz), 7.53-7.44 (2H, m), 6.96 (1H, dt, J = 15.2, 5.9Hz), 6.45 (1H, t, J = 5.6Hz), 6.33 (1H, d, J = 15.2Hz), 4.68 (1H, d, J = 6.6Hz), 3.74-3.32 (6H, m), 3.10 (2H, d, J = 5.9Hz), 2.52-2.43 (2H, m), 2.27 (6H, s), 1.89-1.65 (8H, m), 0.99 (3H, t, J = 7.4Hz) |
| 7-34 | 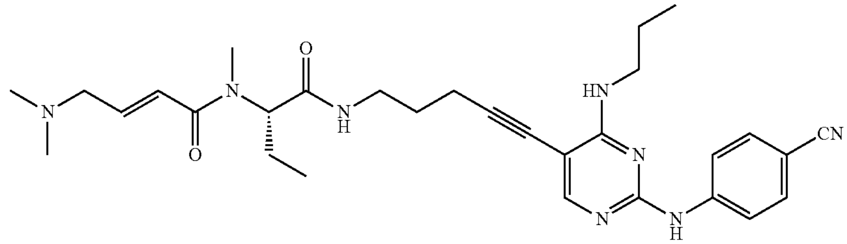 [SMILES: CCCNc1nc(Nc2ccc(C#N)cc2)ncc1C#CCCCNC(=O)[C@H](CC)N(C)C(=O)/C=C/CN(C)C] | ¹H-NMR (CDCl₃) δ: 7.97 (1H, s), 7.78 (2H, d, J = 8.6Hz), 7.70 (1H, brs), 7.56 (2H, d, J = 8.6Hz), 6.94 (1H, dt, J = 15.2, 5.9Hz), 6.60 (1H, brs), 6.48-6.42 (2H, m), 4.92 (1H, t, J = 7.9Hz), 3.53-3.42 (4H, m), 3.11 (2H, d, J = 5.9Hz), 3.01 (3H, s), 2.44 (2H, t, J = 6.6Hz), 2.28 (6H, s), 2.04-1.92 (1H, m), 1.78-1.65 (5H, m), 1.00 (3H, t, J = 7.4Hz), 0.91 (3H, t, J = 7.4Hz) |

TABLE 101

| Compound No. | Structure | Physicochemical data |
|---|---|---|
| 7-35 | 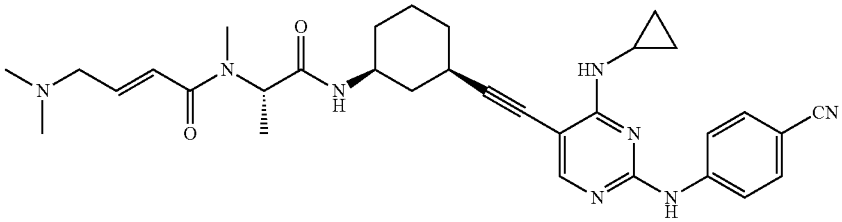 [SMILES: C[C@@H](C(=O)N[C@H]1CCC[C@@H](C#Cc2cnc(Nc3ccc(C#N)cc3)nc2NC2CC2)C1)N(C)C(=O)/C=C/CN(C)C] | ¹H-NMR (CDCl₃) δ: 8.00 (1H, s), 7.88 (2H, d, J = 9.2Hz), 7.56 (2H, d, J = 9.2Hz), 7.45 (1H, s), 6.93 (1H, dt, J = 15.2, 5.9Hz), 6.47-6.37 (1H, m), 6.34 (1H, d, J = 7.9Hz), 5.61 (1H, s), 5.15 (1H, q, J = 7.0Hz), 3.78-3.64 (1H, m), 3.10 (2H, dd, J = 5.9, 1.3Hz), 2.98 (3H, s), 2.87-2.77 (1H, m), 2.67-2.52 (1H, m), 2.35-2.21 (7H, m), 2.05-1.93 (1H, m), 1.92-1.75 (2H, m), 1.47-0.99 (7H, m), 0.98-0.87 (2H, m), 0.72-0.61 (2H, m) |
| 7-36 | 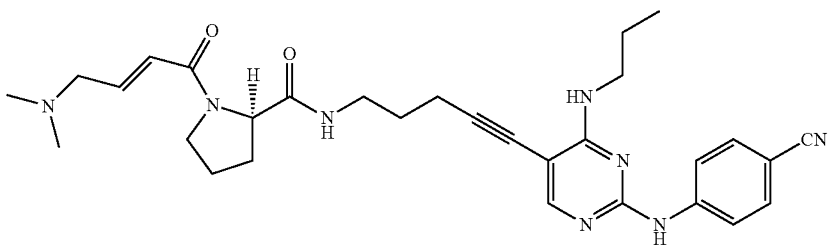 [SMILES: CCCNc1nc(Nc2ccc(C#N)cc2)ncc1C#CCCCNC(=O)[C@H]1CCCN1C(=O)/C=C/CN(C)C] | ¹H-NMR (CDCl₃) δ: 7.97 (1H, s), 7.77 (2H, d, J = 8.8Hz), 7.56 (2H, d, J = 8.8Hz), 7.50-7.36 (2H, m), 6.96 (1H, dt, J = 15.2, 5.9Hz), 6.45 (1H, t, J = 5.9Hz), 6.33 (1H, d, J = 15.2Hz), 4.68 (1H, d, J = 6.6Hz), 3.73-3.32 (6H, m), 3.11 (2H, d, J = 5.6Hz), 2.47 (2H, t, J = 6.6Hz), 2.27 (6H, s), 1.90-1.65 (8H, m), 1.00 (3H, t, J = 7.3Hz) |
| 7-37 | 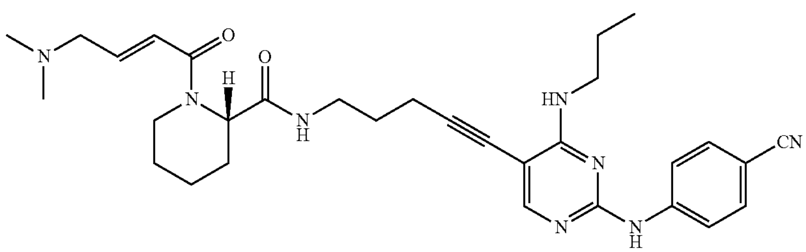 [SMILES: CCCNc1nc(Nc2ccc(C#N)cc2)ncc1C#CCCCNC(=O)[C@@H]1CCCCN1C(=O)/C=C/CN(C)C] | ¹H-NMR (CDCl₃) δ: 7.98 (1H, s), 7.76 (2H, d, J = 8.8Hz), 7.57 (2H, d, J = 8.8Hz), 7.19 (1H, s), 6.91 (1H, dt, J = 15.2, 5.9Hz), 6.55-6.30 (3H, m), 5.20 (1H, d, J = 4.6Hz), 3.99-3.87 (1H, m), 3.57-3.36 (4H, m), 3.14-3.00 (3H, m), 2.46 (2H, t, J = 6.6Hz), 2.28 (6H, s), 1.95-1.20 (10H, m), 1.00 (3H, t, J = 7.4Hz) |
| 7-38 | 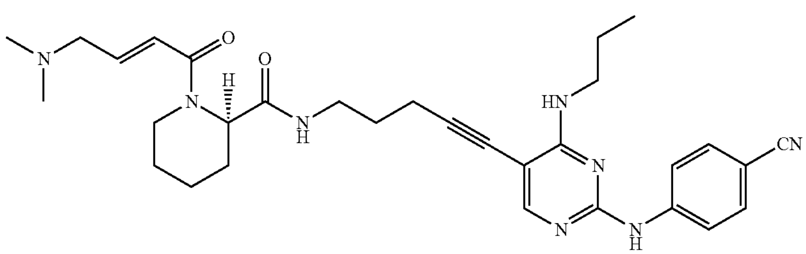 [SMILES: CCCNc1nc(Nc2ccc(C#N)cc2)ncc1C#CCCCNC(=O)[C@H]1CCCCN1C(=O)/C=C/CN(C)C] | ¹H-NMR (CDCl₃) δ: 7.98 (1H, s), 7.76 (2H, d, J = 8.8Hz), 7.57 (2H, d, J = 8.8Hz), 7.16 (1H, s), 6.91 (1H, dt, J = 15.2, 5.9Hz), 6.55-6.30 (3H, m), 5.20 (1H, d, J = 5.3Hz), 3.99-3.87 (1H, m), 3.57-3.36 (4H, m), 3.14-3.00 (3H, m), 2.46 (2H, t, J = 6.6Hz), 2.28 (6H, s), 1.95-1.20 (10H, m), 1.00 (3H, t, J = 7.4Hz) |

TABLE 101-continued

| Compound No. | Structure | Physicochemical data |
|---|---|---|
| 7-39 | 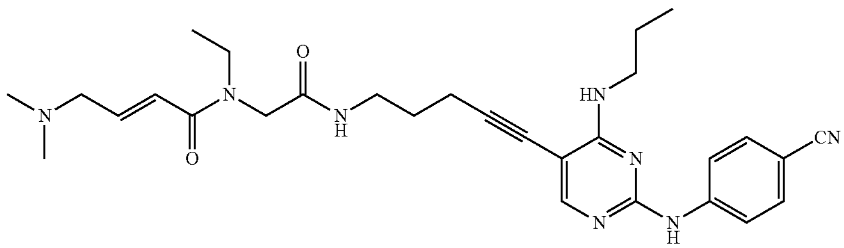 [SMILES: CCCNc1nc(Nc2ccc(C#N)cc2)ncc1C#CCCCNC(=O)CN(CC)C(=O)/C=C/CN(C)C] | $^1$H-NMR (CDCl$_3$) δ: 7.97 (1H, s), 7.77 (2H, d, J = 9.2Hz), 7.56 (2H, d, J = 9.2Hz), 7.47 (1H, s), 6.98 (1H, dt J = 15.2, 5.9Hz), 6.85 (1H, brs), 6.43 (1H, d, J = 15.2Hz), 6.29 (1H, brs), 4.02 (2H, s), 3.57-3.41 (6H, m), 3.12-3.07 (2H, m), 2.47 (2H, t, J = 6.6Hz), 2.27 (6H, s), 1.83-1.65 (4H, m), 1.25 (3H, t, J = 7.3Hz), 1.00 (3H, t, J = 7.3Hz) |

TABLE 102

| Compound No. | Structure | Physicochemical data |
|---|---|---|
| 7-40 | 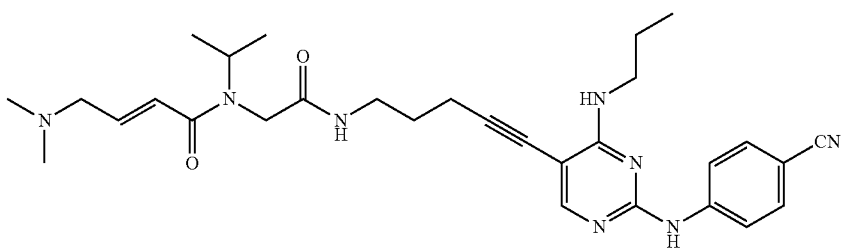 [SMILES: CCCNc1nc(Nc2ccc(C#N)cc2)ncc1C#CCCCNC(=O)CN(C(=O)/C=C/CN(C)C)C(C)C] | $^1$H-NMR (CDCl$_3$) δ: 7.97 (1H, s), 7.77 (2H, d, J = 9.2Hz), 7.56 (2H, d, J = 9.2Hz), 7.47 (1H, s), 7.09 (1H, brs), 6.98-6.89 (1H, m), 6.49 (1H, d, J = 15.2Hz), 6.38 (1H, brs), 4.31-4.20 (1H, m), 3.97 (2H, s), 3.52-3.42 (4H, m), 3.12-3.07 (2H, m), 2.47 (2H, t, J = 6.9Hz), 2.28 (6H, s), 1.80-1.65 (4H, m), 1.26 (6H, d, J = 6.9Hz), 1.00 (3H, t, J = 7.6Hz) |
| 7-41 | 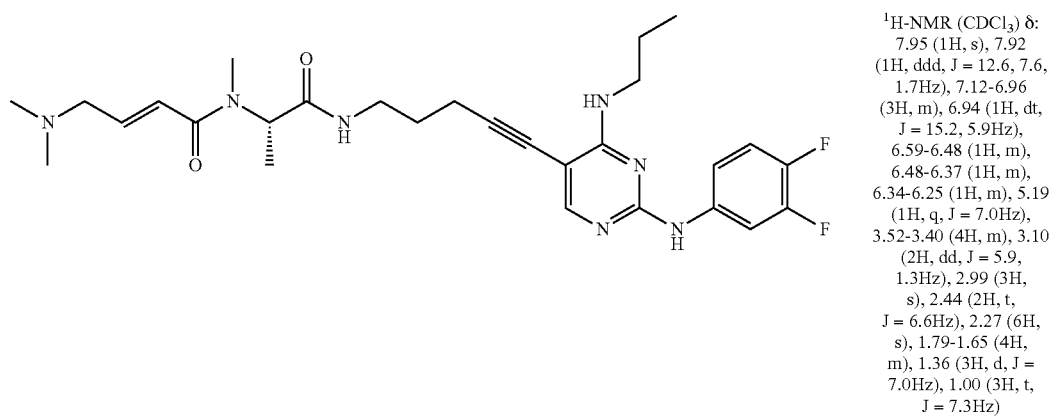 | $^1$H-NMR (CDCl$_3$) δ: 7.95 (1H, s), 7.92 (1H, ddd, J = 12.6, 7.6, 1.7Hz), 7.12-6.96 (3H, m), 6.94 (1H, dt, J = 15.2, 5.9Hz), 6.59-6.48 (1H, m), 6.48-6.37 (1H, m), 6.34-6.25 (1H, m), 5.19 (1H, q, J = 7.0Hz), 3.52-3.40 (4H, m), 3.10 (2H, dd, J = 5.9, 1.3Hz), 2.99 (3H, s), 2.44 (2H, t, J = 6.6Hz), 2.27 (6H, s), 1.79-1.65 (4H, m), 1.36 (3H, d, J = 7.0Hz), 1.00 (3H, t, J = 7.3Hz) |

TABLE 102-continued

| Compound No. | Structure | Physicochemical data |
|---|---|---|
| 7-42 | 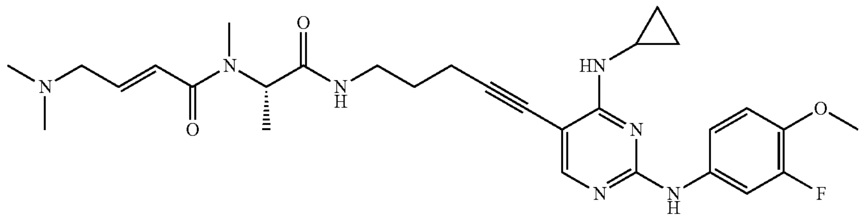 | ¹H-NMR (CDCl₃) δ: 8.06 (1H, dd, J = 14.2, 2.3Hz), 7.95 (1H, s), 7.10-7.01 (2H, m), 6.94 (1H, dt, J = 15.2, 5.9Hz), 6.88 (1H, t, J = 9.2Hz), 6.60-6.48 (1H, m), 6.42 (1H, d, J = 15.2Hz), 6.21 (1H, s), 5.18 (1H, q, J = 7.0Hz), 3.87 (3H, s), 3.41 (2H, q, J = 6.4Hz), 3.10 (2H, d, J = 5.9Hz), 3.00 (3H, s), 2.91-2.80 (1H, m), 2.42 (2H, t, J = 6.6Hz), 2.27 (6H, s), 1.78-1.69 (2H, m), 1.37 (3H, d, J = 7.0Hz), 0.93-0.86 (2H, m), 0.72 (2H, q, J = 5.3Hz) |
| 7-43 | 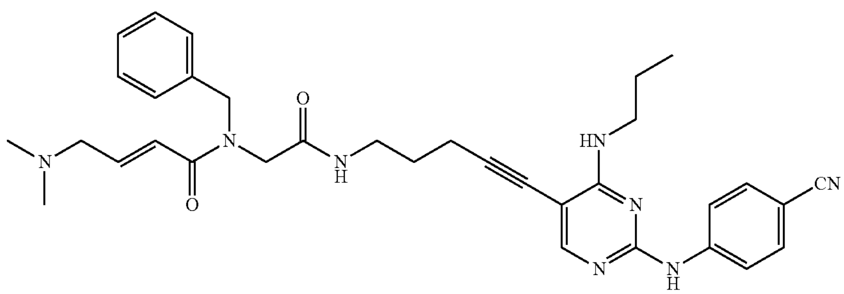 [SMILES: CCCNc1nc(Nc2ccc(C#N)cc2)ncc1C#CCCCNC(=O)CN(Cc1ccccc1)C(=O)/C=C/CN(C)C] | ¹H-NMR (CDCl₃) δ: 7.98 (1H, s), 7.77 (2H, d, J = 8.6Hz), 7.57 (2H, d, J = 8.6Hz), 7.37-7.18 (6H, m), 7.08-6.99 (1H, m), 6.69 (1H, brs), 6.48 (1H, d, J = 15.2Hz), 6.29 (1H, brs), 4.73 (2H, s), 4.01 (2H, s), 3.49-3.36 (4H, m), 3.09-3.01 (2H, m), 2.48 (2H, t, J = 6.0Hz), 2.26 (6H, s), 1.84-1.66 (4H, m), 1.00 (3H, t, J = 7.6Hz) |

TABLE 103

| Compound No. | Structure | Physicochemical data |
|---|---|---|
| 7-44 | 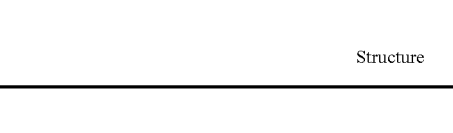 | ¹H-NMR (CDCl₃) δ: 7.98 (1H, s), 7.76 (2H, d, J = 8.6Hz), 7.57 (2H, d, J = 8.6Hz), 7.26 (1H, brs), 6.89 (1H, dt, J = 15.2, 5.3Hz), 6.53 (1H, brs), 6.42 (1H, brs), 6.25 (1H, brs), 6.02 (1H, d, J = 15.2Hz), 4.60-4.55 (1H, m), 3.88 (1H, dd, J = 8.9, 3.6Hz), 3.54-3.46 (5H, m), 3.41 (3H, s), 3.07 (2H, d, J = 5.9Hz), 2.50 (2H, t, J = 6.6Hz), 2.26 (6H, s), 1.84-1.68 (4H, m), 1.01 (3H, t, J = 7.3Hz) |

TABLE 103-continued

| Compound No. | Structure | Physicochemical data |
|---|---|---|
| 7-45 | 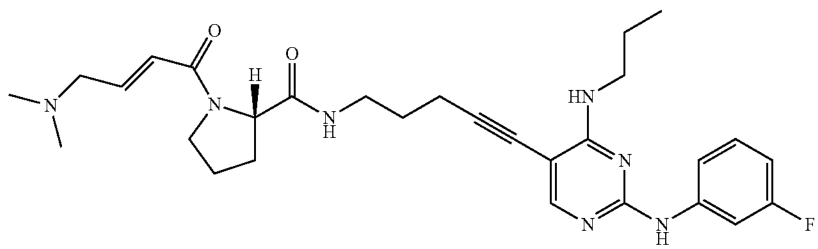 [SMILES: CCCNc1nc(Nc2cccc(F)c2)ncc1C#CCCCNC(=O)[C@@H]1CCCN1C(=O)/C=C/CN(C)C] | ¹H-NMR (CDCl₃) δ: 7.95 (1H, s), 7.82 (1H, d, J = 12.1Hz), 7.47-7.41 (1H, m), 7.24-7.16 (1H, m), 7.10-7.07 (1H, m), 7.08-7.05 (1H, m), 6.96 (1H, dt, J = 15.2, 5.9Hz), 6.67 (1H, td, J = 8.1, 2.4Hz), 6.33 (1H, d, J = 15.2Hz), 6.32-6.28 (1H, m), 4.68 (1H, d, J = 7.3Hz), 3.70-3.63 (1H, m), 3.59-3.45 (4H, m), 3.46-3.33 (1H, m), 3.10 (2H, d, J = 5.9Hz), 2.55-2.48 (1H, m), 2.46 (2H, t, J = 6.6Hz), 2.27 (6H, s), 2.22-1.97 (2H, m), 1.88-1.69 (1H, m), 1.82-1.65 (4H, m), 1.00 (3H, t, J = 6.6Hz) |
| 7-46 | 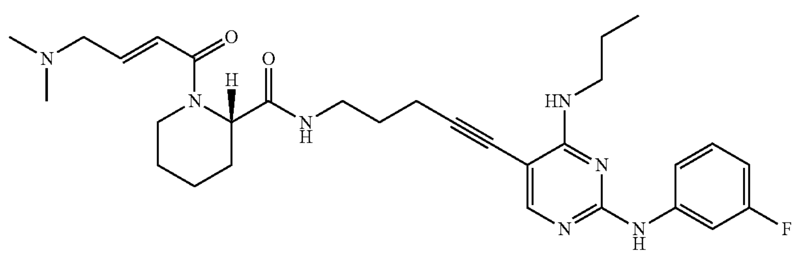 [SMILES: CCCNc1nc(Nc2cccc(F)c2)ncc1C#CCCCNC(=O)[C@@H]1CCCCN1C(=O)/C=C/CN(C)C] | ¹H-NMR (CDCl₃) δ: 7.96 (1H, s), 7.82 (1H, d, J = 11.9Hz), 7.24-7.17 (1H, m), 7.11-7.06 (1H, m), 7.08-7.05 (1H, m), 6.91 (1H, dt, J = 15.2, 5.9Hz), 6.67 (1H, td, J = 8.3, 2.0Hz), 6.48 (1H, d, J = 15.2Hz), 6.38-6.33 (1H, m), 5.20 (1H, d, J = 5.3Hz), 3.93 (1H, d, J = 13.2Hz), 3.54-3.42 (4H, m), 3.10-3.00 (2H, m), 3.10 (2H, d, J = 5.9Hz), 2.46 (2H, t, J = 6.6Hz), 2.27 (6H, s), 1.90-1.80 (2H, m), 1.82-1.65 (6H, m), 1.58-1.47 (2H, m), 1.00 (3H, t, J = 7.3Hz) |
| 7-47 | 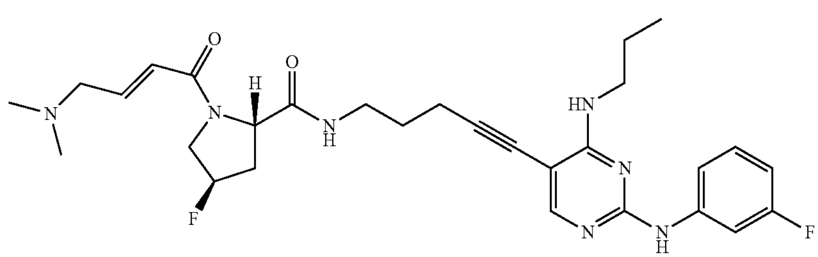 [SMILES: CCCNc1nc(Nc2cccc(F)c2)ncc1C#CCCCNC(=O)[C@@H]1C[C@@H](F)CN1C(=O)/C=C/CN(C)C] | ¹H-NMR (CDCl₃) δ: 7.96 (1H, s), 7.85-7.78 (1H, m), 7.27-7.17 (2H, m), 7.10-7.06 (1H, m), 7.06-7.03 (1H, m), 6.95 (1H, dt, J = 15.2, 5.9Hz), 6.67 (1H, td, J = 8.1, 2.2Hz), 6.27 (1H, d, J = 15.2Hz), 6.20-6.14 (1H, m), 5.33 (1H, d, J = 53.5Hz), 4.83-4.76 (1H, m), 3.98 (1H, dd, J = 20.5, 12.6Hz), 3.70 (1H, ddd, J = 32.4, 12.2, 3.6Hz), 3.52-3.39 (4H, m), 3.10 (2H, d, J = 5.9Hz), 2.90-2.70 (1H, m), 2.48 (2H, t, J = 6.9Hz), 2.45-2.25 (1H, m), 2.26 (6H, s), 1.85-1.74 (2H, m), 1.76-1.65 (2H, m), 1.00 (3H, t, J = 7.6Hz) |

TABLE 104

| Compound No. | Structure | Physicochemical data |
|---|---|---|
| 7-48 | 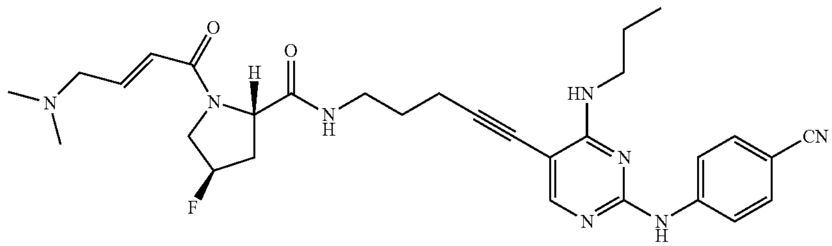 [SMILES: CCCNc1nc(Nc2ccc(C#N)cc2)ncc1C#CCCCNC(=O)[C@@H]1C[C@@H](F)CN1C(=O)/C=C/CN(C)C] | ¹H-NMR (CDCl₃) δ: 7.97 (1H, s), 7.76 (2H, d, J = 8.6Hz), 7.57 (2H, d, J = 8.6Hz), 7.29-7.26 (2H, m), 6.95 (1H, dt, J = 15.2, 5.9Hz), 6.30-6.26 (1H, m), 6.28 (1H, d, J = 15.2Hz), 5.33 (1H, d, J = 52.8Hz), 4.83-4.76 (1H, m), 3.99 (1H, dd, J = 20.1, 12.2Hz), 3.70 (1H, ddd, J = 32.4, 12.2,3.6Hz), 3.50-3.43 (4H, m), 3.10 (2H, d, J = 5.9Hz), 2.89-2.69 (1H, m), 2.48 (2H, t, J = 6.6Hz), 2.45-2.28 (1H, m), 2.26 (6H, s), 1.85-1.73 (2H, m), 1.75-1.64 (2H, m), 0.99 (3H, t, J = 7.6Hz) |
| 7-49 | 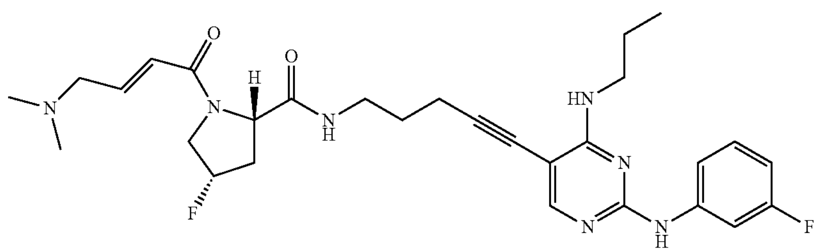 [SMILES: CCCNc1nc(Nc2cccc(F)c2)ncc1C#CCCCNC(=O)[C@@H]1C[C@H](F)CN1C(=O)/C=C/CN(C)C] | MS m/z (M + H): 554.4 |
| 7-50 | 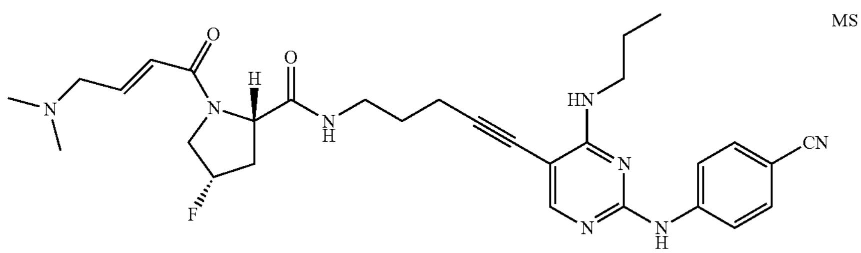 | MS m/z (M + H): 561.4 |
| 7-51 | 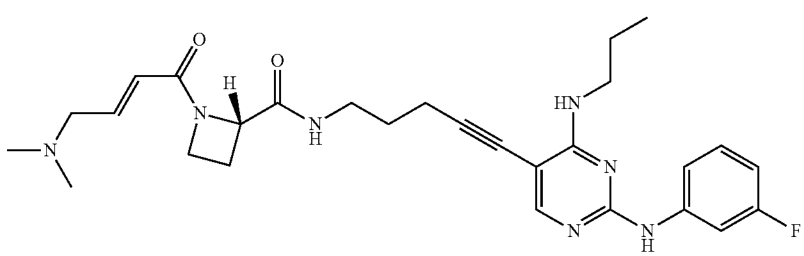 [SMILES: CCCNc1nc(Nc2cccc(F)c2)ncc1C#CCCCNC(=O)[C@@H]1CCN1C(=O)/C=C/CN(C)C] | ¹H-NMR (CDCl₃) δ: 8.03-8.00 (1H, m), 7.96 (1H, s), 7.82 (1H, d, J = 12.1Hz), 7.25-7.16 (1H, m), 7.11-7.05 (1H, m), 7.04-7.00 (1H, m), 6.94 (1H, dt, J = 15.2, 5.9Hz), 6.67 (1H, td, J = 8.3, 2.2Hz), 6.25-6.17 (1H, m), 6.04 (1H, d, J = 15.2Hz), 4.95 (1H, dd, J = 9.2, 6.6Hz), 4.17-4.09 (2H, m), 3.58-3.37 (4H, m), 3.10 (2H, d, J = 5.9Hz), 2.81-2.70 (1H, m), 2.52-2.40 (1H, m), 2.50 (2H, t, J = 6.6Hz), 2.26 (6H, s), 1.85-1.75 (2H, m), 1.78-1.65 (2H, m), 1.01 (3H, t, J = 7.3Hz) |

TABLE 104-continued

| Compound No. | Structure | Physicochemical data |
|---|---|---|
| 7-52 | 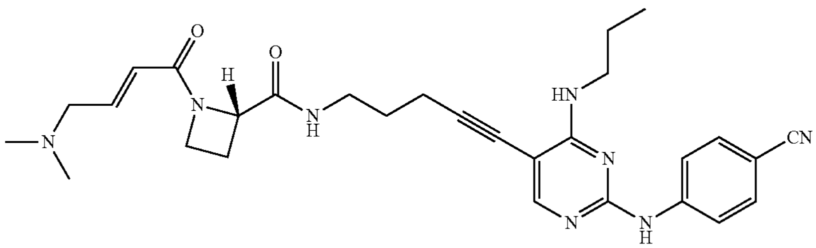 [SMILES: CCCNc1nc(Nc2ccc(C#N)cc2)ncc1C#CCCCNC(=O)[C@@H]1CCN1C(=O)/C=C/CN(C)C] | ¹H-NMR (CDCl₃) δ: 8.06-7.99 (1H, m), 7.98 (1H, s), 7.76 (2H, d, J = 8.6Hz), 7.57 (2H, d, J = 8.6Hz), 7.25-7.20 (1H, m), 6.94 (1H, dt, J = 15.2, 5.9Hz), 6.37-6.30 (1H, m), 6.04 (1H, d, J = 15.2Hz), 4.95 (1H, dd, J = 9.2, 6.6Hz), 4.20-4.11 (2H, m), 3.62-3.33 (4H, m), 3.10 (2H, d, J = 5.9Hz), 2.81-2.70 (1H, m), 2.50 (2H, t, J = 6.6Hz), 2.50-2.40 (1H, m), 2.26 (6H, s), 1.85-1.75 (2H, m), 1.76-1.65 (2H, m), 1.00 (3H, t, J = 7.3Hz) |

TABLE 105

| Compound No. | Structure | Physicochemical data |
|---|---|---|
| 7-53 | 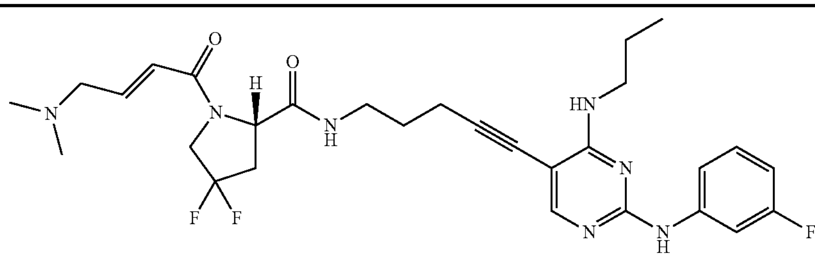 | ¹H-NMR (CDCl₃) δ: 7.96 (1H, s), 7.81 (1H, d, J = 13.0Hz), 7.28-7.16 (2H, m), 7.16-7.06 (1H, m), 7.07-6.97 (1H, m), 7.06-7.02 (1H, m), 6.71-6.64 (1H, m), 6.22 (1H, d, J = 15.2Hz), 6.21-6.17 (1H, m), 4.88 (1H, dd, J = 9.2, 4.6Hz), 4.07-3.80 (2H, m), 3.54-3.40 (4H, m), 3.24-3.05 (1H, m), 3.11 (2H, d, J = 5.0Hz), 2.58-2.43 (1H, m), 2.48 (2H, t, J = 6.6Hz), 2.26 (6H, s), 1.83-1.73 (2H, m), 1.76-1.65 (2H, m), 1.00 (3H, t, J = 7.3Hz) |
| 7-54 | 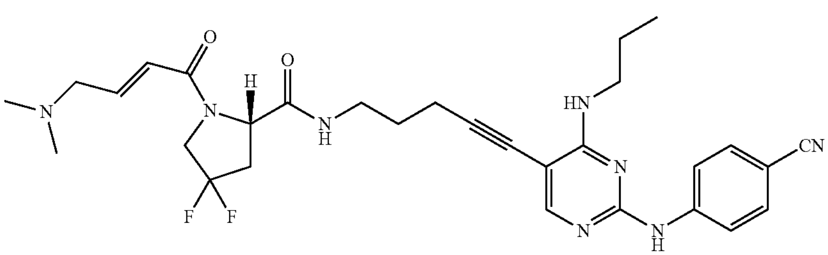 [SMILES: CCCNc1nc(Nc2ccc(C#N)cc2)ncc1C#CCCCNC(=O)[C@@H]1CC(F)(F)CN1C(=O)/C=C/CN(C)C] | ¹H-NMR (CDCl₃) δ: 7.97 (1H, s), 7.76 (2H, d, J = 8.6Hz), 7.57 (2H, d, J = 8.6Hz), 7.25-7.21 (1H, m), 7.15-7.09 (1H, m), 7.01 (1H, dt, J = 15.2, 5.9Hz), 6.37-6.31 (1H, m), 6.22 (1H, d, J = 15.2Hz), 4.88 (1H, dd, J = 9.6, 5.0Hz), 4.10-3.80 (2H, m), 3.53-3.43 (4H, m), 3.18-3.05 (1H, m), 3.11 (2H, d, J = 5.3Hz), 2.57-2.44 (1H, m), 2.48 (2H, t, J = 6.6Hz), 2.27 (6H, s), 1.83-1.73 (2H, m), 1.75-1.65 (2H, m), 1.00 (3H, t, J = 7.6Hz) |

TABLE 105-continued

| Compound No. | Structure | Physicochemical data |
|---|---|---|
| 7-55 | 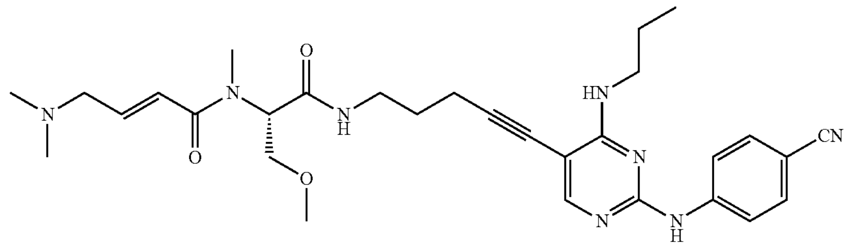 [SMILES: CCCNc1nc(Nc2ccc(C#N)cc2)ncc1C#CCCCNC(=O)[C@H](COC)N(C)C(=O)/C=C/CN(C)C] | ¹H-NMR (CDCl₃) δ: 7.98 (1H, s), 7.76 (2H, d, J = 8.6Hz), 7.57 (2H, d, J = 8.6Hz), 7.21 (1H, brs), 6.94 (1H, dt, J = 15.2, 5.9Hz), 6.64 (1H, brs), 6.46 (1H, d, J = 15.2Hz), 6.35 (1H, brs), 5.22 (1H, t, J = 7.3Hz), 3.80 (2H, d, J = 7.3Hz), 3.51-3.41 (4H, m), 3.38 (3H, s), 3.11-3.04 (5H, m), 2.46 (2H, t, J = 6.6Hz), 2.27 (6H, s), 1.78-1.70 (4H, m), 1.00 (3H, t, J = 7.6Hz) |
| 7-56 | 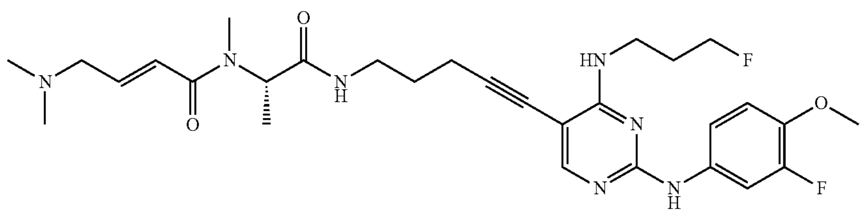 | ¹H-NMR (CDCl₃) δ: 7.95 (1H, s), 7.71 (1H, dd, J = 13.5, 2.3Hz), 7.10-7.03 (1H, m), 6.94 (1H, dt, J = 15.2, 5.9Hz), 6.89 (1H, t, J = 9.2Hz), 6.86 (1H, brs), 6.61-6.48 (2H, m), 6.42 (1H, dt, J = 15.2, 1.3Hz), 5.18 (1H, q, J = 6.8Hz), 4.59 (2H, dt, J = 47.1, 5.6Hz), 3.87 (3H, s), 3.69 (2H, q, J = 6.6Hz), 3.45 (2H, q, J = 6.6Hz), 3.11 (2H, dd, J = 5.9, 1.3Hz), 2.99 (3H, s), 2.43 (2H, t, J = 6.3Hz), 2.27 (6H, s), 2.21-2.02 (2H, m), 1.79-1.69 (2H, m), 1.36 (3H, d, J = 6.8Hz) |

TABLE 106

| Compound No. | Structure | Physicochemical data |
|---|---|---|
| 7-57 | 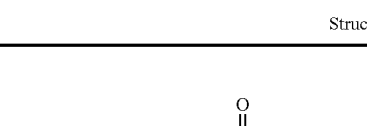 | ¹H-NMR (CDCl₃) δ: 7.98 (1H, s), 7.77 (2H, d, J = 8.6Hz), 7.56 (2H, d, J = 8.6Hz), 7.51 (1H, brs), 6.87 (1H, dt, J = 15.3, 6.0Hz), 6.62 (1H, brs), 6.54 (1H, brs), 6.13 (1H, t, J = 5.3 Hz), 6.02 (1H, d, J = 15.3Hz), 4.01 (2H, d, J = 5.3Hz), 3.57-3.42 (4H, m), 3.06 (2H, d, J = 6.0Hz), 2.51 (2H, t, J = 6.9Hz), 2.25 (6H, s), 1.87-1.76 (2H, m), 1.76-1.65 (2H, m), 1.00 (3H, t, J = 7.6Hz) |

TABLE 106-continued

| Compound No. | Structure | Physicochemical data |
|---|---|---|
| 7-58 | 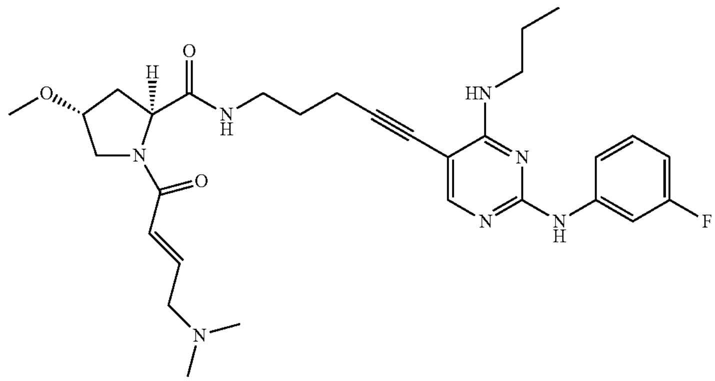 [SMILES: CCCNc1nc(Nc2cccc(F)c2)ncc1C#CCCCNC(=O)[C@@H]1C[C@@H](OC)CN1C(=O)/C=C/CN(C)C] | ¹H-NMR (CDCl₃) δ: 7.96 (1H, s), 7.86-7.78 (1H, m), 7.36-7.29 (1H, m), 7.25-7.16 (1H, m), 7.11-7.05 (1H, m), 7.04-7.01 (1H, m), 6.94 (1H, dt, J = 15.2, 5.9Hz), 6.67 (1H, dt, J = 8.1, 2.2Hz), 6.28 (1H, d, J = 15.2Hz), 6.27-6.22 (1H, m), 4.73 (1H, dd, J = 8.6, 4.0Hz), 4.23-4.16 (1H, m), 3.76 (1H, dd, J = 10.6, 5.9Hz), 3.58 (1H, dd, J = 10.6, 4.6Hz), 3.53-3.41 (2H, m), 3.43-3.30 (2H, m), 3.35 (3H, s), 3.10 (2H, d, J = 5.9Hz), 2.73-2.64 (1H, m), 2.47 (2H, t, J = 6.9Hz), 2.26 (6H, s), 2.06-1.91 (1H, m), 1.80-1.67 (4H, m), 1.00 (3H, t, J = 7.6Hz) |
| 7-59 | 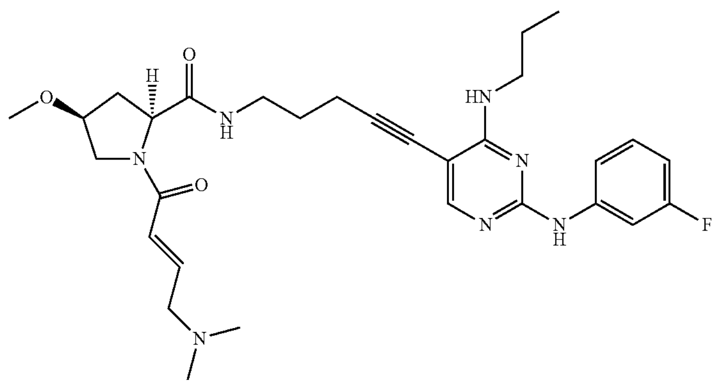 [SMILES: CCCNc1nc(Nc2cccc(F)c2)ncc1C#CCCCNC(=O)[C@@H]1C[C@H](OC)CN1C(=O)/C=C/CN(C)C] | MS m/z (M + H): 566.4 |
| 7-60 | 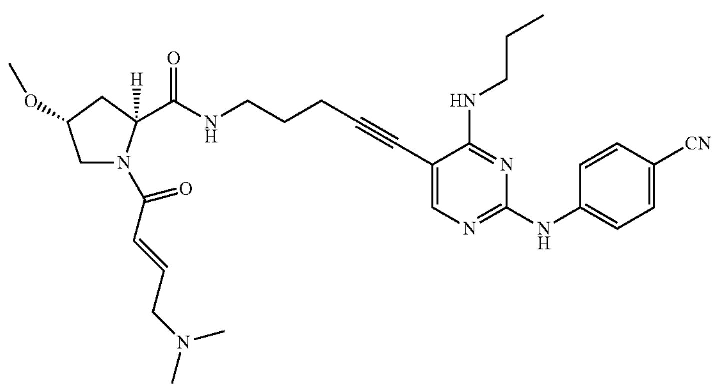 [SMILES: CCCNc1nc(Nc2ccc(C#N)cc2)ncc1C#CCCCNC(=O)[C@@H]1C[C@@H](OC)CN1C(=O)/C=C/CN(C)C] | ¹H-NMR (CDCl₃) δ: 7.97 (1H, s), 7.76 (2H, d, J = 9.2Hz), 7.56 (2H, d, J = 9.2Hz), 7.36-7.31 (1H, m), 7.26-7.23 (1H, m), 6.94 (1H, dt, J = 15.2, 5.9Hz), 6.39-6.33 (1H, m), 6.28 (1H, d, J = 15.2Hz), 4.73 (1H, dd, J = 8.3, 4.3Hz), 4.22-4.15 (1H, m), 3.76 (1H, dd, J = 10.6, 5.9Hz), 3.58 (1H, dd, J = 10.6, 4.6Hz), 3.52-3.41 (4H, m), 3.35 (3H, s), 3.10 (2H, d, J = 5.9Hz), 2.72-2.64 (1H, m), 2.47 (2H, t, J = 6.9Hz), 2.26 (6H, s), 2.02-1.92 (1H, m), 1.81-1.67 (4H, m), 1.00 (3H, t, J = 7.3Hz) |

TABLE 107

| Compound No. | Structure | Physicochemical data |
|---|---|---|
| 7-61 | 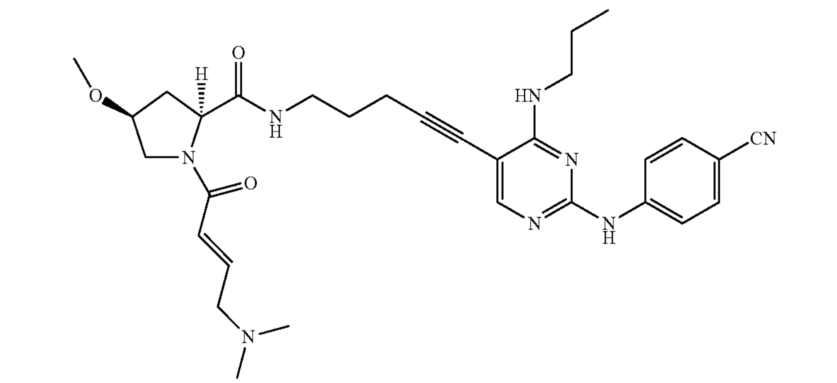 [SMILES: CCCNc1nc(Nc2ccc(C#N)cc2)ncc1C#CCCCNC(=O)[C@@H]1C[C@H](OC)CN1C(=O)/C=C/CN(C)C] | MS m/z (M + H): 573.4 |
| 7-62 | 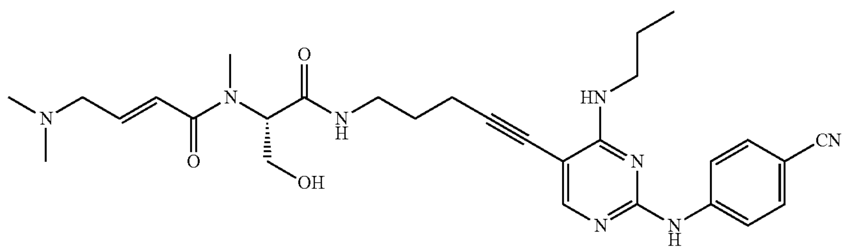 [SMILES: CCCNc1nc(Nc2ccc(C#N)cc2)ncc1C#CCCCNC(=O)[C@H](CO)N(C)C(=O)/C=C/CN(C)C] | ¹H-NMR (CDCl₃) δ: 7.98 (1H, s), 7.76 (2H, d, J = 9.0Hz), 7.57 (2H, d, J = 9.0Hz), 7.22 (1H, brs), 6.97 (1H, dt, J = 15.0, 6.0Hz), 6.66 (1H, brs), 6.47 (1H, d, J = 15.0Hz), 6.23 (1H, brs), 5.05 (1H, t, J = 5.0Hz), 4.16-3.95 (2H, m), 3.52-3.45 (4H, m), 3.14-3.10 (5H, m), 2.48 (2H, t, J = 6.6Hz), 2.28 (6H, s), 1.83-1.65 (5H, m), 1.00 (3H, t, J = 7.8Hz) |
| 7-63 | 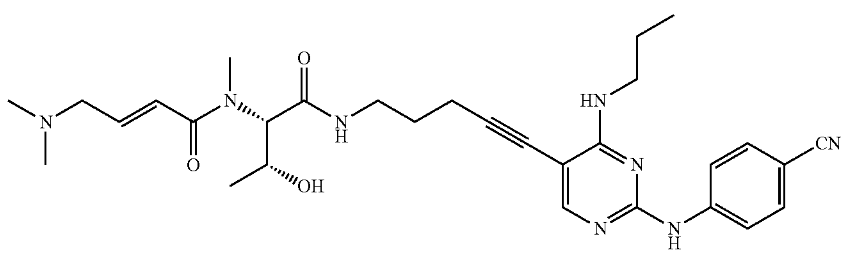 [SMILES: CCCNc1nc(Nc2ccc(C#N)cc2)ncc1C#CCCCNC(=O)[C@H]([C@@H](C)O)N(C)C(=O)/C=C/CN(C)C] | ¹H-NMR (CDCl₃) δ: 7.99 (1H, s), 7.76 (2H, d, J = 9.0Hz), 7.57 (2H, d, J = 9.0Hz), 7.17 (1H, brs), 6.97 (1H, dt, J = 15.0, 6.0Hz), 6.57 (1H, brs), 6.51 (1H, d, J = 15.0Hz), 6.24 (1H, brs), 4.86 (1H, d, J = 5.4Hz), 4.47-4.38 (1H, m), 3.52-3.45 (4H, m), 3.23 (3H, s), 3.13-3.08 (2H, m), 2.47 (2H, t, J = 7.5Hz), 2.28 (6H, s), 1.82-1.59 (5H, m), 1.21 (3H, d, J = 6.0 Hz), 1.00 (3H, t, J = 7.2Hz) |
| 7-64 | 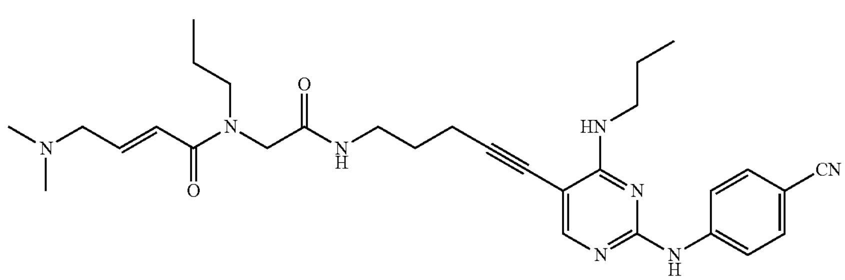 [SMILES: CCCNc1nc(Nc2ccc(C#N)cc2)ncc1C#CCCCNC(=O)CN(CCC)C(=O)/C=C/CN(C)C] | ¹H-NMR (CDCl₃) δ: 7.98 (1H, s), 7.76 (2H, d, J = 9.0Hz), 7.57 (2H, d, J = 9.0Hz), 7.18 (1H, brs), 6.97 (1H, dt, J = 15.0, 6.0Hz), 6.86 (1H, brs), 6.43 (1H, d, J = 15.0Hz), 6.26 (1H, brs), 4.02 (2H, s), 3.52-3.39 (6H, m), 3.11 (2H, d, J = 6.0Hz), 2.47 (2H, t, J = 6.6Hz), 2.28 (6H, s), 1.81-1.63 (6H, m), 1.00 (3H, t, J = 7.2Hz), 0.93 (3H, t, J = 7.2Hz) |

TABLE 107-continued
| Compound No. | Structure | Physicochemical data |
|---|---|---|
| 7-65 | 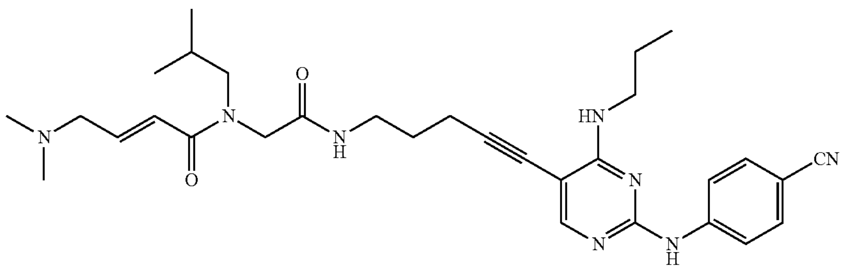 [SMILES: CCCNc1nc(Nc2ccc(C#N)cc2)ncc1C#CCCCNC(=O)CN(CC(C)C)C(=O)/C=C/CN(C)C] | ¹H-NMR (CDCl₃) δ: 7.98 (1H, s), 7.76 (2H, d, J = 9.0Hz), 7.56 (2H, d, J = 9.0Hz), 7.23 (1H, brs), 6.97 (2H, dt, J = 15.0, 6.0Hz), 6.44 (1H, d, J = 15.0Hz), 6.27 (1H, brs), 4.03 (2H, s), 3.54-3.40 (4H, m), 3.28 (2H, d, J = 7.2Hz), 3.10 (2H, d, J = 6.0Hz), 2.47 (2H, t, J = 6.6Hz), 2.27 (6H, s), 2.13-1.90 (1H, m), 1.81-1.66 (4H, m), 1.00 (3H, t, J = 7.5Hz), 0.93 (6H, d, J = 6.6Hz) |
TABLE 108
| Compound No. | Structure | Physicochemical data |
|---|---|---|
| 7-66 | 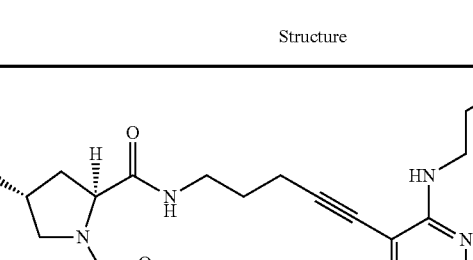 | ¹H-NMR (CDCl₃) δ: 7.95 (1H, s), 7.85-7.78 (1H, m), 7.36-7.30 (1H, m), 7.24-7.17 (1H, m), 7.11-7.05 (1H, m), 7.08-7.05 (1H, m), 6.94 (1H, dt, J = 15.2, 5.9Hz), 6.67 (1H, td, J = 8.3, 2.4Hz), 6.28 (1H, d, J = 15.2Hz), 6.24-6.17 (1H, m), 4.76 (1H, dd, J = 8.3, 5.0Hz). 4.70-4.64 (1H, m), 3.77 (1H, dd, J = 10.6, 5.0Hz), 3.56 (1H, dd, J = 10.6, 5.0Hz), 3.55-3.37 (4H, m), 3.10 (2H, d, J = 5.9Hz), 2.72-2.63 (1H, m), 2.47 (2H, t, J = 6.9Hz), 2.28-2.22 (1H, m), 2.26 (6H, s), 2.03-1.92 (1H, m), 1.82-1.63 (4H, m), 1.00 (3H, t, J = 7.6Hz) |

| Compound No. | Structure | Physicochemical data |
|---|---|---|
| 7-67 | 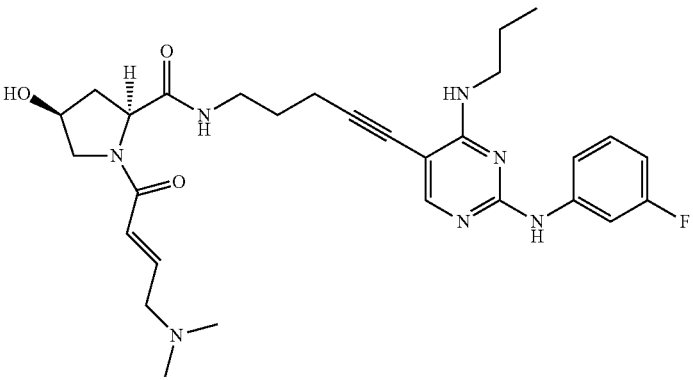 [SMILES: CCCNc1nc(Nc2cccc(F)c2)ncc1C#CCCCNC(=O)[C@@H]1C[C@H](O)CN1C(=O)/C=C/CN(C)C] | ¹H-NMR (CDCl₃) δ: 7.96 (1H, s), 7.84-7.78 (1H, m), 7.74-7.69 (1H, m), 7.26-7.16 (1H, m), 7.15-7.11 (1H, m), 7.15-7.09 (1H, m), 6.97 (1H, dt, J = 15.2, 5.9Hz), 6.71-6.63 (1H, m), 6.26 (1H, d, J = 15.2Hz), 6.04-5.98 (1H, m), 5.62-5.55 (1H, m), 4.79 (1H, d, J = 8.6Hz), 4.53-4.46 (1H, m), 3.77-3.67 (2H, m), 3.52-3.42 (4H, m), 3.10 (2H, d, J = 5.9Hz), 2.50 (2H, t, J = 6.9Hz), 2.45-2.38 (1H, m), 2.26 (6H, s), 2.18-2.09 (1H, m), 1.85-1.76 (2H, m), 1.74-1.65 (2H, m), 1.00 (3H, t, J = 7.3Hz) |
| 7-68 | 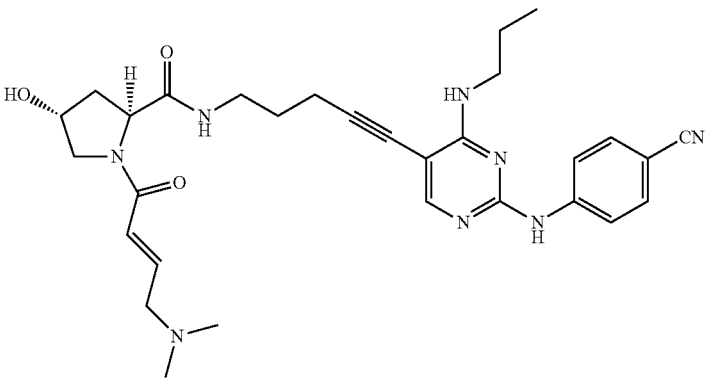 [SMILES: CCCNc1nc(Nc2ccc(C#N)cc2)ncc1C#CCCCNC(=O)[C@@H]1C[C@@H](O)CN1C(=O)/C=C/CN(C)C] | ¹H-NMR (CDCl₃) δ: 7.97 (1H, s), 7.76 (2H, d, J = 8.6Hz), 7.57 (2H, d, J = 8.6Hz), 7.36-7.28 (1H, m), 7.31-7.23 (1H, m), 6.94 (1H, dt, J = 15.2, 5.9Hz), 6.34-6.28 (1H, m), 6.29 (1H, d, J = 15.2Hz), 4.76 (1H, dd, J = 8.3, 5.0Hz), 4.70-4.64 (1H, m), 3.77 (1H, dd, J = 10.9, 5.6Hz), 3.57 (1H, dd, J = 10.6, 4.6Hz), 3.51-3.41 (4H, m), 3.10 (2H, d, J = 5.9Hz), 2.72-2.63 (1H, m), 2.47 (2H, t, J = 6.6Hz), 2.28-2.21 (1H, m), 2.26 (6H, s), 2.04-1.94 (1H, m), 1.80-1.66 (4H, m), 1.00 (3H, t, J = 7.6Hz) |

TABLE 109

| Compound No. | Structure | Physicochemical data |
|---|---|---|
| 7-69 | 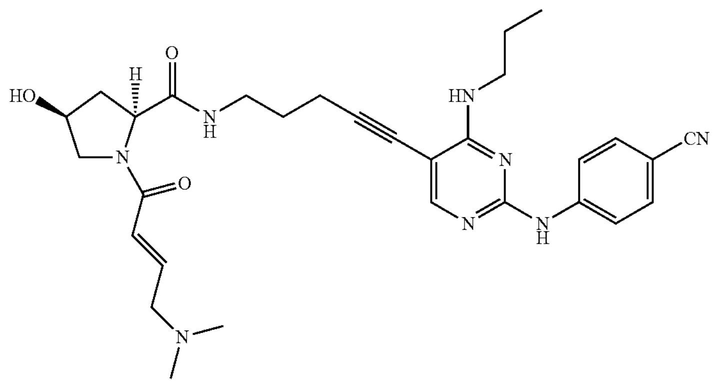 [SMILES: CCCNc1nc(Nc2ccc(C#N)cc2)ncc1C#CCCCNC(=O)[C@@H]1C[C@H](O)CN1C(=O)/C=C/CN(C)C] | ¹H-NMR (CDCl₃) δ: 7.97 (1H, s), 7.78 (2H, d, J = 8.6Hz), 7.76-7.69 (1H, m), 7.56 (2H, d, J = 8.6Hz), 7.41-7.38 (1H, m), 6.96 (1H, dt, J = 15.2, 5.9Hz), 6.27 (1H, d, J = 15.2Hz), 6.14-6.08 (1H, m), 5.60-5.54 (1H, m), 4.79 (1H, d, J = 8.6Hz), 4.53-4.47 (1H, m), 3.79-3.66 (2H, m), 3.51-3.42 (4H, m), 3.10 (2H, d, J = 5.9Hz), 2.50 (2H, t, J = 6.6Hz), 2.46-2.37 (1H, m), 2.26 (6H, s), 2.20-2.09 (1H, m), 1.86-1.76 (2H, m), 1.75-1.63 (2H, m), 0.99 (3H, t, J = 7.3Hz) |
| 7-70 | 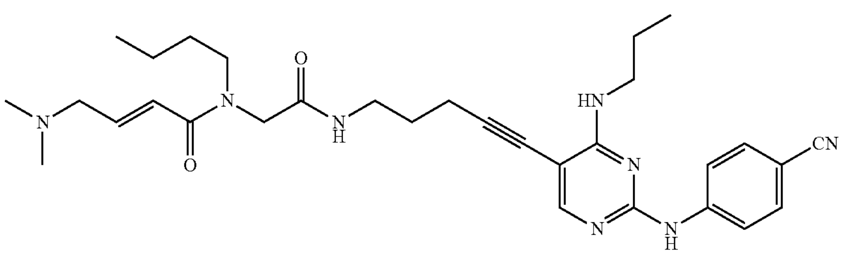 [SMILES: CCCCN(CC(=O)NCCCC#Cc1cnc(Nc2ccc(C#N)cc2)nc1NCCC)C(=O)/C=C/CN(C)C] | ¹H-NMR (CDCl₃) δ: 7.98 (1H, s), 7.76 (2H, d, J = 9.0Hz), 7.56 (2H, d, J = 9.0Hz), 7.26 (1H, brs), 6.97 (1H, dt, J = 15.0, 6.0Hz), 6.86 (1H, brs), 6.42 (1H, d, J = 15.0Hz), 6.29 (1H, brs), 4.02 (2H, s), 3.52-3.40 (6H, m), 3.11 (2H, d, J = 6.0Hz), 2.47 (2H, t, J = 7.5Hz), 2.27 (6H, s), 1.81-1.56 (6H, m), 1.39-1.26 (2H, m), 1.00 (3H, t, J = 7.5Hz), 0.94 (3H, t, J = 7.5Hz) |
| 7-71 | 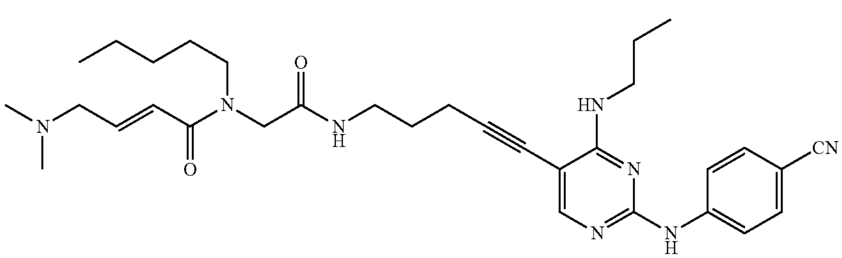 [SMILES: CCCCCN(CC(=O)NCCCC#Cc1cnc(Nc2ccc(C#N)cc2)nc1NCCC)C(=O)/C=C/CN(C)C] | ¹H-NMR (CDCl₃) δ: 7.98 (1H, s), 7.76 (2H, d, J = 9.0Hz), 7.56 (2H, d, J = 9.0Hz), 7.34 (1H, brs), 6.97 (1H, dt, J = 15.0, 6.0Hz), 6.87 (1H, brs), 6.42 (1H, d, J = 15.0Hz), 6.29 (1H, brs), 4.02 (2H, s), 3.52-3.41 (6H, m), 3.10 (2H, d, J = 6.0Hz), 2.47 (2H, t, J = 7.5Hz), 2.27 (6H, s), 1.79-1.58 (6H, m), 1.37-1.23 (4H, m), 1.00 (3H, t, J = 7.5Hz), 0.90 (3H, t, J = 7.5Hz) |

TABLE 109-continued

| Compound No. | Structure | Physicochemical data |
|---|---|---|
| 7-72 | 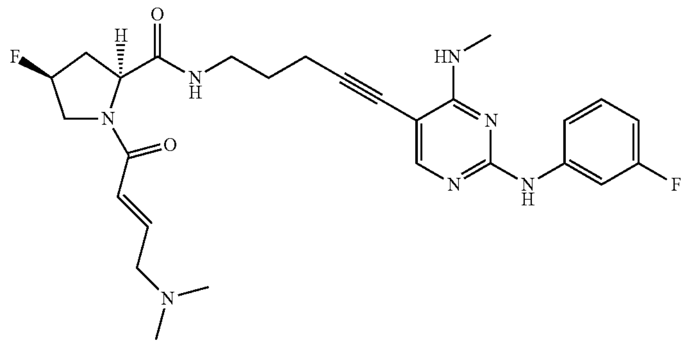 [SMILES: CNc1nc(Nc2cccc(F)c2)ncc1C#CCCCNC(=O)[C@@H]1C[C@H](F)CN1C(=O)/C=C/CN(C)C] | MS m/z (M + H): 526.4 |
| 7-73 | 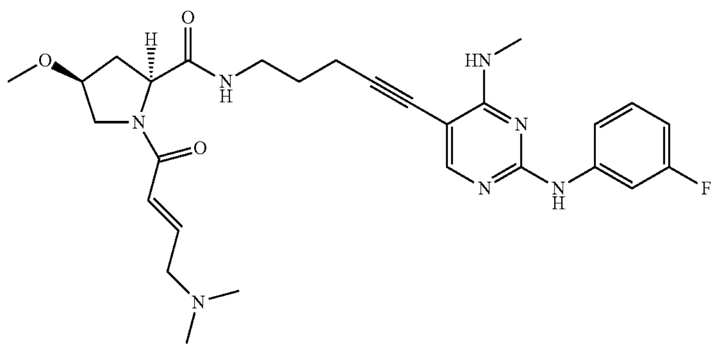 [SMILES: CNc1nc(Nc2cccc(F)c2)ncc1C#CCCCNC(=O)[C@@H]1C[C@H](OC)CN1C(=O)/C=C/CN(C)C] | MS m/z (M + H): 538.4 |

TABLE 110

| Compound No. | Structure | Physicochemical data |
|---|---|---|
| 7-74 | 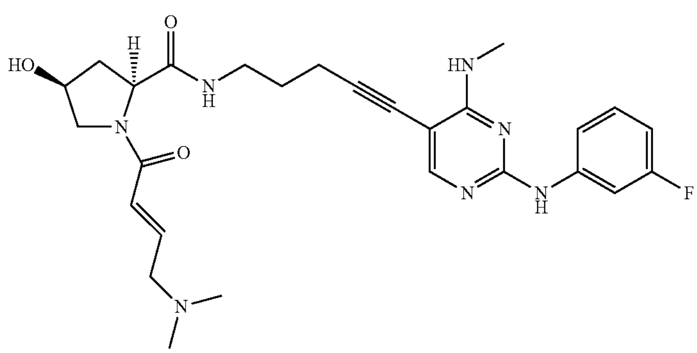 [SMILES: CNc1nc(Nc2cccc(F)c2)ncc1C#CCCCNC(=O)[C@@H]1C[C@H](O)CN1C(=O)/C=C/CN(C)C] | $^1$H-NMR (CDCl$_3$) δ: 7.95 (1H, s), 7.84-7.78 (1H, m), 7.76-7.70 (1H, m), 7.26-7.16 (1H, m), 7.20-7.15 (1H, m), 7.19-7.13 (1H, m), 6.96 (1H, dt, J = 15.2, 5.9Hz), 6.71-6.64 (1H, m), 6.27 (1H, d, J = 15.2Hz), 6.12-6.06 (1H, m), 5.67-5.60 (1H, m), 4.80 (1H, d, J = 8.6Hz), 4.53-4.47 (1H, m), 3.79-3.67 (2H, m), 3.53-3.45 (2H, m), 3.11 (2H, d, J = 5.9Hz), 3.08 (3H, d, J = 4.6Hz), 2.49 (2H, t, J = 6.6Hz), 2.46-2.38 (1H, m), 2.27 (6H, s), 2.20-2.09 (1H, m), 1.88-1.73 (2H, m) |

TABLE 110-continued

| Compound No. | Structure | Physicochemical data |
|---|---|---|
| 7-75 | 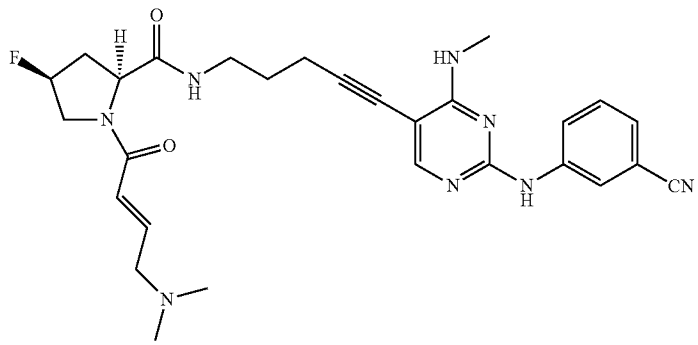 [SMILES: CNc1nc(Nc2cccc(C#N)c2)ncc1C#CCCCNC(=O)[C@@H]1C[C@H](F)CN1C(=O)/C=C/CN(C)C] | MS m/z (M + H): 533.4 |
| 7-76 | 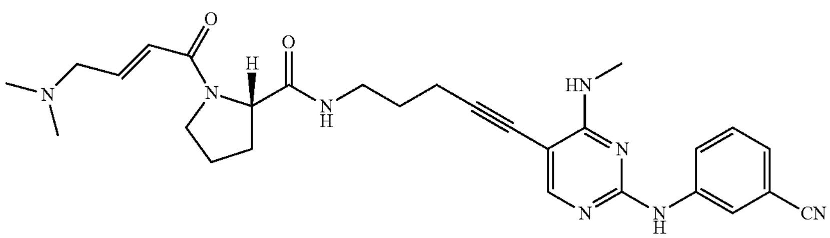 [SMILES: CNc1nc(Nc2cccc(C#N)c2)ncc1C#CCCCNC(=O)[C@@H]1CCCN1C(=O)/C=C/CN(C)C] | ¹H-NMR (CDCl₃) δ: 8.39 (1H, s), 7.99 (1H, s), 7.95 (1H, s), 7.67-7.59 (2H, m), 7.35 (1H, t, J = 7.9Hz), 7.23 (1H, d, J = 7.9Hz), 6.96 (1H, dt, J = 15.2, 5.9Hz), 6.52-6.49 (1H, m), 6.34 (1H, d, J = 15.2Hz), 4.69 (1H, d, J = 6.6Hz), 3.73-3.66 (1H, m), 3.58-3.42 (3H, m), 3.12-3.08 (5H, m), 2.49-2.31 (3H, m), 2.26 (6H, s), 2.21-1.85 (3H, m), 1.78-1.73 (2H, m) |
| 7-77 | 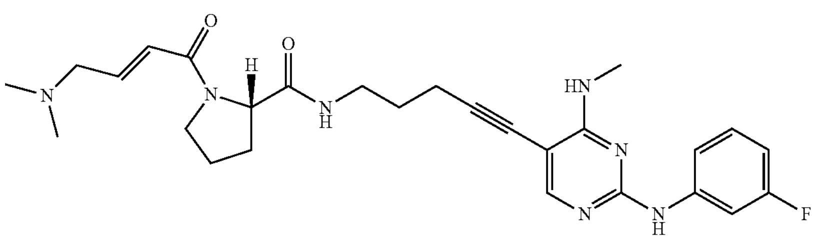 [SMILES: CNc1nc(Nc2cccc(F)c2)ncc1C#CCCCNC(=O)[C@@H]1CCCN1C(=O)/C=C/CN(C)C] | ¹H-NMR (CDCl₃) δ: 7.95 (1H, s), 7.85-7.79 (1H, m), 7.45 (1H, brs), 7.20 (1H, dd, J = 7.9, 6.6Hz), 7.11 (1H, d, J = 7.9Hz), 7.00-6.92 (2H, m), 6.70-6.65 (1H, dt, J = 8.1, 1.8Hz), 6.39-6.30 (2H, m), 4.69 (1H, d, J = 6.6Hz), 3.71-3.64 (1H, m), 3.59-3.37 (3H, m), 3.11-3.09 (5H, m), 2.55-2.43 (4H, m), 2.27 (6H, s), 1.88-1.71 (4H, m) |
| 7-78 | 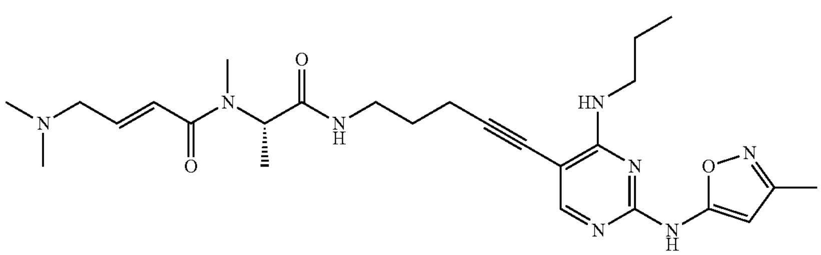 | ¹H-NMR (CDCl₃) δ: 8.22 (1H, s), 6.95 (1H, dt, J = 15.2, 5.9Hz), 6.59-6.49 (2H, m), 6.43 (2H, d, J = 15.2Hz), 6.18 (1H, s), 5.20 (1H, q, J = 7.2Hz), 3.56-3.32 (4H, m), 3.11 (2H, d, J = 5.9Hz), 3.00 (3H, s), 2.43 (2H, t, J = 6.6Hz), 2.28 (3H, s), 2.27 (6H, s), 1.86-1.66 (4H, m), 1.36 (3H, d, J = 7.2Hz), 1.01 (3H, t, J = 7.3Hz) |

TABLE 111
| Compound No. | Structure | Physicochemical data |
|---|---|---|
| 7-79 | 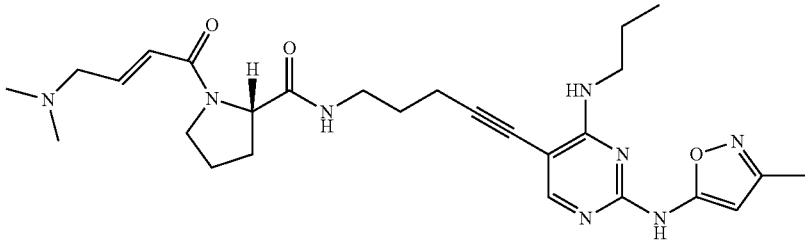 | ¹H-NMR (CDCl₃) δ: 8.21 (1H, s), 7.41 (1H, t, J = 5.9Hz), 6.97 (1H, dt, J = 15.2, 5.9Hz), 6.57 (1H, t, J = 5.9Hz), 6.34 (1H, d, J = 15.2Hz), 6.18 (1H, s), 4.69 (1H, dd, J = 6.6, 3.3Hz), 3.75-3.34 (6H, m), 3.11 (2H, d, J = 5.9Hz), 2.55-2.50 (1H, m), 2.46 (2H, t, J = 6.9Hz), 2.28 (3H, s), 2.27 (6H, s), 2.22-1.96 (2H, m), 1.92-1.61 (6H, m), 1.00 (3H, t, J = 7.6Hz) |
| 7-80 | 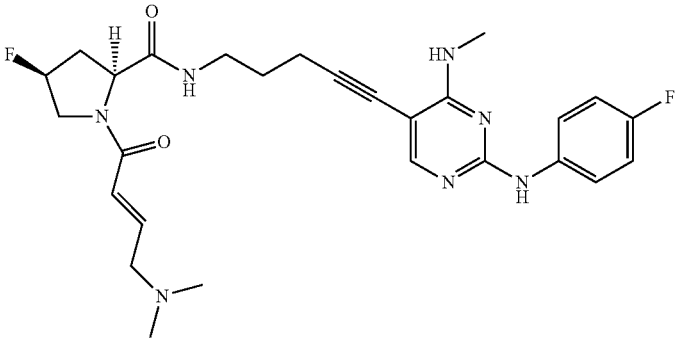 [SMILES: CNc1nc(Nc2ccc(F)cc2)ncc1C#CCCCNC(=O)[C@@H]1C[C@H](F)CN1C(=O)/C=C/CN(C)C] | MS m/z (M + H): 526.5 |
| 7-81 | 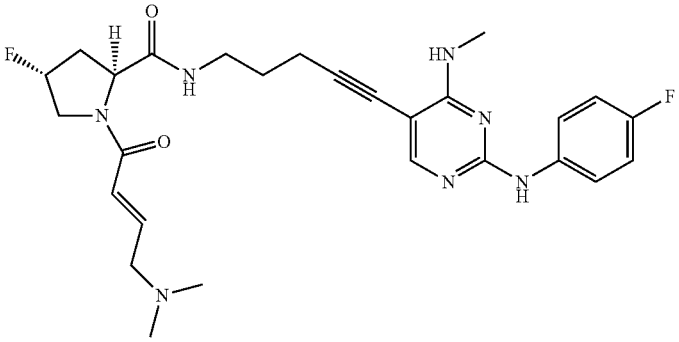 [SMILES: CNc1nc(Nc2ccc(F)cc2)ncc1C#CCCCNC(=O)[C@@H]1C[C@@H](F)CN1C(=O)/C=C/CN(C)C] | ¹H-NMR (CDCl₃) δ: 7.93 (1H, s), 7.63-7.56 (2H, m), 7.44-7.38 (1H, m), 7.24-7.21 (1H, m), 7.03-6.96 (2H, m), 6.94 (1H, dt, J = 15.2, 5.9Hz), 6.27 (1H, d, J = 15.2Hz), 6.17-6.12 (1H, m), 5.34 (1H, d, J = 52.8Hz), 4.84-4.77 (1H, m), 3.98 (1H, dd, J = 20.1, 12.2Hz), 3.73 (1H, ddd, J = 32.4, 12.2, 3.6Hz), 3.51-3.41 (2H, m), 3.10 (2H, d, J = 5.9Hz), 3.04 (3H, d, J = 4.6Hz), 2.87-2.67 (1H, m), 2.47 (2H, t, J = 6.6Hz), 2.42-2.29 (1H, m), 2.26 (6H, s), 1.83-1.72 (2H, m) |
| 7-82 | 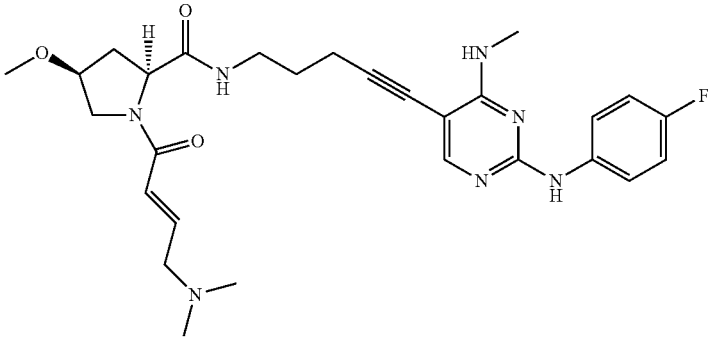 [SMILES: CNc1nc(Nc2ccc(F)cc2)ncc1C#CCCCNC(=O)[C@@H]1C[C@H](OC)CN1C(=O)/C=C/CN(C)C] | MS m/z (M + H): 538.5 |

TABLE 111-continued

| Compound No. | Structure | Physicochemical data |
|---|---|---|
| 7-83 | 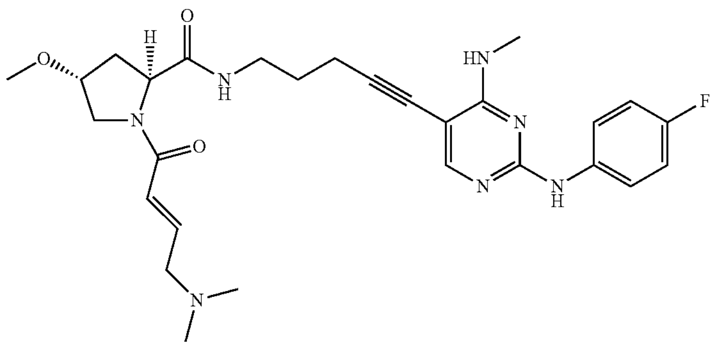 [SMILES: CNc1nc(Nc2ccc(F)cc2)ncc1C#CCCCNC(=O)[C@@H]1C[C@@H](OC)CN1C(=O)/C=C/CN(C)C] | ¹H-NMR (CDCl₃) δ: 7.93 (1H, s), 7.62-7.55 (2H, m), 7.37-7.32 (1H, m), 7.04-6.96 (2H, m), 7.04-6.99 (1H, m), 6.94 (1H, dt, J = 15.2, 5.9Hz), 6.28 (1H, d, J = 15.2Hz), 6.27-6.20 (1H, m), 4.74 (1H, dd, J = 8.3, 5.0Hz), 4.23-4.16 (1H, m), 3.76 (1H, dd, J = 10.6, 5.0Hz), 3.58 (1H, dd, J = 10.9, 5.0Hz), 3.49-3.40 (2H, m), 3.35 (3H, s), 3.10 (2H, d, J = 5.9Hz), 3.06 (3H, d, J = 4.6Hz), 2.72-2.64 (1H, m), 2.46 (2H, t, J = 6.9Hz), 2.26 (6H, s), 2.02-1.93 (1H, m), 1.82-1.73 (2H, m) |

TABLE 112

| Compound No. | Structure | Physicochemical data |
|---|---|---|
| 7-84 | 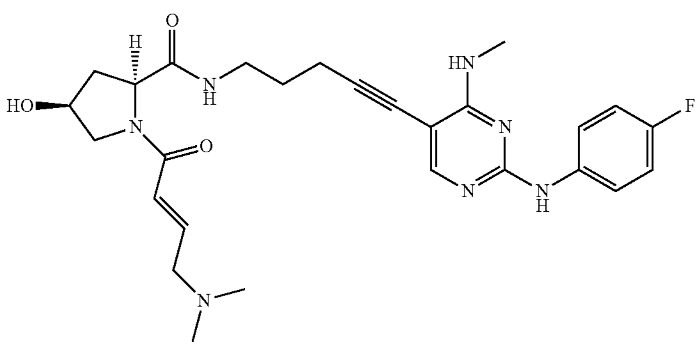 [SMILES: CNc1nc(Nc2ccc(F)cc2)ncc1C#CCCCNC(=O)[C@@H]1C[C@H](O)CN1C(=O)/C=C/CN(C)C] | ¹H-NMR (CDCl₃) δ: 7.90 (1H, s), 7.80-7.74 (1H, m), 7.65-7.57 (2H, m), 7.52-7.49 (1H, m), 7.04-6.95 (2H, m), 7.01-6.95 (1H, m), 6.96 (1H, dt, J = 15.2, 5.9 Hz), 6.27 (1H, d, J = 15.2 Hz), 6.09-6.05 (1H, m), 4.79 (1H, d, J = 8.6 Hz), 4.52-4.47 (1H, m), 3.79-3.66 (2H, m), 3.54-3.44 (2H, m), 3.11 (2H, d, J = 5.9 Hz), 3.04 (3H, d, J = 5.3 Hz), 2.49 (2H, t, J = 6.6 Hz), 2.41-2.37 (1H, m), 2.26 (6H, s), 2.20-2.10 (1H, m), 1.87-1.74 (2H, m) |
| 7-85 | 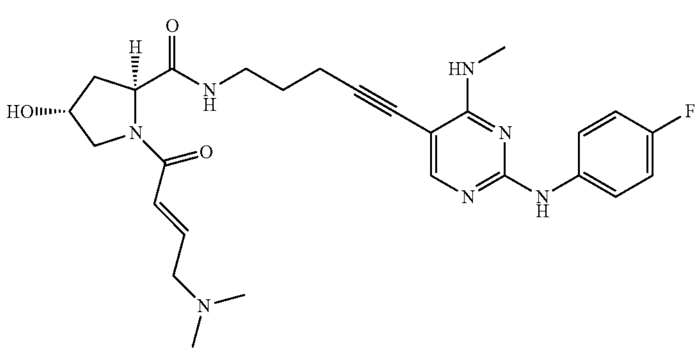 [SMILES: CNc1nc(Nc2ccc(F)cc2)ncc1C#CCCCNC(=O)[C@@H]1C[C@@H](O)CN1C(=O)/C=C/CN(C)C] | ¹H-NMR (CDCl₃) δ: 7.92 (1H, s), 7.62-7.55 (2H, m), 7.32-7.24 (1H, m), 7.15-7.11 (1H, m), 7.05-6.95 (2H, m), 6.97-6.89 (1H, m), 6.30 (1H, d, J = 15.2 Hz), 6.29-6.24 (1H, m), 4.77 (1H, dd, J = 7.9, 4.6 Hz), 4.71-4.65 (1H, m), 3.77 (1H, dd, J = 10.6, 4.6 Hz), 3.57 (1H, dd J = 10.9, 4.6 Hz), 3.50-3.40 (2H, m), 3.12 (2H, d, J = 5.9 Hz), 3.06 (3H, d, J = 4.6 Hz), 2.76-2.66 (1H, m), 2.46 (2H, t, J = 6.6 Hz), 2.36-2.33 (1H, m), 2.28 (6H, s), 2.04-1.93 (1H, m), 1.80-1.73 (2H, m) |

TABLE 112-continued

| Compound No. | Structure | Physicochemical data |
|---|---|---|
| 7-86 | 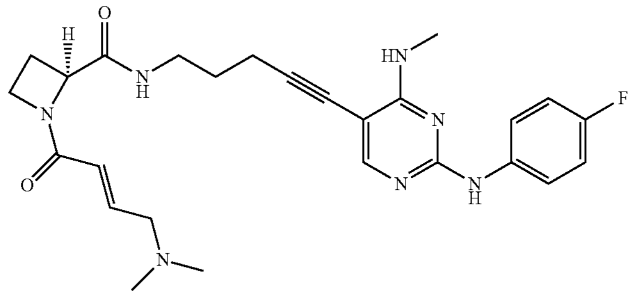 [SMILES: CNc1nc(Nc2ccc(F)cc2)ncc1C#CCCCNC(=O)[C@@H]1CCN1C(=O)/C=C/CN(C)C] | ¹H-NMR (CDCl₃) δ: 8.06-7.99 (1H, m), 7.94 (1H, s), 7.62-7.55 (2H, m), 7.13-7.10 (1H, m), 7.00 (2H, dd, J = 8.6, 8.6 Hz), 6.93 (1H, dt, J = 15.2, 5.9 Hz), 6.29-6.20 (1H, m), 6.04 (1H, d, J = 15.2 Hz), 4.95 (1H, dd, J = 9.2, 6.6 Hz). 4.19-4.11 (2H, m), 3.59-3.39 (2H, m), 3.10 (2H, d, J = 5.9 Hz), 3.06 (3H, d, J = 5.3 Hz), 2.81-2.70 (1H, m), 2.49 (2H, t, J = 6.6 Hz), 2.48-2.40 (1H, m), 2.26 (6H, s), 1.84-1.75 (2H, m) |
| 7-87 | 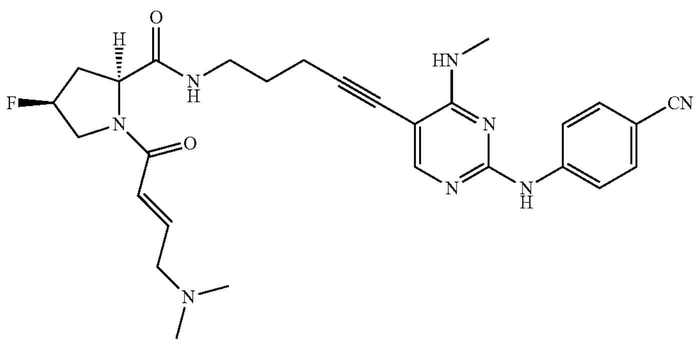 [SMILES: CNc1nc(Nc2ccc(C#N)cc2)ncc1C#CCCCNC(=O)[C@@H]1C[C@H](F)CN1C(=O)/C=C/CN(C)C] | MS m/z (M + H): 533.5 |

TABLE 113

| Compound No. | Structure | Physicochemical data |
|---|---|---|
| 7-88 | 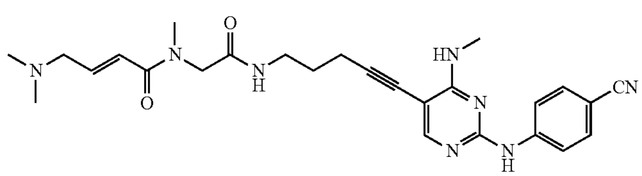 [SMILES: CNc1nc(Nc2ccc(C#N)cc2)ncc1C#CCCCNC(=O)CN(C)C(=O)/C=C/CN(C)C] | ¹H-NMR (CDCl₃) δ: 7.97 (1H, s), 7.79 (2H, d, J = 9.2 Hz), 7.73 (1H, s), 7.57 (2H, d, J = 8.6 Hz), 6.95 (1H, dt, J = 15.2, 5.9 Hz), 6.73 (1H, t, J = 5.9 Hz), 6.47 (1H, d, J = 15.2 Hz), 6.41-6.28 (1H, m), 4.06 (2H, s), 3.55-3.41 (2H, m), 3.22 (3H, s), 3.12-3.07 (5H, m), 2.47 (2H, t, J = 6.6 Hz), 2.27 (6H, s), 1.80-1.72 (2H, m) |
| 7-89 | 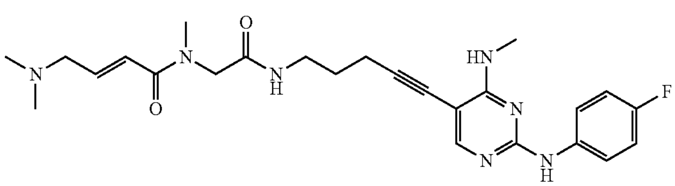 [SMILES: CNc1nc(Nc2ccc(F)cc2)ncc1C#CCCCNC(=O)CN(C)C(=O)/C=C/CN(C)C] | ¹H-NMR (CDCl₃) δ: 7.93 (1H, s), 7.63-7.55 (2H, m), 7.30 (1H, brs), 7.02-6.89 (3H, m), 6.73 (1H, brs), 6.46 (1H, d, J = 15.2 Hz), 6.17-6.14 (1H, m), 4.05 (2H, s), 3.54-3.41 (2H, m), 3.20 (3H, s), 3.10 (2H, d, J = 5.9 Hz), 3.05 (3H, d, J = 4.6 Hz), 2.46 (2H, t, J = 6.6 Hz), 2.26 (6H, s), 1.80-1.71 (2H, m) |
| 7-90 | 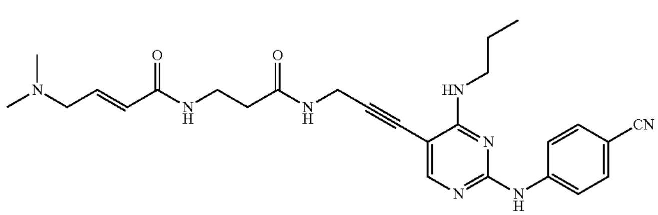 [SMILES: CCCNc1nc(Nc2ccc(C#N)cc2)ncc1C#CCNC(=O)CCNC(=O)/C=C/CN(C)C] | ¹H-NMR (CDCl₃) δ: 7.95 (1H, s), 7.82 (2H, d, J = 9.0 Hz), 7.57 (2H, d, J = 9.0 Hz), 6.74 (1H, dt, J = 15.0, 6.0 Hz), 6.33 (1H, brs), 5.94 (1H, d, J = 15.0 Hz), 4.21 (2H, s), 3.55-3.44 (4H, m), 3.35 (3H, brs), 3.05 (2H, d, J = 6.0 Hz), 2.47 (2H, t, J = 6.0 Hz), 2.25 (6H, s), 1.78-1.66 (2H, m), 1.02 (3H, t, J = 7.5 Hz) |

TABLE 113-continued

| Compound No. | Structure | Physicochemical data |
| --- | --- | --- |
| 7-91 | 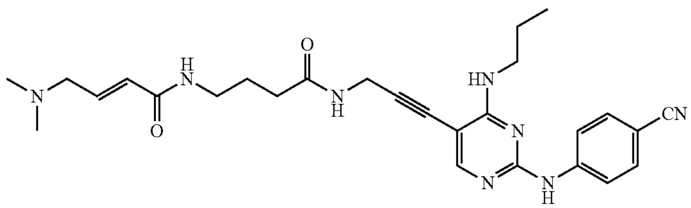 [SMILES: CCCNc1nc(Nc2ccc(C#N)cc2)ncc1C#CCNC(=O)CCCNC(=O)/C=C/CN(C)C] | ¹H-NMR (CDCl₃) δ: 7.95 (1H, s), 7.81 (2H, d, J = 9.0 Hz), 7.57 (2H, d, J = 9.0 Hz), 6.73 (1H, dt, J = 15.0, 6.0 Hz), 6.37 (1H, brs), 5.98 (1H, d, J = 15.0 Hz), 4.22 (2H, s), 3.46-3.27 (7H, m), 3.08 (2H, d, J = 6.0 Hz), 2.28-2.22 (8H, m), 1.87-1.83 (2H, m), 1.74-1.67 (2H, m), 1.0 (3H, t, J = 7.5 Hz) |
| 7-92 | 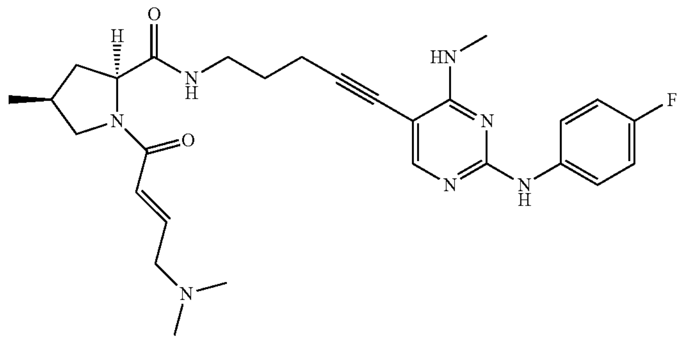 [SMILES: CNc1nc(Nc2ccc(F)cc2)ncc1C#CCCCNC(=O)[C@@H]1C[C@H](C)CN1C(=O)/C=C/CN(C)C] | ¹H-NMR (CDCl₃) δ: 7.93 (1H, s), 7.62-7.55 (2H, m), 7.13-7.07 (1H, m), 7.03-6.95 (2H, m), 6.97-6.92 (1H, m), 6.91 (1H, dt, J = 15.2, 5.9 Hz), 6.31-6.25 (1H, m), 6.31 (1H, d, J = 15.2 Hz), 4.59-4.53 (1H, m), 3.84 (1H, dd, J = 9.9, 7.3 Hz), 3.51-3.43 (2H, m), 3.16-3.05 (1H, m), 3.08 (2H, d, J = 5.9 Hz), 3.05 (3H, d, J = 5.3 Hz), 2.48 (2H, t, J = 6.6 Hz), 2.26 (6H, s), 2.24-2.18 (2H, m), 2.20-2.08 (1H, m), 1.81-1.71 (2H, m), 1.11 (3H, d, J = 5.9 Hz) |

TABLE 114

| Compound No. | Structure | Physicochemical data |
| --- | --- | --- |
| 7-93 | 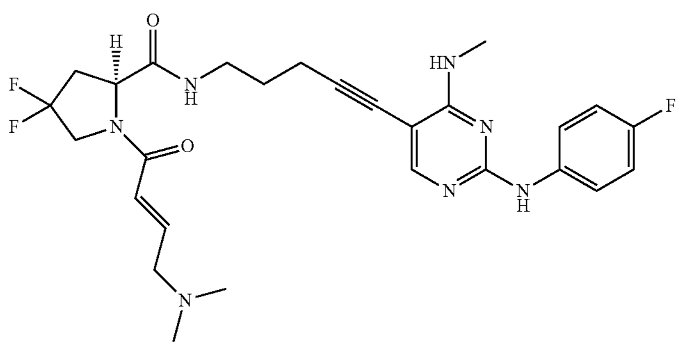 [SMILES: CNc1nc(Nc2ccc(F)cc2)ncc1C#CCCCNC(=O)[C@@H]1CC(F)(F)CN1C(=O)/C=C/CN(C)C] | ¹H-NMR (CDCl₃) δ: 7.94 (1H, s), 7.61-7.54 (2H, m), 7.14-7.09 (1H, m), 7.05-6.97 (2H, m), 7.03-6.98 (1H, m), 6.88-6.85 (1H, m), 6.22-6.17 (1H, m), 6.21 (1H, d. J = 15.2 Hz), 4.89 (1H, dd, J = 9.6, 5.0 Hz), 4.09-3.80 (2H, m), 3.52-3.45 (2H, m), 3.23-3.06 (1H, m), 3.10 (2H, d, J = 5.9 Hz), 3.06 (3H, d, J = 4.6 Hz), 2.58-2.44 (1H, m), 2.47 (2H, t, J = 6.6 Hz), 2.27 (6H, s), 1.81-1.73 (2H, m) |
| 7-94 | 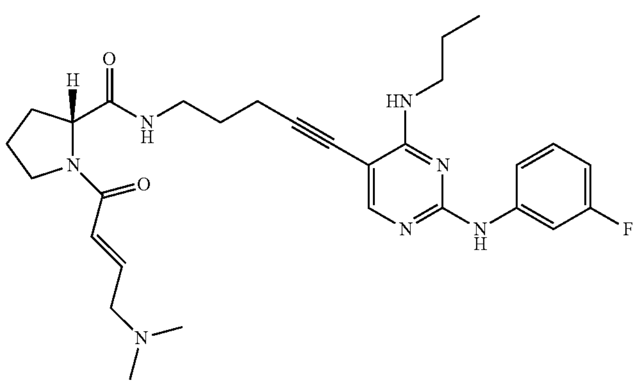 [SMILES: CCCNc1nc(Nc2cccc(F)c2)ncc1C#CCCCNC(=O)[C@H]1CCCN1C(=O)/C=C/CN(C)C] | ¹H-NMR (CDCl₃) δ: 7.95 (1H, s), 7.85-7.79 (1H, m), 7.47-7.41 (1H, m), 7.25-7.17 (1H, m), 7.11-7.05 (1H, m), 7.01-6.96 (1H, m), 6.96 (1H, dt, J = 15.2, 5.9 Hz), 6.71-6.62 (1H, m), 6.36-6.29 (1H, m), 6.33 (1H, d, J = 15.2 Hz), 4.68 (1H, d, J = 6.6 Hz), 3.70-3.63 (1H, m), 3.59-3.45 (4H, m), 3.44-3.35 (1H, m), 3.11 (2H, d, J = 5.9 Hz), 2.54-2.49 (1H, m), 2.46 (2H, t, J = 6.6 Hz), 2.27 (6H, s), 2.17-1.95 (2H, m), 1.87-1.81 (1H, m), 1.85-1.66 (4H, m), 1.01 (3H, t, J = 7.4 Hz) |

TABLE 114-continued

| Compound No. | Structure | Physicochemical data |
|---|---|---|
| 7-95 | 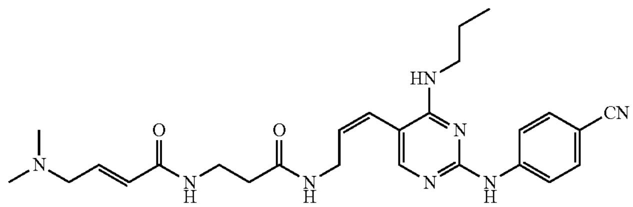 [SMILES: CCCNc1nc(Nc2ccc(C#N)cc2)ncc1/C=C\CNC(=O)CCNC(=O)/C=C/CN(C)C] | ¹H-NMR (CDCl₃) δ: 7.82 (2H, d, J = 9.0 Hz), 7.67 (1H, s), 7.57 (2H, d, J = 9.0 Hz), 6.75 (1H, dt, J = 15.0, 6.0 Hz), 6.17 (1H, d, J = 11.0 Hz), 5.95 (1H, d, J = 15.0 Hz), 5.77 (1H, dt, J = 11.0, 6.0 Hz), 5.59 (1H, brs), 3.92-3.85 (2H, m), 3.50-3.39 (4H, m), 3.14-3.00 (5H, m), 2.48-2.38 (2H, m), 2.26 (6H, s), 1.75-1.64 (2H, m), 1.00 (3H, t. J = 7.5 Hz) |
| 7-96 | 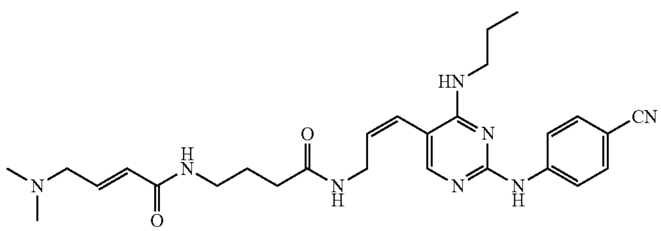 [SMILES: CCCNc1nc(Nc2ccc(C#N)cc2)ncc1/C=C\CNC(=O)CCCNC(=O)/C=C/CN(C)C] | ¹H-NMR (CDCl₃) δ: 7.82 (2H, d, J = 9.0 Hz), 7.68 (1H, s), 7.57 (2H, d, J = 9.0 Hz), 6.72 (1H, dt, J = 15.0, 6.0 Hz), 6.16 (1H, d, J = 11.0 Hz), 5.96 (1H, d, J = 15.0 Hz), 5.79 (1H, dt, J = 11.0, 6.0 Hz), 5.66 (1H, brs), 3.90-3.88 (2H, m), 3.46-3.39 (2H, m), 3.32-3.28 (2H, m), 3.07 (2H, d, J = 6.0 Hz), 3.00 (3H, brs), 2.27 (6H, s), 2.22-2.18 (2H, m), 1.84-1.80 (2H, m), 1.72-1.65 (2H, m), 1.00 (3H, t, J = 7.5 Hz) |

Example 38

1

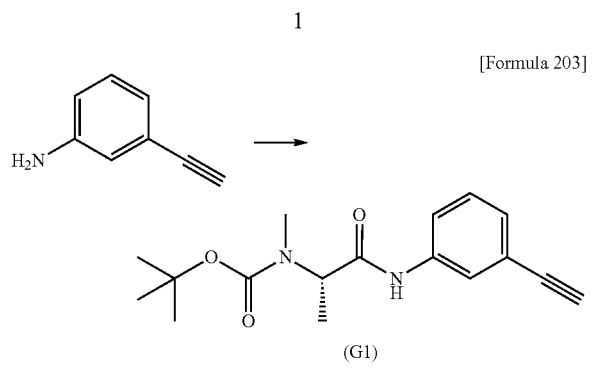

[Formula 203]

To N-Boc-N-methyl-L-alanine (2.03 g), 1-ethyl-3-(3-dimethylaminopropyl)carbodiimide hydrochloride (3.81 g) and 1-hydroxybenzotriazole monohydrate (2.70 g), N,N-dimethylformamide (20 mL) was added at room temperature, and the mixture was stirred at the same temperature for 2 hours. To the reaction mixture, N,N-diisopropylethylamine (5.2 mL) and 3-ethynylaniline (1.17 g) were added at room temperature, and the mixture was stirred at the same temperature for 1 hour and 30 minutes. To the reaction mixture, saturated aqueous sodium hydrogencarbonate and ethyl acetate were added. The organic layer was separated, washed successively with saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 80 to 50% hexane in ethyl acetate) to obtain (S)-tert-butyl (1-((3-ethynylphenyl)amino)-1-oxopropan-2-yl)(methyl)carbamate (G1, 626 mg) as white solid.

¹H-NMR (DMSO-d₆) δ: 10.04-9.86 (1H, m), 7.79 (1H, s), 7.59 (1H, d, J=7.3 Hz), 7.32 (1H, t, J=7.9 Hz), 7.15 (1H, d, J=7.9 Hz), 4.70-4.30 (1H, m), 4.18 (1H, s), 2.85 (3H, s), 1.46-1.26 (12H, m)

2

[Formula 204]

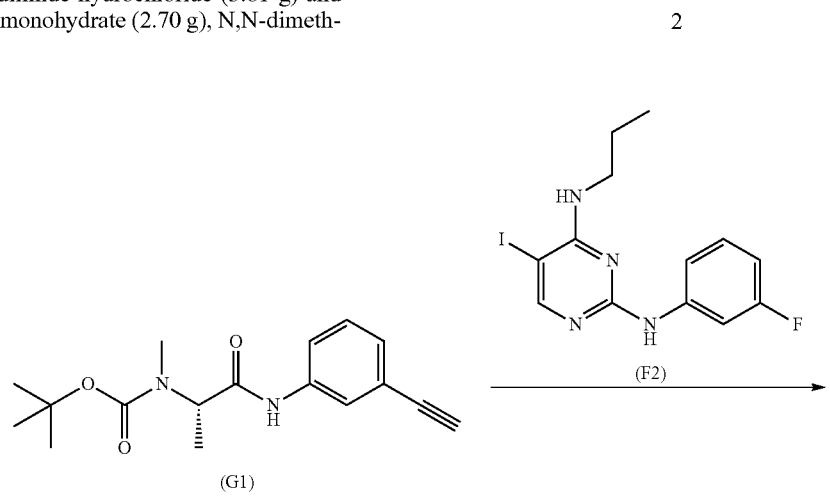

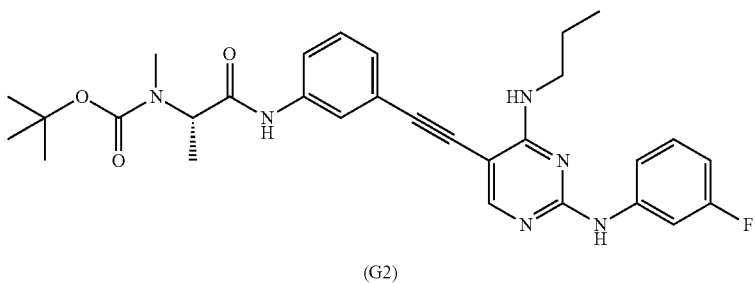

(G2)

To $N^2$-(3-fluorophenyl)-5-iodo-$N^4$-propylpyrimidine-2,4-diamine (F2, 186 mg), bis(triphenylphosphine)palladium(II) dichloride (35 mg) and copper(I) iodide (19 mg), N,N-dimethylformamide (5 mL), triethylamine (348 μL), and (S)-tert-butyl (1-(3-ethynylphenyl)amino)-1-oxopropan-2-yl)(methyl)carbamate (G1, 166 mg) were added at room temperature, and the mixture was stirred at the same temperature for 1 hour and 20 minutes. To the reaction mixture, saturated aqueous sodium hydrogencarbonate and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 80 to 35% hexane in ethyl acetate) to obtain oily (S)-tert-butyl (1-((3-((2-((3-fluorophenyl)amino)-4-(propylamino)pyrimidin-5-yl)ethynyl)phenyl)amino)-1-oxopropan-2-yl)(methyl)carbamate (G2, 265 mg).

MS m/z (M+H): 547.2

To a solution of (S)-tert-butyl (1-((3-((2-((3-fluorophenyl)amino)-4-(propylamino)pyrimidin-5-yl)ethynyl)phenyl)amino)-1-oxopropan-2-yl)(methyl)carbamate (G2, 265 mg) in 1,4-dioxane (4 mL), a 4.0 mol/L solution of hydrochloric acid in 1,4-dioxane (4 mL) was added at room temperature, and the mixture was stirred at the same temperature for 2 hours. The solvent was evaporated under reduced pressure. To the obtained residue, saturated aqueous sodium hydrogencarbonate and ethyl acetate were added. The organic layer was separated, and washed successively with saturated aqueous sodium hydrogencarbonate and saturated aqueous sodium chloride, and then the solvent was evaporated under reduced pressure. The obtained solid matter was recrystallized from a mixed solvent of ethyl acetate and methanol to obtain (S)—N-(3-((2-((3-fluorophenyl)amino)-4-(propylamino)pyrimidin-5-yl)ethynyl)phenyl)-2-(methylamino)propanamide (G3, 105 mg).

MS m/z (M+H): 447.2

[Formula 205]

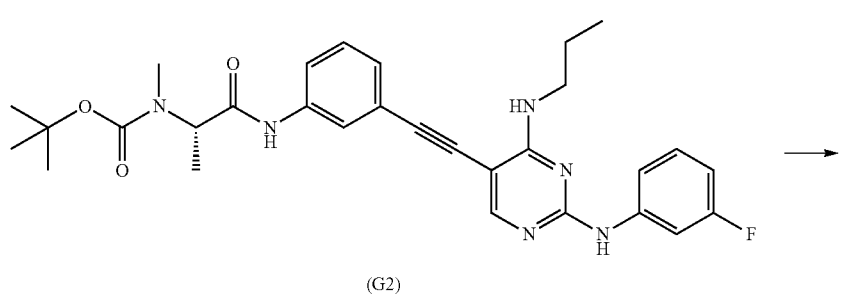

(G2)

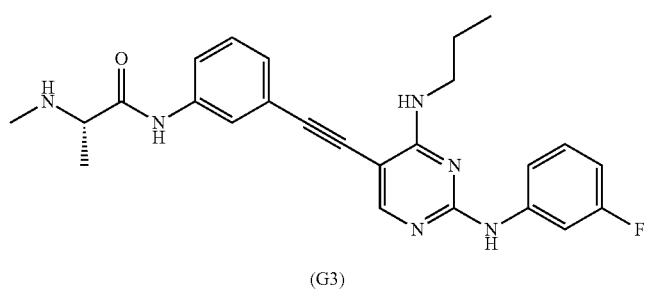

(G3)

[Formula 206]

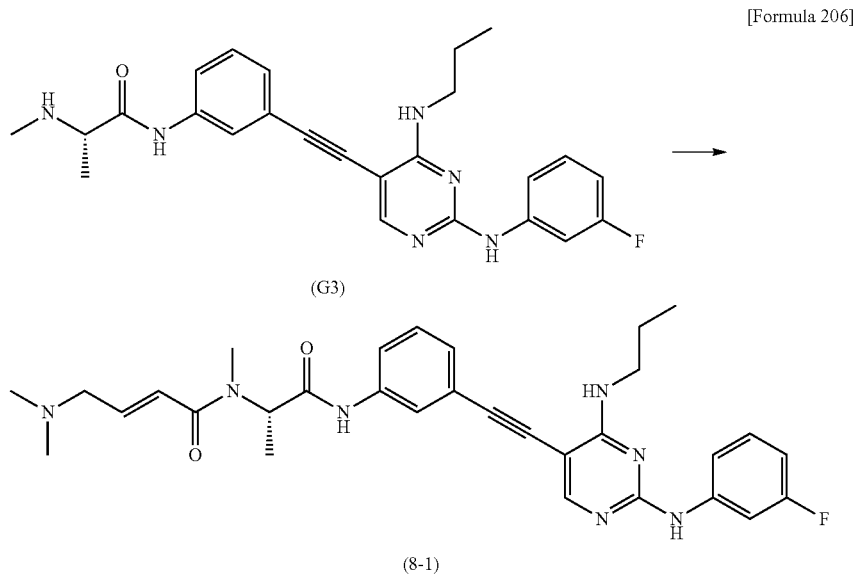

To (S)—N-(3-((2-((3-fluorophenyl)amino)-4-(propylamino)pyrimidin-5-yl)ethynyl)phenyl)-2-(methylamino)propanamide (G3, 67 mg), 4-dimethylaminocrotonic acid hydrochloride (50 mg) and 1-ethyl-3-(3-dimethylaminopropyl)carbodiimide hydrochloride (58 mg), N,N-dimethylformamide (1.5 mL) and N,N-diisopropylethylamine (105 μL) were added at room temperature, and the mixture was stirred at the same temperature for 13 hours. To the reaction mixture, saturated aqueous sodium hydrogencarbonate and ethyl acetate were added. The organic layer was separated, washed successively with saturated aqueous sodium hydrogencarbonate and saturated aqueous sodium chloride, and then dried over anhydrous sodium sulfate, and the solvent was evaporated under reduced pressure. The obtained residue was purified by basic silica gel column chromatography (eluent, 100 to 94% ethyl acetate in methanol). The obtained solid matter was washed with water, and then dried under reduced pressure to obtain (S,E)-4-(dimethylamino)-N-(1-((3-((2-((3-fluorophenyl)amino)-4-(propylamino)pyrimidin-5-yl)ethynyl)phenyl)amino)-1-oxopropan-2-yl)-N-methyl-2-butenamide (8-1, 50 mg).

$^1$H-NMR (CDCl$_3$) δ: 8.84 (1H, s), 8.12 (1H, s), 7.82 (1H, dt, J=12.1, 2.1 Hz), 7.74 (1H, s), 7.46 (1H, d, J=8.6 Hz), 7.32-7.18 (4H, m), 7.11 (1H, d, J=9.2 Hz), 7.00 (1H, dt, J=15.2, 5.9 Hz), 6.70 (1H, td, J=8.3, 2.2 Hz), 6.44 (1H, d, J=15.2 Hz), 5.62 (1H, brs), 5.30 (1H, q, J=7.0 Hz), 3.56-3.48 (2H, m), 3.12 (2H, d, J=5.9 Hz), 3.03 (3H, s), 2.28 (6H, s), 1.76-1.72 (2H, m), 1.44 (3H, d, J=7.3 Hz), 1.04 (3H, t, J=7.6 Hz)

5

By using 4-pentynoic acid, Intermediates (G52) to (G54) were obtained in the same manner as that of Example 38, (1).

TABLE 115

| Compound No. | Structure | Physicochemical data |
|---|---|---|
| G52 | ![structure] | — |
| G53 | ![structure] | — |
| G54 | ![structure] | — |

6

[Formula 207]

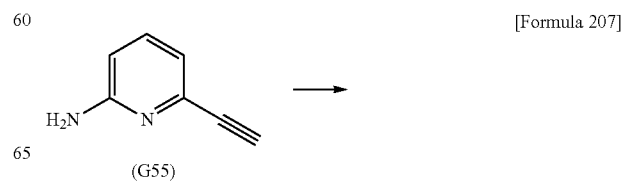

-continued

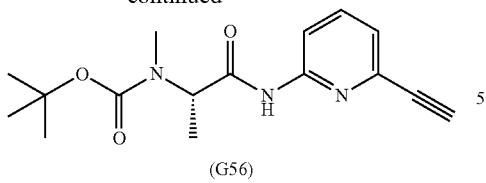

(G56)

To 2-amino-6-ethynylpyridine (G55, 203 mg) synthesized according to the method described in WO2012/052451 A1, N-Boc-N-methyl-L-alanine (524 mg), and O-(7-azabenzotriazol-1-yl)-1,1,3,3-tetramethyluronium hexafluorophosphate (1.31 g), N,N-diisopropylethylamine (1.2 mL) and N,N-dimethylformamide (4.5 mL) were added at room temperature, and the mixture was stirred at 45° C. for 12 hours. The reaction mixture was cooled on ice, and then saturated aqueous sodium hydrogencarbonate and ethyl acetate were added to the reaction mixture. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain tert-butyl (1-((6-ethynylpyridin-2-yl) amino)-1-oxopropan-2-yl)(methyl)carbamate (G56, 180 mg) as white solid.

MS m/z (M+H): 304.3

Example 39

1

[Formula 208]

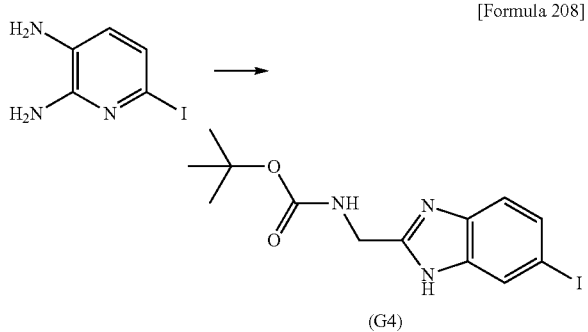

(G4)

To a solution of N-Boc-glycine (129 mg) in tetrahydrofuran (3.5 mL), isobutyl chloroformate (97 μL) and N-methylmorpholine (81 μL) were added under ice cooling, and the mixture was stirred at the same temperature for 30 minutes. To the reaction mixture, 4-iodobenzene-1,2-diamine (200 mg) synthesized according to the method described in WO2010/065668 A1 was added under ice cooling, and the mixture was stirred at room temperature for 1 hour, and then acetic acid (3.5 mL) was added, and the mixture was stirred at 70° C. for 2 hours. The reaction mixture was cooled to room temperature, and then water and ethyl acetate were added to the reaction mixture. The organic layer was separated, washed successively with saturated aqueous sodium hydrogencarbonate and saturated aqueous sodium chloride, and then dried over anhydrous sodium sulfate, and the solvent was evaporated under reduced pressure. The obtained residue was purified by silica gel column chromatography (eluent, 80 to 0% hexane in ethyl acetate) to obtain tert-butyl ((6-iodo-1H-benzo[d]imidazol-2-yl)methyl)carbamate (G4, 216 mg).

MS m/z (M+H): 374.0

2

[Formula 209]

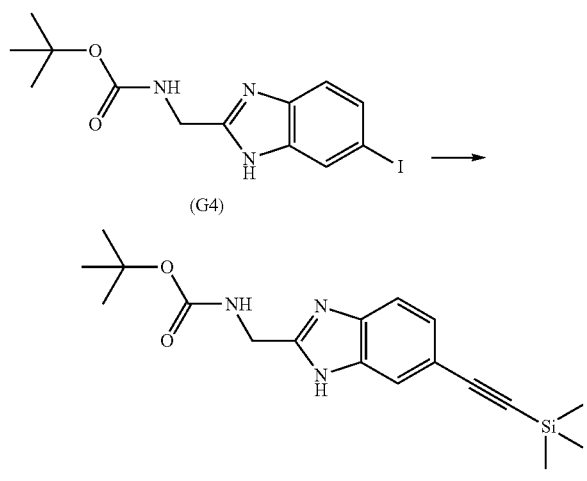

To a suspension of tert-butyl ((6-iodo-1H-benzo[d]imidazol-2-yl)methyl)carbamate (G4, 216 mg), bis(triphenylphosphine)palladium(II) dichloride (40 mg) and copper(I) iodide (22 mg) in tetrahydrofuran (2 mL), triethylamine (243 μL) and trimethylsilylacetylene (96 μL) were added at room temperature, and the mixture was stirred at the same temperature for 3 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 70 to 0% hexane in ethyl acetate) to obtain tert-butyl ((6-((trimethylsilyl)ethynyl)-1H-benzo[d] imidazol-2-yl)methyl)carbamate (G5, 82 mg).

MS m/z (M+H): 344.1

3

[Formula 210]

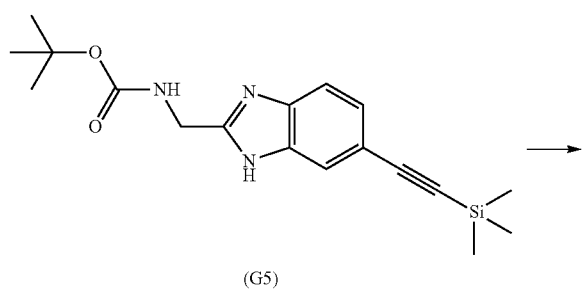

(G5)

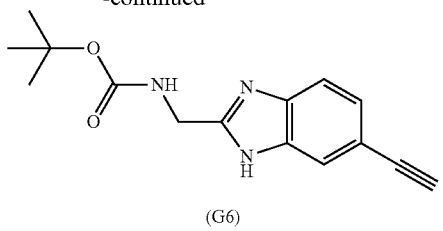

(G6)

To tert-butyl ((6-((trimethylsilyl)ethynyl)-1H-benzo[d]imidazol-2-yl)methyl)carbamate (G5, 82 mg) and potassium carbonate (99 mg), methanol (1 mL) was added at room temperature, and the mixture was stirred at the same temperature for 1 hour. The solvent was evaporated under reduced pressure, and the obtained residue was purified by silica gel column chromatography (eluent, 80 to 30% hexane in ethyl acetate) to obtain tert-butyl ((6-ethynyl-1H-benzo[d]imidazol-2-yl)methyl)carbamate (G6, 62 mg).

MS m/z (M+H): 272.1

4

[Formula 211]

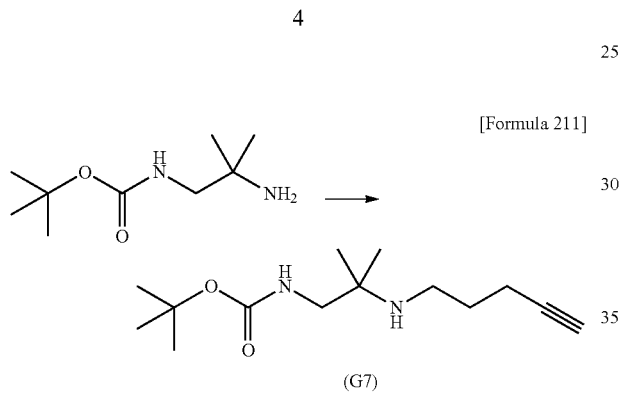

(G7)

To a solution of 4-pentynal (631 mg) synthesized according to the method described in U.S. Pat. No. 4,877,779 A1 and tert-butyl (2-amino-2-methylpropyl)carbamate (328 mg) in methylene chloride (10 mL), sodium triacetoxyborohydride (921 mg) and acetic acid (99 μL) were added at room temperature, and the mixture was stirred at the same temperature for 2 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 80% ethyl acetate in methanol) to obtain tert-butyl (2-methyl-2-((4-pentyn-1-yl)amino)propyl)carbamate (G7, 172 mg).

MS m/z (M+H): 255.5

5

[Formula 212]

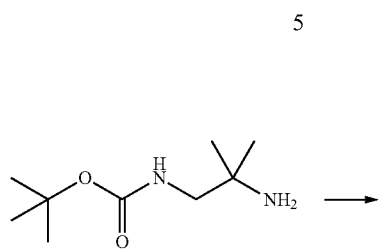

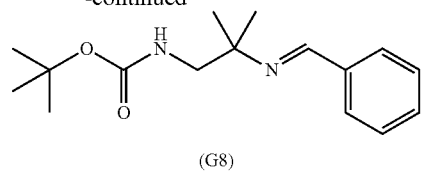

(G8)

To a suspension of tert-butyl (2-amino-2-methylpropyl)carbamate (1.98 g) and anhydrous sodium sulfate (3.00 g) in toluene (5 mL), benzaldehyde (1.07 mL) was added at room temperature, and the mixture was stirred for 11 hours under reflux by heating. The reaction mixture was cooled to room temperature, and then the solvent was evaporated under reduced pressure to obtain (E)-tert-butyl (2-(benzylideneamino)-2-methylpropyl)carbamate (G8).

MS m/z (M+H): 277.3

6

[Formula 213]

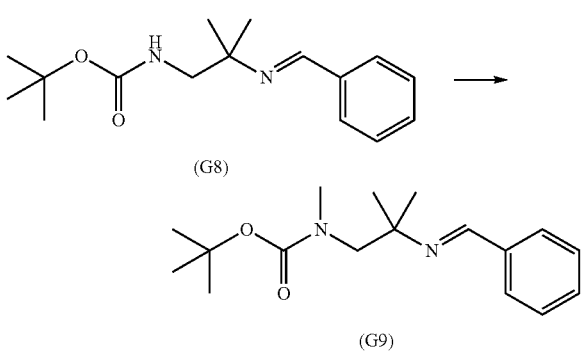

To a solution of (E)-tert-butyl (2-(benzylideneamino)-2-methylpropyl)carbamate (G8) obtained above in N,N-dimethylformamide (20 mL), iodomethane (1.96 mL) and sodium hydride(60% wt, 1.26 g) were added at room temperature, and the mixture was stirred at the same temperature for 30 minutes. To the reaction mixture, iodomethane (1.00 mL) was added at room temperature, and the mixture was stirred at the same temperature for 1 hour. To the reaction mixture, ethyl acetate and water were added. The organic layer was separated, washed with saturated aqueous sodium chloride, and then dried over anhydrous sodium sulfate, and the solvent was evaporated under reduced pressure to obtain (E)-tert-butyl (2-(benzylideneamino)-2-methylpropyl)(methyl)carbamate (G9, 3.17 g).

7

[Formula 214]

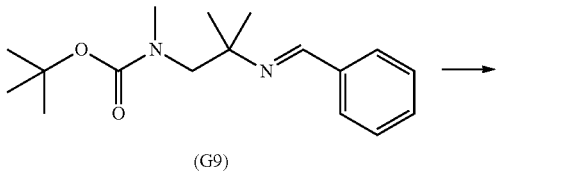

(G9)

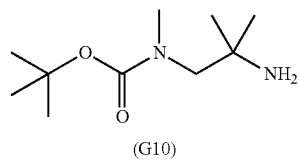

(G10)

To a solution of (E)-tert-butyl (2-(benzylideneamino)-2-methylpropyl)(methyl)carbamate (G9, 3.17 g) in tetrahydrofuran (25 mL), 5% aqueous citric acid (25 mL) was added at room temperature, and the mixture was stirred at the same temperature for 3 hours. To the reaction mixture, ethyl acetate and saturated aqueous sodium hydrogencarbonate were added. The organic layer was separated, and the aqueous layer was extracted with methylene chloride. The organic layer and the extract were combined, and dried over anhydrous sodium sulfate, and the solvent was evaporated under reduced pressure. The obtained residue was purified by silica gel column chromatography (eluent, 100 to 0% hexane in ethyl acetate) to obtain tert-butyl (2-amino-2-methylpropyl)(methyl)carbamate (G10, 506 mg).

MS m/z (M+H): 203.2

8

[Formula 215]

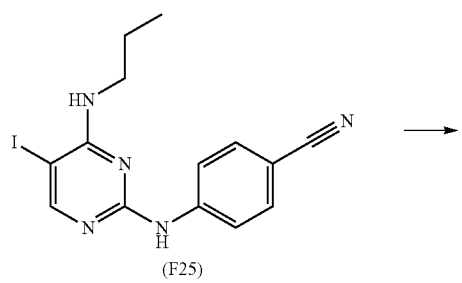

(F25)

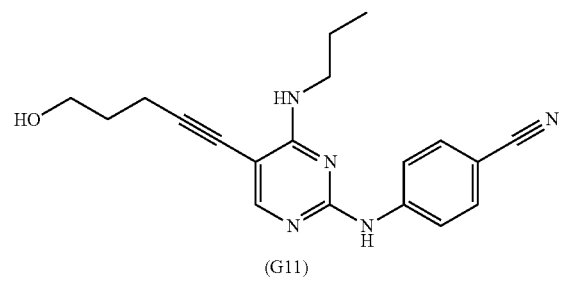

(G11)

To a suspension of 4-((5-iodo-4-(propylamino)pyrimidin-2-yl)amino)benzonitrile (F25, 289 mg), bis(triphenylphosphine)palladium(II) dichloride (53 mg) and copper(I) iodide (28 mg) in N,N-dimethylformamide (4 mL), triethylamine (322 μL), 4-pentyn-1-ol (304 mg), and tetrakis(triphenylphosphine)palladium(0) (88 mg) were added at room temperature, and the mixture was stirred at the same temperature for 3 hours. To the reaction mixture, ethyl acetate and water were added, and the insoluble matter was removed by filtration through Cerite. The organic layer was separated, washed successively with water, saturated aqueous ammonium chloride and saturated aqueous sodium chloride, and then dried over anhydrous sodium sulfate, and the solvent was evaporated under reduced pressure. The obtained residue was purified by silica gel column chromatography (eluent, 90 to 0% hexane in ethyl acetate) to obtain 4-((5-(5-hydroxy-1-pentyn-1-yl)-4-(propylamino)pyrimidin-2-yl)amino)benzonitrile (G11, 195 mg).

MS m/z (M+H): 336.3

9

[Formula 216]

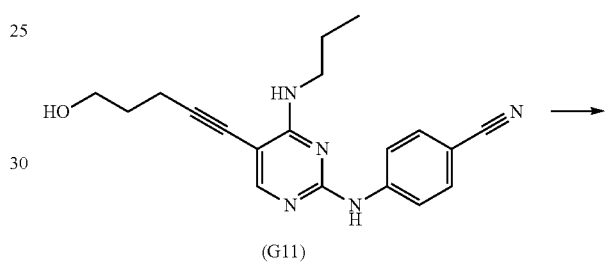

(G11)

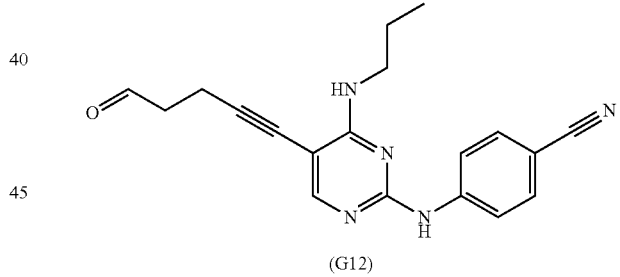

(G12)

To a solution of 4-((5-(5-hydroxy-1-pentyn-1-yl)-4-(propylamino)pyrimidin-2-yl)amino)benzonitrile (G11, 124 mg) in methylene chloride (4 mL), 1,1,1-triacetoxy-1,1-dihydro-1,2-benziodoxol-3(1H)-one (313 mg) was added at room temperature, and the mixture was stirred at the same temperature for 3 hours. To the reaction mixture, ethyl acetate and 10% aqueous sodium thiosulfate were added. The organic layer was separated, washed successively with water and saturated aqueous sodium chloride, and then dried over anhydrous sodium sulfate, and the solvent was evaporated under reduced pressure to obtain 4-((5-(5-oxo-1-pentyn-1-yl)-4-(propylamino)pyrimidin-2-yl)amino)benzonitrile (G12, 300 mg).

MS m/z (M+H): 334.3

10

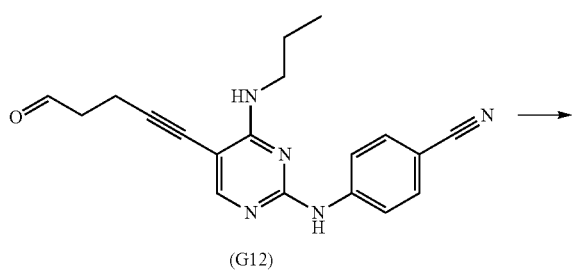

(G12)

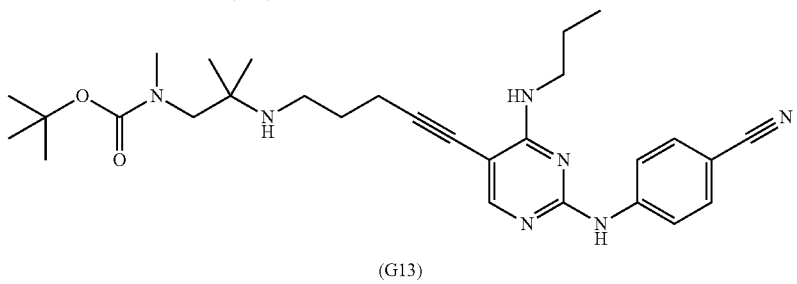

(G13)

To a solution of 4-((5-(5-oxo-1-pentyn-1-yl)-4-(propylamino)pyrimidin-2-yl)amino)benzonitrile (G12, 300 mg) and tert-butyl (2-amino-2-methylpropyl)(methyl)carbamate (G10, 112 mg) in methylene chloride (4 mL), sodium triacetoxyborohydride (195 mg) and acetic acid (21 µL) were added at room temperature, and the mixture was stirred at the same temperature for 3 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 80% ethyl acetate in methanol) to obtain tert-butyl (2-((5-(2-((4-cyanophenyl)amino)-4-(propylamino)pyrimidin-5-yl)-4-pentyn-1-yl)amino)-2-methylpropyl)(methyl)carbamate (G13, 80 mg).

MS m/z (M+H): 520.5

11

[Formula 218]

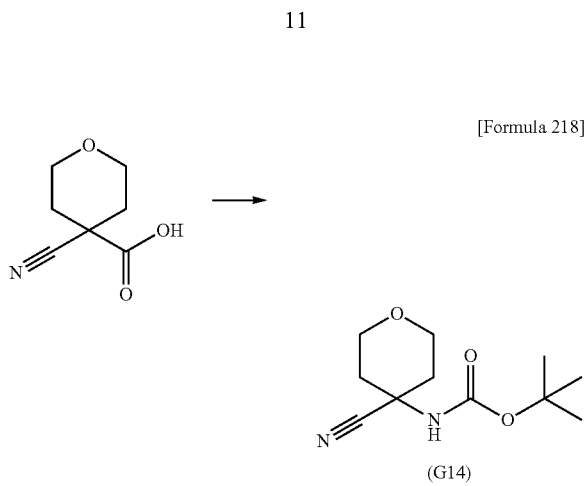

To a solution of 4-cyanotetrahydro-2H-pyrane-4-carboxylic acid (1.69 g) synthesized according to the method described in Journal of the American Chemical Society, 1942, vol. 64, p. 1672 in tetrahydrofuran (20 mL) and tert-butanol (80 mL), diphenylphosphonyl azide (2.32 mL) and triethylamine (1.51 mL) were added at room temperature, and the mixture was stirred at 80° C. for 3 hours. The reaction mixture was cooled to room temperature, and then ethyl acetate and saturated aqueous sodium chloride were added. The organic layer was separated, and dried over anhydrous sodium sulfate, and the solvent was evaporated under reduced pressure. The obtained residue was purified by silica gel column chromatography (eluent, 100 to 0% hexane in ethyl acetate) to obtain tert-butyl (4-cyanotetrahydro-2H-pyran-4-yl)carbamate (G14, 1.38 g).

MS m/z (M+H): 227.2

12

[Formula 219]

To a suspension of tert-butyl (4-cyanotetrahydro-2H-pyran-4-yl)carbamate (G14, 210 mg) and cobalt(II) chloride (241 mg) in methanol (9 mL), sodium borohydride (175 mg) was added at room temperature, and the mixture was stirred at the same temperature for 1 hour. To the reaction mixture, cobalt(II) chloride (241 mg) and sodium borohydride (175 mg) were added at room temperature, and the mixture was stirred at the same temperature for 2 hours. To the reaction mixture, ethyl acetate and 1.0 mol/L aqueous sodium hydroxide were added. The organic layer was separated, washed with saturated aqueous sodium chloride, and then dried over anhydrous sodium sulfate, and the solvent was evaporated under reduced pressure to obtain tert-butyl (4-(aminomethyl)tetrahydro-2H-pyran-4-yl)carbamate (G15, 195 mg).

13

[Formula 220]

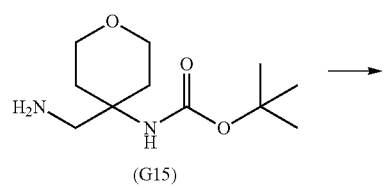

(G15)

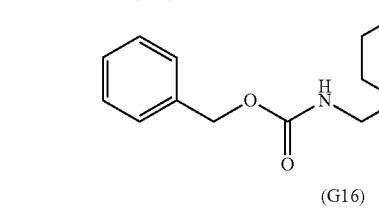

(G16)

To a suspension of tert-butyl (4-(aminomethyl)tetrahydro-2H-pyran-4-yl)carbamate (G15, 195 mg) and sodium carbonate (449 mg) in acetone (5 mL) and water (2 mL), benzyloxycarbonyl chloride (241 µL) was added at room temperature, and the mixture was stirred at the same temperature for 2 hours. To the reaction mixture, ethyl acetate and saturated aqueous sodium chloride were added. The organic layer was separated, and dried over anhydrous sodium sulfate, and the solvent was evaporated under reduced pressure. The obtained residue was purified by silica gel column chromatography (eluent, 100 to 0% hexane in ethyl acetate) to obtain tert-butyl (4-(((benzyloxycarbonyl)amino)methyl)tetrahydro-2H-pyran-4-yl)carbamate (G16, 141 mg).

MS m/z (M+H): 365.3

14

[Formula 221]

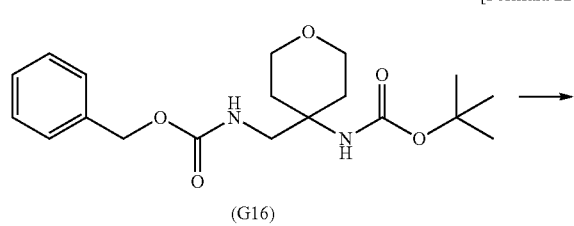

To a solution of tert-butyl (4-(((benzyloxycarbonyl)amino)methyl)tetrahydro-2H-pyran-4-yl)carbamate (G16, 141 mg) in methylene chloride (2 mL), trifluoroacetic acid (2 mL) was added at room temperature, and the mixture was stirred at the same temperature for 1 hour. The solvent was evaporated under reduced pressure, and then ethyl acetate and saturated aqueous sodium hydrogencarbonate were added to the residue. The organic layer was separated, washed with saturated aqueous sodium chloride, and then dried over anhydrous sodium sulfate, and the solvent was evaporated under reduced pressure to obtain benzyl ((4-aminotetrahydro-2H-pyran-4-yl)methyl)carbamate (G17, 106 mg).

MS m/z (M+H): 265.2

15

[Formula 222]

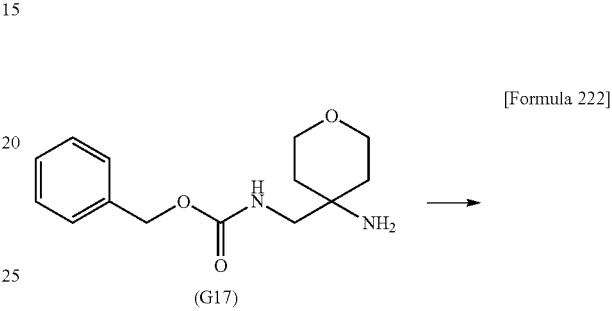

(G17)

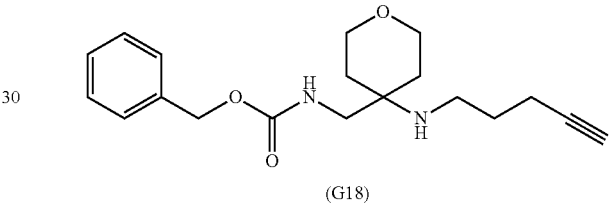

(G18)

To a solution of benzyl ((4-aminotetrahydro-2H-pyran-4-yl)methyl)carbamate (G17, 106 mg) and 4-pentynal (34 mg) in methylene chloride (4 mL), sodium triacetoxyborohydride (205 mg) and acetic acid (22 µL) were added at room temperature, and the mixture was stirred at the same temperature for 2 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 100 to 0% hexane in ethyl acetate) to obtain benzyl ((4-((4-pentyn-1-yl)amino)tetrahydro-2H-pyran-4-yl)methyl)carbamate (G18, 74 mg).

$^1$H-NMR (CDCl$_3$) δ: 7.38-7.30 (5H, m), 5.10 (2H, s), 3.73-3.64 (4H, m), 3.22 (2H, d), 2.59 (2H, dt), 2.31 (2H, dt), 2.17 (1H, d), 1.69-1.45 (6H, m)

16

[Formula 223]

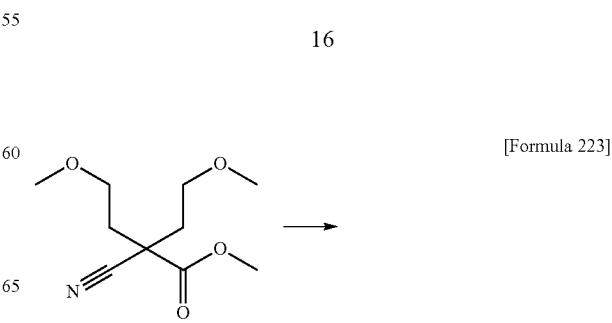

17

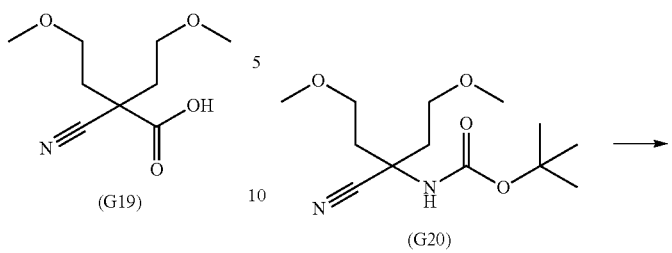

(G19)

To a solution of methyl 2-cyano-4-methoxy-2-(2-methoxyethyl)butanoate (1.13 g) synthesized according to the method described in European Journal of Organic Chemistry, 2005, vol. 20, pp. 4313-4321 in tetrahydrofuran (10 mL), 1.0 mol/L aqueous sodium hydroxide (20 mL) was added at room temperature, and the mixture was stirred at the same temperature for 7 hours. To the reaction mixture, hexane and tert-butyl methyl ether were added. The aqueous layer was separated, and ethyl acetate and 1.0 mol/L aqueous hydrochloric acid were added. The organic layer was separated, and dried over anhydrous sodium sulfate, and the solvent was evaporated under reduced pressure to obtain 2-cyano-4-methoxy-2-(2-methoxyethyl)butyric acid (G19, 957 mg).

17

[Formula 224]

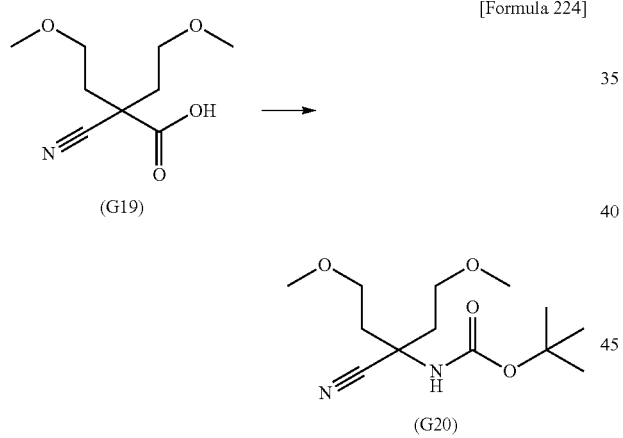

To a solution of 2-cyano-4-methoxy-2-(2-methoxyethyl) butyric acid (G19, 957 mg) in tetrahydrofuran (8 mL) and tert-butanol (32 mL), diphenylphosphonyl azide (1.63 mL) and triethylamine (1.00 mL) were added at room temperature, and the mixture was stirred at 80° C. for 2 hours. The solvent was evaporated under reduced pressure, and to the obtained residue, ethyl acetate and saturated aqueous sodium chloride were added. The organic layer was separated, washed successively with saturated aqueous sodium hydrogencarbonate and saturated aqueous sodium chloride, and then dried over anhydrous sodium sulfate, and the solvent was evaporated under reduced pressure. The obtained residue was purified by silica gel column chromatography (eluent, 100 to 0% hexane in ethyl acetate) to obtain tert-butyl (3-cyano-1,5-dimethoxypentan-3-yl)carbamate (G20, 519 mg).

MS m/z (M+H): 273.3

18

[Formula 225]

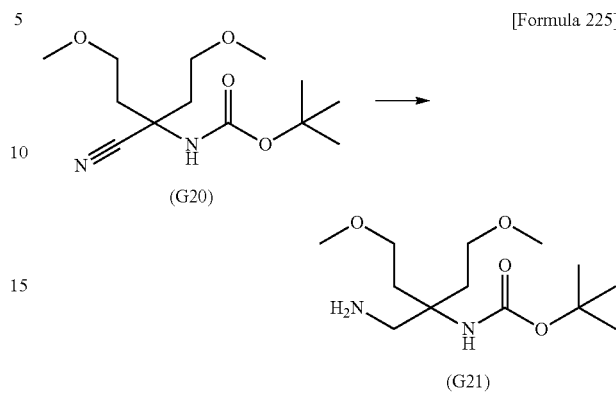

To a suspension of tert-butyl (3-cyano-1,5-dimethoxypentan-3-yl)carbamate (G20, 192 mg) and cobalt(II) chloride (183 mg) in methanol (7 mL), sodium borohydride (134 mg) was added at room temperature, and the mixture was stirred at the same temperature for 4 hours. To the reaction mixture, ethyl acetate and 1.0 mol/L aqueous sodium hydroxide were added. The organic layer was separated, washed with saturated aqueous sodium chloride, and then dried over anhydrous sodium sulfate, and the solvent was evaporated under reduced pressure to obtain tert-butyl (3-(aminomethyl)-1,5-dimethoxypentan-3-yl)carbamate (G21, 275 mg).

19

[Formula 226]

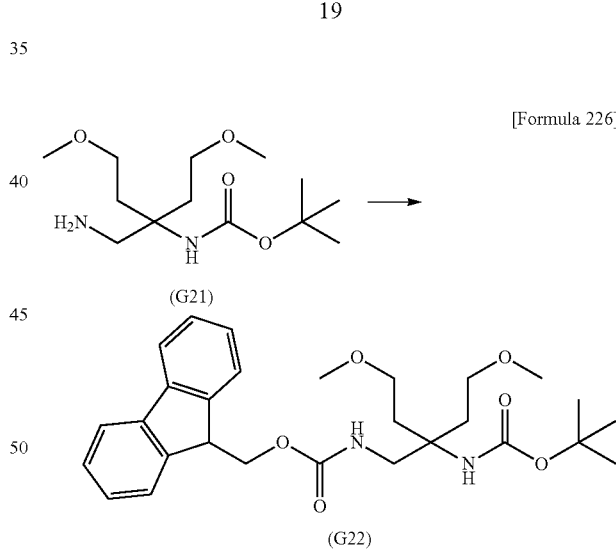

To a suspension of tert-butyl (3-(aminomethyl)-1,5-dimethoxypentan-3-yl)carbamate (G21, 275 mg) and sodium hydrogencarbonate (400 mg) in 1,4-dioxane (4 mL) and water (4 mL), 9-fluorenylmethyl succinimidyl carbonate (261 mg) was added under ice cooling, and the mixture was stirred at the same temperature for 2 hours, and then stirred at room temperature for 1 hour. To the reaction mixture, ethyl acetate and saturated aqueous sodium chloride were added. The organic layer was separated, and dried over anhydrous sodium sulfate, and the solvent was evaporated under reduced pressure. The obtained residue was purified by silica gel column chromatography (eluent, 100 to 30% hexane in ethyl acetate) to obtain (9H-fluoren-9-yl)methyl tert-butyl (4-methoxy-2-(2-methoxyethyl)butane-1,2-diyl)dicarbamate (G22, 269 mg).

$^1$H-NMR (CDCl$_3$) δ: 7.77 (2H, d), 7.60 (2H, d), 7.40 (2H, t), 7.31 (2H, t), 4.41-4.35 (2H, m), 4.24 (1H, t), 3.52-3.42 (4H, m), 3.33-3.29 (4H, m), 2.17 (6H, s), 1.43 (9H, s).

20

[Formula 227]

(G22)

(G23)

To a solution of (9H-fluoren-9-yl)methyl tert-butyl (4-methoxy-2-(2-methoxyethyl)butane-1,2-diyl)dicarbamate (G22, 269 mg) in methylene chloride (2 mL), trifluoroacetic acid (2 mL) was added at room temperature, and the mixture was stirred at the same temperature for 5 hours. The solvent was evaporated under reduced pressure, and then ethyl acetate and saturated aqueous sodium hydrogencarbonate were added to the residue. The organic layer was separated, washed with saturated aqueous sodium chloride, and then dried over anhydrous sodium sulfate, and the solvent was evaporated under reduced pressure to obtain (9H-fluoren-9-yl)methyl (2-amino-4-methoxy-2-(2-methoxyethyl)butyl)carbamate (G23, 186 mg).

MS m/z (M+H): 399.4

21

[Formula 228]

(G23)

(G24)

To a solution of (9H-fluoren-9-yl)methyl (2-amino-4-methoxy-2-(2-methoxyethyl)butyl)carbamate (G23, 186 mg) and 4-pentynal (42 mg) in methylene chloride (5 mL), sodium triacetoxyborohydride (247 mg) and acetic acid (26 μL) were added at room temperature, and the mixture was stirred at the same temperature for 3 hours. To the reaction mixture, ethyl acetate and saturated aqueous sodium hydrogencarbonate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 60 to 0% hexane in ethyl acetate) to obtain (9H-fluoren-9-yl)methyl (4-methoxy-2-(2-methoxyethyl)-2-((4-pentyn-1-yl)amino)butyl)carbamate (G24, 102 mg).

MS m/z (M+H): 465.4

22

[Formula 229]

(G25)

(G26)

A solution of (S)-4-((5-(((3-(2-(methylamino)propanamido)phenyl)ethynyl)-4-(propylamino)pyrimidin-2-yl)amino)benzamide (G25, 47 mg) synthesized in the same manner as that of Example 38, (1) to (3) in a mixture of acetic acid (2.5 mL) and methanol (80 mL) was prepared, and hydrogenation was performed at room temperature and a flow rate of 1 mL/minute in a flow type hydrogenation reactor set with a 10% palladium-carbon cartridge. The solvent was evaporated under reduced pressure to obtain (S)-4-((5-(3-(2-(methylamino)propaneamido)phenethyl)-4-(propylamino)pyrimidin-2-yl)amino)benzamide (G26, 38 mg) as white solid.

MS m/z (M+H): 476.2

23

[Formula 230]

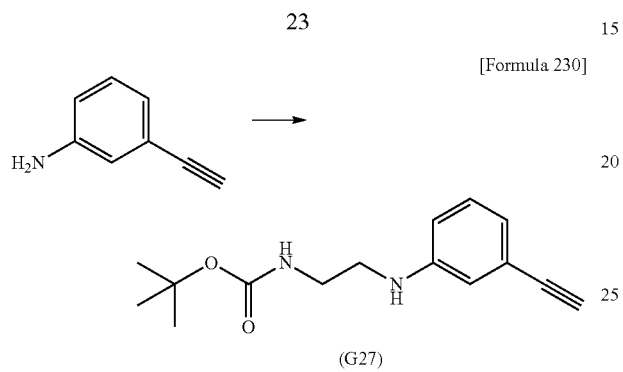

(G27)

To a solution of 3-ethynylaniline (100 mg) and N-Boc-2-aminoacetaldehyde (407 mg) in ethyl acetate (5 mL) and methylene chloride (5 mL), acetic acid (2 drops) and sodium triacetoxyborohydride (543 mg) were added at room temperature, and the mixture was stirred at the same temperature for 3 hours and 30 minutes. To the reaction mixture, N-Boc-2-aminoacetaldehyde (200 mg) and sodium triacetoxyborohydride (200 mg) were added at room temperature, and the mixture was stirred at the same temperature. To the reaction mixture, saturated aqueous sodium hydrogencarbonate and ethyl acetate were added. The organic layer was separated, and dried over anhydrous sodium sulfate, and the solvent was evaporated under reduced pressure. The obtained residue was purified by basic silica gel column chromatography (eluent, 75% hexane/25% ethyl acetate) to obtain tert-butyl (2-((3-ethynylphenyl)amino)ethyl)carbamate (G27).

MS m/z (M+H): 261.1

24

[Formula 231]

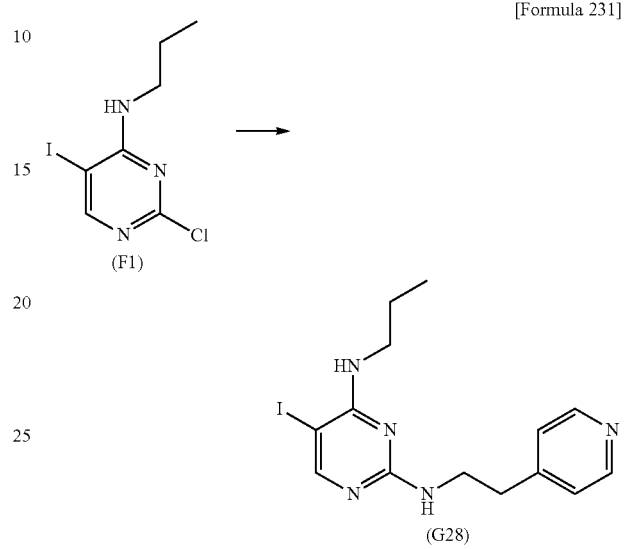

By using 2-chloro-5-iodo-N-propylpyrimidin-4-amine (F1), 5-iodo-N$^4$-propyl-N$^2$-(2-(pyridin-4-yl)ethyl)pyrimidine-2,4-diamine (G28) was obtained in the same manner as that of Example 36, (11).

25

In the same manner as that of Example 38, (2), Intermediates (G29) to (G37) and Intermediates (G57) to (G64) were obtained.

TABLE 116

| Compound No. | Structure | Physicochemical data |
|---|---|---|
| G29 | 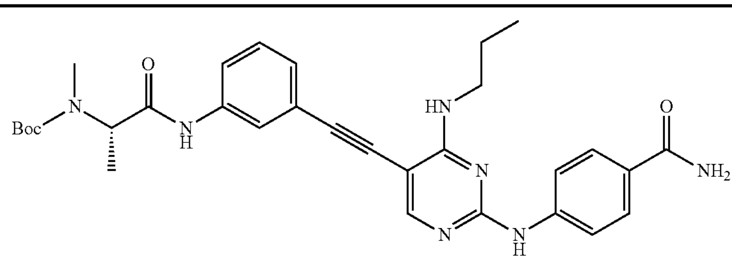 | MS m/z (M + H): 572.3 |
| G30 | 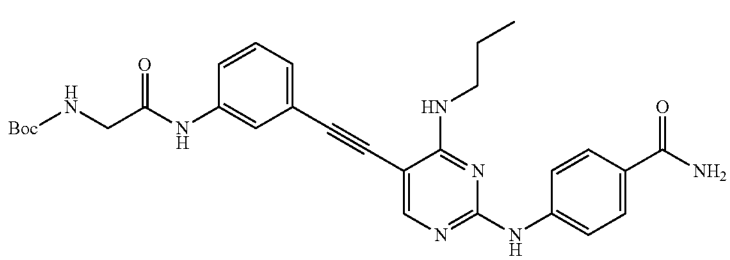 [SMILES: CCCNc1nc(Nc2ccc(C(N)=O)cc2)ncc1C#Cc1cccc(NC(=O)CNC(=O)OC(C)(C)C)c1] | — |

TABLE 116-continued

| Compound No. | Structure | Physico-chemical data |
|---|---|---|
| G31 | 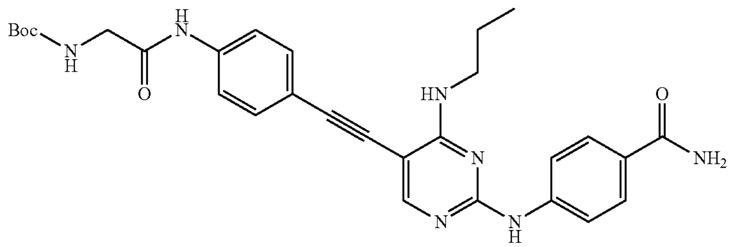 [SMILES: CCCNc1nc(Nc2ccc(C(N)=O)cc2)ncc1C#Cc1ccc(NC(=O)CNC(=O)OC(C)(C)C)cc1] | — |
| G32 | 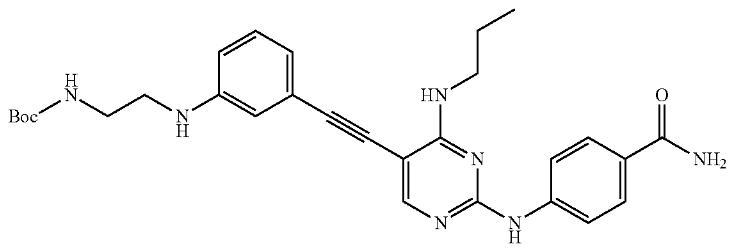 [SMILES: CCCNc1nc(Nc2ccc(C(N)=O)cc2)ncc1C#Cc1cccc(NCCNC(=O)OC(C)(C)C)c1] | MS m/z (M + H): 530.2 |
| G33 | 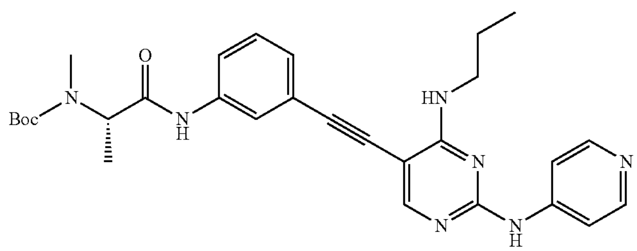 | MS m/z (M + H): 558.3 |
| G34 | 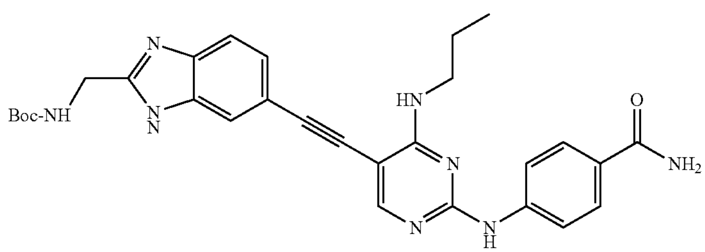 | — |
| G35 | 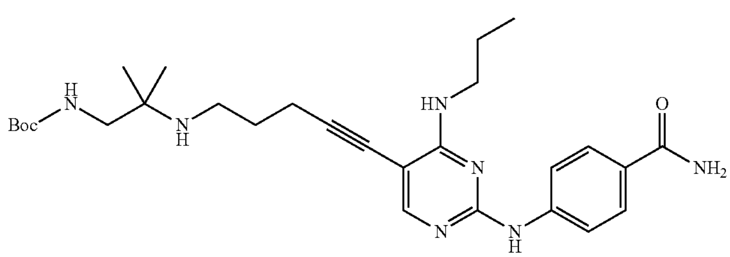 [SMILES: CCCNc1nc(Nc2ccc(C(N)=O)cc2)ncc1C#CCCCNC(C)(C)CNC(=O)OC(C)(C)C] | — |
| G36 | 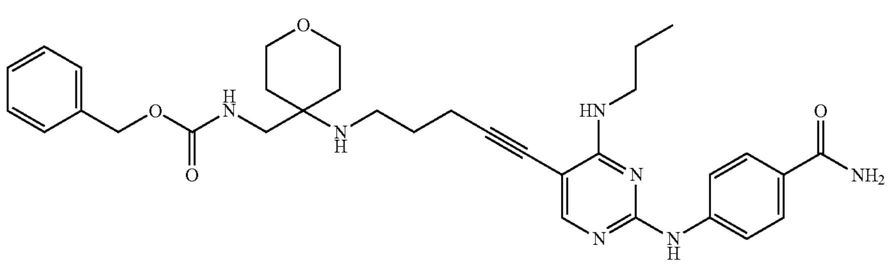 [SMILES: CCCNc1nc(Nc2ccc(C(N)=O)cc2)ncc1C#CCCCNC1(CNC(=O)OCc2ccccc2)CCOCC1] | |

TABLE 116-continued
| Compound No. | Structure | Physicochemical data |
|---|---|---|
| G37 | 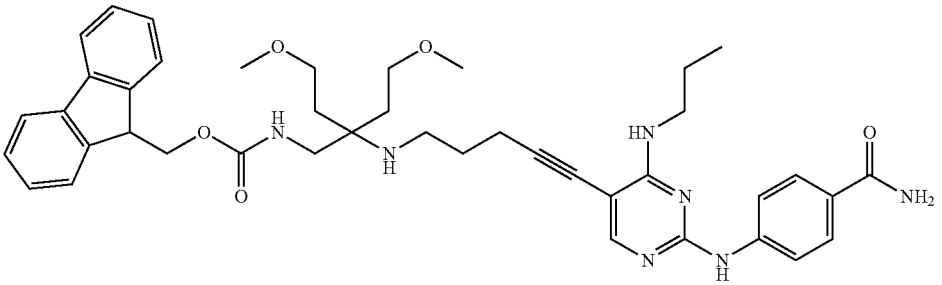 [SMILES: CCCNc1nc(Nc2ccc(C(N)=O)cc2)ncc1C#CCCCNC(CCOC)(CCOC)CNC(=O)OCC1c2ccccc2-c2ccccc21] | — |
| G57 | 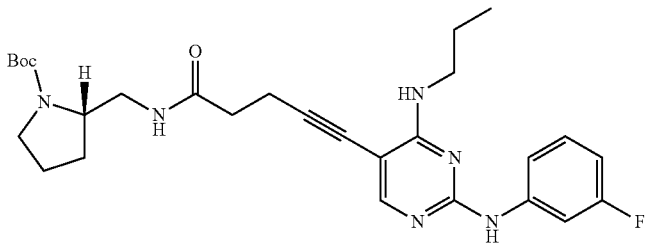 [SMILES: CCCNc1nc(Nc2cccc(F)c2)ncc1C#CCCC(=O)NC[C@@H]1CCCN1C(=O)OC(C)(C)C] | MS m/z (M − H): 523.4 |
TABLE 117
| Compound No. | Structure | Physicochemical data |
|---|---|---|
| G58 | 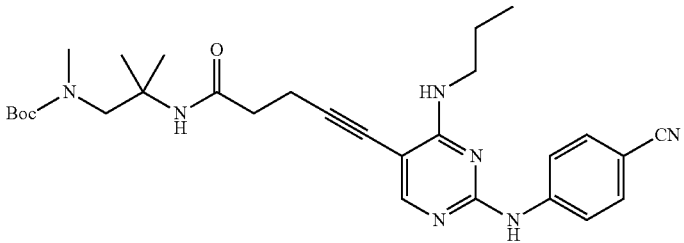 [SMILES: CCCNc1nc(Nc2ccc(C#N)cc2)ncc1C#CCCC(=O)NC(C)(C)CN(C)C(=O)OC(C)(C)C] | MS m/z (M + H): 534.4 |
| G59 | 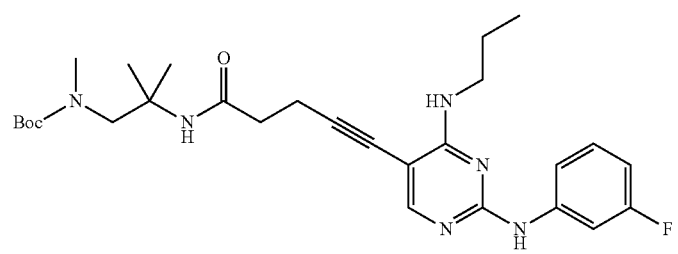 [SMILES: CCCNc1nc(Nc2cccc(F)c2)ncc1C#CCCC(=O)NC(C)(C)CN(C)C(=O)OC(C)(C)C] | MS m/z (M + H): 527.2 |
| G60 | 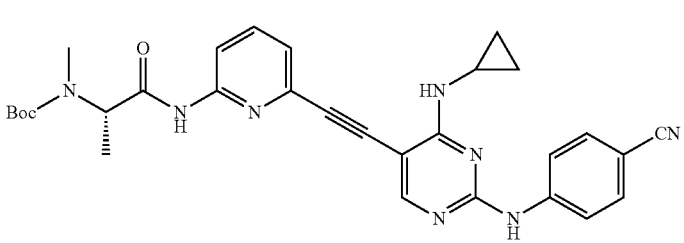 [SMILES: C[C@@H](C(=O)Nc1cccc(C#Cc2cnc(Nc3ccc(C#N)cc3)nc2NC2CC2)n1)N(C)C(=O)OC(C)(C)C] | — |

TABLE 117-continued

| Compound No. | Structure | Physicochemical data |
|---|---|---|
| G61 | 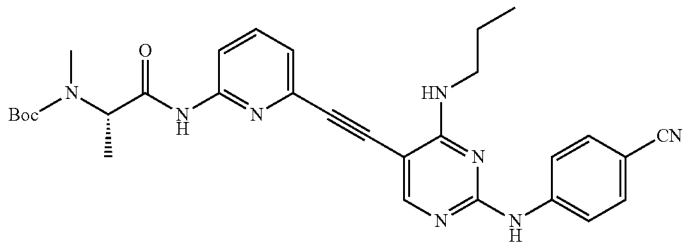 [SMILES: CCCNc1nc(Nc2ccc(C#N)cc2)ncc1C#Cc1cccc(NC(=O)[C@H](C)N(C)C(=O)OC(C)(C)C)n1] | — |
| G62 | 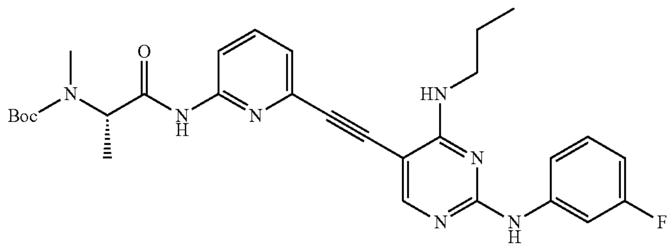 [SMILES: CCCNc1nc(Nc2cccc(F)c2)ncc1C#Cc1cccc(NC(=O)[C@H](C)N(C)C(=O)OC(C)(C)C)n1] | MS m/z (M + H): 548.4 |
| G63 | 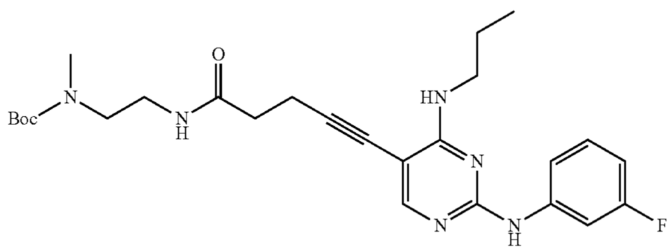 [SMILES: CCCNc1nc(Nc2cccc(F)c2)ncc1C#CCCC(=O)NCCN(C)C(=O)OC(C)(C)C] | MS m/z (M + H): 499.4 |
| G64 | 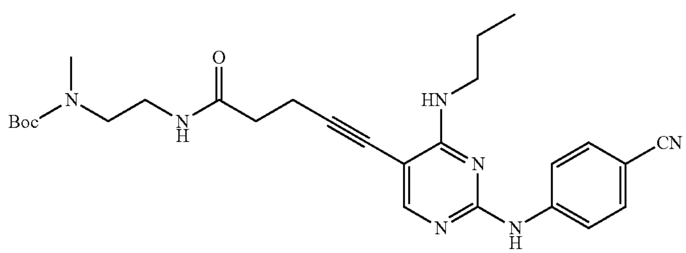 [SMILES: CCCNc1nc(Nc2ccc(C#N)cc2)ncc1C#CCCC(=O)NCCN(C)C(=O)OC(C)(C)C] | MS m/z (M + H): 506.4 |

26

In the same manner as that of Example 38, (3), Intermediates (G38) to (G47), Intermediates (G65) to (G72) and Intermediates (G74) were obtained.

TABLE 118

| Compound No. | Structure | Physicochemical data |
|---|---|---|
| G38 | 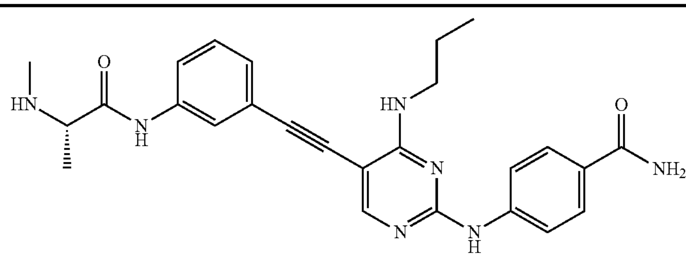 | MS m/z (M + H): 472.2 |

TABLE 118-continued

| Compound No. | Structure | Physicochemical data |
|---|---|---|
| G39 | 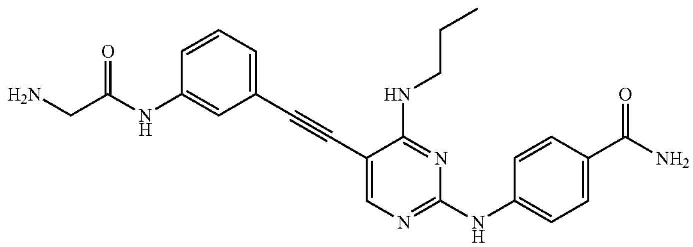 [SMILES: CCCNc1nc(Nc2ccc(C(N)=O)cc2)ncc1C#Cc1cccc(NC(=O)CN)c1] | — |
| G40 | 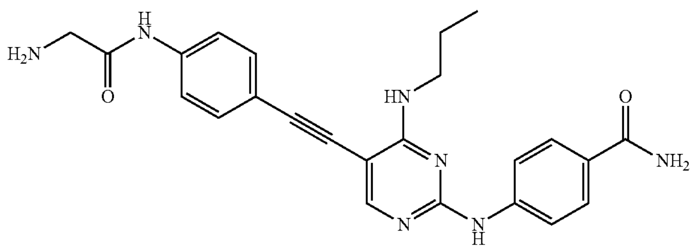 [SMILES: CCCNc1nc(Nc2ccc(C(N)=O)cc2)ncc1C#Cc1ccc(NC(=O)CN)cc1] | — |
| G41 | 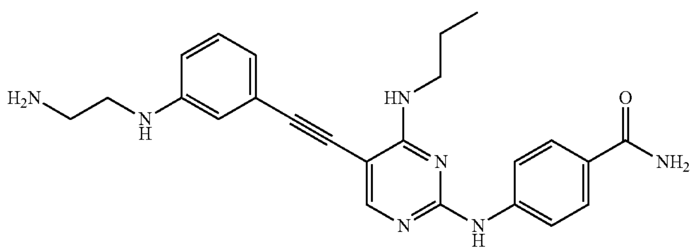 [SMILES: CCCNc1nc(Nc2ccc(C(N)=O)cc2)ncc1C#Cc1cccc(NCCN)c1] | — |
| G42 | 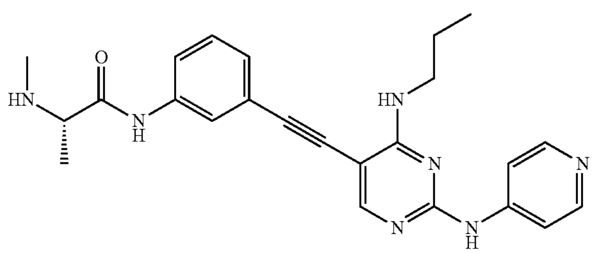 [SMILES: CCCNc1nc(Nc2ccncc2)ncc1C#Cc1cccc(NC(=O)[C@H](C)NC)c1] | — |
| G43 | 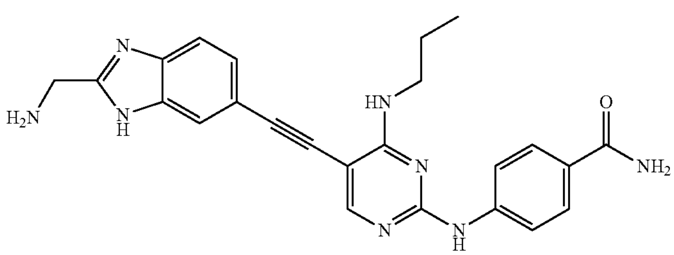 [SMILES: CCCNc1nc(Nc2ccc(C(N)=O)cc2)ncc1C#Cc1ccc2nc(CN)[nH]c2c1] | — |
| G44 | 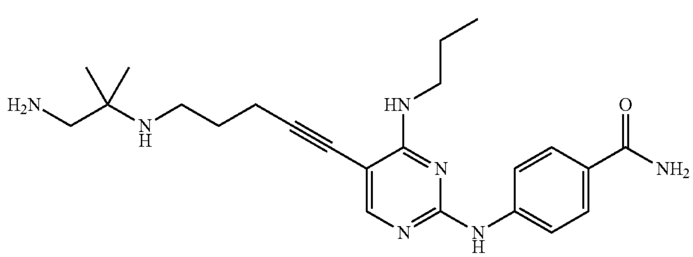 [SMILES: CCCNc1nc(Nc2ccc(C(N)=O)cc2)ncc1C#CCCCNC(C)(C)CN] | — |

TABLE 118-continued

| Compound No. | Structure | Physicochemical data |
|---|---|---|
| G45 | 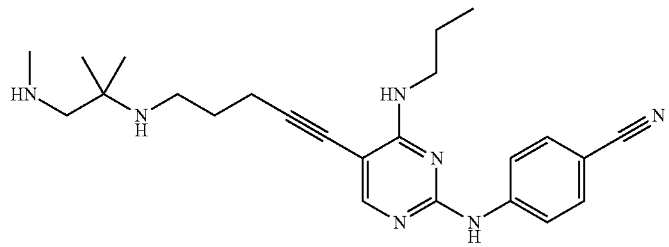 [SMILES: CCCNc1nc(Nc2ccc(C#N)cc2)ncc1C#CCCCNC(C)(C)CNC] | — |
| G46 | 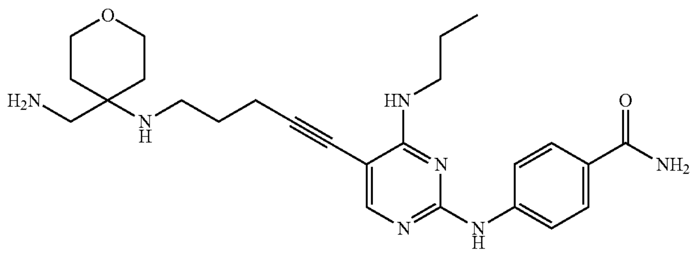 [SMILES: CCCNc1nc(Nc2ccc(C(N)=O)cc2)ncc1C#CCCCNC1(CN)CCOCC1] | — |
| G47 | 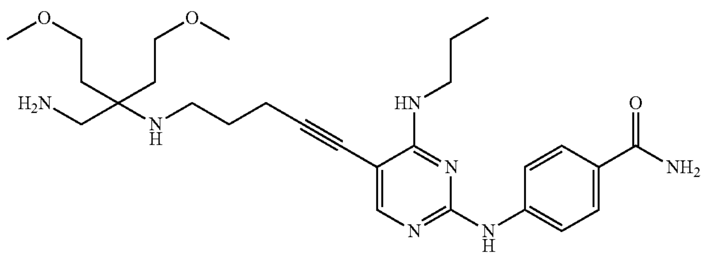 [SMILES: CCCNc1nc(Nc2ccc(C(N)=O)cc2)ncc1C#CCCCNC(CN)(CCOC)CCOC] | — |

TABLE 119

| Compound No. | Structure | Physicochemical data |
|---|---|---|
| G65 | 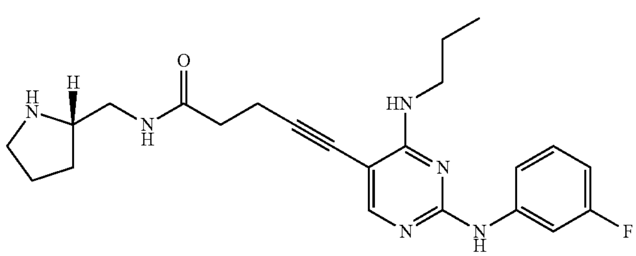 [SMILES: CCCNc1nc(Nc2cccc(F)c2)ncc1C#CCCC(=O)NC[C@@H]1CCCN1] | MS m/z (M + H): 425.3 |
| G66 | 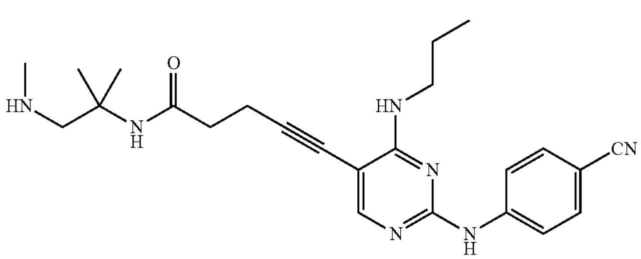 [SMILES: CCCNc1nc(Nc2ccc(C#N)cc2)ncc1C#CCCC(=O)NC(C)(C)CNC] | MS m/z (M + H): 434.4 |

TABLE 119-continued

| Compound No. | Structure | Physicochemical data |
|---|---|---|
| G67 | 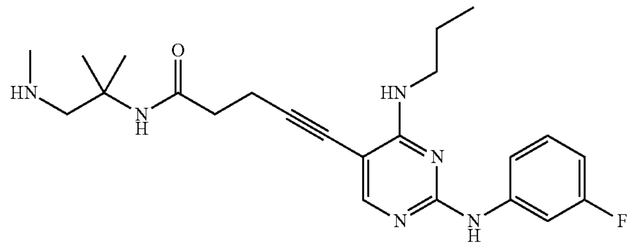 [SMILES: CCCNc1nc(Nc2cccc(F)c2)ncc1C#CCCC(=O)NC(C)(C)CNC] | MS m/z (M + H): 427.3 |
| G68 | 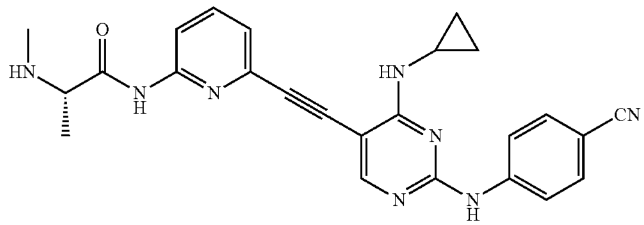 [SMILES: CN[C@@H](C)C(=O)Nc1cccc(C#Cc2cnc(Nc3ccc(C#N)cc3)nc2NC2CC2)n1] | MS m/z (M + H): 453.3 |
| G69 | 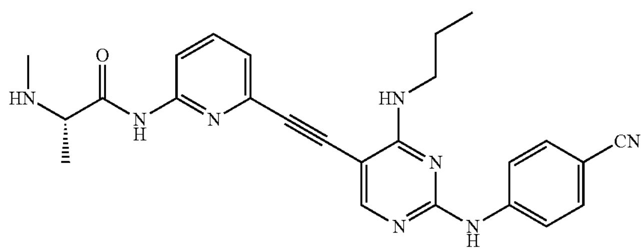 [SMILES: CCCNc1nc(Nc2ccc(C#N)cc2)ncc1C#Cc1cccc(NC(=O)[C@H](C)NC)n1] | MS m/z (M + H): 455.3 |
| G70 | 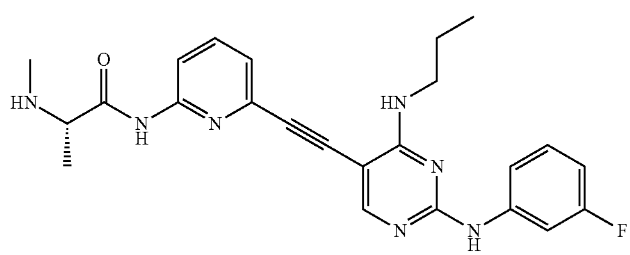 [SMILES: CCCNc1nc(Nc2cccc(F)c2)ncc1C#Cc1cccc(NC(=O)[C@H](C)NC)n1] | MS m/z (M + H): 448.3 |
| G71 | 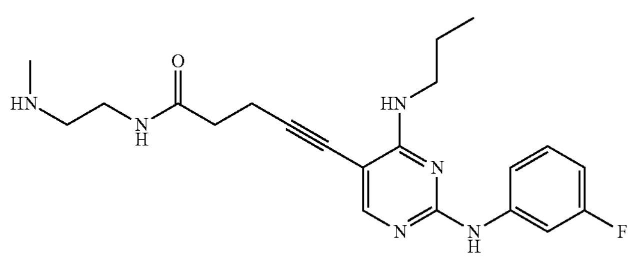 [SMILES: CCCNc1nc(Nc2cccc(F)c2)ncc1C#CCCC(=O)NCCNC] | MS m/z (M + H): 399.3 |
| G72 | 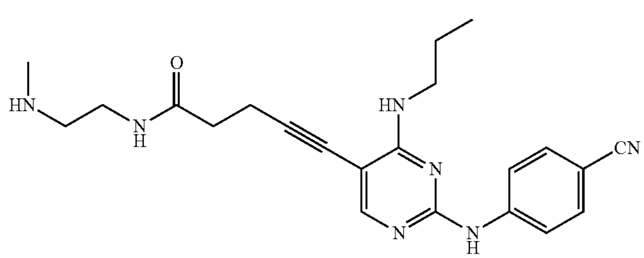 [SMILES: CCCNc1nc(Nc2ccc(C#N)cc2)ncc1C#CCCC(=O)NCCNC] | MS m/z (M + H): 406.3 |

TABLE 119-continued

| Compound No. | Structure | Physicochemical data |
|---|---|---|
| G74 | 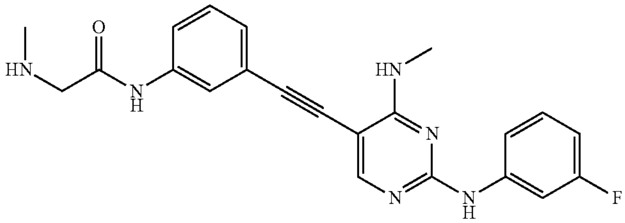 [SMILES: CNCC(=O)Nc1cccc(C#Cc2cnc(Nc3cccc(F)c3)nc2NC)c1] | MS m/z (M + H): 405.3 |

27

[Formula 232]

(F2)

(G48)

By using N²-(3-fluorophenyl)-5-iodo-N⁴-propylpyrimidine-2,4-diamine (F2), 5-((5-amino-2-fluorophenyl)ethynyl)-N²-(3-fluorophenyl)-N⁴-propylpyrimidine-2,4-diamine (G48) was obtained in the same manner as that of Example 38, (2).

28

[Formula 233]

(G48)

(G49)

By using 5-((5-amino-2-fluorophenyl)ethynyl)-N²-(3-fluorophenyl)-N⁴-propylpyrimidine-2,4-diamine (G48), (S)-tert-butyl (1-((4-fluoro-3-((2-((3-fluorophenyl)amino)-4-(propylamino)pyrimidin-5-yl)ethynyl)phenyl)amino)-1-oxopropan-2-yl)(methyl)carbamate (G49) was obtained in the same manner as that of Example 1, (5).

29

[Formula 234]

(G49)

(G50)

By using (S)-tert-butyl (1-((4-fluoro-3-((2-((3-fluorophenyl)amino)-4-(propylamino)pyrimidin-5-yl)ethynyl)phenyl)amino)-1-oxopropan-2-yl)(methyl)carbamate (G49), (S)—N-(4-fluoro-3-((2-(3-fluorophenyl)amino)-4-(propylamino) pyrimidin-5-yl)ethynyl)phenyl)-2-(methylamino) propanamide (G50) was obtained in the same manner as that of Example 38, (3).

30

[Formula 235]

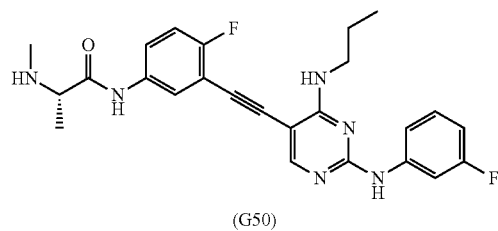

(G50)

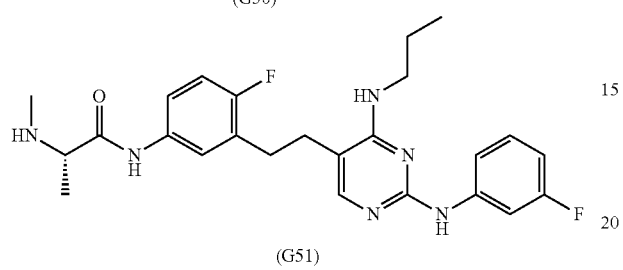

(G51)

By using (S)—N-(4-fluoro-3-((2-((3-fluorophenyl)amino)-4-(propylamino)pyrimidin-5-yl)ethynyl)phenyl)-2-(methylamino)propanamide (G50), (S)—N-(4-fluoro-3-(2-(2-((3-fluorophenyl)amino)-4-(propylamino)pyrimidin-5-yl)ethyl)phenyl)-2-(methylamino)propanamide (G51) was obtained in the same manner as that of Example 36, (4) or Example 38, (22).

Example 40

1

In the same manner as that of Example 1, (7), Example 1, (8) or Example 35, (7), Compounds (8-2) to (8-23) were obtained.

TABLE 120

| Compound No. | Structure | Physicochemical data |
|---|---|---|
| 8-2 | 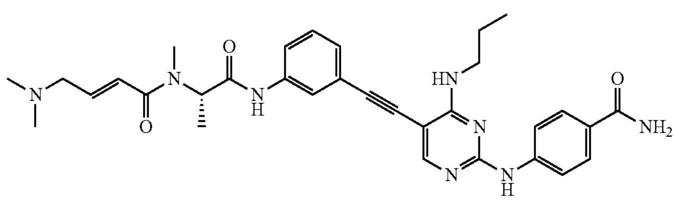 [SMILES: CCCNc1nc(Nc2ccc(C(N)=O)cc2)ncc1C#Cc1cccc(NC(=O)[C@H](C)N(C)C(=O)/C=C/CN(C)C)c1] | $^1$H-NMR (CD$_3$OD) δ: 8.03 (1H, s), 7.83 (4H, s), 7.79 (1H, brs), 7.51-7.47 (1H, m), 7.34-7.29 (2H, m), 6.84-6.76 (1H, m), 6.64 (1H, d, J = 15.2 Hz), 5.17 (1H, q, J = 7.3 Hz), 3.51 (2H, t, J = 7.3 Hz), 3.21-3.12 (5H, m), 2.28 (6H, s), 1.74-1.69 (2H, m), 1.48 (3H, d, J = 7.3 Hz), 1.01 (3H, t, J = 7.3 Hz) |
| 8-3 | 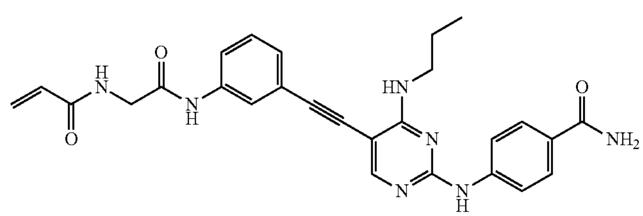 [SMILES: C=CC(=O)NCC(=O)Nc1cccc(C#Cc2cnc(Nc3ccc(C(N)=O)cc3)nc2NCCC)c1] | $^1$H-NMR (CD$_3$OD) δ: 8.05 (1H, s), 7.84-7.80 (1H, m), 7.84 (4H, s), 7.50-7.48 (1H, m), 7.34-7.31 (2H, m), 6.37-6.27 (2H, m), 5.72 (1H, dd, J = 9.9, 5.0 Hz), 4.10 (2H, s), 3.52 (2H, t, J = 7.6 Hz), 1.75-1.71 (2H, m), 1.02 (3H, t, J = 7.6 Hz) |
| 8-4 | 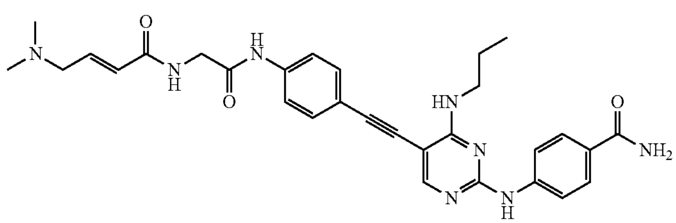 [SMILES: CCCNc1nc(Nc2ccc(C(N)=O)cc2)ncc1C#Cc1ccc(NC(=O)CNC(=O)/C=C/CN(C)C)cc1] | $^1$H-NMR (CD$_3$OD) δ: 8.03 (1H, s), 7.83 (4H, s), 7.60 (2H, dd, J = 9.2, 2.6 Hz), 7.50-7.47 (2H, m), 6.86-6.76 (1H, m), 6.20 (1H, d, J = 15.5 Hz), 4.09 (2H, s), 3.52 (2H, t, J = 7.3 Hz), 3.15 (2H, d, J = 6.6 Hz), 2.28 (6H, s), 1.75-1.70 (2H, m), 1.02 (3H, t, J = 7.3 Hz) |
| 8-5 | 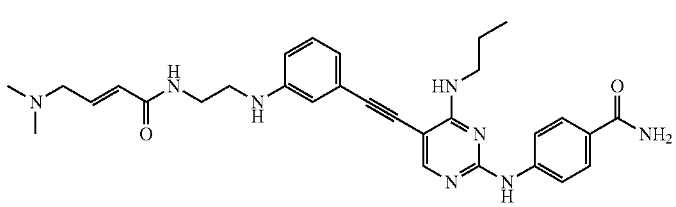 [SMILES: CCCNc1nc(Nc2ccc(C(N)=O)cc2)ncc1C#Cc1cccc(NCCNC(=O)/C=C/CN(C)C)c1] | $^1$H-NMR (CD$_3$OD) δ: 8.03 (1H, s), 7.83 (4H, s), 7.10 (1H, t, J = 7.9 Hz), 6.84-6.63 (4H, m), 6.08 (1H, d, J = 15.2 Hz), 3.53-3.46 (4H, m), 3.37-3.22 (2H, m), 3.14-3.09 (2H, m), 2.25 (6H, s), 1.75-1.70 (2H, m), 1.02 (3H, t, J = 7.3 Hz) |

TABLE 120-continued

| Compound No. | Structure | Physicochemical data |
|---|---|---|
| 8-6 | 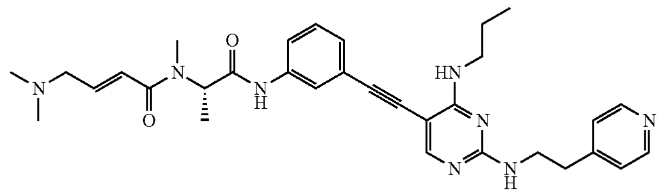 [SMILES: CCCNc1nc(NCCc2ccncc2)ncc1C#Cc1cccc(NC(=O)[C@H](C)N(C)C(=O)/C=C/CN(C)C)c1] | ¹H-NMR (CDCl₃ + CD₃OD) δ: 8.41 (2H, dd, J = 4.6. 2.0 Hz), 7.86 (1H, s), 7.76 (1H, s), 7.46 (1H, d, J = 7.3 Hz), 7.33-7.20 (4H, m), 6.87-6.66 (1H, m), 6.59 (1H, d, J = 13.2 Hz), 5.17 (1H, q, J = 7.0 Hz), 3.64 (2H, t, J = 6.9 Hz), 3.44 (2H, t, J = 7.3 Hz), 3.19-3.12 (5H, m), 2.96 (2H, t, J = 7.3 Hz), 2.28 (6H, s), 1.72-1.59 (2H, m), 1.47 (3H, d, J = 7.3 Hz), 0.96 (3H, t, J = 7.3 Hz) |
| 8-7 | 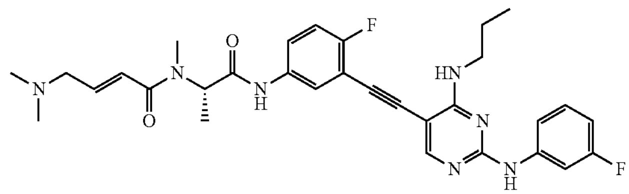 [SMILES: CCCNc1nc(Nc2cccc(F)c2)ncc1C#Cc1cc(NC(=O)[C@H](C)N(C)C(=O)/C=C/CN(C)C)ccc1F] | ¹H-NMR (CDCl₃) δ: 8.86 (1H, s), 8.12 (1H, s), 7.81 (1H, dt, J = 11.7, 2.1 Hz), 7.70 (1H, dd, J = 5.9, 2.6 Hz), 7.47-7.39 (1H, m), 7.26-6.96 (5H, m), 6.71 (1H, td, J = 8.1, 2.4 Hz), 6.44 (1H, d, J = 15.2 Hz), 5.75 (1H, t, J = 4.6 Hz), 5.26 (1H, q, J = 7.0 Hz), 3.58-3.47 (2H, m), 3.13 (2H, d, J = 6.3 Hz), 3.03 (3H, s), 2.29 (6H, s), 1.79-1.68 (2H, m), 1.44 (3H, d, J = 7.3 Hz), 1.04 (3H, t, J = 7.6 Hz) |

TABLE 121

| Compound No. | Structure | Physicochemical data |
|---|---|---|
| 8-8 | 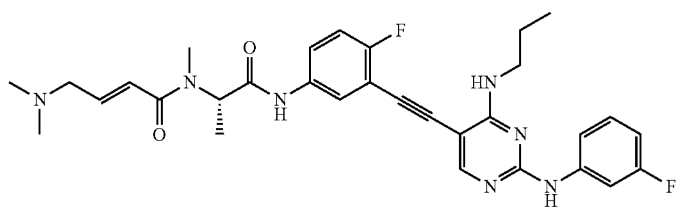 [SMILES: CCCNc1nc(Nc2cccc(F)c2)ncc1C#Cc1cc(NC(=O)[C@H](C)N(C)C(=O)/C=C/CN(C)C)ccc1F] | ¹H-NMR (CDCl₃) δ: 8.74 (1H, s), 7.80 (1H, dt, J = 11.9, 2.0 Hz), 7.69 (1H, s), 7.45 (1H, dd, J = 6.6, 2.6 Hz), 7.32-7.08 (4H, m), 7.05-6.93 (2H, m), 6.65 (1H, td, J = 8.6, 2.0 Hz), 6.43 (1H, d, J = 15.2 Hz), 5.26 (1H, q, J = 7.3 Hz), 4.95-4.85 (1H, m), 3.53-3.44 (2H, m), 3.14-3.08 (2H, m), 3.02 (3H, s), 2.84-2.76 (2H, m), 2.61-2.53 (2H, m), 2.27 (6H, s), 1.75-1.64 (2H, m), 1.42 (3H, d, J = 6.6 Hz), 1.02 (3H, t, J = 7.3 Hz) |
| 8-9 | 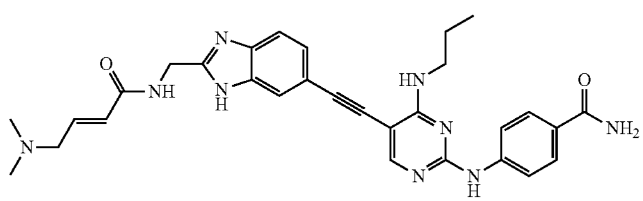 [SMILES: CCCNc1nc(Nc2ccc(C(N)=O)cc2)ncc1C#Cc1ccc2nc(CNC(=O)/C=C/CN(C)C)[nH]c2c1] | ¹H-NMR (CD₃OD) δ: 8.06 (1H, s), 7.84 (4H, s), 7.54-7.31 (3H, m), 6.90-6.78 (1H, m), 6.23-6.14 (1H, m), 4.70 (2H, s), 3.54 (2H, t), 3.17-3.13 (2H, m), 2.29 (6H, s), 1.74 (2H, dt), 1.03 (3H, t) |
| 8-10 | 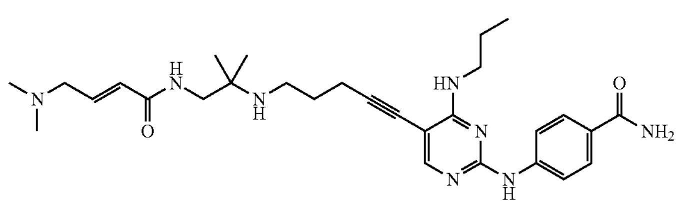 [SMILES: CCCNc1nc(Nc2ccc(C(N)=O)cc2)ncc1C#CCCCNC(C)(C)CNC(=O)/C=C/CN(C)C] | ¹H-NMR (CD₃OD) δ: 7.90 (1H, s), 7.82-7.80 (4H, brs), 6.76 (1H, dt), 6.14 (1H, dt), 3.47 (2H, t), 3.32-3.28 (2H, t), 3.09 (2H, dd), 2.73 (2H, t), 2.57 (2H, t), 2.15 (6H, s), 1.81-1.61 (4H, m), 1.16 (6H, s), 1.00 (3H, t) |
| 8-11 | 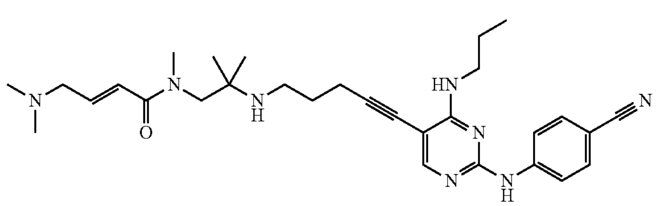 [SMILES: CCCNc1nc(Nc2ccc(C#N)cc2)ncc1C#CCCCNC(C)(C)CN(C)C(=O)/C=C/CN(C)C] | ¹H-NMR (CD₃OD) δ: 7.90 (1H, s), 7.90 (2H, d), 7.58 (2H, d), 6.81-6.69 (1H, m), 6.60 (1H, d), 3.50-3.42 (4H, m), 3.16-3.12 (2H, m), 2.80-2.71 (2H, m), 2.61-2.53 (2H, m), 2.26 (6H, s), 2.24 (3H, s), 1.81-1.61 (4H, m), 1.13 (6H, s), 0.98 (3H, t) |

TABLE 121-continued

| Compound No. | Structure | Physicochemical data |
|---|---|---|
| 8-12 | 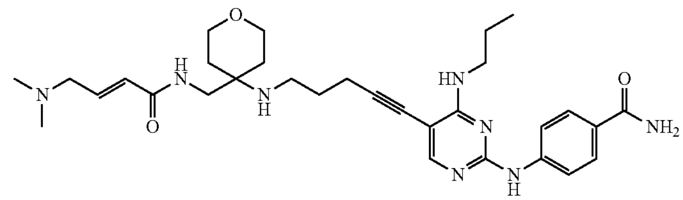 [SMILES: CCCNc1nc(Nc2ccc(C(N)=O)cc2)ncc1C#CCCCNC1(CNC(=O)/C=C/CN(C)C)CCOCC1] | $^1$H-NMR (CDCl$_3$) δ: 7.90 (1H, s), 7.80-7.80 (4H, brs), 7.77 (1H, dt), 6.16 (1H, d), 3.85-3.55 (8H, m), 3.36-3.32 (2H, m), 3.12 (2H, d), 2.66-2.58 (2H, t), 2.26 (6H, s), 1.80-1.48 (8H, m), 1.00 (3H, t) |
| 8-13 | 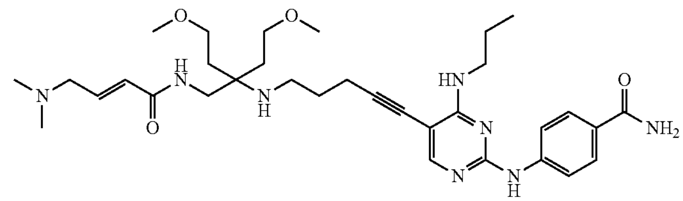 [SMILES: CCCNc1nc(Nc2ccc(C(N)=O)cc2)ncc1C#CCCCNC(CCOC)(CCOC)CNC(=O)/C=C/CN(C)C] | $^1$H-NMR (CDCl$_3$) δ: 7.90 (1H, s), 7.80-7.80 (4H, brs), 7.77 (1H, dt), 6.16 (1H, d), 3.62-3.52 (8H, m), 3.34 (6H, s) 3.36-3.32 (2H, m), 3.12 (2H, d), 2.66-2.58 (2H, t), 2.26 (6H, s), 1.80-1.48 (8H, m), 1.00 (3H, t) |

TABLE 122

| Compound No. | Structure | Physicochemical data |
|---|---|---|
| 8-14 | 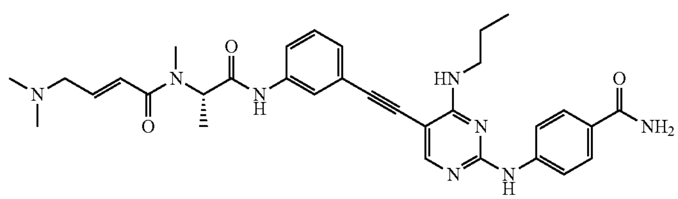 [SMILES: CCCNc1nc(Nc2ccc(C(N)=O)cc2)ncc1C#Cc1cccc(NC(=O)[C@H](C)N(C)C(=O)/C=C/CN(C)C)c1] | $^1$H-NMR (CD$_3$OD) δ: 7.90 (1H, s), 7.81-7.77 (4H, m), 7.37-7.34 (2H, m), 7.20 (1H, t. J = 7.6 Hz), 6.93 (1H, d, J = 7.3 Hz), 6.85-6.75 (1H, m), 6.59 (1H, d, J = 15.2 Hz), 5.15 (1H, q, J = 7.3 Hz), 3.45 (2H, t, J = 7.3 Hz), 3.15 (2H, d, J = 6.6 Hz), 3.10 (3H, s), 2.86-2.83 (2H, m), 2.68 (2H, t, J = 6.9 Hz), 2.27 (6H, s), 1.71-1.66 (2H, m), 1.43 (3H, d, J = 7.3 Hz), 1.01 (3H, t, J = 7.3 Hz) |
| 8-15 | 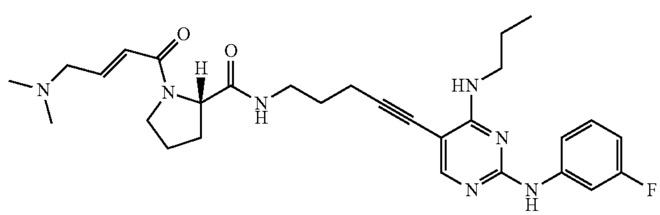 [SMILES: CCCNc1nc(Nc2cccc(F)c2)ncc1C#CCCCNC(=O)[C@@H]1CCCN1C(=O)/C=C/CN(C)C] | $^1$H-NMR (CDCl$_3$) δ: 7.93 (1H, s), 7.86-7.74 (2H, m), 7.29-7.14 (2H, m), 7.12-7.05 (1H, m), 6.92 (1H, dt, J = 15.2, 5.9 Hz), 6.67 (1H, dt, J = 8.1. 2.4 Hz), 6.33-6.25 (1H, m), 6.24-6.14 (1H, m), 4.43-4.31 (1H, m), 3.66-3.40 (5H, m), 3.30-3.18 (1H, m), 3.09 (2H, d, J = 5.9 Hz), 2.74 (2H, t, J = 6.9 Hz), 2.47 (2H, t, J = 6.9 Hz), 2.26 (6H, s), 2.07-1.88 (4H, m), 1.80-1.64 (2H, m), 1.01 (3H, t, J = 7.6 Hz) |
| 8-16 | 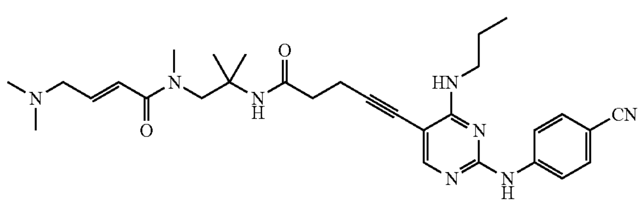 [SMILES: CCCNc1nc(Nc2ccc(C#N)cc2)ncc1C#CCCC(=O)NC(C)(C)CN(C)C(=O)/C=C/CN(C)C] | $^1$H-NMR (CDCl$_3$) δ: 8.07 (1H, s), 7.93 (1H, s), 7.76 (2H, d, J = 8.6 Hz), 7.56 (2H, d, J = 9.2 Hz), 7.29-7.22 (1H, m), 6.93 (1H, dt, J = 15.3, 5.9 Hz), 6.53-6.42 (2H, m), 3.46 (2H, dd, J = 14.5, 5.9 Hz), 3.41 (2H, s), 3.20 (3H, s), 3.11 (2H, dd, J = 5.9, 1.3 Hz), 2.69 (2H, t, J = 6.9 Hz), 2.37 (2H, t, J = 6.9 Hz), 2.28 (6H, s), 1.81-1.68 (2H, m), 1.46 (6H, s), 1.01 (3H, t, J = 7.3 Hz) |
| 8-17 | 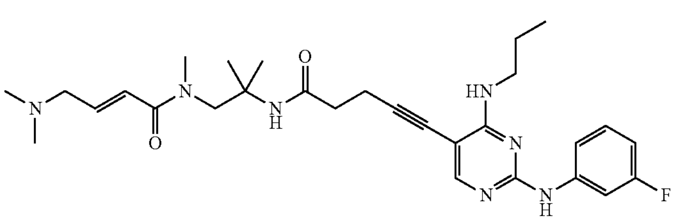 [SMILES: CCCNc1nc(Nc2cccc(F)c2)ncc1C#CCCC(=O)NC(C)(C)CN(C)C(=O)/C=C/CN(C)C] | $^1$H-NMR (CDCl$_3$) δ: 8.03 (1H, s), 7.91 (1H, s), 7.82 (1H, dt, J = 12.1, 2.0 Hz), 7.31-7.23 (1H, m), 7.20 (1H, dt, J = 8.3, 6.6 Hz), 7.09 (1H, dd, J = 8.3, 2.0 Hz), 6.93 (1H, dt, J = 15.2, 6.0 Hz), 6.67 (1H, dt, J = 8.3, 2.0 Hz), 6.46 (1H, dt, J = 15.2, 1.7 Hz), 6.35 (1H, t, J = 6.3 Hz), 3.47 (2H, dd, J = 14.9, 6.3 Hz), 3.41 (2H, s), 3.19 (3H, s), 3.10 (2H, dd, J = 6.0, 1.7 Hz), 2.69 (2H, t, J = 6.9 Hz), 2.36 (2H, t, J = 6.9 Hz), 2.27 (6H, s), 1.80-1.65 (2H, m), 1.45 (6H, s), 1.01 (3H, t, J = 7.3 Hz) |

TABLE 123

| Compound No. | Structure | Physicochemical data |
|---|---|---|
| 8-18 | 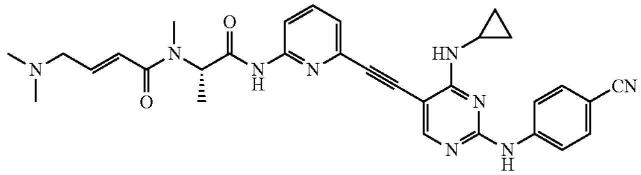 [SMILES: C[C@@H](C(=O)Nc1cccc(C#Cc2cnc(Nc3ccc(C#N)cc3)nc2NC2CC2)n1)N(C)C(=O)/C=C/CN(C)C] | ¹H-NMR (CDCl₃) δ: 8.87-8.83 (1H, m), 8.21 (1H, s), 8.16 (1H, d, J = 7.9 Hz), 7.90 (2H, d, J = 9.2 Hz), 7.69 (1H, t, J = 7.9 Hz), 7.59 (2H, d, J = 9.2 Hz), 7.41-7.37 (1H, m), 7.22 (1H, d, J = 7.9 Hz), 7.04 (1H, dt, J = 15.2, 5.9 Hz), 6.51-6.41 (1H, m), 6.14-6.11 (1H, m), 5.40 (1H, q, J = 7.3 Hz), 3.13 (2H, dd, J = 5.9, 1.3 Hz), 3.04 (3H, s), 2.94-2.83 (1H, m), 2.28 (6H, s), 1.44 (3H, d, J = 7.3 Hz), 0.99-0.88 (2H, m), 0.78-0.68 (2H, m) |
| 8-19 | 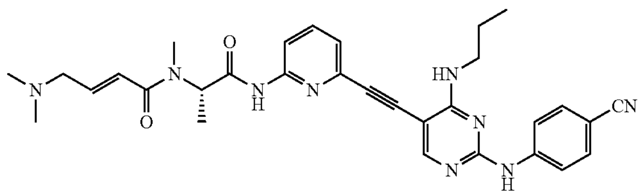 [SMILES: CCCNc1nc(Nc2ccc(C#N)cc2)ncc1C#Cc1cccc(NC(=O)[C@H](C)N(C)C(=O)/C=C/CN(C)C)n1] | ¹H-NMR (CDCl₃) δ: 8.83 (1H, s), 8.19 (1H, s), 8.16 (1H, d, J = 8.3 Hz), 7.78 (2H, d, J = 8.6 Hz), 7.69 (1H, t, J = 8.3 Hz), 7.59 (2H, d, J = 8.6 Hz), 7.32 (1H, s), 7.22 (1H, d, J = 8.3 Hz), 7.03 (1H, dt, J = 15.2, 5.9 Hz), 6.51-6.41 (1H, m), 6.09-5.97 (1H, m), 5.40 (1H, q, J = 6.8 Hz), 3.59-3.47 (2H, m), 3.12 (2H, d, J = 5.9 Hz), 3.04 (3H, s), 2.28 (6H, s), 1.83-1.64 (2H, m), 1.44 (3H, d, J = 6.8 Hz), 1.04 (3H, t, J = 7.6 Hz) |
| 8-20 | 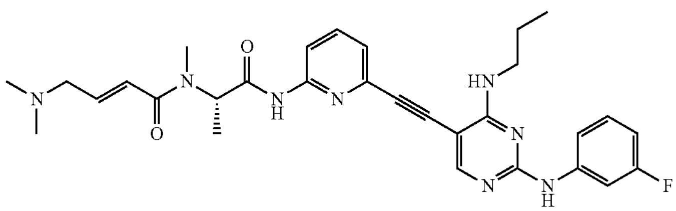 [SMILES: CCCNc1nc(Nc2cccc(F)c2)ncc1C#Cc1cccc(NC(=O)[C@H](C)N(C)C(=O)/C=C/CN(C)C)n1] | ¹H-NMR (CDCl₃) δ: 8.78 (1H, s), 8.18 (1H, s), 8.15 (1H, d, J = 7.9 Hz), 7.81 (1H, dt, J = 11.7, 2.3 Hz), 7.68 (1H, t, J = 7.9 Hz), 7.29-7.18 (3H, m), 7.11 (1H, dd, J = 7.9, 2.3 Hz), 7.03 (1H, dt, J = 15.3, 5.9 Hz), 6.71 (1H, dt, J = 8.3, 2.3 Hz), 6.51-6.39 (1H, m), 5.98-5.87 (1H, m), 5.48-5.33 (1H, m), 3.61-3.45 (2H, m), 3.12 (2H, dd, J = 5.9, 1.3 Hz), 3.04 (3H, s), 2.28 (6H, s), 1.83-1.67 (2H, m), 1.44 (3H, d, J = 7.3 Hz), 1.04 (3H, t, J = 7.6 Hz) |
| 8-21 | 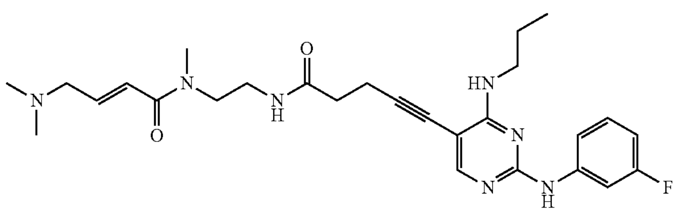 [SMILES: CCCNc1nc(Nc2cccc(F)c2)ncc1C#CCCC(=O)NCCN(C)C(=O)/C=C/CN(C)C] | ¹H-NMR (CDCl₃) δ: 7.93 (1H, s), 7.86-7.76 (1H, m), 7.31-7.15 (2H, m), 7.14-7.06 (1H, m), 6.95-6.77 (2H, m), 6.67 (1H, dt, J = 8.3, 2.0 Hz), 6.40 (1H, d, J = 15.2 Hz), 6.31-6.22 (1H, m), 3.66-3.56 (2H, m), 3.53-3.42 (4H, m), 3.13-3.03 (5H, m), 2.72 (2H, t, J = 6.9 Hz), 2.44 (2H, t, J = 6.9 Hz), 2.26 (6H, s), 1.81-1.66 (2H, m), 1.02 (3H, t, J = 7.6 Hz) |

TABLE 124

| Compound No. | Structure | Physicochemical data |
|---|---|---|
| 8-22 | 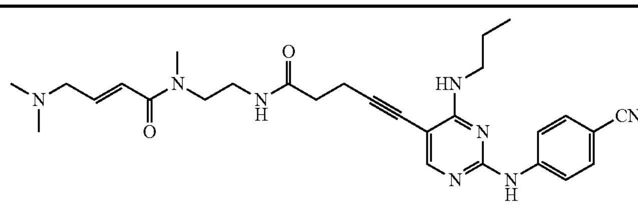 | ¹H-NMR (CDCl₃) δ: 7.94 (1H, s), 7.77 (2H, d, J = 8.6 Hz), 7.61-7.47 (3H, m), 6.97-6.81 (2H, m), 6.48-6.34 (2H, m), 3.66-3.57 (2H, m), 3.53-3.40 (4H, m), 3.14-3.04 (5H, m), 2.72 (2H, t, J = 6.9 Hz), 2.45 (2H, t, J = 6.9 Hz), 2.26 (6H, s), 1.81-1.64 (2H, m), 1.01 (3H, t, J = 7.6 Hz) |
| 8-23 | 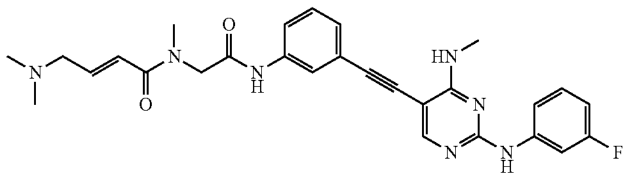 [SMILES: CNc1nc(Nc2cccc(F)c2)ncc1C#Cc1cccc(NC(=O)CN(C)C(=O)/C=C/CN(C)C)c1] | ¹H-NMR (CDCl₃) δ: 8.94 (1H, s), 8.12 (1H, s), 7.84-7.79 (1H, m), 7.73 (1H, s), 7.45 (1H, d, J = 7.9 Hz), 7.32-7.13 (5H, m), 7.00 (1H, dt, J = 15.3, 5.7 Hz), 6.73-6.68 (1H, m), 6.48 (1H, d, J = 15.2 Hz), 5.59 (1H, brs), 4.17 (2H, s), 3.26 (3H, s), 3.16-3.12 (5H, m), 2.28 (6H, s) |

Example 41

1

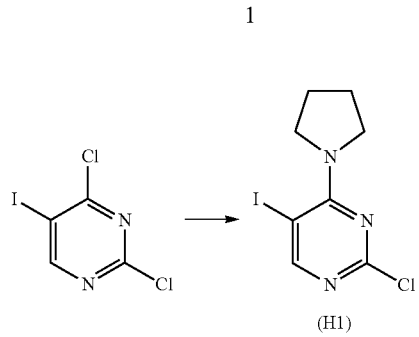

To a solution of 2,4-dichloro-5-iodopyrimidine (5.00 g) synthesized according to the method described in WO2008/155140A1 in tetrahydrofuran (50 mL), N,N-diisopropylethylamine (3.49 mL) and pyrrolidine (1.65 mL) were added under ice cooling, and the mixture was stirred at the same temperature for 3 hours. To the reaction mixture, 1.0 mol/L aqueous hydrochloric acid was added. The solid matter was taken by filtration, washed with water, and then dried under reduced pressure to obtain 2-chloro-5-iodo-4-(pyrrolidin-1-yl)pyrimidine (H1, 4.49 g).

MS m/z (M+H): 310.1

2

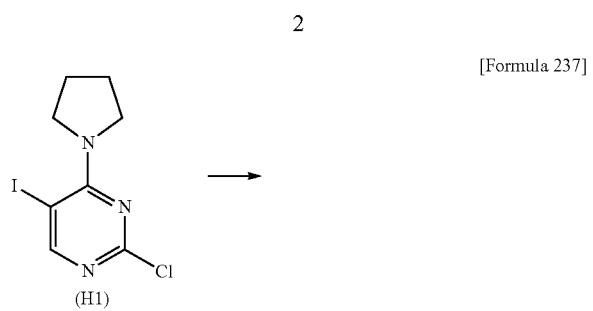

To a suspension of bis(triphenylphosphine)palladium(II) dichloride (1.02 g) and copper(I) iodide (558 mg) in N,N-dimethylformamide (90 mL), triethylamine (10.2 mL), 2-chloro-5-iodo-4-(pyrrolidin-1-yl)pyrimidine (H1, 4.49 g), and N-(4-pentynyl)phthalimide (4.65 g) were added at room temperature under a nitrogen atmosphere, and the mixture was stirred at the same temperature for 4 hours. To the reaction mixture, water was added. The solid matter was taken by filtration, washed with water, then dried under reduced pressure, and purified by silica gel column chromatography. The obtained solid matter was washed with ethyl acetate, and then dried under reduced pressure to obtain 2-(5-(2-chloro-4-(pyrrolidin-1-yl)pyrimidin-5-yl)-4-pentyn-1-yl)isoindoline-1,3-dione (H2, 3.66 g).

MS m/z (M+H): 395.2

3

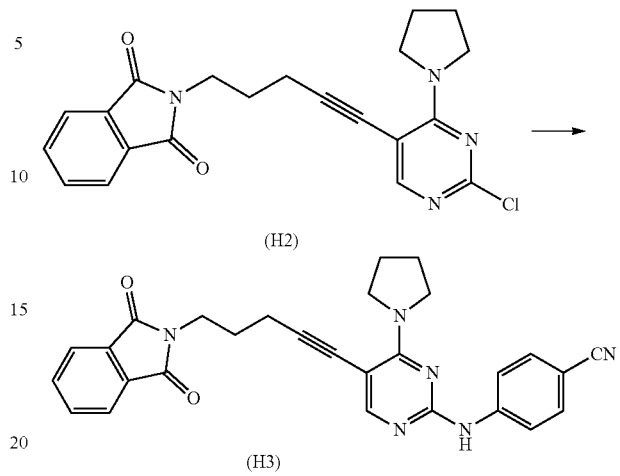

To a solution of tris(dibenzylideneacetone)dipalladium(0) (835 mg) and 4,5'-bis(diphenylphosphino)-9,9'-dimethylxanthene (1.06 g) in 1,4-dioxane (125 mL), 2-(5-(2-chloro-4-(pyrrolidin-1-yl)pyrimidin-5-yl)-4-pentyn-1-yl)isoindoline-1,3-dione (H2, 3.60 g), 4-aminobenzonitrile (2.69 g) and cesium carbonate (8.90 g) were added at room temperature under a nitrogen atmosphere, and the mixture was stirred at 90° C. for 7 hours. The reaction mixture was cooled to room temperature, and then ethyl acetate was added to the reaction mixture. The insoluble matter was removed by filtration through Cerite, and then the solvent was evaporated under reduced pressure. To the obtained residue, water was added. The solid matter was taken by filtration, and washed with water to obtain 4-((5-(5-(1,3-dioxoisoindolin-2-yl)-1-pentyn-1-yl)-4-(pyrrolidin-1-yl)pyrimidin-2-yl)amino)benzonitrile (H3).

MS m/z (M+H): 477.3

4

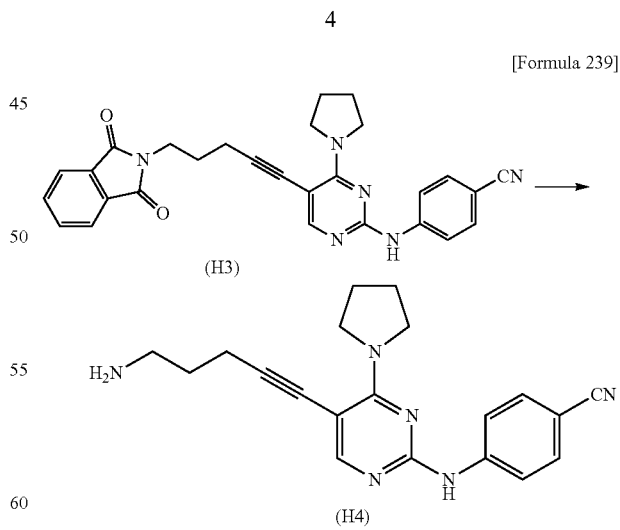

To a solution of 4-((5-(5-(1,3-dioxoisoindolin-2-yl)-1-pentyn-1-yl)-4-(pyrrolidin-1-yl)pyrimidin-2-yl)amino)benzonitrile (H3) obtained above in tetrahydrofuran (80 mL) and ethanol (80 mL), hydrazine monohydrate (16 mL) was added at room temperature, and the mixture was stirred at 80° C. for 3 hours. The reaction mixture was cooled to room temperature, and then ethyl acetate was added to the reaction mixture. The insoluble matter was removed by filtration, and then the solvent was evaporated under reduced pressure. The obtained residue was purified by basic silica gel column chromatography (eluent, 98 to 85% ethyl acetate in methanol) to obtain 4-((5-(5-amino-1-pentyn-1-yl)-4-(pyrrolidin-1-yl)pyrimidin-2-yl)amino)benzonitrile (H4, 2.64 g).

MS m/z (M+H): 347.3

5

[Formula 240]

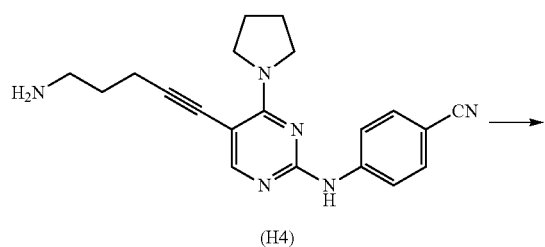

(H4)

N-Boc-N-methyl-L-alanine (3.10 g), 1-ethyl-3-(3-dimethylaminopropyl)carbodiimide hydrochloride (2.92 g) and 1-hydroxybenzotriazole monohydrate (2.06 g) in N,N-dimethylformamide (40 mL), N,N-diisopropylethylamine (3.98 mL) was added at room temperature, and the mixture was stirred at the same temperature for 3 hours. The solvent was evaporated under reduced pressure, and to the obtained residue, saturated aqueous sodium hydrogencarbonate and ethyl acetate were added. The organic layer was separated, washed successively with saturated aqueous sodium hydrogencarbonate and saturated aqueous sodium chloride, and then dried over anhydrous sodium sulfate, and the solvent was evaporated under reduced pressure. The obtained residue was purified by silica gel column chromatography (eluent, 30 to 5% hexane in ethyl acetate). The obtained solid matter was washed with a mixed solvent of ethyl acetate and hexane, and then dried under reduced pressure to obtain (S)-tert-butyl (1 -((5-(2-((4-cyanophenyl)amino)-4-(pyrrolidin-1-yl)pyrimidin-5-yl)-4-pentyn-1-yl)amino)-1-oxopropan-2-yl)(methyl)carbamate (H5, 2.39 g) as white solid.

MS m/z (M+H): 532.5

6

[Formula 241]

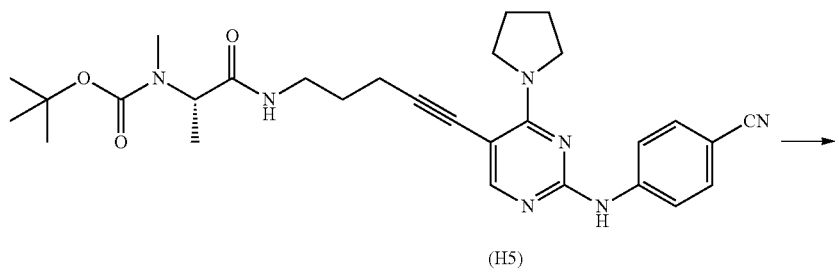

(H5)

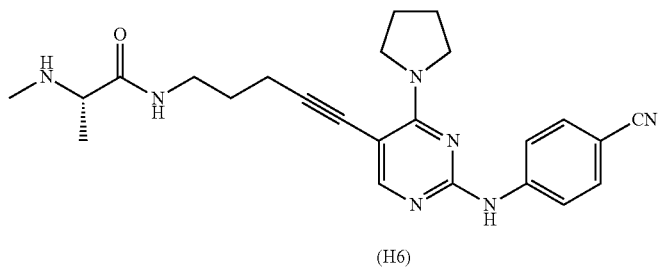

(H6)

-continued

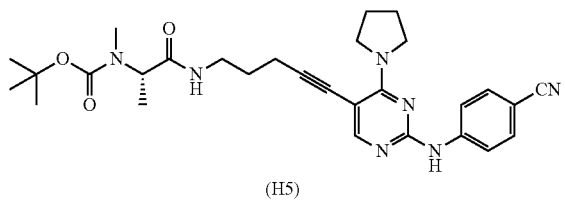

(H5)

To a solution of 4-((5-(5-amino-1-pentyn-1-yl)-4-(pyrrolidin-1-yl)pyrimidin-2-yl)amino)benzonitrile (H4, 2.64 g), To a solution of (S)-tert-butyl (1-((5-(2-((4-cyanophenyl)amino)-4-(pyrrolidin-1-yl)pyrimidin-5-yl)-4-pentyn-1-yl)amino)-1-oxopropan-2-yl)(methyl)carbamate (H5, 2.39 g) in 1,4-dioxane (40 mL), a 4.0 mol/L solution of hydrochloric acid in 1,4-dioxane (20 mL) was added at room temperature, and the mixture was stirred at the same temperature for 6 hours. The solvent was evaporated under reduced pressure. The obtained solid matter was washed with ethyl acetate, and then dried under reduced pressure to obtain (S)—N-(5-(2-((4-cyanophenyl)amino)-4-(pyrrolidin-1-yl)pyrimidin-5-yl)-4-pentyn-1-yl)-2-(methylamino)propanamide (H6) dihydrochloride (2.36 g) as white solid.

MS m/z (M–H): 430.4

[Formula 242]

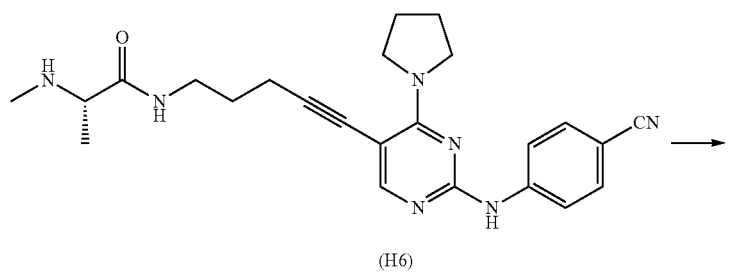

(H6)

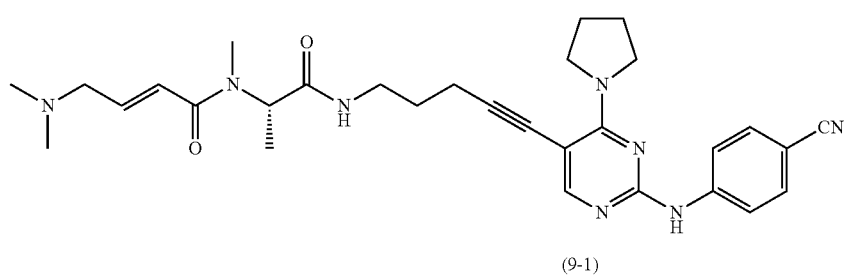

(9-1)

To a solution of (S)—N-(5-(2-((4-cyanophenyl)amino)-4-(pyrrolidin-1-yl)pyrimidin-5-yl)-4-pentyn-1-yl)-2-(methylamino)propanamide (H6) dihydrochloride (252 mg) and 4-dimethylaminocrotonic acid hydrochloride (331 mg) in N,N-dimethylformamide (8 mL), N-methylmorpholine (660 µL) and isobutyl chloroformate were added under ice cooling, and the mixture was stirred at the same temperature for 1 hour. To the reaction mixture, saturated aqueous sodium hydrogencarbonate (5 drop) was added, and the solvent was evaporated under reduced pressure. The obtained residue was purified by basic silica gel column chromatography (eluent, 100 to 90% ethyl acetate in methanol). The obtained solid matter was washed with a mixed solvent of ethyl acetate and hexane, and then dried under reduced pressure to obtain (S,E)-N-(1-((5-(2-((4-cyanophenyl)amino)-4-(pyrrolidin-1-yl)pyrimidin-5-yl)-4-pentyn-1-yl)amino)-1-oxopropan-2-yl)-4-(dimethylamino)-N-methyl-2-butenamide (9-1, 132 mg) as white solid.

$^{1}$H-NMR (CDCl$_{3}$) δ: 8.03 (1H, s), 7.74 (2H, d, J=8.6 Hz), 7.56 (2H, d, J=8.6 Hz), 7.30 (1H, s), 6.93 (1H, dt, J=15.2, 5.9 Hz), 6.57 (1H, brs), 6.42 (1H, d, J=15.2 Hz), 5.17 (1H, q, J=7.0 Hz), 3.84 (4H, brs), 3.42-3.26 (2H, m), 3.10 (2H, d, J=5.9 Hz), 2.99 (3H, s), 2.40 (2H, t, J=6.9 Hz), 2.27 (6H, s), 2.00-1.94 (4H, m), 1.78-1.72 (2H, m), 1.35 (3H, d, J=6.6 Hz)

Example 42

1

[Formula 243]

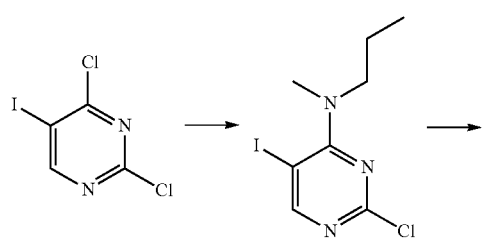

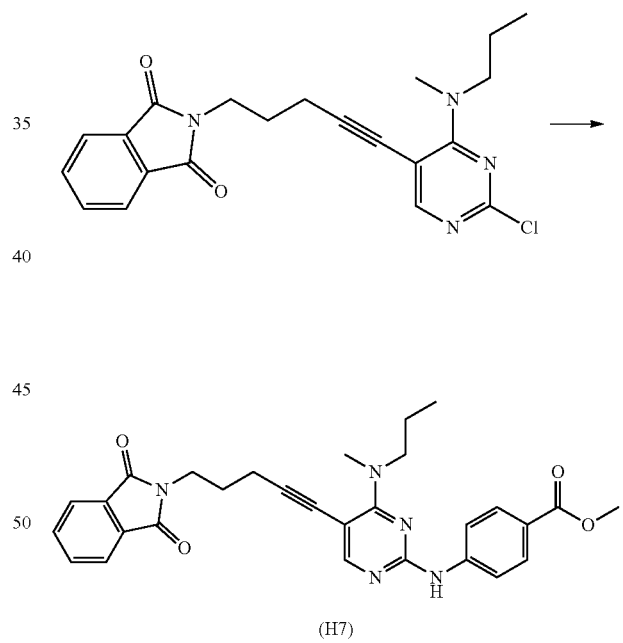

(H7)

By using N-methyl-propylamine and methyl 4-aminobenzoate, methyl 4-((5-(5-(1,3-dioxoisoindolin-2-yl)-1-pentyn-1-yl)-4-(methyl(propyl)amino)pyrimidin-2-yl)amino)benzoate (H7) was obtained in the same manner as that of Example 41.

MS m/z (M+H): 512.4

[Formula 244]

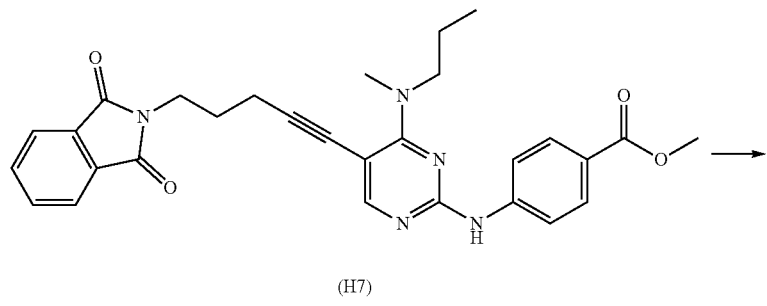

(H7)

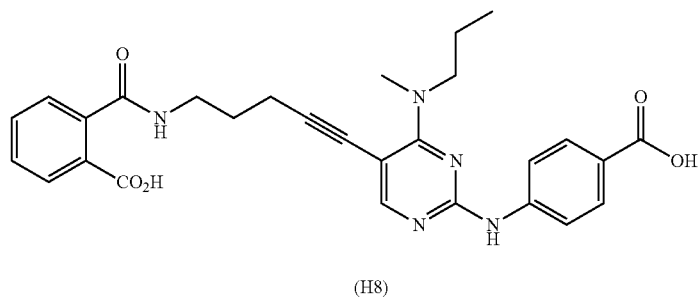

(H8)

To a solution of methyl 4-((5-(5-(1,3-dioxoisoindolin-2-yl)-1-pentyn-1-yl)-4-(methyl(propyl)amino)pyrimidin-2-yl)amino)benzoate (H7, 634 mg) in tetrahydrofuran (6.2 mL), 2.0 mol/L aqueous sodium hydroxide (3.1 mL) was added at room temperature, and the mixture was stirred at 80° C. for 4 hours. The reaction mixture was cooled to room temperature, and then 1.0 mol/L aqueous hydrochloric acid was added to the reaction mixture until the mixture became acidic. The solid matter was taken by filtration, washed with water, and then dried under reduced pressure to obtain 2-((5-(2-((4-carboxyphenyl)amino)-4-(methyl(propyl)amino)pyrimidin-5-yl)-4-pentyn-1-yl)carbamoyl)benzoic acid (H8, 526 mg) as white solid.

MS m/z (M+H): 516.4

3

[Formula 245]

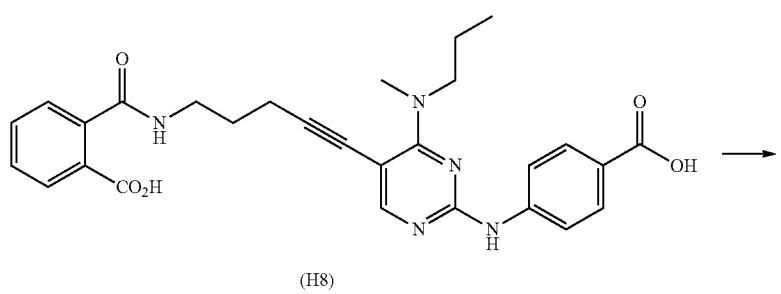

(H8)

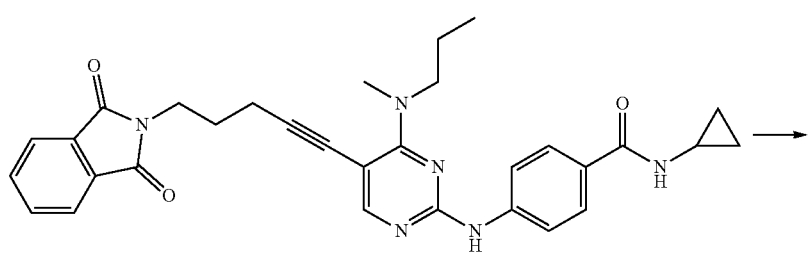

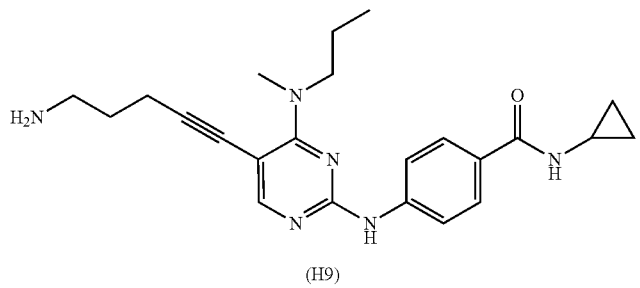

(H9)

To a solution of 2-((5-(2-((4-carboxyphenyl)amino)-4-(methyl(propyl)amino)pyrimidin-5-yl)-4-pentyn-1-yl)carbamoyl)benzoic acid (H8, 200 mg) in N,N-dimethylformamide (4 mL), 1-ethyl-3-(3-dimethylaminopropyl)carbodiimide hydrochloride (297 mg) and 1-hydroxybenzotriazole monohydrate (210 mg) were added at room temperature, and the mixture was stirred at the same temperature for 3 hours. To the reaction mixture, N,N-diisopropylethylamine (541 μL) and cyclopropylamine (215 μL) were added at room temperature, and the mixture was stirred at the same temperature for 2 hours. To the reaction mixture, water was added. The solid matter was taken by filtration, and dried under reduced pressure to obtain white solid (218 mg).

To a solution of the white solid (218 mg) obtained above in ethanol (3 mL) and tetrahydrofuran (3 mL), hydrazine monohydrate (0.5 mL) was added at room temperature, and the mixture was stirred for 1 hour under reflux by heating. The reaction mixture was cooled to room temperature, and then ethyl acetate was added to the reaction mixture. The insoluble matter was removed by filtration, and then water was added. The organic layer was separated, washed successively with water and saturated aqueous sodium chloride, and then dried over anhydrous sodium sulfate, and the solvent was evaporated under reduced pressure. The obtained residue was purified by basic silica gel column chromatography (eluent, 100 to 88% ethyl acetate in methanol) to obtain 4-((5-(5-amino-1-pentyn-1-yl)-4-(methyl(propyl)amino)pyrimidin-2-yl)amino)-N-cyclopropylbenzamide (H9, 112 mg) as white solid.

MS m/z (M+H): 407.4

4

[Formula 246]

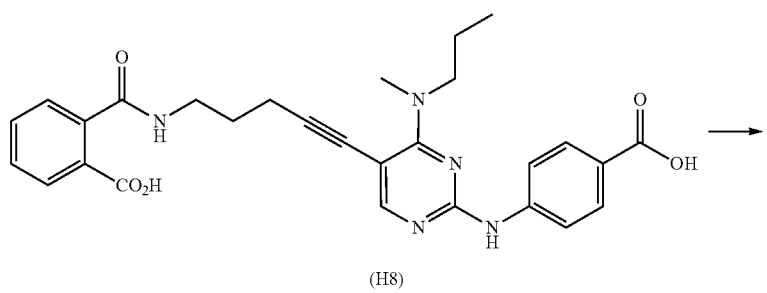

(H8)

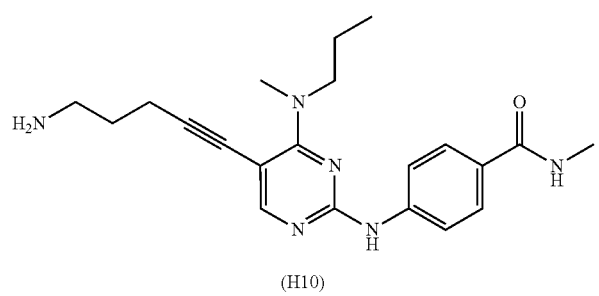

(H10)

By using methylamine, 4-((5-(5-amino-1-pentyn-1-yl)-4-(methyl(propyl)amino)pyrimidin-2-yl)amino)-N-methyl-benzamide (H10) was obtained in the same manner as that of Example 42, (3).

5

By using 2,4-dichloro-5-iodopyrimidine, Intermediates (H11) to (H14) were obtained in the same manner as that of Example 41, (1).

TABLE 125

| Compound No. | Structure | Physicochemical data |
|---|---|---|
| H11 | 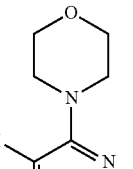 | — |
| H12 | 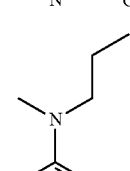 | — |

TABLE 125-continued

| Compound No. | Structure | Physicochemical data |
|---|---|---|
| H13 | 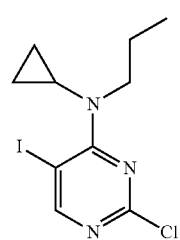 | — |
| H14 | 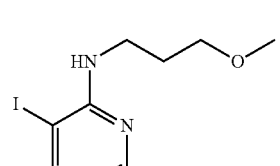 | — |

6

In the same manner as that of Example 41, (2), Intermediates (H15) to (H23) and Intermediates (H125) were obtained.

TABLE 126

| Compound No. | Structure | Physicochemical data |
|---|---|---|
| H15 | 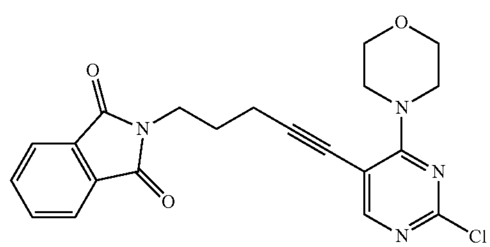 [SMILES: O=C1c2ccccc2C(=O)N1CCCC#Cc1cnc(Cl)nc1N1CCOCC1] | — |
| H16 | 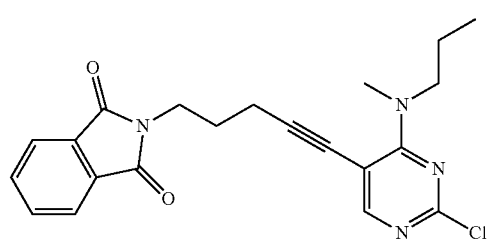 [SMILES: CCCN(C)c1nc(Cl)ncc1C#CCCCN1C(=O)c2ccccc2C1=O] | MS m/z (M + H): 397.1 |

TABLE 126-continued
| Compound No. | Structure | Physicochemical data |
|---|---|---|
| H17 | 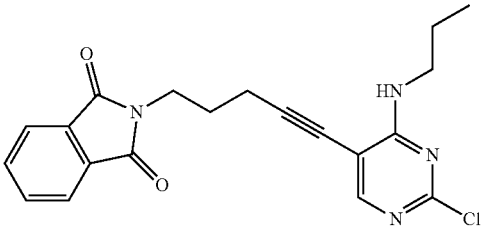 [SMILES: CCCNc1nc(Cl)ncc1C#CCCCN1C(=O)c2ccccc2C1=O] | — |
| H18 | 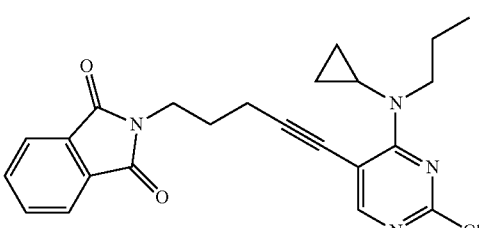 | — |
| H19 | 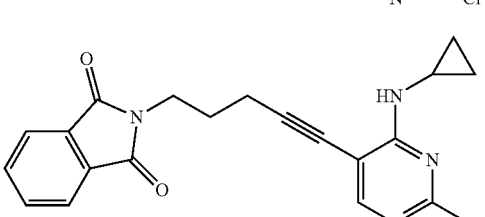 | — |
| H20 | 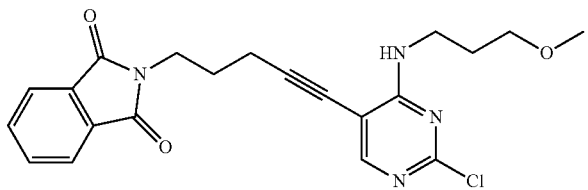 [SMILES: COCCCNc1nc(Cl)ncc1C#CCCCN1C(=O)c2ccccc2C1=O] | MS m/z (M + H): 413.3 |
| H21 | 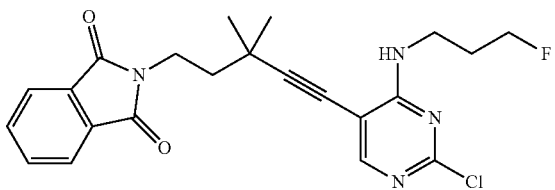 [SMILES: CC(C)(C#Cc1cnc(Cl)nc1NCCCF)CCN1C(=O)c2ccccc2C1=O] | — |
| H22 | 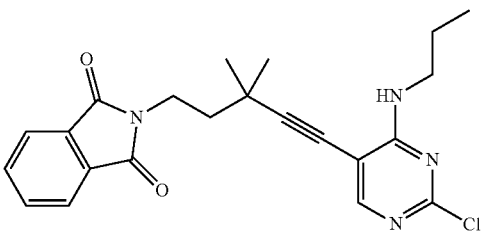 [SMILES: CCCNc1nc(Cl)ncc1C#CC(C)(C)CCN1C(=O)c2ccccc2C1=O] | — |
| H23 | 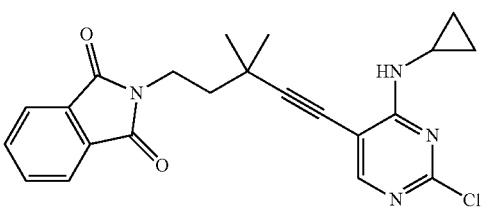 [SMILES: CC(C)(C#Cc1cnc(Cl)nc1NC1CC1)CCN1C(=O)c2ccccc2C1=O] | — |

TABLE 126-continued
| Compound No. | Structure | Physicochemical data |
|---|---|---|
| H125 | 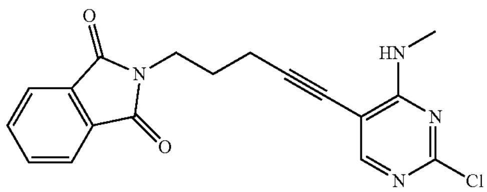 [SMILES: CNc1nc(Cl)ncc1C#CCCCN1C(=O)c2ccccc2C1=O] | MS m/z (M + H): 355.2 |
7 15
In the same manner as that of Example 41, (3), Intermediates (H25) to (H47) and Intermediates (H126) to (H130) were obtained.
TABLE 127
| Compound No. | Structure | Physicochemical data |
|---|---|---|
| H25 | 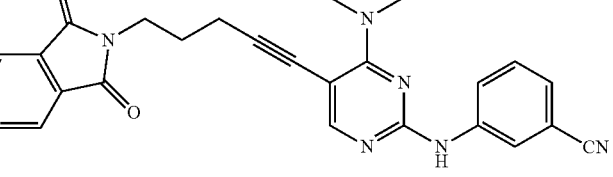 | — |
| H26 | 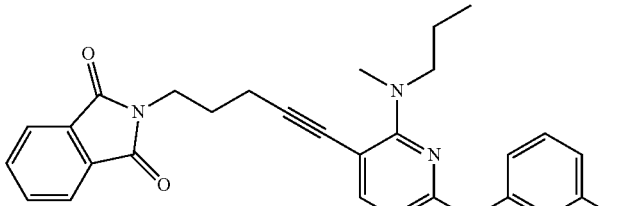 | — |
| H27 | 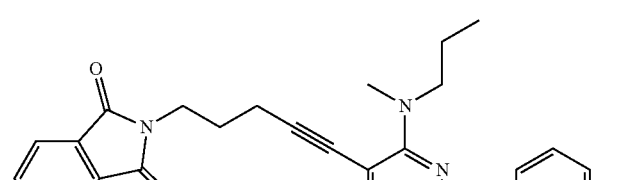 | MS m/z (M + H): 472.2 |
| H28 | 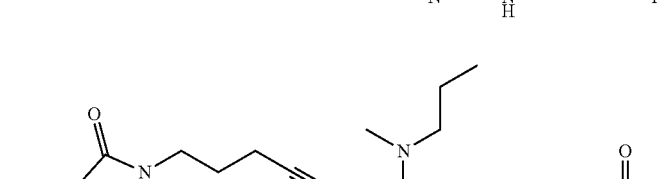 | — |

TABLE 127-continued
| Compound No. | Structure | Physicochemical data |
|---|---|---|
| H29 | 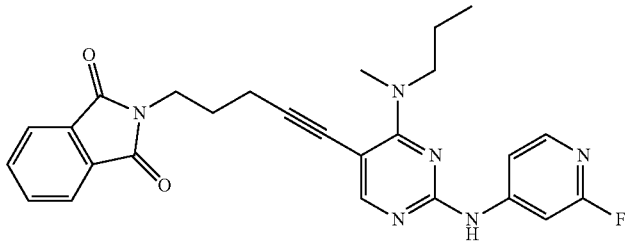 [SMILES: CCCN(C)c1nc(Nc2ccnc(F)c2)ncc1C#CCCCN1C(=O)c2ccccc2C1=O] | — |
| H30 | 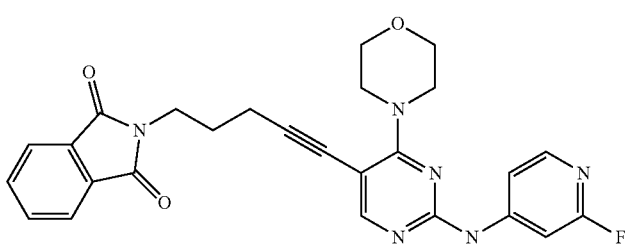 | — |
| H31 | 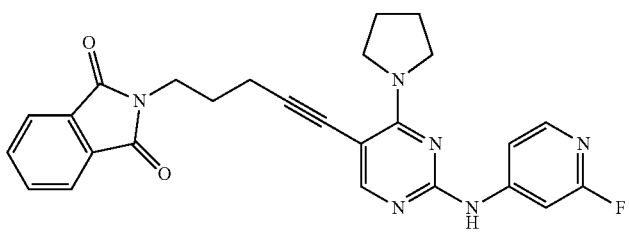 [SMILES: O=C1c2ccccc2C(=O)N1CCCC#Cc1cnc(Nc2ccnc(F)c2)nc1N1CCCC1] | — |
| H32 | 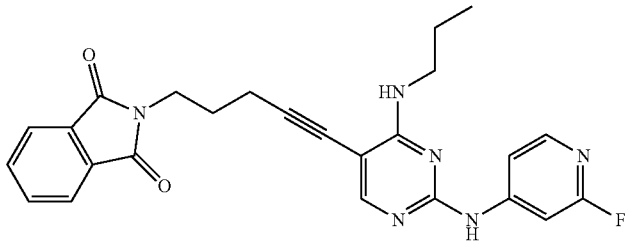 [SMILES: CCCNc1nc(Nc2ccnc(F)c2)ncc1C#CCCCN1C(=O)c2ccccc2C1=O] | — |
TABLE 128
| Compound No. | Structure | Physicochemical data |
|---|---|---|
| H33 | 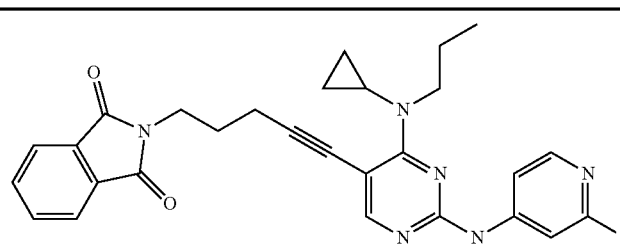 | — |
| H34 | 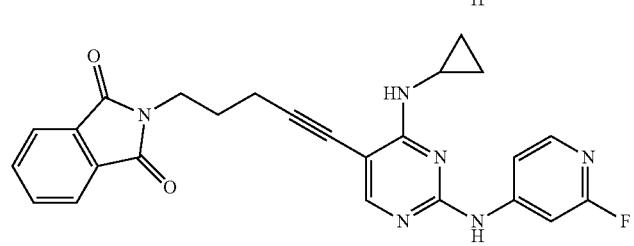 | — |

TABLE 128-continued
| Compound No. | Structure | Physicochemical data |
|---|---|---|
| H35 | 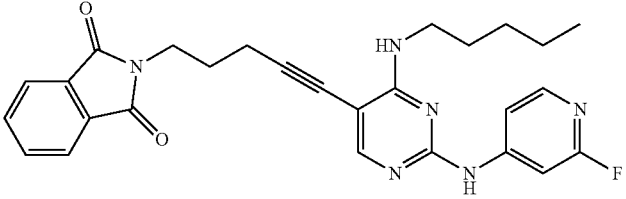 [SMILES: CCCCCNc1nc(Nc2ccnc(F)c2)ncc1C#CCCCN1C(=O)c2ccccc2C1=O] | — |
| H36 | 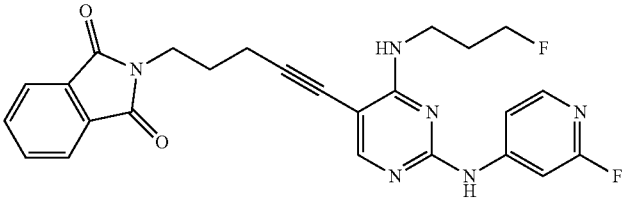 [SMILES: O=C1c2ccccc2C(=O)N1CCCC#Cc1cnc(Nc2ccnc(F)c2)nc1NCCCF] | — |
| H37 | 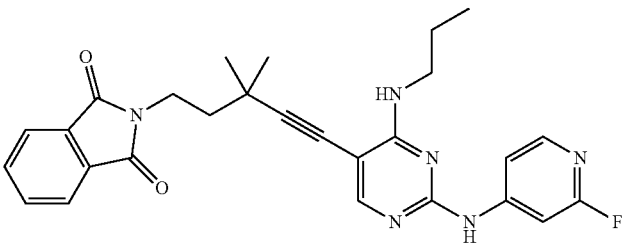 [SMILES: CCCNc1nc(Nc2ccnc(F)c2)ncc1C#CC(C)(C)CCN1C(=O)c2ccccc2C1=O] | — |
| H38 | 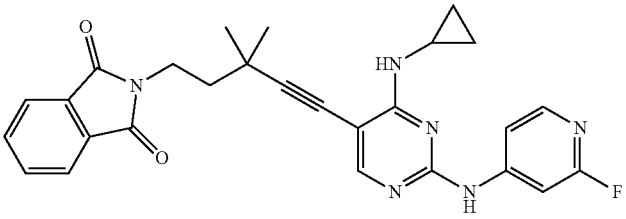 [SMILES: CC(C)(C#Cc1cnc(Nc2ccnc(F)c2)nc1NC1CC1)CCN1C(=O)c2ccccc2C1=O] | — |
| H39 | 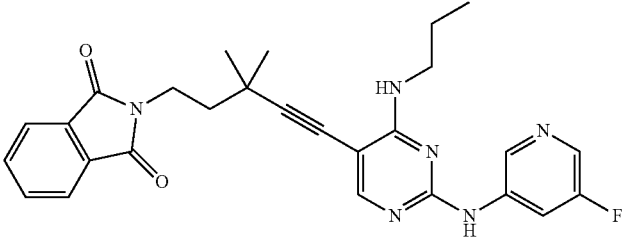 [SMILES: CCCNc1nc(Nc2cncc(F)c2)ncc1C#CC(C)(C)CCN1C(=O)c2ccccc2C1=O] | — |
| H40 | 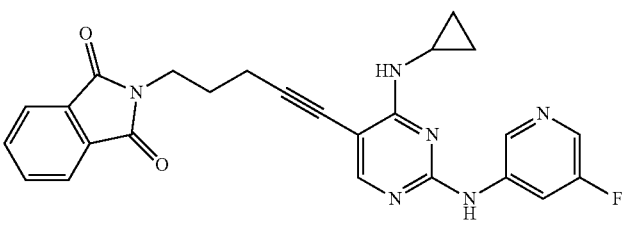 [SMILES: O=C1c2ccccc2C(=O)N1CCCC#Cc1cnc(Nc2cncc(F)c2)nc1NC1CC1] | — |

TABLE 128-continued

| Compound No. | Structure | Physicochemical data |
|---|---|---|
| H41 | 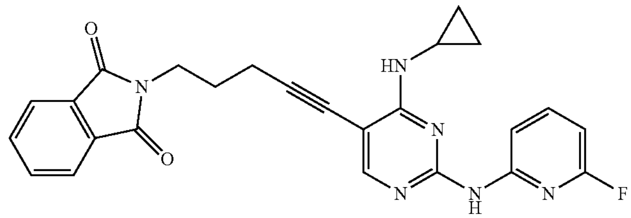 [SMILES: O=C1c2ccccc2C(=O)N1CCCC#Cc1cnc(Nc2cccc(F)n2)nc1NC1CC1] | — |

TABLE 129

| Compound No. | Structure | Physicochemical data |
|---|---|---|
| H42 | 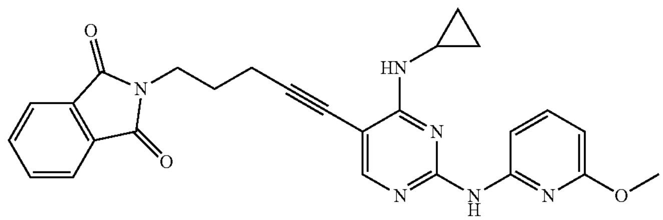 [SMILES: COc1cccc(Nc2ncc(C#CCCCN3C(=O)c4ccccc4C3=O)c(NC3CC3)n2)n1] | — |
| H43 | 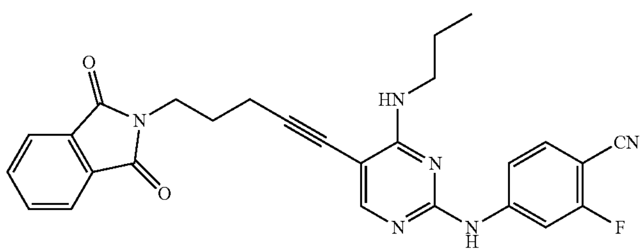 [SMILES: CCCNc1nc(Nc2ccc(C#N)c(F)c2)ncc1C#CCCCN1C(=O)c2ccccc2C1=O] | — |
| H44 | 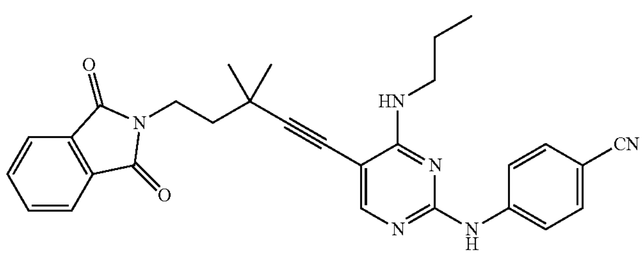 [SMILES: CCCNc1nc(Nc2ccc(C#N)cc2)ncc1C#CC(C)(C)CCN1C(=O)c2ccccc2C1=O] | — |
| H45 | 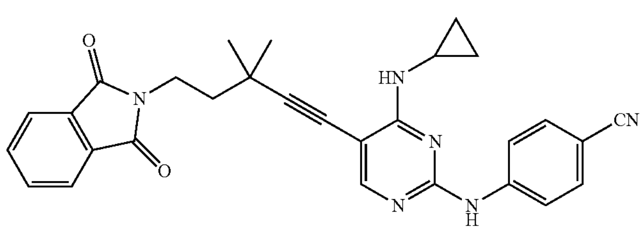 [SMILES: CC(C)(C#Cc1cnc(Nc2ccc(C#N)cc2)nc1NC1CC1)CCN1C(=O)c2ccccc2C1=O] | — |
| H46 | 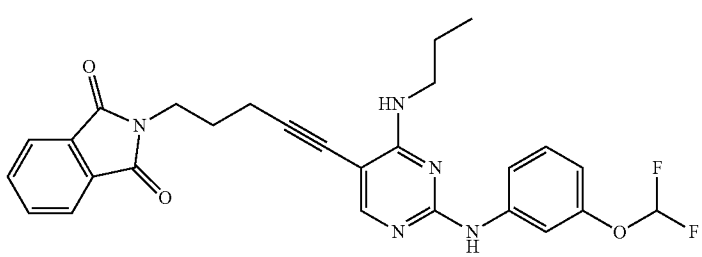 [SMILES: CCCNc1nc(Nc2cccc(OC(F)F)c2)ncc1C#CCCCN1C(=O)c2ccccc2C1=O] | — |

TABLE 129-continued

| Compound No. | Structure | Physicochemical data |
|---|---|---|
| H47 | 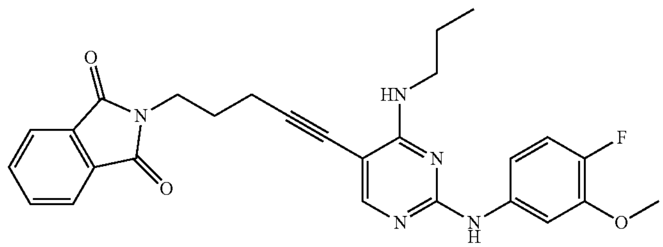 [SMILES: CCCNc1nc(Nc2ccc(F)c(OC)c2)ncc1C#CCCCN1C(=O)c2ccccc2C1=O] | — |
| H126 | 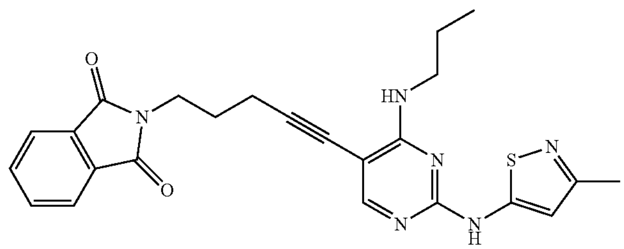 [SMILES: CCCNc1nc(Nc2cc(C)ns2)ncc1C#CCCCN1C(=O)c2ccccc2C1=O] | MS m/z (M + H): 461.3 |
| H127 | 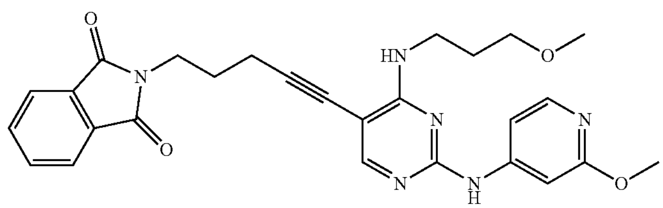 [SMILES: COCCCNc1nc(Nc2ccnc(OC)c2)ncc1C#CCCCN1C(=O)c2ccccc2C1=O] | — |

TABLE 130

| Compound No. | Structure | Physicochemical data |
|---|---|---|
| H128 | 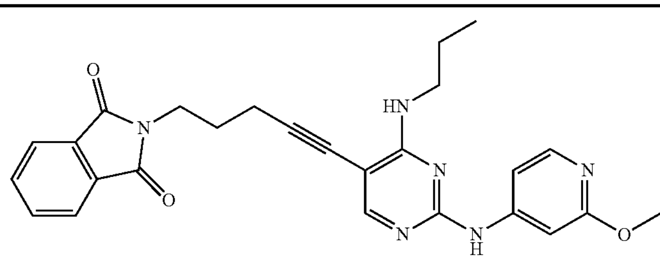 | — |
| H129 | 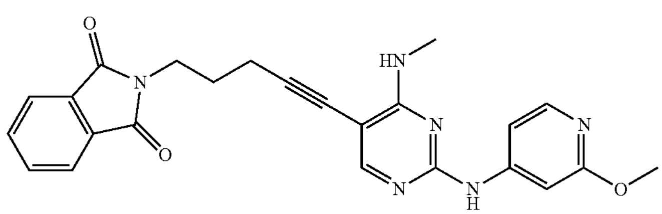 [SMILES: CNc1nc(Nc2ccnc(OC)c2)ncc1C#CCCCN1C(=O)c2ccccc2C1=O] | MS m/z (M + H): 443.3 |
| H130 | 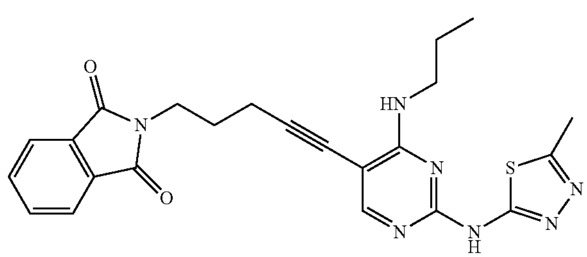 [SMILES: CCCNc1nc(Nc2nnc(C)s2)ncc1C#CCCCN1C(=O)c2ccccc2C1=O] | MS m/z (M + H): 462.3 |

In the same manner as that of Example 41, (4), Intermediates (H48) to (H70) and Intermediates (H131) to (H135) were obtained.

TABLE 131

| Compound No. | Structure | Physicochemical data |
|---|---|---|
| H48 | 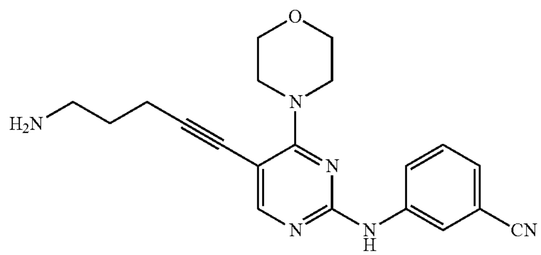 [SMILES: N#Cc1cccc(Nc2ncc(C#CCCCN)c(N3CCOCC3)n2)c1] | — |
| H49 | 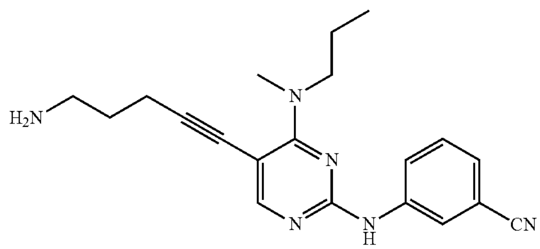 [SMILES: CCCN(C)c1nc(Nc2cccc(C#N)c2)ncc1C#CCCCN] | — |
| H50 | 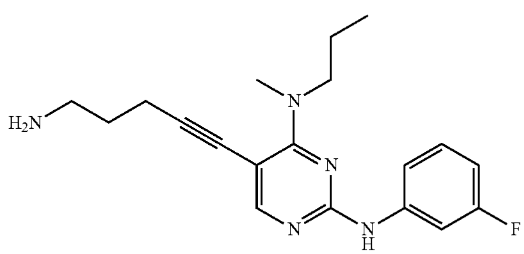 [SMILES: CCCN(C)c1nc(Nc2cccc(F)c2)ncc1C#CCCCN] | MS m/z (M + H): 342.2 |
| H51 | 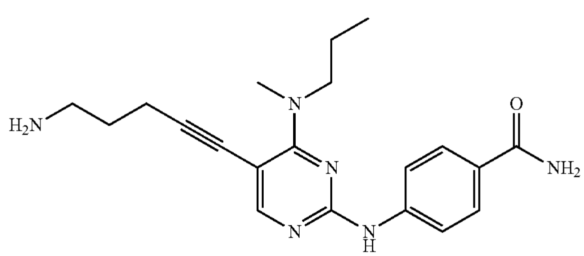 [SMILES: CCCN(C)c1nc(Nc2ccc(C(N)=O)cc2)ncc1C#CCCCN] | MS m/z (M + H): 367.3 |
| H52 | 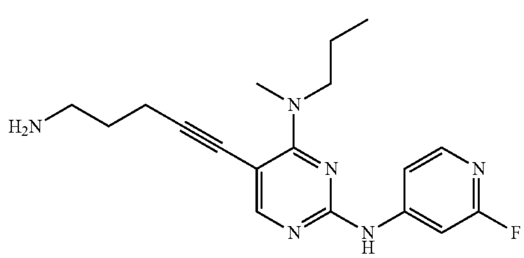 [SMILES: CCCN(C)c1nc(Nc2ccnc(F)c2)ncc1C#CCCCN] | — |

TABLE 131-continued

| Compound No. | Structure | Physicochemical data |
|---|---|---|
| H53 | 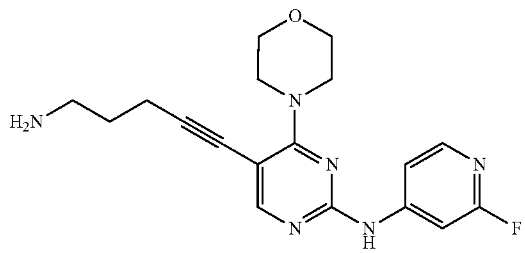 [SMILES: NCCCC#Cc1cnc(Nc2ccnc(F)c2)nc1N1CCOCC1] | — |
| H54 | 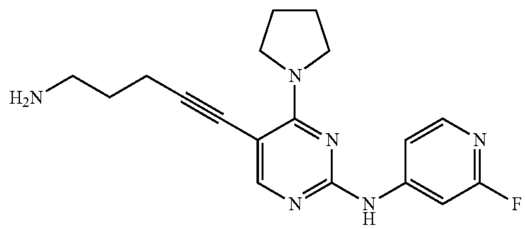 [SMILES: NCCCC#Cc1cnc(Nc2ccnc(F)c2)nc1N1CCCC1] | — |
| H55 | 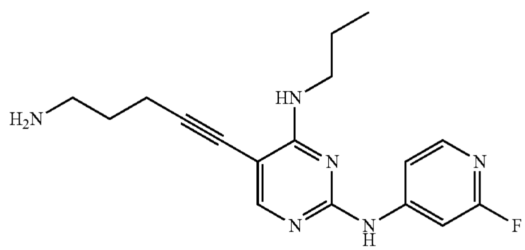 [SMILES: CCCNc1nc(Nc2ccnc(F)c2)ncc1C#CCCCN] | — |

TABLE 132

| Compound No. | Structure | Physicochemical data |
|---|---|---|
| H56 | 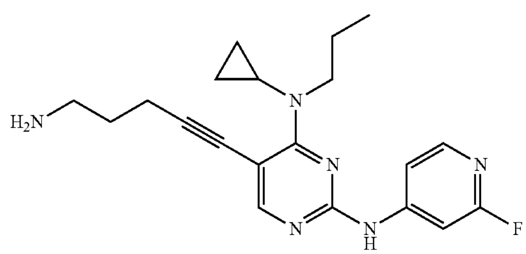 [SMILES: CCCN(c1nc(Nc2ccnc(F)c2)ncc1C#CCCCN)C1CC1] | — |
| H57 | 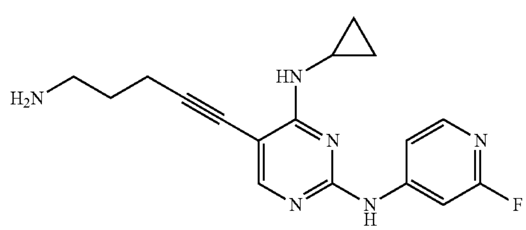 [SMILES: NCCCC#Cc1cnc(Nc2ccnc(F)c2)nc1NC1CC1] | — |
| H58 | 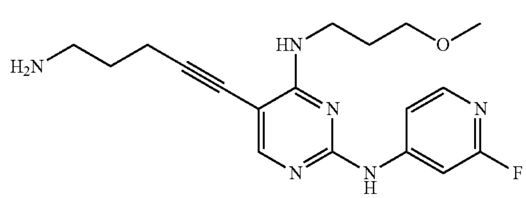 [SMILES: COCCCNc1nc(Nc2ccnc(F)c2)ncc1C#CCCCN] | — |

TABLE 132-continued

| Compound No. | Structure | Physicochemical data |
|---|---|---|
| H59 | 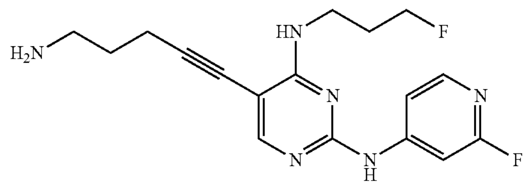 [SMILES: NCCCC#Cc1cnc(Nc2ccnc(F)c2)nc1NCCCF] | — |
| H60 | 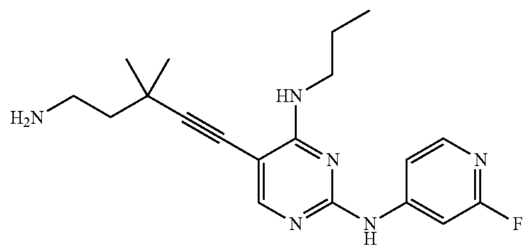 [SMILES: CCCNc1nc(Nc2ccnc(F)c2)ncc1C#CC(C)(C)CCN] | — |
| H61 | 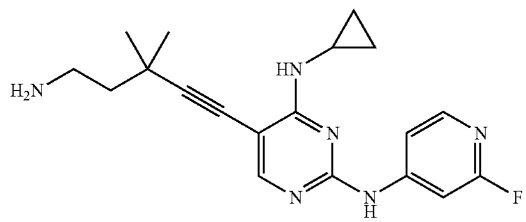 [SMILES: CC(C)(C#Cc1cnc(Nc2ccnc(F)c2)nc1NC1CC1)CCN] | — |
| H62 | 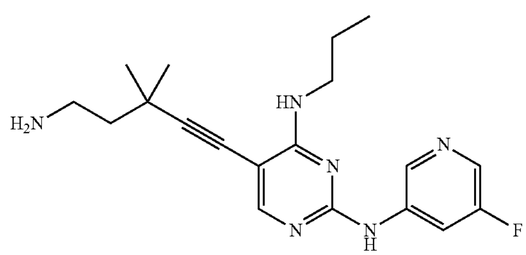 [SMILES: CCCNc1nc(Nc2cncc(F)c2)ncc1C#CC(C)(C)CCN] | — |
| H63 | 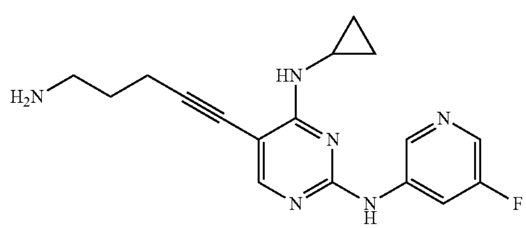 [SMILES: NCCCC#Cc1cnc(Nc2cncc(F)c2)nc1NC1CC1] | — |
| H64 | 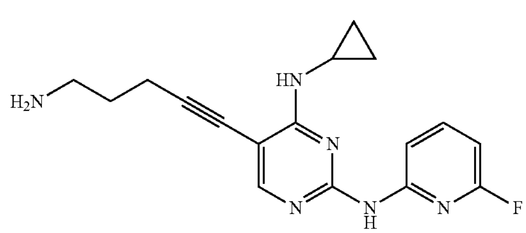 [SMILES: NCCCC#Cc1cnc(Nc2cccc(F)n2)nc1NC1CC1] | — |

TABLE 133

| Compound No. | Structure | Physicochemical data |
|---|---|---|
| H65 | 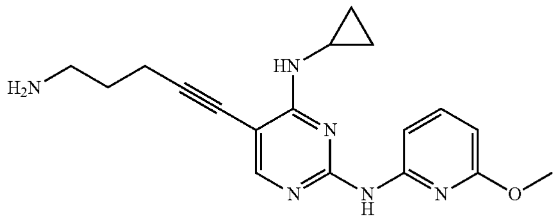 [SMILES: COc1cccc(Nc2ncc(C#CCCCN)c(NC3CC3)n2)n1] | — |
| H66 | 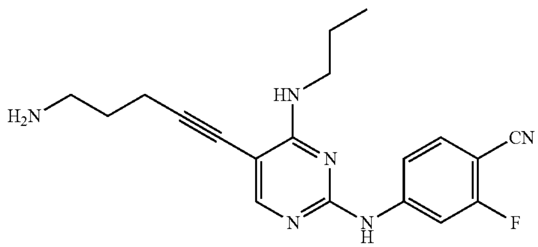 [SMILES: CCCNc1nc(Nc2ccc(C#N)c(F)c2)ncc1C#CCCCN] | — |
| H67 | 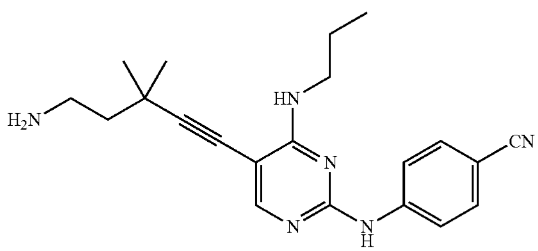 [SMILES: CCCNc1nc(Nc2ccc(C#N)cc2)ncc1C#CC(C)(C)CCN] | — |
| H68 | 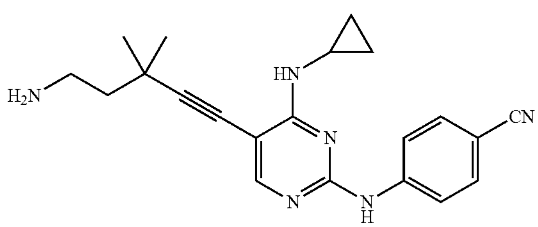 [SMILES: CC(C)(C#Cc1cnc(Nc2ccc(C#N)cc2)nc1NC1CC1)CCN] | — |
| H69 | 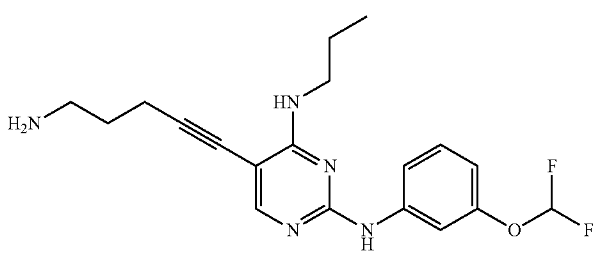 [SMILES: CCCNc1nc(Nc2cccc(OC(F)F)c2)ncc1C#CCCCN] | — |
| H70 | 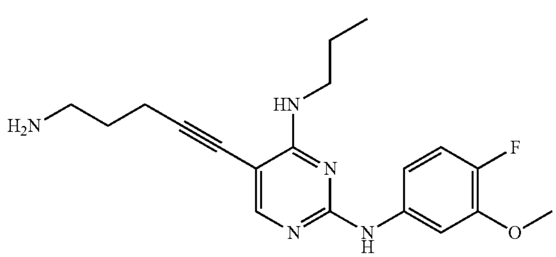 [SMILES: CCCNc1nc(Nc2ccc(F)c(OC)c2)ncc1C#CCCCN] | — |

TABLE 133-continued
| Compound No. | Structure | Physicochemical data |
|---|---|---|
| H131 | 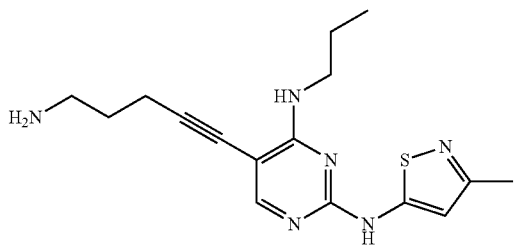 [SMILES: CCCNc1nc(Nc2cc(C)ns2)ncc1C#CCCCN] | — |
| H132 | 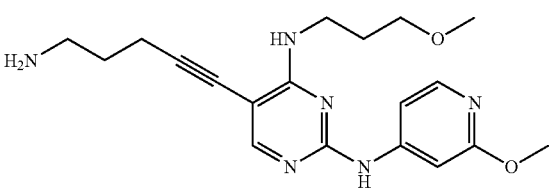 [SMILES: COCCCNc1nc(Nc2ccnc(OC)c2)ncc1C#CCCCN] | MS m/z (M + H): 371.3 |
TABLE 134
| Compound No. | Structure | Physicochemical data |
|---|---|---|
| H133 | 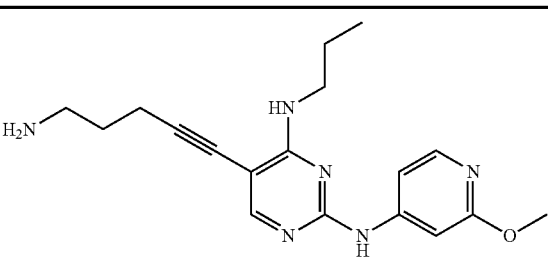 | — |
| H134 | 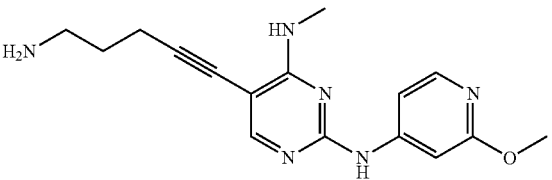 [SMILES: CNc1nc(Nc2ccnc(OC)c2)ncc1C#CCCCN] | MS m/z (M + H): 313.3 |
| H135 | 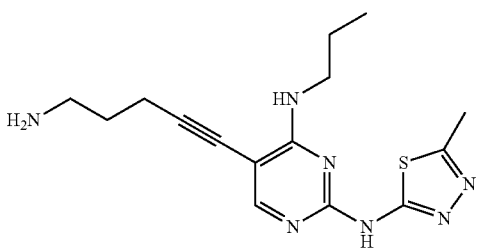 [SMILES: CCCNc1nc(Nc2nnc(C)s2)ncc1C#CCCCN] | MS m/z (M + H): 332.3 |
In the same manner as that of Example 41, (5), Intermediates (H71) to (H97) and Intermediates (H136) to (H146) were obtained.

TABLE 135

| Compound No. | Structure | Physicochemical data |
|---|---|---|
| H71 | 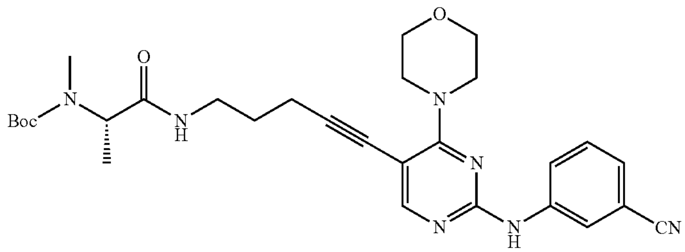 [SMILES: C[C@@H](C(=O)NCCCC#Cc1cnc(Nc2cccc(C#N)c2)nc1N1CCOCC1)N(C)C(=O)OC(C)(C)C] | — |
| H72 | 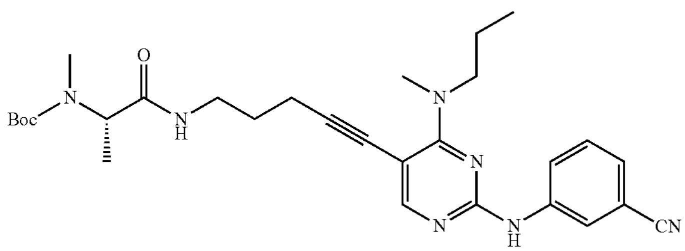 [SMILES: CCCN(C)c1nc(Nc2cccc(C#N)c2)ncc1C#CCCCNC(=O)[C@H](C)N(C)C(=O)OC(C)(C)C] | — |
| H73 | 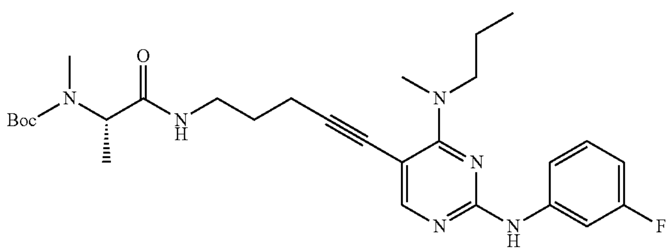 [SMILES: CCCN(C)c1nc(Nc2cccc(F)c2)ncc1C#CCCCNC(=O)[C@H](C)N(C)C(=O)OC(C)(C)C] | MS m/z (M + H): 527.3 |
| H74 | 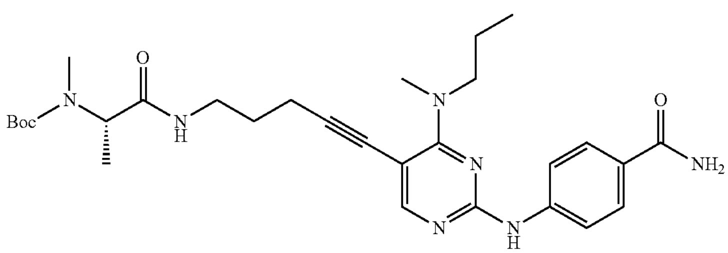 [SMILES: CCCN(C)c1nc(Nc2ccc(C(N)=O)cc2)ncc1C#CCCCNC(=O)[C@H](C)N(C)C(=O)OC(C)(C)C] | MS m/z (M + H): 552.4 |
| H75 | 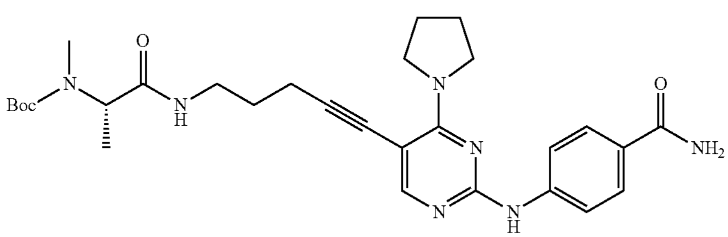 [SMILES: C[C@@H](C(=O)NCCCC#Cc1cnc(Nc2ccc(C(N)=O)cc2)nc1N1CCCC1)N(C)C(=O)OC(C)(C)C] | MS m/z (M + H): 550.4 |
| H76 | 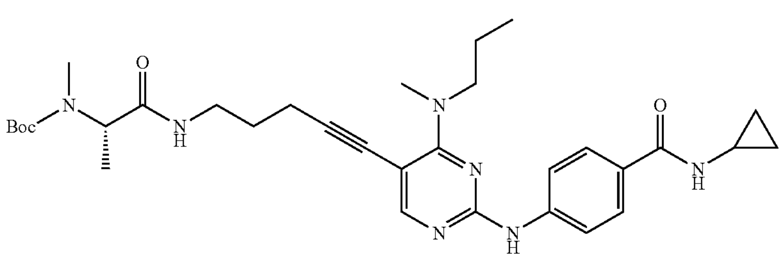 [SMILES: CCCN(C)c1nc(Nc2ccc(C(=O)NC3CC3)cc2)ncc1C#CCCCNC(=O)[C@H](C)N(C)C(=O)OC(C)(C)C] | MS m/z (M + H): 592.5 |

TABLE 135-continued
| Compound No. | Structure | Physicochemical data |
|---|---|---|
| H77 | 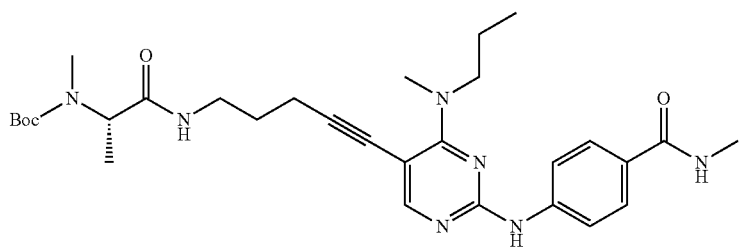 [SMILES: CCCN(C)c1nc(Nc2ccc(C(=O)NC)cc2)ncc1C#CCCCNC(=O)[C@H](C)N(C)C(=O)OC(C)(C)C] | MS m/z (M + H): 566.5 |
| H78 | 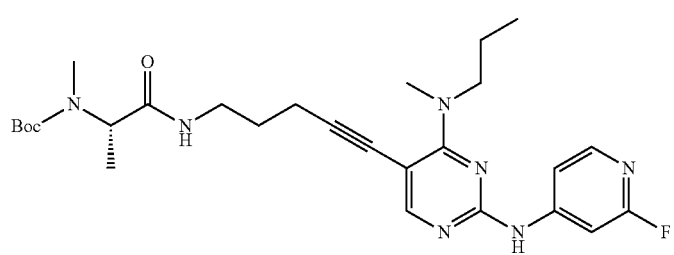 [SMILES: CCCN(C)c1nc(Nc2ccnc(F)c2)ncc1C#CCCCNC(=O)[C@H](C)N(C)C(=O)OC(C)(C)C] | — |
| H79 | 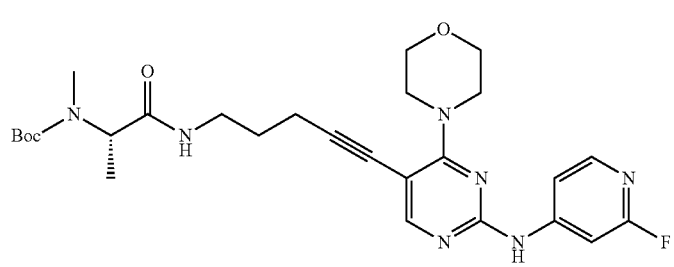 [SMILES: C[C@@H](C(=O)NCCCC#Cc1cnc(Nc2ccnc(F)c2)nc1N1CCOCC1)N(C)C(=O)OC(C)(C)C] | — |
| H80 | 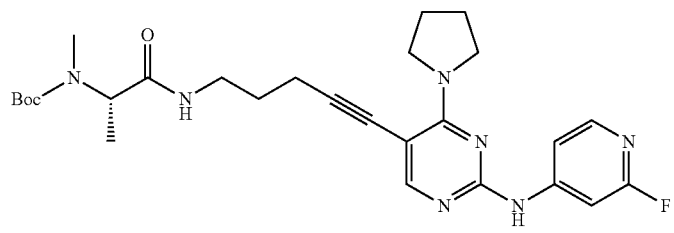 [SMILES: C[C@@H](C(=O)NCCCC#Cc1cnc(Nc2ccnc(F)c2)nc1N1CCCC1)N(C)C(=O)OC(C)(C)C] | — |
| H81 | 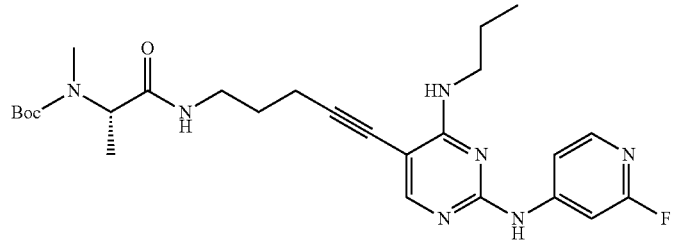 [SMILES: CCCNc1nc(Nc2ccnc(F)c2)ncc1C#CCCCNC(=O)[C@H](C)N(C)C(=O)OC(C)(C)C] | — |

TABLE 136

| Compound No. | Structure | Physicochemical data |
|---|---|---|
| H82 | 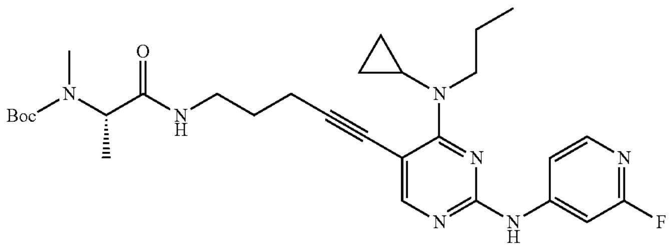 [SMILES: CCCN(c1nc(Nc2ccnc(F)c2)ncc1C#CCCCNC(=O)[C@H](C)N(C)C(=O)OC(C)(C)C)C1CC1] | — |
| H83 | 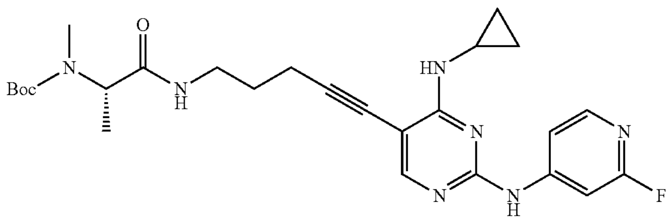 [SMILES: C[C@@H](C(=O)NCCCC#Cc1cnc(Nc2ccnc(F)c2)nc1NC1CC1)N(C)C(=O)OC(C)(C)C] | MS m/z (M + H): 512.4 |
| H84 | 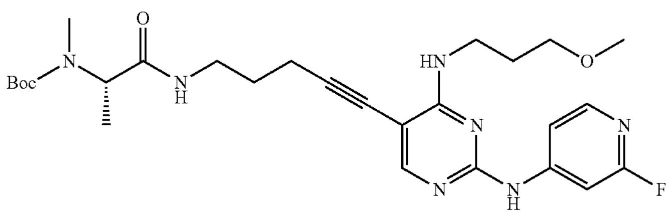 [SMILES: COCCCNc1nc(Nc2ccnc(F)c2)ncc1C#CCCCNC(=O)[C@H](C)N(C)C(=O)OC(C)(C)C] | — |
| H85 | 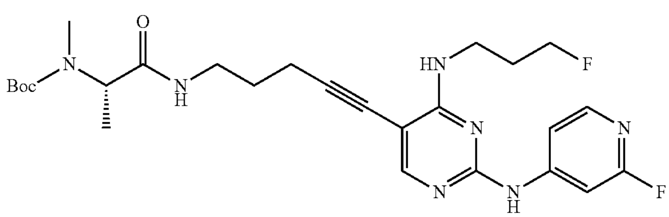 [SMILES: C[C@@H](C(=O)NCCCC#Cc1cnc(Nc2ccnc(F)c2)nc1NCCCF)N(C)C(=O)OC(C)(C)C] | — |
| H86 | 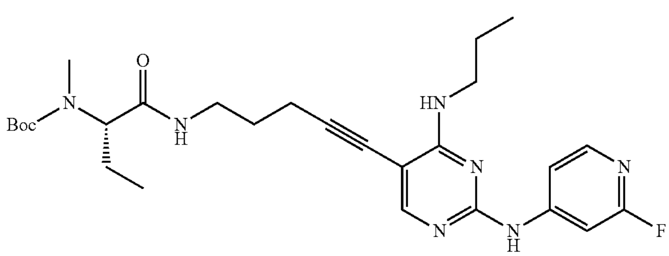 | — |
| H87 | 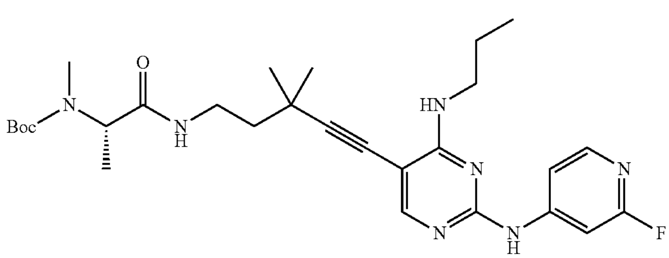 | — |

TABLE 136-continued

| Compound No. | Structure | Physicochemical data |
|---|---|---|
| H88 | 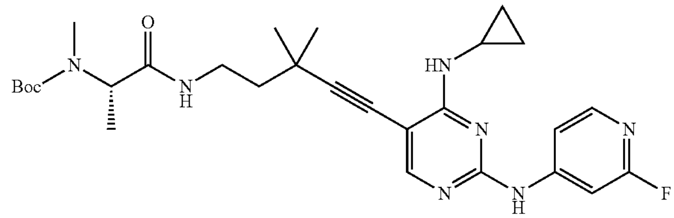 [SMILES: C[C@@H](C(=O)NCCC(C)(C)C#Cc1cnc(Nc2ccnc(F)c2)nc1NC1CC1)N(C)C(=O)OC(C)(C)C] | — |
| H89 | 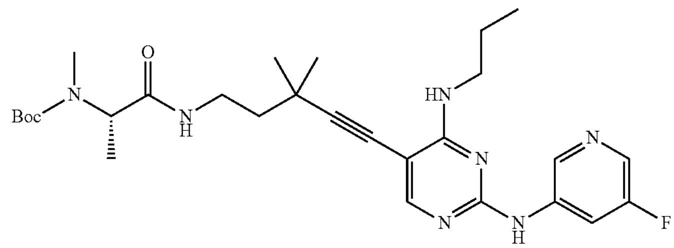 | — |
| H90 | 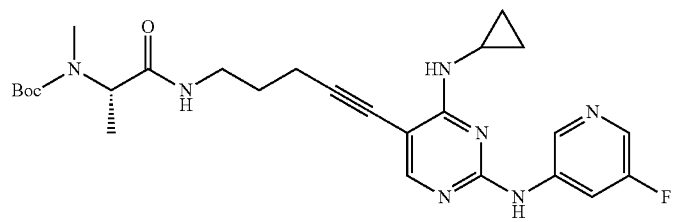 [SMILES: C[C@@H](C(=O)NCCCC#Cc1cnc(Nc2cncc(F)c2)nc1NC1CC1)N(C)C(=O)OC(C)(C)C] | — |
| H91 | 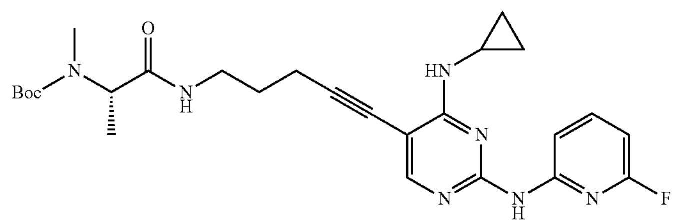 [SMILES: C[C@@H](C(=O)NCCCC#Cc1cnc(Nc2cccc(F)n2)nc1NC1CC1)N(C)C(=O)OC(C)(C)C] | — |

TABLE 137

| Compound No. | Structure | Physicochemical data |
|---|---|---|
| H92 | 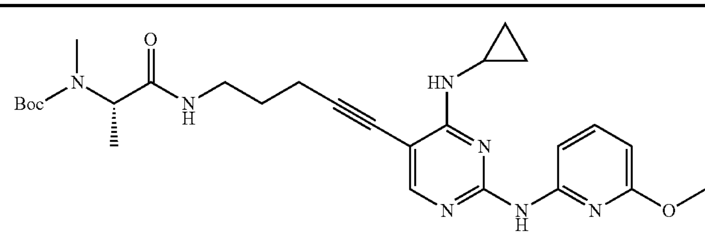 | — |
| H93 | 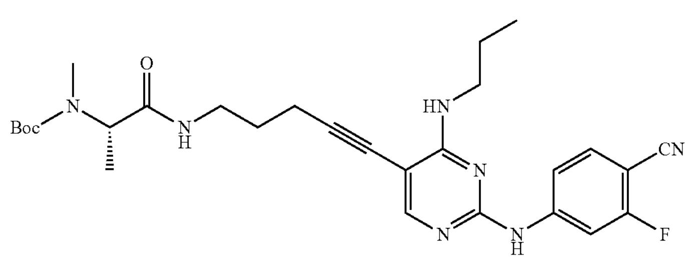 [SMILES: CCCNc1nc(Nc2ccc(C#N)c(F)c2)ncc1C#CCCCNC(=O)[C@H](C)N(C)C(=O)OC(C)(C)C] | — |

TABLE 137-continued

| Compound No. | Structure | Physicochemical data |
|---|---|---|
| H94 | 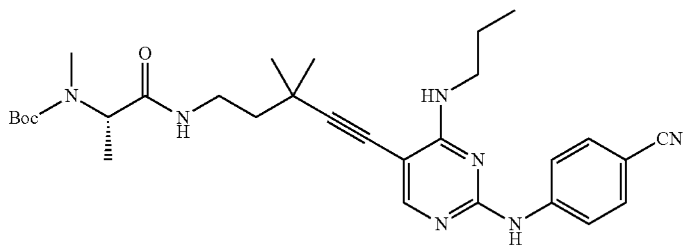 [SMILES: CCCNc1nc(Nc2ccc(C#N)cc2)ncc1C#CC(C)(C)CCNC(=O)[C@H](C)N(C)C(=O)OC(C)(C)C] | — |
| H95 | 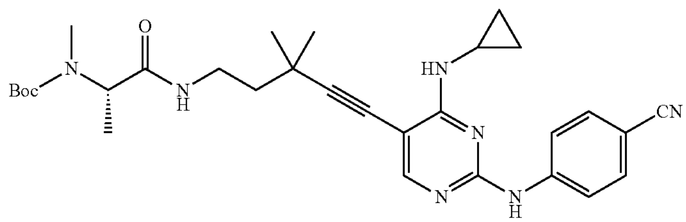 [SMILES: C[C@@H](C(=O)NCCC(C)(C)C#Cc1cnc(Nc2ccc(C#N)cc2)nc1NC1CC1)N(C)C(=O)OC(C)(C)C] | — |
| H96 | 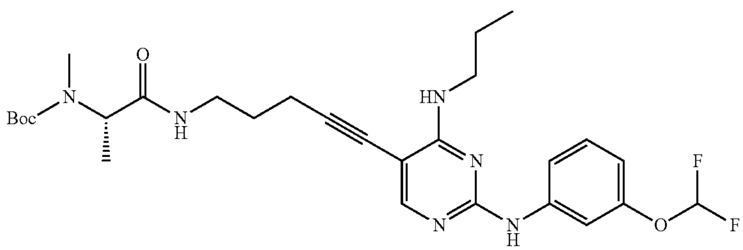 [SMILES: CCCNc1nc(Nc2cccc(OC(F)F)c2)ncc1C#CCCCNC(=O)[C@H](C)N(C)C(=O)OC(C)(C)C] | — |
| H97 | 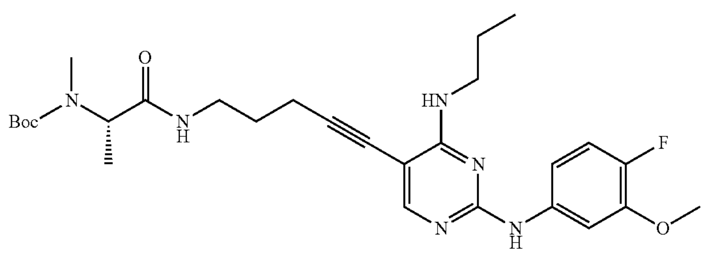 [SMILES: CCCNc1nc(Nc2ccc(F)c(OC)c2)ncc1C#CCCCNC(=O)[C@H](C)N(C)C(=O)OC(C)(C)C] | — |
| H136 | 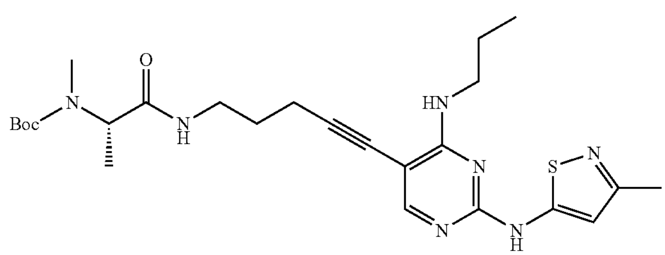 [SMILES: CCCNc1nc(Nc2cc(C)ns2)ncc1C#CCCCNC(=O)[C@H](C)N(C)C(=O)OC(C)(C)C] | — |
| H137 | 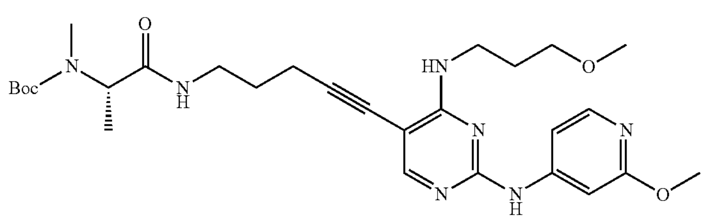 [SMILES: COCCCNc1nc(Nc2ccnc(OC)c2)ncc1C#CCCCNC(=O)[C@H](C)N(C)C(=O)OC(C)(C)C] | — |

TABLE 137-continued

| Compound No. | Structure | Physicochemical data |
| --- | --- | --- |
| H138 | 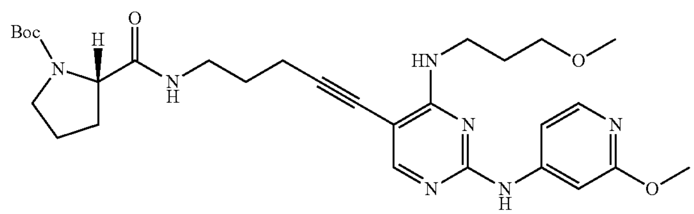 [SMILES: COCCCNc1nc(Nc2ccnc(OC)c2)ncc1C#CCCCNC(=O)[C@@H]1CCCN1C(=O)OC(C)(C)C] | — |
| H139 | 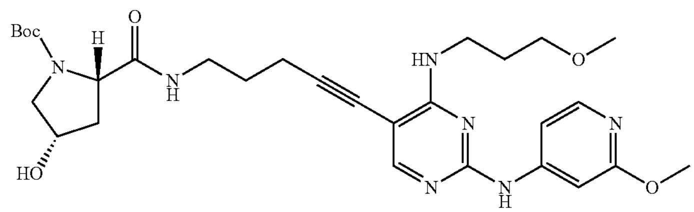 [SMILES: COCCCNc1nc(Nc2ccnc(OC)c2)ncc1C#CCCCNC(=O)[C@@H]1C[C@H](O)CN1C(=O)OC(C)(C)C] | — |

TABLE 138

| Compound No. | Structure | Physicochemical data |
| --- | --- | --- |
| H140 | 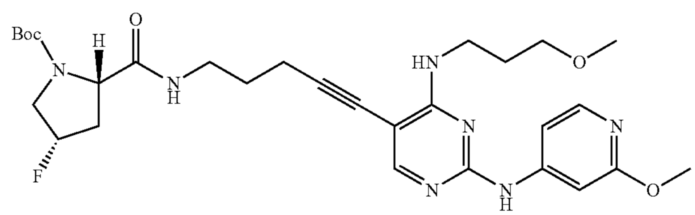 [SMILES: COCCCNc1nc(Nc2ccnc(OC)c2)ncc1C#CCCCNC(=O)[C@@H]1C[C@H](F)CN1C(=O)OC(C)(C)C] | — |
| H141 | 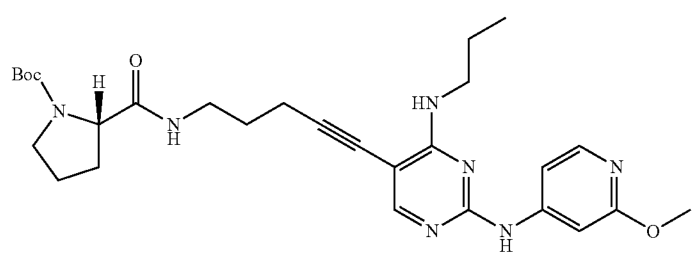 [SMILES: CCCNc1nc(Nc2ccnc(OC)c2)ncc1C#CCCCNC(=O)[C@@H]1CCCN1C(=O)OC(C)(C)C] | MS m/z (M + H): 538.5 |
| H142 | 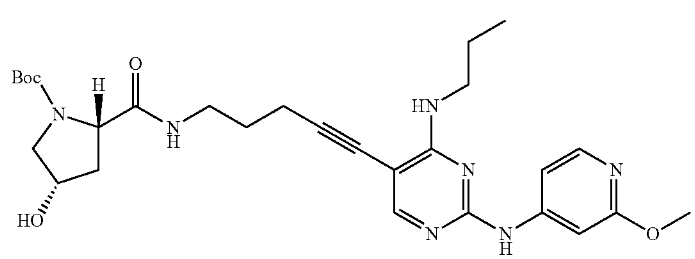 [SMILES: CCCNc1nc(Nc2ccnc(OC)c2)ncc1C#CCCCNC(=O)[C@@H]1C[C@H](O)CN1C(=O)OC(C)(C)C] | MS m/z (M + H): 554.4 |
| H143 | 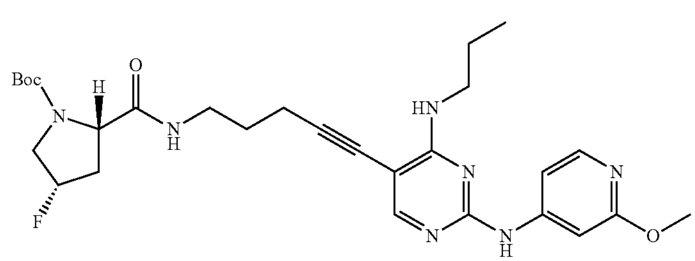 [SMILES: CCCNc1nc(Nc2ccnc(OC)c2)ncc1C#CCCCNC(=O)[C@@H]1C[C@H](F)CN1C(=O)OC(C)(C)C] | MS m/z (M + H): 556.4 |

TABLE 138-continued

| Compound No. | Structure | Physicochemical data |
| --- | --- | --- |
| H144 | 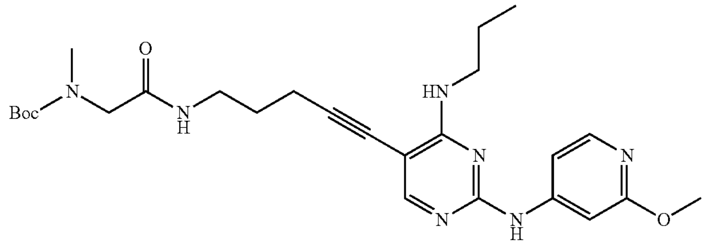 [SMILES: CCCNc1nc(Nc2ccnc(OC)c2)ncc1C#CCCCNC(=O)CN(C)C(=O)OC(C)(C)C] | MS m/z (M + H): 512.4 |
| H145 | 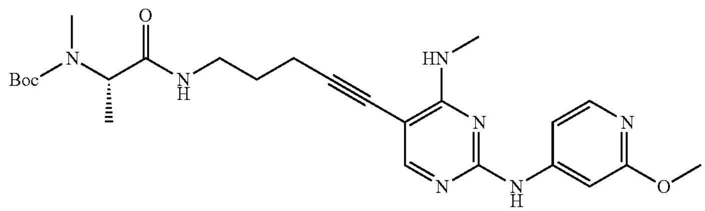 [SMILES: CNc1nc(Nc2ccnc(OC)c2)ncc1C#CCCCNC(=O)[C@H](C)N(C)C(=O)OC(C)(C)C] | MS m/z (M + H): 498.4 |
| H146 | 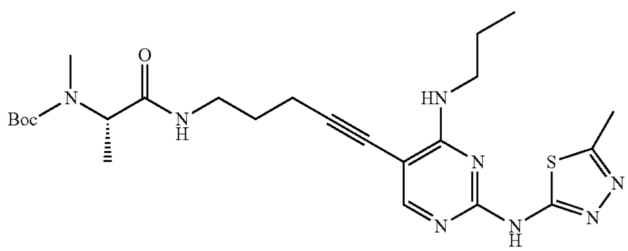 [SMILES: CCCNc1nc(Nc2nnc(C)s2)ncc1C#CCCCNC(=O)[C@H](C)N(C)C(=O)OC(C)(C)C] | MS m/z (M + H): 517.4 |

In the same manner as that of Example 41, (6), Intermediates (H98) to (H124) and Intermediates (H147) to (H157) were obtained.

TABLE 139

| Compound No. | Structure | Physicochemical data |
| --- | --- | --- |
| H98 | 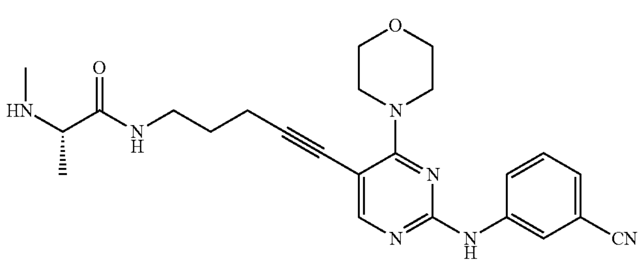 [SMILES: CN[C@@H](C)C(=O)NCCCC#Cc1cnc(Nc2cccc(C#N)c2)nc1N1CCOCC1] | — |
| H99 | 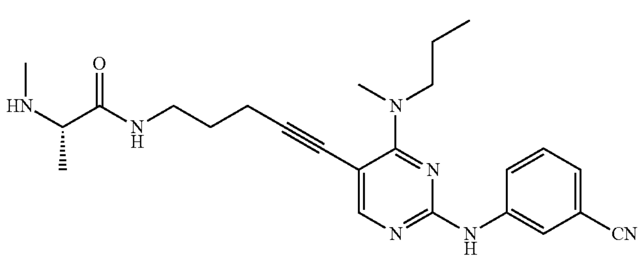 [SMILES: CCCN(C)c1nc(Nc2cccc(C#N)c2)ncc1C#CCCCNC(=O)[C@H](C)NC] | — |

TABLE 139-continued

| Compound No. | Structure | Physicochemical data |
|---|---|---|
| H100 | 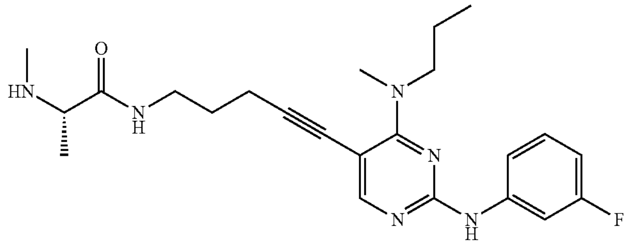 [SMILES: CCCN(C)c1nc(Nc2cccc(F)c2)ncc1C#CCCCNC(=O)[C@H](C)NC] | MS m/z (M + H): 427.3 |
| H101 | 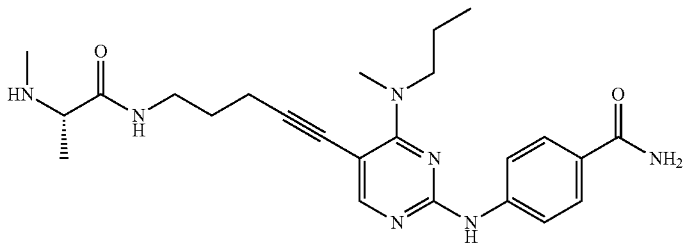 [SMILES: CCCN(C)c1nc(Nc2ccc(C(N)=O)cc2)ncc1C#CCCCNC(=O)[C@H](C)NC] | MS m/z (M + H): 452.4 |
| H102 | 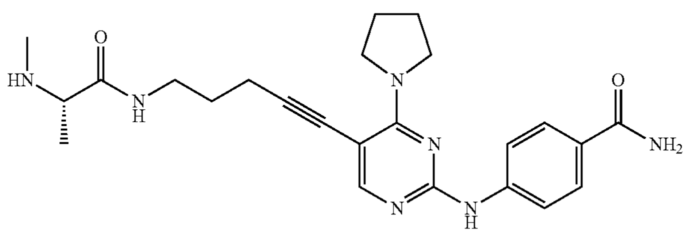 [SMILES: CN[C@@H](C)C(=O)NCCCC#Cc1cnc(Nc2ccc(C(N)=O)cc2)nc1N1CCCC1] | MS m/z (M + H): 450.4 |
| H103 | 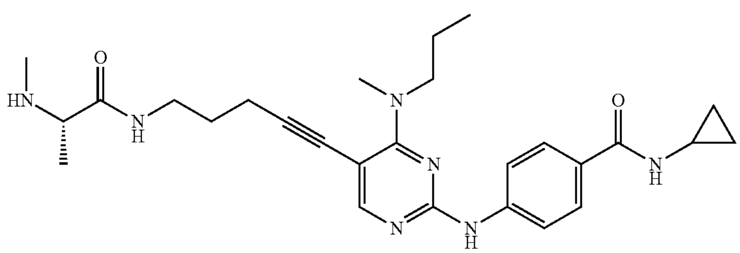 [SMILES: CCCN(C)c1nc(Nc2ccc(C(=O)NC3CC3)cc2)ncc1C#CCCCNC(=O)[C@H](C)NC] | MS m/z (M + H): 492.5 |
| H104 | 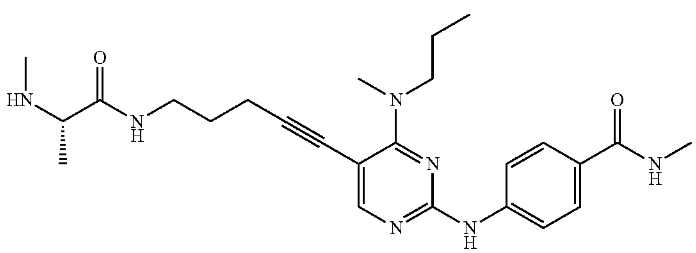 [SMILES: CCCN(C)c1nc(Nc2ccc(C(=O)NC)cc2)ncc1C#CCCCNC(=O)[C@H](C)NC] | — |
| H105 | 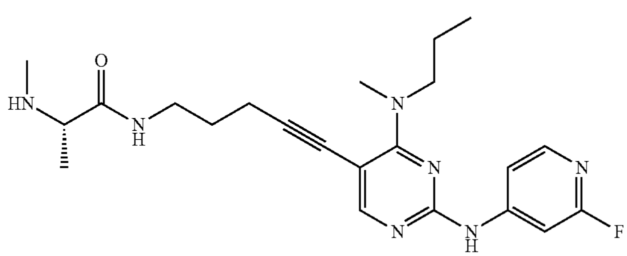 [SMILES: CCCN(C)c1nc(Nc2ccnc(F)c2)ncc1C#CCCCNC(=O)[C@H](C)NC] | — |

TABLE 140

| Compound No. | Structure | Physicochemical data |
|---|---|---|
| H106 | 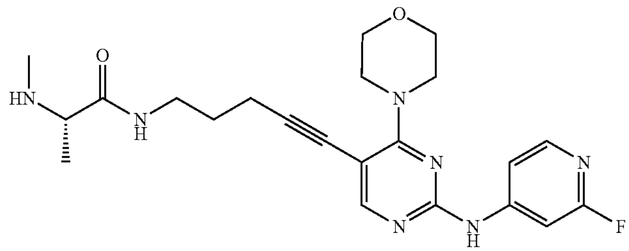 [SMILES: CN[C@@H](C)C(=O)NCCCC#Cc1cnc(Nc2ccnc(F)c2)nc1N1CCOCC1] | — |
| H107 | 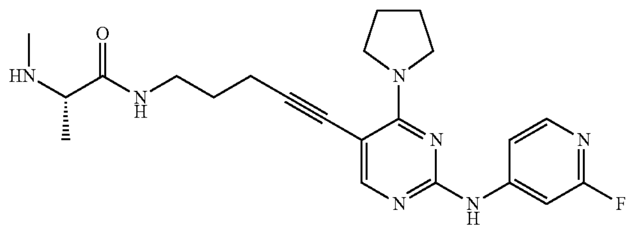 [SMILES: CN[C@@H](C)C(=O)NCCCC#Cc1cnc(Nc2ccnc(F)c2)nc1N1CCCC1] | — |
| H108 | 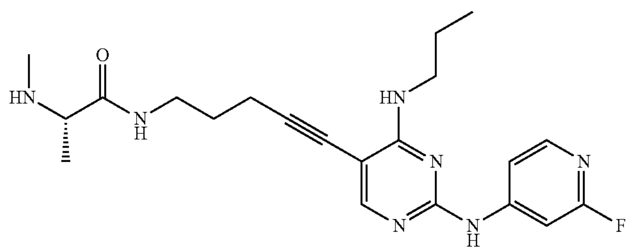 [SMILES: CCCNc1nc(Nc2ccnc(F)c2)ncc1C#CCCCNC(=O)[C@H](C)NC] | — |
| H109 | 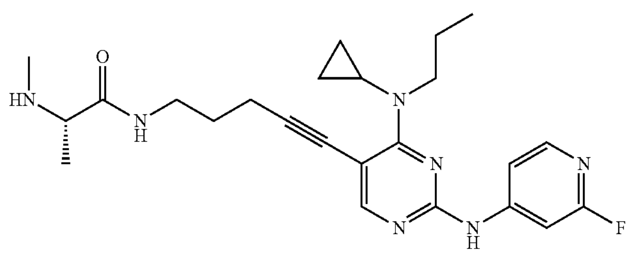 [SMILES: CCCN(c1nc(Nc2ccnc(F)c2)ncc1C#CCCCNC(=O)[C@H](C)NC)C1CC1] | — |
| H110 | 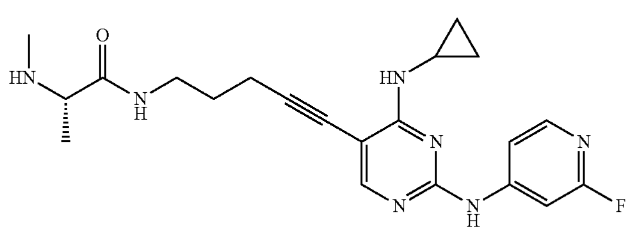 [SMILES: CN[C@@H](C)C(=O)NCCCC#Cc1cnc(Nc2ccnc(F)c2)nc1NC1CC1] | — |
| H111 | 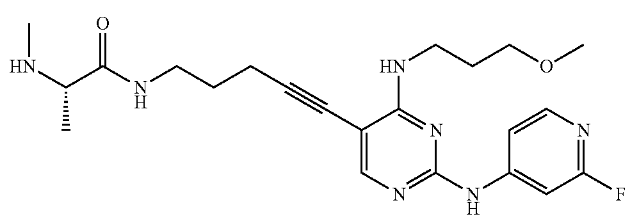 [SMILES: CN[C@@H](C)C(=O)NCCCC#Cc1cnc(Nc2ccnc(F)c2)nc1NCCCOC] | — |

TABLE 140-continued

| Compound No. | Structure | Physicochemical data |
|---|---|---|
| H112 | 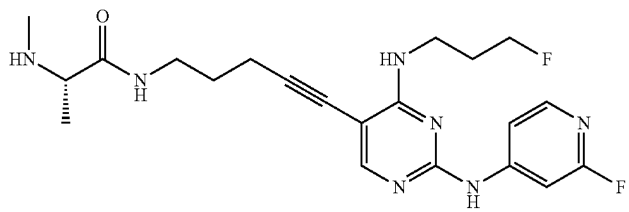 [SMILES: CN[C@@H](C)C(=O)NCCCC#Cc1cnc(Nc2ccnc(F)c2)nc1NCCCF] | — |
| H113 | 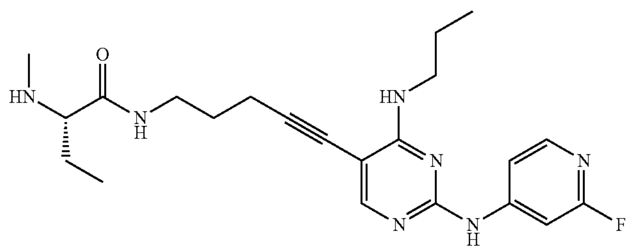 | — |
| H114 | 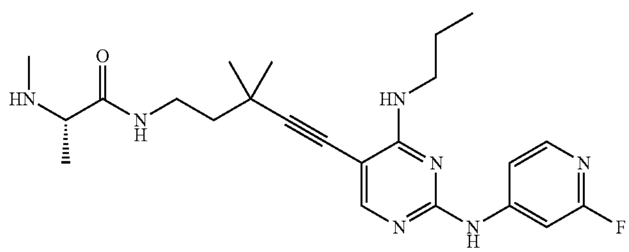 [SMILES: CCCNc1nc(Nc2ccnc(F)c2)ncc1C#CC(C)(C)CCNC(=O)[C@H](C)NC] | — |
| H115 | 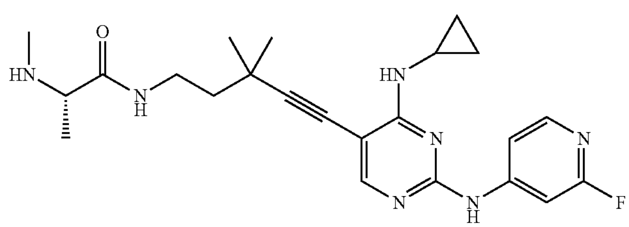 [SMILES: CN[C@@H](C)C(=O)NCCC(C)(C)C#Cc1cnc(Nc2ccnc(F)c2)nc1NC1CC1] | — |

TABLE 141

| Compound No. | Structure | Physicochemical data |
|---|---|---|
| H116 | 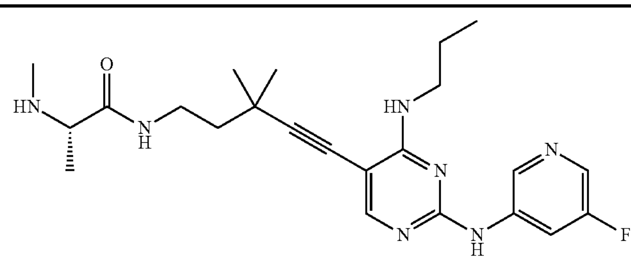 | — |
| H117 | 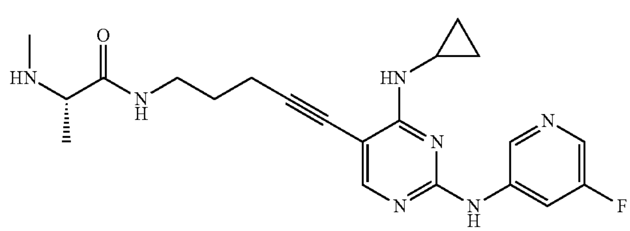 [SMILES: CN[C@@H](C)C(=O)NCCCC#Cc1cnc(Nc2cncc(F)c2)nc1NC1CC1] | — |

TABLE 141-continued
| Compound No. | Structure | Physicochemical data |
|---|---|---|
| H118 | 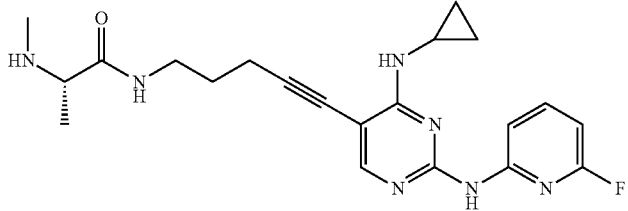 [SMILES: CN[C@@H](C)C(=O)NCCCC#Cc1cnc(Nc2cccc(F)n2)nc1NC1CC1] | — |
| H119 | 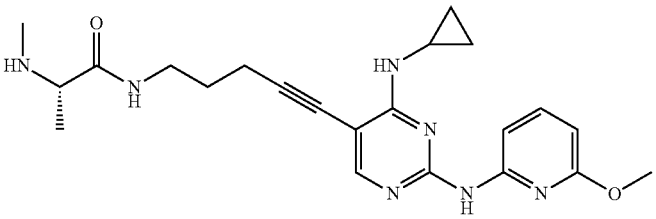 [SMILES: CN[C@@H](C)C(=O)NCCCC#Cc1cnc(Nc2cccc(OC)n2)nc1NC1CC1] | — |
| H120 | 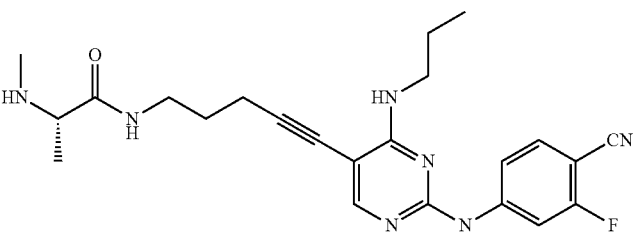 | — |
| H121 | 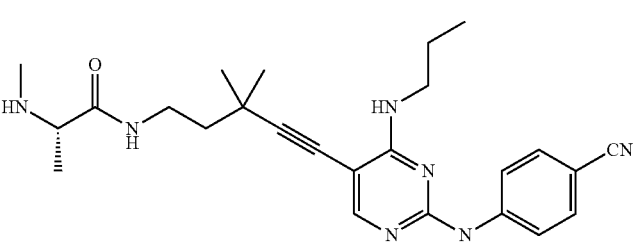 | — |
| H122 | 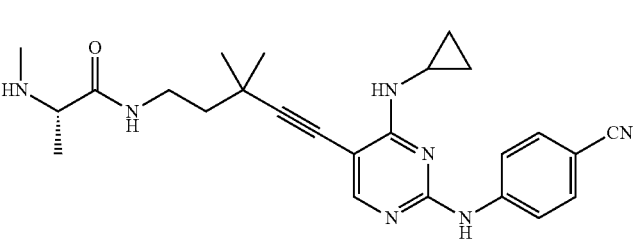 [SMILES: CN[C@@H](C)C(=O)NCCC(C)(C)C#Cc1cnc(Nc2ccc(C#N)cc2)nc1NC1CC1] | — |
| H123 | 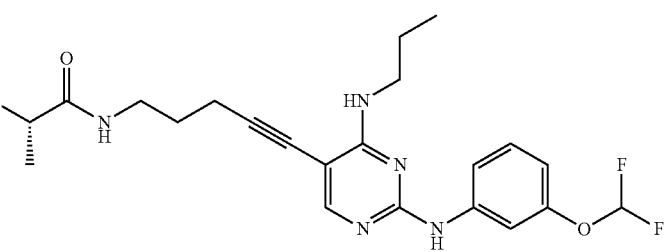 | — |

TABLE 141-continued
| Compound No. | Structure | Physicochemical data |
|---|---|---|
| H124 | 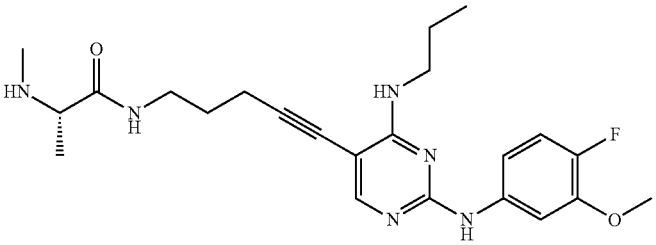 [SMILES: CCCNc1nc(Nc2ccc(F)c(OC)c2)ncc1C#CCCCNC(=O)[C@H](C)NC] | — |
| H147 | 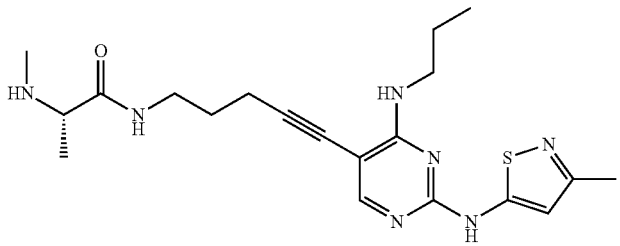 [SMILES: CCCNc1nc(Nc2cc(C)ns2)ncc1C#CCCCNC(=O)[C@H](C)NC] | — |
TABLE 142
| Compound No. | Structure | Physicochemical data |
|---|---|---|
| H148 | 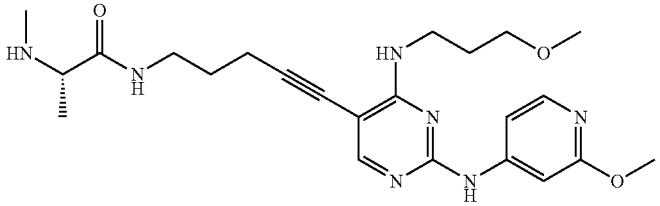 | — |
| H149 | 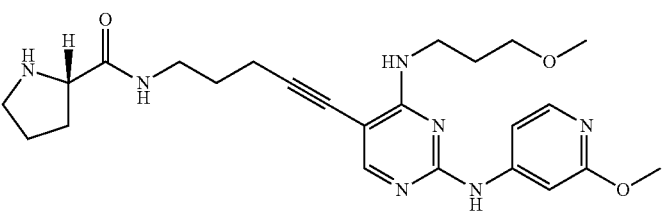 [SMILES: COCCCNc1nc(Nc2ccnc(OC)c2)ncc1C#CCCCNC(=O)[C@@H]1CCCN1] | — |
| H150 | 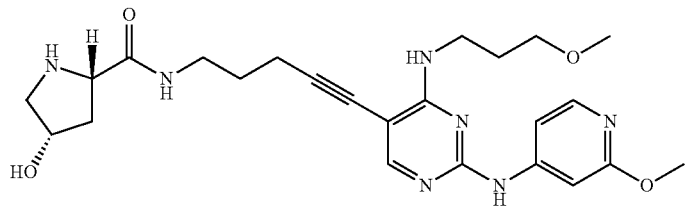 [SMILES: COCCCNc1nc(Nc2ccnc(OC)c2)ncc1C#CCCCNC(=O)[C@@H]1C[C@H](O)CN1] | — |
| H151 | 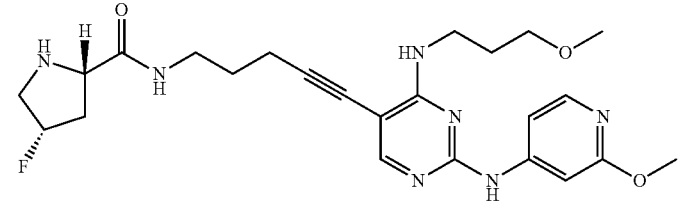 [SMILES: COCCCNc1nc(Nc2ccnc(OC)c2)ncc1C#CCCCNC(=O)[C@@H]1C[C@H](F)CN1] | — |

TABLE 142-continued

| Compound No. | Structure | Physicochemical data |
|---|---|---|
| H152 | 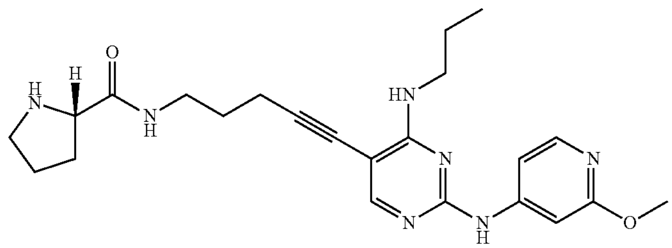 [SMILES: CCCNc1nc(Nc2ccnc(OC)c2)ncc1C#CCCCNC(=O)[C@@H]1CCCN1] | MS m/z (M + H): 438.3 |
| H153 | 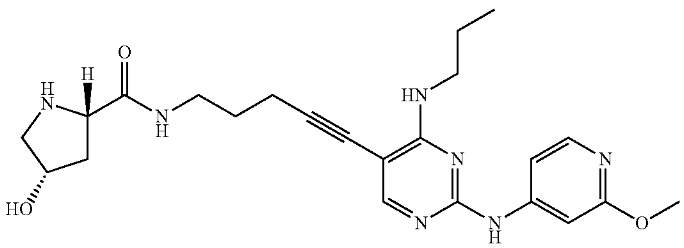 [SMILES: CCCNc1nc(Nc2ccnc(OC)c2)ncc1C#CCCCNC(=O)[C@@H]1C[C@H](O)CN1] | MS m/z (M + H): 454.4 |
| H154 | 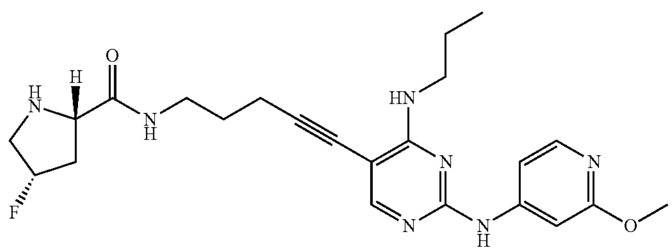 [SMILES: CCCNc1nc(Nc2ccnc(OC)c2)ncc1C#CCCCNC(=O)[C@@H]1C[C@H](F)CN1] | — |
| H155 | 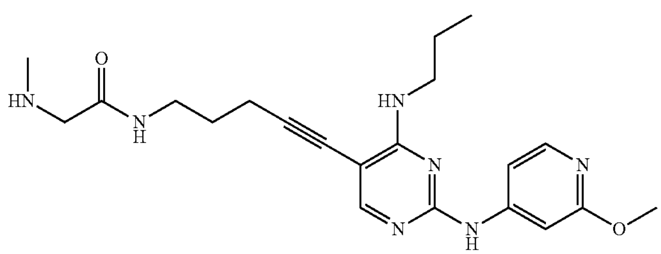 [SMILES: CCCNc1nc(Nc2ccnc(OC)c2)ncc1C#CCCCNC(=O)CNC] | MS m/z (M + H): 412.4 |
| H156 | 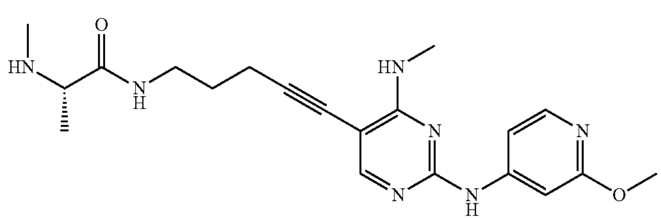 [SMILES: CNc1nc(Nc2ccnc(OC)c2)ncc1C#CCCCNC(=O)[C@H](C)NC] | — |
| H157 | 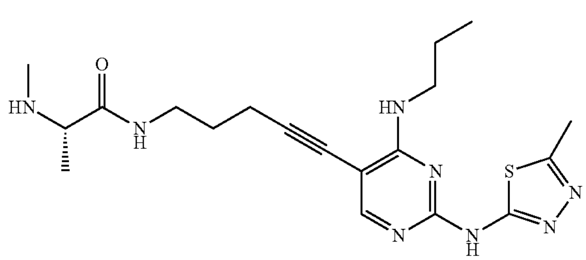 [SMILES: CCCNc1nc(Nc2nnc(C)s2)ncc1C#CCCCNC(=O)[C@H](C)NC] | MS m/z (M + H): 417.4 |

Example 43

In the same manner as that of Example 41, Compounds (9-2) to (9-40) were obtained.

TABLE 143

| Compound No. | Structure | Physicochemical data |
|---|---|---|
| 9-2 | 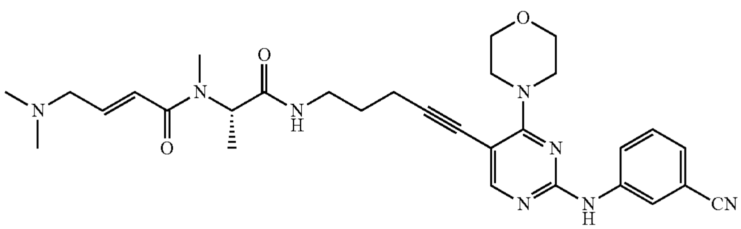 [SMILES: C[C@@H](C(=O)NCCCC#Cc1cnc(Nc2cccc(C#N)c2)nc1N1CCOCC1)N(C)C(=O)/C=C/CN(C)C] | ¹H-NMR (CDCl₃) δ: 8.16 (1H, brs), 8.12 (1H, s), 7.63 (1H, s), 7.60 (1H, brs), 7.41-7.35 (1H, m), 7.25 (1H, brs), 7.02-6.89 (1H, m), 6.67 (1H, t, J = 5.6 Hz), 6.43 (1H, d, J = 15.2 Hz), 5.17 (1H, q, J = 7.3 Hz), 3.99-3.93 (4H, m), 3.83-3.76 (4H, m), 3.48-3.23 (2H, m), 3.10 (2H, d, J = 5.9 Hz), 3.00 (3H, s), 2.44 (2H, t, J = 6.9 Hz), 2.27 (6H, s), 1.80-1.71 (2H, m), 1.35 (3H, d, J = 7.3 Hz) |
| 9-3 | 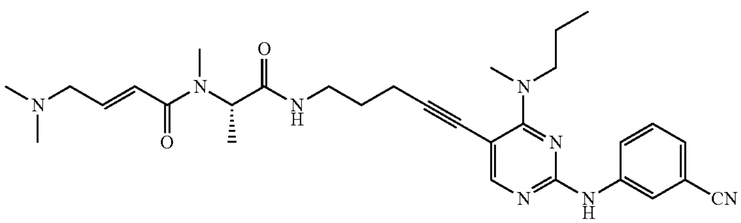 [SMILES: CCCN(C)c1nc(Nc2cccc(C#N)c2)ncc1C#CCCCNC(=O)[C@H](C)N(C)C(=O)/C=C/CN(C)C] | ¹H-NMR (CDCl₃) δ: 8.22 (1H, s), 8.14 (1H, s), 8.02 (1H, s), 7.74-7.19 (3H, m), 6.93-6.85 (2H, m), 6.44 (1H, d, J = 15.2 Hz), 5.20 (1H, q, J = 7.3 Hz), 3.74 (2H, t, J = 7.6 Hz), 3.39-3.35 (2H, m), 3.29 (3H, s), 3.12-3.10 (2H, m), 3.02 (3H, s), 2.42 (2H, t, J = 6.9 Hz), 2.27 (6H, s), 1.77-1.67 (4H, m), 1.36 (3H, d, J = 7.3 Hz), 0.93 (3H, t, J = 7.6 Hz) |
| 9-4 | 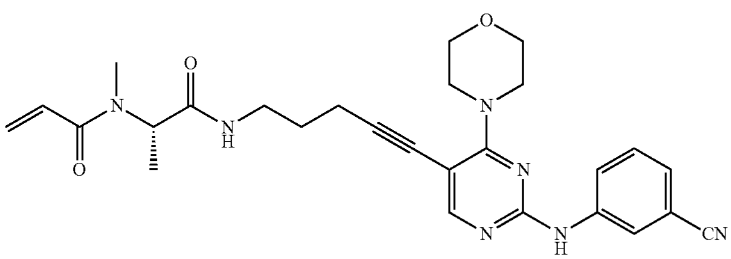 [SMILES: C=CC(=O)N(C)[C@@H](C)C(=O)NCCCC#Cc1cnc(Nc2cccc(C#N)c2)nc1N1CCOCC1] | ¹H-NMR (CDCl₃) δ: 8.16 (1H, brs), 8.13 (1H, s), 7.59 (1H, dd, J = 7.6, 1.7 Hz), 7.40-7.26 (4H, m), 6.64-6.33 (2H, m), 5.79 (1H, dd, J = 10.2, 1.7 Hz), 5.16 (1H, q, J = 7.3 Hz), 3.99-3.93 (4H, m), 3.83-3.76 (4H, m), 3.44-3.24 (2H, m), 3.00 (3H, s), 2.44 (2H, t, J = 6.9 Hz), 1.81-1.72 (2H, m), 1.36 (3H, d, J = 7.3 Hz) |
| 9-5 | 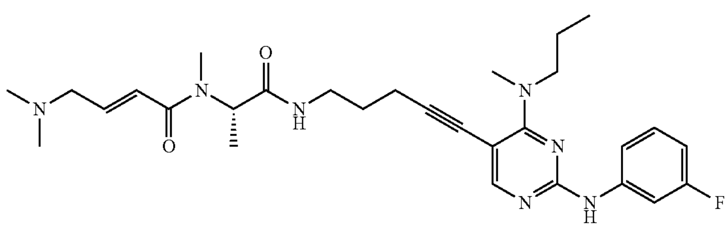 [SMILES: CCCN(C)c1nc(Nc2cccc(F)c2)ncc1C#CCCCNC(=O)[C@H](C)N(C)C(=O)/C=C/CN(C)C] | ¹H-NMR (CDCl₃) δ: 8.03 (1H, s), 7.76-7.68 (1H, m), 7.24-7.16 (2H, m), 7.07 (1H, d, J = 7.6 Hz), 6.98-6.88 (1H, m), 6.67 (1H, dt, J = 8.3, 2.0 Hz), 6.58 (1H, brs), 6.42 (1H, d, J = 15.2 Hz), 5.18 (1H, q, J = 7.0 Hz), 3.78-3.70 (2H, m), 3.42-3.32 (2H, m), 3.30 (3H, s), 3.12-3.06 (2H, m), 2.99 (3H, s), 2.42 (2H, t, J = 6.9 Hz), 2.26 (6H, s), 1.80-1.64 (4H, m), 1.35 (3H, d, J = 7.3 Hz), 0.94 (3H, t, J = 7.3 Hz) |
| 9-6 | 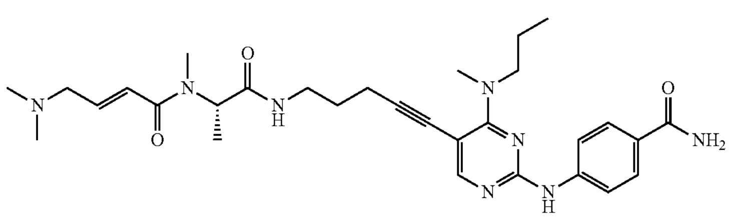 [SMILES: CCCN(C)c1nc(Nc2ccc(C(N)=O)cc2)ncc1C#CCCCNC(=O)[C@H](C)N(C)C(=O)/C=C/CN(C)C] | MS m/z (M + H): 563.5 |
| 9-7 | 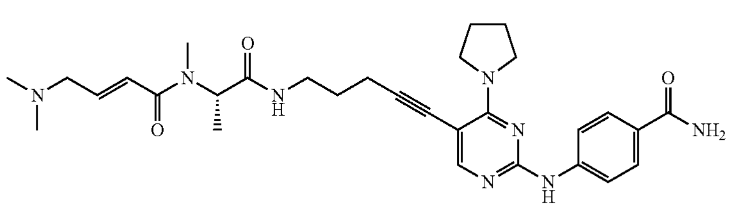 [SMILES: C[C@@H](C(=O)NCCCC#Cc1cnc(Nc2ccc(C(N)=O)cc2)nc1N1CCCC1)N(C)C(=O)/C=C/CN(C)C] | ¹H-NMR (CDCl₃) δ: 8.02 (1H, s), 7.77 (2H, d, J = 8.6 Hz), 7.70 (2H, d, J = 8.6 Hz), 6.93 (1H, dt, J = 15.0, 6.1 Hz), 6.57 (1H, brs), 6.42 (1H, d, J = 15.2 Hz), 5.18 (1H, d, J = 7.3 Hz), 3.84 (4H, s), 3.42-3.28 (2H, m), 3.09 (2H, d, J = 5.9 Hz), 2.99 (3H, s), 2.40 (2H, t, J = 6.9 Hz), 2.26 (6H, s), 2.00-1.92 (4H, m), 1.75 (2H, t, J = 7.3 Hz), 1.35 (3H, d, J = 7.3 Hz) |

TABLE 144

| Compound No. | Structure | Physicochemical data |
|---|---|---|
| 9-8 | 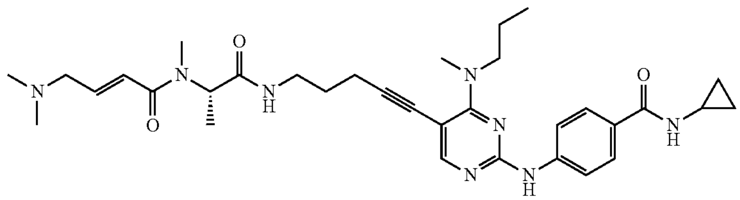 [SMILES: CCCN(C)c1nc(Nc2ccc(C(=O)NC3CC3)cc2)ncc1C#CCCCNC(=O)[C@H](C)N(C)C(=O)/C=C/CN(C)C] | ¹H-NMR (CDCl₃) δ: 8.03 (1H, s), 7.70 (2H, d, J = 8.6 Hz), 7.64 (2H, d, J = 8.6 Hz), 7.61 (1H, s), 6.93 (1H, dt, J = 15.0, 6.1 Hz), 6.64 (1H, brs), 6.42 (1H, d, J = 15.2 Hz), 6.38-6.32 (1H, m), 5.18 (1H, q, J = 7.0 Hz), 3.78-3.70 (2H, m), 3.42-3.30 (2H, m), 3.28 (3H, s), 3.09 (2H, d, J = 5.3 Hz), 2.99 (3H, s), 2.94-2.84 (1H, m), 2.42 (2H, t, J = 7.3 Hz), 2.26 (6H, s), 1.82-1.64 (4H, m), 1.35 (3H, d, J = 6.6 Hz), 0.93 (3H, t, J = 7.6 Hz), 0.88-0.82 (2H, m), 0.64-0.58 (2H, m) |
| 9-9 | 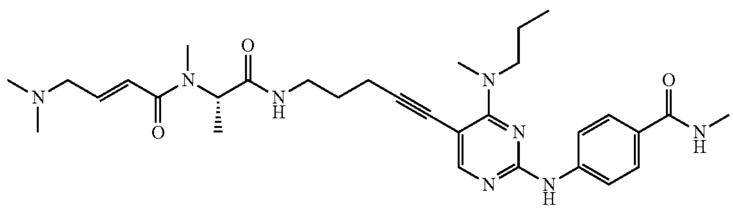 | ¹H-NMR (CDCl₃) δ: 8.04 (1H, s), 7.71 (2H, d, J = 8.9 Hz), 7.64 (2H, d, J = 8.9 Hz), 7.16 (1H, s), 6.93 (1H, dt, J = 15.0, 5.9 Hz), 6.53 (1H, brs), 6.41 (1H, d, J = 15.2 Hz), 6.12-6.04 (1H, m), 5.17 (1H, q, J = 6.8 Hz), 3.79-3.70 (2H, m), 3.42-3.32 (2H, m), 3.29 (3H, s), 3.10 (2H, d, J = 5.9 Hz), 3.01 (3H, d, J = 5.0 Hz), 2.98 (3H, s), 2.46-2.38 (2H, m), 2.26 (6H, s), 1.80-1.68 (4H, m), 1.35 (3H, d, J = 7.3 Hz), 0.94 (3H, t, J = 7.3 Hz) |
| 9-10 | 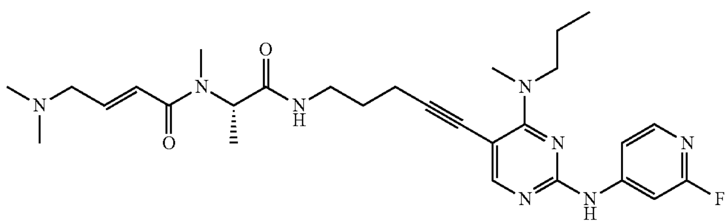 [SMILES: CCCN(C)c1nc(Nc2ccnc(F)c2)ncc1C#CCCCNC(=O)[C@H](C)N(C)C(=O)/C=C/CN(C)C] | ¹H-NMR (CDCl₃) δ: 8.50 (1H, s), 8.03 (1H, s), 7.97 (1H, d, J = 5.9 Hz), 7.55 (1H, d, J = 1.3 Hz), 7.17 (1H, d, J = 5.3 Hz), 6.97-6.88 (2H, m), 6.42 (1H, d, J = 15 Hz), 5.20 (1H, q, J = 7.0 Hz), 3.75-3.65 (2H, m), 3.39-3.32 (2H, m), 3.30 (3H, s). 3.10 (2H, d, J = 5.3 Hz), 3.02 (3H, s), 2.42 (2H, t, J = 6.9 Hz), 2.26 (6H, s), 1.84-1.62 (4H, m), 1.36 (3H, d, J = 6.6 Hz), 0.94 (3H, t, J = 7.6 Hz) |
| 9-11 | 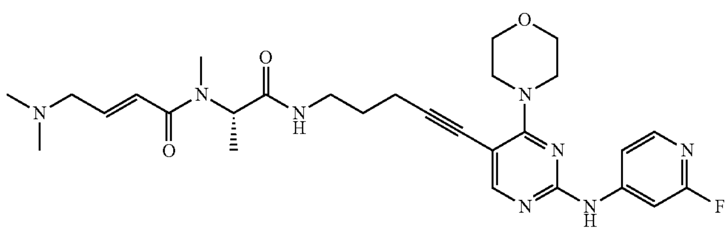 [SMILES: C[C@@H](C(=O)NCCCC#Cc1cnc(Nc2ccnc(F)c2)nc1N1CCOCC1)N(C)C(=O)/C=C/CN(C)C] | ¹H-NMR (CDCl₃) δ: 8.15 (1H, s), 8.01 (1H, d, 5.9 Hz), 7.83 (1H, s), 7.47 (1H, d, J = 1.3 Hz), 7.17 (1H, dd, J = 4.6, 2.6 Hz), 6.94 (1H, dt, J = 15.2, 5.9 Hz), 6.68 (1H, t, J = 5.3 Hz), 6.43 (1H, d, J = 15.2 Hz), 5.17 (1H, q, J = 7.0 Hz), 4.05-3.96 (4H, m), 3.83-3.79 (4H, m), 3.45-3.23 (2H, m), 3.10 (2H, dd, J = 5.9, 1.3 Hz), 3.00 (3H, s), 2.44 (2H, t, 7.3 Hz), 2.25 (6H, s), 1.83-1.69 (2H, m), 1.36 (3H, d, J = 7.3 Hz) |
| 9-12 | 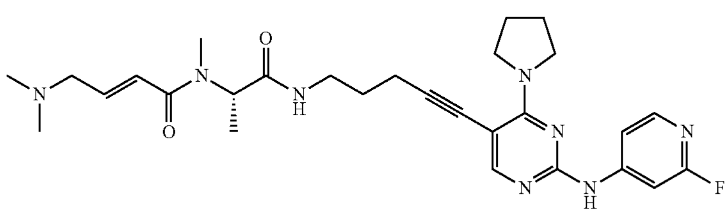 [SMILES: C[C@@H](C(=O)NCCCC#Cc1cnc(Nc2ccnc(F)c2)nc1N1CCCC1)N(C)C(=O)/C=C/CN(C)C] | ¹H-NMR (CDCl₃) δ: 8.26 (1H, s), 8.06-7.94 (2H, m), 7.60 (1H, s), 7.23-7.14 (1H, m), 7.01-6.81 (2H, m), 6.43 (1H, d, 15.2 Hz), 5.27-5.13 (1H, m), 4.05-3.62 (4H, m), 3.46-3.26 (2H, m), 3.19-3.07 (2H, m), 3.02 (3H, s), 2.51-2.36 (2H, m), 2.30 (6H, s), 2.00 (4H, brs), 1.86-1.64 (2H, m), 1.36 (3H, d, J = 7.3 Hz) |

TABLE 145

| Compound No. | Structure | Physicochemical data |
|---|---|---|
| 9-13 | 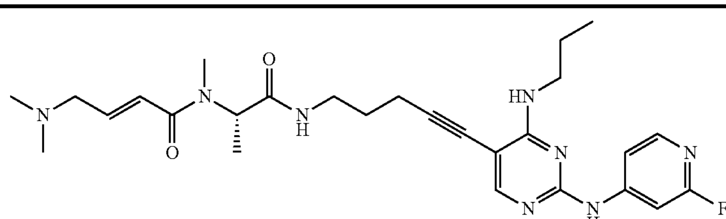 | ¹H-NMR (CDCl₃) δ: 8.99 (1H, s), 7.97 (2H, t, J = 3.0 Hz), 7.69 (1H, s), 7.18 (1H, d, J = 5.3 Hz), 6.96-6.89 (2H, m), 6.59 (1H, t, J = 5.3 Hz), 6.44 (1H, d, J = 15.2 Hz), 5.23 (1H, q, J = 7.2 Hz), 3.60-3.38 (4H, m), 3.10 (2H, d, J = 5.9 Hz), 3.03 (3H, s), 2.53-2.37 (2H, m), 2.26 (6H, s), 1.83-1.61 (4H, m), 1.38 (3H, d, J = 7.2 Hz), 1.01 (3H, t, J = 7.3 Hz) |

TABLE 145-continued

| Compound No. | Structure | Physicochemical data |
|---|---|---|
| 9-14 | 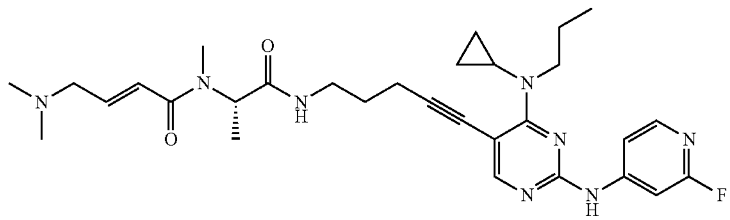 [SMILES: CCCN(c1nc(Nc2ccnc(F)c2)ncc1C#CCCCNC(=O)[C@H](C)N(C)C(=O)/C=C/CN(C)C)C1CC1] | ¹H-NMR (CDCl₃) δ: 8.57 (1H, s), 8.12 (1H, s), 7.97 (1H, d, J = 5.3 Hz), 7.71 (1H, d, J = 2.0 Hz), 7.14 (1H, d, J = 5.9 Hz), 6.93 (1H, dt, 15.2, 5.9 Hz), 6.80 (1H, t, J = 5.6 Hz), 6.43 (1H, d, 15.0 Hz), 6.40 (1H, s), 5.19 (1H, q, J = 7.0 Hz), 3.81-3.72 (2H, m), 3.43-3.24 (2H, m), 3.15-3.03 (3H, m), 3.01 (3H, s), 2.69-2.55 (1H, m), 2.41 (2H, t, J = 7.3 Hz), 2.26 (6H, s), 1.83-1.64 (4H, m), 1.35 (3H, d, J = 7.3 Hz), 1.00-0.88 (5H, m), 0.76-0.71 (2H, m) |
| 9-15 | 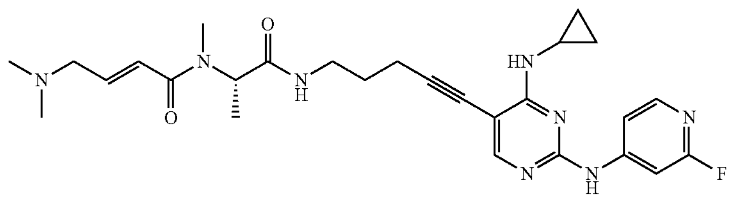 [SMILES: C[C@@H](C(=O)NCCCC#Cc1cnc(Nc2ccnc(F)c2)nc1NC1CC1)N(C)C(=O)/C=C/CN(C)C] | ¹H-NMR (CDCl₃) δ: 8.30 (1H, s), 8.02-7.95 (3H, m), 7.17-7.10 (1H, m), 6.94 (1H, dt, J = 15.2, 5.9 Hz), 6.70 (1H, t, J = 5.9 Hz), 6.51 (1H, s), 6.44 (1H, dt, J = 15.2, 1.7 Hz), 5.20 (1H, q, J = 6.8 Hz), 3.44 (2H, q, J = 6.4 Hz), 3.11 (2H, dd, J = 5.9, 1.3 Hz), 3.02 (3H, s), 2.92-2.81 (1H, m), 2.43 (2H, t, J = 6.6 Hz), 2.27 (6H, s), 1.78-1.69 (2H, m), 1.38 (3H, d, J = 6.8 Hz), 0.96-0.90 (2H, m), 0.79-0.74 (2H, m) |
| 9-16 | 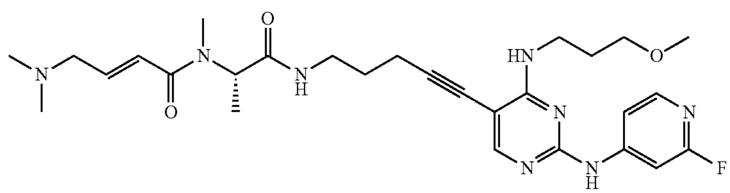 [SMILES: COCCCNc1nc(Nc2ccnc(F)c2)ncc1C#CCCCNC(=O)[C@H](C)N(C)C(=O)/C=C/CN(C)C] | ¹H-NMR (CDCl₃) δ: 8.24 (1H, s), 8.01-7.96 (2H, m), 7.63 (1H, d, J = 1.3 Hz), 7.18 (1H, d, J = 5.9 Hz), 6.94 (1H, dt, J = 15.2, 5.9 Hz), 6.81-6.65 (2H, m), 6.43 (1H, d, J = 15.2 Hz), 5.20 (1H, q, J = 7.3 Hz), 3.65 (2H, q, J = 6.4 Hz), 3.54 (2H, t, J = 5.9 Hz), 3.43 (2H, q, J = 6.4 Hz), 3.35 (3H, s), 3.11 (2H, dd, J = 5.9, 1.3 Hz), 3.02 (3H, s), 2.49-2.40 (2H, m), 2.27 (6H, s), 2.01-1.97 (2H, m), 1.80-1.71 (2H, m), 1.37 (3H, d, J = 7.3 Hz) |

TABLE 146

| Compound No. | Structure | Physicochemical data |
|---|---|---|
| 9-17 | 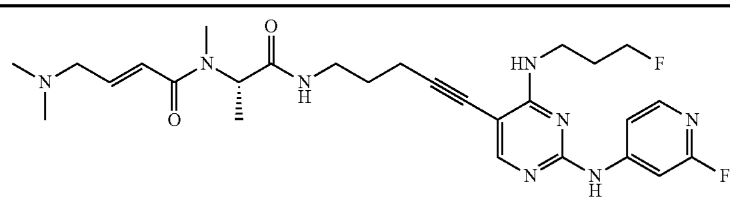 | ¹H-NMR (CDCl₃) δ: 8.00 (1H, s), 8.00 (1H, d, J = 5.3 Hz), 7.60 (1H, d, J = 2.0 Hz), 7.30 (1H, s), 7.16-7.09 (1H, m), 6.94 (1H, dt, J = 15.2, 5.9 Hz), 6.89-6.80 (1H, m), 6.61-6.51 (1H, m), 6.48-6.37 (1H, m), 5.19 (1H, q, J = 7.0 Hz), 4.61 (2H, dt, J = 47.3, 5.6 Hz), 3.73 (2H, q, J = 6.6 Hz), 3.53-3.40 (2H, m), 3.11 (2H, dd, J = 5.9, 1.3 Hz), 3.00 (3H, s), 2.52-2.37 (2H, m), 2.27 (6H, s), 2.22-2.05 (2H, m), 1.78-1.69 (2H, m), 1.36 (3H, d, J = 7.0 Hz) |
| 9-18 | 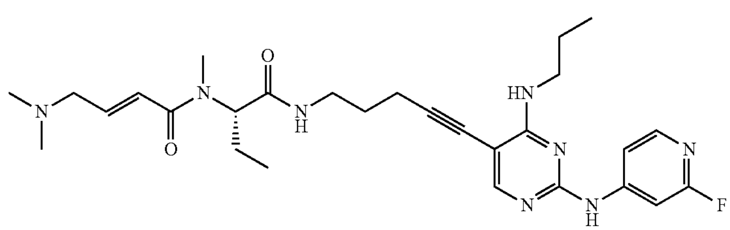 [SMILES: CCCNc1nc(Nc2ccnc(F)c2)ncc1C#CCCCNC(=O)[C@H](CC)N(C)C(=O)/C=C/CN(C)C] | ¹H-NMR (CDCl₃) δ: 8.52 (1H, s), 7.98 (2H, dd, J = 5.9, 1.3 Hz), 7.68 (1H, d, J = 1.3 Hz), 7.17 (1H, d, J = 5.9 Hz), 6.94 (1H, dt, J = 15.2, 5.9 Hz), 6.83 (1H, t, J = 6.3 Hz), 6.59 (1H, t, J = 5.9 Hz), 6.45 (1H, d, J = 15.2 Hz), 4.94 (1H, t, J = 7.9 Hz), 3.54-3.42 (4H, m), 3.13-3.08 (2H, m), 3.03 (3H, s), 2.44 (2H, t, J = 6.3 Hz), 2.27 (6H, s), 2.06-1.95 (1H, m), 1.77-1.67 (5H, m), 1.01 (3H, t, J = 7.3 Hz), 0.91 (3H, t, J = 7.3 Hz) |
| 9-19 | 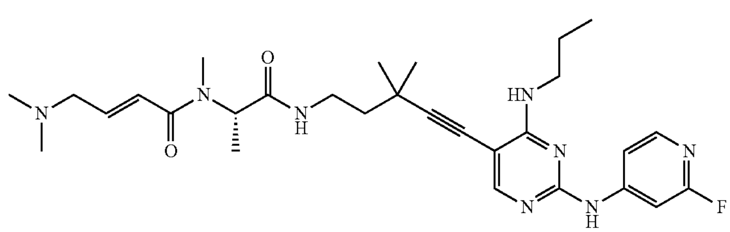 [SMILES: CCCNc1nc(Nc2ccnc(F)c2)ncc1C#CC(C)(C)CCNC(=O)[C@H](C)N(C)C(=O)/C=C/CN(C)C] | ¹H-NMR (CDCl₃) δ: 8.00 (1H, s), 7.99 (1H, d, J = 5.9 Hz), 7.65 (1H, d, J = 2.0 Hz), 7.30 (1H, s), 7.12-7.06 (1H, m), 6.94 (1H, dt, J = 15.2, 5.9 Hz), 6.64-6.53 (1H, m), 6.47-6.36 (1H, m), 6.32-6.22 (1H, m), 5.17 (1H, q, J = 7.0 Hz), 3.59-3.36 (4H, m), 3.10 (2H, dd, J = 5.9, 1.3 Hz), 2.98 (3H, s), 2.27 (6H, s), 1.78-1.64 (4H, m), 1.35 (3H, d, J = 7.0 Hz), 1.30 (3H, s), 1.29 (3H, s), 1.01 (3H, t, J = 7.3 Hz) |

TABLE 146-continued

| Compound No. | Structure | Physicochemical data |
|---|---|---|
| 9-20 | 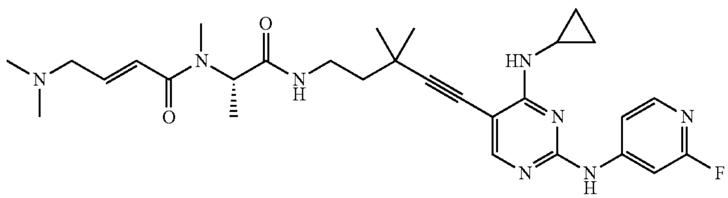 [SMILES: C[C@@H](C(=O)NCCC(C)(C)C#Cc1cnc(Nc2ccnc(F)c2)nc1NC1CC1)N(C)C(=O)/C=C/CN(C)C] | $^1$H-NMR (CDCl$_3$) δ: 8.02 (1H, s), 7.99 (1H, d, J = 5.3 Hz), 7.95 (1H, d, J = 2.0 Hz), 7.38 (1H, s), 7.12-7.04 (1H, m), 6.94 (1H, dt, J = 15.2, 5.9 Hz), 6.61-6.51 (1H, m), 6.41 (1H, d, J = 15.2 Hz), 6.09 (1H, s), 5.16 (1H, q, J = 7.0 Hz), 3.51-3.37 (2H, m), 3.10 (2H, d, J = 5.9 Hz), 2.99 (3H, s), 2.87-2.82 (1H, m), 2.27 (6H, s), 1.66 (2H, t, J = 9.6 Hz), 1.36 (3H, d, J = 7.0 Hz), 1.30 (3H, s), 1.29 (3H, s), 1.01-0.88 (2H, m), 0.77-0.67 (2H, m) |

TABLE 147

| Compound No. | Structure | Physicochemical data |
|---|---|---|
| 9-21 | 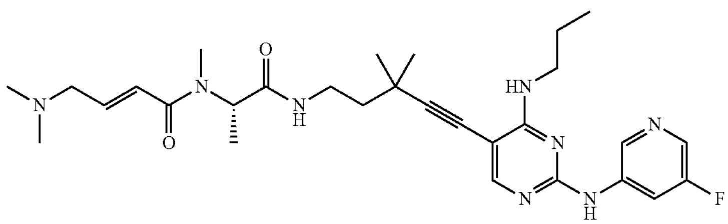 [SMILES: CCCNc1nc(Nc2cncc(F)c2)ncc1C#CC(C)(C)CCNC(=O)[C@H](C)N(C)C(=O)/C=C/CN(C)C] | $^1$H-NMR (CDCl$_3$) δ: 8.37 (1H, dt, J = 11.7, 2.3 Hz), 8.34-8.31 (1H, m), 8.07 (1H, d, J = 2.6 Hz), 7.98 (1H, s), 7.52 (1H, s), 6.94 (1H, dt, J = 15.2, 5.9 Hz), 6.64-6.55 (1H, m), 6.46-6.37 (1H, m), 6.24-6.15 (1H, m), 5.17 (1H, q, J = 7.0 Hz), 3.57-3.35 (4H, m), 3.10 (2H, dd, J = 5.9, 1.3 Hz), 2.98 (3H, s), 2.27 (6H, s), 1.79-1.61 (4H, m), 1.35 (3H, d, J = 7.3 Hz), 1.30 (3H, s), 1.29 (3H, s), 1.00 (3H, t, J = 7.3 Hz) |
| 9-22 | 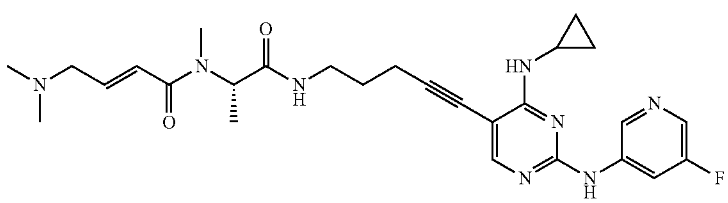 | $^1$H-NMR (CDCl$_3$) δ: 8.67 (1H, dt, J = 11.9, 2.3 Hz), 8.35 (1H, s), 8.07 (1H, d, J = 2.3 Hz), 8.00 (1H, s), 7.60 (1H, s), 6.94 (1H, dt, J = 15.2, 5.9 Hz), 6.62-6.51 (1H, m), 6.48-6.38 (2H, m), 5.19 (1H, q, J = 7.0 Hz), 3.43 (2H, q, J = 6.4 Hz), 3.11 (2H, dd, J = 5.9, 1.3 Hz), 3.00 (3H, s), 2.91-2.80 (1H, m), 2.42 (2H, t, J = 6.6 Hz), 2.27 (6H, s), 1.78-1.69 (2H, m), 1.37 (3H, d, J = 7.0 Hz), 0.95-0.89 (2H, m), 0.79-0.72 (2H, m) |
| 9-23 | 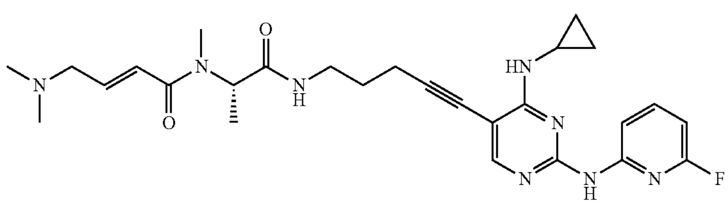 [SMILES: C[C@@H](C(=O)NCCCC#Cc1cnc(Nc2cccc(F)n2)nc1NC1CC1)N(C)C(=O)/C=C/CN(C)C] | $^1$H-NMR (CDCl$_3$) δ: 8.48 (1H, dd, J = 8.3, 2.3 Hz), 8.05 (1H, s), 7.76 (1H, s), 7.70 (1H, q, J = 8.3 Hz), 6.94 (1H, dt, J = 15.2, 5.9 Hz), 6.57-6.51 (1H, m), 6.49 (1H, dd, J = 8.3, 2.3 Hz), 6.46-6.37 (1H, m), 6.34 (1H, s), 5.18 (1H, q, J = 7.0 Hz), 3.43 (2H, q, J = 6.4 Hz), 3.10 (2H, dd, J = 5.9, 1.3 Hz), 3.00 (3H, s), 2.93-2.81 (1H, m), 2.42 (2H, t, J = 6.6 Hz), 2.27 (6H, s), 1.78-1.68 (2H, m), 1.37 (3H, d, J = 7.0 Hz), 0.90-0.84 (2H, m), 0.77-0.72 (2H, m) |
| 9-24 | 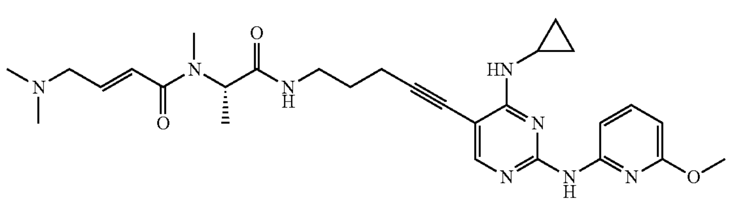 | $^1$H-NMR (CDCl$_3$) δ: 8.12 (1H, d, J = 7.9 Hz), 8.02 (1H, s), 7.60 (1H, s), 7.53 (1H, t, J = 7.9 Hz), 6.94 (1H, dt, J = 15.2, 5.9 Hz), 6.57-6.48 (1H, m), 6.46-6.38 (1H, m), 6.35 (1H, d, J = 7.9 Hz), 6.24 (1H, s), 5.18 (1H, q, J = 7.3 Hz), 3.87 (3H, s), 3.42 (2H, q, J = 6.4 Hz), 3.10 (2H, dd, J = 5.9, 1.3 Hz), 3.00 (3H, s), 2.94-2.83 (1H, m), 2.42 (2H, t, J = 6.9 Hz), 2.27 (6H, s), 1.78-1.69 (2H, m), 1.37 (3H, d, J = 7.3 Hz), 0.90-0.84 (2H, m), 0.77-0.70 (2H, m) |

TABLE 148

| Compound No. | Structure | Physicochemical data |
| --- | --- | --- |
| 9-25 | 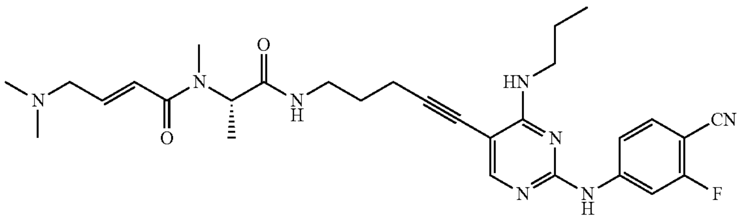 [SMILES: CCCNc1nc(Nc2ccc(C#N)c(F)c2)ncc1C#CCCCNC(=O)[C@H](C)N(C)C(=O)/C=C/CN(C)C] | $^1$H-NMR (CDCl$_3$) δ: 8.11 (1H, dd, J = 12.6, 2.0 Hz), 7.97 (1H, s), 7.62 (1H, s), 7.46 (1H, dd, J = 8.6, 7.3 Hz), 7.13 (1H, dd, J = 8.6, 2.0 Hz), 6.94 (1H, dt, J = 15.2, 5.9 Hz), 6.63-6.49 (2H, m), 6.48-6.38 (1H, m), 5.19 (1H, q, J = 7.0 Hz), 3.56-3.39 (4H, m), 3.11 (2H, dd, J = 5.9, 1.3 Hz), 3.00 (3H, s), 2.44 (2H, t, J = 6.3 Hz), 2.27 (6H, s), 1.81-1.65 (4H, m), 1.36 (3H, d, J = 7.3 Hz), 1.01 (3H, t, J = 7.0 Hz) |
| 9-26 | 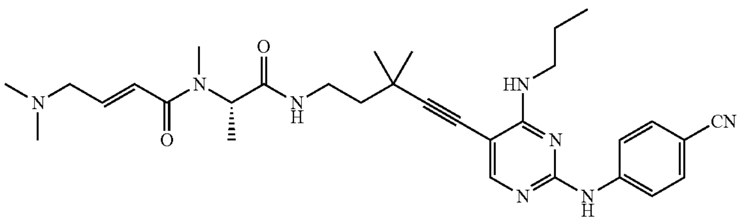 [SMILES: CCCNc1nc(Nc2ccc(C#N)cc2)ncc1C#CC(C)(C)CCNC(=O)[C@H](C)N(C)C(=O)/C=C/CN(C)C] | $^1$H-NMR (CDCl$_3$) δ: 7.98 (1H, s), 7.76 (2H, d, J = 8.6 Hz), 7.57 (2H, d, J = 8.6 Hz), 7.23 (1H, s), 6.94 (1H, dt, J = 15.2, 5.9 Hz), 6.62-6.52 (1H, m), 6.41 (1H, d, J = 15.2 Hz), 6.22-6.10 (1H, m), 5.17 (1H, q, J = 7.0 Hz), 3.53-3.39 (4H, m), 3.10 (2H, d, J = 5.9 Hz), 2.98 (3H, s), 2.27 (6H, s), 1.78-1.62 (4H, m), 1.35 (3H, d, J = 7.0 Hz), 1.30 (3H, s), 1.29 (3H, s), 1.00 (3H, t, J = 7.3 Hz) |
| 9-27 | 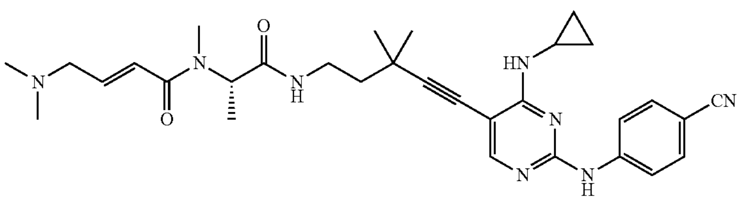 [SMILES: C[C@@H](C(=O)NCCC(C)(C)C#Cc1cnc(Nc2ccc(C#N)cc2)nc1NC1CC1)N(C)C(=O)/C=C/CN(C)C] | $^1$H-NMR (CDCl$_3$) δ: 8.00 (1H, s), 7.88 (2H, d, J = 9.2 Hz), 7.56 (2H, d, J = 9.2 Hz), 7.33 (1H, s), 6.93 (1H, dt, J = 15.2, 5.9 Hz), 6.59-6.50 (1H, m), 6.41 (1H, d, J = 15.2 Hz), 6.00 (1H, s), 5.16 (1H, q, J = 7.0 Hz), 3.55-3.32 (2H, m), 3.10 (2H, d, J = 5.9 Hz), 2.99 (3H, s), 2.90-2.79 (1H, m), 2.27 (6H, s), 1.66 (2H, t, J = 7.6 Hz), 1.36 (3H, d, J = 7.0 Hz), 1.30 (3H, s), 1.29 (3H, s), 0.94-0.84 (2H, m), 0.74-0.69 (2H, m) |
| 9-28 | 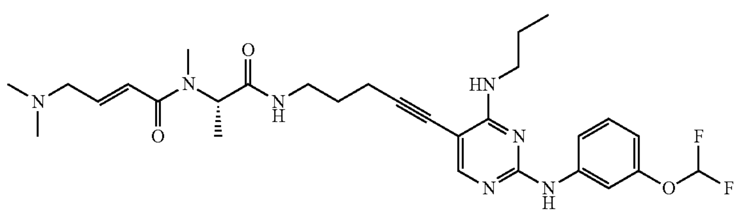 [SMILES: CCCNc1nc(Nc2cccc(OC(F)F)c2)ncc1C#CCCCNC(=O)[C@H](C)N(C)C(=O)/C=C/CN(C)C] | $^1$H-NMR (CDCl$_3$) δ: 7.96 (1H, s), 7.86 (1H, t, J = 2.0 Hz), 7.28-7.14 (2H, m), 7.05 (1H, s), 6.94 (1H, dt, J = 15.2, 5.9 Hz), 6.73 (1H, dd, J = 7.6, 2.0 Hz), 6.57-6.48 (1H, m), 6.53 (1H, t, J = 74.3 Hz), 6.48-6.37 (1H, m), 6.27-6.18 (1H, m), 5.18 (1H, q, J = 7.0 Hz), 3.51 (2H, q, J = 6.3 Hz), 3.43 (2H, q, J = 6.4 Hz), 3.10 (2H, dd, J = 5.9, 1.3 Hz), 2.99 (3H, s), 2.44 (2H, t, J = 6.9 Hz), 2.27 (6H, s), 1.84-1.65 (4H, m), 1.36 (3H, d, J = 7.0 Hz), 1.00 (3H, t, J = 7.6 Hz) |

TABLE 149

| Compound No. | Structure | Physicochemical data |
| --- | --- | --- |
| 9-29 | 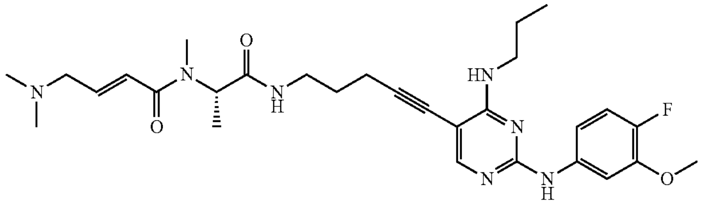 | $^1$H-NMR (CDCl$_3$) δ: 7.95 (1H, s), 7.57 (1H, dd, J = 7.9, 2.0 Hz), 7.09-6.86 (4H, m), 6.60-6.49 (1H, m), 6.42 (1H, d, J = 15.2 Hz), 6.21-6.08 (1H, m), 5.18 (1H, q, J = 7.0 Hz), 3.90 (3H, s), 3.50 (2H, q, J = 6.6 Hz), 3.43 (2H, q, J = 6.6 Hz), 3.10 (2H, d, J = 5.9 Hz), 2.99 (3H, s), 2.44 (2H, t, J = 6.6 Hz), 2.27 (6H, s), 1.79-1.62 (4H, m), 1.35 (3H, d, J = 7.0 Hz), 0.97 (3H, t, J = 7.3 Hz) |

//

TABLE 149-continued

| Compound No. | Structure | Physicochemical data |
|---|---|---|
| 9-30 | 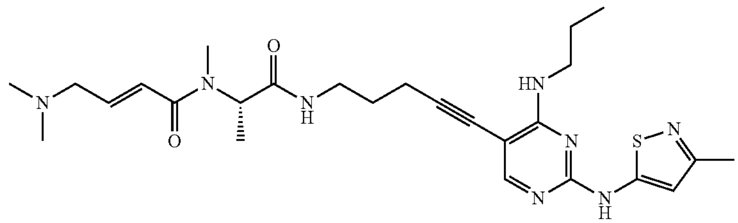 | ¹H-NMR (CDCl₃) δ: 8.01 (1H, s), 7.01-6.88 (1H, m), 6.84-6.70 (1H, m), 6.69-6.58 (1H, m), 6.57-6.33 (2H, m), 5.27-5.15 (1H, m), 3.97-3.86 (1H, m), 3.80-3.61 (2H, m), 3.59-3.36 (2H, m), 3.11 (2H, d, J = 5.9 Hz), 3.02 (3H, s), 2.52-2.41 (2H, m), 2.40 (3H, s), 2.27 (6H, s), 1.91-1.66 (4H, m), 1.37 (3H, d, J = 7.3 Hz), 1.03 (3H, t, J = 7.6 Hz) |
| 9-31 | 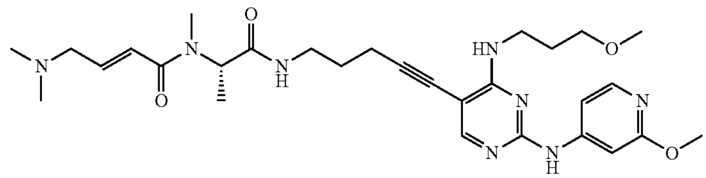 | ¹H-NMR (CDCl₃) δ: 7.97 (2H, brs), 7.41-7.13 (2H, m), 7.11-6.88 (2H, m), 6.70-6.51 (2H, m), 6.42 (1H, d, J = 14.5 Hz), 5.19 (1H, brs), 3.93 (3H, s), 3.79-3.61 (2H, m), 3.61-3.51 (2H, m), 3.51-3.39 (2H, m), 3.36 (3H, s), 3.11 (2H, d, J = 5.3 Hz), 3.00 (3H, s), 2.45 (2H, t, J = 6.3 Hz), 2.27 (6H, s), 2.14-1.67 (4H, m), 1.36 (3H, d, J = 6.6 Hz) |
| 9-32 | 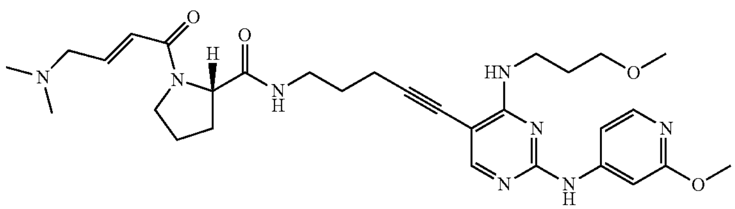 | ¹H-NMR (CDCl₃) δ: 7.99 (2H, brs), 7.23-7.09 (1H, m), 7.09-6.86 (2H, m), 6.48-6.36 (1H, m), 6.36-6.18 (2H, m), 5.54 (1H, brs), 4.90-4.42 (1H, m), 3.92 (3H, s), 3.86-3.43 (8H, m), 3.36 (3H, s), 3.11 (2H, brs), 2.52 (2H, brs), 2.26 (6H, s), 2.22-1.51 (8H, m) |
| 9-33 | 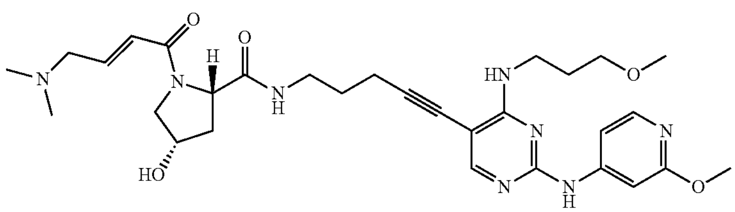 | ¹H-NMR (CDCl₃) δ: 7.98 (2H, brs), 7.31-7.13 (2H, m), 7.13-6.87 (3H, m), 6.60 (1H, brs), 6.33 (1H, d, J = 13.9 Hz), 4.68 (1H, brs), 3.93 (3H, s), 3.77-3.45 (10H, m), 3.36 (3H, s), 3.12 (2H, brs), 2.49 (2H, brs), 2.27 (6H, s), 2.10-1.50 (6H, m) |

TABLE 150

| Compound No. | Structure | Physicochemical data |
|---|---|---|
| 9-34 | 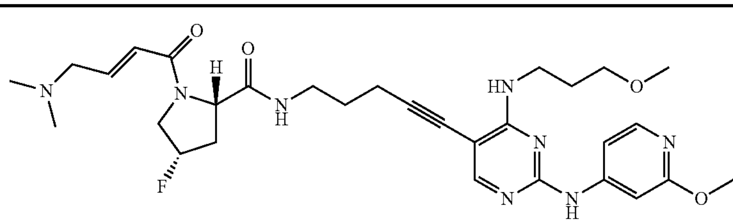 | ¹H-NMR (CDCl₃) δ: 8.03-7.93 (2H, m), 7.14-6.96 (3H, m), 6.95-6.82 (1H, m), 6.63-6.40 (1H, m), 6.36-6.12 (2H, m), 5.47-5.18 (1H, m), 4.88-4.51 (1H, m), 3.93 (3H, s), 3.81-3.41 (8H, m), 3.36 (3H, s), 3.13-3.05 (2H, m), 2.48 (2H, t, J = 5.3 Hz), 2.28 (3H, s), 2.23 (3H, s), 2.03-1.90 (2H, m), 1.84-1.70 (2H, m), 1.68-1.56 (2H, m) |
| 9-35 | 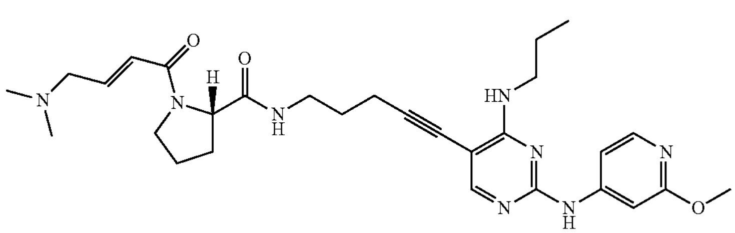 | ¹H-NMR (CDCl₃) δ: 7.98 (2H, d, J = 5.3 Hz), 7.54-7.41 (1H, m), 7.41-7.24 (1H, m), 7.21-7.06 (1H, m), 7.06-6.86 (2H, m), 6.52-6.09 (2H, m), 4.69 (1H, brs), 3.92 (3H, s), 3.83-3.28 (6H, m), 3.11 (2H, s), 2.49 (2H, brs), 2.27 (6H, s), 2.18-1.51 (8H, m), 1.00 (3H, t, J = 5.9 Hz) |

TABLE 150-continued

| Compound No. | Structure | Physicochemical data |
|---|---|---|
| 9-36 | 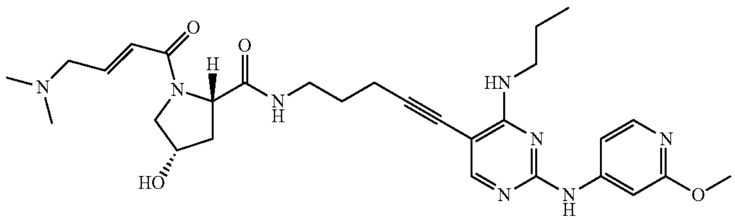 | ¹H-NMR (CDCl₃) δ: 8.06-7.93 (2H, m), 7.85 (1H, brs), 7.43-7.27 (2H, m), 7.11-6.88 (2H, m), 6.27 (1H, d, J = 15.2 Hz), 6.04 (1H, s), 5.68 (1H, s), 4.79 (1H, d, J = 8.6 Hz), 4.51 (1H, brs), 3.92 (3H, s), 3.84-3.66 (2H, m), 3.59-3.38 (4H, m), 3.12 (2H, brs), 2.50 (2H, t, J = 5.6 Hz), 2.27 (6H, s), 1.92-1.59 (6H, m), 1.00 (3H, t, J = 7.6 Hz) |
| 9-37 | 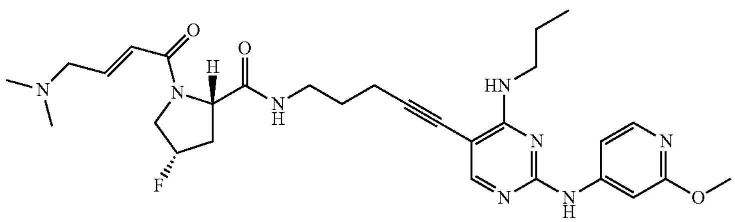 | ¹H-NMR (CDCl₃) δ: 7.99 (2H, s), 7.42-7.23 (2H, m), 7.19-6.84 (2H, m), 6.50-6.12 (2H, m), 5.48-5.16 (1H, m), 4.92-4.50 (1H, m), 3.93 (3H, s), 3.90-3.36 (5H, m), 3.21-2.89 (4H, m), 2.48 (2H, t, J = 5.6 Hz), 2.28 (3H, s), 2.23 (3H, s), 1.95-1.51 (6H, m), 1.02 (3H, t, J = 6.9 Hz) |
| 9-38 | 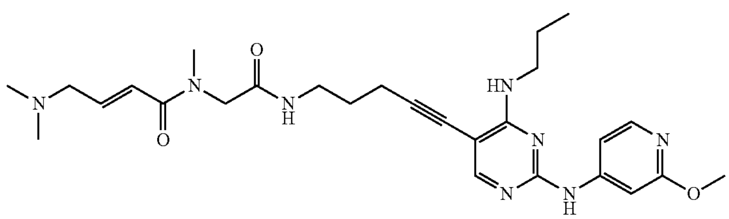 | ¹H-NMR (CDCl₃) δ: 8.00-7.96 (2H, m), 7.35-7.25 (2H, m), 7.06-6.89 (2H, m), 6.66 (1H, brs), 6.47 (1H, d, J = 15.2 Hz), 6.22 (1H, brs), 4.04 (2H, s), 3.92 (3H, s), 3.59-3.40 (4H, m), 3.20 (3H, s), 3.11 (2H, d, J = 5.9 Hz), 2.48 (2H, t, J = 6.6 Hz), 2.27 (6H, s), 1.93-1.64 (4H, m), 1.01 (3H, t, J = 7.3 Hz) |

TABLE 151

| Compound No. | Structure | Physicochemical data |
|---|---|---|
| 9-39 | 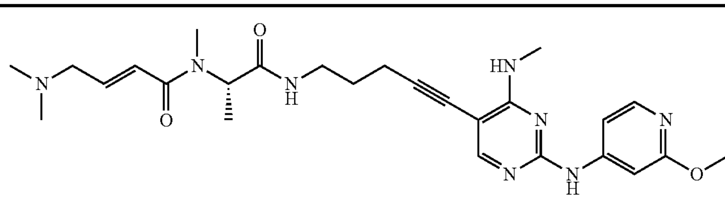 | ¹H-NMR (CDCl₃) δ: 7.98 (1H, d, J = 5.9 Hz), 7.96 (1H, s), 7.43 (1H, s), 7.34 (1H, d, J = 2.0 Hz), 7.02 (1H, dd, J = 5.9, 2.0 Hz), 6.94 (1H, dt, J = 15.2, 5.9 Hz), 6.63 (1H, t, J = 5.9 Hz), 6.45-6.40 (2H, m), 5.19 (1H, q, J = 6.8 Hz), 3.93 (3H, s), 3.48-3.40 (2H, m), 3.15-3.08 (5H, m), 3.00 (3H, s), 2.43 (2H, t, J = 6.3 Hz), 2.27 (6H, s), 1.78-1.70 (2H, m), 1.37 (3H, d, J = 6.8 Hz) |
| 9-40 | 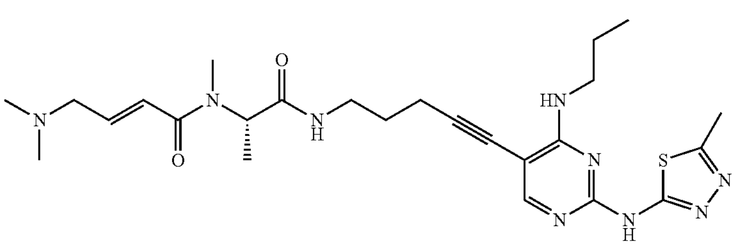 [SMILES: CCCNc1nc(Nc2nnc(C)s2)ncc1C#CCCCNC(=O)[C@H](C)N(C)C(=O)/C=C/CN(C)C] | ¹H-NMR (CDCl₃) δ: 8.33 (1H, brs), 6.97-6.92 (2H, m), 6.66-6.53 (2H, m), 6.45-6.40 (2H, m), 5.28-5.11 (1H, m), 3.67-3.53 (1H, m), 3.53-3.37 (2H, m), 3.11 (2H, d, J = 5.9 Hz), 3.00 (3H, s), 2.68 (3H, s), 2.43 (2H, t, J = 5.9 Hz), 2.27 (6H, s), 1.88-1.53 (4H, m), 1.36 (3H, d, J = 7.3 Hz), 1.02 (3H, t, J = 7.6 Hz) |

Example 44

1

[Formula 247]

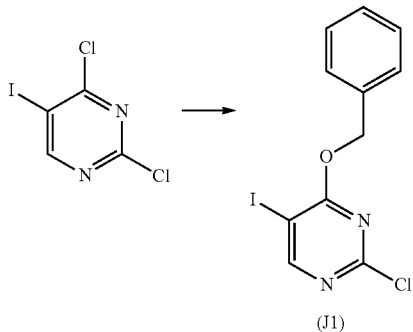

To a solution of benzyl alcohol (10.4 mL) in tetrahydrofuran (100 mL), tert-butoxypotassium (6.2 g) was added under a nitrogen atmosphere with ice cooling, and the mixture was stirred for 40 minutes under reflux by heating (Reaction mixture A).

To a solution of 2,4-dichloro-5-iodopyrimidine (13.7 g) synthesized according to the method described in WO2008/155140 A1 in N,N-dimethylformamide (100 mL), Reaction mixture A mentioned above was added dropwise at a temperature below 10° C., and the mixture was stirred for 2 hours under ice cooling. To the reaction mixture, water (800 mL) was added. The solid matter was taken by filtration, washed with water, and then recrystallized from acetonitrile, and dried under reduced pressure to obtain 4-(benzyloxy)-2-chloro-5-iodopyrimidine (J1, 10.3 g) as white solid.

MS m/z (M+H): 347.0

2

[Formula 248]

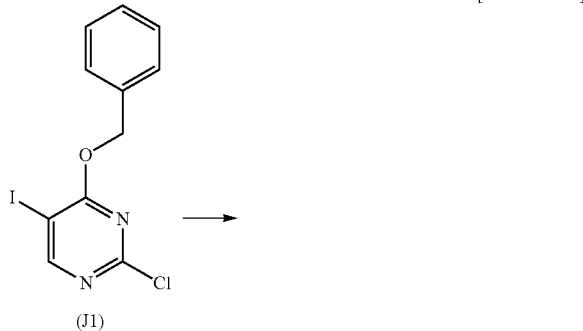

To a solution of 4-(benzyloxy)-2-chloro-5-iodopyrimidine (J1, 158 mg) in N-methylpyrrolidone (2.5 mL), 3-fluoroaniline (66 μL) and (1S)-(+)-10-camphorsulfonic acid (159 mg) were added at room temperature, and the mixture was stirred at 60° C. for 2 hours, and then stirred at 80° C. for 7 hours. The reaction mixture was cooled to room temperature, and then saturated aqueous sodium hydrogencarbonate and ethyl acetate were added. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain 4-(benzyloxy)-N-(3-fluorophenyl)-5-iodopyrimidin-2-amine (J2, 60 mg) as white solid.

MS m/z (M+H): 422.0

3

[Formula 249]

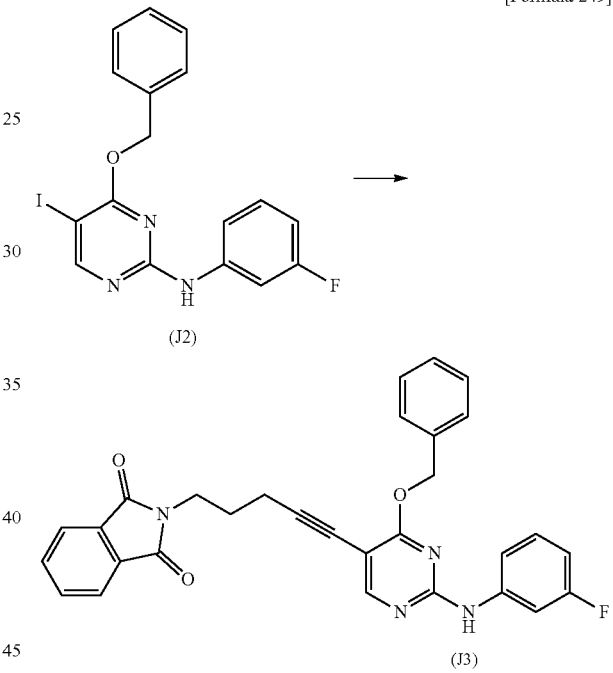

To a solution of 4-(benzyloxy)-N-(3-fluorophenyl)-5-iodopyrimidin-2-amine (J2, 60 mg) and N-(4-pentynyl)phthalimide (76 mg) in N,N-dimethylformamide (500 μL), triethylamine (98 μL), copper(I) iodide (14 mg) and bis(triphenylphosphine)palladium(II) dichloride (10 mg) were added at room temperature, and the mixture was stirred at the same temperature for 1 hour. To the reaction mixture, ethyl acetate and water were added. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain 2-(5-(4-(benzyloxy)-2-((3-fluorophenyl)amino)pyrimidin-5-yl)-4-pentyn-1-yl)isoindoline-1,3-dione (J3, 69 mg) as pale green solid.

MS m/z (M+H): 507.2

4

[Formula 250]

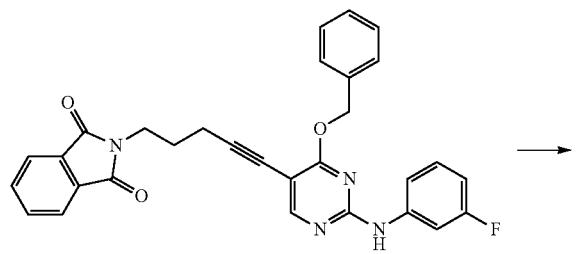

(J3)

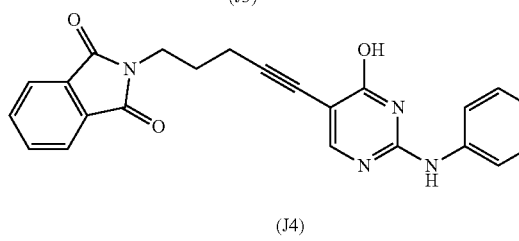

(J4)

To 2-(5-(4-(benzyloxy)-2-((3-fluorophenyl)amino)pyrimidin-5-yl)-4-pentyn-1-yl)isoindoline-1,3-dione (J3, 69 mg), trifluoroacetic acid (1 mL) was added at room temperature, and the mixture was stirred overnight at the same temperature. The solvent was evaporated under reduced pressure, and then ethyl acetate and water were added to the mixture. The organic layer was separated, washed with saturated aqueous sodium chloride, and then dried over anhydrous sodium sulfate, and the solvent was evaporated under reduced pressure. The obtained solid matter was washed with diisopropyl ether, and then dried under reduced pressure to obtain 2-(5-(2-((3-fluorophenyl)amino)-4-hydroxypyrimidin-5-yl)-4-pentyn-1-yl)isoindoline-1,3-dione (J4, 62 mg) as pale pink solid.

MS m/z (M+H): 417.1

5

[Formula 251]

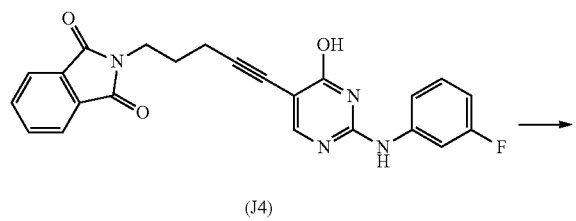

(J4)

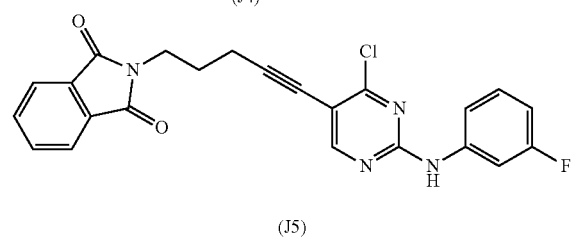

(J5)

To 2-(5-(2-((3-fluorophenyl)amino)-4-hydroxypyrimidin-5-yl)-4-pentyn-1-yl)isoindoline-1,3-dione (J4, 36 mg), phosphorus oxychloride (1 mL) was added at room temperature, and the mixture was stirred at 80° C. for 45 minutes. The reaction mixture was cooled to room temperature, and then poured into ice, and then ethyl acetate was added to the mixture. The organic layer was separated, washed successively with water, saturated aqueous sodium hydrogencarbonate and saturated aqueous sodium chloride, and then dried over anhydrous sodium sulfate, and the solvent was evaporated under reduced pressure. The obtained solid matter was washed with diisopropyl ether, and then dried under reduced pressure to obtain 2-(5-(4-chloro-2-((3-fluorophenyl)amino)pyrimidin-5-yl)-4-pentyn-1-yl)isoindoline-1,3-dione (J5, 21 mg) as pale yellow solid.

MS m/z (M+H): 435.1

6

[Formula 252]

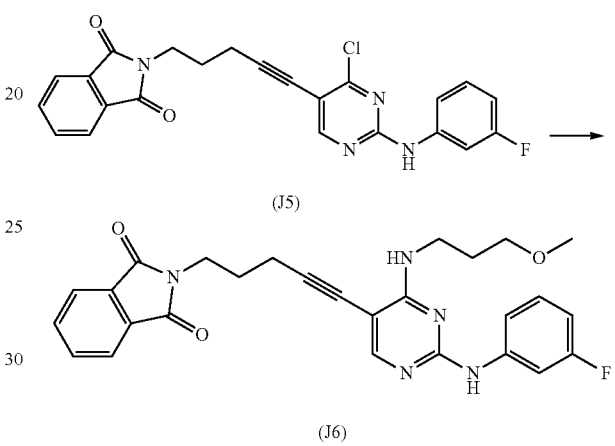

To a solution of 2-(5-(4-chloro-2-((3-fluorophenyl)amino)pyrimidin-5-yl)-4-pentyn-1-yl)isoindoline-1,3-dione (J5, 124 mg) in 1,4-dioxane (2 mL), triethylamine (119 μL) and 3-methoxypropylamine (88 μL) were added at room temperature, and the mixture was stirred overnight at 50° C. in a sealed tube. The reaction mixture was cooled to room temperature, and then ethyl acetate and water were added to the reaction mixture. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain 2-(5-(2-((3-fluorophenyl)amino)-4-((3-methoxypropyl)amino)pyrimidin-5-yl)-4-pentyn-1-yl)isoindoline-1,3-dione (J6, 90 mg) as pale yellow solid.

MS m/z (M+H): 488.2

7

[Formula 253]

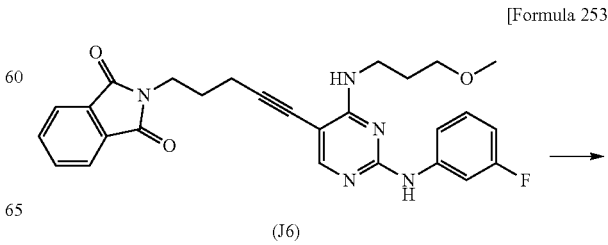

(J6)

531

-continued

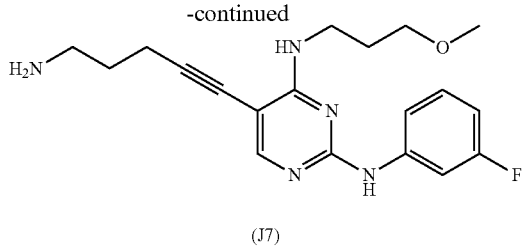

(J7)

To a solution of 2-(5-(2-((3-fluorophenyl)amino)-4-((3-methoxypropyl)amino)pyrimidin-5-yl)-4-pentyn-1-yl)isoindoline-1,3-dione (J6, 90 mg) in tetrahydrofuran (1 mL) and ethanol (0.5 mL), hydrazine monohydrate (100 μL) was added at room temperature, and the mixture was stirred for 1 hour under reflux by heating. The reaction mixture was cooled to room temperature, and then ethyl acetate was added to the reaction mixture. The insoluble matter was removed by filtration, and then 1.0 mol/L aqueous hydrochloric acid was added to the reaction mixture until the mixture became acidic. The aqueous layer was separated, 3.0 mol/L aqueous sodium hydroxide was added until the mixture became basic, and the reaction mixture was extracted with ethyl acetate. The extract was dried over anhydrous sodium sulfate, and the solvent was evaporated under reduced pressure to obtain 5-(5-amino-1-pentyn-1-yl)-$N^2$-(3-fluorophenyl)-$N^4$-(3-methoxypropyl)pyrimidine-2,4-diamine (J7, 55 mg) as pale yellow solid.

MS m/z (M+H): 358.2

8

[Formula 254]

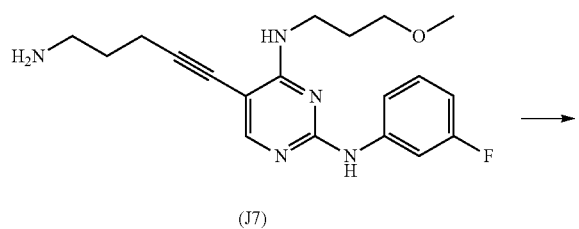

532

-continued

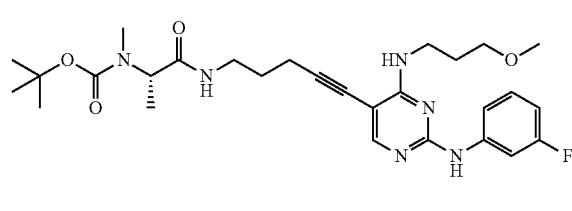

(J8)

To a solution of 5-(5-amino-1-pentyn-1-yl)-$N^2$-(3-fluorophenyl)-$N^4$-(3-methoxypropyl)pyrimidine-2,4-diamine (J7, 55 mg), N-Boc-N-methyl-L-alanine (63 mg), 1-ethyl-3-(3-dimethylaminopropyl)carbodiimide hydrochloride (59 mg) and 1-hydroxybenzotriazole monohydrate (42 mg) in N,N-dimethylformamide (700 μL), N,N-diisopropylethylamine (108 μL) was added at room temperature, and the mixture was stirred at the same temperature for 3 hours. To the reaction mixture, water and ethyl acetate were added. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain (S)-tert-butyl (1-((5-(2-((3-fluorophenyl)amino)-4-((3-methoxypropyl)amino)pyrimidin-5-yl)-4-pentyn-1-yl)amino)-1-oxopropan-2-yl)(methyl)carbamate (J8, 84 mg).

MS m/z (M+H): 543.1

9

[Formula 255]

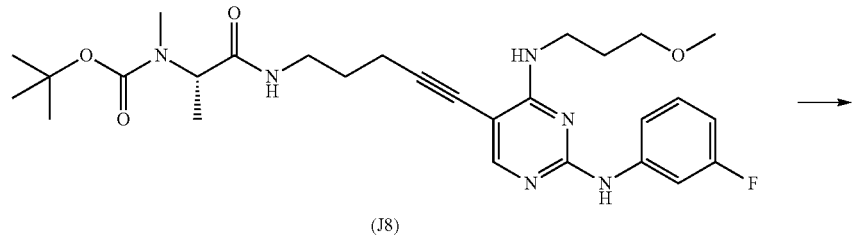

(J8)

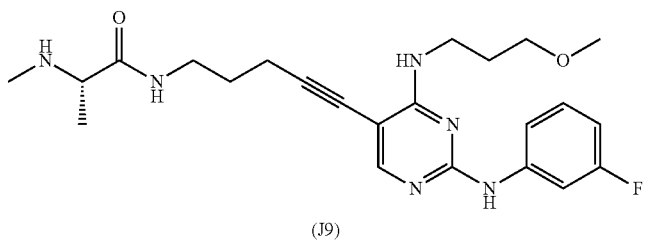

(J9)

533

To (S)-tert-butyl (1-((5-(2-((3-fluorophenyl)amino)-4-((3-methoxypropyl)amino)pyrimidin-5-yl)-4-pentyn-1-yl)amino)-1-oxopropan-2-yl)(methyl)carbamate (J8, 81 mg), a 4.0 mol/L solution of hydrochloric acid in 1,4-dioxane (1 mL) was added at room temperature, and the mixture was stirred at the same temperature for 30 minutes. The solvent was evaporated under reduced pressure. The obtained solid matter was washed with diisopropyl ether, and then dried under reduced pressure to obtain (S)—N-(5-(2-((3-fluorophenyl)amino)-4-((3-methoxypropyl)amino)pyrimidin-5-yl)-4-pentyn-1-yl)-2-(methylamino)propanamide (J9) dihydrochloride (55 mg) as pale yellow solid.

MS m/z (M+H): 443.3

10

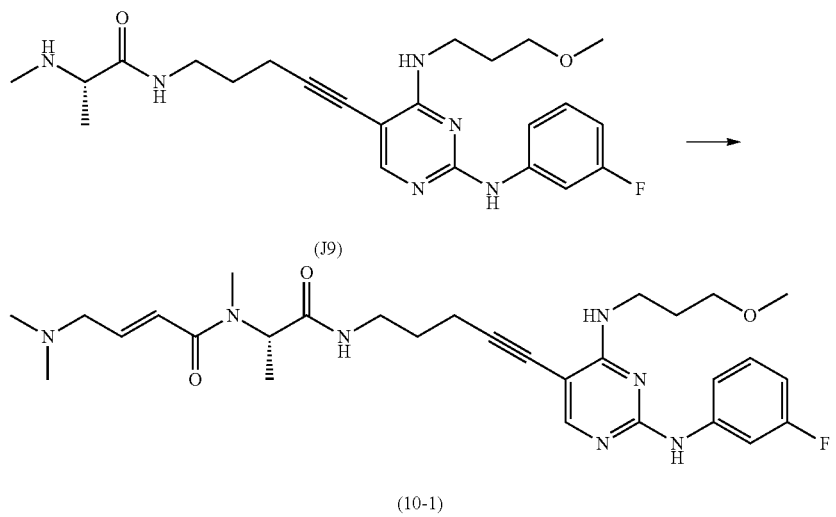

(J9)

(10-1)

To a solution of 4-dimethylaminocrotonic acid hydrochloride (61 mg) in N,N-dimethylformamide (0.5 mL), N-methylmorpholine (135 μL) and isobutyl chloroformate (40 μL) were added under ice cooling, then (S)—N-(5-(2-((3-fluorophenyl)amino)-4-((3-methoxypropyl)amino)pyrimidin-5-yl)-4-pentyn-1-yl)-2-(methylamino)propanamide (J9) dihydrochloride (55 mg) was further added, and the mixture was stirred at the same temperature for 1 hour. To the reaction mixture, saturated aqueous sodium hydrogencarbonate (10 drops) was added, and the solvent was evaporated under reduced pressure. The obtained residue was purified by basic silica gel column chromatography to obtain (S,E)-4-(dimethylamino)-N-(1-((5-(2-((3-fluorophenyl)amino)-4-((3-methoxypropyl)amino)pyrimidin-5-yl)-4-pentyn-1-yl)amino)-1-oxopropan-2-yl)-N-methyl-2-butenamide (10-1, 45 mg).

$^1$H-NMR (CDCl$_3$) δ: 7.96 (1H, s), 7.79 (1H, dt, J=12.1, 2.1 Hz), 7.26-7.15 (1H, m), 7.09 (1H, dd, J=8.1, 2.1 Hz), 7.05 (1H, s), 6.94 (1H, dt, J=15.2, 5.9 Hz), 6.67 (1H, dt, J=8.1, 2.1 Hz), 6.60-6.50 (1H, m), 6.50-6.36 (2H, m), 5.18 (1H, q, J=7.3 Hz), 3.64 (2H, q, J=6.4 Hz), 3.53 (2H, t, J=6.3 Hz), 3.42 (2H, q, J=6.4 Hz), 3.35 (3H, s), 3.10 (2H, dd, J=5.9, 1.3 Hz), 2.99 (3H, s), 2.44 (2H, t, J=6.6 Hz), 2.26 (6H, s), 2.01-1.93 (2H, m), 1.80-1.71 (2H, m), 1.36 (3H, d, J=7.3 Hz)

534

Example 45

1 [Formula 257]

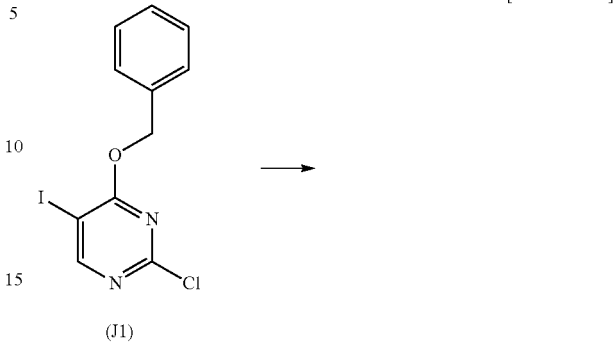

(J1)

[Formula 256]

-continued

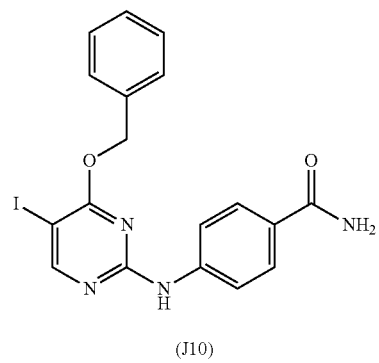

(J10)

To a solution of 4-(benzyloxy)-2-chloro-5-iodopyrimidine (J1, 2.02 g) and 4-aminobenzamide (3.97 g) in N-methylpyrrolidone (20 mL), (1S)-(+)-10-camphorsulfonic acid (6.76 g) was added at room temperature, and the mixture was stirred at 60° C. for 9 hours. The reaction mixture was cooled on ice, and then poured into saturated aqueous sodium hydrogencarbonate. The solid matter was taken by filtration, washed with a mixed solvent of ethyl acetate and methanol, and then dried under reduced pressure to obtain 4-((4-(benzyloxy)-5-iodopyrimidin-2-yl)amino)benzamide (J10, 3.05 g) as white solid.

MS m/z (M+H): 447.2

2

[Formula 258]

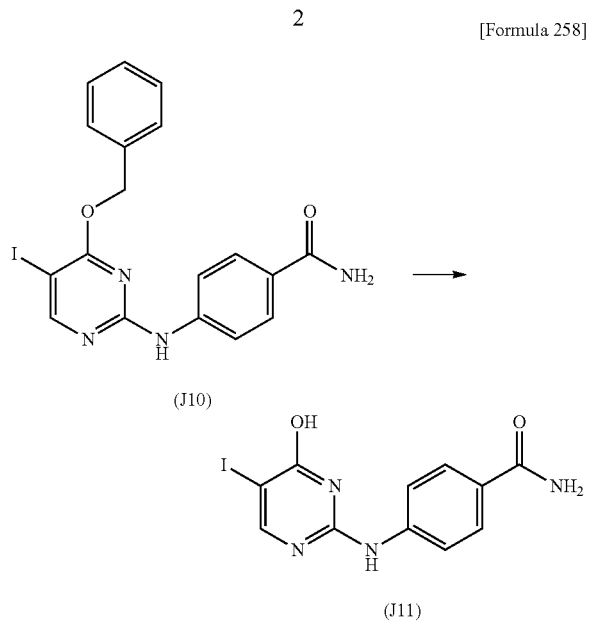

To 4-((4-(benzyloxy)-5-iodopyrimidin-2-yl)amino)benzamide (J10, 2.84 g), trifluoroacetic acid (25 mL) was added at room temperature, and the mixture was stirred at 40 to 50° C. for 8 hours. The reaction mixture was cooled to room temperature, and then the solvent was evaporated under reduced pressure. The obtained solid matter was washed with a mixed solvent of diisopropyl ether and chloroform, and then dried under reduced pressure to obtain 4-((4-hydroxy-5-iodopyrimidin-2-yl)amino)benzamide (J11, 1.35 g) as pale brown solid.

MS m/z (M+H): 357.1

3

[Formula 259]

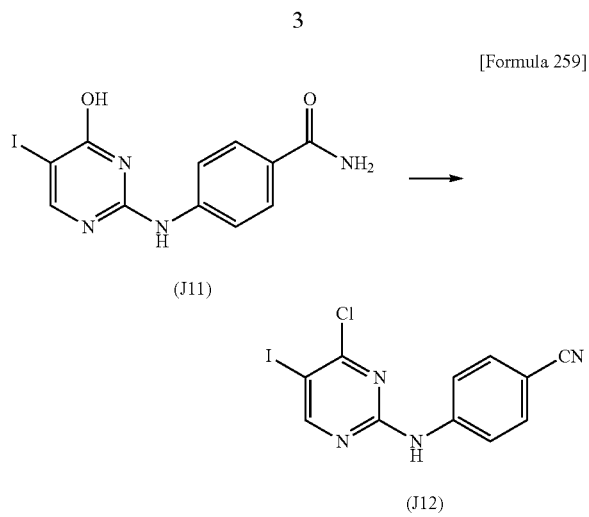

To 4-((4-hydroxy-5-iodopyrimidin-2-yl)amino)benzamide (J11, 1.35 g), phosphorus oxychloride (14 mL) was added at room temperature, and the mixture was stirred at 90° C. for 1 hour and 30 minutes. The reaction mixture was cooled to room temperature, and then poured into ice, and then ethyl acetate was added to the mixture. The organic layer was separated, washed successively with water, saturated aqueous sodium hydrogencarbonate and saturated aqueous sodium chloride, and then dried over anhydrous sodium sulfate, and the solvent was evaporated under reduced pressure. The obtained solid matter was washed with a mixed solvent of diisopropyl ether and chloroform, and then dried under reduced pressure to obtain 4-((4-chloro-5-iodopyrimidin-2-yl)amino)benzonitrile (J12, 764 mg) as pale yellow solid.

MS m/z (M+H): 357.0

4

[Formula 260]

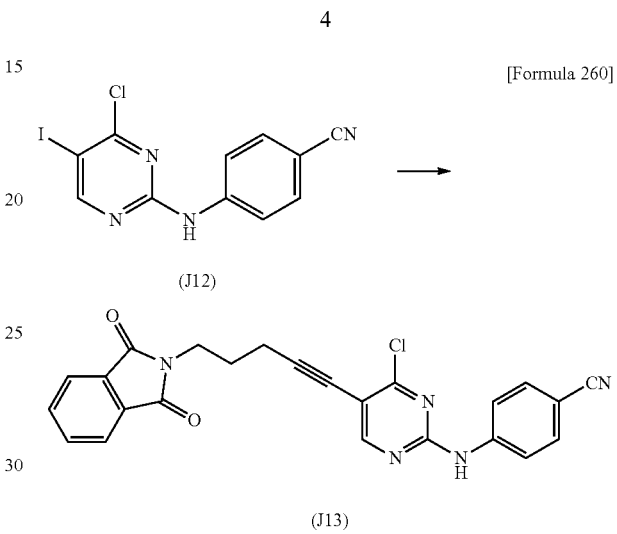

To a solution of 4-((4-chloro-5-iodopyrimidin-2-yl)amino)benzonitrile (J12, 53 mg) and N-(4-pentynyl)phthalimide (47 mg) in N,N-dimethylformamide (1 mL), triethylamine (103 μL), copper(I) iodide (14 mg), and bis(triphenylphosphine)palladium(II) dichloride (10 mg) were added at room temperature, and the mixture was stirred overnight at the same temperature. To the reaction mixture, ethyl acetate and water were added. The organic layer was separated, washed successively with water and saturated aqueous sodium chloride, and then dried over anhydrous sodium sulfate, and the solvent was evaporated under reduced pressure. The obtained solid matter was washed with chloroform, and then dried under reduced pressure to obtain 4-((4-chloro-5-(5-(1,3-dioxoisoindolin-2-yl)-1-pentyn-1-yl)pyrimidin-2-yl)amino)benzonitrile (J13, 44 mg) as white solid.

MS m/z (M+H): 442.2

5

[Formula 261]

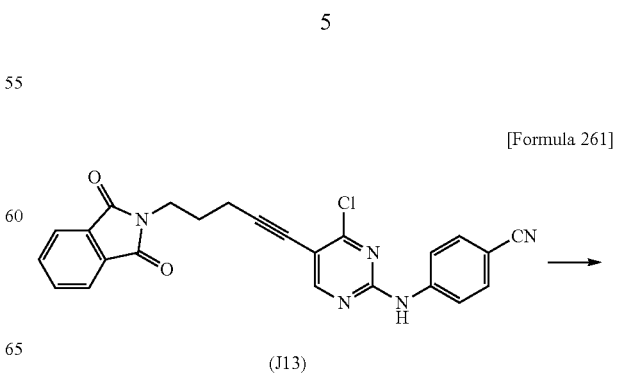

-continued

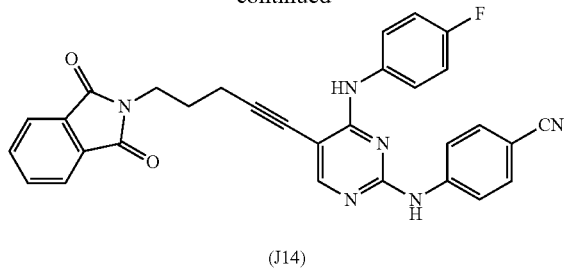

(J14)

To a solution of 4-((4-chloro-5-(5-(1,3-dioxoisoindolin-2-yl)-1-pentyn-1-yl)pyrimidin-2-yl)amino)benzonitrile (J13, 41 mg) in 1,4-dioxane (1.5 mL), 4-fluoroaniline (79 μL) and triethylamine (115 μL) were added at room temperature, and the mixture was stirred at 95° C. for 2 hours in a sealed tube. The reaction mixture was cooled to room temperature, and then ethyl acetate and water were added to the reaction mixture. The organic layer was separated, washed successively with 1.0 mol/L aqueous hydrochloric acid, saturated aqueous sodium hydrogencarbonate and saturated aqueous sodium chloride, and then dried over anhydrous sodium sulfate, and the solvent was evaporated under reduced pressure. The obtained solid matter was washed with a mixed solvent of chloroform and methanol, and then dried under reduced pressure to obtain 4-((5-(5-(1,3-dioxoisoindolin-2-yl)-1-pentyn-1-yl)-4-((4-fluorophenyl)amino)pyrimidin-2-yl)amino)benzonitrile (J14, 32 mg) as pale green solid.

MS m/z (M+H): 517.3

6

[Formula 262]

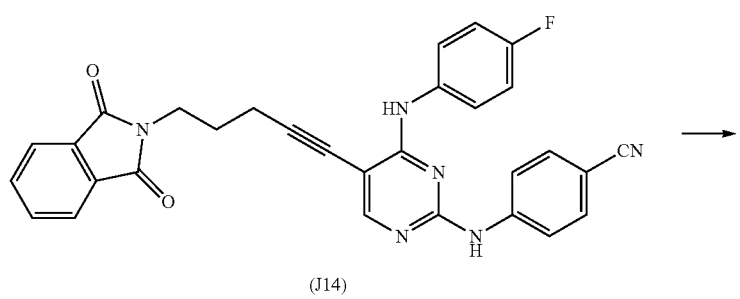

(J14)

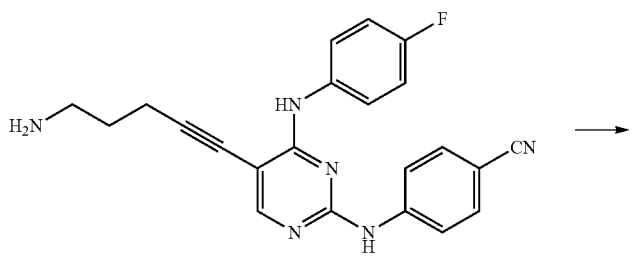

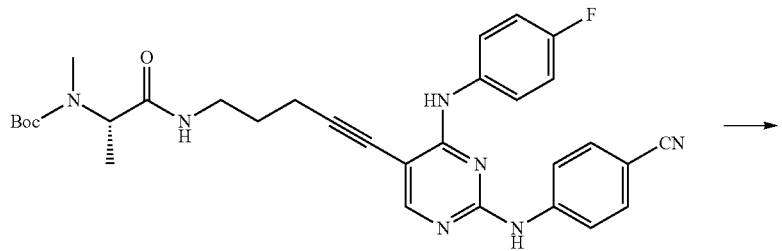

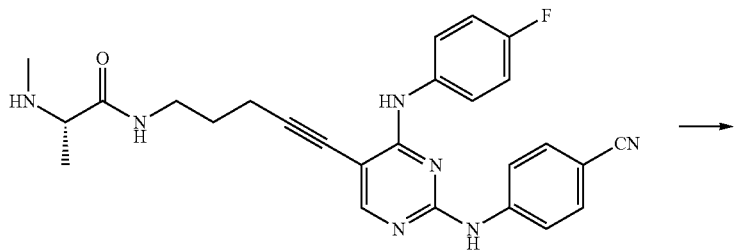

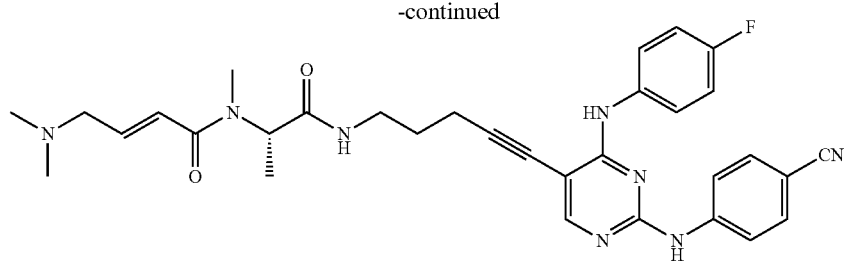

(10-2)

In the same manner as that of Example 44, (7) to (10), (S,E)-N-(1--((5-(2-((4-cyanophenyl)amino)-4-((4-fluorophenyl)amino)pyrimidin-5-yl)-4-pentyn-1-yl)amino)-1-oxopropan-2-yl)-4-(dimethylamino)-N-methyl-2-butenamide (10-2) was obtained from 4-((5-(5-(1,3-dioxoisoindolin-2-yl)-1-pentyn-1-yl)-4-((4-fluorophenyl)amino)pyrimidin-2-yl)amino)benzonitrile (J14).

$^1$H-NMR (CDCl$_3$) δ: 8.26 (1H, s), 8.15 (1H, s), 7.64 (2H, d, J=8.6 Hz), 7.59 (2H, dd, J=8.6, 4.6 Hz), 7.49 (2H, d, J=8.6 Hz), 7.45 (1H, brs), 7.07 (2H, t, J=8.6 Hz), 6.93 (1H, dt, J=15.0, 6.1 Hz), 6.67-6.57 (1H, m), 6.41 (1H, dt, J=15.0, 1.3 Hz), 5.17 (1H, q, J=7.0 Hz), 3.54-3.49 (2H, m), 3.10 (2H, dd, J=5.9, 1.3 Hz), 2.95 (3H, s), 2.54-2.43 (2H, m), 2.27 (6H, s), 1.81-1.68 (2H, m), 1.32 (3H, d, J=7.0 Hz)

7

[Formula 263]

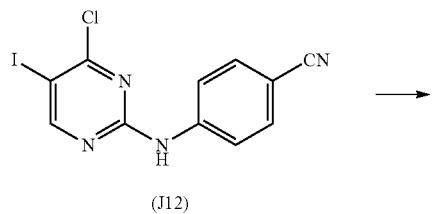

(J12)

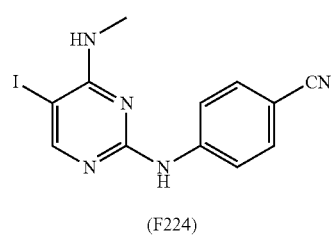

(F224)

To a solution of 4-((4-chloro-5-iodopyrimidin-2-yl)amino)benzonitrile (J12, 25 mg) in tetrahydrofuran (1 mL), N,N-diisopropylethylamine (37 μL) and a 2.0 mol/L solution of methylamine in tetrahydrofuran (105 μL) were added at room temperature, and the mixture was stirred at room temperature for 19 hours. To the reaction mixture, water (5 mL) was added. The solid matter was taken by filtration, washed with water, and then dried under reduced pressure to obtain 4-((5-iodo-4-(methylamino)pyrimidin-2-yl)amino)benzonitrile (F224, 27 mg).

8

[Formula 264]

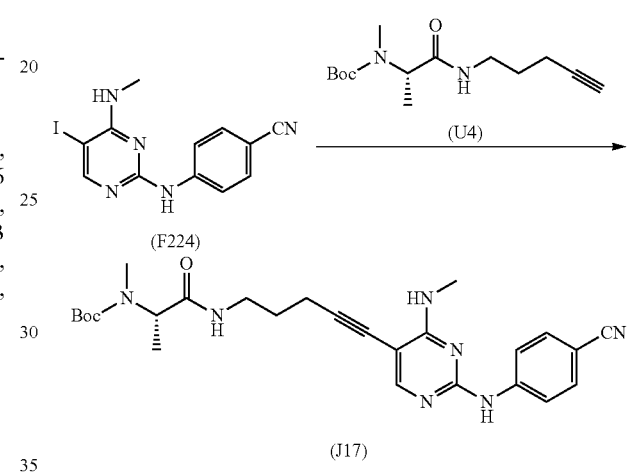

By using 4-((5-iodo-4-(methylamino)pyrimidin-2-yl)amino)benzonitrile (F224) and (S)-tert-butyl methyl(1-oxo-1-(4-pentyn-1-ylamino)propan-2-yl)carbamate (U4), (S)-tert-butyl (1-((5-(2-((4-cyanophenyl)amino)-4-(methylamino)pyrimidin-5-yl)-4-pentyn-1-yl)amino)-1-oxopropan-2-yl)(methyl)carbamate (J17) was obtained in the same manner as that of Example 38, (2).

MS m/z (M+H): 492.4

9

By using Intermediates (J12), Intermediates (J18) to (J23) were obtained in the same manner as that of Example 45, (7).

TABLE 152

| Compound No. | Structure | Physicochemical data |
|---|---|---|
| J18 | 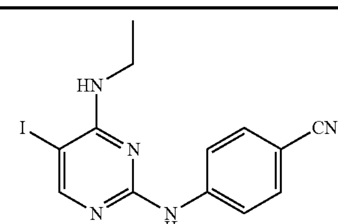 | MS m/z (M + H): 366.1 |

TABLE 152-continued
| Compound No. | Structure | Physicochemical data |
|---|---|---|
| J19 | 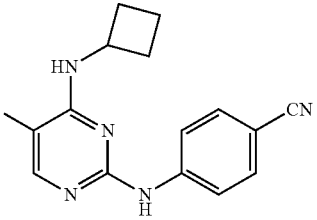 | MS m/z (M + H): 392.1 |
| J20 | 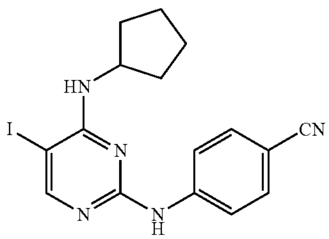 [SMILES: N#Cc1ccc(Nc2ncc(I)c(NC3CCCC3)n2)cc1] | MS m/z (M + H): 406.1 |
| J21 | 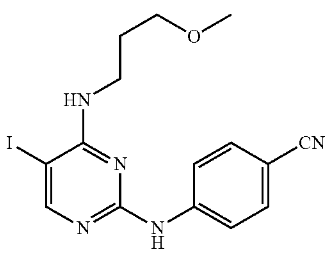 [SMILES: COCCCNc1nc(Nc2ccc(C#N)cc2)ncc1I] | MS m/z (M + H): 410.1 |
| J22 | 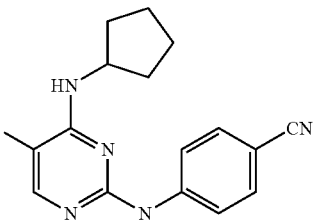 | MS m/z (M + H): 396.1 |
| J23 | 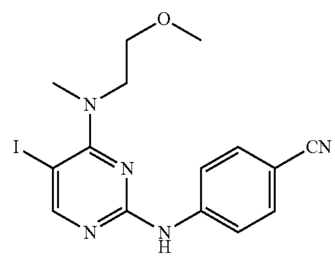 [SMILES: COCCN(C)c1nc(Nc2ccc(C#N)cc2)ncc1I] | MS m/z (M + H): 410.1 |
By using Intermediates (J18) to (J23), Intermediates (J24) to (J29) were obtained in the same manner as that of Example 45, (8).
TABLE 153
| Compound No. | Structure | Physicochemical data |
|---|---|---|
| J24 | 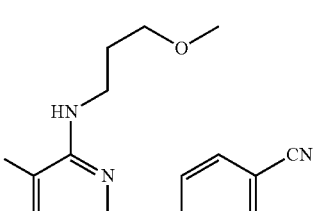 | MS m/z (M + H): 506.4 |
| J25 | 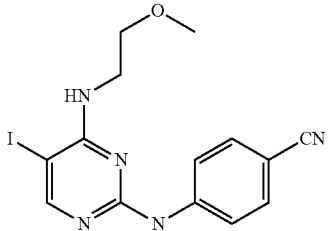 | MS m/z (M + H): 532.4 |
| J26 | 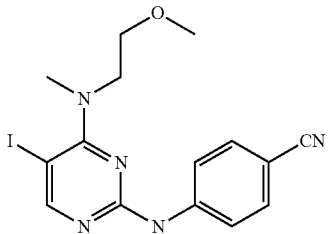 | MS m/z (M + H): 546.4 |

TABLE 153-continued

| Compound No. | Structure | Physicochemical data |
|---|---|---|
| J27 | 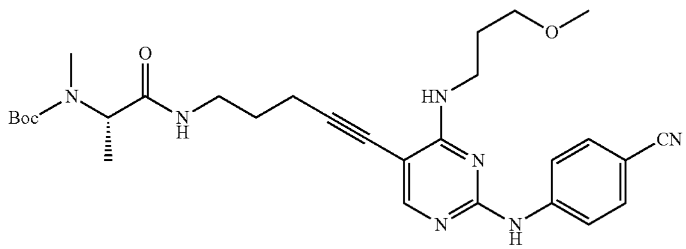 [SMILES: COCCCNc1nc(Nc2ccc(C#N)cc2)ncc1C#CCCCNC(=O)[C@H](C)N(C)C(=O)OC(C)(C)C] | MS m/z (M + H): 550.4 |
| J28 | 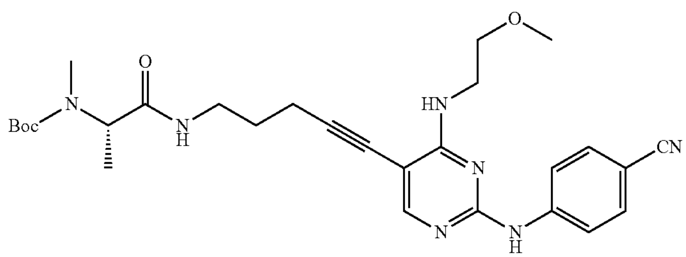 [SMILES: COCCNc1nc(Nc2ccc(C#N)cc2)ncc1C#CCCCNC(=O)[C@H](C)N(C)C(=O)OC(C)(C)C] | MS m/z (M + H): 536.4 |
| J29 | 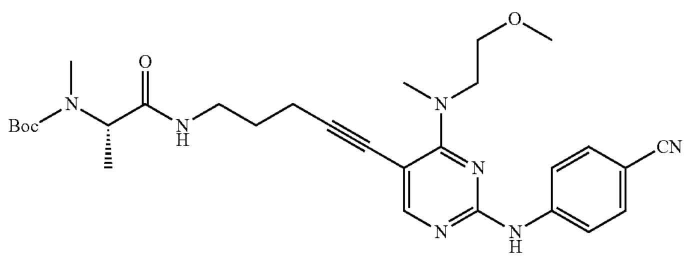 [SMILES: COCCN(C)c1nc(Nc2ccc(C#N)cc2)ncc1C#CCCCNC(=O)[C@H](C)N(C)C(=O)OC(C)(C)C] | MS m/z (M + H): 550.4 |

By using 4-(benzyloxy)-2-chloro-5-iodopyrimidine (J1), Intermediates (J30) to (J33) were obtained in the same manner as that of Example 45, (1) to (3).

TABLE 154

| Compound No. | Structure | Physicochemical data |
|---|---|---|
| J30 | 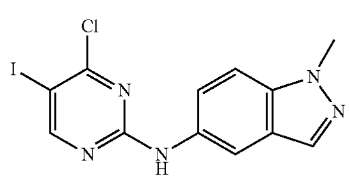 [SMILES: Cn1ncc2cc(Nc3ncc(I)c(Cl)n3)ccc21] | MS m/z (M + H): 385.9 |
| J31 | 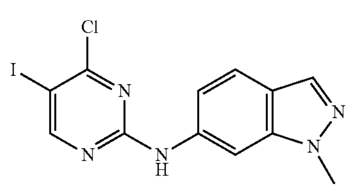 [SMILES: Cn1ncc2ccc(Nc3ncc(I)c(Cl)n3)cc21] | MS m/z (M + H): 385.9 |

TABLE 154-continued

| Compound No. | Structure | Physicochemical data |
|---|---|---|
| J32 | 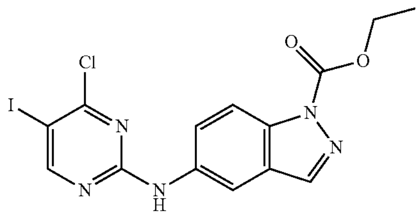 [SMILES: CCOC(=O)n1ncc2cc(Nc3ncc(I)c(Cl)n3)ccc21] | MS m/z (M + H): 444.0 |
| J33 | 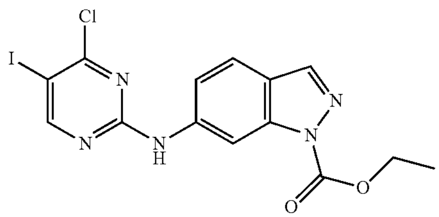 [SMILES: CCOC(=O)n1ncc2ccc(Nc3ncc(I)c(Cl)n3)cc21] | MS m/z (M + H): 444.0 |

By using Intermediates (J30) to (J33), Intermediates (J34) to (J39) were obtained in the same manner as that of Example 45, (8).

TABLE 155

| Compound No. | Structure | Physicochemical data |
|---|---|---|
| J34 | 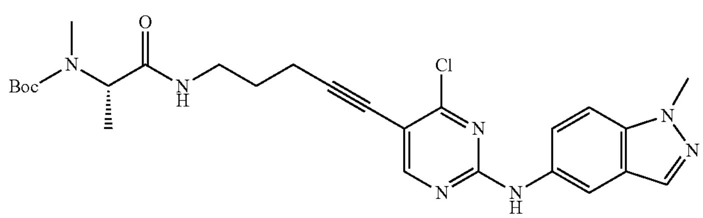 [SMILES: C[C@@H](C(=O)NCCCC#Cc1cnc(Nc2ccc3c(cnn3C)c2)nc1Cl)N(C)C(=O)OC(C)(C)C] | MS m/z (M + H): 526.3 |
| J35 | 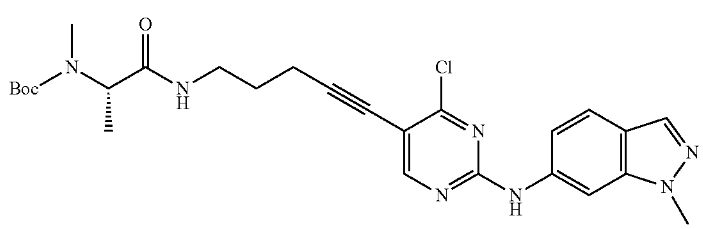 [SMILES: C[C@@H](C(=O)NCCCC#Cc1cnc(Nc2ccc3cnn(C)c3c2)nc1Cl)N(C)C(=O)OC(C)(C)C] | MS m/z (M + H): 526.3 |
| J36 | 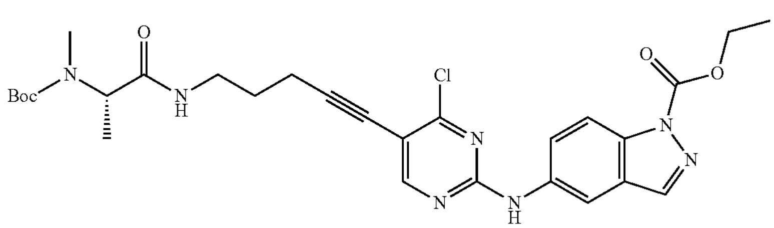 [SMILES: CCOC(=O)n1ncc2cc(Nc3ncc(C#CCCCNC(=O)[C@H](C)N(C)C(=O)OC(C)(C)C)c(Cl)n3)ccc21] | MS m/z (M + H): 584.4 |

TABLE 155-continued

| Compound No. | Structure | Physicochemical data |
| --- | --- | --- |
| J37 | 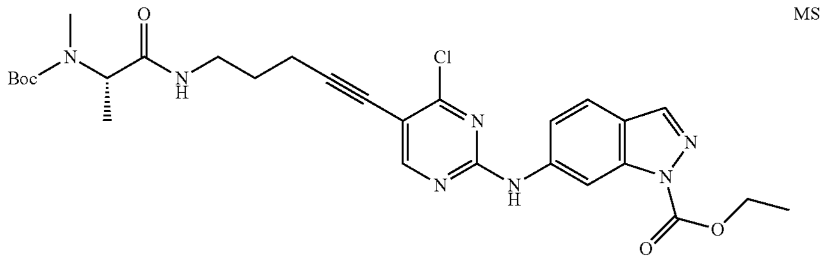 | MS m/z (M + H): 584.4 |
| J38 | 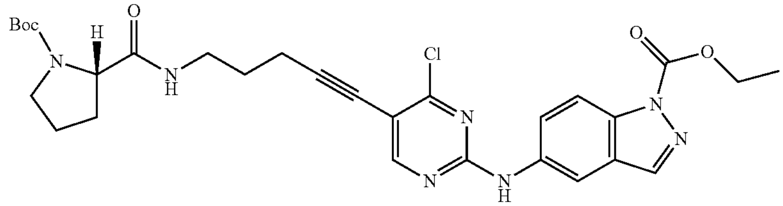 [SMILES: CCOC(=O)n1ncc2cc(Nc3ncc(C#CCCCNC(=O)[C@@H]4CCCN4C(=O)OC(C)(C)C)c(Cl)n3)ccc21] | MS m/z (M + H): 596.4 |
| J39 | 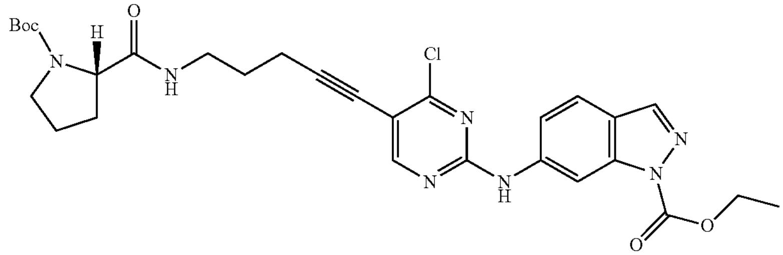 [SMILES: CCOC(=O)n1ncc2ccc(Nc3ncc(C#CCCCNC(=O)[C@@H]4CCCN4C(=O)OC(C)(C)C)c(Cl)n3)cc21] | MS m/z (M + H): 596.4 |

13

By using Intermediates (J34) to (J39), Intermediates (J40) to (J63) were obtained in the same manner as that of Example 45, (7).

TABLE 156

| Compound No. | Structure | Physicochemical data |
| --- | --- | --- |
| J40 | 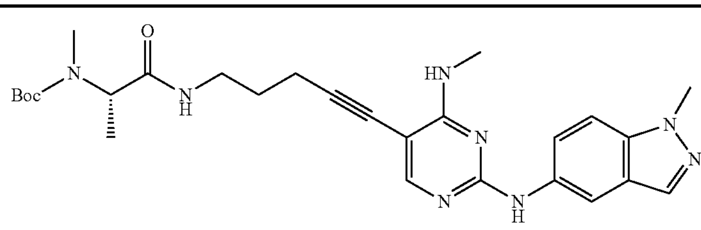 | MS m/z (M + H): 521.4 |
| J41 | 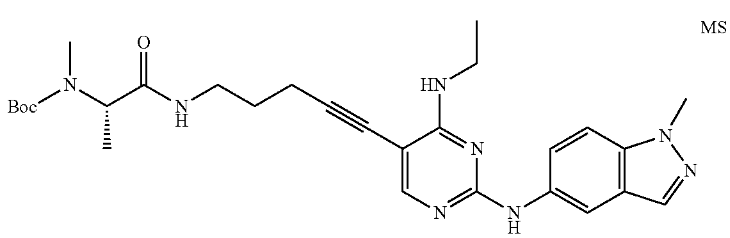 | MS m/z (M + H): 535.5 |

TABLE 156-continued
| Compound No. | Structure | Physicochemical data |
|---|---|---|
| J42 | 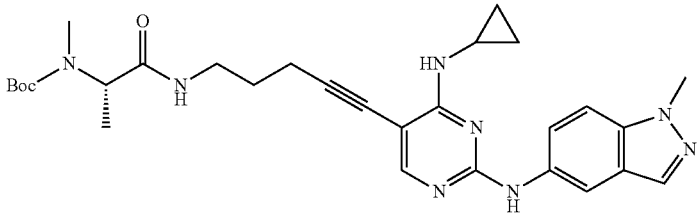 [SMILES: C[C@@H](C(=O)NCCCC#Cc1cnc(Nc2ccc3c(cnn3C)c2)nc1NC1CC1)N(C)C(=O)OC(C)(C)C] | MS m/z (M + H): 547.5 |
| J43 | 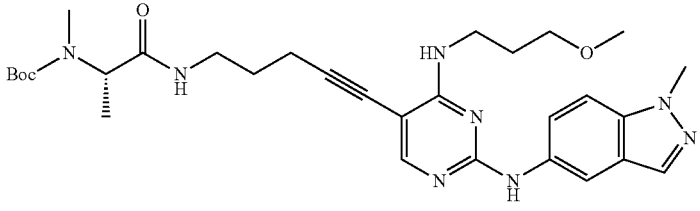 [SMILES: COCCCNc1nc(Nc2ccc3c(cnn3C)c2)ncc1C#CCCCNC(=O)[C@H](C)N(C)C(=O)OC(C)(C)C] | MS m/z (M + H): 579.5 |
| J44 | 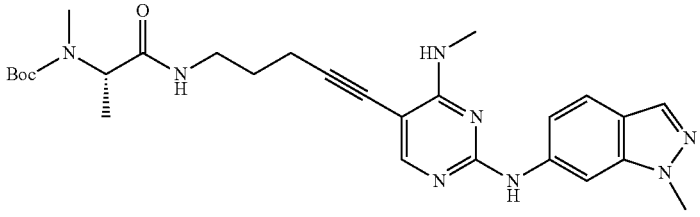 [SMILES: CNc1nc(Nc2ccc3cnn(C)c3c2)ncc1C#CCCCNC(=O)[C@H](C)N(C)C(=O)OC(C)(C)C] | MS m/z (M + H): 521.5 |
| J45 | 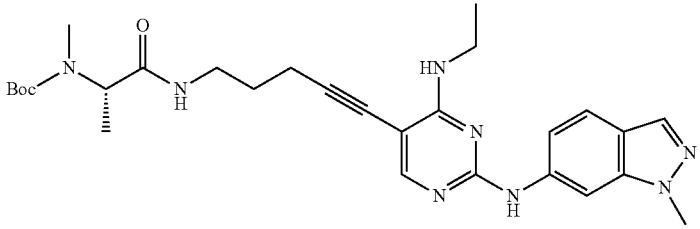 [SMILES: CCNc1nc(Nc2ccc3cnn(C)c3c2)ncc1C#CCCCNC(=O)[C@H](C)N(C)C(=O)OC(C)(C)C] | MS m/z (M + H): 535.5 |
| J46 | 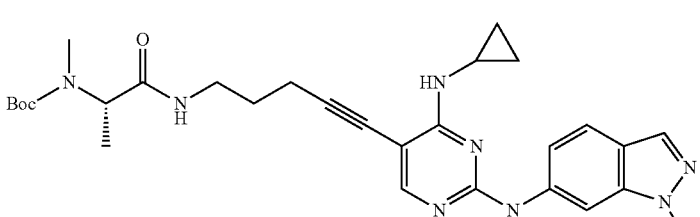 | MS m/z (M + H): 547.5 |
| J47 | 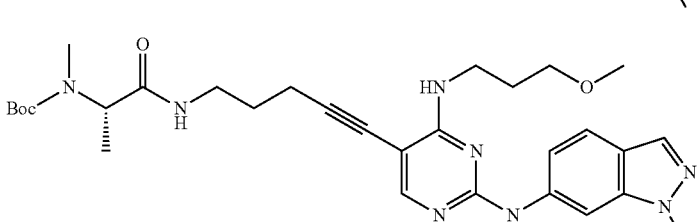 | MS m/z (M + H): 579.5 |
| J48 | 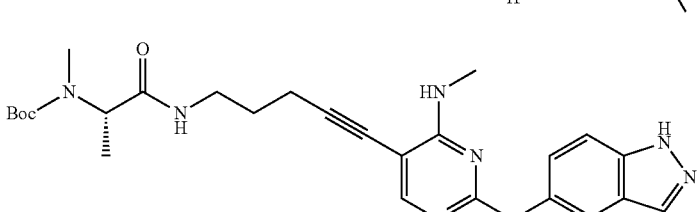 | MS m/z (M + H): 507.4 |

TABLE 156-continued
| Compound No. | Structure | Physicochemical data |
|---|---|---|
| J49 | 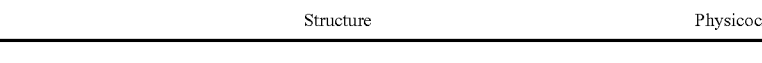 | MS m/z (M + H): 521.5 |
TABLE 157
| Compound No. | Structure | Physicochemical data |
|---|---|---|
| J50 | 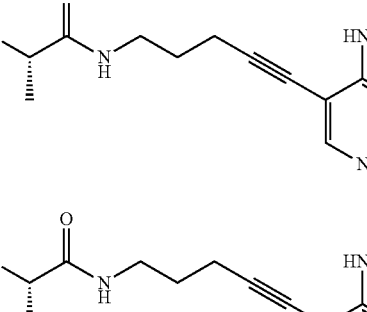 | MS m/z (M + H): 565.5 |
| J51 | 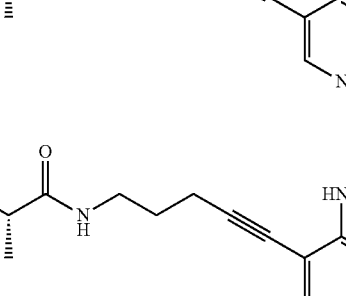 | MS m/z (M + H): 507.4 |
| J52 | 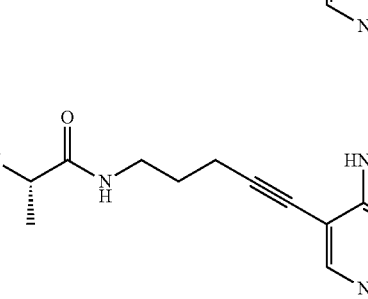 | MS m/z (M + H): 521.5 |
| J53 | 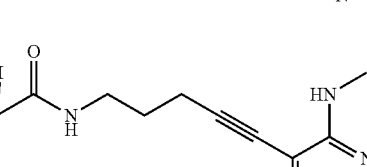 | MS m/z (M + H): 565.5 |
| J54 | 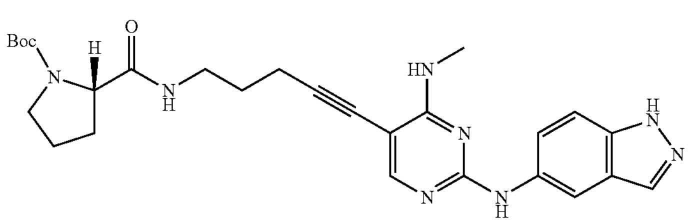 [SMILES: CNc1nc(Nc2ccc3[nH]ncc3c2)ncc1C#CCCCNC(=O)[C@@H]1CCCN1C(=O)OC(C)(C)C] | MS m/z (M + H): 519.5 |

TABLE 157-continued
| Compound No. | Structure | Physicochemical data |
|---|---|---|
| J55 | 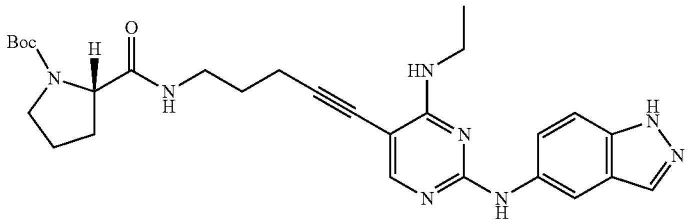 [SMILES: CCNc1nc(Nc2ccc3[nH]ncc3c2)ncc1C#CCCCNC(=O)[C@@H]1CCCN1C(=O)OC(C)(C)C] | MS m/z (M + H): 533.5 |
| J56 | 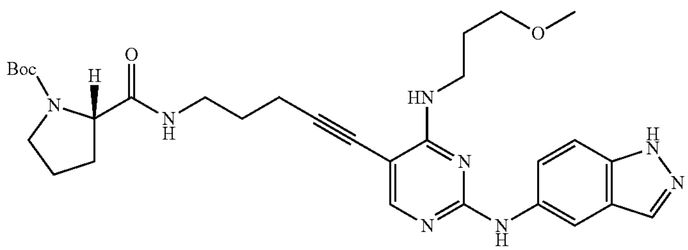 [SMILES: COCCCNc1nc(Nc2ccc3[nH]ncc3c2)ncc1C#CCCCNC(=O)[C@@H]1CCCN1C(=O)OC(C)(C)C] | MS m/z (M + H): 577.5 |
| J57 | 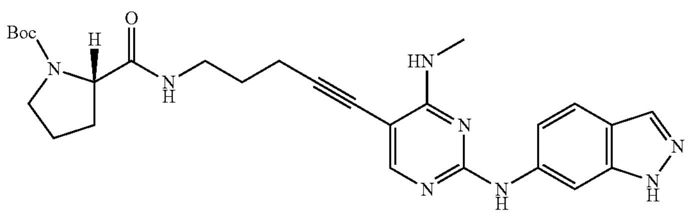 [SMILES: CNc1nc(Nc2ccc3cn[nH]c3c2)ncc1C#CCCCNC(=O)[C@@H]1CCCN1C(=O)OC(C)(C)C] | MS m/z (M + H): 519.3 |
| J58 | 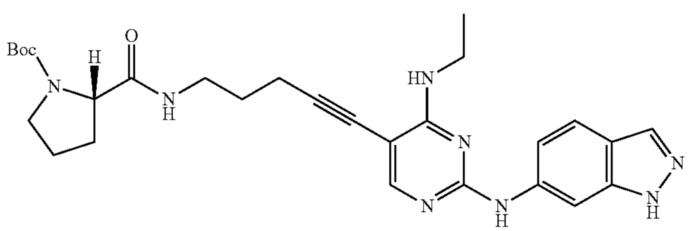 [SMILES: CCNc1nc(Nc2ccc3cn[nH]c3c2)ncc1C#CCCCNC(=O)[C@@H]1CCCN1C(=O)OC(C)(C)C] | MS m/z (M + H): 533.3 |
| J59 | 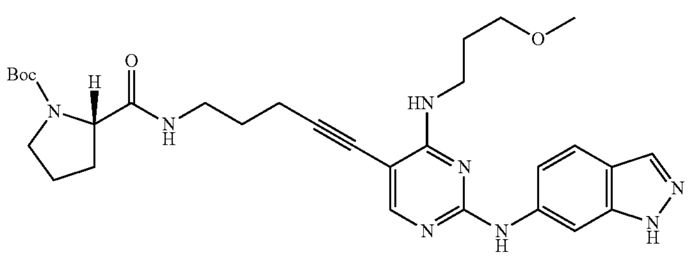 [SMILES: COCCCNc1nc(Nc2ccc3cn[nH]c3c2)ncc1C#CCCCNC(=O)[C@@H]1CCCN1C(=O)OC(C)(C)C] | MS m/z (M + H): 577.3 |
TABLE 158
| Compound No. | Structure | Physicochemical data |
|---|---|---|
| J60 | 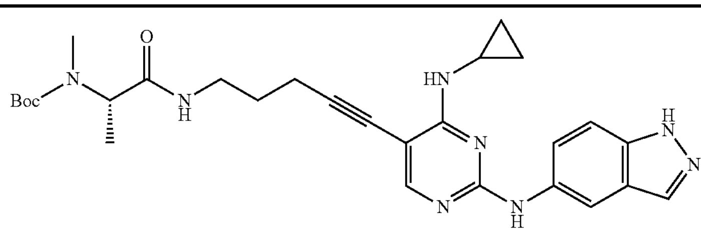 | — |

TABLE 158-continued

| Compound No. | Structure | Physicochemical data |
|---|---|---|
| J61 | 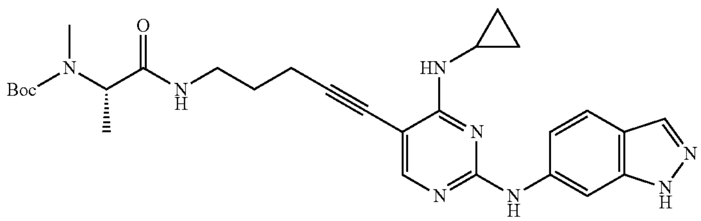 [SMILES: C[C@@H](C(=O)NCCCC#Cc1cnc(Nc2ccc3cn[nH]c3c2)nc1NC1CC1)N(C)C(=O)OC(C)(C)C] | — |
| J62 | 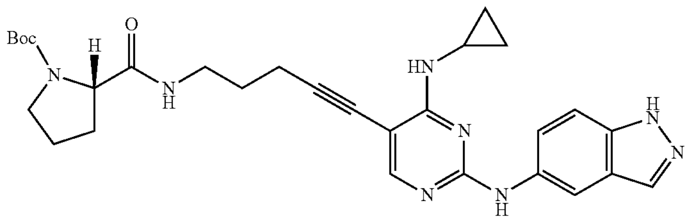 [SMILES: CC(C)(C)OC(=O)N1CCC[C@H]1C(=O)NCCCC#Cc1cnc(Nc2ccc3[nH]ncc3c2)nc1NC1CC1] | — |
| J63 | 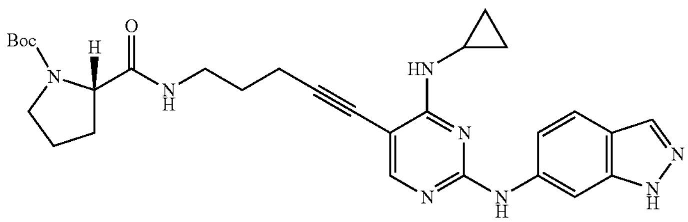 [SMILES: CC(C)(C)OC(=O)N1CCC[C@H]1C(=O)NCCCC#Cc1cnc(Nc2ccc3cn[nH]c3c2)nc1NC1CC1] | — |

Example 46

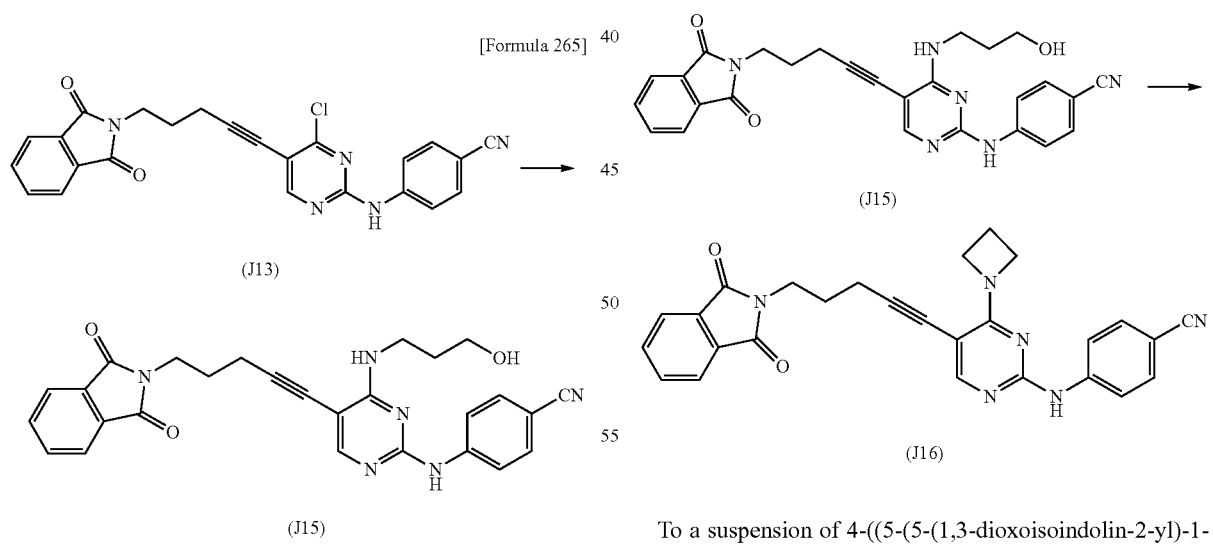

(J13)

(J15)

(J15)

(J16)

By using 4-((4-chloro-5-(5-(1,3-dioxoisoindolin-2-yl)-1-pentyn-1-yl)pyrimidin-2-yl)amino)benzonitrile (J13), 4-((5-(5-(1,3-dioxoisoindolin-2-yl)-1-pentyn-1-yl)-4-((3-hydroxypropyl)amino)pyrimidin-2-yl)amino)benzonitrile (J15) was obtained in the same manner as that of Example 45, (5).

MS m/z (M+H): 481.3

To a suspension of 4-((5-(5-(1,3-dioxoisoindolin-2-yl)-1-pentyn-1-yl)-4-((3-hydroxypropyl)amino)pyrimidin-2-yl)amino)benzonitrile (J15, 51 mg) in methylene chloride (1 mL), bis(2-methoxyethyl)aminosulfur trifluoride (188 μL) was added under ice cooling, and the mixture was stirred at the same temperature for 1 hour. To the reaction mixture, water and ethyl acetate were added. The solid matter was taken by filtration, washed successively with water and ethyl acetate, and then dried under reduced pressure to obtain 4-((4-

(azetidin-1-yl)-5-(5-(1,3-dioxoisoindolin-2-yl)-1-pentyn-1-yl)pyrimidin-2-yl)amino)benzonitrile (J16, 48 mg) as pale yellow solid.

MS m/z (M+H): 463.3

Example 47

In the same manner as that of Example 44 and Example 45, Compounds (10-3) to (10-75) were obtained.

TABLE 159

| Compound No. | Structure | Physicochemical data |
|---|---|---|
| 10-3 | 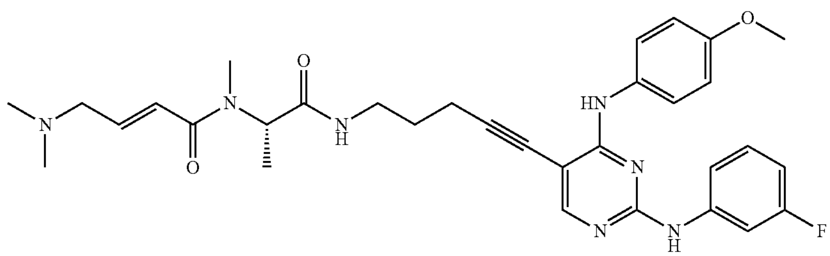 [SMILES: COc1ccc(Nc2nc(Nc3cccc(F)c3)ncc2C#CCCCNC(=O)[C@H](C)N(C)C(=O)/C=C/CN(C)C)cc1] | $^1$H-NMR (CDCl$_3$) δ: 8.11 (1H, s), 7.90 (1H, s), 7.65 (1H, dt, J = 11.9, 2.3 Hz), 7.54-7.50 (2H, m), 7.21-7.11 (1H, m), 7.08 (1H, s), 7.04-6.87 (4H, m), 6.65 (1H, dt, J = 8.3, 2.3 Hz), 6.60-6.52 (1H, m), 6.41 (1H, d, J = 15.2 Hz), 5.17 (1H, q, J = 7.3 Hz), 3.84 (3H, s), 3.47 (2H, q, J = 6.4 Hz), 3.09 (2H, d, J = 5.3 Hz), 2.95 (3H, s), 2.48 (2H, t, J = 6.6 Hz), 2.26 (6H, s), 1.81-1.73 (2H, m), 1.33 (3H, d, J = 7.3 Hz) |
| 10-4 | 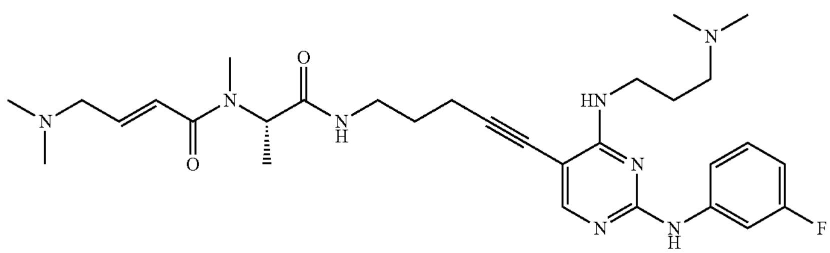 [SMILES: C[C@@H](C(=O)NCCCC#Cc1cnc(Nc2cccc(F)c2)nc1NCCCN(C)C)N(C)C(=O)/C=C/CN(C)C] | $^1$H-NMR (CDCl$_3$) δ: 7.96 (1H, s), 7.81 (1H, dt, J = 11.9, 2.0 Hz), 7.26-7.15 (2H, m), 7.12-7.05 (1H, m), 7.00-6.80 (2H, m), 6.73-6.55 (2H, m), 6.42 (1H, d, J = 15.2 Hz), 5.19 (1H, q, J = 7.0 Hz), 3.67-3.54 (2H, m), 3.51-3.35 (2H, m), 3.10 (2H, d, J = 5.3 Hz), 2.99 (3H, s), 2.46-2.39 (4H, m), 2.27 (6H, s), 2.25 (6H, s), 1.91-1.70 (4H, m), 1.36 (3H, d, J = 6.6 Hz) |
| 10-5 | 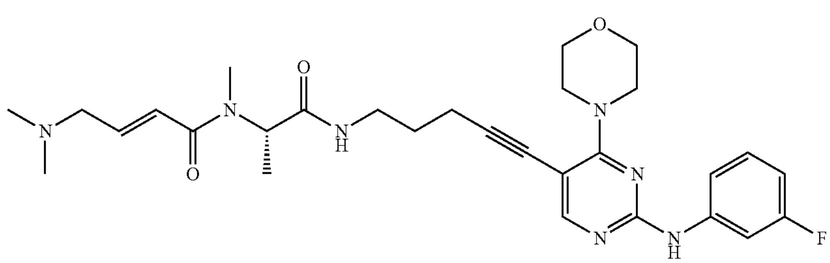 [SMILES: C[C@@H](C(=O)NCCCC#Cc1cnc(Nc2cccc(F)c2)nc1N1CCOCC1)N(C)C(=O)/C=C/CN(C)C] | $^1$H-NMR (CDCl$_3$) δ: 8.11 (1H, s), 7.61 (1H, dt, J = 11.7, 2.1 Hz), 7.27-7.18 (2H, m), 7.13-7.04 (1H, m), 6.93 (1H, dt, J = 15.2, 5.9 Hz), 6.70 (1H, dt, J = 8.1, 2.1 Hz), 6.65-6.54 (1H, m), 6.47-6.35 (1H, m), 5.16 (1H, q, J = 7.0 Hz), 4.00-3.90 (4H, m), 3.85-3.75 (4H, m), 3.43-3.23 (2H, m), 3.10 (2H, dd, J = 5.9, 1.3 Hz), 2.99 (3H, s), 2.43 (2H, t, J = 7.3 Hz), 2.27 (6H, s), 1.80-1.71 (2H, m), 1.35 (3H, d, J = 7.0 Hz) |
| 10-6 | 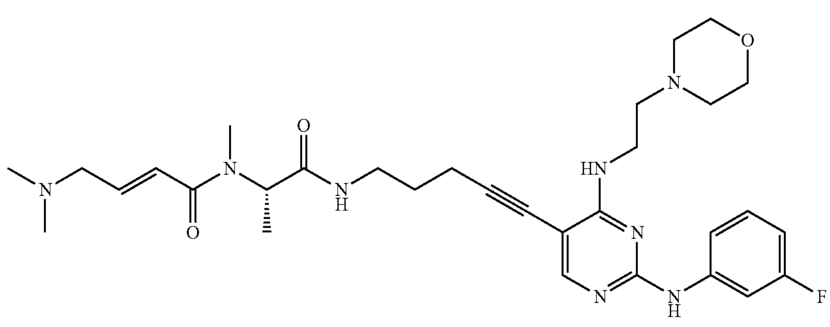 [SMILES: C[C@@H](C(=O)NCCCC#Cc1cnc(Nc2cccc(F)c2)nc1NCCN1CCOCC1)N(C)C(=O)/C=C/CN(C)C] | $^1$H-NMR (CDCl$_3$) δ: 7.97 (1H, s), 7.78 (1H, dt, J = 11.9, 2.0 Hz), 7.28 (1H, s), 7.25-7.15 (1H, m), 7.09 (1H, dd, J = 7.6, 2.0 Hz), 6.93 (1H, dt, J = 15.2, 5.9 Hz), 6.73-6.57 (2H, m), 6.49-6.35 (2H, m), 5.18 (1H, q, J = 7.0 Hz), 3.75-3.68 (4H, m), 3.64 (2H, q, J = 5.9 Hz), 3.42 (2H, q, J = 6.6 Hz), 3.13-3.07 (2H, m), 2.99 (3H, s), 2.67 (2H, t, J = 6.6 Hz), 2.59-2.49 (4H, m), 2.46 (2H, t, J = 6.9 Hz), 2.26 (6H, s), 1.82-1.73 (2H, m), 1.35 (3H, d, J = 7.0 Hz) |

TABLE 159-continued

| Compound No. | Structure | Physicochemical data |
|---|---|---|
| 10-7 | 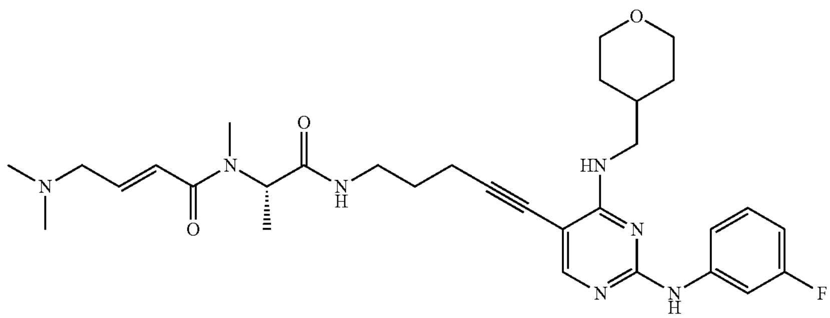 [SMILES: C[C@@H](C(=O)NCCCC#Cc1cnc(Nc2cccc(F)c2)nc1NCC1CCOCC1)N(C)C(=O)/C=C/CN(C)C] | $^1$H-NMR (CDCl$_3$) δ: 7.97 (1H, s), 7.87 (1H, dt, J = 11.9, 2.0 Hz), 7.24 (1H, s), 7.20 (1H, dt, J = 8.3, 6.6 Hz), 7.04 (1H, dd, J = 8.3, 2.0 Hz), 6.94 (1H, dt, J = 15.2, 5.9 Hz), 6.68 (1H, dt, J = 8.3, 2.0 Hz), 6.62-6.51 (2H, m), 6.48-6.37 (1H, m), 5.19 (1H, q, J = 7.0 Hz), 3.99 (2H, dd, J = 11.6, 3.6 Hz), 3.52-3.32 (6H, m), 3.11 (2H, dd, J = 5.9, 1.3 Hz), 3.00 (3H, s), 2.43 (2H, t, J = 6.3 Hz), 2.27 (6H, s), 2.13-2.02 (1H, m), 1.80-1.66 (4H, m), 1.49-1.30 (5H, m) |

TABLE 160

| Compound No. | Structure | Physicochemical data |
|---|---|---|
| 10-8 | 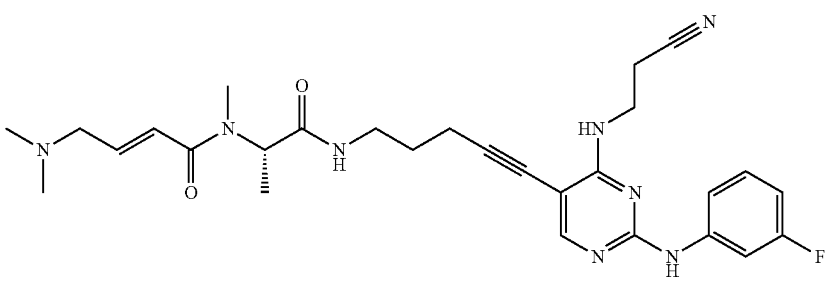 [SMILES: C[C@@H](C(=O)NCCCC#Cc1cnc(Nc2cccc(F)c2)nc1NCCC#N)N(C)C(=O)/C=C/CN(C)C] | $^1$H-NMR (CDCl$_3$) δ: 8.01 (1H, s), 7.65 (1H, dt, J = 11.9, 2.3 Hz), 7.24 (1H, dt, J = 8.6, 6.2 Hz), 7.18-7.08 (3H, m), 6.94 (1H, dt, J = 15.2, 5.9 Hz), 6.70 (1H, dt, J = 8.6, 2.3 Hz), 6.63-6.56 (1H, m), 6.48-6.37 (1H, m), 5.21 (1H, q, J = 7.0 Hz), 3.93-3.81 (2H, m), 3.60-3.43 (2H, m), 3.11 (2H, dd, J = 5.9, 1.3 Hz), 3.01 (3H, s), 2.82 (2H, q, J = 6.4 Hz), 2.46-2.39 (2H, m), 2.27 (6H, s), 1.80-1.65 (2H, m), 1.38 (3H, d, J = 7.0 Hz) |
| 10-9 | 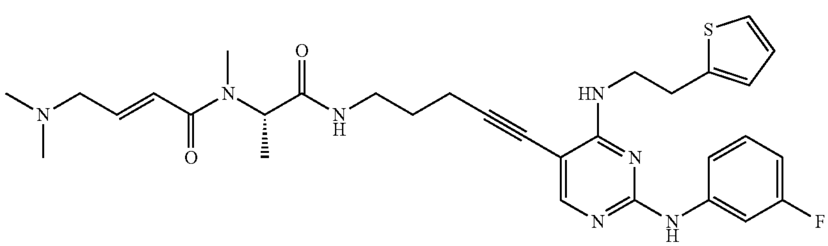 [SMILES: C[C@@H](C(=O)NCCCC#Cc1cnc(Nc2cccc(F)c2)nc1NCCc1cccs1)N(C)C(=O)/C=C/CN(C)C] | $^1$H-NMR (CDCl$_3$) δ: 7.98 (1H, s), 7.75-7.66 (1H, m), 7.23-7.16 (4H, m), 7.00-6.86 (3H, m), 6.72-6.65 (1H, m), 6.58-6.48 (2H, m), 6.42 (1H, dt, J = 15.0, 1.7 Hz), 5.18 (1H, q, J = 7.0 Hz), 3.90-3.77 (2H, m), 3.49-3.35 (2H, m), 3.23 (2H, t, J = 7.3 Hz), 3.11-3.07 (2H, m), 2.99 (3H, s), 2.41 (2H, t, J = 6.6 Hz), 2.27 (6H, s), 1.75-1.67 (2H, m), 1.36 (3H, d, J = 7.0 Hz) |
| 10-10 | 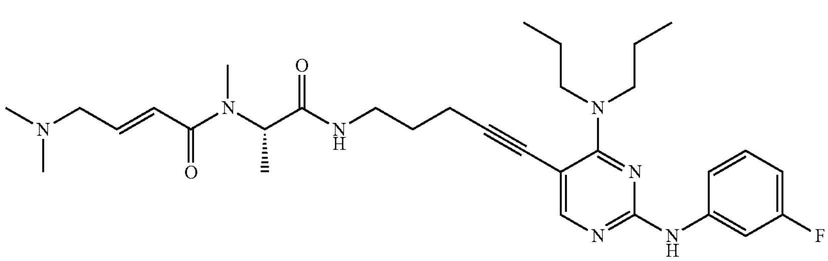 [SMILES: CCCN(CCC)c1nc(Nc2cccc(F)c2)ncc1C#CCCCNC(=O)[C@H](C)N(C)C(=O)/C=C/CN(C)C] | $^1$H-NMR (CDCl$_3$) δ: 8.02 (1H, s), 7.67 (1H, dt, J = 11.7, 2.1 Hz), 7.25-7.13 (2H, m), 7.05 (1H, dd, J = 7.9, 2.1 Hz), 6.94 (1H, dt, J = 15.2, 5.9 Hz), 6.66 (1H, dt, J = 8.1, 2.1 Hz), 6.61-6.52 (1H, m), 6.46-6.37 (1H, m), 5.17 (1H, q, J = 7.0 Hz), 3.74-3.61 (4H, m), 3.45-3.25 (2H, m), 3.10 (2H, dd, J = 5.9, 1.3 Hz), 2.99 (3H, s), 2.42 (2H, t, J = 7.3 Hz), 2.27 (6H, s), 1.83-1.62 (6H, m), 1.35 (3H, d, J = 7.3 Hz), 0.94 (6H, t, J = 7.0 Hz) |

TABLE 160-continued

| Compound No. | Structure | Physicochemical data |
|---|---|---|
| 10-11 | 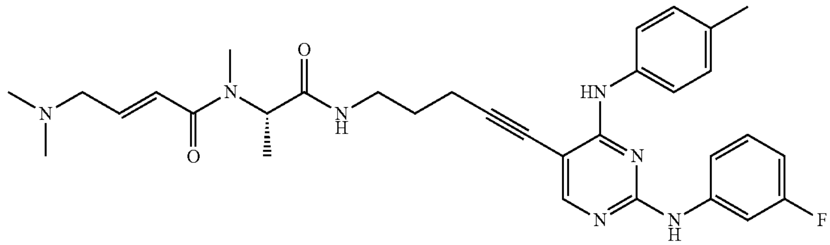 [SMILES: Cc1ccc(Nc2nc(Nc3cccc(F)c3)ncc2C#CCCCNC(=O)[C@H](C)N(C)C(=O)/C=C/CN(C)C)cc1] | ¹H-NMR (CDCl₃) δ: 8.12 (1H, s), 7.87 (1H, s), 7.64 (1H, dt, J = 11.9, 2.3 Hz), 7.52 (2H, d, J = 8.6 Hz), 7.27 (1H, s), 7.22-7.12 (3H, m), 7.06 (1H, dd, J = 7.6, 2.3 Hz), 6.93 (1H, dt, J = 15.2, 5.9 Hz), 6.73-6.56 (2H, m), 6.41 (1H, dt, J = 15.2, 1.7 Hz), 5.18 (1H, q, J = 7.3 Hz), 3.46 (2H, q, J = 6.4 Hz), 3.14-3.04 (2H, m), 2.97 (3H, s), 2.48 (2H, t, J = 6.6 Hz), 2.37 (3H, s), 2.26 (6H, s), 1.82-1.73 (2H, m), 1.34 (3H, d, J = 7.3 Hz) |

TABLE 161

| Compound No. | Structure | Physicochemical data |
|---|---|---|
| 10-12 | 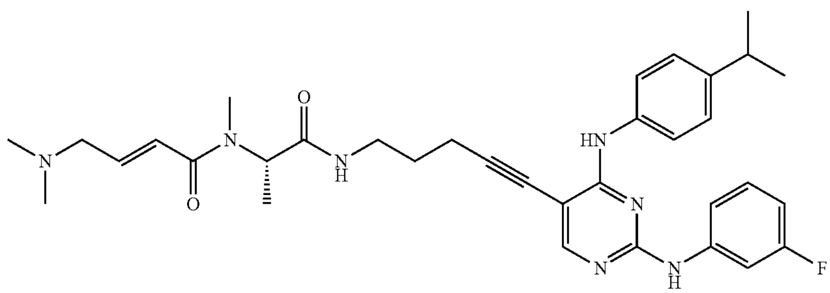 [SMILES: CC(C)c1ccc(Nc2nc(Nc3cccc(F)c3)ncc2C#CCCCNC(=O)[C@H](C)N(C)C(=O)/C=C/CN(C)C)cc1] | ¹H-NMR (CDCl₃) δ: 8.12 (1H, s), 7.88 (1H, s), 7.68 (1H, dt, J = 11.7, 2.3 Hz), 7.55 (2H, d, J = 8.6 Hz), 7.30-7.11 (4H, m), 7.04 (1H, dd, J = 7.9, 2.3 Hz), 6.93 (1H, dt, J = 15.2, 5.9 Hz), 6.66 (1H, dt, J = 8.1, 2.3 Hz), 6.62-6.52 (1H, m), 6.47-6.35 (1H, m), 5.18 (1H, q, J = 7.0 Hz), 3.46 (2H, q, J = 6.4 Hz), 3.10 (2H, dd, J = 5.9, 1.3 Hz), 2.99-2.88 (4H, m), 2.48 (2H, t, J = 6.6 Hz), 2.26 (6H, s), 1.82-1.73 (2H, m), 1.34 (3H, d, J = 7.0 Hz), 1.29 (3H, s), 1.27 (3H, s) |
| 10-13 | 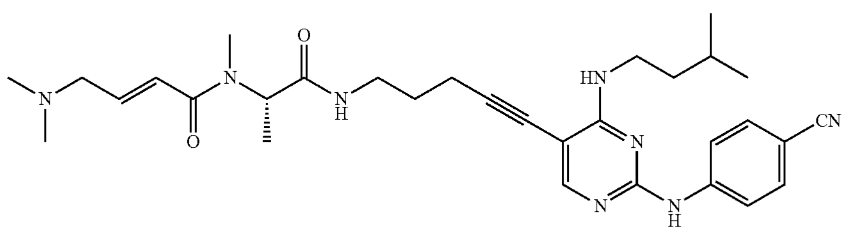 [SMILES: CC(C)CCNc1nc(Nc2ccc(C#N)cc2)ncc1C#CCCCNC(=O)[C@H](C)N(C)C(=O)/C=C/CN(C)C] | ¹H-NMR (CDCl₃) δ: 7.97 (1H, s), 7.77 (2H, d, J = 8.6 Hz), 7.56 (2H, d, J = 8.6 Hz), 7.30 (1H, s), 6.94 (1H, dt, J = 15.2, 5.9 Hz), 6.60-6.51 (1H, m), 6.47-6.31 (2H, m), 5.19 (1H, q, J = 7.0 Hz), 3.60-3.50 (2H, m), 3.45 (2H, q, J = 6.4 Hz), 3.11 (2H, dd, J = 5.9, 1.3 Hz), 3.00 (3H, s), 2.44 (2H, t, J = 6.3 Hz), 2.27 (6H, s), 1.82-1.56 (5H, m), 1.36 (3H, d, J = 7.3 Hz), 0.99 (6H, d, J = 7.0 Hz) |
| 10-14 | 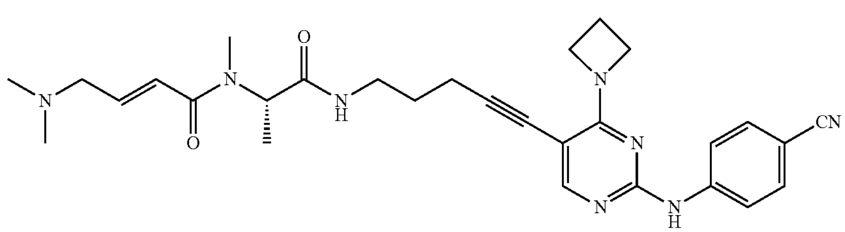 [SMILES: C[C@@H](C(=O)NCCCC#Cc1cnc(Nc2ccc(C#N)cc2)nc1N1CCC1)N(C)C(=O)/C=C/CN(C)C] | ¹H-NMR (CDCl₃) δ: 7.79 (1H, s), 7.58 (1H, s), 7.54-7.48 (2H, m), 7.17-7.11 (2H, m), 6.94 (1H, dt, J = 15.2, 5.9 Hz), 6.61-6.51 (1H, m), 6.49-6.36 (1H, m), 5.19 (1H, q, J = 7.0 Hz), 4.12-4.05 (2H, m), 3.63-3.37 (4H, m), 3.11 (2H, dd, J = 5.9, 1.3 Hz), 2.99 (3H, s), 2.50-2.34 (2H, m), 2.28 (6H, s), 2.21-2.12 (2H, m), 1.82-1.64 (2H, m), 1.36 (3H, d, J = 7.0 Hz) |

TABLE 161-continued

| Compound No. | Structure | Physicochemical data |
|---|---|---|
| 10-15 | 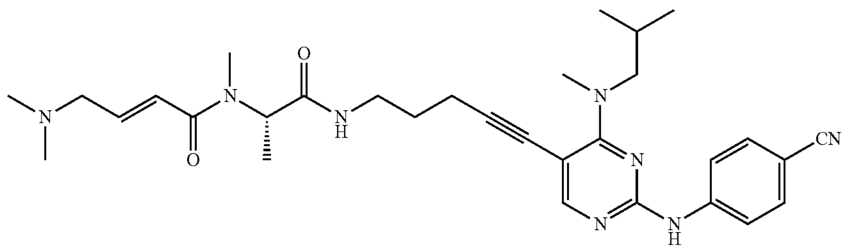 [SMILES: CC(C)CN(C)c1nc(Nc2ccc(C#N)cc2)ncc1C#CCCCNC(=O)[C@H](C)N(C)C(=O)/C=C/CN(C)C] | ¹H-NMR (CDCl₃) δ: 8.05 (1H, s), 7.72 (2H, d, J = 9.2 Hz), 7.60-7.46 (3H, m), 6.93 (1H, dt, J = 15.2, 5.9 Hz), 6.66-6.55 (1H, m), 6.42 (1H, d, J = 15.2 Hz), 5.17 (1H, q, J = 7.0 Hz), 3.70 (2H, d, J = 7.3 Hz), 3.47-3.24 (5H, m), 3.10 (2H, d, J = 5.9 Hz), 2.99 (3H, s), 2.50-2.35 (2H, m), 2.26 (6H, s), 2.20-2.07 (1H, m), 1.84-1.69 (2H, m), 1.35 (3H, d, J = 7.3 Hz), 0.93 (6H, d, J = 7.0 Hz) |
| 10-16 | 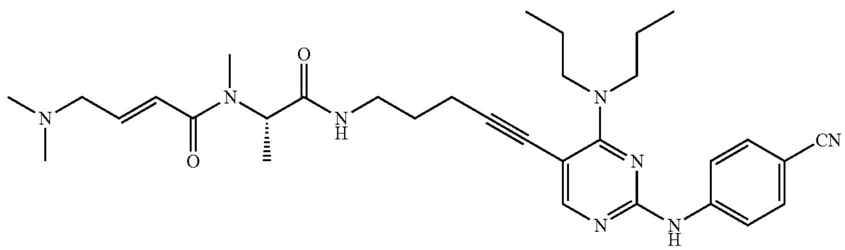 [SMILES: CCCN(CCC)c1nc(Nc2ccc(C#N)cc2)ncc1C#CCCCNC(=O)[C@H](C)N(C)C(=O)/C=C/CN(C)C] | ¹H-NMR (CDCl₃) δ: 8.04 (1H, s), 7.70 (2H, d, J = 8.6 Hz), 7.55 (2H, d, J = 8.6 Hz), 7.50 (1H, s), 6.94 (1H, dt, J = 15.0, 6.1 Hz), 6.66-6.57 (1H, m), 6.48-6.35 (1H, m), 5.17 (1H, q, J = 7.0 Hz), 3.72-3.61 (4H, m), 3.46-3.22 (2H, m), 3.10 (2H, dd, J = 6.1, 1.3 Hz), 2.99 (3H, s), 2.42 (2H, t, J = 7.3 Hz), 2.27 (6H, s), 1.82-1.60 (6H, m), 1.35 (3H, d, J = 7.0 Hz), 0.94 (6H, t, J = 7.6 Hz) |

TABLE 162

| Compound No. | Structure | Physicochemical data |
|---|---|---|
| 10-17 | 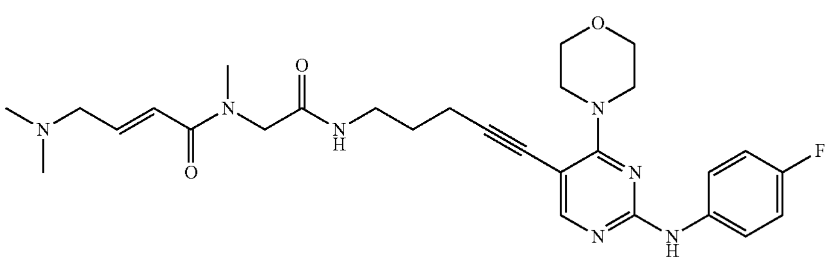 [SMILES: CN(C)C/C=C/C(=O)N(C)CC(=O)NCCCC#Cc1cnc(Nc2ccc(F)cc2)nc1N1CCOCC1] | ¹H-NMR (CDCl₃) δ: 8.09 (1H, s), 7.52-7.42 (2H, m), 7.12-6.88 (4H, m), 6.70-6.59 (1H, m), 6.46 (1H, d, J = 15.2 Hz), 4.02 (2H, s), 3.97-3.88 (4H, m), 3.83-3.74 (4H, m), 3.35 (2H, dd, J = 13.2, 6.6 Hz), 3.19 (3H, s), 3.10 (2H, d, J = 5.9 Hz), 2.45 (2H, t, J = 7.3 Hz), 2.27 (6H, s), 1.85-1.72 (2H, m) |
| 10-18 | 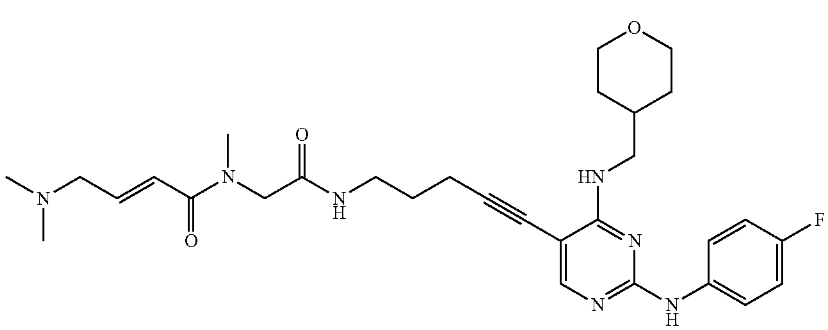 [SMILES: CN(C)C/C=C/C(=O)N(C)CC(=O)NCCCC#Cc1cnc(Nc2ccc(F)cc2)nc1NCC1CCOCC1] | ¹H-NMR (CDCl₃) δ: 7.95 (1H, s), 7.60-7.50 (2H, m), 7.12 (1H, s), 7.04-6.88 (3H, m), 6.69-6.57 (1H, m), 6.47 (1H, d, J = 15.2 Hz), 6.36-6.23 (1H, m), 4.03 (2H, s), 3.99 (2H, dd, J = 11.2, 3.3 Hz), 3.54-3.28 (6H, m), 3.20 (3H, s), 3.11 (2H, d, J = 5.9 Hz), 2.47 (2H, t, J = 6.6 Hz), 2.27 (6H, s), 2.10-1.90 (1H, m), 1.84-1.60 (4H, m), 1.47-1.26 (2H, m) |

TABLE 162-continued

| Compound No. | Structure | Physicochemical data |
|---|---|---|
| 10-19 | 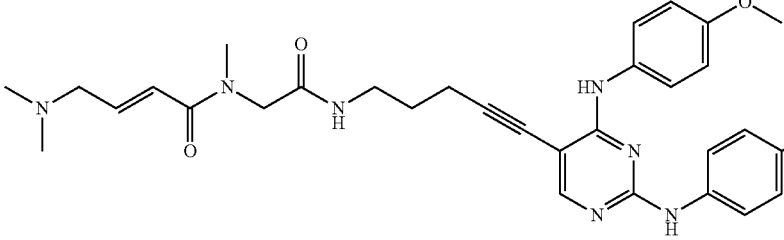 | $^1$H-NMR (CDCl$_3$) δ: 8.08 (1H, s), 7.71 (1H, s), 7.56-7.41 (4H, m), 7.11 (1H, s), 6.98-6.87 (5H, m), 6.73-6.59 (1H, m), 6.45 (1H, d, J = 15.2 Hz), 4.03 (2H, s), 3.84 (3H, s), 3.47 (2H, q, J = 6.4 Hz), 3.17 (3H, s), 3.10 (2H, d, J = 5.9 Hz), 2.52 (2H, t, J = 6.6 Hz), 2.26 (6H, s), 1.84-1.75 (2H, m) |
| 10-20 | 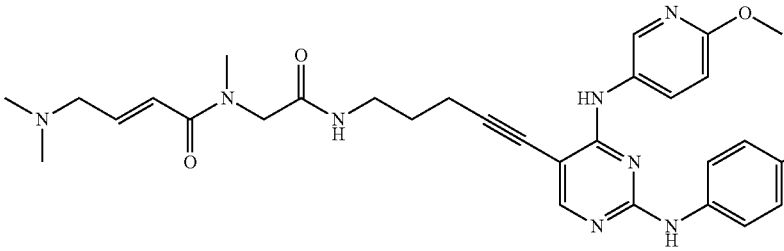 | $^1$H-NMR (CDCl$_3$) δ: 8.39 (1H, d, J = 2.6 Hz), 8.10 (1H, s), 8.07 (1H, s), 7.91 (1H, dd, J = 9.2, 2.6 Hz), 7.49-7.38 (2H, m), 7.03 (1H, s), 6.97-6.89 (3H, m), 6.73 (1H, d, J = 9.2 Hz), 6.68-6.58 (1H, m), 6.45 (1H, d, J = 15.2 Hz), 4.03 (2H, s), 3.96 (3H, s), 3.52 (2H, q, J = 6.2 Hz), 3.17 (3H, s), 3.10 (2H, d, J = 5.9 Hz), 2.51 (2H, t, J = 6.6 Hz), 2.26 (6H, s), 1.87-1.67 (2H, m) |
| 10-21 | 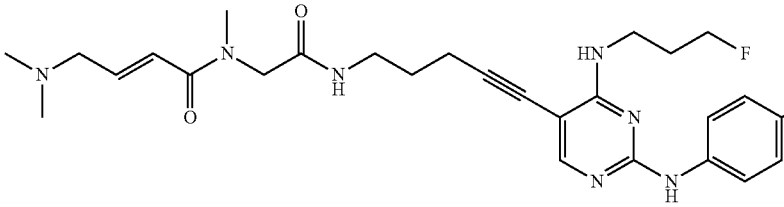 | $^1$H-NMR (CDCl$_3$) δ: 7.95 (1H, s), 7.58-7.52 (2H, m), 7.04-6.90 (4H, m), 6.65-6.54 (1H, m), 6.47 (1H, d, J = 15.2 Hz), 6.46-6.36 (1H, m), 4.57 (2H, m), 4.03 (2H, s), 3.66 (2H, q, J = 6.6 Hz), 3.45 (2H, q, J = 6.4 Hz), 3.20 (3H, s), 3.11 (2H, d, J = 5.9 Hz), 2.46 (2H, t, J = 6.6 Hz), 2.27 (6H, s), 2.16-1.98 (2H, m), 1.80-1.67 (2H, m) |
| 10-22 | 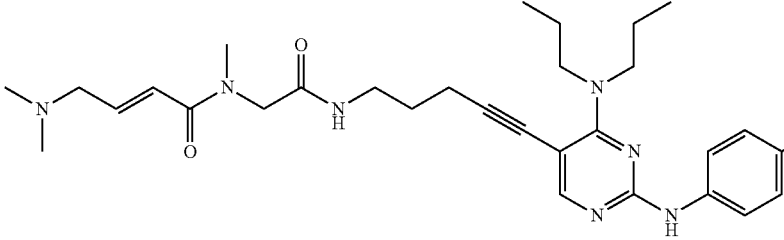 | $^1$H-NMR (CDCl$_3$) δ: 8.00 (1H, s), 7.52-7.46 (2H, m), 7.05-6.86 (4H, m), 6.70-6.59 (1H, m), 6.45 (1H, d, J = 15.2 Hz), 4.03 (2H, s), 3.69-3.61 (4H, m), 3.36 (2H, q, J = 6.8 Hz), 3.19 (3H, s), 3.10 (2H, d, J = 5.9 Hz), 2.43 (2H, t, J = 6.9 Hz), 2.26 (6H, s), 1.83-1.61 (6H, m), 0.91 (6H, t, J = 7.3 Hz) |

TABLE 163

| Compound No. | Structure | Physicochemical data |
|---|---|---|
| 10-23 | 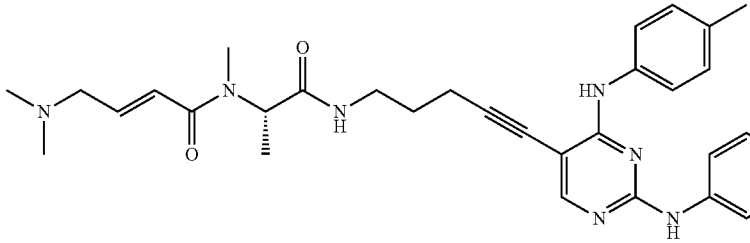 | $^1$H-NMR (CDCl$_3$) δ: 8.14 (1H, s), 8.03 (1H, s), 7.71-7.63 (2H, m), 7.51-7.47 (4H, m), 7.32 (1H, s), 7.19 (2H, d, J = 7.9 Hz), 6.93 (1H, dt, J = 15.2, 5.9 Hz), 6.66-6.54 (1H, m), 6.47-6.35 (1H, m), 5.17 (1H, q, J = 7.0 Hz), 3.55-3.42 (2H, m), 3.10 (2H, dd, J = 5.9, 1.3 Hz), 2.96 (3H, s), 2.49 (2H, t, J = 6.3 Hz), 2.40 (3H, s), 2.26 (6H, s), 1.85-1.71 (2H, m), 1.34 (3H, d, J = 7.0 Hz) |

TABLE 163-continued

| Compound No. | Structure | Physicochemical data |
|---|---|---|
| 10-24 | 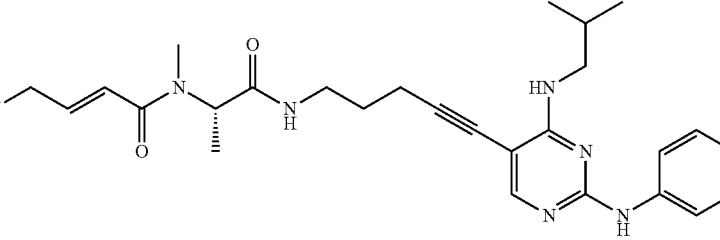 | ¹H-NMR (CDCl₃) δ: 7.97 (1H, s), 7.77 (2H, d, J = 9.2 Hz), 7.56 (2H, d, J = 9.2 Hz), 7.47 (1H, s), 6.94 (1H, dt, J = 15.2, 5.9 Hz), 6.63-6.54 (1H, m), 6.51-6.37 (2H, m), 5.18 (1H, q, J = 7.0 Hz), 3.44 (2H, q, J = 6.4 Hz), 3.35 (2H, t, J = 6.6 Hz), 3.10 (2H, dd, J = 5.9, 1.3 Hz), 3.00 (3H, s), 2.44 (2H, t, J = 6.6 Hz), 2.27 (6H, s), 2.13-1.97 (1H, m), 1.80-1.67 (2H, m), 1.36 (3H, d, J = 7.0 Hz), 0.99 (6H, d, J = 6.6 Hz) |
| 10-25 | 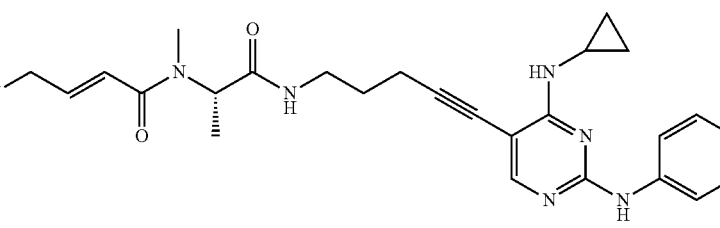 | ¹H-NMR (CDCl₃) δ: 7.99 (1H, s), 7.89 (2H, d, J = 9.2 Hz), 7.62 (1H, s), 7.56 (2H, d, J = 9.2 Hz), 6.94 (1H, dt, J = 15.2, 5.9 Hz), 6.65-6.54 (1H, m), 6.48-6.36 (2H, m), 5.19 (1H, q, J = 7.0 Hz), 3.43 (2H, q, J = 6.4 Hz), 3.11 (2H, dd, J = 5.9, 1.3 Hz), 3.01 (3H, s), 2.92-2.81 (1H, m), 2.43 (2H, t, J = 6.6 Hz), 2.27 (6H, s), 1.78-1.69 (2H, m), 1.37 (3H, d, J = 7.0 Hz), 0.91-0.85 (2H, m), 0.79-0.70 (2H, m) |
| 10-26 | 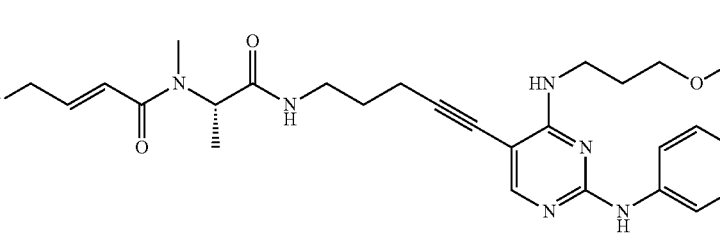 | ¹H-NMR (CDCl₃) δ: 7.95 (1H, s), 7.60-7.52 (2H, m), 7.15 (1H, s), 7.04-6.88 (3H, m), 6.59 (1H, brs), 6.46-6.34 (2H, m), 5.19 (1H, q, J = 7.0 Hz), 3.99 (3H, s), 3.60 (2H, q, J = 6.4 Hz), 3.51 (2H, t, J = 5.9 Hz), 3.42 (2H, q, J = 6.4 Hz), 3.35 (3H, s), 3.12-3.08 (2H, m), 2.99 (3H, s), 2.44 (2H, t, J = 6.6 Hz), 2.27 (6H, s), 1.98-1.88 (2H, m), 1.80-1.71 (2H, m), 1.35 (3H, d, J = 7.3 Hz) |
| 10-27 | 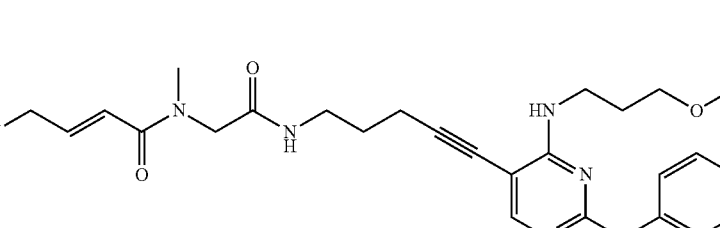 | ¹H-NMR (CDCl₃) δ: 7.94 (1H, s), 7.60-7.53 (2H, m), 7.22 (1H, s), 7.04-6.88 (3H, m), 6.69 (1H, brs), 6.46 (1H, d, J = 15.2 Hz), 6.34-6.24 (1H, m), 4.04 (2H, s), 3.59 (2H, q, J = 6.4 Hz), 3.51 (2H, t, J = 5.9 Hz), 3.42 (2H, q, J = 6.4 Hz), 3.35 (3H, s), 3.20 (3H, s), 3.12-3.04 (2H, m), 2.47 (2H, t, J = 6.6 Hz), 2.26 (6H, s), 1.98-1.88 (2H, m), 1.82-1.73 (2H, m) |

TABLE 164

| Compound No. | Structure | Physicochemical data |
|---|---|---|
| 10-28 | 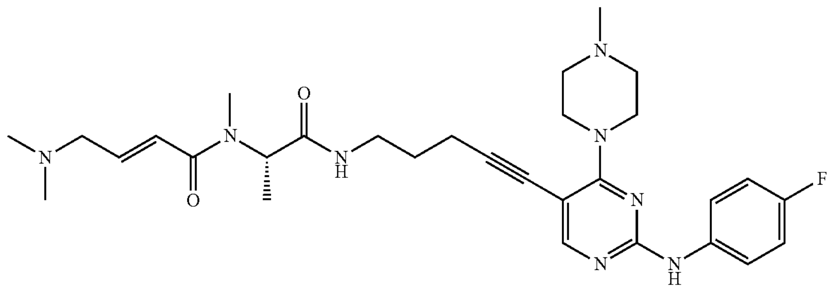 [SMILES: C[C@@H](C(=O)NCCCC#Cc1cnc(Nc2ccc(F)cc2)nc1N1CCN(C)CC1)N(C)C(=O)/C=C/CN(C)C] | ¹H-NMR (CDCl₃) δ: 8.07 (1H, s), 7.51-7.46 (2H, m), 7.08-6.88 (4H, m), 6.55 (1H, brs), 6.42 (1H, d, J = 15.2 Hz), 5.17 (1H, q, J = 6.8 Hz), 3.98-3.90 (4H, m), 3.44-3.24 (2H, m), 3.10 (2H, d, J = 5.9 Hz), 2.99 (3H, s), 2.52-2.40 (6H, m), 2.33 (3H, s), 2.27 (6H, s), 1.82-1.70 (2H, m), 1.35 (3H, d, J = 6.6 Hz) |
| 10-29 | 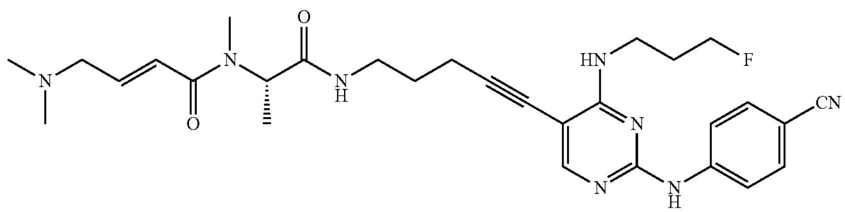 [SMILES: C[C@@H](C(=O)NCCCC#Cc1cnc(Nc2ccc(C#N)cc2)nc1NCCCF)N(C)C(=O)/C=C/CN(C)C] | ¹H-NMR (CDCl₃) δ: 7.98 (1H, s), 7.77 (2H, d, J = 9.2 Hz), 7.57 (2H, d, J = 9.2 Hz), 7.47 (1H, s), 6.94 (1H, dt, J = 15.2, 5.9 Hz), 6.81-6.70 (1H, m), 6.64-6.52 (1H, m), 6.43 (1H, dt, J = 15.2, 1.7 Hz), 5.19 (1H, q, J = 7.0 Hz), 4.59 (2H, dt, J = 47.3, 5.6 Hz), 3.72 (2H, q, J = 6.4 Hz), 3.46 (2H, q, J = 6.6 Hz), 3.11 (2H, dd, J = 5.9, 1.7 Hz), 3.00 (3H, s), 2.50-2.38 (2H, m), 2.27 (6H, s), 2.22-2.02 (2H, m), 1.78-1.69 (2H, m), 1.36 (3H, d, J = 7.0 Hz) |
| 10-30 | 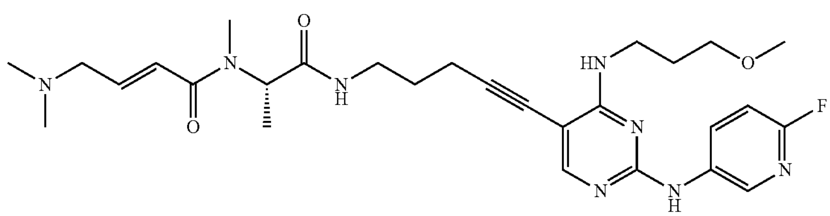 [SMILES: COCCCNc1nc(Nc2ccc(F)nc2)ncc1C#CCCCNC(=O)[C@H](C)N(C)C(=O)/C=C/CN(C)C] | ¹H-NMR (CDCl₃) δ: 8.37 (1H, s), 8.21 (1H, dt, J = 11.2, 4.1 Hz), 7.94 (1H, s), 7.34 (1H, brs), 6.98-6.86 (2H, m), 6.53 (2H, brs), 6.42 (1H, dt, J = 15.2, 1.7 Hz), 5.18 (1H, q, J = 7.0 Hz), 3.60 (2H, q, J = 6.2 Hz), 3.54-3.39 (4H, m), 3.35 (3H, s), 3.11 (2H, d, J = 4.6 Hz), 2.99 (3H, s), 2.53-2.39 (2H, m), 2.27 (6H, s), 1.97-1.89 (2H, m), 1.83-1.71 (2H, m), 1.36 (3H, d, J = 7.0 Hz) |
| 10-31 | 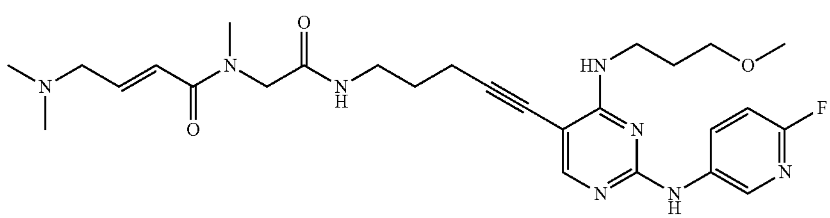 [SMILES: COCCCNc1nc(Nc2ccc(F)nc2)ncc1C#CCCCNC(=O)CN(C)C(=O)/C=C/CN(C)C] | ¹H-NMR (CDCl₃) δ: 8.37 (1H, s), 8.24-8.18 (1H, m), 7.95 (1H, s), 7.38 (1H, s), 6.99-6.86 (2H, m), 6.65 (1H, brs), 6.47 (2H, d, J = 15.2 Hz), 4.04 (2H, s), 3.62-3.40 (6H, m), 3.35 (3H, s), 3.20 (3H, s), 3.11-3.08 (2H, m), 2.48 (2H, t, J = 6.6 Hz), 2.27 (6H, s), 1.96-1.88 (2H, m), 1.82-1.74 (2H, m) |
| 10-32 | 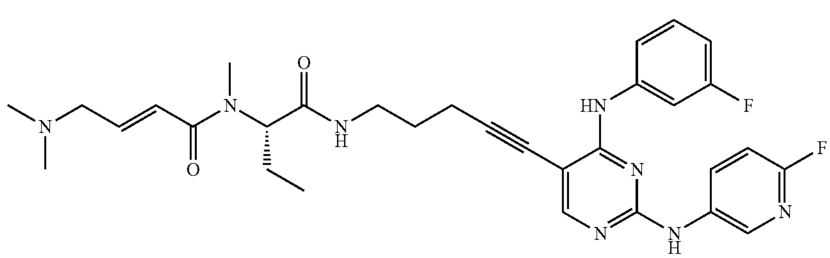 [SMILES: CC[C@@H](C(=O)NCCCC#Cc1cnc(Nc2ccc(F)nc2)nc1Nc1cccc(F)c1)N(C)C(=O)/C=C/CN(C)C] | ¹H-NMR (CDCl₃) δ: 8.29-8.15 (4H, m), 7.58 (1H, dt, J = 11.0, 2.1 Hz), 7.44 (1H, d, J = 7.9 Hz), 7.29-7.22 (2H, m), 6.97-6.79 (3H, m), 6.57 (1H, t, J = 6.3 Hz), 6.43 (1H, d, J = 15.2 Hz), 4.90 (1H, t, J = 7.6 Hz), 3.60-3.43 (2H, m), 3.10 (2H, dd, J = 6.3, 2.1 Hz), 2.99 (3H, s), 2.46 (2H, dt, J = 6.4, 2.4 Hz), 2.27 (6H, s), 2.06-1.62 (4H, m), 0.90 (3H, t, J = 7.6 Hz) |

TABLE 165

| Compound No. | Structure | Physicochemical data |
|---|---|---|
| 10-33 | 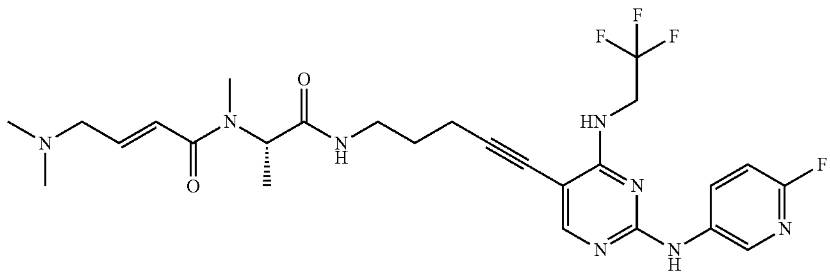 [SMILES: C[C@@H](C(=O)NCCCC#Cc1cnc(Nc2ccc(F)nc2)nc1NCC(F)(F)F)N(C)C(=O)/C=C/CN(C)C] | ¹H-NMR (CDCl₃) δ: 8.26 (1H, s), 8.21 (1H, t, J = 7.5 Hz), 8.04 (1H, s), 7.18 (2H, brs), 6.99-6.88 (2H, m), 6.58 (1H, brs), 6.43 (1H, d, J = 15.2 Hz), 5.19 (1H, d, J = 7.3 Hz), 4.26-4.12 (2H, m), 3.49 (2H, t, J = 5.6 Hz), 3.11 (2H, d, J = 5.9 Hz), 2.98 (3H, s), 2.43-2.41 (2H, m), 2.28 (6H, s), 1.72 (2H, brs), 1.35 (3H, d, J = 7.3 Hz) |
| 10-34 | 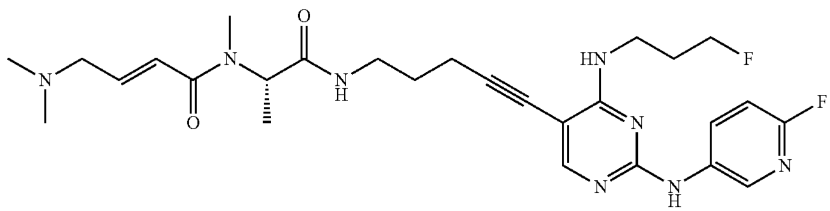 [SMILES: C[C@@H](C(=O)NCCCC#Cc1cnc(Nc2ccc(F)nc2)nc1NCCCF)N(C)C(=O)/C=C/CN(C)C] | ¹H-NMR (CDCl₃) δ: 8.34 (1H, s), 8.25-8.19 (1H, m), 7.96 (1H, s), 7.08 (1H, s), 6.99-6.87 (2H, m), 6.66 (1H, brs), 6.54 (1H, brs), 6.43 (1H, d, J = 15.2 Hz), 5.19 (1H, q, J = 7.0 Hz), 4.66 (1H, t, J = 5.6 Hz), 4.50 (1H, t, J = 5.6 Hz), 3.68 (2H, q, J = 6.4 Hz), 3.46 (2H, q, J = 6.4 Hz), 3.11 (2H, d, J = 5.9 Hz), 2.99 (3H, s), 2.43 (2H, t, J = 5.9 Hz), 2.27 (6H, s), 2.17-1.99 (2H, m), 1.75-1.68 (2H, m), 1.36 (3H, d, J = 7.0 Hz) |
| 10-35 | 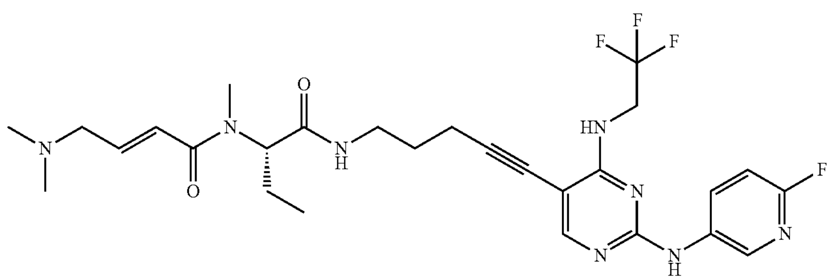 [SMILES: CC[C@@H](C(=O)NCCCC#Cc1cnc(Nc2ccc(F)nc2)nc1NCC(F)(F)F)N(C)C(=O)/C=C/CN(C)C] | ¹H-NMR (CDCl₃) δ: 8.27 (1H, s), 8.20 (1H, dt, J = 8.8, 3.5 Hz), 8.02 (1H, s), 7.32 (1H, brs), 7.22 (1H, brs), 6.98-6.88 (2H, m), 6.57 (1H, brs), 6.44 (1H, d, J = 15.2 Hz), 4.90 (1H, t, J = 7.6 Hz), 4.24-4.16 (2H, m), 3.50 (2H, d, J = 6.0 Hz), 3.11 (2H, d, J = 6.0 Hz), 2.99 (3H, s), 2.41 (2H, d, J = 5.3 Hz), 2.28 (6H, s), 2.02-1.96 (1H, m), 1.73-1.69 (3H, m), 0.90 (3H, t, J = 7.3 Hz) |
| 10-36 | 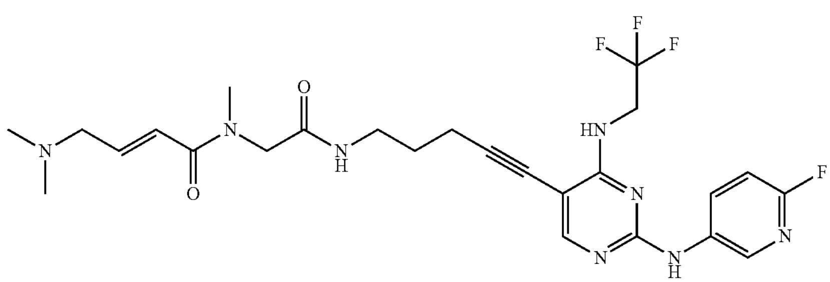 | ¹H-NMR (CDCl₃) δ: 8.26 (1H, s), 8.19 (1H, dt, J = 8.8, 3.5 Hz), 8.03 (1H, s), 7.30 (1H, brs), 7.06 (1H, brs), 6.99-6.88 (2H, m), 6.63 (1H, brs), 6.47 (1H, d, J = 15.2 Hz), 4.25-4.14 (2H, m), 4.03 (2H, s), 3.50 (2H, q, J = 6.4 Hz), 3.20 (3H, s), 3.11 (2H, t, J = 5.9 Hz), 2.46 (2H, t, J = 6.3 Hz), 2.28 (6H, s), 1.78-1.70 (2H, m) |
| 10-37 | 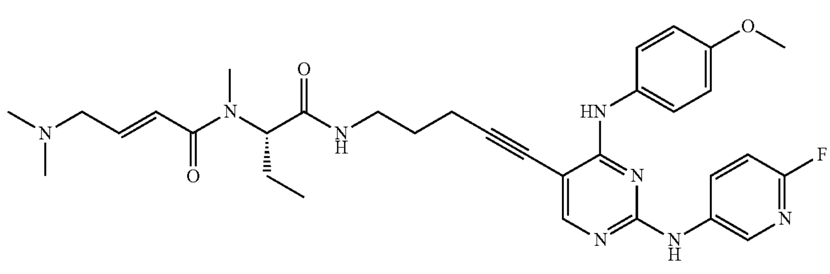 [SMILES: CC[C@@H](C(=O)NCCCC#Cc1cnc(Nc2ccc(F)nc2)nc1Nc1ccc(OC)cc1)N(C)C(=O)/C=C/CN(C)C] | ¹H-NMR (CDCl₃) δ: 8.23 (1H, dt, J = 8.8, 3.5 Hz), 8.13 (1H, s), 8.09 (1H, s), 7.98 (1H, s), 7.49 (2H, d, J = 6.6 Hz), 7.42 (1H, s), 6.95-6.87 (3H, m), 6.77 (1H, dd, J = 8.8, 3.5 Hz), 6.59 (1H, brs), 6.42 (1H, d, J = 15.2 Hz), 4.89 (1H, t, J = 7.6 Hz), 3.84 (3H, s), 3.49 (2H, d, J = 5.9 Hz), 3.10 (2H, d, J = 5.9 Hz), 2.95 (3H, s), 2.47 (2H, s), 2.27 (6H, s), 2.00-1.61 (4H, m), 0.88 (3H, t, J = 7.3 Hz) |

TABLE 166

| Compound No. | Structure | Physicochemical data |
|---|---|---|
| 10-38 | 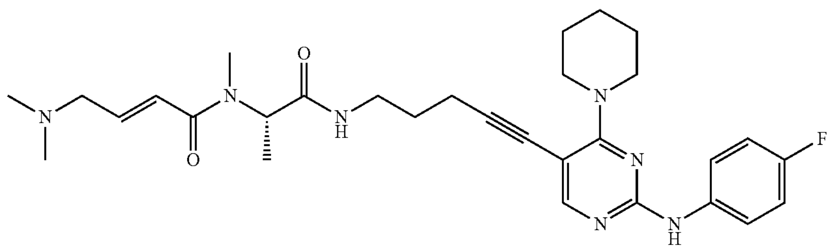 [SMILES: C[C@@H](C(=O)NCCCC#Cc1cnc(Nc2ccc(F)cc2)nc1N1CCCCC1)N(C)C(=O)/C=C/CN(C)C] | ¹H-NMR (CDCl₃) δ: 8.04 (1H, s), 7.54-7.46 (2H, m), 7.17 (1H, s), 7.04-6.87 (3H, m), 6.57 (1H, brs), 6.42 (1H, d, J = 15.2 Hz), 5.18 (1H, q, J = 7.0 Hz), 3.88-3.82 (4H, m), 3.40-3.26 (2H, m), 3.10 (2H, d, J = 5.9 Hz), 2.99 (3H, s), 2.43 (2H, t, J = 6.9 Hz), 2.26 (6H, s), 1.82-1.58 (8H, m), 1.35 (3H, d, J = 7.8 Hz) |
| 10-39 | 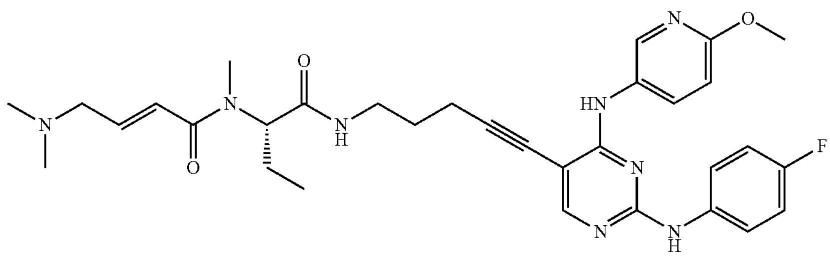 [SMILES: CC[C@@H](C(=O)NCCCC#Cc1cnc(Nc2ccc(F)cc2)nc1Nc1ccc(OC)nc1)N(C)C(=O)/C=C/CN(C)C] | ¹H-NMR (CDCl₃) δ: 8.40 (1H, d, J = 2.6 Hz), 8.19 (1H, s), 8.10 (1H, s), 7.90 (1H, dd, J = 8.6, 2.6 Hz), 7.47-7.40 (2H, m), 7.23 (1H, s), 6.98-6.88 (3H, m), 6.72 (1H, d, J = 8.6 Hz), 6.60 (1H, brs), 6.42 (1H, d, J = 15.2 Hz), 4.89 (1H, t, J = 7.6 Hz), 3.96 (3H, s), 3.57-3.45 (2H, m), 3.09 (2H, d, J = 5.9 Hz), 2.95 (3H, s), 2.48-2.43 (2H, m), 2.26 (6H, s), 2.04-1.86 (1H, m), 1.78-1.60 (3H, m), 0.87 (3H, t, J = 7.6 Hz) |
| 10-40 | 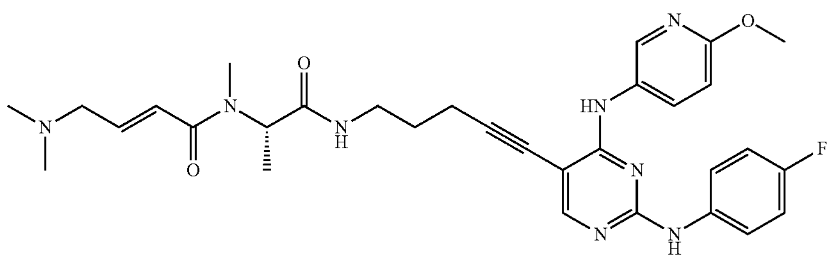 [SMILES: COc1ccc(Nc2nc(Nc3ccc(F)cc3)ncc2C#CCCCNC(=O)[C@H](C)N(C)C(=O)/C=C/CN(C)C)cn1] | ¹H-NMR (CDCl₃) δ: 8.41 (1H, d, J = 2.6 Hz), 8.15 (1H, s), 8.11 (1H, s), 7.90 (1H, dd, J = 8.6, 2.6 Hz), 7.47-7.40 (2H, m), 6.98-6.88 (4H, m), 6.73 (1H, d, J = 8.6 Hz), 6.58 (1H, brs), 6.41 (1H, d, J = 15.2 Hz), 5.17 (1H, q, J = 7.3 Hz), 3.96 (3H, s), 3.50 (2H, q, J = 6.2 Hz), 3.10 (2H, d, J = 5.9 Hz), 2.95 (3H, s), 2.46 (2H, t, J = 5.9 Hz), 2.26 (6H, s), 1.76 (2H, q, J = 6.2 Hz), 1.32 (3H, d, J = 7.3 Hz) |
| 10-41 | 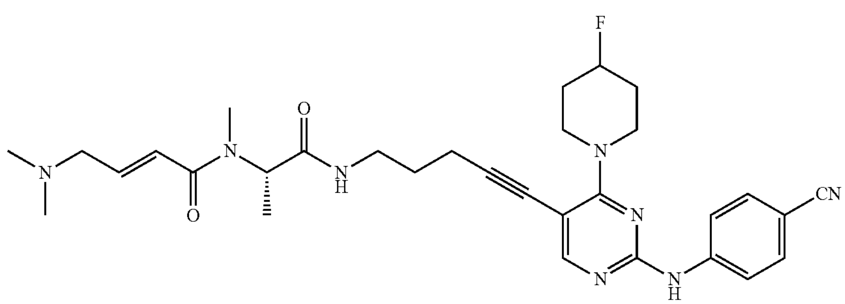 [SMILES: C[C@@H](C(=O)NCCCC#Cc1cnc(Nc2ccc(C#N)cc2)nc1N1CCC(F)CC1)N(C)C(=O)/C=C/CN(C)C] | ¹H-NMR (CDCl₃) δ: 8.12 (1H, s), 7.69 (2H, d, J = 9.0 Hz), 7.58 (2H, d, J = 9.0 Hz), 7.23 (1H, brs), 6.94 (1H, dt, J = 15.0, 6.0 Hz), 6.54 (1H, brs), 6.42 (1H, d, J = 15.0 Hz), 5.15 (1H, q, J = 6.6 Hz), 4.99-4.82 (1H, m), 4.12 (2H, t, J = 13.2 Hz), 3.90 (2H, t, J = 7.2 Hz), 3.11-3.07 (4H, m), 2.99 (3H, s), 2.45 (2H, t, J = 7.2 Hz), 2.27 (6H, s), 2.03-1.92 (4H, m), 1.82-1.64 (2H, m), 1.36 (3H, d, J = 7.5 Hz) |
| 10-42 | 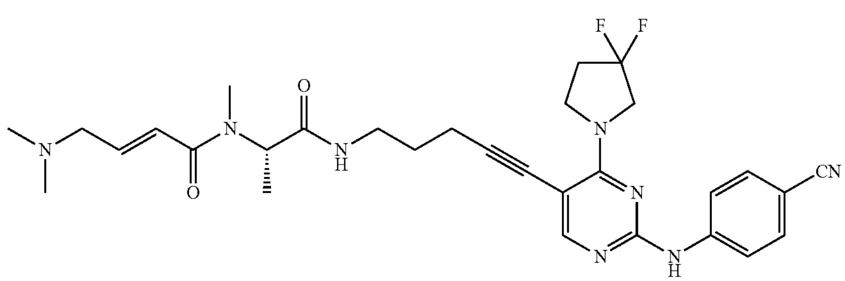 [SMILES: C[C@@H](C(=O)NCCCC#Cc1cnc(Nc2ccc(C#N)cc2)nc1N1CCC(F)(F)C1)N(C)C(=O)/C=C/CN(C)C] | ¹H-NMR (CDCl₃) δ: 8.11 (1H, s), 7.69 (2H, d, J = 9.0 Hz), 7.58 (2H, d, J = 9.0 Hz), 6.93 (1H, dt, J = 15.0, 6.0 Hz), 6.55 (1H, brs), 6.42 (2H, d, J = 15.0 Hz), 5.16 (1H, q, J = 6.6 Hz), 4.21 (2H, t, J = 13.2 Hz), 4.10 (2H, t, J = 7.2 Hz), 3.11-3.07 (4H, m), 2.99 (3H, s), 2.52-2.39 (2H, m), 2.26 (6H, s), 1.81-1.71 (4H, m), 1.35 (3H, d, J = 7.2 Hz) |

TABLE 167

| Compound No. | Structure | Physicochemical data |
|---|---|---|
| 10-43 | 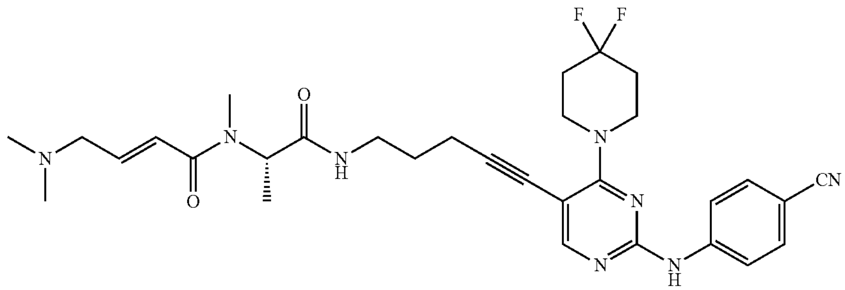 [SMILES: C[C@@H](C(=O)NCCCC#Cc1cnc(Nc2ccc(C#N)cc2)nc1N1CCC(F)(F)CC1)N(C)C(=O)/C=C/CN(C)C] | ¹H-NMR (CDCl₃) δ: 8.16 (1H, s), 7.68 (2H, d, J = 9.0 Hz), 7.58 (2H, d, J = 9.0 Hz), 7.23 (1H, brs), 6.94 (1H, dt, J = 15.0, 6.0 Hz), 6.55 (1H, brs), 6.42 (1H, d, J = 15.0 Hz), 5.16 (1H, q, J = 6.6 Hz), 4.04 (4H, t, J = 6.0 Hz), 3.11-3.07 (4H, m), 2.99 (3H, s), 2.45 (2H, t, J = 7.2 Hz), 2.27 (6H, s), 2.15-2.02 (4H, m), 1.82-1.64 (2H, m), 1.36 (3H, d, J = 7.5 Hz) |
| 10-44 | 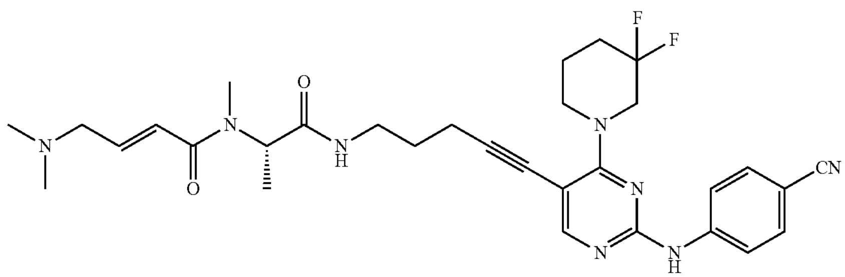 [SMILES: C[C@@H](C(=O)NCCCC#Cc1cnc(Nc2ccc(C#N)cc2)nc1N1CCCC(F)(F)C1)N(C)C(=O)/C=C/CN(C)C] | ¹H-NMR (CDCl₃) δ: 8.16 (1H, s), 7.69 (2H, d, J = 9.0 Hz), 7.58 (2H, d, J = 9.0 Hz), 7.23 (1H, brs), 6.94 (1H, dt, J = 15.0, 6.0 Hz), 6.52 (1H, brs) 6.42 (1H, d, J = 15.0 Hz), 5.17 (1H, q, J = 7.2 Hz), 4.00 (2H, t, J = 11.4 Hz), 3.91 (2H, t, J = 5.4 Hz), 3.11-3.07 (4H, m), 2.98 (3H, s), 2.46 (2H, t, J = 7.5 Hz), 2.27 (6H, s), 2.17-2.04 (2H, m), 1.94-1.86 (2H, m), 1.83-1.68 (2H, m), 1.35 (3H, d, J = 6.6 Hz) |
| 10-45 | 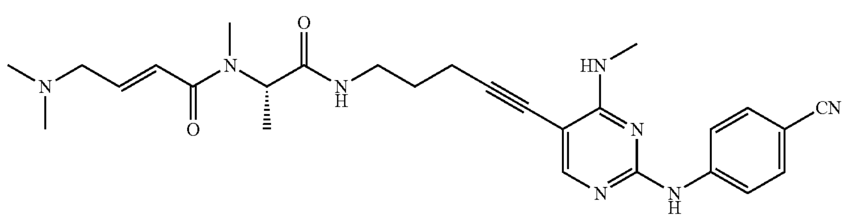 [SMILES: CNc1nc(Nc2ccc(C#N)cc2)ncc1C#CCCCNC(=O)[C@H](C)N(C)C(=O)/C=C/CN(C)C] | ¹H-NMR (CDCl₃) δ: 7.97 (1H, s), 7.79 (2H, d, J = 8.9 Hz), 7.57 (2H, d, J = 8.9 Hz), 7.54-7.48 (1H, m), 6.95 (1H, dt, J = 15.2, 5.9 Hz), 6.67-6.37 (3H, m), 5.20 (1H, q, J = 7.3 Hz), 3.53-3.40 (2H, m), 3.16-3.06 (5H, m), 3.01 (3H, s), 2.49-2.39 (2H, m), 2.27 (6H, s), 1.83-1.67 (2H, m), 1.38 (3H, d, J = 6.9 Hz) |
| 10-46 | 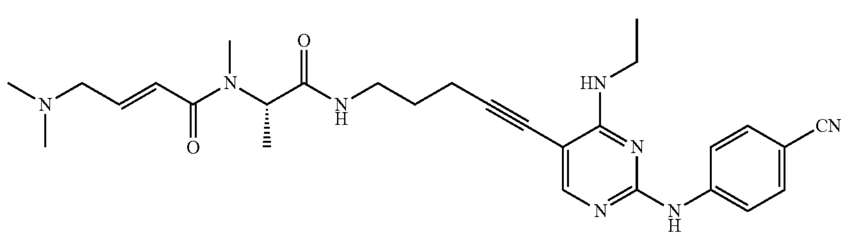 [SMILES: CCNc1nc(Nc2ccc(C#N)cc2)ncc1C#CCCCNC(=O)[C@H](C)N(C)C(=O)/C=C/CN(C)C] | ¹H-NMR (CDCl₃) δ: 7.98 (1H, s), 7.77 (2H, d, J = 8.6 Hz), 7.65-7.55 (1H, m), 7.57 (2H, d, J = 8.6 Hz), 6.95 (1H, dt, J = 15.2, 5.9 Hz), 6.68-6.55 (1H, m), 6.43 (1H, d, J = 15.2 Hz), 6.38-6.29 (1H, m), 5.19 (1H, q, J = 7.0 Hz), 3.64-3.52 (2H, m), 3.50-3.40 (2H, m), 3.15-3.05 (2H, m), 3.00 (3H, s), 2.45 (2H, t, J = 6.4 Hz), 2.27 (6H, s), 1.83-1.67 (2H, m), 1.37 (3H, d, J = 7.3 Hz), 1.31 (3H, t, J = 7.3 Hz) |

TABLE 168

| Compound No. | Structure | Physicochemical data |
|---|---|---|
| 10-47 | 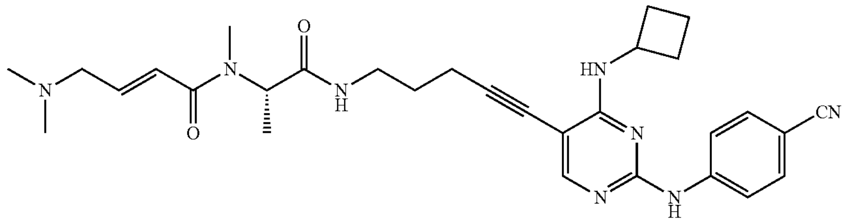 [SMILES: C[C@@H](C(=O)NCCCC#Cc1cnc(Nc2ccc(C#N)cc2)nc1NC1CCC1)N(C)C(=O)/C=C/CN(C)C] | ¹H-NMR (CDCl₃) δ: 7.99 (1H, s), 7.76 (2H, d, J = 8.9 Hz), 7.58 (2H, d, J = 8.9 Hz), 7.52-7.45 (1H, m), 6.95 (1H, dt, J = 15.2, 5.9 Hz), 6.64-6.52 (1H, m), 6.43 (1H, d, J = 15.2 Hz), 6.36-6.23 (1H, m), 5.20 (1H, q, J = 7.0 Hz), 4.68-4.51 (1H, m), 3.52-3.40 (2H, m), 3.14-3.07 (2H, m), 3.01 (3H, s), 2.51-2.35 (4H, m), 2.27 (6H, s), 2.21-2.06 (2H, m), 1.88-1.69 (4H, m), 1.38 (3H, d, J = 7.3 Hz) |
| 10-48 | 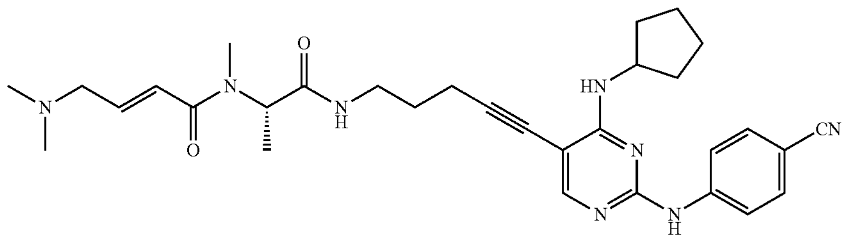 [SMILES: C[C@@H](C(=O)NCCCC#Cc1cnc(Nc2ccc(C#N)cc2)nc1NC1CCCC1)N(C)C(=O)/C=C/CN(C)C] | ¹H-NMR (CDCl₃) δ: 7.98 (1H, s), 7.77 (2H, d, J = 8.8 Hz), 7.56 (2H, d, J = 8.8 Hz), 7.44-7.35 (1H, m), 6.95 (1H, dt, J = 15.2, 5.9 Hz), 6.62-6.50 (1H, m), 6.47-6.38 (1H, m), 5.96-5.82 (1H, m), 5.18 (1H, q, J = 7.0 Hz), 4.48-4.33 (1H, m), 3.50-3.34 (2H, m), 3.13-3.07 (2H, m), 2.99 (3H, s), 2.45 (2H, t, J = 6.8 Hz), 2.27 (6H, s), 2.17-2.03 (2H, m), 1.86-1.55 (8H, m), 1.36 (3H, d, J = 6.9 Hz) |
| 10-49 | 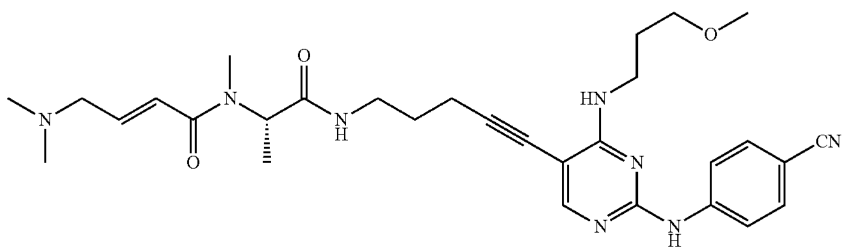 [SMILES: COCCCNc1nc(Nc2ccc(C#N)cc2)ncc1C#CCCCNC(=O)[C@H](C)N(C)C(=O)/C=C/CN(C)C] | ¹H-NMR (CDCl₃) δ: 7.98 (1H, s), 7.83-7.72 (1H, m), 7.78 (2H, d, J = 8.6 Hz), 7.56 (2H, d, J = 8.6 Hz), 6.95 (1H, dt, J = 15.2, 5.9 Hz), 6.72-6.52 (2H, m), 6.43 (1H, d, J = 15.2 Hz), 5.20 (1H, q, J = 7.0 Hz), 3.68-3.57 (2H, m), 3.56-3.47 (2H, m), 3.47-3.38 (2H, m), 3.36 (3H, s), 3.15-3.05 (2H, m), 3.00 (3H, s), 2.45 (2H, t, J = 6.6 Hz), 2.27 (6H, s), 2.02-1.90 (2H, m), 1.84-1.68 (2H, m), 1.36 (3H, d, J = 6.9 Hz) |
| 10-50 | 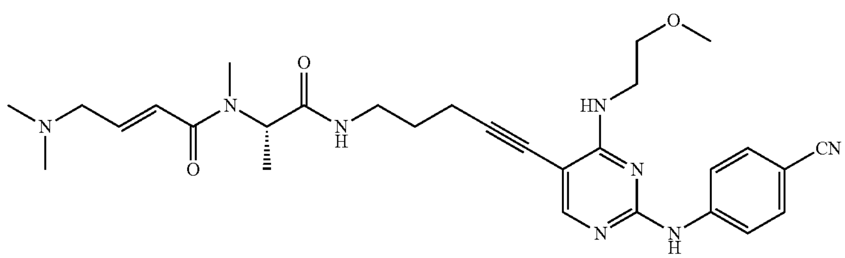 [SMILES: COCCNc1nc(Nc2ccc(C#N)cc2)ncc1C#CCCCNC(=O)[C@H](C)N(C)C(=O)/C=C/CN(C)C] | ¹H-NMR (CDCl₃) δ: 8.00 (1H, s), 7.75 (2H, d, J = 8.9 Hz), 7.57 (2H, d, J = 8.9 Hz), 7.45-7.37 (1H, m), 6.95 (1H, dt, J = 15.2, 5.9 Hz), 6.67-6.53 (1H, m), 6.45-6.34 (1H, m), 6.43 (1H, d, J = 15.2 Hz), 5.19 (1H, q, J = 7.0 Hz), 3.78-3.67 (2H, m), 3.67-3.58 (2H, m), 3.48-3.34 (2H, m), 3.40 (3H, s), 3.14-3.06 (2H, m), 3.00 (3H, s), 2.52-2.37 (2H, m), 2.27 (6H, s), 1.84-1.67 (2H, m), 1.36 (3H, d, J = 7.3 Hz) |
| 10-51 | 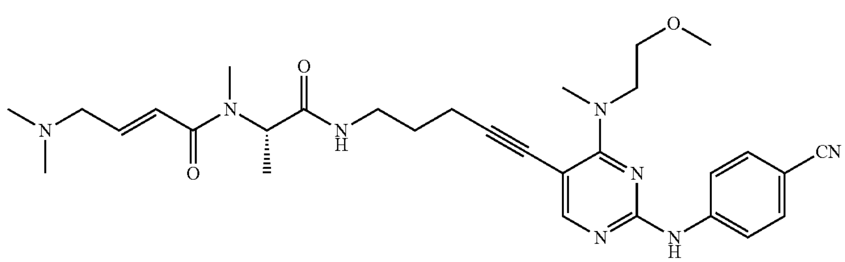 [SMILES: COCCN(C)c1nc(Nc2ccc(C#N)cc2)ncc1C#CCCCNC(=O)[C@H](C)N(C)C(=O)/C=C/CN(C)C] | ¹H-NMR (CDCl₃) δ: 8.07 (1H, s), 7.71 (2H, d, J = 8.8 Hz), 7.56 (2H, d, J = 8.8 Hz), 7.46-7.36 (1H, m), 6.95 (1H, dt, J = 15.2, 5.9 Hz), 6.66-6.52 (1H, m), 6.42 (1H, d, J = 15.2 Hz), 5.17 (1H, q, J = 7.0 Hz), 4.00 (2H, t, J = 5.9 Hz), 3.64 (2H, t, J = 5.9 Hz), 3.45-3.20 (8H, m), 3.15-3.05 (2H, m), 2.99 (3H, s), 2.41 (2H, t, J = 7.1 Hz), 2.27 (6H, s), 1.84-1.66 (2H, m), 1.35 (3H, d, J = 6.9 Hz) |

TABLE 169

| Compound No. | Structure | Physicochemical data |
|---|---|---|
| 10-52 | 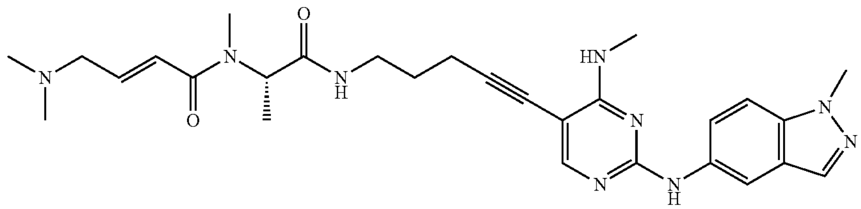 [SMILES: CNc1nc(Nc2ccc3c(cnn3C)c2)ncc1C#CCCCNC(=O)[C@H](C)N(C)C(=O)/C=C/CN(C)C] | ¹H-NMR (CDCl₃) δ: 8.14 (1H, d, J = 2.0 Hz), 7.95 (1H, s), 7.91 (1H, s), 7.47 (1H, dd, J = 8.6, 2.0 Hz), 7.32 (1H, d, J = 8.6 Hz), 7.13 (1H, s), 6.94 (1H, dt, J = 15.2, 5.9 Hz), 6.62-6.54 (1H, m), 6.48-6.37 (1H, m), 6.28-6.19 (1H, m), 5.19 (1H, q, J = 7.0 Hz), 4.06 (3H, s), 3.53-3.37 (2H, m), 3.15-3.05 (5H, m), 3.00 (3H, s), 2.43 (2H, t, J = 6.6 Hz), 2.27 (6H, s), 1.82-1.67 (2H, m), 1.37 (3H, d, J = 7.0 Hz) |
| 10-53 | 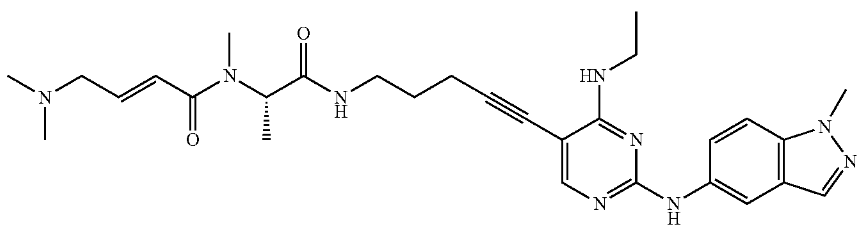 [SMILES: CCNc1nc(Nc2ccc3c(cnn3C)c2)ncc1C#CCCCNC(=O)[C@H](C)N(C)C(=O)/C=C/CN(C)C] | ¹H-NMR (CDCl₃) δ: 8.12 (1H, d, J = 2.0 Hz), 7.97 (1H, s), 7.90 (1H, s), 7.46 (1H, dd, J = 8.6, 2.0 Hz), 7.32 (1H, d, J = 8.6 Hz), 7.03 (1H, s), 6.94 (1H, dt, J = 15.2, 5.9 Hz), 6.60-6.51 (1H, m), 6.47-6.36 (1H, m), 6.12-6.03 (1H, m), 5.19 (1H, q, J = 7.3 Hz), 4.06 (3H, s), 3.64-3.50 (2H, m), 3.50-3.37 (2H, m), 3.10 (2H, dd, J = 5.9, 1.3 Hz), 2.99 (3H, s), 2.44 (2H, t, J = 6.9 Hz), 2.27 (6H, s), 1.80-1.68 (2H, m), 1.36 (3H, d, J = 7.3 Hz), 1.30 (3H, t, J = 7.3 Hz) |
| 10-54 | 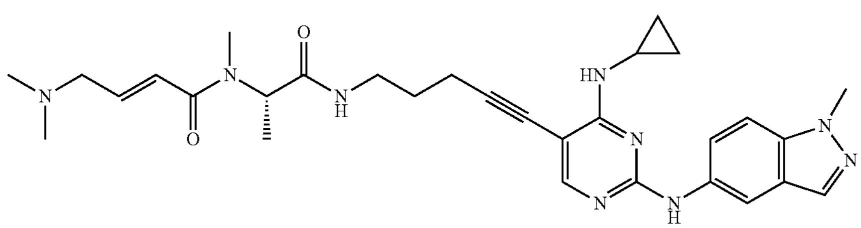 [SMILES: C[C@@H](C(=O)NCCCC#Cc1cnc(Nc2ccc3c(cnn3C)c2)nc1NC1CC1)N(C)C(=O)/C=C/CN(C)C] | ¹H-NMR (CDCl₃) δ: 8.34 (1H, d, J = 2.0 Hz), 7.98 (1H, s), 7.89 (1H, s), 7.49 (1H, dd, J = 8.6, 2.0 Hz), 7.31 (1H, d, J = 8.6 Hz), 7.16 (1H, s), 6.94 (1H, dt, J = 15.2, 5.9 Hz), 6.60-6.51 (1H, m), 6.48-6.37 (1H, m), 6.20-6.14 (1H, m), 5.19 (1H, q, J = 7.0 Hz), 4.06 (3H, s), 3.48-3.37 (2H, m), 3.10 (2H, dd, J = 5.9, 1.3 Hz), 3.00 (3H, s), 2.94-2.83 (1H, m), 2.43 (2H, t, J = 6.6 Hz), 2.27 (6H, s), 1.79-1.67 (2H, m), 1.37 (3H, d, J = 7.0 Hz), 0.94-0.83 (2H, m), 0.81-0.71 (2H, m) |
| 10-55 | 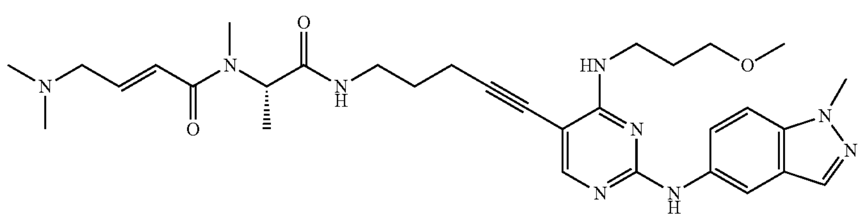 [SMILES: COCCCNc1nc(Nc2ccc3c(cnn3C)c2)ncc1C#CCCCNC(=O)[C@H](C)N(C)C(=O)/C=C/CN(C)C] | ¹H-NMR (CDCl₃) δ: 8.13 (1H, d, J = 2.0 Hz), 7.97 (1H, s), 7.91 (1H, s), 7.44 (1H, dd, J = 9.2, 2.0 Hz), 7.32 (1H, d, J = 9.2 Hz), 7.08 (1H, s), 6.94 (1H, dt, J = 15.2, 5.9 Hz), 6.62-6.53 (1H, m), 6.47-6.31 (2H, m), 5.19 (1H, q, J = 7.0 Hz), 4.06 (3H, s), 3.68-3.58 (2H, m), 3.52 (2H, t, J = 5.9 Hz), 3.48-3.38 (2H, m), 3.35 (3H, s), 3.10 (2H, d, J = 5.9 Hz), 3.00 (3H, s), 2.45 (2H, t, J = 6.9 Hz), 2.27 (6H, s), 2.02-1.91 (2H, m), 1.82-1.69 (2H, m), 1.36 (3H, d, J = 7.0 Hz) |

TABLE 170

| Compound No. | Structure | Physicochemical data |
|---|---|---|
| 10-56 | 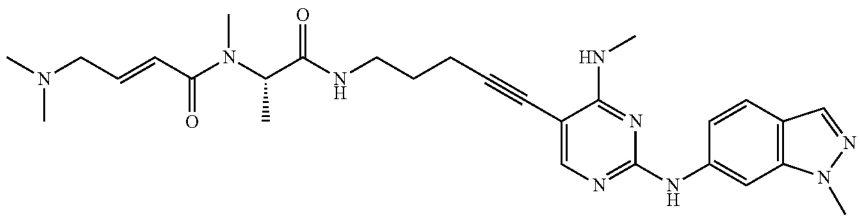 [SMILES: CNc1nc(Nc2ccc3cnn(C)c3c2)ncc1C#CCCCNC(=O)[C@H](C)N(C)C(=O)/C=C/CN(C)C] | ¹H-NMR (CDCl₃) δ: 8.40 (1H, s), 8.00 (1H, s), 7.87 (1H, s), 7.58 (1H, d, J = 8.6 Hz), 7.20 (1H, s), 7.01-6.88 (2H, m), 6.61-6.52 (1H, m), 6.48-6.33 (2H, m), 5.20 (1H, q, J = 7.0 Hz), 4.04 (3H, s), 3.53-3.40 (2H, m), 3.18 (3H, d, J = 4.6 Hz), 3.10 (2H, d, J = 5.9 Hz), 3.00 (3H, s), 2.44 (2H, t, J = 6.3 Hz), 2.27 (6H, s), 1.81-1.71 (2H, m), 1.37 (3H, d, J = 7.0 Hz) |
| 10-57 | 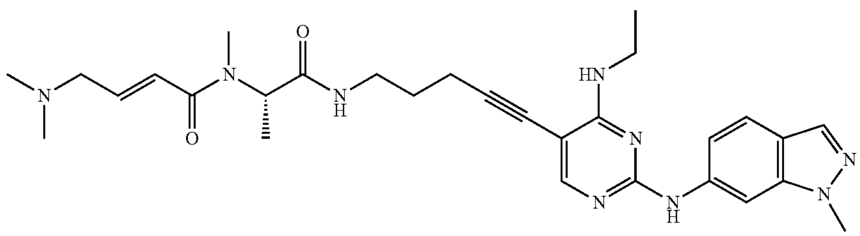 [SMILES: CCNc1nc(Nc2ccc3cnn(C)c3c2)ncc1C#CCCCNC(=O)[C@H](C)N(C)C(=O)/C=C/CN(C)C] | ¹H-NMR (CDCl₃) δ: 8.36 (1H, s), 8.00 (1H, s), 7.87 (1H, s), 7.58 (1H, d, J = 8.6 Hz), 7.28-7.22 (1H, m), 7.01-6.86 (2H, m), 6.61-6.50 (1H, m), 6.43 (1H, d, J = 15.2 Hz), 6.33-6.23 (1H, m), 5.19 (1H, q, J = 7.0 Hz), 4.04 (3H, s), 3.74-3.61 (2H, m), 3.54-3.39 (2H, m), 3.11 (2H, d, J = 5.3 Hz), 3.00 (3H, s), 2.45 (2H, t, J = 6.6 Hz), 2.27 (6H, s), 1.82-1.67 (2H, m), 1.43-1.31 (6H, m) |
| 10-58 | 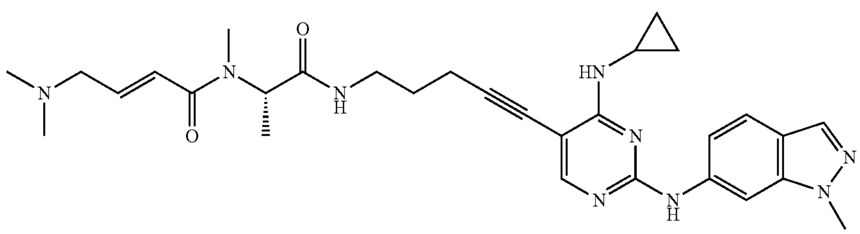 [SMILES: C[C@@H](C(=O)NCCCC#Cc1cnc(Nc2ccc3cnn(C)c3c2)nc1NC1CC1)N(C)C(=O)/C=C/CN(C)C] | ¹H-NMR (CDCl₃) δ: 8.36 (1H, s), 8.02 (1H, s), 7.87 (1H, s), 7.58 (1H, d, J = 8.6 Hz), 7.31-7.24 (1H, m), 7.03-6.89 (2H, m), 6.59-6.48 (1H, m), 6.47-6.38 (1H, m), 6.29-6.22 (1H, m), 5.19 (1H, q, J = 6.8 Hz), 4.02 (3H, s), 3.49-3.38 (2H, m), 3.11 (2H, dd, J = 5.9, 1.3 Hz), 3.04-2.93 (4H, m), 2.43 (2H, t, J = 6.6 Hz), 2.27 (6H, s), 1.80-1.69 (2H, m), 1.37 (3H, d, J = 6.8 Hz), 0.95-0.83 (2H, m), 0.83-0.74 (2H, m) |
| 10-59 | 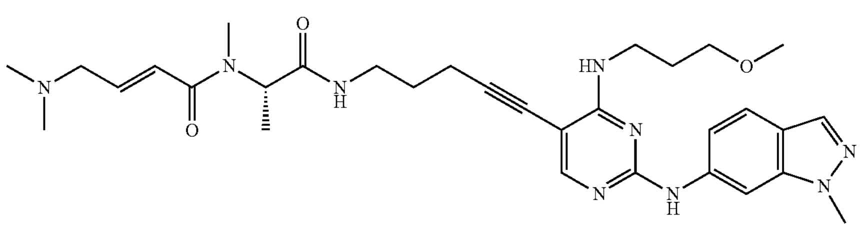 [SMILES: COCCCNc1nc(Nc2ccc3cnn(C)c3c2)ncc1C#CCCCNC(=O)[C@H](C)N(C)C(=O)/C=C/CN(C)C] | ¹H-NMR (CDCl₃) δ: 8.31 (1H, s), 8.01 (1H, s), 7.87 (1H, s), 7.58 (1H, d, J = 8.6 Hz), 7.29 (1H, s), 7.00-6.87 (2H, m), 6.62-6.51 (1H, m), 6.48-6.36 (2H, m), 5.19 (1H, q, J = 7.0 Hz), 4.05 (3H, s), 3.78-3.68 (2H, m), 3.53 (2H, t, J = 5.9 Hz), 3.49-3.38 (2H, m), 3.32 (3H, s), 3.11 (2H, dd, J = 5.9, 1.3 Hz), 3.00 (3H, s), 2.46 (2H, t, J = 6.9 Hz), 2.27 (6H, s), 2.06-1.94 (2H, m), 1.83-1.70 (2H, m), 1.36 (3H, d, J = 7.0 Hz) |
| 10-60 | 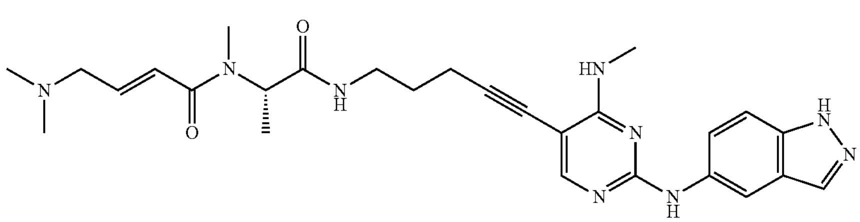 [SMILES: CNc1nc(Nc2ccc3[nH]ncc3c2)ncc1C#CCCCNC(=O)[C@H](C)N(C)C(=O)/C=C/CN(C)C] | MS m/z (M + H): 518.5 |

TABLE 170-continued

| Compound No. | Structure | Physicochemical data |
| --- | --- | --- |
| 10-61 | 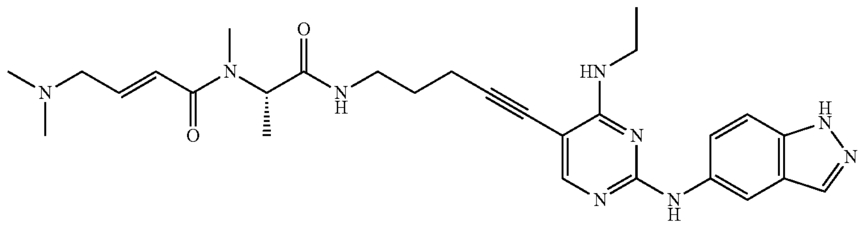 [SMILES: CCNc1nc(Nc2ccc3[nH]ncc3c2)ncc1C#CCCCNC(=O)[C@H](C)N(C)C(=O)/C=C/CN(C)C] | MS m/z (M + H): 532.5 |

TABLE 171

| Compound No. | Structure | Physicochemical data |
| --- | --- | --- |
| 10-62 | 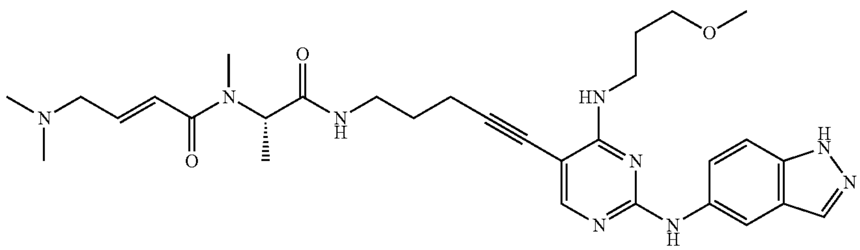 [SMILES: COCCCNc1nc(Nc2ccc3[nH]ncc3c2)ncc1C#CCCCNC(=O)[C@H](C)N(C)C(=O)/C=C/CN(C)C] | MS m/z (M + H): 576.5 |
| 10-63 | 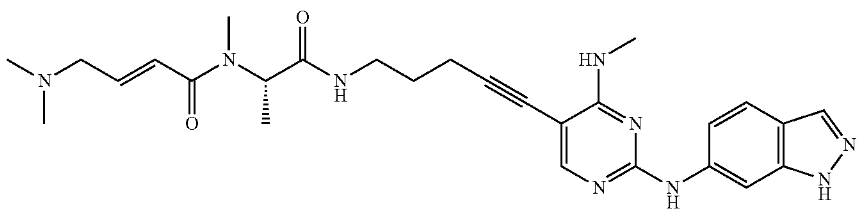 [SMILES: CNc1nc(Nc2ccc3cn[nH]c3c2)ncc1C#CCCCNC(=O)[C@H](C)N(C)C(=O)/C=C/CN(C)C] | MS m/z (M + H): 518.5 |
| 10-64 | 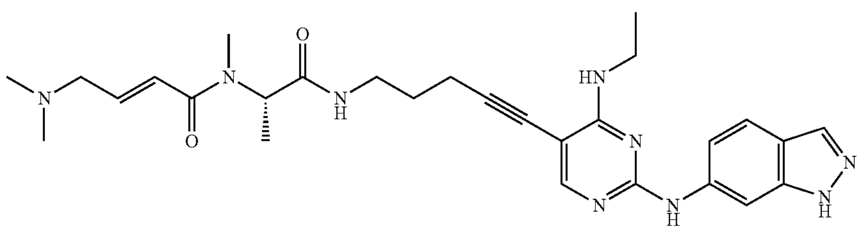 [SMILES: CCNc1nc(Nc2ccc3cn[nH]c3c2)ncc1C#CCCCNC(=O)[C@H](C)N(C)C(=O)/C=C/CN(C)C] | MS m/z (M + H): 532.5 |
| 10-65 | 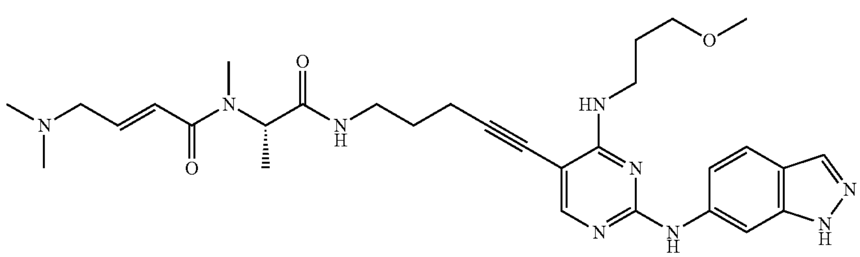 [SMILES: COCCCNc1nc(Nc2ccc3cn[nH]c3c2)ncc1C#CCCCNC(=O)[C@H](C)N(C)C(=O)/C=C/CN(C)C] | MS m/z (M + H): 576.5 |
| 10-66 | 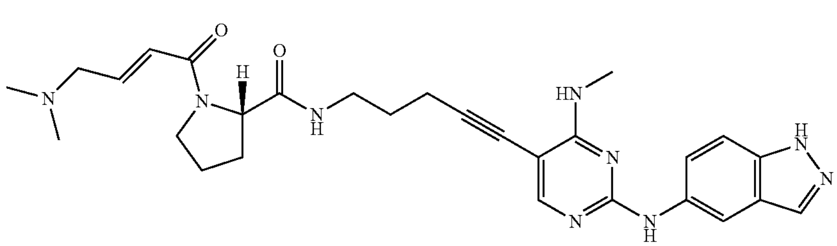 [SMILES: CNc1nc(Nc2ccc3[nH]ncc3c2)ncc1C#CCCCNC(=O)[C@@H]1CCCN1C(=O)/C=C/CN(C)C] | MS m/z (M + H): 530.5 |

TABLE 171-continued

| Compound No. | Structure | Physicochemical data |
|---|---|---|
| 10-67 | 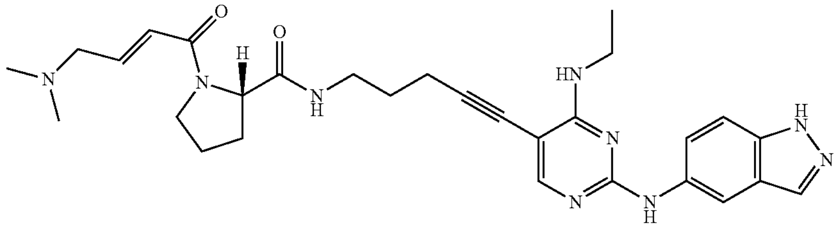 [SMILES: CCNc1nc(Nc2ccc3[nH]ncc3c2)ncc1C#CCCCNC(=O)[C@@H]1CCCN1C(=O)/C=C/CN(C)C] | MS m/z (M + H): 544.5 |
| 10-68 | 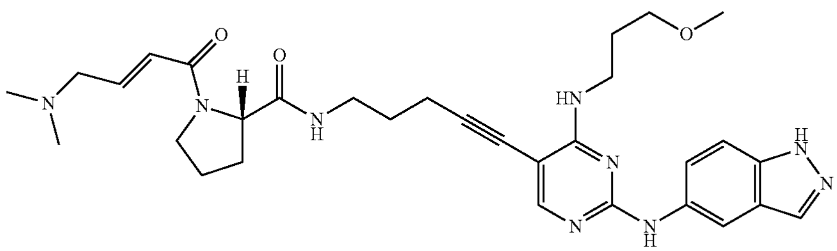 [SMILES: COCCCNc1nc(Nc2ccc3[nH]ncc3c2)ncc1C#CCCCNC(=O)[C@@H]1CCCN1C(=O)/C=C/CN(C)C] | MS m/z (M + H): 588.5 |
| 10-69 | 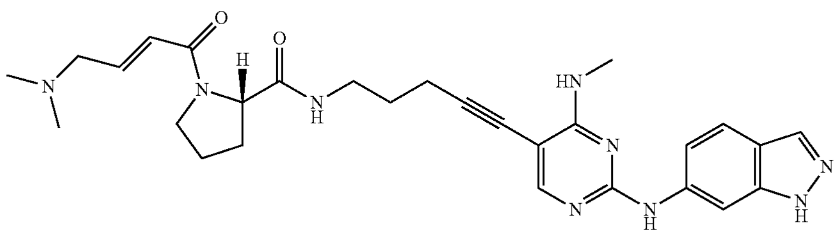 [SMILES: CNc1nc(Nc2ccc3cn[nH]c3c2)ncc1C#CCCCNC(=O)[C@@H]1CCCN1C(=O)/C=C/CN(C)C] | MS m/z (M + H): 530.5 |
| 10-70 | 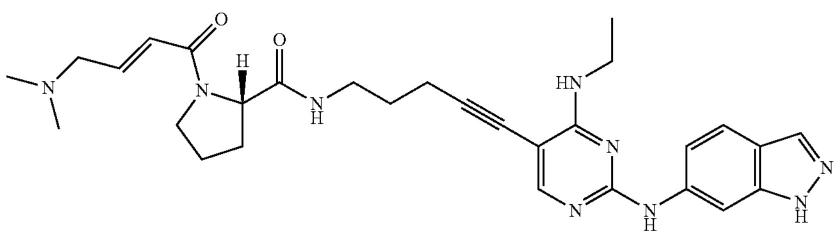 [SMILES: CCNc1nc(Nc2ccc3cn[nH]c3c2)ncc1C#CCCCNC(=O)[C@@H]1CCCN1C(=O)/C=C/CN(C)C] | MS m/z (M + H): 544.5 |

TABLE 172

| Compound No. | Structure | Physicochemical data |
|---|---|---|
| 10-71 | 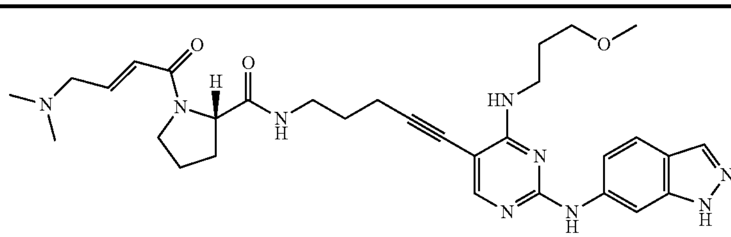 | $^1$H-NMR (CDCl$_3$:CD$_3$OD = 10:1) δ: 8.39 (1H, s), 7.97-7.86 (2H, m), 7.61 (1H, d, J = 8.6 Hz), 7.03 (1H, d, J = 8.6 Hz), 6.91 (1H, dt, J = 15.2, 6.3 Hz), 6.35 (1H, d, J = 15.2 Hz), 4.56 (1H, d, J = 6.6 Hz), 3.78-3.63 (2H, m), 3.63-3.50 (2H, m), 3.50-3.22 (7H, m), 3.18-3.09 (2H, m), 2.58-2.42 (2H, m), 2.29 (6H, s), 2.20-1.64 (8H, m) |

TABLE 172-continued

| Compound No. | Structure | Physicochemical data |
|---|---|---|
| 10-72 | 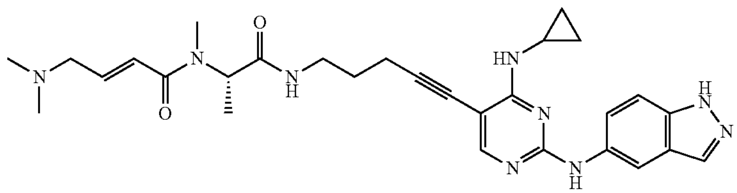 [SMILES: C[C@@H](C(=O)NCCCC#Cc1cnc(Nc2ccc3[nH]ncc3c2)nc1NC1CC1)N(C)C(=O)/C=C/CN(C)C] | MS m/z (M + H): 544.5 |
| 10-73 | 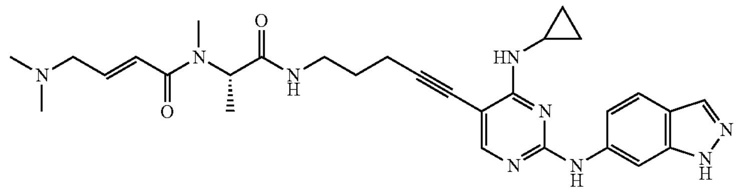 [SMILES: C[C@@H](C(=O)NCCCC#Cc1cnc(Nc2ccc3cn[nH]c3c2)nc1NC1CC1)N(C)C(=O)/C=C/CN(C)C] | — |
| 10-74 | 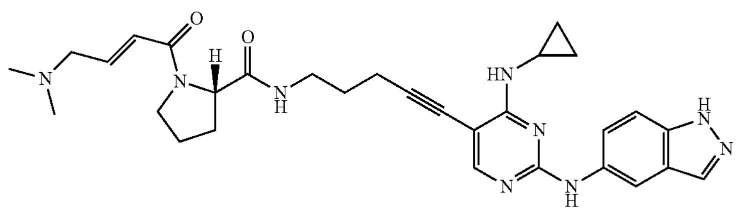 [SMILES: CN(C)C/C=C/C(=O)N1CCC[C@H]1C(=O)NCCCC#Cc1cnc(Nc2ccc3[nH]ncc3c2)nc1NC1CC1] | $^1$H-NMR (CDCl$_3$:CD$_3$OD = 10:1) δ: 8.39 (1H, s), 7.95 (1H, s), 7.91 (1H, s), 7.51 (1H, dd, J = 8.9, 2.0 Hz), 7.44 (1H, d, J = 8.9 Hz), 6.91 (1H, dt, J = 15.2, 6.3 Hz), 6.36 (1H, d, J = 15.2 Hz), 4.59-4.51 (2H, m), 3.80-3.51 (2H, m), 3.50-3.26 (2H, m), 3.18-3.07 (2H, m), 2.90-2.78 (1H, m), 2.47 (2H, t, J = 6.9 Hz), 2.30 (6H, s), 2.22-1.88 (4H, m), 1.87-1.60 (2H, m), 0.96-0.82 (2H, m), 0.78-0.68 (2H, m) |
| 10-75 | 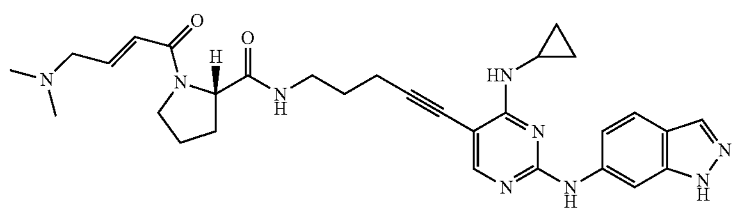 [SMILES: CN(C)C/C=C/C(=O)N1CCC[C@H]1C(=O)NCCCC#Cc1cnc(Nc2ccc3cn[nH]c3c2)nc1NC1CC1] | MS m/z (M + H): 556.5 |

Example 48

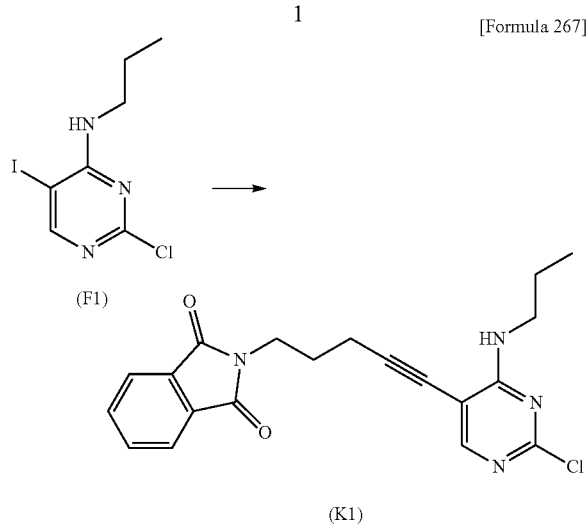

To a solution of 2-chloro-5-iodo-N-propylpyrimidin-4-amine (F1, 1.45 g), N-(4-pentynyl)phthalimide (2.08 g), bis(triphenylphosphine)palladium(II) dichloride (171 mg) and copper(I) iodide (47 mg) in N,N-dimethylformamide (15 mL), triethylamine (3.4 mL) was added at room temperature, and the mixture was stirred at 60° C. for 1 hour and 15 minutes. The reaction mixture was cooled to room temperature, and then water and ethyl acetate were added to the reaction mixture. The organic layer was separated, washed successively with saturated aqueous sodium hydrogencarbonate, water and saturated aqueous sodium chloride, and then dried over anhydrous sodium sulfate, and the solvent was evaporated under reduced pressure. The obtained residue was purified by basic silica gel column chromatography (eluent, 70 to 40% hexane in ethyl acetate) to obtain 2-(5-(2-chloro-4-(propylamino)pyrimidin-5-yl)-4-pentyn-1-yl)isoindoline-1,3-dione (K1, 2.00 g).

[Formula 268]

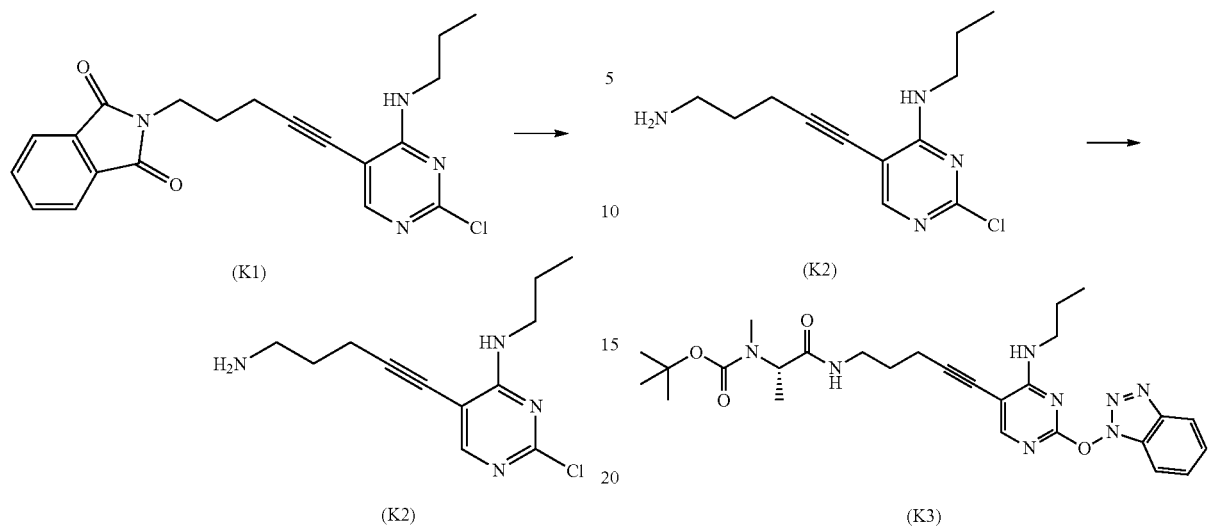

To a solution of 2-(5-(2-chloro-4-(propylamino)pyrimidin-5-yl)-4-pentyn-1-yl)isoindoline-1,3-dione (K1, 2.0 g) in ethanol (15 mL) and tetrahydrofuran (15 mL), hydrazine monohydrate (2.6 mL) was added at room temperature, and the mixture was stirred at the same temperature for 3 hours and 30 minutes. The reaction mixture was cooled on ice, and then neutralized by adding 1.0 mol/L aqueous hydrochloric acid. The insoluble matter was removed by filtration, and then water and ethyl acetate were added. The organic layer was separated, and the aqueous layer was extracted with ethyl acetate. The organic layer and the extract were combined, washed with saturated aqueous sodium hydrogencarbonate, and then dried over anhydrous sodium sulfate, and the solvent was evaporated under reduced pressure. The obtained residue was purified by basic silica gel column chromatography (eluent, 95 to 93% ethyl acetate in methanol) to obtain oily 5-(5-amino-1-pentyn-1-yl)-2-chloro-N-propylpyrimidin-4-amine (K2, 510 mg).

MS m/z (M+H): 253.1

[Formula 269]

To a solution of 5-(5-amino-1-pentyn-1-yl)-2-chloro-N-propylpyrimidin-4-amine (K2, 510 mg), N-Boc-N-methyl-L-alanine (493 mg), 1-ethyl-3-(3-dimethylaminopropyl)carbodiimide hydrochloride (1.16 g) and 1-hydroxybenzotriazole monohydrate (930 mg) in N,N-dimethylformamide (10 mL), N,N-diisopropylethylamine (690 μL) was added at room temperature, and the mixture was stirred at the same temperature for 12 hours. To the reaction mixture, water and ethyl acetate were added. The organic layer was separated, and the aqueous layer was extracted with ethyl acetate. The organic layer and the extract were combined, washed successively with water and saturated aqueous sodium chloride, and then dried over anhydrous sodium sulfate, and the solvent was evaporated under reduced pressure. The obtained residue was purified by silica gel column chromatography (eluent, 70 to 40% hexane in ethyl acetate) to obtain (S)-tert-butyl (1-((5-(2-((1H-benzo[d][1,2,3]triazol-1-yl)oxy)-4-(propylamino)pyrimidin-5-yl)-4-pentyn-1-yl)amino)-1-oxopropan-2-yl)(methyl)carbamate (K3, 380 mg).

MS m/z (M+H): 537.3

[Formula 270]

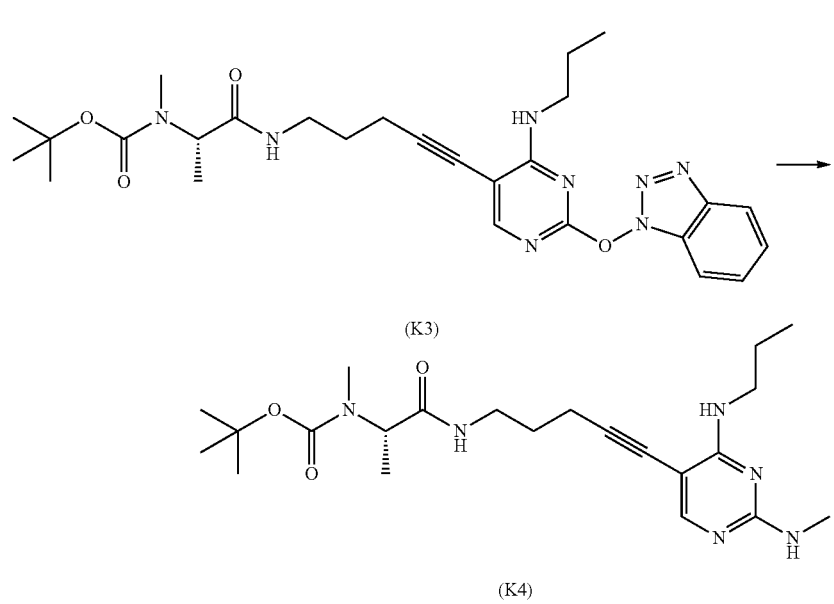

To (S)-tert-butyl (1-((5-(2-((1H-benzo[d][1,2,3]triazol-1-yl)oxy)-4-(propylamino)pyrimidin-5-yl)-4-pentyn-1-yl)amino)-1-oxopropan-2-yl)(methyl)carbamate (K3, 50 mg), a 2.0 mol/L solution of methylamine in tetrahydrofuran (1 mL) was added at room temperature, the reaction vessel was sealed, and then the mixture was stirred at 50° C. for 5 hours by using a microwave reaction system. The reaction mixture was cooled to room temperature, and then the solvent was evaporated under reduced pressure. The obtained residue was purified by silica gel column chromatography (eluent, 40 to 0% hexane in ethyl acetate) to obtain oily (S)-tert-butyl methyl(1-((5-(2-(methylamino)-4-(propylamino)pyrimidin-5-yl)-4-pentyn-1-yl)amino)-1-oxopropan-2-yl)carbamate (K4, 35 mg).

MS m/z (M+H): 433.3

5 [Formula 271]

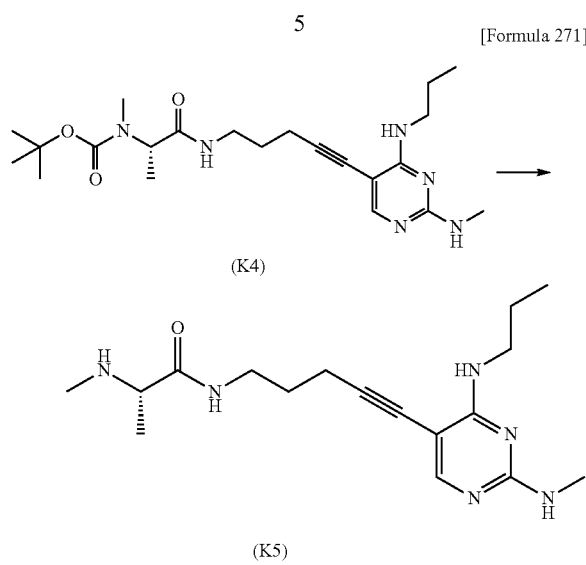

(K4)

(K5)

To a solution of (S)-tert-butyl methyl(1-((5-(2-(methylamino)-4-(propylamino)pyrimidin-5-yl)-4-pentyn-1-yl)amino)-1-oxopropan-2-yl)carbamate (K4, 35 mg) in 1,4-dioxane (1 mL), a 4.0 mol/L solution of hydrochloric acid in 1,4-dioxane (1 mL) was added at room temperature, and the mixture was stirred at the same temperature for 30 minutes. The solvent was evaporated under reduced pressure. The obtained solid matter was dried under reduced pressure to obtain (S)-2-(methylamino)-N-(5-(2-(methylamino)-4-(propylamino)pyrimidin-5-yl)-4-pentyn-1-yl)propanamide (K5) dihydrochloride.

6 [Formula 272]

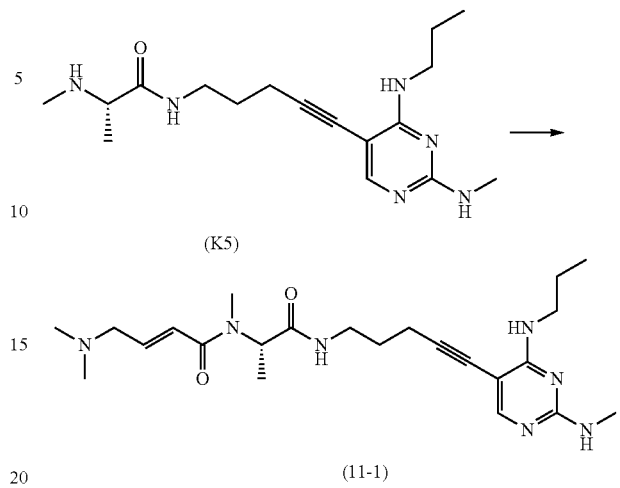

(K5)

(11-1)

To a solution of 4-dimethylaminocrotonic acid hydrochloride (67 mg) and N-methylmorpholine (90 μL) in N,N-dimethylformamide (1 mL), isobutyl chloroformate (43 μL) was added under ice cooling, a solution of (S)-2-(methylamino)-N-(5-(2-(methylamino)-4-(propylamino)pyrimidin-5-yl)-4-pentyn-1-yl)propanamide (K5) dihydrochloride obtained above in N,N-dimethylformamide (2 mL) was further added to the mixture, and the mixture was stirred at the same temperature for 30 minutes. The solvent was evaporated under reduced pressure. The obtained residue was purified by basic silica gel column chromatography (eluent, 99 to 96% ethyl acetate in methanol) to obtain oily (S,E)-4-(dimethylamino)-N-methyl-N-(1-((5-(2-(methylamino)-4-(propylamino)pyrimidin-5-yl)-4-pentyn-1-yl)amino)-1-oxopropan-2-yl)-2-butenamide (11-1, 9 mg).

$^1$H-NMR (CDCl$_3$) δ: 7.86 (1H, s), 6.94 (1H, dt, J=15.2, 6.1 Hz), 6.50 (1H, brs), 6.41 (1H, d, J=15.2 Hz), 5.90 (1H, brs), 5.18 (1H, q, J=7.3 Hz), 5.04 (1H, brs), 3.47-3.37 (4H, m), 3.10 (2H, d, J=6.1 Hz), 2.98-2.94 (6H, m), 2.42 (2H, t, J=6.6 Hz), 2.27 (6H, s), 1.78-1.59 (4H, m), 1.35 (3H, d, J=7.3 Hz), 0.96 (3H, t, J=7.3 Hz)

Example 49

1

By using (S)-tert-butyl (1-((5-(2-((1H-benzo[d][1,2,3]triazol-1-yl)oxy)-4-(propylamino)pyrimidin-5-yl)-4-pentyn-1-yl)amino)-1-oxopropan-2-yl)(methyl)carbamate (K3), Intermediates (K6) to (K13), (K22) and (K23) were obtained in the same manner as that of Example 48, (4).

TABLE 173

| Compound No. | Structure | Physicochemical data |
|---|---|---|
| K6 | 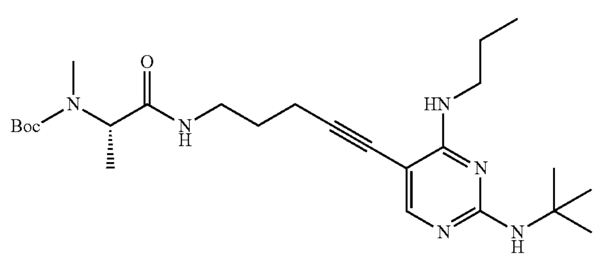 [SMILES: CCCNc1nc(NC(C)(C)C)ncc1C#CCCCNC(=O)[C@H](C)N(C)C(=O)OC(C)(C)C] | MS m/z (M + H): 475.4 |

TABLE 173-continued

| Compound No. | Structure | Physicochemical data |
|---|---|---|
| K7 | 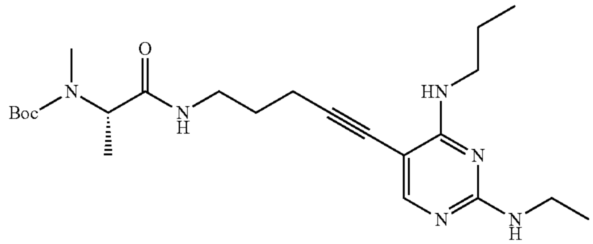 [SMILES: CCCNc1nc(NCC)ncc1C#CCCCNC(=O)[C@H](C)N(C)C(=O)OC(C)(C)C] | — |
| K8 | 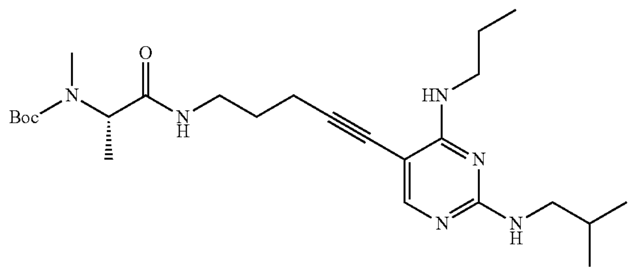 [SMILES: CCCNc1nc(NCC(C)C)ncc1C#CCCCNC(=O)[C@H](C)N(C)C(=O)OC(C)(C)C] | — |
| K9 | 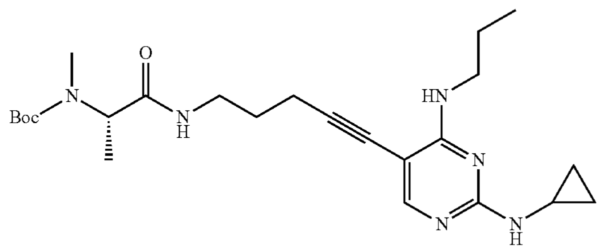 [SMILES: CCCNc1nc(NC2CC2)ncc1C#CCCCNC(=O)[C@H](C)N(C)C(=O)OC(C)(C)C] | — |
| K10 | 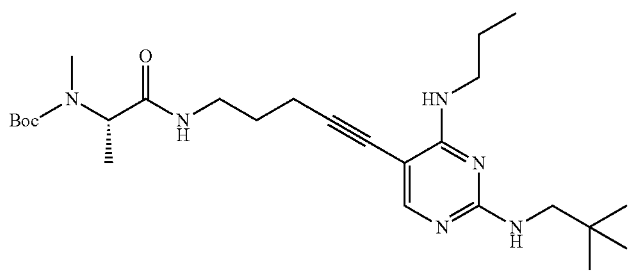 [SMILES: CCCNc1nc(NCC(C)(C)C)ncc1C#CCCCNC(=O)[C@H](C)N(C)C(=O)OC(C)(C)C] | — |
| K11 | 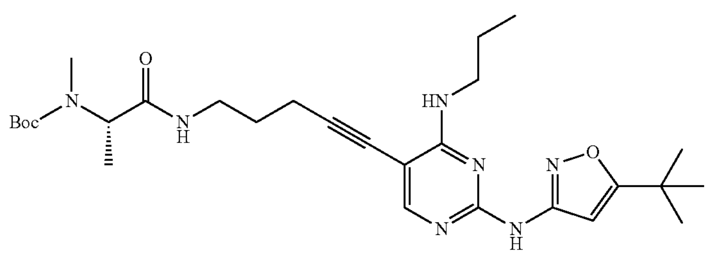 [SMILES: CCCNc1nc(Nc2cc(C(C)(C)C)on2)ncc1C#CCCCNC(=O)[C@H](C)N(C)C(=O)OC(C)(C)C] | — |
| K12 | 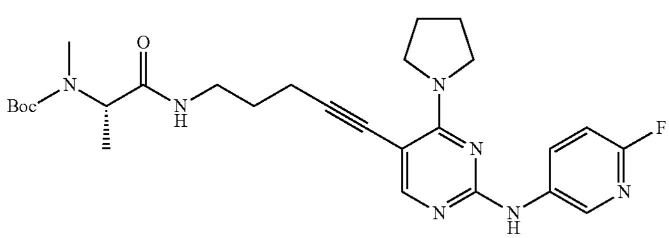 [SMILES: C[C@@H](C(=O)NCCCC#Cc1cnc(Nc2ccc(F)nc2)nc1N1CCCC1)N(C)C(=O)OC(C)(C)C] | — |

TABLE 173-continued

| Compound No. | Structure | Physicochemical data |
|---|---|---|
| K13 | 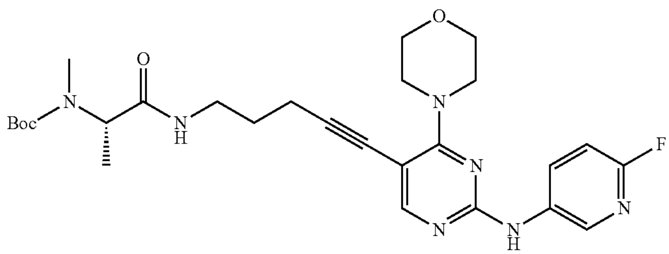 [SMILES: C[C@@H](C(=O)NCCCC#Cc1cnc(Nc2ccc(F)nc2)nc1N1CCOCC1)N(C)C(=O)OC(C)(C)C] | — |
| K22 | 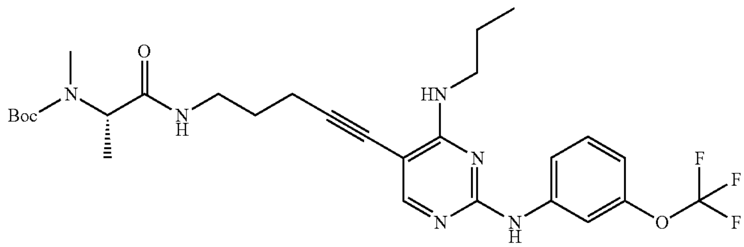 [SMILES: CCCNc1nc(Nc2cccc(OC(F)(F)F)c2)ncc1C#CCCCNC(=O)[C@H](C)N(C)C(=O)OC(C)(C)C] | MS m/z (M + H): 579.4 |
| K23 | 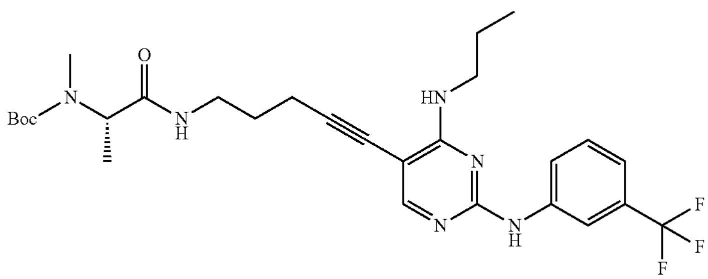 [SMILES: CCCNc1nc(Nc2cccc(C(F)(F)F)c2)ncc1C#CCCCNC(=O)[C@H](C)N(C)C(=O)OC(C)(C)C] | MS m/z (M + H): 563.4 |

2

In the same manner as that of Example 48, (5), Intermediates (K14) to (K21), (K24) and (K25) were obtained.

TABLE 174

| Compound No. | Structure | Physicochemical data |
|---|---|---|
| K14 | 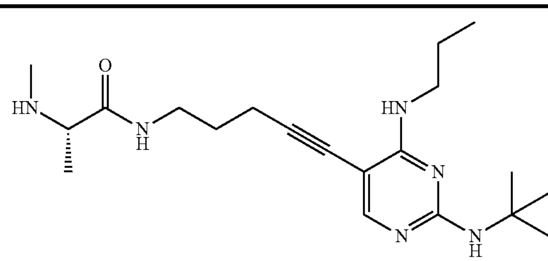 | — |
| K15 | 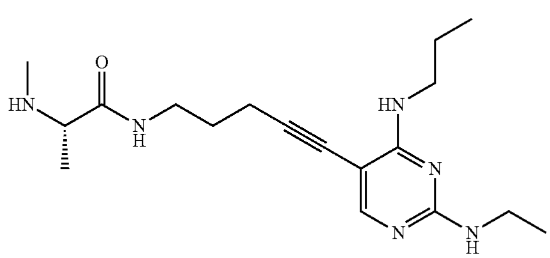 [SMILES: CCCNc1nc(NCC)ncc1C#CCCCNC(=O)[C@H](C)NC] | — |

TABLE 174-continued
| Compound No. | Structure | Physicochemical data |
|---|---|---|
| K16 | 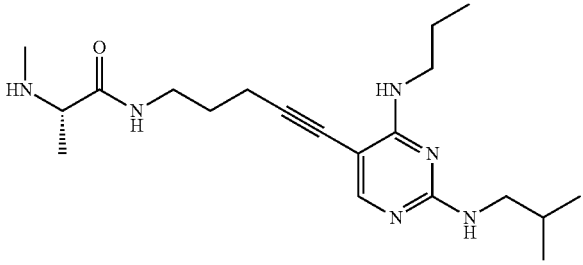 [SMILES: CCCNc1nc(NCC(C)C)ncc1C#CCCCNC(=O)[C@H](C)NC] | — |
| K17 | 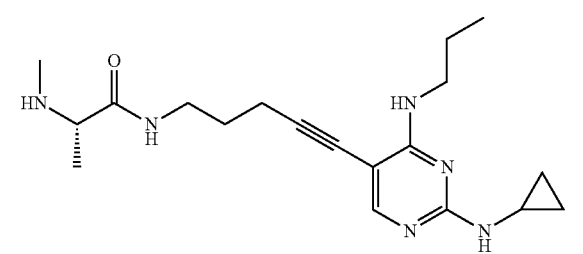 [SMILES: CCCNc1nc(NC2CC2)ncc1C#CCCCNC(=O)[C@H](C)NC] | — |
| K18 | 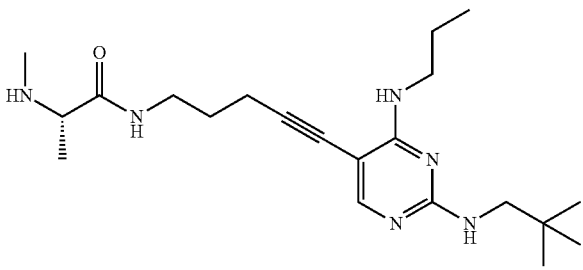 [SMILES: CCCNc1nc(NCC(C)(C)C)ncc1C#CCCCNC(=O)[C@H](C)NC] | — |
| K19 | 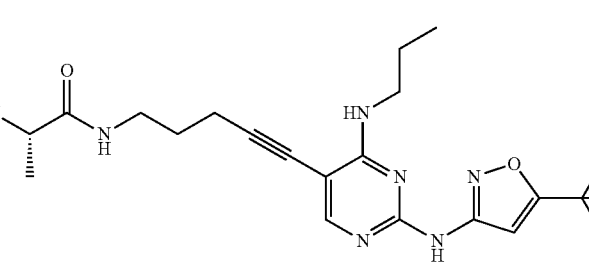 | — |
| K20 | 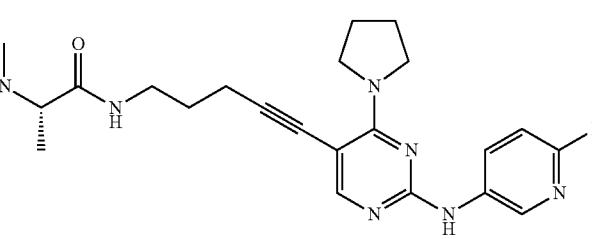 | — |
| K21 | 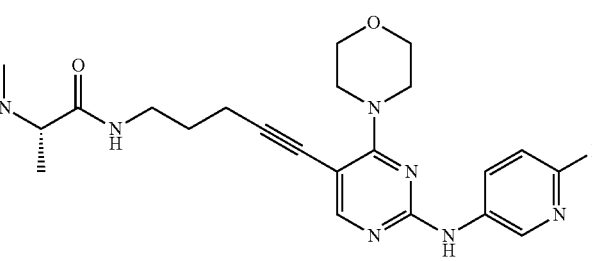 | — |

TABLE 174-continued

| Compound No. | Structure | Physicochemical data |
|---|---|---|
| K24 | 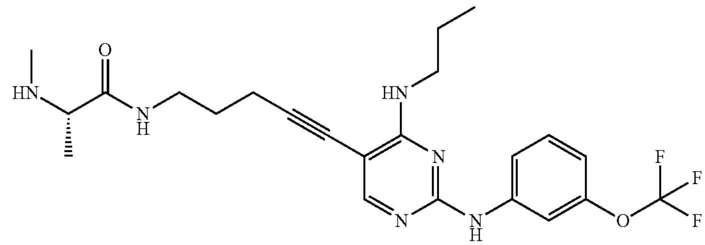 [SMILES: CCCNc1nc(Nc2cccc(OC(F)(F)F)c2)ncc1C#CCCCNC(=O)[C@H](C)NC] | — |
| K25 | 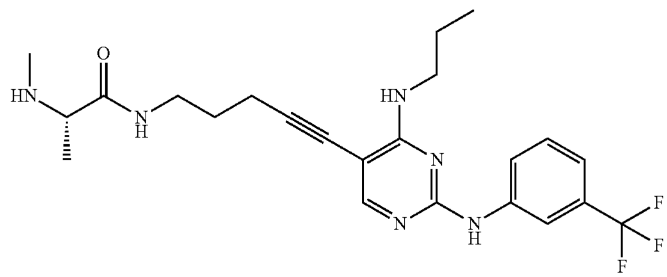 [SMILES: CCCNc1nc(Nc2cccc(C(F)(F)F)c2)ncc1C#CCCCNC(=O)[C@H](C)NC] | — |

In the same manner as that of Example 48, (6), Compounds (11-2) to (11-11) were obtained.

TABLE 175

| Compound No. | Structure | Physicochemical data |
|---|---|---|
| 11-2 | 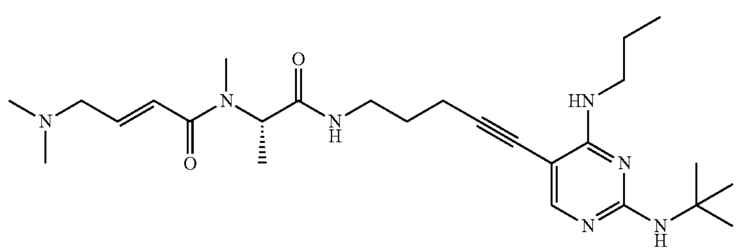 [SMILES: CCCNc1nc(NC(C)(C)C)ncc1C#CCCCNC(=O)[C@H](C)N(C)C(=O)/C=C/CN(C)C] | $^1$H-NMR (CDCl$_3$) δ: 7.80 (1H, s), 6.89 (1H, dt, J = 15.2, 5.6 Hz), 6.52 (1H, brs), 6.42 (1H, d, J = 15.2 Hz), 5.92 (1H, brs), 5.18 (1H, q, J = 7.0 Hz), 5.09 (1H, brs), 3.47-3.37 (4H, m), 3.00 (2H, d, J = 5.6 Hz), 2.98 (3H, s), 2.41 (2H, t, J = 6.6 Hz), 2.26 (6H, s), 1.77-1.59 (4H, m), 1.43 (9H, s), 1.35 (3H, d, J = 7.0 Hz), 0.96 (3H, t, J = 7.3 Hz) |
| 11-3 | 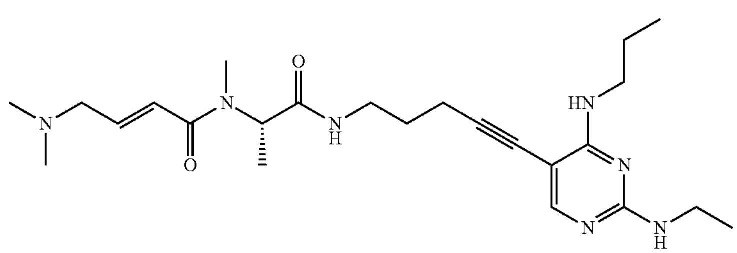 [SMILES: CCCNc1nc(NCC)ncc1C#CCCCNC(=O)[C@H](C)N(C)C(=O)/C=C/CN(C)C] | $^1$H-NMR (CDCl$_3$) δ: 7.85 (1H, s), 6.93 (1H, dt, J = 15.2, 5.9 Hz), 6.52 (1H, brs), 6.42 (1H, d, J = 15.2 Hz), 5.89 (1H, brs), 5.18 (1H, q, J = 7.0 Hz), 5.02 (1H, brs), 3.48-3.36 (6H, m), 3.10 (2H, d, J = 5.9 Hz), 2.98 (3H, s), 2.41 (2H, t, J = 7.0 Hz), 2.27 (6H, s), 1.78-1.59 (4H, m), 1.35 (3H, d, J = 7.0 Hz), 1.20 (3H, t, J = 7.3 Hz), 0.96 (3H, t, J = 7.3 Hz) |

TABLE 175-continued

| Compound No. | Structure | Physicochemical data |
|---|---|---|
| 11-4 | 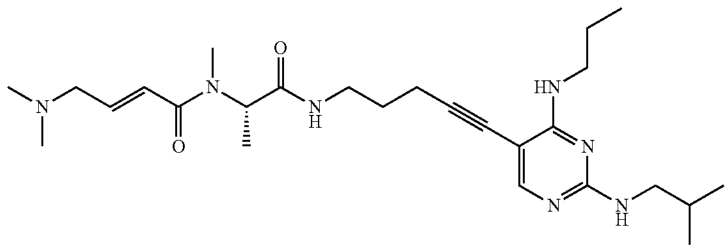 [SMILES: CCCNc1nc(NCC(C)C)ncc1C#CCCCNC(=O)[C@H](C)N(C)C(=O)/C=C/CN(C)C] | ¹H-NMR (CDCl₃) δ: 7.84 (1H, s), 6.93 (1H, dt, J = 15.2, 5.9 Hz), 6.51 (1H, brs), 6.42 (1H, d, J = 15.2 Hz), 5.91 (1H, brs), 5.18 (2H, q, J = 7.0 Hz), 3.46-3.37 (4H, m), 3.20 (2H, t, J = 6.6 Hz), 3.10 (2H, d, J = 5.9 Hz), 2.98 (3H, s), 2.42 (2H, t, J = 6.6 Hz), 2.27 (6H, s), 1.91-1.59 (5H, m), 1.35 (3H, d, J = 7.0 Hz), 0.96 (9H, t, J = 6.6 Hz) |
| 11-5 | 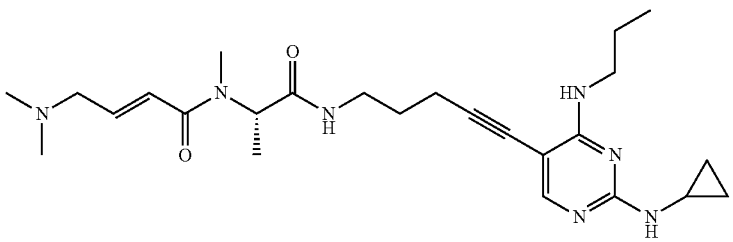 [SMILES: CCCNc1nc(NC2CC2)ncc1C#CCCCNC(=O)[C@H](C)N(C)C(=O)/C=C/CN(C)C] | ¹H-NMR (CDCl₃) δ: 7.91 (1H, s), 6.95 (1H, dt, J = 15.2, 5.9 Hz), 6.53 (1H, brs), 6.42 (1H, d, J = 15.2 Hz), 5.88 (1H, brs), 5.21-5.12 (2H, m), 3.45-3.37 (4H, m), 3.09 (2H, d, J = 5.9 Hz), 3.00 (3H, s), 2.78-2.70 (1H, m), 2.42 (2H, t, J = 6.6 Hz), 2.27 (6H, s), 1.78-1.59 (4H, m), 1.35 (3H, d, J = 7.3 Hz), 0.95 (3H, t, J = 7.6 Hz), 0.76 (2H, dt, J = 7.0, 4.0 Hz), 0.52 (2H, dt, J = 7.0, 4.0 Hz) |
| 11-6 | 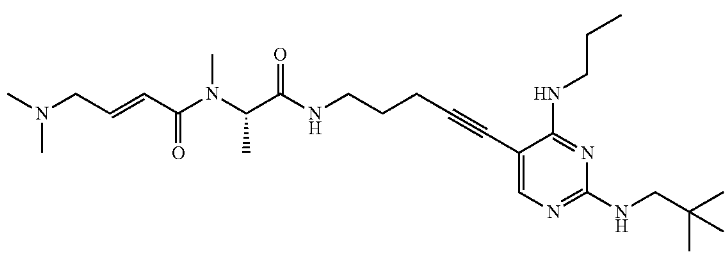 [SMILES: CCCNc1nc(NCC(C)(C)C)ncc1C#CCCCNC(=O)[C@H](C)N(C)C(=O)/C=C/CN(C)C] | ¹H-NMR (CDCl₃) δ: 7.82 (1H, s), 6.93 (1H, dt, J = 15.2, 5.9 Hz), 6.55 (1H, brs), 6.42 (1H, d, J = 15.2 Hz), 5.93 (1H, brs), 5.37 (1H, brs), 5.18 (1H, q, J = 6.8 Hz), 3.46-3.37 (4H, m), 3.24 (2H, d, J = 6.6 Hz), 3.10 (2H, d, J = 5.9 Hz), 2.97 (3H, s), 2.42 (2H, t, J = 6.6 Hz), 2.27 (6H, s), 1.76-1.59 (4H, m), 1.35 (3H, d, J = 6.8 Hz), 0.96 (3H, t, J = 7.6 Hz), 0.94 (9H, s) |

TABLE 176

| Compound No. | Structure | Physicochemical data |
|---|---|---|
| 11-7 | 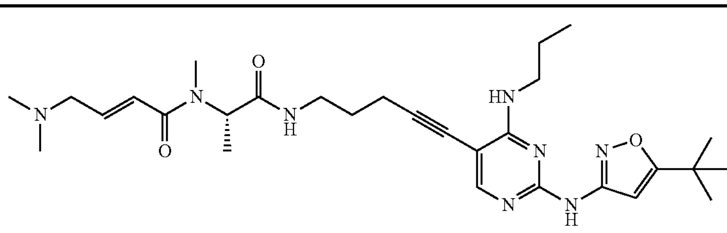 | ¹H-NMR (CDCl₃) δ: 8.02 (1H, s), 6.99-6.88 (2H, m), 6.82 (1H, s), 6.54 (1H, brs), 6.41 (1H, dd, J = 15.2, 5.3 Hz), 6.33 (1H, brs), 5.22-5.13 (1H, m), 3.52-3.43 (4H, m), 3.10 (2H, d, J = 6.6 Hz), 2.99 (3H, s), 2.45 (2H, t, J = 6.6 Hz), 2.27 (6H, s), 1.77-1.65 (7H, m), 1.35 (9H, s), 0.98 (3H, t, J = 7.6 Hz) |

TABLE 176-continued

| Compound No. | Structure | Physicochemical data |
|---|---|---|
| 11-8 | 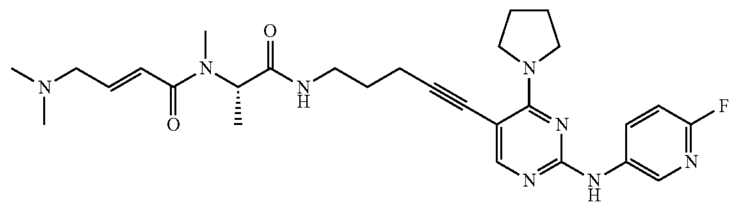 [SMILES: C[C@@H](C(=O)NCCCC#Cc1cnc(Nc2ccc(F)nc2)nc1N1CCCC1)N(C)C(=O)/C=C/CN(C)C] | ¹H-NMR (CDCl₃) δ: 8.48 (1H, s), 8.14-8.08 (1H, m), 7.99 (1H, s), 7.81 (1H, brs), 6.97-6.82 (2H, m), 6.71 (1H, brs), 6.42 (1H, d, J = 15.2 Hz), 5.18 (1H, q, J = 7.3 Hz), 3.80 (4H, brs), 3.43-3.26 (2H, m), 3.10 (2H, d, J = 5.9 Hz), 3.00 (3H, s), 2.48-2.37 (2H, m), 2.30 (6H, s), 1.93 (4H, brs), 1.79-1.70 (2H, m), 1.35 (3H, d, J = 7.3 Hz) |
| 11-9 | 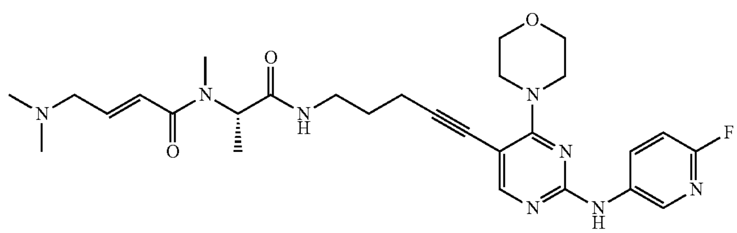 [SMILES: C[C@@H](C(=O)NCCCC#Cc1cnc(Nc2ccc(F)nc2)nc1N1CCOCC1)N(C)C(=O)/C=C/CN(C)C] | ¹H-NMR (CDCl₃) δ: 8.39 (1H, s), 8.11-8.00 (2H, m), 7.91-7.78 (1H, m), 6.97-6.82 (2H, m), 6.74 (1H, s), 6.42 (1H, d, J = 15.2 Hz), 5.28-5.11 (1H, m), 4.06-3.87 (4H, m), 3.87-3.70 (4H, m), 3.47-3.20 (2H, m), 3.10 (2H, dd, J = 5.9, 1.3 Hz), 3.00 (3H, s), 2.54-2.36 (2H, m), 2.26 (6H, s), 1.83-1.69 (2H, m), 1.36 (3H, d, J = 7.3 Hz) |
| 11-10 | 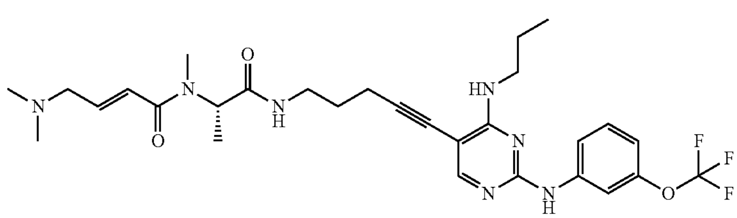 [SMILES: CCCNc1nc(Nc2cccc(OC(F)(F)F)c2)ncc1C#CCCCNC(=O)[C@H](C)N(C)C(=O)/C=C/CN(C)C] | ¹H-NMR (CDCl₃) δ: 8.39 (1H, s), 7.99-7.94 (1H, m), 7.87 (1H, s), 7.54 (1H, d, J = 8.6 Hz), 7.37 (1H, t, J = 7.9 Hz), 7.22 (1H, d, J = 7.9 Hz), 6.94 (1H, dt, J = 15.1, 6.0 Hz), 6.77-6.68 (1H, m), 6.43 (1H, d, J = 15.1 Hz), 6.28 (1H, t, J = 5.6 Hz), 5.21 (1H, q, J = 6.5 Hz), 3.59-3.41 (4H, m), 3.10 (2H, d, J = 6.0 Hz), 3.01 (3H, s), 2.44 (2H, t, J = 6.6 Hz), 2.26 (6H, s), 1.79-1.65 (4H, m), 1.36 (3H, d, J = 6.5 Hz), 0.98 (3H, t, J = 6.9 Hz) |
| 11-11 | 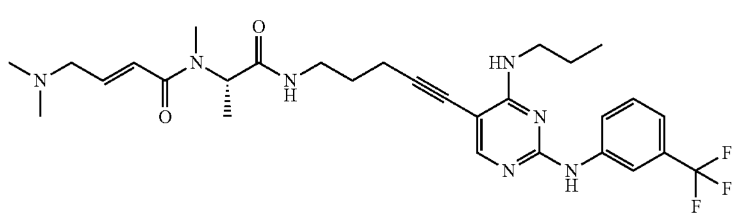 [SMILES: CCCNc1nc(Nc2cccc(C(F)(F)F)c2)ncc1C#CCCCNC(=O)[C@H](C)N(C)C(=O)/C=C/CN(C)C] | ¹H-NMR (CDCl₃) δ: 8.09-7.89 (2H, m), 7.60-7.35 (1H, m), 7.25 (2H, s), 7.03-6.88 (1H, m), 6.84 (1H, brs), 6.62 (1H, brs), 6.43 (1H, d, J = 15.2 Hz), 6.27 (1H, brs), 5.22-5.19 (1H, m), 3.62-3.37 (4H, m), 3.18-3.07 (2H, m), 3.00 (3H, s), 2.44 (2H, brs), 2.27 (6H, s), 2.14-1.62 (4H, m), 1.37 (3H, d, J = 6.6 Hz), 1.00 (3H, t, J = 6.9 Hz) |

Example 50

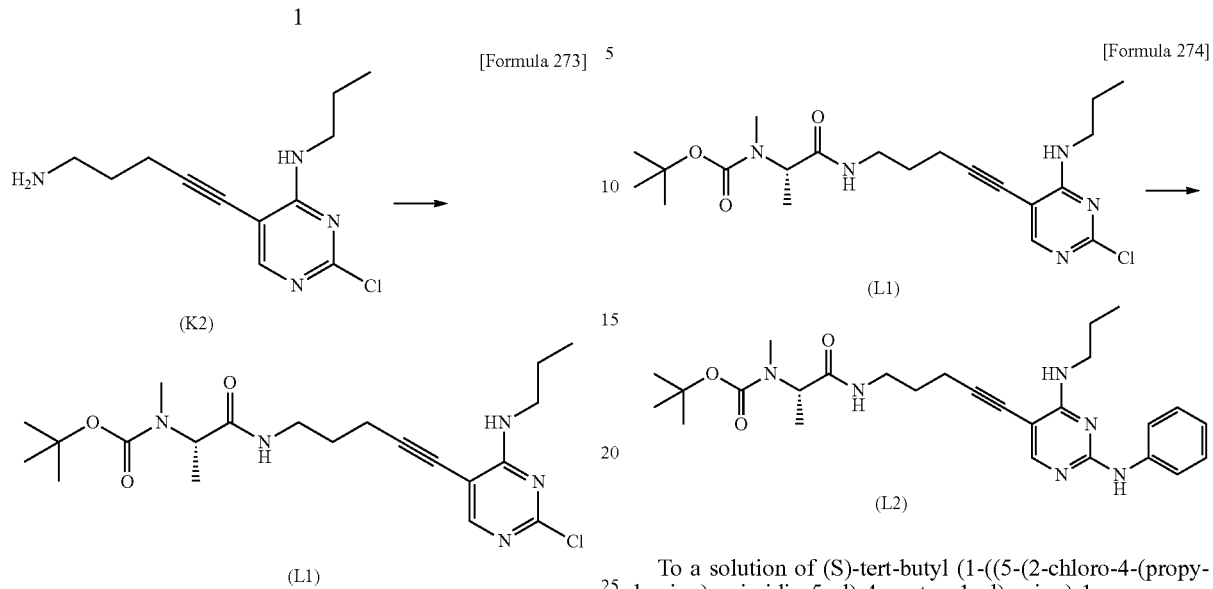

(K2)

(L1)

To a solution of 5-(5-amino-1-pentyn-1-yl)-2-chloro-N-propylpyrimidin-4-amine (K2, 505 mg) and N-Boc-N-methyl-L-alanine (270 mg) in N,N-dimethylformamide (5 mL), 1-ethyl-3-(3-dimethylaminopropyl)carbodiimide hydrochloride (635 mg) and N,N-diisopropylethylamine (378 µL) were added at room temperature, and the mixture was stirred overnight at the same temperature. To the reaction mixture, saturated aqueous sodium carbonate and ethyl acetate were added. The organic layer was separated, washed with water, and then dried over anhydrous sodium sulfate, and the solvent was evaporated under reduced pressure. The obtained residue was purified by basic silica gel column chromatography (eluent, 50% hexane/50% ethyl acetate) to obtain (S)-tert-butyl (1-((5-(2-chloro-4-(propylamino)pyrimidin-5-yl)-4-pentyn-1-yl)amino)-1-oxopropan-2-yl)(methyl)carbamate (L1, 660 mg).

MS m/z (M+H): 438.3

(L1)

(L2)

To a solution of (S)-tert-butyl (1-((5-(2-chloro-4-(propylamino)pyrimidin-5-yl)-4-pentyn-1-yl)amino)-1-oxopropan-2-yl)(methyl)carbamate (L1, 57 mg) and (1S)-(+)-10-camphorsulfonic acid (150 mg) in N-methylpyrrolidone (1 mL), aniline (60 µL) was added at room temperature, and the mixture was stirred at 60° C. for 2 hours and 30 minutes. The reaction mixture was cooled to room temperature, and then saturated aqueous sodium hydrogencarbonate and ethyl acetate were added to the reaction mixture. The organic layer was separated, and the aqueous layer was extracted with ethyl acetate. The organic layer and the extract were combined, washed successively with water and saturated aqueous sodium chloride, and then dried over anhydrous sodium sulfate, and the solvent was evaporated under reduced pressure. The obtained residue was purified by silica gel column chromatography (eluent, 50 to 25% hexane in ethyl acetate) to obtain oily (S)-tert-butyl methyl(1-oxo-1-((5-(2-(phenylamino)-4-(propylamino)pyrimidin-5-yl)-4-pentyn-1-yl)amino)propan-2-yl)carbamate (L2, 52 mg).

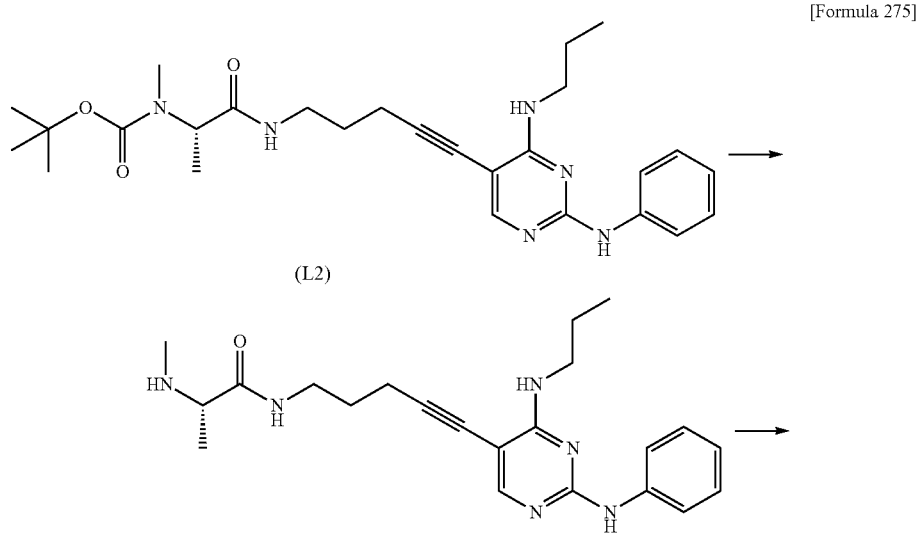

(L2)

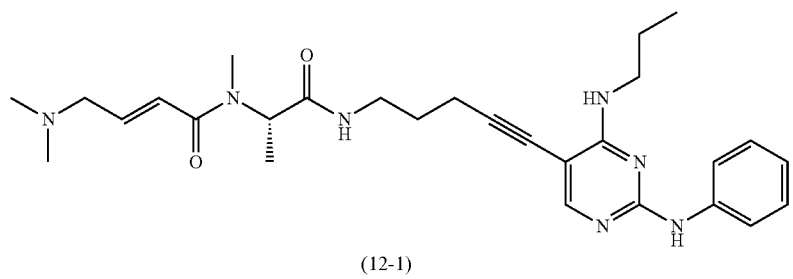

(12-1)

By using (S)-tert-butyl methyl(1-oxo-1-((5-(2-(phenylamino)-4-(propylamino)pyrimidin-5-yl)-4-pentyn-1-yl)amino)propan-2-yl)carbamate (L2), (S,E)-4-(dimethylamino)-N-methyl-N-(1-oxo-1-((5-(2-(phenylamino)-4-(propylamino)pyrimidin-5-yl)-4-pentyn-1-yl)amino)propan-2-yl)-2-butenamide (12-1) was obtained in the same manner as that of Example 35, (6) and (7).

$^1$H-NMR (CDCl$_3$) δ: 7.95 (1H, s), 7.64 (2H, d, J=7.3 Hz), 7.34-7.27 (2H, m), 7.01-6.80 (2H, m), 6.63 (1H, t, J=5.6 Hz), 6.42 (1H, d, J=15.2 Hz), 6.18 (1H, t, J=5.6 Hz), 5.19 (1H, q, J=6.6 Hz), 3.53-3.40 (4H, m), 3.11-3.07 (2H, m), 2.99 (3H, s), 2.72 (1H, brs), 2.44 (2H, t, J=6.6 Hz), 2.26 (6H, s), 1.79-1.65 (4H, m), 1.36 (3H, d, J=6.6 Hz), 0.99 (3H, t, J=7.3 Hz)

4

[Formula 276]

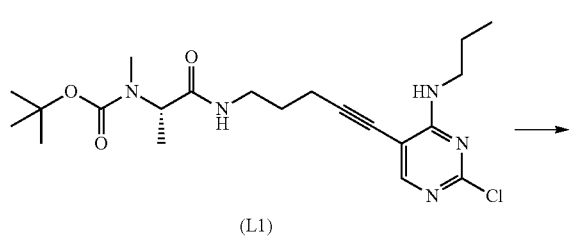

(L1)

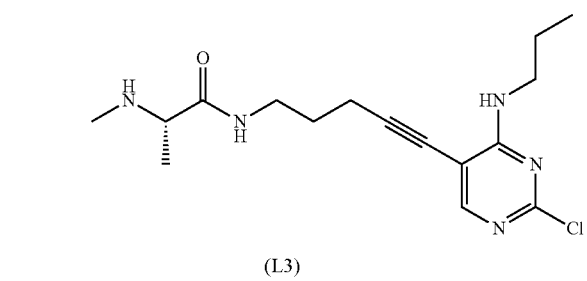

(L3)

To a solution of (S)-tert-butyl (1-((5-(2-chloro-4-(propylamino)pyrimidin-5-yl)-4-pentyn-1-yl)amino)-1-oxopropan-2-yl)(methyl)carbamate (L1, 910 mg) in 1,4-dioxane (10 mL), a 4.0 mol/L solution of hydrochloric acid in dioxane (7 mL) was added at room temperature, and the mixture was stirred at the same temperature for 1 hour. The solvent was evaporated under reduced pressure to obtain (S)—N-(5-(2-chloro-4-(propylamino)pyrimidin-5-yl)-4-pentyn-1-yl)-2-(methylamino)propanamide (L3) hydrochloride.

MS m/z (M+H): 338.2

5

[Formula 277]

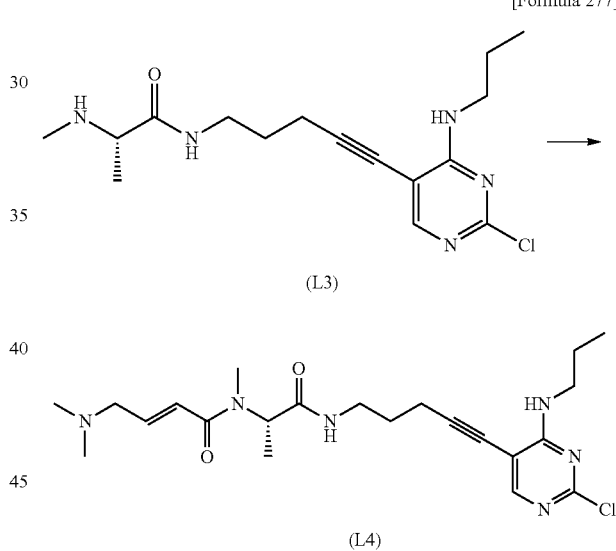

(L3)

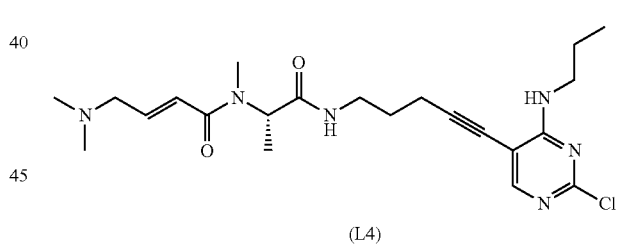

(L4)

To a solution of 4-dimethylaminocrotonic acid hydrochloride (1.0 g) in N,N-dimethylformamide (10 mL), N-methylmorpholine (2.3 mL) and isobutyl chloroformate (0.8 mL) were added under ice cooling, a solution of (S)—N-(5-(2-chloro-4-(propylamino)pyrimidin-5-yl)-4-pentyn-1-yl)-2-(methylamino)propanamide (L3) hydrochloride obtained above in N,N-dimethylformamide was further added, and the mixture was stirred at the same temperature for 2 hours. The solvent was evaporated under reduced pressure, and the obtained residue was purified by basic silica gel column chromatography (eluent, 100 to 90% ethyl acetate in methanol) to obtain (S,E)-N-(1-((5-(2-chloro-4-(propylamino)pyrimidin-5-yl)-4-pentyn-1-yl)amino)-1-oxopropan-2-yl)-4-(dimethylamino)-N-methyl-2-butenamide (L4, 610 mg).

MS m/z (M+H): 449.4

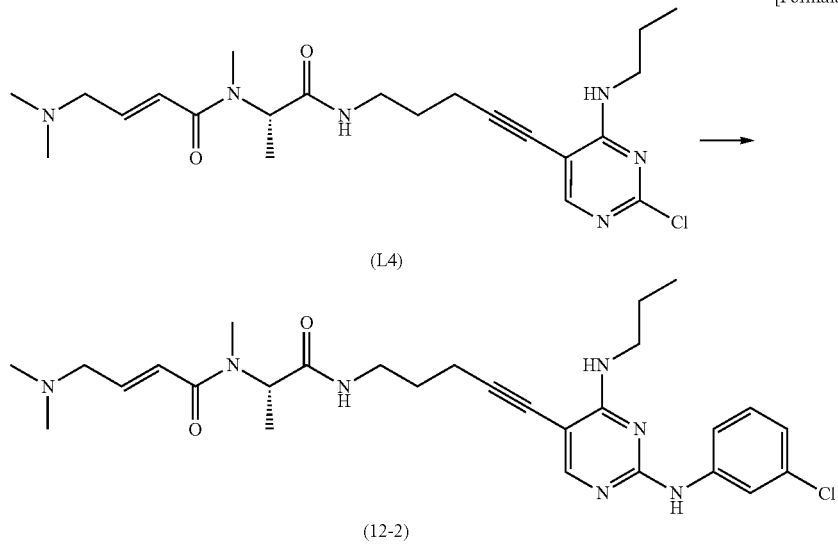

[Formula 278]

To a solution of (S,E)-N-(1-((5-(2-chloro-4-(propylamino)pyrimidin-5-yl)-4-pentyn-1-yl)amino)-1-oxopropan-2-yl)-4-(dimethylamino)-N-methyl-2-butenamide (L4, 20 mg) and 3-chloroaniline (28 mg) in tetrahydrofuran (3 mL), (1S)-(+)-10-camphorsulfonic acid (52 mg) was added at room temperature, and the mixture was stirred at 70° C. for 2 hours. The reaction mixture was cooled to room temperature, and then diethylamine was added until the mixture became basic. The solvent was evaporated under reduced pressure, and the obtained residue was purified by basic silica gel column chromatography to obtain (S,E)-N-(1-((5-(2-((3-chlorophenyl)amino)-4-(propylamino)pyrimidin-5-yl)-4-pentyn-1-yl)amino)-1-oxopropan-2-yl)-4-(dimethylamino)-N-methyl-2-butenamide (12-2, 4 mg).

$^1$H-NMR (CDCl$_3$) δ: 8.03 (1H, s), 7.95 (1H, s), 7.24-7.21 (1H, m), 7.02-6.97 (3H, m), 6.52-6.44 (2H, m), 6.28 (1H, brs), 5.21-5.18 (1H, m), 3.50-3.47 (4H, m), 3.13 (3H, d, J=7.9 Hz), 2.99 (3H, s), 2.46-2.42 (2H, m), 2.27 (6H, s), 1.74-1.66 (4H, m), 1.39-1.35 (3H, m), 1.01 (3H, t, J=7.3 Hz)

Example 51

1

By using (S)-tert-butyl (1-((5-(2-chloro-4-(propylamino)pyrimidin-5-yl)-4-pentyn-1-yl)amino)-1-oxopropan-2-yl)(methyl)carbamate (L1), Compounds (12-3) to (12-12) were obtained in the same manner as that of Example 50.

TABLE 177

| Compound No. | Structure | Physicochemical data |
|---|---|---|
| 12-3 | 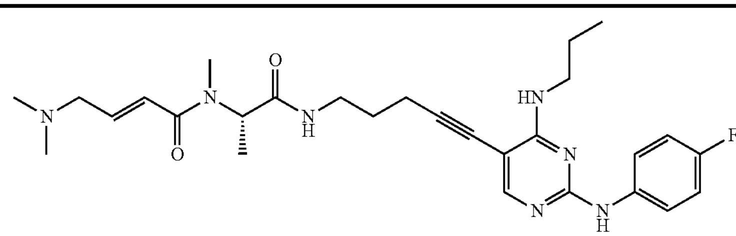 | $^1$H-NMR (CDCl$_3$) δ: 7.95 (1H, brs), 7.59-7.54 (2H, m), 7.12 (1H, brs), 7.06-6.95 (2H, m), 6.58-6.40 (2H, m), 6.17 (1H, brs), 5.92 (1H, d, J = 15.2 Hz), 5.20-5.17 (1H, m), 3.55-3.33 (4H, m), 3.10 (2H, d, J = 5.3 Hz), 2.99 (3H, s), 2.44 (2H, t, J = 6.3 Hz), 2.27 (6H, s), 1.77-1.63 (4H, m), 1.35 (3H, d, J = 7.3 Hz), 0.98 (3H, t, J = 7.6 Hz) |
| 12-4 | 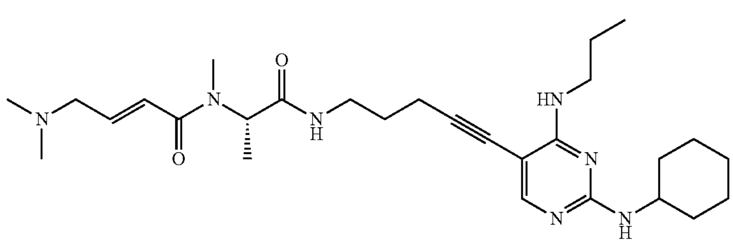 [SMILES: CCCNc1nc(NC2CCCCC2)ncc1C#CCCCNC(=O)[C@H](C)N(C)C(=O)/C=C/CN(C)C] | $^1$H-NMR (CDCl$_3$) δ: 7.84 (1H, s), 6.93 (1H, dt, J = 15.2, 5.9 Hz), 6.51 (1H, brs), 6.42 (1H, d, J = 15.2 Hz), 5.91 (1H, brs), 5.18 (1H, q, J = 7.0 Hz), 4.93 (1H, brs), 3.82-3.72 (1H, m), 3.44-3.38 (4H, m), 3.09 (2H, d, J = 5.9 Hz), 2.98 (3H, s), 2.42 (2H, t, J = 6.6 Hz), 2.27 |

TABLE 177-continued

| Compound No. | Structure | Physicochemical data |
|---|---|---|
| | | (6H, s), 1.76-1.59 (8H, m), 1.46-1.14 (9H, m), 0.96 (3H, t, J = 7.3 Hz) |
| 12-5 | 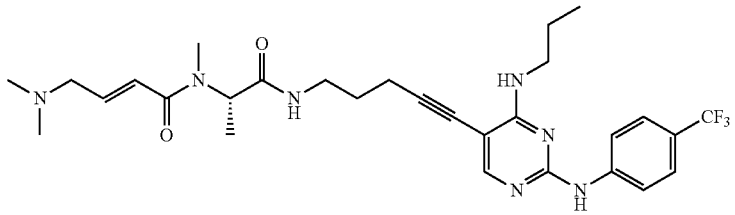 [SMILES: CCCNc1nc(Nc2ccc(C(F)(F)F)cc2)ncc1C#CCCCNC(=O)[C@H](C)N(C)C(=O)/C=C/CN(C)C] | ¹H-NMR (CDCl₃) δ: 7.97 (1H, s), 7.76 (2H, d, J = 8.6 Hz), 7.53 (2H, d, J = 9.2 Hz), 7.32 (1H, brs), 6.94 (1H, dt, J = 15.2, 5.9 Hz), 6.58 (1H, brs), 6.43 (1H, d, J = 15.2 Hz), 6.31 (1H, brs), 5.19 (1H, q, J = 6.6 Hz), 3.53-3.44 (4H, m), 3.10 (2H, d, J = 5.9 Hz), 3.00 (3H, s), 2.44 (2H, t, J = 6.6 Hz), 2.27 (6H, s), 1.87-1.64 (4H, m), 1.36 (3H, d, J = 6.6 Hz), 1.01 (3H, t, J = 7.6 Hz) |

TABLE 178

| Compound No. | Structure | Physicochemical data |
|---|---|---|
| 12-6 | 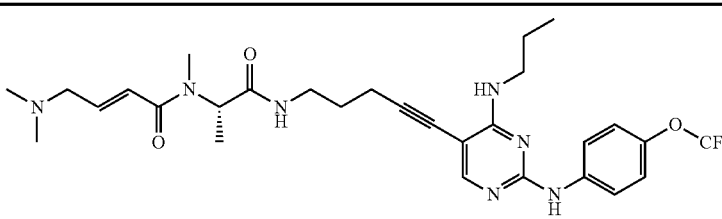 | ¹H-NMR (CDCl₃) δ: 7.95 (1H, s), 7.65 (2H, d, J = 7.3 Hz), 7.16-7.13 (3H, m), 7.02-6.76 (1H, m), 6.57 (1H, brs), 6.42 (1H, dd, J = 15.2, 1.3 Hz), 6.23 (1H, brs), 5.19 (1H, q, J = 7.0 Hz), 3.48-3.43 (4H, m), 3.14-3.07 (2H, m), 2.99 (3H, s), 2.44 (2H, t, J = 6.6 Hz), 2.27 (6H, s), 1.79-1.64 (4H, m), 1.36 (3H, d, J = 7.0 Hz), 0.99 (3H, t, J = 7.3 Hz) |
| 12-7 | 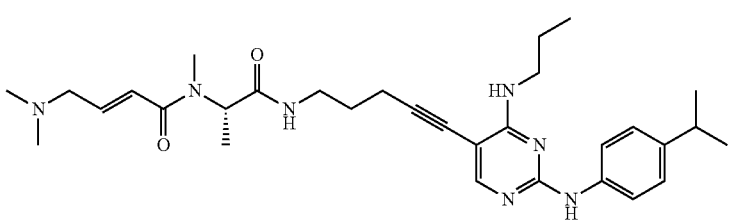 [SMILES: CCCNc1nc(Nc2ccc(C(C)C)cc2)ncc1C#CCCCNC(=O)[C@H](C)N(C)C(=O)/C=C/CN(C)C] | ¹H-NMR (CDCl₃) δ: 7.94 (1H, s), 7.54 (2H, d, J = 7.9 Hz), 7.23-7.18 (3H, m), 6.95-6.92 (2H, m), 6.50-6.43 (1H, m), 6.11 (1H, s), 5.19-5.17 (1H, m), 3.49-3.45 (4H, m), 3.13-3.10 (2H, m), 2.99 (3H, s), 2.88-2.86 (1H, m), 2.46-2.44 (2H, m), 2.27 (6H, s), 1.86-1.66 (4H, m), 1.35 (3H, d, J = 6.6 Hz), 1.25 (6H, s), 1.00 (3H, t, J = 7.3 Hz) |
| 12-8 | 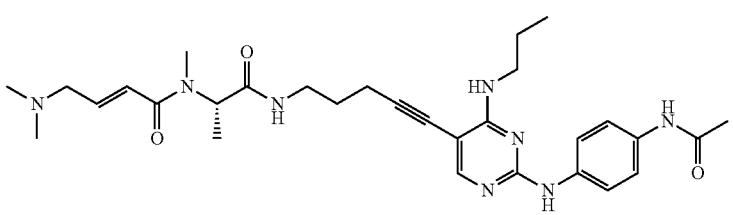 [SMILES: CCCNc1nc(Nc2ccc(NC(C)=O)cc2)ncc1C#CCCCNC(=O)[C@H](C)N(C)C(=O)/C=C/CN(C)C] | ¹H-NMR (CDCl₃) δ: 7.94 (1H, s), 7.58 (1H, d, J = 9.2 Hz), 7.46-7.42 (2H, m), 7.15-6.94 (4H, m), 6.51-6.43 (2H, m), 6.14 (1H, brs), 5.19 (1H, brs), 3.49-3.46 (4H, m), 3.13-3.10 (2H, m), 2.99 (3H, s), 2.45-2.42 (2H, m), 2.27 (6H, s), 2.17 (3H, s), 1.67-1.63 (4H, m), 1.38-1.35 (3H, m), 0.99 (3H, t, J = 7.3 Hz) |

TABLE 178-continued

| Compound No. | Structure | Physicochemical data |
|---|---|---|
| 12-9 | 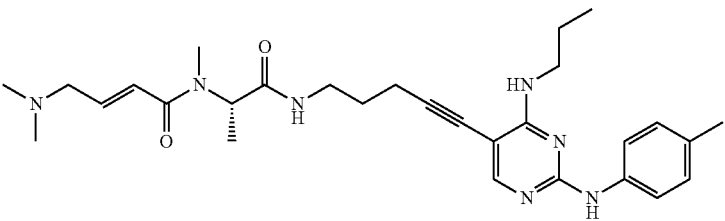 | ¹H-NMR (CDCl₃) δ: 7.93 (1H, s), 7.50 (1H, d, J = 8.6 Hz), 7.25-7.22 (1H, brs), 7.11 (2H, d, J = 8.6 Hz), 6.95-6.91 (2H, m), 6.51 (1H, brs), 6.43 (1H, d, J = 15.9 Hz), 6.14 (1H, brs), 5.18 (1H, q, J = 7.0 Hz), 3.50-3.44 (4H, m), 3.11 (2H, d, J = 5.3 Hz), 2.99 (3H, s), 2.43 (2H, t, J = 6.6 Hz), 2.31 (3H, s), 2.28 (6H, s), 1.77-1.67 (4H, m), 1.35 (3H, d, J = 7.0 Hz), 0.99 (3H, t, J = 7.6 Hz) |
| 12-10 | 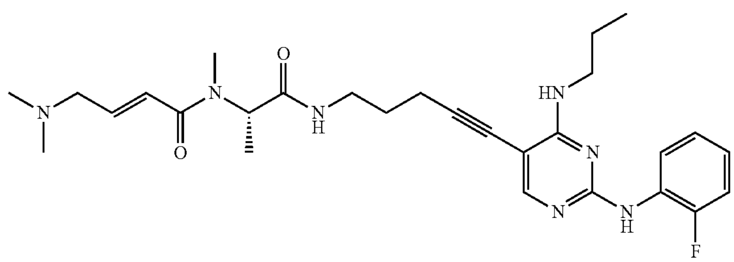 [SMILES: CCCNc1nc(Nc2ccccc2F)ncc1C#CCCCNC(=O)[C@H](C)N(C)C(=O)/C=C/CN(C)C] | ¹H-NMR (CDCl₃) δ: 8.55-8.52 (1H, m), 7.98 (1H, s), 7.11-7.06 (3H, m), 6.94-6.91 (2H, m), 6.49-6.44 (2H, m), 6.22 (1H, brs), 5.19-5.17 (1H, m), 3.59-3.37 (4H, m), 3.15-3.12 (2H, m), 2.99 (3H, s), 2.46-2.42 (2H, m), 2.29 (6H, s), 1.72-1.63 (4H, m), 1.36 (3H, d, J = 7.3 Hz), 1.00 (3H, t, J = 7.6 Hz) |

TABLE 179

| Compound No. | Structure | Physicochemical data |
|---|---|---|
| 12-11 | 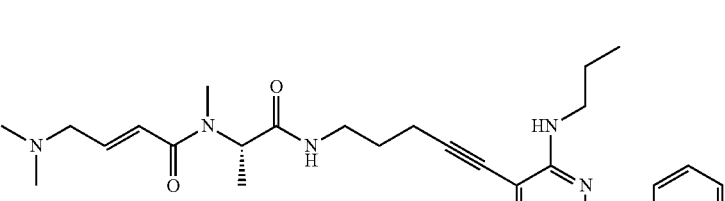 | ¹H-NMR (CDCl₃) δ: 8.03 (1H, s), 7.96 (1H, d, J = 2.6 Hz), 7.67 (2H, d, J = 8.6 Hz), 7.30-7.22 (3H, m), 6.95 (1H, dt, J = 15.2, 5.9 Hz), 6.67 (1H, t, J = 5.6 Hz), 6.46 (1H, d, J = 15.2 Hz), 6.30 (1H, brs), 6.11 (1H, t, J = 5.6 Hz), 5.29 (2H, s), 4.04 (2H, s), 3.50-3.40 (4H, m), 3.20 (2H, s), 3.09 (3H, t, J = 5.6 Hz), 2.47 (2H, t, J = 6.6 Hz), 2.26 (6H, s), 1.81-1.63 (4H, m), 0.98 (3H, t, J = 7.3 Hz) |
| 12-12 | 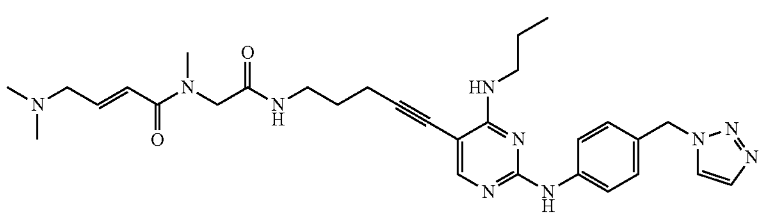 [SMILES: CCCNc1nc(Nc2ccc(Cn3ccnn3)cc2)ncc1C#CCCCNC(=O)CN(C)C(=O)/C=C/CN(C)C] | ¹H-NMR (CDCl₃) δ: 7.96 (1H, s), 7.66 (3H, t, J = 8.3 Hz), 7.45 (1H, s), 7.22 (2H, d, J = 8.3 Hz), 7.00-6.91 (2H, m), 6.59 (1H, brs), 6.46 (1H, d, J = 15.2 Hz), 6.10 (1H, t, J = 5.6 Hz), 5.51 (2H, s), 4.03 (2H, s), 3.50-3.41 (4H, m), 3.20 (3H, s), 3.09 (2H, t, J = 5.9 Hz), 2.47 (2H, t, J = 6.6 Hz), 2.27 (6H, s), 1.82-1.68 (4H, m), 0.99 (3H, t, J = 7.3 Hz) |

Example 52

1

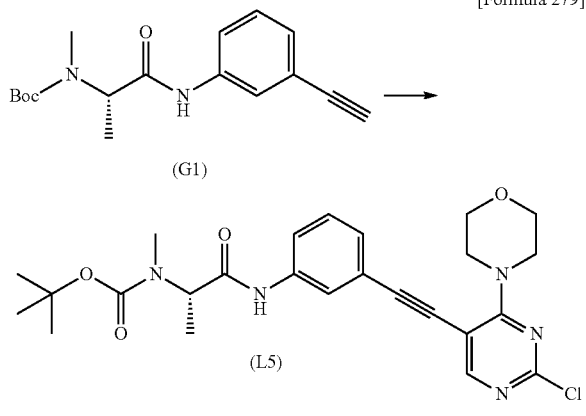

To a solution of 4-(2-chloro-5-iodopyrimidin-4-yl)morpholine (H11, 300 mg), (S)-tert-butyl (1-((3-ethynylphenyl)amino)-1-oxopropan-2-yl)(methyl)carbamate (G1, 558 mg), bis(triphenylphosphine)palladium(II) dichloride (32 mg) and copper(I) iodide (9 mg) in N,N-dimethylformamide (5 mL), triethylamine (640 μL) was added at room temperature, and the mixture was stirred at the same temperature for 2 hours. To the reaction mixture, water and ethyl acetate were added. The organic layer was separated, washed successively with water and saturated aqueous sodium chloride, and then dried over anhydrous sodium sulfate, and the solvent was evaporated under reduced pressure. The obtained residue was purified by basic silica gel column chromatography (eluent, 85 to 70% hexane in ethyl acetate) to obtain (S)-tert-butyl (1-((3-((2-chloro-4-morpholinopyrimidin-5-yl)ethynyl)phenyl)amino)-1-oxopropan-2-yl)(methyl)carbamate (L5, 437 mg).

2

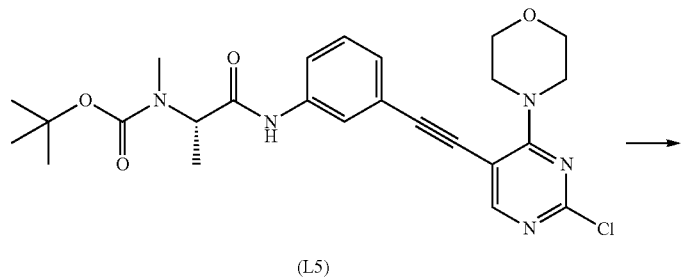

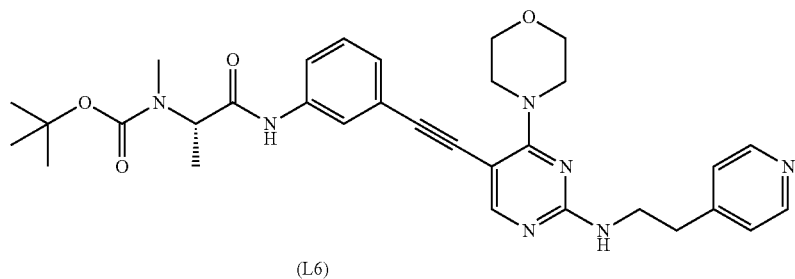

To (S)-tert-butyl (1-((3-((2-chloro-4-morpholinopyrimidin-5-yl)ethynyl)phenyl)amino)-1-oxopropan-2-yl)(methyl)carbamate (L5, 437 mg), 4-(2-aminoethyl)pyridine (214 mg), tris(dibenzylideneacetone)dipalladium(0) (80 mg), 4,5'-bis(diphenylphosphino)-9,9'-dimethylxanthene (101 mg) and cesium carbonate (856 mg), 1,4-dioxane (10 mL) was added at room temperature, and the mixture was stirred at 100° C. for 12 hours. The reaction mixture was cooled to room temperature, then the insoluble matter was removed by filtration through Cerite, and then the solvent was evaporated under reduced pressure. The obtained residue was purified by silica gel column chromatography (eluent, 95% ethyl acetate/5% methanol) to obtain (S)-tert-butyl methyl(1-((3-((4-morpholino-2-((2-(pyridin-4-yl)ethyl)amino)pyrimidin-5-yl)ethynyl)phenyl)amino)-1-oxopropan-2-yl)carbamate (L6, 104 mg).

[Formula 281]

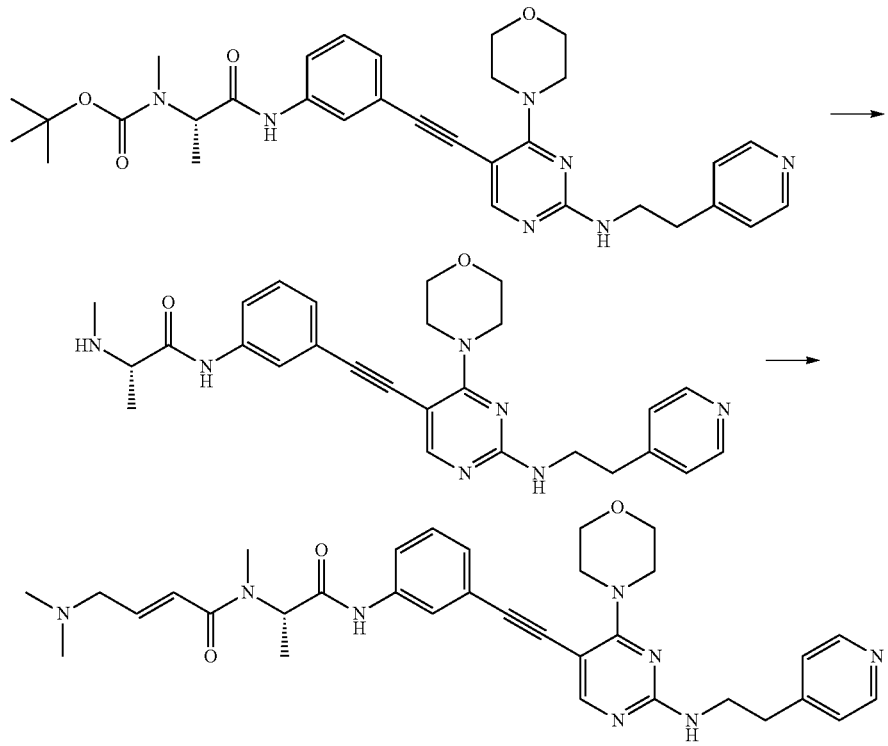

(12-13)

By using (S)-tert-butyl methyl(1-((3-((4-morpholino-2-((2-(pyridin-4-yl)ethyl)amino)pyrimidin-5-yl)ethynyl)phenyl)amino)-1-oxopropan-2-yl)carbamate (L6), (S,E)-4-(dimethylamino)-N-methyl-N-(1-((3-((4-morpholino-2-((2-(pyridin-4-yl)ethyl)amino)pyrimidin-5-yl)ethynyl)phenyl)amino)-1-oxopropan-2-yl)-2-butenamide (12-13) was obtained in the same manner as that of Example 35, (6) and (7).

$^1$H-NMR (CD$_3$OD) δ: 8.40 (2H, d, J=5.9 Hz), 8.00 (1H, s), 7.71 (1H, s), 7.45 (1H, d, J=7.3 Hz), 7.30-7.24 (3H, m), 7.11 (1H, d, J=7.3 Hz), 6.87-6.70 (1H, m), 6.63 (1H, d, J=15.2 Hz), 5.16 (1H, q, J=6.6 Hz), 3.94 (4H, t, J=4.3 Hz), 3.76 (4H, t, J=4.3 Hz), 3.62 (2H, t, J=6.9 Hz), 3.15 (5H, m), 2.93 (3H, t, J=6.9 Hz), 2.27 (6H, s), 1.46 (3H, d, J=6.6 Hz)

4

[Formula 282]

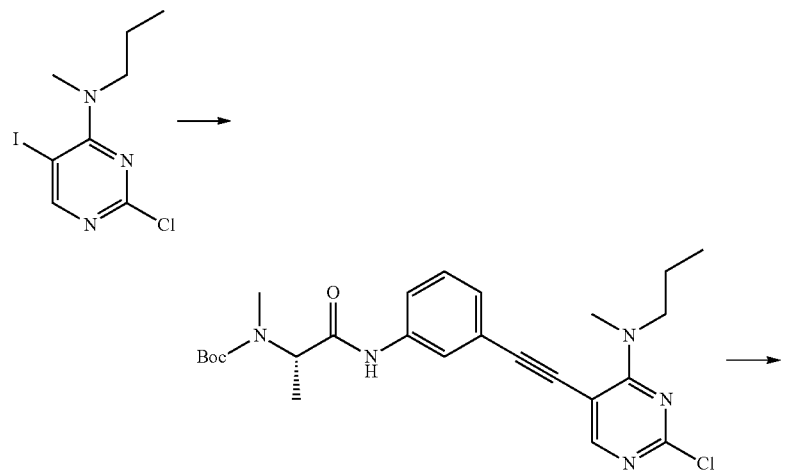

-continued

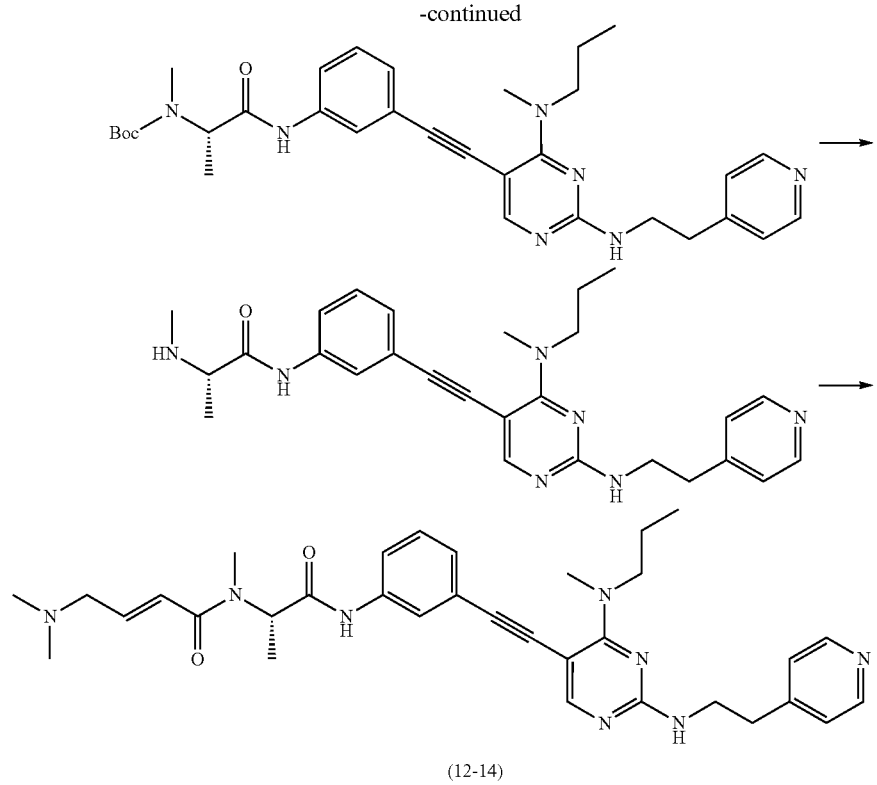

(12-14)

By using 2-chloro-5-iodo-4-(N-methyl-N-propylamino)pyrimidine (H12), (S,E)-4-(dimethylamino)-N-methyl-N-(1-((3-((4-(methyl(propyl)amino)-2-((2-(pyridin-4-yl)ethyl)amino)pyrimidin-5-yl)ethynyl)phenyl)amino)-1-oxopropan-2-yl)-2-butenamide (12-14) was obtained in the same manner as that of Example 52, (1) to (3).

$^1$H-NMR (CD$_3$OD) δ: 8.40 (2H, d, J=5.9 Hz), 7.93 (1H, s), 7.69 (1H, s), 7.46 (1H, d, J=7.9 Hz), 7.32-7.25 (3H, m), 7.14 (1H, d, J=7.9 Hz), 6.87-6.72 (1H, m), 6.64 (1H, d, J=15.2 Hz), 5.16 (1H, q, J=7.3 Hz), 3.81 (2H, t, J=7.6 Hz), 3.63 (2H, t, J=7.3 Hz), 3.30 (3H, s), 3.19-3.15 (5H, m), 2.95 (2H, t, J=6.9 Hz), 2.28 (6H, s), 1.79-1.67 (2H, m), 1.47 (3H, d, J=7.3 Hz), 0.91 (3H, t, J=7.6 Hz)

Example 53

1

[Formula 283]

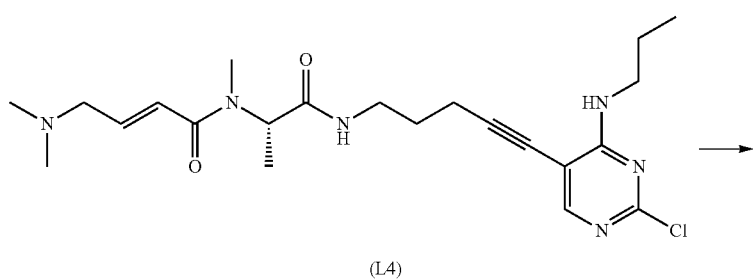

(12-15)

To (S,E)-N-(1-((5-(2-chloro-4-(propylamino)pyrimidin-5-yl)-4-pentyn-1-yl)amino)-1-oxopropan-2-yl)-4-(dimethylamino)-N-methyl-2-butenamide (L4, 30 mg), 4-(2-aminoethyl)morpholine (18 μL), tris(dibenzylideneacetone)dipalladium(0) (6.1 mg), 4,5'-bis(diphenylphosphino)-9,9'-dimethylxanthene (7.7 mg) and cesium carbonate (65 mg), 1,4-dioxane (2 mL) was added at room temperature, the reaction vessel was sealed, and then the mixture was stirred at 150° C. for 30 minutes by using a microwave reaction system. The reaction mixture was cooled to room temperature, then the insoluble matter was removed by filtration, and the solvent was evaporated under reduced pressure. The obtained residue was purified by basic silica gel column chromatography (eluent, 95% ethyl acetate/5% methanol) to obtain oily (S,E)-4-(dimethylamino)-N-methyl-N-(1-((5-(2-((2-morpholinoethyl)amino)-4-(propylamino)pyrimidin-5-yl)-4-pentyn-1-yl)amino)-1-oxopropan-2-yl)-2-butenamide (12-15, 2.9 mg).

$^1$H-NMR (CDCl$_3$) δ: 7.92 (1H, s), 6.98 (1H, dt, J=15.2, 5.9 Hz), 6.43 (2H, d, J=15.2 Hz), 6.15 (1H, brs), 5.75 (1H, brs), 5.17 (1H, q, J=7.0 Hz), 3.70 (4H, t, J=4.6 Hz), 3.47-3.36 (4H, m), 3.14 (6H, s), 3.00-2.95 (5H, m), 2.73 (2H, t, J=5.9 Hz), 2.52-2.43 (8H, m), 1.76-1.60 (4H, m), 1.33 (3H, d, J=7.0 Hz), 0.96 (3H, t, J=7.6 Hz)

2

In the same manner as that of Example 53, (1), Compounds (12-16) to (12-19) were obtained.

TABLE 180

| Compound No. | Structure | Physicochemical data |
|---|---|---|
| 12-16 | 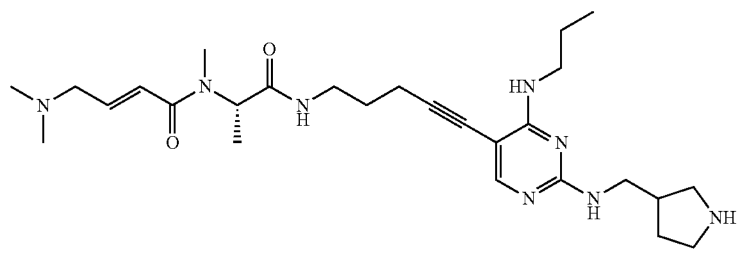 [SMILES: CCCNc1nc(NCC2CCNC2)ncc1C#CCCCNC(=O)[C@H](C)N(C)C(=O)/C=C/CN(C)C] | $^1$H-NMR (CD$_3$OD) δ: 7.71 (1H, s), 6.95 (1H, d, J = 15.2 Hz), 6.72 (1H, dt, J = 15.0, 8.6 Hz), 3.92 (2H, d, J = 5.9 Hz), 3.75-3.37 (10H, m), 3.25-2.93 (10H, m), 2.80 (1H, t, J = 7.9 Hz), 2.50 (2H, t, J = 6.3 Hz), 2.38-2.32 (1H, m), 1.90-1.64 (5H, m), 1.41 (3H, d, J = 7.3 Hz), 0.96 (3H, t, J = 7.6 Hz) |
| 12-17 | 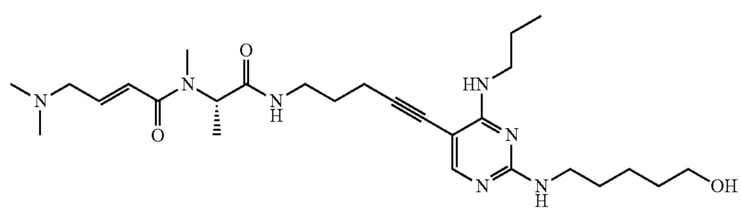 [SMILES: CCCNc1nc(NCCCCCO)ncc1C#CCCCNC(=O)[C@H](C)N(C)C(=O)/C=C/CN(C)C] | $^1$H-NMR (CDCl$_3$) δ: 7.91 (1H, s), 6.98 (1H, dt, J = 15.2, 5.9 Hz), 6.51 (1H, brs), 6.42 (1H, d, J = 15.2 Hz), 5.74 (1H, brs), 5.18 (1H, q, J = 7.3 Hz), 3.64 (3H, t, J = 6.6 Hz), 3.47-3.35 (6H, m), 3.14 (6H, s), 3.07-2.92 (5H, m), 2.66 (2H, t, J = 6.6 Hz), 2.42 (2H, t, J = 6.6 Hz), 1.50-1.26 (12H, m), 0.96 (3H, t, J = 7.6 Hz) |
| 12-18 | 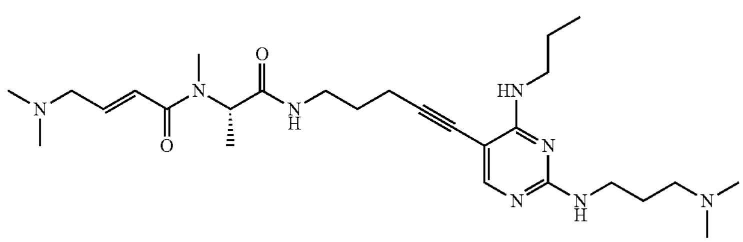 | $^1$H-NMR (CDCl$_3$) δ: 7.92 (1H, s), 6.99 (1H, dt, J = 15.2, 5.9 Hz), 6.51-6.41 (2H, m), 5.75 (1H, brs), 5.18 (2H, q, J = 7.3 Hz), 3.47-3.36 (6H, m), 3.14 (6H, s), 2.98 (3H, s), 2.70 (2H, t, J = 5.9 Hz), 2.43 (2H, t, J = 6.6 Hz), 2.36 (2H, t, J = 6.9 Hz), 2.24 (6H, s), 1.76-1.64 (6H, m), 1.34 (3H, d, J = 7.3 Hz), 0.96 (3H, t, J = 7.6 Hz) |
| 12-19 | 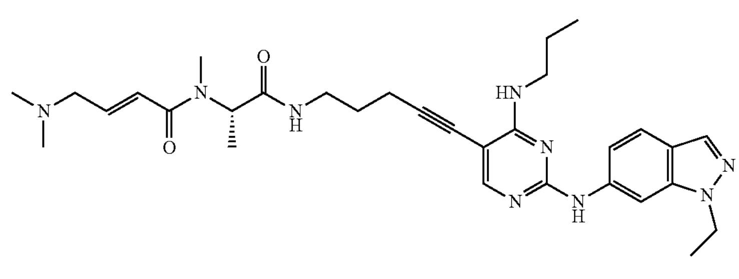 [SMILES: CCCNc1nc(Nc2ccc3cnn(CC)c3c2)ncc1C#CCCCNC(=O)[C@H](C)N(C)C(=O)/C=C/CN(C)C] | $^1$H-NMR (CDCl$_3$): 8.32 (1H, s), 7.99 (1H, s), 7.89 (1H, s), 7.58 (1H, d, J = 8.6 Hz), 7.00-6.80 (3H, m), 6.57-6.47 (1H, m), 6.42 (1H, dd, J = 15.2, 1.7 Hz), 6.28-6.19 (1H, m), 5.17 (1H, q, J = 7.3 Hz), 4.41 (2H, q, J = 7.3 Hz), 3.65-3.55 (2H, m), 3.50-3.40 (2H, m), 3.15-2.95 (5H, m), 2.49-2.41 (2H, m), 2.27 (6H, s), 1.85-1.65 (4H, m), 1.52 (3H, t, J = 7.3 Hz), 1.36 (3H, d, J = 6.9 Hz), 1.02 (3H, t, J = 7.3 Hz) |

Example 54

1

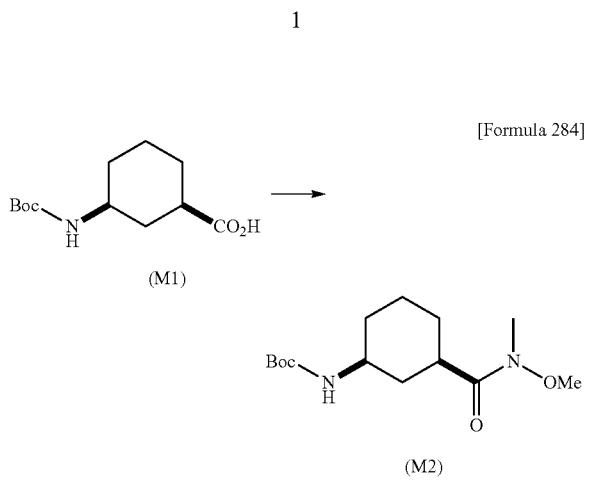

[Formula 284]

To a solution of (1R*,3S*)-3-((tert-butoxycarbonyl)amino)cyclohexanecarboxylic acid (M1, 3.00 g) as racemate synthesized according to the method described in Chemistry A European Journal, 2005, 11, pp. 6543-6551 in methylene chloride (30 mL), carbonyldiimidazole (2.60 g) was added under ice cooling, and the mixture was stirred at the same temperature for 10 minutes. To the reaction mixture, N,N-diisopropylethylamine (2.72 mL) and methoxyamine hydrochloride (1.56 g) were added under ice cooling, and the mixture was stirred at room temperature for 1 hour. To the reaction mixture, 1.0 mol/L aqueous hydrochloric acid and methylene chloride were added. The organic layer was separated, and the aqueous layer was extracted with methylene chloride. The organic layer and the extract were combined, washed successively with water, saturated aqueous sodium hydrogencarbonate and saturated aqueous sodium chloride, and then dried over anhydrous magnesium sulfate, and the solvent was evaporated under reduced pressure to obtain oily tert-butyl ((1S*,3R*)-3-(methoxy(methyl)carbamoyl)cyclohexyl)carbamate (M2, 3.60 g).

MS m/z (M+H): 287.0

2

[Formula 285]

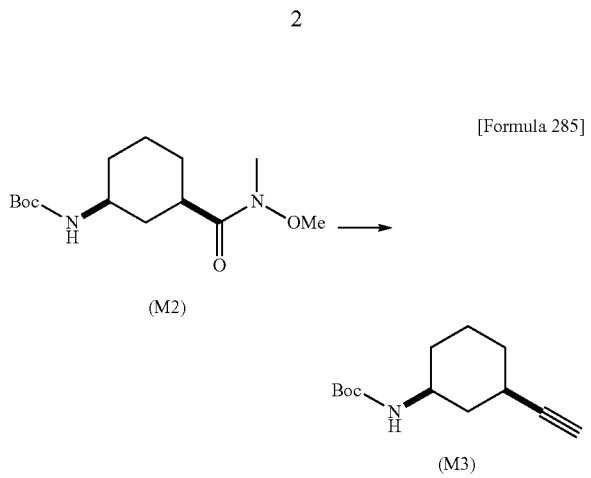

To a solution of tert-butyl ((1S*,3R*)-3-(methoxy(methyl)carbamoyl)cyclohexyl)carbamate (M2, 200 mg) in tetrahydrofuran (2 mL), lithium aluminum hydride (80 mg) was added under ice cooling, and the mixture was stirred at the same temperature for 40 minutes. To the reaction mixture, saturated aqueous sodium sulfate was added, the mixture was stirred at room temperature 30 minutes, and then ethyl acetate was added to the reaction mixture. The organic layer was separated, and the aqueous layer was extracted with ethyl acetate. The organic layer and the extract were combined, and dried over anhydrous magnesium sulfate, and the solvent was evaporated under reduced pressure.

To a solution of the residue obtained above and dimethyl (1-diazo-2-oxopropyl)phosphonate (126 μL) in methanol (6.5 mL), potassium carbonate (193 mg) was added under ice cooling, and the mixture was stirred at the same temperature for 35 minutes. To the reaction mixture, saturated aqueous ammonium chloride and ethyl acetate were added. The organic layer was separated, and the aqueous layer was extracted with ethyl acetate. The organic layer and the extract were combined, washed successively with saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 96 to 80% hexane in ethyl acetate) to obtain tert-butyl ((1S*,3R*)-3-ethynylcyclohexyl)carbamate (M3, 119 mg) as white solid.

MS m/z (M+H): 224.2

3

[Formula 286]

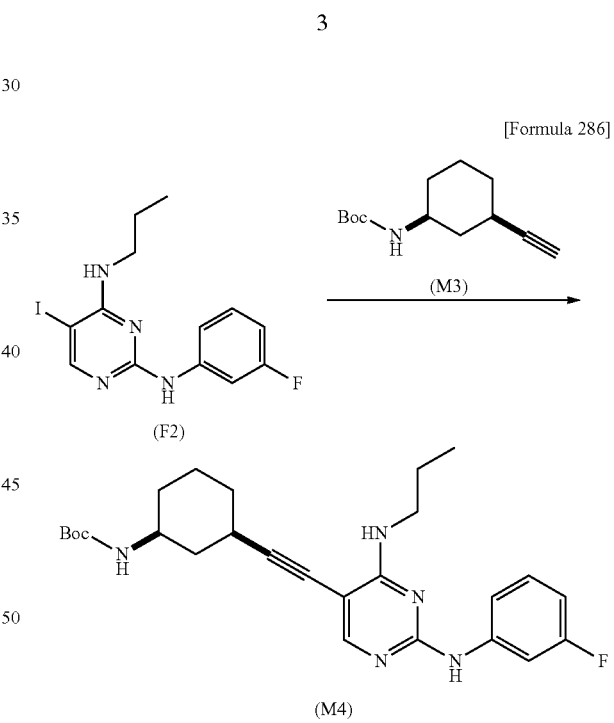

To a solution of N²-(3-fluorophenyl)-5-iodo-N⁴-propylpyrimidine-2,4-diamine (F2, 100 mg), bis(triphenylphosphine)palladium(II) dichloride (19 mg) and copper(I) iodide (10 mg) in N,N-dimethylformamide (2.7 mL), triethylamine (188 μL) and tert-butyl ((1S*,3R*)-3-ethynylcyclohexyl)carbamate (M3, 90 mg) were added at room temperature, and the mixture was stirred at the same temperature for 1 hour and 45 minutes. To the reaction mixture, water and ethyl acetate were added. The organic layer was separated, washed successively with saturated ammonium chloride and saturated aqueous sodium chloride, and then dried over anhydrous magnesium sulfate, and the solvent was evaporated under reduced pressure. The obtained residue was purified by silica gel column chromatography (eluent, 94 to 60% hexane in ethyl acetate) to obtain tert-butyl ((1S*,3R*)-3-((2-((3-fluorophenyl)amino)-4-(propylamino)pyrimidin-5-yl)ethynyl)cyclohexyl)carbamate (M4, 130 mg) as yellow solid.

MS m/z (M+H): 468.4

4

[Formula 287]

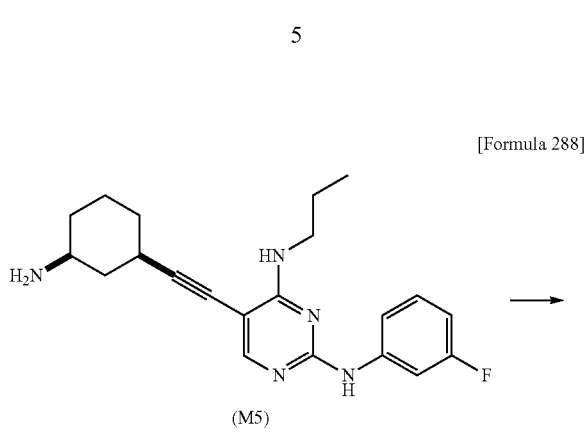

To a solution of tert-butyl ((1S*,3R*)-3-((2-((3-fluorophenyl)amino)-4-(propylamino)pyrimidin-5-yl)ethynyl)cyclohexyl)carbamate (M4, 130 mg) in 1,4-dioxane (3 mL), a 4.0 mol/L solution of hydrochloric acid in 1,4-dioxane (3 mL) was added at room temperature, and the mixture was stirred at the same temperature for 1 hour and 30 minutes. To the reaction mixture, 1,4-dioxane (2 mL) and a 4.0 mol/L solution of hydrochloric acid in 1,4-dioxane (2 mL) were added at room temperature, and the mixture was stirred at the same temperature for 3 hours. The solvent was evaporated under reduced pressure to obtain 5-(((1R*,3S*)-3-aminocyclohexyl)ethynyl)-N²-(3-fluorophenyl)-N⁴-propylpyrimidine-2,4-diamine (M5) dihydrochloride.

MS m/z (M+H): 368.3

5

[Formula 288]

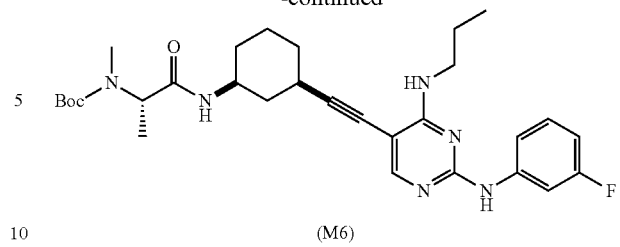

To a solution of 5-(((1R*,3S*)-3-aminocyclohexyl)ethynyl)-N²-(3-fluorophenyl)-N⁴-propylpyrimidine-2,4-diamine (M5) dihydrochloride obtained above, N-Boc-N-methyl-L-alanine (114 mg), 1-ethyl-3-(3-dimethylaminopropyl)carbodiimide hydrochloride (107 mg) and 1-hydroxybenzotriazole monohydrate (76 mg) in N,N-dimethylformamide (3 mL), N,N-diisopropylethylamine (286 μL) was added at room temperature, and the mixture was stirred at the same temperature for 40 minutes. To the reaction mixture, saturated aqueous sodium hydrogencarbonate and ethyl acetate were added. The organic layer was separated, and the aqueous layer was extracted with ethyl acetate. The organic layer and the extract were combined, washed successively with water, saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 88 to 20% hexane in ethyl acetate) to obtain tert-butyl ((S)-1-((1S,3R)-3-((2-((3-fluorophenyl)amino)-4-(propylamino)pyrimidin-5-yl)ethynyl)cyclohexyl)amino)-1-oxopropan-2-yl)(methyl)carbamate (M6, 113 mg).

MS m/z (M+H): 553.5

6

[Formula 289]

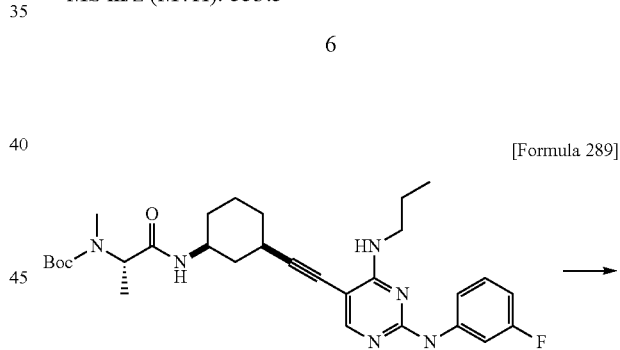

To a solution of tert-butyl ((S)-1-((1S*,3R*)-3-((2-((3-fluorophenyl)amino)-4-(propylamino)pyrimidin-5-yl)ethynyl)cyclohexyl)amino)-1-oxopropan-2-yl)(methyl)carbamate (M6, 113 mg) in 1,4-dioxane (2 mL), a 4.0 mol/L solution of hydrochloric acid in 1,4-dioxane (2 mL) was added at room temperature, and the mixture was stirred at the same temperature for 2 hours and 45 minutes. The solvent was evaporated under reduced pressure, and to the obtained residue, ethyl acetate was added. The solid matter was taken by filtration, and then ethyl acetate and saturated aqueous sodium hydrogencarbonate were added. The organic layer was separated, washed successively with saturated aqueous sodium hydrogencarbonate and saturated aqueous sodium chloride, and then dried over anhydrous sodium sulfate, and the solvent was evaporated under reduced pressure to obtain (S)—N-((1S*,3R*)-3-((2-((3-fluorophenyl)amino)-4-(propylamino)pyrimidin-5-yl)ethynyl)cyclohexyl)-2-(methylamino)propanamide (M7, 27 mg).

MS m/z (M+H): 453.4

By using a supercritical fluid chromatography purification apparatus (column, CHIRALPAKIA), stereoisomers of (S)—N-((1S*,3R*)-3-((2-((3-fluorophenyl)amino)-4-(propylamino)pyrimidin-5-yl)ethynyl)cyclohexyl)-2-(methylamino)propanamide (M7, 27 mg) were separated to obtain (S)—N-((1S,3R)-3-((2-((3-fluorophenyl)amino)-4-(propylamino)pyrimidin-5-yl)ethynyl)cyclohexyl)-2-(methylamino)propanamide (M8, 13.2 mg) and (S)—N-((1R,3S)-3-((2-((3-fluorophenyl)amino)-4-(propylamino)pyrimidin-5-yl)ethynyl)cyclohexyl)-2-(methylamino)propanamide (M9, 11.6 mg).

MS m/z (M+H): 453.4

7

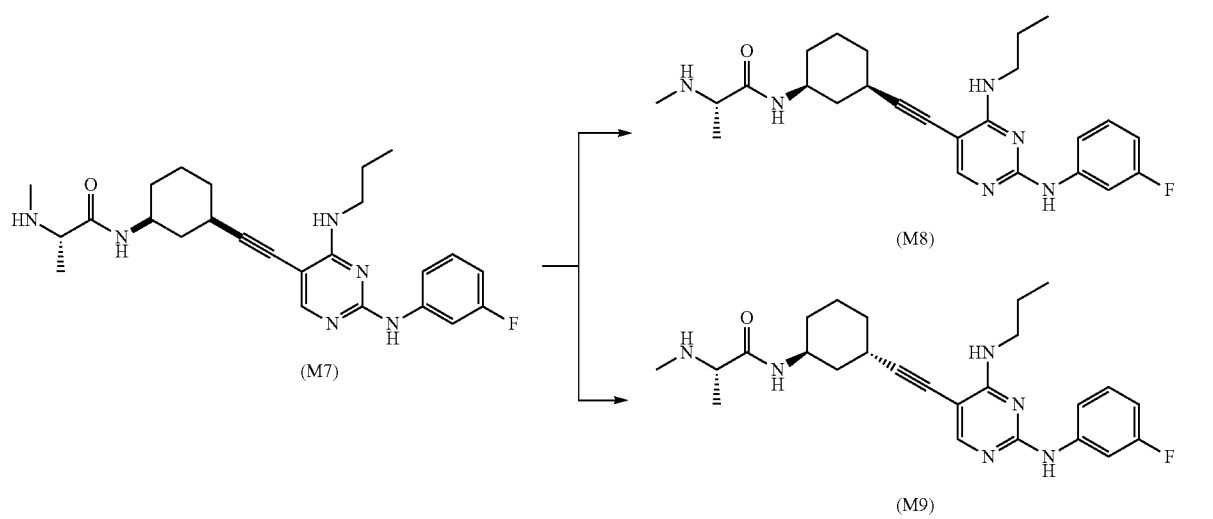

[Formula 290]

8

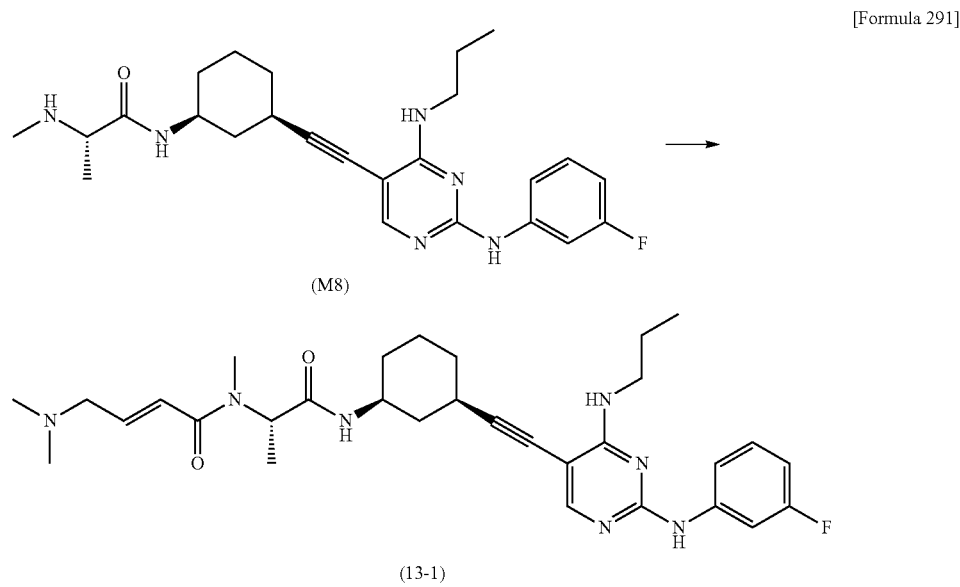

[Formula 291]

In the same manner as that of Example 35, (7), (E)-4-(dimethylamino)-N—((S)-1-(((1S,3R)-3-((2-((3-fluorophenyl)amino)-4-(propylamino)pyrimidin-5-yl)ethynyl)cyclohexyl)amino)-1-oxopropan-2-yl)-N-methyl-2-butenamide (13-1) was obtained from (S)—N-((1S,3R)-3-((2-((3-fluorophenyl)amino)-4-(propylamino)pyrimidin-5-yl)ethynyl)cyclohexyl)-2-(methylamino)propanamide (M8).

$^1$H-NMR (CDCl$_3$) δ: 7.96 (1H, s), 7.79 (1H, dt, J=11.8, 2.0 Hz), 7.20 (1H, dd, J=7.9, 6.6 Hz), 7.11-7.03 (2H, m), 6.93 (1H, dt, J=15.2, 5.9 Hz), 6.68 (1H, dt, J=8.3, 2.2 Hz), 6.42 (1H, d, J=15.2 Hz), 6.28 (1H, d, J=8.6 Hz), 5.51-5.43 (1H, m), 5.15 (1H, q, J=7.0 Hz), 3.74-3.72 (1H, m), 3.52-3.44 (3H, m), 3.11 (3H, d, J=5.9 Hz), 2.98 (4H, s), 2.68-2.56 (1H, m), 2.35-2.28 (1H, m), 2.28 (6H, s), 2.06-1.96 (1H, m), 1.88-1.78 (1H, m), 1.80-1.61 (2H, m), 1.43-1.20 (2H, m), 1.33 (3H, d, J=7.0 Hz), 1.02 (3H, t, J=7.6 Hz)

9

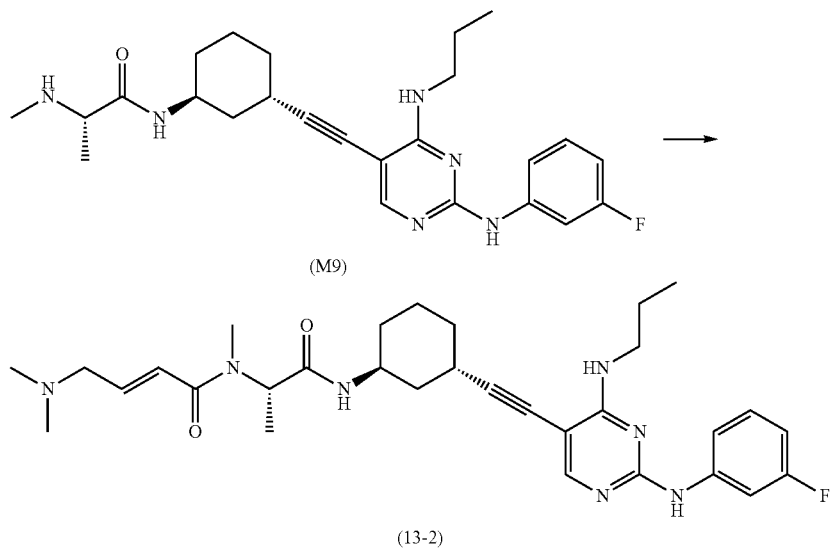

Example 55

1

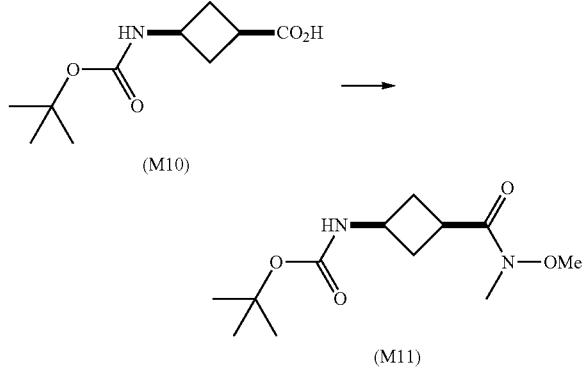

In the same manner as that of Example 35, (7), (E)-4-(dimethylamino)-N—((S)-1-(((1R,3S)-3-((2-((3-fluorophenyl)amino)-4-(propylamino)pyrimidin-5-yl)ethynyl)cyclohexyl)amino)-1-oxopropan-2-yl)-N-methyl-2-butenamide (13-2) was obtained from (S)—N-((1R,3S)-3-((2-((3-fluorophenyl)amino)-4-(propylamino)pyrimidin-5-yl)ethynyl)cyclohexyl)-2-(methylamino)propanamide (M9).

$^1$H-NMR (CDCl$_3$) δ: 7.95 (1H, s), 7.79 (1H, dt, J=11.9, 2.0 Hz), 7.27-7.16 (1H, m), 7.20-7.13 (1H, m), 7.12-7.05 (1H, m), 6.94 (1H, dt, J=15.2, 5.9 Hz), 6.68 (1H, dt, J=8.3, 2.2 Hz), 6.43 (1H, d, J=15.2 Hz), 6.30-6.23 (1H, m), 5.48 (1H, t, J=5.6 Hz), 5.17 (1H, q, J=7.0 Hz), 3.79-3.69 (1H, m), 3.52-3.43 (2H, m), 3.12 (2H, d, J=5.9 Hz), 2.97 (3H, s), 2.67-2.55 (1H, m), 2.31-2.19 (1H, m), 2.27 (6H, s), 2.06-1.83 (4H, m), 1.76-1.64 (2H, m), 1.43-1.10 (4H, m), 1.33 (2H, d, J=7.3 Hz), 1.02 (3H, t, J=8.0 Hz)

To a solution of (1S*,3S*)-3-((tert-butoxycarbonyl)amino)cyclobutanecarboxylic acid (M10, 500 mg) in methylene chloride (5 mL), carbonyldiimidazole (490 mg), N,N-diisopropylethylamine (510 μL) and methoxyamine hydrochloride (293 mg) were added under ice cooling, and the mixture was stirred at room temperature for 1 hour. To the reaction mixture, 1.0 mol/L aqueous hydrochloric acid and methylene chloride were added. The organic layer was separated, and the aqueous layer was extracted with methylene chloride. The organic layer and the extract were combined, washed successively with water, saturated aqueous sodium hydrogencarbonate and saturated aqueous sodium chloride, and then dried over anhydrous magnesium sulfate, and the solvent was evaporated under reduced pressure to obtain tert-butyl ((1S*,3S*)-3-(methoxy(methyl)carbamoyl)cyclobutyl)carbamate (M11, 510 mg) as white solid.

MS m/z (M+H): 259.0

2

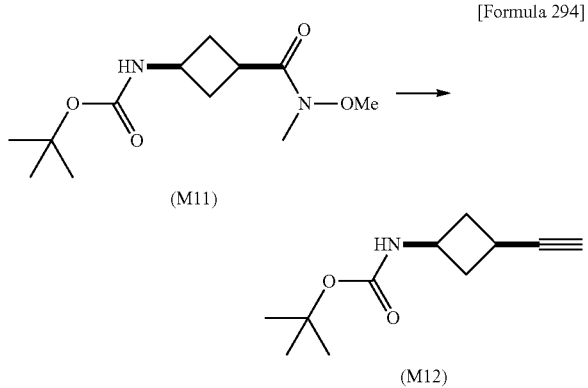

To a solution of tert-butyl ((1S,3S)-3-(methoxy(methyl)carbamoyl)cyclobutyl)carbamate (M11, 510 mg) in tetrahydrofuran (6.5 mL), lithium aluminum hydride (261 mg) was added under ice cooling, and the mixture was stirred at the same temperature for 25 minutes. To the reaction mixture, saturated aqueous sodium sulfate and ethyl acetate were added. The organic layer was separated, and dried over anhydrous magnesium sulfate, and the solvent was evaporated under reduced pressure.

To a solution of the residue obtained above and dimethyl (1-diazo-2-oxopropyl)phosphonate (414 μL) in methanol (20 mL), potassium carbonate (636 mg) was added under ice cooling, and the mixture was stirred at room temperature for 15 hours. To the reaction mixture, saturated aqueous ammonium chloride and ethyl acetate were added. The organic layer was separated, washed successively with saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 94-80% hexane in ethyl acetate) to obtain tert-butyl ((1S,3S)-3-ethynylcyclobutyl)carbamate (M12, 207 mg) as white solid.

MS m/z (M+H): 196.1

3

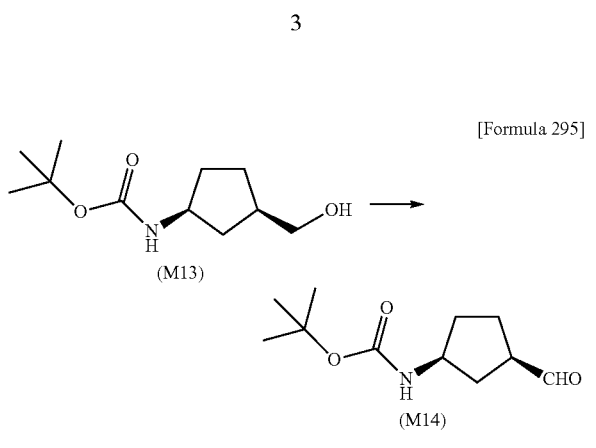

To a suspension of tert-butyl ((1S,3R)-3-(hydroxymethyl)cyclopentyl)carbamate (M13, 1.0 g) synthesized according to the method described in Journal of the American Chemical Society, 2005, 127, pp. 8846-8855, 4-methylmorpholine-N-oxide (1.1 g) and anhydrous sodium sulfate (2.0 g) in methylene chloride (20 mL), tetrapropylammonium perruthenate (81 mg) was added at room temperature, and the mixture was stirred at the same temperature for 1 hour. The reaction mixture was purified by silica gel column chromatography (eluent, ethyl acetate) to obtain oily tert-butyl ((1S,3R)-3-(formylcyclopentyl)carbamate (M14, 583 mg).

4

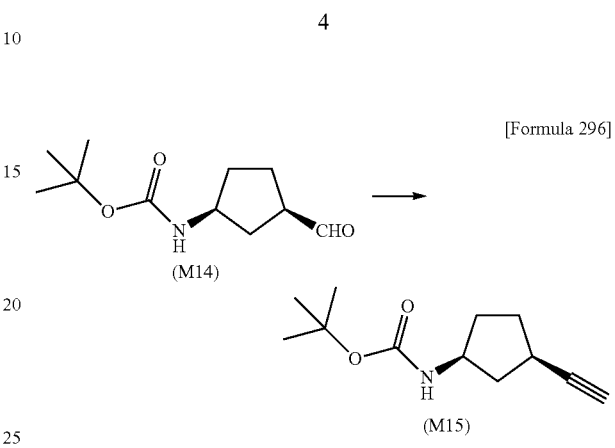

To a solution of tert-butyl ((1S,3R)-3-(formylcyclopentyl)carbamate (M14, 583 mg) and dimethyl (1-diazo-2-oxopropyl)phosphonate (608 μL) in methanol (20 mL), potassium carbonate (746 mg) was added under ice cooling, and the mixture was stirred at the same temperature for 1 hour and 15 minutes, and then stirred at room temperature for 15 hours. To the reaction mixture, saturated aqueous ammonium chloride and ethyl acetate were added. The organic layer was separated, and the aqueous layer was extracted with ethyl acetate. The organic layer and the extract were combined, washed successively with saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 96 to 80% hexane in ethyl acetate) to obtain tert-butyl ((1S,3R)-3-ethynylcyclopentyl)carbamate (M15, 465 mg) as white solid.

MS m/z (M+H): 210.1

5

By using tert-butyl ((1S*,3R*)-3-ethynylcyclohexyl)carbamate (M3), tert-butyl ((1S*,3S*)-3-ethynylcyclobutyl)carbamate (M12), tert-butyl ((1S,3R)-3-ethynylcyclopentyl)carbamate (M15), or tert-butyl ((1S,3R)-3-ethynylcyclohexyl)carbamate (P0), Intermediates (M16) to (M23) and Intermediates (M50) to (M59) were obtained in the same manner as that of Example 54, (3).

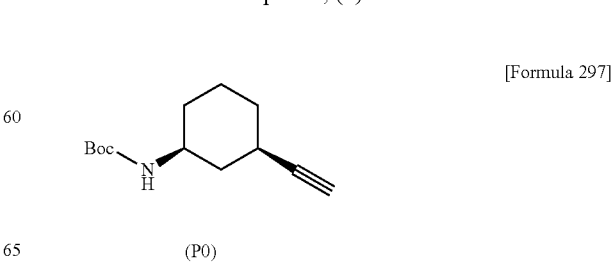

TABLE 181
| Compound No. | Structure | Physicochemical data |
|---|---|---|
| M16 | 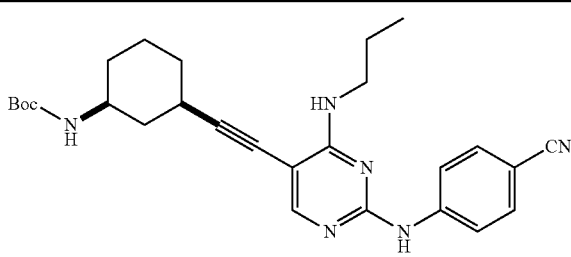 | — |
| M17 | 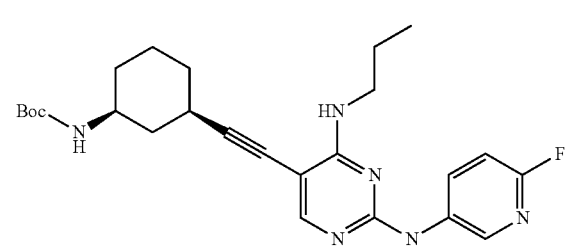 | — |
| M18 | 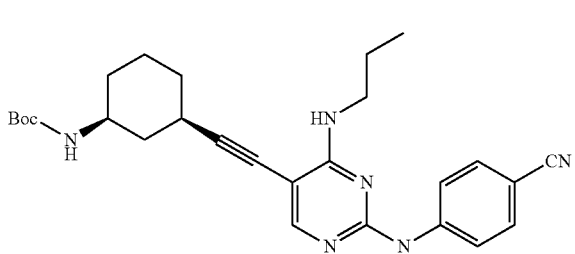 | — |
| M19 | 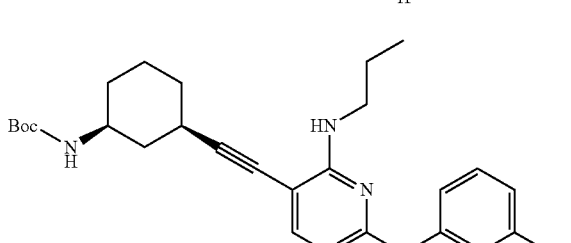 | — |
| M20 | 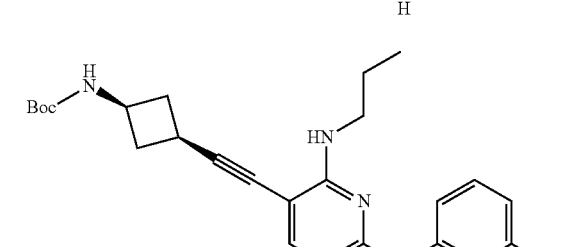 | MS m/z (M + H): 440.3 |
| M21 | 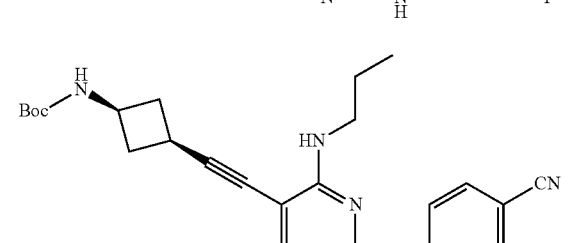 | — |

TABLE 182

| Compound No. | Structure | Physicochemical data |
|---|---|---|
| M22 | 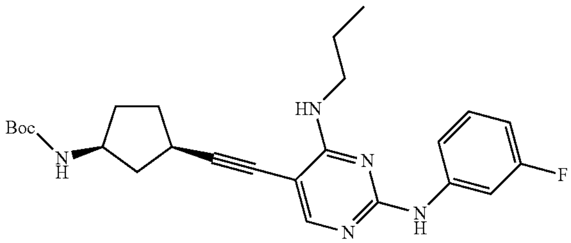 [SMILES: CCCNc1nc(Nc2cccc(F)c2)ncc1C#C[C@@H]1CC[C@H](NC(=O)OC(C)(C)C)C1] | — |
| M23 | 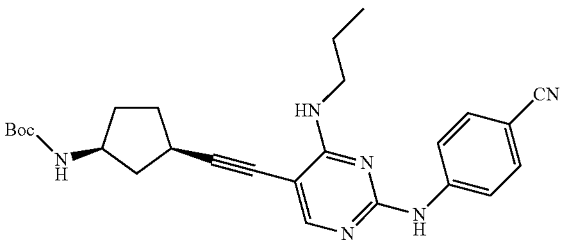 [SMILES: CCCNc1nc(Nc2ccc(C#N)cc2)ncc1C#C[C@@H]1CC[C@H](NC(=O)OC(C)(C)C)C1] | — |
| M50 | 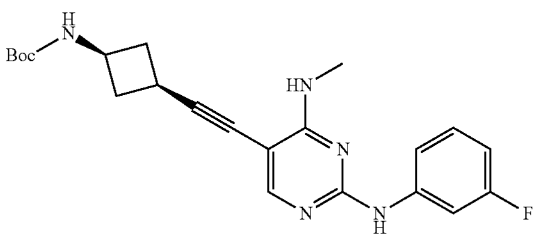 [SMILES: CNc1nc(Nc2cccc(F)c2)ncc1C#C[C@H]1C[C@@H](NC(=O)OC(C)(C)C)C1] | MS m/z (M + H): 412.3 |
| M51 | 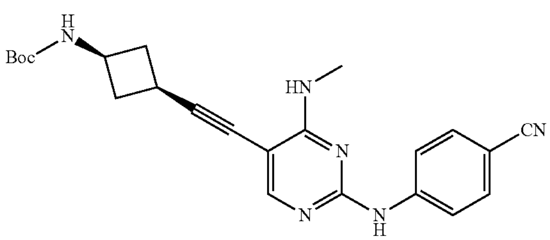 [SMILES: CNc1nc(Nc2ccc(C#N)cc2)ncc1C#C[C@H]1C[C@@H](NC(=O)OC(C)(C)C)C1] | MS m/z (M + H): 419.3 |
| M52 | 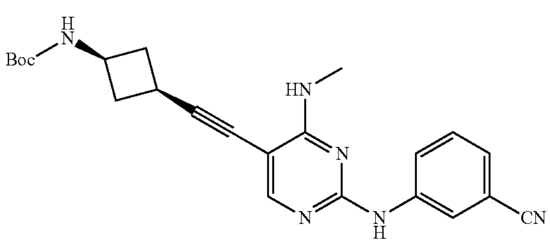 [SMILES: CNc1nc(Nc2cccc(C#N)c2)ncc1C#C[C@H]1C[C@@H](NC(=O)OC(C)(C)C)C1] | MS m/z (M + H): 419.3 |
| M53 | 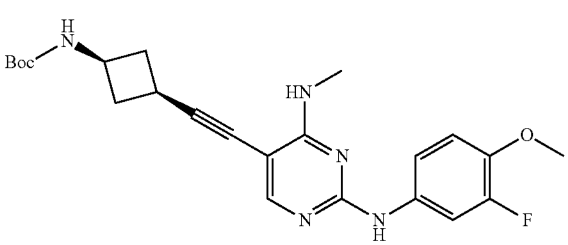 [SMILES: CNc1nc(Nc2ccc(OC)c(F)c2)ncc1C#C[C@H]1C[C@@H](NC(=O)OC(C)(C)C)C1] | MS m/z (M + H): 442.3 |

TABLE 182-continued

| Compound No. | Structure | Physicochemical data |
|---|---|---|
| M54 | 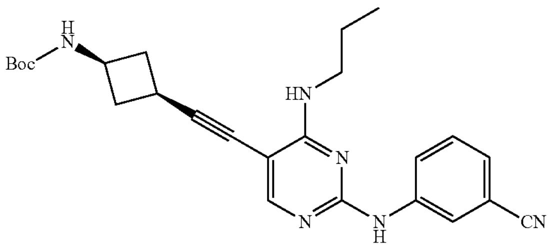 [SMILES: CCCNc1nc(Nc2cccc(C#N)c2)ncc1C#C[C@H]1C[C@@H](NC(=O)OC(C)(C)C)C1] | MS m/z (M + H): 447.3 |
| M55 | 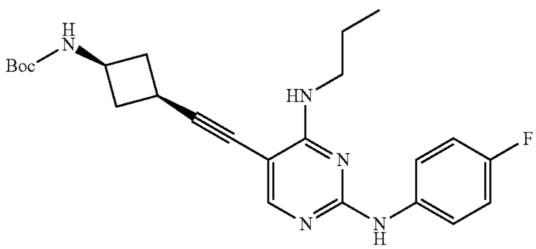 [SMILES: CCCNc1nc(Nc2ccc(F)cc2)ncc1C#C[C@H]1C[C@@H](NC(=O)OC(C)(C)C)C1] | MS m/z (M + H): 440.3 |
| M56 | 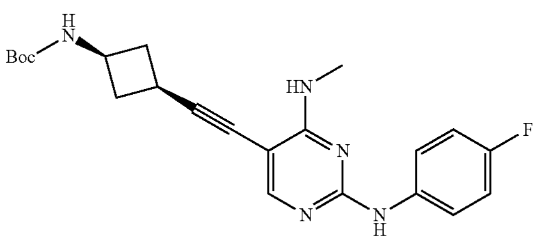 [SMILES: CNc1nc(Nc2ccc(F)cc2)ncc1C#C[C@H]1C[C@@H](NC(=O)OC(C)(C)C)C1] | MS m/z (M + H): 412.3 |

TABLE 183

| Compound No. | Structure | Physicochemical data |
|---|---|---|
| M57 | 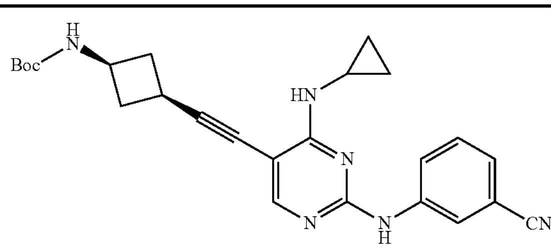 | MS m/z (M + H): 445.4 |
| M58 | 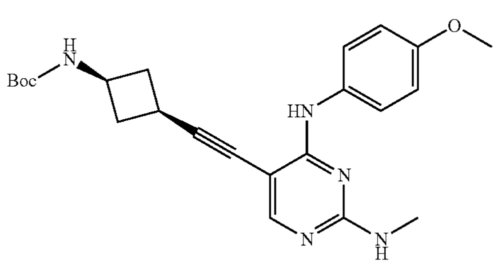 [SMILES: CNc1ncc(C#C[C@H]2C[C@@H](NC(=O)OC(C)(C)C)C2)c(Nc2ccc(OC)cc2)n1] | MS m/z (M + H): 424.4 |

TABLE 183-continued

| Compound No. | Structure | Physicochemical data |
|---|---|---|
| M59 | 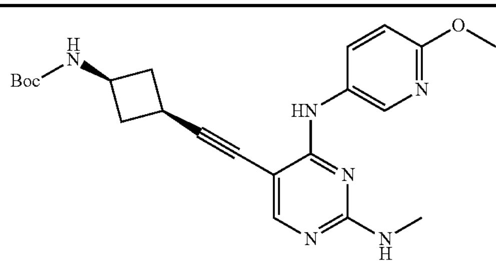 | MS m/z (M + H): 425.4 |

In the same manner as that of Example 54, (4), Intermediates (M24) to (M31) and Intermediates (M60) to (M69) were obtained.

TABLE 184

| Compound No. | Structure | Physicochemical data |
|---|---|---|
| M24 | 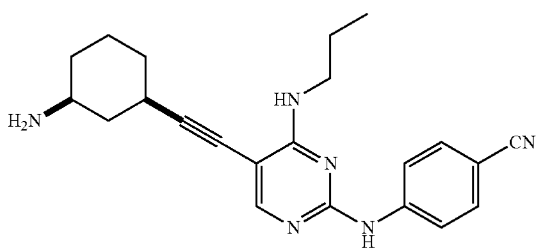 [SMILES: CCCNc1nc(Nc2ccc(C#N)cc2)ncc1C#C[C@@H]1CCC[C@H](N)C1] | — |
| M25 | 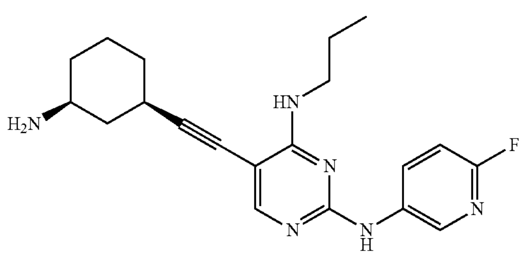 [SMILES: CCCNc1nc(Nc2ccc(F)nc2)ncc1C#C[C@@H]1CCC[C@H](N)C1] | — |
| M26 | 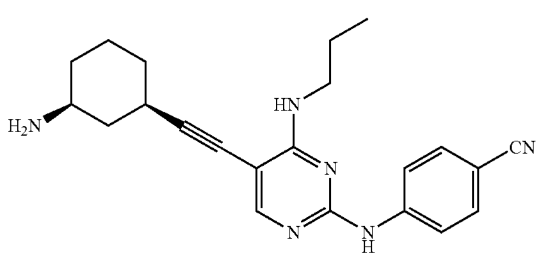 [SMILES: CCCNc1nc(Nc2ccc(C#N)cc2)ncc1C#C[C@@H]1CCC[C@H](N)C1] | — |
| M27 | 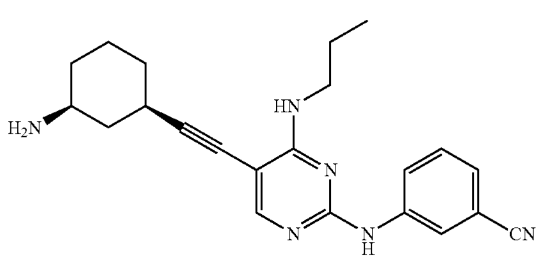 [SMILES: CCCNc1nc(Nc2cccc(C#N)c2)ncc1C#C[C@@H]1CCC[C@H](N)C1] | — |

TABLE 185

| Compound No. | Structure | Physicochemical data |
| --- | --- | --- |
| M28 | 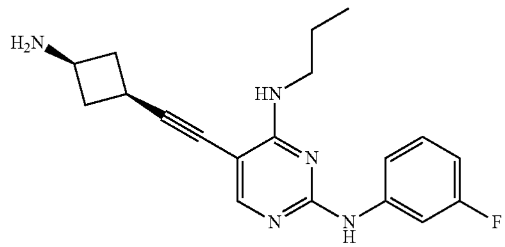 [SMILES: CCCNc1nc(Nc2cccc(F)c2)ncc1C#C[C@H]1C[C@@H](N)C1] | MS m/z (M + H): 340.2 |
| M29 | 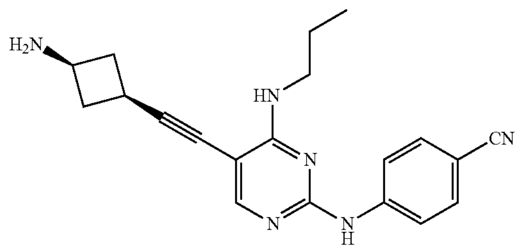 [SMILES: CCCNc1nc(Nc2ccc(C#N)cc2)ncc1C#C[C@H]1C[C@@H](N)C1] | — |
| M30 | 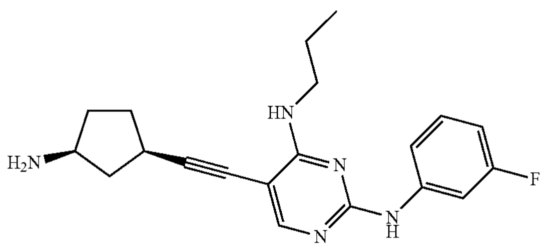 [SMILES: CCCNc1nc(Nc2cccc(F)c2)ncc1C#C[C@@H]1CC[C@H](N)C1] | — |
| M31 | 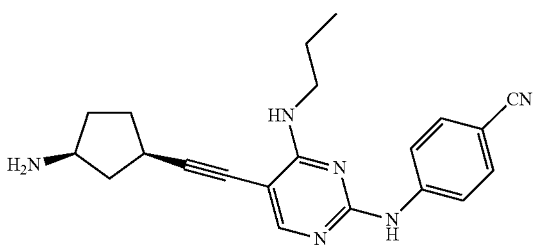 [SMILES: CCCNc1nc(Nc2ccc(C#N)cc2)ncc1C#C[C@@H]1CC[C@H](N)C1] | — |
| M60 | 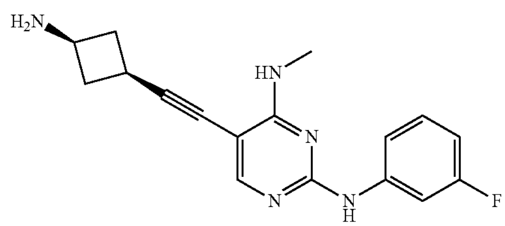 [SMILES: CNc1nc(Nc2cccc(F)c2)ncc1C#C[C@H]1C[C@@H](N)C1] | — |
| M61 | 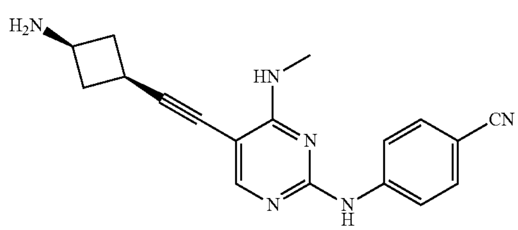 [SMILES: CNc1nc(Nc2ccc(C#N)cc2)ncc1C#C[C@H]1C[C@@H](N)C1] | — |

TABLE 185-continued

| Compound No. | Structure | Physicochemical data |
|---|---|---|
| M62 | 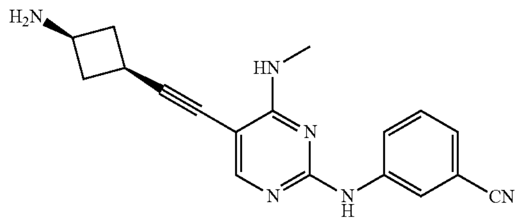 [SMILES: CNc1nc(Nc2cccc(C#N)c2)ncc1C#C[C@H]1C[C@@H](N)C1] | — |
| M63 | 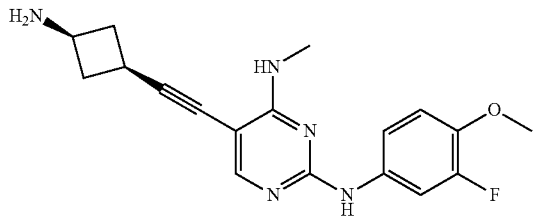 [SMILES: CNc1nc(Nc2ccc(OC)c(F)c2)ncc1C#C[C@H]1C[C@@H](N)C1] | MS m/z (M + H): 342.1 |
| M64 | 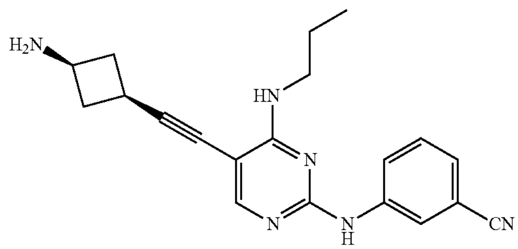 [SMILES: CCCNc1nc(Nc2cccc(C#N)c2)ncc1C#C[C@H]1C[C@@H](N)C1] | — |

TABLE 186

| Compound No. | Structure | Physicochemical data |
|---|---|---|
| M65 | 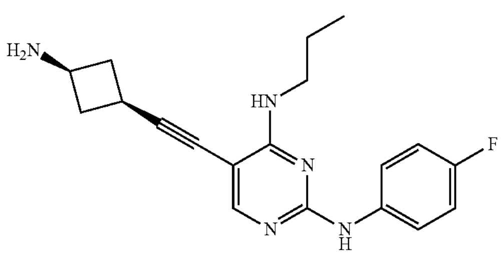 [SMILES: CCCNc1nc(Nc2ccc(F)cc2)ncc1C#C[C@H]1C[C@@H](N)C1] | MS m/z (M + H): 340.3 |
| M66 | 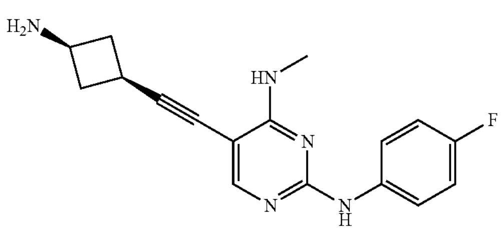 [SMILES: CNc1nc(Nc2ccc(F)cc2)ncc1C#C[C@H]1C[C@@H](N)C1] | MS m/z (M + H): 312.2 |
| M67 | 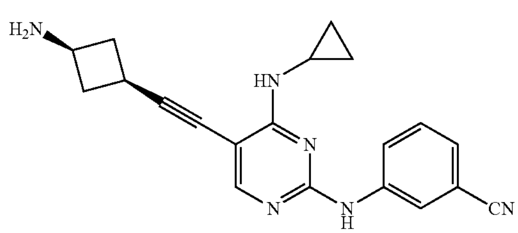 [SMILES: N#Cc1cccc(Nc2ncc(C#C[C@H]3C[C@@H](N)C3)c(NC3CC3)n2)c1] | MS m/z (M + H): 345.3 |

TABLE 186-continued

| Compound No. | Structure | Physicochemical data |
|---|---|---|
| M68 | 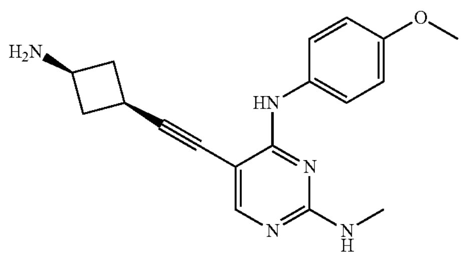 [SMILES: CNc1ncc(C#C[C@H]2C[C@@H](N)C2)c(Nc2ccc(OC)cc2)n1] | — |
| M69 | 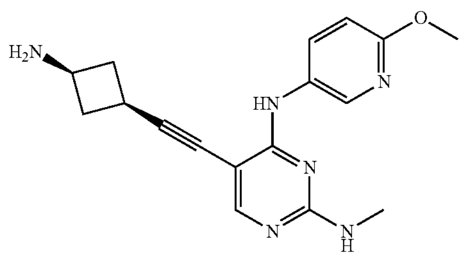 [SMILES: CNc1ncc(C#C[C@H]2C[C@@H](N)C2)c(Nc2ccc(OC)nc2)n1] | — |

In the same manner as that of Example 54, (5), Intermediates (M32) to (M39) and Intermediates (M70) to (M79) were obtained.

TABLE 187

| Compound No. | Structure | Physicochemical data |
|---|---|---|
| M32 | 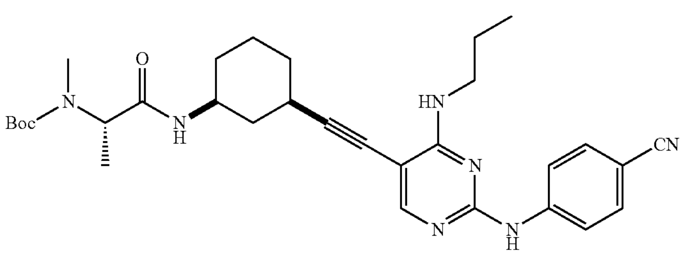 | — |
| M33 | 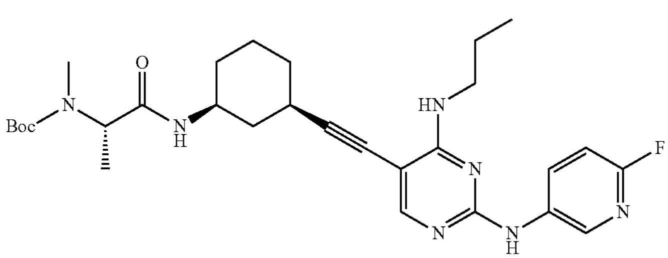 [SMILES: CCCNc1nc(Nc2ccc(F)nc2)ncc1C#C[C@@H]1CCC[C@H](NC(=O)[C@H](C)N(C)C(=O)OC(C)(C)C)C1] | — |

TABLE 188

| Compound No. | Structure | Physicochemical data |
|---|---|---|
| M34 | 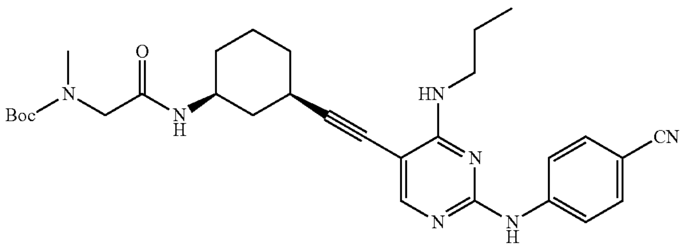 [SMILES: CCCNc1nc(Nc2ccc(C#N)cc2)ncc1C#C[C@@H]1CCC[C@H](NC(=O)CN(C)C(=O)OC(C)(C)C)C1] | — |
| M35 | 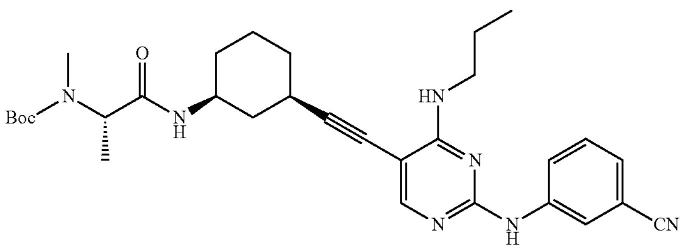 [SMILES: CCCNc1nc(Nc2cccc(C#N)c2)ncc1C#C[C@@H]1CCC[C@H](NC(=O)[C@H](C)N(C)C(=O)OC(C)(C)C)C1] | — |
| M36 | 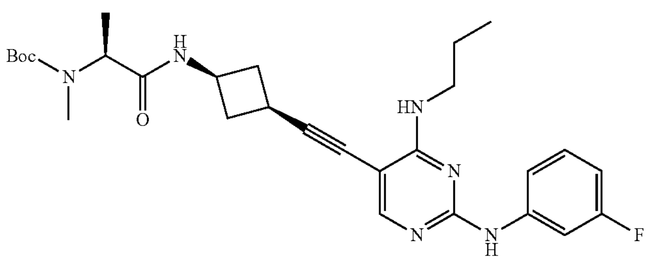 [SMILES: CCCNc1nc(Nc2cccc(F)c2)ncc1C#C[C@H]1C[C@@H](NC(=O)[C@H](C)N(C)C(=O)OC(C)(C)C)C1] | MS m/z (M + H): 525.4 |
| M37 | 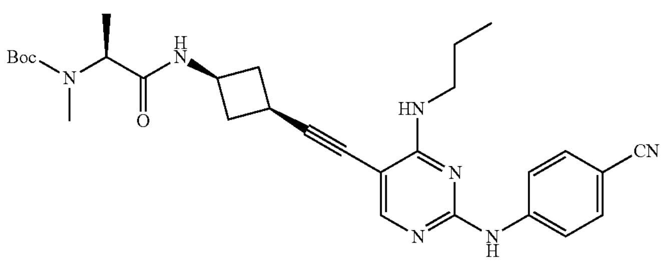 [SMILES: CCCNc1nc(Nc2ccc(C#N)cc2)ncc1C#C[C@H]1C[C@@H](NC(=O)[C@H](C)N(C)C(=O)OC(C)(C)C)C1] | — |
| M38 | 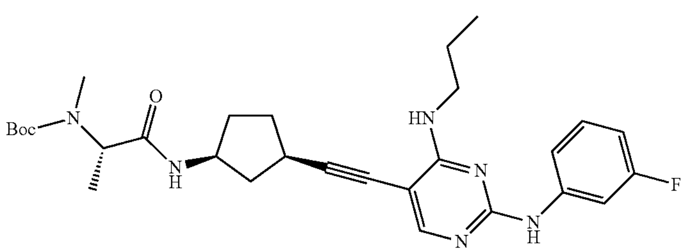 [SMILES: CCCNc1nc(Nc2cccc(F)c2)ncc1C#C[C@@H]1CC[C@H](NC(=O)[C@H](C)N(C)C(=O)OC(C)(C)C)C1] | — |
| M39 | 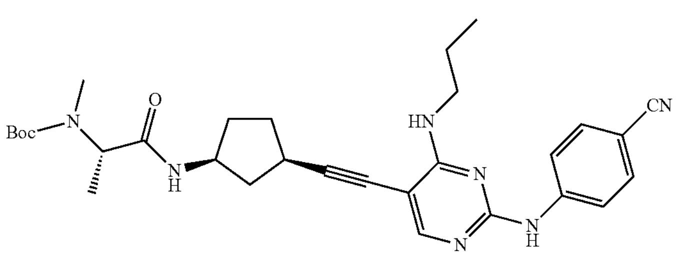 [SMILES: CCCNc1nc(Nc2ccc(C#N)cc2)ncc1C#C[C@@H]1CC[C@H](NC(=O)[C@H](C)N(C)C(=O)OC(C)(C)C)C1] | — |

TABLE 188-continued

| Compound No. | Structure | Physicochemical data |
|---|---|---|
| M70 | 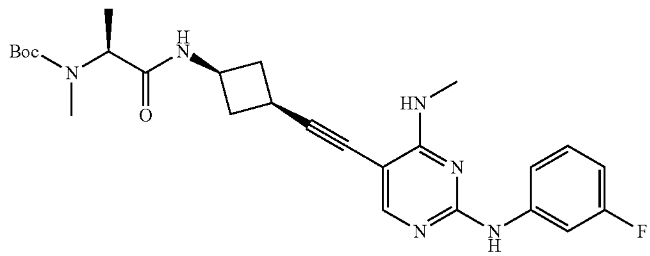 [SMILES: CNc1nc(Nc2cccc(F)c2)ncc1C#C[C@H]1C[C@@H](NC(=O)[C@H](C)N(C)C(=O)OC(C)(C)C)C1] | MS m/z (M + H): 497.4 |
| M71 | 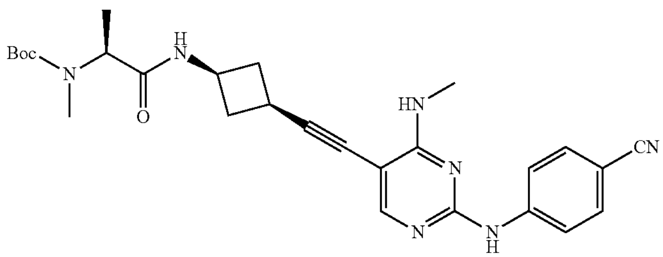 [SMILES: CNc1nc(Nc2ccc(C#N)cc2)ncc1C#C[C@H]1C[C@@H](NC(=O)[C@H](C)N(C)C(=O)OC(C)(C)C)C1] | MS m/z (M + H): 504.4 |

TABLE 189

| Compound No. | Structure | Physicochemical data |
|---|---|---|
| M72 | 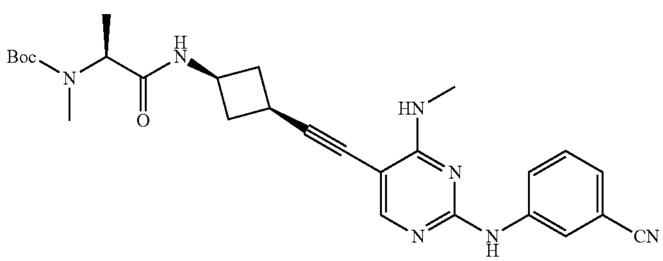 [SMILES: CNc1nc(Nc2cccc(C#N)c2)ncc1C#C[C@H]1C[C@@H](NC(=O)[C@H](C)N(C)C(=O)OC(C)(C)C)C1] | MS m/z (M + H): 504.4 |
| M73 | 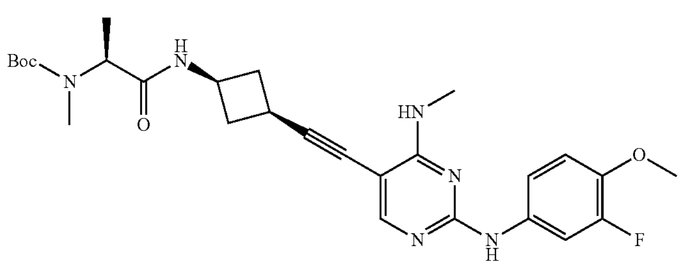 [SMILES: CNc1nc(Nc2ccc(OC)c(F)c2)ncc1C#C[C@H]1C[C@@H](NC(=O)[C@H](C)N(C)C(=O)OC(C)(C)C)C1] | MS m/z (M + H): 527.4 |
| M74 | 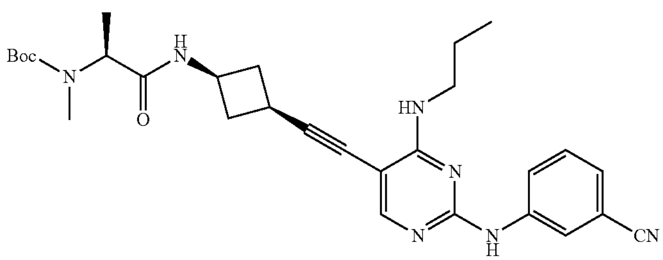 [SMILES: CCCNc1nc(Nc2cccc(C#N)c2)ncc1C#C[C@H]1C[C@@H](NC(=O)[C@H](C)N(C)C(=O)OC(C)(C)C)C1] | MS m/z (M + H): 532.4 |

TABLE 189-continued

| Compound No. | Structure | Physicochemical data |
|---|---|---|
| M75 | 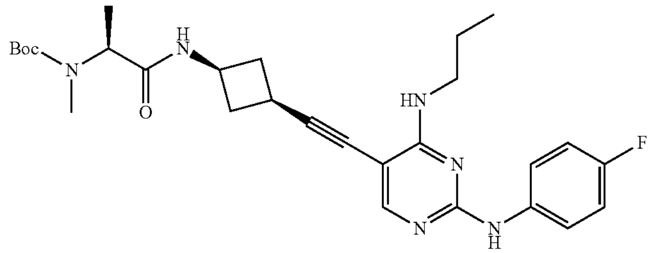 [SMILES: CCCNc1nc(Nc2ccc(F)cc2)ncc1C#C[C@H]1C[C@@H](NC(=O)[C@H](C)N(C)C(=O)OC(C)(C)C)C1] | MS m/z (M + H): 525.4 |
| M76 | 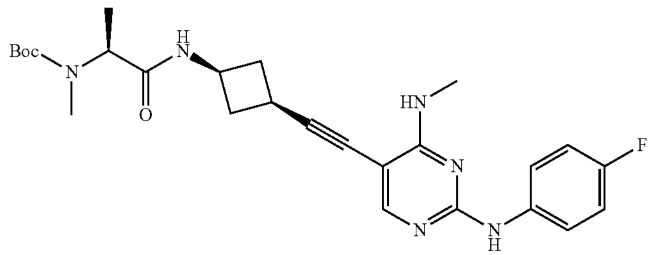 [SMILES: CNc1nc(Nc2ccc(F)cc2)ncc1C#C[C@H]1C[C@@H](NC(=O)[C@H](C)N(C)C(=O)OC(C)(C)C)C1] | MS m/z (M + H): 497.4 |
| M77 | 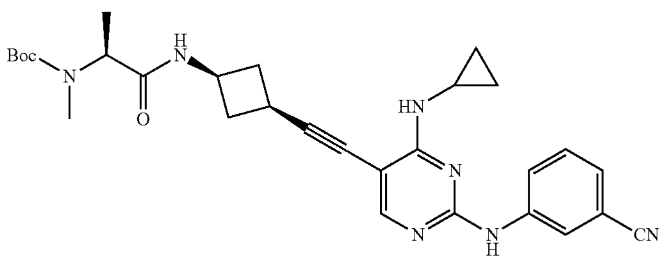 [SMILES: C[C@@H](C(=O)N[C@H]1C[C@@H](C#Cc2cnc(Nc3cccc(C#N)c3)nc2NC2CC2)C1)N(C)C(=O)OC(C)(C)C] | MS m/z (M + H): 530.5 |
| M78 | 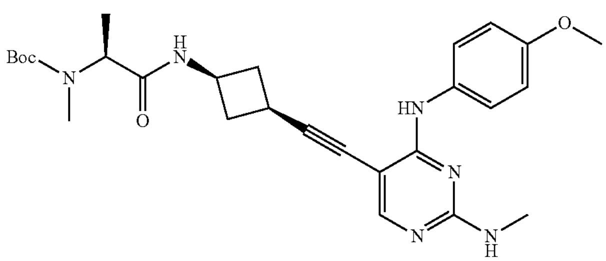 [SMILES: CNc1ncc(C#C[C@H]2C[C@@H](NC(=O)[C@H](C)N(C)C(=O)OC(C)(C)C)C2)c(Nc2ccc(OC)cc2)n1] | MS m/z (M + H): 509.5 |
| M79 | 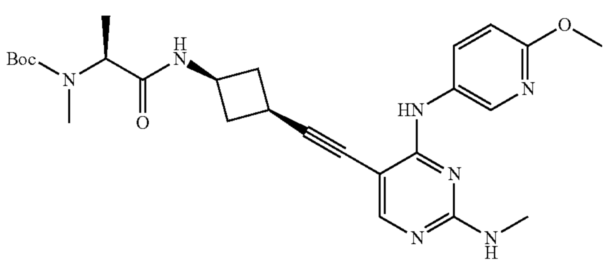 [SMILES: CNc1ncc(C#C[C@H]2C[C@@H](NC(=O)[C@H](C)N(C)C(=O)OC(C)(C)C)C2)c(Nc2ccc(OC)nc2)n1] | MS m/z (M + H): 510.4 |

In the same manner as that of Example 54, (6), Intermediates (M40) to (M47) and Intermediates (M80) to (M89) were obtained.

TABLE 190

| Compound No. | Structure | Physicochemical data |
|---|---|---|
| M40 | 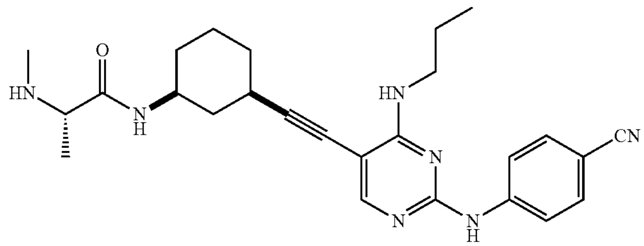 | — |
| M41 | 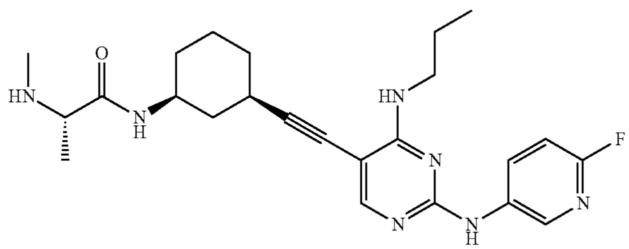 [SMILES: CCCNc1nc(Nc2ccc(F)nc2)ncc1C#C[C@@H]1CCC[C@H](NC(=O)[C@H](C)NC)C1] | — |
| M42 | 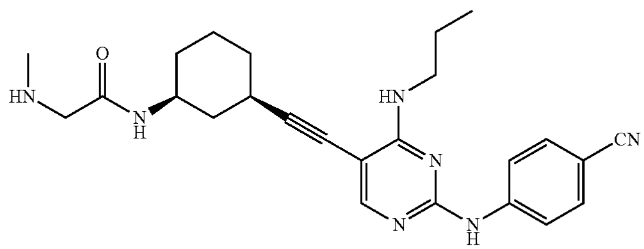 [SMILES: CCCNc1nc(Nc2ccc(C#N)cc2)ncc1C#C[C@@H]1CCC[C@H](NC(=O)CNC)C1] | — |
| M43 | 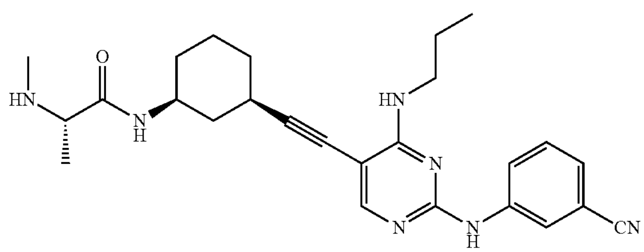 [SMILES: CCCNc1nc(Nc2cccc(C#N)c2)ncc1C#C[C@@H]1CCC[C@H](NC(=O)[C@H](C)NC)C1] | — |
| M44 | 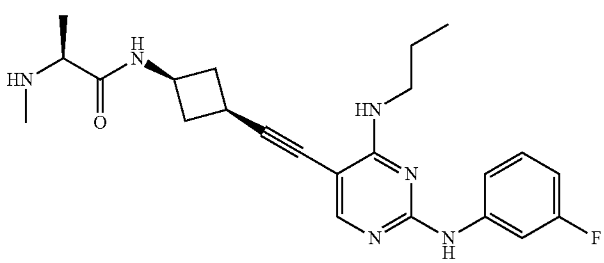 [SMILES: CCCNc1nc(Nc2cccc(F)c2)ncc1C#C[C@H]1C[C@@H](NC(=O)[C@H](C)NC)C1] | MS m/z (M + H): 425.3 |
| M45 | 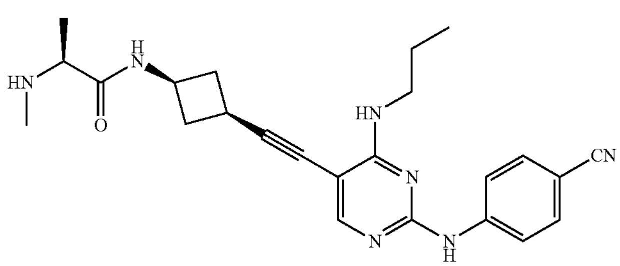 [SMILES: CCCNc1nc(Nc2ccc(C#N)cc2)ncc1C#C[C@H]1C[C@@H](NC(=O)[C@H](C)NC)C1] | — |

TABLE 190-continued

| Compound No. | Structure | Physicochemical data |
|---|---|---|
| M46 | 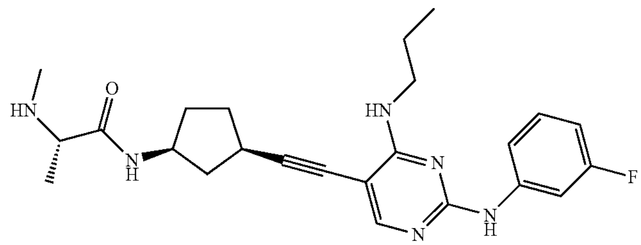 [SMILES: CCCNc1nc(Nc2cccc(F)c2)ncc1C#C[C@@H]1CC[C@H](NC(=O)[C@H](C)NC)C1] | — |
| M47 | 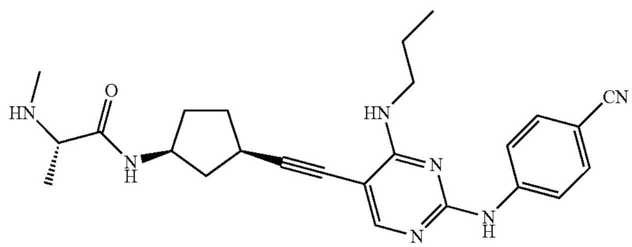 [SMILES: CCCNc1nc(Nc2ccc(C#N)cc2)ncc1C#C[C@@H]1CC[C@H](NC(=O)[C@H](C)NC)C1] | — |

TABLE 191

| Compound No. | Structure | Physicochemical data |
|---|---|---|
| M80 | 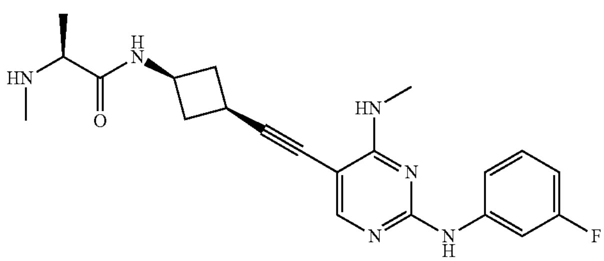 [SMILES: CNc1nc(Nc2cccc(F)c2)ncc1C#C[C@H]1C[C@@H](NC(=O)[C@H](C)NC)C1] | — |
| M81 | 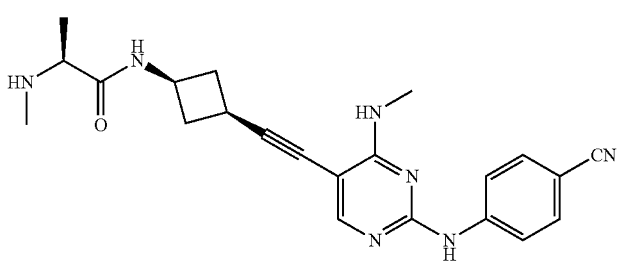 [SMILES: CNc1nc(Nc2ccc(C#N)cc2)ncc1C#C[C@H]1C[C@@H](NC(=O)[C@H](C)NC)C1] | — |
| M82 | 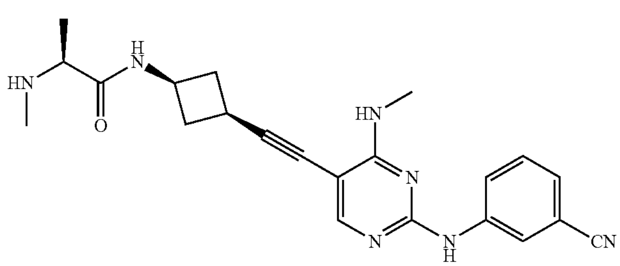 [SMILES: CNc1nc(Nc2cccc(C#N)c2)ncc1C#C[C@H]1C[C@@H](NC(=O)[C@H](C)NC)C1] | — |

TABLE 191-continued

| Compound No. | Structure | Physicochemical data |
|---|---|---|
| M83 | 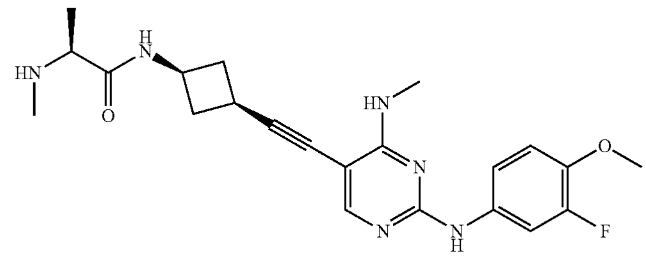 [SMILES: CNc1nc(Nc2ccc(OC)c(F)c2)ncc1C#C[C@H]1C[C@@H](NC(=O)[C@H](C)NC)C1] | — |
| M84 | 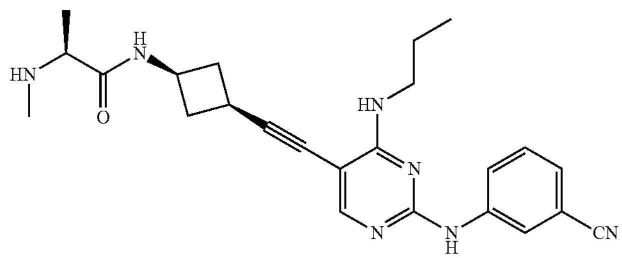 [SMILES: CCCNc1nc(Nc2cccc(C#N)c2)ncc1C#C[C@H]1C[C@@H](NC(=O)[C@H](C)NC)C1] | — |
| M85 | 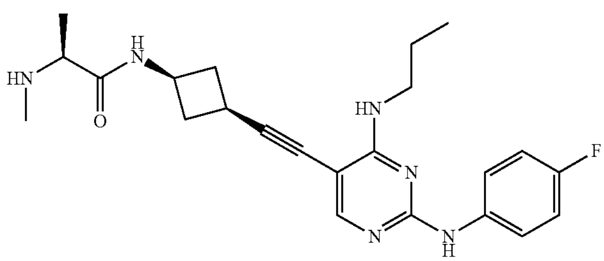 [SMILES: CCCNc1nc(Nc2ccc(F)cc2)ncc1C#C[C@H]1C[C@@H](NC(=O)[C@H](C)NC)C1] | MS m/z (M + H): 425.4 |
| M86 | 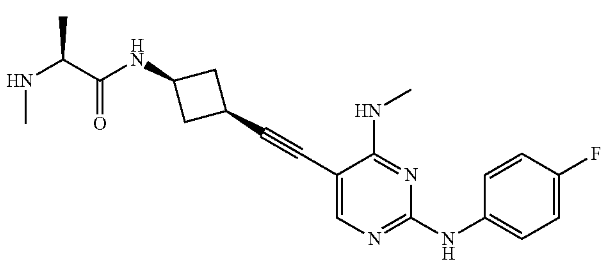 [SMILES: CNc1nc(Nc2ccc(F)cc2)ncc1C#C[C@H]1C[C@@H](NC(=O)[C@H](C)NC)C1] | MS m/z (M + H): 397.4 |
| M87 | 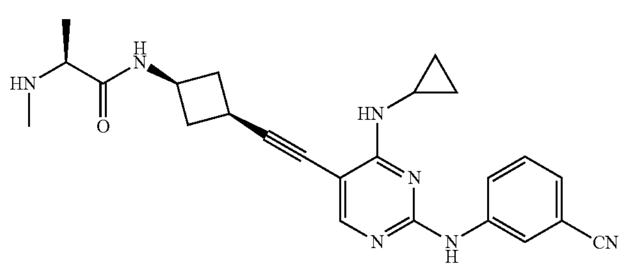 [SMILES: CN[C@@H](C)C(=O)N[C@H]1C[C@@H](C#Cc2cnc(Nc3cccc(C#N)c3)nc2NC2CC2)C1] | MS m/z (M + H): 430.4 |

TABLE 192

| Compound No. | Structure | Physicochemical data |
|---|---|---|
| M88 | 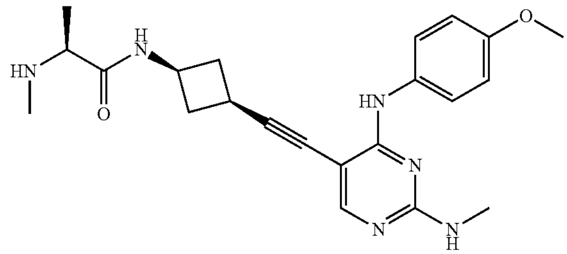 [SMILES: CNc1ncc(C#C[C@H]2C[C@@H](NC(=O)[C@H](C)NC)C2)c(Nc2ccc(OC)cc2)n1] | MS m/z (M + H): 409.4 |
| M89 | 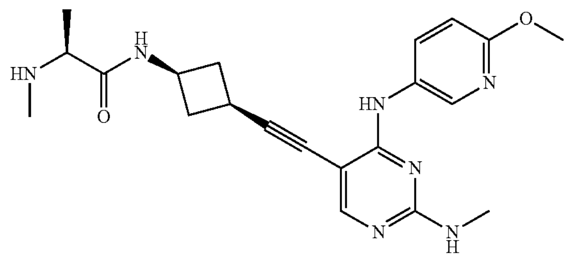 [SMILES: CNc1ncc(C#C[C@H]2C[C@@H](NC(=O)[C@H](C)NC)C2)c(Nc2ccc(OC)nc2)n1] | MS m/z (M + H): 410.4 |

By using (S)—N-((1S*,3R*)-3-((2-((4-cyanophenyl)amino)-4-(propylamino)pyrimidin-5-yl)ethynyl)cyclohexyl)-2-(methylamino)propanamide (M40), Intermediates (M48) and (M49) were obtained in the same manner as that of Example 54, (7).

TABLE 193

| Compound No. | Structure | Physicochemical data |
|---|---|---|
| M48 | 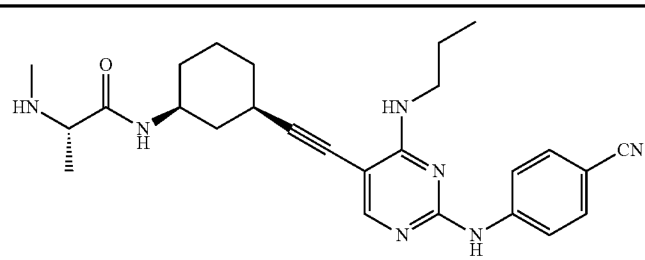 | — |
| M49 | 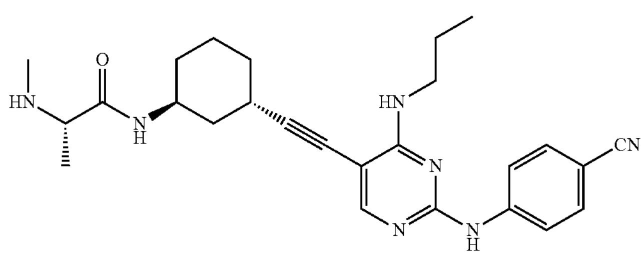 [SMILES: CCCNc1nc(Nc2ccc(C#N)cc2)ncc1C#C[C@H]1CCC[C@H](NC(=O)[C@H](C)NC)C1] | — |

Example 56

In the same manner as that of Example 54, Compounds (13-3) to (13-22) were obtained.

TABLE 194

| Compound No. | Structure | Physicochemical data |
|---|---|---|
| 13-3 | 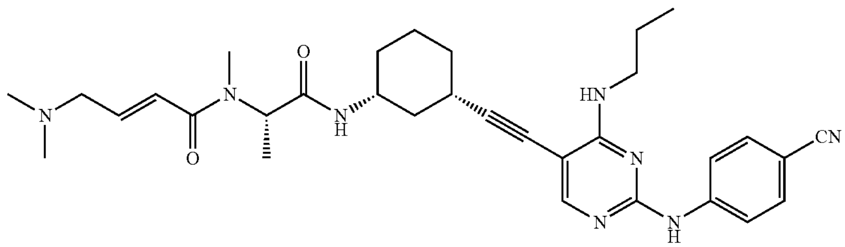 [SMILES: CCCNc1nc(Nc2ccc(C#N)cc2)ncc1C#C[C@H]1CCC[C@@H](NC(=O)[C@H](C)N(C)C(=O)/C=C/CN(C)C)C1] | ¹H-NMR (CDCl₃) δ: 7.98 (1H, s), 7.75 (2H, d, J = 9.2 Hz), 7.57 (2H, d, J = 9.2 Hz), 7.18-7.12 (1H, m), 6.93 (1H, dt, J = 15.2, 5.9 Hz), 6.42 (1H, d, J = 15.2 Hz), 6.31-6.21 (1H, m), 5.55-5.44 (1H, m), 5.16 (1H, q, J = 6.6 Hz), 3.83-3.63 (1H, m), 3.53-3.40 (2H, m), 3.10 (2H, d, J = 5.9 Hz), 2.97 (3H, s), 2.71-2.52 (1H, m), 2.28 (6H, s), 2.28-2.19 (1H, m), 2.05-1.80 (3H, m), 1.76-1.62 (2H, m), 1.48-1.11 (4H, m), 1.32 (3H, d, J = 8.9 Hz), 1.02 (3H, t, J = 6.6 Hz) |
| 13-4 | 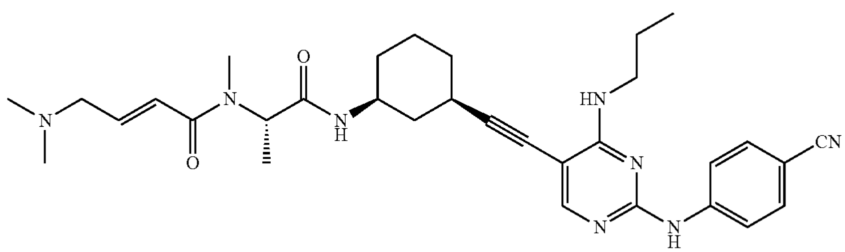 [SMILES: CCCNc1nc(Nc2ccc(C#N)cc2)ncc1C#C[C@@H]1CCC[C@H](NC(=O)[C@H](C)N(C)C(=O)/C=C/CN(C)C)C1] | ¹H-NMR (CDCl₃) δ: 7.98 (1H, s), 7.75 (2H, d, J = 8.6 Hz), 7.57 (2H, d, J = 8.6 Hz), 7.17 (1H, s), 6.93 (1H, dt, J = 15.2, 5.9 Hz), 6.42 (1H, d, J = 15.2 Hz), 6.34-6.25 (1H, m), 5.55-5.45 (1H, m), 5.16 (1H, q, J = 7.2 Hz), 3.83-3.65 (1H, m), 3.52-3.41 (2H, m), 3.11 (2H, d, J = 5.9 Hz), 2.98 (3H, s), 2.71-2.54 (1H, m), 2.29 (6H, s), 2.25-2.37 (1H, m), 2.10-1.93 (1H, m), 1.89-1.75 (2H, m), 1.77-1.63 (2H, m), 1.48-1.27 (4H, m), 1.34 (3H, d, J = 7.3 Hz), 1.02 (3H, t, J = 7.0 Hz) |
| 13-5 | 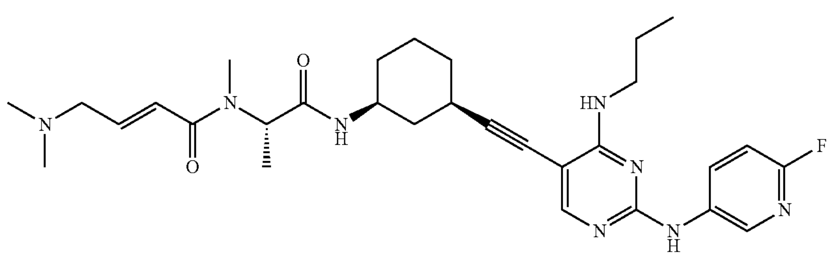 [SMILES: CCCNc1nc(Nc2ccc(F)nc2)ncc1C#C[C@@H]1CCC[C@H](NC(=O)[C@H](C)N(C)C(=O)/C=C/CN(C)C)C1] | ¹H-NMR (CDCl₃) δ: 8.37 (1H, s), 8.21-8.13 (1H, m), 7.95 (1H, s), 7.08-7.03 (1H, m), 6.98-6.89 (1H, m), 6.88 (1H, dd, J = 8.9, 3.6 Hz), 6.42 (1H, d, J = 15.2 Hz), 6.32 (1H, d, J = 7.3 Hz), 5.46 (1H, t, J = 5.6 Hz), 5.15 (1H, q, J = 7.0 Hz), 3.79-3.65 (1H, m), 3.49-3.39 (2H, m), 3.11 (2H, d, J = 5.9 Hz), 2.98 (3H, s), 2.67-2.55 (1H, m), 2.34-2.25 (1H, m), 2.28 (6H, s), 2.04-1.95 (1H, m), 1.86-1.76 (2H, m), 1.72-1.62 (2H, m), 1.50-1.26 (4H, m), 1.34 (3H, d, J = 7.0 Hz), 1.00 (3H, t, J = 7.3 Hz) |

TABLE 195

| Compound No. | Structure | Physicochemical data |
|---|---|---|
| 13-6 | 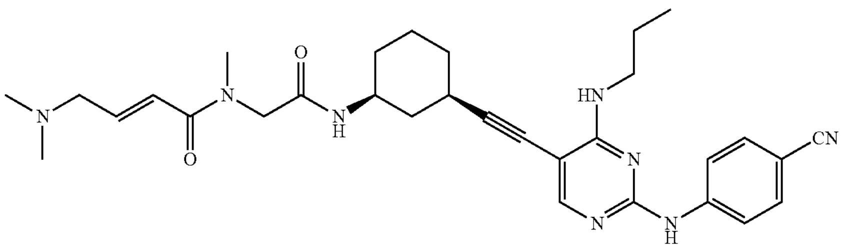 [SMILES: CCCNc1nc(Nc2ccc(C#N)cc2)ncc1C#C[C@@H]1CCC[C@H](NC(=O)CN(C)C(=O)/C=C/CN(C)C)C1] | ¹H-NMR (CDCl₃) δ: 7.98 (1H, s), 7.75 (2H, d, J = 8.6 Hz), 7.57 (2H, d, J = 8.6 Hz), 6.94 (1H, dt, J = 15.2, 5.9 Hz), 6.46 (1H, d, J = 15.2 Hz), 6.38 (1H, d, J = 7.9 Hz), 5.54-5.46 (1H, m), 4.01 (2H, s), 3.81-3.71 (1H, m), 3.51-3.42 (2H, m), 3.18 (3H, s), 3.10 (3H, d, J = 5.9 Hz), 2.68-2.58 (1H, m), 2.32-2.24 (1H, m), 2.26 (6H, s), 2.05-1.81 (3H, m), 1.75-1.64 (2H, m), 1.47-1.10 (3H, m), 1.01 (3H, t, J = 6.6 Hz) |
| 13-7 | 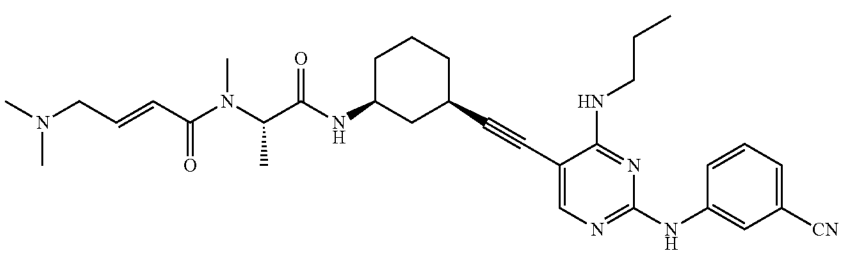 [SMILES: CCCNc1nc(Nc2cccc(C#N)c2)ncc1C#C[C@@H]1CCC[C@H](NC(=O)[C@H](C)N(C)C(=O)/C=C/CN(C)C)C1] | ¹H-NMR (CDCl₃) δ: 8.31 (1H, s), 7.97 (1H, s), 7.61-7.54 (1H, m), 7.36 (1H, dd, J = 7.9, 7.9 Hz), 7.26-7.22 (1H, m), 7.14-7.10 (1H, m), 6.93 (1H, dt, J = 15.2, 5.9 Hz), 6.42 (1H, d, J = 15.2 Hz), 6.33 (1H, d, J = 7.9 Hz), 5.51 (1H, t, J = 5.6 Hz), 5.15 (1H, q, J = 7.0 Hz), 3.79-3.67 (1H, m), 3.52-3.43 (2H, m), 3.11 (2H, d, J = 5.9 Hz), 2.98 (3H, s), 2.70-2.55 (1H, m), 2.35-2.28 (1H, m), 2.28 (6H, s), 2.05-1.98 (1H, m), 1.89-1.76 (2H, m), 1.77-1.64 (2H, m), 1.50-1.24 (4H, m), 1.34 (3H, d, J = 7.0 Hz), 1.04 (3H, t, J = 7.3 Hz) |
| 13-8 | 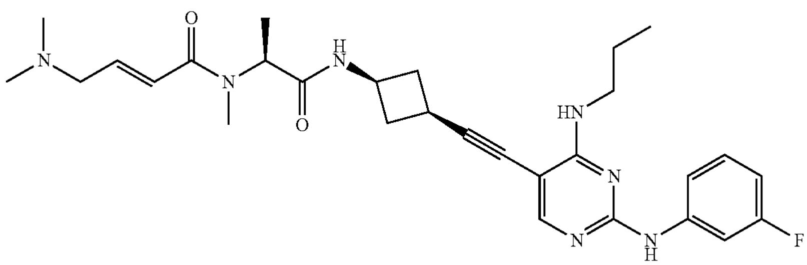 [SMILES: CCCNc1nc(Nc2cccc(F)c2)ncc1C#C[C@H]1C[C@@H](NC(=O)[C@H](C)N(C)C(=O)/C=C/CN(C)C)C1] | ¹H-NMR (CDCl₃) δ: 7.99 (1H, s), 7.84-7.75 (1H, m), 7.27-7.17 (1H, m), 7.11-7.09 (1H, m), 7.09-7.06 (1H, m), 6.95 (1H, dt, J = 15.2, 5.9 Hz), 6.73-6.64 (1H, m), 6.66-6.58 (1H, m), 6.43 (1H, d, J = 15.2 Hz), 5.57-5.46 (1H, m), 5.16 (1H, q, J = 7.0 Hz), 4.35-4.20 (1H, m), 3.54-3.44 (2H, m), 3.11 (2H, d, J = 5.9 Hz), 3.01-2.88 (1H, m), 2.98 (3H, s), 2.84-2.70 (2H, m), 2.27 (6H, s), 2.14-1.98 (2H, m), 1.76-1.65 (2H, m), 1.34 (3H, d, J = 7.0 Hz), 1.02 (3H, t, J = 7.3 Hz) |

TABLE 196

| Compound No. | Structure | Physicochemical data |
|---|---|---|
| 13-9 | 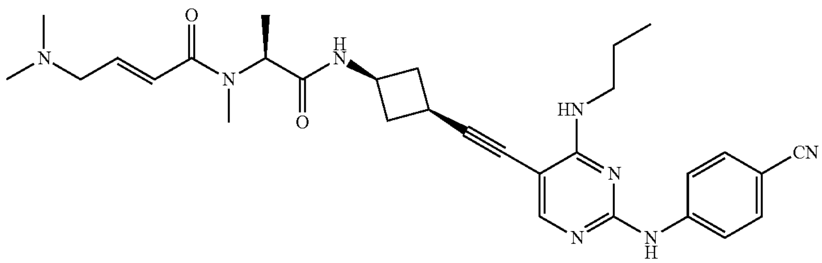 [SMILES: CCCNc1nc(Nc2ccc(C#N)cc2)ncc1C#C[C@H]1C[C@@H](NC(=O)[C@H](C)N(C)C(=O)/C=C/CN(C)C)C1] | ¹H-NMR (CDCl₃) δ: 8.01 (1H, s), 7.76 (2H, d, J = 8.6 Hz), 7.57 (2H, d, J = 8.6 Hz), 7.26-7.22 (1H, m), 6.95 (1H, dt, J = 15.2, 5.9 Hz), 6.67-6.60 (1H, m), 6.43 (1H, d, J = 15.2 Hz), 5.61-5.51 (1H, m), 5.15 (1H, q, J = 7.0 Hz), 4.35-4.20 (1H, m), 3.53-3.42 (2H, m), 3.11 (2H, d, J = 5.9 Hz), 3.01-2.88 (1H, m), 2.98 (3H, s), 2.84-2.70 (2H, m), 2.28 (6H, s), 2.16-2.00 (2H, m), 1.76-1.65 (2H, m), 1.34 (3H, d, J = 7.3 Hz), 1.02 (3H, t, J = 7.6 Hz) |
| 13-10 | 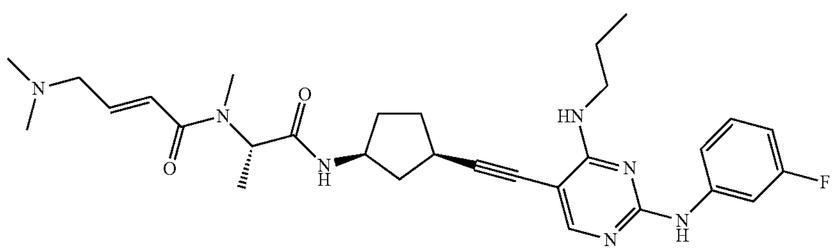 [SMILES: CCCNc1nc(Nc2cccc(F)c2)ncc1C#C[C@@H]1CC[C@H](NC(=O)[C@H](C)N(C)C(=O)/C=C/CN(C)C)C1] | ¹H-NMR (CDCl₃) δ: 8.00 (1H, s), 7.81 (1H, d, J = 11.9 Hz), 7.26-7.17 (1H, m), 7.12-7.05 (2H, m), 6.91 (1H, dt, J = 15.2, 5.9 Hz), 6.68 (1H, td, J = 8.3, 2.6 Hz), 6.62-6.56 (1H, m), 6.40 (1H, d, J = 15.2 Hz), 5.74-5.65 (1H, m), 5.13 (1H, q, J = 7.0 Hz), 4.28-4.19 (1H, m), 3.52-3.43 (2H, m), 3.08 (2H, d, J = 5.9 Hz), 2.97 (3H, s), 2.49-2.38 (1H, m), 2.26 (6H, s), 2.08-1.94 (2H, m), 1.94-1.50 (4H, m), 1.76-1.64 (2H, m), 1.34 (3H, d, J = 7.0 Hz), 1.01 (3H, t, J = 7.3 Hz) |
| 13-11 | 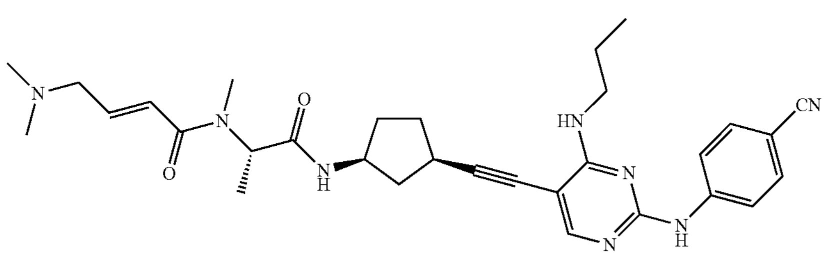 [SMILES: CCCNc1nc(Nc2ccc(C#N)cc2)ncc1C#C[C@@H]1CC[C@H](NC(=O)[C@H](C)N(C)C(=O)/C=C/CN(C)C)C1] | ¹H-NMR (CDCl₃) δ: 8.02 (1H, s), 7.76 (2H, d, J = 8.6 Hz), 7.57 (2H, d, J = 8.6 Hz), 7.22-7.18 (1H, m), 6.91 (1H, dt, J = 15.2, 5.9 Hz), 6.65-6.58 (1H, m), 6.41 (1H, d, J = 15.2 Hz), 5.78-5.73 (1H, m), 5.13 (1H, q, J = 7.0 Hz), 4.30-4.19 (1H, m), 3.50-3.42 (2H, m), 3.09 (2H, d, J = 5.9 Hz), 2.98 (3H, s), 2.49-2.39 (1H, m), 2.26 (6H, s), 2.11-1.94 (2H, m), 1.90-1.55 (4H, m), 1.75-1.65 (2H, m), 1.34 (3H, d, J = 7.0 Hz), 1.01 (3H, t, J = 7.6 Hz) |

TABLE 196-continued

| Compound No. | Structure | Physicochemical data |
|---|---|---|
| 13-12 | 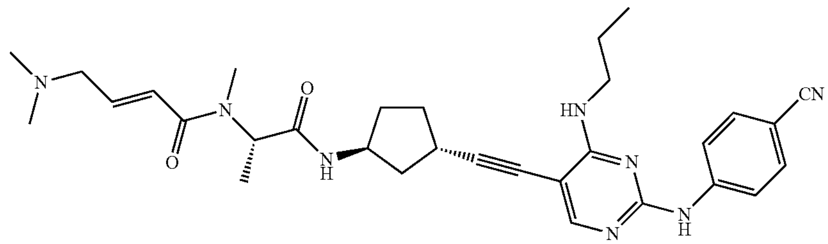 [SMILES: CCCNc1nc(Nc2ccc(C#N)cc2)ncc1C#C[C@H]1CC[C@H](NC(=O)[C@H](C)N(C)C(=O)/C=C/CN(C)C)C1] | ¹H-NMR (CDCl₃) δ: 7.97 (1H, s), 7.76 (2H, d, J = 9.2 Hz), 7.57 (2H, d, J = 9.2 Hz), 7.39-7.35 (1H, m), 6.93 (1H, dt, J = 15.2, 5.9 Hz), 6.53-6.47 (1H, m), 6.43 (1H, d, J = 15.2 Hz), 5.55-5.48 (1H, m), 5.12 (1H, q, J = 7.0 Hz), 4.41-4.30 (1H, m), 3.51-3.42 (2H, m), 3.15-3.01 (1H, m), 3.12 (2H, d, J = 4.6 Hz), 2.98 (3H, s), 2.29 (6H, s), 2.22-1.88 (4H, m), 1.79-1.64 (2H, m), 1.46-1.23 (2H, m), 1.34 (3H, d, J = 7.0 Hz), 1.02 (3H, t, J = 7.6 Hz) |

TABLE 197

| Compound No. | Structure | Physicochemical data |
|---|---|---|
| 13-13 | 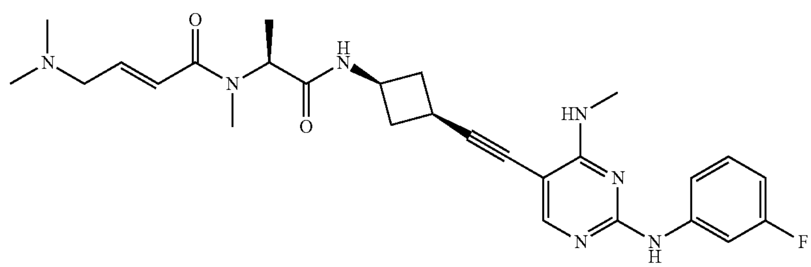 [SMILES: CNc1nc(Nc2cccc(F)c2)ncc1C#C[C@H]1C[C@@H](NC(=O)[C@H](C)N(C)C(=O)/C=C/CN(C)C)C1] | ¹H-NMR (CDCl₃) δ: 7.98 (1H, s), 7.84-7.76 (1H, m), 7.25-7.18 (1H, m), 7.15-7.12 (1H, m), 7.13-7.09 (1H, m), 6.94 (1H, dt, J = 15.2, 5.9 Hz), 6.72-6.65 (1H, m), 6.68-6.63 (1H, m), 6.53 (1H, d, J = 15.2 Hz), 5.56-5.51 (1H, m), 5.15 (1H, q, J = 7.3 Hz), 4.32-4.23 (1H, m), 3.22 (2H, d, J = 5.9 Hz), 3.11 (3H, d, J = 4.6 Hz), 3.00 (3H, s), 2.98-2.90 (1H, m), 2.80-2.73 (2H, m), 2.37 (6H, s), 2.17-2.01 (2H, m), 1.34 (3H, d, J = 7.3 Hz) |
| 13-14 | 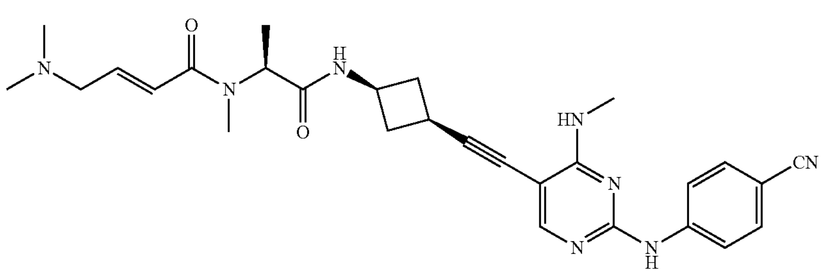 [SMILES: CNc1nc(Nc2ccc(C#N)cc2)ncc1C#C[C@H]1C[C@@H](NC(=O)[C@H](C)N(C)C(=O)/C=C/CN(C)C)C1] | ¹H-NMR (CDCl₃) δ: 8.00 (1H, s), 7.78 (2H, d, J = 9.2 Hz), 7.58-7.52 (1H, m), 7.57 (2H, d, J = 9.2 Hz), 6.94 (1H, dt, J = 15.2, 5.9 Hz), 6.76-6.69 (1H, m), 6.48 (1H, d, J = 15.2 Hz), 5.61-5.55 (1H, m), 5.15 (1H, q, J = 7.0 Hz), 4.33-4.23 (1H, m), 3.16 (2H, d, J = 5.9 Hz), 3.10 (3H, d, J = 4.3 Hz), 2.99 (3H, s), 2.98-2.88 (1H, m), 2.84-2.66 (2H, m), 2.32 (6H, s), 2.17-2.05 (2H, m), 1.34 (3H, d, J = 7.0 Hz) |

TABLE 197-continued

| Compound No. | Structure | Physicochemical data |
|---|---|---|
| 13-15 | 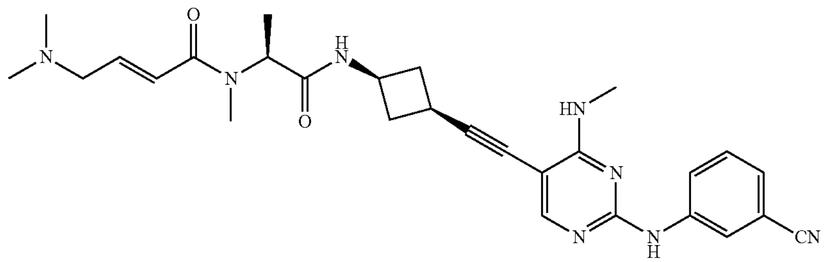 [SMILES: CNc1nc(Nc2cccc(C#N)c2)ncc1C#C[C@H]1C[C@@H](NC(=O)[C@H](C)N(C)C(=O)/C=C/CN(C)C)C1] | ¹H-NMR (CDCl₃) δ: 8.34 (1H, s), 8.00 (1H, s), 7.65-7.59 (1H, m), 7.36 (1H, dd, J = 7.0, 7.0 Hz), 7.35-7.30 (1H, m), 7.28-7.24 (1H, m), 6.95 (1H, dt, J = 15.2, 5.9 Hz), 6.73-6.67 (1H, m), 6.53 (1H, d, J = 15.2 Hz), 5.61-5.55 (1H, m), 5.15 (1H, q, J = 7.3 Hz), 4.34-4.23 (1H, m), 3.22 (2H, d, J = 5.9 Hz), 3.11 (3H, d, J = 4.6 Hz), 3.00 (3H, s), 2.99-2.89 (1H, m), 2.83-2.71 (2H, m), 2.37 (6H, s), 2.17-2.05 (2H, m), 1.35 (3H, d, J = 7.3 Hz) |
| 13-16 | 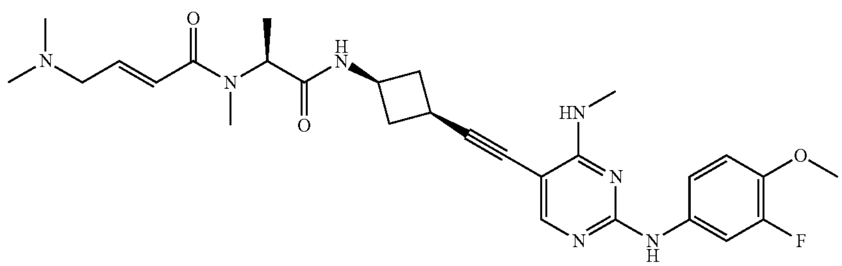 | ¹H-NMR (CDCl₃) δ: 7.95 (1H, s), 7.79-7.71 (1H, m), 7.12-7.09 (1H, m), 7.09-7.06 (1H, m), 6.99-6.90 (1H, m), 6.94-6.86 (1H, m), 6.67-6.63 (1H, m), 6.55 (1H, d, J = 15.2 Hz), 5.54-5.50 (1H, m), 5.15 (1H, q, J = 7.3 Hz), 4.32-4.23 (1H, m), 3.87 (3H, s), 3.24 (2H, d, J = 5.9 Hz), 3.09 (3H, d, J = 4.0 Hz), 3.00 (3H, s), 2.97-2.87 (1H, m), 2.81-2.73 (2H, m), 2.39 (6H, s), 2.15-2.05 (2H, m), 1.34 (3H, d, J = 7.3 Hz) |

TABLE 198

| Compound No. | Structure | Physicochemical data |
|---|---|---|
| 13-17 | 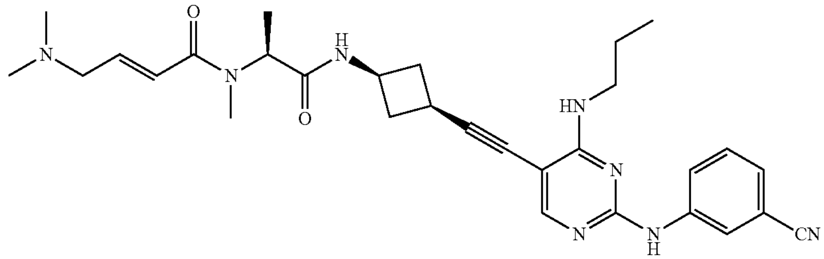 [SMILES: CCCNc1nc(Nc2cccc(C#N)c2)ncc1C#C[C@H]1C[C@@H](NC(=O)[C@H](C)N(C)C(=O)/C=C/CN(C)C)C1] | ¹H-NMR (CDCl₃) δ: 8.33 (1H, s), 7.99 (1H, s), 7.62-7.55 (1H, m), 7.59-7.53 (1H, m), 7.36 (1H, dd, J = 7.9, 7.9 Hz), 7.28-7.23 (1H, m), 6.94 (1H, dt, J = 15.2, 5.9 Hz), 6.73-6.66 (1H, m), 6.60 (1H, d, J = 15.2 Hz), 5.62-5.55 (1H, m), 5.14 (1H, q, J = 7.3 Hz), 4.33-4.23 (1H, m), 3.53-3.47 (2H, m), 3.29 (2H, d, J = 5.9 Hz), 3.01 (3H, s), 3.00-2.89 (1H, m), 2.83-2.72 (2H, m), 2.43 (6H, s), 2.17-2.05 (2H, m), 1.77-1.68 (2H, m), 1.35 (3H, d, J = 7.3 Hz), 1.04 (3H, t, J = 7.6 Hz) |

TABLE 198-continued

| Compound No. | Structure | Physicochemical data |
|---|---|---|
| 13-18 | 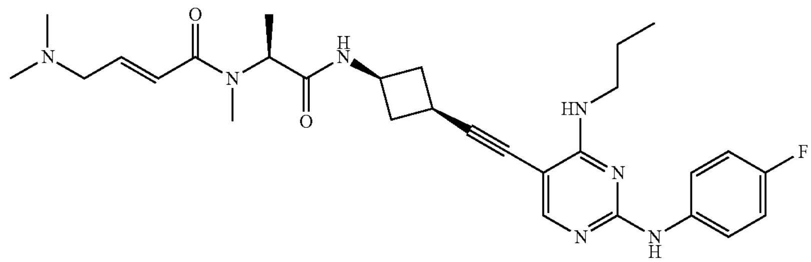 [SMILES: CCCNc1nc(Nc2ccc(F)cc2)ncc1C#C[C@H]1C[C@@H](NC(=O)[C@H](C)N(C)C(=O)/C=C/CN(C)C)C1] | ¹H-NMR (CDCl₃) δ: 7.97 (1H, s), 7.60-7.52 (2H, m), 7.10-7.07 (1H, m), 7.04-6.96 (2H, m), 6.99-6.89 (1H, m), 6.68-6.62 (1H, m), 6.43 (1H, d, J = 15.2 Hz), 5.50-5.44 (1H, m), 5.16 (1H, q, J = 7.3 Hz), 4.32-4.23 (1H, m), 3.48-3.41 (2H, m), 3.12 (2H, d, J = 5.9 Hz), 2.98 (3H, s), 2.97-2.88 (1H, m), 2.81-2.71 (2H, m), 2.30 (6H, s), 2.12-2.00 (2H, m), 1.73-1.64 (2H, m), 1.34 (3H, d, J = 7.3 Hz), 1.00 (3H, t, J = 7.6 Hz) |
| 13-19 | 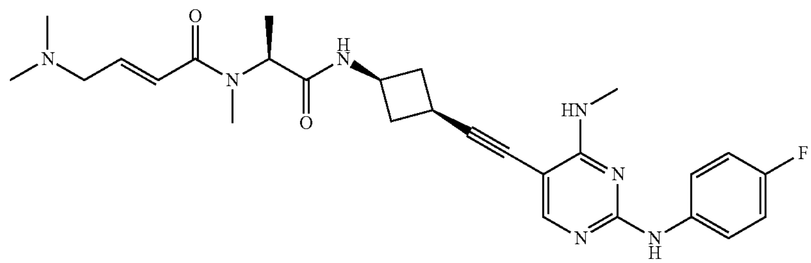 [SMILES: CNc1nc(Nc2ccc(F)cc2)ncc1C#C[C@H]1C[C@@H](NC(=O)[C@H](C)N(C)C(=O)/C=C/CN(C)C)C1] | ¹H-NMR (CDCl₃) δ: 7.97 (1H, s), 7.61-7.54 (2H, m), 7.18-7.15 (1H, m), 7.05-6.96 (2H, m), 6.99-6.89 (1H, m), 6.72-6.66 (1H, m), 6.43 (1H, d, J = 15.2 Hz), 5.48-5.43 (1H, m), 5.16 (1H, q, J = 7.0 Hz), 4.32-4.23 (1H, m), 3.11 (2H, d, J = 5.9 Hz), 3.07 (3H, d, J = 4.6 Hz), 2.98-2.87 (1H, m), 2.98 (3H, s), 2.81-2.71 (2H, m), 2.28 (6H, s), 2.13-1.99 (2H, m), 1.34 (3H, d, J = 7.0 Hz) |
| 13-20 | 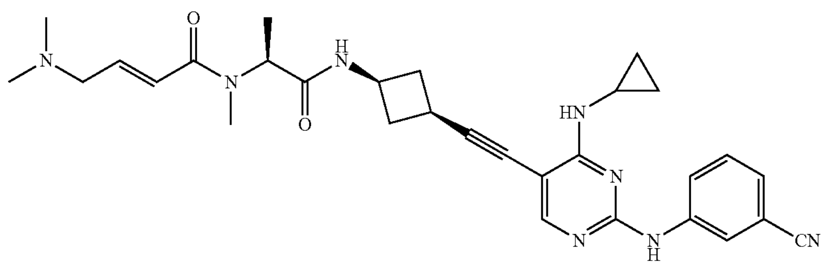 [SMILES: C[C@@H](C(=O)N[C@H]1C[C@@H](C#Cc2cnc(Nc3cccc(C#N)c3)nc2NC2CC2)C1)N(C)C(=O)/C=C/CN(C)C] | ¹H-NMR (CDCl₃) δ: 8.73 (1H, s), 8.01 (1H, s), 7.53-7.48 (1H, m), 7.36-7.31 (1H, m), 7.36 (1H, dd, J = 7.0, 7.0 Hz), 7.27-7.23 (1H, m), 6.95 (1H, dt, J = 15.2, 5.9 Hz), 6.73-6.63 (1H, m), 6.45 (1H, d, J = 15.2 Hz), 5.68-5.65 (1H, m), 5.15 (1H, q, J = 7.3 Hz), 4.33-4.23 (1H, m), 3.14 (2H, d, J = 5.9 Hz), 2.99 (3H, s), 2.96-2.89 (1H, m), 2.92-2.82 (1H, m), 2.84-2.68 (2H, m), 2.30 (6H, s), 2.11-2.02 (2H, m), 1.34 (3H, d, J = 7.3 Hz), 1.04-0.98 (2H, m), 0.72-0.66 (2H, m) |

TABLE 199

| Compound No. | Structure | Physicochemical data |
|---|---|---|
| 13-21 | 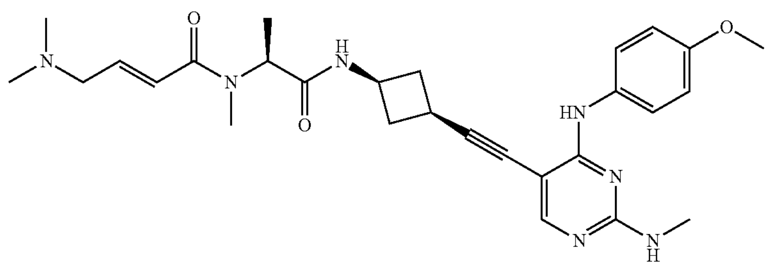 | ¹H-NMR (CDCl₃) δ: 8.04 (1H, s), 7.54 (2H, d, J = 8.6 Hz), 7.08-6.84 (4H, m), 6.65 (1H, d, J = 7.3 Hz), 6.42 (1H, d, J = 15.2 Hz), 5.16 (1H, q, J = 7.0 Hz), 5.09-4.98 (1H, m), 4.37-4.20 (1H, m), 3.81 (3H, s), 3.10 (2H, d, J = 4.6 Hz), 3.05-2.90 (7H, m), 2.87-2.69 (2H, m), 2.26 (6H, s), 2.21-1.99 (2H, m), 1.33 (3H, d, J = 7.0 Hz) |

TABLE 199-continued

| Compound No. | Structure | Physicochemical data |
|---|---|---|
| 13-22 | (structure) | $^1$H-NMR (CDCl$_3$) δ: 8.42-8.35 (1H, m), 8.06 (1H, s), 7.95-7.82 (1H, m), 7.02-6.88 (2H, m), 6.75 (1H, d, J = 9.2 Hz), 6.71-6.61 (1H, m), 6.42 (1H, d, J = 15.2 Hz), 5.15 (1H, q, J = 7.0 Hz), 5.09-4.97 (1H, m), 4.35-4.21 (1H, m), 3.94 (3H, s), 3.10 (2H, d, J = 4.6 Hz), 3.04-2.87 (7H, m), 2.87-2.69 (2H, m), 2.27 (6H, s), 2.21-2.01 (2H, m), 1.33 (3H, d, J = 7.0 Hz) |

Example 57

1

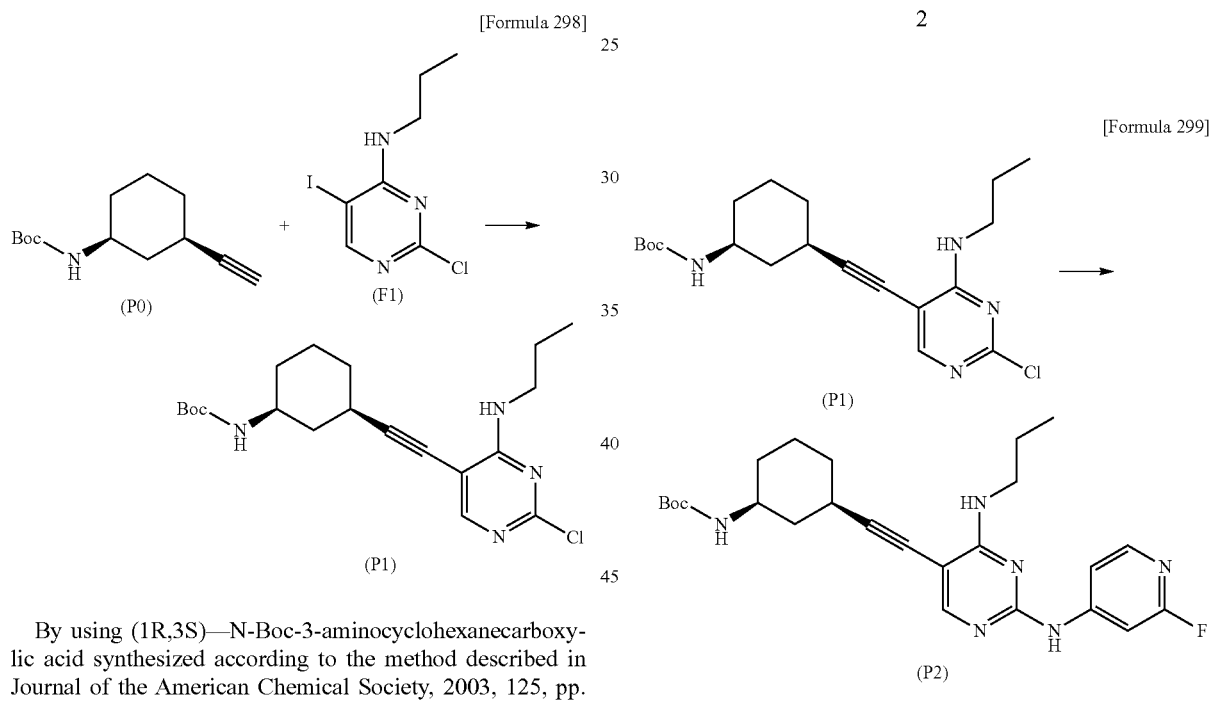

[Formula 298]

[Formula 299]

By using (1R,3S)—N-Boc-3-aminocyclohexanecarboxylic acid synthesized according to the method described in Journal of the American Chemical Society, 2003, 125, pp. 2844-2845, tert-butyl ((1S,3R)-3-ethynylcyclohexyl)carbamate (P0) was obtained in the same manner as that of Example 54, (1) and (2).

To a solution of 2-chloro-5-iodo-N-propylpyrimidin-4-amine (F1, 78 mg), bis(triphenylphosphine)palladium(II) dichloride (18 mg) and copper(I) iodide (10 mg) in N,N-dimethylformamide (2 mL), triethylamine (181 μL) and tert-butyl ((1S,3R)-3-ethynylcyclohexyl)carbamate (P0, 70 mg) were added at room temperature, and the mixture was stirred at the same temperature for 8 hours. To the reaction mixture, ethyl acetate and saturated aqueous ammonium chloride were added. The organic layer was separated, washed successively with saturated aqueous ammonium chloride, water and saturated aqueous sodium chloride, and then dried over anhydrous magnesium sulfate, and the solvent was evaporated under reduced pressure. The obtained residue was purified by silica gel column chromatography (eluent, 94 to 60% hexane in ethyl acetate) to obtain tert-butyl ((1S,3R)-3-((2-chloro-4-(propylamino)pyrimidin-5-yl)ethynyl)cyclohexyl)carbamate (P1, 83 mg).

MS m/z (M+H): 393.3

2

To tert-butyl ((1S,3R)-3-((2-chloro-4-(propylamino)pyrimidin-5-yl)ethynyl)cyclohexyl)carbamate (P1, 155 mg), 4-amino-2-fluoropyridine (89 mg), tris(dibenzylideneacetone)dipalladium(0) (36 mg), 4,5'-bis(diphenylphosphino)-9,9'-dimethylxanthene (45 mg) and cesium carbonate (381 mg), 1,4-dioxane (5 mL) was added at room temperature, the reaction vessel was sealed, and then the mixture was stirred at 150° C. for 1 hour by using a microwave reaction system. The reaction mixture was cooled to room temperature, and then the solvent was evaporated under reduced pressure. The obtained residue was purified by silica gel column chromatography (eluent, 88 to 30% hexane in ethyl acetate) to obtain tert-butyl ((1S,3R)-3-((2-((2-fluoropyridin-4-yl)amino)-4-(propylamino)pyrimidin-5-yl)ethynyl)cyclohexyl)carbamate (P2).

MS m/z (M+H): 469.4

3

[Formula 300]

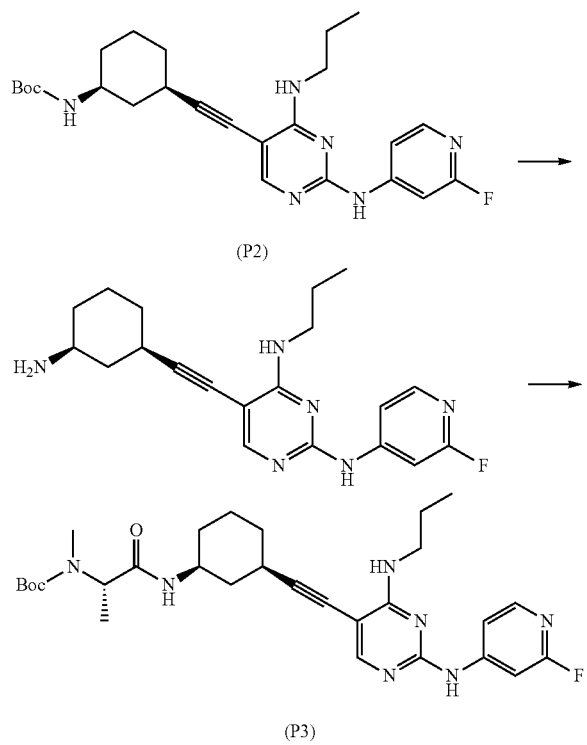

To a solution of tert-butyl ((1S,3R)-3-((2-((2-fluoropyridin-4-yl)amino)-4-(propylamino)pyrimidin-5-yl)ethynyl)cyclohexyl)carbamate (P2) obtained above in 1,4-dioxane (2 mL), a 4.0 mol/L solution of hydrochloric acid in 1,4-dioxane (4 mL) was added at room temperature, and the mixture was stirred at the same temperature for 2 hours and 30 minutes. The solvent was evaporated under reduced pressure.

To a solution of the residue obtained above, N-Boc-N-methyl-L-alanine (163 mg), 1-ethyl-3-(3-dimethylaminopropyl)carbodiimide hydrochloride (153 mg) and 1-hydroxybenzotriazole monohydrate (108 mg) in N,N-dimethylformamide (3 mL), N,N-diisopropylethylamine (408 μL) was added at room temperature, and the mixture was stirred at the same temperature for 2 hours. To the reaction mixture, ethyl acetate and saturated aqueous sodium hydrogencarbonate were added. The organic layer was separated, washed successively with saturated aqueous sodium hydrogencarbonate, water and saturated aqueous sodium chloride, and then dried over anhydrous magnesium sulfate, and the solvent was evaporated under reduced pressure. The obtained residue was purified by silica gel column chromatography (eluent, 70 to 20% hexane in ethyl acetate) to obtain tert-butyl ((S)-1-(((1S,3R)-3-((2-((2-fluoropyridin-4-yl)amino)-4-(propylamino)pyrimidin-5-yl)ethynyl)cyclohexyl)amino)-1-oxopropan-2-yl)(methyl)carbamate (P3, 32 mg).

MS m/z (M+H): 554.4

4

[Formula 301]

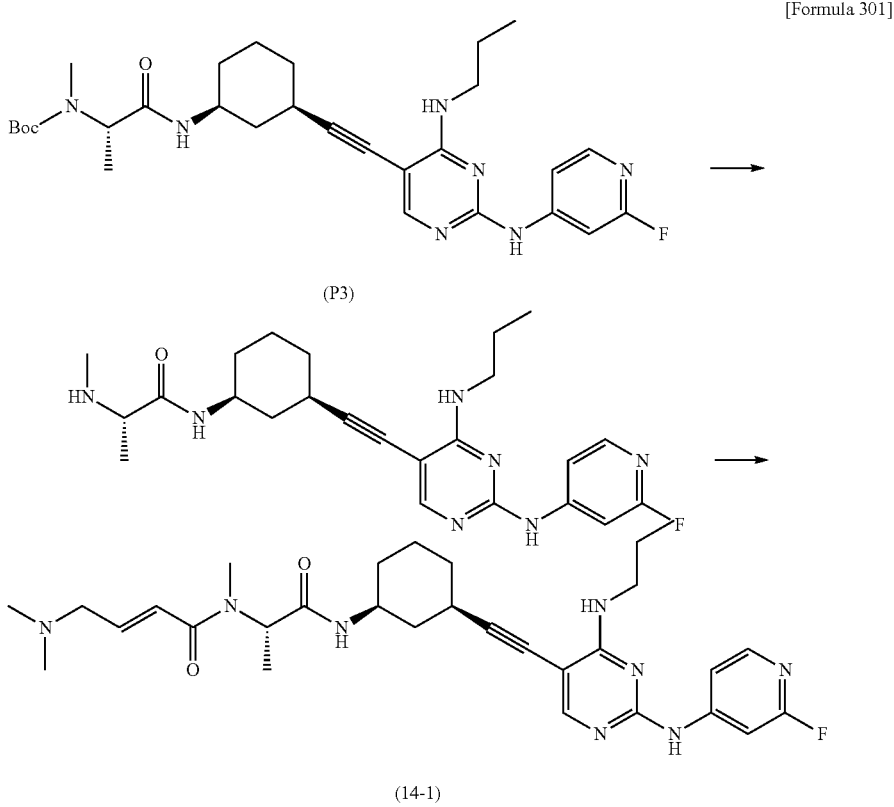

(14-1)

By using tert-butyl ((S)-1-(((1S,3R)-3-((2-((2-fluoropyridin-4-yl)amino)-4-(propylamino)pyrimidin-5-yl)ethynyl)cyclohexyl)amino)-1-oxopropan-2-yl)(methyl)carbamate (P3), (E)-4-(dimethylamino)-N—((S)-1-(((1S,3R)-3-((2-((2-fluoropyridin-4-yl)amino)-4-(propylamino)pyrimidin-5-yl)ethynyl)cyclohexyl)amino)-1-oxopropan-2-yl)-N-methyl-2-butenamido(14-1) was obtained in the same manner as that of Example 35, (6) and (7).

¹H-NMR (CDCl₃) δ: 8.02-7.97 (2H, m), 7.62 (1H, d, J=2.0 Hz), 7.10 (1H, d, J=5.9 Hz), 6.93 (1H, dt, J=15.2, 5.9 Hz), 6.42 (1H, d, J=15.2 Hz), 6.35-6.29 (1H, m), 5.59-5.52 (1H, m), 5.15 (1H, q, J=7.0 Hz), 3.81-3.65 (1H, m), 3.52-3.44 (2H, m), 3.11 (2H, d, J=5.9 Hz), 2.98 (3H, s), 2.69-2.57 (1H, m), 2.35-2.28 (1H, m), 2.28 (6H, s), 2.05-1.97 (1H, m), 1.88-1.78 (2H, m), 1.80-1.66 (2H, m), 1.40-1.27 (5H, m), 1.34 (3H, d, J=7.3 Hz), 1.03 (3H, t, J=6.6 Hz)

Example 58

1

In the same manner as that of Example 57, (1), Intermediates (P4) to (P6) were obtained.

TABLE 200

| Compound No. | Structure | Physicochemical data |
|---|---|---|
| P4 | 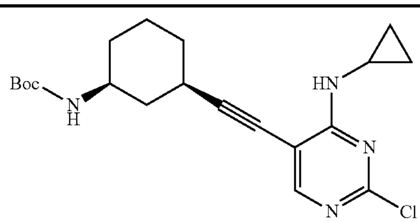 | — |
| P5 | 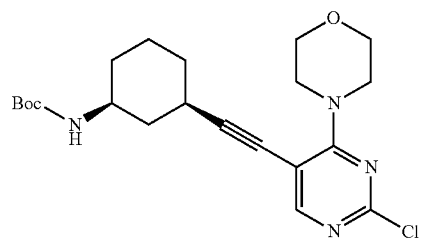 [SMILES: CC(C)(C)OC(=O)N[C@H]1CCC[C@@H](C#Cc2cnc(Cl)nc2N2CCOCC2)C1] | — |
| P6 | 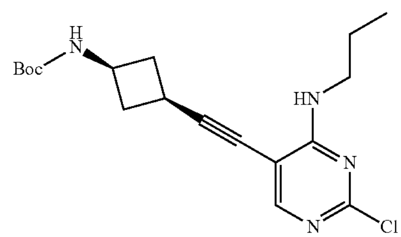 [SMILES: CCCNc1nc(Cl)ncc1C#C[C@H]1C[C@@H](NC(=O)OC(C)(C)C)C1] | MS m/z (M + H): 365.2 |

2

In the same manner as that of Example 57, (2), Intermediates (P7) to (P10) and Intermediates (P15) were obtained.

TABLE 201

| Compound No. | Structure | Physicochemical data |
|---|---|---|
| P7 | 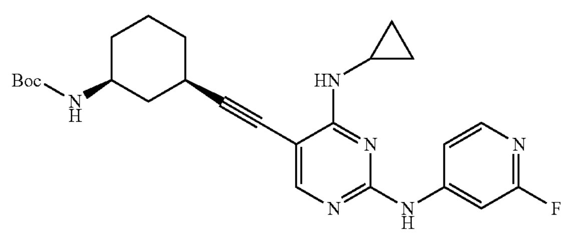 [SMILES: CC(C)(C)OC(=O)N[C@H]1CCC[C@@H](C#Cc2cnc(Nc3ccnc(F)c3)nc2NC2CC2)C1] | — |
| P8 | 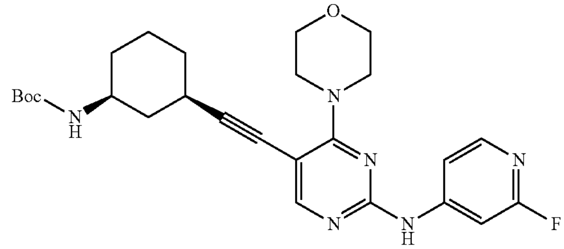 [SMILES: CC(C)(C)OC(=O)N[C@H]1CCC[C@@H](C#Cc2cnc(Nc3ccnc(F)c3)nc2N2CCOCC2)C1] | — |

TABLE 201-continued

| Compound No. | Structure | Physicochemical data |
|---|---|---|
| P9 | 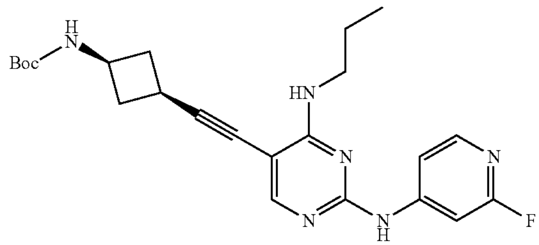 [SMILES: CCCNc1nc(Nc2ccnc(F)c2)ncc1C#C[C@H]1C[C@@H](NC(=O)OC(C)(C)C)C1] | — |
| P10 | 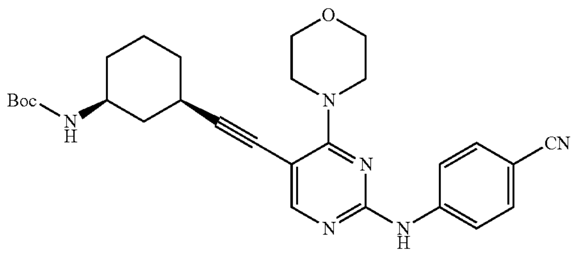 [SMILES: CC(C)(C)OC(=O)N[C@H]1CCC[C@@H](C#Cc2cnc(Nc3ccc(C#N)cc3)nc2N2CCOCC2)C1] | — |
| P15 | 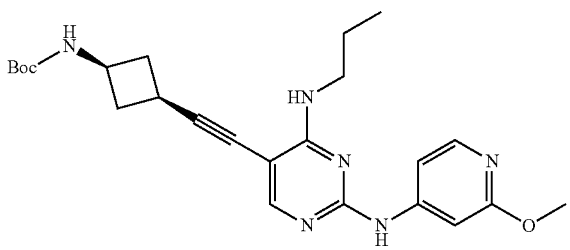 [SMILES: CCCNc1nc(Nc2ccnc(OC)c2)ncc1C#C[C@H]1C[C@@H](NC(=O)OC(C)(C)C)C1] | MS m/z (M + H): 453.4 |

3

In the same manner as that of Example 57, (3), Intermediates (P11) to (P14) and Intermediates (P16) were obtained.

TABLE 202

| Compound No. | Structure | Physicochemical data |
|---|---|---|
| P11 | 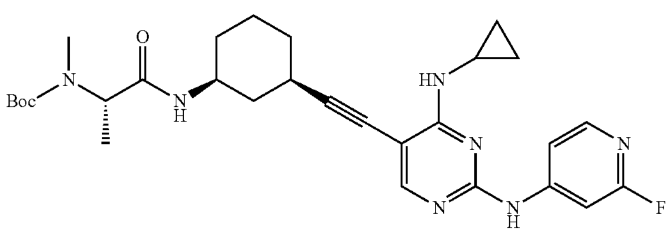 [SMILES: C[C@@H](C(=O)N[C@H]1CCC[C@@H](C#Cc2cnc(Nc3ccnc(F)c3)nc2NC2CC2)C1)N(C)C(=O)OC(C)(C)C] | — |
| P12 | 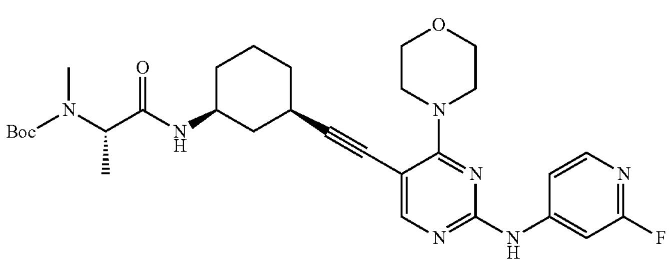 [SMILES: C[C@@H](C(=O)N[C@H]1CCC[C@@H](C#Cc2cnc(Nc3ccnc(F)c3)nc2N2CCOCC2)C1)N(C)C(=O)OC(C)(C)C] | — |

TABLE 202-continued

| Compound No. | Structure | Physicochemical data |
|---|---|---|
| P13 | 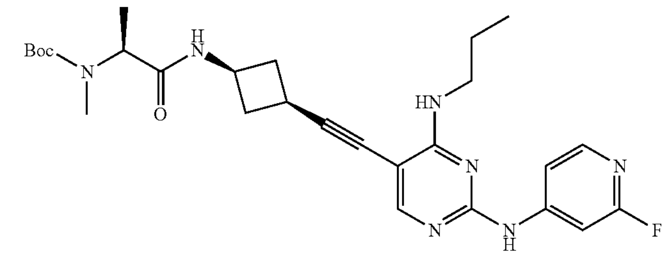 [SMILES: CCCNc1nc(Nc2ccnc(F)c2)ncc1C#C[C@H]1C[C@@H](NC(=O)[C@H](C)N(C)C(=O)OC(C)(C)C)C1] | — |
| P14 | 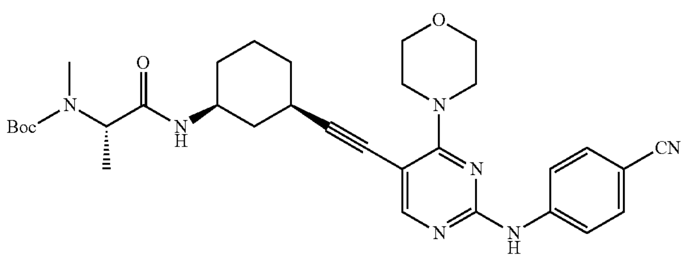 [SMILES: C[C@@H](C(=O)N[C@H]1CCC[C@@H](C#Cc2cnc(Nc3ccc(C#N)cc3)nc2N2CCOCC2)C1)N(C)C(=O)OC(C)(C)C] | — |
| P16 | 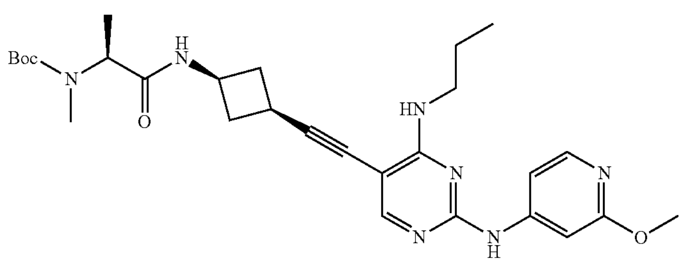 [SMILES: CCCNc1nc(Nc2ccnc(OC)c2)ncc1C#C[C@H]1C[C@@H](NC(=O)[C@H](C)N(C)C(=O)OC(C)(C)C)C1] | MS m/z (M + H): 538.5 |

In the same manner as that of Example 57, (4), Compounds (14-2) to (14-6) were obtained.

TABLE 203

| Compound No. | Structure | Physicochemical data |
|---|---|---|
| 14-2 | 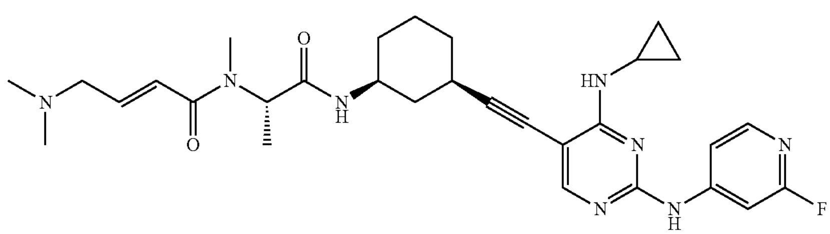 | $^1$H-NMR (CDCl$_3$) δ: 8.02-7.97 (2H, m), 7.92 (1H, d, J = 2.6 Hz), 7.41-7.38 (1H, m), 7.12-7.06 (1H, m), 6.93 (1H, dt, J = 15.2, 5.9 Hz), 6.42 (1H, d, J = 15.2 Hz), 6.32 (1H, d, J = 7.9 Hz), 5.69-5.63 (1H, m), 5.15 (1H, q, J = 6.8 Hz), 3.77-3.68 (1H, m), 3.11 (2H, d, J = 5.0 Hz), 2.98 (3H, s), 2.65-2.55 (1H, m), 2.33-2.27 (1H, m), 2.28 (6H, s), 2.05-1.94 (1H, m), 1.87-1.78 (2H, m), 1.39-1.25 (1H, m), 1.34 (3H, d, J = 7.3 Hz), 1.25 (3H, t, J = 6.2 Hz), 1.15-1.01 (1H, m), 1.00-0.94 (2H, m), 0.70-0.65 (2H, m) |

TABLE 203-continued

| Compound No. | Structure | Physicochemical data |
|---|---|---|
| 14-3 | 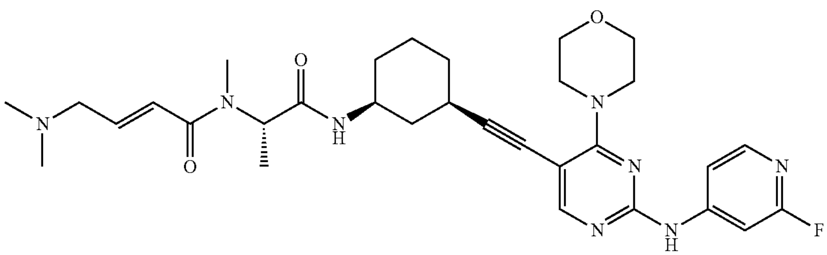 [SMILES: C[C@@H](C(=O)N[C@H]1CCC[C@@H](C#Cc2cnc(Nc3ccnc(F)c3)nc2N2CCOCC2)C1)N(C)C(=O)/C=C/CN(C)C] | ¹H-NMR (CDCl₃) δ: 8.13 (1H, s), 8.01 (1H, d, J = 5.9 Hz), 7.47 (1H, d, J = 2.0 Hz), 7.35-7.30 (1H, m), 7.11 (1H, d, J = 5.3 Hz), 6.92 (1H, dt, J = 15.2, 5.9 Hz), 6.42 (1H, d, J = 15.2 Hz), 6.32 (1H, d, J = 7.9 Hz), 5.15 (1H, q, J = 7.0 Hz), 4.00-3.93 (4H, m), 3.84-3.78 (4H, m), 3.78-3.66 (1H, m), 3.11 (2H, d, J = 5.9 Hz), 2.98 (3H, s), 2.65-2.52 (1H, m), 2.30-2.24 (1H, m), 2.28 (6H, s), 2.01-1.92 (1H, m), 1.87-1.77 (2H, m), 1.40-1.04 (4H, m), 1.34 (3H, d, J = 7.0 Hz) |
| 14-4 | 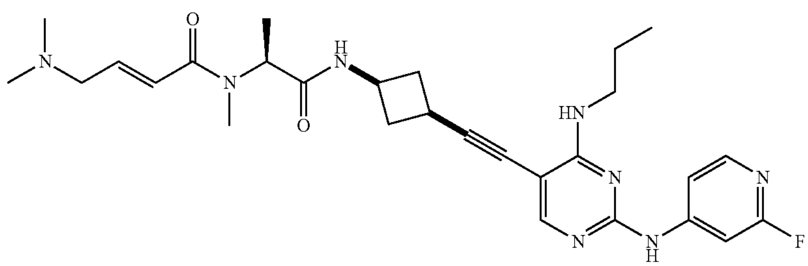 [SMILES: CCCNc1nc(Nc2ccnc(F)c2)ncc1C#C[C@H]1C[C@@H](NC(=O)[C@H](C)N(C)C(=O)/C=C/CN(C)C)C1] | ¹H-NMR (CDCl₃) δ: 8.03 (1H, s), 8.00 (1H, d, J = 5.9 Hz), 7.63 (1H, d, J = 1.3 Hz), 7.99-7.46 (1H, m), 7.13-7.09 (1H, m), 6.95 (1H, dt, J = 15.2, 5.9 Hz), 6.72-6.65 (1H, m), 6.43 (1H, d, J = 15.2 Hz), 5.67-5.58 (1H, m), 5.15 (1H, q, J = 7.0 Hz), 4.37-4.20 (1H, m), 3.54-3.45 (2H, m), 3.11 (2H, d, J = 5.9 Hz), 3.03-2.88 (1H, m), 2.98 (3H, s), 2.86-2.71 (2H, m), 2.28 (6H, s), 2.16-2.01 (2H, m), 1.79-1.68 (2H, m), 1.34 (3H, d, J = 6.6 Hz), 1.03 (3H, t, J = 7.3 Hz) |
| 14-5 | 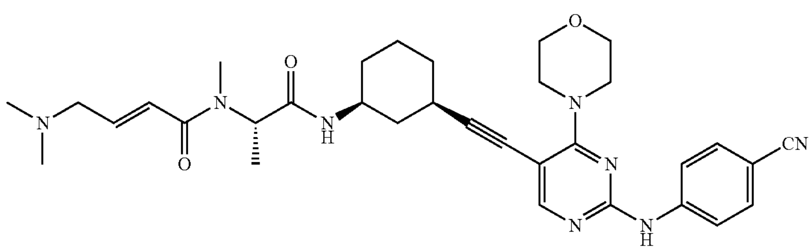 [SMILES: C[C@@H](C(=O)N[C@H]1CCC[C@@H](C#Cc2cnc(Nc3ccc(C#N)cc3)nc2N2CCOCC2)C1)N(C)C(=O)/C=C/CN(C)C] | ¹H-NMR (CDCl₃) δ: 8.11 (1H, s), 7.68 (2H, d, J = 8.6 Hz), 7.58 (2H, d, J = 8.6 Hz), 7.36 (1H, s), 6.93 (1H, dt, J = 15.2, 5.9 Hz), 6.41 (1H, d, J = 15.2 Hz), 6.34 (1H, d, J = 7.9 Hz), 5.15 (1H, q, J = 7.0 Hz), 4.00-3.88 (4H, m), 3.86-3.64 (5H, m), 3.10 (2H, d, J = 5.9 Hz), 2.98 (3H, s), 2.66-2.52 (1H, m), 2.32-2.20 (7H, m), 2.02-1.74 (3H, m), 1.45-0.86 (7H, m) |

TABLE 204

| Compound No. | Structure | Physicochemical data |
|---|---|---|
| 14-6 | 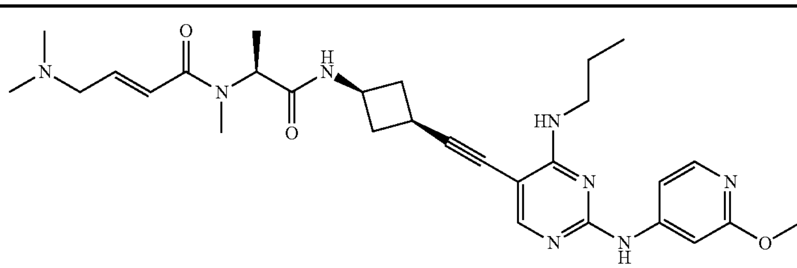 | ¹H-NMR (CDCl₃) δ: 8.00 (1H, s), 7.98 (1H, d, J = 5.9 Hz), 7.29 (1H, d, J = 2.0 Hz), 7.07 (1H, s), 7.01-6.87 (2H, m), 6.67-6.60 (1H, m), 6.43 (1H, d, J = 15.2 Hz), 5.56 (1H, t, J = 6.6 Hz), 5.15 (1H, q, J = 6.7 Hz), 4.36-4.20 (1H, m), 3.93 (3H, s), 3.54-3.44 (2H, m), 3.12 (2H, d, J = 5.3 Hz), 2.98 (3H, s), 2.85-2.69 (1H, m), 2.28 (6H, s), 2.10 (2H, dt, J = 17.8, 9.5 Hz), 1.78-1.64 (4H, m), 1.34 (3H, d, J = 6.7 Hz), 1.03 (3H, t, J = 7.3 Hz) |

Example 59

1

[Formula 302]

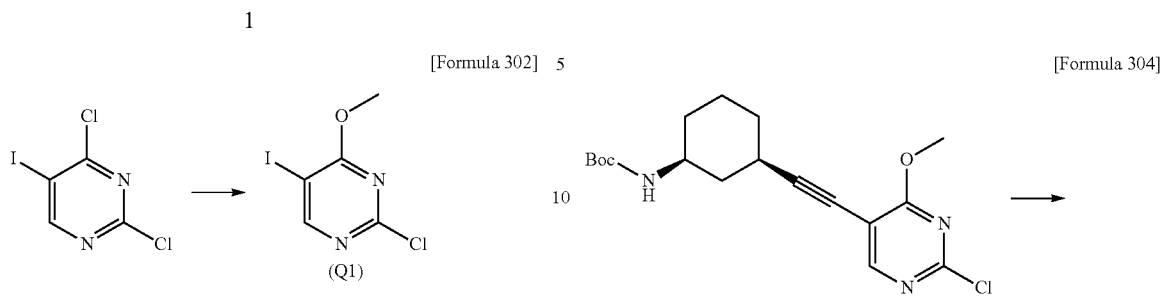

To a solution of 2,4-dichloro-5-iodopyrimidine (500 mg) in tetrahydrofuran (4 mL) and N,N-dimethylformamide (4 mL), a 5.0 mol/L a solution of sodium methoxide in methanol (360 μL) was added under ice cooling, and the mixture was stirred at the same temperature for 1 hour. To the reaction mixture, water and ethyl acetate were added. The organic layer was separated, washed successively with water and saturated aqueous sodium chloride, and then dried over anhydrous magnesium sulfate to obtain 2-chloro-5-iodo-4-methoxypyrimidine (Q1, 460 mg).

$^1$H-NMR (CDCl$_3$) δ: 8.59 (1H, s), 4.08 (3H, s)

2

[Formula 303]

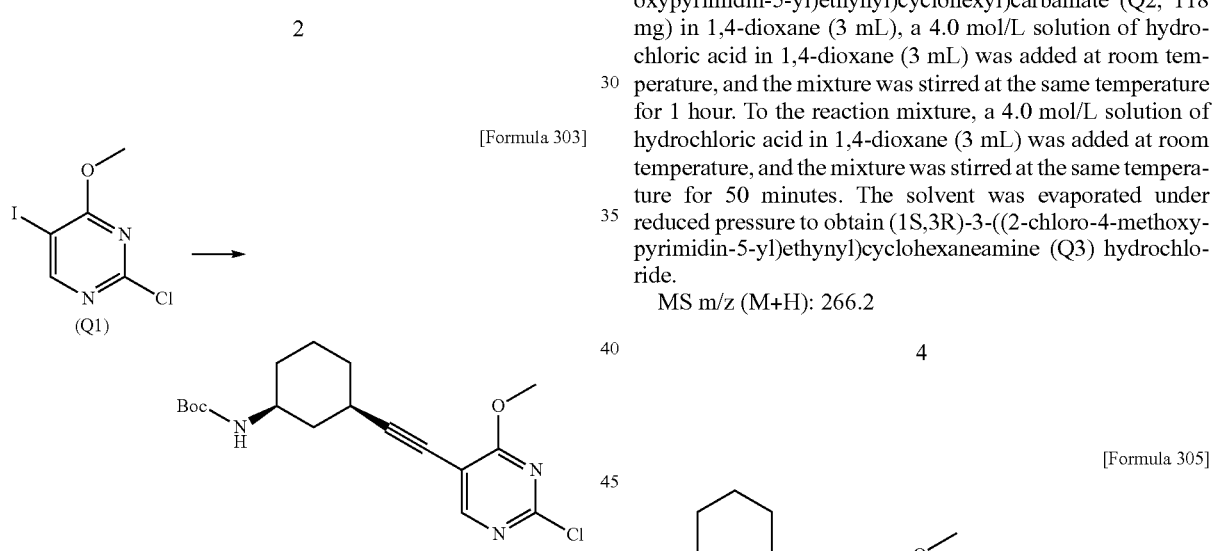

To a solution of 2-chloro-5-iodo-4-methoxypyrimidine (Q1, 101 mg), tert-butyl ((1S,3R)-3-ethynylcyclohexyl)carbamate (P0, 100 mg), bis(triphenylphosphine)palladium(II) dichloride (26 mg) and copper(I) iodide (14 mg) in N,N-dimethylformamide (3 mL), triethylamine (258 μL) was added at room temperature, and the mixture was stirred at the same temperature for 1 hour. To the reaction mixture, ethyl acetate and saturated aqueous ammonium chloride were added. The organic layer was separated, washed successively with water and saturated aqueous sodium chloride, and then dried over anhydrous magnesium sulfate, and the solvent was evaporated under reduced pressure. The obtained residue was purified by silica gel column chromatography (eluent, 88 to 50% hexane in ethyl acetate) to obtain tert-butyl ((1S,3R)-3-((2-chloro-4-methoxypyrimidin-5-yl)ethynyl)cyclohexyl)carbamate (Q2, 118 mg).

MS m/z (M+H): 366.2

3

[Formula 304]

To a solution of tert-butyl ((1S,3R)-3-((2-chloro-4-methoxypyrimidin-5-yl)ethynyl)cyclohexyl)carbamate (Q2, 118 mg) in 1,4-dioxane (3 mL), a 4.0 mol/L solution of hydrochloric acid in 1,4-dioxane (3 mL) was added at room temperature, and the mixture was stirred at the same temperature for 1 hour. To the reaction mixture, a 4.0 mol/L solution of hydrochloric acid in 1,4-dioxane (3 mL) was added at room temperature, and the mixture was stirred at the same temperature for 50 minutes. The solvent was evaporated under reduced pressure to obtain (1S,3R)-3-((2-chloro-4-methoxypyrimidin-5-yl)ethynyl)cyclohexaneamine (Q3) hydrochloride.

MS m/z (M+H): 266.2

4

[Formula 305]

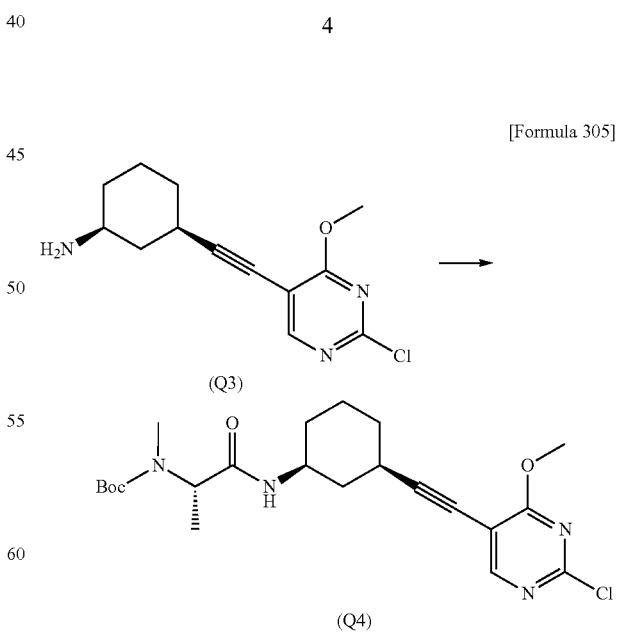

To a solution of N-Boc-N-methyl-L-alanine (195 mg) in N,N-dimethylformamide (2.5 mL), N-methylmorpholine (246 μL) and isobutyl chloroformate (105 μL) were added under ice cooling, and the mixture was stirred at the same temperature for 2 minutes. To the reaction mixture, a solution of (1S,3R)-3-((2-chloro-4-methoxypyrimidin-5-yl)ethynyl)cyclohexaneamine (Q3) hydrochloride in N,N-dimethylformamide (2 mL) was added under ice cooling, and the mixture was stirred at the same temperature for 1 hour and 30 minutes. To the reaction mixture, saturated aqueous sodium hydrogencarbonate and ethyl acetate were added. The organic layer was separated, washed successively with water, saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 88 to 40% hexane in ethyl acetate) to obtain tert-butyl ((S)-1-(((1S,3R)-3-((2-chloro-4-methoxypyrimidin-5-yl)ethynyl)cyclohexyl)amino)-1-oxopropan-2-yl)(methyl)carbamate (Q4, 120 mg).

MS m/z (M+H): 451.3

5

[Formula 306]

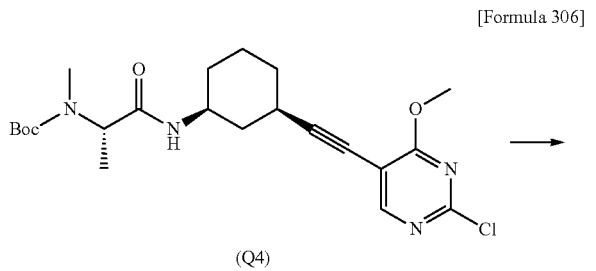

(Q4)

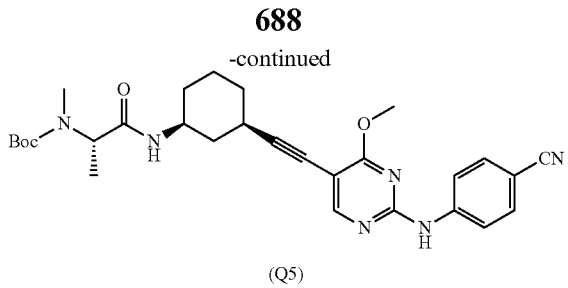

(Q5)

To a solution of tert-butyl ((S)-1-(((1S,3R)-3-((2-chloro-4-methoxypyrimidin-5-yl)ethynyl)cyclohexyl)amino)-1-oxopropan-2-yl)(methyl)carbamate (Q4, 32 mg) in N-methylpyrrolidone (0.5 mL), 4-aminobenzonitrile (42 mg) and (1S)-(+)-10-camphorsulfonic acid (81 mg) were added at room temperature, and the mixture was stirred at 60° C. for 7 hours and 30 minutes. The reaction mixture was cooled to room temperature, and then saturated aqueous sodium hydrogencarbonate and ethyl acetate were added to the reaction mixture. The organic layer was separated, washed successively with saturated aqueous sodium hydrogencarbonate, water and saturated aqueous sodium chloride, and then dried over anhydrous magnesium sulfate, and the solvent was evaporated under reduced pressure. The obtained residue was purified by silica gel column chromatography (eluent, 88 to 25% hexane in ethyl acetate) to obtain tert-butyl ((S)-1-(((1S,3R)-3-((2-((4-cyanophenyl)amino)-4-methoxypyrimidin-5-yl)ethynyl)cyclohexyl)amino)-1-oxopropan-2-yl)(methyl)carbamate (Q5, 11 mg).

MS m/z (M+H): 533.4

6

[Formula 307]

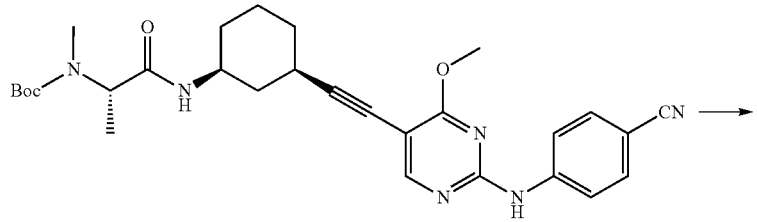

(Q5)

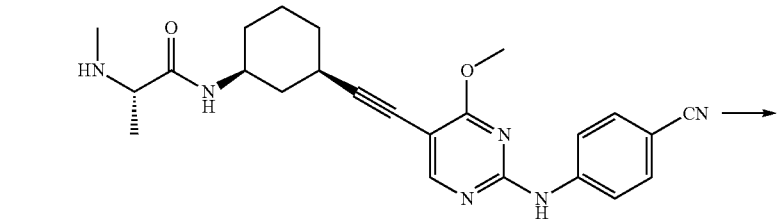

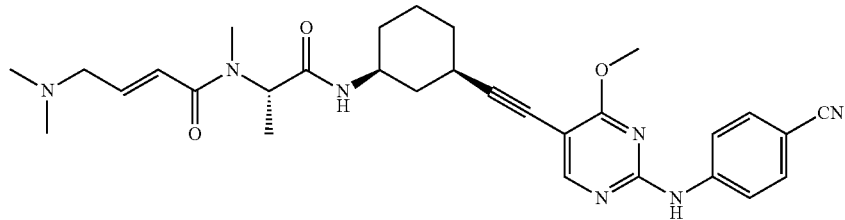

(15-1)

In the same manner as that of Example 35, (6) and (7), (E)-N—((S)-1-(((1S,3R)-3-((2-((4-cyanophenyl)amino)-4-methoxypyrimidin-5-yl)ethynyl)cyclohexyl)amino)-1-oxopropan-2-yl)-4-(dimethylamino)-N-methyl-2-butenamide (15-1) was obtained from tert-butyl ((S)-1-(((1S,3R)-3-((2-((4-cyanophenyl)amino)-4-methoxypyrimidin-5-yl)ethynyl)cyclohexyl)amino)-1-oxopropan-2-yl)(methyl)carbamate (Q5).

$^1$H-NMR (CDCl$_3$) δ: 8.22 (1H, s), 7.76 (2H, d, J=9.2 Hz), 7.61 (2H, d, J=9.2 Hz), 6.92 (1H, dt, J=15.2, 5.9 Hz), 6.42 (1H, d, J=15.2 Hz), 6.30-6.24 (1H, m), 5.15 (1H, q, J=6.6 Hz), 4.05 (3H, s), 3.82-3.65 (1H, m), 3.13 (2H, d, J=5.9 Hz), 2.97 (3H, s), 2.67-2.58 (1H, m), 2.34-2.28 (1H, m), 2.29 (6H, s), 2.02-1.75 (4H, m), 1.42-1.31 (2H, m), 1.33 (3H, d, J=6.6 Hz), 1.21-1.01 (1H, m).

Example 60

1

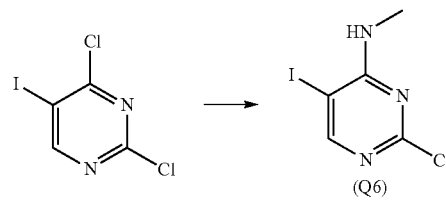

[Formula 308]

2-Chloro-5-iodo-N-methylpyrimidin-4-amine (Q6) was obtained in the same manner as that of Example 35, (1).
MS m/z (M+H): 270.0

2

In the same manner as that of Example 59, (2), Intermediates (Q7), (Q8), (Q25) and (Q26) were obtained.

TABLE 205

| Compound No. | Structure | Physicochemical data |
|---|---|---|
| Q7 | 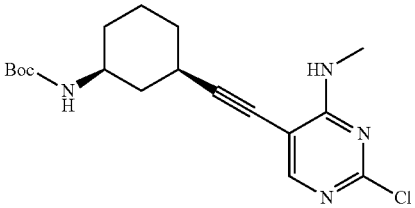 [SMILES: CNc1nc(Cl)ncc1C#C[C@@H]1CCC[C@H](NC(=O)OC(C)(C)C)C1] | — |
| Q8 | 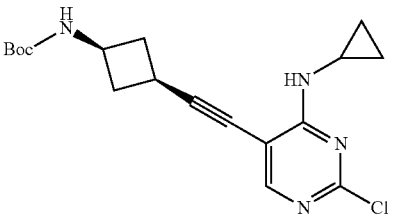 [SMILES: CC(C)(C)OC(=O)N[C@H]1C[C@@H](C#Cc2cnc(Cl)nc2NC2CC2)C1] | MS m/z (M + H): 363.2 |
| Q25 | 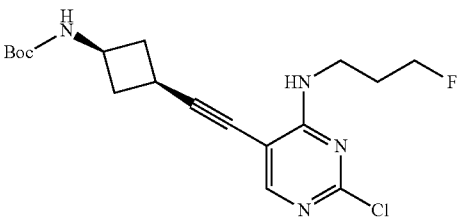 [SMILES: CC(C)(C)OC(=O)N[C@H]1C[C@@H](C#Cc2cnc(Cl)nc2NCCCF)C1] | MS m/z (M + H): 383.2 |
| Q26 | 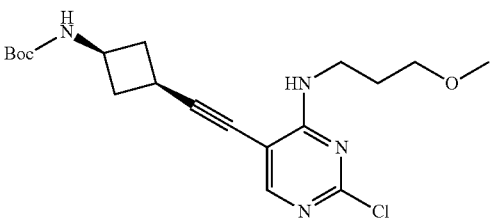 [SMILES: COCCCNc1nc(Cl)ncc1C#C[C@H]1C[C@@H](NC(=O)OC(C)(C)C)C1] | MS m/z (M + H): 395.3 |

3

In the same manner as that of Example 59, (3), Intermediates (Q9), (Q10), (Q27) and (Q28) were obtained.

TABLE 206

| Compound No. | Structure | Physicochemical data |
| --- | --- | --- |
| Q9 | 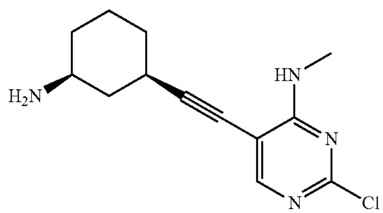 [SMILES: CNc1nc(Cl)ncc1C#C[C@@H]1CCC[C@H](N)C1] | — |
| Q10 | 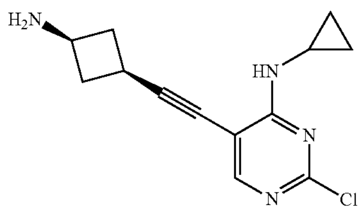 [SMILES: N[C@H]1C[C@@H](C#Cc2cnc(Cl)nc2NC2CC2)C1] | MS m/z (M + H): 263.1 |
| Q27 | 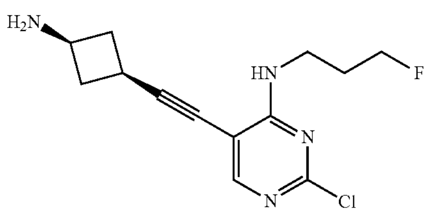 [SMILES: N[C@H]1C[C@@H](C#Cc2cnc(Cl)nc2NCCCF)C1] | MS m/z (M + H): 283.2 |
| Q28 | 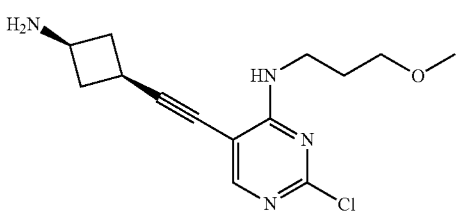 [SMILES: COCCCNc1nc(Cl)ncc1C#C[C@H]1C[C@@H](N)C1] | MS m/z (M + H): 295.2 |

4

In the same manner as that of Example 59, (4), Intermediates (Q11) to (Q13), (Q29) and (Q30) were obtained.

TABLE 207

| Compound No. | Structure | Physicochemical data |
| --- | --- | --- |
| Q11 | 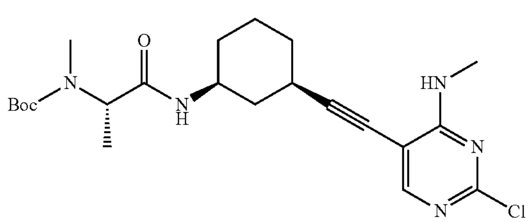 [SMILES: CNc1nc(Cl)ncc1C#C[C@@H]1CCC[C@H](NC(=O)[C@H](C)N(C)C(=O)OC(C)(C)C)C1] | — |

TABLE 207-continued
| Compound No. | Structure | Physicochemical data |
|---|---|---|
| Q12 | 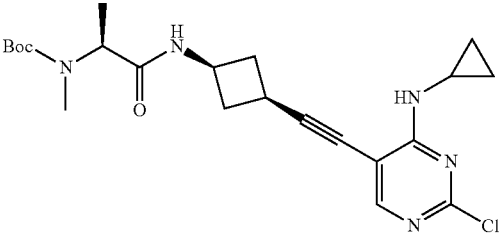 [SMILES: C[C@@H](C(=O)N[C@H]1C[C@@H](C#Cc2cnc(Cl)nc2NC2CC2)C1)N(C)C(=O)OC(C)(C)C] | MS m/z (M + H): 448.3 |
| Q13 | 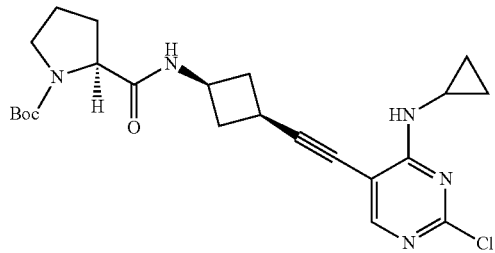 [SMILES: CC(C)(C)OC(=O)N1CCC[C@H]1C(=O)N[C@H]1C[C@@H](C#Cc2cnc(Cl)nc2NC2CC2)C1] | — |
| Q29 | 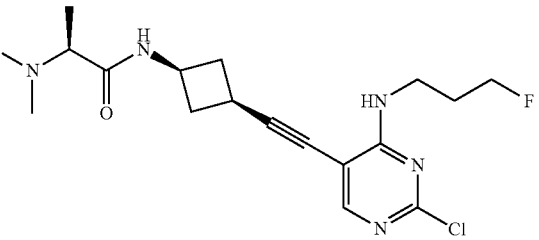 | MS m/z (M + H): 468.3 |
| Q30 | 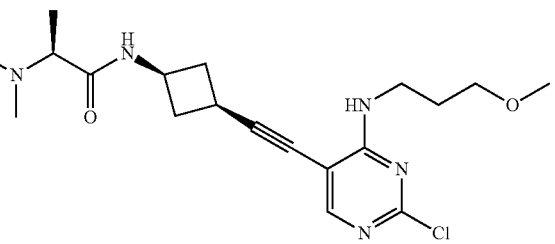 | MS m/z (M + H): 480.3 |
In the same manner as that of Example 59, (5), Intermediates (Q14) to (Q24) and Intermediates (Q31) to (Q34) were obtained.
TABLE 208
| Compound No. | Structure | Physicochemical data |
|---|---|---|
| Q14 | 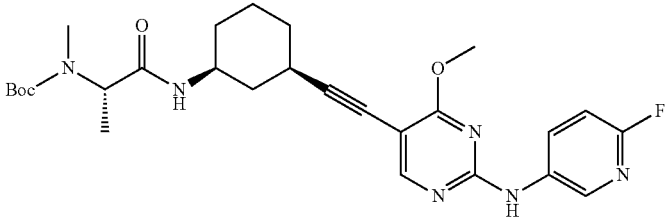 [SMILES: COc1nc(Nc2ccc(F)nc2)ncc1C#C[C@@H]1CCC[C@H](NC(=O)[C@H](C)N(C)C(=O)OC(C)(C)C)C1] | — |

TABLE 208-continued

| Compound No. | Structure | Physicochemical data |
|---|---|---|
| Q15 | 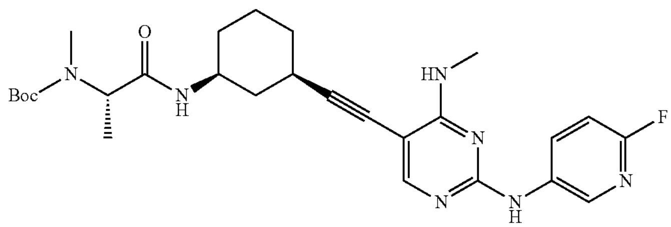 [SMILES: CNc1nc(Nc2ccc(F)nc2)ncc1C#C[C@@H]1CCC[C@H](NC(=O)[C@H](C)N(C)C(=O)OC(C)(C)C)C1] | — |
| Q16 | 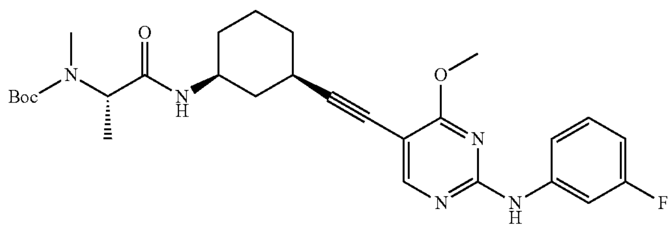 [SMILES: COc1nc(Nc2cccc(F)c2)ncc1C#C[C@@H]1CCC[C@H](NC(=O)[C@H](C)N(C)C(=O)OC(C)(C)C)C1] | — |
| Q17 | 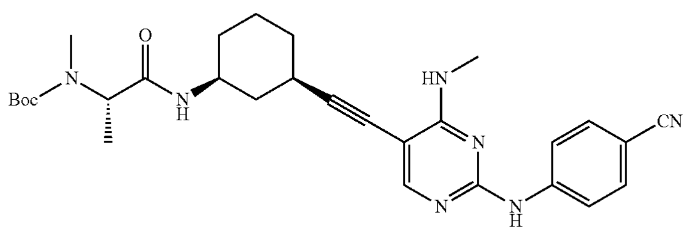 [SMILES: CNc1nc(Nc2ccc(C#N)cc2)ncc1C#C[C@@H]1CCC[C@H](NC(=O)[C@H](C)N(C)C(=O)OC(C)(C)C)C1] | — |
| Q18 | 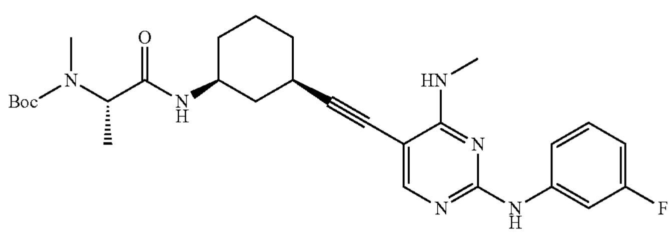 [SMILES: CNc1nc(Nc2cccc(F)c2)ncc1C#C[C@@H]1CCC[C@H](NC(=O)[C@H](C)N(C)C(=O)OC(C)(C)C)C1] | — |
| Q19 | 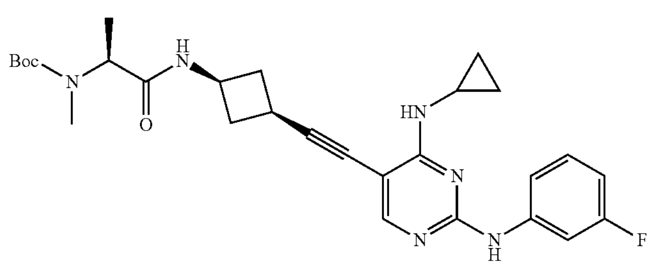 [SMILES: C[C@@H](C(=O)N[C@H]1C[C@@H](C#Cc2cnc(Nc3cccc(F)c3)nc2NC2CC2)C1)N(C)C(=O)OC(C)(C)C] | — |
| Q20 | 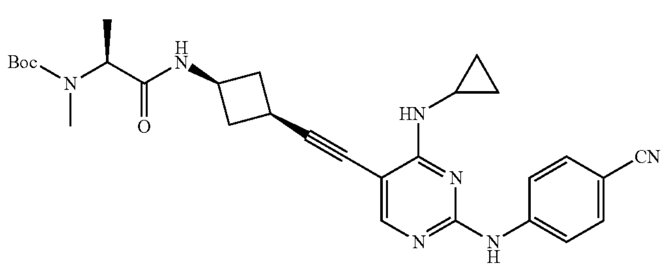 [SMILES: C[C@@H](C(=O)N[C@H]1C[C@@H](C#Cc2cnc(Nc3ccc(C#N)cc3)nc2NC2CC2)C1)N(C)C(=O)OC(C)(C)C] | — |

TABLE 208-continued

| Compound No. | Structure | Physicochemical data |
|---|---|---|
| Q21 | 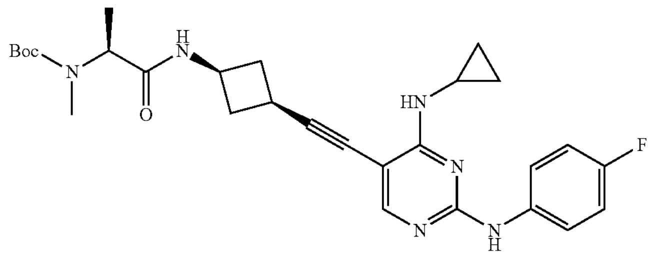 [SMILES: C[C@@H](C(=O)N[C@H]1C[C@@H](C#Cc2cnc(Nc3ccc(F)cc3)nc2NC2CC2)C1)N(C)C(=O)OC(C)(C)C] | MS m/z (M + H): 523.4 |
| Q22 | 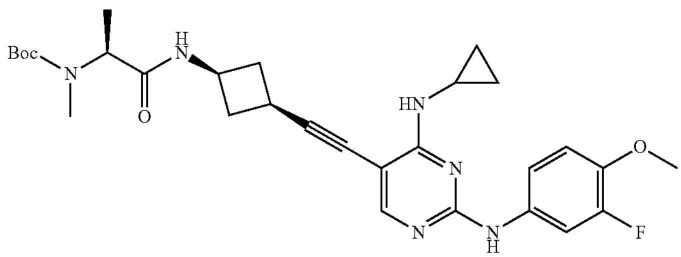 [SMILES: COc1ccc(Nc2ncc(C#C[C@H]3C[C@@H](NC(=O)[C@H](C)N(C)C(=O)OC(C)(C)C)C3)c(NC3CC3)n2)cc1F] | — |

TABLE 209

| Compound No. | Structure | Physicochemical data |
|---|---|---|
| Q23 | 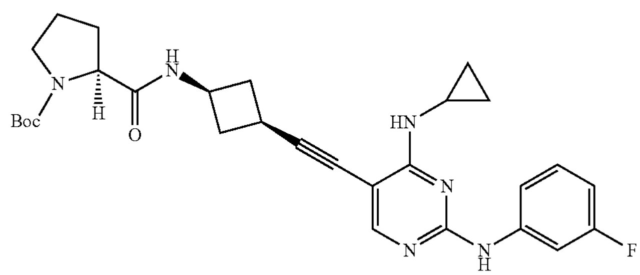 [SMILES: CC(C)(C)OC(=O)N1CCC[C@H]1C(=O)N[C@H]1C[C@@H](C#Cc2cnc(Nc3cccc(F)c3)nc2NC2CC2)C1] | — |
| Q24 | 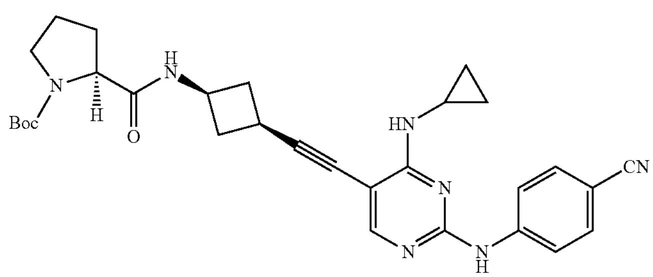 [SMILES: CC(C)(C)OC(=O)N1CCC[C@H]1C(=O)N[C@H]1C[C@@H](C#Cc2cnc(Nc3ccc(C#N)cc3)nc2NC2CC2)C1] | — |
| Q31 | 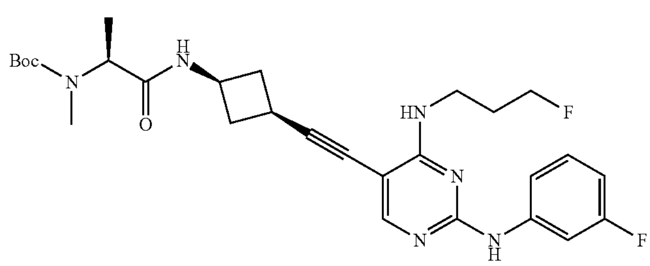 [SMILES: C[C@@H](C(=O)N[C@H]1C[C@@H](C#Cc2cnc(Nc3cccc(F)c3)nc2NCCCF)C1)N(C)C(=O)OC(C)(C)C] | MS m/z (M + H): 543.4 |

TABLE 209-continued

| Compound No. | Structure | Physicochemical data |
|---|---|---|
| Q32 | 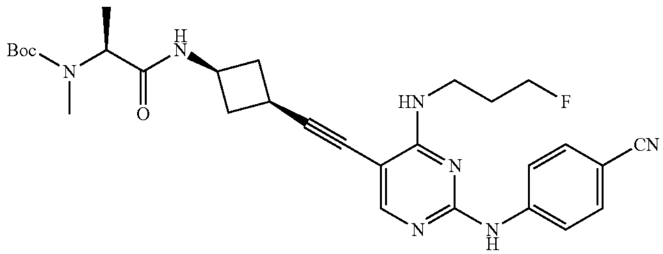 [SMILES: C[C@@H](C(=O)N[C@H]1C[C@@H](C#Cc2cnc(Nc3ccc(C#N)cc3)nc2NCCCF)C1)N(C)C(=O)OC(C)(C)C] | MS m/z (M + H): 550.4 |
| Q33 | 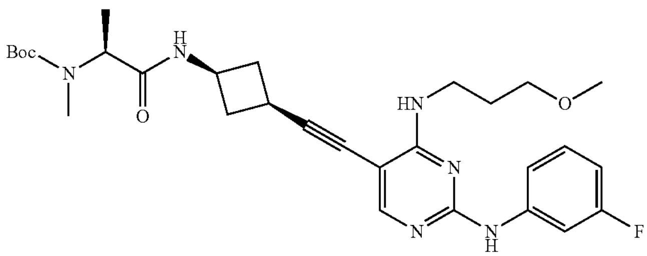 [SMILES: COCCCNc1nc(Nc2cccc(F)c2)ncc1C#C[C@H]1C[C@@H](NC(=O)[C@H](C)N(C)C(=O)OC(C)(C)C)C1] | MS m/z (M + H): 555.4 |
| Q34 | 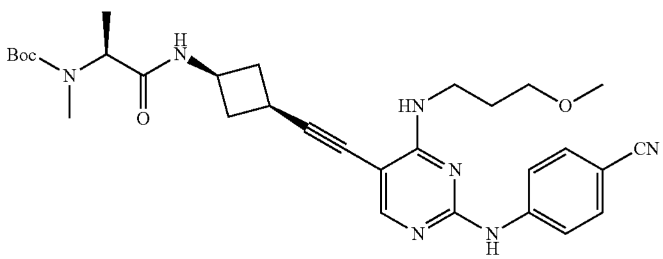 [SMILES: COCCCNc1nc(Nc2ccc(C#N)cc2)ncc1C#C[C@H]1C[C@@H](NC(=O)[C@H](C)N(C)C(=O)OC(C)(C)C)C1] | MS m/z (M + H): 562.4 |

6

In the same manner as that of Example 59, (6), Compounds (15-2) to (15-16) were obtained.

TABLE 210

| Compound No. | Structure | Physicochemical data |
|---|---|---|
| 15-2 | 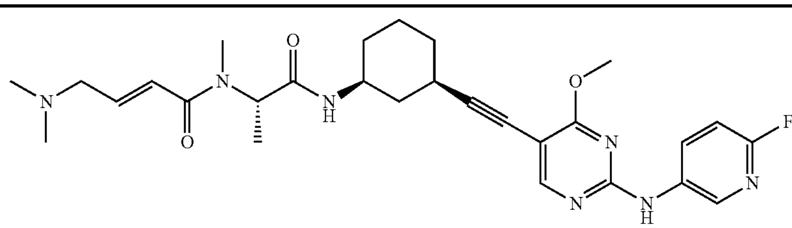 | $^1$H-NMR (CDCl$_3$) δ: 8.38 (1H, s), 8.21-8.13 (1H, m), 8.20 (1H, s), 7.12-7.03 (1H, m), 6.98-6.86 (2H, m), 6.42 (1H, d, J = 15.2 Hz), 6.30-6.23 (1H, m), 5.15 (1H, q, J = 7.3 Hz), 4.00 (3H, s), 3.80-3.66 (1H, m), 3.11 (2H, d, J = 5.9 Hz), 2.97 (3H, s), 2.69-2.55 (1H, m), 2.33-2.26 (1H, m), 2.28 (6H, s), 2.05-1.95 (1H, m), 1.88-1.75 (2H, m), 1.63-1.30 (3H, m), 1.33 (3H, d, J = 7.3 Hz), 1.14-1.02 (1H, m) |
| 15-3 | 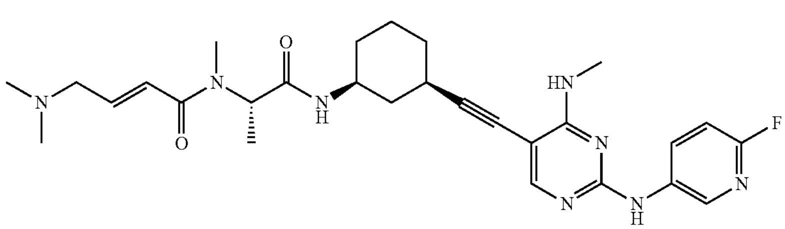 [SMILES: CNc1nc(Nc2ccc(F)nc2)ncc1C#C[C@@H]1CCC[C@H](NC(=O)[C@H](C)N(C)C(=O)/C=C/CN(C)C)C1] | $^1$H-NMR (CDCl$_3$) δ: 8.40 (1H, s), 8.23-8.15 (1H, m), 7.95 (1H, s), 7.08-7.00 (1H, m), 6.98-6.89 (1H, m), 6.89 (1H, dd, J = 8.9, 3.6 Hz), 6.42 (1H, d, J = 15.2 Hz), 6.35-6.29 (1H, m), 5.47-5.39 (1H, m), 5.15 (1H, q, J = 7.3 Hz), 3.80-3.65 (1H, m), 3.11 (2H, d, J = 5.9 Hz), 3.05 (3H, d, J = 4.6 Hz), 2.98 (3H, s), 2.66-2.55 (1H, m), 2.35-2.31 (1H, m), 2.28 (6H, |

TABLE 210-continued

| Compound No. | Structure | Physicochemical data |
|---|---|---|
| 15-4 | 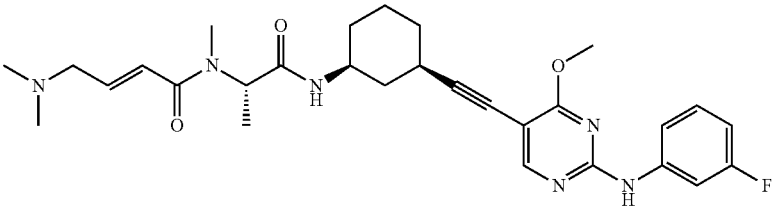 [SMILES: COc1nc(Nc2cccc(F)c2)ncc1C#C[C@@H]1CCC[C@H](NC(=O)[C@H](C)N(C)C(=O)/C=C/CN(C)C)C1] | ¹H-NMR (CDCl₃) δ: 8.21 (1H, s), 7.70 (1H, d, J = 11.2 Hz), 7.28-7.21 (1H, m), 7.16-7.10 (2H, m), 6.92 (1H, dt, J = 15.2, 5.9 Hz), 6.77-6.69 (1H, m), 6.42 (1H, d, J = 15.2 Hz), 6.29-6.22 (1H, m), 5.15 (1H, q, J = 7.3 Hz), 4.04 (3H, s), 3.82-3.65 (1H, m), 3.11 (2H, d, J = 5.9 Hz), 2.97 (3H, s), 2.66-2.58 (1H, m), 2.33-2.27 (1H, m), 2.28 (6H, s), 2.06-1.95 (1H, m), 1.90-1.75 (2H, m), 1.39-1.30 (3H, m), 1.33 (3H, d, J = 7.3 Hz), 1.14-1.02 (1H, m) |
| 15-5 | 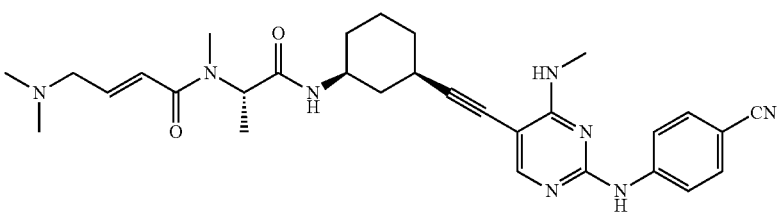 [SMILES: CNc1nc(Nc2ccc(C#N)cc2)ncc1C#C[C@@H]1CCC[C@H](NC(=O)[C@H](C)N(C)C(=O)/C=C/CN(C)C)C1] | ¹H-NMR (CDCl₃) δ: 7.98 (1H, s), 7.77 (2H, d, J = 8.6 Hz), 7.57 (2H, d, J = 8.6 Hz), 7.28-7.21 (1H, m), 6.93 (1H, dt, J = 15.2, 5.9 Hz), 6.42 (1H, d, J = 15.2 Hz), 6.32 (1H, d, J = 7.9 Hz), 5.52-5.42 (1H, m), 5.15 (1H, q, J = 7.3 Hz), 3.79-3.67 (1H, m), 3.12 (3H, s), 3.09 (2H, d, J = 5.9 Hz), 2.98 (3H, s) 2.66-2.58 (1H, m), 2.37-2.25 (1H, m), 2.28 (6H, s), 2.08-1.96 (1H, m), 1.88-1.77 (2H, m), 15.0-1.25 (3H, m), 1.34 (3H, d, J = 8.3 Hz), 1.16-1.04 (1H, m) |

TABLE 211

| Compound No. | Structure | Physicochemical data |
|---|---|---|
| 15-6 | 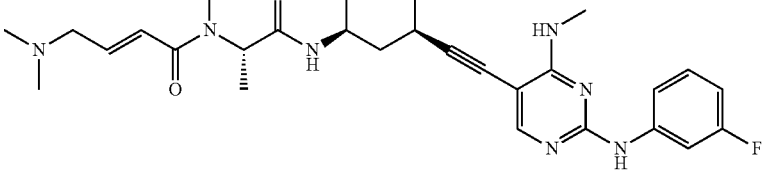 | ¹H-NMR (CDCl₃) δ: 7.97 (1H, s), 7.79 (1H, dt, J = 12.6, 2.0 Hz), 7.26-7.18 (1H, m), 7.14-7.09 (1H, m), 7.09-7.03 (1H, m), 6.93 (1H, dt, J = 15.2, 5.9 Hz), 6.68 (1H, td, J = 8.1, 2.2 Hz), 6.42 (1H, d, J = 15.2 Hz), 6.30 (1H, d, J = 7.9 Hz), 5.45-5.37 (1H, m), 5.15 (1H, q, J = 7.0 Hz), 3.78-3.68 (1H, m), 3.12 (3H, s), 3.10 (2H, d, J = 5.9 Hz), 2.98 (3H, s), 2.66-2.55 (1H, m), 2.34-2.27 (1H, m), 2.28 (6H, s), 2.05-1.97 (1H, m), 1.92-1.57 (3H, m), 1.50-1.20 (2H, m), 1.34 (3H, d, J = 7.3 Hz), 1.19-1.01 (1H, m) |
| 15-7 | 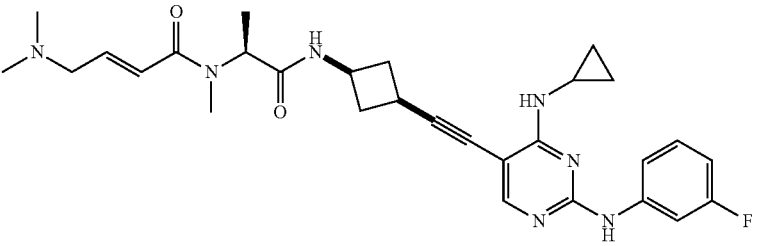 [SMILES: C[C@@H](C(=O)N[C@H]1C[C@@H](C#Cc2cnc(Nc3cccc(F)c3)nc2NC2CC2)C1)N(C)C(=O)/C=C/CN(C)C] | ¹H-NMR (CDCl₃) δ: 8.11 (1H, d, J = 9.9 Hz), 8.01 (1H, s), 7.26-7.16 (1H, m), 7.16-7.12 (1H, m), 7.10-7.04 (1H, m), 6.96 (1H, dt, J = 15.2, 5.9 Hz), 6.68 (1H, td, J = 7.9, 2.0 Hz), 6.64-6.58 (1H, m), 6.43 (1H, d, J = 15.2 Hz), 5.62-5.58 (1H, m), 5.15 (1H, q, J = 7.0 Hz), 4.35-4.20 (1H, m), 3.11 (2H, d, J = 5.9 Hz), 2.98-2.88 (1H, m), 2.98 (3H, s), 2.90-2.80 (1H, m), 2.81-2.70 (2H, m), 2.28 (6H, s), 2.13-1.97 (2H, m), 1.34 (3H, d, J = 7.0 Hz), 0.98-0.92 (2H, m), 0.70-0.64 (2H, m) |

TABLE 211-continued

| Compound No. | Structure | Physicochemical data |
|---|---|---|
| 15-8 | 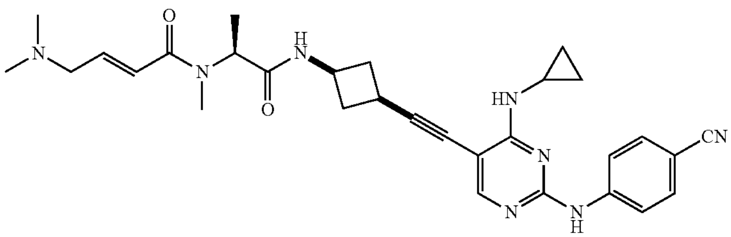 [SMILES: C[C@@H](C(=O)N[C@H]1C[C@@H](C#Cc2cnc(Nc3ccc(C#N)cc3)nc2NC2CC2)C1)N(C)C(=O)/C=C/CN(C)C] | ¹H-NMR (CDCl₃) δ: 8.03 (1H, s), 7.87 (2H, d, J = 9.2 Hz), 7.57 (2H, d, J = 9.2 Hz), 7.32-7.29 (1H, m), 6.95 (1H, dt, J = 15.2, 5.9 Hz), 6.67-6.61 (1H, m), 6.43 (1H, d, J = 15.2 Hz), 5.66-5.61 (1H, m), 5.15 (1H, q, J = 7.0 Hz), 4.35-4.20 (1H, m), 3.11 (2H, d, J = 5.9 Hz), 2.98-2.88 (1H, m), 2.98 (3H, s), 2.87-2.79 (1H, m), 2.82-2.70 (2H, m), 2.28 (6H, s), 2.13-1.99 (2H, m), 1.34 (3H, d, J = 7.0 Hz), 0.95-0.89 (2H, m), 0.71-0.64 (2H, m) |
| 15-9 | 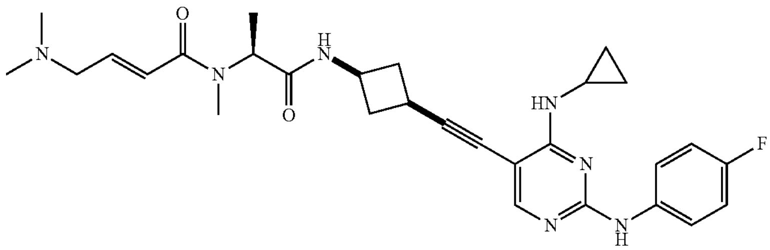 [SMILES: C[C@@H](C(=O)N[C@H]1C[C@@H](C#Cc2cnc(Nc3ccc(F)cc3)nc2NC2CC2)C1)N(C)C(=O)/C=C/CN(C)C] | ¹H-NMR (CDCl₃) δ: 7.99 (1H, s), 7.70-7.63 (2H, m), 7.03-6.95 (2H, m), 6.99-6.94 (1H, m), 6.98-6.89 (1H, m), 6.63-6.58 (1H, m), 6.43 (1H, d, J = 15.2 Hz), 5.57-5.51 (1H, m), 5.15 (1H, q, J = 7.0 Hz), 4.35-4.20 (1H, m), 3.11 (2H, d, J = 5.9 Hz), 3.01-2.85 (1H, m), 2.97 (3H, s), 2.86-2.78 (1H, m), 2.82-2.70 (2H, m), 2.28 (6H, s), 2.14-1.95 (2H, m), 1.33 (3H, d, J = 7.3 Hz), 0.91-0.84 (2H, m), 0.67-0.62 (2H, m) |

TABLE 212

| Compound No. | Structure | Physicochemical data |
|---|---|---|
| 15-10 | 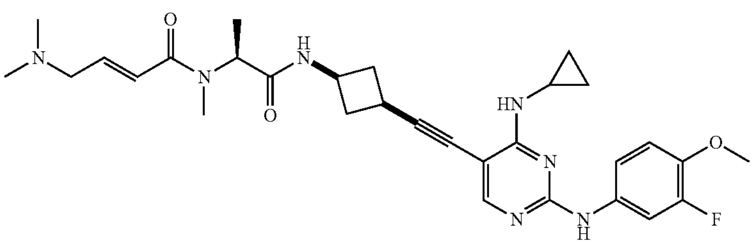 | ¹H-NMR (CDCl₃) δ: 8.05 (1H, d, J = 14.2 Hz), 7.98 (1H, s), 7.07-7.01 (1H, m), 7.00-6.97 (1H, m), 7.00-6.91 (1H, m), 6.93-6.85 (1H, m), 6.64-6.57 (1H, m), 6.43 (1H, d, J = 15.2 Hz), 5.58-5.55 (1H, m), 5.15 (1H, q, J = 6.8 Hz), 4.35-4.20 (1H, m), 3.87 (3H, s), 3.11 (2H, d, J = 5.9 Hz), 2.99-2.88 (1H, m), 2.98 (3H, s), 2.87-2.77 (1H, m), 2.84-2.69 (2H, m), 2.28 (6H, s), 2.13-1.97 (2H, m), 1.33 (3H, d, J = 7.3 Hz), 0.96-0.90 (2H, m), 0.68-0.63 (2H, m) |
| 15-11 | 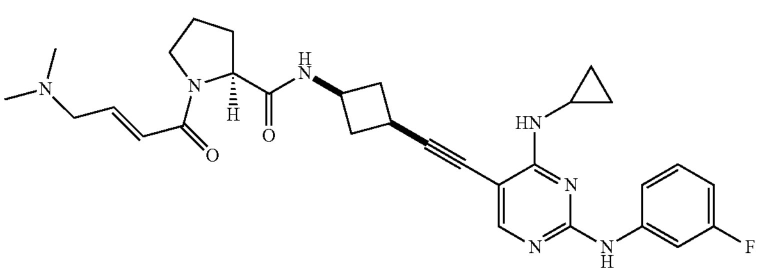 [SMILES: CN(C)C/C=C/C(=O)N1CCC[C@H]1C(=O)N[C@H]1C[C@@H](C#Cc2cnc(Nc3cccc(F)c3)nc2NC2CC2)C1] | ¹H-NMR (CDCl₃) δ: 8.11 (1H, d, J = 12.6 Hz), 8.01 (1H, s), 7.68-7.60 (1H, m), 7.25-7.16 (1H, m), 7.17-7.13 (1H, m), 7.10-7.05 (1H, m), 6.98 (1H, dt, J = 15.2, 5.9 Hz), 6.71-6.64 (1H, m), 6.33 (1H, d, J = 15.2 Hz), 5.63-5.59 (1H, m), 4.64 (1H, d, J = 5.9 Hz), 4.34-4.20 (1H, m), 3.72-3.63 (1H, m), 3.57-3.47 (1H, m), 3.11 (2H, d, J = 5.9 Hz), 2.97-2.85 (1H, m), 2.88-2.80 (1H, m), 2.80-2.68 (2H, m), 2.53-2.45 (1H, m), 2.27 (6H, s), 2.17-2.02 (2H, m), 2.10-1.96 (2H, m), 1.84-1.72 (1H, m), 0.96-0.93 (2H, m), 0.70-0.65 (2H, m) |

TABLE 212-continued

| Compound No. | Structure | Physicochemical data |
|---|---|---|
| 15-12 | 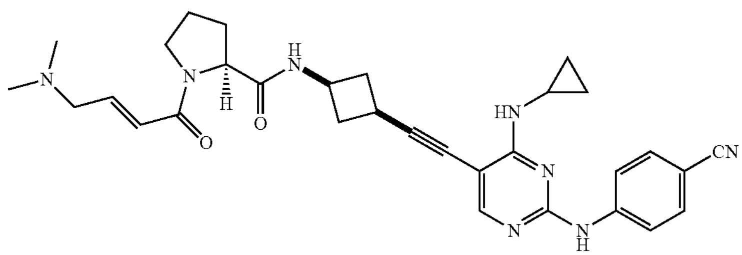 [SMILES: CN(C)C/C=C/C(=O)N1CCC[C@H]1C(=O)N[C@H]1C[C@@H](C#Cc2cnc(Nc3ccc(C#N)cc3)nc2NC2CC2)C1] | $^1$H-NMR (CDCl$_3$) δ: 8.03 (1H, s), 7.88 (2H, d, J = 8.6 Hz), 7.70-7.65 (1H, m), 7.57 (2H, d, J = 8.6 Hz), 7.38-7.35 (1H, m), 6.97 (1H, dt, J = 15.2, 5.9 Hz), 6.33 (1H, d, J = 15.2 Hz), 5.67-5.64 (1H, m), 4.64 (1H, d, J = 6.6 Hz), 4.33-4.21 (1H, m), 3.72-3.62 (1H, m), 3.56-3.48 (1H, m), 3.11 (2H, d, J = 5.9 Hz), 2.97-2.86 (1H, m), 2.87-2.79 (1H, m), 2.83-2.69 (2H, m), 2.53-2.45 (1H, m), 2.27 (6H, s), 2.17-2.04 (2H, m), 2.07-1.95 (2H, m), 1.86-1.71 (1H, m), 0.95-0.88 (2H, m), 0.70-0.66 (2H, m) |

TABLE 213

| Compound No. | Structure | Physicochemical data |
|---|---|---|
| 15-13 | 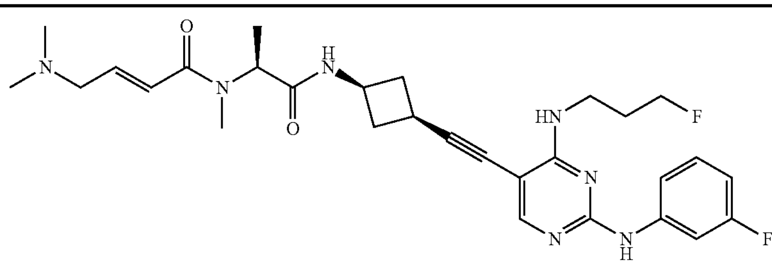 | $^1$H-NMR (CDCl$_3$) δ: 8.00 (1H, s), 7.79-7.71 (1H, m), 7.26-7.18 (1H, m), 7.12-7.07 (1H, m), 7.05-7.02 (1H, m), 6.95 (1H, dt, J = 15.2, 5.9 Hz), 6.69 (1H, td, J = 8.3, 2.0 Hz), 6.64-6.57 (1H, m), 6.43 (1H, d, J = 15.2 Hz), 5.79-5.71 (1H, m), 5.16 (1H, q, J = 7.3 Hz), 4.64 (2H, dt, J = 46.9, 5.2 Hz), 4.33-4.23 (1H, m), 3.75-3.66 (2H, m), 3.11 (2H, d, J = 5.9 Hz), 2.98 (3H, s), 2.97-2.88 (1H, m), 2.82-2.72 (2H, m), 2.28 (6H, s), 2.19-2.10 (2H, m), 2.10-2.02 (2H, m), 1.33 (3H, d, J = 7.3 Hz) |
| 15-14 | 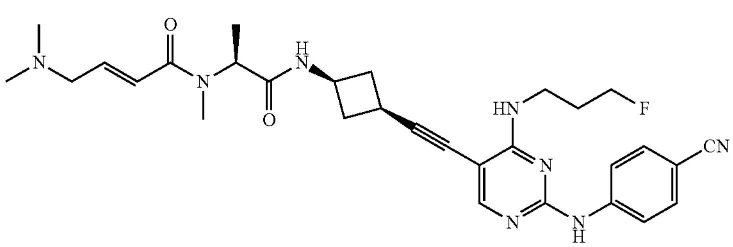 [SMILES: C[C@@H](C(=O)N[C@H]1C[C@@H](C#Cc2cnc(Nc3ccc(C#N)cc3)nc2NCCCF)C1)N(C)C(=O)/C=C/CN(C)C] | $^1$H-NMR (CDCl$_3$) δ: 8.02 (1H, s), 7.75 (2H, d, J = 9.0 Hz), 7.58 (2H, d, J = 9.0 Hz), 7.24-7.21 (1H, m), 6.94 (1H, dt, J = 15.2, 5.9 Hz), 6.65-6.61 (1H, m), 6.43 (1H, d, J = 15.2 Hz), 5.83-5.77 (1H, m), 5.15 (1H, q, J = 7.3 Hz), 4.64 (2H, dt, J = 47.6, 5.3 Hz), 4.34-4.22 (1H, m), 3.74-3.68 (2H, m), 3.11 (2H, d, J = 5.9 Hz), 2.98 (3H, s), 2.97-2.89 (1H, m), 2.82-2.73 (2H, m), 2.28 (6H, s), 2.17-2.10 (2H, m), 2.10-2.01 (2H, m), 1.34 (3H, d, J = 7.3 Hz) |
| 15-15 | 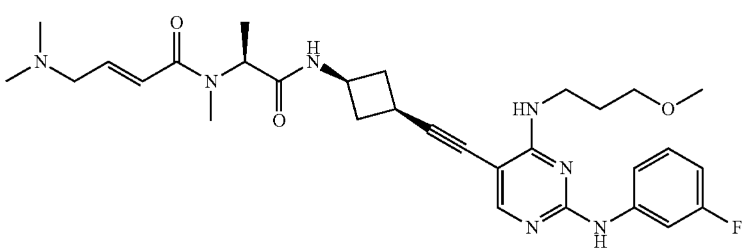 [SMILES: COCCCNc1nc(Nc2cccc(F)c2)ncc1C#C[C@H]1C[C@@H](NC(=O)[C@H](C)N(C)C(=O)/C=C/CN(C)C)C1] | $^1$H-NMR (CDCl$_3$) δ: 7.99 (1H, s), 7.81-7.74 (1H, m), 7.25-7.17 (1H, m), 7.11-7.07 (1H, m), 7.06-7.03 (1H, m), 6.95 (1H, dt, J = 15.2, 5.9 Hz), 6.68 (1H, td, J = 8.4, 2.2 Hz), 6.67-6.60 (1H, m), 6.43 (1H, d, J = 15.2 Hz), 6.01-5.95 (1H, m), 5.16 (1H, q, J = 6.9 Hz), 4.32-4.23 (1H, m), 3.67-3.59 (2H, m), 3.55 (2H, t, J = 5.6 Hz), 3.36 (3H, s), 3.11 (2H, d, J = 5.9 Hz), 2.98-2.89 (1H, m), 2.98 (3H, s), 2.81-2.73 (2H, m), 2.28 (6H, s), 2.15-2.02 (2H, m), 1.99-1.91 (2H, m), 1.33 (3H, d, J = 6.9 Hz) |

| Compound No. | Structure | Physicochemical data |
|---|---|---|
| 15-16 | 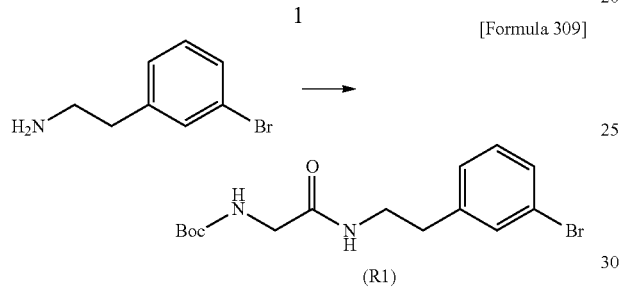 | ¹H-NMR (CDCl₃) δ: 8.01 (1H, s), 7.75 (2H, d, J = 8.6 Hz), 7.57 (2H, d, J = 8.6 Hz), 7.25-7.21 (1H, m), 6.95 (1H, dt, J = 15.2, 5.9 Hz), 6.67-6.62 (1H, m), 6.43 (1H, d, J = 15.2 Hz), 6.09-6.04 (1H, m), 5.15 (1H, q, J = 6.8 Hz), 4.32-4.24 (1H, m), 3.67-3.58 (2H, m), 3.55 (2H, t, J = 5.6 Hz), 3.37 (3H, s), 3.11 (2H, d, J = 5.9 Hz), 2.98 (3H, s), 2.98-2.89 (1H, m), 2.81-2.73 (2H, m), 2.28 (6H, s), 2.16-2.04 (2H, m), 1.98-1.90 (2H, m), 1.33 (3H, d, J = 6.8 Hz) |

Example 61

1

[Formula 309]

To a solution of N-Boc-glycine (175 mg) in tetrahydrofuran (1 mL), N-methylmorpholine (165 μL) and isobutyl chloroformate (131 μL) were added under ice cooling, and the mixture was stirred at the same temperature for 40 minutes. To the reaction mixture, 3-bromophenethylamine (100 μL) was added under ice cooling, and the mixture was stirred at room temperature for 5 hours. To the reaction mixture, saturated aqueous sodium hydrogencarbonate and ethyl acetate were added. The organic layer was separated, and dried over anhydrous sodium sulfate, and the solvent was evaporated under reduced pressure to obtain tert-butyl (2-((3-bromophenethyl)amino)-2-oxoethyl)carbamate (R1, 290 mg).

MS m/z (M+H): 357.1

2

[Formula 310]

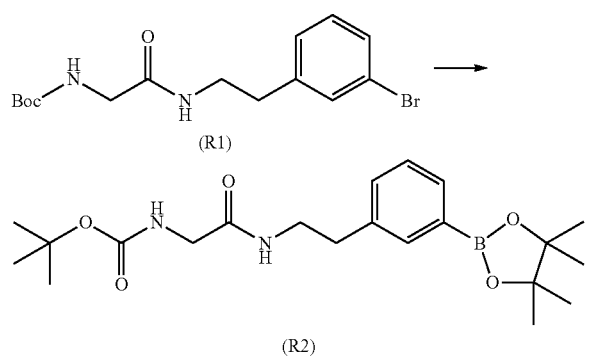

To a solution of tert-butyl (2-((3-bromophenethyl)amino)-2-oxoethyl)carbamate (R1, 290 mg) in dimethyl sulfoxide (40 mL), bis(pinacolato)diboron (618 mg), 1,1'-bis(diphenylphosphino)ferrocene-palladium(II) dichloride-dichloromethane complex (99 mg) and potassium acetate (478 mg) were added at room temperature, and the mixture was stirred at 80° C. for 14 hours. The reaction mixture was cooled to room temperature, and then saturated aqueous sodium hydrogencarbonate and ethyl acetate were added to the reaction mixture. The organic layer was separated, and dried over anhydrous sodium sulfate, and the solvent was evaporated under reduced pressure to obtain tert-butyl (2-oxo-2-((3-(4,4,5,5-tetramethyl-1,3,2-dioxaborolan-2-yl)phenethyl)amino)ethyl)carbamate (R2).

3

[Formula 311]

To a solution of 4-((5-iodo-4-(propylamino)pyrimidin-2-yl)amino)benzamide (F23, 55 mg) and tert-butyl (2-oxo-2-((3-(4,4,5,5-tetramethyl-1,3,2-dioxaborolan-2-yl)phenethyl)amino)ethyl)carbamate (R2) obtained above in dimethoxyethane and water (5/1, 1 mL), bis(di-tert-butyl(4-dimethylaminophenyl)phosphine)dichloropalladium(II) (10 mg) and sodium carbonate (44 mg) were added at room temperature, and the mixture was stirred at 80° C. for 4 hours and 40 minutes. The reaction mixture was cooled to room temperature, and then saturated aqueous sodium hydrogencarbonate and ethyl acetate were added to the reaction mixture. The organic layer was separated, and dried over anhydrous sodium sulfate, and the solvent was evaporated under reduced pressure. The obtained residue was purified by basic silica gel column chromatography (eluent, 91% chloroform/9% methanol) to obtain tert-butyl (2-((3-(2-((4-carbamoylphenyl)amino)-4-(propylamino)pyrimidin-5-yl)phenethyl)amino)-2-oxoethyl)carbamate (R3, 123 mg).

4

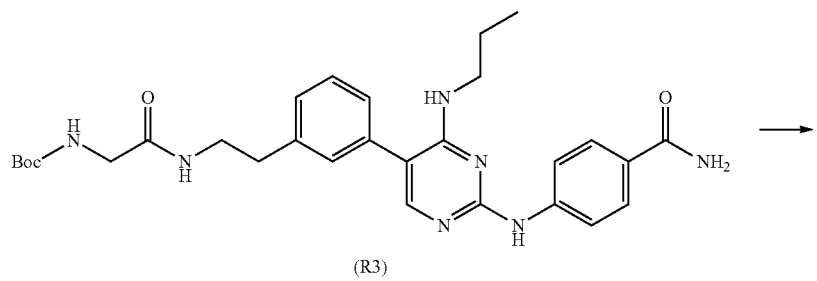

(R3)

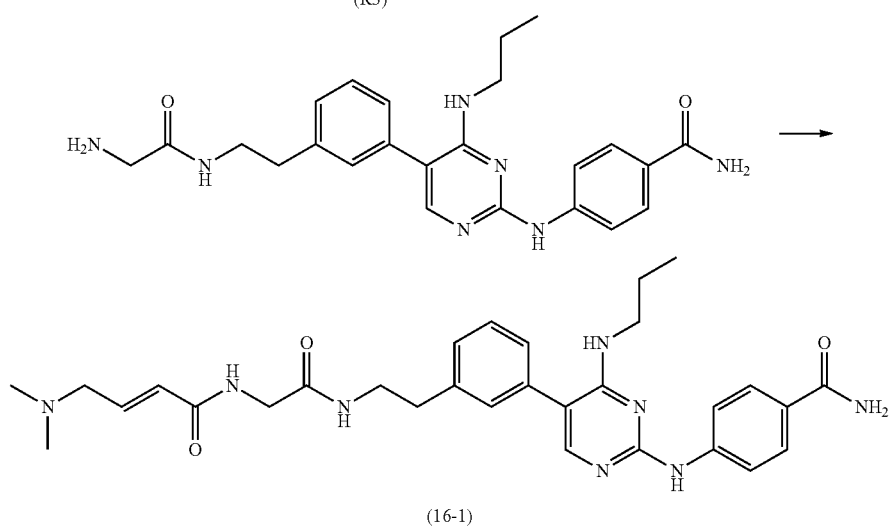

(16-1)

In the same manner as that of Example 35, (6) and (7), (E)-4-((5-(3-(2-(2-(4-(dimethylamino)-2-butenamido)acetamido)ethyl)phenyl)-4-(propylamino)pyrimidin-2-yl)amino)benzamide (16-1) was obtained from tert-butyl (2-((3-(2-((4-carbamoylphenyl)amino)-4-(propylamino)pyrimidin-5-yl)phenethyl)amino)-2-oxoethyl)carbamate (R3).

$^1$H-NMR (CD$_3$ OD) δ: 7.86-7.82 (4H, m), 7.71 (1H, s), 7.39 (1H, t, J=7.6 Hz), 7.27-7.20 (3H, m), 6.75-6.68 (1H, m), 6.11 (1H, d, J=15.2 Hz), 3.83 (2H, s), 3.59-3.37 (4H, m), 3.13 (2H, t, J=6.6 Hz), 2.85 (2H, t, J=6.9 Hz), 2.26 (6H, s), 1.69-1.65 (2H, m), 0.98 (3H, t, J=7.3 Hz)

5

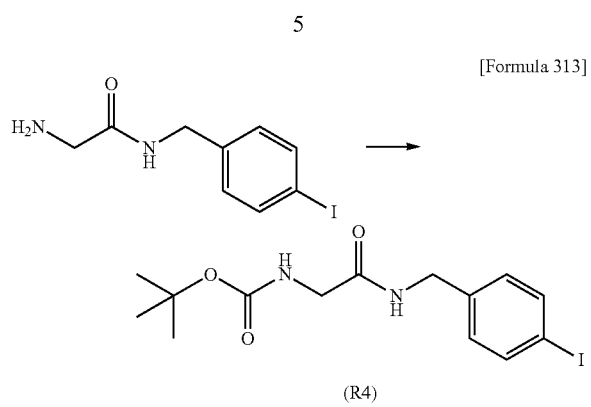

(R4)

To a solution of N-Boc-glycine (325 mg) in tetrahydrofuran (3 mL), N-methylmorpholine (1.0 mL) and isobutyl chloroformate (244 μL) were added under ice cooling, and the mixture was stirred at the same temperature for 30 minutes. To the reaction mixture, 4-iodobenzylamine hydrochloride (250 mg) was added under ice cooling, and the mixture was stirred at the same temperature for 1 hour and 30 minutes. To the reaction mixture, saturated aqueous sodium hydrogencarbonate and ethyl acetate were added. The organic layer was separated, and dried over anhydrous sodium sulfate, and the solvent was evaporated under reduced pressure to obtain tert-butyl (2-((4-iodobenzyl)amino)-2-oxoethyl)carbamate (R4, 430 mg).

MS m/z (M+H): 391.1

6

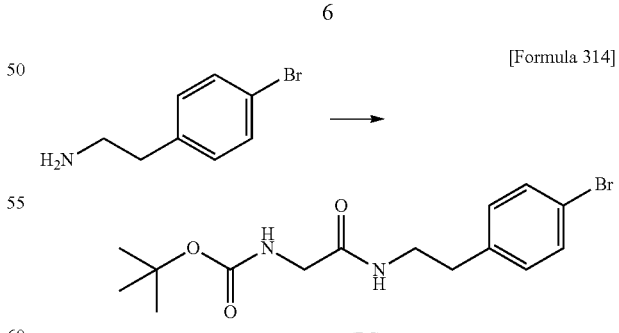

(R5)

To a solution of N-Boc-glycine (175 mg) in tetrahydrofuran (2 mL), N-methylmorpholine (165 μL) and isobutyl chloroformate (131 μL) were added under ice cooling, and the mixture was stirred at the same temperature for 40 minutes. To the reaction mixture, 2-(4-bromophenyl)ethylamine (100 μL) was added under ice cooling, and the mixture was stirred at room temperature for 5 hours. To the reaction mixture, saturated aqueous sodium hydrogencarbonate and ethyl acetate were added. The organic layer was separated, and dried over anhydrous sodium sulfate, and the solvent was evaporated under reduced pressure to obtain tert-butyl (2-((4-bromophenethyl)amino)-2-oxoethyl)carbamate (R5).

7

By using Intermediates (R4) and (R5), Intermediates (R6) and (R7) were obtained in the same manner as that of Example 61, (2).

TABLE 214

| Compound No. | Structure | Physicochemical data |
|---|---|---|
| R6 | ![structure] | — |
| R7 | ![structure] | — |

8

By using Intermediates (R6) and (R7), Intermediates (R8) and (R9) were obtained in the same manner as that of Example 61, (3).

TABLE 215

| Compound No. | Structure | Physicochemical data |
|---|---|---|
| R8 | ![structure] | MS m/z (M + H): 534.3 |
| R9 | ![structure] | — |

9

By using Intermediates (R8) and (R9), Compounds (16-2) and (16-3) were obtained in the same manner as that of Example 61, (4).

TABLE 216

| Compound No. | Structure | Physicochemical data |
|---|---|---|
| 16-2 | 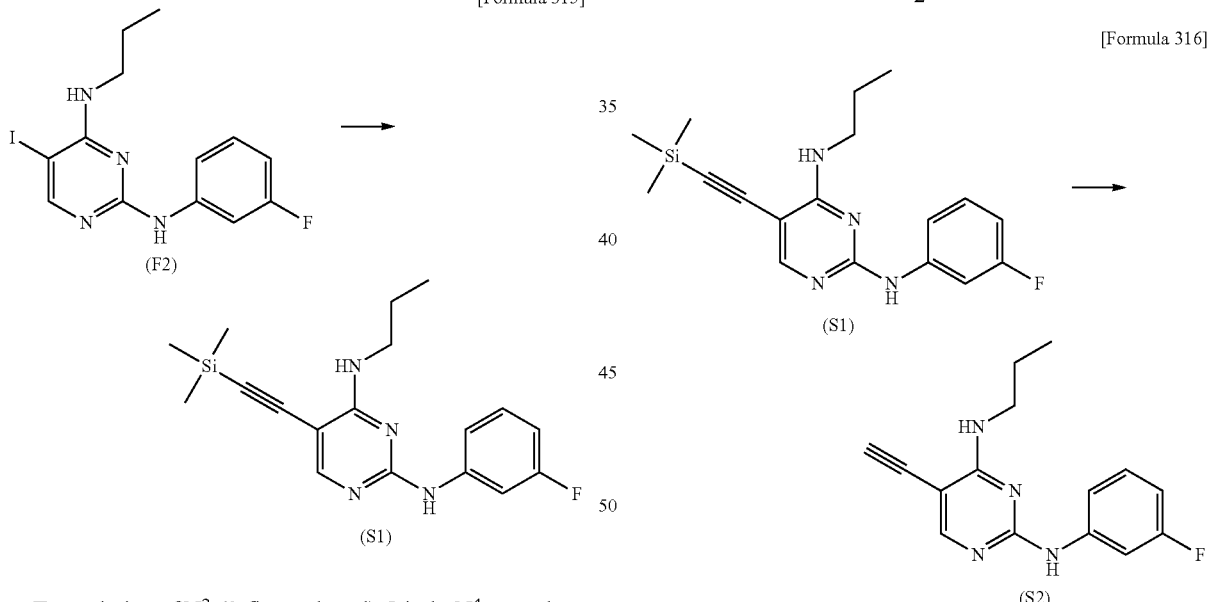 | $^1$H-NMR (CD$_3$OD) δ: 7.84 (4H, s), 7.68 (1H, s), 7.40-7.33 (4H, m), 6.80 (1H, dt, J = 15.2, 6.6 Hz), 6.16 (1H, d, J = 15.2 Hz), 4.44 (2H, s), 3.97 (2H, s), 3.43 (2H, t, J = 7.3 Hz), 3.14 (2H, d, J = 6.6 Hz), 2.27 (6H, s), 1.68-1.63 (2H, m), 0.97 (3H, t, J = 7.6 Hz) |
| 16-3 | 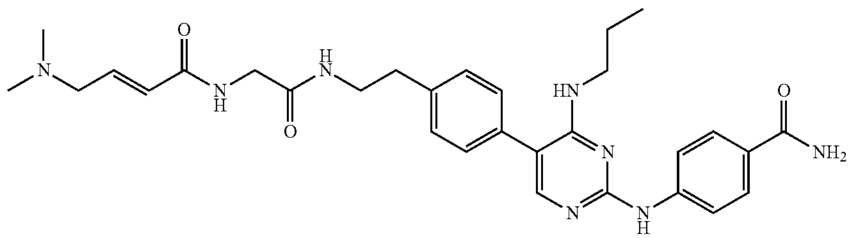 [SMILES: CCCNc1nc(Nc2ccc(C(N)=O)cc2)ncc1-c1ccc(CCNC(=O)CNC(=O)/C=C/CN(C)C)cc1] | $^1$H-NMR (CD$_3$OD) δ: 7.84 (4H, s), 7.68 (1H, s), 7.34-7.28 (4H, m), 6.78-6.73 (1H, m), 6.13 (1H, d, J = 15.2 Hz), 3.87 (2H, s), 3.73-3.54 (2H, m), 3.49-3.39 (2H, m), 3.12-3.08 (2H, m), 2.90-2.82 (2H, m), 2.25 (6H, s), 1.68-1.63 (2H, m), 0.97 (3H, t, J = 7.6 Hz) |

Example 62

[Formula 315]

[Formula 316]

To a solution of N$^2$-(3-fluorophenyl)-5-iodo-N$^4$-propylpyrimidine-2,4-diamine (F2, 500 mg), bis(triphenylphosphine) palladium(II) dichloride (94 mg) and copper(I) iodide (51 mg) in N,N-dimethylformamide (10 mL), triethylamine (934 μL) and trimethylsilylacetylene (285 μL) were added at room temperature, and the mixture was stirred at the same temperature for 1 hour. To the reaction mixture, ethyl acetate and saturated aqueous ammonium chloride were added. The organic layer was separated, washed successively with saturated aqueous ammonium chloride, water and saturated aqueous sodium chloride, and then dried over anhydrous magnesium sulfate, and the solvent was evaporated under reduced pressure. The obtained residue was purified by silica gel column chromatography (eluent, 95 to 85% hexane in ethyl acetate) to obtain N$^2$-(3-fluorophenyl)-N$^4$-propyl-5-((trimethylsilyl)ethynyl)pyrimidine-2,4-diamine (S1, 509 mg).

MS m/z (M+H): 343.2

To a solution of N$^2$-(3-fluorophenyl)-N$^4$-propyl-5-((trimethylsilyl)ethynyl)pyrimidine-2,4-diamine (S1, 509 mg) in methanol (10 mL) and tetrahydrofuran (10 mL), potassium carbonate (246 mg) was added at room temperature, and the mixture was stirred at the same temperature for 30 minutes. To the reaction mixture, ethyl acetate and saturated aqueous ammonium chloride were added. The organic layer was separated, washed successively with saturated aqueous ammonium chloride and saturated aqueous sodium chloride, and then dried over anhydrous magnesium sulfate, and the solvent was evaporated under reduced pressure. The obtained residue was purified by silica gel column chromatography (eluent, 94 to 60% hexane in ethyl acetate) to obtain 5-ethynyl-$N^2$-(3-fluorophenyl)-$N^4$-propylpyrimidine-2,4-diamine (S2, 226 mg).

MS m/z (M+H): 271.2

3

[Formula 317]

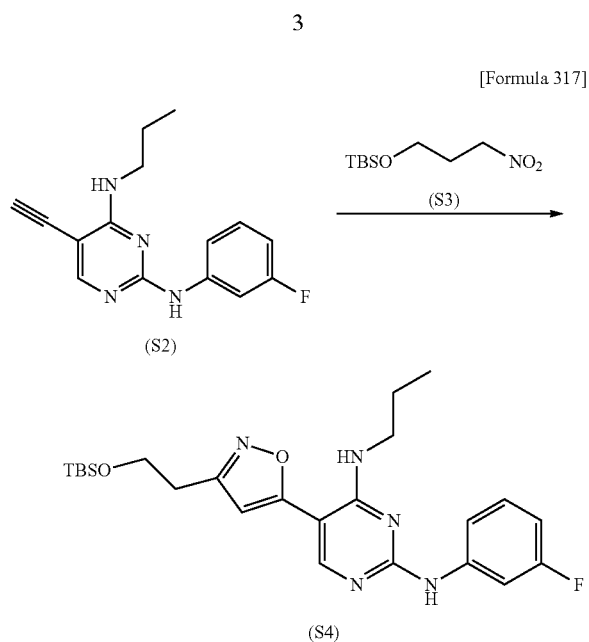

To a solution of 5-ethynyl-$N^2$-(3-fluorophenyl)-$N^4$-propylpyrimidine-2,4-diamine (S2, 30 mg) and tert-butyldimethyl (3-nitropropyloxy)silane (S3, 146 mg) synthesized according to the method described in Journal of Medicinal Chemistry, 2011, 54, pp. 7280-7288 in toluene (1 mL), phenyl isocyanate (36 μL) and triethylamine (46 μL) were added at room temperature, and the mixture was stirred at 60° C. for 4 hours and 40 minutes. To the reaction mixture, phenyl isocyanate (36 μL) and triethylamine (46 μL) were added, and the mixture was further stirred at 60° C. for 6 hours. The reaction mixture was cooled to room temperature, and then water and ethyl acetate were added to the reaction mixture. The organic layer was separated, and dried over anhydrous magnesium sulfate, and the solvent was evaporated under reduced pressure to obtain 5-(3-(2-((tert-butyldimethylsilyl)oxy)ethyl)isoxazol-5-yl)-$N^2$-(3-fluorophenyl)-$N^4$-propylpyrimidine-2,4-diamine (S4, 22 mg).

MS m/z (M+H): 472.3

4

[Formula 318]

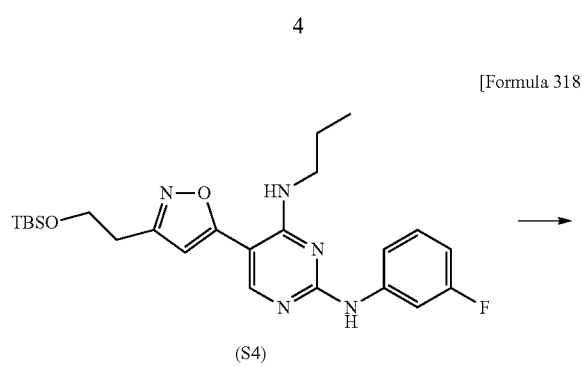

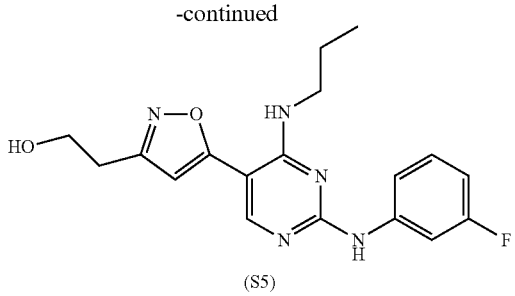

To a solution of 5-(3-(2-((tert-butyldimethylsilyl)oxy) ethyl)isoxazol-5-yl)-$N^2$-(3-fluorophenyl)-$N^4$-propylpyrimidine-2,4-diamine (S4, 22 mg) in tetrahydrofuran (1 mL), a 1.0 mol/L solution of tetrabutylammonium fluoride in tetrahydrofuran (69 μL) was added under ice cooling, and the mixture was stirred at room temperature for 3 hours. To the reaction mixture, saturated aqueous sodium hydrogencarbonate and ethyl acetate were added. The organic layer was separated, washed successively with water and saturated aqueous sodium chloride, and then dried over anhydrous magnesium sulfate, and the solvent was evaporated under reduced pressure. The obtained residue was purified by silica gel column chromatography (eluent, 70 to 5% hexane in ethyl acetate) to obtain 2-(5-(2-((3-fluorophenyl)amino)-4-(propylamino)pyrimidin-5-yl)isoxazol-3-yl)ethanol (S5, 5.3 mg) as white solid.

MS m/z (M+H): 358.2

5

[Formula 319]

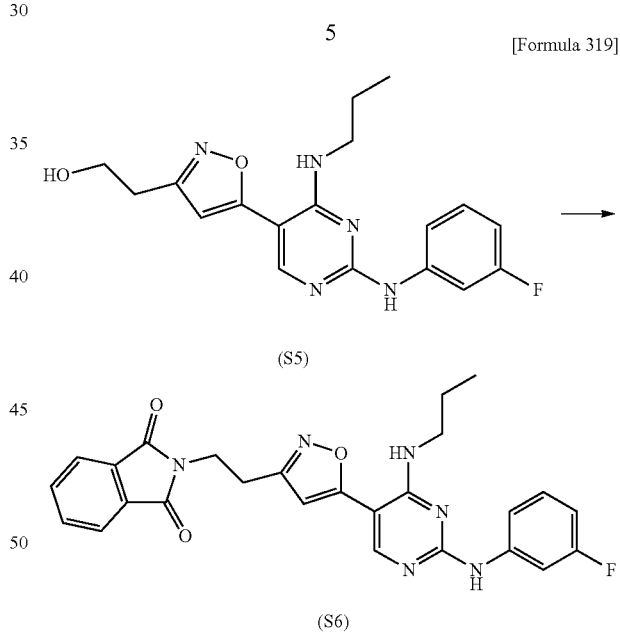

To a solution of 2-(5-(2-((3-fluorophenyl)amino)-4-(propylamino)pyrimidin-5-yl)isoxazol-3-yl)ethanol (S5, 5.3 mg), phthalimide (10.9 mg) and triphenylphosphine (19.4 mg) in tetrahydrofuran (1 mL), a 1.9 mol/L solution of diisopropyl azodicarboxylate in toluene (39 μL) was added under ice cooling, and the mixture was stirred at the same temperature for 35 minutes, and then stirred at room temperature for 2 hours and 30 minutes. The solvent was evaporated under reduced pressure, and the obtained residue was purified by silica gel column chromatography (eluent, 84 to 35% hexane in ethyl acetate) to obtain 2-(2-(5-(2-((3-fluorophenyl)amino)-4-(propylamino)pyrimidin-5-yl)isoxazol-3-yl)ethyl)isoindoline-1,3-dione (S6, 8.9 mg) as white solid.

MS m/z (M+H): 487.3

[Formula 320]

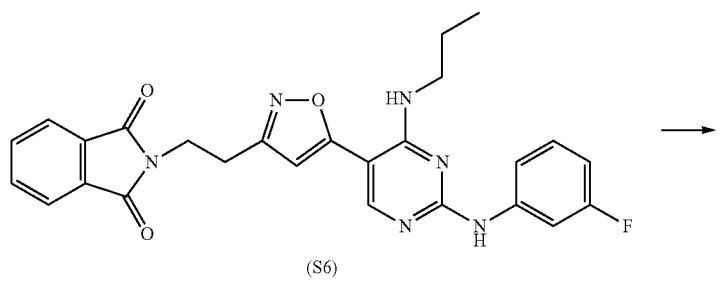

(S6)

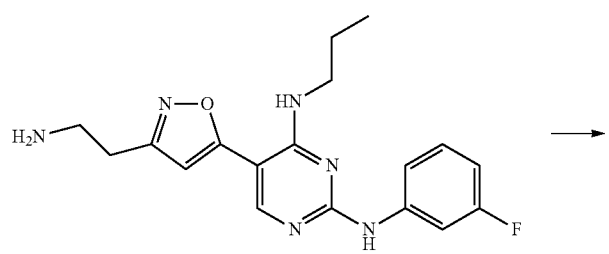

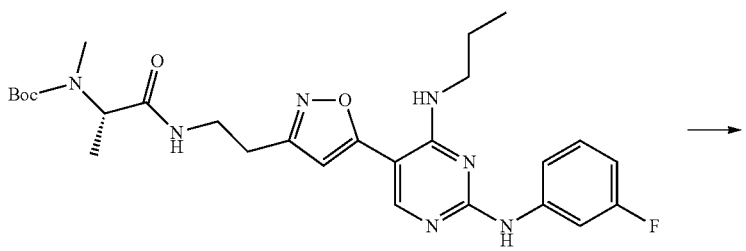

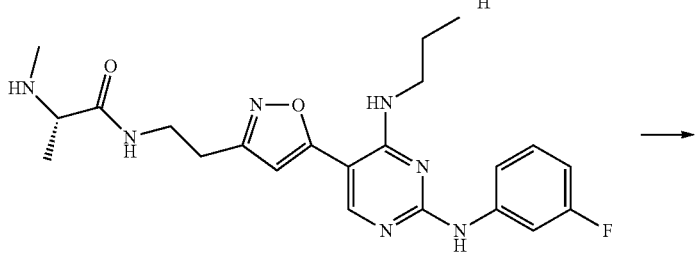

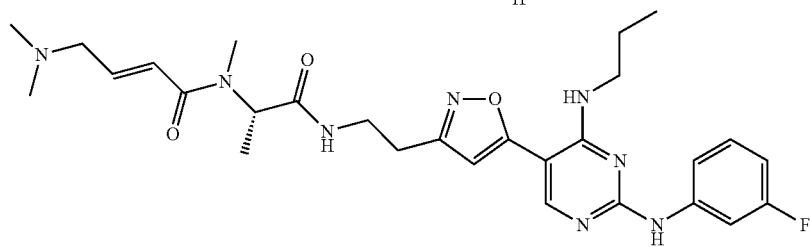

(17-1)

In the same manner as that of Example 35, (4) to (7), (S,E)-4-(dimethylamino)-N-(1-((2-(5-(2-(((3-fluorophenyl)amino)-4-(propylamino)pyrimidin-5-yl)isoxazol-3-yl)ethyl)amino)-1-oxopropan-2-yl)-N-methyl-2-butenamide (17-1) was obtained from 2-(2-(5-(2-(((3-fluorophenyl)amino)-4-(propylamino)pyrimidin-5-yl)isoxazol-3-yl)ethyl)isoindoline-1,3-dione (S6).

$^1$H-NMR (CDCl$_3$) δ: 8.26 (1H, s), 7.82 (1H, d, J=11.9 Hz), 7.29-7.20 (1H, m), 7.22-7.18 (1H, m), 7.16-7.10 (1H, m), 6.89 (1H, dt, J=15.2, 5.9 Hz), 6.76-6.67 (1H, m), 6.72-6.64 (1H, m), 6.61-6.56 (1H, m), 6.39 (1H, d, J=15.2 Hz), 6.26 (1H, s), 5.15 (1H, q, J=7.0 Hz), 3.71-3.57 (2H, m), 3.60-3.50 (2H, m), 3.07 (2H, d, J=5.9 Hz), 2.94 (3H, s), 2.90 (2H, t, J=6.6 Hz), 2.26 (6H, s), 1.80-1.69 (2H, m), 1.34 (3H, d, J=7.3 Hz), 1.04 (3H, t, J=7.6 Hz)

7

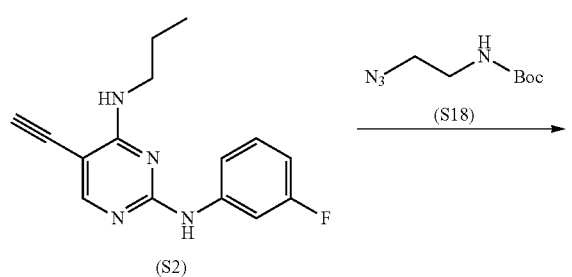

[Formula 321]

To 5-ethynyl-$N^2$-(3-fluorophenyl)-$N^4$-propylpyrimidine-2,4-diamine (S2, 62.4 mg) and tert-butyl(2-azidoethyl)carbamate (S18, 51.6 mg), tert-butanol (0.6 mL), water (0.6 mL), N,N-dimethylformamide (1.2 mL), sodium ascorbate (9.15 mg) and copper sulfate (3.69 mg) were added at room temperature, and the mixture was stirred at the same temperature for 12 hours. To the reaction mixture, ethyl acetate and water were added. The organic layer was separated, washed successively with water and saturated aqueous sodium chloride, and then dried over anhydrous sodium sulfate, and the solvent was evaporated under reduced pressure to obtain tert-butyl (2-(4-(2-((3-fluorophenyl)amino)-4-(propylamino)pyrimidin-5-yl)-1H-1,2,3-triazol-1-yl)ethyl)carbamate (S19, 32.5 mg).

MS m/z (M+H): 457.4

8

[Formula 322]

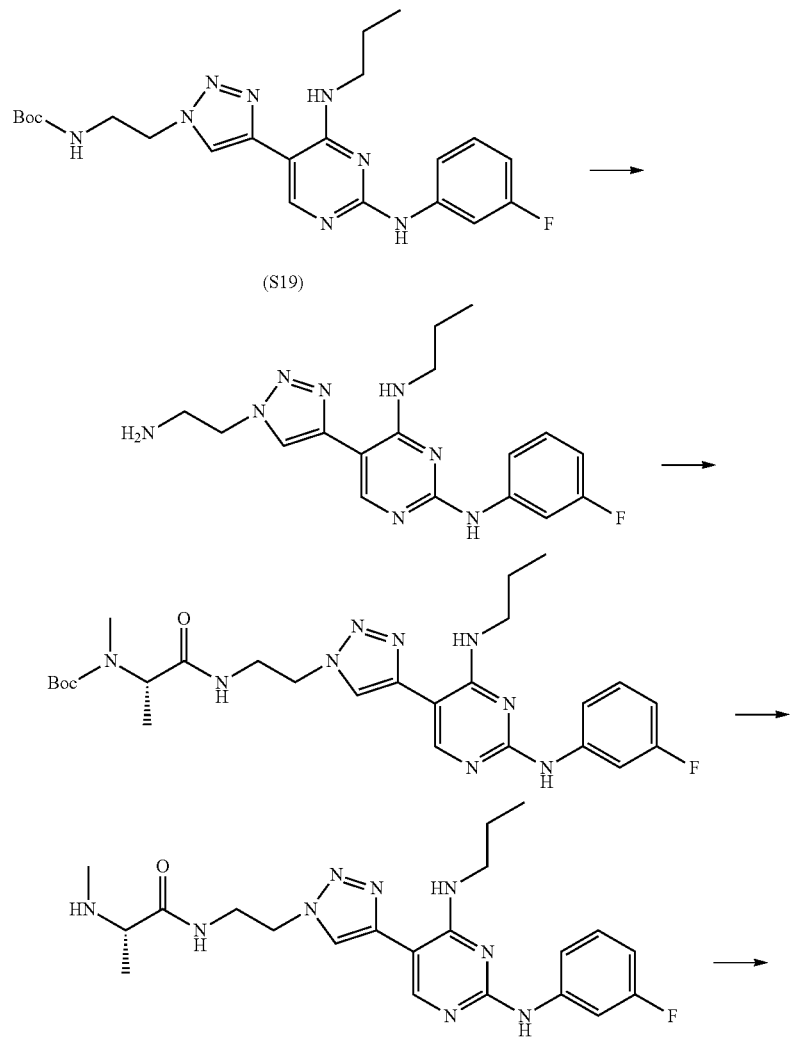

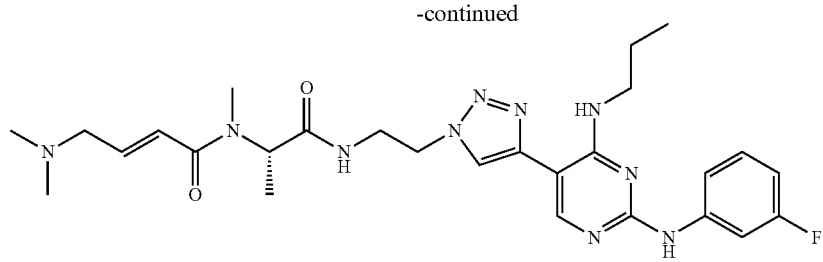

(17-2)

By using tert-butyl (2-(4-(2-((3-fluorophenyl)amino)-4-(propylamino)pyrimidin-5-yl)-1H-1,2,3-triazol-1-yl)ethyl)carbamate (S19), (S,E)-4-(dimethylamino)-N-(1-((2-(4-(2-((3-fluorophenyl)amino)-4-(propylamino)pyrimidin-5-yl)-1H-1,2,3-triazol-1-yl)ethyl)amino)-1-oxopropan-2-yl)-N-methyl-2-butenamide (17-2) was obtained in the same manner as that of Example 54, (4) to (6) and Example 54, (8).

$^1$H-NMR (CDCl$_3$) δ: 8.55-8.45 (1H, m), 8.18 (1H, s), 7.87 (1H, dt, J=11.9, 2.3 Hz), 7.82 (1H, s), 7.29-7.04 (3H, m), 6.87 (1H, dt, J=15.2, 5.9 Hz), 6.81-6.72 (1H, m), 6.68 (1H, dt, J=8.1, 2.3 Hz), 6.35 (1H, d, J=15.2 Hz), 5.05 (1H, q, J=7.3 Hz), 4.64-4.46 (2H, m), 3.92-3.76 (1H, m), 3.76-3.52 (3H, m), 3.04 (2H, d, J=5.9 Hz), 2.94 (3H, s), 2.22 (6H, s), 1.85-1.70 (2H, m), 1.35 (3H, d, J=7.3 Hz), 1.06 (3H, t, J=7.6 Hz)

9

[Formula 323]

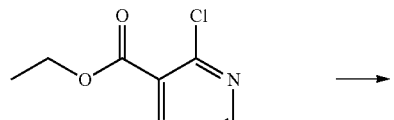

10

[Formula 324]

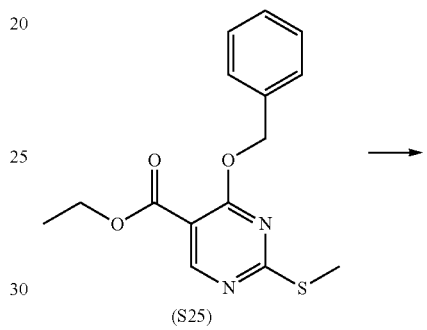

(S25)

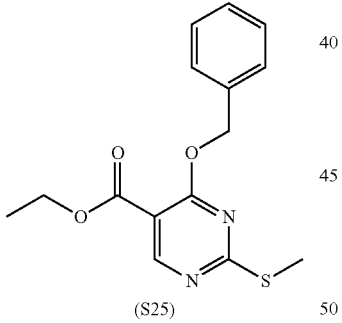

(S25)

To a solution of 4-chloro-2-(methylthio)pyrimidine-5-carboxylic acid ethyl ester (5.0 g) in tetrahydrofuran (50 mL) and N,N-dimethylformamide (5 mL), benzyl alcohol (2.66 mL) and sodium hydride (60% wt, 946 mg) were added under ice cooling, and the mixture was stirred at the same temperature for 2 hours. To the reaction mixture, saturated aqueous sodium hydrogencarbonate and ethyl acetate were added. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain oily ethyl 4-(benzyloxy)-2-(methylthio)pyrimidine-5-carboxylate (S25, 5.37 g).

MS m/z (M+H): 305.2

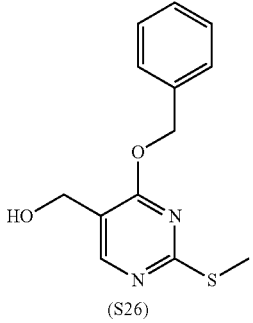

(S26)

To a solution of ethyl 4-(benzyloxy)-2-(methylthio)pyrimidine-5-carboxylate (S25, 3.02 g) in tetrahydrofuran (50 mL), lithium aluminum hydride (1.51 g) was added portion-wise under ice cooling, and the mixture was stirred at the same temperature for 45 minutes. To the reaction mixture, saturated aqueous sodium hydrogencarbonate (300 mL) and ethyl acetate (200 mL) were added. The insoluble matter was removed by filtration through Cerite. The organic layer was separated, washed successively with water and saturated aqueous sodium chloride, and then dried over anhydrous sodium sulfate, and the solvent was evaporated under reduced pressure. The obtained residue was purified by silica gel column chromatography (eluent, 70 to 30% hexane in ethyl acetate) to obtain oily (4-(benzyloxy)-2-(methylthio)pyrimidin-5-yl)methanol (S26, 818 mg).

MS m/z (M+H): 263.2

11

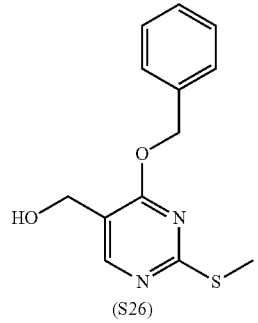 

(S26)

[Formula 325]

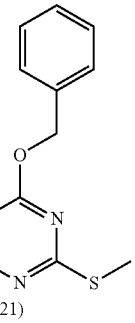

(S21)

To a solution of 4-(benzyloxy)-2-(methylthio)pyrimidine-5-carbaldehyde (S20, 223 mg) in pyridine (4.0 mL), hydroxylamine hydrochloride (95.8 mg) was added at room temperature, and the mixture was stirred at room temperature for 2 hours. To the reaction mixture, ethyl acetate and water were added. The organic layer was separated, washed successively with water and saturated aqueous sodium chloride, and then dried over anhydrous sodium sulfate, and the solvent was evaporated under reduced pressure to obtain 4-(benzyloxy)-2-(methylthio)pyrimidine-5-carbaldehyde oxime (S21, 233 mg).

MS m/z (M+H): 276.2

13

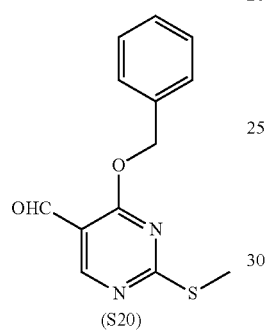

(S20)

To a solution of (4-(benzyloxy)-2-(methylthio)pyrimidin-5-yl)methanol (S26, 818 mg) in toluene (30 mL), manganese dioxide (8.13 g) was added at room temperature, and the mixture was stirred at 50° C. for 1 hour. The reaction mixture was cooled to room temperature, and then the insoluble matter was removed by filtration through Cerite. The solvent was evaporated under reduced pressure to obtain oily 4-(benzyloxy)-2-(methylthio)pyrimidine-5-carbaldehyde (S20, 666 mg).

MS m/z (M+H): 261.2

12

[Formula 326]

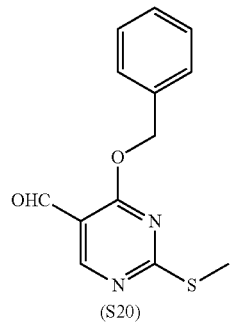 

(S20)

[Formula 327]

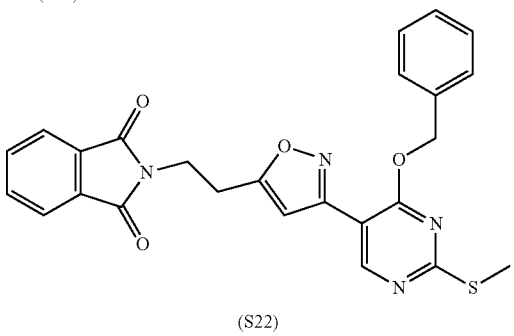

(S21)

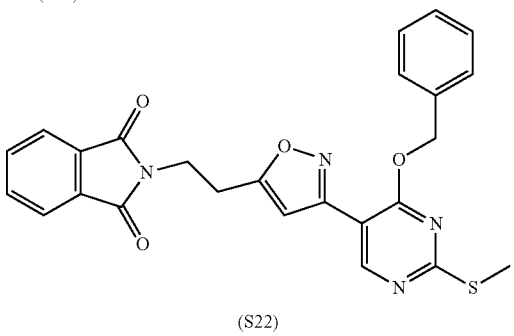

(S22)

To a solution of 4-(benzyloxy)-2-(methylthio)pyrimidine-5-carbaldehyde oxime (S21, 705 mg) in N,N-dimethylformamide (6.0 mL), pyridine (20.6 μL) and N-chlorosuccinimide (471 mg) were added under ice cooling, and the mixture was stirred at 50° C. for 1 hour. The reaction mixture was cooled to room temperature, then a solution of N-(3-butynyl)phthalimide (765 mg) and triethylamine (603 μL) in tetrahydrofuran (8.5 mL) was added to the reaction mixture, and the mixture was stirred at 50° C. for 2 hours. The reaction mixture was cooled to room temperature, and then ethyl acetate and water were added to the reaction mixture. The organic layer was separated, washed successively with water and saturated aqueous sodium chloride, and then dried over anhydrous sodium sulfate, and the solvent was evaporated under reduced pressure. The obtained residue was purified by silica gel column chromatography to obtain 2-(2-(3-(4-(benzyloxy)-2-(methylthio)pyrimidin-5-yl)isoxazol-5-yl)ethyl)isoindoline-1,3-dione (S22, 439 mg).

MS m/z (M+H): 473.3

14

[Formula 328]

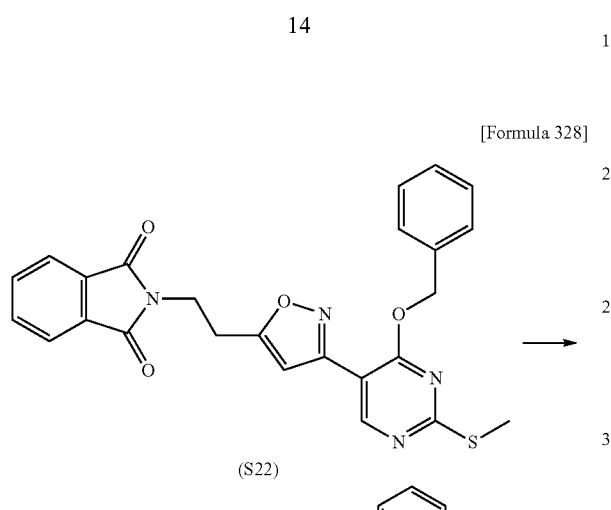

(S22)

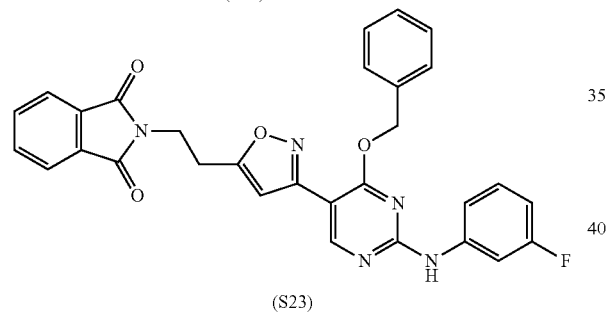

(S23)

To a solution of 2-(2-(3-(4-(benzyloxy)-2-(methylthio)pyrimidin-5-yl)isoxazol-5-yl)ethyl)isoindoline-1,3-dione (S22, 329 mg) in N-methylpyrrolidone (4.0 mL), meta-chloroperbenzoic acid (70 to 75% wt, 561 mg) was added under ice cooling, and the mixture was stirred at room temperature for 30 minutes. To the reaction mixture, ethyl acetate and saturated aqueous sodium hydrogencarbonate were added. The organic layer was separated, washed successively with saturated aqueous sodium hydrogencarbonate, water and saturated aqueous sodium chloride, and then dried over anhydrous sodium sulfate, and the solvent was evaporated under reduced pressure. To a solution of the obtained white solid in N-methylpyrrolidone (4.0 mL), 3-fluoroaniline (267 μL) and (1S)-(+)-10-camphorsulfonic acid (648 mg) were added at room temperature, and the mixture was stirred at 70° C. for 12 hours. The reaction mixture was cooled to room temperature, and then ethyl acetate and water were added to the reaction mixture. The organic layer was separated, washed successively with water, saturated aqueous sodium hydrogencarbonate and saturated aqueous sodium chloride, and then dried over anhydrous sodium sulfate, and the solvent was evaporated under reduced pressure to obtain 2-(2-(3-(4-(benzyloxy)-2-((3-fluorophenyl)amino)pyrimidin-5-yl)isoxazol-5-yl)ethyl)isoindoline-1,3-dione (S23, 235 mg) as white solid.

MS m/z (M+H): 536.4

15

[Formula 329]

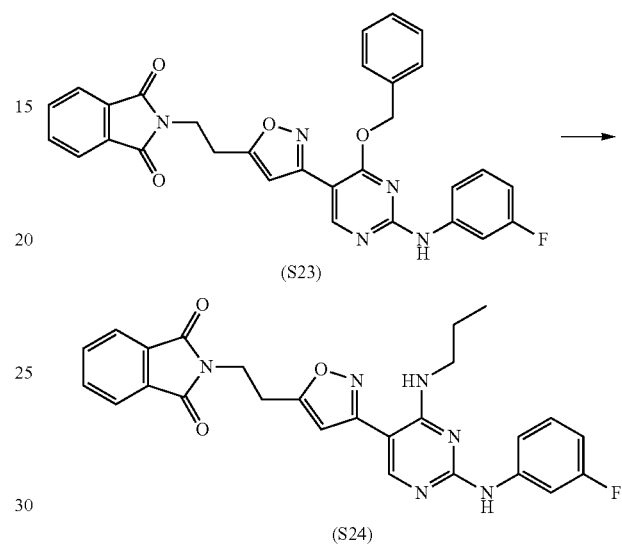

By using 2-(2-(3-(4-(benzyloxy)-2-((3-fluorophenyl)amino)pyrimidin-5-yl)isoxazol-5-yl)ethyl)isoindoline-1,3-dione (S23), 2-(2-(3-(2-((3-fluorophenyl)amino)-4-(propylamino)pyrimidin-5-yl)isoxazol-5-yl)ethyl)isoindoline-1,3-dione (S24) was obtained in the same manner as that of Example 44, (4) to (6).

MS m/z (M+H): 487.5

16

[Formula 330]

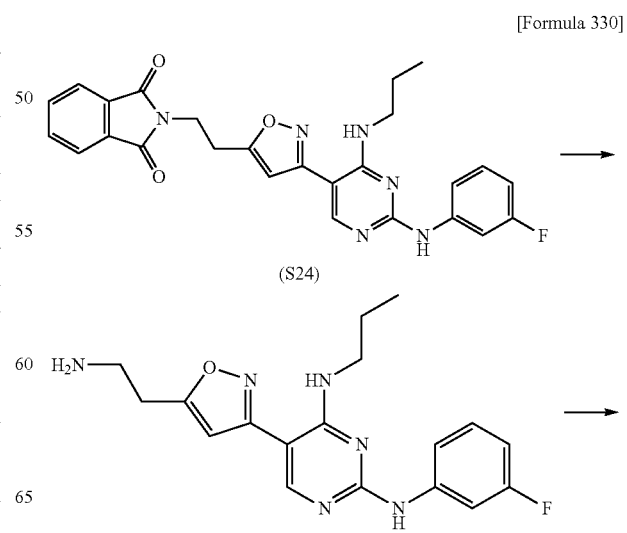

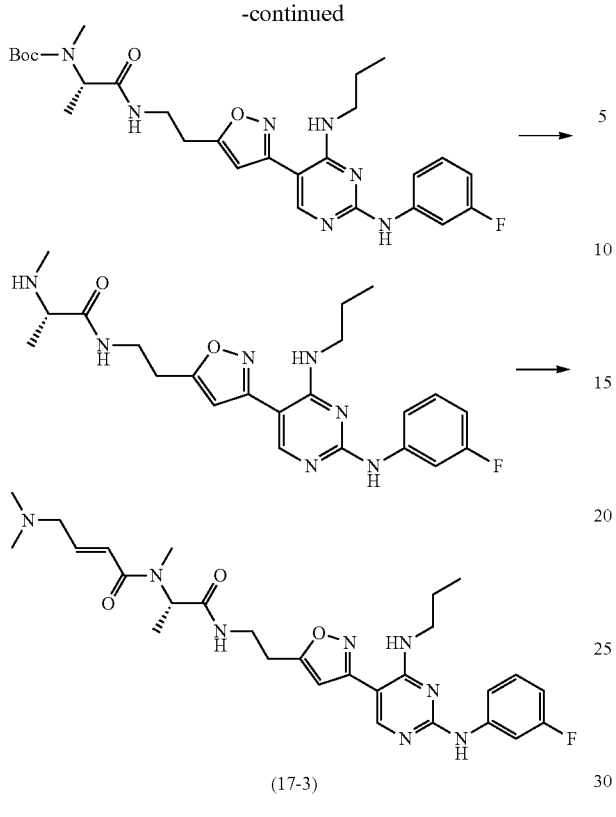

(17-3)

In the same manner as that of Example 35, (4) to (7), (S,E)-4-(dimethylamino)-N-(1-((2-(3-(2-(((3-fluorophenyl)amino)-4-(propylamino)pyrimidin-5-yl)isoxazol-5-yl)ethyl)amino)-1-oxopropan-2-yl)-N-methyl-2-butenamide (17-3) was obtained from 2-(2-(3-(2-(((3-fluorophenyl)amino)-4-(propylamino)pyrimidin-5-yl)isoxazol-5-yl)ethyl)isoindoline-1,3-dione (S24).

$^1$H-NMR (CDCl$_3$) δ: 8.23 (1H, s), 7.97-7.89 (1H, m), 7.85 (1H, dt, J=11.9, 2.0 Hz), 7.30-7.18 (2H, m), 7.18-7.11 (1H, m), 6.89 (1H, dt, J=15.2, 5.9 Hz), 6.81-6.66 (2H, m), 6.41-6.31 (2H, m), 5.14 (1H, q, J=7.0 Hz), 3.73-3.46 (4H, m), 3.10-2.97 (4H, m), 2.94 (3H, s), 2.23 (6H, s), 1.80-1.68 (2H, m), 1.34 (3H, d, J=7.0 Hz), 1.05 (3H, t, J=7.6 Hz)

Example 63

1

[Formula 331]

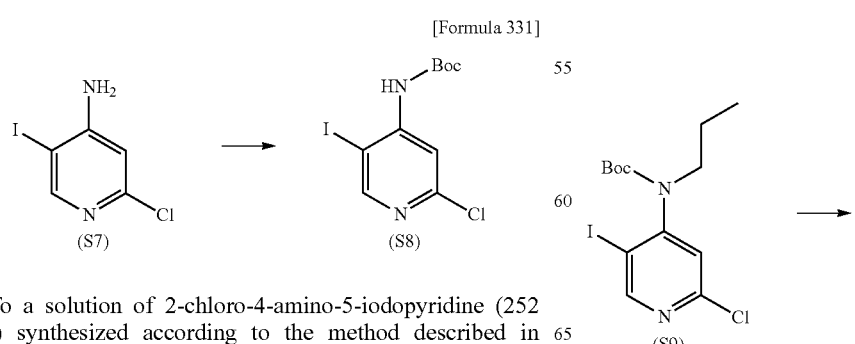

To a solution of 2-chloro-4-amino-5-iodopyridine (252 mg) synthesized according to the method described in EP2108641 A1 and 4-dimethylaminopyridine (241 mg) in tetrahydrofuran (5 mL), triethylamine (208 μL) and di-tert-butyl dicarbonate (273 μL) were added at room temperature, and the mixture was stirred at the same temperature for 1 hour and 20 minutes, and then stirred for 2 hours under reflux by heating. The reaction mixture was cooled to room temperature, and then ethyl acetate and water were added to the reaction mixture. The organic layer was separated, washed with saturated aqueous sodium chloride, and then dried over anhydrous sodium sulfate, and the solvent was evaporated under reduced pressure. The obtained residue was purified by silica gel chromatography (eluent, 100 to 60% hexane in ethyl acetate) to obtain tert-butyl (2-chloro-5-iodopyridin-4-yl)carbamate (S8, 239 mg).

MS m/z (M+H): 355.0

2

[Formula 332]

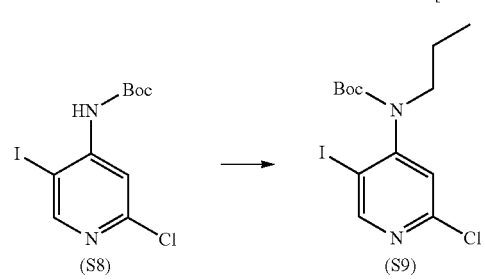

To a solution of tert-butyl (2-chloro-5-iodopyridin-4-yl)carbamate (S8, 239 mg) and propyl iodide (131 μL) in N-methylpyrrolidone (3 mL), sodium hydride (60% wt, 80 mg) was added under ice cooling, and the mixture was stirred at room temperature for 2 hours, and then stirred at 50° C. for 3 hours. The reaction mixture was cooled to room temperature, and then ethyl acetate and water were added to the reaction mixture. The organic layer was separated, washed with saturated aqueous sodium chloride, and then dried over anhydrous sodium sulfate, and the solvent was evaporated under reduced pressure. The obtained residue was purified by silica gel chromatography (eluent, 100 to 70% hexane in ethyl acetate) to obtain tert-butyl (2-chloro-5-iodopyridin-4-yl)(propyl)carbamate (S9, 155 mg).

MS m/z (M+H): 397.1

3

[Formula 333]

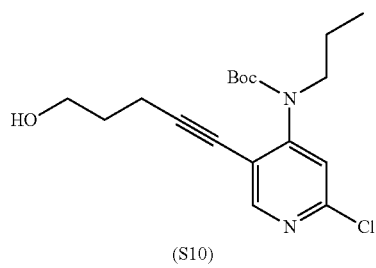

(S10)

To a solution of tert-butyl (2-chloro-5-iodopyridin-4-yl)(propyl)carbamate (S9, 155 mg), bis(triphenylphosphine)palladium(II) dichloride (27 mg) and copper(I) iodide (15 mg) in N,N-dimethylformamide (4 mL), triethylamine (137 μL) and 4-butyn-1-ol (72 μL) were added at room temperature, and the mixture was stirred at the same temperature for 3 hours, and then stirred at 50° C. for 3 hours. The reaction mixture was cooled to room temperature, and then ethyl acetate and water were added to the reaction mixture. The insoluble matter was removed by filtration through Cerite. The organic layer was separated, washed successively with water, saturated aqueous ammonium chloride and saturated aqueous sodium chloride, and then dried over anhydrous sodium sulfate, and the solvent was evaporated under reduced pressure. The obtained residue was purified by silica gel chromatography (eluent, 60 to 0% hexane in ethyl acetate) to obtain tert-butyl (2-chloro-5-(5-hydroxy-1-pentyn-1-yl)pyridin-4-yl)(propyl)carbamate (S10, 88 mg).

MS m/z (M+H): 353.2

4

[Formula 334]

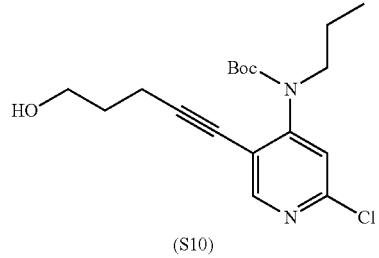

(S10)

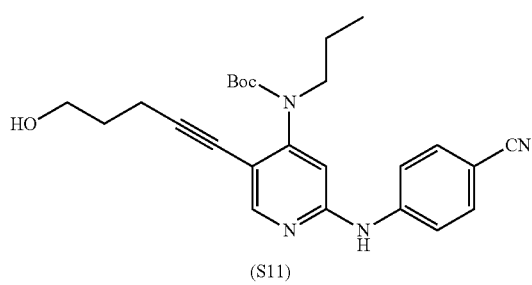

(S11)

To tert-butyl (2-chloro-5-(5-hydroxy-1-pentyn-1-yl)pyridin-4-yl)(propyl)carbamate (S10, 88 mg), 4-aminobenzonitrile (59 mg), tris(dibenzylideneacetone)dipalladium(0) (22 mg), 4,5'-bis(diphenylphosphino)-9,9'-dimethylxanthene (29 mg) and cesium carbonate (203 mg), 1,4-dioxane (2.5 mL) was added at room temperature, and the mixture was stirred at 100° C. for 10 hours. The reaction mixture was cooled to room temperature, and then ethyl acetate and water were added to the reaction mixture. The insoluble matter was removed by filtration through Cerite. The organic layer was separated, washed with saturated aqueous sodium chloride, and then dried over anhydrous sodium sulfate, and the solvent was evaporated under reduced pressure. The obtained residue was purified by silica gel chromatography (eluent, 100 to 30% hexane in ethyl acetate) to obtain tert-butyl (2-((4-cyanophenyl)amino)-5-(5-hydroxy-1-pentyn-1-yl)pyridin-4-yl)(propyl)carbamate (S11, 17 mg).

MS m/z (M+H): 435.3

5

[Formula 335]

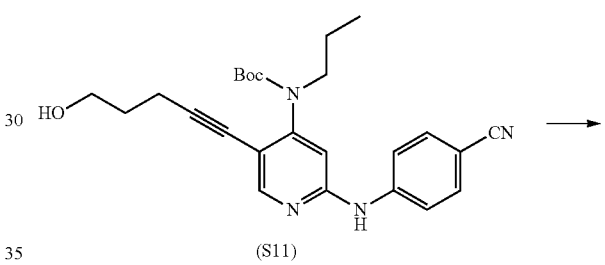

(S11)

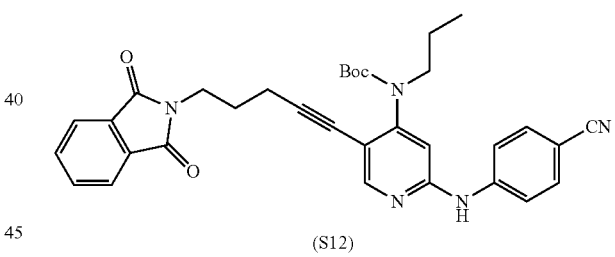

(S12)

To a solution of tert-butyl (2-((4-cyanophenyl)amino)-5-(5-hydroxy-1-pentyn-1-yl)pyridin-4-yl)(propyl)carbamate (S11, 17 mg), phthalimide (12 mg) and triphenylphosphine (21 mg) in tetrahydrofuran (1 mL), a 2.2 mol/mL solution of diethyl azodicarboxylate in toluene (36 μL) was added under ice cooling, and the mixture was stirred at room temperature for 2 hours. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by silica gel chromatography (eluent, 100 to 40% hexane in ethyl acetate) to obtain tert-butyl (2-((4-cyanophenyl)amino)-5-(5-(1,3-dioxoisoindolin-2-yl)-1-pentyn-1-yl)pyridin-4-yl)(propyl)carbamate (S12, 20 mg).

MS m/z (M+H): 564.4

731
6
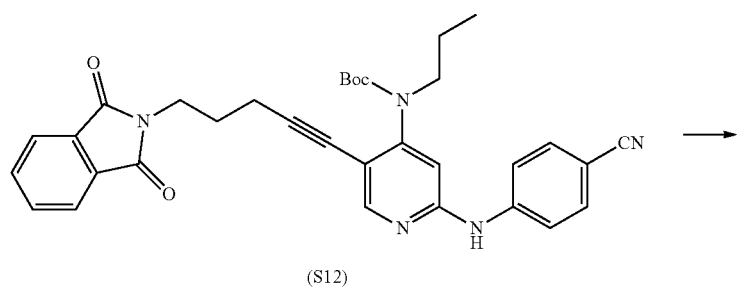
(S12)
[Formula 336]
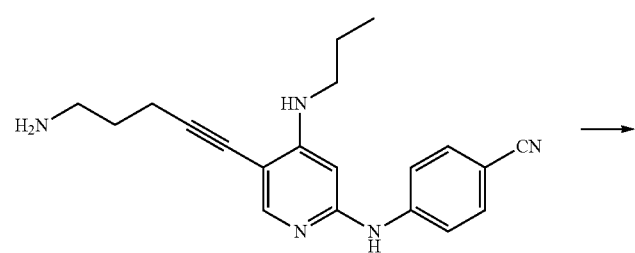
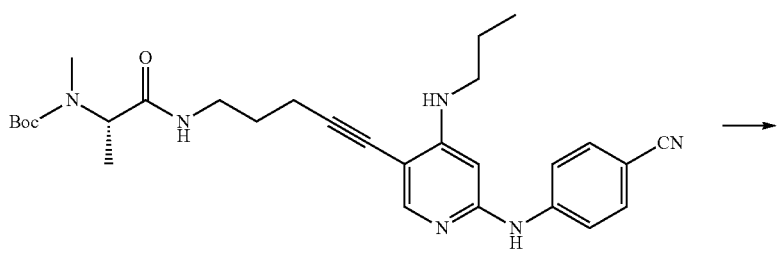
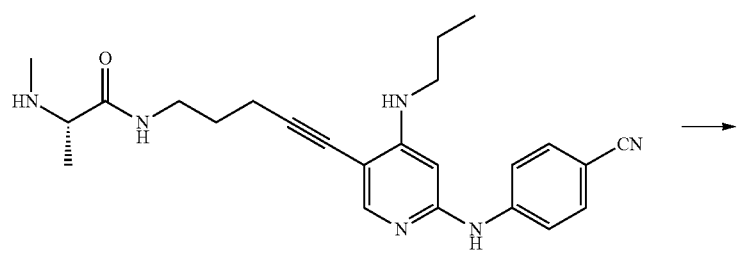
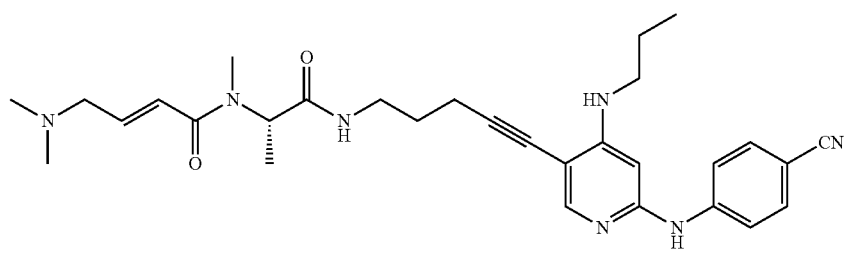
(18-1)
732

In the same manner as that of Example 35, (4) to (7), (S,E)-N-(1-((5-(6-((4-cyanophenyl)amino)-4-(propylamino)pyridin-3-yl)-4-pentyn-1-yl)amino)-1-oxopropan-2-yl)-4-(dimethylamino)-N-methyl-2-butenamide (18-1) was obtained from tert-butyl (2-((4-cyanophenyl)amino)-5-(5-(1,3-dioxoisoindolin-2-yl)-1-pentyn-1-yl)pyridin-4-yl)(propyl)carbamate (S12).

Example 64

1

[Formula 337]

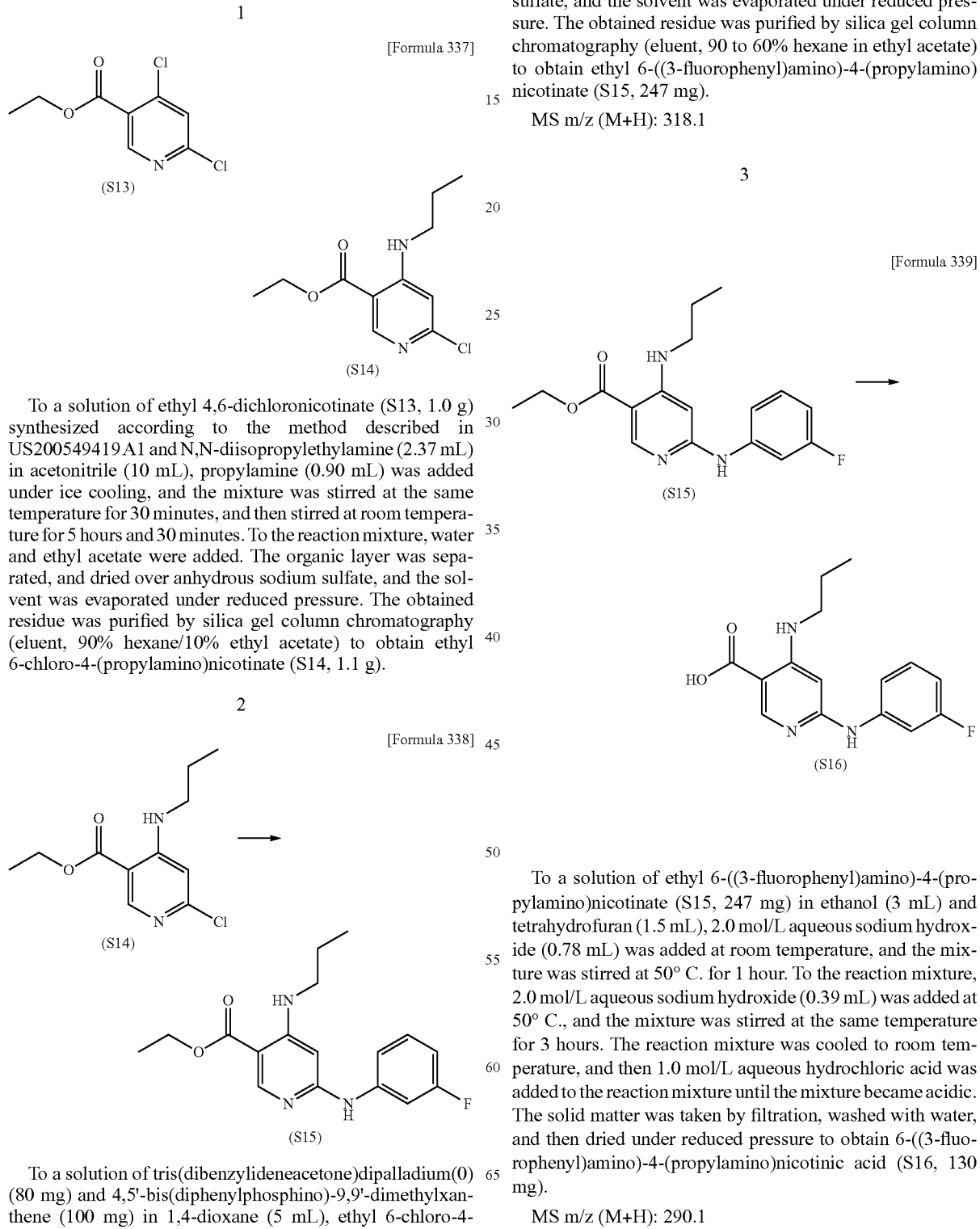

To a solution of ethyl 4,6-dichloronicotinate (S13, 1.0 g) synthesized according to the method described in US200549419A1 and N,N-diisopropylethylamine (2.37 mL) in acetonitrile (10 mL), propylamine (0.90 mL) was added under ice cooling, and the mixture was stirred at the same temperature for 30 minutes, and then stirred at room temperature for 5 hours and 30 minutes. To the reaction mixture, water and ethyl acetate were added. The organic layer was separated, and dried over anhydrous sodium sulfate, and the solvent was evaporated under reduced pressure. The obtained residue was purified by silica gel column chromatography (eluent, 90% hexane/10% ethyl acetate) to obtain ethyl 6-chloro-4-(propylamino)nicotinate (S14, 1.1 g).

2

[Formula 338]

To a solution of tris(dibenzylideneacetone)dipalladium(0) (80 mg) and 4,5'-bis(diphenylphosphino)-9,9'-dimethylxanthene (100 mg) in 1,4-dioxane (5 mL), ethyl 6-chloro-4-(propylamino)nicotinate (S14, 210 mg), 3-fluoroaniline (193 mg) and cesium carbonate (565 mg) were added at room temperature, and the mixture was stirred at 80 to 90° C. for 5 hours. The reaction mixture was cooled to room temperature, and then saturated aqueous sodium hydrogencarbonate and ethyl acetate were added to the reaction mixture. The insoluble matter was removed by filtration through Florisil. The organic layer was separated, washed with saturated aqueous sodium chloride, and then dried over anhydrous sodium sulfate, and the solvent was evaporated under reduced pressure. The obtained residue was purified by silica gel column chromatography (eluent, 90 to 60% hexane in ethyl acetate) to obtain ethyl 6-((3-fluorophenyl)amino)-4-(propylamino)nicotinate (S15, 247 mg).

MS m/z (M+H): 318.1

3

[Formula 339]

To a solution of ethyl 6-((3-fluorophenyl)amino)-4-(propylamino)nicotinate (S15, 247 mg) in ethanol (3 mL) and tetrahydrofuran (1.5 mL), 2.0 mol/L aqueous sodium hydroxide (0.78 mL) was added at room temperature, and the mixture was stirred at 50° C. for 1 hour. To the reaction mixture, 2.0 mol/L aqueous sodium hydroxide (0.39 mL) was added at 50° C., and the mixture was stirred at the same temperature for 3 hours. The reaction mixture was cooled to room temperature, and then 1.0 mol/L aqueous hydrochloric acid was added to the reaction mixture until the mixture became acidic. The solid matter was taken by filtration, washed with water, and then dried under reduced pressure to obtain 6-((3-fluorophenyl)amino)-4-(propylamino)nicotinic acid (S16, 130 mg).

MS m/z (M+H): 290.1

4

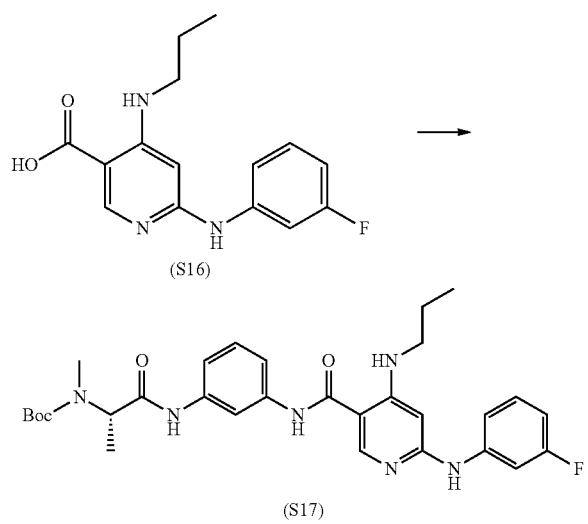

[Formula 340]

To a solution of 6-((3-fluorophenyl)amino)-4-(propylamino)nicotinic acid (S16, 87 mg), (S)-tert-butyl (1-((3-aminophenyl)amino)-1-oxopropan-2-yl)(methyl)carbamate (B9, 115 mg), 1-ethyl-3-(3-dimethylaminopropyl)carbodiimide hydrochloride (115 mg) and 1-hydroxybenzotriazole monohydrate (81 mg) in N,N-dimethylformamide (2 mL), N,N-diisopropylethylamine (157 μL) was added at room temperature, and the mixture was stirred at 40° C. for 15 hours. The reaction mixture was cooled to room temperature, and then saturated aqueous sodium hydrogencarbonate was added to the reaction mixture. The solid matter was taken by filtration, washed with water, and then purified by silica gel column chromatography (eluent, 75 to 35% hexane in ethyl acetate) to obtain (S)-tert-butyl (1-((3-(6-((3-fluorophenyl)amino)-4-(propylamino)nicotinamido)phenyl)amino)-1-oxopropan-2-yl)(methyl)carbamate (S17, 123 mg).

MS m/z (M+H): 565.3

5

[Formula 341]

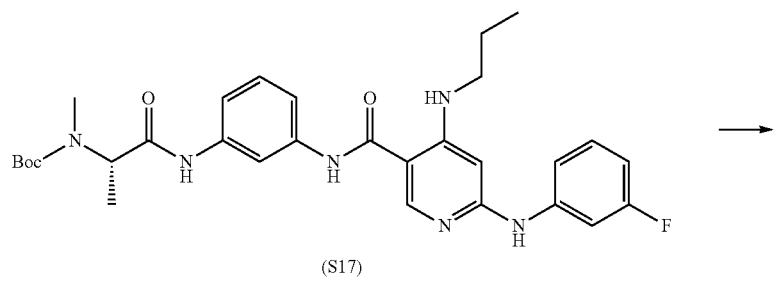

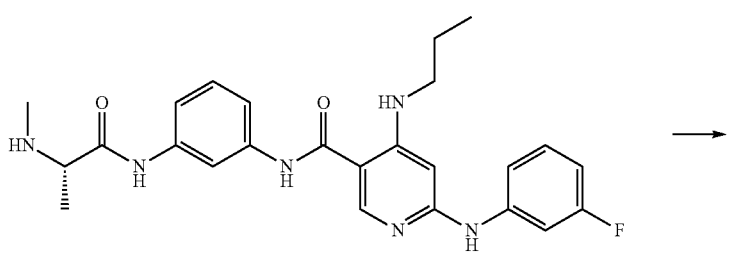

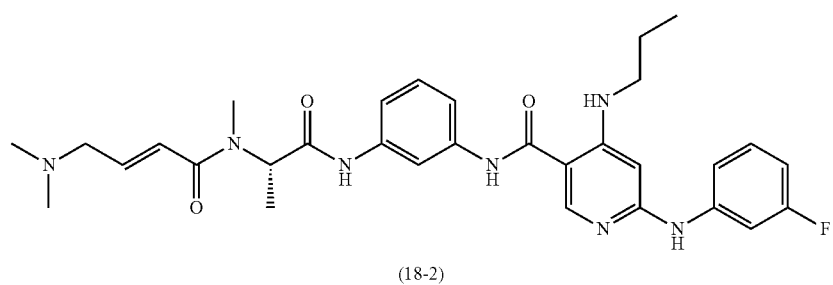

In the same manner as that of Example 35, (6) and (7), (S,E)-N-(3-(2-(4-(dimethylamino)-N-methyl-2-butenamido)propanamido)phenyl)-6-((3-fluorophenyl)amino)-4-(propylamino)nicotinamide (18-2) was obtained from (S)-tert-butyl (1-((3-(6-((3-fluorophenyl)amino)-4-(propylamino)nicotinamido)phenyl)amino)-1-oxopropan-2-yl)(methyl)carbamate (S17).

$^1$H-NMR (CDCl$_3$) δ: 8.73 (1H, s), 8.31 (1H, s), 8.13 (1H, brs), 7.82 (1H, s), 7.72 (1H, s), 7.38-7.16 (5H, m), 7.06-6.94 (2H, m), 6.79-6.72 (1H, m), 6.66 (1H, s), 6.43 (1H, d, J=15.2 Hz), 6.03 (1H, s), 5.31 (1H, q, J=7.3 Hz), 3.14-3.04 (4H, m), 3.02 (3H, s), 2.27 (6H, s), 1.72-1.64 (2H, m), 1.43 (3H, d, J=6.6 Hz), 1.00 (3H, t, J=7.3 Hz)

Example 65

1

[Formula 342]

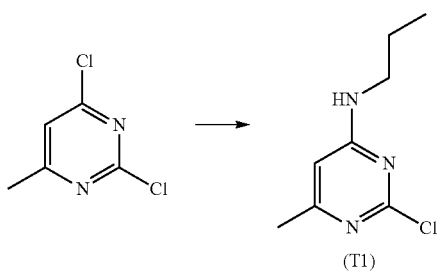

To a solution of 2,4-dichloro-6-methylpyrimidine (1.00 g) in dimethyl sulfoxide (10 mL), N,N-diisopropylethylamine (1.07 mL) and propylamine (0.51 mL) were added at room temperature, and the mixture was stirred at the same temperature for 2 hours. To the reaction mixture, N,N-diisopropylethylamine (1.07 mL) and propylamine (0.51 mL) were added at room temperature, and the mixture was stirred at the same temperature for 2 hours. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by silica gel column chromatography (eluent, 90 to 70% hexane in ethyl acetate) to obtain 2-chloro-6-methyl-N-propylpyrimidin-4-amine (T1, 776 mg).

MS m/z (M+H): 186.1, 188.1

2

[Formula 343]

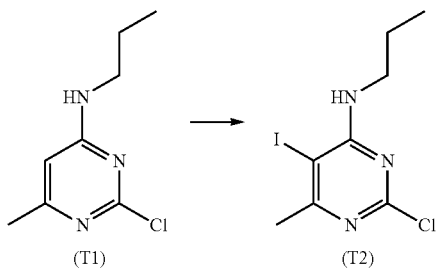

To a suspension of 2-chloro-6-methyl-N-propylpyrimidin-4-amine (T1, 200 mg) in acetic acid (4 mL), N-iodosuccinimide (485 mg) was added at room temperature, and the mixture was stirred at 80° C. for 30 minutes. The reaction mixture was cooled to room temperature, and then saturated aqueous sodium hydrogensulfite, saturated aqueous sodium hydrogencarbonate and ethyl acetate were added to the reaction mixture. The organic layer was separated, washed with saturated aqueous sodium chloride, and then dried over anhydrous sodium sulfate, and the solvent was evaporated under reduced pressure. The obtained residue was purified by silica gel column chromatography (eluent, 90-75% hexane in ethyl acetate) to obtain 2-chloro-5-iodo-6-methyl-N-propylpyrimidin-4-amine (T2, 252 mg).

MS m/z (M+H): 312.0, 314.0

3

[Formula 344]

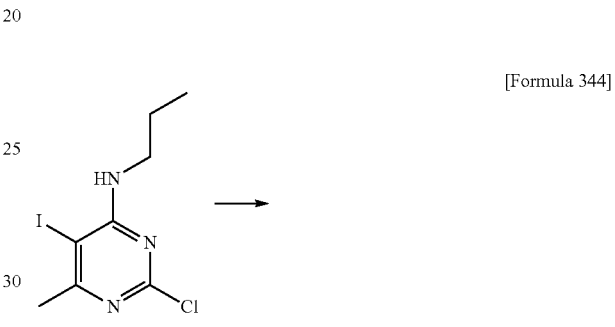

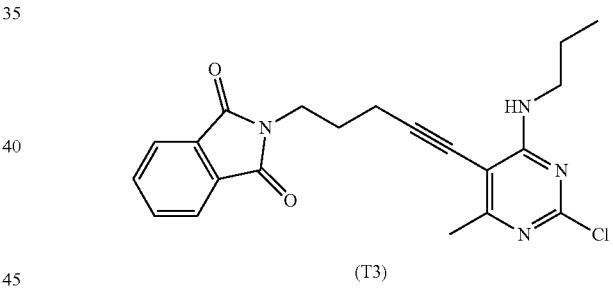

To a solution of 2-chloro-5-iodo-6-methyl-N-propylpyrimidin-4-amine (T2, 150 mg) in N,N-dimethylformamide (3 mL), N-(4-pentynyl)phthalimide (133 mg), bis(triphenylphosphine)palladium(II) dichloride (34 mg), copper(I) iodide (18 mg) and triethylamine (334 μL) were added at room temperature, and the mixture was stirred at 45° C. for 1 hour under a nitrogen atmosphere. The reaction mixture was cooled to room temperature, and then saturated aqueous ammonium chloride and ethyl acetate were added to the reaction mixture. The organic layer was separated, and the aqueous layer was extracted with ethyl acetate. The organic layer and the extract were combined, washed with saturated aqueous sodium chloride, and then dried over anhydrous sodium sulfate, and the solvent was evaporated under reduced pressure. The obtained residue was purified by silica gel column chromatography (eluent, 90 to 70% hexane in ethyl acetate) to obtain 2-(5-(2-chloro-4-methyl-6-(propylamino)pyrimidin-5-yl)-4-pentyn-1-yl)isoindoline-1,3-dione (T3, 131 mg).

MS m/z (M+H): 397.2, 399.2

4

[Formula 345]

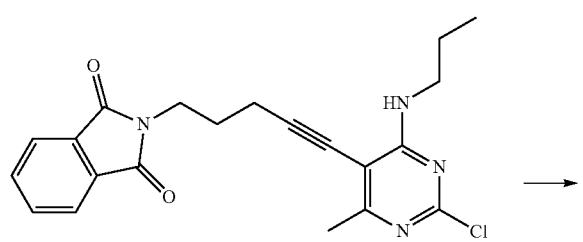

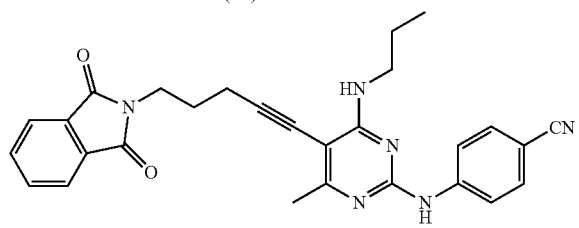

To a solution of 2-(5-(2-chloro-4-methyl-6-(propylamino)pyrimidin-5-yl)-4-pentyn-1-yl)isoindoline-1,3-dione (T3, 65 mg) in 1,4-dioxane (3 mL), 4-aminobenzonitrile (29 mg), cesium carbonate (133 mg), tris(dibenzylideneacetone)dipalladium(0) (30 mg) and 4,5'-bis(diphenylphosphino)-9,9'-dimethylxanthene (38 mg) were added at room temperature, the reaction vessel was sealed, and then by using a microwave reaction system, the mixture was stirred at 160° C. for 20 minutes. The reaction mixture was cooled to room temperature, and then ethyl acetate was added to the reaction mixture. The insoluble matter was removed by filtration through Cerite, and then the solvent was evaporated under reduced pressure. The obtained residue was purified by silica gel column chromatography (eluent, 90 to 50% hexane in ethyl acetate) to obtain 4-((5-(5-(1,3-dioxoisoindolin-2-yl)-1-pentyn-1-yl)-4-methyl-6-(propylamino)pyrimidin-2-yl)amino)benzonitrile (T4, 72 mg) as pale yellow solid.

MS m/z (M+H): 479.3

5

[Formula 346]

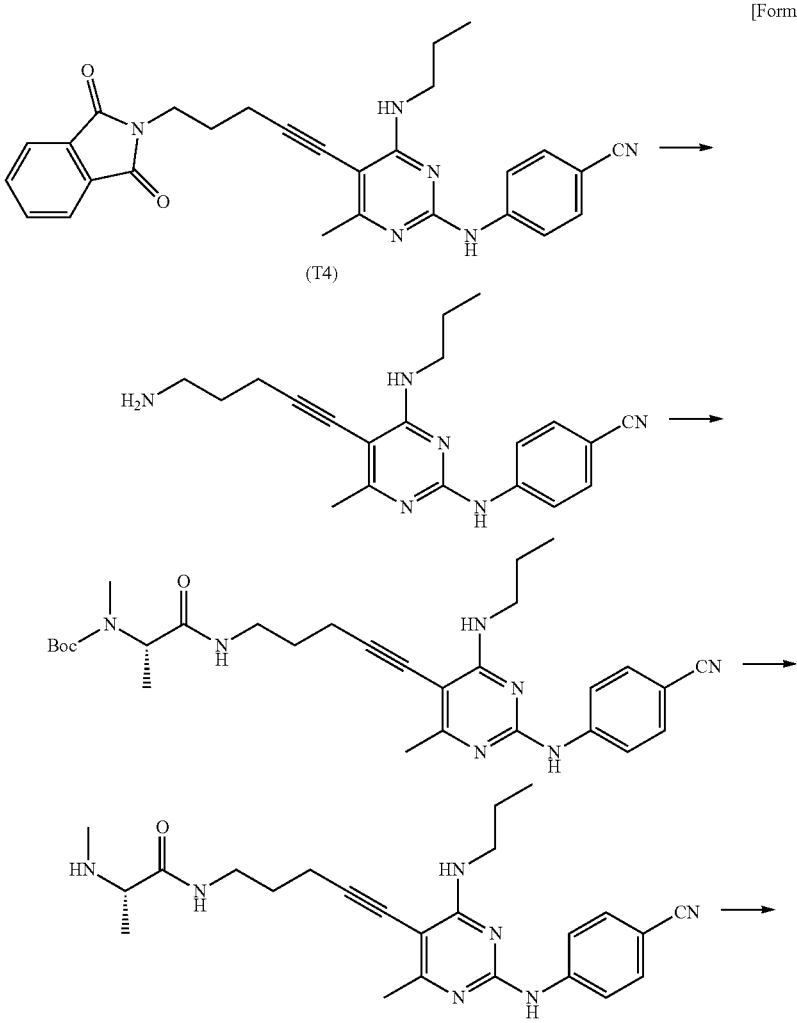

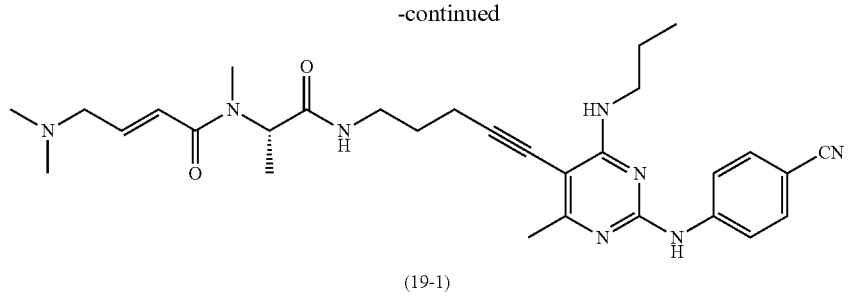

(19-1)

By using 4-((5-(5-(1,3-dioxoisoindolin-2-yl)-1-pentyn-1-yl)-4-methyl-6-(propylamino)pyrimidin-2-yl)amino)benzonitrile (T4), (S,E)-N-(1-((5-(2-((4-cyanophenyl)amino)-4-methyl-6-(propylamino)pyrimidin-5-yl)-4-pentyn-1-yl)amino)-1-oxopropan-2-yl)-4-(dimethylamino)-N-methyl-2-butenamide (19-1) was obtained in the same manner as that of Example 35, (4) to (7).

¹H-NMR (CDCl₃) δ: 7.77 (2H, d, J=8.8 Hz), 7.55 (2H, d, J=8.8 Hz), 7.21 (1H, s), 6.94 (1H, dt, J=15.2, 5.9 Hz), 6.60-6.50 (1H, m), 6.43 (1H, d, J=15.2 Hz), 6.32-6.22 (1H, m), 5.19 (1H, q, J=7.0 Hz), 3.54-3.39 (4H, m), 3.14-3.07 (2H, m), 3.00 (3H, s), 2.49 (2H, t, J=6.6 Hz), 2.37 (3H, s), 2.27 (6H, s), 1.82-1.62 (4H, m), 1.36 (3H, d, J=6.9 Hz), 1.00 (3H, t, J=7.4 Hz)

6

In the same manner as that of Example 65, (1) to (5), Compounds (19-2) to (19-5) were obtained.

TABLE 217

| Compound No. | Structure | Physicochemical data |
|---|---|---|
| 19-2 | 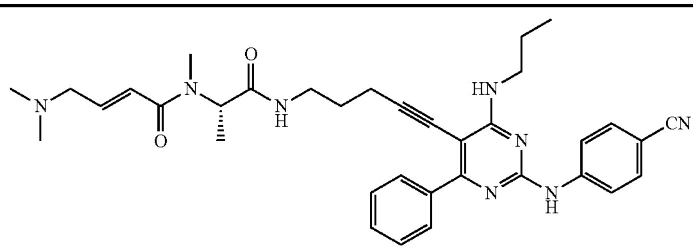 | ¹H-NMR (CDCl₃) δ: 7.98-7.85 (2H, m), 7.80 (2H, d, J = 8.9 Hz), 7.56 (2H, d, J = 8.9 Hz), 7.48-7.33 (3H, m), 7.32 (1H, s), 6.94 (1H, dt, J = 15.2, 5.9 Hz), 6.54-6.34 (2H, m), 6.42 (1H, d, J = 15.2 Hz), 5.17 (1H, q, J = 7.0 Hz), 3.59-3.49 (2H, m), 3.42-3.28 (2H, m), 3.10 (2H, dd, J = 5.9, 1.3 Hz), 2.99 (3H, s), 2.41 (2H, t, J = 6.6 Hz), 2.27 (6H, s), 1.87-1.62 (4H, m), 1.36 (3H, d, J = 7.3 Hz), 1.03 (3H, t, J = 7.4 Hz) |
| 19-3 | 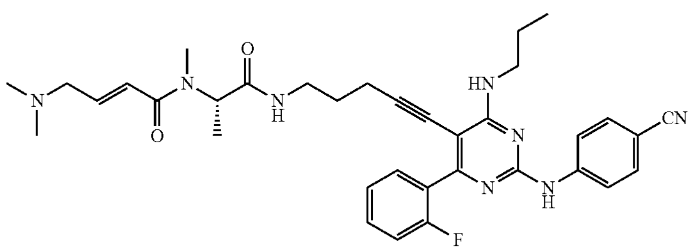 [SMILES: CCCNc1nc(Nc2ccc(C#N)cc2)nc(-c2ccccc2F)c1C#CCCCNC(=O)[C@H](C)N(C)C(=O)/C=C/CN(C)C] | ¹H-NMR (CDCl₃) δ: 7.78 (2H, d, J = 8.6 Hz), 7.57-7.48 (1H, m), 7.56 (2H, d, J = 8.6 Hz), 7.45-7.35 (1H, m), 7.33-7.08 (3H, m), 6.94 (1H, dt, J = 15.2, 5.9 Hz), 6.50-6.36 (3H, m), 5.16 (1H, q, J = 7.0 Hz), 3.59-3.49 (2H, m), 3.30-3.22 (2H, m), 3.13-3.08 (2H, m), 2.98 (3H, s), 2.36-2.28 (2H, m), 2.27 (6H, s), 1.83-1.54 (4H, m), 1.35 (3H, d, J = 6.9 Hz), 1.03 (3H, t, J = 7.4 Hz) |
| 19-4 | 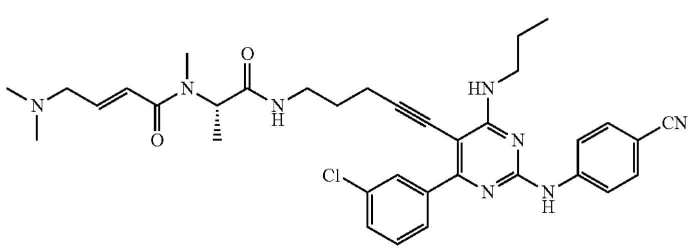 [SMILES: CCCNc1nc(Nc2ccc(C#N)cc2)nc(-c2cccc(Cl)c2)c1C#CCCCNC(=O)[C@H](C)N(C)C(=O)/C=C/CN(C)C] | MS m/z (M + H): 641.4, 643.4 |
| 19-5 | 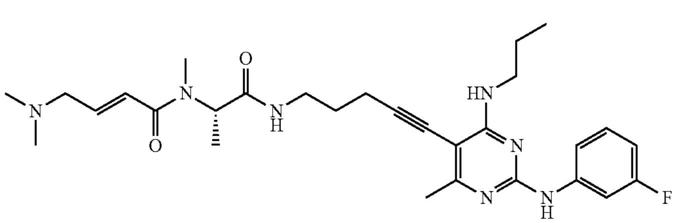 [SMILES: CCCNc1nc(Nc2cccc(F)c2)nc(C)c1C#CCCCNC(=O)[C@H](C)N(C)C(=O)/C=C/CN(C)C] | ¹H-NMR (CDCl₃) δ: 7.86 (1H, dt, J = 12.2, 2.3 Hz), 7.24-7.15 (1H, m), 7.10-7.04 (1H, m), 7.02-6.88 (2H, m), 6.70-6.60 (1H, m), 6.60-6.47 (1H, m), 6.42 (1H, d, J = 15.2 Hz), 6.22-6.07 (1H, m), 5.24-5.12 (1H, m), 3.55-3.37 (4H, m), 3.13-3.08 (2H, m), 2.99 (3H, s), 2.53-2.45 (2H, m), 2.36 (3H, s), 2.27 (6H, s), 1.80-1.64 (4H, m), 1.36 (3H, d, J = 6.9 Hz), 1.00 (3H, t, J = 7.4 Hz) |

Example 66

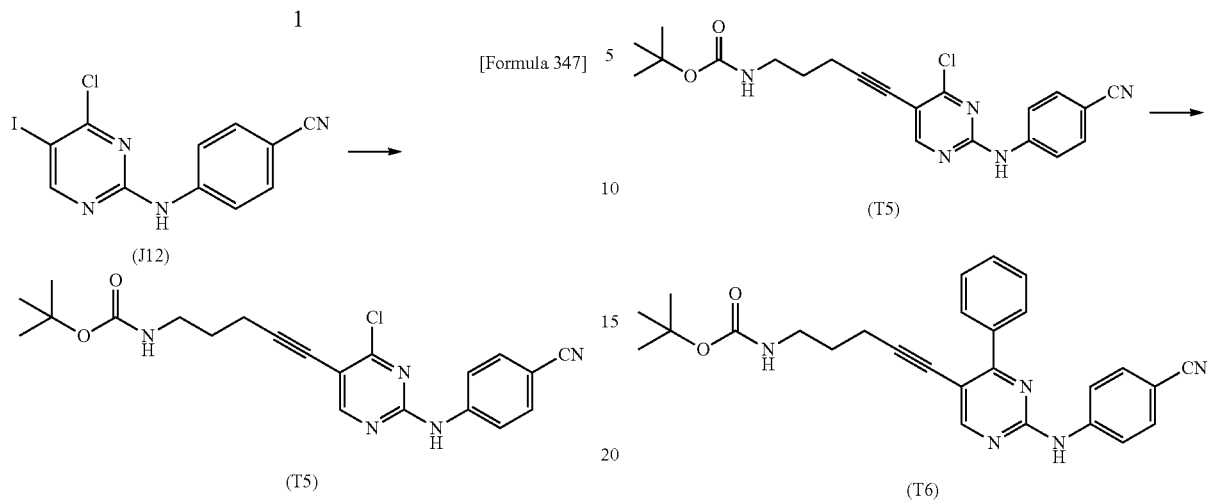

To a solution of 4-((4-chloro-5-iodopyrimidin-2-yl)amino)benzonitrile (J12, 100 mg) and tert-butyl(4-pentynyl)carbamate (77 mg) in N,N-dimethylformamide (3 mL), bis(triphenylphosphine)palladium(II) dichloride (20 mg), triethylamine (195 μL) and copper(I) iodide (11 mg) were added at room temperature, and the mixture was stirred at the same temperature for 1 hour. To the reaction mixture, saturated aqueous ammonium chloride and ethyl acetate were added. The organic layer was separated, washed with saturated aqueous sodium chloride, and then dried over anhydrous sodium sulfate, and the solvent was evaporated under reduced pressure. The obtained solid matter was washed with a mixture of hexane and ethyl acetate (5:1), and then air-dried to obtain tert-butyl (5-(4-chloro-2-((4-cyanophenyl)amino)pyrimidin-5-yl)-4-pentyn-1-yl)carbamate (T5, 73 mg) as pale yellow solid.

MS m/z (M+H): 412.4, 414.2

To a solution of tert-butyl (5-(4-chloro-2-((4-cyanophenyl)amino)pyrimidin-5-yl)-4-pentyn-1-yl)carbamate (T5, 30 mg) in 1,4-dioxane (146 μL), 1.0 mol/L aqueous sodium carbonate (146 μL), phenylboronic acid (10 mg), triphenylphosphine (2 mg) and palladium(II) acetate (1 mg) were added at room temperature, and the mixture was stirred at 60° C. for 3 hours. The reaction mixture was cooled to room temperature, and then water and ethyl acetate were added to the reaction mixture. The organic layer was separated, washed with saturated aqueous sodium chloride, and then dried over anhydrous sodium sulfate, and the solvent was evaporated under reduced pressure. The obtained residue was purified by silica gel column chromatography (eluent, 90 to 55% hexane in ethyl acetate) to obtain tert-butyl (5-(2-(4-cyanophenyl)amino)-4-phenylpyrimidin-5-yl)-4-pentyn-1-yl)carbamate (T6, 31 mg).

MS m/z (M+H): 454.3

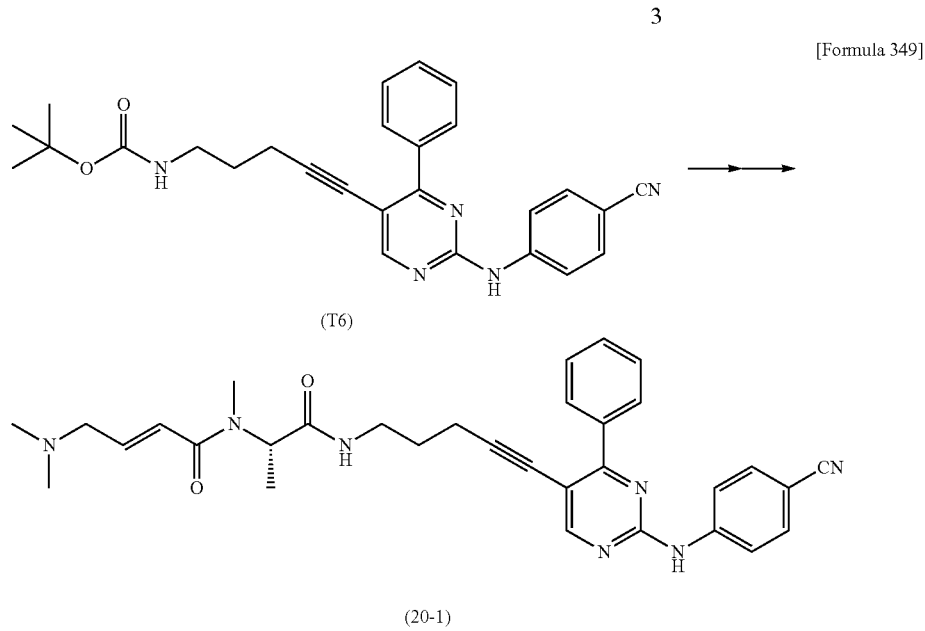

In the same manner as that of Example 54, (4) to (6) and Example 35, (7), (S,E)-N-(1-((5-(2-((4-cyanophenyl)amino)-4-phenylpyrimidin-5-yl)-4-pentyn-1-yl)amino)-1-oxopropan-2-yl)-4-(dimethylamino)-N-methyl-2-butenamide (20-1) was obtained from tert-butyl (5-(2-((4-cyanophenyl)amino)-4-phenylpyrimidin-5-yl)-4-pentyn-1-yl)carbamate (T6).

¹H-NMR (CDCl₃) δ: 8.57 (1H, s), 8.12-8.05 (2H, m), 7.83 (2H, d, J=10.9 Hz), 7.62 (2H, d, J=10.9 Hz), 7.55-7.45 (4H, m), 6.93 (1H, dt, J=15.2, 5.9 Hz), 6.55-6.45 (1H, m), 6.42 (1H, d, J=15.2 Hz), 5.16 (1H, q, J=6.9 Hz), 3.40-3.17 (2H, m), 3.13-3.06 (2H, m), 2.98 (3H, s), 2.41 (2H, t, J=6.9 Hz), 2.26 (6H, s), 1.82-1.68 (2H, m), 1.35 (3H, d, J=6.9 Hz)

Example 67

1

[Formula 350]

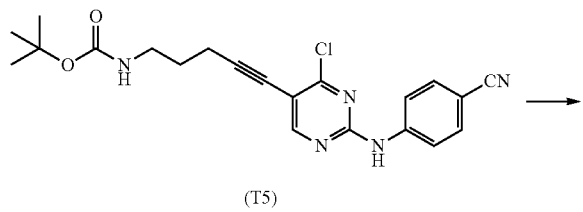

(T5)

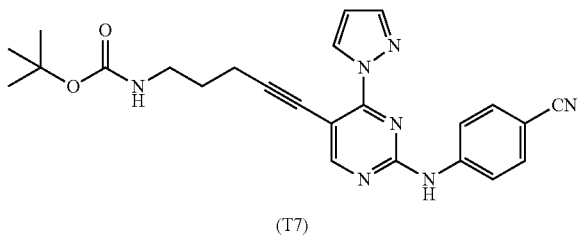

(T7)

To a solution of tert-butyl (5-(4-chloro-2-((4-cyanophenyl)amino)pyrimidin-5-yl)-4-pentyn-1-yl)carbamate (T5, 30 mg) and pyrazole (7 mg) in N-methylpyrrolidone (1 mL), cesium carbonate (71 mg) was added at room temperature, and the mixture was stirred at 60° C. for 3 hours. The reaction mixture was cooled to room temperature, and then water and ethyl acetate were added to the reaction mixture. The organic layer was separated, washed with saturated aqueous sodium chloride, and then dried over anhydrous sodium sulfate, and the solvent was evaporated under reduced pressure. The obtained residue was purified by silica gel column chromatography (eluent, 90 to 40% hexane in ethyl acetate) to obtain tert-butyl (5-(2-((4-cyanophenyl)amino)-4-(1H-pyrazol-1-yl)pyrimidin-5-yl)-4-pentyn-1-yl)carbamate (T7, 20 mg).

MS m/z (M+H): 444.3

2

[Formula 351]

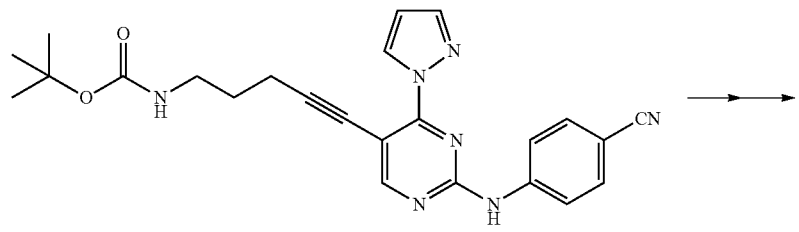

(T7)

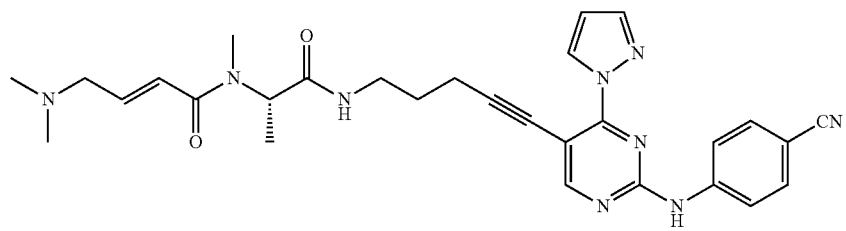

(20-2)

In the same manner as that of Example 54, (4) to (6) and Example 35, (7), (S,E)-N-(1-((5-(2-((4-cyanophenyl)amino)-4-(1H-pyrazol-1-yl)pyrimidin-5-yl)-4-pentyn-1-yl)amino)-1-oxopropan-2-yl)-4-(dimethylamino)-N-methyl-2-butenamide (20-2) was obtained from tert-butyl (5-(2-((4-cyanophenyl)amino)-4-(1H-pyrazol-1-yl)pyrimidin-5-yl)-4-pentyn-1-yl)carbamate (T7).

$^1$H-NMR (CDCl$_3$) δ: 8.67-8.60 (2H, m), 7.88-7.83 (1H, m), 7.78 (2H, d, J=8.9 Hz), 7.65 (2H, d, J=8.9 Hz), 7.62-7.59 (1H, m), 6.89 (1H, dt, J=15.2, 5.9 Hz), 6.80-6.67 (1H, m), 6.54 (1H, dd, J=2.6, 1.0 Hz), 6.38 (1H, d, J=15.2 Hz), 5.17 (1H, q, J=7.3 Hz), 3.54-3.32 (2H, m), 3.07 (2H, d, J=5.9 Hz), 2.99 (3H, s), 2.52 (2H, t, J=6.9 Hz), 2.25 (6H, s), 1.93-1.72 (2H, m), 1.34 (3H, d, J=7.3 Hz)

Example 68

By using tert-butyl (5-(4-chloro-2-((4-cyanophenyl)amino)pyrimidin-5-yl)-4-pentyn-1-yl)carbamate (T5), Compounds (20-3) and (20-4) were obtained in the same manner as that of Example 67.

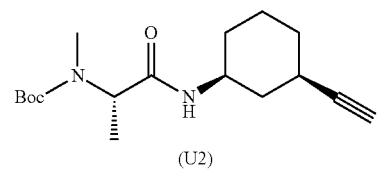

(U2)

To tert-butyl ((1S,3R)-3-ethynylcyclohexyl)carbamate (P0, 1.4 g), a 4.0 mol/L solution of hydrochloric acid in 1,4-dioxane (30 mL) was added at room temperature, and the mixture was stirred at room temperature for 1 hour. The solvent was evaporated under reduced pressure to obtain (1S,3R)-3-ethynylcyclohexaneamine (U1) hydrochloride as white solid.

TABLE 218

| Compound No. | Structure | Physicochemical data |
|---|---|---|
| 20-3 | 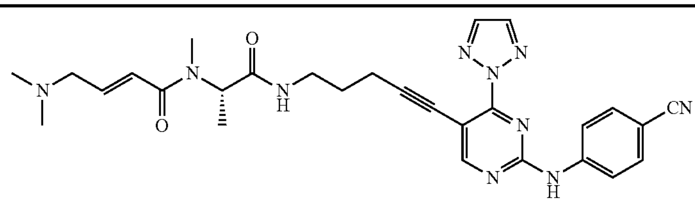 | $^1$H-NMR (CDCl$_3$) δ: 8.73 (1H, s), 8.03 (2H, s), 7.84 (2H, d, J = 8.9 Hz), 7.70-7.62 (1H, m), 7.65 (2H, d, J = 8.9 Hz), 6.90 (1H, dt, J = 15.2, 5.9 Hz), 6.68-6.57 (1H, m), 6.39 (1H, d, J = 15.2 Hz), 5.17 (1H, q, J = 6.9 Hz), 3.54-3.33 (2H, m), 3.08 (2H, d, J = 6.9 Hz), 2.99 (3H, s), 2.50 (2H, t, J = 6.9 Hz), 2.25 (6H, s), 1.88-1.75 (2H, m), 1.35 (3H, d, J = 6.9 Hz) |
| 20-4 | 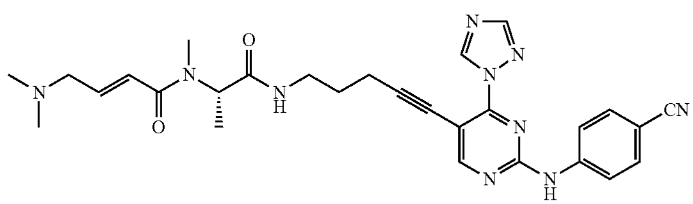 [SMILES: C[C@@H](C(=O)NCCCC#Cc1cnc(Nc2ccc(C#N)cc2)nc1-n1cncn1)N(C)C(=O)/C=C/CN(C)C] | $^1$H-NMR (CDCl$_3$) δ: 9.32 (1H, s), 8.71 (1H, s), 8.21 (1H, s), 7.79 (2H, d, J = 8.6 Hz), 7.69-7.60 (3H, m), 7.00-6.83 (1H, m), 6.70-6.60 (1H, m), 6.40 (1H, d, J = 15.2 Hz), 5.16 (1H, q, J = 6.9 Hz), 3.51-3.28 (2H, m), 3.12-3.06 (2H, m), 2.99 (3H, s), 2.52 (2H, t, J = 6.9 Hz), 2.26 (6H, s), 1.90-1.75 (2H, m), 1.35 (3H, d, J = 6.9 Hz) |

Example 69

1

[Formula 352]

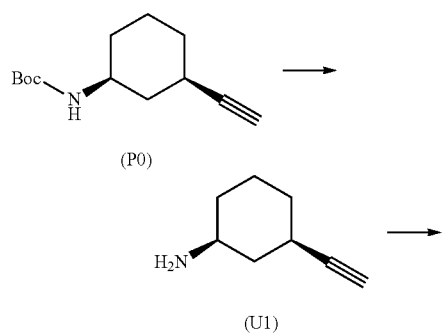

To (1S,3R)-3-ethynylcyclohexaneamine (U1) hydrochloride obtained above, N-Boc-N-methyl-L-alanine (1.9 g), 1-ethyl-3-(3-dimethylaminopropyl)carbodiimide hydrochloride (1.8 g) and 1-hydroxybenzotriazole monohydrate (1.28 g), N,N-dimethylformamide (16 mL) and N,N-diisopropylethylamine (5.4 mL) were added under ice cooling, and the mixture was stirred at room temperature for 1 hour. To the reaction mixture, saturated aqueous sodium hydrogencarbonate and ethyl acetate were added. The organic layer was separated, and the aqueous layer was extracted twice with ethyl acetate. The organic layer and the extracts were combined, washed successively with saturated aqueous sodium hydrogencarbonate and saturated aqueous sodium chloride, and then dried over anhydrous magnesium sulfate, and the solvent was evaporated under reduced pressure. The obtained residue was purified by silica gel column chromatography (eluent, 88 to 50% hexane in ethyl acetate) to obtain oily tert-butyl ((S)-1-(((1S,3R)-3-ethynylcyclohexyl)amino)-1-oxopropan-2-yl)(methyl)carbamate (U2, 2.0 g).

2

[Formula 353]

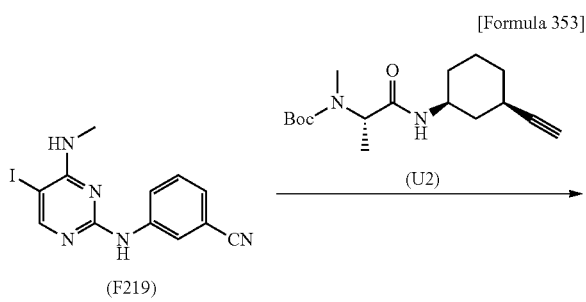

To 3-((5-iodo-4-(methylamino)pyrimidin-2-yl)amino) benzonitrile (F219, 30 mg), tert-butyl ((S)-1-(((1S,3R)-3-ethynylcyclohexyl)amino)-1-oxopropan-2-yl)(methyl)car- bamate (U2, 39.5 mg), bis(triphenylphosphine)palladium(II) dichloride (5.96 mg) and copper(I) iodide (3.24 mg), N,N-dimethylformamide (1 mL) and triethylamine (59 µL) were added at room temperature, and the mixture was stirred at the same temperature for 4 hours. To the reaction mixture, saturated aqueous sodium hydrogencarbonate and ethyl acetate were added. The organic layer was separated, washed successively with saturated aqueous ammonium chloride, water and saturated aqueous sodium chloride, and then dried over anhydrous sodium sulfate, and the solvent was evaporated under reduced pressure. The obtained residue was purified by silica gel column chromatography (eluent, 84 to 25% hexane in ethyl acetate) to obtain tert-butyl ((S)-1-(((1S,3R)-3-((2-((3-cyanophenyl)amino)-4-(methylamino)pyrimidin-5-yl)ethynyl)cyclohexyl)amino)-1-oxopropan-2-yl)(methyl)carbamate (U3, 27.4 mg) as pale yellow solid.

MS m/z (M+H): 532.4

3

[Formula 354]

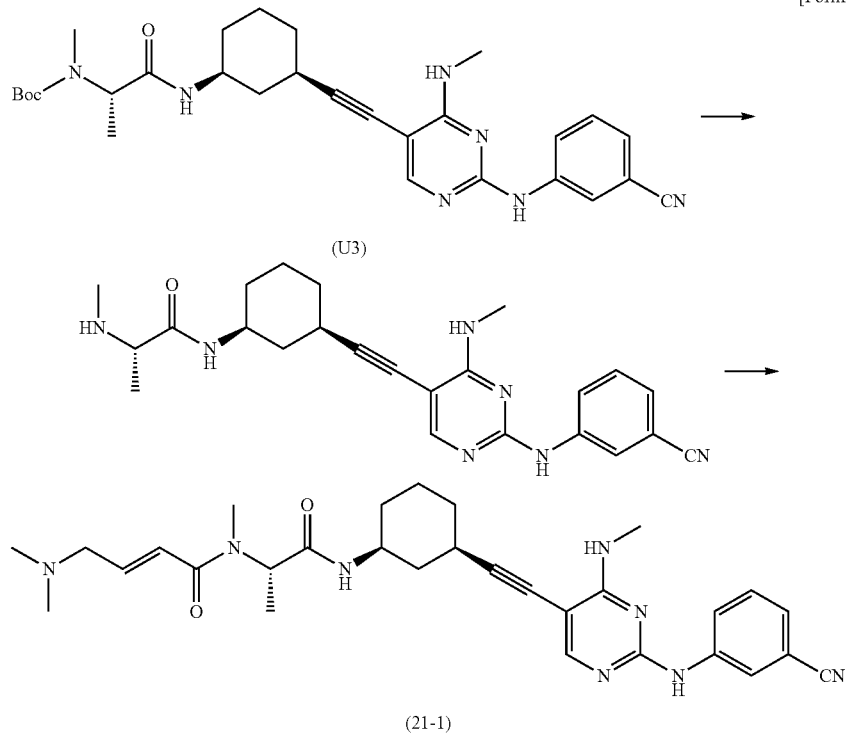

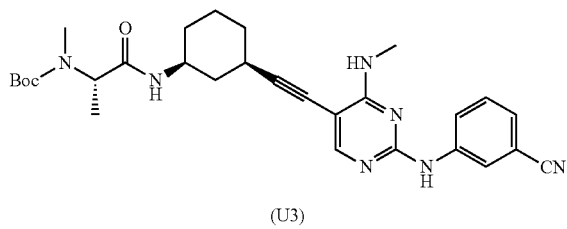

By using tert-butyl ((S)-1-(((1S,3R)-3-((2-((3-cyanophenyl)amino)-4-(methylamino)pyrimidin-5-yl)ethynyl)cyclohexyl)amino)-1-oxopropan-2-yl)(methyl)carbamate (U3), (E)-N—((S)-1-(((1S,3R)-3-((2-((3-cyanophenyl)amino)-4-(methylamino)pyrimidin-5-yl)ethynyl)cyclohexyl)amino)-1-oxopropan-2-yl)-4-(dimethylamino)-N-methyl-2-butenamide (21-1) was obtained in the same manner as that of Example 35, (6) and (7).

$^1$H-NMR (CDCl$_3$) δ: 8.33 (1H, s), 7.97 (1H, s), 7.66-7.61 (1H, m), 7.40-7.32 (2H, m), 7.27-7.21 (1H, m), 6.93 (1H, dt, J=15.2, 5.9 Hz), 6.43 (1H, d, J=15.2 Hz), 6.43-6.35 (1H, m), 5.50-5.43 (1H, m), 5.16 (1H, q, J=7.0 Hz), 3.77-3.68 (1H, m), 3.13 (2H, d, J=5.9 Hz), 3.10 (3H, d, J=4.6 Hz), 2.98 (3H, s), 2.66-2.56 (1H, m), 2.43-2.27 (1H, m), 2.29 (6H, s), 2.07-1.98 (1H, m), 1.88-1.78 (2H, m), 1.44-1.24 (3H, m), 1.34 (3H, d, J=7.0 Hz), 1.14-1.04 (1H, m)

4

In the same manner as that of Example 69, (1), Intermediates (U4) and (U5) were obtained.

TABLE 219

| Compound No. | Structure | Physicochemical data |
|---|---|---|
| U4 | Boc-N(Me)-CH(Me)-C(O)-NH-CH2CH2CH2-C≡CH | — |

TABLE 219-continued

| Compound No. | Structure | Physicochemical data |
|---|---|---|
| U5 | Boc-pyrrolidine-C(O)-NH-CH2CH2-C≡CH | — |

In the same manner as that of Example 69, (2), Intermediates (U6) to (U56) were obtained.

TABLE 220

| Compound No. | Structure | Physicochemical data |
|---|---|---|
| U6 | (structure) | MS m/z (M + H): 529.4 |
| U7 | (structure) | MS m/z (M + H): 534.3 |
| U8 | (structure) | MS m/z (M + H): 525.2 |
| U9 | (structure) | MS m/z (M + H): 549.4 |
| U10 | (structure) | MS m/z (M + H): 549.4 |

TABLE 220-continued

| Compound No. | Structure | Physicochemical data |
|---|---|---|
| U11 | 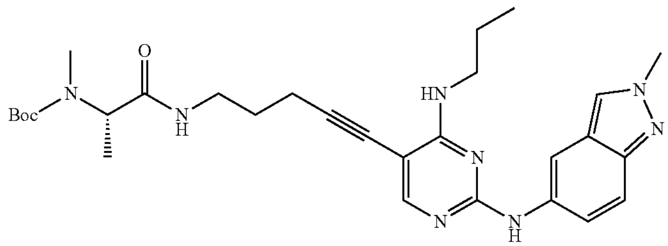 [SMILES: CCCNc1nc(Nc2ccc3nn(C)cc3c2)ncc1C#CCCCNC(=O)[C@H](C)N(C)C(=O)OC(C)(C)C] | MS m/z (M + H): 549.4 |
| U12 | 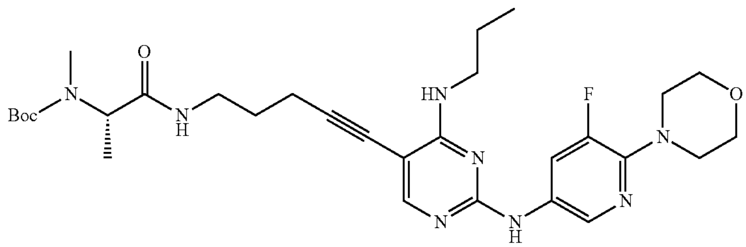 [SMILES: CCCNc1nc(Nc2cnc(N3CCOCC3)c(F)c2)ncc1C#CCCCNC(=O)[C@H](C)N(C)C(=O)OC(C)(C)C] | MS m/z (M + H): 599.5 |

TABLE 221

| Compound No. | Structure | Physicochemical data |
|---|---|---|
| U13 | 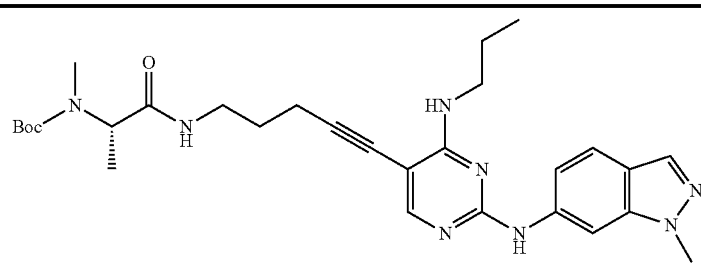 | MS m/z (M + H): 549.4 |
| U14 | 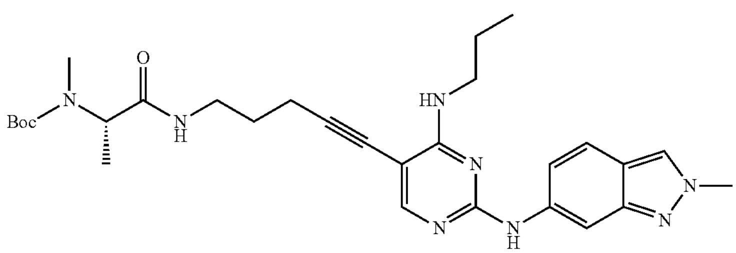 [SMILES: CCCNc1nc(Nc2ccc3cn(C)nc3c2)ncc1C#CCCCNC(=O)[C@H](C)N(C)C(=O)OC(C)(C)C] | MS m/z (M + H): 549.4 |
| U15 | 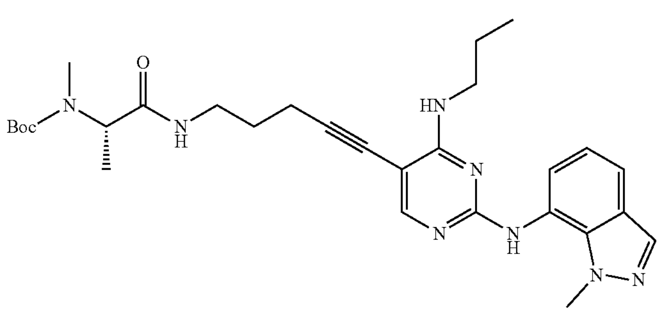 [SMILES: CCCNc1nc(Nc2cccc3cnn(C)c23)ncc1C#CCCCNC(=O)[C@H](C)N(C)C(=O)OC(C)(C)C] | MS m/z (M + H): 549.5 |

TABLE 221-continued

| Compound No. | Structure | Physicochemical data |
|---|---|---|
| U16 | 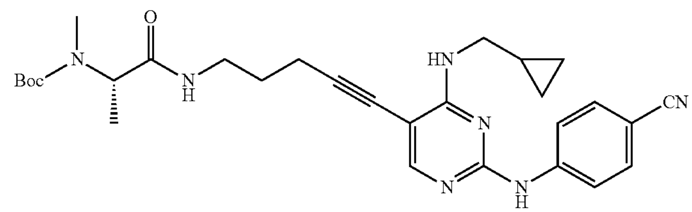 [SMILES: C[C@@H](C(=O)NCCCC#Cc1cnc(Nc2ccc(C#N)cc2)nc1NCC1CC1)N(C)C(=O)OC(C)(C)C] | MS m/z (M + H): 532.4 |
| U17 | 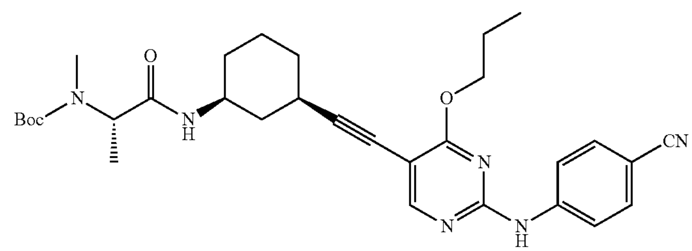 [SMILES: CCCOc1nc(Nc2ccc(C#N)cc2)ncc1C#C[C@@H]1CCC[C@H](NC(=O)[C@H](C)N(C)C(=O)OC(C)(C)C)C1] | MS m/z (M + H): 561.4 |
| U18 | 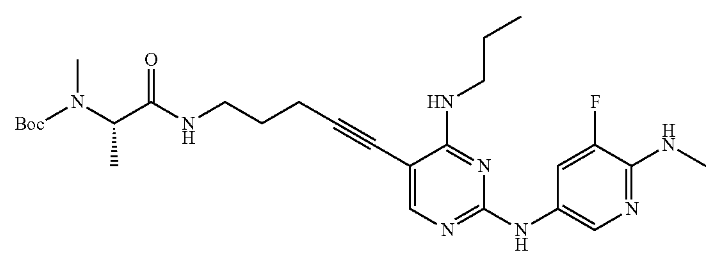 [SMILES: CCCNc1nc(Nc2cnc(NC)c(F)c2)ncc1C#CCCCNC(=O)[C@H](C)N(C)C(=O)OC(C)(C)C] | MS m/z (M + H): 543.4 |
| U19 | 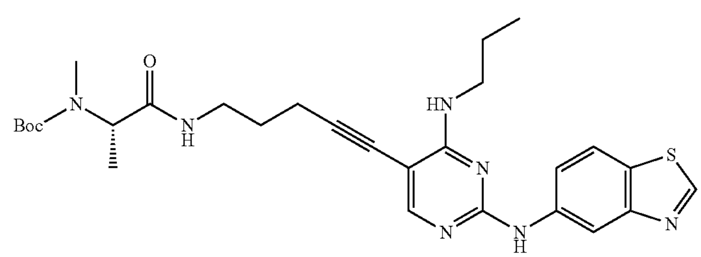 [SMILES: CCCNc1nc(Nc2ccc3scnc3c2)ncc1C#CCCCNC(=O)[C@H](C)N(C)C(=O)OC(C)(C)C] | MS m/z (M + H): 552.4 |
| U20 | 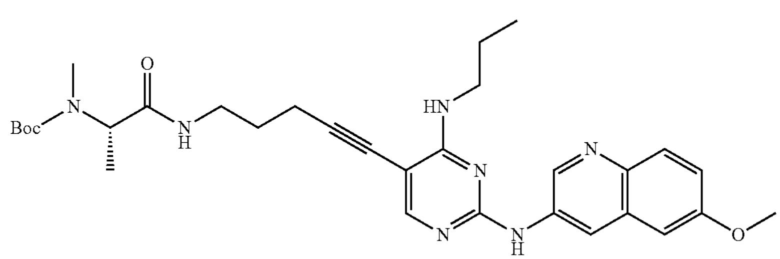 [SMILES: CCCNc1nc(Nc2cnc3ccc(OC)cc3c2)ncc1C#CCCCNC(=O)[C@H](C)N(C)C(=O)OC(C)(C)C] | MS m/z (M + H): 576.4 |
| U21 | 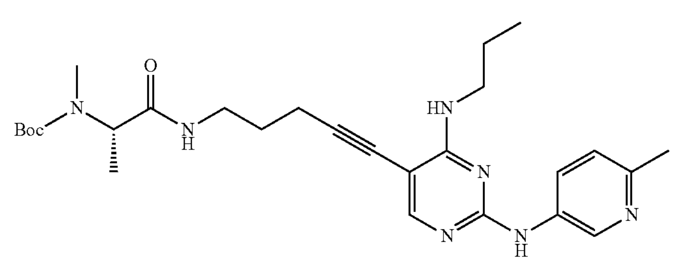 | MS m/z (M + H): 510.4 |

TABLE 222

| Compound No. | Structure | Physicochemical data |
|---|---|---|
| U22 | 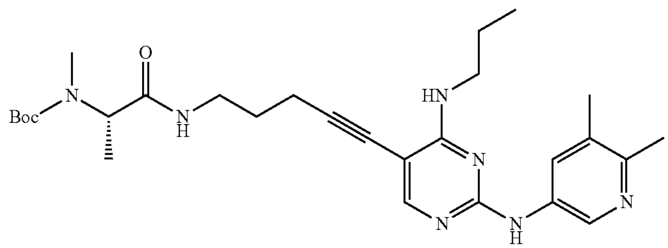 [SMILES: CCCNc1nc(Nc2cnc(C)c(C)c2)ncc1C#CCCCNC(=O)[C@H](C)N(C)C(=O)OC(C)(C)C] | MS m/z (M + H): 524.4 |
| U23 | 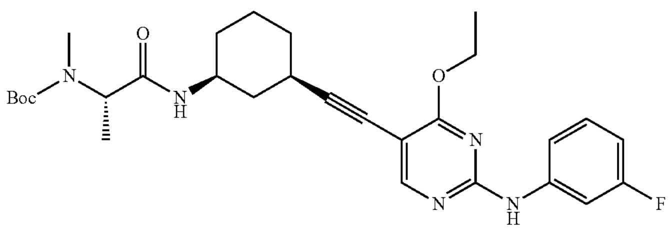 [SMILES: CCOc1nc(Nc2cccc(F)c2)ncc1C#C[C@@H]1CCC[C@H](NC(=O)[C@H](C)N(C)C(=O)OC(C)(C)C)C1] | MS m/z (M + H): 540.4 |
| U24 | 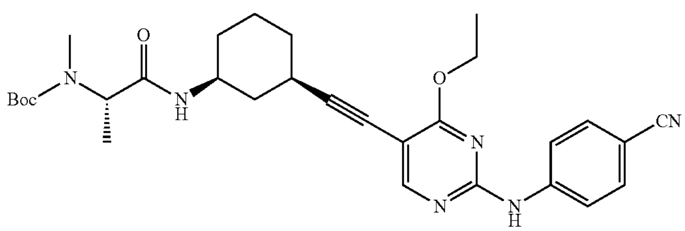 [SMILES: CCOc1nc(Nc2ccc(C#N)cc2)ncc1C#C[C@@H]1CCC[C@H](NC(=O)[C@H](C)N(C)C(=O)OC(C)(C)C)C1] | MS m/z (M + H): 547.4 |
| U25 | 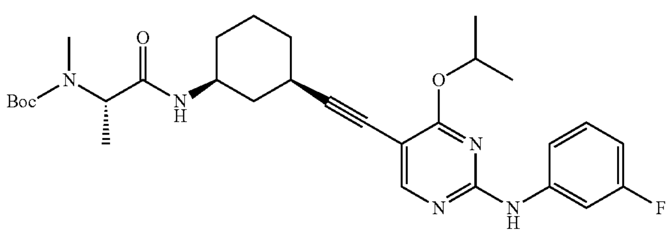 [SMILES: CC(C)Oc1nc(Nc2cccc(F)c2)ncc1C#C[C@@H]1CCC[C@H](NC(=O)[C@H](C)N(C)C(=O)OC(C)(C)C)C1] | MS m/z (M + H): 554.4 |
| U26 | 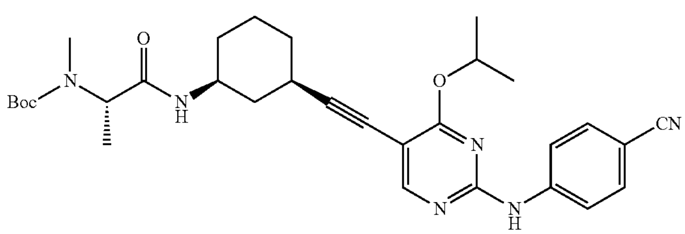 [SMILES: CC(C)Oc1nc(Nc2ccc(C#N)cc2)ncc1C#C[C@@H]1CCC[C@H](NC(=O)[C@H](C)N(C)C(=O)OC(C)(C)C)C1] | MS m/z (M + H): 561.4 |
| U27 | 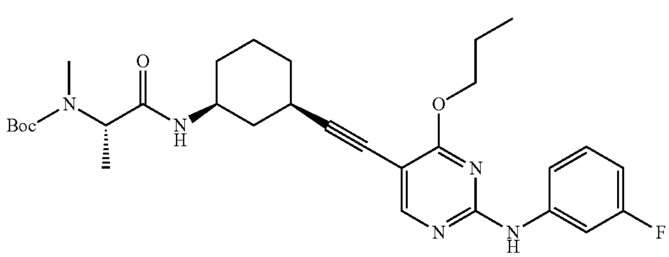 [SMILES: CCCOc1nc(Nc2cccc(F)c2)ncc1C#C[C@@H]1CCC[C@H](NC(=O)[C@H](C)N(C)C(=O)OC(C)(C)C)C1] | MS m/z (M + H): 554.4 |

TABLE 222-continued

| Compound No. | Structure | Physicochemical data |
|---|---|---|
| U28 | 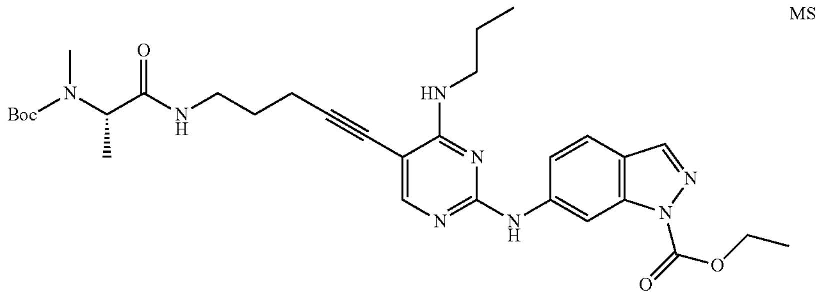 | MS m/z (M + H): 607.4 |
| U29 | 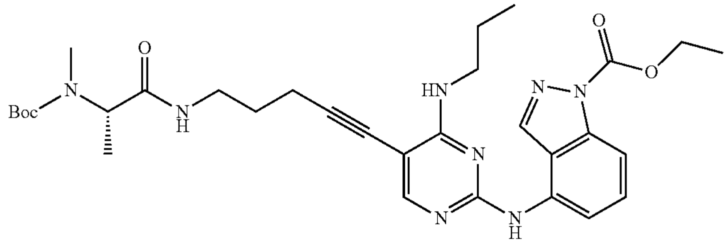 [SMILES: CCCNc1nc(Nc2cccc3c2cnn3C(=O)OCC)ncc1C#CCCCNC(=O)[C@H](C)N(C)C(=O)OC(C)(C)C] | MS m/z (M + H): 607.4 |
| U30 | 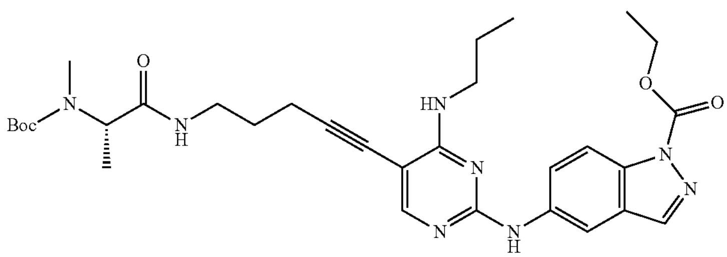 [SMILES: CCCNc1nc(Nc2ccc3c(cnn3C(=O)OCC)c2)ncc1C#CCCCNC(=O)[C@H](C)N(C)C(=O)OC(C)(C)C] | MS m/z (M + H): 607.4 |

TABLE 223

| Compound No. | Structure | Physicochemical data |
|---|---|---|
| U31 | 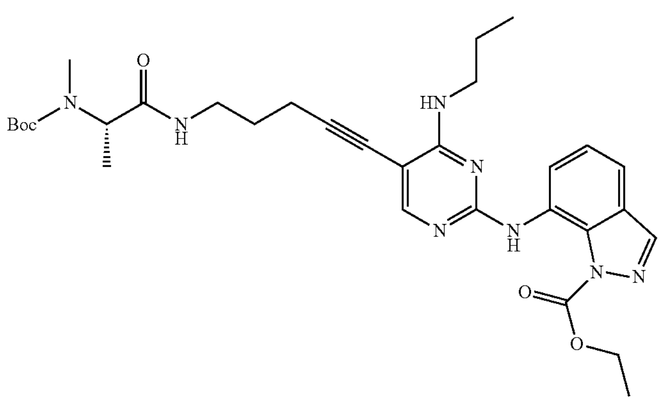 [SMILES: CCCNc1nc(Nc2cccc3cnn(C(=O)OCC)c23)ncc1C#CCCCNC(=O)[C@H](C)N(C)C(=O)OC(C)(C)C] | MS m/z (M + H): 607.4 |

TABLE 223-continued

| Compound No. | Structure | Physicochemical data |
|---|---|---|
| U32 | 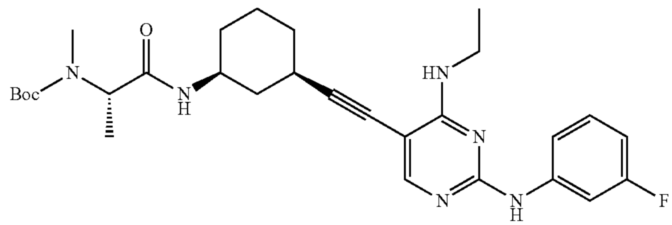 [SMILES: CCNc1nc(Nc2cccc(F)c2)ncc1C#C[C@@H]1CCC[C@H](NC(=O)[C@H](C)N(C)C(=O)OC(C)(C)C)C1] | MS m/z (M + H): 539.4 |
| U33 | 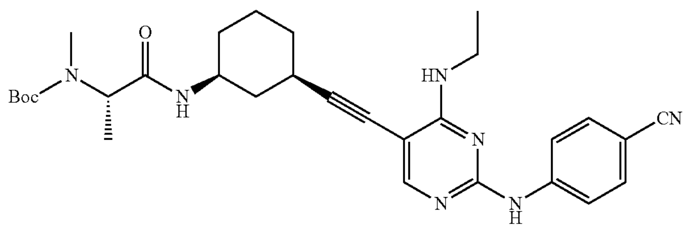 [SMILES: CCNc1nc(Nc2ccc(C#N)cc2)ncc1C#C[C@@H]1CCC[C@H](NC(=O)[C@H](C)N(C)C(=O)OC(C)(C)C)C1] | MS m/z (M + H): 546.4 |
| U34 | 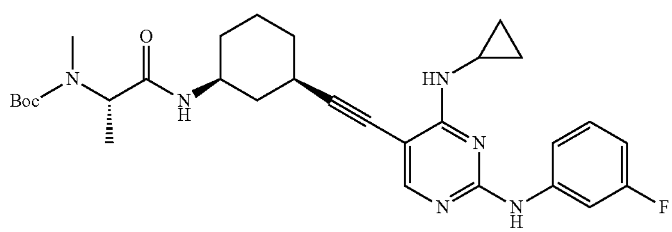 [SMILES: C[C@@H](C(=O)N[C@H]1CCC[C@@H](C#Cc2cnc(Nc3cccc(F)c3)nc2NC2CC2)C1)N(C)C(=O)OC(C)(C)C] | MS m/z (M + H): 551.4 |
| U35 | 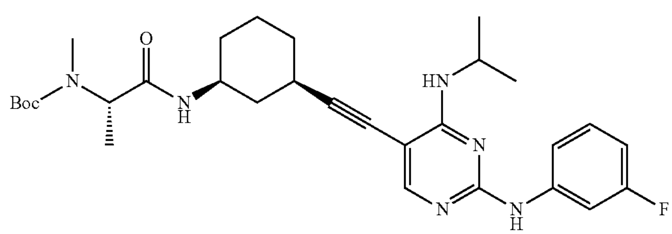 [SMILES: CC(C)Nc1nc(Nc2cccc(F)c2)ncc1C#C[C@@H]1CCC[C@H](NC(=O)[C@H](C)N(C)C(=O)OC(C)(C)C)C1] | MS m/z (M + H): 553.4 |
| U36 | 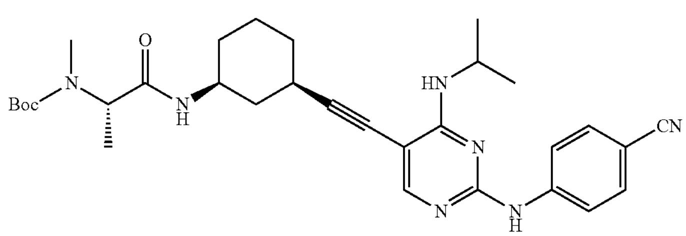 [SMILES: CC(C)Nc1nc(Nc2ccc(C#N)cc2)ncc1C#C[C@@H]1CCC[C@H](NC(=O)[C@H](C)N(C)C(=O)OC(C)(C)C)C1] | MS m/z (M + H): 560.4 |
| U37 | 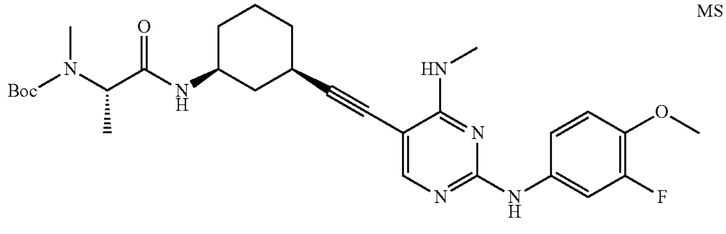 | MS m/z (M + H): 555.4 |

TABLE 223-continued

| Compound No. | Structure | Physicochemical data |
|---|---|---|
| U38 | 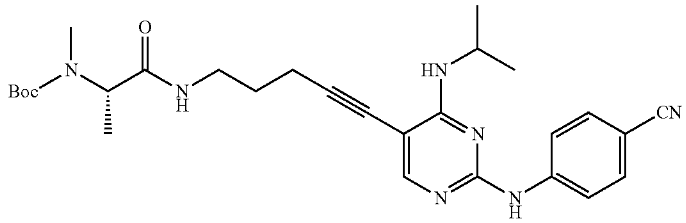 [SMILES: CC(C)Nc1nc(Nc2ccc(C#N)cc2)ncc1C#CCCCNC(=O)[C@H](C)N(C)C(=O)OC(C)(C)C] | MS m/z (M + H): 520.4 |
| U39 | 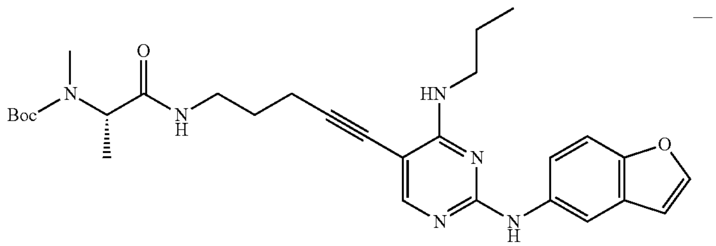 | — |

TABLE 224

| Compound No. | Structure | Physicochemical data |
|---|---|---|
| U40 | 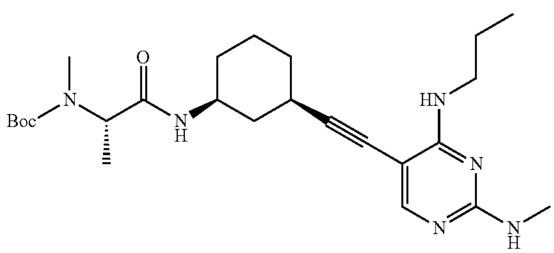 [SMILES: CCCNc1nc(NC)ncc1C#C[C@@H]1CCC[C@H](NC(=O)[C@H](C)N(C)C(=O)OC(C)(C)C)C1] | MS m/z (M + H): 473.4 |
| U41 | 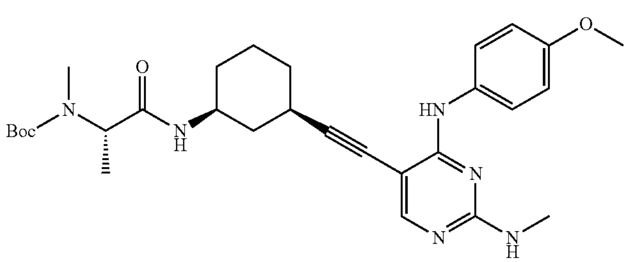 [SMILES: CNc1ncc(C#C[C@@H]2CCC[C@H](NC(=O)[C@H](C)N(C)C(=O)OC(C)(C)C)C2)c(Nc2ccc(OC)cc2)n1] | MS m/z (M + H): 537.4 |
| U42 | 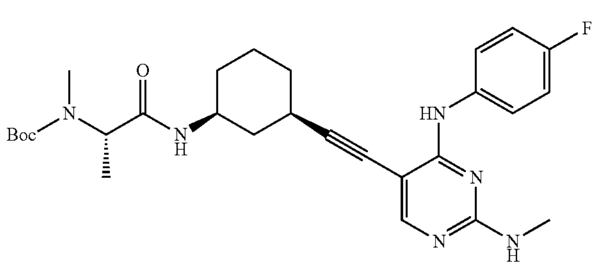 [SMILES: CNc1ncc(C#C[C@@H]2CCC[C@H](NC(=O)[C@H](C)N(C)C(=O)OC(C)(C)C)C2)c(Nc2ccc(F)cc2)n1] | MS m/z (M + H): 525.4 |

TABLE 224-continued

| Compound No. | Structure | Physicochemical data |
|---|---|---|
| U43 | 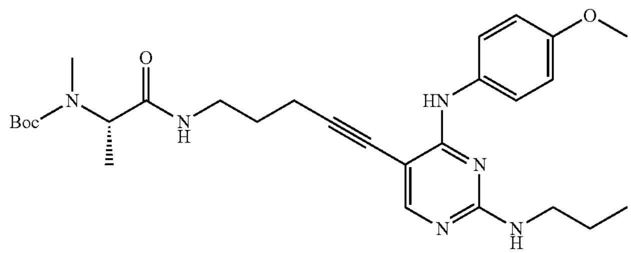 [SMILES: CCCNc1ncc(C#CCCCNC(=O)[C@H](C)N(C)C(=O)OC(C)(C)C)c(Nc2ccc(OC)cc2)n1] | MS m/z (M + H): 525.4 |
| U44 | 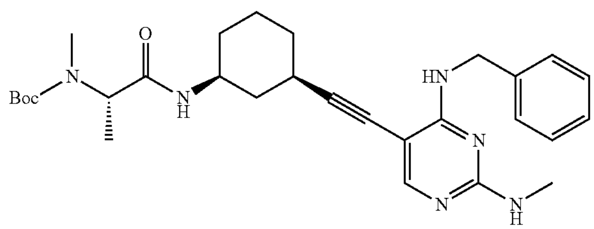 [SMILES: CNc1ncc(C#C[C@@H]2CCC[C@H](NC(=O)[C@H](C)N(C)C(=O)OC(C)(C)C)C2)c(NCc2ccccc2)n1] | MS m/z (M − H): 519.5 |
| U45 | 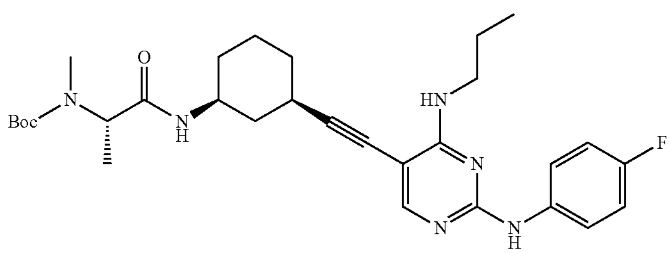 | MS m/z (M + H): 553.5 |
| U46 | 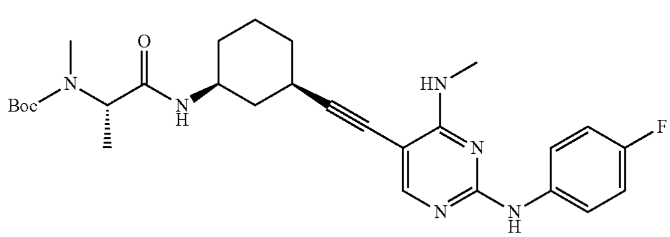 [SMILES: CNc1nc(Nc2ccc(F)cc2)ncc1C#C[C@@H]1CCC[C@H](NC(=O)[C@H](C)N(C)C(=O)OC(C)(C)C)C1] | MS m/z (M + H): 525.4 |
| U47 | 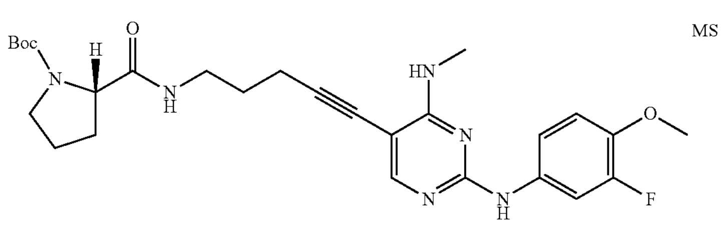 | MS m/z (M + H): 527.4 |
| U48 | 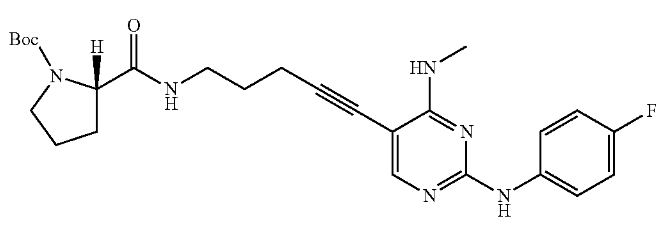 [SMILES: CNc1nc(Nc2ccc(F)cc2)ncc1C#CCCCNC(=O)[C@@H]1CCCN1C(=O)OC(C)(C)C] | MS m/z (M + H): 497.4 |

TABLE 224-continued

| Compound No. | Structure | Physicochemical data |
|---|---|---|
| U49 | 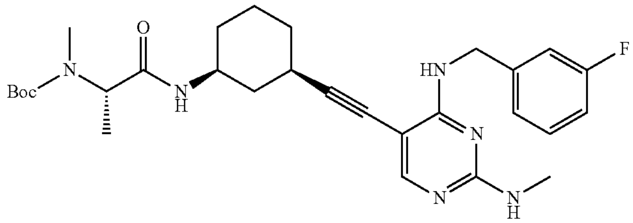 [SMILES: CNc1ncc(C#C[C@@H]2CCC[C@H](NC(=O)[C@H](C)N(C)C(=O)OC(C)(C)C)C2)c(NCc2cccc(F)c2)n1] | MS m/z (M + H): 539.4 |

TABLE 225

| Compound No. | Structure | Physicochemical data |
|---|---|---|
| U50 | 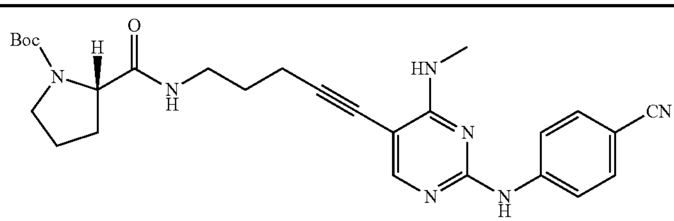 | MS m/z (M + H): 504.4 |
| U51 | 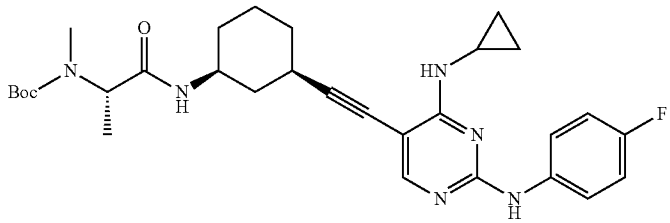 [SMILES: C[C@@H](C(=O)N[C@H]1CCC[C@@H](C#Cc2cnc(Nc3ccc(F)cc3)nc2NC2CC2)C1)N(C)C(=O)OC(C)(C)C] | MS m/z (M + H): 551.5 |
| U52 | 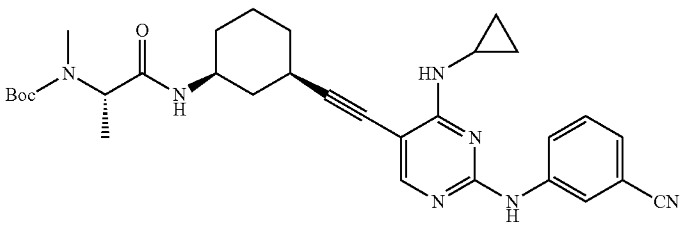 [SMILES: C[C@@H](C(=O)N[C@H]1CCC[C@@H](C#Cc2cnc(Nc3cccc(C#N)c3)nc2NC2CC2)C1)N(C)C(=O)OC(C)(C)C] | MS m/z (M + H): 558.5 |
| U53 | 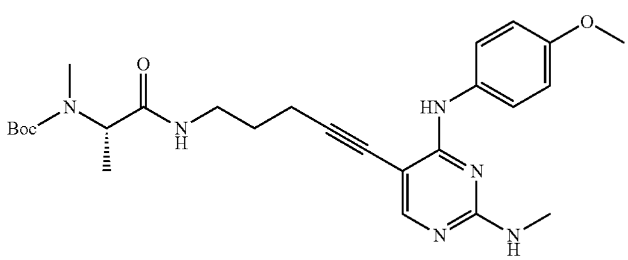 [SMILES: CNc1ncc(C#CCCCNC(=O)[C@H](C)N(C)C(=O)OC(C)(C)C)c(Nc2ccc(OC)cc2)n1] | MS m/z (M + H): 497.4 |
| U54 | 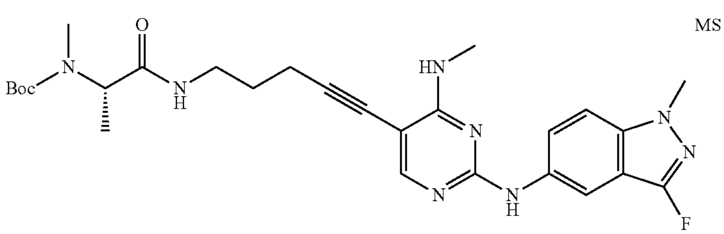 | MS m/z (M + H): 539.5 |

TABLE 225-continued

| Compound No. | Structure | Physicochemical data |
|---|---|---|
| U55 | 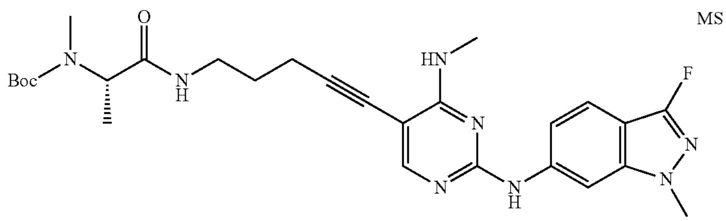 | MS m/z (M + H): 539.5 |
| U56 | 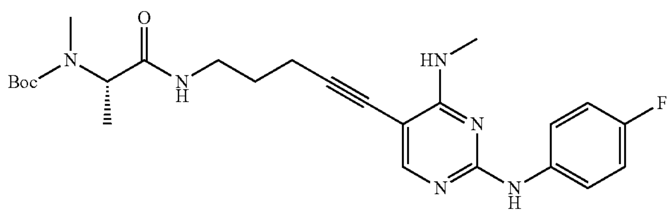 [SMILES: CNc1nc(Nc2ccc(F)cc2)ncc1C#CCCCNC(=O)[C@H](C)N(C)C(=O)OC(C)(C)C] | MS m/z (M + H): 485.4 |

In the same manner as that of Example 69, (3), Compounds (21-2) to (21-52) were obtained.

TABLE 226

| Compound No. | Structure | Physicochemical data |
|---|---|---|
| 21-2 | 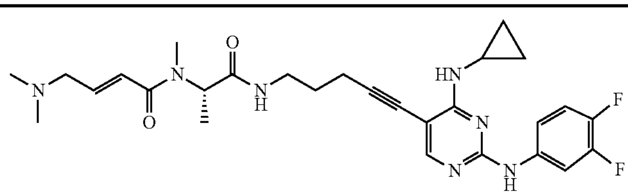 | $^1$H-NMR (CDCl$_3$) δ: 8.24 (1H, ddd, J = 13.8, 7.2, 2.4 Hz), 7.96 (1H, s), 7.12-6.88 (4H, m), 6.57-6.48 (1H, m), 6.42 (1H, d, J = 15.2 Hz), 6.29 (1H, s), 5.18 (1H, q, J = 7.0 Hz), 3.42 (2H, q, J = 6.4 Hz), 3.11 (2H, d, J = 5.3 Hz), 3.00 (3H, s), 2.90-2.80 (1H, m), 2.42 (2H, t, J = 6.9 Hz), 2.27 (6H, s), 1.80-1.68 (2H, m), 1.37 (3H, d, J = 7.0 Hz), 0.95-0.85 (2H, m), 0.79-0.68 (2H, m) |
| 21-3 | 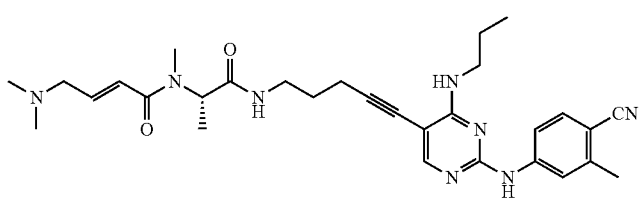 [SMILES: CCCNc1nc(Nc2ccc(C#N)c(C)c2)ncc1C#CCCCNC(=O)[C@H](C)N(C)C(=O)/C=C/CN(C)C] | $^1$H-NMR (CDCl$_3$) δ: 7.95 (1H, s), 7.66 (1H, s), 7.57-7.46 (2H, m), 7.17 (1H, s), 6.93 (1H, dt, J = 15.2, 5.9 Hz), 6.57-6.48 (1H, m), 6.47-6.34 (2H, m), 5.17 (1H, q, J = 7.0 Hz), 3.55-3.38 (4H, m), 3.10 (2H, d, J = 5.9 Hz), 2.98 (3H, s), 2.51 (3H, s), 2.43 (2H, t, J = 6.6 Hz), 2.26 (6H, s), 1.80-1.67 (4H, m), 1.35 (3H, d, J = 7.0 Hz), 0.99 (3H, t, J = 7.3 Hz) |
| 21-4 | 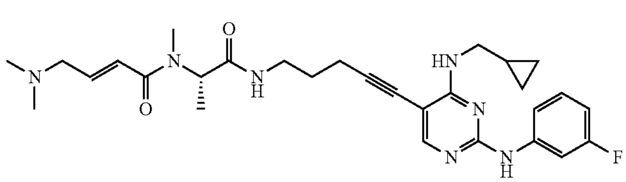 [SMILES: C[C@@H](C(=O)NCCCC#Cc1cnc(Nc2cccc(F)c2)nc1NCC1CC1)N(C)C(=O)/C=C/CN(C)C] | $^1$H-NMR (CDCl$_3$) δ: 7.97 (1H, s), 7.79 (1H, dt, J = 11.9, 2.0 Hz), 7.35-7.07 (3H, m), 6.94 (1H, dt, J = 15.2, 5.9 Hz), 6.67 (1H, dt, J = 8.3, 2.0 Hz), 6.62-6.52 (1H, m), 6.48-6.37 (1H, m), 6.32-6.20 (1H, m), 5.19 (1H, q, J = 7.0 Hz), 3.50-3.36 (4H, m), 3.10 (2H, dd, J = 5.9, 1.3 Hz), 2.99 (3H, s), 2.45 (2H, t, J = 6.6 Hz), 2.27 (6H, s), 1.83-1.70 (2H, m), 1.35 (3H, d, J = 7.0 Hz), 1.01-0.83 (1H, m), 0.59-0.49 (2H, m), 0.37-0.28 (2H, m) |
| 21-5 | 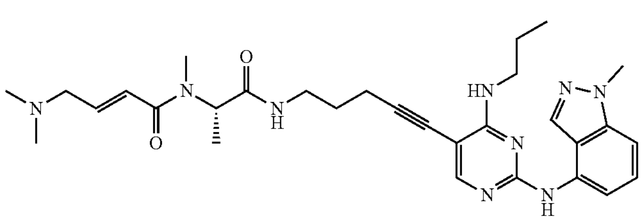 [SMILES: CCCNc1nc(Nc2cccc3c2cnn3C)ncc1C#CCCCNC(=O)[C@H](C)N(C)C(=O)/C=C/CN(C)C] | $^1$H-NMR (CDCl$_3$) δ: 8.09-7.99 (3H, m), 7.41-7.32 (1H, m), 7.27-7.23 (1H, m), 7.03 (1H, d, J = 8.3 Hz), 6.95 (1H, dt, J = 14.9, 5.9 Hz), 6.57-6.48 (1H, m), 6.47-6.38 (1H, m), 6.29-6.21 (1H, m), 5.19 (1H, q, J = 7.0 Hz), 4.07 (3H, s), 3.58-3.40 (4H, m), 3.14-3.06 (2H, m), 2.99 (3H, s), 2.50-2.40 (2H, m), 2.27 (6H, s), 1.82-1.63 (4H, m), 1.36 (3H, d, J = 6.9 Hz), 1.03 (3H, t, J = 7.4 Hz) |

TABLE 227

| Compound No. | Structure | Physicochemical data |
|---|---|---|
| 21-6 | 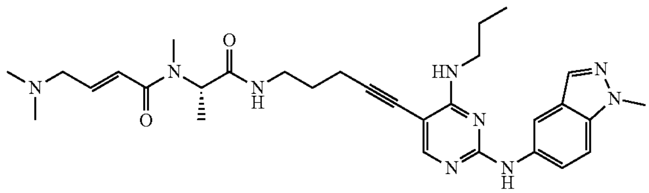 | ¹H-NMR (CDCl₃) δ: 8.15 (1H, d, J = 1.7 Hz), 7.97 (1H, s), 7.90 (1H, s), 7.44 (1H, dd, J = 6.9, 2.0 Hz), 7.32 (1H, d, J = 8.9 Hz), 7.09-7.02 (1H, m), 6.94 (1H, dt, J = 15.2, 5.9 Hz), 6.59-6.49 (1H, m), 6.42 (1H, d, J = 15.2 Hz), 6.23-6.12 (1H, m), 5.19 (1H, q, J = 7.0 Hz), 4.06 (3H, s), 3.45-3.38 (4H, m), 3.13-3.06 (2H, m), 2.99 (3H, s), 2.50-2.39 (2H, m), 2.27 (6H, s), 1.85-1.65 (4H, m), 1.36 (3H, d, J = 7.3 Hz), 1.01 (3H, t, J = 7.4 Hz) |
| 21-7 | 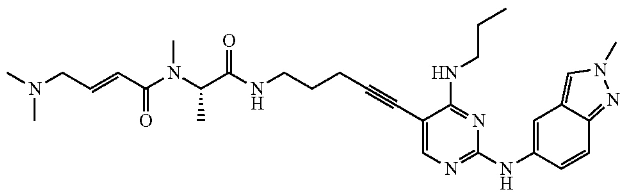 | ¹H-NMR (CDCl₃) δ: 8.14 (1H, d, J = 2.0 Hz), 7.97 (1H, s), 7.78 (1H, s), 7.61 (1H, d, J = 9.2 Hz), 7.24 (1H, dd, J = 9.2, 2.0 Hz), 7.02-6.87 (2H, m), 6.58-6.48 (1H, m), 6.42 (1H, d, J = 15.2 Hz), 6.20-6.11 (1H, m), 5.19 (1H, q, J = 7.2 Hz), 4.19 (3H, s), 3.55-3.37 (4H, m), 3.13-3.07 (2H, m), 2.99 (3H, s), 2.50-2.37 (2H, m), 2.27 (6H, s), 1.80-1.65 (4H, m), 1.36 (3H, d, J = 6.9 Hz), 1.01 (3H, t, J = 7.4 Hz) |
| 21-8 | 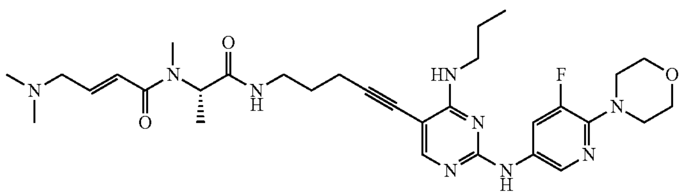 [SMILES: CCCNc1nc(Nc2cnc(N3CCOCC3)c(F)c2)ncc1C#CCCCNC(=O)[C@H](C)N(C)C(=O)/C=C/CN(C)C] | ¹H-NMR (CDCl₃) δ: 8.18 (1H, dd, J = 15.0, 2.0 Hz), 7.99 (1H, d, J = 2.0 Hz), 7.95 (1H, s), 7.74-7.61 (1H, m), 6.94 (1H, dt, J = 15.2, 5.9 Hz), 6.68-6.54 (1H, m), 6.43 (1H, d, J = 15.2 Hz), 6.35-6.25 (1H, m), 5.19 (1H, q, J = 7.0 Hz), 3.90-3.81 (4H, m), 3.52-3.40 (4H, m), 3.40-3.32 (4H, m), 3.14-3.06 (2H, m), 3.00 (3H, s), 2.50-2.38 (2H, m), 2.27 (6H, s), 1.82-1.63 (4H, m), 1.36 (3H, d, J = 7.3 Hz), 0.99 (3H, t, J = 7.4 Hz) |
| 21-9 | 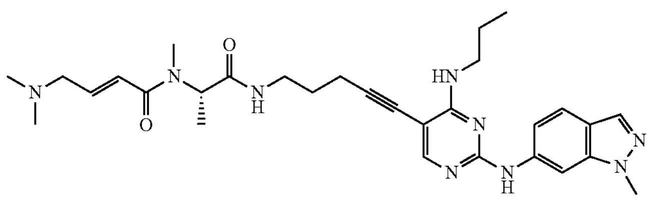 [SMILES: CCCNc1nc(Nc2ccc3cnn(C)c3c2)ncc1C#CCCCNC(=O)[C@H](C)N(C)C(=O)/C=C/CN(C)C] | ¹H-NMR (CDCl₃) δ: 8.31 (1H, s), 8.01 (1H, s), 7.87 (1H, s), 7.58 (1H, d, J = 8.6 Hz), 7.35-7.28 (1H, m), 7.01-6.87 (2H, m), 6.62-6.51 (1H, m), 6.43 (1H, d, J = 15.2 Hz), 6.30-6.20 (1H, m), 5.20 (1H, q, J = 6.9 Hz), 4.04 (3H, s), 3.65-3.54 (2H, m), 3.50-3.39 (2H, m), 3.13-3.06 (2H, m), 3.00 (3H, s), 2.45 (2H, t, J = 6.6 Hz), 2.27 (6H, s), 1.84-1.68 (4H, m), 1.36 (3H, d, J = 6.9 Hz), 1.01 (3H, t, J = 7.4 Hz) |

TABLE 228

| Compound No. | Structure | Physicochemical data |
|---|---|---|
| 21-10 | 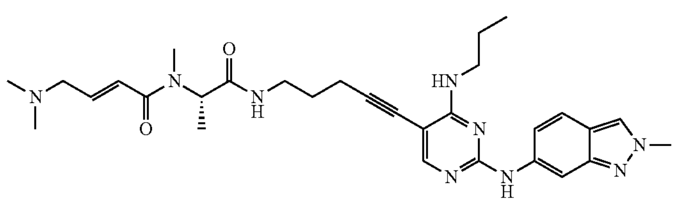 | ¹H-NMR (CDCl₃) δ: 8.18 (1H, s), 7.97 (1H, s), 7.79 (1H, s), 7.53 (1H, d, J = 9.2 Hz), 7.16-7.07 (2H, m), 6.94 (1H, dt, J = 15.2, 5.9 Hz), 6.60-6.48 (1H, m), 6.42 (1H, d, J = 15.2 Hz), 6.17-6.04 (1H, m), 5.19 (1H, q, J = 7.1 Hz), 4.17 (3H, s), 3.60-3.50 (2H, m), 3.48-3.38 (2H, m), 3.12-3.06 (2H, m), 2.99 (3H, s), 2.44 (2H, t, J = 6.8 Hz), 2.27 (6H, s), 1.83-1.66 (4H, m), 1.36 (3H, d, J = 6.9 Hz), 1.02 (3H, t, J = 7.4 Hz) |
| 21-11 | 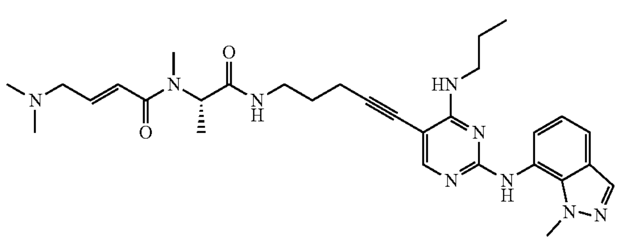 [SMILES: CCCNc1nc(Nc2cccc3cnn(C)c23)ncc1C#CCCCNC(=O)[C@H](C)N(C)C(=O)/C=C/CN(C)C] | ¹H-NMR (CDCl₃) δ: 7.96 (1H, s), 7.91 (1H, s), 7.58 (1H, d, J = 8.3 Hz), 7.32 (1H, d, J = 7.3 Hz), 7.09 (1H, dd, J = 7.6, 7.6 Hz), 6.98-6.86 (2H, m), 6.57-6.46 (1H, m), 6.41 (1H, d, J = 15.2 Hz), 6.17-6.06 (1H, m), 5.16 (1H, q, J = 7.0 Hz), 4.13 (3H, s), 3.47-3.35 (2H, m), 3.22-3.12 (2H, m), 3.12-3.05 (2H, m), 2.97 (3H, s), 2.41 (2H, t, J = 6.6 Hz), 2.26 (6H, s), 1.78-1.66 (2H, m), 1.50-1.37 (2H, m), 1.33 (3H, d, J = 6.9 Hz), 0.75 (3H, t, J = 7.4 Hz) |

TABLE 228-continued

| Compound No. | Structure | Physicochemical data |
|---|---|---|
| 21-12 | 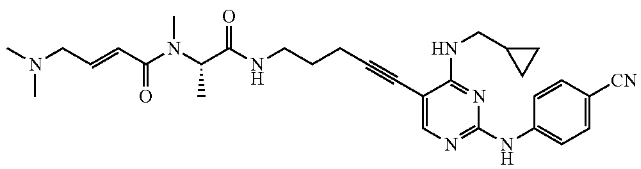 [SMILES: C[C@@H](C(=O)NCCCC#Cc1cnc(Nc2ccc(C#N)cc2)nc1NCC1CC1)N(C)C(=O)/C=C/CN(C)C] | ¹H-NMR (CDCl₃) δ: 7.98 (1H, s), 7.77 (2H, d, J = 8.6 Hz), 7.64-7.52 (3H, m), 6.94 (1H, dt, J = 15.2, 5.9 Hz), 6.65-6.56 (1H, m), 6.48-6.36 (2H, m), 5.19 (1H, q, J = 7.3 Hz), 3.51-3.36 (4H, m), 3.11 (2H, dd, J = 5.9, 1.3 Hz), 3.00 (3H, s), 2.46 (2H, t, J = 6.6 Hz), 2.27 (6H, s), 1.83-1.69 (2H, m), 1.36 (3H, d, J = 7.3 Hz), 1.29-1.16 (1H, m), 0.60-0.50 (2H, m), 0.37-0.27 (2H, m) |
| 21-13 | 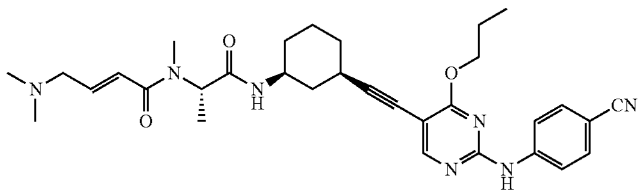 [SMILES: CCCOc1nc(Nc2ccc(C#N)cc2)ncc1C#C[C@@H]1CCC[C@H](NC(=O)[C@H](C)N(C)C(=O)/C=C/CN(C)C)C1] | ¹H-NMR (CDCl₃) δ: 8.22 (1H, s), 7.74 (2H, d, J = 8.6 Hz), 7.60 (2H, d, J = 8.6 Hz), 7.30-7.27 (1H, m), 6.92 (1H, dt, J = 15.2, 5.9 Hz), 6.41 (1H, d, J = 15.2 Hz), 6.31-6.24 (1H, m), 5.16 (1H, q, J = 7.3 Hz), 4.35 (2H, t, J = 6.6 Hz), 3.78-3.70 (1H, m), 3.10 (2H, d, J = 5.9 Hz), 2.97 (3H, s), 2.65-2.56 (1H, m), 2.32-2.26 (1H, m), 2.28 (6H, s), 2.04-1.96 (1H, m), 1.93-1.82 (2H, m), 1.86-1.78 (2H, m), 1.48-1.25 (3H, m), 1.33 (3H, d, J = 7.3 Hz), 1.14-1.05 (1H, m), 1.09 (3H, t, J = 8.9 Hz) |

TABLE 229

| Compound No. | Structure | Physicochemical data |
|---|---|---|
| 21-14 | 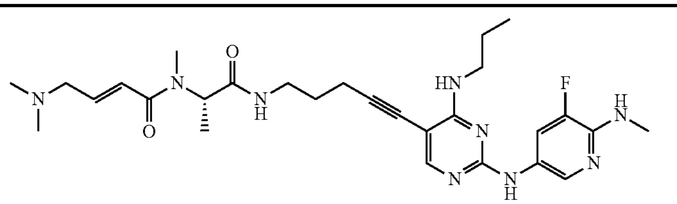 | ¹H-NMR (CDCl₃) δ: 7.98-7.85 (3H, m), 6.94 (1H, dt, J = 15.2, 5.9 Hz), 6.80-6.73 (1H, m), 6.56-6.46 (1H, m), 6.42 (1H, d, J = 15.2 Hz), 6.22-6.12 (1H, m), 5.18 (1H, q, J = 7.0 Hz), 4.47-4.35 (1H, m), 3.52-3.37 (4H, m), 3.15-3.06 (2H, m), 3.03 (3H, d, J = 5.0 Hz), 2.99 (3H, s), 2.43 (2H, t, J = 6.8 Hz), 2.27 (6H, s), 1.85-1.58 (4H, m), 1.35 (3H, d, J = 6.9 Hz), 0.97 (3H, t, J = 7.3 Hz) |
| 21-15 | 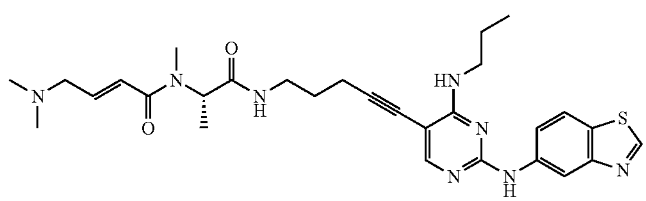 [SMILES: CCCNc1nc(Nc2ccc3scnc3c2)ncc1C#CCCCNC(=O)[C@H](C)N(C)C(=O)/C=C/CN(C)C] | MS m/z (M + H): 563.4 |
| 21-16 | 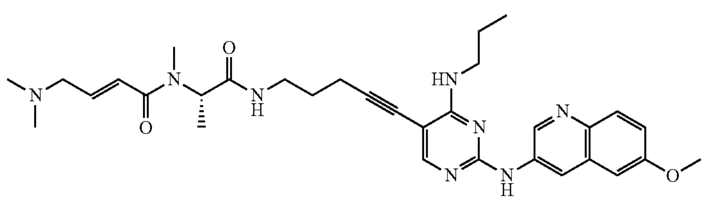 | ¹H-NMR (CDCl₃) δ: 8.75-8.68 (2H, m), 8.02 (1H, s), 7.90 (1H, d, J = 9.2 Hz), 7.34-7.27 (1H, m), 7.21 (1H, dd, J = 9.2, 2.6 Hz), 7.02 (1H, d, J = 2.6 Hz), 6.95 (1H, dt, J = 15.2, 5.9 Hz), 6.60-6.48 (1H, m), 6.43 (1H, d, J = 15.2 Hz), 6.42-6.32 (1H, m), 5.20 (1H, q, J = 7.1 Hz), 3.93 (3H, s), 3.62-3.51 (2H, m), 3.50-3.40 (2H, m), 3.13-3.07 (2H, m), 3.00 (3H, s), 2.45 (2H, t, J = 6.6 Hz), 2.27 (6H, s), 1.85-1.68 (4H, m), 1.37 (3H, d, J = 7.3 Hz), 1.05 (3H, t, J = 7.4 Hz) |
| 21-17 | 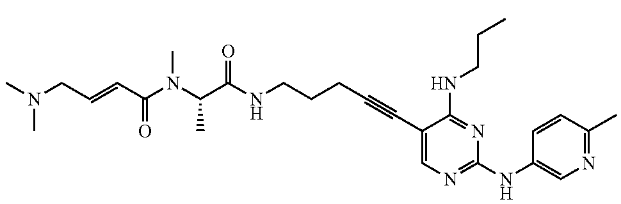 | ¹H-NMR (CDCl₃) δ: 8.62 (1H, d, J = 2.6 Hz), 8.04 (1H, dd, J = 8.6, 2.6 Hz), 7.95 (1H, s), 7.09 (1H, d, J = 8.3 Hz), 6.99-6.93 (1H, m), 6.95 (1H, dt, J = 15.2, 5.9 Hz), 6.57-6.47 (1H, m), 6.42 (1H, d, J = 15.2 Hz), 6.25-6.15 (1H, m), 5.18 (1H, q, J = 7.2 Hz), 3.53-3.38 (4H, m), 3.14-3.06 (2H, m), 2.99 (3H, s), 2.51 (3H, s), 2.44 (2H, t, J = 6.6 Hz), 2.27 (6H, s), 1.82-1.62 (4H, m), 1.36 (3H, d, J = 6.9 Hz), 0.99 (3H, t, J = 7.4 Hz) |

TABLE 229-continued

| Compound No. | Structure | Physicochemical data |
| --- | --- | --- |
| 21-18 | 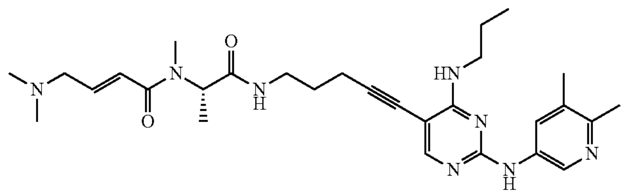 | $^1$H-NMR (CDCl$_3$) δ: 8.45 (1H, d, J = 2.3 Hz), 7.94 (1H, s), 7.92 (1H, d, J = 2.0 Hz), 7.00-6.87 (2H, m), 6.58-6.47 (1H, m), 6.42 (1H, d, J = 15.2 Hz), 6.25-6.15 (1H, m), 5.18 (1H, q, J = 7.2 Hz), 3.57-3.38 (4H, m), 3.12-3.07 (2H, m), 2.99 (3H, s), 2.52-2.38 (2H, m), 2.45 (3H, s), 2.28 (3H, s), 2.27 (6H, s), 1.83-1.63 (4H, m), 1.36 (3H, d, J = 6.9 Hz), 0.99 (3H, t, J = 7.3 Hz) |

TABLE 229

| Compound No. | Structure | Physicochemical data |
| --- | --- | --- |
| 21-19 | 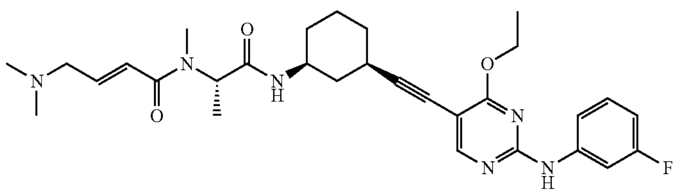 [SMILES: CCOc1nc(Nc2cccc(F)c2)ncc1C#C[C@@H]1CCC[C@H](NC(=O)[C@H](C)N(C)C(=O)/C=C/CN(C)C)C1] | $^1$H-NMR (CDCl$_3$) δ: 8.20 (1H, s), 7.72-7.65 (1H, m), 7.28-7.21 (1H, m), 7.14-7.09 (1H, m), 7.12-7.09 (1H, m), 6.92 (1H, dt, J = 15.2, 5.9 Hz), 6.72 (1H, td, J = 8.1, 2.2 Hz), 6.41 (1H, d, J = 15.2 Hz), 6.28-6.23 (1H, m), 5.16 (1H, q, J = 7.0 Hz), 4.47 (2H, q, J = 7.0 Hz), 3.78-3.72 (1H, m), 3.10 (2H, d, J = 5.9 Hz), 2.97 (3H, s), 2.65-2.57 (1H, m), 2.32-2.26 (1H, m), 2.27 (6H, s), 2.06-1.96 (1H, m), 1.88-1.77 (2H, m), 1.46 (3H, t, J = 7.0 Hz), 1.37-1.26 (3H, m), 1.33 (3H, d, J = 7.0 Hz), 1.14-1.04 (1H, m) |
| 21-20 | 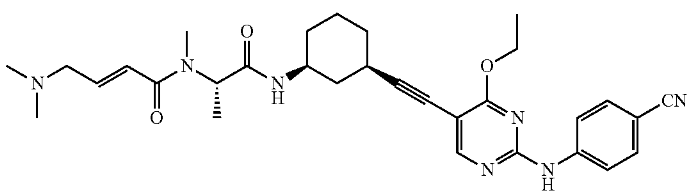 [SMILES: CCOc1nc(Nc2ccc(C#N)cc2)ncc1C#C[C@@H]1CCC[C@H](NC(=O)[C@H](C)N(C)C(=O)/C=C/CN(C)C)C1] | $^1$H-NMR (CDCl$_3$) δ: 8.23 (1H, s), 7.74 (2H, d, J = 8.6 Hz), 7.60 (2H, d, J = 8.6 Hz), 7.34-7.31 (1H, m), 6.92 (1H, dt, J = 15.2, 5.9 Hz), 6.41 (1H, d, J = 15.2 Hz), 6.32-6.25 (1H, m), 5.16 (1H, q, J = 7.0 Hz), 4.46 (2H, q, J = 7.0 Hz), 3.78-3.70 (1H, m), 3.10 (2H, d, J = 5.9 Hz), 2.97 (3H, s), 2.65-2.58 (1H, m), 2.34-2.26 (1H, m), 2.27 (6H, s), 2.05-1.96 (1H, m), 1.87-1.78 (2H, m), 1.47 (3H, t, J = 7.3 Hz), 1.38-1.25 (3H, m), 1.33 (3H, d, J = 7.0 Hz), 1.14-1.04 (1H, m) |
| 21-21 | 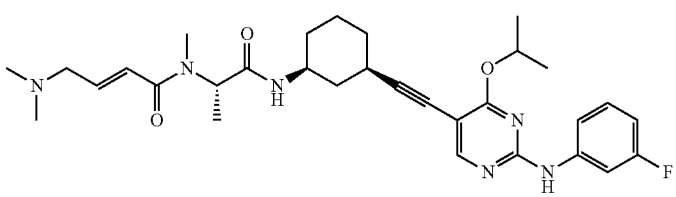 [SMILES: CC(C)Oc1nc(Nc2cccc(F)c2)ncc1C#C[C@@H]1CCC[C@H](NC(=O)[C@H](C)N(C)C(=O)/C=C/CN(C)C)C1] | $^1$H-NMR (CDCl$_3$) δ: 8.18 (1H, s), 7.72-7.65 (1H, m), 7.28-7.19 (1H, m), 7.17-7.14 (1H, m), 7.13-7.08 (1H, m), 6.92 (1H, dt, J = 15.2, 5.9 Hz), 6.72 (1H, td, J = 8.3, 2.2 Hz), 6.42 (1H, d, J = 15.2 Hz), 6.29-6.21 (1H, m), 5.38-5.30 (1H, m), 5.16 (1H, q, J = 7.0 Hz), 3.78-3.70 (1H, m), 3.11 (2H, d, J = 5.9 Hz), 2.97 (3H, s), 2.64-2.56 (1H, m), 2.32-2.25 (1H, m), 2.28 (6H, s), 2.06-1.96 (1H, m), 1.86-1.74 (2H, m), 1.43 (6H, d, J = 6.6 Hz), 1.39-1.25 (3H, m), 1.33 (3H, d, J = 7.0 Hz), 1.14-1.04 (1H, m) |
| 21-22 | 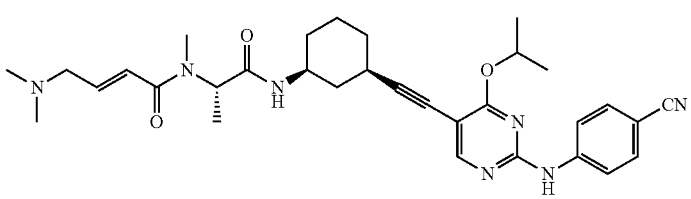 [SMILES: CC(C)Oc1nc(Nc2ccc(C#N)cc2)ncc1C#C[C@@H]1CCC[C@H](NC(=O)[C@H](C)N(C)C(=O)/C=C/CN(C)C)C1] | $^1$H-NMR (CDCl$_3$) δ: 8.21 (1H, s), 7.73 (2H, d, J = 8.6 Hz), 7.60 (2H, d, J = 8.6 Hz), 7.29-7.25 (1H, m), 6.92 (1H, dt, J = 15.2, 5.9 Hz), 6.41 (1H, d, J = 15.2 Hz), 6.30-6.23 (1H, m), 5.37-5.28 (1H, m), 5.16 (1H, q, J = 7.0 Hz), 3.79-3.69 (1H, m), 3.10 (2H, d, J = 5.9 Hz), 2.97 (3H, s), 2.64-2.57 (1H, m), 2.32-2.26 (1H, m), 2.28 (6H, s), 2.05-1.95 (1H, m), 1.87-1.77 (2H, m), 1.43 (6H, d, J = 5.9 Hz), 1.39-1.31 (3H, m), 1.33 (3H, d, J = 7.0 Hz), 1.14-1.04 (1H, m) |

TABLE 231

| Compound No. | Structure | Physicochemical data |
|---|---|---|
| 21-23 | 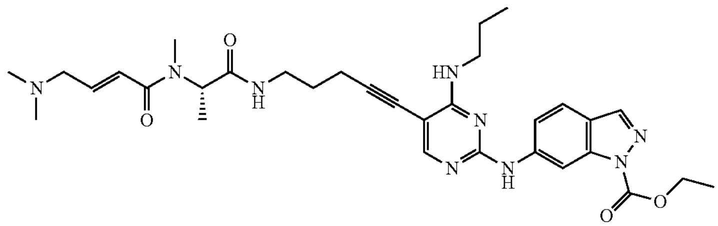 [SMILES: CCCNc1nc(Nc2ccc3cnn(C(=O)OCC)c3c2)ncc1C#CCCCNC(=O)[C@H](C)N(C)C(=O)/C=C/CN(C)C] | MS m/z (M + H): 618.5 |
| 21-24 | 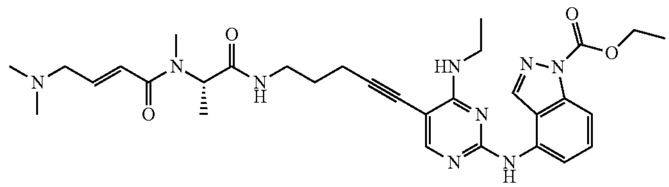 | MS m/z (M + H): 618.5 |
| 21-25 | 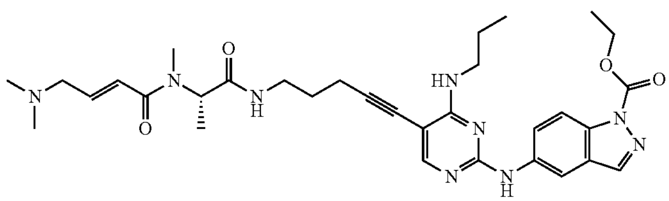 [SMILES: CCCNc1nc(Nc2ccc3c(cnn3C(=O)OCC)c2)ncc1C#CCCCNC(=O)[C@H](C)N(C)C(=O)/C=C/CN(C)C] | MS m/z (M + H): 618.5 |
| 21-26 | 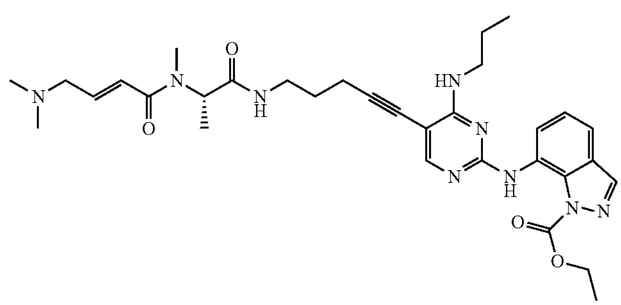 [SMILES: CCCNc1nc(Nc2cccc3cnn(C(=O)OCC)c23)ncc1C#CCCCNC(=O)[C@H](C)N(C)C(=O)/C=C/CN(C)C] | — |
| 21-27 | 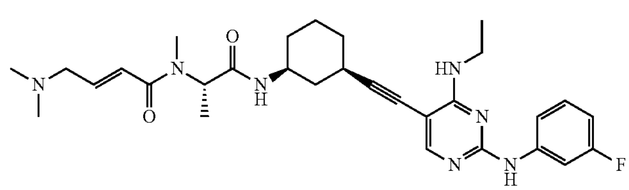 [SMILES: CCNc1nc(Nc2cccc(F)c2)ncc1C#C[C@@H]1CCC[C@H](NC(=O)[C@H](C)N(C)C(=O)/C=C/CN(C)C)C1] | ¹H-NMR (CDCl₃) δ: 7.96 (1H, s), 7.82-7.74 (1H, m), 7.31-7.25 (1H, m), 7.27-7.21 (1H, m), 7.14-7.09 (1H, m), 6.93 (1H, dt, J = 15.2, 5.9 Hz), 6.72-6.64 (1H, m), 6.43 (1H, d, J = 15.2 Hz), 6.37-6.31 (1H, m), 5.43-5.35 (1H, m), 5.16 (1H, q, J = 7.0 Hz), 3.78-3.68 (1H, m), 3.61-3.50 (2H, m), 3.12 (2H, d, J = 5.9 Hz), 2.98 (3H, s), 2.66-2.57 (1H, m), 2.34-2.27 (1H, m), 2.29 (6H, s), 2.07-1.95 (1H, m), 1.88-1.78 (2H, m), 1.41-1.27 (3H, m), 1.33 (3H, t, J = 6.3 Hz), 1.32 (3H, d, J = 7.0 Hz), 1.16-1.05 (1H, m) |
| 21-28 | 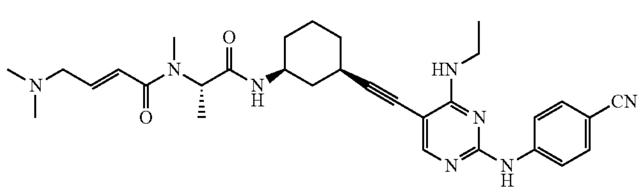 [SMILES: CCNc1nc(Nc2ccc(C#N)cc2)ncc1C#C[C@@H]1CCC[C@H](NC(=O)[C@H](C)N(C)C(=O)/C=C/CN(C)C)C1] | ¹H-NMR (CDCl₃) δ: 7.98 (1H, s), 7.77 (2H, d, J = 8.6 Hz), 7.62-7.57 (1H, m), 7.57 (2H, d, J = 8.6 Hz), 6.93 (1H, dt, J = 15.2, 5.9 Hz), 6.49 (1H, d, J = 15.2 Hz), 6.40-6.35 (1H, m), 5.47-5.41 (1H, m), 5.15 (1H, q, J = 7.0 Hz), 3.78-3.70 (1H, m), 3.59-3.49 (2H, m), 3.18 (2H, d, J = 5.9 Hz), 3.01 (3H, s), 2.68-2.58 (1H, m), 2.36-2.28 (1H, m), 2.34 (6H, s), 2.08-1.96 (1H, m), 1.89-1.77 (2H, m), 1.47-1.24 (3H, m), 1.31 (3H, t, J = 7.3 Hz), 1.30 (3H, d, J = 7.0 Hz), 1.15-1.05 (1H, m) |

TABLE 232

| Compound No. | Structure | Physicochemical data |
|---|---|---|
| 21-29 | 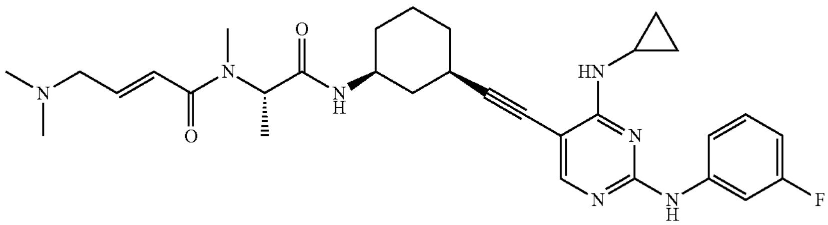 [SMILES: C[C@@H](C(=O)N[C@H]1CCC[C@@H](C#Cc2cnc(Nc3cccc(F)c3)nc2NC2CC2)C1)N(C)C(=O)/C=C/CN(C)C] | ¹H-NMR (CDCl₃) δ: 8.15-8.08 (1H, m), 7.97 (1H, s), 7.37-7.33 (1H, m), 7.25-7.16 (1H, m), 7.12-7.05 (1H, m), 6.92 (1H, dt, J = 15.2, 5.9 Hz), 6.68 (1H, td, J = 8.3, 2.2 Hz), 6.51 (1H, d, J = 15.2 Hz), 6.35-6.28 (1H, m), 5.61-5.57 (1H, m), 5.15 (1H, q, J = 6.9 Hz), 3.78-3.68 (1H, m), 3.21 (2H, d, J = 5.9 Hz), 2.99 (3H, s), 2.88-2.81 (1H, m), 2.67-2.56 (1H, m), 2.36 (6H, s), 2.36-2.26 (1H, m), 2.03-1.95 (1H, m), 1.87-1.79 (2H, m), 1.47-1.28 (3H, m), 1.35 (3H, d, J = 7.0 Hz), 1.14-1.05 (1H, m), 0.98-0.88 (2H, m), 0.70-0.63 (2H, m) |
| 21-30 | 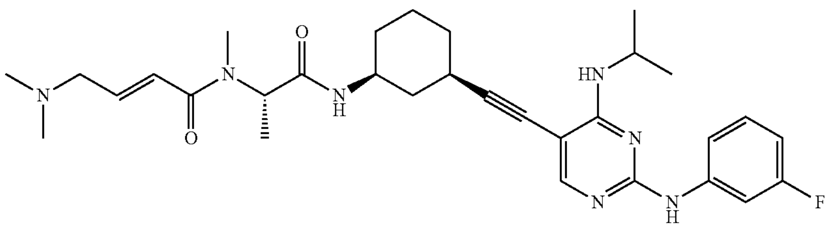 [SMILES: CC(C)Nc1nc(Nc2cccc(F)c2)ncc1C#C[C@@H]1CCC[C@H](NC(=O)[C@H](C)N(C)C(=O)/C=C/CN(C)C)C1] | ¹H-NMR (CDCl₃) δ: 7.95 (1H, s), 7.82-7.74 (1H, m), 7.29-7.25 (1H, m), 7.25-7.17 (1H, m), 7.13-7.07 (1H, m), 6.92 (1H, dt, J = 15.2, 5.9 Hz), 6.68 (1H, td, J = 8.3, 2.0 Hz), 6.51 (1H, d, J = 15.2 Hz), 6.35-6.28 (1H, m), 5.25-5.18 (1H, m), 5.15 (1H, q, J = 7.3 Hz), 4.34-4.23 (1H, m), 3.79-3.69 (1H, m), 3.21 (2H, d, J = 5.9 Hz), 3.00 (3H, s), 2.68-2.58 (1H, m), 2.38-2.27 (1H, m), 2.36 (6H, s), 2.05-1.97 (1H, m), 1.89-1.77 (2H, m), 1.47-1.24 (3H, m), 1.34 (3H, d, J = 7.3 Hz), 1.30 (6H, d, J = 7.0 Hz), 1.15-1.05 (1H, m) |
| 21-31 | 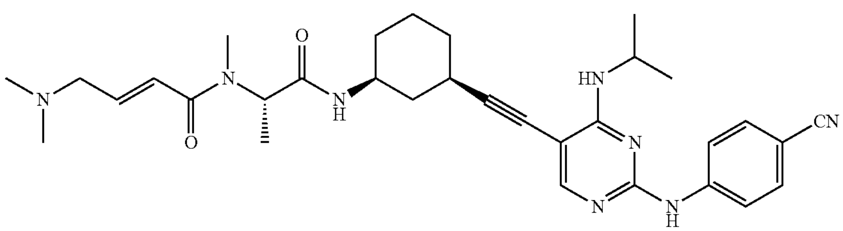 [SMILES: CC(C)Nc1nc(Nc2ccc(C#N)cc2)ncc1C#C[C@@H]1CCC[C@H](NC(=O)[C@H](C)N(C)C(=O)/C=C/CN(C)C)C1] | ¹H-NMR (CDCl₃) δ: 7.97 (1H, s), 7.76 (2H, d, J = 8.6 Hz), 7.66-7.63 (1H, m), 7.57 (2H, d, J = 8.6 Hz), 6.92 (1H, dt, J = 15.2, 5.9 Hz), 6.50 (1H, d, J = 15.2 Hz), 6.41-6.35 (1H, m), 5.29-5.24 (1H, m), 5.16 (1H, q, J = 7.0 Hz), 4.32-4.20 (1H, m), 3.79-3.70 (1H, m), 3.19 (2H, d, J = 5.9 Hz), 3.00 (3H, s), 2.66-2.58 (1H, m), 2.35-2.26 (1H, m), 2.34 (6H, s), 2.05-1.97 (1H, m), 1.88-1.79 (2H, m), 1.47-1.27 (3H, m), 1.34 (3H, d, J = 7.0 Hz), 1.31 (6H, d, J = 6.6 Hz), 1.14-1.04 (1H, m) |
| 21-32 | 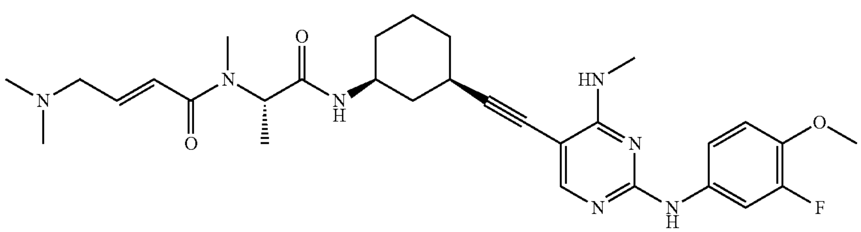 | ¹H-NMR (CDCl₃) δ: 7.94 (1H, s), 7.77-7.70 (1H, m), 7.11-7.06 (1H, m), 7.09-7.03 (1H, m), 6.97-6.87 (1H, m), 6.94-6.85 (1H, m), 6.43 (1H, d, J = 15.2 Hz), 6.37-6.30 (1H, m), 5.43-5.35 (1H, m), 5.15 (1H, q, J = 7.3 Hz), 3.87 (3H, s), 3.76-3.67 (1H, m), 3.12 (2H, d, J = 5.9 Hz), 3.07 (3H, d, J = 5.3 Hz), 2.98 (3H, s), 2.64-2.56 (1H, m), 2.43-2.29 (1H, m), 2.29 (6H, s), 2.09-1.98 (1H, m), 1.90-1.78 (2H, m), 1.43-1.24 (3H, m), 1.34 (3H, d, J = 7.3 Hz), 1.15-1.02 (1H, m) |

TABLE 233

| Compound No. | Structure | Physicochemical data |
|---|---|---|
| 21-33 | 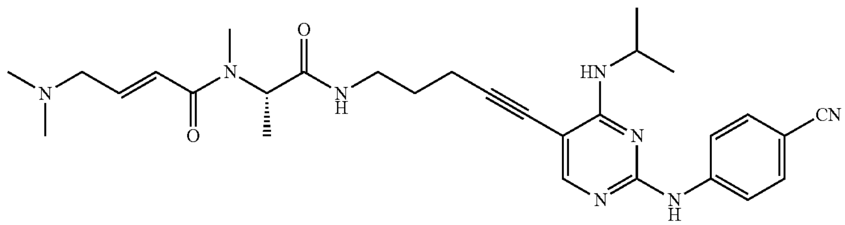 [SMILES: CC(C)Nc1nc(Nc2ccc(C#N)cc2)ncc1C#CCCCNC(=O)[C@H](C)N(C)C(=O)/C=C/CN(C)C] | ¹H-NMR (CDCl₃) δ: 7.98 (1H, s), 7.75 (2H, d, J = 8.6 Hz), 7.57 (2H, d, J = 8.6 Hz), 7.49-7.46 (1H, m), 6.94 (1H, dt, J = 15.2, 5.9 Hz), 6.59-6.54 (1H, m), 6.44 (1H, d, J = 15.2 Hz), 5.88-5.83 (1H, m), 5.18 (1H, q, J = 7.0 Hz), 4.38-4.28 (1H, m), 3.46-3.39 (2H, m), 3.12 (2H, d, J = 5.9 Hz), 3.00 (3H, s), 2.45 (2H, t, J = 6.9 Hz), 2.29 (6H, s), 1.80-1.72 (2H, m), 1.36 (3H, d, J = 7.0 Hz), 1.32 (6H, d, J = 6.6 Hz) |
| 21-34 | 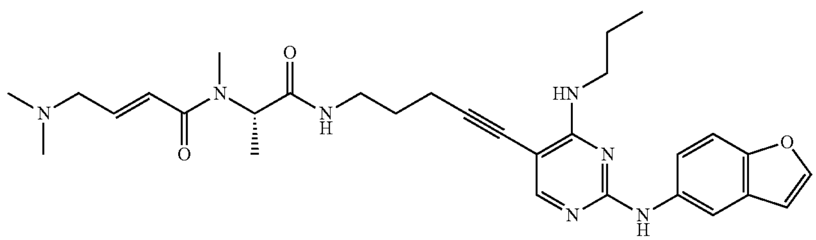 [SMILES: CCCNc1nc(Nc2ccc3occc3c2)ncc1C#CCCCNC(=O)[C@H](C)N(C)C(=O)/C=C/CN(C)C] | ¹H-NMR (CDCl₃) δ: 8.02 (1H, d, J = 1.3 Hz), 7.95 (1H, t, J = 2.3 Hz), 7.59 (1H, d, J = 2.0 Hz), 7.53 (1H, s), 7.39 (2H, d, J = 2.6 Hz), 6.93 (1H, dt, J = 15.1, 6.0 Hz), 6.79 (1H, s), 6.71 (1H, brs), 6.42 (1H, d, J = 15.1 Hz), 6.17 (1H, t, J = 5.9 Hz), 5.19 (1H, q, J = 7.2 Hz), 3.54-3.37 (4H, m), 3.10 (2H, d, J = 6.0 Hz), 3.00 (3H, s), 2.44 (2H, t, J = 6.6 Hz), 2.26 (6H, s), 1.82-1.62 (4H, m), 1.35 (3H, d, J = 7.2 Hz), 0.99 (3H, t, J = 7.3 Hz) |
| 21-35 | 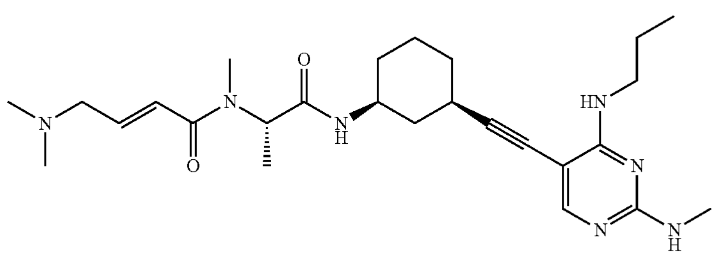 | ¹H-NMR (CDCl₃) δ: 7.87 (1H, s), 6.92 (1H, dt, J = 15.2, 5.9 Hz), 6.41 (1H, d, J = 15.2 Hz), 6.25 (1H, d, J = 7.9 Hz), 5.32-5.20 (1H, m), 5.15 (1H, q, J = 7.0 Hz), 4.88-4.77 (1H, m), 3.81-3.63 (1H, m), 3.47-3.34 (2H, m), 3.10 (2H, d, J = 5.9 Hz), 3.02-2.90 (6H, m), 2.67-2.53 (1H, m), 2.33-2.19(7H, m), 2.07-1.95 (1H, m), 1.89-1.74 (2H, m), 1.70-1.57 (2H, m), 1.40-1.18 (6H, m), 1.14-1.02 (1H, m), 0.97 (3H, t, J = 7.6 Hz) |
| 21-36 | 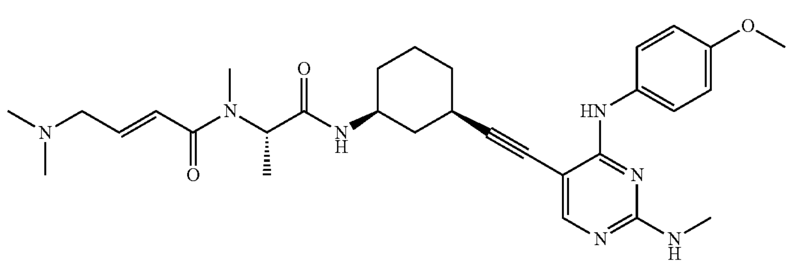 | ¹H-NMR (CDCl₃) δ: 8.01 (1H, s), 7.54 (2H, d, J = 8.6 Hz), 7.05 (1H, s), 6.98-6.84 (3H, m), 6.41 (1H, d, J = 15.2 Hz), 6.31 (1H, d, J = 7.3 Hz), 5.15 (1H, q, J = 7.0 Hz), 5.08-4.96 (1H, m), 3.81 (3H, s), 3.80-3.68 (1H, m), 3.10 (2H, d, J = 5.3 Hz), 3.01-2.92 (6H, m), 2.72-2.59 (1H, m), 2.39-2.17 (7H, m), 2.10-1.77 (3H, m), 1.48-1.25 (6H, m), 1.18-1.02 (1H, m) |
| 21-37 | 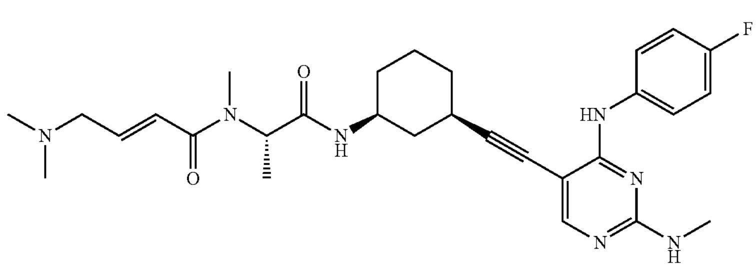 [SMILES: CNc1ncc(C#C[C@@H]2CCC[C@H](NC(=O)[C@H](C)N(C)C(=O)/C=C/CN(C)C)C2)c(Nc2ccc(F)cc2)n1] | ¹H-NMR (CDCl₃) δ: 8.03 (1H, s), 7.67-7.55 (2H, m), 7.12 (1H, s), 7.09-6.99 (2H, m), 6.92 (1H, dt, J = 15.2, 5.9 Hz), 6.42 (1H, d, J = 15.2 Hz), 6.31 (1H, d, J = 7.9 Hz), 5.15 (1H, q, J = 7.0 Hz), 5.10-5.00 (1H, m), 3.87-3.68 (1H, m), 3.11 (2H, d, J = 5.9 Hz), 3.02-2.91 (6H, m), 2.72-2.58 (1H, m), 2.42-2.23 (7H, m), 2.12-1.75 (3H, m), 1.51-1.20 (6H, m), 1.18-1.04 (1H, m) |

TABLE 234

| Compound No. | Structure | Physicochemical data |
|---|---|---|
| 21-38 | 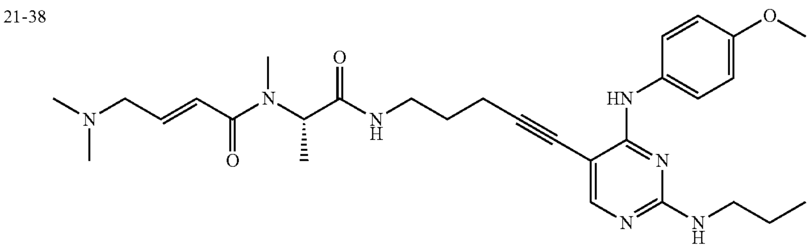 | ¹H-NMR (CDCl₃) δ: 8.01 (1H, s), 7.66-7.53 (3H, m), 6.94 (1H, dt, J = 15.2, 6.6 Hz), 6.87 (2H, d, J = 9.2 Hz), 6.56-6.47 (1H, m), 6.41 (1H, d, J = 15.2 Hz), 5.18 (1H, q, J = 7.0 Hz), 5.04-4.93 (1H, m), 3.81 (3H, s), 3.50-3.38 (2H, m), 3.37-3.26 (2H, m), 3.09 (2H, d, J = 6.6 Hz), 2.97 (3H, s), 2.46 (2H, t, J = 6.6 Hz), 2.26 (6H, s), 1.84-1.69 (2H, m), 1.63-1.51 (2H, m), 1.34 (3H, d, J = 6.6 Hz), 0.96 (3H, t, J = 7.6 Hz) |
| 21-39 | 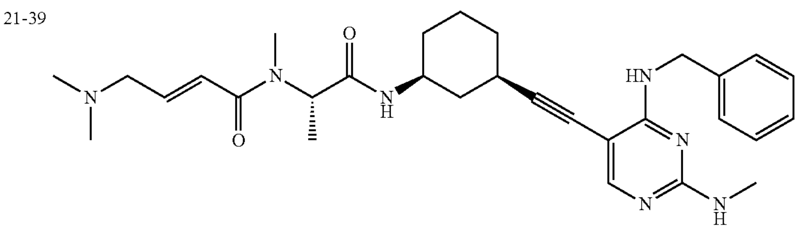 | ¹H-NMR (CDCl₃) δ: 7.91 (1H, s), 7.41-7.22 (5H, m), 6.92 (1H, dt, J = 15.2, 5.9 Hz), 6.40 (1H, d, J = 15.2 Hz), 6.25 (1H, d, J = 7.9 Hz), 5.66-5.55 (1H, m), 5.13 (1H, q, J = 7.0 Hz), 5.02-4.89 (1H, m), 4.72-4.64 (2H, m), 3.81-3.62 (1H, m), 3.10 (2H, d, J = 5.9 Hz), 3.03-2.85 (6H, m), 2.66-2.48 (1H, m), 2.32-2.16 (7H, m), 2.12-1.70 (3H, m), 1.45-1.16 (6H, m), 1.14-0.85 (1H, m) |
| 21-40 | 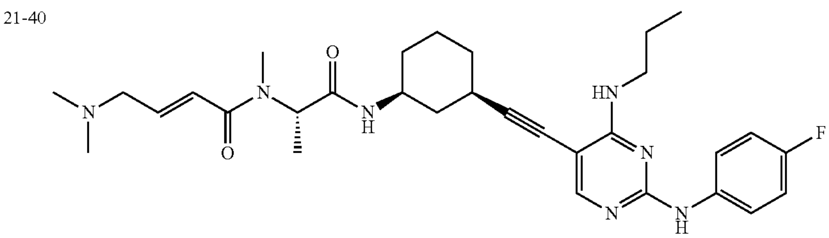 | ¹H-NMR (CDCl₃) δ: 7.94 (1H, s), 7.59-7.53 (2H, m), 7.22-7.16 (1H, m), 7.04-6.95 (2H, m), 6.93 (1H, dt, J = 15.2, 5.9 Hz), 6.42 (1H, d, J = 15.2 Hz), 6.37-6.31 (1H, m), 5.47-5.39 (1H, m), 5.16 (1H, q, J = 7.3 Hz), 3.78-3.68 (1H, m), 3.48-3.40 (2H, m), 3.11 (2H, d, J = 5.9 Hz), 2.98 (3H, s), 2.66-2.56 (1H, m), 2.35-2.26 (1H, m), 2.28 (6H, s), 2.05-1.96 (1H, m), 1.89-1.77 (2H, m), 1.74-1.61 (2H, m), 1.45-1.25 (3H, m), 1.34 (3H, d, J = 7.3 Hz), 1.16-1.02 (1H, m), 1.00 (3H, t, J = 7.3 Hz) |
| 21-41 | 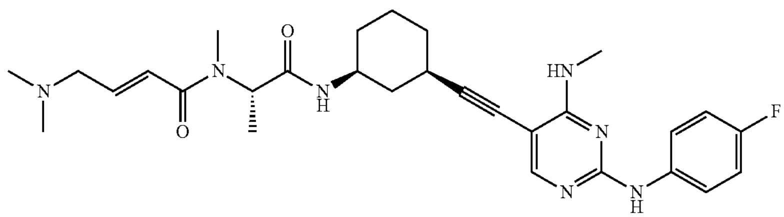 [SMILES: CNc1nc(Nc2ccc(F)cc2)ncc1C#C[C@@H]1CCC[C@H](NC(=O)[C@H](C)N(C)C(=O)/C=C/CN(C)C)C1] | ¹H-NMR (CDCl₃) δ: 7.95 (1H, s), 7.60-7.54 (2H, m), 7.04-6.96 (2H, m), 6.97-6.87 (1H, m), 6.96-6.91 (1H, m), 6.42 (1H, d, J = 15.2 Hz), 6.34-6.27 (1H, m), 5.40-5.35 (1H, m), 5.15 (1H, q, J = 7.0 Hz), 3.76-3.68 (1H, m), 3.11 (2H, d, J = 5.9 Hz), 3.06 (3H, d, J = 5.3 Hz), 2.98 (3H, s), 2.65-2.56 (1H, m), 2.34-2.25 (1H, m), 2.28 (6H, s), 2.05-1.98 (1H, m), 1.88-1.78 (2H, m), 1.40-1.28 (3H, m), 1.34 (3H, d, J = 7.0 Hz), 1.15-1.04 (1H, m) |

TABLE 235

| Compound No. | Structure | Physicochemical data |
|---|---|---|
| 21-42 | 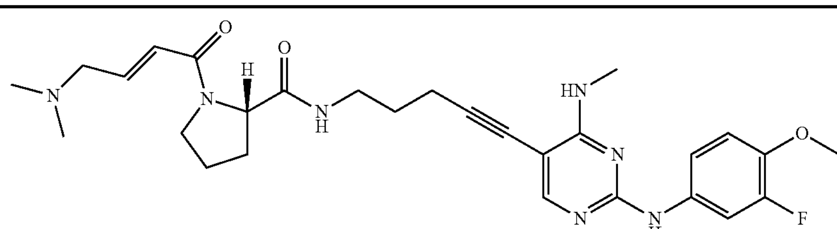 | ¹H-NMR (CDCl₃) δ: 7.92 (1H, s), 7.78 (1H, dd, J = 14.2, 2.3 Hz), 7.49 (1H, t, J = 5.9 Hz), 7.17 (1H, brs), 7.11-7.08 (1H, m), 7.01-6.86 (2H, m), 6.36-6.30 (2H, m), 4.68 (1H, d, J = 6.6 Hz), 3.87 (3H, s), 3.68 (1H, dt, J = 9.1, 2.4 Hz), 3.55-3.41 (3H, m), 3.10 (2H, d, J = 5.9 Hz), 3.07 (3H, d, J = 4.6 Hz), 2.48-2.43 (3H, m), 2.26 (6H, s), 1.96 (3H, brs), 1.78-1.73 (2H, m) |

TABLE 235-continued

| Compound No. | Structure | Physicochemical data |
|---|---|---|
| 21-43 | 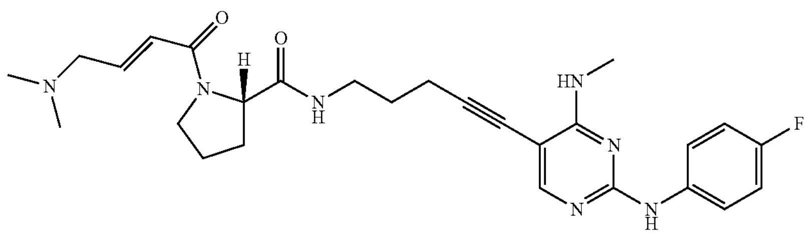 [SMILES: CNc1nc(Nc2ccc(F)cc2)ncc1C#CCCCNC(=O)[C@@H]1CCCN1C(=O)/C=C/CN(C)C] | ¹H-NMR (CDCl₃) δ: 7.93 (1H, s), 7.63-7.55 (2H, m), 7.49 (1H, t, J = 5.9 Hz), 7.30 (1H, brs), 7.03-6.91 (3H, m), 6.35-6.28 (2H, m), 4.68 (1H, d, J = 6.6 Hz), 3.71-3.64 (1H, m), 3.56-3.38 (3H, m), 3.10 (2H, d, J = 5.3 Hz), 3.05 (3H, d, J = 5.1 Hz), 2.48-2.43 (3H, m), 2.26 (6H, s), 2.10 (3H, brs), 1.78-1.73 (2H, m) |
| 21-44 | 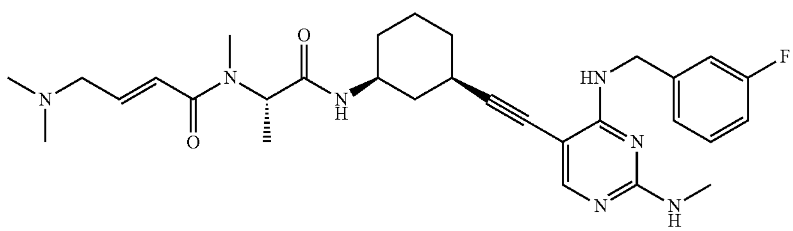 [SMILES: CNc1ncc(C#C[C@@H]2CCC[C@H](NC(=O)[C@H](C)N(C)C(=O)/C=C/CN(C)C)C2)c(NCc2cccc(F)c2)n1] | ¹H-NMR (CDCl₃) δ: 7.93 (1H, s), 7.36-7.23 (1H, m), 7.15-7.00 (2H, m), 7.00-6.85 (2H, m), 6.40 (1H, d, J = 15.2 Hz), 6.27 (1H, d, J = 7.9 Hz), 5.70-5.55 (1H, m), 5.13 (1H, q, J = 7.0 Hz), 5.00-4.86 (1H, m), 4.74-4.62 (2H, m), 3.78-3.61 (1H, m), 3.09 (2H, d, J = 5.3 Hz), 3.01-2.86 (6H, m), 2.67-2.51 (1H, m), 2.34-2.19 (7H, m), 2.08-1.71 (3H, m), 1.49-1.19 (6H, m), 1.15-0.97 (1H, m) |
| 21-45 | 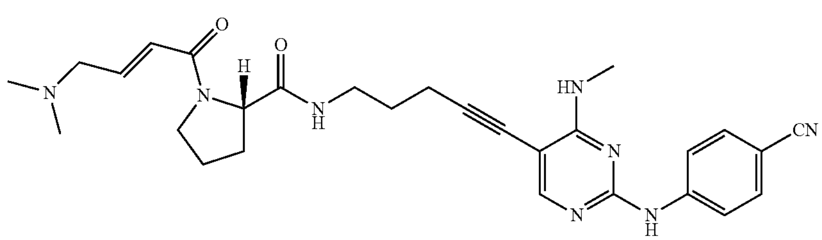 [SMILES: CNc1nc(Nc2ccc(C#N)cc2)ncc1C#CCCCNC(=O)[C@@H]1CCCN1C(=O)/C=C/CN(C)C] | ¹H-NMR (CDCl₃) δ: 7.96 (1H, s), 7.80 (2H, d, J = 8.6 Hz), 7.71 (1H, brs), 7.56 (2H, d, J = 8.6 Hz), 7.51 (1H, t, J = 5.9 Hz), 6.96 (1H, dt, J = 15.2, 5.9 Hz), 6.54 (1H, brs), 6.33 (1H, d, J = 15.2 Hz), 4.69 (1H, d, J = 6.6 Hz), 3.72-3.65 (1H, m), 3.59-3.36 (3H, m), 3.12-3.07 (5H, m), 2.49-2.26 (3H, m), 2.26 (6H, s), 1.97 (3H, brs), 1.80-1.71 (2H, m) |
| 21-46 | 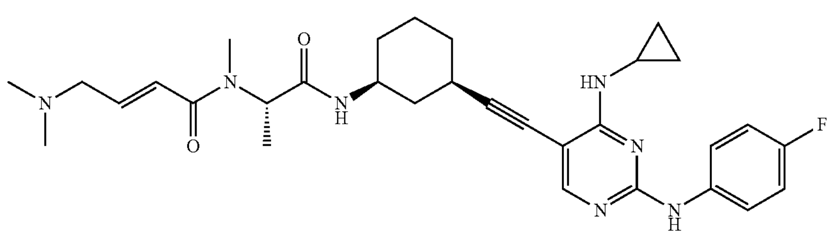 [SMILES: C[C@@H](C(=O)N[C@H]1CCC[C@@H](C#Cc2cnc(Nc3ccc(F)cc3)nc2NC2CC2)C1)N(C)C(=O)/C=C/CN(C)C] | ¹H-NMR (CDCl₃) δ: 7.96 (1H, s), 7.69-7.63 (2H, m), 7.04-6.98 (1H, m), 7.03-6.95 (2H, m), 6.93 (1H, dt, J = 15.2, 5.9 Hz), 6.41 (1H, d, J = 15.2 Hz), 6.33-6.26 (1H, m), 5.53-5.50 (1H, m), 5.15 (1H, q, J = 7.0 Hz), 3.78-3.68 (1H, m), 3.10 (2H, d, J = 5.9 Hz), 2.97 (3H, s), 2.85-2.77 (1H, m), 2.64-2.55 (1H, m), 2.31-2.24 (1H, m), 2.28 (6H, s), 2.05-1.95 (1H, m), 1.88-1.75 (2H, m), 1.41-1.24 (3H, m), 1.34 (3H, d, J = 7.0 Hz), 1.15-1.02 (1H, m), 0.92-0.84 (2H, m), 0.67-0.59 (2H, m) |

TABLE 236

| Compound No. | Structure | Physicochemical data |
|---|---|---|
| 21-47 | 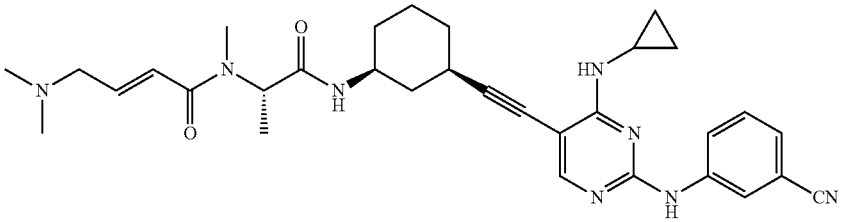 [SMILES: C[C@@H](C(=O)N[C@H]1CCC[C@@H](C#Cc2cnc(Nc3cccc(C#N)c3)nc2NC2CC2)C1)N(C)C(=O)/C=C/CN(C)C] | $^1$H-NMR (CDCl$_3$) δ: 8.74 (1H, s), 7.98 (1H, s), 7.87-7.84 (1H, m), 7.59-7.53 (1H, m), 7.35 (1H, dd, J = 7.6, 7.6 Hz), 7.27-7.22 (1H, m), 6.93 (1H, dt, J = 15.2, 5.9 Hz), 6.53-6.45 (1H, m), 6.43 (1H, d, J = 15.2 Hz), 5.65-5.62 (1H, m), 5.17 (1H, q, J = 7.0 Hz), 3.78-3.69 (1H, m), 3.12 (2H, d, J = 5.9 Hz), 3.00 (3H, s), 2.87-2.80 (1H, m), 2.65-2.56 (1H, m), 2.37-2.28 (1H, m), 2.28 (6H, s), 2.06-1.95 (1H, m), 1.89-1.76 (2H, m), 1.42-1.22 (3H, m), 1.34 (3H, d, J = 7.0 Hz), 1.14-1.07 (1H, m), 1.05-0.97 (2H, m), 0.74-0.65 (2H, m) |
| 21-48 | 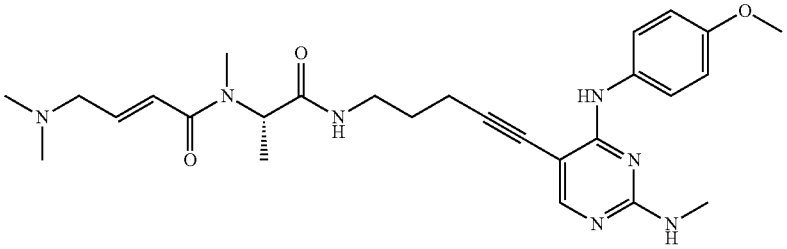 | $^1$H-NMR (CDCl$_3$) δ: 8.01 (1H, s), 7.69-7.55 (3H, m), 6.99-6.81 (3H, m), 6.57-6.49 (1H, m), 6.41 (1H, dt, J = 15.2, 1.3 Hz), 5.18 (1H, q, J = 6.8 Hz), 5.11-4.98 (1H, m), 3.81 (3H, s), 3.52-3.38 (2H, m), 3.10 (2H, dd, J = 5.9, 1.3 Hz), 3.01-2.89 (6H, m), 2.47 (2H, t, J = 6.9 Hz), 2.26 (6H, s), 1.87-1.62 (2H, m), 1.34 (3H, d, J = 6.8 Hz) |
| 21-49 | 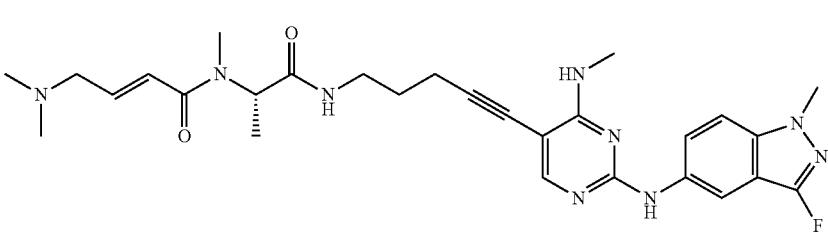 [SMILES: CNc1nc(Nc2ccc3c(c2)c(F)nn3C)ncc1C#CCCCNC(=O)[C@H](C)N(C)C(=O)/C=C/CN(C)C] | $^1$H-NMR (CDCl$_3$) δ: 8.20 (1H, d, J = 2.0 Hz), 7.95 (1H, s), 7.42 (1H, dd, J = 8.6, 2.0 Hz), 7.22 (1H, dd, J = 8.6, 2.0 Hz), 7.14-7.05 (1H, m), 6.94 (1H, dt, J = 15.2, 5.9 Hz), 6.61-6.51 (1H, m), 6.43 (1H, d, J = 15.2 Hz), 6.34-6.24 (1H, m), 5.19 (1H, q, J = 7.0 Hz), 3.90 (3H, s), 3.52-3.39 (2H, m), 3.15-3.06 (5H, m), 3.00 (3H, s), 2.44 (2H, t, J = 6.6 Hz), 2.27 (6H, s), 1.82-1.68 (2H, m), 1.37 (3H, d, J = 7.0 Hz) |
| 21-50 | 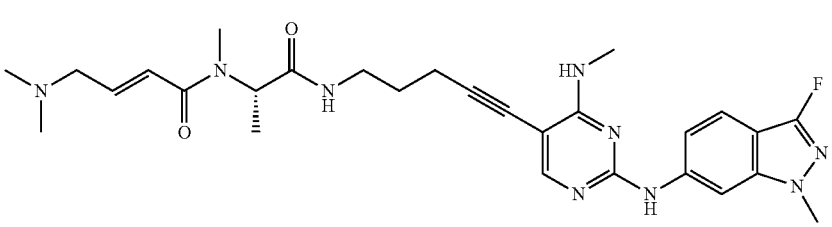 [SMILES: CNc1nc(Nc2ccc3c(F)nn(C)c3c2)ncc1C#CCCCNC(=O)[C@H](C)N(C)C(=O)/C=C/CN(C)C] | $^1$H-NMR (CDCl$_3$) δ: 8.35 (1H, s), 8.00 (1H, s), 7.49 (1H, d, J = 8.6 Hz), 7.31 (1H, s), 7.01-6.84 (2H, m), 6.64-6.54 (1H, m), 6.48-6.38 (2H, m), 5.20 (1H, q, J = 7.0 Hz), 3.87 (3H, s), 3.52-3.41 (2H, m), 3.17 (3H, d, J = 5.3 Hz), 3.11 (2H, d, J = 5.3 Hz), 3.01 (3H, s), 2.44 (2H, t, J = 6.3 Hz), 2.27 (6H, s), 1.83-1.70 (2H, m), 1.38 (3H, d, J = 7.0 Hz) |

TABLE 237

| Compound No. | Structure | Physicochemical data |
|---|---|---|
| 21-51 | 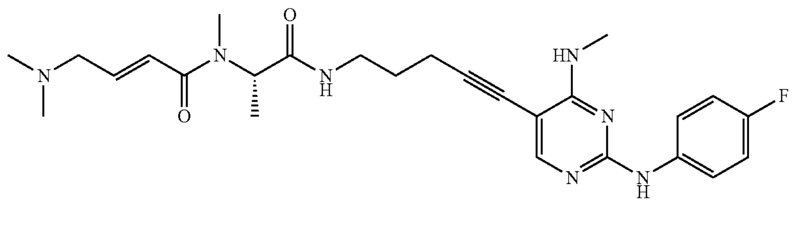 [SMILES: CNc1nc(Nc2ccc(F)cc2)ncc1C#CCCCNC(=O)[C@H](C)N(C)C(=O)/C=C/CN(C)C] | ¹H-NMR (CDCl₃) δ: 7.94 (1H, s), 7.61-7.55 (2H, m), 7.04-6.96 (2H, m), 6.98-6.94 (1H, m), 6.98-6.89 (1H, m), 6.57-6.51 (1H, m), 6.42 (1H, d, J = 15.2 Hz), 6.28-6.22 (1H, m), 5.19 (1H, q, J = 7.0 Hz), 3.51-3.38 (2H, m), 3.10 (2H, d, J = 5.9 Hz), 3.07 (3H, d, J = 5.3 Hz), 2.99 (3H, s), 2.43 (2H, t, J = 6.3 Hz), 2.27 (6H, s), 1.77-1.69 (2H, m), 1.36 (3H, d, J = 7.0 Hz) |
| 21-52 | 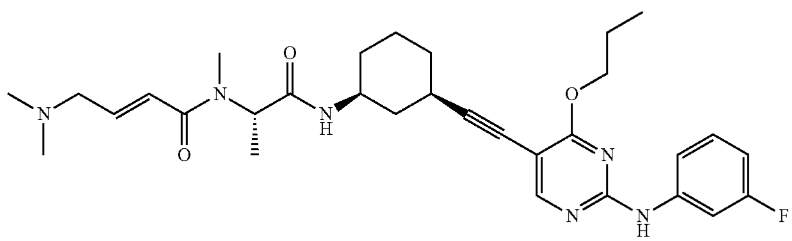 [SMILES: CCCOc1nc(Nc2cccc(F)c2)ncc1C#C[C@@H]1CCC[C@H](NC(=O)[C@H](C)N(C)C(=O)/C=C/CN(C)C)C1] | ¹H-NMR (CDCl₃) δ: 8.19 (1H, s), 7.72-7.66 (1H, m), 7.28-7.21 (1H, m), 7.14-7.11 (1H, m), 7.14-7.09 (1H, m), 6.92 (1H, dt, J = 15.2, 5.9 Hz), 6.72 (1H, td, J = 8.3, 2.0 Hz), 6.41 (1H, d, J = 15.2 Hz), 6.29-6.22 (1H, m), 5.16 (1H, q, J = 7.0 Hz), 4.36 (2H, t, J = 6.6 Hz), 3.79-3.70 (1H, m), 3.10 (2H, d, J = 5.9 Hz), 2.97 (3H, s), 2.65-2.56 (1H, m), 2.32-2.25 (1H, m), 2.27 (6H, s), 2.03-1.96 (1H, m), 1.91-1.81 (2H, m), 1.86-1.77 (2H, m), 1.38-1.26 (3H, m), 1.33 (3H, d, J = 7.0 Hz), 1.10-1.03 (1H, m), 1.06 (3H, t, J = 7.6 Hz) |

7

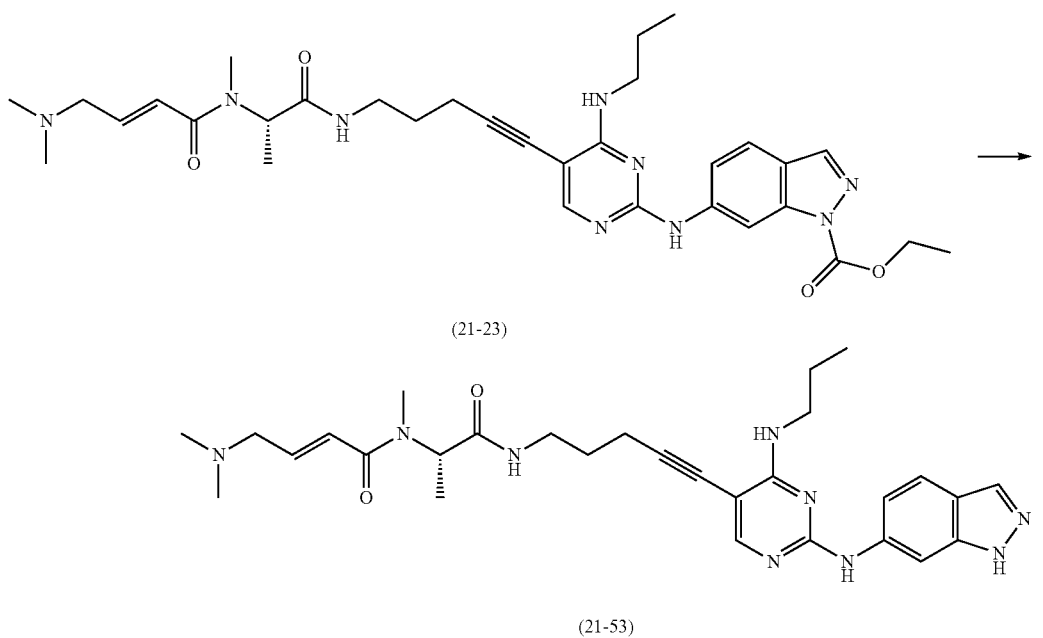

[Formula 355]

(21-23)

(21-53)

To (S,E)-ethyl 6-((5-(5-(2-(4-(dimethylamino)-N-methyl-2-butenamido)propaneamido)-1-pentyn-1-yl)-4-(propylamino)pyrimidin-2-yl)amino)-1H-indazole-1-carboxylate (21-23, 17.3 mg), tetrahydrofuran (1.0 mL) and 1.0 mol/L aqueous lithium hydroxide (1.0 mL) were added at room temperature, and the mixture was stirred at the same temperature for 30 minutes. To the reaction mixture, water and ethyl acetate were added. The organic layer was separated, washed with saturated aqueous sodium chloride, and then dried over anhydrous sodium sulfate, and the solvent was evaporated under reduced pressure. The obtained residue was purified by basic silica gel column chromatography (eluent, 100 to 90% ethyl acetate in methanol) to obtain (S,E)-N-(1-((5-(2 -((1H-indazol-6-yl)amino)-4-(propylamino)pyrimidin-5-yl)-4-pentyn-1-yl)amino)-1-oxopropan-2-yl)-4-(dimethylamino)-N-methyl-2-butenamide (21-53, 9.8 mg) as pale yellow solid.

$^1$H-NMR (CDCl$_3$) δ: 10.6-10.2 (1H, m), 8.26 (1H, s), 8.03-7.92 (2H, m), 7.62 (1H, d, J=8.6 Hz), 7.50-7.40 (1H, m), 7.17-7.05 (1H, m), 6.95 (1H, dt, J=15.2, 5.9 Hz), 6.78-6.64 (1H, m), 6.44 (1H, d, J=15.2 Hz), 6.26-6.12 (1H, m), 5.20 (1H, q, J=7.0 Hz), 3.57-3.38 (4H, m), 3.16-3.08 (2H, m), 3.01 (3H, s), 2.45 (2H, t, J=6.6 Hz), 2.28 (6H, s), 1.83-1.65 (4H, m), 1.37 (3H, d, J=6.9 Hz), 1.01 (3H, t, J=7.4 Hz)

8

By using Compounds (21-24) to (21-26), Compounds (21-54) to (21-56) were obtained in the same manner as that of Example 69, (7).

Example 70

1

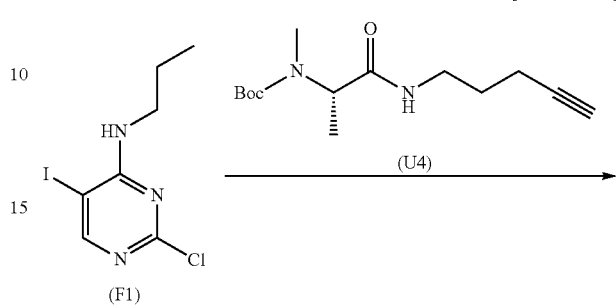

(F1) + (U4) →

[Formula 356]

TABLE 238

| Compound No. | Structure | Physicochemical data |
|---|---|---|
| 21-54 | 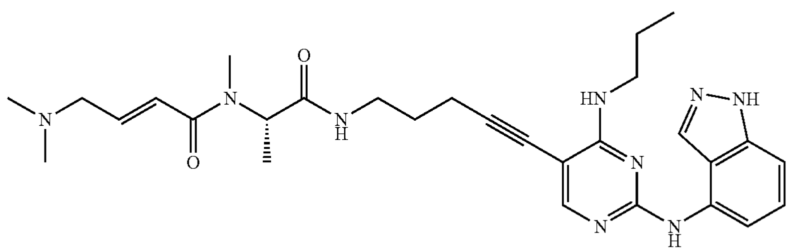 [SMILES: CCCNc1nc(Nc2cccc3[nH]ncc23)ncc1C#CCCCNC(=O)[C@H](C)N(C)C(=O)/C=C/CN(C)C] | $^1$H-NMR (CDCl$_3$) δ: 10.9-10.6 (1H, m), 8.31 (1H, s), 8.09 (1H, d, J = 7.6 Hz), 8.04 (1H, s), 7.82-7.68 (1H, m), 7.37 (1H, dd, J = 8.3, 7.9 Hz), 7.15 (1H, d, J = 8.3 Hz), 6.95 (1H, dt, J = 15.2, 5.9 Hz), 6.62-6.50 (1H, m), 6.44 (1H, d, J = 15.2 Hz), 6.32-6.20 (1H, m), 5.20 (1H, q, J = 7.2 Hz), 3.59-3.40 (4H, m), 3.16-3.07 (2H, m), 3.00 (3H, s), 2.45 (2H, t, J = 6.8 Hz), 2.28 (6H, s), 1.85-1.58 (4H, m), 1.37 (3H, d, J = 6.9 Hz), 1.01 (3H, t, J = 7.4 Hz) |
| 21-55 | 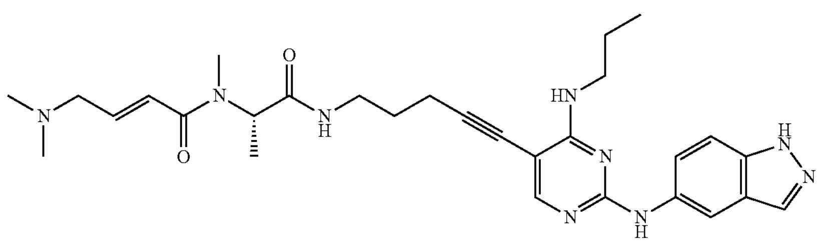 [SMILES: CCCNc1nc(Nc2ccc3[nH]ncc3c2)ncc1C#CCCCNC(=O)[C@H](C)N(C)C(=O)/C=C/CN(C)C] | $^1$H-NMR (CDCl$_3$) δ: 10.5-10.0 (1H, m), 8.20 (1H, s), 8.00 (1H, s), 7.97 (1H, s), 7.48-7.37 (2H, m), 7.16-7.05 (1H, m), 6.95 (1H, dt, J = 15.2, 5.9 Hz), 6.63-6.50 (1H, m), 6.43 (1H, d, J = 15.2 Hz), 6.25-6.08 (1H, m), 5.20 (1H, q, J = 7.0 Hz), 3.65-3.37 (4H, m), 3.14-3.07 (2H, m), 3.00 (3H, s), 2.44 (2H, t, J = 6.6 Hz), 2.27 (6H, s), 1.85-1.61 (4H, m), 1.36 (3H, d, J = 6.9 Hz), 1.01 (3H, t, J = 7.4 Hz) |
| 21-56 | 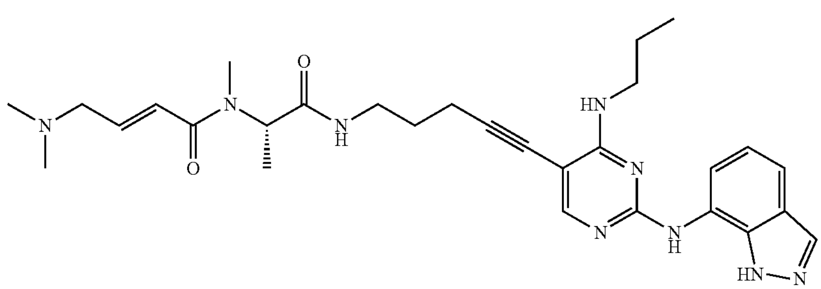 [SMILES: CCCNc1nc(Nc2cccc3cn[nH]c23)ncc1C#CCCCNC(=O)[C@H](C)N(C)C(=O)/C=C/CN(C)C] | $^1$H-NMR (CDCl$_3$) δ: 12.7-12.3 (1H, m), 8.06 (1H, s), 7.98 (1H, s), 7.52-7.43 (1H, m), 7.37-7.29 (1H, m), 7.12-7.03 (2H, m), 6.95 (1H, dt, J = 15.2, 5.9 Hz), 6.70-6.58 (1H, m), 6.43 (1H, d, J = 15.2 Hz), 6.32-6.24 (1H, m), 5.20 (1H, q, J = 7.0 Hz), 3.53-3.35 (4H, m), 3.15-3.05 (2H, m), 3.00 (3H, s), 2.45 (2H, t, J = 6.6 Hz), 2.27 (6H, s), 1.85-1.58 (4H, m), 1.36 (3H, d, J = 6.9 Hz), 0.95 (3H, t, J = 7.4 Hz) |

-continued

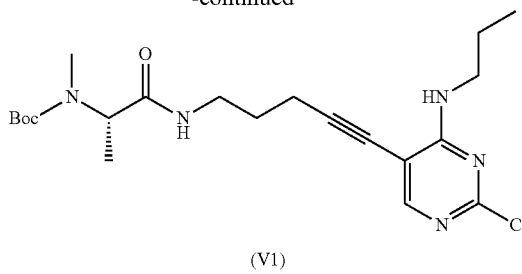

(V1)

To a solution of 2-chloro-5-iodo-N-propylpyrimidin-4-amine (F1, 2.00 g) and (S)-tert-butyl methyl(1-oxo-1-(4-pentyn-1-ylamino)propan-2-yl)carbamate (U4, 2.16 g) in N,N-dimethylformamide (40 mL), triethylamine (4.67 mL), bis(triphenylphosphine)palladium(II) dichloride (0.47 g) and copper(I) iodide (0.26 g) were added at room temperature, and the mixture was stirred at the same temperature for 1.5 hours, and then further stirred at 45° C. for 0.5 hour. The reaction mixture was cooled to room temperature, and then saturated aqueous ammonium chloride and ethyl acetate were added to the reaction mixture. The organic layer was separated, washed with saturated aqueous sodium chloride, and then dried over anhydrous sodium sulfate, and the solvent was evaporated under reduced pressure. The obtained residue was purified by silica gel column chromatography (eluent, 80 to 30% hexane in ethyl acetate) to obtain (S)-tert-butyl (1-((5-(2-chloro-4-(propylamino)pyrimidin-5-yl)-4-pentyn-1-yl)amino)-1-oxopropan-2-yl)(methyl)carbamate (V1, 2.49 g) as pale yellow oil.

MS m/z (M+H): 438.3

To a solution of tris(dibenzylideneacetone)dipalladium(0) (1.0 mg) in 1,4-dioxane (0.86 mL), 2-(dicyclohexylphosphino)-3,6-dimethoxy-2',4',6'-triisopropyl-1,1'-biphenyl (1.5 mg) was added at room temperature under a nitrogen atmosphere, and the mixture was stirred at 100° C. for 5 minutes. The reaction mixture was cooled to room temperature, and then (S)-tert-butyl (1-((5-(2-chloro-4-(propylamino)pyrimidin-5-yl)-4-pentyn-1-yl)amino)-1-oxopropan-2-yl)(methyl)carbamate (V1, 12.5 mg), 2-methyl-4-aminopyridine (4.0 mg) and cesium carbonate (19 mg) were added, and the mixture was stirred at 70° C. for 1 hour. The reaction mixture was cooled to room temperature, and then ethyl acetate was added to the reaction mixture. The insoluble matter was removed by filtration through Cerite, and then the solvent was evaporated under reduced pressure. The obtained residue was purified by silica gel column chromatography (eluent, 80 to 0% hexane in ethyl acetate) to obtain (S)-tert-butyl methyl(1-((5-(2-((2-methylpyridin-4-yl)amino)-4-(propylamino)pyrimidin-5-yl)-4-pentyn-1-yl)amino)-1-oxopropan-2-yl)carbamate (V2, 5.6 mg) as yellow oil.

MS m/z (M+H): 510.4

[Formula 357]

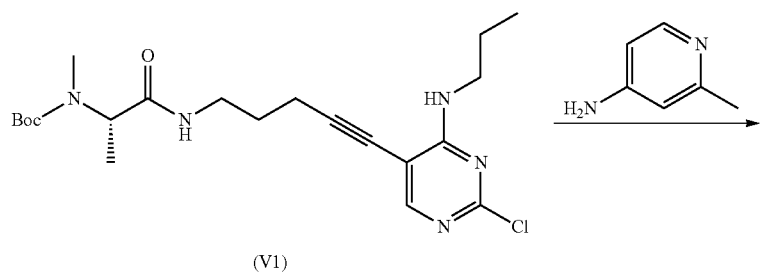

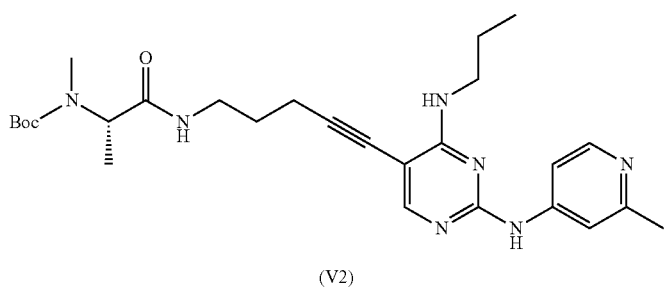

(V2)

3

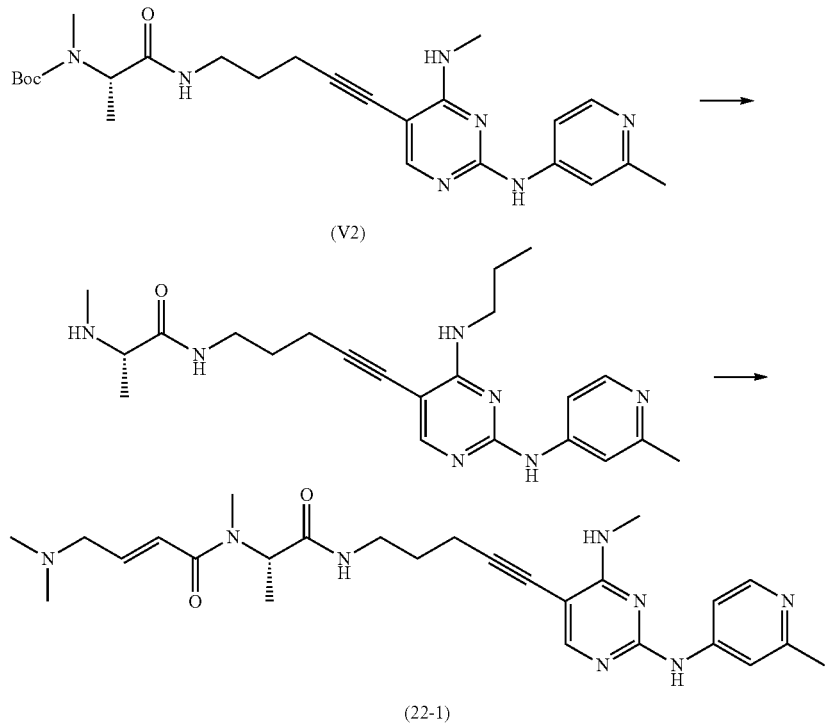

[Formula 358]

By using (S)-tert-butyl methyl(1-((5-(2-((2-methylpyridin-4-yl)amino)-4-(propylamino)pyrimidin-5-yl)-4-pentyn-1-yl)amino)-1-oxopropan-2-yl)carbamate (V2), (S,E)-4-(dimethylamino)-N-methyl-N-(1-((5-(2-((2-methylpyridin-4-yl)amino)-4-(propylamino)pyrimidin-5-yl)-4-pentyn-1-yl)amino)-1-oxopropan-2-yl)-2-butenamide (22-1) was obtained in the same manner as that of Example 35, (6) and (7).

$^1$H-NMR (CDCl$_3$) δ: 8.30 (1H, d, J=5.6 Hz), 7.98 (1H, s), 7.50 (1H, d, J=2.0 Hz), 7.37 (1H, dd, J=5.6, 2.0 Hz), 7.07-7.00 (1H, m), 6.95 (1H, dt, J=15.2, 5.9 Hz), 6.59-6.48 (1H, m), 6.47-6.35 (2H, m), 5.19 (1H, q, J=7.0 Hz), 3.60-3.40 (4H, m), 3.14-3.07 (2H, m), 3.00 (3H, s), 2.52 (3H, s), 2.44 (2H, t, J=6.6 Hz), 2.27 (6H, s), 1.85-1.65 (4H, m), 1.36 (3H, d, J=6.9 Hz), 1.01 (3H, t, J=7.3 Hz)

4

In the same manner as that of Example 70, (1), Intermediates (V3) to (V5) were obtained.

TABLE 239

| Compound No. | Structure | Physicochemical data |
|---|---|---|
| V3 | 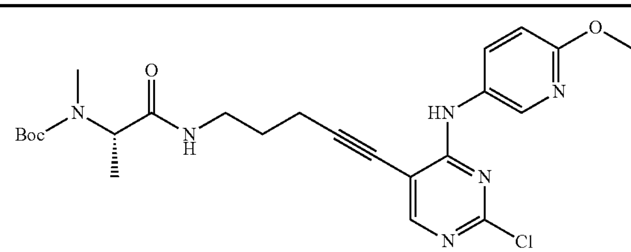 | MS m/z (M + H): 503.4 |
| V4 | 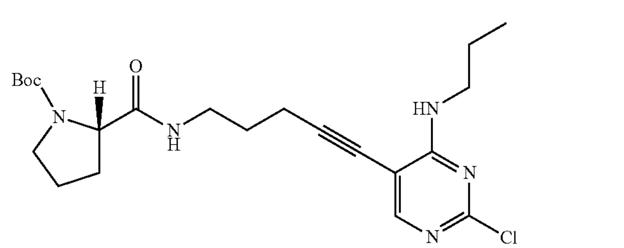 [SMILES: CCCNc1nc(Cl)ncc1C#CCCCNC(=O)[C@@H]1CCCN1C(=O)OC(C)(C)C] | MS m/z (M + H): 450.3 |

TABLE 239-continued

| Compound No. | Structure | Physicochemical data |
|---|---|---|
| V5 | 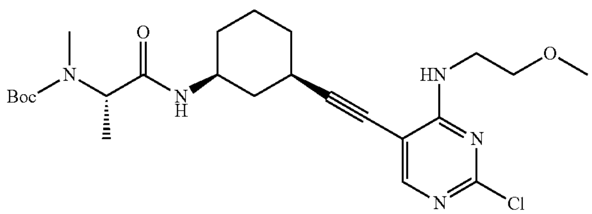 [SMILES: COCCNc1nc(Cl)ncc1C#C[C@@H]1CCC[C@H](NC(=O)[C@H](C)N(C)C(=O)OC(C)(C)C)C1] | MS m/z (M + H): 494.3 |

In the same manner as that of Example 70, (2), Intermediates (V6) to (V59) were obtained.

TABLE 240

| Compound No. | Structure | Physicochemical data |
|---|---|---|
| V6 | 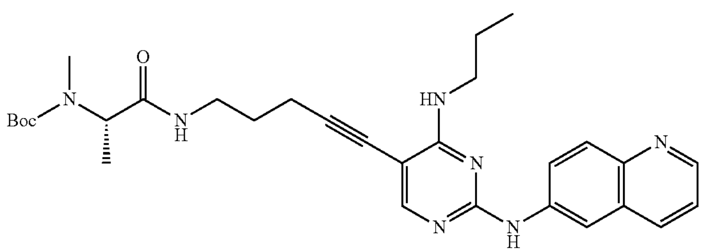 [SMILES: CCCNc1nc(Nc2ccc3ncccc3c2)ncc1C#CCCCNC(=O)[C@H](C)N(C)C(=O)OC(C)(C)C] | MS m/z (M + H): 546.4 |
| V7 | 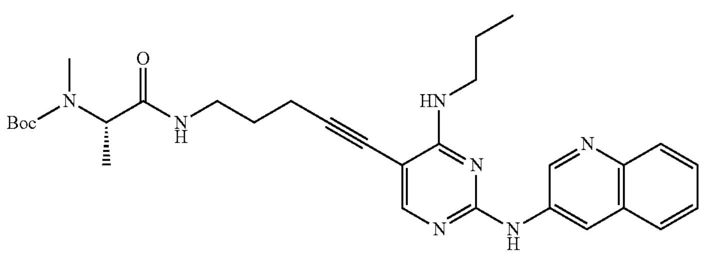 [SMILES: CCCNc1nc(Nc2cnc3ccccc3c2)ncc1C#CCCCNC(=O)[C@H](C)N(C)C(=O)OC(C)(C)C] | MS m/z (M + H): 546.4 |
| V8 | 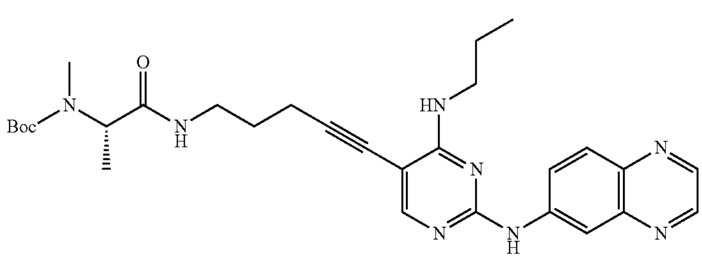 [SMILES: CCCNc1nc(Nc2ccc3nccnc3c2)ncc1C#CCCCNC(=O)[C@H](C)N(C)C(=O)OC(C)(C)C] | MS m/z (M + H): 547.4 |
| V9 | 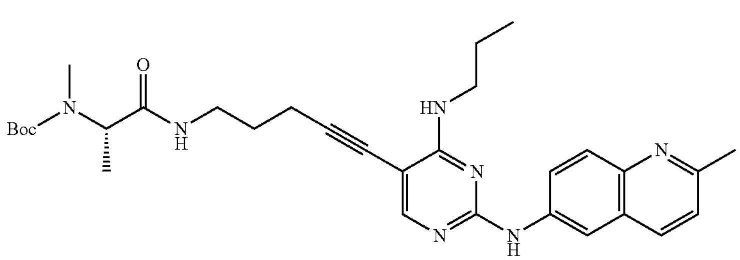 [SMILES: CCCNc1nc(Nc2ccc3nc(C)ccc3c2)ncc1C#CCCCNC(=O)[C@H](C)N(C)C(=O)OC(C)(C)C] | MS m/z (M + H): 560.5 |

TABLE 240-continued

| Compound No. | Structure | Physicochemical data |
|---|---|---|
| V10 | 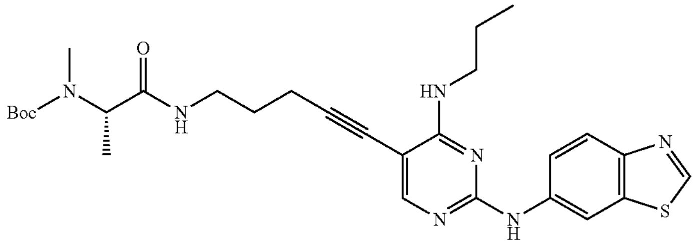 [SMILES: CCCNc1nc(Nc2ccc3ncsc3c2)ncc1C#CCCCNC(=O)[C@H](C)N(C)C(=O)OC(C)(C)C] | MS m/z (M + H): 552.4 |
| V11 | 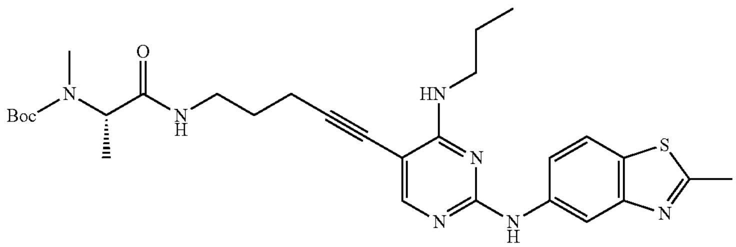 [SMILES: CCCNc1nc(Nc2ccc3sc(C)nc3c2)ncc1C#CCCCNC(=O)[C@H](C)N(C)C(=O)OC(C)(C)C] | MS m/z (M + H): 566.4 |
| V12 | 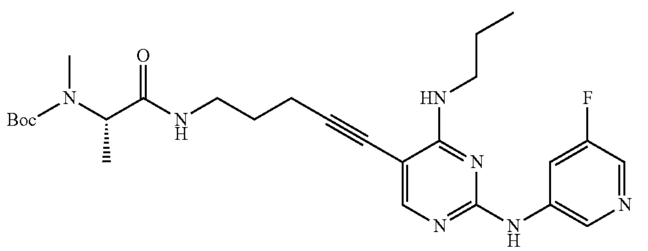 [SMILES: CCCNc1nc(Nc2cncc(F)c2)ncc1C#CCCCNC(=O)[C@H](C)N(C)C(=O)OC(C)(C)C] | MS m/z (M + H): 514.4 |
| V13 | 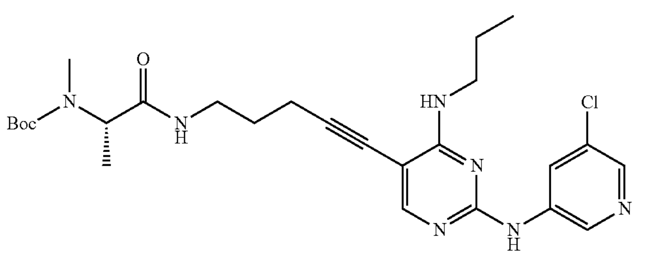 [SMILES: CCCNc1nc(Nc2cncc(Cl)c2)ncc1C#CCCCNC(=O)[C@H](C)N(C)C(=O)OC(C)(C)C] | MS m/z (M + H): 530.4 |
| V14 | 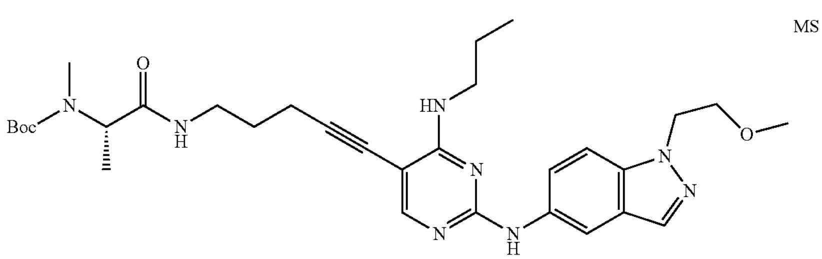 | MS m/z (M + H): 593.5 |

TABLE 241

| Compound No. | Structure | Physicochemical data |
|---|---|---|
| V15 | 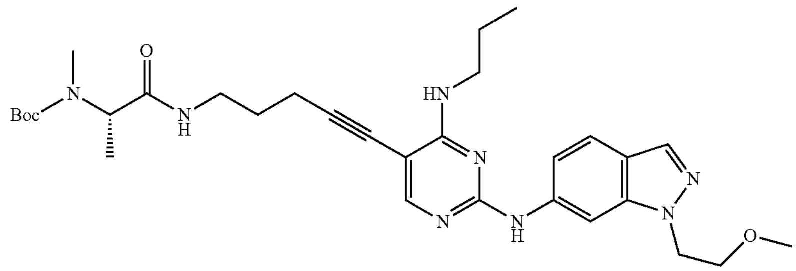 [SMILES: CCCNc1nc(Nc2ccc3cnn(CCOC)c3c2)ncc1C#CCCCNC(=O)[C@H](C)N(C)C(=O)OC(C)(C)C] | MS m/z (M + H): 593.5 |
| V16 | 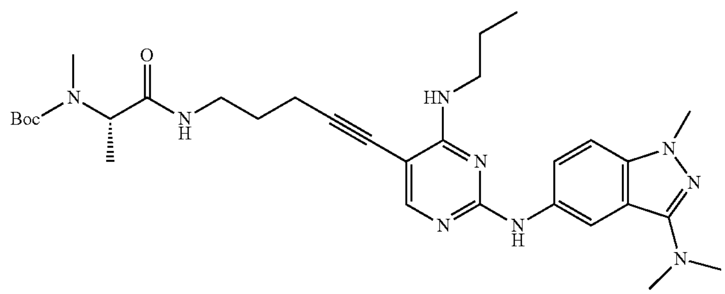 [SMILES: CCCNc1nc(Nc2ccc3c(c2)c(N(C)C)nn3C)ncc1C#CCCCNC(=O)[C@H](C)N(C)C(=O)OC(C)(C)C] | MS m/z (M + H): 592.5 |
| V17 | 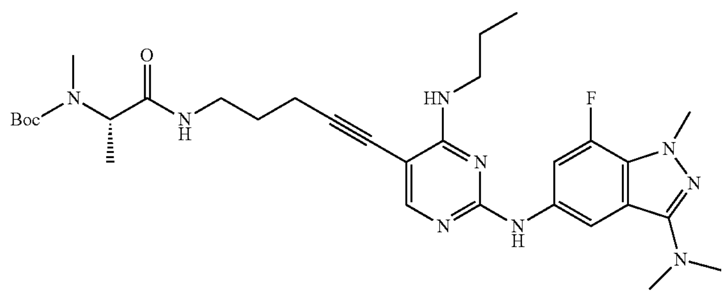 [SMILES: CCCNc1nc(Nc2cc(F)c3c(c2)c(N(C)C)nn3C)ncc1C#CCCCNC(=O)[C@H](C)N(C)C(=O)OC(C)(C)C] | MS m/z (M + H): 610.5 |
| V18 | 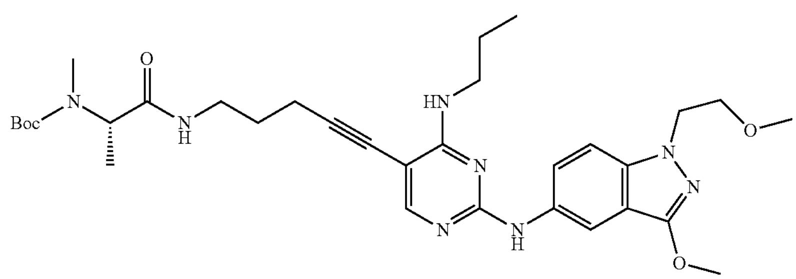 [SMILES: CCCNc1nc(Nc2ccc3c(c2)c(OC)nn3CCOC)ncc1C#CCCCNC(=O)[C@H](C)N(C)C(=O)OC(C)(C)C] | MS m/z (M + H): 623.5 |
| V19 | 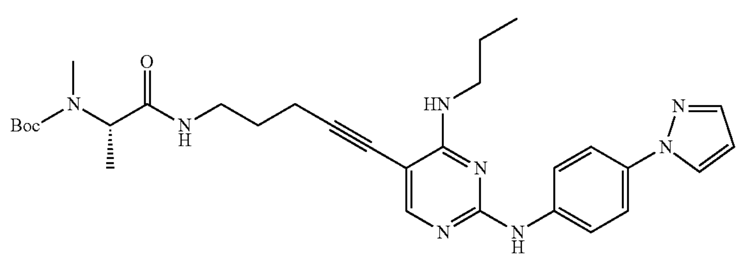 [SMILES: CCCNc1nc(Nc2ccc(-n3cccn3)cc2)ncc1C#CCCCNC(=O)[C@H](C)N(C)C(=O)OC(C)(C)C] | MS m/z (M + H): 561.5 |

TABLE 241-continued
| Compound No. | Structure | Physicochemical data |
|---|---|---|
| V20 | 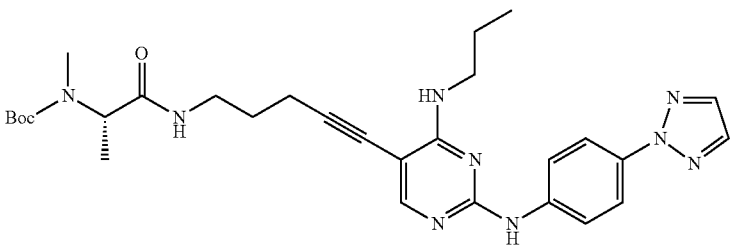 | MS m/z (M + H): 562.4 |
| V21 | 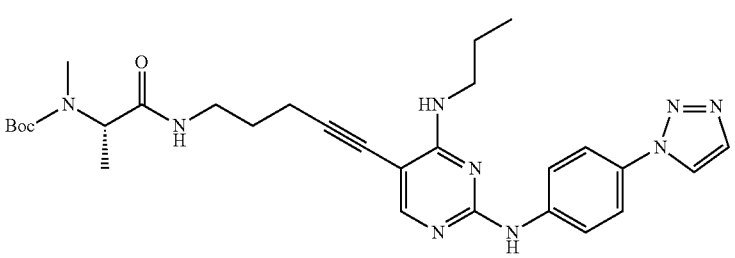 [SMILES: CCCNc1nc(Nc2ccc(-n3ccnn3)cc2)ncc1C#CCCCNC(=O)[C@H](C)N(C)C(=O)OC(C)(C)C] | MS m/z (M + H): 562.4 |
| V22 | 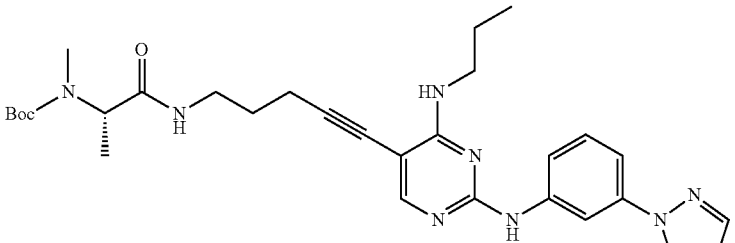 | MS m/z (M + H): 561.5 |
| V23 | 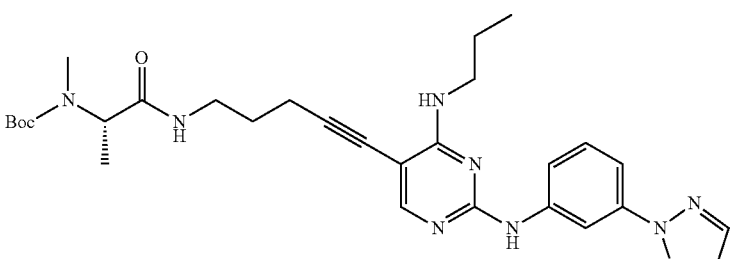 | MS m/z (M + H): 562.4 |
TABLE 242
| Compound No. | Structure | Physicochemical data |
|---|---|---|
| V24 | 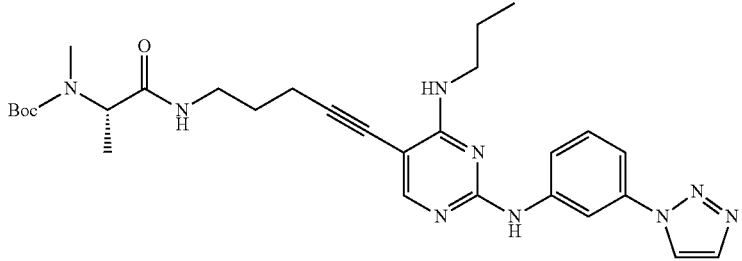 [SMILES: CCCNc1nc(Nc2cccc(-n3ccnn3)c2)ncc1C#CCCCNC(=O)[C@H](C)N(C)C(=O)OC(C)(C)C] | MS m/z (M + H): 562.4 |

TABLE 242-continued

| Compound No. | Structure | Physicochemical data |
|---|---|---|
| V25 | 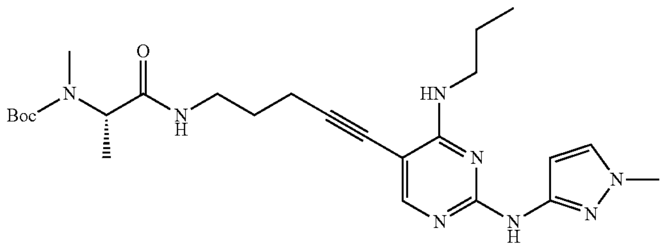 [SMILES: CCCNc1nc(Nc2ccn(C)n2)ncc1C#CCCCNC(=O)[C@H](C)N(C)C(=O)OC(C)(C)C] | MS m/z (M + H): 499.4 |
| V26 | 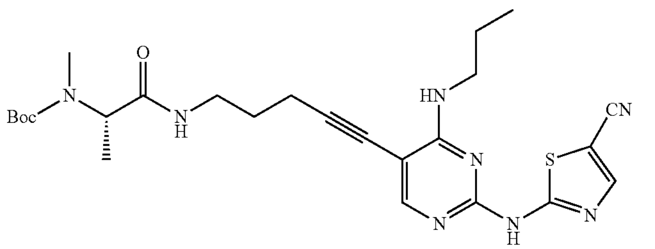 [SMILES: CCCNc1nc(Nc2ncc(C#N)s2)ncc1C#CCCCNC(=O)[C@H](C)N(C)C(=O)OC(C)(C)C] | MS m/z (M + H): 527.4 |
| V27 | 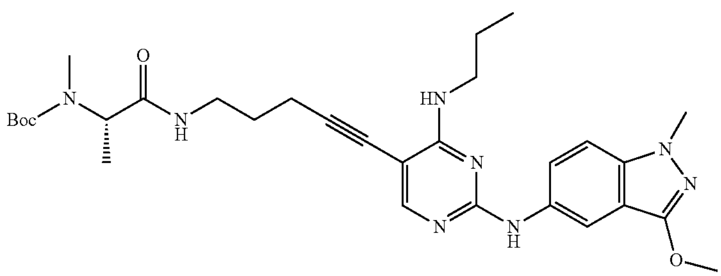 [SMILES: CCCNc1nc(Nc2ccc3c(c2)c(OC)nn3C)ncc1C#CCCCNC(=O)[C@H](C)N(C)C(=O)OC(C)(C)C] | MS m/z (M + H): 579.5 |
| V28 | 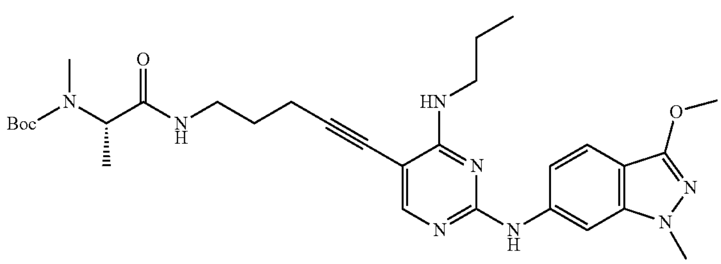 [SMILES: CCCNc1nc(Nc2ccc3c(OC)nn(C)c3c2)ncc1C#CCCCNC(=O)[C@H](C)N(C)C(=O)OC(C)(C)C] | MS m/z (M + H): 579.5 |
| V29 | 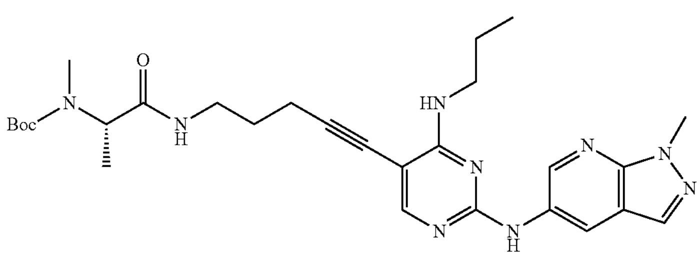 [SMILES: CCCNc1nc(Nc2cnc3c(cnn3C)c2)ncc1C#CCCCNC(=O)[C@H](C)N(C)C(=O)OC(C)(C)C] | MS m/z (M + H): 550.5 |
| V30 | 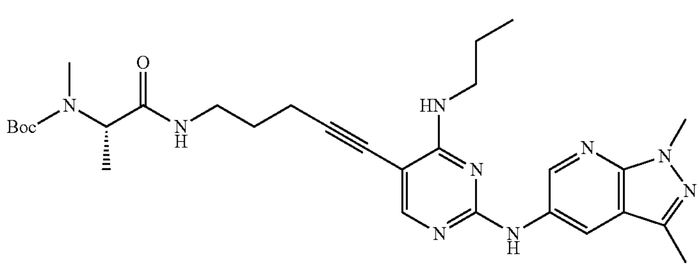 [SMILES: CCCNc1nc(Nc2cnc3c(c2)c(C)nn3C)ncc1C#CCCCNC(=O)[C@H](C)N(C)C(=O)OC(C)(C)C] | MS m/z (M + H): 564.5 |

TABLE 242-continued

| Compound No. | Structure | Physicochemical data |
|---|---|---|
| V31 | 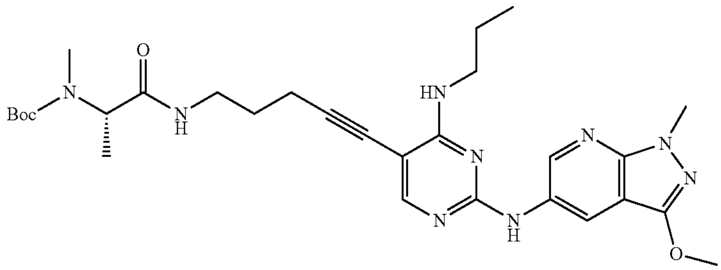 [SMILES: CCCNc1nc(Nc2cnc3c(c2)c(OC)nn3C)ncc1C#CCCCNC(=O)[C@H](C)N(C)C(=O)OC(C)(C)C] | MS m/z (M + H): 580.5 |
| V32 | 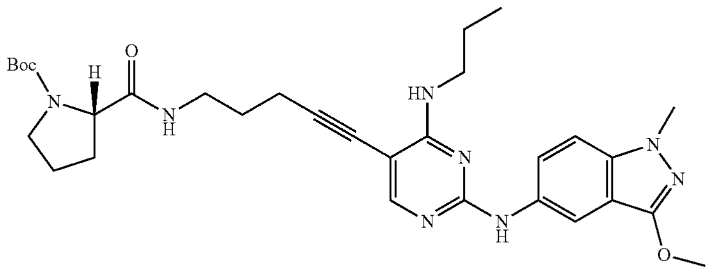 [SMILES: CCCNc1nc(Nc2ccc3c(c2)c(OC)nn3C)ncc1C#CCCCNC(=O)[C@@H]1CCCN1C(=O)OC(C)(C)C] | MS m/z (M + H): 591.5 |
| V33 | 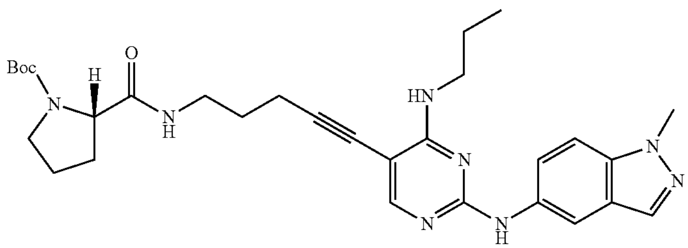 [SMILES: CCCNc1nc(Nc2ccc3c(cnn3C)c2)ncc1C#CCCCNC(=O)[C@@H]1CCCN1C(=O)OC(C)(C)C] | MS m/z (M + H): 561.5 |

TABLE 243

| Compound No. | Structure | Physicochemical data |
|---|---|---|
| V34 | 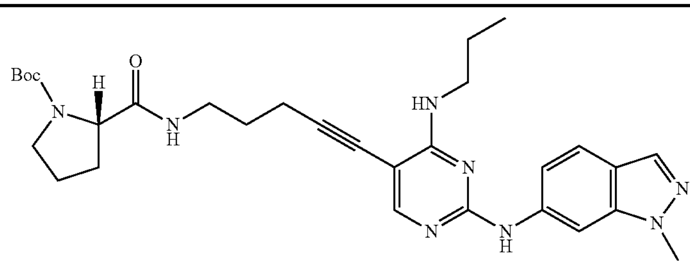 | MS m/z (M + H): 561.5 |
| V35 | 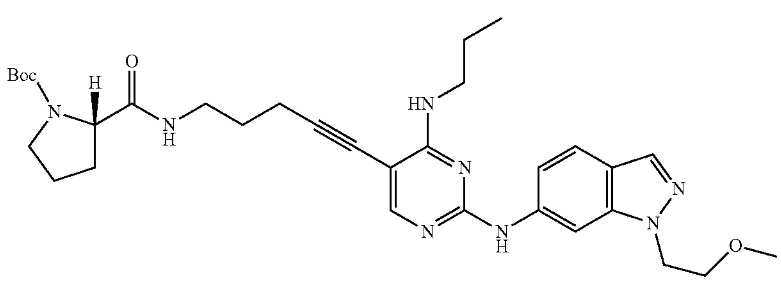 [SMILES: CCCNc1nc(Nc2ccc3cnn(CCOC)c3c2)ncc1C#CCCCNC(=O)[C@@H]1CCCN1C(=O)OC(C)(C)C] | MS m/z (M + H): 605.5 |

TABLE 243-continued

| Compound No. | Structure | Physicochemical data |
|---|---|---|
| V36 | 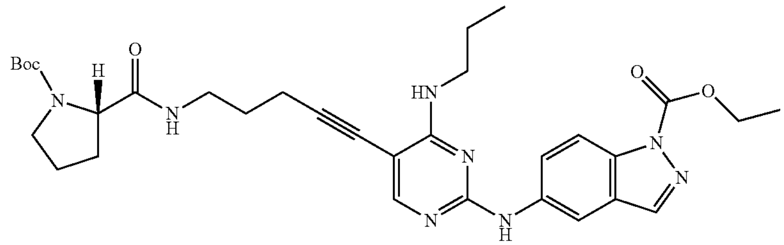 [SMILES: CCCNc1nc(Nc2ccc3c(cnn3C(=O)OCC)c2)ncc1C#CCCCNC(=O)[C@@H]1CCCN1C(=O)OC(C)(C)C] | MS m/z (M + H): 619.5 |
| V37 | 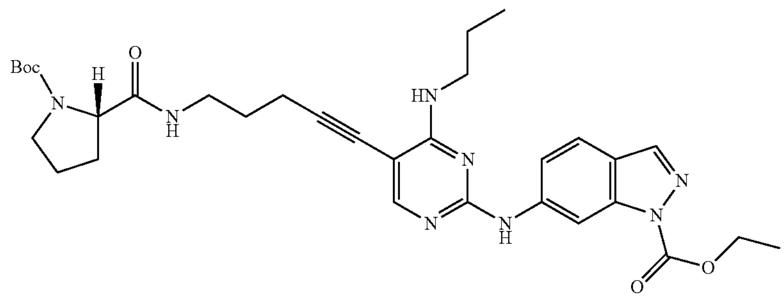 [SMILES: CCCNc1nc(Nc2ccc3cnn(C(=O)OCC)c3c2)ncc1C#CCCCNC(=O)[C@@H]1CCCN1C(=O)OC(C)(C)C] | MS m/z (M + H): 619.5 |
| V38 | 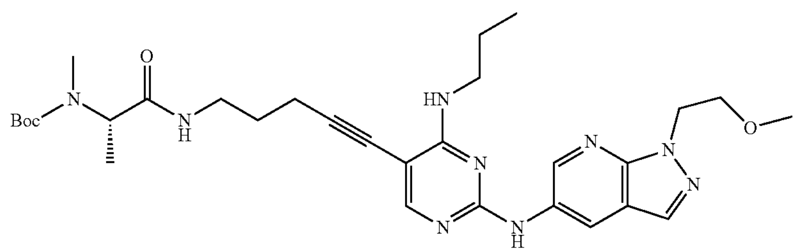 [SMILES: CCCNc1nc(Nc2cnc3c(cnn3CCOC)c2)ncc1C#CCCCNC(=O)[C@H](C)N(C)C(=O)OC(C)(C)C] | MS m/z (M + H): 594.5 |
| V39 | 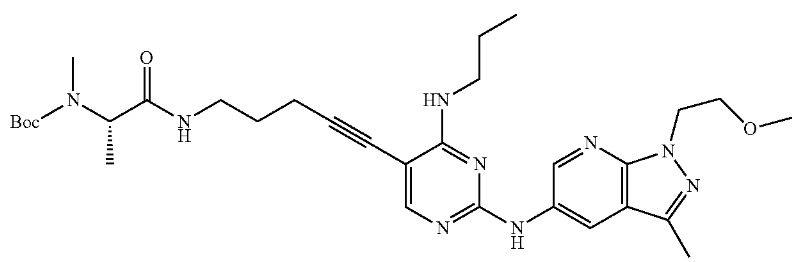 [SMILES: CCCNc1nc(Nc2cnc3c(c2)c(C)nn3CCOC)ncc1C#CCCCNC(=O)[C@H](C)N(C)C(=O)OC(C)(C)C] | MS m/z (M + H): 608.5 |
| V40 | 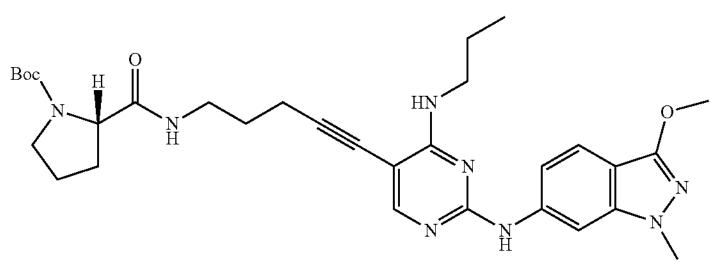 [SMILES: CCCNc1nc(Nc2ccc3c(OC)nn(C)c3c2)ncc1C#CCCCNC(=O)[C@@H]1CCCN1C(=O)OC(C)(C)C] | MS m/z (M + H): 591.5 |
| V41 | 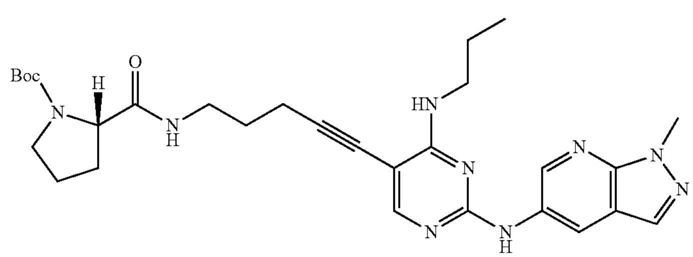 [SMILES: CCCNc1nc(Nc2cnc3c(cnn3C)c2)ncc1C#CCCCNC(=O)[C@@H]1CCCN1C(=O)OC(C)(C)C] | MS m/z (M + H): 562.5 |

TABLE 243-continued

| Compound No. | Structure | Physicochemical data |
|---|---|---|
| V42 | 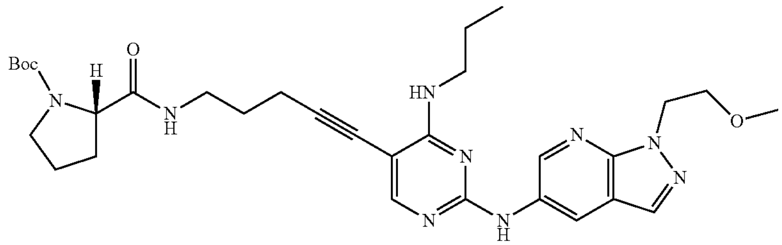 [SMILES: CCCNc1nc(Nc2cnc3c(cnn3CCOC)c2)ncc1C#CCCCNC(=O)[C@@H]1CCCN1C(=O)OC(C)(C)C] | MS m/z (M + H): 606.5 |
| V43 | 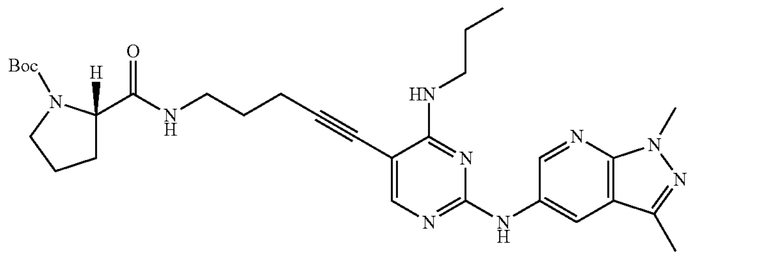 [SMILES: CCCNc1nc(Nc2cnc3c(c2)c(C)nn3C)ncc1C#CCCCNC(=O)[C@@H]1CCCN1C(=O)OC(C)(C)C] | MS m/z (M + H): 576.5 |

TABLE 244

| Compound No. | Structure | Physicochemical data |
|---|---|---|
| V44 | 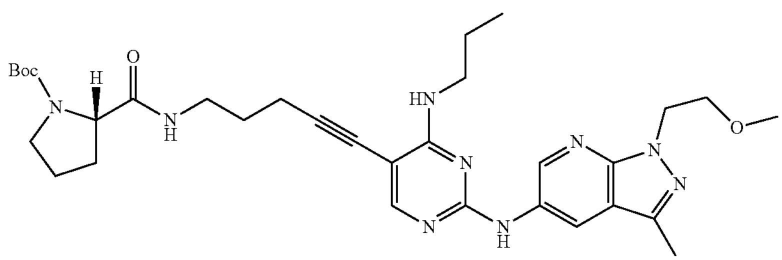 [SMILES: CCCNc1nc(Nc2cnc3c(c2)c(C)nn3CCOC)ncc1C#CCCCNC(=O)[C@@H]1CCCN1C(=O)OC(C)(C)C] | MS m/z (M + H): 620.5 |
| V45 | 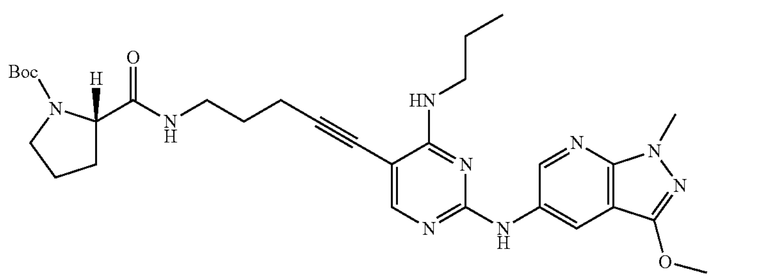 [SMILES: CCCNc1nc(Nc2cnc3c(c2)c(OC)nn3C)ncc1C#CCCCNC(=O)[C@@H]1CCCN1C(=O)OC(C)(C)C] | MS m/z (M + H): 592.5 |
| V46 | 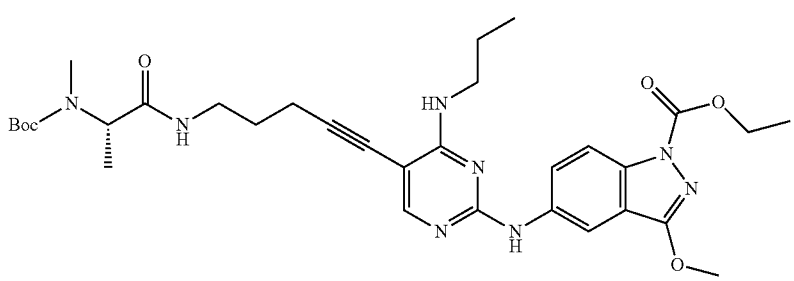 | MS m/z (M + H): 637.6 |

TABLE 244-continued

| Compound No. | Structure | Physicochemical data |
|---|---|---|
| V47 | 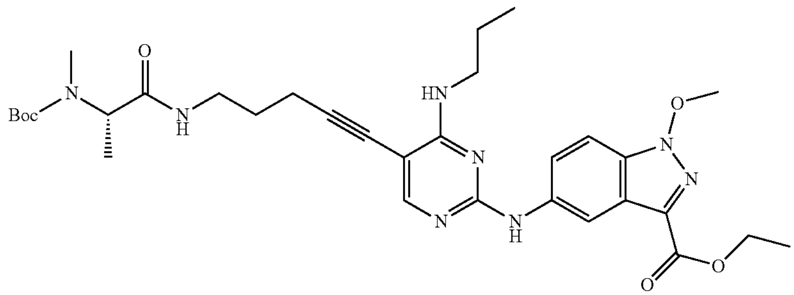 [SMILES: CCCNc1nc(Nc2ccc3c(c2)c(C(=O)OCC)nn3OC)ncc1C#CCCCNC(=O)[C@H](C)N(C)C(=O)OC(C)(C)C] | MS m/z (M + H): 637.5 |
| V48 | 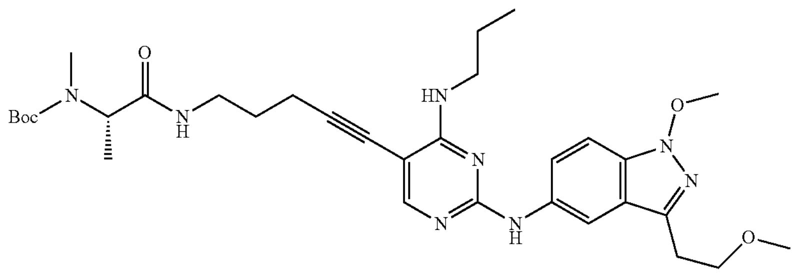 [SMILES: CCCNc1nc(Nc2ccc3c(c2)c(CCOC)nn3OC)ncc1C#CCCCNC(=O)[C@H](C)N(C)C(=O)OC(C)(C)C] | MS m/z (M + H): 623.5 |
| V49 | 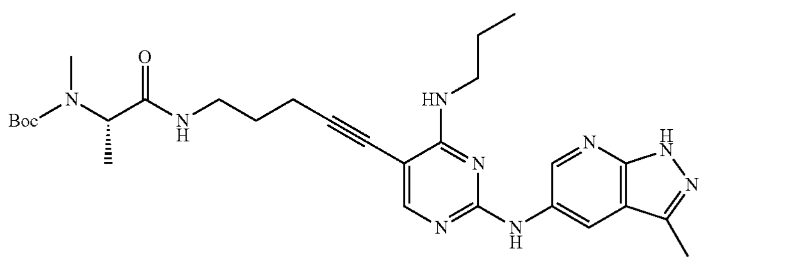 [SMILES: CCCNc1nc(Nc2cnc3[nH]nc(C)c3c2)ncc1C#CCCCNC(=O)[C@H](C)N(C)C(=O)OC(C)(C)C] | MS m/z (M + H): 550.5 |
| V50 | 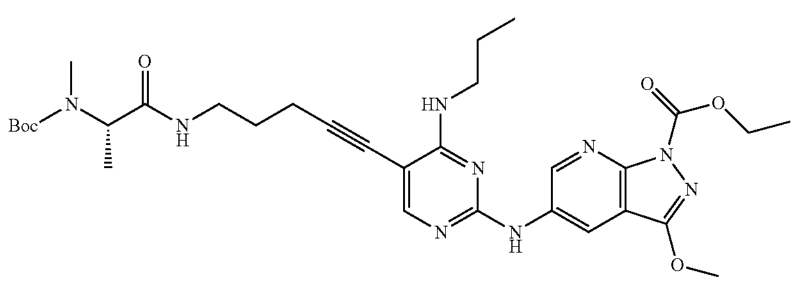 [SMILES: CCCNc1nc(Nc2cnc3c(c2)c(OC)nn3C(=O)OCC)ncc1C#CCCCNC(=O)[C@H](C)N(C)C(=O)OC(C)(C)C] | MS m/z (M + H): 638.5 |
| V51 | 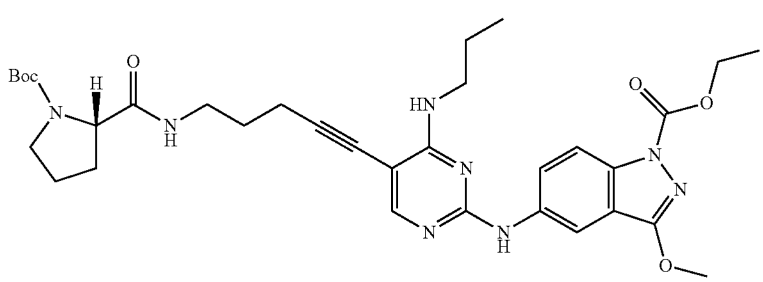 [SMILES: CCCNc1nc(Nc2ccc3c(c2)c(OC)nn3C(=O)OCC)ncc1C#CCCCNC(=O)[C@@H]1CCCN1C(=O)OC(C)(C)C] | MS m/z (M + H): 649.5 |

TABLE 244-continued

| Compound No. | Structure | Physicochemical data |
|---|---|---|
| V52 | 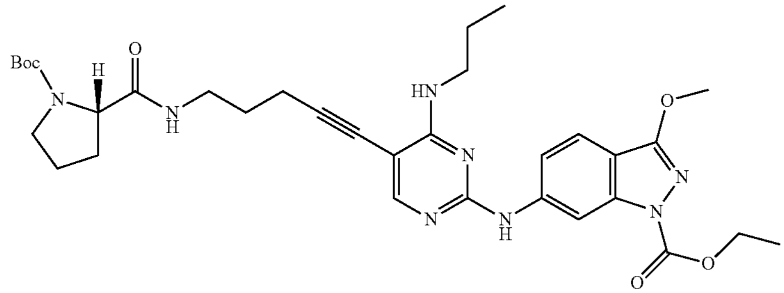 [SMILES: CCCNc1nc(Nc2ccc3c(OC)nn(C(=O)OCC)c3c2)ncc1C#CCCCNC(=O)[C@@H]1CCCN1C(=O)OC(C)(C)C] | MS m/z (M + H): 649.5 |
| V53 | 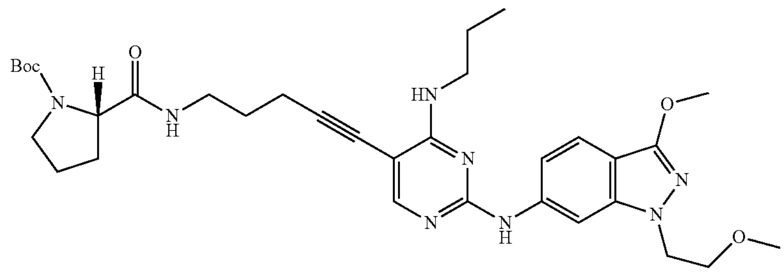 [SMILES: CCCNc1nc(Nc2ccc3c(OC)nn(CCOC)c3c2)ncc1C#CCCCNC(=O)[C@@H]1CCCN1C(=O)OC(C)(C)C] | MS m/z (M + H): 635.6 |

TABLE 245

| Compound No. | Structure | Physicochemical data |
|---|---|---|
| V54 | 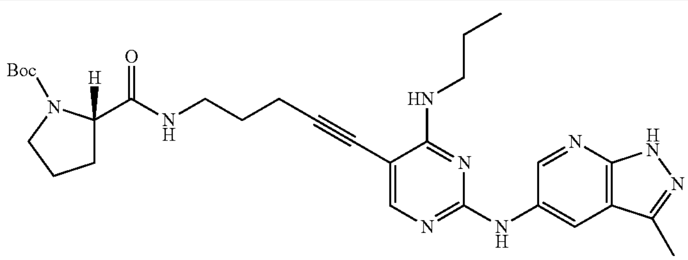 [SMILES: CCCNc1nc(Nc2cnc3[nH]nc(C)c3c2)ncc1C#CCCCNC(=O)[C@@H]1CCCN1C(=O)OC(C)(C)C] | MS m/z (M + H): 562.5 |
| V55 | 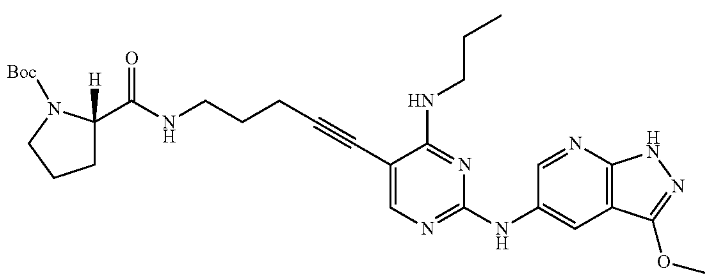 [SMILES: CCCNc1nc(Nc2cnc3[nH]nc(OC)c3c2)ncc1C#CCCCNC(=O)[C@@H]1CCCN1C(=O)OC(C)(C)C] | MS m/z (M + H): 578.5 |
| V56 | 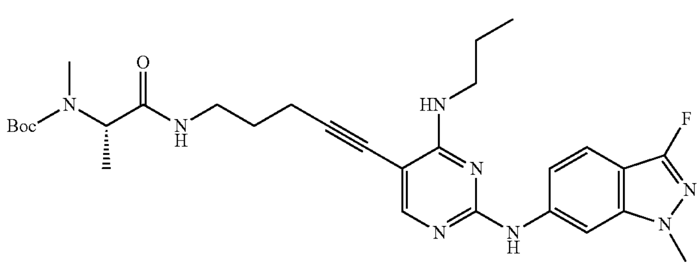 [SMILES: CCCNc1nc(Nc2ccc3c(F)nn(C)c3c2)ncc1C#CCCCNC(=O)[C@H](C)N(C)C(=O)OC(C)(C)C] | MS m/z (M + H): 567.5 |

TABLE 245-continued

| Compound No. | Structure | Physicochemical data |
|---|---|---|
| V57 | 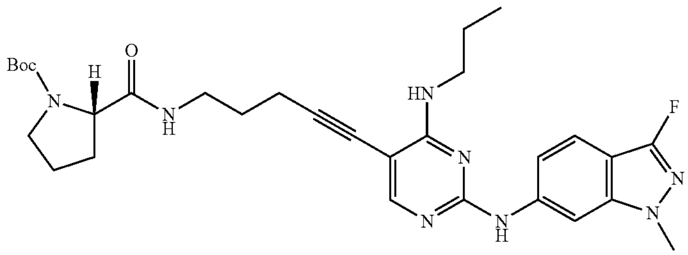 [SMILES: CCCNc1nc(Nc2ccc3c(F)nn(C)c3c2)ncc1C#CCCCNC(=O)[C@@H]1CCCN1C(=O)OC(C)(C)C] | MS m/z (M + H): 579.5 |
| V58 | 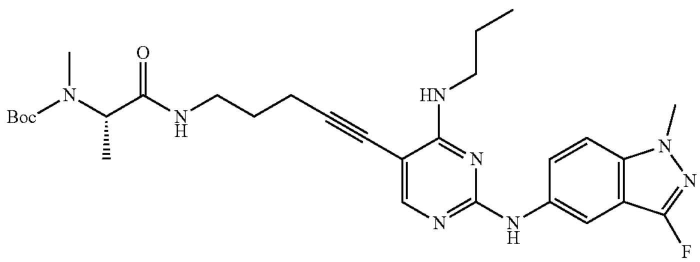 [SMILES: CCCNc1nc(Nc2ccc3c(c2)c(F)nn3C)ncc1C#CCCCNC(=O)[C@H](C)N(C)C(=O)OC(C)(C)C] | MS m/z (M + H): 567.3 |
| V59 | 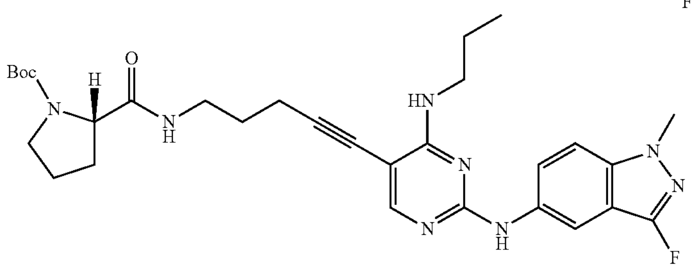 | MS m/z (M + H): 579.5 |

6

By using Intermediates (V3), Intermediates (V60) and (V61) were obtained in the same manner as that of Example 36, (11).

TABLE 246

| Compound No. | Structure | Physicochemical data |
|---|---|---|
| V60 | 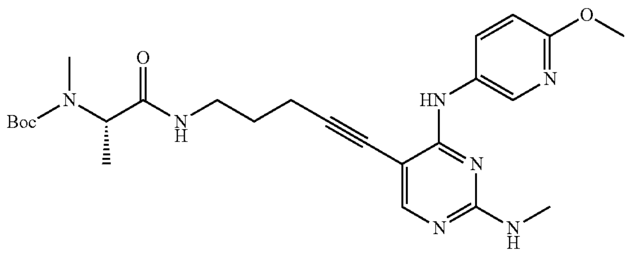 [SMILES: CNc1ncc(C#CCCCNC(=O)[C@H](C)N(C)C(=O)OC(C)(C)C)c(Nc2ccc(OC)nc2)n1] | MS m/z (M + H): 498.4 |
| V61 | 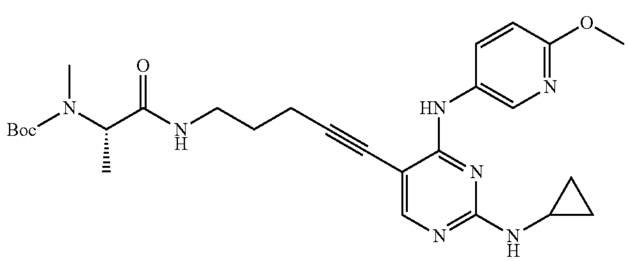 [SMILES: COc1ccc(Nc2nc(NC3CC3)ncc2C#CCCCNC(=O)[C@H](C)N(C)C(=O)OC(C)(C)C)cn1] | MS m/z (M + H): 524.5 |

7

By using Intermediates (V5), Intermediates (V62) to (V65) were obtained in the same manner as that of Example 35, (2).

TABLE 247

| Compound No. | Structure | Physicochemical data |
|---|---|---|
| V62 | 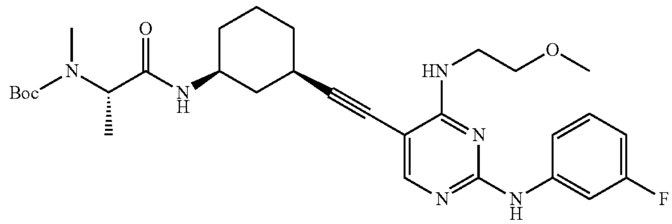 [SMILES: COCCNc1nc(Nc2cccc(F)c2)ncc1C#C[C@@H]1CCC[C@H](NC(=O)[C@H](C)N(C)C(=O)OC(C)(C)C)C1] | MS m/z (M + H): 569.4 |
| V63 | 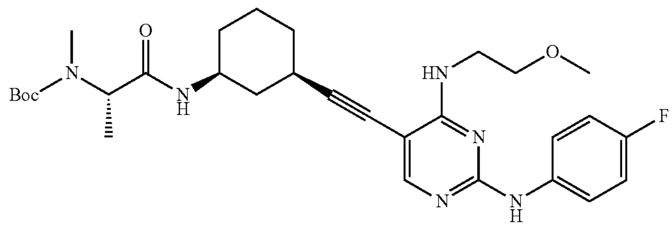 [SMILES: COCCNc1nc(Nc2ccc(F)cc2)ncc1C#C[C@@H]1CCC[C@H](NC(=O)[C@H](C)N(C)C(=O)OC(C)(C)C)C1] | MS m/z (M + H): 569.4 |
| V64 | 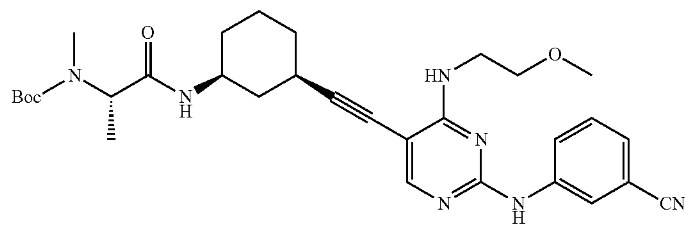 [SMILES: COCCNc1nc(Nc2cccc(C#N)c2)ncc1C#C[C@@H]1CCC[C@H](NC(=O)[C@H](C)N(C)C(=O)OC(C)(C)C)C1] | MS m/z (M + H): 576.4 |
| V65 | 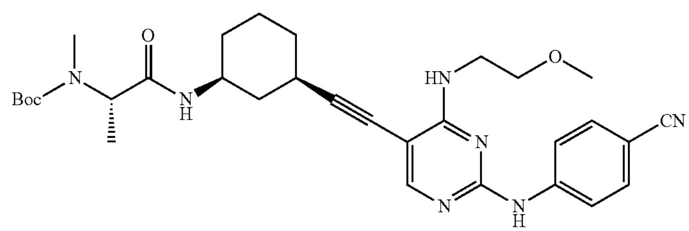 [SMILES: COCCNc1nc(Nc2ccc(C#N)cc2)ncc1C#C[C@@H]1CCC[C@H](NC(=O)[C@H](C)N(C)C(=O)OC(C)(C)C)C1] | MS m/z (M + H): 576.4 |

8

In the same manner as that of Example 35, (6) and (7), Compounds (22-2) to (22-61) were obtained.

TABLE 248

| Compound No. | Structure | Physicochemical data |
|---|---|---|
| 22-2 | 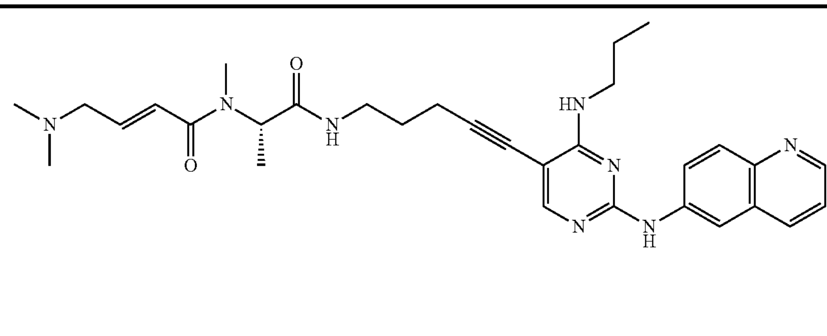 | $^1$H-NMR (CDCl$_3$) δ: 8.77 (1H, dd, J = 4.0, 1.5 Hz), 8.40 (1H, d, J = 2.3 Hz), 8.10-7.96 (3H, m), 7.72 (1H, dd, J = 8.9, 2.3 Hz), 7.35 (1H, dd, J = 8.3, 4.0 Hz), 7.30-7.21 (1H, m), 6.95 (1H, dt, J = 15.2, 5.9 Hz), 6.62-6.50 (1H, m), 6.43 (1H, d, J = |

| Compound No. | Structure | Physicochemical data |
|---|---|---|
| | | 15.2 Hz), 6.38-6.27 (1H, m), 5.20 (1H, q, J = 7.0 Hz), 3.63-3.51 (2H, m), 3.50-3.39 (2H, m), 3.14-3.07 (2H, m), 3.00 (3H, s), 2.45 (2H, t, J = 6.6 Hz), 2.27 (6H, s), 1.86-1.68 (4H, m), 1.37 (3H, d, J = 7.3 Hz), 1.04 (3H, t, J = 7.4 Hz) |
| 22-3 | 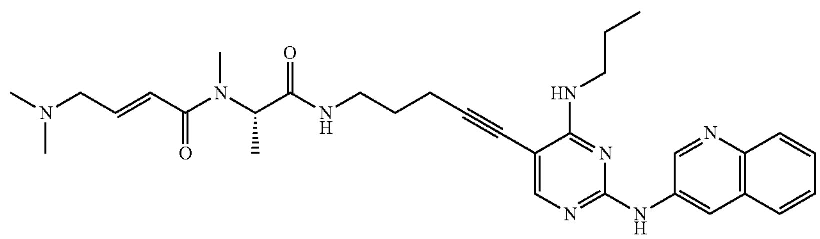 [SMILES: CCCNc1nc(Nc2cnc3ccccc3c2)ncc1C#CCCCNC(=O)[C@H](C)N(C)C(=O)/C=C/CN(C)C] | ¹H-NMR (CDCl₃) δ: 8.87 (1H, d, J = 2.6 Hz), 8.81 (1H, d, J = 2.6 Hz), 8.07-7.98 (2H, m), 7.78-7.72 (1H, m), 7.63-7.40 (3H, m), 6.95 (1H, dt, J = 15.2, 5.9 Hz), 6.64-6.50 (1H, m), 6.50-6.33 (2H, m), 5.20 (1H, q, J = 7.0 Hz), 3.64-3.51 (2H, m), 3.51-3.40 (2H, m), 3.15-3.06 (2H, m), 3.00 (3H, s), 2.45 (2H, t, J = 6.6 Hz), 2.27 (6H, s), 1.87-1.67 (4H, m), 1.37 (3H, d, J = 7.3 Hz), 1.04 (3H, t, J = 7.4 Hz) |
| 22-4 | 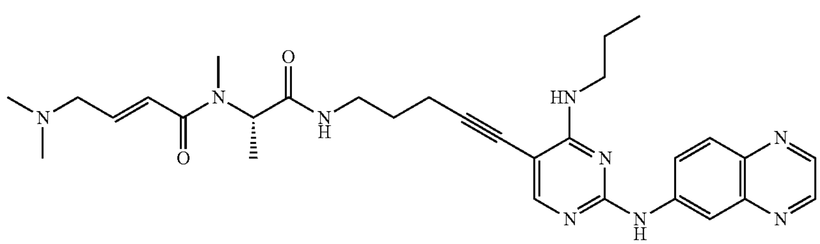 [SMILES: CCCNc1nc(Nc2ccc3nccnc3c2)ncc1C#CCCCNC(=O)[C@H](C)N(C)C(=O)/C=C/CN(C)C] | ¹H-NMR (CDCl₃) δ: 8.76 (1H, d, J = 2.0 Hz), 8.67 (1H, d, J = 2.0 Hz), 8.58 (1H, d, J = 2.3 Hz), 8.10-7.82 (3H, m), 7.55-7.45 (1H, m), 6.95 (1H, dt, J = 15.2, 5.9 Hz), 6.63-6.51 (1H, m), 6.48-6.30 (2H, m), 5.20 (1H, q, J = 6.9 Hz), 3.64-3.53 (2H, m), 3.50-3.40 (2H, m), 3.13-3.07 (2H, m), 3.00 (3H, s), 2.45 (2H, t, J = 6.6 Hz), 2.27 (6H, s), 1.85-1.68 (4H, m), 1.37 (3H, d, J = 6.9 Hz), 1.04 (3H, t, J = 7.4 Hz) |
| 22-5 | 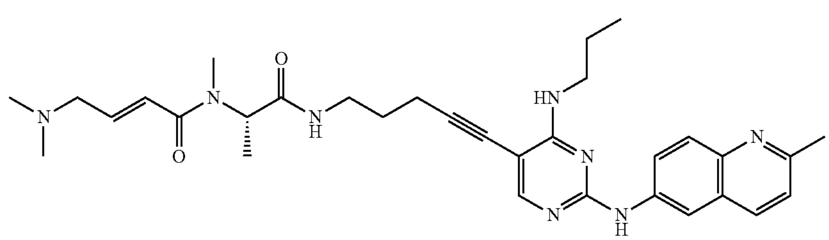 | ¹H-NMR (CDCl₃) δ: 8.33 (1H, d, J = 2.3 Hz), 8.03-7.85 (3H, m), 7.70 (1H, dd, J = 9.1, 2.5 Hz), 7.28-7.15 (2H, m), 6.95 (1H, dt, J = 15.2, 5.9 Hz), 6.60-6.48 (1H, m), 6.46-6.38 (1H, m), 6.35-6.22 (1H, m), 5.20 (1H, q, J = 7.0 Hz), 3.62-3.50 (2H, m), 3.50-3.37 (2H, m), 3.14-3.06 (2H, m), 3.00 (3H, s), 2.71 (3H, s), 2.45 (2H, t, J = 6.6 Hz), 2.27 (6H, s), 1.86-1.66 (4H, m), 1.36 (3H, d, J = 7.3 Hz), 1.03 (3H, t, J = 7.3 Hz) |

TABLE 249

| Compound No. | Structure | Physicochemical data |
|---|---|---|
| 22-6 | 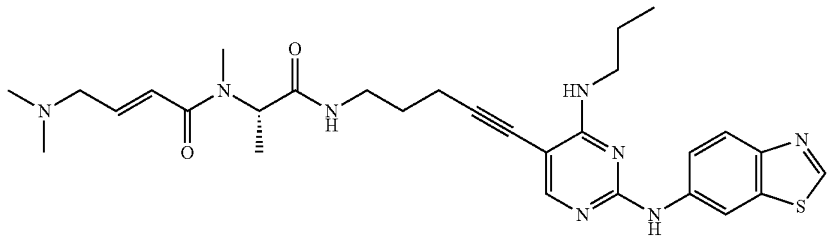 [SMILES: CCCNc1nc(Nc2ccc3ncsc3c2)ncc1C#CCCCNC(=O)[C@H](C)N(C)C(=O)/C=C/CN(C)C] | ¹H-NMR (CDCl₃) δ: 8.84 (1H, s), 8.69 (1H, d, J = 2.0 Hz), 8.05-7.94 (2H, m), 7.44 (1H, dd, J = 8.9, 2.3 Hz), 7.34-7.27 (1H, m), 6.95 (1H, dt, J = 15.2, 5.9 Hz), 6.62-6.50 (1H, m), 6.48-6.37 (1H, m), 6.37-6.25 (1H, m), 5.20 (1H, q, J = 7.0 Hz), 3.58-3.38 (4H, m), 3.14-3.05 (2H, m), 3.00 (3H, s), 2.45 (2H, t, J = 6.6 Hz), 2.27 (6H, s), 1.82-1.67 (4H, m), 1.36 (3H, d, J = 6.9 Hz), 1.03 (3H, t, J = 7.4 Hz) |
| 22-7 | 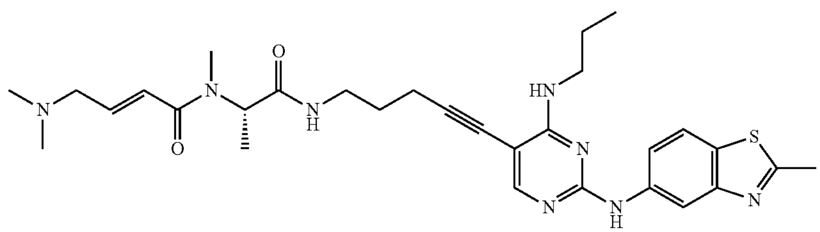 | ¹H-NMR (CDCl₃) δ: 8.28 (1H, d, J = 2.0 Hz), 7.97 (1H, s), 7.75-7.60 (2H, m), 7.17-7.08 (1H, m), 6.95 (1H, dt, J = 15.2, 5.9 Hz), 6.59-6.48 (1H, m), 6.42 (1H, d, J = 15.2 Hz), 6.25-6.10 (1H, m), 5.19 (1H, q, J = 7.0 Hz), 3.58-3.37 (4H, m), 3.15-3.06 (2H, m), 2.99 (3H, s), 2.82 (3H, s), 2.44 (2H, t, J = 6.6 Hz), 2.27 (6H, s), 1.85-1.65 (4H, m), 1.36 (3H, d, J = 7.3 Hz), 1.01 (3H, t, J = 7.4 Hz) |
| 22-8 | 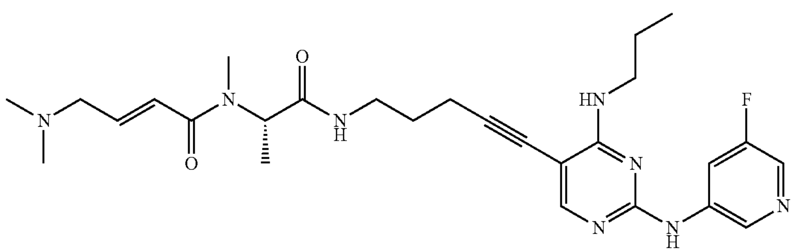 [SMILES: CCCNc1nc(Nc2cncc(F)c2)ncc1C#CCCCNC(=O)[C@H](C)N(C)C(=O)/C=C/CN(C)C] | ¹H-NMR (CDCl₃) δ: 8.42-8.29 (2H, m), 8.08 (1H, d, J = 2.6 Hz), 7.97 (1H, s), 7.28-7.20 (1H, m), 6.95 (1H, dt, J = 15.2, 5.9 Hz), 6.60-6.48 (1H, m), 6.48-6.37 (2H, m), 5.19 (1H, q, J = 7.0 Hz), 3.67-3.38 (4H, m), 3.14-3.07 (2H, m), 3.00 (3H, s), 2.44 (2H, t, J = 6.6 Hz), 2.28 (6H, s), 1.85-1.61 (4H, m), 1.36 (3H, d, J = 6.9 Hz), 1.01 (3H, t, J = 7.4 Hz) |
| 22-9 | 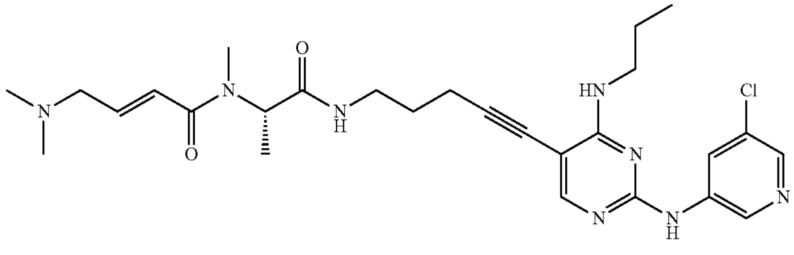 [SMILES: CCCNc1nc(Nc2cncc(Cl)c2)ncc1C#CCCCNC(=O)[C@H](C)N(C)C(=O)/C=C/CN(C)C] | ¹H-NMR (CDCl₃) δ: 8.55 (1H, dd, J = 2.0, 2.0 Hz), 8.42 (1H, d, J = 2.0 Hz), 8.17 (1H, d, J = 2.0 Hz), 7.96 (1H, s), 7.27-7.20 (1H, m), 7.11-7.02 (1H, m), 7.00-6.89 (1H, m), 6.58-6.39 (2H, m), 5.18 (1H, q, J = 7.3 Hz), 3.57-3.39 (4H, m), 3.17-3.08 (2H, m), 3.00 (3H, s), 2.44 (2H, t, J = 6.9 Hz), 2.29 (6H, s), 1.83-1.65 (4H, m), 1.38 (3H, d, J = 6.9 Hz), 1.02 (3H, t, J = 7.4 Hz) |

TABLE 250

| Compound No. | Structure | Physicochemical data |
|---|---|---|
| 22-10 | 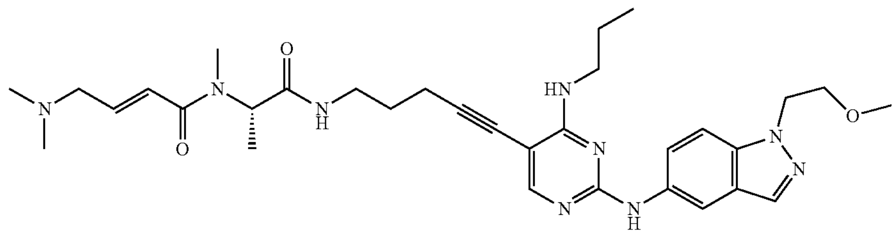 | $^1$H-NMR (CDCl$_3$) δ: 8.15 (1H, s), 7.99-7.85 (2H, m), 7.50-7.32 (2H, m), 7.24-7.13 (1H, m), 6.95 (1H, dt, J = 15.2, 5.9 Hz), 6.65-6.54 (1H, m), 6.43 (1H, d, J = 15.2 Hz), 6.25-6.11 (1H, m), 5.18 (1H, q, J = 6.9 Hz), 4.59-4.43 (2H, m), 3.88-3.75 (2H, m), 3.57-3.35 (4H, m), 3.29 (3H, s), 3.15-3.05 (2H, m), 3.00 (3H, s), 2.51-2.39 (2H, m), 2.27 (6H, s), 1.85-1.60 (4H, m), 1.36 (3H, d, J = 6.9 Hz), 1.01 (3H, t, J = 7.4 Hz) |
| 22-11 | 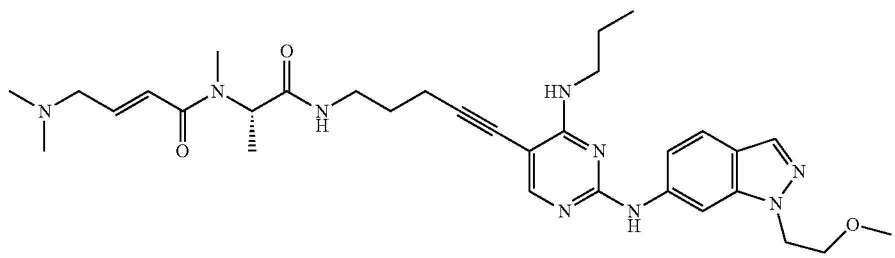 | MS m/z (M + H): 604.5 |
| 22-12 | 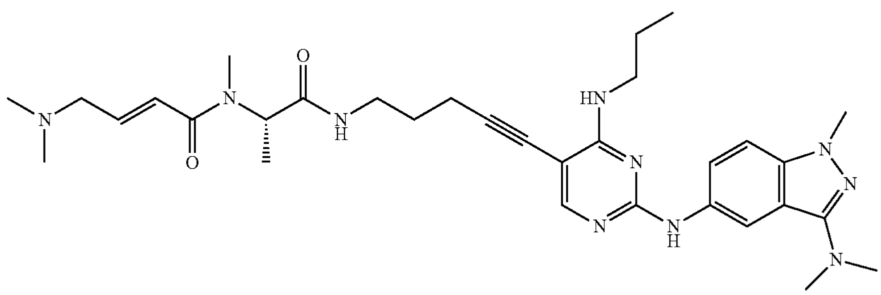 | MS m/z (M + H): 603.5 |
| 22-13 | 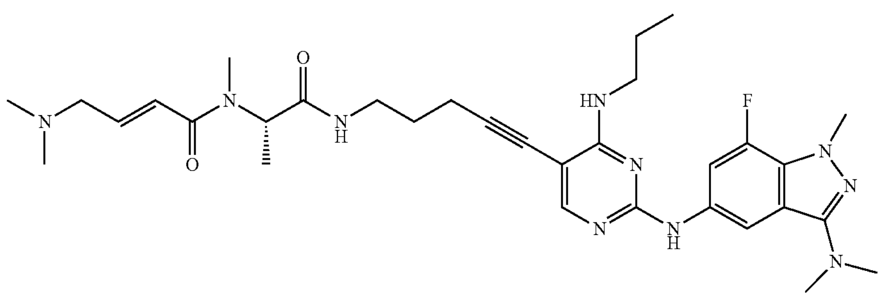 | MS m/z (M + H): 621.5 |
| 22-14 | 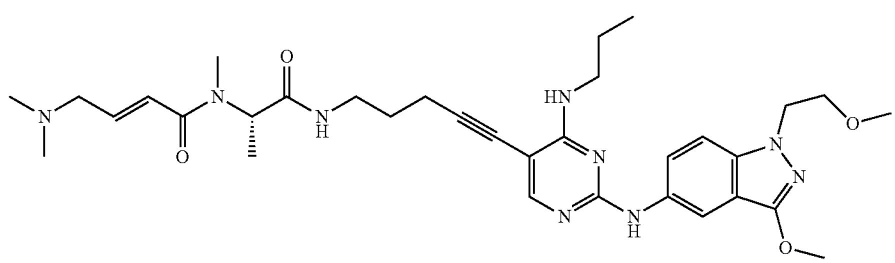 | $^1$H-NMR (CDCl$_3$) δ: 8.08 (1H, s), 7.98-7.88 (1H, m), 7.38 (1H, dd, J = 8.9, 2.0 Hz), 7.21 (1H, d, J = 8.9 Hz), 7.16-7.10 (1H, m), 6.95 (1H, dt, J = 15.2, 5.9 Hz), 6.63-6.53 (1H, m), 6.43 (1H, d, J = 15.2 Hz), 6.20-6.10 (1H, m), 5.19 (1H, q, J = 7.3 Hz), 4.37-4.23 (2H, m), 4.06 (3H, s), 3.80-3.70 |

TABLE 250-continued

| Compound No. | Structure | Physicochemical data |
|---|---|---|
| | | (2H, m), 3.68-3.35 (4H, m), 3.29 (3H, s), 3.15-3.06 (2H, m), 3.00 (3H, s), 2.50-2.37 (2H, m), 2.27 (6H, s), 1.85-1.62 (4H, m), 1.36 (3H, d, J = 7.3 Hz), 1.01 (3H, t, J = 7.4 Hz) |
| 22-15 | 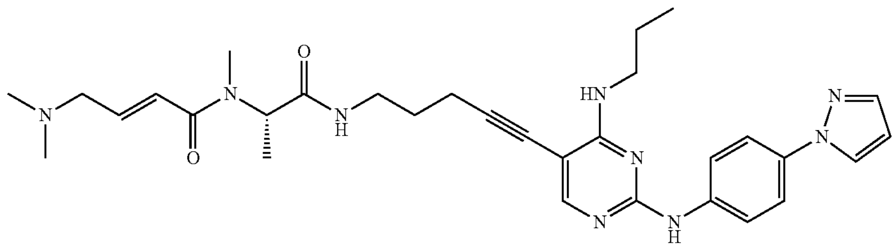 [SMILES: CCCNc1nc(Nc2ccc(-n3cccn3)cc2)ncc1C#CCCCNC(=O)[C@H](C)N(C)C(=O)/C=C/CN(C)C] | MS m/z (M + H): 572.5 |

TABLE 251

| Compound No. | Structure | Physicochemical data |
|---|---|---|
| 22-16 | 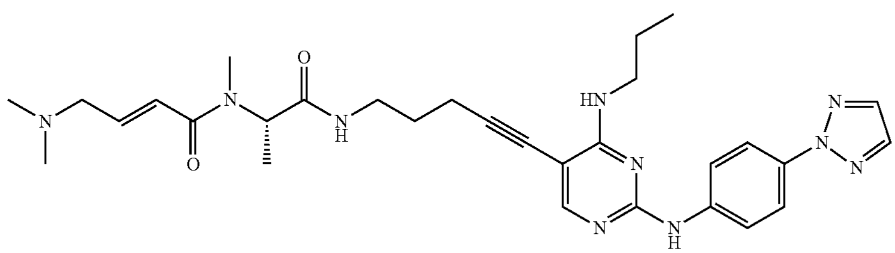 [SMILES: CCCNc1nc(Nc2ccc(-n3nccn3)cc2)ncc1C#CCCCNC(=O)[C@H](C)N(C)C(=O)/C=C/CN(C)C] | MS m/z (M + H): 573.5 |
| 22-17 | 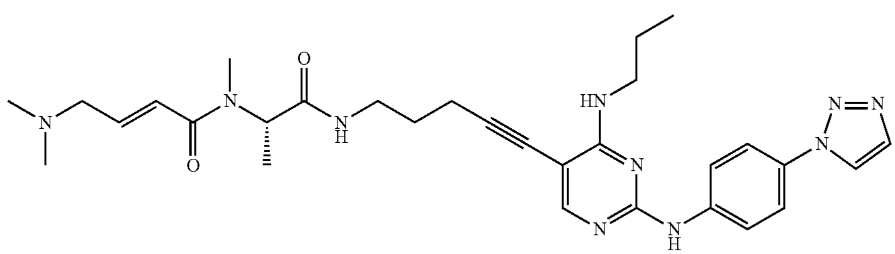 [SMILES: CCCNc1nc(Nc2ccc(-n3ccnn3)cc2)ncc1C#CCCCNC(=O)[C@H](C)N(C)C(=O)/C=C/CN(C)C] | MS m/z (M + H): 573.5 |
| 22-18 | 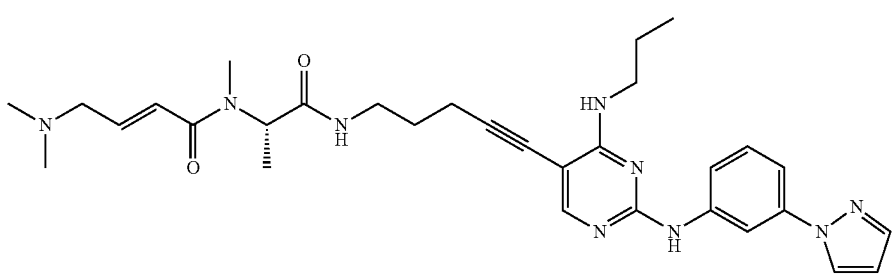 [SMILES: CCCNc1nc(Nc2cccc(-n3cccn3)c2)ncc1C#CCCCNC(=O)[C@H](C)N(C)C(=O)/C=C/CN(C)C] | MS m/z (M + H): 572.5 |

TABLE 251-continued

| Compound No. | Structure | Physicochemical data |
|---|---|---|
| 22-19 | 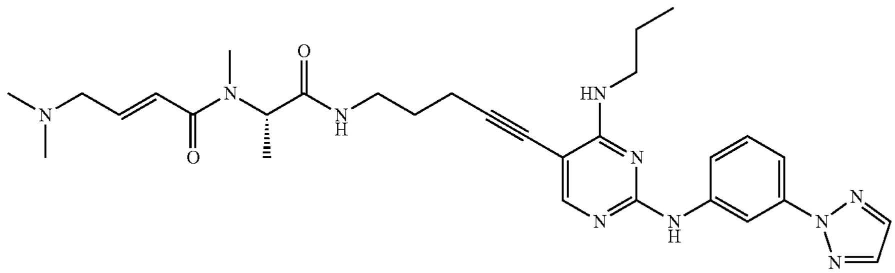 [SMILES: CCCNc1nc(Nc2cccc(-n3nccn3)c2)ncc1C#CCCCNC(=O)[C@H](C)N(C)C(=O)/C=C/CN(C)C] | $^1$H-NMR (CDCl$_3$) δ: 8.77 (1H, s), 8.00-7.92 (1H, m), 7.79 (2H, s), 7.73-7.64 (1H, m), 7.47-7.32 (2H, m), 7.23-7.15 (1H, m), 6.95 (1H, dt, J = 15.2, 5.9 Hz), 6.60-6.48 (1H, m), 6.43 (1H, d, J = 15.2 Hz), 6.24-6.14 (1H, m), 5.19 (1H, q, J = 6.8 Hz), 3.66-3.52 (2H, m), 3.52-3.37 (2H, m), 3.15-3.06 (2H, m), 3.00 (3H, s), 2.53-2.40 (2H, m), 2.27 (6H, s), 1.84-1.61 (4H, m), 1.36 (3H, d, J = 7.3 Hz), 0.98 (3H, t, J = 7.4 Hz) |
| 22-20 | 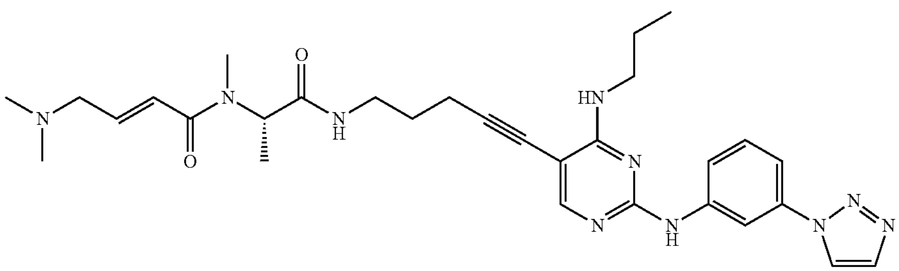 [SMILES: CCCNc1nc(Nc2cccc(-n3ccnn3)c2)ncc1C#CCCCNC(=O)[C@H](C)N(C)C(=O)/C=C/CN(C)C] | MS m/z (M + H): 573.5 |
| 22-21 | 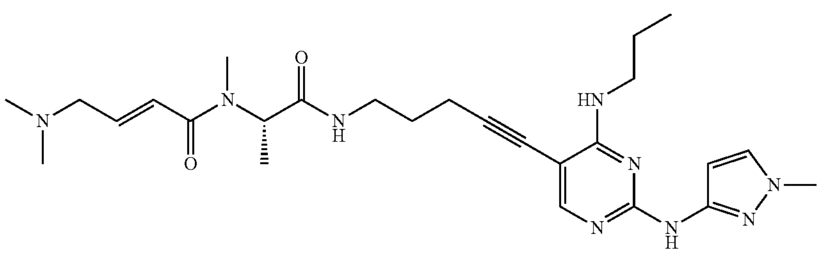 | $^1$H-NMR (CDCl$_3$) δ: 7.95 (1H, s), 7.30-7.20 (2H, m), 6.95 (1H, dt, J = 15.2, 5.9 Hz), 6.71 (1H, d, J = 2.3 Hz), 6.56-6.43 (1H, m), 6.42 (1H, d, J = 15.2 Hz), 6.14-6.01 (1H, m), 5.18 (1H, q, J = 7.0 Hz), 3.80 (3H, s), 3.54-3.36 (4H, m), 3.13-3.06 (2H, m), 2.98 (3H, s), 2.43 (2H, t, J = 6.6 Hz), 2.27 (6H, s), 1.80-1.60 (4H, m), 1.35 (3H, d, J = 7.3 Hz), 0.98 (3H, t, J = 7.4 Hz) |

TABLE 252

| Compound No. | Structure | Physicochemical data |
|---|---|---|
| 22-22 | 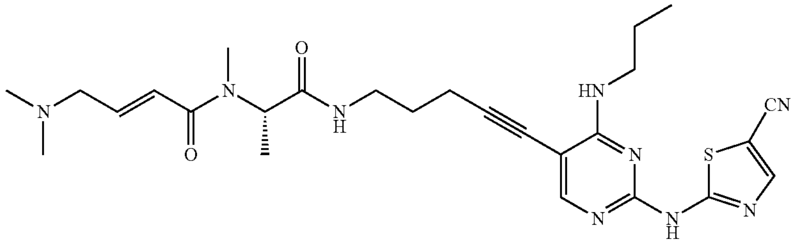 [SMILES: CCCNc1nc(Nc2ncc(C#N)s2)ncc1C#CCCCNC(=O)[C@H](C)N(C)C(=O)/C=C/CN(C)C] | $^1$H-NMR (CDCl$_3$) δ: 8.22 (1H, s), 8.01 (1H, s), 7.32-7.25 (1H, m), 6.95 (1H, dt, J = 15.2, 5.9 Hz), 6.91-6.82 (1H, m), 6.62-6.52 (1H, m), 6.43 (1H, d, J = 15.2 Hz), 5.19 (1H, q, J = 6.9 Hz), 3.70-3.59 (2H, m), 3.53-3.43 (2H, m), 3.15-3.08 (2H, m), |

TABLE 252-continued

| Compound No. | Structure | Physicochemical data |
|---|---|---|
| | | 3.01 (3H, s), 2.52-2.42 (2H, m), 2.28 (6H, s), 1.87-1.69 (4H, m), 1.38 (3H, d, J = 7.3 Hz), 1.04 (3H, t, J = 7.4 Hz) |
| 22-23 | 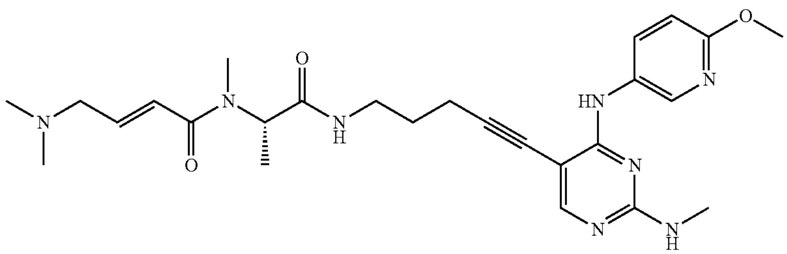 | ¹H-NMR (CDCl₃) δ: 8.51 (1H, d, J = 2.0 Hz), 8.07-7.94 (2H, m), 7.87 (1H, s), 6.93 (1H, dt, J = 15.2, 5.9 Hz), 6.71 (1H, d, J = 8.6 Hz), 6.62-6.53 (1H, m), 6.46-6.34 (1H, m), 5.17 (1H, q, J = 7.0 Hz), 5.08-4.95 (1H, m), 3.93 (3H, s), 3.48 (2H, q, J = 6.2 Hz), 3.09 (2H, dd, J = 5.9, 1.3 Hz), 3.01-2.90 (6H, m), 2.45 (2H, t, J = 6.6 Hz), 2.26 (6H, s), 1.81-1.67 (2H, m), 1.33 (3H, d, J = 7.0 Hz) |
| 22-24 | 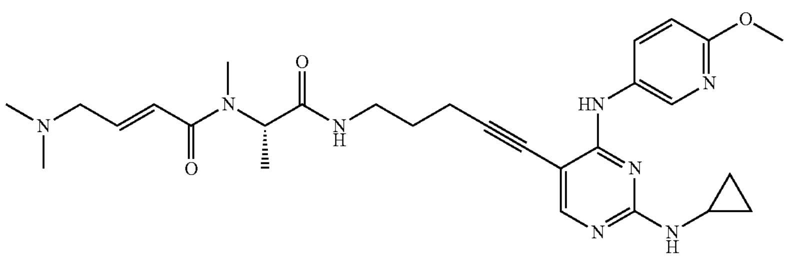 | ¹H-NMR (CDCl₃) δ: 8.53 (1H, d, J = 2.0 Hz), 8.13-8.02 (2H, m), 7.91 (1H, s), 6.93 (1H, dt, J = 15.2, 5.9 Hz), 6.70 (1H, d, J = 8.6 Hz), 6.62-6.53 (1H, m), 6.46-6.36 (1H, m), 5.28-5.22 (1H, m), 5.17 (1H, q, J = 7.3 Hz), 3.92 (3H, s), 3.54-3.42 (2H, m), 3.10 (2H, dd, J = 5.9, 1.3 Hz), 2.96 (3H, s), 2.77-2.67 (1H, m), 2.45 (2H, t, J = 6.6 Hz), 2.26 (6H, s), 1.81-1.68 (2H, m), 1.33 (3H, d, J = 7.3 Hz), 0.83-0.73 (2H, m), 0.57-0.48 (2H, m) |
| 22-25 | 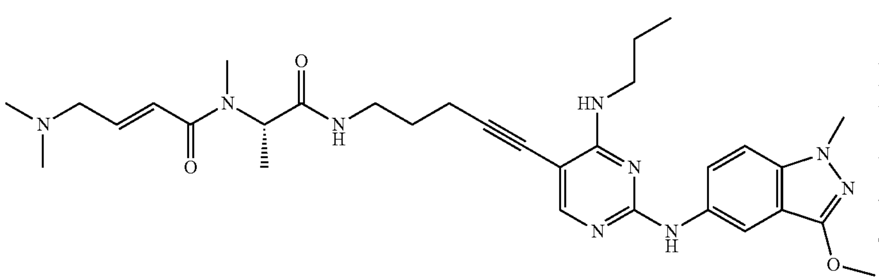 | ¹H-NMR (CDCl₃) δ: 8.07-8.03 (1H, m), 7.97-7.85 (1H, m), 7.45-7.35 (1H, m), 7.20-7.04 (2H, m), 6.95 (1H, dt, J = 15.2, 5.9 Hz), 6.58-6.47 (1H, m), 6.43 (1H, d, J = 15.2 Hz), 6.23-6.12 (1H, m), 5.20 (1H, q, J = 7.0 Hz), 4.07 (3H, s), 3.85 (3H, s), 3.58-3.37 (4H, m), 3.17-3.05 (2H, m), 2.99 (3H, s), 2.57-2.37 (2H, m), 2.27 (6H, s), 1.88-1.62 (4H, m), 1.36 (3H, d, J = 6.9 Hz), 1.01 (3H, t, J = 7.3 Hz) |

TABLE 253

| Compound No. | Structure | Physicochemical data |
|---|---|---|
| 22-26 | 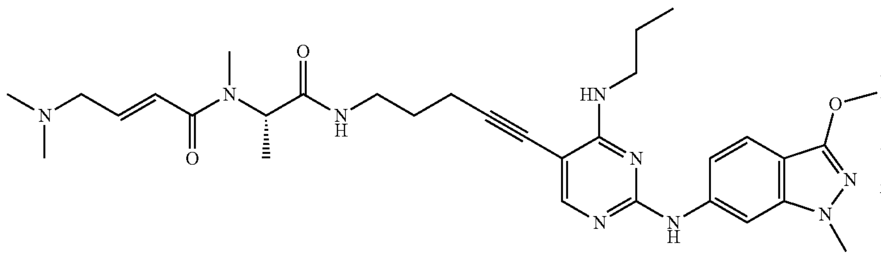 | ¹H-NMR (CDCl₃) δ: 8.16-8.05 (1H, m), 8.02-7.93 (1H, m), 7.52-7.44 (1H, m), 7.35-7.28 (1H, m), 6.95 (1H, dt, J = 15.2, 5.9 Hz), 6.87-6.78 (1H, m), 6.60-6.51 (1H, m), 6.43 (1H, d, J = 15.2 Hz), 6.30-6.19 (1H, m), 5.19 (1H, q, J = 6.9 Hz), 4.06 (3H, s), 3.84 (3H, s), 3.63-3.38 (4H, m), 3.15-3.05 (2H, m), 3.00 (3H, s), 2.63-2.48 (2H, m), 2.27 (6H, s), 1.86-1.65 (4H, m), 1.36 (3H, d, J = 7.3 Hz), 1.01 (3H, t, J = 7.4 Hz) |
| 22-27 | 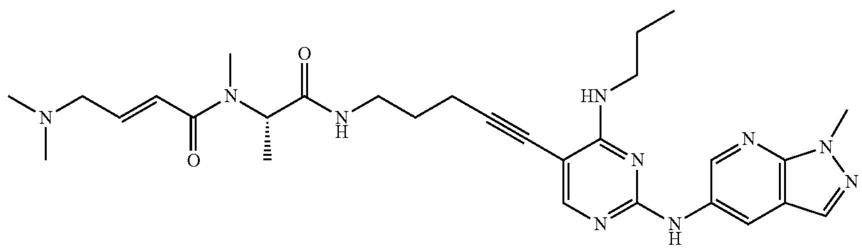 [SMILES: CCCNc1nc(Nc2cnc3c(cnn3C)c2)ncc1C#CCCCNC(=O)[C@H](C)N(C)C(=O)/C=C/CN(C)C] | MS m/z (M + H): 561.5 |
| 22-28 | 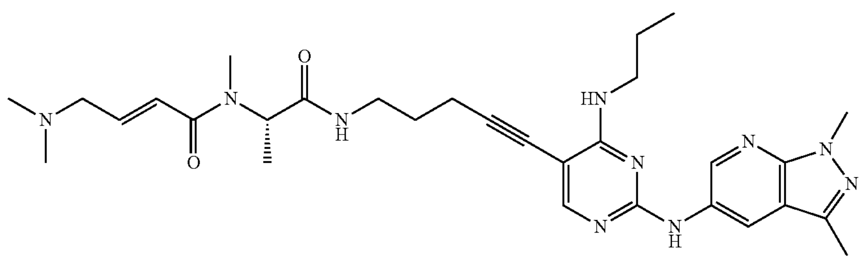 [SMILES: CCCNc1nc(Nc2cnc3c(c2)c(C)nn3C)ncc1C#CCCCNC(=O)[C@H](C)N(C)C(=O)/C=C/CN(C)C] | ¹H-NMR (CDCl₃) δ: 8.58-8.43 (2H, m), 8.00-7.91 (1H, m), 7.23-7.13 (1H, m), 6.95 (1H, dt, J = 15.2, 5.9 Hz), 6.60-6.48 (1H, m), 6.43 (1H, d, J = 15.2 Hz), 6.28-6.18 (1H, m), 5.18 (1H, q, J = 7.0 Hz), 4.07 (3H, s), 3.57-3.37 (4H, m), 3.14-3.07 (2H, m), 2.99 (3H, s), 2.55 (3H, s), 2.52-2.38 (2H, m), 2.27 (6H, s), 1.72-1.63 (4H, m), 1.36 (3H, d, J = 6.9 Hz), 0.98 (3H, t, J = 7.3 Hz) |
| 22-29 | 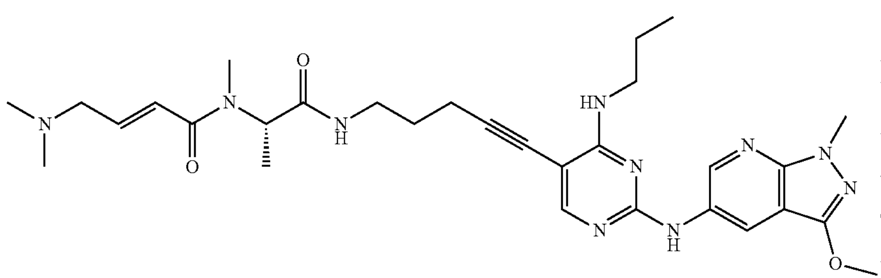 | ¹H-NMR (CDCl₃) δ: 8.54-8.41 (2H, m), 7.97-7.90 (1H, m), 7.11-7.02 (1H, m), 6.95 (1H, dt, J = 15.2, 5.9 Hz), 6.57-6.47 (1H, m), 6.43 (1H, d, J = 15.2 Hz), 6.30-6.20 (1H, m), 5.18 (1H, q, J = 7.3 Hz), 4.07 (3H, s), 3.95 (3H, s), 3.56-3.36 (4H, m), 3.16-3.07 (2H, m), 2.99 (3H, s), 2.50-2.38 (2H, m), 2.28 (6H, s), 1.85-1.62 (4H, m), 1.36 (3H, d, J = 7.3 Hz), 0.99 (3H, t, J = 7.3 Hz) |

TABLE 253-continued

| Compound No. | Structure | Physicochemical data |
|---|---|---|
| 22-30 | 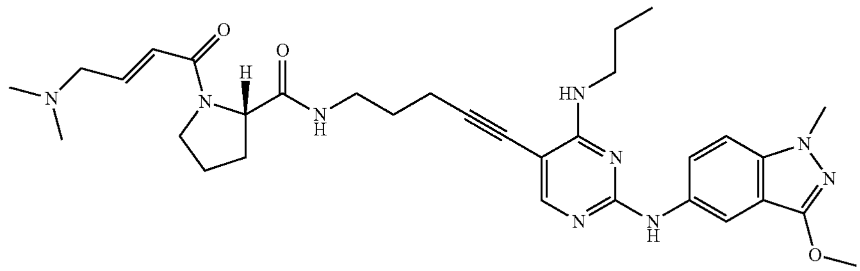 | MS m/z (M + H): 602.5 |

TABLE 254

| Compound No. | Structure | Physicochemical data |
|---|---|---|
| 22-31 | 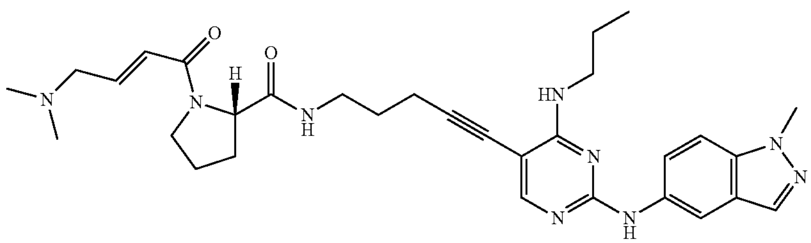 [SMILES: CCCNc1nc(Nc2ccc3c(cnn3C)c2)ncc1C#CCCCNC(=O)[C@@H]1CCCN1C(=O)/C=C/CN(C)C] | ¹H-NMR (CDCl₃) δ: 8.19-8.10 (1H, m), 7.95 (1H, s), 7.93-7.85 (1H, m), 7.50-7.37 (1H, m), 7.44 (1H, dd, J = 8.9, 2.0 Hz), 7.31 (1H, d, J = 8.9 Hz), 7.10-7.03 (1H, m), 6.95 (1H, dt, J = 15.2, 5.9 Hz), 6.37-6.27 (1H, m), 6.27-6.17 (1H, m), 4.73-4.62 (1H, m), 4.06 (3H, s), 3.73-3.61 (2H, m), 3.60-3.28 (6H, m), 3.10 (2H, d, J = 5.9 Hz), 2.52-2.40 (2H, m), 2.27 (6H, s), 2.16-1.61 (6H, m), 1.00 (3H, t, J = 4.7 Hz |
| 22-32 | 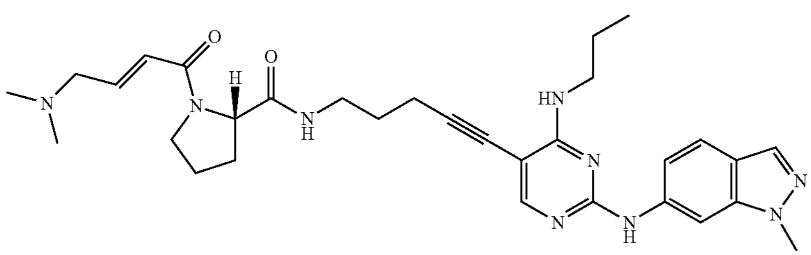 [SMILES: CCCNc1nc(Nc2ccc3cnn(C)c3c2)ncc1C#CCCCNC(=O)[C@@H]1CCCN1C(=O)/C=C/CN(C)C] | MS m/z (M + H): 572.5 |
| 22-33 | 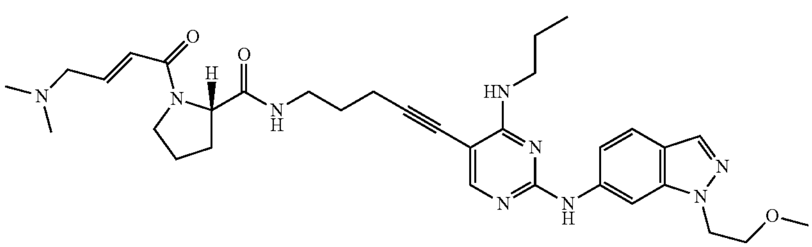 | ¹H-NMR (CDCl₃) δ: 8.30 (1H, s), 7.99 (1H, s), 7.90 (1H, s), 7.57 (1H, d, J = 8.6 Hz), 7.48-7.38 (1H, m), 7.10-6.90 (3H, m), 6.33 (1H, d, J = 15.2 Hz), 6.28-6.17 (1H, m), 4.72-4.64 (1H, m), 4.51 (2H, t, J = 5.8 Hz), 3.84 (2H, t, J = 5.8 Hz), 3.75-3.33 (6H, m), 3.31 (3H, s), 3.11 (2H, d, J = 6.3 Hz), 2.57-2.41 (2H, m), 2.27 (6H, s), 2 20-1.65 (8H, m), 1.02 (3H, t, J = 7.4 Hz) |

TABLE 254-continued

| Compound No. | Structure | Physicochemical data |
|---|---|---|
| 22-34 | 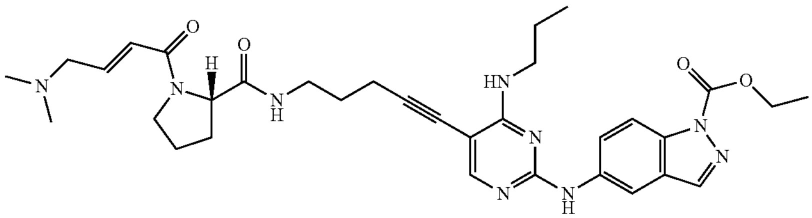 [SMILES: CCCNc1nc(Nc2ccc3c(cnn3C(=O)OCC)c2)ncc1C#CCCCNC(=O)[C@@H]1CCCN1C(=O)/C=C/CN(C)C] | MS m/z (M + H): 630.5 |
| 22-35 | 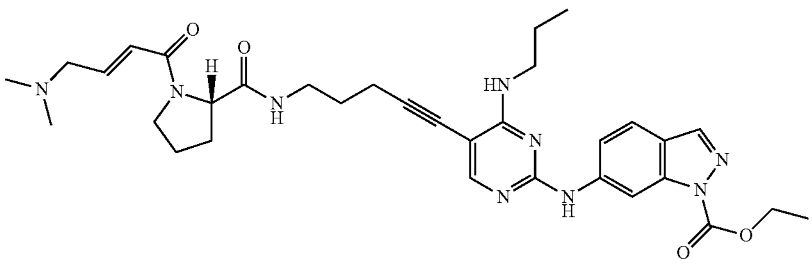 [SMILES: CCCNc1nc(Nc2ccc3cnn(C(=O)OCC)c3c2)ncc1C#CCCCNC(=O)[C@@H]1CCCN1C(=O)/C=C/CN(C)C] | MS m/z (M + H): 630.5 |

TABLE 255

| Compound No. | Structure | Physicochemical data |
|---|---|---|
| 22-36 | 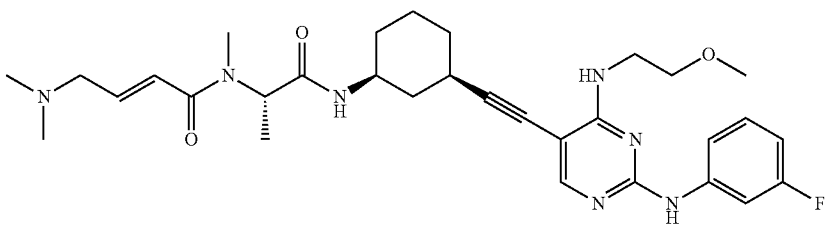 [SMILES: COCCNc1nc(Nc2cccc(F)c2)ncc1C#C[C@@H]1CCC[C@H](NC(=O)[C@H](C)N(C)C(=O)/C=C/CN(C)C)C1] | $^1$H-NMR (CDCl$_3$) δ: 7.97 (1H, s), 7.76-7.69 (1H, m), 7.26-7.16 (1H, m), 7.11-7.05 (1H, m), 7.09-7.05 (1H, m), 6.92 (1H, dt, J = 15.2, 5.9 Hz), 6.68 (1H, td, J = 8.3, 2.2 Hz), 6.42 (1H, d, J = 15.2 Hz), 6.33-6.26 (1H, m), 5.83-5.77 (1H, m), 5.15 (1H, q, J = 7.0 Hz), 3.77-3.66 (1H, m), 3.74-3.69 (2H, m), 3.65-3.59 (2H, m), 3.42 (3H, s), 3.11 (2H, d, J = 5.3 Hz), 2.98 (3H, s), 2.66-2.57 (1H, m), 2.35-2.27 (1H, m), 2.29 (6H, s), 2.05-1.97 (1H, m), 1.88-1.77 (2H, m), 1.42-1.28 (3H, m), 1.33 (3H, d, J = 7.0 Hz), 1.16-1.04 (1H, m) |
| 22-37 | 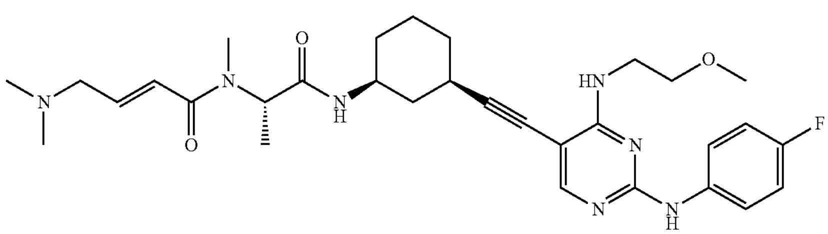 [SMILES: COCCNc1nc(Nc2ccc(F)cc2)ncc1C#C[C@@H]1CCC[C@H](NC(=O)[C@H](C)N(C)C(=O)/C=C/CN(C)C)C1] | $^1$H-NMR (CDCl$_3$) δ: 7.95 (1H, s), 7.55-7.49 (2H, m), 7.05-6.95 (2H, m), 6.97-6.88 (1H, m), 6.95-6.89 (1H, m), 6.41 (1H, d, J = 15.2 Hz), 6.32-6.26 (1H, m), 5.78-5.73 (1H, m), 5.14 (1H, q, J = 7.3 Hz), 3.77-3.63 (1H, m), 3.69-3.63 (2H, m), 3.61-3.56 (2H, m), 3.41 (3H, s), 3.11 (2H, d, J = 5.9 Hz), 2.97 (3H, s), 2.66-2.57 (1H, m), 2.34-2.26 (1H, |

TABLE 255-continued

| Compound No. | Structure | Physicochemical data |
|---|---|---|
| | | m), 2.28 (6H, s), 2.06-1.95 (1H, m), 1.88-1.77 (2H, m), 1.45-1.26 (3H, m), 1.33 (3H, d, J = 7.3 Hz), 1.15-1.04 (1H, m) |
| 22-38 | 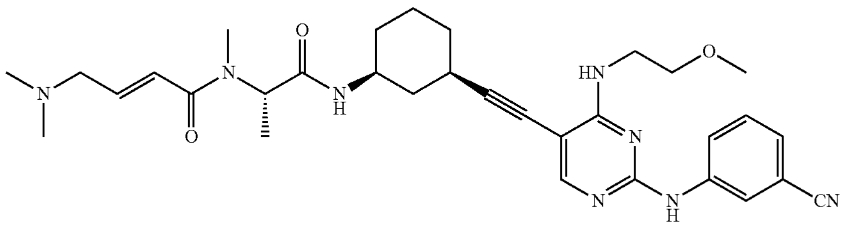 [SMILES: COCCNc1nc(Nc2cccc(C#N)c2)ncc1C#C[C@@H]1CCC[C@H](NC(=O)[C@H](C)N(C)C(=O)/C=C/CN(C)C)C1] | ¹H-NMR (CDCl₃) δ: 8.28 (1H, s), 7.98 (1H, s), 7.74 (1H, s), 7.66-7.60 (1H, m), 7.36 (1H, dd, J = 7.9, 7.9 Hz), 7.27-7.23 (1H, m), 6.93 (1H, dt, J = 15.2, 5.9 Hz), 6.54-6.48 (1H, m), 6.43 (1H, d, J = 15.2 Hz), 5.90-5.83 (1H, m), 5.17 (1H, q, J = 7.0 Hz), 3.78-3.68 (1H, m), 3.74-3.66 (2H, m), 3.67-3.60 (2H, m), 3.42 (3H, s), 3.12 (2H, d, J = 5.9 Hz), 3.00 (3H, s), 2.66-2.56 (1H, m), 2.47-2.31 (1H, m), 2.28 (6H, s), 2.07-1.96 (1H, m), 1.88-1.76 (2H, m), 1.47-1.26 (3H, m), 1.34 (3H, d, J = 7.0 Hz), 1.15-1.04 (1H, m) |

TABLE 256

| Compound No. | Structure | Physicochemical data |
|---|---|---|
| 22-39 | 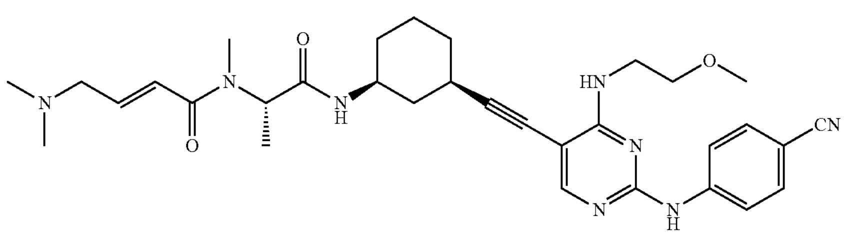 [SMILES: COCCNc1nc(Nc2ccc(C#N)cc2)ncc1C#C[C@@H]1CCC[C@H](NC(=O)[C@H](C)N(C)C(=O)/C=C/CN(C)C)C1] | ¹H-NMR (CDCl₃) δ: 7.99 (1H, s), 7.73 (2H, d, J = 9.2 Hz), 7.57 (2H, d, J = 9.2 Hz), 7.26-7.20 (1H, m), 6.92 (1H, dt, J = 15.2, 5.9 Hz), 6.42 (1H, d, J = 15.2 Hz), 6.35-6.28 (1H, m), 5.88-5.81 (1H, m), 5.14 (1H, q, J = 7.0 Hz), 3.78-3.65 (1H, m), 3.72-3.64 (2H, m), 3.64-3.58 (2H, m), 3.42 (3H, s), 3.11 (2H, d, J = 5.9 Hz), 2.98 (3H, s), 2.67-2.57 (1H, m), 2.36-2.27 (1H, m), 2.28 (6H, s), 2.05-1.97 (1H, m), 1.89-1.77 (2H, m), 1.45-1.24 (3H, m), 1.33 (3H, d, J = 7.0 Hz), 1.15-1.05 (1H, m) |

TABLE 256-continued

| Compound No. | Structure | Physicochemical data |
|---|---|---|
| 22-40 | 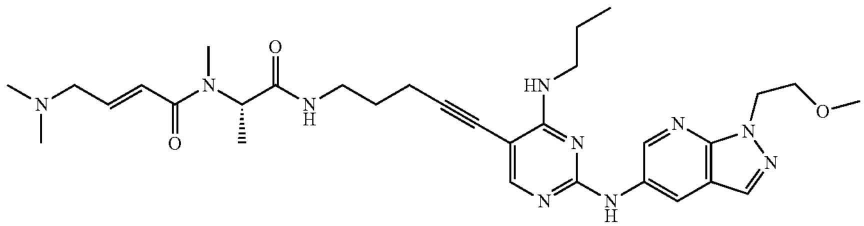 | ¹H-NMR (CDCl₃:CD₃OD = 10:1) δ: 8.65-8.52 (2H, m), 7.96 (1H, s), 7.91 (1H, s), 6.91 (1H, dt, J = 15.2, 6.2 Hz), 6.44 (1H, d, J = 15.2 Hz), 5.23-5.08 (1H, m), 4.75-4.65 (2H, m), 3.95-3.85 (2H, m), 3.53-3.30 (7H, m), 3.18-3.08 (2H, m), 3.04 (3H, s), 2.56-2.42 (2H, m), 2.30 (6H, s), 1.88-1.63 (4H, m), 1.37 (3H, d, J = 6.9 Hz), 0.99 (3H, t, J = 6.8 Hz) |
| 22-41 | 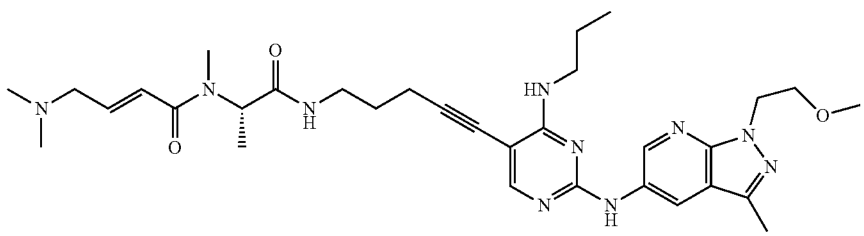 | ¹H-NMR (CDCl₃:CD₃OD = 10:1) δ: 8.58-8.50 (2H, m), 7.91 (1H, s), 6.92-6.75 (1H, m), 6.44 (1H, d, J = 15.9 Hz), 5.21-5.10 (1H, m), 4.67-4.56 (2H, m), 3.92-3.82 (2H, m), 3.55-3.28 (7H, m), 3.23-2.97 (5H, m), 2.56 (3H, s), 2.53-2.42 (2H, m), 2.28 (6H, s), 1.88-1.63 (4H, m), 1.36 (3H, d, J = 6.9 Hz), 0.98 (3H, t, J = 7.3 Hz) |
| 22-42 | 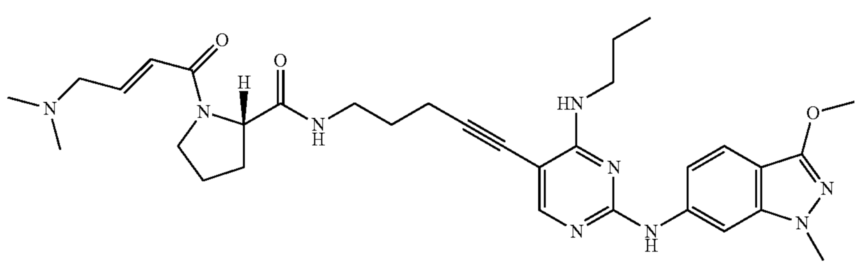 | MS m/z (M + H): 602.5 |
| 22-43 | 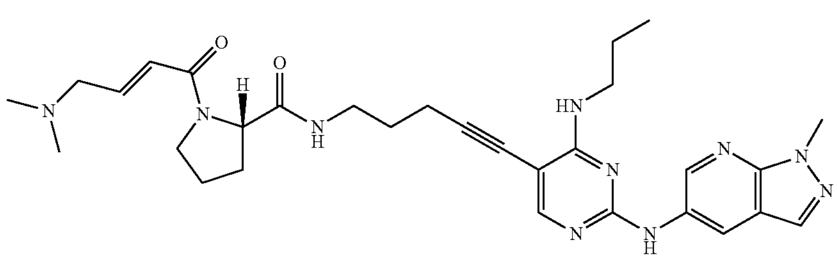 [SMILES: CCCNc1nc(Nc2cnc3c(cnn3C)c2)ncc1C#CCCCNC(=O)[C@@H]1CCCN1C(=O)/C=C/CN(C)C] | MS m/z (M + H): 573.5 |

TABLE 257

| Compound No. | Structure | Physicochemical data |
|---|---|---|
| 22-44 | 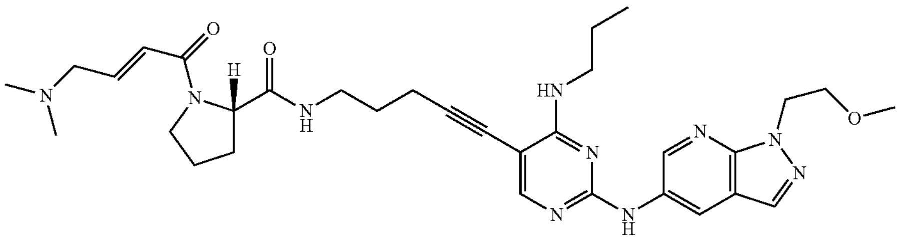 | ¹H-NMR (CDCl₃:CD₃OD = 10:1) δ: 8.60 (1H, d, J = 2.3 Hz), 8.58 (1H, d, J = 2.3 Hz), 7.96 (1H, s), 7.90 (1H, s), 6.91 (1H, dt, J = 15.2, 6.3 Hz), 6.35 (1H, d, J = 15.2 Hz), 4.69 (2H, t, J = 5.6 Hz), 4.59-4.51 (1H, m), 3.90 (2H, t, J = 5.6 Hz), 3.80-3.27 (9H, m), 3.25-3.09 (2H, m), 2.57-2.43 (2H, m), 2.29 (6H, s), 2.25-1.89 (4H, m), 1.88-1.60 (4H, m), 0.98 (3H, t, J = 7.4 Hz) |
| 22-45 | 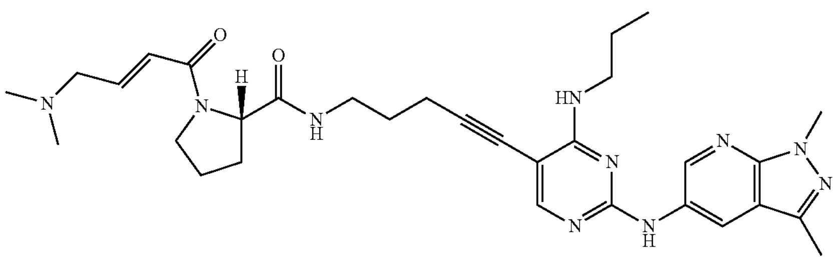 [SMILES: CCCNc1nc(Nc2cnc3c(c2)c(C)nn3C)ncc1C#CCCCNC(=O)[C@@H]1CCCN1C(=O)/C=C/CN(C)C] | MS m/z (M + H): 587.5 |
| 22-46 | 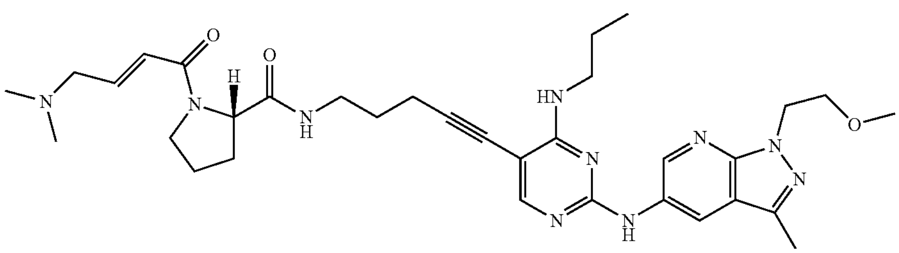 | ¹H-NMR (CDCl₃:CD₃OD = 10:1) δ: 8.55 (1H, s), 8.54 (1H, s), 7.90 (1H, s), 6.91 (1H, dt, J = 15.2, 6.3 Hz), 6.35 (1H, d, J = 15.2 Hz), 4.61 (2H, t, J = 5.6 Hz), 4.60-4.52 (1H, m), 3.86 (2H, t, J = 5.6 Hz), 3.77-3.27 (9H, m), 3.20-3.07 (2H, m), 2.56 (3H, s), 2.53-2.42 (2H, m), 2.28 (6H, s), 2.22-1.89 (4H, m), 1.88-1.61 (4H, m), 0.97 (3H, t, J = 7.4 Hz) |
| 22-47 | 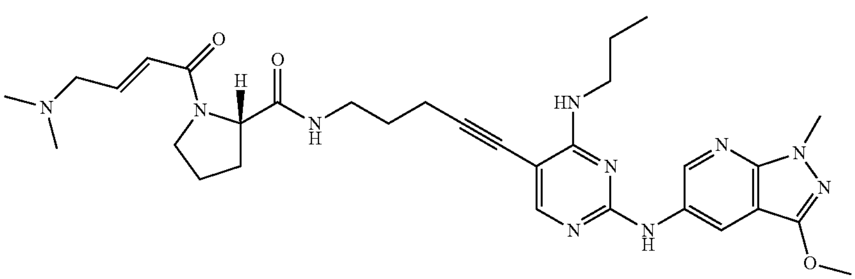 | MS m/z (M + H): 603.6 |

TABLE 257-continued

| Compound No. | Structure | Physicochemical data |
|---|---|---|
| 22-48 | 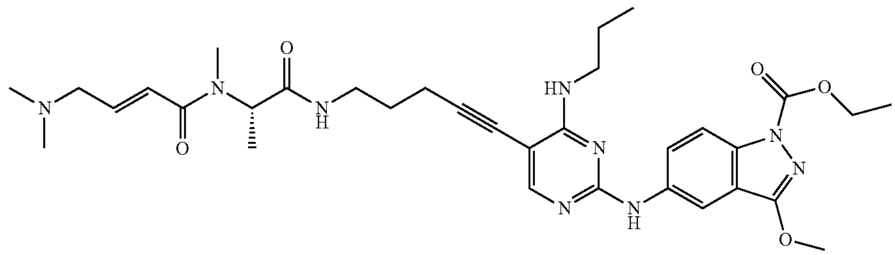 [SMILES: CCCNc1nc(Nc2ccc3c(c2)c(OC)nn3C(=O)OCC)ncc1C#CCCCNC(=O)[C@H](C)N(C)C(=O)/C=C/CN(C)C] | MS m/z (M + H): 648.6 |
| 22-49 | 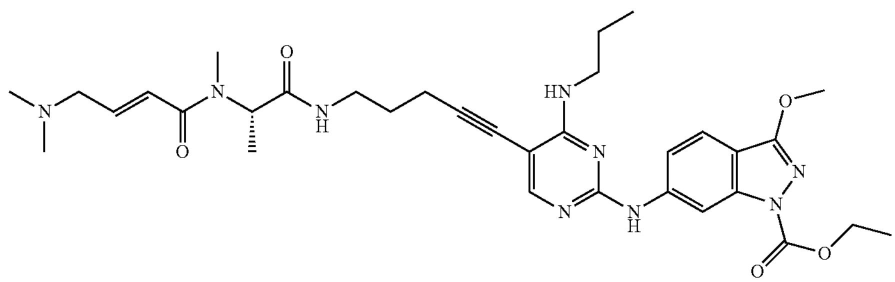 [SMILES: CCCNc1nc(Nc2ccc3c(OC)nn(C(=O)OCC)c3c2)ncc1C#CCCCNC(=O)[C@H](C)N(C)C(=O)/C=C/CN(C)C] | MS m/z (M + H): 648.6 |
| 22-50 | 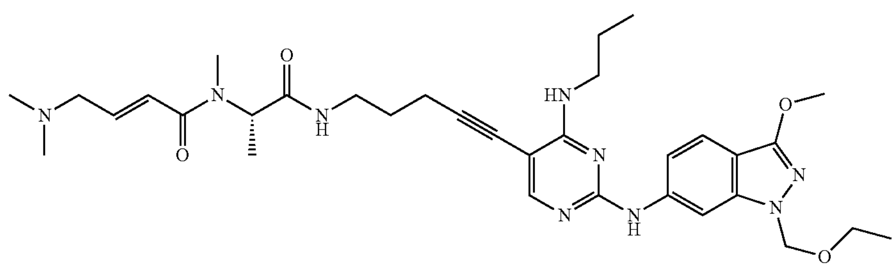 [SMILES: CCCNc1nc(Nc2ccc3c(OC)nn(COCC)c3c2)ncc1C#CCCCNC(=O)[C@H](C)N(C)C(=O)/C=C/CN(C)C] | MS m/z (M + H): 634.6 |

TABLE 258

| Compound No. | Structure | Physicochemical data |
|---|---|---|
| 22-51 | 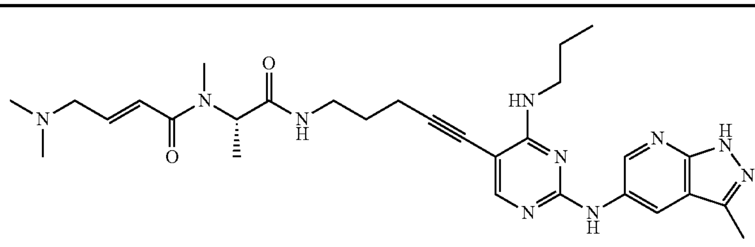 | $^1$H-NMR (CDCl$_3$:CD$_3$OD = 10:1) δ: 8.58(1H, s), 8.55 (1H, s), 7.91 (1H, s), 6.91 (1H, dt, J = 14.9, 6.3 Hz), 6.44 (1H, d, J = 14.9 Hz), 5.15 (1H, q, J = 7.6 Hz), 3.55-3.22 (4H, m), 3.19-3.09 (2H, m), 3.03 (3H, s), 2.57 (3H, s), 2.53-2.43 (2H, m), 2.29 (6H, s), 1.87-1.62 (4H, m), 1.36 (3H, d, J = 6.9 Hz), 0.97 (3H, t, J = 7.3 Hz) |

TABLE 258-continued
| Compound No. | Structure | Physicochemical data |
|---|---|---|
| 22-52 | 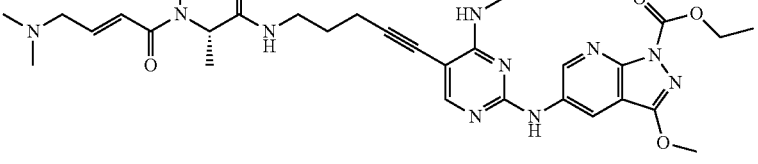 | MS m/z (M + H): 649.6 |
| 22-53 | 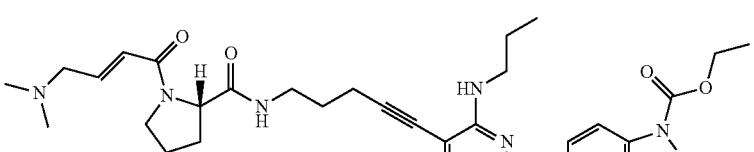 | MS m/z (M + H): 660.6 |
| 22-54 | 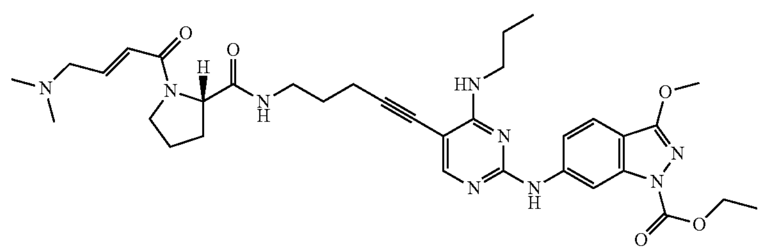 [SMILES: CCCNc1nc(Nc2ccc3c(OC)nn(C(=O)OCC)c3c2)ncc1C#CCCCNC(=O)[C@@H]1CCCN1C(=O)/C=C/CN(C)C] | MS m/z (M + H): 660.6 |
| 22-55 | 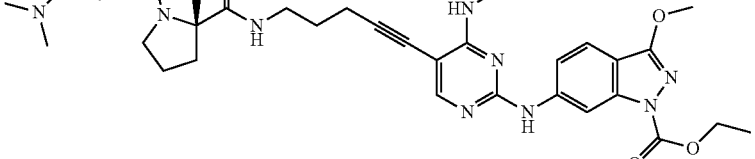 | MS m/z (M + H): 646.6 |
| 22-56 | 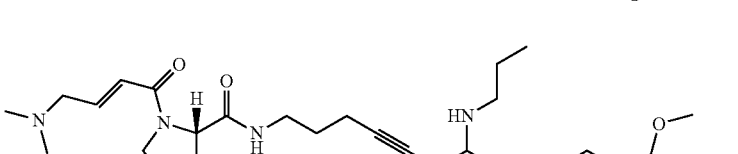 | MS m/z (M + H): 573.5 |
| 22-57 | 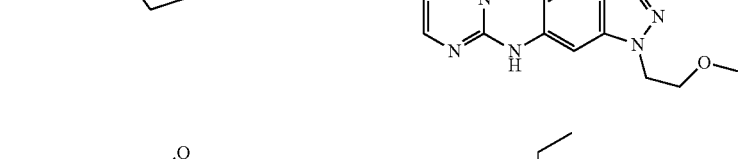 | MS m/z (M + H): 589.5 |

TABLE 259

| Compound No. | Structure | Physicochemical data |
|---|---|---|
| 22-58 | 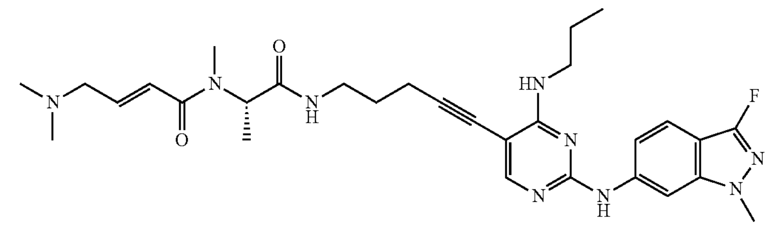 [SMILES: CCCNc1nc(Nc2ccc3c(F)nn(C)c3c2)ncc1C#CCCCNC(=O)[C@H](C)N(C)C(=O)/C=C/CN(C)C] | ¹H-NMR (CDCl₃) δ: 8.27-8.22 (1H, m), 8.00 (1H, s), 7.49 (1H, d, J = 8.6 Hz), 7.30-7.23 (1H, m), 7.01-6.85 (2H, m), 6.59-6.50 (1H, m), 6.43 (1H, dt, J = 15.0, 1.3 Hz), 6.34-6.26 (1H, m), 5.19 (1H, q, J = 7.0 Hz), 3.88 (3H, s), 3.63-3.52 (2H, m), 3.50-3.39 (2H, m), 3.11 (2H, dd, J = 5.9, 1.3 Hz), 3.00 (3H, s), 2.45 (2H, t, J = 6.6 Hz), 2.27 (6H, s), 1.82-1.72 (4H, m), 1.36 (3H, d, J = 7.0 Hz), 1.01 (3H, t, J = 7.3 Hz) |
| 22-59 | 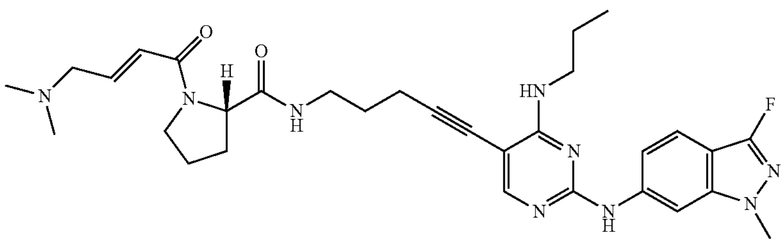 [SMILES: CCCNc1nc(Nc2ccc3c(F)nn(C)c3c2)ncc1C#CCCCNC(=O)[C@@H]1CCCN1C(=O)/C=C/CN(C)C] | ¹H-NMR (CDCl₃) δ: 8.27-8.23 (1H, m), 8.00 (1H, s), 7.49 (1H, d, J = 8.6 Hz), 7.47-7.40 (1H, m), 7.28-7.22 (1H, m), 6.97 (1H, dt, J = 15.2, 5.9 Hz), 6.90 (1H, dd, J = 8.6, 1.7 Hz), 6.38-6.27 (2H, m), 4.72-4.64 (1H, m), 3.88 (3H, s), 3.71-3.33 (6H, m), 3.11 (2H, d, J = 5.9 Hz), 2.48 (2H, t, J = 6.6 Hz), 2.27 (6H, s), 2.20-1.96 (2H, m), 1.88-1.70 (6H, m), 1.00 (3H, t, J = 7.6 Hz) |
| 22-60 | 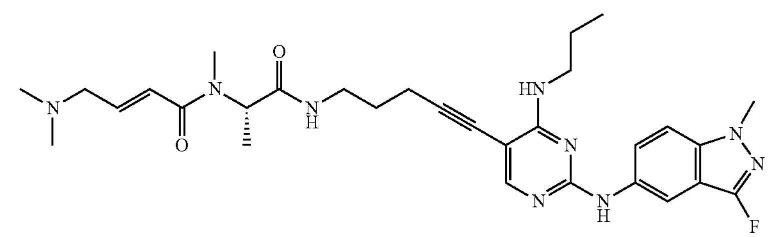 [SMILES: CCCNc1nc(Nc2ccc3c(c2)c(F)nn3C)ncc1C#CCCCNC(=O)[C@H](C)N(C)C(=O)/C=C/CN(C)C] | ¹H-NMR (CDCl₃) δ: 8.25-8.19 (1H, m), 7.95 (1H, s), 7.37 (1H, dd, J = 9.2, 2.0 Hz), 7.28-7.15 (2H, m), 6.94 (1H, dt, J = 15.2, 5.9 Hz), 6.58-6.49 (1H, m), 6.48-6.38 (1H, m), 6.32-6.22 (1H, m), 5.18 (1H, q, J = 7.3 Hz), 3.90 (3H, s), 3.57-3.38 (4H, m), 3.11 (2H, dd, J = 5.9, 1.3 Hz), 2.99 (3H, s), 2.44 (2H, t, J = 6.6 Hz), 2.27 (6H, s), 1.81-1.65 (4H, m), 1.36 (3H, d, J = 7.3 Hz), 1.01 (3H, t, J = 7.3 Hz) |
| 22-61 | 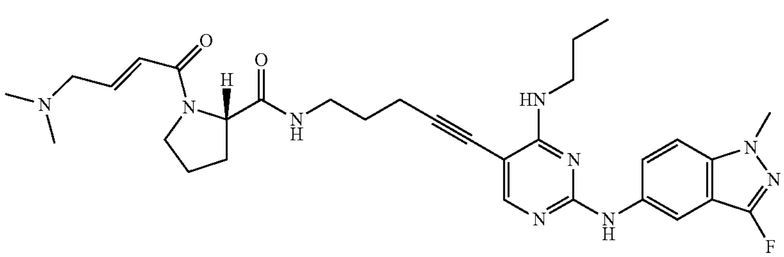 [SMILES: CCCNc1nc(Nc2ccc3c(c2)c(F)nn3C)ncc1C#CCCCNC(=O)[C@@H]1CCCN1C(=O)/C=C/CN(C)C] | ¹H-NMR (CDCl₃) δ: 8.26-8.20 (1H, m), 7.94 (1H, s), 7.47-7.34 (2H, m), 7.30-7.16 (2H, m), 6.96 (1H, dt, J = 15.2, 5.9 Hz), 6.38-6.28 (2H, m), 4.71-4.63 (1H, m), 3.90 (3H, s), 3.73-3.30 (6H, m), 3.11 (2H, d, J = 5.9 Hz), 2.47 (2H, t, |

TABLE 259-continued

| Compound No. | Structure | Physicochemical data |
|---|---|---|
| | | J = 6.6 Hz), 2.27 (6H, s), 2.19-1.96 (2H, m), 1.89-1.66 (6H, m), 1.00 (3H, t, J = 7.6 Hz) |

9

In the same manner as that of Example 40, (2), Compounds (22-62) to (22-68) were obtained.

TABLE 260

| Compound No. | Structure | Physicochemical data |
|---|---|---|
| 22-62 | 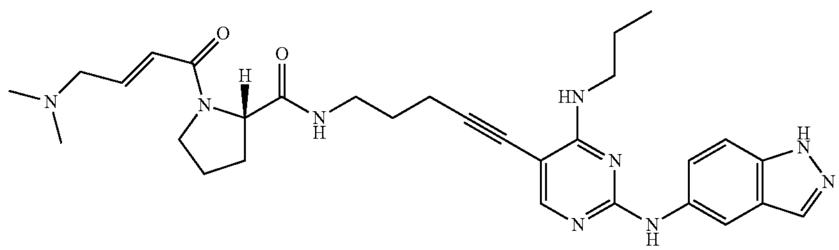 [SMILES: CCCNc1nc(Nc2ccc3[nH]ncc3c2)ncc1C#CCCCNC(=O)[C@@H]1CCCN1C(=O)/C=C/CN(C)C] | MS m/z (M + H): 558.5 |
| 22-63 | 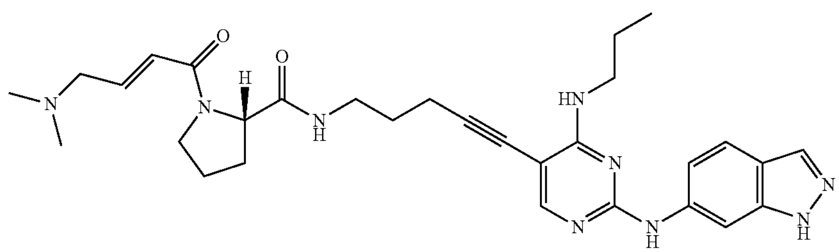 [SMILES: CCCNc1nc(Nc2ccc3cn[nH]c3c2)ncc1C#CCCCNC(=O)[C@@H]1CCCN1C(=O)/C=C/CN(C)C] | $^1$H-NMR (CDCl$_3$:CD$_3$OD = 10:1) δ: 8.15 (1H, s), 7.93 (1H, s), 7.92 (1H, s), 7.63 (1H, d, J = 8.9 Hz), 7.17 (1H, dd, J = 8.6, 1.7 Hz), 6.91 (1H, dt, J = 15.2, 6.3 Hz), 6.36 (1H, d, J = 15.2 Hz), 4.62-4.48 (1H, m), 3.57-3.47 (2H, m), 3.46-3.32 (4H, m), 3.23-3.15 (2H, m), 2.56-2.43 (2H, m), 2.31 (6H, s), 2.24-1.89 (4H, m), 1.86-1.63 (4H, m), 1.01 (3H, t, J = 7.4 Hz) |
| 22-64 | 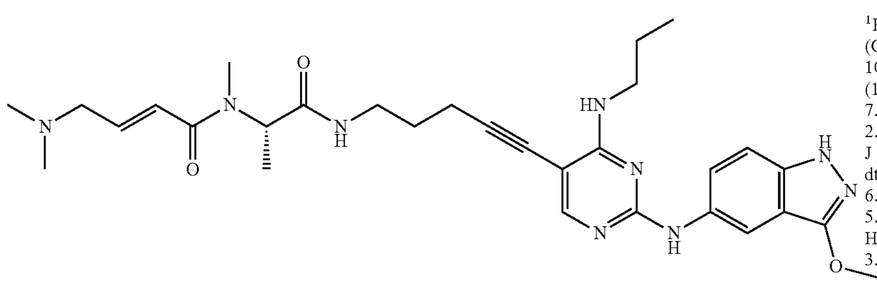 | $^1$H-NMR (CDCl$_3$:CD$_3$OD = 10:1) δ: 8.16 (1H, s), 7.88 (1H, s), 7.40 (1H, dd, J = 8.9, 2.0 Hz), 7.24 (1H, d, J = 8.9 Hz), 6.91 (1H, dt, J = 15.2, 6.3 Hz), 6.45 (1H, d, J = 15.2 Hz), 5.15 (1H, q, J = 6.9 Hz), 4.07 (3H, s), 3.55-3.45 (2H, m), 3.44-3.35 (2H, m), 3.17-3.09 (2H, m), 3.03 (3H, s), 2.54-2.40 (2H, m), 2.29 (6H, s), 1.88-1.63 (4H, m), 1.36 (3H, d, J = 7.3 Hz), 1.01 (3H, t, J = 7.3 Hz) |

TABLE 260-continued

| Compound No. | Structure | Physicochemical data |
|---|---|---|
| 22-65 | 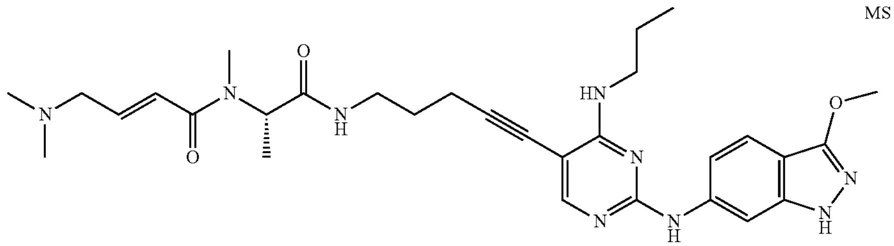 | MS m/z (M + H): 576.5 |
| 22-66 | 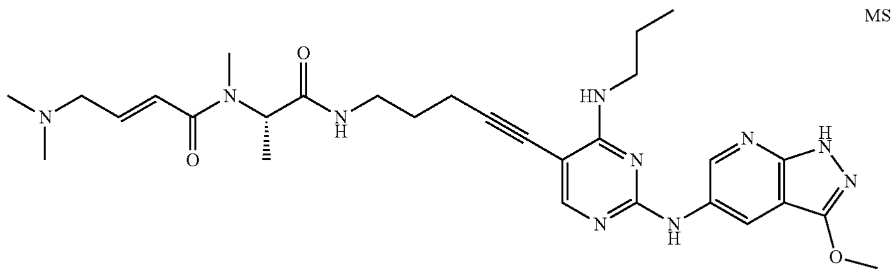 | MS m/z (M + H): 577.5 |

TABLE 261

| Compound No. | Structure | Physicochemical data |
|---|---|---|
| 22-67 | 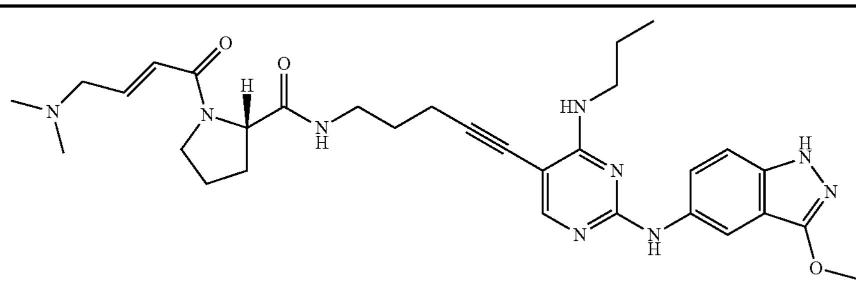 | $^1$H-NMR (CDCl$_3$:CD$_3$OD = 10:1) δ: 8.16 (1H, s), 7.87 (1H, s), 7.39 (1H, d, J = 8.8 Hz), 7.24 (1H, d, J = 8.8 Hz), 6.91 (1H, dt, J = 15.2, 6.3 Hz), 6.36 (1H, d, J = 15.2 Hz), 4.60-4.48 (1H, m), 4.07 (3H, s), 3.78-3.30 (6H, m), 3.13-3.05 (2H, m), 2.57-2.42 (2H, m), 2.31 (6H, s), 2.25-1.88 (4H, m), 1.87-1.60 (4H, m), 1.00 (3H, t, J = 6.9 Hz) |
| 22-68 | 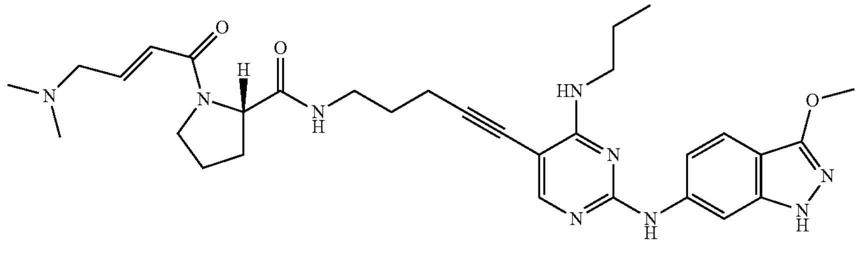 | $^1$H-NMR (CDCl$_3$:CD$_3$OD = 10:1) δ: 7.96 (1H, s), 7.91 (1H, s), 7.53 (1H, d, J = 8.8 Hz), 7.07 (1H, d, J = 8.8 Hz), 6.91 (1H, dt, J = 15.2, 6.3 Hz), 6.35 (1H, d, J = 15.2 Hz), 4.61-4.42 (1H, m), 4.07 (3H, s), 3.80-3.33 (6H, m), 3.20-3.06 (2H, m), 2.57-2.44 (2H, m), 2.29 (6H, s), 2.22-1.88 (4H, m), 1.88-1.63 (4H, m), 1.01 (3H, t, J = 6.9 Hz) |

The invention claimed is:
1. A compound represented by the general formula [1]:

[Formula 1]

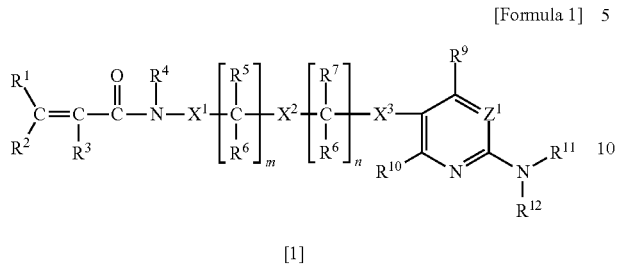

[1]

wherein,
R$^1$ represents hydrogen atom or a C$_{1-6}$ alkyl group which may be substituted,
R$^2$ represents hydrogen atom, a C$_{1-6}$ alkyl group which may be substituted, a C$_{2-6}$ alkenyl group which may be substituted or a C$_{2-6}$ alkynyl group which may be substituted,
R$^3$ represents hydrogen atom, a C$_{1-6}$ alkyl group which may be substituted, a C$_{2-6}$ alkenyl group which may be substituted or a C$_{2-6}$ alkynyl group which may be substituted, or
R$^2$ and R$^3$ may bind together to form an atomic bond,
R$^4$ represents hydrogen atom, a C$_{1-6}$ alkyl group which may be substituted, a C$_{2-6}$ alkenyl group which may be substituted, a C$_{2-6}$ alkynyl group which may be substituted, a C$_{3-8}$ cycloalkyl group which may be substituted or an imino protecting group,
m of R$^5$ are the same or different, and represent hydrogen atom or a C$_{1-6}$ alkyl group which may be substituted,
m of R$^6$ are the same or different, and represent hydrogen atom or a C$_{1-6}$ alkyl group which may be substituted, or
R$^5$ and R$^6$ binding to the same carbon atom may bind together to form a C$_{2-6}$ alkylene group which may be substituted, an O—(C$_{1-6}$ alkylene) group which may be substituted, an N(R$^{13}$)—(C$_{1-6}$ alkylene) group which may be substituted wherein R$^{13}$ represents hydrogen atom, a C$_{1-6}$ alkyl group which may be substituted or an imino protecting group, a (C$_{1-3}$ alkylene)—O—(C$_{1-3}$ alkylene) group which may be substituted or a (C$_{1-3}$ alkylene)-N(R$^{13}$)—(C$_{1-3}$ alkylene) group which may be substituted wherein R$^{13}$ has the same meanings as that defined above,
n of R$^7$ are the same or different, and represent hydrogen atom or a C$_{1-6}$ alkyl group which may be substituted,
n of R$^8$ are the same or different, and represent hydrogen atom or a C$_{1-6}$ alkyl group which may be substituted, or
R$^7$ and R$^8$ binding to the same carbon atom may bind together to form a C$_{2-6}$ alkylene group which may be substituted, an O—(C$_{1-6}$ alkylene) group which may be substituted, an N(R$^{14}$)—(C$_{1-6}$ alkylene) group which may be substituted wherein R$^{14}$ represents hydrogen atom, a C$_{1-6}$ alkyl group which may be substituted or an imino protecting group, a (C$_{1-3}$ alkylene)-O—(C$_{1-3}$ alkylene) group which may be substituted or a (C$_{1-3}$ alkylene)-N(R$^{14}$)—(C$_{1-3}$ alkylene) group which may be substituted wherein R$^{14}$ has the same meaning as that defined above,
R$^9$ represents a C$_{1-6}$ alkyl group which may be substituted, a C$_{3-8}$ cycloalkyl group which may be substituted, an aryl group which may be substituted, a C$_{1-6}$ alkoxy group which may be substituted, a heterocyclic group which may be substituted or N(R$^{15}$)(R$^{16}$) wherein R$^{15}$ represents hydrogen atom, a C$_{1-6}$ alkyl group which may be substituted, a C$_{2-6}$ alkenyl group which may be substituted, a C$_{2-6}$ alkynyl group which may be substituted or a C$_{3-8}$ cycloalkyl group which may be substituted, and R$^{16}$ represents a C$_{1-6}$ alkyl group which may be substituted, a C$_{2-6}$ alkenyl group which may be substituted, a C$_{2-6}$ alkynyl group which may be substituted, a C$_{3-8}$ cycloalkyl group which may be substituted, an aryl group which may be substituted or a heterocyclic group which may be substituted, or R$^{15}$ and R$^{16}$ may form a cyclic amino group which may be substituted together with the nitrogen atom to which they bind,
R$^{10}$ represents hydrogen atom, a halogen atom, a C$_{1-6}$ alkyl group which may be substituted, a C$_{3-8}$ cycloalkyl group which may be substituted, an aryl group which may be substituted, a C$_{1-6}$ alkoxy group which may be substituted or a heterocyclic group which may be substituted,
R$^{11}$ represents hydrogen atom, a C$_{1-6}$ alkyl group which may be substituted, a C$_{2-6}$ alkenyl group which may be substituted, a C$_{2-6}$ alkynyl group which may be substituted or a C$_{3-8}$ cycloalkyl group which may be substituted,
R$^{12}$ represents a C$_{1-6}$ alkyl group which may be substituted with one or more groups selected from a halogen atom, cyano group, amino group which may be protected, hydroxyl group which may be protected, a carbamoyl group which may be substituted with one or more groups selected from the substituent group A, a C$_{1-6}$ alkyl group which may be substituted with one or more groups selected from the substituent group A, an aryl group which may be substituted with one or more groups selected from the substituent group A, a C$_{1-6}$ alkoxy group which may be substituted with one or more groups selected from the substituent group A, an acyl group which may be substituted with one or more groups selected from the substituent group A, a C$_{1-6}$ alkoxycarbonyl group which may be substituted with one or more groups selected from the substituent group A, a C$_{1-6}$ alkylamino group which may be substituted with one or more groups selected from the substituent group A, a di(C$_{1-6}$ alkyl)amino group which may be substituted with one or more groups selected from the substituent group A, a C$_{1-6}$ alkylsulfonyl group which may be substituted with one or more groups selected from the substituent group A, a C$_{1-6}$ alkylsulfonylamino group which may be substituted with one or more groups selected from the substituent group A, and a heterocyclic group which may be substituted with one or more groups selected from the substituent group A, a C$_{2-6}$ alkenyl group which may be substituted, a C$_{2-6}$ alkynyl group which may be substituted, a C$_{3-8}$ cycloalkyl group which may be substituted, an aryl group which may be substituted, a heterocyclic group which may be substituted or a carbamoyl group which may be substituted,
X$^1$ represents a group represented by the general formula [2]:

[Formula 2]

—X$^4$—X$^5$—     [2]

wherein X$^4$ represents a divalent alicyclic hydrocarbon group which may be substituted, a divalent aromatic hydrocarbon group which may be substituted, a divalent heterocyclic group which may be substituted, a group represented by the general formula [3]

[Formula 3]

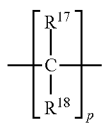

[3]

wherein p of $R^{17}$ are the same or different, and represent hydrogen atom or a $C_{1-6}$ alkyl group which may be substituted, or one $R^{17}$ selected from p of $R^{17}$ may bind with $R^4$ to form a $C_{1-6}$ alkylene group which may be substituted, a $(C_{1-3}$ alkylene)-O group which may be substituted, a $(C_{1-3}$ alkylene)-$N(R^{19})$ group which may be substituted wherein $R^{19}$ represents hydrogen atom, a $C_{1-6}$ alkyl group which may be substituted or an imino protecting group, a $(C_{1-3}$ alkylene)-O—$(C_{1-3}$ alkylene) group which may be substituted or a $(C_{1-3}$ alkylene)-N$(R^{19})$—$(C_{1-3}$ alkylene) group which may be substituted wherein $R^{19}$ has the same meanings as that defined above, p of $R^{18}$ are the same or different, and represent hydrogen atom or a $C_{1-6}$ alkyl group which may be substituted, or $R^{17}$ and $R^{18}$ binding to the same carbon atom may bind together to form a $C_{2-6}$ alkylene group which may be substituted, an O—$(C_{1-6}$ alkylene) group which may be substituted, an $N(R^{20})$—$(C_{1-6}$ alkylene) group which may be substituted wherein $R^{20}$ represents hydrogen atom, a $C_{1-6}$ alkyl group which may be substituted or an imino protecting group, a $(C_{1-3}$ alkylene)-O—$(C_{1-3}$ alkylene) group which may be substituted or a $(C_{1-3}$ alkylene)-$N(R^{20})$—$(C_{1-3}$ alkylene) group which may be substituted wherein $R^{20}$ has the same meanings as that defined above, and p represents an integer of 1 to 6, and $X^5$ represents oxygen atom, $N(R^{21})$ wherein $R^{21}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group, or $R^{21}$ may bind with $R^4$ to form a $C_{1-6}$ alkylene group which may be substituted, C(=O), C(=O)—$N(R^{21})$ wherein $R^{21}$ has the same meaning as that defined above, or an atomic bond, $X^2$ represents a $C_{1-6}$ alkylene group which may be substituted, a divalent alicyclic hydrocarbon group which may be substituted, a divalent aromatic hydrocarbon group which may be substituted or a divalent heterocyclic group which may be substituted, $X^3$ represents a $C_{1-6}$ alkylene group which may be substituted, a $C_{2-6}$ alkenylene group which may be substituted, a $C_{2-6}$ alkynylene group which may be substituted, an O—$(C_{1-6}$ alkylene) group which may be substituted, an $S(O)_q$—$(C_{1-6}$ alkylene) group which may be substituted wherein q represents 0, 1 or 2, an $N(R^{22})$—$(C_{1-6}$ alkylene) group which may be substituted wherein $R^{22}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group, $N(R^{22})$—C(=O) wherein $R^{22}$ has the same meaning as that defined above, or an atomic bond, $Z^1$ represents nitrogen atom or $C(R^{23})$ wherein $R^{23}$ represents hydrogen atom, a halogen atom, a $C_{1-6}$ alkyl group which may be substituted, a $C_{3-8}$ cycloalkyl group which may be substituted, an aryl group which may be substituted, a $C_{1-6}$ alkoxy group which may be substituted or a heterocyclic group which may be substituted, m represents an integer of 0 to 6, n represents an integer of 0 to 6 or a salt thereof substituent group A represents a halogen atom, cyano group, amino group which may be protected, hydroxyl group which may be protected, a $C_{1-6}$ alkyl group which may be substituted with one or more groups selected from substituent group B, a $C_{3-8}$ cycloalkyl group which may be substituted with one or more groups selected from the substituent group B, an aryl group which may be substituted with one or more groups selected from the substituent group B, a $C_{1-6}$ alkoxy group which may be substituted with one or more groups selected from the substituent group B, a $C_{1-6}$ alkylamino group which may be substituted with one or more groups selected from the substituent group B, a di($C_{1-6}$ alkyl)amino group which may be substituted with one or more groups selected from the substituent group B, a heterocyclic group which may be substituted with one or more groups selected from the substituent group B, or an oxo group, and substituent group B represents a halogen atom, cyano group, amino group which may be protected, hydroxyl group which may be protected, a $C_{1-6}$ alkyl group which may be substituted with a halogen atom or hydroxyl group, a $C_{1-6}$ alkoxy group which may be substituted with a halogen atom or hydroxyl group, an aryl group, a heterocyclic group, or an oxo group.

2. The compound or a salt thereof according to claim 1, wherein $Z^1$ is nitrogen atom.

3. The compound or a salt thereof according to claim 1, wherein $X^3$ is a $C_{2-6}$ alkynylene group which may be substituted or $N(R^{22})$—C(=O) wherein $R^{22}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group.

4. The compound or a salt thereof according to claim 1, wherein $R^1$ is hydrogen atom, and $R^2$ is a $C_{1-6}$ alkyl group which may be substituted.

5. The compound or a salt thereof according to claim 1, wherein $R^9$ is $N(R^{15})(R^{16})$ wherein $R^{15}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, and $R^{16}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted, or $R^{15}$ and $R^{16}$ may form a cyclic amino group which may be substituted together with the nitrogen atom to which they bind.

6. The compound or a salt thereof according to claim 1, wherein $R^{11}$ is hydrogen atom, and $R^{12}$ is an aryl group which may be substituted or a heterocyclic group which may be substituted.

7. The compound or a salt thereof according to claim 1, wherein $R^{11}$ is hydrogen atom, and $R^{12}$ is phenyl group which may be substituted, pyridyl group which may be substituted, pyrazolyl group which may be substituted, thienyl group which may be substituted, oxazoyl group which may be substituted, thiazolyl group which may be substituted, isothiazolyl group which may be substituted, indazolyl group which may be substituted, pyrazolopyridinyl group which may be substituted, quinolyl group which may be substituted, isoquinolyl group which may be substituted, cinnolinyl group which may be substituted, phthalazinyl group which may be substituted, quinoxalinyl group which may be substituted, benzofuranyl group which may be substituted or benzothiazolyl group which may be substituted.

8. The compound or a salt thereof according to claim 1, wherein $R^4$ is hydrogen atom or a $C_{1-6}$ alkyl group which may be substituted.

9. The compound or as salt thereof according to claim 1, wherein $X^2$ is a $C_{1-6}$ alkylene group which may be substituted or a divalent alicyclic hydrocarbon group which may be substituted.

10. The compound or a salt thereof according to claim 1, wherein $X^1$ is a group represented by the general formula [2]:

[Formula 4]

$$-X^4-X^5- \qquad [2]$$

wherein $X^4$ represents as group represented by the general formula [3]

[Formula 5]

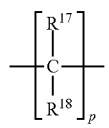

[3]

wherein p of $R^{17}$ the same or different, and represent hydrogen atom or a $C_{1-6}$ alkyl group which may be substituted, p of $R^{18}$ are the same or different, and represent hydrogen atom or a $C_{1-6}$ alkyl group which may be substituted, and p represents an integer of 1 to 6, and $X^5$ represents a group represented as $C(=O)-N(R^{21})$ wherein $R^{21}$ represents hydrogen atom.

11. The compound or a salt thereof according to claim 1, wherein $R^3$ is hydrogen atom or a $C_{1-6}$ alkyl group which may be substituted.

12. The compound or a salt thereof according to claim 1, wherein $R^5$, $R^6$, $R^7$ and $R^8$ are hydrogen atoms.

13. The compound or a salt thereof according to claim 1, wherein $R^{10}$ is hydrogen atom.

14. A compound represented by general formula [1]-(1):

[Formula 6]

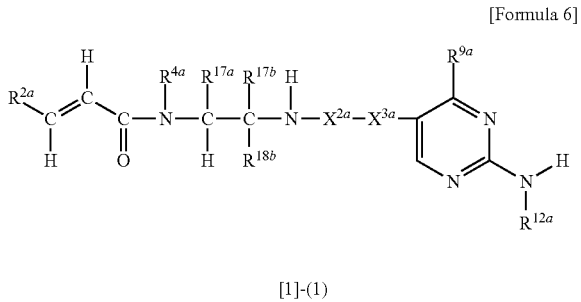

[1]-(1)

wherein
$R^{2a}$ represents hydrogen atom or a $C_{1-6}$ alkyl group which may be substituted,
$R^{4a}$ represents hydrogen atom or a $C_{1-6}$ alkyl group which may be substituted,
$R^{17a}$ represents hydrogen atom or a $C_{1-6}$ alkyl group which may be substituted, provided that $R^{17a}$ may form a divalent nitrogen-containing heterocyclic group which may be substituted together with $R^{4a}$, the nitrogen atom to which $R^{4a}$ binds, and the carbon atom to which $R^{17a}$ binds,
$R^{17b}$ and $R^{18b}$ are the same or different, and represent hydrogen atom or a $C_{1-6}$ alkyl group which may be substituted, provided that $R^{17b}$ and $R^{18b}$ may form $C(=O)$ together with the carbon atom to which they bind, or $R^{17b}$ and $R^{18b}$ may form a heterocyclic group which may be substituted together with the carbon atom to which they bind,
$R^{9a}$ represents a $C_{1-6}$ alkyl group which may be substituted, a $C_{1-6}$ alkoxy group which may be substituted, a heterocyclic group which may be substituted or $N(R^{15})(R^{16})$ wherein $R^{15}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, and $R^{16}$ represents a $C_{1-6}$ alkyl group which may be substituted, a $C_{2-6}$ alkenyl group which may be substituted, a $C_{2-6}$ alkyl group which may be substituted, a $C_{3-8}$ cycloalkyl group which may be substituted, an aryl group which may be substituted or a heterocyclic group which may be substituted, or $R^{15}$ and $R^{16}$ may form a cyclic amino group which may be substituted together with the nitrogen atom to which they bind,
$R^{12a}$ represents a $C_{1-6}$ alkyl group which may be substituted, an aryl group which may be substituted or a heterocyclic group which may be substituted,
$X^{2a}$ represents a $C_{1-6}$ alkylene group which may be substituted, a divalent alicyclic hydrocarbon group which may be substituted or a divalent aromatic hydrocarbon group which may be substituted, and
$X^{3a}$ represents a $C_{2-6}$ alkynylene group which may be substituted or $N(R^{22})-C(=O)$ wherein $R^{22}$ represents hydrogen atom, a $C_{1-6}$ alkyl group which may be substituted, a $C_{2-6}$ alkenyl group which may be substituted, a $C_{2-6}$ alkynyl group which may be substituted or an imino protecting group or a salt thereof.

15. The compound or a salt thereof according to claim 14, wherein $R^{2a}$ is a $C_{1-6}$ alkyl group which may be substituted, substituent of the $C_{1-6}$ alkyl group which may be substituted as $R^{2a}$ is a halogen atom, hydroxyl group, a $C_{1-6}$ alkylamino group which may be substituted with one or more groups selected from the substituent group A-3, a di($C_{1-6}$ alkyl) amino group which may be substituted with one or more groups selected from the substituent group A-3 or a heterocyclic group which may be substituted with one or more groups selected from the substituent group A-3, and the substituent group A-3 consists of a halogen atom, hydroxyl group which may be protected, and a $C_{1-6}$ alkyl group which may be substituted with hydroxyl group.

16. The compound or a salt thereof according to claim 14, wherein
$R^{4a}$ is hydrogen atom or a $C_{1-6}$ alkyl group;
$R^{17a}$ is hydrogen atom or a $C_{1-6}$ alkyl group;
$R^{17b}$ and $R^{18b}$ are the same or different, and represent a $C_{1-6}$ alkyl group, or $R^{17b}$ and $R^{18b}$ form $C(=O)$ together with the carbon atom to which they bind;
$R^{9a}$ is $N(R^{15})(R^{16})$ wherein $R^{15}$ represents hydrogen atom, a $C_{1-6}$ alkyl group which may be substituted, a $C_{2-6}$ alkenyl group which may be substituted, a $C_{2-6}$ alkynyl group which may be substituted or a $C_{3-8}$ cycloalkyl group which may be substituted, and $R^{16}$ represents a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, an aryl group which may be substituted or a heterocyclic group which may be substituted, or R$^{15}$ and R$^{16}$ form a cyclic amino group which may be substituted together with the nitrogen atom to which they bind;

R$^{12a}$ is an aryl group which may be substituted;

X$^{2a}$ is a C$_{1-6}$ alkylene group which may be substituted or a divalent alicyclic hydrocarbon group which may be substituted; and/or X$^{3a}$ is a C$_{2-6}$ alkynylene group which may be substituted.

17. The compound or a salt thereof according to claim 1, which is a compound selected from (S,E)-N-(3-(2-(4-(dimethylamino)-N-methyl-2-butenamido)propanamido)phenyl)-4-(propylamino)-2-((2-(pyridin-4-yl)ethyl)amino)pyrimidine-5-carboxamide, carbamoylphenyl)amino)-N-(3-(2-(4-(dimethylamino)-N-methyl-2-butenamido)propanamido)phenyl)-4-(propylamino)pyrimidine-5-carboxamide, (E)-2-((4-carbamoylphenyl)amino)-N-(3-(2-(4-(dimethylamino)-N-methyl-2-butenamido)actamido)cyclohexyl)-4-(propylamino)pyrimidine-5-carboxamide, (S,E)-2-((4-carbamoylphenyl)amino)-N-(3-(2-(4-(diethylamino)-N-methyl-2-butenamido)propanamido)phenyl)-4-(propylamino)pyrimidine-5-carboxamide, (S,E)-2-((4-carbamoylphenyl)amino)-N-(3-(2-(4-(dimethylamino)-N-methyl-2-butenamido)propaneamido)propyl)-4-(propylamino)pyrimidine-5-carboxamide, (S,E)-N-(3-(2-(4-(dimethylamino)-N-methyl-2-butenamido)propanamido)phenyl)-2-(isoquinolin-6-ylamino)-4-(propylamino)pyrimidine-5-carboxamide, (S,E)-2-(cinnolin-6-ylamino)-N-(3-(2-(4-(dimethylamino)-N-methyl-2-butenamido)propanamido)phenyl)-4-(propylamino)pyrimidine-5-carboxamide, (S,E)-4-(dimethylamino)-N-(1-((5-(2-((3-fluorophenyl)amino)-4-(propylamino)pyrimidin-5-yl)-4-pentyn-1-yl)amino)-1-oxopropan-2-yl)-N-methyl-2-butenamide, (S,E)-N-(1-((5-(2-((3-cyanophenyl)amino)-4-(propylamino)pyrimidin-5-yl)-4-pentyn-1-yl)amino)-1-oxopropan-2-yl)-4-(dimethylamino)-N-methyl-2-butenamide, (S,E)-4-((5-(5-(2-(4-(dimethylamino)-N-methyl-2-butenamido)propaneamido)-1-pentyn-1-yl)-4-(propylamino)pyrimidin-2-yl)amino)benzamide, (S,E)-N-(1-((5-(2-((4-cyanophenyl)amino)-4-(propylamino)pyrimidin-5-yl)-4-pentyn-1-yl)amino)-1-oxopropan-2-yl)-4-(dimethylamino)-N-methyl-2-butenamide, (E)-4-(dimethylamino)-N-(2-((5-(2-((4-fluorophenyl)amino)-4-(propylamino)pyrimidin-5-yl)-4-pentyn-1-yl)amino)-2-oxoethyl)-N-methyl-2-butenamide, (E)-N-(2-((5-(2-((4-cyanophenyl)amino)-4-(propylamino)pyrimidin-5-yl)-4-pentyn-1-yl)amino)-2-oxoethyl)-4-(dimethylamino)-N-methyl-2-butenamide, (S,E)-4-(dimethylamino)-N-(1-((5-(2-((3-fluorophenyl)amino)-4-(propylamino)pyrimidin-5-yl)-4-pentyn-1-yl)amino)-1-oxobutan-2-yl)-N-methyl-2-butenamide, (S,E)-4-(dimethylamino)-N-(1-((5-(2-((3-fluoro-4-methoxyphenyl)amino)-4-(propylamino)pyrimidin-5-yl)-4-pentyn-yl)amino)-1-oxopropan-2-yl)-N-methyl-2-butenamide, (S,E)-4-(dimethylamino)-N-(1-((5-(2-((6-fluoropyridin-3-yl)amino)-4-(propylamino)pyrimidin-5-yl)-4-pentyn-1-yl)amino)-1-oxopropan-2-yl)-N-methyl-2-butenamide, (S,E)-4-(dimethylamino)-N-(1-((5-(2-((6-fluoropyridin-3-yl)amino)-4-((4-methoxyphenyl)amino)pyrimidin-5-yl)-4-pentyn-1-yl)amino)-1-oxopropan-2-yl)-N-methyl-2-butenamide, (E)-4-(dimethylamino)-N-(2-((5-(2-((3-fluorophenyl)amino)-4-(propylamino)pyrimidin-5-yl)-4-pentyn-1-yl)amino)-2-oxoethyl)-N-methyl-2-butenamide, (S,E)-N-(5-(2-((4-cyanophenyl)amino)-4-(propylamino)pyrimidin-5-yl)-4-pentyn-1-yl)-1-(4-(dimethylamino)-2-butenoyl)pyrrolidine-2-carboxamide, (S,E)-N-(1-((5-(4-(cyclopropylamino)-2-((3-fluoro-4-methoxyphenyl)amino)pyrimidin-5-yl)-4-pentyn-1-yl)amino)-1-oxopropan-2-yl)-4-(dimethylamino)-N-methyl-2-butenamide, (S,E)-4-(dimethylamino)-N-(1-((5-(2-((3-fluoro-4-methoxyphenyl)amino)-4-((3-fluoropropyl)amino) pyrimidin-5-yl)-4-pentyn-1-yl)amino)-1-oxopropan-2-yl)-N-methyl-2-butenamide, (S,E)-N-(1-((5-(2-((4-cyanophenyl)amino)-4-(propylamino)pyrimidin-5-yl)-4-pentyn-1-yl)amino)-3-hydroxy-1-oxopropan-2-yl)-4-(dimethylamino)-N-methyl-2-butenamide, (2S,4R)-1-((E)-4-(dimethylamino)-2-butenoyl)-N-(5-(2-((3-fluorophenyl)amino)-4-(propylamino)pyrimidin-5-yl)-4-pentyn-1-yl)-4-hydroxypyrrolidine-2-carboxamide, (2S,4S)-1-((E)-4-(dimethylamino)-2-butenoyl)-4-fluoro-N-(5-(2-((3-fluorophenyl)amino)-4-(methylamino)pyrimidin-5-yl)-4-pentyn-1-yl)pyrrolidine-2-carboxamide, (2S,4S)-1-((E)-4-(dimethylamino)-2-butenoyl)-N-(5-(2-((3-fluorophenyl)amino)-4-(methylamino)pyrimidin-5-yl)-4-pentyn-1-yl)-4-methoxypyrrolidine-2-carboxamide, (2S,4S)-1-((E)-4-(dimethylamino)-2-butenoyl)-4-fluoro-N-(5-(2-((4-fluorophenyl)amino)-4-(methylamino)pyrimidin-5-yl)-4-pentyn-1-yl)pyrrolidine-2-carboxamide, (2S,4R)-1-((E)-4-(dimethylamino)-2-butenoyl)-4-fluoro-N-(5-(2-((4-fluorophenyl)amino)-4-(methylamino)pyrimidin-5-yl)-4-pentyn-1-yl)pyrrolidine-2-carboxamide, (2S,4S)-1-((E)-4-(dimethylamino)-2-butenoyl)-N-(5-(2-((4-fluorophenyl)amino)-4-(methylamino)pyrimidin-5-yl)-4-pentyn-1-yl)-4-methoxypyrrolidine-2-carboxamide, (2S,4R)-1-((E)-4-(dimethylamino)-2-butenoyl)-N-(5-(2-((4-fluorophenyl)amino)-4-(methylamino)pyrimidin-5-yl)-4-pentyn-1-yl)-4-methoxypyrrolidine-2-carboxamide, (S,E)-1-(4-(dimethylamino)-2-butenoyl)-N-(5-(2-((4-fluorophenyl)amino)-4-(methylamino)pyrimidin-5-yl)-4-pentyn-1-yl)azetidine-2-carboxamide, (2S,4S)—N-(5-(2-((4-cyanophenyl)amino)-4-(methylamino)pyrimidin-5-yl)-4-pentyn-1-yl)-1-((E)-4-(dimethylamino)-2-butenoyl)-4-fluoropyrrolidine-2-carboxamide, (E)-N-(2-((5-(2-((4-cyanophenyl)amino)-4-(methylamino)pyrimidin-5-yl)-4-pentyn-1-yl)amino)-2-oxoethyl)-4-(dimethylamino)-N-methyl-2-butenamide, (S,E)-4-(dimethylamino)-N-(1-((3-((2-((3-fluorophenyl)amino)-4-(propylamino)pyrimidin-5-yl)ethynyl)phenyl)amino)-1-oxopropan-2-yl)-N-methyl-2-butenamide, (S,E)-4-((5-((3-(2-(4-(dimethylamino)-N-methyl-2-butenamido)propanamido)phenyl)ethynyl)-4-(propylamino)pyrimidin-2-yl)amino)benzamide, (S,E)-N-(1-((5-(2-((4-cyanophenyl)amino)-4-(pyrrolidin-1-yl)pyrimidin-5-yl)-4-pentyn-1-yl)amino)-1-oxopropan-2-yl)-4-(dimethylamino)-N-methyl-2-butenamide, (S,E)-4-(dimethylamino)-N-(1-((5-(2-((2-fluoropyridin-4-yl)amino)-4-(pyrrolidin-1-yl)pyrimidin-5-yl)-4-pentyn-1-yl)amino)-1-oxopropan-2-yl)-N-methyl-2-butenamide, (S,E)-4-(dimethylamino)-N-(1-((5-(2-((2-fluoropyridin-4-yl)amino)-4-(propylamino)pyrimidin-5-yl)-4-pentyn-1-yl)amino)-1-oxopropan-2-yl)-N-methyl-2-butenamide, (S,E)-N-(1-((5-(4-(cyclopropylamino)-2-((2 fluoropyridin-4-yl)amino)pyrimidin-5-yl)-4-pentyn-1-yl)amino)-1-oxopropan-2-yl)-4-(dimethylamino)-N-methyl-2-butenamide, (S,E)-4-(dimethylamino)-N-methyl-N-(1-((5-(2-((3-methylisothiazol-5-yl)amino)-4-(propylamino)pyrimidin-5-yl)-4-pentyn-1-yl)amino)-1-oxopropan-2-yl)-2-butenamide, (S,E)-4-(dimethylamino)-N-(1-((5-(4-((3-methoxypropyl)amino)-2-((2-methoxypyridin-4-yl)amino)pyrimidin-5-yl)-4-pentyn-1-yl)amino)-1-oxopropan-2-yl)-N-methyl-2-butenamide, (S,E)-1-(4-(dimethylamino)-2-butenoyl)-N-(5-(4-((3-methoxypropyl)amino)-2-((methoxypyridin-4-yl)amino)pyrimidin-5-yl)-4-pentyn-1-yl)pyrrolidine-2-carboxamide, (2S,4S)-1-((E)-4-(dimethylamino)-2-butenoyl)-4-fluoro-N-(5-(4-((3-methoxypropyl)amino)-2-

((methoxypyridin-4-yl)amino)pyrimidin-5-yl)-4-pentyn-1-yl)pyrrolidine-2-carboxamide, (S,E)-1-(4-(dimethylamino)-2-butenoyl)-N-(5-(2-((2-methoxypyridin-4-yl)amino)-4-(propylamino)pyrimidin-5-yl)-4-pentyn-1-yl)pyrrolidine-2-carboxamide, (2S,4S)-1-((E)-4-(dimethylamino)-2-butenoyl)-4-fluoro-N-(5-(2-((2-methoxypyridin-4-yl)amino)-4-(propylamino)pyrimidin-5-yl)-4-pentyn-1-yl)pyrrolidine-2-carboxamide, (E)-4-(dimethylamino)-N-(2-((5-(2-((2-methoxypyridin-4-yl)amino)-4-(propylamino)pyrimidin-5-yl)-4-pentyn-1-yl)amino)-2-oxoethyl)-N-methyl-2-butenamide, (S,E)-4-(dimethylamino)-N-(1-((5-(2-((3-fluorophenyl)amino)-4-((methoxyphenyl)amino)pyrimidin-5-yl)-4-pentyn-1-yl)amino)-1-oxopropan-2-yl)-N-methyl-2-butenamide, (S,E)-4-(dimethylamino)-N-(1-((5-(2-((3-fluorophenyl)amino)-4-morpholinopyrimidin-5-yl)-4-pentyn-1-yl)amino)-1-oxopropan-2-yl)-N-methyl-2-butenamide, (E)-4-(dimethylamino)-N-(2-((5-(2-((4-fluorophenyl)amino)-4-((3-fluoropropyl)amino)pyrimidin-5-yl)-4-pentyn-1-yl)amino)-2-oxoethyl)-N-methyl-2-butenamide, (S,E)-N-(1-((5-(2-((4-cyanophenyl)amino)-4-(cyclopropylamino)pyrimidin-5-yl)-4-pentyn-1-yl)amino)-1-oxopropan-2-yl)-4-(dimethylamino))-N-methyl-2-butenamide, (S,E)-N-(1-((5-(2-((4-cyanophenyl)amino)-4-((3-fluoropropyl)amino)pyrimidin-5-yl)-4-pentyn-1-yl)amino)-1-oxopropan-2-yl)-4-(dimethylamino))-N-methyl-2-butenamide, (S,E)-4-(dimethylamino))-N-(1-((5-(4-(ethylamino)-2-((1-methyl-1H-indazol-5-yl)amino)pyrimidin-5-yl)-4-pentyn-1-yl)amino)-1-oxopropan-2-yl)-N-methyl-2-butenamide, (S,E)-N-(1-((5-(4-(cyclopropylamino)-2-((1-methyl-1H-indazol-5-yl)amino)pyrimidin-5-yl)-4-pentyn-1-yl)amino)-1-oxopropan-2-yl)-4-(dimethylamino))-N-methyl-2-butenamide, (S,E)-4-(dimethylamino))-N-methyl-N-(1-((5-(2-((1-methyl-1H-indazol-5-yl)amino)-4-(methylamino)pyrimidin-5-yl)-4-pentyn-1-yl)amino)-1-oxopropan-2-yl)-2-butenamide, (S,E)-N-(5-(2-((1H-indazol-5-yl)amino)-4-(methylamino)pyrimidin-5-yl)-4-pentyn-1-yl)-1-(4-(dimethylamino)-2-butenoyl)pyrrolidine-2-carboxamide, (S,E)-N-(5-(2-((1H-indazol-5-yl)amino)-4-(ethylamino)pyrimidin-5-yl)-4-pentyn-1-yl)-1-(4-(dimethylamino)-2-butenoyl)pyrrolidine-2-carboxamide, (S,E)-N-(5-(2-((1H-indazol-5-yl)amino)-4-((3-methoxypropyl)amino)pyrimidin-5-yl)-4-pentyn-1-yl)-1-(4-(dimethylamino)-2-butenoyl)pyrrolidine-2-carboxamide, (E)-4-(dimethylamino)-N—((S)-1-(((1S,3R)-3-((2-((3-fluorophenyl)amino)-4-(propylamino)pyrimidin-5-yl)ethynyl)cyclohexyl)amino)-1-oxopropan-2-yl)-N-methyl-2-butenamide, (E)-4-(dimethylamino)-N—((S)-1-(((1S,3R)-3-((2-((3-fluorophenyl)amino)-4-(propylamino)pyrimidin-5-yl)ethynyl)cyclobutyl)amino)-1-oxopropan-2-yl)-N-methyl-2-butenamide, (E)-N—((S)1-(((1S,3R)-3-((2-((4-cyanophenyl)amino)-4-(methylamino)pyrimidin-5-yl)ethynyl)cyclobutyl)amino)-1-oxopropan-2-yl)-4-(dimethylamino)-N-methyl-2-butenamide, (E)-4-(dimethylamino)-N—((S)-1-(((1S,3R)-3-((2-((3-fluorophenyl)amino)4-(methylamino)pyrimidin-5-yl)ethynyl)cyclobutyl)amino)-1-oxopropan-2-yl)-N-methyl-2-butenamide, (E)-N—((S)-1-(((1S,3R)-3-((2-((4-cyanophenyl)amino)-4-(methylamino)pyrimidin-5-yl)ethynyl)cyclobutyl)amino)-1-oxopropan-2-yl)-4-(dimethylamino)-N-methyl-2-butenamide, (E)-N—((S)-1-(((1S,3R)-3-((2-((3-cyanophenyl)amino)-4-(methylamino)pyrimidin-5-yl)ethynyl)cyclobutyl)amino)-1-oxopropan-2-yl)-4-(dimethylamino)-N-methyl-2-butenamide, (E)-4-(dimethylamino)-N—((S)-1-(((1S,3R)-3-((2-((3-fluoro-4-methoxyphenyl)amino)-4-(methylamino)pyrimidin-5-yl)ethynyl)cyclobutyl)amino)-1-oxopropan-2-yl)-N-methyl-2-butenamide, (E)-4-(dimethylamino)-N—((S)-1-(((1S,3R)-3-((2-((4-fluorophenyl)amino)-4-(methylamino)pyrimidin-5-yl)ethynyl)cyclobutyl)amino)-1-oxopropan-2-yl)-N-methyl-2-butenamide, (E)-N—((S)-1-(((1S,3R)-3-((2-((3-cyanophenyl)amino)-4-(cyclopropylamino)pyrimidin-5-yl)ethynyl)cyclobutyl)amino)-1-oxopropan-2-yl)-4-(dimethylamino)-N-methyl-2-butenamide, (E)-4-(dimethylamino)-N—((S)-1-(((1S*,3R*)-3-((2-((2-fluoropyridin-4-yl)amino)-4-(propylamino)pyrimidin-5-yl)ethynyl)cyclobutyl)amino)-1-oxopropan-2-yl)-N-methyl-2-butenamide, (E)-4-(dimethylamino)-N—((S)-1-(((1S,3R)-3-((2-((2-methoxypyridin-4-yl)amino)-4-(propylamino)pyrimidin-5-yl)ethynyl)cyclobutyl)amino)-1-oxopropan-2-yl)-N-methyl-2-butenamide, (E)-N—((S)-1-(((1S,3R)-3-((2-((4-cyanophenyl)amino)-4-(methylamino)pyrimidin-5-yl)ethynyl)cyclohexyl)amino)-1-oxopropan-2-yl)-4-(dimethylamino)-N-methyl-2-butenamide, (E)-N—((S)-1-(((1S*,3R*)-3-((2-((4-cyanophenyl)amino)-4-(cyclopropylamino)pyrimidin-5-yl)ethynyl)cyclobutyl)amino)-1-oxopropan-2-yl)-4-(dimethylamino)-N-methyl-2-butenamide, (E)-N—((S)-1-(((1S*,3R*)-3-((4-(cyclopropylamino)-2-((4-fluorophenyl)amino)pyrimidin-5-yl)ethynyl)cyclobutyl)amino)-1-oxopropan-2-yl)-4-(dimethylamino)-N-methyl-2-butenamide, (E)-N—((S)-1-(((1S*,3R*)-3-((4-(cyclopropylamino)-2-((3-fluoro-4-methoxyphenyl)amino)pyrimidin-5-yl)ethynyl)cyclobutyl)amino)-1-oxopropan-2-yl)-4-(dimethylamino)-N-methyl-2-butenamide, (E)-4-(dimethylamino)-N—((S)-1-(((1S,3R)-3-((2-((3-fluorophenyl)amino)-4-((3-fluoropropyl)amino)pyrimidin-5-yl)ethynyl)cyclobutyl)amino)-1-oxopropan-2-yl)-N-methyl-2-butenamide, (E)-N—((S)-1-(((1S,3R)-3-((2-((4-cyanophenyl)amino)-4-((3-fluoropropyl)amino)pyrimidin-5-yl)ethynyl)cyclobutyl)amino)-1-oxopropan-2-yl)-4-(dimethylamino)-N-methyl-2-butenamide, (E)-4-(dimethylamino)-N—((S)-1-(((1S,3R)-3-((2-((3-fluorophenyl)amino)-4-((3-methylpropyl)amino)pyrimidin-5-yl)ethynyl)cyclobutyl)amino)-1-oxopropan-2-yl)-N-methyl-2-butenamide, (E)-N—((S)-1-(((1S,3R)-3-((2-((4-cyanophenyl)amino)-4-((3-methoxypropyl)amino)pyrimidin-5-yl)ethynyl)cyclobutyl)amino)-1-oxopropan-2-yl)-4-(dimethylamino)-N-methy-2-butenamide, (E)-4-(dimethylamino)-N—((S)-1-(((1S,3R)-3-((2-((3-fluoro-4-methoxyphenyl)amino)-4-(methylamino)pyrimidin-5-yl)ethynyl)cyclohexyl)amino)-1-oxopropan-2-yl)-N-methyl-2-butenamide, (S,E)-4-(dimethylamino)-N-methyl-N-(1-((5-(2-((2-methylpyridin-4-yl)amino)-4-(propylamino)pyrimidin-5-yl)-4-pentyn-1-yl)amino)-1-oxopropan-2-yl)-2-butenamide, (S,E)-N-(1-((5-(2-(benzo[d]thiazol-6-ylamino)-4-(propylamino)pyrimidin-5-yl)-4-pentyn-1-yl)amino)-1-oxopropan-2-yl)-4-(dimethylamino)-N-methyl-2-butenamide, (S,E)-1-(4-(dimethylamino)-2-butenoyl)-N-(5-(2-((1-methyl-1H-indazol-5-yl)amino)-4-(propylamino)pyrimidin-5-yl)-4-pentyn-1-yl)pyrrolidine-2-carboxamide, (S,E)-1-(4-(dimethylamino)-2-butenoyl)-N-(5-(2-((1-methyl-1H-pyrazolo[3,4-b]pyridin-5-yl)amino)-4-(propylamino)pyrimidin-5-yl)-4-pentyn-1-yl)pyrolidine-2-carboxamide, (S,E)-1-(4-(dimethylamino)-2-butenoyl)-N-(5-(2-((1-(2-methoxyethyl)-1H-pyrazolo[3,4-b]pyridin-5-yl)amino)-4-(propylamino)pyrimidin-5-yl)-4-pentyn-1-yl)pyrrolidine-2-carboxamide, (S,E)-4-(dimethylamino)-N-methyl-N-(1-((5-(2-((3-methyl-1H-pyrazolo[3,4-b]pyridin-5-yl)amino)-4-(propylamino)pyrimidin-5-yl)-4-pentyn-1-yl)amino)-oxopropan-2-yl)-2-butenamide, (S,E)-1-(4-(dimethylamino)-2-butenoyl)-N-(5-(2-((3-methyl-1H-pyrazolo[3,4-b]pyridin-5-yl)amino)-4-(propylamino)pyrimidin-5-yl)-4-pentyn-1-yl)pyrrolidine-2-carboxamide, and (S,E)-1-(4-dimethylamino)-2-butenoyl)-N-(5-(2-((3- methoxy-1H-pyrazolo[3,4-b]pyridin-5-yl)amino)-4-(propylamino)pyrimidin-5-yl)-4-pentyn-1-yl)pyrrolidine-2-carboxamide.

18. A pharmaceutical composition containing the compound or a salt thereof according to claim 1 together with a pharmaceutically acceptable additive.

19. A method for treatment of a disease or condition selected from the group consisting of acute lymphocytic leukemia, acute myeloid leukemia, acute promyelocytic leukemia, chronic lymphocytic leukemia, chronic myeloid leukemia, chronic neutrophilic leukemia, acute undifferentiated leukemia, anaplastic large cell lymphoma, prolymphocytic leukemia, juvenile myelomonocytic leukemia, adult T cell ALL, myelodysplastic syndrome, and myeloproliferative disorder in a subject in need of such treatment comprising the step of administering to the subject a compound or a salt thereof according to claim 1.

20. A method for inhibiting FLT3, comprising contacting FLT3 with a compound or a salt thereof according to claim 1.

* * * * *